United States Patent
Nakamura et al.

(10) Patent No.: US 8,962,648 B2
(45) Date of Patent: Feb. 24, 2015

(54) TRICYCLIC COMPOUNDS AND PBK INHIBITORS CONTAINING THE SAME

(75) Inventors: Yusuke Nakamura, Tokyo (JP); Yo Matsuo, Kanagawa (JP); Shoji Hisada, Kanagawa (JP); Feryan Ahmed, Latham, NY (US); Raymond Huntley, Albany, NY (US); Zohreh Sajjadi-Hashemi, Schenectady, NY (US); David M. Jenkins, Cohoes, NY (US); Robert B. Kargbo, Guilderland, NY (US); Wenge Cui, Clifton Park, NY (US); Polivina Jolicia F. Gauuan, Schenectady, NY (US); Joel R. Walker, Schenectady, NY (US); Helene Decornez, Clifton Park, NY (US); Mahender Gurram, Guilderland, NY (US)

(73) Assignee: OncoTherapy Science, Inc., Kanagawa (JP)

( * ) Notice: Subject to any disclaimer, the term of this patent is extended or adjusted under 35 U.S.C. 154(b) by 607 days.

(21) Appl. No.: 13/202,544

(22) PCT Filed: Mar. 29, 2011

(86) PCT No.: PCT/US2011/030278
§ 371 (c)(1),
(2), (4) Date: Aug. 19, 2011

(87) PCT Pub. No.: WO2011/123419
PCT Pub. Date: Oct. 6, 2011

(65) Prior Publication Data
US 2013/0178459 A1 Jul. 11, 2013

Related U.S. Application Data

(60) Provisional application No. 61/318,606, filed on Mar. 29, 2010.

(51) Int. Cl.
| | | |
|---|---|---|
| *A61K 31/44* | (2006.01) | |
| *A61K 31/38* | (2006.01) | |
| *C07D 455/04* | (2006.01) | |
| *C07D 333/50* | (2006.01) | |
| *C07D 495/04* | (2006.01) | |
| *C07D 221/06* | (2006.01) | |
| *C07D 487/04* | (2006.01) | |
| *C07D 513/04* | (2006.01) | |
| *C07D 221/16* | (2006.01) | |
| *C07D 401/10* | (2006.01) | |

(52) U.S. Cl.
CPC ............ *C07D 495/04* (2013.01); *C07D 221/06* (2013.01); *C07D 487/04* (2013.01); *C07D 513/04* (2013.01); *C07D 221/16* (2013.01); *C07D 401/10* (2013.01)
USPC ................ 514/291; 514/443; 546/80; 549/41

(58) Field of Classification Search
None
See application file for complete search history.

(56) References Cited

U.S. PATENT DOCUMENTS

| | | |
|---|---|---|
| 5,189,055 A | 2/1993 | Thal et al. |
| 7,253,180 B2 | 8/2007 | Chen et al. |
| 2003/0166929 A1 | 9/2003 | Snow et al. |
| 2004/0138230 A1 | 7/2004 | Andreana et al. |
| 2006/0247217 A1 | 11/2006 | Berger et al. |
| 2009/0105233 A1 | 4/2009 | Chua et al. |
| 2009/0239859 A1 | 9/2009 | Chua et al. |
| 2010/0183551 A1 | 7/2010 | Harper et al. |
| 2011/0263581 A1 | 10/2011 | Chua et al. |

FOREIGN PATENT DOCUMENTS

| | | |
|---|---|---|
| JP | 53077096 A * | 7/1978 |
| WO | 2004/026864 A1 | 4/2004 |
| WO | WO 2006/120573 A2 | 11/2006 |
| WO | 2008/028168 A3 | 3/2008 |
| WO | 2009/010804 A1 | 1/2009 |

OTHER PUBLICATIONS

Bew et al. Journal of the Chemical Society (1955) 1775-8.*
STN Abstract JP 53077096 A.*
STN Abstract Ombetta 1989.*
Park, J-H., et al., "PDZ-Binding Kinase/T-LAK Cell-Originated Protein Kinase, a Putative Cancer/Testis Antigen with an Oncogenic Activity in Breast Cancer," Cancer Res., vol. 66(18), Abstract Only, 2 pgs (2006), http://cancerres.aacrjournals.org/content/66/18/9186.abstract.
Park, J-H. et al., "PDZ-Binding Kinase/T-LAK Cell-Originated Protein Kinase, a Putative Cancer/Testis Antigen with an Oncogenic Activity in Breast Cancer," Cancer Res., vol. 66(18), abstract only, 2 pgs. (2006).
Abe, et al., "Cloning and Expression of a Novel MAPKK-like Protein Kinase, Lymphokine-activated Killer T-cell-originated Protein Kinase, Specifically Expressed in the Testis and Activated Lymphoid Cells " *J. Biol Chem.*, vol. 275(28), pp. 21525-21531 (Jul. 14, 2000).
Bailey, et al., "The Reactions of p-Toluensulphonyl Azide with Substituted Indoles," *Tetrahedron Letters*, No. 34, pp. 2979-2982 (1970).
Beccalli, et al., "Synthesis of Tricyclic Quinolones and Naphthyridones by Intramolecular Heck Cyclization of Functionalized Electron-Rich Heterocycles," *Eur. J. Org. Chem.*, pp. 2091-2096 (2005).
Brown, et al., The Reaction of Ethyl 2-Oxocyclopentanecarboxylate with Arylamines. Part I. The Preparation of 2,3-Dihydro-α-quinindones (2, 3, 4, 5-Tetrahydro-4-oxo-IH-cyclopenta[c]quinolines), *Journal of the Chemical Society*, pp. 4295-4298 (1961).
Ferraccioli, et al., "Synthesis of 6-Phenanthridinones and Their Heterocyclic Analogues through Palladium-Catalyzed Sequential Aryl-Aryl and N-Aryl Coupling," *Organic Letters*, vol. 6, No. 25, pp. 4759-4762 (2004).

(Continued)

*Primary Examiner* — Jeffrey S. Lundgren
*Assistant Examiner* — Michael Schmitt
(74) *Attorney, Agent, or Firm* — Kilpatrick Townsend & Stockton LLP

(57) ABSTRACT

Tricyclic compounds are provided. These compounds are PBK inhibitors, and are useful for the treatment of PBK related diseases, including cancer.

14 Claims, No Drawings

(56) References Cited

OTHER PUBLICATIONS

Fujibuchi, et al., "Expression and phosphorylation of TOPK during spermatogenesis," *Dev Growth Differ.*, vol. 47(9), pp. 637-644 (Dec. 2005).

Gaudet, et al., "Characterization of PDZ-binding kinase, a mitotic kinase," *Proc Natl Acad Sci. USA*, vol. 97(10), pp. 5167-5172 (May 9, 2000).

Gorlitzer, et al., "Thieno[2,3-c]chinoline—Synthese and biologische Prufung" *Pharmazie*, vol. 59, pp. 439-442 (2004).

Jaroch, et al., "Dihydroquinolines as Novel n-NOS Inhibitors," *Bioorganic & Medicinal Chemistry Letters*, vol. 12, pp. 2561-2564 (2002).

Jaroch, et al., "Fluorinated dihydroquinolines as potent *n*-NOS inhibitors," *Bioorganic & Medicinal Chemistry Letters*, vol. 14, pp. 743-746 (2004).

Matsumoto, et al., "Characterization of a MAPKK-like protein kinase TOPK," *Biochem Biophys Res Commun.*, vol. 325(3), pp. 997-1004 (Dec. 2004).

Nandi, et al., "Protein expression of PDZ-binding kinase is up-regulated in hematologic malignancies and strongly down-regulated during terminal differentiation of HL-60 leukemic cells," *Blood Cells Mol Dis.*, vol. 32(1), pp. 240-245 (Jan. 2004-Feb. 2004).

Simons-Evelyn, et al., "PBK/TOPK is a Novel Mitotic Kinase Which is Upregulated in Burkitt's Lymphoma and Other Highly Proliferative Malignant Cells," *Blood Cells Mol Dis.*, vol. 27(5), pp. 825-829 (Sep. 2001-Oct. 2001).

Temciuc, et al., "An Unexpected [2+2]-Cycloaddition Reaction of 4-Methyldithieno-[3,4-*b*:3',2'-*d*]pyridinium Iodide with Dimethyl Acetylenedicarboxylate," *Tetrahedron*, vol. 51, No. 48, pp. 13185-13196 (1995).

Vaillard, et al., "Synthesis of novel fused azaheterocycles by photostimulated intramolecular $S_{RN}1$ reactions with nitrogen nucleophiles," *Tetrahedron Letters*, vol. 50, pp. 3829-3832 (2009).

European Search Report for European Application No. EP 11763307.3, 11 pages, issued on Jul. 17, 2013.

Office Action issued in EP 11 763 307.3 on Mar. 5, 2014, 4 pages.

Ombetta et al.; "Préparation et approche pharmacologique d'une série de dihydro-4,5 thiéno [2,3-c] quinoléiones-4," Annales pharmaceutiques françaises, 1988, vol. 46, No. 6, pp. 377-389.

* cited by examiner

TRICYCLIC COMPOUNDS AND PBK INHIBITORS CONTAINING THE SAME

PRIORITY

The present application is a U.S. National Phase Application of PCT/US2011/030278, filed Mar. 29, 2011, which claims the benefit of U.S. Provisional Application No. 61/318,606, filed on Mar. 29, 2010, the contents of each of which are hereby incorporated herein by reference in their entirety for all purposes.

TECHNICAL FIELD

The present invention relates to a compound for inhibiting PBK activity, a method for the preparation thereof, and a pharmaceutical composition containing the compound as an active ingredient.

BACKGROUND ART

Previous studies revealed that PDZ binding kinase (PBK) is a serine/threonine kinase related to the dual specific mitogen-activated protein kinase kinase (MAPKK) family (Abe Y, et al., J Biol. Chem. 275: 21525-21531, 2000, Gaudet S, et al., Proc Natl Acad. Sci. 97: 5167-5172, 2000 and Matsumoto S, et al., Biochem Biophys Res Commun. 325: 997-1004, 2004). PBK was also indicated to be involved in mitosis as shown by its significant role in highly proliferating spermatocytes (Gaudet S, et al., Proc Natl Acad. Sci. 97: 5167-5172, 2000 and Fujibuchi T, et al., Dev Growth Differ. 47:637-44, 2005). In fact, abundant expression of PBK was observed in testis, while almost no PBK expression was detected in other normal organs (Park J H, et al., Cancer Res. 66: 9186-95, 2006). PBK regulates cell cycle progression. In accordance with this, its significant overexpression was detected in clinical breast cancer samples (Park J H, et al., Cancer Res. 66: 9186-95, 2006), Burkitt's lymphoma (Simons-Evelyn M, et al., Blood Cells Mol Dis. 27: 825-829, 2001) and a variety of hematologic malignancies (Nandi A, et al., Blood Cells Mol Dis. 32: 240-5, 2004).

Immunohistochemical analysis of testis revealed the expression of PBK protein around the outer region of seminiferous tubules where repeated mitosis of sperm germ cells followed by meiosis occurs (Fujibuchi T, et al., Dev Growth Differ. 47: 637-44, 2005). Especially, at prophase and metaphase, the subcellular localization of PBK was detected around the condensed chromosome in breast cancer cells (Park J H, et al., Cancer Res. 66: 9186-95, 2006). Moreover the knockdown of PBK expression with gene specific siRNAs caused dysfunction of cytokinesis and subsequently led to apoptosis of the cancer cells (Park J H, et al., Cancer Res. 66: 9186-95, 2006). These indicated the critical function of PBK at mitosis, in testicular and cancer cells.

Taken together, PBK-specific inhibitors can be used as a drug applicable for a broad spectrum of cancers. PBK is an excellent target for cancer therapy for the following reasons: i) almost no expression in normal organs (except for testis); ii) frequent overexpression in clinical cancer samples; iii) a serine/threonine kinase related to the essential function for cell mitosis.

The present inventors have found that a Tricyclic compound can selectively inhibit the activity of PBK.

SUMMARY OF INVENTION

Accordingly, it is an object of the present invention to provide a PBK inhibitor having high inhibitory activity against PBK.

It is another object of the present invention to provide a method for preparing such inhibitor.

It is a further object of the present invention to provide a pharmaceutical composition including the compound, a pharmaceutically acceptable salt, hydrate, solvate, or isomer thereof.

In accordance with one aspect of the present invention, there is provided a compound of formula (I), and a pharmaceutically acceptable salt, hydrate, solvate, or isomer thereof:

A compound represented by general formula I:

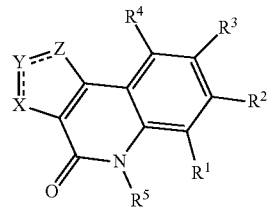

I or a pharmaceutically acceptable salt thereof,
wherein $R^1$, $R^2$, $R^3$, and $R^4$ are each independently a group selected from the group consisting of:
hydrogen,
hydroxyl,
halogen,
cyano,
nitro,
amino,
$C_1$-$C_6$ alkyl,
$C_2$-$C_6$ alkenyl,
$C_2$-$C_6$ alkynyl,
$C_3$-$C_{10}$ cycloalkyl,
$C_3$-$C_{10}$ cycloalkenyl,
$C_1$-$C_6$ alkoxy,
$C_6$-$C_{10}$ aryl,
indanyl,
heteroaryl,
3- to 8-membered heterocycloalkyl,
—$OSO_2CH_3$,
—$OSO_2CF_3$, and
—$CONH_2$,
wherein each of the groups of $R^1$ to $R^4$ is optionally substituted with a substituent selected from the group consisting of substituent A below:
substituent A:
  hydroxyl;
  oxo (=O);
  cyano;
  halogen;
  $C_1$-$C_6$ alkyl (wherein the $C_1$-$C_6$ alkyl is optionally substituted with a substituent selected from the group consisting of substituent B below);
  $C_3$-$C_{10}$ cycloalkyl [wherein the $C_3$-$C_{10}$ cycloalkyl is optionally substituted with cyano, or $C_1$-$C_6$ alkyl substituted with —$NR^{31}R^{32}$ (wherein $R^{31}$ and $R^{32}$ each independently represent hydrogen or $C_1$-$C_6$ alkyl)];
  —$NR^{21}R^{22}$ [wherein $R^{21}$ and $R^{22}$ each independently represent hydrogen, or $C_1$-$C_6$ alkyl (wherein the $C_1$-$C_6$ alkyl is optionally substituted with di($C_1$-$C_6$ alkyl) amino, $C_1$-$C_6$ alkylsulfonyl (—$SO_2$($C_1$-$C_6$ alkyl)), or 3- to 8-membered heterocycloalkyl)];
  $C_1$-$C_6$ alkoxy {wherein the $C_1$-$C_6$ alkoxy is optionally substituted with halogen, 3- to 8-membered heterocycloalkyl (wherein the 3- to 8-membered heterocycloalkyl is optionally substituted with $C_1$-$C_6$ alkyl), or —$NR^{33}R^{34}$ [wherein $R^{33}$ and $R^{34}$ each independently represent hydrogen, $C_1$-$C_6$ alkyl (wherein the $C_1$-$C_6$ alkyl is optionally substituted with $C_1$-$C_6$ alkylsulfonyl or di($C_1$-$C_6$ alkyl)amino), or $C_1$-$C_6$ alkylsulfonyl]};

—$SO_2NR^{23}R^{24}$ {wherein $R^{23}$ and $R^{24}$ each independently represent hydrogen, $C_1$-$C_6$ alkyl [wherein the $C_1$-$C_6$ alkyl is optionally substituted with hydroxyl, $C_1$-$C_6$ alkoxy, halogen, $C_3$-$C_{10}$ cycloalkyl, or —$NR^{35}R^{36}$ (wherein $R^{35}$ and $R^{36}$ each independently represent hydrogen or $C_1$-$C_6$ alkyl)], $C_3$-$C_{10}$ cycloalkyl (wherein the $C_3$-$C_{10}$ cycloalkyl is optionally substituted with $C_1$-$C_6$ hydroxyalkyl), or 3- to 8-membered heterocycloalkyl; or $R^{23}$ and $R^{24}$ may together form 3- to 8-membered heterocycloalkyl wherein the 3- to 8-membered heterocycloalkyl is optionally substituted with amino};

$C_1$-$C_6$ alkylsulfonyl (wherein the $C_1$-$C_6$ alkyl moiety is optionally substituted with hydroxyl);

$C_1$-$C_6$ alkylsulfonylamino (—$NHSO_2(C_1$-$C_6$ alkyl)) [wherein the $C_1$-$C_6$ alkyl moiety is optionally substituted with —$NR^{37}R^{38}$ (wherein $R^{37}$ and $R^{38}$ each independently represent hydrogen or $C_1$-$C_6$ alkyl)];

3- to 8-membered heterocycloalkyl {wherein the 3- to 8-membered heterocycloalkyl is optionally substituted with —$NR^{39}R^{40}$ (wherein $R^{39}$ and $R^{40}$ each independently represent hydrogen, $C_1$-$C_6$ alkyl, or $C_1$-$C_6$ alkylsulfonyl), $C_1$-$C_6$ alkyl [wherein the $C_1$-$C_6$ alkyl is optionally substituted with —$NR^{41}R^{42}$ (wherein $R^{41}$ and $R^{42}$ each independently represent hydrogen or $C_1$-$C_6$ alkyl)], hydroxyl, or $C_1$-$C_6$ alkylsulfonyl};

heteroaryl;

—$COOR^{11}$ (wherein $R^{11}$ represents hydrogen or $C_1$-$C_6$ alkyl); and

—$COR^{12}$ [wherein $R^{12}$ represents $C_1$-$C_6$ alkyl, $C_3$-$C_{10}$ cycloalkyl, cyanomethyl, —$NR^{25}R^{26}$ {wherein $R^{25}$ and $R^{26}$ each independently represent, or $C_1$-$C_6$ alkyl [wherein the $C_1$-$C_6$ alkyl is optionally substituted with hydroxyl or —$NR^{43}R^{44}$ (wherein $R^{43}$ and $R^{44}$ each independently represent hydrogen or $C_1$-$C_6$ alkyl)]}, or 3- to 8-membered heterocycloalkyl which is optionally substituted with $C_1$-$C_6$ alkyl], substituent B:

halogen;

hydroxyl;

cyano;

3- to 8-membered heterocycloalkyl (wherein the 3- to 8-membered heterocycloalkyl is optionally substituted with $C_1$-$C_6$ alkyl, hydroxyl, amino, $C_1$-$C_6$ aminoalkyl, or $C_1$-$C_6$ alkyl substituted with $C_2$-$C_7$ alkyloxycarbonylamino);

—$NR^{51}R^{52}$ {wherein $R^{51}$ and $R^{52}$ each independently represent hydrogen, $C_1$-$C_6$ alkyl [wherein the $C_1$-$C_6$ alkyl is optionally substituted with $C_1$-$C_6$ alkylsulfonyl, or 3- to 8-membered heterocycloalkyl optionally substituted with —$COOR^{53}$ (wherein $R^{53}$ represents hydrogen or $C_1$-$C_6$ alkyl)], 3- to 8-membered heterocycloalkyl, $C_1$-$C_6$ alkylsulfonyl, $C_3$-$C_{10}$ cycloalkyl, —$COR^{55}$ (wherein $R^{55}$ represents $C_1$-$C_6$ alkyl), —$COOR^{56}$ (wherein $R^{56}$ represents $C_1$-$C_6$ alkyl), or —$CONR^{57}R^{58}$ (wherein $R^{57}$ and $R^{58}$ each independently represent hydrogen or $C_1$-$C_6$ alkyl)}; and —$COOR^{54}$ (wherein $R^{54}$ represents hydrogen or $C_1$-$C_6$ alkyl)];

wherein $R^5$ is hydrogen or $C_1$-$C_6$ alkyl; and wherein $$—X\!=\!\!=\!Y\!=\!\!=\!Z—$$

is a structure selected from the group consisting of
(i) —S—$CR^7$=$CR^6$—,
(ii) —$CH_2$—$CH_2$—$CH_2$—,
(iii) —NH—CH=$CCH_3$—, and
(iv) —N=CH—S—, wherein $R^6$ is
hydrogen,
hydroxyl,
$C_1$-$C_6$ alkyl,
$C_6$-$C_{10}$ aryl (wherein the $C_6$-$C_{10}$ aryl is optionally substituted with hydroxyl), or 3- to 8-membered heterocycloalkyl [wherein the 3- to 8-membered heterocycloalkyl is optionally substituted with —$NR^{61}R^{62}$ (wherein $R^{61}$ and $R^{62}$ each independently represent hydrogen or $C_1$-$C_6$ alkyl)], and wherein $R^7$ is
hydrogen,
$C_1$-$C_6$ alkyl (wherein the $C_1$-$C_6$ alkyl is optionally substituted with hydroxyl, —$NR^{71}R^{72}$ [wherein $R^{71}$ and $R^{72}$ each independently represent hydrogen, $C_1$-$C_6$ alkyl (wherein the $C_1$-$C_6$ alkyl is optionally substituted with dimethylamino), $C_3$-$C_{10}$ cycloalkyl (wherein the $C_3$-$C_{10}$ cycloalkyl is optionally substituted with amino), or 3- to 8-membered heterocycloalkyl], or 3- to 8-membered heterocycloalkyl (wherein the 3- to 8-membered heterocycloalkyl is optionally substituted with $C_1$-$C_6$ aminoalkyl)),
$C_6$-$C_{10}$ aryl (wherein the $C_6$-$C_{10}$ aryl is optionally substituted with hydroxyl), or
—$COR^{73}$ {wherein $R^{73}$ represents 3- to 8-membered heterocycloalkyl (wherein the 3- to 8-membered heterocycloalkyl is optionally substituted with amino), or —$NR^{74}R^{75}$ [wherein $R^{74}$ and $R^{75}$ each independently represent hydrogen, 3- to 8-membered heterocycloalkyl, or $C_3$-$C_{10}$ cycloalkyl (wherein the $C_3$-$C_{10}$ cycloalkyl is optionally substituted with amino)]}.

It must be noted that as used in the specification and in the appended claims, the singular forms "a", "an", and "the" include plural reference unless the context clearly dictates otherwise. Thus, for example, reference to "a group" is a reference to one or more groups.

DESCRIPTION OF EMBODIMENTS

In this invention, "alkyl" group refers to a straight chain or a branched chain hydrocarbon group which does not contain any hetero atoms or unsaturated carbon-carbon bonds. "$C_1$-$C_6$ alkyl" refers to an alkyl group which has 1-6 carbon atom(s). "$C_1$-$C_4$ alkyl" refers to an alkyl group which has 1-4 carbon atom(s).

Examples of "C1-C6 alkyl" include, but are not limited to, methyl, ethyl, 1-propyl, 2-propyl, 2-methyl-1-propyl, 2-methyl-2-propyl(tert-butyl(1,1-dimethyl-ethyl), 1-butyl, 2-butyl, 1-pentyl, 2-pentyl, 3-pentyl, 2-methyl-1-butyl, 3-methyl-1-butyl, 2-methyl-2-butyl, 3-methyl-2-butyl, 2,2-dimethyl-1-propyl, 1-hexyl, 2-hexyl, 3-hexyl, 2-methyl-1-pentyl, 3-methyl-1-pentyl, 4-methyl-1-pentyl, 2-methyl-2-pentyl, 3-methyl-2-pentyl, 4-methyl-2-pentyl, 2-methyl-3-pentyl, 3-methyl-3-pentyl, 2,3-dimethyl-1-butyl, 3,3-dimethyl-1- butyl, 2,2-dimethyl-1-butyl, 2-ethyl-1-butyl, 3,3-dimethyl-2-butyl, and 2,3-dimethyl-2-butyl.

In this invention, "alkenyl" group refers to a straight chain or a branched chain hydrocarbon group which contains one or more than one unsaturated carbon-carbon bond(s) and does not contain any hetero atoms. "$C_2$-$C_6$ alkenyl" refers to an alkenyl group which has 2-6 carbon atoms.

Examples of "$C_2$-$C_6$ alkenyl" include, but are not limited to, vinyl(ethenyl), 1-propenyl, 2-propenyl, 3-propenyl, 2-methyl-prop-1-en-1-yl(2-methyl-1-propenyl), 2-methyl-prop-1-en-3-yl(2-methyl-2-propenyl), but-1-en-1-yl, but-1-en-2-yl, but-1-en-3-yl, but-2-en-1-yl, but-2-en-2-yl, pent-1-en-1-yl, pent-1-en-2-yl, pent-1-en-3-yl, pent-1-en-4-yl, pent-1-en-5-yl, pent-2-en-1-yl, pent-2-en-2-yl, pent-2-en-3-yl(1-ethyl-1-propenyl), pent-2-en-4-yl, pent-2-en-5-yl, 2-methyl-but-1-en-1-yl, 2-methyl-but-1-en-2-yl, 2-methyl-but-1-en-3-yl, 2-methyl-but-1-en-4-yl, 2-methyl-but-2-en-1-yl, 2-methyl-but-2-en-3-yl, 2-methyl-but-2-en-4-yl, 3-methyl-but-1-en-1-yl, 3-methyl-but-1-en-2-yl, 3-methyl-but-1-en-3-yl, 3-methyl-but-1-en-4-yl, 2,2-dimethyl-prop-1-en-1-yl, 2,2-dimethyl-prop-1-en-2-yl, hex-1-en-1-yl, hex-1-en-2-yl, hex-1-en-3-yl, hex-1-en-4-yl, hex-1-en-5-yl, hex-1-en-6-yl, hex-2-en-1-yl, hex-2-en-2-yl, hex-2-en-3-yl, hex-2-en-4-yl, hex-2-en-5-yl, hex-2-en-6-yl, hex-3-en-1-yl, hex-3-en-2-yl, hex-3-en-3-yl, 2-methyl-pent-1-en-1-yl, 2-methyl-pent-1-en-3-yl, 2-methyl-pent-1-en-4-yl, 2-methyl-pent-1-en-5-yl, 2-methyl-pent-2-en-1-yl, 2-methyl-pent-2-en-3-yl, 2-methyl-pent-2-en-4-yl, 2-methyl-pent-2-en-5-yl, 3-methyl-pent-1-en-1-yl, 3-methyl-pent-1-en-2-yl, 3-methyl-pent-1-en-3-yl, 3-methyl-pent-1-en-4-yl, 3-methyl-pent-1-en-5-yl, 3-methyl-pent-2-en-1-yl, 3-methyl-pent-2-en-2-yl, 3-methyl-pent-2-en-4-yl, 3-methyl-pent-2-en-5-yl, 4-methyl-pent-1-en-1-yl, 4-methyl-pent-1-en-2-yl, 4-methyl-pent-1-en-3-yl, 4-methyl-pent-1-en-4-yl, 4-methyl-pent-1-en-5-yl, 4-methyl-pent-2-en-1-yl, 4-methyl-pent-2-en-2-yl, 4-methyl-pent-2-en-3-yl, 4-methyl-pent-2-en-4-yl, 4-methyl-pent-2-en-5-yl, 2,3-dimethyl-but-1-en-1-yl, 2,3-dimethyl-but-1-en-3-yl, 2,3-dimethyl-but-1-en-4-yl, 2,3-dimethyl-but-2-en-1-yl, 3,3-dimethyl-but-1-en-1-yl, 3,3-dimethyl-but-1-en-2-yl, 3,3-dimethyl-but-1-en-4-yl, 2-ethyl-but-1-en-1-yl, 2-ethyl-but-1-en-3-yl, 2-ethyl-but-1-en-4-yl, 3-ethyl-but-1-en-1-yl, 3-ethyl-but-1-en-2-yl, 3-ethyl-but-1-en-3-yl, 3-ethyl-but-1-en-4-yl, 2-ethyl-but-2-en-1-yl, 2-ethyl-but-2-en-3-yl and 2-ethyl-but-2-en-4-yl.

In this invention, "alkynyl" group refers to a straight chain or a branched chain hydrocarbon group which contains at least one triple carbon-carbon bond and does not contain any hetero atoms. "$C_2$-$C_6$ alkynyl" refers to an alkynyl group which has 2-6 carbon atoms.

Examples of "$C_2$-$C_6$ alkynyl" include, but are not limited to, ethinyl, 1-propinyl, 2-propinyl, 3-propinyl, 2-methyl-prop-1-in-1-yl, 2-methyl-prop-1-in-3-yl, but-1-in-1-yl, but-1-in-2-yl, but-1-in-3-yl, but-2-in-1-yl, but-2-in-2-yl, pent-1-in-1-yl, pent-1-in-2-yl, pent-1-in-3-yl, pent-1-in-4-yl, pent-1-in-5-yl, pent-2-in-1-yl, pent-2-in-2-yl, pent-2-in-3-yl, pent-2-in-4-yl, pent-2-in-5-yl, 2-methyl-but-1-in-1-yl, 2-methyl-but-1-in-2-yl, 2-methyl-but-1-in-3-yl, 2-methyl-but-1-in-4-yl, 2-methyl-but-2-in-1-yl, 2-methyl-but-2-in-3-yl, 2-methyl-but-2-in-4-yl, 3-methyl-but-1-in-1-yl, 3-methyl-but-1-in-2-yl, 3-methyl-but-1-in-3-yl, 3-methyl-but-1-in-4-yl, 2,2-dimethyl-prop-1-in-1-yl, 2,2-dimethyl-prop-1-in-2-yl, hex-1-in-1-yl, hex-1-in-2-yl, hex-1-in-3-yl, hex-1-in-4-yl, hex-1-in-5-yl, hex-1-in-6-yl, hex-2-in-1-yl, hex-2-in-2-yl, hex-2-in-3-yl, hex-2-in-4-yl, hex-2-in-5-yl, hex-2-in-6-yl, hex-3-in-1-yl, hex-3-in-2-yl, hex-3-in-3-yl, 2-methyl-pent-1-in-1-yl, 2-methyl-pent-1-in-3-yl, 2-methyl-pent-1-in-4-yl, 2-methyl-pent-1-in-5-yl, 2-methyl-pent-2-in-1-yl, 2-methyl-pent-2-in-3-yl, 2-methyl-pent-2-in-4-yl, 2-methyl-pent-2-in-5-yl, 3-methyl-pent-1-in-1-yl, 3-methyl-pent-1-in-2-yl, 3-methyl-pent-1-in-3-yl, 3-methyl-pent-1-in-4-yl, 3-methyl-pent-1-in-5-yl, 3-methyl-pent-2-in-1-yl, 3-methyl-pent-2-in-2-yl, 3-methyl-pent-2-in-4-yl, 3-methyl-pent-2-in-5-yl, 4-methyl-pent-1-in-1-yl, 4-methyl-pent-1-in-2-yl, 4-methyl-pent-1-in-3-yl, 4-methyl-pent-1-in-4-yl, 4-methyl-pent-1-in-5-yl, 4-methyl-pent-2-in-1-yl, 4-methyl-pent-2-in-2-yl, 4-methyl-pent-2-in-3-yl, 4-methyl-pent-2-in-4-yl, 4-methyl-pent-2-in-5-yl, 2,3-dimethyl-but-1-in-1-yl, 2,3-dimethyl-but-1-in-3-yl, 2,3-dimethyl-but-1-in-4-yl, 2,3-dimethyl-but-2-in-1-yl, 3,3-dimethyl-but-1-in-1-yl, 3,3-dimethyl-but-1-in-2-yl, 3,3-dimethyl-but-1-in-4-yl, 2-ethyl-but-1-in-1-yl, 2-ethyl-but-1-in-3-yl, 2-ethyl-but-1-in-4-yl, 3-ethyl-but-1-in-1-yl, 3-ethyl-but-1-in-2-yl, 3-ethyl-but-1-in-3-yl, 3-ethyl-but-1-in-4-yl, 2-ethyl-but-2-in-1-yl, 2-ethyl-but-2-in-3-yl and 2-ethyl-but-2-in-4-yl.

In the present invention, "alkoxy" group refers to a group represented by —OR, wherein R is alkyl.

"$C_1$-$C_6$ alkoxy" group refers to an alkoxy group which has 1-6 carbon atom(s). "$C_1$-$C_4$ alkoxy" refers to an alkoxy group which has 1-4 carbon atom(s).

Examples of "$C_1$-$C_6$ alkoxy" include, but are not limited to, methoxy, ethoxy, 1-propyloxy, 2-propyloxy, 2-methyl-1-propyloxy, 2-methyl-2-propyloxy, and 1-butyloxy, and 2-butyloxy.

In the present invention, "cycloalkyl" group refers to a saturated carbon ring system. "$C_3$-$C_{10}$ cycloalkyl" group refers to 3-10 membered cycloalkyl.

Examples of "$C_3$-$C_{10}$ cycloalkyl" include, but are not limited to, cyclopropyl, cyclobutyl, cyclopentyl, cyclohexyl, cycloheptanyl, cyclooctanyl, and adamantyl. For example, 3-8 membered cycloalkyl is also included in "$C_3$-$C_{10}$ cycloalkyl".

In the present invention, "$C_3$-$C_{10}$cycloalkenyl" group refers to a cyclic unsaturated aliphatic hydrocarbon group of 3 to 10 carbon atoms with at least one double bond (two adjacent $SP^2$ carbon atoms).

Specific examples of "$C_3$-$C_{10}$cycloalkenyl" include cyclopropenyl, cyclobutenyl, cyclopentenyl, cyclohexenyl, cycloheptenyl, and cyclooctenyl.

In the present invention, "$C_6$-$C_{10}$aryl" refers to an aromatic cyclic hydrocarbon group of 6 to 10 carbon atoms.

Specific examples of "$C_6$-$C_{10}$aryl" include phenyl, 1-naphthyl, and 2-naphthyl.

In the present invention, "halogen" refers to a fluorine atom, a chlorine atom, a bromine atom, or an iodine atom.

As used herein, "hetero atom" refers to a sulfur atom, an oxygen atom, or a nitrogen atom.

In this invention, "amino" refers to a group represented by —$NH_2$ whose hydrogens may each be optionally substituted by a substituent.

In the present invention, "$C_1$-$C_6$ alkylamino" refers to an amino group bound to the $C_1$-$C_6$ alkyl.

Examples of "$C_1$-$C_6$ alkylamino" include, but are not limited to, methylamino, ethylamino, propylamino, isopropylamino, n-butylamino, s-butylamino, t-butylamino, and 2-ethylbutylamino.

In the present invention, "di($C_1$-$C_6$alkyl)amino" refers to an amino group bound to two "$C_1$-$C_6$alkyls" defined above.

Specific examples of "di($C_1$-$C_6$alkyl)amino" include dimethylamino, diethylamino, dipropylamino, diisopropylamino, di-n-butylamino, di-s-butylamino, di-t-butylamino, and di-2-ethylbutylamino.

In the present invention, "C$_2$-C$_7$alkyloxycarbonylamino" refers to a group represented by (C$_1$-C$_6$alkyl)-O—C=O—NH—, or a group in which the "C$_1$-C$_6$alkyl" defined above is bound to —OCONH—.

In the present invention, "C$_1$-C$_6$aminoalkyl" refers to a group in which an amino group is bound to the "C$_1$-C$_6$alkyl" defined above.

In the present invention, "C$_1$-C$_6$hydroxyalkyl" refers to a group in which one or more hydroxy groups are bound to the "C$_1$-C$_6$alkyl" defined above.

In this invention, "sulfonyl" is a group represented by —SO$_2$—.

In this invention, "C$_1$-C$_6$ alkylsulfonyl" refers to R—SO$_2$— wherein R is the C$_1$-C$_6$ alkyl. "C$_1$-C$_4$ alkylsulfonyl" refers to R—SO$_2$— wherein R is C$_1$-C$_4$ alkyl.

Examples of "C$_1$-C$_6$ alkylsulfonyl" include, but are not limited to, methylsulfonyl, ethylsulfonyl, propylsulfonyl, isopropylsulfonyl, n-butylsulfonyl, s-butylsulfonyl, t-butylsulfonyl, and 2-ethylbutylsulfonyl.

In this invention, "C$_6$-C$_{10}$ arylsulfonyl" refers to R—SO$_2$— wherein R is the C$_6$-C$_{10}$ aryl.

Examples of "C$_6$-C$_{10}$ arylsulfonyl" include, but are not limited to, phenylsulfonyl.

In the present invention, "C$_1$-C$_6$alkylsulfonylamino" refers to R—SO$_2$—NH— wherein R is "C$_1$-C$_6$ alkyl". "C$_1$-C$_4$ alkylsulfonylamino" refers to R—SO$_2$—NH— wherein R is R—SO$_2$—NH— wherein R is "C$_1$-C$_4$ alkyl".

Examples of "C$_1$-C$_6$ alkylsulfonylamino" include, but are not limited to, methylsulfonylamino, ethylsulfonylamino, propylsulfonylamino, isopropylsulfonylamino, n-butylsulfonylamino, s-butylsulfonylamino, t-butylsulfonylamino, and 2-ethylbutylsulfonylamino.

In this invention, "sulfinyl" is a group represented by —SO—.

In this invention, "C$_1$-C$_6$ alkylsulfinyl" refers to R—SO— wherein R is the C$_1$-C$_6$ alkyl. "C$_1$-C$_4$ alkylsulfinyl" refers to R—SO— wherein R is C$_1$-C$_4$ alkyl.

Examples of "C$_1$-C$_6$ alkylsulfinyl" include, but are not limited to, methylsulfinyl, ethylsulfinyl, propylsulfinyl, isopropylsulfinyl, n-butylsulfinyl, s-butylsulfinyl, t-butylsulfinyl, and 2-ethylbutylsulfinyl.

In the present invention, "heteroaryl" refers to a monocyclic or fused aromatic heterocyclic group that includes at least one hetero atom selected from O, S, and N. When the aromatic heterocyclic group is a fused ring, those including a partially hydrogenated ring are also included in "heteroaryl".

Examples of such heteroaryls include pyrazolyl, thiazolyl, isothiazolyl, thiadiazolyl, imidazolyl, furyl, thienyl, oxazolyl, isooxazolyl, pyrrolyl, imidazolyl, (1,2,3)- and (1,2,4)-triazolyl, tetrazolyl, pyranyl, pyridyl, pyrimidinyl, pyrazinyl, pyridazinyl, quinolyl, isoquinolyl, tetrahydroisoquinolyl, benzofuranyl, isobenzofuranyl, indolynyl, indolyl, isoindolyl, indazolyl, benzoimidazolyl, benzotriazolyl, benzooxazolyl, benzothiazolyl, benzo[b]thiophenyl, (1,2)- and (1,3)-benzooxathiol, chromenyl, 2-oxochromenyl, benzothiadiazolyl, quinolizinyl, phthalazinyl, naphthyridinyl, quinoxalinyl, quinazolinyl, cinnolinyl, carbazolyl, tetrahydroisoquinolyl, tetrazolyl, [1,2,4]triazo[1.5-a]pyridyl, 1H-pyrrolo[2,3-b]pyridyl, and 2,3-dihydrobenzooxazolyl.

Preferable examples include pyrazolyl, furyl, thienyl, pyridyl, pyrimidinyl, tetrahydroisoquinolyl, indolynyl, indazolyl, benzoimidazolyl, benzooxazolyl, tetrahydroisoquinolyl, tetrazolyl, [1,2,4]triazo[1.5-a]pyridyl, 1H-pyrrolo[2,3-b]pyridyl, and 2,3-dihydrobenzooxazolyl.

In the present invention, "3- to 8-membered heterocycloalkyl" refers to a non-aromatic monovalent 3- to 8-membered ring that includes 1 to 3 hetero atoms in the atoms forming the ring, and that may have a double bond within the ring.

Examples of "3- to 8-membered heterocycloalkyl" include aziridinyl, azetidinyl, pyrrolidinyl, imidazolidinyl, piperidyl, piperazinyl, azepanyl, morpholinyl, oxetanyl, and 1,2,5,6-tetrahydropyridyl.

A salt is defined as the product formed from the neutralisation reaction of acids and bases. Salts are ionic compounds composed of cations (positively charged ions) and anions (negative ions) so that the product is electrically neutral. These component ions can be inorganic as well as organic.

Hydrate is a term used in inorganic chemistry and organic chemistry to indicate that a substance contains water. Solvate refers to a molecule in a solution complexed by solvent molecules. Isomers are compounds with the same molecular formula but different structural formulae. More specifically, isomer includes geometric isomer, optical isomer, stereoisomer, tautomer of the compound, and mixtures thereof.

In a preferred embodiments, the present invention provides
[1] a compound represented by formula (I) or a pharmaceutically acceptable salt thereof:

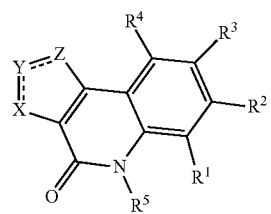

I or a pharmaceutically acceptable salt thereof,
wherein R$^1$, R$^2$, R$^3$, and R$^4$ are each independently a group selected from the group consisting of:
hydrogen,
hydroxyl,
halogen,
cyano,
nitro,
amino,
C$_1$-C$_6$ alkyl,
C$_2$-C$_6$ alkenyl,
C$_2$-C$_6$ alkynyl,
C$_3$-C$_{10}$ cycloalkyl,
C$_3$-C$_{10}$ cycloalkenyl,
C$_1$-C$_6$ alkoxy,
C$_6$-C$_{10}$ aryl,
indanyl,
heteroaryl,
3- to 8-membered heterocycloalkyl,
—OSO$_2$CH$_3$,
—OSO$_2$CF$_3$,
—CONH$_2$,
—OCONR$^{101}$R$^{102}$, wherein R$^{101}$ and R$^{102}$ each independently is hydrogen, C$_1$-C$_6$ alkyl, or R$^{101}$ and R$^{102}$ taken together form morpholinyl,
—OCOR$^{103}$, wherein R$^{103}$ represents C$_1$-C$_6$ alkyl, and
—OCOOR$^{104}$, wherein R$^{104}$ represents C$_1$-C$_6$ alkyl,
wherein R$^1$, R$^2$, R$^3$, and R$^4$ are optionally substituted with a substituent independently selected from the group consisting of substituent A;

wherein substituent A is independently selected from the group consisting of:
hydroxyl;
oxo (=O);
cyano;
halogen;
$C_1$-$C_6$ alkyl optionally substituted with substituent B;
$C_3$-$C_{10}$ cycloalkyl optionally substituted with cyano or $C_1$-$C_6$ alkyl substituted with —$NR^{31}R^{32}$, wherein $R^{31}$ and $R^{32}$ each independently represent hydrogen or $C_1$-$C_6$ alkyl;
—$NR^{21}R^{22}$, wherein $R^{21}$ and $R^{22}$ each independently represent hydrogen; $C_1$-$C_6$ alkyl optionally substituted with hydroxyl, amino, di($C_1$-$C_6$ alkyl)amino, —$SO_2$($C_1$-$C_6$ alkyl), 3- to 8-membered heterocycloalkyl, or cyano; or a 3- to 8-membered heterocycloalkyl optionally substituted with —$COOR^{105}$ wherein $R^{105}$ represents $C_1$-$C_6$ alkyl;
$C_1$-$C_6$ alkoxy optionally substituted with halogen, 3- to 8-membered heterocycloalkyl optionally substituted with $C_1$-$C_6$ alkyl, or —$NR^{33}R^{34}$ wherein $R^{33}$ and $R^{34}$ each independently represent hydrogen, $C_1$-$C_6$ alkylsulfonyl, or $C_1$-$C_6$ alkyl optionally substituted with $C_1$-$C_6$ alkylsulfonyl or di($C_1$-$C_6$ alkyl)amino;
—$SO_2NR^{23}R^{24}$, wherein $R^{23}$ and $R^{24}$ each independently represent hydrogen; $C_1$-$C_6$ alkyl optionally substituted with hydroxyl, $C_1$-$C_6$ alkoxy, halogen, $C_3$-$C_{10}$ cycloalkyl, heteroaryl, or —$NR^{35}R^{36}$ wherein $R^{35}$ and $R^{36}$ each independently represent hydrogen or $C_1$-$C_6$ alkyl; $C_3$-$C_{10}$ cycloalkyl optionally substituted with $C_1$-$C_6$ hydroxyalkyl; 3- to 8-membered heterocycloalkyl; or $R^{23}$ and $R^{24}$ taken together form 3- to 8-membered heterocycloalkyl optionally substituted with amino or halogen;
$C_1$-$C_6$ alkylsulfonyl optionally substituted with hydroxyl;
—$NHSO_2$($C_1$-$C_6$ alkyl), wherein the carbon atoms are optionally substituted with —$NR^{37}R^{38}$ wherein $R^{37}$ and $R^{38}$ each independently represent hydrogen or $C_1$-$C_6$ alkyl;
3- to 8-membered heterocycloalkyl optionally substituted with —$NR^{39}R^{40}$, wherein $R^{39}$ and $R^{40}$ each independently represent hydrogen, $C_1$-$C_6$ alkyl, or $C_1$-$C_6$ alkylsulfonyl; $C_1$-$C_6$ alkyl optionally substituted with —$NR^{41}R^{42}$, wherein $R^{41}$ and $R^{42}$ each independently represent hydrogen or $C_1$-$C_6$ alkyl; hydroxyl; or $C_1$-$C_6$ alkylsulfonyl;
aryl optionally substituted with $C_1$-$C_6$ alkyl optionally substituted with cyano or amino;
heteroaryl;
—$COOR^{11}$, wherein $R^{11}$ represents hydrogen or $C_1$-$C_6$ alkyl; and
—$COR^{12}$, wherein $R^{12}$ represents $C_1$-$C_6$ alkyl; $C_3$-$C_{10}$ cycloalkyl; cyanomethyl; aminomethyl; —$NR^{25}R^{26}$ wherein $R^{25}$ and $R^{26}$ each independently represent hydrogen or $C_1$-$C_6$ alkyl optionally substituted with hydroxyl or —$NR^{43}R^{44}$, wherein $R^{43}$ and $R^{44}$ each independently represent hydrogen or $C_1$-$C_6$ alkyl; or 3- to 8-membered heterocycloalkyl optionally substituted with $C_1$-$C_6$ alkyl;
wherein substituent B is independently selected from the group consisting of:
halogen;
hydroxyl;
$C_1$-$C_6$ alkoxy;
cyano;
cycloalkyl;
$C_6$-$C_{10}$ aryl optionally substituted with cyano;
heteroaryl;
3- to 8-membered heterocycloalkyl optionally substituted with $C_1$-$C_6$ alkyl, hydroxyl, amino, $C_1$-$C_6$ aminoalkyl, or $C_1$-$C_6$ alkyl substituted with $C_2$-$C_7$ alkyloxycarbonylamino;
—$NR^{51}R^{52}$, wherein $R^{51}$ and $R^{52}$ each independently represent hydrogen; $C_1$-$C_6$ alkyl optionally substituted with $C_1$-$C_6$ alkylsulfonyl or 3- to 8-membered heterocycloalkyl optionally substituted with —$COOR^{56}$ wherein $R^{53}$ represents hydrogen or $C_1$-$C_6$ alkyl; 3- to 8-membered heterocycloalkyl; $C_1$-$C_6$ alkylsulfonyl; $C_3$-$C_{10}$ cycloalkyl; —$COR^{55}$ wherein $R^{55}$ represents $C_1$-$C_6$ alkyl; —$COOR^{56}$ wherein $R^{56}$ represents $C_1$-$C_6$ alkyl; or —$CONR^{57}R^{58}$ wherein $R^{57}$ and $R^{58}$ each independently represent hydrogen or $C_1$-$C_6$ alkyl;
—$COOR^{54}$, wherein $R^{54}$ represents hydrogen or $C_1$-$C_6$ alkyl;
—$CONH_2$;
—$SO_2NR^{106}R^{107}$, wherein $R^{106}$ and $R^{107}$ each independently represent hydrogen, $C_1$-$C_6$ alkyl, or $C_3$-$C_{10}$ cycloalkyl;
$C_1$-$C_6$ alkylsulfinyl; and
$C_1$-$C_6$ alkylsulfonyl;
wherein $R^5$ is hydrogen or $C_1$-$C_6$ alkyl; and
wherein $$-X\!=\!Y\!=\!Z-$$

is a structure selected from the group consisting of
(i) —S—$CR^7$=$CR^6$—,
(ii) —$CH_2$—$CH_2$—$CH_2$—,
(iii) —$NR^{108}$—CH=$CR^{109}$—, wherein $R^{108}$ represents hydrogen, or $C_1$-$C_6$ alkyl optionally substituted with hydroxyl, and $R^{109}$ represents hydrogen, $CH_3$, or phenyl substituted with $C_1$-$C_6$ aminoalkyl, and
(iv) —N=CH—S—,
wherein $R^6$ is selected from the group consisting of:
hydrogen,
hydroxyl,
$C_1$-$C_6$ alkyl,
$C_6$-$C_{10}$ aryl optionally substituted with hydroxyl, and
3- to 8-membered heterocycloalkyl optionally substituted with —$NR^{61}R^{62}$, wherein $R^{61}$ and $R^{62}$ each independently represent hydrogen or $C_1$-$C_6$ alkyl;
wherein $R^7$ is selected from the group consisting of:
hydrogen;
halogen;
$C_1$-$C_6$ alkyl optionally substituted with hydroxyl, —$NR^{71}R^{72}$ wherein $R^{71}$ and $R^{72}$ each independently represent hydrogen; $C_1$-$C_6$ alkyl optionally substituted with dimethylamino; $C_3$-$C_{10}$ cycloalkyl optionally substituted with amino or 3- to 8-membered heterocycloalkyl; or 3- to 8-membered heterocycloalkyl optionally substituted with $C_1$-$C_6$ aminoalkyl;
$C_6$-$C_{10}$ aryl optionally substituted with hydroxyl;
$C_6$-$C_{10}$ arylsulfonyl; and
—$COR^{73}$, wherein $R^{73}$ represents 3- to 8-membered heterocycloalkyl optionally substituted with amino; or —$NR^{74}R^{75}$ wherein $R^{74}$ and $R^{75}$ each independently represent hydrogen, 3- to 8-membered heterocycloalkyl, or $C_3$-$C_{10}$ cycloalkyl optionally substituted with amino.

[2] The compound of [1], or a pharmaceutically acceptable salt thereof, wherein

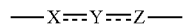

is —S—CR$^7$=CR$^6$—.

[3] The compound of [2], or a pharmaceutically acceptable salt thereof, wherein R$^1$ is hydrogen, cyano, C$_1$-C$_6$ alkyl optionally substituted with hydroxyl or halogen, C$_3$-C$_{10}$ cycloalkyl, C$_2$-C$_6$ alkenyl, C$_2$-C$_6$ alkynyl, or halogen.

[4] The compound of [2], or a pharmaceutically acceptable salt thereof, wherein R$^2$ is hydrogen, hydroxyl, halogen, C$_1$-C$_6$ alkoxy, or C$_6$-C$_{10}$ aryl optionally substituted with hydroxyl.

[5] The compound of [2] or a pharmaceutically acceptable salt, wherein R$^2$ is hydrogen, hydroxyl, halogen, C$_1$-C$_6$ alkoxy, or dihydroxyphenyl.

[6] The compound of [2], or a pharmaceutically acceptable salt thereof, wherein R$^3$ is selected from the group consisting of: hydrogen; hydroxyl; C$_1$-C$_6$ alkyl optionally substituted with hydroxyl, halogen, or hydroxyethylamino; halogen; C$_1$-C$_6$ alkoxy optionally substituted with dimethylamino or morpholinyl; C$_1$-C$_6$ alkylphenyl, wherein the aliphatic carbons are optionally substituted with —NR$^{51}$R$^{52}$; cyano; nitro; amino; 3- to 8-membered heterocycloalkyl optionally substituted with amino; heteroaryl; —OSO$_2$CH$_3$; —OSO$_2$CF$_3$; —OCOR$^{103}$, wherein R$^{103}$ represents C$_1$-C$_6$ alkyl; —OCOOR$^{104}$ wherein R$^{104}$ represents C$_1$-C$_6$ alkyl; —OCONR$^{101}$R$^{1022}$ wherein R$^{101}$ and R$^{102}$ each independently represent hydrogen or C$_1$-C$_6$ alkyl, or R$^{101}$ and R$^{102}$ taken together form morpholinyl; and —CONH$_2$.

[7] The compound of [6], or a pharmaceutically acceptable salt thereof, wherein when R$^3$ is a 3- to 8-membered heterocycloalkyl, the 3- to 8-membered heterocycloalkyl is selected from the group consisting of piperidyl, pyrrolidinyl, morpholinyl, or piperazinyl and optionally substituted with amino; and when R$^3$ is heteroaryl, the heteroaryl is pyridyl.

[8]. The compound of [2], or a pharmaceutically acceptable salt thereof, wherein R$^4$ is selected from the group consisting of hydrogen, hydroxyl, halogen, amino, C$_1$-C$_6$ alkyl, C$_2$-C$_6$ alkenyl, C$_3$-C$_{10}$ cycloalkyl, C$_3$-C$_{10}$ cycloalkenyl, C$_1$-C$_6$ alkoxy, C$_6$-C$_{10}$ aryl, indanyl, heteroaryl, and 3- to 8-membered heterocycloalkyl, and R$^4$ is optionally substituted with substituent A.

[9] The compound of [8], or a pharmaceutically acceptable salt thereof, wherein when R$^4$ is heteroaryl, the heteroaryl is selected from the group consisting of pyridyl, 1H-indazolyl, 1H-tetrazolyl, [1,2,4]triazolo[1,5-a]pyridyl, benzoimidazolyl, 2,3-dihydrobenzooxazolyl, pyrazolyl, pyrrolo[2,3-b]pyridyl, pyrimidinyl, indolinyl, furyl, thienyl, and tetrahydroisoquinolyl); and wherein the 3- to 8-membered heterocycloalkyl is selected from the group consisting of aziridinyl, azetidinyl, pyrrolidinyl, imidazolidinyl, piperidyl, piperazinyl, azepanyl, morpholinyl, and 1,2,3,6-tetrahydropyridyl; wherein each of the groups of R$^4$ is optionally substituted with substituent A-1;
wherein substituent A-1 is selected from the group consisting of:
hydroxyl;
oxo;
cyano;
halogen;
C$_1$-C$_6$ alkyl optionally substituted with a substituent selected from the group consisting of substituent B-1;
C$_3$-C$_{10}$ cycloalkyl optionally substituted with cyano, or C$_1$-C$_6$ alkyl substituted with —NR$^{31}$R$^{32}$;
—NR$^{21A}$R$^{22A}$, wherein R$^{21A}$ and R$^{22A}$ each independently represent hydrogen; C$_1$-C$_6$ alkyl optionally substituted with amino, di(C$_1$-C$_6$ alkyl)amino, —SO$_2$(C$_1$-C$_6$ alkyl), piperidyl, or cyano; or piperidyl optionally substituted with —COOR$^{105}$;
C$_1$-C$_6$ alkoxy optionally substituted with halogen; a 3- to 8-membered heterocycloalkyl selected from piperidyl and piperazinyl, either of which is optionally substituted with C$_1$-C$_6$ alkyl; or —NR$^{33}$R$^{34}$;
—SO$_2$NR$^{23A}$R$^{24A}$, wherein R$^{23A}$ and R$^{24A}$ each independently represent hydrogen, C$_1$-C$_6$ alkyl optionally substituted with hydroxyl, C$_1$-C$_6$ alkoxy, halogen, C$_3$-C$_{10}$ cycloalkyl, pyrazolyl, imidazolyl, or —NR$^{35}$R$^{36}$; C$_3$-C$_{10}$ cycloalkyl optionally substituted with C$_1$-C$_6$ hydroxyalkyl; azetidinyl; pyrrolidinyl, or R$^{23A}$ and R$^{24A}$ taken together form pyrrolidinyl optionally substituted with amino or halogen;
C$_1$-C$_6$ alkylsulfonyl optionally substituted with hydroxyl; —NHSO$_2$(C$_1$-C$_6$ alkyl), wherein the carbon atoms are optionally substituted with NR$^{37}$R$^{38}$;
3- to 8-membered heterocycloalkyl selected from the group consisting of azetidinyl, pyrrolidinyl, piperidyl, piperazinyl, and tetrahydropyridyl any of which is optionally substituted with —NR$^{39}$R$^{40}$; C$_1$-C$_6$ alkyl optionally substituted with —NR$^{41}$R$^{42}$; hydroxyl; or C$_1$-C$_6$ alkylsulfonyl;
1H-tetrazolyl;
aryl optionally substituted with C$_1$-C$_6$ alkyl, wherein C$_1$-C$_6$ is the aliphatic carbons are optionally substituted with cyano or amino;
—COOR$^{11}$; and
—COR$^{12A}$, wherein R$^{12A}$ represents piperazinyl optionally substituted with C$_1$-C$_6$ alkyl; C$_3$-C$_{10}$ cycloalkyl; cyanomethyl; aminomethyl; —NR$^{25}$R$^{26}$ wherein R$^{25}$ and R$^{26}$ each independently represent hydrogen or C$_1$-C$_6$ alkyl optionally substituted with hydroxyl or —NR$^{43}$R$^{44}$; or C$_1$-C$_6$ alkylsulfonyl;
wherein substituent B-1 is selected from the group consisting of:
halogen;
hydroxyl;
C$_1$-C$_6$ alkoxy;
cyano;
cycloalkyl;
phenyl optionally substituted with cyano;
heteroaryl selected from the group consisting of imidazolyl, pyrazolyl, and thiazolyl;
3- to 8-membered heterocycloalkyl selected from the group consisting of pyrrolidinyl, piperidyl, piperazinyl, morpholinyl, and oxetanyl any of which are optionally substituted with hydroxyl, amino, C$_1$-C$_6$ aminoalkyl, or C$_1$-C$_6$ alkyl optionally substituted with C$_2$-C$_7$ alkyloxycarbonylamino;
—NR$^{51A}$R$^{52A}$, wherein R$^{51A}$ and R$^{52A}$ each independently represent hydrogen; C$_1$-C$_6$ alkyl optionally substituted with C$_1$-C$_6$ alkylsulfonyl or piperidyl optionally substituted with —COOR$^{53}$; piperidyl; C$_1$-C$_6$ alkylsulfonyl; C$_3$-C$_{10}$ cycloalkyl; —COR$^{55}$, —COOR$^{56}$, or —CONR$^{57}$R$^{58}$;
—COOR$^{54}$;
—CONH$_2$;
—SO$_2$NR$^{106}$R$^{107}$;

$C_1$-$C_6$ alkylsulfinyl; and
$C_1$-$C_6$ alkylysulfonyl.

[10] The compound of [9], or a pharmaceutically acceptable salt thereof, wherein $R^4$ is a group selected from group (p):

wherein group (p) is independently selected from the group consisting of:
hydrogen,
hydroxyl,
halogen,
amino optionally substituted with a substituent selected from the group consisting of substituent (g),
$C_1$-$C_6$ alkyl optionally substituted with a substituent selected from the group consisting of substituent (a),
$C_2$-$C_6$ alkenyl optionally substituted with a substituent selected from the group consisting of substituent (b),
$C_3$-$C_{10}$ cycloalkyl,
$C_3$-$C_{10}$ cycloalkenyl,
$C_1$-$C_6$ alkoxy,
$C_6$-$C_{10}$ aryl optionally substituted with a substituent selected from the group consisting of substituent (c),
indanyl optionally substituted with a substituent selected from the group consisting of substituent (d),
heteroaryl selected from the group consisting of pyridyl, 1H-indazolyl, 1H-tetrazolyl, [1,2,4]triazolo[1,5-a]pyridyl, benzoimidazolyl, 2,3-dihydrobenzooxazolyl, pyrazolyl, pyrrolo[2,3-b]pyridyl, pyrimidinyl, indolinyl, furyl, thienyl, and tetrahydroisoquinolyl any of which is optionally substituted with a substituent selected from the group consisting of substituent (e); and
3- to 8-membered heterocycloalkyl selected from the group consisting of pyrrolidinyl, piperidyl, piperazinyl, morpholinyl, and 1,2,3,6-tetrahydropyridyl any of which is optionally substituted with a substituent selected from the group consisting of substituent (f);

wherein substituent (a) is selected from the group consisting of:
—$NR^{21A}R^{22A}$, wherein $R^{21A}$ and $R^{22A}$ each independently represent hydrogen; $C_1$-$C_6$ alkyl optionally substituted with piperidyl; or piperidyl optionally substituted with —$COOR^{105}$;
3- to 8-membered heterocycloalkyl selected from the group consisting of pyrrolidinyl and piperidyl either of which is optionally substituted with $C_1$-$C_6$ alkyl optionally substituted with —$NR^{41}R^{42}$ or —$NR^{39}R^{40}$ wherein $R^{39}$ and $R^4$ each independently represent hydrogen or $C_1$-$C_6$ alkyl; and
—$NHSO_2(C_1$-$C_6$ alkyl);

wherein substituent (b) is selected from the group consisting of:
—$COOR^{11}$;
—$NR^{21a}R^{22a}$, wherein $R^{21a}$ and $R^{22a}$ each independently represent hydrogen, or $C_1$-$C_6$ alkyl optionally substituted with di($C_1$-$C_6$ alkyl)amino or $C_1$-$C_6$ alkylsulfonyl;
3- to 8-membered heterocycloalkyl selected from the group consisting of azetidinyl, pyrrolidinyl, and piperidyl any of which are optionally substituted with —$NR^{39}R^{40}$, $C_1$-$C_6$ alkyl optionally substituted with —$NR^{41}R^{42}$, hydroxyl, or $C_1$-$C_6$ alkylsulfonyl;
cyano; and
$C_1$-$C_6$ alkoxy;

wherein substituent (c) is selected from the group consisting of:
hydroxyl;
cyano;
halogen;
$C_1$-$C_6$ alkyl optionally substituted with a substituent selected from the group consisting of substituent B-c below;
$C_3$-$C_{10}$ cycloalkyl optionally substituted with cyano, or $C_1$-$C_6$ alkyl substituted with —$NR^{31}R^{32}$;
—$NR^{21c}R^{22c}$, wherein $R^{21c}$ and $R^{22c}$ each independently represent hydrogen or $C_1$-$C_6$ alkyl optionally substituted with amino or cyano;
$C_1$-$C_6$ alkoxy optionally substituted with halogen, 3- to 8-membered heterocycloalkyl selected from the group consisting of piperidyl and piperazinyl either of which are optionally substituted with $C_1$-$C_6$ alkyl, or —$NR^{33}R^{34}$;
—$SO_2NR^{23c}R^{24c}$, wherein $R^{23c}$ and $R^{24c}$ each independently represent hydrogen, $C_1$-$C_6$ alkyl optionally substituted with hydroxyl, $C_1$-$C_6$ alkoxy, halogen, $C_3$-$C_{10}$ cycloalkyl, pyrazolyl, imidazolyl, or —$NR^{35}R^{36}$; $C_3$-$C_{10}$ cycloalkyl optionally substituted with $C_1$-$C_6$ hydroxyalkyl; azetidinyl, pyrrolidinyl, or wherein $R^{23c}$ and $R^{24c}$ taken together form pyrrolidinyl which is optionally substituted with amino or halogen;
$C_1$-$C_6$ alkylsulfonyl optionally substituted with hydroxyl;
—$NHSO_2(C_1$-$C_6$ alkyl), wherein the carbon atoms are optionally substituted with $NR^{37}R^{38}$;
piperazinyl optionally substituted with $C_1$-$C_6$ alkyl or $C_1$-$C_6$ alkylsulfonyl;
piperidyl optionally substituted with hydroxyl;
1H-tetrazolyl;
1,2,3,6-tetrahydropyridyl; and
—$COR^{12c}$, wherein $R^{12c}$ represents piperazinyl which is optionally substituted with $C_1$-$C_6$ alkyl, $C_3$-$C_{10}$ cycloalkyl, cyanomethyl, aminomethyl, —$NR^{25}R^{26}$, or $C_1$-$C_6$ alkyl; and wherein substituent B-c is selected from the group consisting of:
halogen;
hydroxyl;
methoxy;
cyano;
$C_3$-$C_{10}$ cycloalkyl;
3- to 8-membered heterocycloalkyl selected from the group consisting of pyrrolidinyl, piperidyl, piperazinyl, morpholinyl, and oxetanyl, any of which is optionally substituted with $C_1$-$C_6$ alkyl, hydroxyl, amino, $C_1$-$C_6$ aminoalkyl, or $C_1$-$C_6$ alkyl substituted with $C_2$-$C_7$ alkyloxycarbonylamino;
—$NR^{51c}R^{52c}$, wherein $R^{51c}$ and $R^{52c}$ each independently represent hydrogen; $C_1$-$C_6$ alkyl optionally substituted with $C_1$-$C_6$ alkylsulfonyl, or piperidyl optionally substituted with —$COOR^{53}$; piperidyl; $C_1$-$C_6$ alkylsulfonyl; $C_3$-$C_{10}$ cycloalkyl; —$COR^{55}$; or —$CONR^{57}R^{58}$;
heteroaryl selected from the group consisting of imidazolyl, pyrazolyl, and thiazolyl;
—$COOR^{54}$;
—$CONH_2$;
—$SO_2NR^{106}R^{107}$;
$C_1$-$C_6$ alkylsufinyl; and
$C_1$-$C_6$ alkylsulfonyl;

wherein substituent (d) is selected from the group consisting of:
—$NR^{21d}R^{22d}$, wherein $R^{21d}$ and $R^{22d}$ each independently represent hydrogen or $C_1$-$C_6$ alkyl;

wherein substituent (e) is selected from the group consisting of:
hydroxyl;
oxo;
cyano;
$C_3$-$C_{10}$ cycloalkyl optionally substituted with cyano;
—$NR^{21e}R^{22e}$, wherein $R^{21e}$ and $R^{22e}$ each independently represent hydrogen or $C_1$-$C_6$ alkyl optionally substituted with amino;
piperidyl;
$C_1$-$C_6$ alkoxy optionally substituted with —$NR^{33}R^{34}$;
$C_1$-$C_6$ alkyl optionally substituted with cyano; —$NR^{51e}R^{52e}$, wherein $R^{51e}$ and $R^{52e}$ each independently represent hydrogen, $C_1$-$C_6$ alkyl, or —$COOR^{56}$; morpholinyl; or cyanophenyl;
—$CONH_2$;
wherein substituent (f) is selected from the group consisting of:
$C_1$-$C_6$ alkyl optionally substituted with —$NR^{51f}R^{52f}$, wherein $R^{51f}$ and $R^{52f}$ each independently represent hydrogen, $C_1$-$C_6$ alkyl, or —$COOR^{56}$; and $C_1$-$C_6$ alkylsulfonyl;
wherein substituent (g) is aryl optionally substituted with $C_1$-$C_6$ alkyl having the aliphatic carbons optionally substituted with cyano or amino.

[11] The compound of [2], or a pharmaceutically acceptable salt thereof, wherein $R^6$ is hydrogen; hydroxyl; $C_1$-$C_6$ alkyl; phenyl optionally substituted with 1 to 3 hydroxyls; piperidyl optionally substituted with amino; or piperazinyl.

[12] The compound of [11], or a pharmaceutically acceptable salt thereof, wherein $R^7$ is hydrogen; $C_1$-$C_6$ alkyl optionally substituted with hydroxyl or piperidyl; or halogen.

[13] The compound of [2], or a pharmaceutically acceptable salt thereof, wherein $R^7$ is hydrogen;
$C_1$-$C_6$ alkyl optionally substituted with hydroxyl; —$NR^{71A}R^{72A}$ wherein $R^{71A}$ and $R^{72A}$ independently represent hydrogen, $C_1$-$C_6$ alkyl optionally substituted with dimethylamino, $C_3$-$C_{10}$ cycloalkyl optionally substituted with amino, or piperidyl; or 3- to 8-membered heterocycloalkyl selected from the group consisting of piperidyl and morpholinyl either of which is optionally substituted with $C_1$-$C_6$ aminoalkyl;
phenyl optionally substituted with 1 to 2 hydroxyls;
phenylsulfonyl; or
—$COR^{73A}$, wherein $R^{73A}$ represents piperidyl optionally substituted with amino, or —$NR^{74A}R^{75A}$, wherein $R^{74A}$ and $R^{75A}$ each independently represent hydrogen, piperidyl, or $C_3$-$C_{10}$ cycloalkyl optionally substituted with amino.

[14] The compound of [1], or a pharmaceutically acceptable salt thereof, wherein

—X═Y═Z— is —$CH_2$—$CH_2$—$CH_2$—.

[15] The compound of [14], or a pharmaceutically acceptable salt thereof, wherein $R^1$ and $R^2$ are hydrogen.

[16] The compound of [14], or a pharmaceutically acceptable salt thereof, wherein $R^3$ is hydroxyl or methoxy.

[17] The compound of [14], or a pharmaceutically acceptable salt thereof, wherein $R^4$ is hydrogen; phenyl substituted with $C_1$-$C_6$ alkyl substituted with —$NR^{51A}R^{52A}$, wherein $R^{51A}$ and $R^{52A}$ each independently represent hydrogen or $C_1$-$C_6$ alkyl, or —$SO_2NR^{53A}R^{54A}$, wherein $R^{53A}$ and $R^{54A}$ each independently represent hydrogen or $C_1$-$C_6$ alkyl optionally substituted with halogen or hydroxy; 1,2,3,6-tetrahydropyridyl; hydroxypyridyl; or methoxypyridyl.

[18] The compound of [1], or a pharmaceutically acceptable salt thereof, wherein

—X═Y═Z— is —$NR^{108}$—CH═$CR^{109}$—,
$R^1$, $R^2$, and $R^4$ are hydrogen, and
$R^3$ is hydrogen, hydroxyl or $C_1$-$C_6$ alkoxy.

[19] The compound of [1], or a pharmaceutically acceptable salt thereof, wherein

—X═Y═Z— is —N═CH—S—,
$R^1$, $R^2$, and $R^4$ are hydrogen, and
$R^3$ is methoxy.

Alternatively, in some embodiments, the present invention also provides a compound represented by formula (I) or a pharmaceutically acceptable salt thereof:

1. A compound represented by general formula I:

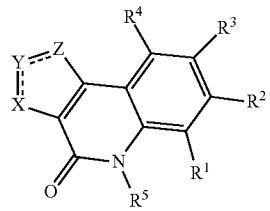

or a pharmaceutically acceptable salt thereof,
wherein $R^1$, $R^2$, $R^3$, and $R^4$ are each independently a group selected from the group consisting of:
hydrogen,
hydroxyl,
halogen,
cyano,
nitro,
amino,
$C_1$-$C_6$ alkyl,
$C_2$-$C_6$ alkenyl,
$C_2$-$C_6$ alkynyl,
$C_3$-$C_{10}$ cycloalkyl,
$C_3$-$C_{10}$ cycloalkenyl,
$C_1$-$C_6$ alkoxy,
$C_6$-$C_{10}$ aryl,
indanyl,
heteroaryl,
3- to 8-membered heterocycloalkyl,
—$OSO_2CH_3$,
—$OSO_2CF_3$,
—$CONH_2$,
—$OCONR^{101}R^{102}$ (wherein $R^{101}$ and $R^{102}$ each independently represent hydrogen or $C_1$-$C_6$ alkyl, or $R^{101}$ and $R^{102}$ together form morpholinyl),
—$OCOR^{103}$ (wherein $R^{103}$ represents $C_1$-$C_6$ alkyl), and
—$OCOOR^{104}$ (wherein $R^{104}$ represents $C_1$-$C_6$ alkyl)

wherein each of the groups of $R^1$ to $R^4$ is optionally substituted with a substituent selected from the group consisting of substituent A below:

substituent A:
- hydroxyl;
- oxo (=O);
- cyano;
- halogen;
- $C_1$-$C_6$ alkyl (wherein the $C_1$-$C_6$ alkyl is optionally substituted with a substituent selected from the group consisting of substituent B below);
- $C_3$-$C_{10}$ cycloalkyl [wherein the $C_3$-$C_{10}$ cycloalkyl is optionally substituted with cyano, or $C_1$-$C_6$ alkyl substituted with —$NR^{31}R^{32}$ (wherein $R^{31}$ and $R^{32}$ each independently represent hydrogen or $C_1$-$C_6$ alkyl)];
- —$NR^{21}R^{22}$ [wherein $R^{21}$ and $R^{22}$ each independently represent hydrogen, $C_1$-$C_6$ alkyl (wherein the $C_1$-$C_6$ alkyl is optionally substituted with hydroxyl, amino, di($C_1$-$C_6$ alkyl)amino, $C_1$-$C_6$ alkylsulfonyl (—$SO_2$($C_1$-$C_6$ alkyl)), 3- to 8-membered heterocycloalkyl, or cyano), or 3- to 8-membered heterocycloalkyl (wherein the 3- to 8-membered heterocycloalkyl is optionally substituted with —$COOR^{105}$ (wherein $R^{105}$ represents $C_1$-$C_6$))];
- $C_1$-$C_6$ alkoxy {wherein the $C_1$-$C_6$ alkoxy is optionally substituted with halogen, 3- to 8-membered heterocycloalkyl (wherein the 3- to 8-membered heterocycloalkyl is optionally substituted with $C_1$-$C_6$ alkyl), or —$NR^{33}R^{34}$ [wherein $R^{33}$ and $R^{34}$ each independently represent hydrogen, $C_1$-$C_6$ alkyl (wherein the $C_1$-$C_6$ alkyl is optionally substituted with $C_1$-$C_6$ alkylsulfonyl or di($C_1$-$C_6$ alkyl)amino), or $C_1$-$C_6$ alkylsulfonyl]};
- —$SO_2NR^{23}R^{24}$ (wherein $R^{23}$ and $R^{24}$ each independently represent hydrogen, $C_1$-$C_6$ alkyl [wherein the $C_1$-$C_6$ alkyl is optionally substituted with hydroxyl, $C_1$-$C_6$ alkoxy, halogen, $C_3$-$C_{10}$ cycloalkyl, heteroaryl, or —$NR^{35}R^{36}$ (wherein $R^{35}$ and $R^{36}$ each independently represent hydrogen or $C_1$-$C_6$ alkyl)], $C_3$-$C_{10}$ cycloalkyl (wherein the $C_3$-$C_{10}$ cycloalkyl is optionally substituted with $C_1$-$C_6$ hydroxyalkyl), or 3- to 8-membered heterocycloalkyl; or $R^{23}$ and $R^{24}$ may together form 3- to 8-membered heterocycloalkyl wherein the 3- to 8-membered heterocycloalkyl is optionally substituted with amino or halogen);
- $C_1$-$C_6$ alkylsulfonyl (wherein the $C_1$-$C_6$ alkyl moiety is optionally substituted with hydroxyl);
- $C_1$-$C_6$ alkylsulfonylamino (—$NHSO_2$($C_1$-$C_6$ alkyl)) [wherein the $C_1$-$C_6$ alkyl moiety is optionally substituted with —$NR^{37}R^{38}$ (wherein $R^{37}$ and $R^{38}$ each independently represent hydrogen or $C_1$-$C_6$ alkyl)];
- 3- to 8-membered heterocycloalkyl (wherein the 3- to 8-membered heterocycloalkyl is optionally substituted with —$NR^{39}R^{40}$ (wherein $R^{39}$ and $R^{40}$ each independently represent hydrogen, $C_1$-$C_6$ alkyl, or $C_1$-$C_6$ alkylsulfonyl), $C_1$-$C_6$ alkyl [wherein the $C_1$-$C_6$ alkyl is optionally substituted with —$NR^{41}R^{42}$ (wherein $R^{41}$ and $R^{42}$ each independently represent hydrogen or $C_1$-$C_6$ alkyl)], hydroxyl, or $C_1$-$C_6$ alkylsulfonyl);
- Aryl (wherein the aryl is optionally substituted with $C_1$-$C_6$ alkyl[wherein $C_1$-$C_6$ alkyl is optionally substituted with cyano or amino]);
- heteroaryl;
- —$COOR^{11}$ (wherein $R^{11}$ represents hydrogen or $C_1$-$C_6$ alkyl); and
- —$COR^{12}$ [wherein $R^{12}$ represents $C_1$-$C_6$ alkyl, $C_3$-$C_{10}$ cycloalkyl, cyanomethyl, aminomethyl, —$NR^{25}R^{26}$ {wherein $R^{25}$ and $R^{26}$ each independently represent hydrogen, or $C_1$-$C_6$ alkyl [wherein the $C_1$-$C_6$ alkyl is optionally substituted with hydroxyl or —$NR^{43}R^{44}$ (wherein $R^{43}$ and $R^{44}$ each independently represent hydrogen or $C_1$-$C_6$ alkyl)]}), or 3- to 8-membered heterocycloalkyl which is optionally substituted with $C_1$-$C_6$ alkyl], substituent B:
- halogen;
- hydroxyl;
- $C_1$-$C_6$ alkoxy;
- cyano;
- cycloalkyl;
- $C_6$-$C_{10}$ aryl (wherein $C_6$-$C_{10}$ aryl is optionally substituted with cyano) heteroaryl;
- 3- to 8-membered heterocycloalkyl (wherein the 3- to 8-membered heterocycloalkyl is optionally substituted with $C_1$-$C_6$ alkyl, hydroxyl, amino, $C_1$-$C_6$ aminoalkyl, or $C_1$-$C_6$ alkyl substituted with $C_2$-$C_7$ alkyloxycarbonylamino);
- —$NR^{51}R^{52}$ {wherein $R^{51}$ and $R^{52}$ each independently represent hydrogen, $C_1$-$C_6$ alkyl [wherein the $C_1$-$C_6$ alkyl is optionally substituted with $C_1$-$C_6$ alkylsulfonyl, or 3- to 8-membered heterocycloalkyl optionally substituted with —$COOR^{53}$ (wherein $R^{53}$ represents hydrogen or $C_1$-$C_6$ alkyl)], 3- to 8-membered heterocycloalkyl, $C_1$-$C_6$ alkylsulfonyl, $C_3$-$C_{10}$ cycloalkyl, —$COR^{55}$ (wherein $R^{55}$ represents $C_1$-$C_6$ alkyl), —$COOR^{56}$ (wherein $R^{56}$ represents $C_1$-$C_6$ alkyl), or —$CONR^{57}R^{58}$ (wherein $R^{57}$ and $R^{58}$ each independently represent hydrogen or $C_1$-$C_6$ alkyl)};
- —$COOR^{54}$ (wherein $R^{54}$ represents hydrogen or $C_1$-$C_6$ alkyl)];
- —$CONH_2$;
- —$SO_2NR^{106}R^{107}$ (wherein $R^{106}$ and $R^{107}$ each independently represent hydrogen, $C_1$-$C_6$ alkyl, or $C_3$-$C_{10}$ cycloalkyl)
- $C_1$-$C_6$ alkylsulfinyl; and
- $C_1$-$C_6$ alkylsulfonyl;

wherein $R^5$ is hydrogen or $C_1$-$C_6$ alkyl; and
wherein $$\text{---}X\text{===}Y\text{===}Z\text{---}$$

is a structure selected from the group consisting of
(i) —S—$CR^7$=$CR^6$—,
(ii) -$CH_2$—$CH_2$—$CH_2$—,
(iii) -$NR^{108}$—CH=$CR^{109}$— (wherein $R^{108}$ represents hydrogen, or $C_1$-$C_6$ alkyl that is optionally substituted with hydroxyl, and $R^{109}$ represents hydrogen, $CH_3$, or phenyl that is substituted with $C_1$-$C_6$ aminoalkyl, and
(iv) —N=CH—S—, wherein $R^6$ is
- hydrogen,
- hydroxyl,
- $C_1$-$C_6$ alkyl,
- $C_6$-$C_{10}$ aryl (wherein the $C_6$-$C_{10}$ aryl is optionally substituted with hydroxyl), or
- 3- to 8-membered heterocycloalkyl [wherein the 3- to 8-membered heterocycloalkyl is optionally substituted with —$NR^{61}R^{62}$ (wherein $R^{61}$ and $R^{62}$ each independently represent hydrogen or $C_1$-$C_6$ alkyl)];

wherein $R^7$ is
hydrogen;
halogen;
$C_1$-$C_6$ alkyl {wherein the $C_1$-$C_6$ alkyl is optionally substituted with hydroxyl, —$NR^{71}R^{72}$ [wherein $R^{71}$ and $R^{72}$ each independently represent hydrogen, $C_1$-$C_6$ alkyl (wherein the $C_1$-$C_6$ alkyl is optionally substituted with dimethylamino), $C_3$-$C_{10}$ cycloalkyl (wherein the $C_3$-$C_{10}$ cycloalkyl is optionally substituted with amino), or 3- to 8-membered heterocycloalkyl], or 3- to 8-membered heterocycloalkyl (wherein the 3- to 8-membered heterocycloalkyl is optionally substituted with $C_1$-$C_6$ aminoalkyl)},
$C_6$-$C_{10}$ aryl (wherein the $C_6$-$C_{10}$ aryl is optionally substituted with hydroxyl);
$C_6$-$C_{10}$ arylsulfonyl; or
—$COR^{73}$ {wherein $R^{73}$ represents 3- to 8-membered heterocycloalkyl (wherein the 3- to 8-membered heterocycloalkyl is optionally substituted with amino), or —$NR^{74}R^{75}$ [wherein $R^{74}$ and $R^{75}$ each independently represent hydrogen, 3- to 8-membered heterocycloalkyl, or $C_3$-$C_{10}$ cycloalkyl (wherein the $C_3$-$C_{10}$ cycloalkyl is optionally substituted with amino)]}.

2. The compound of above 1, or a pharmaceutically acceptable salt thereof, wherein $$-X\!\!=\!\!\!=\!\!Y\!\!=\!\!\!=\!\!Z-$$

is —S—$CR^7$=$CR^6$—.

3. The compound of above 2, or a pharmaceutically acceptable salt thereof, wherein $R^1$ is hydrogen, cyano, $C_1$-$C_6$ alkyl (wherein $C_1$-$C_6$ alkyl is optionally substituted with hydroxyl or halogen), $C_3$-$C_{10}$ cycloalkyl, $C_2$-$C_6$ alkenyl, $C_2$-$C_6$ alkynyl, or halogen.

4. The compound of above 2, or a pharmaceutically acceptable salt thereof, wherein $R^2$ is hydrogen, hydroxyl, halogen, $C_1$-$C_6$ alkoxy, or $C_6$-$C_{10}$ aryl which is optionally substituted with hydroxyl.

5. The compound of above 2 or a pharmaceutically acceptable salt, wherein $R^2$ is hydrogen, hydroxyl, halogen, $C_1$-$C_6$ alkoxy, or dihydroxyphenyl.

6. The compound of above 2, or a pharmaceutically acceptable salt thereof, wherein $R^3$ is hydrogen; hydroxyl; $C_1$-$C_6$ alkyl (wherein alkyl is optionally substituted with hydroxyl, halogen, or hydroxyethylamino); halogen; $C_1$-$C_6$ alkoxy optionally substituted with dimethylamino or morpholinyl; $C_1$-$C_6$ alkylphenyl [wherein $C_1$-$C_6$ alkyl of the $C_1$-$C_6$ alkylphenyl is optionally substituted with —$NR^{51}R^{52}$ {wherein $R^{51}$ and $R^{52}$ each independently represent hydrogen, $C_1$-$C_6$ alkyl, or —$COOR^{56}$ (wherein $R^{56}$ represents $C_1$-$C_6$ alkyl))}]; cyano; nitro; amino; 3- to 8-membered heterocycloalkyl which is optionally substituted with amino; heteroaryl; —$OSO_2CH_3$; —$OSO_2CF_3$; —$OCOR^{103}$ ($R^{103}$ represents $C_1$-$C_6$ alkyl); —$OCOOR^{104}$ (wherein $R^{104}$ represents $C_1$-$C_6$ alkyl); —$OCONR^{101}R^{102}$ (wherein $R^{101}$, $R^{102}$ each independently represent hydrogen or $C_1$-$C_6$ alkyl, or $R^{101}$ and $R^{102}$ together form morpholinyl); or —$CONH_2$.

7. The compound of above 2, or a pharmaceutically acceptable salt thereof, wherein $R^3$ is hydrogen; hydroxyl; $C_1$-$C_6$ alkyl (wherein alkyl is optionally substituted with hydroxyl, halogen, or hydroxyethylamino); halogen; $C_1$-$C_6$ alkoxy that is optionally substituted with dimethylamino or morpholinyl; $C_1$-$C_6$ alkylphenyl (wherein $C_1$-$C_6$ alkyl of the $C_1$-$C_6$ alkylphenyl is optionally substituted with —$NR^{51}R^{52}$ (wherein $R^{51}$ and $R^{52}$ each independently represent hydrogen, $C_1$-$C_6$ alkyl, or —$COOR^{56}$ (wherein $R^{56}$ represents $C_1$-$C_6$ alkyl) cyano; nitro; amino; 3- to 8-membered heterocycloalkyl which is optionally substituted with amino (wherein the 3- to 8-membered heterocycloalkyl is piperidyl, pyrrolidinyl, morpholinyl, or piperazinyl); pyridyl; —$OSO_2CH_3$; —$OSO_2CF_3$; —$OCOR^{103}$ ($R^{103}$ represents $C_1$-$C_6$ alkyl); —$OCOOR^{104}$ (wherein $R^{104}$ represents $C_1$-$C_6$ alkyl); —$OCONR^{101}R^{102}$ (wherein $R^{101}$, $R^{102}$ each independently represent hydrogen or $C_1$-$C_6$ alkyl, or $R^{101}$ and $R^{102}$ together form morpholinyl); or —$CONH_2$.

8. The compound of above 2, or a pharmaceutically acceptable salt thereof, wherein $R^4$ is a group selected from the group consisting of hydrogen, hydroxyl, halogen, amino, $C_1$-$C_6$ alkyl, $C_2$-$C_6$ alkenyl, $C_3$-$C_{10}$ cycloalkyl, $C_3$-$C_{10}$ cycloalkenyl, $C_1$-$C_6$ alkoxy, $C_6$-$C_{10}$ aryl, indanyl, heteroaryl, and 3- to 8-membered heterocycloalkyl, wherein each of the groups of $R^4$ is optionally substituted with a substituent selected from the group consisting of substituent A above.

9. The compound of above 2, or a pharmaceutically acceptable salt thereof, wherein $R^4$ is a group selected from the group consisting of hydrogen, hydroxyl, halogen, amino, $C_1$-$C_6$ alkyl, $C_2$-$C_6$ alkenyl, $C_3$-$C_{10}$ cycloalkyl, $C_3$-$C_{10}$ cycloalkenyl, $C_1$-$C_6$ alkoxy, $C_6$-$C_{10}$ aryl, indanyl, heteroaryl (wherein the heteroaryl is selected from the group consisting of pyridyl, 1H-indazolyl, 1H-tetrazolyl, [1,2,4]triazolo[1,5-a]pyridyl, benzoimidazolyl, 2,3-dihydrobenzooxazolyl, pyrazolyl, pyrrolo[2,3-b]pyridyl, pyrimidinyl, indolinyl, furyl, thienyl, and tetrahydroisoquinolyl), and 3- to 8-membered heterocycloalkyl (wherein the 3- to 8-membered heterocycloalkyl is selected from the group consisting of aziridinyl, azetidinyl, pyrrolidinyl, imidazolidinyl, piperidyl, piperazinyl, azepanyl, morpholinyl, and 1,2,3,6-tetrahydropyridyl), wherein each of the groups of $R^4$ is optionally substituted with a substituent selected from the group consisting of substituent A-1 below:
substituent A-1:
hydroxyl;
oxo;
cyano;
halogen;
$C_1$-$C_6$ alkyl (wherein the $C_1$-$C_6$ alkyl is optionally substituted with a substituent selected from the group consisting of substituent B-1 below);
$C_3$-$C_{10}$ cycloalkyl [wherein the $C_3$-$C_{10}$ cycloalkyl is optionally substituted with cyano, or $C_1$-$C_6$ alkyl substituted with —$NR^{31}R^{32}$ (wherein $R^{31}$ and $R^{32}$ each independently represent hydrogen or $C_1$-$C_6$ alkyl)];
—$NR^{21A}R^{22A}$ [wherein $R^{21A}$ and $R^{22A}$ each independently represent hydrogen, $C_1$-$C_6$ alkyl (wherein $C_1$-$C_6$ alkyl is optionally substituted with amino, di($C_1$-$C_6$ alkyl)amino, $C_1$-$C_6$ alkylsulfonyl (—$SO_2$ ($C_1$-$C_6$ alkyl)), piperidyl, or cyano), or piperidyl (wherein piperidyl is optionally substituted with —$COOR^{105}$ (wherein $R^{105}$ represents $C_1$-$C_6$ alkyl))];
$C_1$-$C_6$ alkoxy {wherein the $C_1$-$C_6$ alkoxy is optionally substituted with 3- to 8-membered heterocycloalkyl selected from halogen, piperidyl, and piperazinyl (wherein the 3- to 8-membered heterocycloalkyl is optionally substituted with $C_1$-$C_6$ alkyl), or —$NR^{33}R^{34}$ [wherein $R^{33}$ and $R^{34}$ each independently represent hydrogen, $C_1$-$C_6$ alkyl (wherein the $C_1$-$C_6$ alkyl is optionally substituted with $C_1$-$C_6$ alkylsulfonyl or di($C_1$-$C_6$ alkyl)amino), or $C_1$-$C_6$ alkylsulfonyl]};

—SO$_2$NR$^{23A}$R$^{24A}$ (wherein R$^{23A}$ and R$^{24A}$ each independently represent hydrogen, C$_1$-C$_6$ alkyl [wherein the C$_1$-C$_6$ alkyl is optionally substituted with hydroxyl, C$_1$-C$_6$ alkoxy, halogen, C$_3$-C$_{10}$ cycloalkyl, pyrazolyl, imidazolyl, or —NR$^{35}$R$^{36}$ (wherein R$^{35}$ and R$^{36}$ each independently represent hydrogen or C$_1$-C$_6$ alkyl)], C$_3$-C$_{10}$ cycloalkyl (wherein the C$_3$-C$_{10}$ cycloalkyl is optionally substituted with C$_1$-C$_6$ hydroxyalkyl), azetidinyl, or pyrrolidinyl, or may together form pyrrolidinyl, wherein the pyrrolidinyl is optionally substituted with amino or halogen);

C$_1$-C$_6$ alkylsulfonyl (wherein the C$_1$-C$_6$ alkyl moiety is optionally substituted with hydroxyl);

C$_1$-C$_6$ alkylsulfonylamino (—NHSO$_2$ (C$_1$-C$_6$ alkyl)) [wherein the C$_1$-C$_6$ alkyl moiety is optionally substituted with —NR$^{37}$R$^{38}$ (wherein R$^{37}$ and R$^{38}$ each independently represent hydrogen or C$_1$-C$_6$ alkyl)];

3- to 8-membered heterocycloalkyl selected from the group consisting of azetidinyl, pyrrolidinyl, piperidyl, piperazinyl, and tetrahydropyridyl {wherein the 3- to 8-membered heterocycloalkyl is optionally substituted with —NR$^{39}$R$^{40}$ (wherein R$^{39}$ and R$^{40}$ each independently represent hydrogen, C$_1$-C$_6$ alkyl, or C$_1$-C$_6$ alkylsulfonyl), C$_1$-C$_6$ alkyl [wherein the C$_1$-C$_6$ alkyl is optionally substituted with —NR$^{41}$R$^{42}$ (wherein R$^{41}$ and R$^{42}$ each independently represent hydrogen or C$_1$-C$_6$ alkyl)], hydroxyl, or C$_1$-C$_6$ alkylsulfonyl};

1H-tetrazolyl;

aryl (wherein aryl is optionally substituted with C$_1$-C$_6$ alkyl [wherein C$_1$-C$_6$ alkyl is optionally substituted with cyano or amino])

—COOR$^{11}$ (wherein R$^{11}$ represents hydrogen or C$_1$-C$_6$ alkyl); and

—COR$^{12A}$ [wherein R$^{12A}$ represents piperazinyl which is optionally substituted with C$_1$-C$_6$ alkyl, C$_3$-C$_{10}$ cycloalkyl, cyanomethyl, aminomethyl, —NR$^{25}$R$^{26}$ {wherein R$^{25}$ and R$^{26}$ each independently represent hydrogen or C$_1$-C$_6$ alkyl [wherein the C$_1$-C$_6$ alkyl is optionally substituted with hydroxyl or —NR$^{43}$R$^{44}$ (wherein R$^{43}$ and R$^{44}$ each independently represent hydrogen or C$_1$-C$_6$ alkyl)]}, or C$_1$-C$_6$ alkyl];

substituent B-1:
halogen;
hydroxyl;
C$_1$-C$_6$ alkoxy;
cyano;
cycloalkyl;
phenyl (wherein phenyl is optionally substituted with cyano);
heteroaryl selected from the group consisting of imidazolyl, pyrazolyl, and thiazolyl
3- to 8-membered heterocycloalkyl selected from the group consisting of pyrrolidinyl, piperidyl, piperazinyl, morpholinyl, and oxetanyl (wherein the 3- to 8-membered heterocycloalkyl is optionally substituted with C$_1$-C$_6$ alkyl, hydroxyl, amino, C$_1$-C$_6$ aminoalkyl, or C$_1$-C$_6$ alkyl substituted with C$_2$-C$_7$ alkyloxycarbonylamino);

—NR$^{51A}$R$^{52A}$ {wherein R$^{51A}$ and R$^{52A}$ each independently represent hydrogen, C$_1$-C$_6$ alkyl [wherein the C$_1$-C$_6$ alkyl is optionally substituted with C$_1$-C$_6$ alkylsulfonyl, or piperidyl which is optionally substituted with, —COOR$^{53}$ (wherein R$^{53}$ represents hydrogen or C$_1$-C$_6$ alkyl)], piperidyl, C$_1$-C$_6$ alkylsulfonyl, C$_3$-C$_{10}$ cycloalkyl, —COR$^{55}$ (wherein R$^{55}$ represents C$_1$-C$_6$ alkyl), —COOR$^{56}$ (wherein R$^{56}$ represents C$_1$-C$_6$ alkyl), or —CONR$^{57}$R$^{58}$ (wherein R$^{57}$ and R$^{58}$ each independently represent hydrogen or C$_1$-C$_6$ alkyl)};

—COOR$^{54}$ (wherein R$^{54}$ represents hydrogen or C$_1$-C$_6$ alkyl);

—CONH$_2$;

—SO$_2$NR$^{106}$R$^{107}$ (wherein R$^{106}$ and R$^{107}$ each independently represent hydrogen, C$_1$-C$_6$ alkyl, or C$_3$-C$_{10}$ cycloalkyl);

C$_1$-C$_6$ alkylsulfinyl; and

C$_1$-C$_6$ alkylsulfonyl

10. The compound of above 9, or a pharmaceutically acceptable salt thereof, wherein R$^4$ is a group selected from the group consisting of (p) below:

(p):
hydrogen,
hydroxyl,
halogen,
amino which is optionally substituted with a substituent selected from the group consisting of substituent (g) below,
C$_1$-C$_6$ alkyl which is optionally substituted with a substituent selected from the group consisting of substituent (a) below,
C$_2$-C$_6$ alkenyl which is optionally substituted with a substituent selected from the group consisting of substituent (b) below,
C$_3$-C$_{10}$ cycloalkyl,
C$_3$-C$_{10}$ cycloalkenyl,
C$_1$-C$_6$ alkoxy,
C$_6$-C$_{10}$ aryl which is optionally substituted with a substituent selected from the group consisting of substituent (c) below,
indanyl which is optionally substituted with a substituent selected from the group consisting of substituent (d) below,
heteroaryl which is optionally substituted with a substituent selected from the group consisting of substituent (e) below, and
3- to 8-membered heterocycloalkyl which is optionally substituted with a substituent selected from the group consisting of substituent (f) below, wherein, in the group (p),
the heteroaryl is selected from the group consisting of pyridyl, 1H-indazolyl, 1H-tetrazolyl, [1,2,4]triazolo[1,5-a]pyridyl, benzoimidazolyl, 2,3-dihydrobenzooxazolyl, pyrazolyl, pyrrolo[2,3-b]pyridyl, pyrimidinyl, indolinyl, furyl, thienyl, and tetrahydroisoquinolyl;

the 3- to 8-membered heterocycloalkyl is selected from the group consisting of pyrrolidinyl, piperidyl, piperazinyl, morpholinyl, and 1,2,3,6-tetrahydropyridyl;

substituent (a):
—NR$^{21A}$R$^{22A}$ [wherein R$^{21A}$ and R$^{22A}$ each independently represent hydrogen, C$_1$-C$_6$ alkyl {wherein C$_1$-C$_6$ alkyl is optionally substituted with piperidyl}, or piperidyl {wherein piperidyl is optionally substituted with —COOR$^{105}$ (wherein R$^{105}$ represents C$_1$-C$_6$ alkyl)}];

3- to 8-membered heterocycloalkyl selected from the group consisting of pyrrolidinyl and piperidyl {wherein the 3- to 8-membered heterocycloalkyl is optionally substituted with —NR$^{39}$R$^{40}$ (wherein R$^{39}$ and R$^{40}$ each independently represent hydrogen or C$_1$-C$_6$ alkyl), or C$_1$-C$_6$ alkyl [wherein the C$_1$-C$_6$ alkyl is optionally substituted with —NR$^{41}$R$^{42}$ (wherein R$^{41}$ and R$^{42}$ each independently represent hydrogen or C$_1$-C$_6$ alkyl)]}; and $C_1$-$C_6$ alkylsulfonylamino (—NHSO$_2$($C_1$-$C_6$ alkyl));
substituent (b):
- —COOR$^{11}$ (wherein R$^{11}$ represents hydrogen or $C_1$-$C_6$ alkyl); —NR$^{21a}$R$^{22a}$ [wherein R$^{21a}$ and R$^{22a}$ each independently represent hydrogen, or $C_1$-$C_6$ alkyl (wherein the $C_1$-$C_6$ alkyl is optionally substituted with di($C_1$-$C_6$ alkyl)amino or $C_1$-$C_6$ alkylsulfonyl)];
- 3- to 8-membered heterocycloalkyl selected from the group consisting of azetidinyl, pyrrolidinyl, and piperidyl {wherein the 3- to 8-membered heterocycloalkyl is optionally substituted with —NR$^{39}$R$^{40}$ (wherein R$^{39}$ and R$^{40}$ each independently represent hydrogen, $C_1$-$C_6$ alkyl, or $C_1$-$C_6$ alkylsulfonyl), $C_1$-$C_6$ alkyl [wherein the $C_1$-$C_6$ alkyl is optionally substituted with —NR$^{41}$R$^{42}$ (wherein R$^{41}$ and R$^{42}$ each independently represent hydrogen or $C_1$-$C_6$ alkyl)], hydroxyl, or $C_1$-$C_6$ alkylsulfonyl};
- cyano; and
- $C_1$-$C_6$ alkoxy;

substituent (c):
- hydroxyl;
- cyano;
- halogen;
- $C_1$-$C_6$ alkyl (wherein the $C_1$-$C_6$ alkyl is optionally substituted with a substituent selected from the group consisting of substituent B-c below);
- $C_3$-$C_{10}$ cycloalkyl [wherein the $C_3$-$C_{10}$ cycloalkyl is optionally substituted with cyano, or $C_1$-$C_6$ alkyl substituted with —NR$^{31}$R$^{32}$ (wherein R$^{31}$ and R$^{32}$ each independently represent hydrogen or $C_1$-$C_6$ alkyl)];
- —NR$^{21c}$R$^{22c}$ [wherein R$^{21c}$ and R$^{22c}$ each independently represent hydrogen or $C_1$-$C_6$ alkyl (wherein $C_1$-$C_6$ alkyl is optionally substituted with amino, or cyano)]];
- $C_1$-$C_6$ alkoxy {wherein the $C_1$-$C_6$ alkoxy is optionally substituted with 3- to 8-membered heterocycloalkyl selected from halogen, piperidyl, and piperazinyl (wherein the 3- to 8-membered heterocycloalkyl is optionally substituted with $C_1$-$C_6$ alkyl), or —NR$^{33}$R$^{34}$ [wherein R$^{33}$ and R$^{34}$ each independently represent hydrogen, $C_1$-$C_6$ alkyl (wherein the $C_1$-$C_6$ alkyl is optionally substituted with di($C_1$-$C_6$ alkyl)amino), or $C_1$-$C_6$ alkylsulfonyl]};
- —SO$_2$NR$^{23c}$R$^{24c}$ {wherein R$^{23c}$ and R$^{24c}$ each independently represent hydrogen, $C_1$-$C_6$ alkyl [wherein the $C_1$-$C_6$ alkyl is optionally substituted with hydroxyl, $C_1$-$C_6$ alkoxy, halogen, $C_3$-$C_{10}$ cycloalkyl, pyrazolyl, imidazolyl, or —NR$^{35}$R$^{36}$ (wherein R$^{35}$ and R$^{36}$ each independently represent hydrogen or $C_1$-$C_6$ alkyl)], $C_3$-$C_{10}$cycloalkyl (wherein the $C_3$-$C_{10}$ cycloalkyl is optionally substituted with $C_1$-$C_6$ hydroxyalkyl), azetidinyl, or pyrrolidinyl, or wherein R$^{23c}$ and R$^{24c}$ may together form pyrrolidinyl which is optionally substituted with amino or halogen};
- $C_1$-$C_6$ alkylsulfonyl (wherein the $C_1$-$C_6$ alkyl moiety is optionally substituted with hydroxyl);
- $C_1$-$C_6$ alkylsulfonylamino (—NHSO$_2$($C_1$-$C_6$ alkyl)) [wherein the $C_1$-$C_6$ alkyl moiety is optionally substituted with —NR$^{37}$R$^{38}$ (wherein R$^{37}$ and R$^{38}$ each independently represent hydrogen or $C_1$-$C_6$ alkyl)];
- piperazinyl {wherein the piperazinyl is optionally substituted with $C_1$-$C_6$ alkyl or $C_1$-$C_6$ alkylsulfonyl};
- piperidyl (wherein piperidyl is optionally substituted with hydroxyl);
- 1H-tetrazolyl;
- 1,2,3,6-tetrahydropyridyl; and
- —COR$^{12c}$ [wherein R$^{12c}$ represents piperazinyl which is optionally substituted with $C_1$-$C_6$ alkyl, $C_3$-$C_{10}$ cycloalkyl, cyanomethyl, aminomethyl, —NR$^{25}$R$^{26}$ {wherein R$^{25}$ and R$^{26}$ each independently represent hydrogen or $C_1$-$C_6$ alkyl [wherein the $C_1$-$C_6$ alkyl is optionally substituted with hydroxyl, or —NR$^{43}$R$^{44}$ (wherein R$^{43}$ and R$^{44}$ each independently represent hydrogen or $C_1$-$C_6$ alkyl)]}, or $C_1$-$C_6$ alkyl]; and substituent B-c:
- halogen;
- hydroxyl;
- methoxy;
- cyano;
- $C_3$-$C_{10}$ cycloalkyl
- 3- to 8-membered heterocycloalkyl selected from the group consisting of pyrrolidinyl, piperidyl, piperazinyl, morpholinyl, and oxetanyl (wherein the 3- to 8-membered heterocycloalkyl is optionally substituted with $C_1$-$C_6$ alkyl, hydroxyl, amino, $C_1$-$C_6$ aminoalkyl, or $C_1$-$C_6$ alkyl substituted with $C_2$-$C_7$ alkyloxycarbonylamino); and
- —NR$^{51c}$R$^{52c}$ {wherein R$^{51c}$ and R$^{52c}$ each independently represent hydrogen, $C_1$-$C_6$ alkyl [wherein the $C_1$-$C_6$ alkyl is optionally substituted with $C_1$-$C_6$ alkylsulfonyl, or piperidyl which is optionally substituted with —COOR$^{53}$ (wherein R$^{53}$ represents hydrogen or $C_1$-$C_6$ alkyl)], piperidyl, $C_1$-$C_6$alkylsulfonyl, $C_3$-$C_{10}$ cycloalkyl, —COR$^{55}$ (wherein R$^{55}$ represents $C_1$-$C_6$ alkyl), or —CONR$^{57}$R$^{58}$ (wherein R$^{57}$ and R$^{58}$ each independently represent hydrogen or $C_1$-$C_6$ alkyl)}];
- heteroaryl selected from the group of imidazolyl, pyrazolyl, and thiazolyl;
- —COOR$^{54}$ (wherein R$^{54}$ represents hydrogen, or $C_1$-$C_6$ alkyl)
- —CONH$_2$;
- —SO$_2$NR$^{106}$R$^{107}$ wherein R$^{106}$ and R$^{107}$ each independently represent hydrogen, $C_1$-$C_6$ alkyl, or $C_3$-$C_{10}$ cycloalkyl);
- $C_1$-$C_6$ alkylsufinyl; and
- $C_1$-$C_6$ alkylsulfonyl;

substituent (d):
- —NR$^{21d}$R$^{22d}$ (wherein R$^{21d}$ and R$^{22d}$ each independently represent hydrogen or $C_1$-$C_6$ alkyl);

substituent (e):
- hydroxyl;
- oxo;
- cyano;
- $C_3$-$C_{10}$ cycloalkyl [wherein $C_3$-$C_{10}$ cycloalkyl is optionally substituted with cyano];
- —NR$^{21}$R$^{22}$ [wherein R$^{21}$ and R$^{22}$ each independently represent hydrogen or $C_1$-$C_6$ alkyl (wherein $C_1$-$C_6$ alkyl is optionally substituted with amino)];
- piperidyl;
- $C_1$-$C_6$ alkoxy (wherein $C_1$-$C_6$ alkoxy is optionally substituted with —NR$^{33}$R$^{34}$ [wherein R$^{33}$ and R$^{34}$ each independently represent hydrogen, or $C_1$-$C_6$ alkyl]); and $C_1$-$C_6$ alkyl {wherein the $C_1$-$C_6$ alkyl is optionally substituted with cyano, —NR$^{51e}$R$^{52e}$ [wherein R$^{51e}$ and R$^{52e}$ each independently represent hydrogen, $C_1$-$C_6$ alkyl, or —COOR$^{56}$ (wherein R$^{56}$ represents $C_1$-$C_6$ alkyl)], morpholinyl, or cyanophenyl}; —CONH$_2$;

substituent (f):

$C_1$-$C_6$ alkyl {wherein the $C_1$-$C_6$ alkyl is optionally substituted with —NR$^{51f}$R$^{52f}$ [wherein R$^{51f}$ and R$^{52f}$ each independently represent hydrogen, $C_1$-$C_6$ alkyl, or —COOR$^{56}$ (wherein R$^{56}$ represents $C_1$-$C_6$ alkyl)]}; and $C_1$-$C_6$ alkylsulfonyl;

substituent (g):

Aryl (wherein aryl is optionally substituted with $C_1$-$C_6$ alkyl [wherein $C_1$-$C_6$ alkyl is optionally substituted with cyano or amino]).

11. The compound of above 2, or a pharmaceutically acceptable salt thereof, wherein R$^6$ is hydrogen; hydroxyl; $C_1$-$C_6$ alkyl; phenyl which is optionally substituted with 1 to 3 hydroxyls; piperidyl which is optionally substituted with amino; or piperazinyl.

12. The compound of above 11, or a pharmaceutically acceptable salt thereof, wherein R$^7$ is hydrogen, $C_1$-$C_6$ alkyl (wherein $C_1$-$C_6$ alkyl is optionally substituted by a substituent selected from the group comprising hydroxyl and piperidyl), or halogen.

13. The compound of above 2, or a pharmaceutically acceptable salt thereof, wherein R$^7$ is hydrogen;

$C_1$-$C_6$ alkyl {wherein the $C_1$-$C_6$ alkyl is optionally substituted with hydroxyl, —NR$^{71A}$R$^{72A}$ [wherein R$^{71A}$ and R$^{72A}$ each independently represent hydrogen, $C_1$-$C_6$ alkyl (wherein the $C_1$-$C_6$ alkyl is optionally substituted with dimethylamino), $C_3$-$C_{10}$ cycloalkyl (wherein the $C_3$-$C_{10}$ cycloalkyl is optionally substituted with amino), or piperidyl], or 3- to 8-membered heterocycloalkyl selected from the group consisting of piperidyl and morpholinyl (wherein the 3- to 8-membered heterocycloalkyl is optionally substituted with $C_1$-$C_6$ aminoalkyl)};

phenyl which is optionally substituted with 1 to 2 hydroxyls;

phenylsulfonyl; or

—COR$^{73A}$ {wherein R$^{73A}$ represents piperidyl (wherein the piperidyl is optionally substituted with amino), or —NR$^{74A}$R$^{75A}$ [wherein R$^{74A}$ and R$^{75A}$ each independently represent hydrogen, piperidyl, or $C_3$-$C_{10}$ cycloalkyl (wherein the $C_3$-$C_{10}$ cycloalkyl is optionally substituted with amino)]}.

14. The compound of above 1, or a pharmaceutically acceptable salt thereof, wherein $$—X\rlap{=}{-}Y\rlap{=}{-}Z—$$

is —CH$_2$—CH$_2$—CH$_2$—.

15. The compound of above 14, or a pharmaceutically acceptable salt thereof, wherein R$^1$ and R$^2$ are hydrogen.

16. The compound of above 14, or a pharmaceutically acceptable salt thereof, wherein R$^3$ is hydroxyl or methoxy.

17. The compound of above 14, or a pharmaceutically acceptable salt thereof, wherein R$^4$ is hydrogen, phenyl [wherein the phenyl is substituted with $C_1$-$C_6$ alkyl substituted with —NR$^{51A}$R$^{52A}$ (wherein R$^{51A}$ and R$^{52A}$ each independently represent hydrogen or $C_1$-$C_6$ alkyl), or —SO$_2$NR$^{53A}$R$^{54A}$ (wherein R$^{53A}$ and R$^{54A}$ each independently represent hydrogen, or $C_1$-$C_6$ alkyl that is optionally substituted with halogen or hydroxyl)], 1,2,3,6-tetrahydropyridyl, hydroxypyridyl, or methoxypyridyl.

18. The compound of above 1, or a pharmaceutically acceptable salt thereof, wherein $$—X\rlap{=}{-}Y\rlap{=}{-}Z—$$

is —NR$^{108}$—CH=CR$^{109}$— (wherein R$^{108}$ represents hydrogen, or $C_1$-$C_6$ alkyl that is optionally substituted with hydroxyl, and R$^{109}$ represents hydrogen, CH$_3$, or phenyl group which is substituted with $C_1$-$C_6$-aminoalkyl), R$^1$, R$^2$, and R$^4$ are hydrogen, and R$^3$ is hydrogen, hydroxyl or $C_1$-$C_6$alkoxy.

19. The compound of above 1, or a pharmaceutically acceptable salt thereof, wherein $$—X\rlap{=}{-}Y\rlap{=}{-}Z—$$

is —N=CH—S—,

R$^1$, R$^2$, and R$^4$ are hydrogen, and

R$^3$ is methoxy.

20. A compound selected from the group consisting of:

(1): 8-methoxy-5-methylthieno[2,3-c]quinolin-4(5H)-one;
(2): 8-hydroxy-5-methylthieno[2,3-c]quinolin-4(5H)-one;
(3): 7,8-dihydroxythieno[2,3-c]quinolin-4(5H)-one;
(4): 7,8-dimethoxythieno[2,3-c]quinolin-4(5H)-one;
(5): 8-methoxythieno[2,3-c]quinolin-4(5H)-one;
(6): 7,9-dimethoxythieno[2,3-c]quinolin-4(5H)-one;
(7): 7,9-dihydroxythieno[2,3-c]quinolin-4(5H)-one;
(8): 7,8,9-trimethoxythieno[2,3-c]quinolin-4(5H)-one;
(9): 8-hydroxythieno[2,3-c]quinolin-4(5H)-one;
(10): 7,8,9-trihydroxythieno[2,3-c]quinolin-4(5H)-one;
(11): 9-(3-(2-aminoethyl)phenyl)-8-methoxythieno[2,3-c]quinolin-4(5H)-one;
(12): 8-chlorothieno[2,3-c]quinolin-4(5H)-one;
(13): 4-oxo-4,5-dihydrothieno[2,3-c]quinoline-8-carbonitrile;
(14): thieno[2,3-c]quinolin-4(5H)-one;
(15): 8-fluorothieno[2,3-c]quinolin-4(5H)-one;
(16): 8-nitrothieno[2,3-c]quinolin-4(5H)-one;
(17): 8-(3-aminopiperidin-1-yl)thieno[2,3-c]quinolin-4(5H)-one;
(18): 1-(4-hydroxyphenyl)thieno[2,3-c]quinolin-4(5H)-one;
(19): 1,8-dihydroxythieno[2,3-c]quinolin-4(5H)-one;
(20): 8-hydroxy-1-(4-hydroxyphenyl)thieno[2,3-c]quinolin-4(5H)-one;
(2H): (R)-8-(3-aminopyrrolidin-1-yl)thieno[2,3-c]quinolin-4(5H)-one;
(22): (S)-8-(3-aminopyrrolidin-1-yl)thieno[2,3-c]quinolin-4(5H)-one;
(23): 8-(pyridin-3-yl)thieno[2,3-c]quinolin-4(5H)-one;
(24): 8-(4-hydroxyphenyl)thieno[2,3-c]quinolin-4(5H)-one;
(25): 1-(3,4-dihydroxyphenyl)-8-hydroxythieno[2,3-c]quinolin-4(5H)-one;
(26): 1-(3-aminopiperidin-1-yl)-8-hydroxythieno[2,3-c]quinolin-4(5H)-one;
(27): 8-morpholinothieno[2,3-c]quinolin-4(5H)-one;
(28): 8-hydroxy-2-methylthieno[2,3-c]quinolin-4(5H)-one;
(29): 8-hydroxy-2-(hydroxymethyl)thieno[2,3-c]quinolin-4(5H)-one;
(30): 8-hydroxy-4-oxo-N-(piperidin-3-yl)-4,5-dihydrothieno[2,3-c]quinoline-2-carboxamide;

(31): 8-hydroxy-2-(4-hydroxyphenyl)thieno[2,3-c]quinolin-4(5H)-one;
(32): 8-hydroxy-1-(piperazin-1-yl)thieno[2,3-c]quinolin-4(5H)-one;
(33): N-((1r,4r)-4-aminocyclohexyl)-8-hydroxy-4-oxo-4,5-dihydrothieno[2,3-c]quinolin-2-carboxamide;
(34): 2-(3-aminopiperidine-1-carbonyl)-8-hydroxythieno[2,3-c]quinolin-4(5H)-one;
(35): 2-(3,4-dihydroxyphenyl)-8-hydroxythieno[2,3-c]quinolin-4(5H)-one;
(36): 2-(((1r,4r)-4-aminocyclohexylamino)methyl)-8-hydroxythieno[2,3-c]quinolin-4(5H)-one;
(37): 8-(piperazin-1-yl)thieno[2,3-c]quinolin-4(5H)-one;
(38): 8-hydroxy-1-methylthieno[2,3-c]quinolin-4(5H)-one;
(39): 2-((2-(dimethylamino)ethylamino)methyl)-8-hydroxythieno[2,3-c]quinolin-(5H)-one;
(40): 8-hydroxy-2-((piperidin-3-ylamino)methyl)thieno[2,3-c]quinolin-4(5H)-one;
(41): 7-hydroxythieno[2,3-c]quinolin-4(5H)-one;
(42): 9-bromo-8-hydroxythieno[2,3-c]quinolin-4(5H)-one;
(43): 9-(3,4-dihydroxyphenyl)-8-hydroxythieno[2,3-c]quinolin-4(5H)-one;
(44): 1-methyl-4-oxo-4,5-dihydrothieno[2,3-c]quinoline-8-carbonitrile;
(45): 7-(3,4-dihydroxyphenyl)-8-hydroxythieno[2,3-c]quinolin-4(5H)-one;
(46): 8-hydroxy-1-methyl-3H-pyrrolo[2,3-c]quinolin-4(5H)-one;
(47): 9-(3,5-dihydroxyphenyl)-8-hydroxythieno[2,3-c]quinolin-4(5H)-one;
(48): 8-hydroxy-9-(3-hydroxyphenyl)thieno[2,3-c]quinolin-4(5H)-one;
(49): 8-hydroxy-9-(4-hydroxyphenyl)thieno[2,3-c]quinolin-4(5H)-one;
(50): 9-(3,4-difluorophenyl)-8-methoxythieno[2,3-c]quinolin-4(5H)-one;
(51): (S)-8-(3-aminopyrrolidin-1-yl)-2-(4-hydroxyphenyl)thieno[2,3-c]quinolin-4(5H)-one;
(52): 5-(8-methoxy-4-oxo-4,5-dihydrothieno[2,3-c]quinolin-9-yl)picolinonitrile;
(53): 9-(6-aminopyridin-3-yl)-8-hydroxythieno[2,3-c]quinolin-4(5H)-one;
(54): 4-(8-hydroxy-4-oxo-4,5-dihydrothieno[2,3-c]quinolin-9-yl)benzamide;
(55): 9-(3-fluoro-4-hydroxyphenyl)-8-hydroxythieno[2,3-c]quinolin-4(5H)-one;
(56): 8-hydroxy-2-(3-hydroxyphenyl)thieno[2,3-c]quinolin-4(5H)-one;
(57): (R)-8-(3-aminopyrrolidin-1-yl)-2-(3,4-dihydroxyphenyl)thieno[2,3-c]quinolin-4(5H)-one;
(58): 9-(3,4-difluorophenyl)-8-hydroxythieno[2,3-c]quinolin-4(5H)-one;
(59): 9-(4-fluoro-3-hydroxyphenyl)-8-hydroxythieno[2,3-c]quinolin-4(5H)-one;
(60): 8-hydroxy-9-(3-hydroxy-5-(trifluoromethyl)phenyl)thieno[2,3-c]quinolin-4(5H)-one;
(61): 8-hydroxy-9-(1H-indazol-6-yl)thieno[2,3-c]quinolin-4(5H)-one;
(62): 8-hydroxy-9-(3,4,5-trihydroxyphenyl)thieno[2,3-c]quinolin-4(5H)-one;
(63): 9-(4-hydroxyphenyl)-8-methoxythieno[2,3-c]quinolin-4(5H)-one;
(64): 9-(4-(1H-tetrazol-5-yl)phenyl)-8-hydroxythieno[2,3-c]quinolin-4(5H)-one;
(65): 4-(8-hydroxy-4-oxo-4,5-dihydrothieno[2,3-c]quinolin-9-yl)benzenesulfonamide;
(66): 9-(3-chloro-4-fluorophenyl)-8-hydroxythieno[2,3-c]quinolin-4(5H)-one;
(67): 9-(4-chloro-3-fluorophenyl)-8-hydroxythieno[2,3-c]quinolin-4(5H)-one;
(68): 9-(3,4-dichlorophenyl)-8-hydroxythieno[2,3-c]quinolin-4(5H)-one;
(69): 9-(4-fluorophenyl)-8-hydroxythieno[2,3-c]quinolin-4(5H)-one;
(70): 8-hydroxy-9-phenylthieno[2,3-c]quinolin-4(5H)-one;
(71): 9-(4-(difluoromethoxy)phenyl)-8-methoxythieno[2,3-c]quinolin-4(5H)-one;
(72): 9-(4-(aminomethyl)phenyl)-8-hydroxythieno[2,3-c]quinolin-4(5H)-one;
(73): 9-(4-(aminomethyl)phenyl)-8-hydroxythieno[2,3-c]quinolin-4(5H)-one;
(74): 9-(3-aminophenyl)-8-hydroxythieno[2,3-c]quinolin-4(5H)-one;
(75): 3-(8-hydroxy-4-oxo-4,5-dihydrothieno[2,3-c]quinolin-9-yl)benzenesulfonamide;
(76): 8-hydroxy-9-(3,4,5-trifluorophenyl)thieno[2,3-c]quinolin-4(5H)-one;
(77): N-(4-(8-hydroxy-4-oxo-4,5-dihydrothieno[2,3-c]quinolin-9-yl)phenyl)methanesulfonamide;
(78): 8-methoxy-9-phenylthieno[2,3-c]quinolin-4(5H)-one;
(79): 8-hydroxy-9-(naphthalen-2-yl)thieno[2,3-c]quinolin-4(5H)-one;
(80): 8-hydroxy-9-(4-(hydroxymethyl)phenyl)thieno[2,3-c]quinolin-4(5H)-one;
(81): 2-(4-(8-hydroxy-4-oxo-4,5-dihydrothieno[2,3-c]quinolin-9-yl)phenyl)acetonitrile;
(82): 8-hydroxy-9-(4-(methylsulfonyl)phenyl)thieno[2,3-c]quinolin-4(5H)-one;
(83): 8-hydroxy-9-(pyridin-4-yl)thieno[2,3-c]quinolin-4(5H)-one;
(84): 8-hydroxy-9-(1,2,3,6-tetrahydropyridin-4-yl)thieno[2,3-c]quinolin-4(5H)-one;
(85): 8-hydroxy-9-(4-hydroxy-3-methoxyphenyl)thieno[2,3-c]quinolin-4(5H)-one;
(86): 9-(3-fluoro-4-(morpholinomethyl)phenyl)-8-hydroxythieno[2,3-c]quinolin-4(5H)-one;
(87): 9-(3-(aminomethyl)phenyl)-8-hydroxythieno[2,3-c]quinolin-4(5H)-one;
(88): 9-(4-(aminomethyl)phenyl)-8-methoxythieno[2,3-c]quinolin-4(5H)-one;
(89): 9-(3-(difluoromethyl)phenyl)-8-methoxythieno[2,3-c]quinolin-4(5H)-one;
(90): 9-(3-(aminomethyl)phenyl)-8-hydroxy-2-methylthieno[2,3-c]quinolin-4(5H)-one;
(91): 9-cyclohexenyl-8-methoxythieno[2,3-c]quinolin-4(5H)-one;
(92): 9-(3,5-difluorophenyl)-8-hydroxythieno[2,3-c]quinolin-4(5H)-one;
(93): 9-(4-(2-(dimethylamino)ethyl)phenyl)-8-hydroxythieno[2,3-c]quinolin-4(5H)-one;
(94): 9-(3-(aminomethyl)phenyl)-8-methoxythieno[2,3-c]quinolin-4(5H)-one;
(95): 9-(4-(aminomethyl)phenyl)-8-hydroxy-2-methylthieno[2,3-c]quinolin-4(5H)-one;
(96): 9-cyclopropyl-8-hydroxythieno[2,3-c]quinolin-4(5H)-one;
(97): 9-([1,2,4]triazolo[1,5-a]pyridin-6-yl)-8-hydroxythieno[2,3-c]quinolin-4(5H)-one;
(98): 8-methoxy-9-(1,2,3,6-tetrahydropyridin-4-yl)thieno[2,3-c]quinolin-4(5H)-one;
(99): 9-cyclohexenyl-8-hydroxythieno[2,3-c]quinolin-4(5H)-one;

(100): 8-methoxy-9-(4-(2-(piperidin-1-yl)ethylamino)phenyl)thieno[2,3-c]quinolin-4(5H)-one;
(101): 9-(4-(aminomethyl)phenyl)-8-hydroxy-2-(morpholinomethyl)thieno[2,3-c]quinolin-4(5H)-one;
(102): 9-(1H-benzo[d]imidazol-5-yl)-8-hydroxythieno[2,3-c]quinolin-4(5H)-one;
(103): 9-(4-(difluoromethyl)phenyl)-8-methoxythieno[2,3-c]quinolin-4(5H)-one;
(104): 9-(4-(aminomethyl)phenyl)-8-methoxy-2-(morpholinomethyl)thieno[2,3-c]quinolin-4(5H)-one;
(105): 8-hydroxy-9-(4-(2-(piperidin-1-yl)ethylamino)phenyl)thieno[2,3-c]quinolin-4(5H)-one;
(106): 8-hydroxy-9-(4-(piperazin-1-yl)phenyl)thieno[2,3-c]quinolin-4(5H)-one;
(107): 8-methoxy-2,3-dihydro-1H-cyclopenta[c]quinolin-4(5H)-one;
(108): 8-hydroxy-2,3-dihydro-1H-cyclopenta[c]quinolin-4(5H)-one;
(109): 5-(8-hydroxy-4-oxo-4,5-dihydrothieno[2,3-c]quinolin-9-yl)benzo[d]oxazol-2(3H)-one;
(110): tert-butyl 4-(2-(hydroxy-4-oxo-4,5-dihydrothieno[2,3-c]quinolin-9-yl)benzylamino)ethyl)piperidine-1-carboxylate;
(111): 8-methoxy-9-(4-(piperazin-1-yl)phenyl)thieno[2,3-c]quinolin-4(5H)-one;
(112): 8-hydroxy-9-(4-(4-(methylsulfonyl)piperazin-1-yl)phenyl)thieno[2,3-c]quinolin-4(5H)-one;
(113): 8-hydroxy-9-(4-((piperidin-3-ylamino)methyl)phenyl)thieno[2,3-c]quinolin-4(5H)-one;
(114): N-(2-(dimethylamino)ethyl)-4-(8-hydroxy-4-oxo-4,5-dihydrothieno[2,3-c]quinolin-9-yl)benzamide;
(115): 9-(4-(3-(dimethylamino)propoxy)phenyl)-8-methoxythieno[2,3-c]quinolin-(5H)-one;
(116): 8-methoxy-9-(1-(piperidin-4-yl)-1H-pyrazol-4-yl)thieno[2,3-c]quinolin-4(5H)-one;
(117): 8-hydroxy-9-(1-(piperidin-4-yl)-1H-pyrazol-4-yl)thieno[2,3-c]quinolin-4(5H)-one;
(118): 8-methoxythiazolo[4,5-c]quinolin-4(5H)-one;
(119): 2-((4-(aminomethyl)piperidin-1-yl)methyl)-8-hydroxythieno[2,3-c]quinolin-4(5H)-one;
(120): N-(2-(dimethylamino)ethyl)-4-(8-methoxy-4-oxo-4,5-dihydrothieno[2,3-c]quinolin-9-yl)benzamide;
(121): 9-(4-(aminomethyl)phenyl)-8-hydroxy-2,3-dihydro-1H-cyclopenta[c]quinolin-4(5H)-one;
(122): (E)-butyl 3-(8-hydroxy-4-oxo-4,5-dihydrothieno[2,3-c]quinolin-9-yl)acrylate;
(123): 8-methoxy-9-(1H-pyrrolo[2,3-b]pyridin-5-yl)thieno[2,3-c]quinolin-4(5H)-one;
(124): 8-hydroxy-9-(1H-pyrrolo[2,3-b]pyridin-5-yl)thieno[2,3-c]quinolin-4(5H)-one;
(125): N-(methoxy-4-oxo-4,5-dihydrothieno[2,3-c]quinolin-9-yl)phenethyl)acetamide;
(126): N-(2-aminoethyl)-4-(8-hydroxy-4-oxo-4,5-dihydrothieno[2,3-c]quinolin-9-yl)benzamide;
(127): N-(2-aminoethyl)-4-(8-methoxy-4-oxo-4,5-dihydrothieno[2,3-c]quinolin-9-yl)benzamide;
(128): N-(hydroxy-4-oxo-4,5-dihydrothieno[2,3-c]quinolin-9-yl)phenethyl)acetamide;
(129): 4-(8-hydroxy-4 oxo-2,3,4,5-tetrahydro-1H-cyclopenta[c]quinolin-9-yl)benzenesulfonamide;
(130): 8-hydroxy-9-(4-(4-methylpiperazine-1-carbonyl)phenyl)thieno[2,3-c]quinolin-4(5H)-one;
(131): 8-methoxy-9-(4-(4-methylpiperazine-1-carbonyl)phenyl)thieno[2,3-c]quinolin-4(5H)-one;
(132): 8-hydroxy-9-(4-((4-methylpiperazin-1-yl)methyl)phenyl)thieno[2,3-c]quinolin-4(5H)-one;
(133): 8-methoxy-9-(4-((4-methylpiperazin-1-yl)methyl)phenyl)thieno[2,3-c]quinolin-4(5H)-one;
(134): (E)-9-(3-(diethylamino)prop-1-enyl)-8-methoxythieno[2,3-c]quinolin-4(5H)-one;
(135): (E)-9-(3-(4-(aminomethyl)piperidin-1-yl)prop-1-enyl)-8-methoxythieno[2,3-c]quinolin-4(5H)-one;
(136): (E)-9-(3-(2-(diethylamino)ethylamino)prop-1-enyl)-8-hydroxythieno[2,3-c]quinolin-4(5H)-one;
(137): N-(4-(8-hydroxy-4-oxo-2,3,4,5-tetrahydro-1H-cyclopenta[c]quinolin-9-yl)phenyl)methanesulfonamide;
(138): 9-(2-(dimethylamino)pyrimidin-5-yl)-8-hydroxythieno[2,3-c]quinolin-4(5H)-one;
(139): tert-butyl(1-(methoxy-4-oxo-4,5-dihydrothieno[2,3-c]quinolin-9-yl)benzyl)piperidin-4-yl)methylcarbamate;
(140): 8-hydroxy-9-(4-(4-methylpiperazin-1-yl)phenyl)thieno[2,3-c]quinolin-4(5H)-one;
(141): 8-methoxy-9-(4-(4-methylpiperazin-1-yl)phenyl)thieno[2,3-c]quinolin-4(5H)-one;
(142): 8-methoxy-9-(1-(methylsulfonyl)-1,2,3,6-tetrahydropyridin-4-yl)thieno[2,3-c]quinolin-4(5H)-one;
(143): (E)-9-(3-(diethylamino)prop-1-enyl)-8-hydroxythieno[2,3-c]quinolin-4(5H)-one;
(144): 9-(3-(4-(aminomethyl)piperidin-1-yl)propyl)-8-methoxythieno[2,3-c]quinolin-4(5H)-one;
(145): 9-(4-(3-(2-(diethylamino)ethylamino)propoxy)phenyl)-8-methoxythieno[2,3-c]quinolin-(5H)-one;
(146): 9-(4-(3-(diethylamino)propoxy)phenyl)-8-methoxythieno[2,3-c]quinolin-4(5H)-one;
(147): 9-(4-(3-(2-(diethylamino)ethylamino)propoxy)phenyl)-8-hydroxythieno[2,3-c]quinolin-(5H)-one;
(148): (E)-9-(3-(4-(aminomethyl)piperidin-1-yl)prop-1-enyl)-8-hydroxythieno[2,3-c]quinolin-4(5H)-one;
(149): 9-(4-(3-(dimethylamino)propoxy)phenyl)-8-hydroxythieno[2,3-c]quinolin-4(5H)-one;
(150): 8-hydroxy-9-(4-(2-(piperidin-1-yl)ethoxy)phenyl)thieno[2,3-c]quinolin-4(5H)-one;
(151): 9-(4-(2-(ethylamino)ethoxy)phenyl)-8-hydroxythieno[2,3-c]quinolin-4(5H)-one;
(152): (E)-9-(3-(4-aminopiperidin-1-yl)prop-1-enyl)-8-methoxythieno[2,3-c]quinolin-4(5H)-one;
(153): 9-(1-(2-aminoethyl)-1,2,3,6-tetrahydropyridin-4-yl)-8-methoxythieno[2,3-c]quinolin-4(5H)-one;
(154): 9-(4-(2-(ethylamino)ethoxy)phenyl)-8-methoxythieno[2,3-c]quinolin-4(5H)-one;
(155): 9-(4-(2-(diethylamino)ethoxy)phenyl)-8-hydroxythieno[2,3-c]quinolin-4(5H)-one;
(156): 9-(4-(2-(diethylamino)ethoxy)phenyl)-8-methoxythieno[2,3-c]quinolin-4(5H)-one;
(157): 9-(4-(2-(dimethylamino)ethoxy)phenyl)-8-hydroxythieno[2,3-c]quinolin-4(5H)-one;
(158): 9-(4-(2-(dimethylamino)ethoxy)phenyl)-8-methoxythieno[2,3-c]quinolin-4(5H)-one;
(159): 8-methoxy-9-(4-(2-(piperidin-1-yl)ethoxy)phenyl)thieno[2,3-c]quinolin-4(5H)-one;
(160): 8-methoxy-9-(3-(2-(4-methylpiperazin-1-yl)ethoxy)phenyl)thieno[2,3-c]quinolin-4(5H)-one;
(161): 9-(3-(2-(diethylamino)ethoxy)phenyl)-8-methoxythieno[2,3-c]quinolin-4(5H)-one;
(162): 9-(3-(3-(diethylamino)propoxy)phenyl)-8-methoxythieno[2,3-c]quinolin-4(5H)-one;
(163): 9-(4-(2-(dimethylamino)ethyl)phenyl)-8-methoxythieno[2,3-c]quinolin-4(5H)-one;
(164): 9-(4-((dimethylamino)methyl)phenyl)-8-methoxythieno[2,3-c]quinolin-4(5H)-one;
(165): 9-(4-((dimethylamino)methyl)phenyl)-8-hydroxythieno[2,3-c]quinolin-4(5H)-one;

(166): 9-(3-(2-(diethylamino)ethoxy)phenyl)-8-hydroxythieno[2,3-c]quinolin-4(5H)-one;
(167): 8-hydroxy-9-(3-(2-(4-methylpiperazin-1-yl)ethoxy)phenyl)thieno[2,3-c]quinolin-4(5H)-one;
(168): N-ethyl-N-(2-(4-(8-methoxy-4-oxo-4,5-dihydrothieno[2,3-c]quinolin-9-yl)phenylmethoxy-4-oxo-4,5-dihydrothieno[2,3-c]quinolin-9-yl)phenoxy)ethyl)methanesulfonamide;
(169): 9-(4-(2-aminoethyl)phenyl)-8-methoxythieno[2,3-c]quinolin-4(5H)-one;
(170): 2-(3-(8-hydroxy-4-oxo-4,5-dihydrothieno[2,3-c]quinolin-9-yl)phenyl)acetonitrile;
(171): 2-(3-(8-methoxy-4-oxo-4,5-dihydrothieno[2,3-c]quinolin-9-yl)phenyl)acetonitrile;
(172): 9-(1-(2-(dimethylamino)ethyl)-1,2,3,6-tetrahydropyridin-4-yl)-8-hydroxythieno[2,3-c]quinolin-4(5H)-one;
(173): N-(hydroxy-4-oxo-4,5-dihydrothieno[2,3-c]quinolin-9-yl)phenethyl)methanesulfonamide;
(174): 9-(1-(2-(diethylamino)ethyl)-1,2,3,6-tetrahydropyridin-4-yl)-8-hydroxythieno[2,3-c]quinolin-4(5H)-one;
(175): 9-(4-(2-aminoethyl)phenyl)-8-hydroxythieno[2,3-c]quinolin-4(5H)-one;
(176): 9-(4-(2-aminoethyl)phenyl)-8-hydroxythieno[2,3-c]quinolin-4(5H)-one;
(177): N-(methoxy-4-oxo-4,5-dihydrothieno[2,3-c]quinolin-9-yl)phenethyl)methanesulfonamide;
(178): N-(methoxy-4-oxo-4,5-dihydrothieno[2,3-c]quinolin-9-yl)phenethyl)methanesulfonamide;
(179): N-(2-aminoethyl)-4-(8-hydroxy-4-oxo-4,5-dihydrothieno[2,3-c]quinolin-9-yl)benzensulfonamide;
(180): 8-hydroxy-9-(1,2,3,6-tetrahydropyridin-4-yl)-2,3-dihydro-1H-cyclopenta[c]quinolin-4(5H)-one;
(181): 9-(4-(1-(dimethylamino)ethyl)phenyl)-8-hydroxy-2,3-dihydro-1H-cyclopenta[c]quinolin-4(5H)-one;
(182): 9-(4-(2-(dimethylamino)ethyl)phenyl)-8-methoxy-2,3-dihydro-1H-cyclopenta[c]quinolin-4(5H)-one;
(183): 9-(4-((diethylamino)methyl)phenyl)-8-methoxythieno[2,3-c]quinolin-4(5H)-one;
(184): 9-(4-((diethylamino)methyl)phenyl)-8-hydroxythieno[2,3-c]quinolin-4(5H)-one;
(185): 9-(3-(2-(dimethylamino)ethyl)phenyl)-8-hydroxythieno[2,3-c]quinolin-4(5H)-one;
(186): 9-(3-(2-aminoethyl)phenyl)-8-hydroxythieno[2,3-c]quinolin-4(5H)-one;
(187): 8-hydroxy-9-(4-((methylamino)methyl)phenyl)thieno[2,3-c]quinolin-4(5H)-one;
(188): 8-methoxy-9-(4-((methylamino)methyl)phenyl)thieno[2,3-c]quinolin-4(5H)-one;
(189): 9-(4-amino-3-methoxyphenyl)-8-methoxythieno[2,3-c]quinolin-4(5H)-one;
(190): 3-(8-hydroxy-4 oxo-4,5-dihydrothieno[2,3-c]quinolin-9-yl)benzonitrile;
(191): 9-(4-(1-(dimethylamino)ethyl)phenyl)-8-hydroxythieno[2,3-c]quinolin-4(5H)-one;
(192): 9-(4-(1-(dimethylamino)ethyl)phenyl)-8-hydroxythieno[2,3-c]quinolin-4(5H)-one;
(193): N-(1-(4-(8-hydroxy-4-oxo-4,5-dihydrothieno[2,3-c]quinolin-9-yl)phenyl)ethyl)methanesulfonamide;
(194): 8-hydroxy-9-(4-(1-(pyrrolidin-1-yl)ethyl)phenyl)thieno[2,3-c]quinolin-4(5H)-one;
(195): 9-(4-(1-aminoethyl)phenyl)-8-hydroxythieno[2,3-c]quinolin-4(5H)-one;
(196): 9-(4-(1-(diethylamino)ethyl)phenyl)-8-hydroxythieno[2,3-c]quinolin-4(5H)-one;
(197): N-(2-aminoethyl)-4-(8-methoxy-4-oxo-4,5-dihydrothieno[2,3-c]quinolin-9-yl)benzensulfonamide;
(198): N-(2-(dimethylamino)ethyl)-4-(8-methoxy-4-oxo-4,5-dihydrothieno[2,3-c]quinolin-9-yl)benzenesulfonamide;
(199): 4-(8-hydroxy-4-oxo-4,5-dihydrothieno[2,3-c]quinolin-9-yl)-N-(pyrrolidin-3-yl)benzenesulfonamide;
(200): N-(azetidin-3-yl)-4-(8-hydroxy-4-oxo-4,5-dihydrothieno[2,3-c]quinolin-9-yl)benzensulfonamide;
(201): 9-(4-(2-(diethylamino)ethyl)phenyl)-8-hydroxythieno[2,3-c]quinolin-4(5H)-one;
(202): 2-amino-N-(3-(8-methoxy-4-oxo-4,5-dihydrothieno[2,3-c]quinolin-9-yl)phenyl)ethanesulfonamide;
(203): 4-(8-hydroxy-4-oxo-4,5-dihydrothieno[2,3-c]quinolin-9-yl)benzonitrile;
(204): 4-(8-methoxy-4-oxo-4,5-dihydrothieno[2,3-c]quinolin-9-yl)benzonitrile;
(205): (E)-9-(3-(3-aminopyrrolidin-1-yl)prop-1-enyl)-8-methoxythieno[2,3-c]quinolin-4(5H)-one;
(206): N-(2-hydroxyethyl)-4-(8-methoxy-4-oxo-4,5-dihydrothieno[2,3-c]quinolin-9-yl)benzenesulfonamide;
(207): 8-methoxy-9-(5-methoxypyridin-3-yl)thieno[2,3-c]quinolin-4(5H)-one;
(208): 8-methoxy-9-(5-methoxypyridin-3-yl)-2,3-dihydro-1H-cyclopenta[c]quinolin-4(5H)-one;
(209): 9-(4-(3-aminopyrrolidin-1-ylsulfonyl)phenyl)-8-hydroxythieno[2,3-c]quinolin-4(5H)-one;
(210): N-(2-bromoethyl)-4-(8-hydroxy-4-oxo-4,5-dihydrothieno[2,3-c]quinolin-9-yl)benzensulfonamide;
(211): 9-(4-((diisopropylamino)methyl)phenyl)-8-methoxythieno[2,3-c]quinolin-4(5H)-one;
(212): N-(hydroxy-4-oxo-4,5-dihydrothieno[2,3-c]quinolin-9-yl)benzyl)methanesulfonamide;
(213): 9-(4-((isopropylamino)methyl)phenyl)-8-methoxythieno[2,3-c]quinolin-4(5H)-one;
(214): 2-(dimethylamino)-N-(3-(8-hydroxy-4-oxo-4,5-dihydrothieno[2,3-c]quinolin-9-yl)phenyl)ethanesulfonamide;
(215): 2-amino-N-(3-(8-hydroxy-4-oxo-4,5-dihydrothieno[2,3-c]quinolin-9-yl)phenyl)ethanesulfonamide;
(216): 8-methoxy-9-(4-(1-(pyrrolidin-1-yl)ethyl)phenyl)thieno[2,3-c]quinolin-4(5H)-one;
(217): 9-(4-amino-3-hydroxyphenyl)-8-hydroxythieno[2,3-c]quinolin-4(5H)-one;
(218): N-(2-methoxy-4-(8-methoxy-4-oxo-4,5-dihydrothieno[2,3-c]quinolin-9-yl)phenyl)methanesulfonamide;
(219): 9-(3,5-difluoro-4-hydroxyphenyl)-8-methoxythieno[2,3-c]quinolin-4(5H)-one;
(220): N-(2-hydroxy-4-(8-hydroxy-4-oxo-4,5-dihydrothieno[2,3-c]quinolin-9-yl)phenyl)methanesulfonamide;
(221): 9-(4-((4-(aminomethyl)piperidin-1-yl)methyl)-3-fluorophenyl)-8-methoxythieno[2,3-c]quinolin-4(5H)-one;
(222): 9-(4-(2-(dimethylamino)ethyl)phenyl)-6-fluoro-8-methoxythieno[2,3-c]quinolin-4(5H)-one;
(223): 9-(3,5-difluoro-4-hydroxyphenyl)-8-hydroxythieno[2,3-c]quinolin-4(5H)-one;
(224): 6-fluoro-8-methoxy-9-(1,2,3,6-tetrahydropyridin-4-yl)thieno[2,3-c]quinolin-4(5H)-one;
(225): 9-(4-(1-(dimethylamino)ethyl)phenyl)-6-fluoro-8-hydroxythieno[2,3-c]quinolin-(5H)-one;
(226): 9-(4-((diethylamino)methyl)-3-fluorophenyl)-8-methoxythieno[2,3-c]quinolin-4(5H)-one;
(227): (E)-9-(3-(3-hydroxypyrrolidin-1-yl)prop-1-enyl)-8-methoxythieno[2,3-c]quinolin-4(5H)-one;
(228): (E)-8-hydroxy-9-(3-(3-hydroxypyrrolidin-1-yl)prop-1-enyl)thieno[2,3-c]quinolin-4(5H)-one (229): 8-hydroxy-9-(4-((isopropylamino)methyl)phenyl) thieno[2,3-c]quinolin-4(5H)-one;
(230): (E)-9-(3-(3-aminoazetidin-1-yl)prop-1-enyl)-8-hydroxythieno[2,3-c]quinolin-4(5H)-one;
(231): (E)-8-methoxy-9-(3-(2-(methylsulfonyl)ethylamino) prop-1-enyl)thieno[2,3-c]quinolin-4(5H)-one;
(232): (S)-9-(4-(1-aminoethyl)phenyl)-8-methoxythieno[2,3-c]quinolin-4(5H)-one;
(233): (S)-9-(4-(1-aminoethyl)phenyl)-8-hydroxythieno[2,3-c]quinolin-4(5H)-one;
(234): 8-hydroxy-9-(5-hydroxypyridin-3-yl)-2,3-dihydro-1H-cyclopenta[c]quinolin-4(5H)-one;
(235): 9-(4-((4-(aminomethyl)piperidin-1-yl)methyl)-3-fluorophenyl)-8-hydroxythieno[2,3-c]quinolin-4(5H)-one;
(236): 8-methoxy-9-(4-(1-(2-(methylsulfonyl)ethylamino) ethyl)phenyl)thieno[2,3-c]quinolin-4(5H)-one;
(237): 9-(4-((3-aminopyrrolidin-1-yl)methyl)-3-fluorophenyl)-8-methoxythieno[2,3-c]quinolin-4(5H)-one;
(238): (E)-9-(3-(3-aminoazetidin-1-yl)prop-1-enyl)-8-methoxythieno[2,3-c]quinolin-4(5H)-one;
(239): (E)-9-(3-(ethylamino)prop-1-enyl)-8-hydroxythieno[2,3-c]quinolin-4(5H)-one;
(240): 9-(4-((3-aminopiperidin-1-yl)methyl)-3-fluorophenyl)-8-hydroxythieno[2,3-c]quinolin-4(5H)-one;
(241): 9-(4-((3-aminopyrrolidin-1-yl)methyl)-3-fluorophenyl)-8-hydroxythieno[2,3-c]quinolin-4(5H)-one;
(242): 9-(4-((3-aminopiperidin-1-yl)methyl)-3-fluorophenyl)-8-methoxythieno[2,3-c]quinolin-4(5H)-one;
(243): 8-hydroxy-9-(4-(1-(2-(methylsulfonyl)ethylamino) ethyl)phenyl)thieno[2,3-c]quinolin-4(5H)-one;
(244): (E)-9-(3-(3-aminopiperidin-1-yl)prop-1-enyl)-8-methoxythieno[2,3-c]quinolin-4(5H)-one;
(245): (E)-9-(3-(3-aminopyrrolidin-1-yl)prop-1-enyl)-8-hydroxythieno[2,3-c]quinolin-4(5H)-one;
(246): (E)-9-(3-(3-aminopiperidin-1-yl)prop-1-enyl)-8-hydroxythieno[2,3-c]quinolin-4(5H)-one;
(247): (E)-8-hydroxy-9-(3-(2-(methylsulfonyl)ethylamino) prop-1-enyl)thieno[2,3-c]quinolin-4(5H)-one;
(248): 8-methoxy-9-(4-(2-(2-(methylsulfonyl)ethylamino) ethyl)phenyl)thieno[2,3-c]quinolin-(5H)-one;
(249): 2-(2-fluoro-4-(8-methoxy-4-oxo-4,5-dihydrothieno [2,3-c]quinolin-9-yl)phenyl)acetonitrile;
(250): (E)-N-(1-(3-(8-methoxy-4-oxo-4,5-dihydrothieno[2,3-c]quinolin-9-yl)allyl)azetidin-3-yl)methanesulfonamide;
(251): 4-(8-methoxy-4-oxo-4,5-dihydrothieno[2,3-c]quinolin-9-yl)-N,N-dimethylbenzenesulfonamide;
(252): 4-(8-hydroxy-4-oxo-4,5-dihydrothieno[2,3-c]quinolin-9-yl)-N-methylbenzenesulfonamide;
(253): tert-butyl (5-(8-methoxy-4-oxo-4,5-dihydrothieno[2,3-c]quinolin-9-yl)furan-2-yl)methylcarbamate;
(254): N-(4-(8-hydroxy-4-oxo-4,5-dihydrothieno[2,3-c] quinolin-9-yl)-2-methylphenyl)methanesulfonamide;
(255): N-(4-(8-methoxy-1-oxo-4,5-dihydrothieno[2,3-c] quinolin-9-yl)-2-methylphenyl)methanesulfonamide;
(256): 9-(4-(aminomethyl)phenyl)-6-fluoro-8-hydroxythieno[2,3-c]quinolin-4(5H)-one;
(257): 9-(4-(aminomethyl)phenyl)-6-fluoro-8-methoxythieno[2,3-c]quinolin-4(5H)-one;
(258): 6-fluoro-8-hydroxy-9-(1,2,3,6-tetrahydropyridin-4-yl)thieno[2,3-c]quinolin-4(5H)-one;
(259): 9-(4-((diethylamino)methyl)-3-fluorophenyl)-8-hydroxythieno[2,3-c]quinolin-4(5H)-one;
(260): 8-methoxy-9-(4-(1-(piperidin-1-yl)ethyl)phenyl) thieno[2,3-c]quinolin-4(5H)-one;
(261): 2-(2-fluoro-4-(8-hydroxy-4-oxo-4,5-dihydrothieno[2,3-c]quinolin-9-yl)phenyl)acetonitrile;
(262): 8-hydroxy-9-(4-(1-(piperidin-1-yl)ethyl)phenyl) thieno[2,3-c]quinolin-4(5H)-one;
(263): (E)-9-(3-(3-(dimethylamino)piperidin-1-yl)prop-1-enyl)-8-hydroxythieno[2,3-c]quinolin-4(5H)-one;
(264): (E)-9-(3-(3-(dimethylamino)pyrrolidin-1-yl)prop-1-enyl)-8-hydroxythieno[2,3-c]quinolin-4(5H)-one;
(265): 9-(4-(2-aminoethyl)-3-fluorophenyl)-8-methoxythieno[2,3-c]quinolin-4(5H)-one;
(266): 9-(5-(aminomethyl)thiophen-2-yl)-8-hydroxythieno[2,3-c]quinolin-4(5H)-one;
(267): 9-(4-((ethylamino)methyl)phenyl)-8-hydroxythieno[2,3-c]quinolin-4(5H)-one;
(268): (E)-9-(3-(4-aminopiperidin-1-yl)prop-1-enyl)-8-hydroxythieno[2,3-c]quinolin-4(5H)-one;
(269): 9-(4-((ethylamino)methyl)phenyl)-8-methoxythieno [2,3-c]quinolin-4(5H)-one;
(270): 9-(4-(aminomethyl)phenyl)-6-bromo-8-hydroxythieno[2,3-c]quinolin-4(5H)-one;
(271): 9-(3-chloro-4-((diethylamino)methyl)phenyl)-8-methoxythieno[2,3-c]quinolin-4(5H)-one;
(272): (R)-9-(4-(1-(dimethylamino)ethyl)phenyl)-8-hydroxythieno[2,3-c]quinolin-4(5H)-one;
(273): 9-(4-(3-aminopropyl)phenyl)-8-hydroxythieno[2,3-c]quinolin-4(5H)-one;
(274): (R)-9-(4-(1-aminoethyl)phenyl)-8-methoxythieno[2,3-c]quinolin-4(5H)-one;
(275): (R)-9-(4-(1-aminoethyl)phenyl)-8-hydroxythieno[2,3-c]quinolin-4(5H)-one;
(276): 9-(4-(2-aminoethyl)-3-fluorophenyl)-8-hydroxythieno[2,3-c]quinolin-4(5H)-one;
(277): 9-(4-(1-amino-2-methylpropan-2-yl)phenyl)-8-hydroxythieno[2,3-c]quinolin-4(5H)-one;
(278): 9-(3-fluoro-4-((3-hydroxypyrrolidin-1-yl)methyl) phenyl)-8-hydroxythieno[2,3-c]quinolin-4(5H)-one;
(279): 9-(3-fluoro-4-((3-hydroxypyrrolidin-1-yl)methyl) phenyl)-8-methoxythieno[2,3-c]quinolin-4(5H)-one;
(280): 4-(8-methoxy-4-oxo-4,5-dihydrothieno[2,3-c]quinolin-9-yl)-N-(2,2,2-trifluoroethyl)benzenesulfonamide;
(281): 4-(8-hydroxy-4-oxo-4,5-dihydrothieno[2,3-c]quinolin-9-yl)-N-(2,2,2-trifluoroethyl)benzenesulfonamide;
(282): N-(2-(dimethylamino)ethyl)-4-(8-hydroxy-4-oxo-4,5-dihydrothieno[2,3-c]quinolin-9-yl)benzenesulfonamide;
(283): 8-hydroxy-9-(4-((2-(methylsulfonyl)ethylamino)methyl)phenyl)thieno[2,3-c]quinolin-4(5H)-one;
(284): 9-(3-(3-(dimethylamino)pyrrolidin-1-yl)propyl)-8-hydroxythieno[2,3-c]quinolin-4(5H)-one;
(285): 9-(1-(2-aminoethyl)-1H-pyrazol-4-yl)-8-methoxythieno[2,3-c]quinolin-4(5H)-one;
(286): 9-(3-chloro-4-((diethylamino)methyl)phenyl)-8-hydroxythieno[2,3-c]quinolin-4(5H)-one;
(287): 4-(7-fluoro-8-methoxy-4-oxo-4,5-dihydrothieno[2,3-c]quinolin-9-yl)-N-(2-hydroxyethyl)benzenesulfonamide;
(288): 9-(3-acetylphenyl)-8-methoxythieno[2,3-c]quinolin-4(5H)-one;
(289): 2-fluoro-4-(8-hydroxy-4-oxo-4,5-dihydrothieno[2,3-c]quinolin-9-yl)-N-(2-hydroxyethyl)benzamide;
(290): 3-(4-(8-hydroxy-4-oxo-4,5-dihydrothieno[2,3-c] quinolin-9-yl)phenyl)propanenitrile;
(291): 9-(4-acetylphenyl)-8-methoxythieno[2,3-c]quinolin-4(5H)-one;
(292): 2-fluoro-N-(2-hydroxyethyl)-4-(8-methoxy-4-oxo-4,5-dihydrothieno[2,3-c]quinolin-9-yl)benzamide;

(293): 4-(8-hydroxy-4-oxo-4,5-dihydrothieno[2,3-c]quinolin-9-yl)-N-(2-hydroxyethyl)benzamide;
(294): 1,1-diethyl-3-(hydroxy-4-oxo-4,5-dihydrothieno[2,3-c]quinolin-9-yl)benzyl)urea;
(295): N-(2-hydroxyethyl)-4-(8-methoxy-4-oxo-4,5-dihydrothieno[2,3-c]quinolin-9-yl)benzamide;
(296): 9-(4-acetylphenyl)-8-hydroxythieno[2,3-c]quinolin-4(5H)-one;
(297): N-(2-bromoethyl)-2-fluoro-4-(8-hydroxy-4-oxo-4,5-dihydrothieno[2,3-c]quinolin-9-yl)benzenesulfonamide;
(298): 9-(3-(3-(dimethylamino)piperidin-1-yl)propyl)-8-hydroxythieno[2,3-c]quinolin-4(5H)-one;
(299): N-(2-fluoro-4-(8-hydroxy-4-oxo-4,5-dihydrothieno[2,3-c]quinolin-9-yl)phenethyl)methanesulfonamide;
(300): 9-(3-fluoro-4-(2-(methylsulfonamido)ethyl)phenyl)-4-oxo-4,5-dihydrothieno[2,3-c]quinolin-8-yl methanesulfonate;
(301): (R)—N-(1-(4-(8-hydroxy-4-oxo-4,5-dihydrothieno[2,3-c]quinolin-9-yl)phenyl)ethyl)methanesulfonamide;
(302): (R)-9-(4-(1-(methylsulfonamido)ethyl)phenyl)-4-oxo-4,5-dihydrothieno[2,3-c]quinolin-8-yl methanesulfonate;
(303): 2-fluoro-N-(2-hydroxyethyl)-4-(8-methoxy-4-oxo-4,5-dihydrothieno[2,3-c]quinolin-9-yl)benzenesulfonamide;
(304): 4-(8-hydroxy-4-oxo-4,5-dihydrothieno[2,3-c]quinolin-9-yl)-N,N-dimethylbenzenesulfonamide;
(305): 9-(4-(2-(dimethylamino)ethyl)phenyl)-7-fluoro-8-methoxythieno[2,3-c]quinolin-4(5H)-one;
(306): N-(2-bromoethyl)-4-(7-fluoro-8-hydroxy-4-oxo-4,5-dihydrothieno[2,3-c]quinolin-9-yl)benzenesulfonamide;
(307): 4-(7-fluoro-8-hydroxy-4-oxo-4,5-dihydrothieno[2,3-c]quinolin-9-yl)-N-(2-hydroxyethyl)benzenesulfonamide;
(308): 9-(4-(1-(dimethylamino)-2-methylpropan-2-yl)phenyl)-8-hydroxythieno[2,3-c]quinolin-4(5H)-one;
(309): N-(2-chloro-4-(8-methoxy-4-oxo-4,5-dihydrothieno[2,3-c]quinolin-9-yl)benzyl)-N-methyl methanesulfonamide;
(310): 4-(8-hydroxy-4 oxo-4,5-dihydrothieno[2,3-c]quinolin-9-yl)-N-(2-methoxyethyl)benzenesulfonamide;
(311): (E)-3-(8-methoxy-4-oxo-4,5-dihydrothieno[2,3-c]quinolin-9-yl)-2-methylacrylonitrile;
(312): N-(2-fluoro-4-(8-methoxy-4-oxo-4,5-dihydrothieno[2,3-c]quinolin-9-yl)phenethyl)methanesulfonamide;
(313): 8-hydroxy-9-(4-(1-hydroxyethyl)phenyl)thieno[2,3-c]quinolin-4(5H)-one;
(314): 9-(4-(1-(cyclopentylamino)ethyl)phenyl)-8-hydroxythieno[2,3-c]quinolin-4(5H)-one;
(315): 9-(4-(1-(cyclopentylamino)ethyl)phenyl)-8-methoxythieno[2,3-c]quinolin-4(5H)-one;
(316): 4-(8-hydroxy-4-oxo-4,5-dihydrothieno[2,3-c]quinolin-9-yl)-N-(2-hydroxyethyl)benzenesulfonamide;
(317): 9-(5-(aminomethyl)furan-2-yl)-8-hydroxythieno[2,3-c]quinolin-4(5H)-one;
(318): 9-(3-chloro-4-((methylamino)methyl)phenyl)-8-methoxythieno[2,3-c]quinolin-4(5H)-one;
(319): 9-(4-(2-aminopropan-2-yl)phenyl)-8-hydroxythieno[2,3-c]quinolin-4(5H)-one;
(320): N-(3-hydroxypropyl)-4-(8-methoxy-4-oxo-4,5-dihydrothieno[2,3-c]quinolin-9-yl)benzenesulfonamide;
(321): 2-fluoro-4-(8-hydroxy-4-oxo-4,5-dihydrothieno[2,3-c]quinolin-9-yl)-N-(2-hydroxyethyl)benzenesulfonamide;
(322): 4-(8-hydroxy-4-oxo-4,5-dihydrothieno[2,3-c]quinolin-9-yl)-N-(3-hydroxypropyl)benzensulfonamide;
(323): N-(3-bromopropyl)-4-(8-hydroxy-4-oxo-4,5-dihydrothieno[2,3-c]quinolin-9-yl)benzenesulfonamide;
(324): 2-fluoro-4-(8-hydroxy-4-oxo-4,5-dihydrothieno[2,3-c]quinolin-9-yl)-N-(2-methoxyethyl)benzenesulfonamide;
(325): 9-(3-chloro-4-((methylamino)methyl)phenyl)-8-hydroxythieno[2,3-c]quinolin-4(5H)-one;
(326): 9-(4-(aminomethyl)phenyl)-4 oxo-4,5-dihydrothieno[2,3-c]quinoline-8-carbonitrile;
(327): 9-(4-(2-(dimethylamino)ethyl)-3-fluorophenyl)-8-hydroxythieno[2,3-c]quinolin-(5H)-one;
(328): 9-(4-(aminomethyl)phenyl)-6,7-dichloro-8-hydroxythieno[2,3-c]quinolin-4(5H)-one;
(329): 9-(4-(aminomethyl)phenyl)-6-chloro-8-hydroxythieno[2,3-c]quinolin-4(5H)-one;
(330): 9-(4-(aminomethyl)phenyl)-4-oxo-4,5-dihydrothieno[2,3-c]quinolin-8-yl trifluoromethanesulfonate;
(331): 9-(4-(2-(dimethylamino)ethyl)phenyl)-8-methoxythieno[2,3-c]quinolin-4(5H)-one;
(332): N-(2-chloroethyl)-4-(8-hydroxy-4-oxo-4,5-dihydrothieno[2,3-c]quinolin-9-yl)benzenesulfonamide;
(333): N-(2-fluoroethyl)-4-(8-methoxy-4-oxo-4,5-dihydrothieno[2,3-c]quinolin-9-yl)benzenesulfonamide;
(334): 9-(4-(2-aminopropan-2-yl)phenyl)-6-chloro-8-hydroxythieno[2,3-c]quinolin-4(5H)-one;
(335): (S)-9-(4-(1-(dimethylamino)ethyl)phenyl)-8-hydroxythieno[2,3-c]quinolin-4(5H)-one;
(336): 9-(4-(1-aminopropyl)phenyl)-8-hydroxythieno[2,3-c]quinolin-4(5H)-one;
(337): 9-(4-(1-aminopropyl)phenyl)-8-methoxythieno[2,3-c]quinolin-4(5H)-one;
(338): 9-(4-(1-(diethylamino)propyl)phenyl)-8-hydroxythieno[2,3-c]quinolin-4(5H)-one;
(339): 9-(4-(1-(dimethylamino)propyl)phenyl)-8-hydroxythieno[2,3-c]quinolin-4(5H)-one;
(340): 9-amino-8-methoxythieno[2,3-c]quinolin-4(5H)-one;
(341): 9-(4-(1-(dimethylamino)ethyl)phenyl)-6,7-difluoro-8-hydroxythieno[2,3-c]quinolin-4(5H)-one;
(342): 9-(4-(1-(dimethylamino)ethyl)phenyl)-6,7-difluoro-8-methoxythieno[2,3-c]quinolin-4(5H)-one;
(343): N-cyclopropyl-4-(8-methoxy-4-oxo-4,5-dihydrothieno[2,3-c]quinolin-9-yl)benzenesulfonamide;
(344): N-cyclopropyl-4-(8-hydroxy-4-oxo-4,5-dihydrothieno[2,3-c]quinolin-9-yl)benzenesulfonamide;
(345): 9-(2-amino-2,3-dihydro-1H-inden-5-yl)-8-hydroxythieno[2,3-c]quinolin-4(5H)-one;
(346): 9-(4-(1-(dimethylamino)ethyl)phenyl)thieno[2,3-c]quinolin-4(5H)-one;
(347): (S)—N-(1-(4-(8-hydroxy-4-oxo-4,5-dihydrothieno[2,3-c]quinolin-9-yl)phenyl)ethyl)methanesulfonamide;
(348): 9-(4-(1-(aminomethyl)cyclopropyl)phenyl)-8-hydroxythieno[2,3-c]quinolin-4(5H)-one;
(349): 9-(4-(1-(dimethylamino)ethyl)-3-fluorophenyl)-8-hydroxythieno[2,3-c]quinolin-4(5H)-one;
(350): N-(1-(hydroxymethyl)cyclopentyl)-4-(8-methoxy-4-oxo-4,5-dihydrothieno[2,3-c]quinolin-9-yl)benzenesulfonamide;
(351): 9-(2-(diethylamino)-2,3-dihydro-1H-inden-5-yl)-8-hydroxythieno[2,3-c]quinolin-4(5H)-one;
(352): 9-(2-(dimethylamino)-2,3-dihydro-1H-inden-5-yl)-8-hydroxythieno[2,3-c]quinolin-4(5H)-one;
(353): 8-hydroxy-9-(1,2,3,4-tetrahydroisoquinolin-7-yl)thieno[2,3-c]quinolin-4(5H)-one;
(354): 8-methoxy-9-(1,2,3,4-tetrahydroisoquinolin-7-yl)thieno[2,3-c]quinolin-4(5H)-one;
(355): 3-(3-(8-hydroxy-4-oxo-4,5-dihydrothieno[2,3-c]quinolin-9-yl)phenyl)propanenitrile;

(356): 9-(4-(1-(diethylamino)ethyl)-3-fluorophenyl)-8-hydroxythieno[2,3-c]quinolin-4(5H)-one;
(357): 1-(4-(8-methoxy-4-oxo-4,5-dihydrothieno[2,3-c]quinolin-9-yl)phenyl)cyclopropanecarbonitrile;
(358): 9-(2-ethyl-1,2,3,4-tetrahydroisoquinolin-7-yl)-8-hydroxythieno[2,3-c]quinolin-4(5H)-one;
(359): 9-(4-(1-aminoethyl)-3-fluorophenyl)-8-hydroxythieno[2,3-c]quinolin-4(5H)-one;
(360): 3-(3-(8-methoxy-4-oxo-4,5-dihydrothieno[2,3-c]quinolin-9-yl)phenyl)propanenitrile;
(361): 1-(4-(8-hydroxy-4-oxo-4,5-dihydrothieno[2,3-c]quinolin-9-yl)phenyl)cyclopropanecarbonitrile;
(362): 9-(2-amino-2,3-dihydro-1H-inden-5-yl)-8-methoxythieno[2,3-c]quinolin-4(5H)-one;
(363): N-isopentyl-4-(8-methoxy-4-oxo-4,5-dihydrothieno[2,3-c]quinolin-9-yl)benzenesulfonamide;
(364): 9-(2-(dimethylamino)-2,3-dihydro-1H-inden-5-yl)-8-methoxythieno[2,3-c]quinolin-4(5H)-one;
(365): 9-(4-(1-(ethylamino)ethyl)phenyl)-8-methoxythieno[2,3-c]quinolin-4(5H)-one;
(366): 6-chloro-9-(4-(1-(dimethylamino)ethyl)phenyl)-8-hydroxythieno[2,3-c]quinolin-4(5H)-one;
(367): 9-(4-(cyclopropanecarbonyl)phenyl)-8-methoxythieno[2,3-c]quinolin-4(5H)-one;
(368): 9-(4-(aminomethyl)phenyl)-4-oxo-4,5-dihydrothieno[2,3-c]quinoline-8-carboxamide;
(369): 9-(2-aminoethyl)-8-methoxythieno[2,3-c]quinolin-4(5H)-one;
(370): 8-hydroxy-9-(4-(2-hydroxyethylsulfonyl)phenyl)thieno[2,3-c]quinolin-4(5H)-one;
(371): 9-(4-(2-hydroxyethylsulfonyl)phenyl)-8-methoxythieno[2,3-c]quinolin-4(5H)-one;
(372): 9-(1-ethylindolin-5-yl)-8-hydroxythieno[2,3-c]quinolin-4(5H)-one;
(373): 9-(4-(1-aminopropan-2-yl)phenyl)-8-methoxythieno[2,3-c]quinolin-4(5H)-one;
(374): 8-hydroxy-9-(2-methyl-1,2,3,4-tetrahydroisoquinolin-7-yl)thieno[2,3-c]quinolin-4(5H)-one;
(375): 9-(4-(1-aminoethyl)-3-fluorophenyl)-8-methoxythieno[2,3-c]quinolin-4(5H)-one;
(376): 8-hydroxy-9-(1-methylindolin-5-yl)thieno[2,3-c]quinolin-4(5H)-one;
(377): 8-hydroxy-9-(indolin-5-yl)thieno[2,3-c]quinolin-4(5H)-one;
(378): 9-(indolin-5-yl)-8-methoxythieno[2,3-c]quinolin-4(5H)-one;
(379): 9-(4-(1-((dimethylamino)methyl)cyclopropyl)phenyl)-8-hydroxythieno[2,3-c]quinolin-4(5H)-one;
(380): 4-(8-methoxy-4-oxo-4,5-dihydrothieno[2,3-c]quinolin-9-yl)-N-propylbenzenesulfonamide;
(381): N-(cyclopropylmethyl)-4-(8-methoxy-4-oxo-4,5-dihydrothieno[2,3-c]quinolin-9-yl)benzenesulfonamide;
(382): N-(3,3-dimethylbutyl)-4-(8-methoxy-4-oxo-4,5-dihydrothieno[2,3-c]quinolin-9-yl)benzenesulfonamide;
(383): 4-(8-hydroxy-4-oxo-4,5-dihydrothieno[2,3-c]quinolin-9-yl)-N-isopentylbenzenesulfonamide;
(384): N-(3,3-dimethylbutyl)-4-(8-hydroxy-4-oxo-4,5-dihydrothieno[2,3-c]quinolin-9-yl)benzenesulfonamide;
(385): 9-(4-(1-(ethylamino)ethyl)phenyl)-8-hydroxythieno[2,3-c]quinolin-4(5H)-one;
(386): 3-(4-(8-methoxy-4-oxo-4,5-dihydrothieno[2,3-c]quinolin-9-yl)phenyl)-3-oxopropanenitrile;
(387): (E)-9-(2-ethoxyvinyl)-8-methoxythieno[2,3-c]quinolin-4(5H)-one;
(388): N-(1-(4-(8-hydroxy-4-oxo-4,5-dihydrothieno[2,3-c]quinolin-9-yl)phenyl)ethyl)acetamide;
(389): 4-(8-methoxy-4-oxo-4,5-dihydrothieno[2,3-c]quinolin-9-yl)-N-(3,3,3-trifluoropropyl)benzenesulfonamide;
(390): 4-(8-hydroxy-4-oxo-4,5-dihydrothieno[2,3-c]quinolin-9-yl)-N-(1-(hydroxymethyl)cyclopentyl)benzenesulfonamide;
(391): N-(2,2-difluoroethyl)-4-(8-methoxy-4-oxo-4,5-dihydrothieno[2,3-c]quinolin-9-yl)benzenesulfonamide;
(1031): 8-methoxy-9-(4-(1-methoxyethyl)phenyl)thieno[2,3-c]quinolin-4(5H)-one;
(1032): 9-(4-(1-aminoethyl)phenyl)-6-bromo-8-hydroxythieno[2,3-c]quinolin-4(5H)-one;
(1033): 8-methoxy-9-(2-((piperidin-3-ylmethyl)amino)ethyl)thieno[2,3-c]quinolin-4(5H)-one;
(1034): 9-(2-(4-((dimethylamino)methyl)piperidin-1-yl)ethyl)-8-methoxythieno[2,3-c]quinolin-4(5H)-one;
(1035): tert-butyl 4-((2-(8-methoxy-4-oxo-4,5-dihydrothieno[2,3-c]quinolin-9-yl)ethyl)amino)piperidine-1-carboxylate;
(1036): 8-methoxy-9-(2-(piperidin-4-ylamino)ethyl)thieno[2,3-c]quinolin-4(5H)-one;
(1037): 4-(8-hydroxy-4-oxo-4,5-dihydrothieno[2,3-c]quinolin-9-yl)-N-(3,3,3-trifluoropropyl)benzenesulfonamide;
(1038): 3H-pyrrolo[2,3-c]quinolin-4(5H)-one;
(1039): 9-(4-(1-aminoethyl)phenyl)-6-cyclopropyl-8-hydroxythieno[2,3-c]quinolin-4(5H)-one;
(1040): 9-(4-(1-aminoethyl)phenyl)-8-hydroxy-4-oxo-4,5-dihydrothieno[2,3-c]quinoline-6-carbonitrile;
(1041): 9-(4-(1-aminoethyl)phenyl)-6-chloro-8-hydroxythieno[2,3-c]quinolin-4(5H)-one;
(1042): 8-hydroxy-9-(2-(4-((methylamino)methyl)piperidin-1-yl)ethyl)thieno[2,3-c]quinolin-4(5H)-one;
(1043): 8-methoxy-9-(2-(4-((methylamino)methyl)piperidin-1-yl)ethyl)thieno[2,3-c]quinolin-4(5H)-one;
(1044): 9-(2-(4-((dimethylamino)methyl)piperidin-1-yl)ethyl)-8-hydroxythieno[2,3-c]quinolin-4(5H)-one;
(1045): 9-(4-(1-hydroxypropyl)phenyl)-8-methoxythieno[2,3-c]quinolin-4(5H)-one;
(1046): (R)-8-methoxy-9-(4-(1-(methylamino)ethyl)phenyl)thieno[2,3-c]quinolin-4(5H)-one;
(1047): (R)-8-(4-(1-aminoethyl)phenyl)thieno[2,3-c]quinolin-4(5H)-one;
(1048): (R)-tert-butyl (1-(4-(4-oxo-4,5-dihydrothieno[2,3-c]quinolin-8-yl)phenyl)ethyl)carbamate;
(1049): 9-(4-(4-hydroxypiperidin-4-yl)phenyl)-8-methoxythieno[2,3-c]quinolin-4(5H)-one;
(1050): (R)-8-(4-(1-(dimethylamino)ethyl)phenyl)thieno[2,3-c]quinolin-4(5H)-one;
(1051): 8-hydroxy-9-(4-(1,2,3,6-tetrahydropyridin-4-yl)phenyl)thieno[2,3-c]quinolin-4(5H)-one;
(1052): (R)-8-hydroxy-9-(4-(1-(methylamino)ethyl)phenyl)thieno[2,3-c]quinolin-4(5H)-one;
(1053): 8-hydroxy-9-(4-(1-hydroxypropyl)phenyl)thieno[2,3-c]quinolin-4(5H)-one;
(1054): (R)-8-hydroxy-9-(4-(1-hydroxyethyl)phenyl)thieno[2,3-c]quinolin-4(5H)-one;
(1055): 8-hydroxy-9-(4-(4-hydroxypiperidin-4-yl)phenyl)thieno[2,3-c]quinolin-4(5H)-one;
(1056): (S)-8-hydroxy-9-(4-(1-hydroxyethyl)phenyl)thieno[2,3-c]quinolin-4(5H)-one;
(1057): N-(1-hydroxypropan-2-yl)-4-(8-methoxy-4-oxo-4,5-dihydrothieno[2,3-c]quinolin-9-yl)benzenesulfonamide;
(1058): 9-(4-(hydroxy(thiazol-2-yl)methyl)phenyl)-8-methoxythieno[2,3-c]quinolin-4(5H)-one;
(1059): 9-(6-(1-aminoethyl)pyridin-3-yl)-8-hydroxythieno[2,3-c]quinolin-4(5H)-one;

(1060): 9-(4-(4-hydroxybutyl)phenyl)-8-methoxythieno[2,3-c]quinolin-4(5H)-one;
(1061): 2-(4-(8-hydroxy-4-oxo-4,5-dihydrothieno[2,3-c]quinolin-9-yl)phenyl)-2-methylpropanamide;
(1062): N-(1-bromopropan-2-yl)-4-(8-hydroxy-4-oxo-4,5-dihydrothieno[2,3-c]quinolin-9-yl)benzenesulfonamide;
(1063): 8-hydroxy-9-(4-(hydroxy(thiazol-2-yl)methyl)phenyl)thieno[2,3-c]quinolin-4(5H)-one;
(1064): (S)-8-methoxy-9-(4-(1-(methylamino)ethyl)phenyl)thieno[2,3-c]quinolin-4(5H)-one;
(1065): 9-(6-(1-(diethylamino)ethyl)pyridin-3-yl)-8-hydroxythieno[2,3-c]quinolin-4(5H)-one;
(1066): 9-(4-(1-aminoethyl)phenyl)-8-hydroxy-6-methylthieno[2,3-c]quinolin-4(5H)-one;
(1067): 9-(6-(1-aminoethyl)pyridin-3-yl)-8-methoxythieno[2,3-c]quinolin-4(5H)-one;
(1068): 8-hydroxy-9-(4-(4-hydroxybutyl)phenyl)thieno[2,3-c]quinolin-4(5H)-one;
(1069): 9-(4-(3-amino-1-hydroxypropyl)phenyl)-8-methoxythieno[2,3-c]quinolin-4(5H)-one;
(1070): 9-(6-(1-(dimethylamino)ethyl)pyridin-3-yl)-8-hydroxythieno[2,3-c]quinolin-4(5H)-one;
(1071): 9-(6-(1-(dimethylamino)ethyl)pyridin-3-yl)-8-methoxythieno[2,3-c]quinolin-4(5H)-one;
(1072): 4-((4-(8-methoxy-4-oxo-4,5-dihydrothieno[2,3-c]quinolin-9-yl)-1H-pyrazol-1-yl)methyl)benzonitrile;
(1073): 8-aminothieno[2,3-c]quinolin-4(5H)-one;
(1074): 9-(4-((1H-pyrazol-1-yl)methyl)phenyl)-8-methoxythieno[2,3-c]quinolin-4(5H)-one;
(1075): 9-(6-(1-aminoethyl)pyridin-3-yl)-8-methoxythieno[2,3-c]quinolin-4(5H)-one;
(1076): 9-(4-(1-aminoethyl)phenyl)-4-oxo-4,5-dihydrothieno[2,3-c]quinolin-8-yl dimethylcarbamate;
(1077): 9-(4-(1-aminoethyl)phenyl)-4-oxo-4,5-dihydrothieno[2,3-c]quinolin-8-yl isopropyl carbonate;
(1078): 9-(4-((1H-imidazol-1-yl)methyl)phenyl)-8-methoxythieno[2,3-c]quinolin-4(5H)-one;
(1079): N-(2-bromopropyl)-4-(8-hydroxy-4-oxo-4,5-dihydrothieno[2,3-c]quinolin-9-yl)benzenesulfonamide;
(1080): (R)-9-(4-(1-aminoethyl)phenyl)-6,7-dichloro-8-hydroxythieno[2,3-c]quinolin-4(5H)-one;
(1081): (R)-9-(4-(1-aminoethyl)phenyl)-6-chloro-8-hydroxythieno[2,3-c]quinolin-4(5H)-one;
(1082): (S)-8-hydroxy-9-(4-(1-(methylamino)ethyl)phenyl)thieno[2,3-c]quinolin-4(5H)-one;
(1083): 9-(4-(1-aminoethyl)phenyl)-4-oxo-4,5-dihydrothieno[2,3-c]quinolin-8-yl diethylcarbamate;
(1084): 4-(8-hydroxy-4-oxo-4,5-dihydrothieno[2,3-c]quinolin-9-yl)-N-(2-hydroxyethyl)-N-methylbenzenesulfonamide;
(1085): N-(2-hydroxyethyl)-4-(8-methoxy-4-oxo-4,5-dihydrothieno[2,3-c]quinolin-9-yl)-N-methylbenzenesulfonamide;
(1086): 9-(4-((1H-pyrazol-1-yl)methyl)phenyl)-8-hydroxythieno[2,3-c]quinolin-4(5H)-one;
(1087): (S)-6-chloro-8-hydroxy-9-(4-(1-(methylamino)ethyl)phenyl)thieno[2,3-c]quinolin-4(5H)-one;
(1088): 9-(4-(1-aminopropyl)phenyl)-6-chloro-8-hydroxythieno[2,3-c]quinolin-4(5H)-one;
(1089): 9-(4-(1-aminoethyl)phenyl)-4-oxo-4,5-dihydrothieno[2,3-c]quinolin-8-yl morpholine-4-carboxylate;
(1090): N-(2-hydroxyethyl)-4-(8-methoxy-4-oxo-2,3,4,5-tetrahydro-1H-cyclopenta[c]quinolin-9-yl)benzenesulfonamide;
(1091): 8-bromothieno[2,3-c]quinolin-4(5H)-one;
(1092): 9-(4-(2-(dimethylamino)propyl)phenyl)-8-hydroxythieno[2,3-c]quinolin-4(5H)-one;
(1093): 9-(4-(2-aminopropyl)phenyl)-8-methoxythieno[2,3-c]quinolin-4(5H)-one;
(1094): N-(2-bromoethyl)-4-(8-hydroxy-4 oxo-2,3,4,5-tetrahydro-1H-cyclopenta[c]quinolin-9-yl)benzenesulfonamide;
(1095): 9-(4-(2-aminopropyl)phenyl)-8-hydroxythieno[2,3-c]quinolin-4(5H)-one;
(1096): 8-methoxy-9-(1-(2-morpholinoethyl)-1H-pyrazol-4-yl)thieno[2,3-c]quinolin-4(5H)-one;
(1097): 9-(4-(2-(diethylamino)propyl)phenyl)-8-hydroxythieno[2,3-c]quinolin-4(5H)-one;
(1098): 9-(4-(1-aminoethyl)phenyl)-8-hydroxy-6-(hydroxymethyl)thieno[2,3-c]quinolin-4(5H)-one;
(1099): 9-(4-(1-aminoethyl)phenyl)-4-oxo-4,5-dihydrothieno[2,3-c]quinolin-8-yl acetate;
(1100): 9-(1-(1-(dimethylamino)propan-2-yl)-1H-pyrazol-4-yl)-8-methoxythieno[2,3-c]quinolin-4(5H)-one;
(1101): 9-(4-((1H-imidazol-1-yl)methyl)phenyl)-8-hydroxythieno[2,3-c]quinolin-4(5H)-one;
(1102): 9-(4-(aminomethyl)phenyl)-8-(2-morpholinoethoxy)thieno[2,3-c]quinolin-4(5H)-one;
(1103): 8-hydroxy-9-(1-(2-morpholinoethyl)-1H-pyrazol-4-yl)thieno[2,3-c]quinolin-4(5H)-one;
(1104): N-(2-(1H-pyrazol-1-yl)ethyl)-4-(8-hydroxy-4-oxo-4,5-dihydrothieno[2,3-c]quinolin-9-yl)benzenesulfonamide;
(1105): 8-hydroxy-9-(4-(2,2,2-trifluoro-1-hydroxyethyl)phenyl)thieno[2,3-c]quinolin-4(5H)-one;
(1106): 9-(4-(2-aminopropyl)phenyl)-6-chloro-8-hydroxythieno[2,3-c]quinolin-4(5H)-one;
(1107): N-(2-(4-(8-hydroxy-4-oxo-4,5-dihydrothieno[2,3-c]quinolin-9-yl)phenyl)-2-methylpropyl)methanesulfonamide;
(1108): 9-(4-(2-(dimethylamino)propyl)phenyl)-8-methoxythieno[2,3-c]quinolin-4(5H)-one;
(1109): 9-(4-(1-aminoethyl)phenyl)thieno[2,3-c]quinolin-4(5H)-one;
(1110): 9-(1-(1-(dimethylamino)propan-2-yl)-1H-pyrazol-4-yl)-8-hydroxythieno[2,3-c]quinolin-4(5H)-one;
(1111): 9-(4-(1-aminopropan-2-yl)phenyl)-8-hydroxythieno[2,3-c]quinolin-4(5H)-one;
(1112): 9-(4-(1-(dimethylamino)propan-2-yl)phenyl)-8-hydroxythieno[2,3-c]quinolin-4(5H)-one;
(1113): 8-methoxy-9-(4-(2,2,2-trifluoro-1-hydroxyethyl)phenyl)thieno[2,3-c]quinolin-4(5H)-one;
(1114): N-(2-bromoethyl)-4-(8-hydroxy-4-oxo-4,5-dihydrothieno[2,3-c]quinolin-9-yl)-N-methylbenzenesulfonamide;
(1115): N-(2-(1H-imidazol-1-yl)ethyl)-4-(8-hydroxy-4-oxo-4,5-dihydrothieno[2,3-c]quinolin-9-yl)benzenesulfonamide;
(1116): 9-(4-(1-(aminomethyl)cyclopropyl)phenyl)-6-chloro-8-hydroxythieno[2,3-c]quinolin-4(5H)-one;
(1117): 3-(4-(8-(2-(dimethylamino)ethoxy)-4-oxo-4,5-dihydrothieno[2,3-c]quinolin-9-yl)phenyl)propanenitrile;
(1118): (R)-9-(4-(1-aminopropyl)phenyl)-8-methoxythieno[2,3-c]quinolin-4(5H)-one;
(1119): N-(2-chloroethyl)-4-(8-hydroxy-4-oxo-4,5-dihydrothieno[2,3-c]quinolin-9-yl)-N-methylbenzenesulfonamide;
(1120): (S)-9-(4-(1-aminopropyl)phenyl)-8-hydroxythieno[2,3-c]quinolin-4(5H)-one;
(1121): (S)-9-(4-(1-aminopropyl)phenyl)-8-methoxythieno[2,3-c]quinolin-4(5H)-one;
(1122): (R)-9-(4-(1-aminoethyl)phenyl)-8-hydroxy-6-methylthieno[2,3-c]quinolin-4(5H)-one;

(1123): (R)-9-(4-(1-aminoethyl)phenyl)-6-bromo-8-hydroxythieno[2,3-c]quinolin-4(5H)-one;
(1124): 9-(4-(1-aminoethyl)phenyl)-4-oxo-4,5-dihydrothieno[2,3-c]quinoline-8-carbonitrile;
(1125): 9-(4-(1-aminoethyl)phenyl)-8-(hydroxymethyl)thieno[2,3-c]quinolin-4(5H)-one;
(1126): (R)-6-chloro-9-(4-(1-(dimethylamino)ethyl)phenyl)-8-hydroxythieno[2,3-c]quinolin-4(5H)-one;
(1127): (S)-9-(4-(1-(ethylamino)propyl)phenyl)-8-hydroxythieno[2,3-c]quinolin-4(5H)-one;
(1128): (S)-9-(4-(1-(dimethylamino)propyl)phenyl)-8-hydroxythieno[2,3-c]quinolin-4(5H)-one;
(1129): 6-chloro-9-(4-(1-(dimethylamino)propan-2-yl)phenyl)-8-hydroxythieno[2,3-c]quinolin-4(5H)-one;
(1130): 9-(4-(1-aminoethyl)phenyl)-6-ethynyl-8-hydroxythieno[2,3-c]quinolin-4(5H)-one;
(1131): (R)-9-(4-(1-aminopropyl)phenyl)-8-hydroxythieno[2,3-c]quinolin-4(5H)-one;
(1132): (R)-6-chloro-8-hydroxy-9-(4-(1-(methylamino)ethyl)phenyl)thieno[2,3-c]quinolin-4(5H)-one;
(1133): 9-(4-(2-aminoethyl)phenyl)-6-chloro-8-hydroxythieno[2,3-c]quinolin-(5H)-one;
(1134): 9-(4-(1-aminoethyl)phenyl)-8-(difluoromethyl)thieno[2,3-c]quinolin-4(5H)-one;
(1135): (R)-6-bromo-8-hydroxy-9-(4-(1-(methylamino)ethyl)phenyl)thieno[2,3-c]quinolin-4(5H)-one;
(1136): 9-(4-(1-aminopropan-2-yl)phenyl)-6-chloro-8-hydroxythieno[2,3-c]quinolin-4(5H)-one;
(1137): 9-(4-butylphenyl)-8-methoxythieno[2,3-c]quinolin-4(5H)-one;
(1138): 9-(4-butylphenyl)-8-hydroxythieno[2,3-c]quinolin-4(5H)-one;
(1139): N-(2-chloroethyl)-4-(8-methoxy-4-oxo-4,5-dihydrothieno[2,3-c]quinolin-9-yl)benzenesulfonamide;
(1140): 9-(4-((3-bromopyrrolidin-1-yl)sulfonyl)phenyl)-8-hydroxythieno[2,3-c]quinolin-4(5H)-one;
(1141): (S)-9-(4-(1-(methylsulfonamido)propyl)phenyl)-4-oxo-4,5-dihydrothieno[2,3-c]quinolin-8-yl methanesulfonate;
(1142): 9-(4-(2-aminoethyl)phenyl)-6-bromo-8-hydroxythieno[2,3-c]quinolin-4(5H)-one;
(1143): 9-(4-(3-(dimethylamino)-1-hydroxypropyl)phenyl)-8-methoxythieno[2,3-c]quinolin-4(5H)-one;
(1144): N-(2-bromoethyl)-4-(6-chloro-8-hydroxy-4-oxo-4,5-dihydrothieno[2,3-c]quinolin-9-yl)benzenesulfonamide;
(1145): N-(2-chloroethyl)-4-(8-hydroxy-4-oxo-2,3,4,5-tetrahydro-1H-cyclopenta[c]quinolin-9-yl)benzenesulfonamide;
(1146): N-(2-bromoethyl)-4-(5-ethyl-8-hydroxy-4-oxo-4,5-dihydrothieno[2,3-c]quinolin-9-yl)benzenesulfonamide;
(1147): (S)-8-methoxy-9-(4-(1-(methylamino)propyl)phenyl)thieno[2,3-c]quinolin-4(5H)-one;
(1148): (S)-8-hydroxy-9-(4-(1-(methylamino)propyl)phenyl)thieno[2,3-c]quinolin-4(5H)-one;
(1149): 9-(4-(1-aminoethyl)phenyl)-8-(((2-hydroxyethyl)amino)methyl)thieno[2,3-c]quinolin-4(5H)-one;
(1150): (R)-9-(4-(1-aminopropyl)phenyl)-6-bromo-8-hydroxythieno[2,3-c]quinolin-4(5H)-one;
(1151): (R)-9-(4-(1-(dimethylamino)propyl)phenyl)-8-hydroxythieno[2,3-c]quinolin-4(5H)-one;
(1152): 8-hydroxy-9-(4-pentylphenyl)thieno[2,3-c]quinolin-4(5H)-one;
(1153): 9-(4-(2-aminoacetyl)phenyl)-8-hydroxythieno[2,3-c]quinolin-4(5H)-one;
(1154): (S)-6-chloro-8-hydroxy-9-(4-(1-(methylamino)propyl)phenyl)thieno[2,3-c]quinolin-4(5H)-one;
(1155): 8-hydroxy-9-(4-(2-(methylamino)ethyl)phenyl)thieno[2,3-c]quinolin-4(5H)-one;
(1156): 8-methoxy-9-(4-(2-(methylamino)ethyl)phenyl)thieno[2,3-c]quinolin-4(5H)-one;
(1157): (R)-9-(4-(1-aminopropyl)phenyl)-8-hydroxy-6-methylthieno[2,3-c]quinolin-4(5H)-one;
(1158): (R)-9-(4-(1-aminopropyl)phenyl)-8-methoxy-6-methylthieno[2,3-c]quinolin-4(5H)-one;
(1159): (R)-9-(4-(1-aminopropyl)phenyl)-6-chloro-8-hydroxythieno[2,3-c]quinolin-4(5H)-one;
(1160): (R)-9-(4-(1-aminopropan-2-yl)phenyl)-8-hydroxythieno[2,3-c]quinolin-4(5H)-one;
(1161): (R)-9-(4-(1-aminopropan-2-yl)phenyl)-8-methoxythieno[2,3-c]quinolin-4(5H)-one;
(1162): 2-(4-(8-hydroxy-4-oxo-4,5-dihydrothieno[2,3-c]quinolin-9-yl)phenyl)butanenitrile;
(1163): (S)-9-(4-(1-aminopropan-2-yl)phenyl)-8-hydroxythieno[2,3-c]quinolin-4(5H)-one;
(1164): (S)-9-(4-(1-aminopropan-2-yl)phenyl)-8-methoxythieno[2,3-c]quinolin-4(5H)-one;
(1165): 6-chloro-8-hydroxy-9-(4-(2-(methylamino)ethyl)phenyl)thieno[2,3-c]quinolin-4(5H)-one;
(1166): (R)-9-(4-(1-aminopropan-2-yl)phenyl)-6-chloro-8-hydroxythieno[2,3-c]quinolin-4(5H)-one;
(1167): 9-(4-(2-aminoethyl)-3,5-difluorophenyl)-8-hydroxythieno[2,3-c]quinolin-4(5H)-one;
(1168): (R)-9-(4-(1-aminopropan-2-yl)phenyl)-8-hydroxy-6-methylthieno[2,3-c]quinolin-4(5H)-one
(1169): (R)-9-(4-(1-aminopropan-2-yl)phenyl)-8-hydroxy-6-methylthieno[2,3-c]quinolin-4(5H)-one
(1170): 6-chloro-8-methoxy-9-(4-(2-(methylamino)ethyl)phenyl)thieno[2,3-c]quinolin-4(5H)-one;
(1171): 9-(4-(2-aminoethyl)-3-chlorophenyl)-8-hydroxythieno[2,3-c]quinolin-4(5H)-one;
(1172): (S)-9-(4-(1-(dimethylamino)propan-2-yl)phenyl)-8-hydroxythieno[2,3-c]quinolin-4(5H)-one;
(1173): 6-bromo-8-methoxy-9-(4-(2-(methylamino)ethyl)phenyl)thieno[2,3-c]quinolin-4(5H)-one;
(1174): 9-(4-(1-aminopropan-2-yl)-3-fluorophenyl)-8-hydroxythieno[2,3-c]quinolin-4(5H)-one;
(1175): (R)-9-(4-(1-aminopropyl)phenyl)-6-chloro-8-methoxythieno[2,3-c]quinolin-4(5H)-one;
(1176): (R)-9-(4-(1-aminopropan-2-yl)phenyl)-6-bromo-8-hydroxythieno[2,3-c]quinolin-4(5H)-one;
(1177): 9-(4-(2-aminoethyl)-3,5-difluorophenyl)-8-methoxythieno[2,3-c]quinolin-4(5H)-one;
(1178): 9-(4-(2-(dimethylamino)ethyl)-3,5-difluorophenyl)-8-hydroxythieno[2,3-c]quinolin-4(5H)-one;
(1179): 9-(4-(1-aminopropan-2-yl)-3-fluorophenyl)-8-methoxythieno[2,3-c]quinolin-4(5H)-one;
(1180): (S)-9-(4-(1-aminopropan-2-yl)phenyl)-6,7-dichloro-8-methoxythieno[2,3-c]quinolin-4(5H)-one;
(1181): (S)-9-(4-(1-aminopropan-2-yl)phenyl)-6-chloro-8-hydroxythieno[2,3-c]quinolin-4(5H)-one;
(1182): (S)-6-chloro-9-(4-(1-(dimethylamino)propan-2-yl)phenyl)-8-hydroxythieno[2,3-c]quinolin-4(5H)-one;
(1183): 6-bromo-8-hydroxy-9-(4-(2-(methylamino)ethyl)phenyl)thieno[2,3-c]quinolin-4(5H)-one;
(1185): N-(2-hydroxyethyl)-4-(8-methoxy-5-methyl-4-oxo-4,5-dihydrothieno[2,3-c]quinolin-9-yl)benzenesulfonamide;
(1186): methyl 3-(4-(8-hydroxy-4-oxo-4,5-dihydrothieno[2,3-c]quinolin-9-yl)phenyl)propanoate;
(1187): (R)-8-hydroxy-9-(4-(1-(methylamino)propan-2-yl)phenyl)thieno[2,3-c]quinolin-4(5H)-one;
(1188): (R)-9-(4-(1-(dimethylamino)propan-2-yl)phenyl)-8-hydroxythieno[2,3-c]quinolin-4(5H)-one;

(1189): (R)-8-methoxy-9-(4-(1-(methylamino)propan-2-yl)phenyl)thieno[2,3-c]quinolin-4(5H)-one;
(1190): 9-(4-(1-aminopropan-2-yl)-3-fluorophenyl)-8-hydroxy-6-methylthieno[2,3-c]quinolin-4(5H)-one;
(1191): 9-(4-(2-aminoethyl)phenyl)-8-hydroxy-6-methylthieno[2,3-c]quinolin-4(5H)-one;
(1192): 9-(4-(2-aminoethyl)phenyl)-8-methoxy-6-methylthieno[2,3-c]quinolin-4(5H)-one;
(1193): 9-(4-(1-(dimethylamino)propan-2-yl)-3-fluorophenyl)-8-hydroxy-6-methylthieno[2,3-c]quinolin-4(5H)-one;
(1194): (S)-6-chloro-8-hydroxy-9-(4-(1-(methylamino)propan-2-yl)phenyl)thieno[2,3-c]quinolin-4(5H)-one;
(1195): (S)-6-chloro-9-(4-(1-(diethylamino)propan-2-yl)phenyl)-8-hydroxythieno[2,3-c]quinolin-4(5H)-one;
(1196): (S)-8-methoxy-9-(4-(1-(methylamino)propan-2-yl)phenyl)thieno[2,3-c]quinolin-4(5H)-one;
(1197): (S)-8-hydroxy-9-(4-(1-(methylamino)propan-2-yl)phenyl)thieno[2,3-c]quinolin-4(5H)-one;
(1198): 4-(8-hydroxy-5-methyl-4-oxo-4,5-dihydrothieno[2,3-c]quinolin-9-yl)-N-(2-hydroxyethyl)benzenesulfonamide;
(1199): N-(2-bromoethyl)-4-(8-hydroxy-5-methyl-4-oxo-4,5-dihydrothieno[2,3-c]quinolin-9-yl)benzenesulfonamide;
(1200): (R)-6-chloro-9-(4-(1-(dimethylamino)propan-2-yl)phenyl)-8-methoxythieno[2,3-c]quinolin-4(5H)-one;
(1201): (R)-9-(4-(1-aminopropan-2-yl)phenyl)-6-chloro-8-methoxythieno[2,3-c]quinolin-4(5H)-one;
(1202): 9-(4-(1-aminobutan-2-yl)phenyl)-8-methoxythieno[2,3-c]quinolin-4(5H)-one;
(1203): 9-(4-(2-aminopropan-2-yl)phenyl)-8-hydroxy-2-(phenylsulfonyl)thieno[2,3-c]quinolin-4(5H)-one;
(1204): N-(1-chloropropan-2-yl)-4-(8-hydroxy-4-oxo-4,5-dihydrothieno[2,3-c]quinolin-9-yl)benzenesulfonamide;
(1205): N-(1-chloropropan-2-yl)-4-(8-methoxy-4-oxo-4,5-dihydrothieno[2,3-c]quinolin-9-yl)benzenesulfonamide;
(1206): 9-(4-(2-aminoethyl)-3-hydroxyphenyl)-8-hydroxythieno[2,3-c]quinolin-4(5H)-one;
(1207): 9-(4-(2-aminoethyl)-3-methoxyphenyl)-8-methoxythieno[2,3-c]quinolin-4(5H)-one;
(1208): 9-(4-(2-aminoethyl)-2-chloro-5-methoxyphenyl)-8-methoxythieno[2,3-c]quinolin-4(5H)-one;
(1209): 9-(4-(3-(aminomethyl)pentan-3-yl)phenyl)-8-hydroxythieno[2,3-c]quinolin-4(5H)-one;
(1210): (R)-9-(4-(1-aminopropyl)phenyl)-8-hydroxy-5,6-dimethylthieno[2,3-c]quinolin-4(5H)-one;
(1211): 9-(4-(2-aminoethyl)-2-chloro-5-hydroxyphenyl)-6-chloro-8-hydroxythieno[2,3-c]quinolin-4(5H)-one;
(1212): 9-(4-(aminomethyl)phenyl)-8-hydroxy-6-methylthieno[2,3-c]quinolin-4(5H)-one;
(1213): 9-(4-(2-aminoethyl)-3-fluorophenyl)-6-bromo-8-hydroxythieno[2,3-c]quinolin-4(5H)-one;
(1214): 9-(4-(2-aminoethyl)-3-fluorophenyl)-6-bromo-8-methoxythieno[2,3-c]quinolin-4(5H)-one;
(1215): (S)-8-hydroxy-6-methyl-9-(4-(1-(methylamino)propan-2-yl)phenyl)thieno[2,3-c]quinolin-4(5H)-one;
(1216): 9-(4-(2-aminoethyl)-3-fluorophenyl)-8-methoxy-6-methylthieno[2,3-c]quinolin-4(5H)-one;
(1217): 9-(4-(2-aminoethyl)-3-fluorophenyl)-8-hydroxy-6-methylthieno[2,3-c]quinolin-4(5H)-one;
(1218): 9-(4-(2-aminoethyl)-3-fluorophenyl)-6-chloro-8-methoxythieno[2,3-c]quinolin-(5H)-one;
(1219): 9-(4-(2-aminoethyl)-3-fluorophenyl)-6-chloro-8-hydroxythieno[2,3-c]quinolin-4(5H)-one;
(1220): 9-(4-(2-aminoethyl)-3-fluorophenyl)-6-cyclopropyl-8-methoxythieno[2,3-c]quinolin-4(5H)-one;
(1221): 9-(4-(2-aminoethyl)-3-fluorophenyl)-6-cyclopropyl-8-hydroxythieno[2,3-c]quinolin-4(5H)-one;
(1222): (S)-8-methoxy-6-methyl-9-(4-(1-(methylamino)propan-2-yl)phenyl)thieno[2,3-c]quinolin-4(5H)-one;
(1223): (S)-9-(4-(1-aminopropan-2-yl)phenyl)-8-methoxy-6-methylthieno[2,3-c]quinolin-4(5H)-one;
(1224): 9-(4-(2-aminoethyl)-2-bromo-5-hydroxyphenyl)-8-hydroxythieno[2,3-c]quinolin-4(5H)-one;
(1225): (S)-9-(4-(1-aminoethyl)phenyl)-8-hydroxy-6-methylthieno[2,3-c]quinolin-4(5H)-one;
(1226): 3-(4-(8-hydroxy-6-methyl-4-oxo-4,5-dihydrothieno[2,3-c]quinolin-9-yl)phenyl)propanenitrile;
(1227): 9-(4-(1-amino-2-methylpropan-2-yl)phenyl)-8-methoxy-6-methylthieno[2,3-c]quinolin-4(5H)-one;
(1228): 9-(4-(1-amino-2-methylpropan-2-yl)phenyl)-8-hydroxy-6-methylthieno[2,3-c]quinolin-4(5H)-one;
(1229): 2-(2-fluoro-4-(8-hydroxy-6-methyl-4-oxo-4,5-dihydrothieno[2,3-c]quinolin-9-yl)phenyl)propanenitrile;
(1230): 6-cyclopropyl-9-(4-(2-(dimethylamino)ethyl)-3-fluorophenyl)-8-hydroxythieno[2,3-c]quinolin-4(5H)-one;
(1231): 6-cyclopropyl-9-(4-(2-(dimethylamino)ethyl)-3-fluorophenyl)-8-methoxythieno[2,3-c]quinolin-4(5H)-one;
(1232): (S)-9-(4-(1-aminopropan-2-yl)phenyl)-8-hydroxy-6-methylthieno[2,3-c]quinolin-4(5H)-one;
(1233): (S)-9-(4-(1-(dimethylamino)propan-2-yl)phenyl)-8-hydroxy-6-methylthieno[2,3-c]quinolin-4(5H)-one;
(1234): 9-(3-fluoro-4-(2-(methylamino)ethyl)phenyl)-8-methoxythieno[2,3-c]quinolin-4(5H)-one;
(1235): 9-(3-fluoro-4-(2-(methylamino)ethyl)phenyl)-8-hydroxythieno[2,3-c]quinolin-4(5H)-one;
(1236): 9-(4-(2-amino-1-cyclopentylethyl)phenyl)-8-hydroxythieno[2,3-c]quinolin-4(5H)-one;
(1237): 9-(4-(2-amino-1,1-dicyclopentylethyl)phenyl)-8-methoxythieno[2,3-c]quinolin-4(5H)-one;
(1238): 3-(4-(8-methoxy-6-methyl-4-oxo-4,5-dihydrothieno[2,3-c]quinolin-9-yl)phenyl)propanenitrile;
(1239): 9-(4-(2-amino-1-cyclopentylethyl)phenyl)-8-methoxythieno[2,3-c]quinolin-4(5H)-one;
(1240): 9-(4-(1-amino-2-methylpropan-2-yl)phenyl)-6-cyclopropyl-8-hydroxythieno[2,3-c]quinolin-4(5H)-one;
(1241): 9-(4-(3-aminopropyl)phenyl)-8-methoxy-6-methylthieno[2,3-c]quinolin-4(5H)-one;
(1242): 9-(4-(2-aminopropyl)phenyl)-8-hydroxy-6-methylthieno[2,3-c]quinolin-4(5H)-one;
(1243): 9-(4-(2-aminopropyl)phenyl)-8-methoxy-6-methylthieno[2,3-c]quinolin-4(5H)-one;
(1244): 9-(4-(1-amino-2-methylpropan-2-yl)phenyl)-6-cyclopropyl-8-methoxythieno[2,3-c]quinolin-4(5H)-one;
(1245): 6-bromo-9-(3-fluoro-4-(2-(methylamino)ethyl)phenyl)-8-hydroxythieno[2,3-c]quinolin-4(5H)-one;
(1246): 6-bromo-9-(3-fluoro-4-(2-(methylamino)ethyl)phenyl)-8-methoxythieno[2,3-c]quinolin-4(5H)-one;
(1247): 9-(4-(1-amino-2-methylpropan-2-yl)phenyl)-6-bromo-8-hydroxythieno[2,3-c]quinolin-4(5H)-one;
(1248): 9-(4-(1-amino-2-methylpropan-2-yl)phenyl)-6-bromo-8-methoxythieno[2,3-c]quinolin-4(5H)-one;
(1249): (R)-9-(4-(1-aminopropan-2-yl)phenyl)-6-methyl-4-oxo-4,5-dihydrothieno[2,3-c]quinolin-8-carbonitrile;
(1250): (R)-9-(4-(1-aminoethyl)phenyl)-8-hydroxy-6-vinylthieno[2,3-c]quinolin-4(5H)-one;
(1251): 9-(4-(1-(aminomethyl)cyclopropyl)phenyl)-8-methoxy-6-methylthieno[2,3-c]quinolin-4(5H)-one;
(1252): 9-(4-(1-amino-3-methylbutan-2-yl)phenyl)-8-hydroxythieno[2,3-c]quinolin-4(5H)-one;

(1253): 9-(4-(1-amino-3-methylbutan-2-yl)phenyl)-8-methoxythieno[2,3-c]quinolin-4(5H)-one;
(1254): 9-(4-(1-(aminomethyl)cyclopropyl)phenyl)-8-hydroxy-6-methylthieno[2,3-c]quinolin-4(5H)-one;
(1255): (R)-9-(4-(1-aminoethyl)phenyl)-6-ethyl-8-hydroxythieno[2,3-c]quinolin-4(5H)-one;
(1256): (R)-9-(4-(1-aminoethyl)phenyl)-6-(difluoromethyl)-8-hydroxythieno[2,3-c]quinolin-4(5H)-one;
(1257): 9-(3-fluoro-4-(2-(methylamino)ethyl)phenyl)-8-methoxy-6-methylthieno[2,3-c]quinolin-4(5H)-one;
(1258): 9-(3-fluoro-4-(2-(methylamino)ethyl)phenyl)-8-hydroxy-6-methylthieno[2,3-c]quinolin-4(5H)-one;
(1259): 6-bromo-9-(4-(1-(dimethylamino)-2-methylpropan-2-yl)phenyl)-8-hydroxythieno[2,3-c]quinolin-4(5H)-one;
(1260): 9-(4-(1-amino-2-methylpropan-2-yl)phenyl)-6-chloro-8-hydroxythieno[2,3-c]quinolin-4(5H)-one;
(1261): 9-(4-(3-aminopropyl)phenyl)-8-hydroxy-6-methylthieno[2,3-c]quinolin-4(5H)-one;
(1262): (R)-8-hydroxy-6-methyl-9-(4-(1-(methylamino)ethyl)phenyl)thieno[2,3-c]quinolin-4(5H)-one;
(1263): 9-(4-(2-aminoethyl)-3-chlorophenyl)-8-methoxy-6-methylthieno[2,3-c]quinolin-4(5H)-one;
(1264): 9-(4-(2-aminoethyl)-3-chlorophenyl)-8-hydroxy-6-methylthieno[2,3-c]quinolin-4(5H)-one;
(1265): (R)-8-methoxy-6-methyl-9-(4-(1-(methylamino)ethyl)phenyl)thieno[2,3-c]quinolin-4(5H)-one;
(1266): 9-(4-(2-aminopropyl)phenyl)-6-ethyl-8-hydroxythieno[2,3-c]quinolin-4(5H)-one;
(1267): (R)-9-(4-(1-aminoethyl)phenyl)-6-butyl-8-hydroxythieno[2,3-c]quinolin-4(5H)-one;
(1268): 9-(4-(2-aminoethyl)-3-chlorophenyl)-6-chloro-8-hydroxythieno[2,3-c]quinolin-(5H)-one;
(1269): 9-(4-(2-aminopropyl)phenyl)-6-ethyl-8-methoxythieno[2,3-c]quinolin-4(5H)-one;
(1270): 2-(4-(8-methoxy-4-oxo-4,5-dihydrothieno[2,3-c]quinolin-9-yl)phenyl)-2-(oxetan-3-yl)acetonitrile;
(1271): 9-(4-(1-amino-2-methylpropan-2-yl)-3-fluorophenyl)-8-hydroxythieno[2,3-c]quinolin-4(5H)-one;
(1272): (R)-6-ethyl-8-hydroxy-9-(4-(1-(methylamino)ethyl)phenyl)thieno[2,3-c]quinolin-4(5H)-one;
(1273): 9-(4-(1-aminopropan-2-yl)-3-fluorophenyl)-8-methoxy-6-methylthieno[2,3-c]quinolin-4(5H)-one;
(1274): 9-(4-(1-amino-3-methylbutan-2-yl)phenyl)-8-hydroxy-6-methylthieno[2,3-c]quinolin-4(5H)-one;
(1275): 9-(4-(1-aminopropan-2-yl)-3-chlorophenyl)-8-methoxy-6-methylthieno[2,3-c]quinolin-4(5H)-one;
(1276): 9-(4-(1-aminopropan-2-yl)-3-chlorophenyl)-8-methoxythieno[2,3-c]quinolin-4(5H)-one;
(1277): 9-(4-(1-aminobutan-2-yl)phenyl)-8-methoxy-6-methylthieno[2,3-c]quinolin-4(5H)-one;
(1278): 9-(4-(1-amino-2-methylpropan-2-yl)-3-fluorophenyl)-8-hydroxy-6-methylthieno[2,3-c]quinolin-4(5H)-one;
(1279): 9-(4-(1-aminopropan-2-yl)-3-chlorophenyl)-8-hydroxy-6-methylthieno[2,3-c]quinolin-4(5H)-one;
(1280): 9-(4-(1-aminopropan-2-yl)-3-chlorophenyl)-8-hydroxythieno[2,3-c]quinolin-4(5H)-one;
(1281): 9-(4-(2-amino-2-methylpropyl)phenyl)-8-methoxythieno[2,3-c]quinolin-4(5H)-one;
(1282): 9-(4-(2-amino-2-methylpropyl)phenyl)-8-hydroxythieno[2,3-c]quinolin-4(5H)-one;
(1283): 9-(4-(1-amino-3-methylbutan-2-yl)-3-fluorophenyl)-8-methoxy-6-methylthieno[2,3-c]quinolin-4(5H)-one;
(1284): 8-methoxy-6-methyl-9-(4-(3-methyl-1-(methylamino)butan-2-yl)phenyl)thieno[2,3-c]quinolin-4(5H)-one;
(1285): 8-hydroxy-6-methyl-9-(4-(3-methyl-1-(methylamino)butan-2-yl)phenyl)thieno[2,3-c]quinolin-4(5H)-one;
(1286): 9-(3-fluoro-4-(1-(methylamino)propan-2-yl)phenyl)-8-methoxy-6-methylthieno[2,3-c]quinolin-4(5H)-one;
(1287): 9-(4-(1-amino-2-methylpropan-2-yl)-3-fluorophenyl)-8-methoxythieno[2,3-c]quinolin-4(5H)-one;
(1288): 9-(4-(1-amino-3-methylbutan-2-yl)-3-fluorophenyl)-8-hydroxy-6-methylthieno[2,3-c]quinolin-4(5H)-one;
(1289): 9-(4-(2-amino-2-methylpropyl)phenyl)-6-bromo-8-methoxythieno[2,3-c]quinolin-4(5H)-one;
(1290): 9-(4-(1-(aminomethyl)cyclobutyl)phenyl)-8-hydroxy-6-methylthieno[2,3-c]quinolin-4(5H)-one;
(1291): 9-(4-(1-aminobutan-2-yl)phenyl)-8-hydroxy-6-methylthieno[2,3-c]quinolin-4(5H)-one;
(1292): 9-(4-(2-amino-2-methylpropyl)phenyl)-6-bromo-8-hydroxythieno[2,3-c]quinolin-4(5H)-one;
(1293): 9-(3-fluoro-4-(1-(methylamino)propan-2-yl)phenyl)-8-hydroxy-6-methylthieno[2,3-c]quinolin-4(5H)-one;
(1294): 9-(3-fluoro-4-(3-methyl-1-(methylamino)butan-2-yl)phenyl)-8-hydroxy-6-methylthieno[2,3-c]quinolin-4(5H)-one;
(1295): 9-(4-(1-(dimethylamino)-3-methylbutan-2-yl)phenyl)-8-methoxy-6-methylthieno[2,3-c]quinolin-4(5H)-one;
(1296): 9-(4-(1-(dimethylamino)-3-methylbutan-2-yl)-3-fluorophenyl)-8-hydroxy-6-methylthieno[2,3-c]quinolin-4(5H)-one;
(1297): 9-(4-(1-(aminomethyl)cyclobutyl)phenyl)-8-methoxy-6-methylthieno[2,3-c]quinolin-4(5H)-one;
(1298): (R)-8-methoxy-6-methyl-9-(4-(1-(methylamino)propan-2-yl)phenyl)thieno[2,3-c]quinolin-4(5H)-one;
(1299): 9-(4-(1-(aminomethyl)cyclobutyl)phenyl)-8-methoxythieno[2,3-c]quinolin-4(5H)-one;
(1300): 9-(4-(1-(aminomethyl)cyclobutyl)phenyl)-8-hydroxythieno[2,3-c]quinolin-4(5H)-one;
(1301): 8-methoxy-6-methyl-9-(4-(piperidin-3-yl)phenyl)thieno[2,3-c]quinolin-4(5H)-one;
(1302): 8-hydroxy-6-methyl-9-(4-(piperidin-3-yl)phenyl)thieno[2,3-c]quinolin-4(5H)-one;
(1303): (S)-9-(4-(1-aminopropan-2-yl)-3-fluorophenyl)-8-hydroxy-6-methylthieno[2,3-c]quinolin-4(5H)-one;
(1304): (S)-9-(4-(1-aminopropan-2-yl)-3-fluorophenyl)-8-hydroxy-6-methylthieno[2,3-c]quinolin-4(5H)-one;
(1305): (R)-9-(4-(1-aminopropan-2-yl)phenyl)-8-methoxy-6-methylthieno[2,3-c]quinolin-4(5H)-one;
(1306): (R)-8-hydroxy-6-methyl-9-(4-(1-(methylamino)propan-2-yl)phenyl)thieno[2,3-c]quinolin-4(5H)-one;
(1307): (R)-8-hydroxy-6-methyl-9-(4-(1-(methylamino)propan-2-yl)phenyl)thieno[2,3-c]quinolin-4(5H)-one;
(1308): 8-methoxy-3-methyl-3H-pyrrolo[2,3-c]quinolin-4(5H)-one;
(1309): 9-(4-(1-aminobutan-2-yl)phenyl)-8-hydroxythieno[2,3-c]quinolin-4(5H)-one;
(1310): (S)-9-(4-(1-aminopropan-2-yl)-3-fluorophenyl)-8-methoxy-6-methylthieno[2,3-c]quinolin-4(5H)-one;
(1311): (R)-9-(4-(1-(dimethylamino)propan-2-yl)-3-fluorophenyl)-8-hydroxy-6-methylthieno[2,3-c]quinolin-4(5H)-one;
(1312): 9-(4-(1-aminobutan-2-yl)phenyl)-6-chloro-8-hydroxythieno[2,3-c]quinolin-4(5H)-one;
(1313): 8-hydroxy-3-methyl-3H-pyrrolo[2,3-c]quinolin-4(5H)-one;

(1314): 9-amino-8-methoxy-6-methylthieno[2,3-c]quinolin-4(5H)-one;

(1315): (R)-9-(3-fluoro-4-(1-(methylamino)propan-2-yl)phenyl)-8-hydroxy-6-methylthieno[2,3-c]quinolin-4(5H)-one;

(1316): (R)-9-(3-fluoro-4-(1-(methylamino)propan-2-yl)phenyl)-8-methoxy-6-methylthieno[2,3-c]quinolin-4(5H)-one;

(1317): (R)-9-(4-(1-aminopropan-2-yl)-3-fluorophenyl)-8-methoxy-6-methylthieno[2,3-c]quinolin-4(5H)-one;

(1318): (R)-9-(4-(1-aminopropan-2-yl)-3-fluorophenyl)-8-hydroxy-6-methylthieno[2,3-c]quinolin-4(5H)-one;

(1319): (R)-9-(4-(1-aminopropan-2-yl)-3-fluorophenyl)-8-hydroxy-6-methylthieno[2,3-c]quinolin-4(5H)-one;

(1320): 9-((4-(2-aminoethyl)phenyl)amino)-8-methoxy-6-methylthieno[2,3-c]quinolin-4(5H)-one;

(1321): 9-(4-(1-(aminomethyl)cyclobutyl)phenyl)-6-chloro-8-methoxythieno[2,3-c]quinolin-(5H)-one;

(1322): (R)-1-(4-(1-aminopropan-2-yl)phenyl)-8-methoxy-3-methyl-3H-pyrrolo[2,3-c]quinolin-4(5H)-one;

(1323): 8-hydroxy-3-(hydroxymethyl)-3H-pyrrolo[2,3-c]quinolin-4(5H)-one;

(1324): (R)-9-(4-(1-(dimethylamino)propan-2-yl)phenyl)-8-hydroxy-6-methylthieno[2,3-c]quinolin-4(5H)-one;

(1325): 9-((4-(aminomethyl)phenyl)amino)-8-hydroxy-6-methylthieno[2,3-c]quinolin-4(5H)-one;

(1326): 9-((4-(aminomethyl)phenyl)amino)-8-methoxy-6-methylthieno[2,3-c]quinolin-4(5H)-one;

(1327): 9-((4-(1-aminopropan-2-yl)phenyl)amino)-8-methoxy-6-methylthieno[2,3-c]quinolin-4(5H)-one;

(1328): 9-((4-(1-aminopropan-2-yl)phenyl)amino)-8-hydroxy-6-methylthieno[2,3-c]quinolin-4(5H)-one;

(1329): 9-(4-(2-aminopropan-2-yl)phenyl)-8-methoxy-6-methylthieno[2,3-c]quinolin-4(5H)-one;

(1330): 9-(4-(2-aminopropan-2-yl)phenyl)-8-hydroxy-6-methylthieno[2,3-c]quinolin-4(5H)-one;

(1331): 9-(4-(3-(aminomethyl)pentan-3-yl)phenyl)-8-methoxy-6-methylthieno[2,3-c]quinolin-4(5H)-one;

(1332): 9-(4-((R)-1-aminopropan-2-yl)phenyl)-8-hydroxy-2-(1-hydroxyethyl)thieno[2,3-c]quinolin-4(5H)-one;

(1333): 9-(4-((R)-1-aminopropan-2-yl)phenyl)-2-(1-hydroxyethyl)-8-methoxythieno[2,3-c]quinolin-4(5H)-one;

(1334): 3-(4-((8-methoxy-6-methyl-4-oxo-4,5-dihydrothieno[2,3-c]quinolin-9-yl)amino)phenyl)propanenitrile;

(1335): 9-((3-(2-aminoethyl)phenyl)amino)-8-methoxy-6-methylthieno[2,3-c]quinolin-4(5H)-one;

(1336): 9-((4-(2-aminoethyl)phenyl)amino)-8-hydroxy-6-methylthieno[2,3-c]quinolin-4(5H)-one;

(1337): 9-(4-(2-(ethylamino)propyl)phenyl)-8-hydroxy-6-methylthieno[2,3-c]quinolin-4(5H)-one;

(1338): 9-(4-(3-(aminomethyl)pentan-3-yl)phenyl)-8-methoxythieno[2,3-c]quinolin-(5H)-one;

(1339): 9-(4-(3-(aminomethyl)pentan-3-yl)phenyl)-8-hydroxy-6-methylthieno[2,3-c]quinolin-4(5H)-one;

(1340): (R)-9-(4-(1-aminopropan-2-yl)phenyl)-8-hydroxy-2,6-dimethylthieno[2,3-c]quinolin-4(5H)-one;

(1341): (R)-9-(4-(1-aminopropan-2-yl)phenyl)-8-methoxy-2,6-dimethylthieno[2,3-c]quinolin-4(5H)-one;

(1342): 9-(4-((R)-1-aminopropan-2-yl)phenyl)-2-(1-hydroxyethyl)-8-methoxy-6-methylthieno[2,3-c]quinolin-4(5H)-one;

(1343): 2-((4-(8-methoxy-6-methyl-4-oxo-4,5-dihydrothieno[2,3-c]quinolin-9-yl)phenyl)amino)acetonitrile;

(1344): (R)-9-(4-(1-aminobutan-2-yl)phenyl)-8-methoxy-6-methylthieno[2,3-c]quinolin-4(5H)-one;

(1345): 9-(3-chloro-4-(2-(ethylamino)ethyl)phenyl)-8-methoxythieno[2,3-c]quinolin-4(5H)-one;

(1346): 9-(4-(3-((dimethylamino)methyl)pentan-3-yl)phenyl)-8-hydroxy-6-methylthieno[2,3-c]quinolin-4(5H)-one;

(1347): (R)-6-chloro-9-(4-(1-(dimethylamino)propan-2-yl)phenyl)-8-hydroxythieno[2,3-c]quinolin-4(5H)-one;

(1348): 9-(4-(2-(ethylamino)ethyl)phenyl)-8-hydroxy-6-methylthieno[2,3-c]quinolin-4(5H)-one;

(1349): 9-(4-(2-(ethylamino)ethyl)phenyl)-8-methoxy-6-methylthieno[2,3-c]quinolin-4(5H)-one;

(1350): 9-(4-(2-(ethyl(methyl)amino)propyl)phenyl)-8-hydroxy-6-methylthieno[2,3-c]quinolin-4(5H)-one;

(1351): 2-(hydroxy(piperidin-4-yl)methyl)-8-methoxy-6-methylthieno[2,3-c]quinolin-4(5H)-one;

(1352): (R)-9-(4-(1-aminobutan-2-yl)phenyl)-8-hydroxy-6-methylthieno[2,3-c]quinolin-4(5H)-one;

(1353): (R)-9-(4-(1-aminopropan-2-yl)phenyl)-2-chloro-8-hydroxy-6-methylthieno[2,3-c]quinolin-4(5H)-one;

(1354): (R)-9-(4-(1-aminopropan-2-yl)phenyl)-2-chloro-8-methoxy-6-methylthieno[2,3-c]quinolin-4(5H)-one;

(1355): 8-methoxy-6-methyl-9-(4-(2-(methylamino)ethyl)phenyl)thieno[2,3-c]quinolin-4(5H)-one;

(1356): 9-(4-(2-(ethyl(methyl)amino)ethyl)phenyl)-8-hydroxy-6-methylthieno[2,3-c]quinolin-4(5H)-one;

(1357): 9-(4-(3-(aminomethyl)pentan-3-yl)phenyl)-6-chloro-8-methoxythieno[2,3-c]quinolin-4(5H)-one;

(1358): 9-(4-(3-((dimethylamino)methyl)pentan-3-yl)phenyl)-8-hydroxythieno[2,3-c]quinolin-4(5H)-one;

(1359): 9-(6-(dimethylamino)pyridin-3-yl)-8-methoxy-6-methylthieno[2,3-c]quinolin-4(5H)-one;

(1360): (R)-9-(4-(1-(dimethylamino)butan-2-yl)phenyl)-8-hydroxy-6-methylthieno[2,3-c]quinolin-4(5H)-one;

(1361): (R)-8-methoxy-6-methyl-9-(4-(1-(methylamino)butan-2-yl)phenyl)thieno[2,3-c]quinolin-4(5H)-one;

(1362): 9-(4-(3-((diethylamino)methyl)pentan-3-yl)phenyl)-8-hydroxy-6-methylthieno[2,3-c]quinolin-4(5H)-one;

(1363): 9-(3-chloro-4-(2-(ethylamino)ethyl)phenyl)-8-hydroxythieno[2,3-c]quinolin-4(5H)-one;

(1364): 8-hydroxy-6-methyl-9-(4-(2-(methylamino)ethyl)phenyl)thieno[2,3-c]quinolin-4(5H)-one;

(1365): (R)-9-(4-(1-(dimethylamino)butan-2-yl)phenyl)-8-methoxy-6-methylthieno[2,3-c]quinolin-4(5H)-one;

(1366): (R)-9-(4-(1-(ethyl(methyl)amino)butan-2-yl)phenyl)-8-methoxy-6-methylthieno[2,3-c]quinolin-4(5H)-one;

(1367): (R)-9-(4-(1-(diethylamino)butan-2-yl)phenyl)-8-hydroxy-6-methylthieno[2,3-c]quinolin-4(5H)-one;

(1368): (R)-9-(4-(1-(ethyl(methyl)amino)butan-2-yl)phenyl)-8-hydroxy-6-methylthieno[2,3-c]quinolin-4(5H)-one;

(1369): 2-((4-(8-methoxy-6-methyl-4-oxo-4,5-dihydrothieno[2,3-c]quinolin-9-yl)phenyl)(methyl)amino)acetonitrile;

(1370): 2-((4-(8-hydroxy-6-methyl-4-oxo-4,5-dihydrothieno[2,3-c]quinolin-9-yl)phenyl)(methyl)amino)acetonitrile;

(1371): 9-(3-chloro-4-(2-(ethyl(methyl)amino)ethyl)phenyl)-8-hydroxythieno[2,3-c]quinolin-4(5H)-one;

(1372): 9-(4-(1-((dimethylamino)methyl)cyclobutyl)phenyl)-8-hydroxy-6-methylthieno[2,3-c]quinolin-4(5H)-one;

(1373): (R)-9-(4-(1-aminopropyl)phenyl)-6-bromo-8-methoxythieno[2,3-c]quinolin-4(5H)-one;

(1374): 9-(6-(2-aminoethoxy)pyridin-3-yl)-8-hydroxy-6-methylthieno[2,3-c]quinolin-4(5H)-one;

(1375): (R)-9-(4-(1-aminopropan-2-yl)phenyl)-2-fluoro-8-methoxy-6-methylthieno[2,3-c]quinolin-4(5H)-one;
(1376): 9-(6-(2-aminoethoxy)pyridin-3-yl)-8-methoxy-6-methylthieno[2,3-c]quinolin-4(5H)-one;
(1377): 9-(4-(1-amino-2,2,2-trifluoroethyl)phenyl)-8-hydroxy-6-methylthieno[2,3-c]quinolin-4(5H)-one;
(1378): 9-(4-(1-amino-2,2,2-trifluoroethyl)phenyl)-8-methoxy-6-methylthieno[2,3-c]quinolin-4(5H)-one;
(1379): (R)-9-(4-(1-(ethyl(methyl)amino)propan-2-yl)phenyl)-8-hydroxy-6-methylthieno[2,3-c]quinolin-4(5H)-one;
(1380): (R)-8-hydroxy-6-methyl-9-(4-(1-(methylamino)butan-2-yl)phenyl)thieno[2,3-c]quinolin-4(5H)-one;
(1381): 9-(4-(1-amino-2,2,2-trifluoroethyl)phenyl)-8-methoxythieno[2,3-c]quinolin-4(5H)-one;
(1382): (R)-1-(4-(1-aminopropan-2-yl)phenyl)-8-hydroxy-3-methyl-3H-pyrrolo[2,3-c]quinolin-4(5H)-one;
(1383): (R)-9-(4-(1-aminopropan-2-yl)phenyl)-2-fluoro-8-hydroxy-6-methylthieno[2,3-c]quinolin-4(5H)-one;
(1384): 9-(6-((2-aminoethyl)amino)pyridin-3-yl)-8-hydroxy-6-methylthieno[2,3-c]quinolin-4(5H)-one;
(1385): 9-(6-((2-aminoethyl)amino)pyridin-3-yl)-8-methoxy-6-methylthieno[2,3-c]quinolin-4(5H)-one;
(1386): (S)-6-chloro-9-(4-(1-(ethyl(methyl)amino)propan-2-yl)phenyl)-8-hydroxythieno[2,3-c]quinolin-4(5H)-one;
(1387): (S)-9-(4-(1-(dimethylamino)propan-2-yl)-3-fluorophenyl)-8-methoxy-6-methylthieno[2,3-c]quinolin-4(5H)-one;
(1388): (R)-9-(4-(1-(diethylamino)propan-2-yl)phenyl)-8-hydroxy-6-methylthieno[2,3-c]quinolin-4(5H)-one;
(1389): 9-(4-(1-amino-2,2,2-trifluoroethyl)phenyl)-8-hydroxythieno[2,3-c]quinolin-4(5H)-one;
(1390): 9-(4-(1-amino-2,2,2-trifluoroethyl)phenyl)-6-bromo-8-methoxythieno[2,3-c]quinolin-4(5H)-one;
(1391): 9-(4-(1-(aminomethyl)cyclopropyl)phenyl)-6-bromo-8-methoxythieno[2,3-c]quinolin-4(5H)-one;
(1392): (4-(8-hydroxy-6-methyl-4-oxo-4,5-dihydrothieno[2,3-c]quinolin-9-yl)phenyl)methanesulfonamide;
(1393): 8-methoxy-6-methyl-9-(4-(2-(methylsulfinyl)ethyl)phenyl)thieno[2,3-c]quinolin-4(5H)-one;
(1394): 8-hydroxy-6-methyl-9-(4-((methylsulfonyl)methyl)phenyl)thieno[2,3-c]quinolin-4(5H)-one;
(1395): (4-(8-methoxy-6-methyl-4-oxo-4,5-dihydrothieno[2,3-c]quinolin-9-yl)phenyl)methanesulfonamide;
(1396): 9-(4-((2-aminoethyl)(methyl)amino)phenyl)-8-methoxy-6-methylthieno[2,3-c]quinolin-4(5H)-one;
(1397): (R)—N-(2-(2-fluoro-4-(8-hydroxy-6-methyl-4-oxo-4,5-dihydrothieno[2,3-c]quinolin-9-yl)phenyl)propyl)methanesulfonamide;
(1398): (R)—N-(2-(2-fluoro-4-(8-methoxy-6-methyl-4-oxo-4,5-dihydrothieno[2,3-c]quinolin-9-yl)phenyl)propyl)methanesulfonamide;
(1399): (S)-9-(4-(1-(dimethylamino)propan-2-yl)-3-fluorophenyl)-8-hydroxy-6-methylthieno[2,3-c]quinolin-4(5H)-one;
(1400): 9-(4-((2-aminoethyl)(methyl)amino)phenyl)-8-hydroxy-6-methylthieno[2,3-c]quinolin-4(5H)-one;
(1401): 9-(4-(1-(aminomethyl)cyclopropyl)phenyl)-6-bromo-8-hydroxythieno[2,3-c]quinolin-4(5H)-one;
(1402): 2-(6-(8-methoxy-6-methyl-4-oxo-4,5-dihydrothieno[2,3-c]quinolin-9-yl)pyridin-3-yl)acetonitrile;
(1403): 8-hydroxy-6-methyl-9-(4-(2-(methylsulfinyl)ethyl)phenyl)thieno[2,3-c]quinolin-4(5H)-one;
(1404): 8-methoxy-6-methyl-9-(4-((methylsulfonyl)methyl)phenyl)thieno[2,3-c]quinolin-4(5H)-one;
(1405): 5-(8-methoxy-6-methyl-4-oxo-4,5-dihydrothieno[2,3-c]quinolin-9-yl)nicotinamide;
(1406): 2-(5-(8-hydroxy-4-oxo-4,5-dihydrothieno[2,3-c]quinolin-9-yl)pyridin-2-yl)propanenitrile;
(1407): 2-(4-(8-methoxy-6-methyl-4-oxo-4,5-dihydrothieno[2,3-c]quinolin-9-yl)phenyl)propanamide;
(1408): 9-(6-(1-aminopropan-2-yl)pyridin-3-yl)-8-methoxy-6-methylthieno[2,3-c]quinolin-4(5H)-one;
(1409): 2-(5-(8-methoxy-6-methyl-4-oxo-4,5-dihydrothieno[2,3-c]quinolin-9-yl)pyridin-2-yl)-2-methylpropanenitrile;
(1410): 2-hydroxy-2-(4-(8-hydroxy-4-oxo-4,5-dihydrothieno[2,3-c]quinolin-9-yl)phenyl)propane-1-sulfonamide;
(1411): N-(tert-butyl)-2-hydroxy-2-(4-(8-methoxy-4-oxo-4,5-dihydrothieno[2,3-c]quinolin-9-yl)phenyl)propane-1-sulfonamide;
(1412): 2-(4-(8-hydroxy-6-methyl-4-oxo-4,5-dihydrothieno[2,3-c]quinolin-9-yl)phenyl)propanamide;
(1413): 2-(4-(8-hydroxy-4-oxo-4,5-dihydrothieno[2,3-c]quinolin-9-yl)phenyl)propane-1-sulfonamide;
(1414): 9-(4-(2-amino-1-fluoroethyl)phenyl)-8-methoxy-6-methylthieno[2,3-c]quinolin-4(5H)-one;
(1415): 9-(6-(1-aminopropan-2-yl)pyridin-3-yl)-8-hydroxy-6-methylthieno[2,3-c]quinolin-4(5H)-one;
(1416): 2-(5-(8-hydroxy-6-methyl-4-oxo-4,5-dihydrothieno[2,3-c]quinolin-9-yl)pyridin-2-yl)-2-methylpropanenitrile;
(1417): 2-(5-(8-hydroxy-4-oxo-4,5-dihydrothieno[2,3-c]quinolin-9-yl)pyridin-2-yl)-2-methylpropanenitrile;
(1418): 2-(5-(8-methoxy-4-oxo-4,5-dihydrothieno[2,3-c]quinolin-9-yl)pyridin-2-yl)-2-methylpropanenitrile;
(1419): 2-(4-(8-hydroxy-6-methyl-4-oxo-4,5-dihydrothieno[2,3-c]quinolin-9-yl)phenyl)propane-1-sulfonamide;
(1420): 9-(4-(2-amino-1-hydroxyethyl)phenyl)-8-methoxy-6-methylthieno[2,3-c]quinolin-4(5H)-one;
(1421): 9-(6-(1-amino-2-methylpropan-2-yl)pyridin-3-yl)-8-hydroxythieno[2,3-c]quinolin-4(5H)-one;
(1422): N-cyclopropyl-1-(4-(8-methoxy-6-methyl-4-oxo-4,5-dihydrothieno[2,3-c]quinolin-9-yl)phenyl)methanesulfonamide;
(1423): 2-(5-(8-methoxy-4-oxo-4,5-dihydrothieno[2,3-c]quinolin-9-yl)pyridin-2-yl)propanenitrile;
(1424): (R)—N-(2-(4-(8-methoxy-6-methyl-4-oxo-4,5-dihydrothieno[2,3-c]quinolin-9-yl)phenyl)propyl)methanesulfonamide;
(1425): N-ethyl-1-(4-(8-methoxy-6-methyl-4-oxo-4,5-dihydrothieno[2,3-c]quinolin-9-yl)phenyl)methanesulfonamide;
(1426): 9-(6-(1-aminopropan-2-yl)pyridin-3-yl)-8-methoxythieno[2,3-c]quinolin-4(5H)-one;
(1427): N-cyclopropyl-1-(4-(8-hydroxy-6-methyl-4-oxo-4,5-dihydrothieno[2,3-c]quinolin-9-yl)phenyl)methanesulfonamide;
(1428): 1-(5-(8-methoxy-4-oxo-4,5-dihydrothieno[2,3-c]quinolin-9-yl)pyridin-2-yl)cyclopropanecarbonitrile;
(1429): N-ethyl-1-(4-(8-hydroxy-6-methyl-4-oxo-4,5-dihydrothieno[2,3-c]quinolin-9-yl)phenyl)methanesulfonamide;
(1430): 1-(4-(8-methoxy-6-methyl-4-oxo-4,5-dihydrothieno[2,3-c]quinolin-9-yl)phenyl)ethanesulfonamide;
(1431): 1-(4-(8-methoxy-4-oxo-4,5-dihydrothieno[2,3-c]quinolin-9-yl)phenyl)ethanesulfonamide;
(1432): (R)—N-(2-(4-(8-methoxy-4-oxo-4,5-dihydrothieno[2,3-c]quinolin-9-yl)phenyl)propyl)methanesulfonamide;
(1433): (R)—N-(2-(4-(8-hydroxy-4-oxo-4,5-dihydrothieno[2,3-c]quinolin-9-yl)phenyl)propyl)-N-methylmethanesulfonamide;

(1434): (R)—N-(2-(4-(8-hydroxy-6-methyl-4-oxo-4,5-dihydrothieno[2,3-c]quinolin-9-yl)phenyl)propyl)methanesulfonamide;

(1435): (R)—N-(2-(4-(8-hydroxy-4-oxo-4,5-dihydrothieno[2,3-c]quinolin-9-yl)phenyl)propyl)methanesulfonamide;

(1436): (R)—N-(2-(4-(8-methoxy-4-oxo-4,5-dihydrothieno[2,3-c]quinolin-9-yl)phenyl)propyl)-N-methylmethanesulfonamide;

(1437): (R)—N-(2-(4-(8-hydroxy-6-methyl-4-oxo-4,5-dihydrothieno[2,3-c]quinolin-9-yl)phenyl)propyl)-N-methylmethanesulfonamide;

(1438): (R)—N-(2-(4-(8-methoxy-6-methyl-4-oxo-4,5-dihydrothieno[2,3-c]quinolin-9-yl)phenyl)propyl)-N-methylmethanesulfonamide;

or a pharmaceutically acceptable salt thereof.

21. A pharmaceutical composition comprising at least one compound of above 1 or 2 or a pharmaceutically acceptable salt thereof, and a pharmaceutically acceptable carrier.

22. The pharmaceutical composition of above 21 which is available for preventing or treating a PBK dependent disease.

23. The pharmaceutical composition of above 22, wherein the PBK dependent disease is cancer.

24. A PBK inhibitor comprising at least one compound of above 1 or 2, or a pharmaceutically acceptable salt thereof.

25. A method for treating a PBK dependent disease in a subject, comprising administering to said subject an effective amount of a compound or a pharmaceutically acceptable salt thereof of above 1 or 2.

26. A compound or pharmaceutically acceptable salt thereof of above 1 or 2 for use in treatment of a PBK dependent disease.

27. Use of a compound of above 1 or 2 or a pharmaceutically acceptable salt thereof in manufacturing a pharmaceutical composition for treating a PBK dependent disease.

Alternatively, the present invention also provides following embodiments:

101. The present invention provides a compound represented by formula (I) or a pharmaceutically acceptable salt thereof:

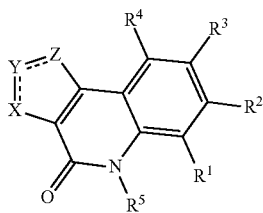

or a pharmaceutically acceptable salt thereof,
wherein $R^1$, $R^2$, $R^3$, and $R^4$ are each independently a group selected from the group consisting of:
hydrogen,
hydroxyl,
halogen,
cyano,
nitro,
amino,
$C_1$-$C_6$ alkyl,
$C_2$-$C_6$ alkenyl,
$C_2$-$C_6$ alkynyl,
$C_3$-$C_{10}$ cycloalkyl,
$C_3$-$C_{10}$ cycloalkenyl,
$C_1$-$C_6$ alkoxy,
$C_6$-$C_{10}$ aryl,
indanyl,
heteroaryl,
3- to 8-membered heterocycloalkyl,
—$OSO_2CH_3$,
—$OSO_2CF_3$, and
—$CONH_2$,
wherein each of the groups of $R^1$ to $R^4$ is optionally substituted with a substituent selected from the group consisting of substituent A below:
substituent A:
hydroxyl;
oxo (=O);
cyano;
halogen;
$C_1$-$C_6$ alkyl (wherein the $C_1$-$C_6$ alkyl is optionally substituted with a substituent selected from the group consisting of substituent B below);
$C_3$-$C_{10}$ cycloalkyl [wherein the $C_3$-$C_{10}$ cycloalkyl is optionally substituted with cyano, or $C_1$-$C_6$ alkyl substituted with —$NR^{31}R^{32}$ (wherein $R^{31}$ and $R^{32}$ each independently represent hydrogen or $C_1$-$C_6$ alkyl)];
—$NR^{21}R^{22}$ [wherein $R^{21}$ and $R^{22}$ each independently represent hydrogen, or $C_1$-$C_6$ alkyl (wherein the $C_1$-$C_6$ alkyl is optionally substituted with di($C_1$-$C_6$ alkyl)amino, $C_1$-$C_6$ alkylsulfonyl (—$SO_2$($C_1$-$C_6$ alkyl)), or 3- to 8-membered heterocycloalkyl)];
$C_1$-$C_6$ alkoxy {wherein the $C_1$-$C_6$ alkoxy is optionally substituted with halogen, 3- to 8-membered heterocycloalkyl (wherein the 3- to 8-membered heterocycloalkyl is optionally substituted with $C_1$-$C_6$ alkyl), or —$NR^{33}R^{34}$ [wherein $R^{33}$ and $R^{34}$ each independently represent hydrogen, $C_1$-$C_6$ alkyl (wherein the $C_1$-$C_6$ alkyl is optionally substituted with $C_1$-$C_6$ alkylsulfonyl or di($C_1$-$C_6$ alkyl)amino), or $C_1$-$C_6$ alkylsulfonyl]};
—$SO_2NR^{23}R^{24}$ {wherein $R^{23}$ and $R^{24}$ each independently represent hydrogen, $C_1$-$C_6$ alkyl [wherein the $C_1$-$C_6$ alkyl is optionally substituted with hydroxyl, $C_1$-$C_6$ alkoxy, halogen, $C_3$-$C_{10}$ cycloalkyl, or —$NR^{35}R^{36}$ (wherein $R^{35}$ and $R^{36}$ each independently represent hydrogen or $C_1$-$C_6$ alkyl)], $C_3$-$C_{10}$ cycloalkyl (wherein the $C_3$-$C_{10}$ cycloalkyl is optionally substituted with $C_1$-$C_6$ hydroxyalkyl), or 3- to 8-membered heterocycloalkyl; or $R^{23}$ and $R^{24}$ may together form 3- to 8-membered heterocycloalkyl wherein the 3- to 8-membered heterocycloalkyl is optionally substituted with amino};
$C_1$-$C_6$ alkylsulfonyl (wherein the $C_1$-$C_6$ alkyl moiety is optionally substituted with hydroxyl);
$C_1$-$C_6$ alkylsulfonylamino (—$NHSO_2$($C_1$-$C_6$ alkyl)) [wherein the $C_1$-$C_6$ alkyl moiety is optionally substituted with —$NR^{37}R^{38}$ (wherein $R^{37}$ and $R^{38}$ each independently represent hydrogen or $C_1$-$C_6$ alkyl)];
3- to 8-membered heterocycloalkyl {wherein the 3- to 8-membered heterocycloalkyl is optionally substituted with —$NR^{39}R^{40}$ (wherein $R^{39}$ and $R^{40}$ each independently represent hydrogen, $C_1$-$C_6$ alkyl, or $C_1$-$C_6$ alkylsulfonyl), $C_1$-$C_6$ alkyl [wherein the $C_1$-$C_6$ alkyl is optionally substituted with —$NR^{41}R^{42}$ (wherein $R^{41}$ and $R^{42}$ each independently represent hydrogen or $C_1$-$C_6$ alkyl)], hydroxyl, or $C_1$-$C_6$ alkylsulfonyl};
heteroaryl;
—$COOR^{11}$ (wherein $R^{11}$ represents hydrogen or $C_1$-$C_6$ alkyl); and —COR$^{12}$ [wherein R$^{12}$ represents C$_1$-C$_6$ alkyl, C$_3$-C$_{10}$ cycloalkyl, cyanomethyl, —NR$^{25}$R$^{26}$ {wherein R$^{25}$ and R$^{26}$ each independently represent hydrogen, or C$_1$-C$_6$ alkyl [wherein the C$_1$-C$_6$ alkyl is optionally substituted with hydroxyl or —NR$^{43}$R$^{44}$ (wherein R$^{43}$ and R$^{44}$ each independently represent hydrogen or C$_1$-C$_6$ alkyl)]}, or 3- to 8-membered heterocycloalkyl which is optionally substituted with C$_1$-C$_6$ alkyl], substituent B:
halogen;
hydroxyl;
cyano;
3- to 8-membered heterocycloalkyl (wherein the 3- to 8-membered heterocycloalkyl is optionally substituted with C$_1$-C$_6$ alkyl, hydroxyl, amino, C$_1$-C$_6$ aminoalkyl, or C$_1$-C$_6$ alkyl substituted with C$_2$-C$_7$ alkyloxycarbonylamino);
—NR$^{51}$R$^{52}$ (wherein R$^{51}$ and R$^{52}$ each independently represent hydrogen, C$_1$-C$_6$ alkyl [wherein the C$_1$-C$_6$ alkyl is optionally substituted with C$_1$-C$_6$ alkylsulfonyl, or 3- to 8-membered heterocycloalkyl optionally substituted with —COOR$^{13}$ (wherein R$^{53}$ represents hydrogen or C$_1$-C$_6$ alkyl)], 3- to 8-membered heterocycloalkyl, C$_1$-C$_6$ alkylsulfonyl, C$_3$-C$_{10}$ cycloalkyl, —COR$^{55}$ (wherein R$^{55}$ represents C$_1$-C$_6$ alkyl), —COOR$^{56}$ (wherein R$^{56}$ represents C$_1$-C$_6$ alkyl), or —CONR$^{57}$R$^{58}$ (wherein R$^{57}$ and R$^{58}$ each independently represent hydrogen or C$_1$-C$_6$ alkyl)); and
—COOR$^{54}$ (wherein R$^{54}$ represents hydrogen or C$_1$-C$_6$ alkyl)];
wherein R$^5$ is hydrogen or C$_1$-C$_6$ alkyl; and
wherein

—X═Y═Z— is a structure selected from the group consisting of
(i) —S—CR$^7$═CR$^6$—,
(ii) —CH$_2$—CH$_2$—CH$_2$—,
(iii) —NH—CH═CCH$_3$—, and
(iv) —═CH—S—,
wherein R$^6$ is
hydrogen,
hydroxyl,
C$_1$-C$_6$ alkyl,
C$_6$-C$_{10}$ aryl (wherein the C$_6$-C$_{10}$ aryl is optionally substituted with hydroxyl), or
3- to 8-membered heterocycloalkyl [wherein the 3- to 8-membered heterocycloalkyl is optionally substituted with —NR$^{61}$R$^{62}$ (wherein R$^{61}$ and R$^{62}$ each independently represent hydrogen or C$_1$-C$_6$ alkyl)], and
wherein R$^7$ is
hydrogen,
C$_1$-C$_6$ alkyl (wherein the C$_1$-C$_6$ alkyl is optionally substituted with hydroxyl, —NR$^{71}$R$^{72}$ [wherein R$^{71}$ and R$^{72}$ each independently represent hydrogen, C$_1$-C$_6$ alkyl (wherein the C$_1$-C$_6$ alkyl is optionally substituted with dimethylamino), C$_3$-C$_{10}$ cycloalkyl (wherein the C$_3$-C$_{10}$ cycloalkyl is optionally substituted with amino), or 3- to 8-membered heterocycloalkyl], or 3- to 8-membered heterocycloalkyl (wherein the 3- to 8-membered heterocycloalkyl is optionally substituted with C$_1$-C$_6$ aminoalkyl)),
C$_6$-C$_{10}$ aryl (wherein the C$_6$-C$_{10}$ aryl is optionally substituted with hydroxyl), or
—COR$^{73}$ {wherein R$^{73}$ represents 3- to 8-membered heterocycloalkyl (wherein the 3- to 8-membered heterocycloalkyl is optionally substituted with amino), or —NR$^{74}$R$^{75}$ [wherein R$^{74}$ and R$^{75}$ each independently represent hydrogen, 3- to 8-membered heterocycloalkyl, or C$_3$-C$_{10}$ cycloalkyl (wherein the C$_3$-C$_{10}$ cycloalkyl is optionally substituted with amino)]}.

102. The compound of above 101, or a pharmaceutically acceptable salt thereof, wherein

—X═Y═Z— is —S—CR$^7$═CR$^6$—.
Specifically, the compound of above 1 which have a following formula II, or a pharmaceutically acceptable salt thereof;

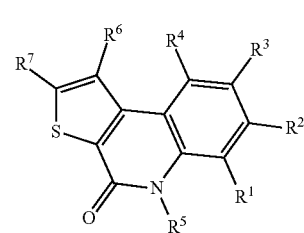

II

103. The compound of above 102, or a pharmaceutically acceptable salt thereof, wherein R$^1$ is hydrogen or halogen.
104. The compound of above 102 or 103, or a pharmaceutically acceptable salt thereof, wherein R$^2$ is hydrogen, hydroxyl, halogen, C$_1$-C$_6$ alkoxy, or C$_6$-C$_{10}$ aryl which is optionally substituted with hydroxyl.
105. The compound of any one of above 102-104 or a pharmaceutically acceptable salt, wherein R$^2$ is hydrogen, hydroxyl, halogen, C$_1$-C$_6$ alkoxy, or dihydroxyphenyl.
106. The compound of any one of above 102-105, or a pharmaceutically acceptable salt thereof, wherein R$^3$ is hydrogen; hydroxyl; halogen; C$_1$-C$_6$ alkoxy; cyano; nitro; 3- to 8-membered heterocycloalkyl which is optionally substituted with amino; heteroaryl; —OSO$_2$CH$_3$; —OSO$_2$CF$_3$; or —CONH$_2$.
107. The compound of any one of above 102-106, or a pharmaceutically acceptable salt thereof, wherein R$^3$ is hydrogen; hydroxyl; halogen; C$_1$-C$_6$ alkoxy; cyano; nitro; 3- to 8-membered heterocycloalkyl which is optionally substituted with amino (wherein the 3- to 8-membered heterocycloalkyl is piperidyl, pyrrolidinyl, morpholinyl, or piperazinyl); pyridyl; —OSO$_2$CH$_3$; —OSO$_2$CF$_3$; or —CONH$_2$.
108. The compound of any one of above 102-107, or a pharmaceutically acceptable salt thereof, wherein R$^4$ is a group selected from the group consisting of hydrogen, hydroxyl, halogen, amino, C$_1$-C$_6$ alkyl, C$_2$-C$_6$ alkenyl, C$_3$-C$_{10}$ cycloalkyl, C$_3$-C$_{10}$ cycloalkenyl, C$_1$-C$_6$ alkoxy, C$_6$-C$_{10}$ aryl, indanyl, heteroaryl, and 3- to 8-membered heterocycloalkyl, wherein each of the groups of R$^4$ is optionally substituted with a substituent selected from the group consisting of substituent A above.
109. The compound of any one of above 102-108, or a pharmaceutically acceptable salt thereof, wherein R$^4$ is a group selected from the group consisting of hydrogen, hydroxyl, halogen, amino, $C_1$-$C_6$ alkyl, $C_2$-$C_6$ alkenyl, $C_3$-$C_{10}$ cycloalkyl, $C_3$-$C_{10}$ cycloalkenyl, $C_1$-$C_6$ alkoxy, $C_6$-$C_{10}$ aryl, indanyl, heteroaryl (wherein the heteroaryl is selected from the group consisting of pyridyl, 1H-indazolyl, 1H-tetrazolyl, [1,2,4]triazolo[1,5-a]pyridyl, benzoimidazolyl, 2,3-dihydrobenzooxazolyl, pyrazolyl, pyrrolo[2,3-b]pyridyl, pyrimidinyl, indolinyl, furyl, thienyl, and tetrahydroisoquinolyl), and 3- to 8-membered heterocycloalkyl (wherein the 3- to 8-membered heterocycloalkyl is selected from the group consisting of aziridinyl, azetidinyl, pyrrolidinyl, imidazolidinyl, piperidyl, piperazinyl, azepanyl, morpholinyl, and 1,2,3,6-tetrahydropyridyl), wherein each of the groups of $R^4$ is optionally substituted with a substituent selected from the group consisting of substituent A-1 below:

substituent A-1:

hydroxyl;

oxo;

cyano;

halogen;

$C_1$-$C_6$ alkyl (wherein the $C_1$-$C_6$ alkyl is optionally substituted with a substituent selected from the group consisting of substituent B-1 below);

$C_3$-$C_{10}$ cycloalkyl [wherein the $C_3$-$C_{10}$ cycloalkyl is optionally substituted with cyano, or $C_1$-$C_6$ alkyl substituted with —$NR^{31}R^{32}$ (wherein $R^{31}$ and $R^{32}$ each independently represent hydrogen or $C_1$-$C_6$ alkyl)];

—$NR^{21A}R^{22A}$ [wherein $R^{21A}$ and $R^{22A}$ each independently represent hydrogen or $C_1$-$C_6$ alkyl (wherein $C_1$-$C_6$ alkyl is optionally substituted with di($C_1$-$C_6$ alkyl)amino, $C_1$-$C_6$ alkylsulfonyl (—$SO_2$ ($C_1$-$C_6$ alkyl)), or piperidyl)];

$C_1$-$C_6$ alkoxy {wherein the $C_1$-$C_6$ alkoxy is optionally substituted with 3- to 8-membered heterocycloalkyl selected from halogen, piperidyl, and piperazinyl (wherein the 3- to 8-membered heterocycloalkyl is optionally substituted with $C_1$-$C_6$ alkyl), or —$NR^{33}R^{34}$ [wherein $R^{33}$ and $R^{34}$ each independently represent hydrogen, $C_1$-$C_6$ alkyl (wherein the $C_1$-$C_6$ alkyl is optionally substituted with $C_1$-$C_6$ alkylsulfonyl or di($C_1$-$C_6$ alkyl)amino), or $C_1$-$C_6$ alkylsulfonyl]};

—$SO_2NR^{23A}R^{24A}$ {wherein $R^{23A}$ and $R^{24A}$ each independently represent hydrogen, $C_1$-$C_6$ alkyl [wherein the $C_1$-$C_6$ alkyl is optionally substituted with hydroxyl, $C_1$-$C_6$ alkoxy, halogen, $C_3$-$C_{10}$ cycloalkyl, or —$NR^{35}R^{36}$ (wherein $R^{35}$ and $R^{36}$ each independently represent hydrogen or $C_1$-$C_6$ alkyl)], $C_3$-$C_{10}$ cycloalkyl (wherein the $C_3$-$C_{10}$ cycloalkyl is optionally substituted with $C_1$-$C_6$ hydroxyalkyl), azetidinyl, or pyrrolidinyl, or may together form pyrrolidinyl, wherein the pyrrolidinyl is optionally substituted with amino};

$C_1$-$C_6$ alkylsulfonyl (wherein the $C_1$-$C_6$ alkyl moiety is optionally substituted with hydroxyl);

$C_1$-$C_6$ alkylsulfonylamino (—$NHSO_2$ ($C_1$-$C_6$ alkyl)) [wherein the $C_1$-$C_6$ alkyl moiety is optionally substituted with —$NR^{37}R^{38}$ (wherein $R^{37}$ and $R^{38}$ each independently represent hydrogen or $C_1$-$C_6$ alkyl)];

3- to 8-membered heterocycloalkyl selected from the group consisting of azetidinyl, pyrrolidinyl, piperidyl, and piperazinyl (wherein the 3- to 8-membered heterocycloalkyl is optionally substituted with —$NR^{39}R^{40}$ (wherein $R^{39}$ and $R^{40}$ each independently represent hydrogen, $C_1$-$C_6$ alkyl, or $C_1$-$C_6$ alkylsulfonyl), $C_1$-$C_6$ alkyl [wherein the $C_1$-$C_6$ alkyl is optionally substituted with —$NR^{41}R^{42}$ (wherein $R^{41}$ and $R^{42}$ each independently represent hydrogen or $C_1$-$C_6$ alkyl)], hydroxyl, or $C_1$-$C_6$ alkylsulfonyl);

1H-tetrazolyl;

—$COOR^{11}$ (wherein $R^{11}$ represents hydrogen or $C_1$-$C_6$ alkyl); and

—$COR^{12A}$ [wherein $R^{12A}$ represents piperazinyl which is optionally substituted with $C_1$-$C_6$ alkyl, $C_3$-$C_{10}$ cycloalkyl, cyanomethyl, —$NR^{25}R^{26}$ {wherein $R^{25}$ and $R^{26}$ each independently represent hydrogen or $C_1$-$C_6$ alkyl [wherein the $C_1$-$C_6$ alkyl is optionally substituted with hydroxyl or —$NR^{43}R^{44}$ (wherein $R^{43}$ and $R^{44}$ each independently represent hydrogen or $C_1$-$C_6$ alkyl)]}), or $C_1$-$C_6$ alkyl];

substituent B-1:

halogen;

hydroxyl;

50 cyano;

3- to 8-membered heterocycloalkyl selected from the group consisting of pyrrolidinyl, piperidyl, piperazinyl, and morpholinyl (wherein the 3- to 8-membered heterocycloalkyl is optionally substituted with $C_1$-$C_6$ alkyl, hydroxyl, amino, $C_1$-$C_6$ aminoalkyl, or $C_1$-$C_6$ alkyl substituted with $C_2$-$C_7$ alkyloxycarbonylamino);

—$NR^{51A}R^{52A}$ {wherein $R^{51A}$ and $R^{52A}$ each independently represent hydrogen, $C_1$-$C_6$ alkyl [wherein the $C_1$-$C_6$ alkyl is optionally substituted with $C_1$-$C_6$ alkylsulfonyl, or piperidyl which is optionally substituted with, —$COOR^{13}$ (wherein $R^{53}$ represents hydrogen or $C_1$-$C_6$ alkyl)], piperidyl, $C_1$-$C_6$ alkylsulfonyl, $C_3$-$C_{10}$ cycloalkyl, —$COR^{55}$ (wherein $R^{55}$ represents $C_1$-$C_6$ alkyl), —$COOR^{56}$ (wherein $R^{56}$ represents $C_1$-$C_6$ alkyl), or —$CONR^{57}R^{58}$ (wherein $R^{57}$ and $R^{58}$ each independently represent hydrogen or $C_1$-$C_6$ alkyl)}; and —$COOR^{54}$ (wherein $R^{54}$ represents hydrogen or $C_1$-$C_6$ alkyl).

1010. The compound of any one of above 102-109, or a pharmaceutically acceptable salt thereof, wherein $R^4$ is a group selected from the group consisting of (p) below:

(p):

hydrogen, hydroxyl, halogen, amino, $C_1$-$C_6$ alkyl which is optionally substituted with a substituent selected from the group consisting of substituent (a) below, $C_2$-$C_6$ alkenyl which is optionally substituted with a substituent selected from the group consisting of substituent (b) below, $C_3$-$C_{10}$ cycloalkyl, $C_3$-$C_{10}$ cycloalkenyl, $C_1$-$C_6$ alkoxy, $C_6$-$C_{10}$ aryl which is optionally substituted with a substituent selected from the group consisting of substituent (c) below, indanyl which is optionally substituted with a substituent selected from the group consisting of substituent (d) below, heteroaryl which is optionally substituted with a substituent selected from the group consisting of substituent (e) below, and 3- to 8-membered heterocycloalkyl which is optionally substituted with a substituent selected from the group consisting of substituent (f) below, wherein, in the group (p), the heteroaryl is selected from the group consisting of pyridyl, 1H-indazolyl, 1H-tetrazolyl, [1,2,4]triazolo[1,5-a]pyridyl, benzoimidazolyl, 2,3-dihydrobenzooxazolyl, pyrazolyl, pyrrolo[2,3-b]pyridyl, pyrimidinyl, indolinyl, furyl, thienyl, and tetrahydroisoquinolyl;

the 3- to 8-membered heterocycloalkyl is selected from the group consisting of pyrrolidinyl, piperidyl, piperazinyl, morpholinyl, and 1,2,3,6-tetrahydropyridyl;

substituent (a):
- 3- to 8-membered heterocycloalkyl selected from the group consisting of pyrrolidinyl and piperidyl {wherein the 3- to 8-membered heterocycloalkyl is optionally substituted with —$NR^{39}R^{40}$ (wherein $R^{39}$ and $R^{40}$ each independently represent hydrogen or $C_1$-$C_6$ alkyl), or $C_1$-$C_6$ alkyl [wherein the $C_1$-$C_6$ alkyl is optionally substituted with —$NR^{41}R^{42}$ (wherein $R^{41}$ and $R^{42}$ each independently represent hydrogen or $C_1$-$C_6$ alkyl)]}; and
- $C_1$-$C_6$ alkylsulfonylamino (—$NHSO_2(C_1$-$C_6$ alkyl));

substituent (b):
- —$COOR^{11}$ (wherein $R^{11}$ represents hydrogen or $C_1$-$C_6$ alkyl);
- —$NR^{21a}R^{22a}$ [wherein $R^{21a}$ and $R^{22a}$ each independently represent hydrogen, or $C_1$-$C_6$ alkyl (wherein the $C_1$-$C_6$ alkyl is optionally substituted with di($C_1$-$C_6$ alkyl)amino or $C_1$-$C_6$ alkylsulfonyl)];
- 3- to 8-membered heterocycloalkyl selected from the group consisting of azetidinyl, pyrrolidinyl, and piperidyl (wherein the 3- to 8-membered heterocycloalkyl is optionally substituted with —$NR^{39}R^{40}$ {wherein $R^{39}$ and $R^{40}$ each independently represent hydrogen, $C_1$-$C_6$ alkyl, or $C_1$-$C_6$ alkylsulfonyl), $C_1$-$C_6$ alkyl [wherein the $C_1$-$C_6$ alkyl is optionally substituted with —$NR^{41}R^{42}$ (wherein $R^{41}$ and $R^{42}$ each independently represent hydrogen or $C_1$-$C_6$ alkyl)], hydroxyl, or $C_1$-$C_6$ alkylsulfonyl};
- cyano; and
- $C_1$-$C_6$ alkoxy;

substituent (c):
- hydroxyl;
- cyano;
- halogen;
- $C_1$-$C_6$ alkyl (wherein the $C_1$-$C_6$ alkyl is optionally substituted with a substituent selected from the group consisting of substituent B-c below);
- $C_3$-$C_{10}$ cycloalkyl [wherein the $C_3$-$C_{10}$ cycloalkyl is optionally substituted with cyano, or $C_1$-$C_6$ alkyl substituted with —$NR^{31}R^{32}$ (wherein $R^{31}$ and $R^{32}$ each independently represent hydrogen or $C_1$-$C_6$ alkyl)];
- —$NR^{21c}R^{22c}$ [wherein $R^{21c}$ and $R^{22c}$ each independently represent hydrogen or $C_1$-$C_6$ alkyl];
- $C_1$-$C_6$ alkoxy {wherein the $C_1$-$C_6$ alkoxy is optionally substituted with 3- to 8-membered heterocycloalkyl selected from halogen, piperidyl, and piperazinyl (wherein the 3- to 8-membered heterocycloalkyl is optionally substituted with $C_1$-$C_6$ alkyl), or —$NR^{33}R^{34}$ [wherein $R^{33}$ and $R^{34}$ each independently represent hydrogen, $C_1$-$C_6$ alkyl (wherein the $C_1$-$C_6$ alkyl is optionally substituted with di($C_1$-$C_6$ alkyl)amino), or $C_1$-$C_6$ alkylsulfonyl]};
- —$SO_2NR^{23c}R^{24c}$ {wherein $R^{23c}$ and $R^{24c}$ each independently represent hydrogen, $C_1$-$C_6$ alkyl [wherein the $C_1$-$C_6$ alkyl is optionally substituted with hydroxyl, $C_1$-$C_6$ alkoxy, halogen, $C_3$-$C_{10}$ cycloalkyl, or —$NR^{35}R^{36}$ (wherein $R^{35}$ and $R^{36}$ each independently represent hydrogen or $C_1$-$C_6$ alkyl)], $C_3$-$C_{10}$ cycloalkyl (wherein the $C_3$-$C_{10}$ cycloalkyl is optionally substituted with $C_1$-$C_6$ hydroxyalkyl), azetidinyl, or pyrrolidinyl, or wherein $R^{23c}$ and $R^{24c}$ may together form pyrrolidinyl which is optionally substituted with amino};
- $C_1$-$C_6$ alkylsulfonyl (wherein the $C_1$-$C_6$ alkyl moiety is optionally substituted with hydroxyl);
- $C_1$-$C_6$ alkylsulfonylamino (—$NHSO_2(C_1$-$C_6$ alkyl)) [wherein the $C_1$-$C_6$ alkyl moiety is optionally substituted with —$NR^{37}R^{38}$ (wherein $R^{37}$ and $R^{38}$ each independently represent hydrogen or $C_1$-$C_6$ alkyl)];
- piperazinyl {wherein the piperazinyl is optionally substituted with $C_1$-$C_6$ alkyl or $C_1$-$C_6$ alkylsulfonyl};
- 1H-tetrazolyl; and
- —$COR^{12c}$ [wherein $R^{12c}$ represents piperazinyl which is optionally substituted with $C_1$-$C_6$ alkyl, $C_3$-$C_{10}$ cycloalkyl, cyanomethyl, —$NR^{25}R^{26}$ {wherein $R^{25}$ and $R^{26}$ each independently represent hydrogen or $C_1$-$C_6$ alkyl [wherein the $C_1$-$C_6$ alkyl is optionally substituted with hydroxyl, or —$NR^{43}R^{44}$ (wherein $R^{43}$ and $R^{44}$ each independently represent hydrogen or $C_1$-$C_6$ alkyl)]}), or $C_1$-$C_6$ alkyl]; and substituent B-c:
- halogen;
- hydroxyl;
- cyano;
- 3- to 8-membered heterocycloalkyl selected from the group consisting of pyrrolidinyl, piperidyl, piperazinyl, and morpholinyl (wherein the 3- to 8-membered heterocycloalkyl is optionally substituted with $C_1$-$C_6$ alkyl, hydroxyl, amino, $C_1$-$C_6$ aminoalkyl, or $C_1$-$C_6$ alkyl substituted with $C_2$-$C_7$ alkyloxycarbonylamino); and
- —$NR^{51c}R^{52c}$ {wherein $R^{51c}$ and $R^{52c}$ each independently represent hydrogen, $C_1$-$C_6$ alkyl [wherein the $C_1$-$C_6$ alkyl is optionally substituted with $C_1$-$C_6$ alkylsulfonyl, or piperidyl which is optionally substituted with —$COOR^{53}$ (wherein $R^{53}$ represents hydrogen or $C_1$-$C_6$ alkyl)], piperidyl, $C_1$-$C_6$alkylsulfonyl, $C_3$-$C_{10}$cycloalkyl, —$COR^{55}$ (wherein $R^{55}$ represents $C_1$-$C_6$ alkyl), or —$CONR^{57}R^{58}$ (wherein $R^{57}$ and $R^{58}$ each independently represent hydrogen or $C_1$-$C_6$ alkyl)}];

substituent (d):
- —$NR^{21d}R^{22d}$ (wherein $R^{21d}$ and $R^{22d}$ each independently represent hydrogen or $C_1$-$C_6$ alkyl);

substituent (e):
- hydroxyl;
- oxo;
- cyano;
- —$NR^{21}R^{22}$ [wherein $R^{21}$ and $R^{22}$ each independently represent hydrogen or $C_1$-$C_6$ alkyl];
- piperidyl;
- $C_1$-$C_6$ alkoxy; and
- $C_1$-$C_6$ alkyl {wherein the $C_1$-$C_6$ alkyl is optionally substituted with —$NR^{51e}R^{52e}$ [wherein $R^{51e}$ and $R^{52e}$ each independently represent hydrogen or —$COOR^{56}$ (wherein $R^{56}$ represents $C_1$-$C_6$ alkyl)]}); and substituent (f):
- $C_1$-$C_6$ alkyl {wherein the $C_1$-$C_6$ alkyl is optionally substituted with —$NR^{51f}R^{52f}$ [wherein $R^{51f}$ and $R^{52f}$ each independently represent hydrogen, $C_1$-$C_6$ alkyl, or —COOR$^{56}$ (wherein R$^{56}$ represents $C_1$-$C_6$ alkyl)]}; and
$C_1$-$C_6$ alkylsulfonyl.
111. The compound of any one of above 102-110, or a pharmaceutically acceptable salt thereof, wherein R$^6$ is hydrogen; hydroxyl; $C_1$-$C_6$ alkyl; phenyl which is optionally substituted with 1 to 3 hydroxyls; piperidyl which is optionally substituted with amino; or piperazinyl.
112. The compound of above 111, or a pharmaceutically acceptable salt thereof, wherein R$^7$ is hydrogen.
113. The compound of any one of above 102-111, or a pharmaceutically acceptable salt thereof, wherein R$^7$ is hydrogen;
$C_1$-$C_6$ alkyl (wherein the $C_1$-$C_6$ alkyl is optionally substituted with hydroxyl, —NR$^{71A}$R$^{72A}$ [wherein R$^{71A}$ and R$^{72A}$ each independently represent hydrogen, $C_1$-$C_6$ alkyl (wherein the $C_1$-$C_6$ alkyl is optionally substituted with dimethylamino), $C_3$-$C_{10}$ cycloalkyl (wherein the $C_3$-$C_{10}$ cycloalkyl is optionally substituted with amino), or piperidyl], or 3- to 8-membered heterocycloalkyl selected from the group consisting of piperidyl and morpholinyl (wherein the 3- to 8-membered heterocycloalkyl is optionally substituted with $C_1$-$C_6$ aminoalkyl));
phenyl which is optionally substituted with 1 to 2 hydroxyls; or
—COR$^{73A}$ {wherein R$^{73A}$ represents piperidyl (wherein the piperidyl is optionally substituted with amino), or —NR$^{74A}$R$^{75A}$ [wherein R$^{74A}$ and R$^{75A}$ each independently represent hydrogen, piperidyl, or $C_3$-$C_{10}$ cycloalkyl (wherein the $C_3$-$C_{10}$ cycloalkyl is optionally substituted with amino)]}.
114. The compound of above 101, or a pharmaceutically acceptable salt thereof, wherein

—X═Y═Z— is —CH$_2$—CH$_2$—CH$_2$—.
Specifically, the compound of above 1 which have a following formula III, or a pharmaceutically acceptable salt thereof:

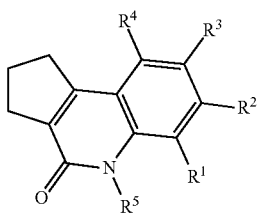

III

115. The compound of above 114, or a pharmaceutically acceptable salt thereof, wherein R$^1$, R$^2$ and R$^5$ are hydrogen.
116. The compound of above 114 or 115, or a pharmaceutically acceptable salt thereof, wherein R$^3$ is hydroxyl or methoxy.
117. The compound of any one of above 114-116, or a pharmaceutically acceptable salt thereof, wherein R$^4$ is hydrogen, phenyl [wherein the phenyl is substituted with $C_1$-$C_6$ alkyl substituted with —NR$^{51A}$R$^{52A}$ (wherein R$^{51A}$ and R$^{52A}$ each independently represent hydrogen or $C_1$-$C_6$ alkyl), or —SO$_2$NH$_2$], 1,2,3,6-tetrahydropyridyl, hydroxypyridyl, or methoxypyridyl.
118. The compound of above 101, or a pharmaceutically acceptable salt thereof, wherein

—X═Y═Z— is —NH—CH═CCH$_3$—,
R$^1$, R$^2$, R$^4$ and R$^5$ are hydrogen, and
R$^3$ is hydroxyl.
119. The compound of above 101, or a pharmaceutically acceptable salt thereof, wherein

—X═Y═Z— is —N═CH—S—,
R$^1$, R$^2$, R$^4$ and R$^5$ are hydrogen, and
R$^3$ is methoxy.
120. A compound selected from the group consisting of:
(1): 8-methoxy-5-methylthieno[2,3-c]quinolin-4(5H)-one;
(2): 8-hydroxy-5-methylthieno[2,3-c]quinolin-4(5H)-one;
(3): 7,8-dihydroxythieno[2,3-c]quinolin-4(5H)-one;
(4): 7,8-dimethoxythieno[2,3-c]quinolin-4(5H)-one;
(5): 8-methoxythieno[2,3-c]quinolin-4(5H)-one;
(6): 7,9-dimethoxythieno[2,3-c]quinolin-4(5H)-one;
(7): 7,9-dihydroxythieno[2,3-c]quinolin-4(5H)-one;
(8): 7,8,9-trimethoxythieno[2,3-c]quinolin-4(5H)-one;
(9): 8-hydroxythieno[2,3-c]quinolin-4(5H)-one;
(10): 7,8,9-trihydroxythieno[2,3-c]quinolin-4(5H)-one;
(11): 9-(3-(2-aminoethyl)phenyl)-8-methoxythieno[2,3-c]quinolin-4(5H)-one;
(12): 8-chlorothieno[2,3-c]quinolin-4(5H)-one;
(13): 4-oxo-4,5-dihydrothieno[2,3-c]quinoline-8-carbonitrile;
(14): thieno[2,3-c]quinolin-4(5H)-one;
(15): 8-fluorothieno[2,3-c]quinolin-4(5H)-one;
(16): 8-nitrothieno[2,3-c]quinolin-4(5H)-one;
(17): 8-(3-aminopiperidin-1-yl)thieno[2,3-c]quinolin-4(5H)-one;
(18): 1-(4-hydroxyphenyl)thieno[2,3-c]quinolin-4(5H)-one;
(19): 1,8-dihydroxythieno[2,3-c]quinolin-4(5H)-one;
(20): 8-hydroxy-1-(4-hydroxyphenyl)thieno[2,3-c]quinolin-4(5H)-one;
(21): (R)-8-(3-aminopyrrolidin-1-yl)thieno[2,3-c]quinolin-4(5H)-one;
(22): (S)-8-(3-aminopyrrolidin-1-yl)thieno[2,3-c]quinolin-4(5H)-one;
(23): 8-(pyridin-3-yl)thieno[2,3-c]quinolin-4(5H)-one;
(24): 8-(4-hydroxyphenyl)thieno[2,3-c]quinolin-4(5H)-one;
(25): 1-(3,4-dihydroxyphenyl)-8-hydroxythieno[2,3-c]quinolin-4(5H)-one;
(26): 1-(3-aminopiperidin-1-yl)-8-hydroxythieno[2,3-c]quinolin-4(5H)-one;
(27): 8-morpholinothieno[2,3-c]quinolin-4(5H)-one;
(28): 8-hydroxy-2-methylthieno[2,3-c]quinolin-4(5H)-one;
(29): 8-hydroxy-2-(hydroxymethyl)thieno[2,3-c]quinolin-4(5H)-one;
(30): 8-hydroxy-4-oxo-N-(piperidin-3-yl)-4,5-dihydrothieno[2,3-c]quinoline-2-carboxamide;
(31): 8-hydroxy-2-(4-hydroxyphenyl)thieno[2,3-c]quinolin-4(5H)-one;
(32): 8-hydroxy-1-(piperazin-1-yl)thieno[2,3-c]quinolin-4(5H)-one;

(33): N-((1r,4r)-4-aminocyclohexyl)-8-hydroxy-4-oxo-4,5-dihydrothieno[2,3-c]quinolin-2-carboxamide;
(34): 2-(3-aminopiperidine-1-carbonyl)-8-hydroxythieno[2,3-c]quinolin-4(5H)-one;
(35): 2-(3,4-dihydroxyphenyl)-8-hydroxythieno[2,3-c]quinolin-4(5H)-one;
(36): 2-(((1r,4r)-4-aminocyclohexylamino)methyl)-8-hydroxythieno[2,3-c]quinolin-4(5H)-one;
(37): 8-(piperazin-1-yl)thieno[2,3-c]quinolin-4(5H)-one;
(38): 8-hydroxy-1-methylthieno[2,3-c]quinolin-4(5H)-one;
(39): 2-((2-(dimethylamino)ethylamino)methyl)-8-hydroxythieno[2,3-c]quinolin-4(5H)-one;
(40): 8-hydroxy-2-((piperidin-3-ylamino)methyl)thieno[2,3-c]quinolin-4(5H)-one;
(41): 7-hydroxythieno[2,3-c]quinolin-4(5H)-one;
(42): 9-bromo-8-hydroxythieno[2,3-c]quinolin-4(5H)-one;
(43): 9-(3,4-dihydroxyphenyl)-8-hydroxythieno[2,3-c]quinolin-4(5H)-one;
(44): 1-methyl-4-oxo-4,5-dihydrothieno[2,3-c]quinoline-8-carbonitrile;
(45): 7-(3,4-dihydroxyphenyl)-8-hydroxythieno[2,3-c]quinolin-4(5H)-one;
(46): 8-hydroxy-1-methyl-3H-pyrrolo[2,3-c]quinolin-4(5H)-one;
(47): 9-(3,5-dihydroxyphenyl)-8-hydroxythieno[2,3-c]quinolin-4(5H)-one;
(48): 8-hydroxy-9-(3-hydroxyphenyl)thieno[2,3-c]quinolin-4(5H)-one;
(49): 8-hydroxy-9-(4-hydroxyphenyl)thieno[2,3-c]quinolin-4(5H)-one;
(50): 9-(3,4-difluorophenyl)-8-methoxythieno[2,3-c]quinolin-4(5H)-one;
(51): (S)-8-(3-aminopyrrolidin-1-yl)-2-(4-hydroxyphenyl)thieno[2,3-c]quinolin-4(5H)-one;
(52): 5-(8-methoxy-4-oxo-4,5-dihydrothieno[2,3-c]quinolin-9-yl)picolinonitrile;
(53): 9-(6-aminopyridin-3-yl)-8-hydroxythieno[2,3-c]quinolin-4(5H)-one;
(54): 4-(8-hydroxy-4-oxo-4,5-dihydrothieno[2,3-c]quinolin-9-yl)benzamide;
(55): 9-(3-fluoro-4-hydroxyphenyl)-8-hydroxythieno[2,3-c]quinolin-4(5H)-one;
(56): 8-hydroxy-2-(3-hydroxyphenyl)thieno[2,3-c]quinolin-4(5H)-one;
(57): (R)-8-(3-aminopyrrolidin-1-yl)-2-(3,4-dihydroxyphenyl)thieno[2,3-c]quinolin-4(5H)-one;
(58): 9-(3,4-difluorophenyl)-8-hydroxythieno[2,3-c]quinolin-4(5H)-one;
(59): 9-(4-fluoro-3-hydroxyphenyl)-8-hydroxythieno[2,3-c]quinolin-4(5H)-one;
(60): 8-hydroxy-9-(3-hydroxy-5-(trifluoromethyl)phenyl)thieno[2,3-c]quinolin-4(5H)-one;
(61): 8-hydroxy-9-(1H-indazol-6-yl)thieno[2,3-c]quinolin-4(5H)-one;
(62): 8-hydroxy-9-(3,4,5-trihydroxyphenyl)thieno[2,3-c]quinolin-4(5H)-one;
(63): 9-(4-hydroxyphenyl)-8-methoxythieno[2,3-c]quinolin-4(5H)-one;
(64): 9-(4-(1H-tetrazol-5-yl)phenyl)-8-hydroxythieno[2,3-c]quinolin-4(5H)-one;
(65): 4-(8-hydroxy-4-oxo-4,5-dihydrothieno[2,3-c]quinolin-9-yl)benzenesulfonamide;
(66): 9-(3-chloro-4-fluorophenyl)-8-hydroxythieno[2,3-c]quinolin-4(5H)-one;
(67): 9-(4-chloro-3-fluorophenyl)-8-hydroxythieno[2,3-c]quinolin-4(5H)-one;
(68): 9-(3,4-dichlorophenyl)-8-hydroxythieno[2,3-c]quinolin-4(5H)-one;
(69): 9-(4-fluorophenyl)-8-hydroxythieno[2,3-c]quinolin-4(5H)-one;
(70): 8-hydroxy-9-phenylthieno[2,3-c]quinolin-4(5H)-one;
(71): 9-(4-(difluoromethoxy)phenyl)-8-methoxythieno[2,3-c]quinolin-4(5H)-one;
(72): 9-(4-(aminomethyl)phenyl)-8-hydroxythieno[2,3-c]quinolin-4(5H)-one;
(73): 9-(4-(aminomethyl)phenyl)-8-hydroxythieno[2,3-c]quinolin-4(5H)-one;
(74): 9-(3-aminophenyl)-8-hydroxythieno[2,3-c]quinolin-4(5H)-one;
(75): 3-(8-hydroxy-4-oxo-4,5-dihydrothieno[2,3-c]quinolin-9-yl)benzenesulfonamide;
(76): 8-hydroxy-9-(3,4,5-trifluorophenyl)thieno[2,3-c]quinolin-4(5H)-one;
(77): N-(4-(8-hydroxy-4-oxo-4,5-dihydrothieno[2,3-c]quinolin-9-yl)phenyl)methanesulfonamide;
(78): 8-methoxy-9-phenylthieno[2,3-c]quinolin-4(5H)-one;
(79): 8-hydroxy-9-(naphthalen-2-yl)thieno[2,3-c]quinolin-4(5H)-one;
(80): 8-hydroxy-9-(4-(hydroxymethyl)phenyl)thieno[2,3-c]quinolin-4(5H)-one;
(81): 2-(4-(8-hydroxy-4-oxo-4,5-dihydrothieno[2,3-c]quinolin-9-yl)phenyl)acetonitrile;
(82): 8-hydroxy-9-(4-(methylsulfonyl)phenyl)thieno[2,3-c]quinolin-4(5H)-one;
(83): 8-hydroxy-9-(pyridin-4-yl)thieno[2,3-c]quinolin-4(5H)-one;
(84): 8-hydroxy-9-(1,2,3,6-tetrahydropyridin-4-yl)thieno[2,3-c]quinolin-4(5H)-one;
(85): 8-hydroxy-9-(4-hydroxy-3-methoxyphenyl)thieno[2,3-c]quinolin-4(5H)-one;
(86): 9-(3-fluoro-4-(morpholinomethyl)phenyl)-8-hydroxythieno[2,3-c]quinolin-4(5H)-one;
(87): 9-(3-(aminomethyl)phenyl)-8-hydroxythieno[2,3-c]quinolin-4(5H)-one;
(88): 9-(4-(aminomethyl)phenyl)-8-methoxythieno[2,3-c]quinolin-4(5H)-one;
(89): 9-(3-(difluoromethyl)phenyl)-8-methoxythieno[2,3-c]quinolin-4(5H)-one;
(90): 9-(3-(aminomethyl)phenyl)-8-hydroxy-2-methylthieno[2,3-c]quinolin-4(5H)-one;
(91): 9-cyclohexenyl-8-methoxythieno[2,3-c]quinolin-4(5H)-one;
(92): 9-(3,5-difluorophenyl)-8-hydroxythieno[2,3-c]quinolin-4(5H)-one;
(93): 9-(4-(2-(dimethylamino)ethyl)phenyl)-8-hydroxythieno[2,3-c]quinolin-4(5H)-one;
(94): 9-(3-(aminomethyl)phenyl)-8-methoxythieno[2,3-c]quinolin-4(5H)-one;
(95): 9-(4-(aminomethyl)phenyl)-8-hydroxy-2-methylthieno[2,3-c]quinolin-4(5H)-one;
(96): 9-cyclopropyl-8-hydroxythieno[2,3-c]quinolin-4(5H)-one;
(97): 9-([1,2,4]triazolo[1,5-a]pyridin-6-yl)-8-hydroxythieno[2,3-c]quinolin-4(5H)-one;
(98): 8-methoxy-9-(1,2,3,6-tetrahydropyridin-4-yl)thieno[2,3-c]quinolin-4(5H)-one;
(99): 9-cyclohexenyl-8-hydroxythieno[2,3-c]quinolin-4(5H)-one;
(100): 8-methoxy-9-(4-(2-(piperidin-1-yl)ethylamino)phenyl)thieno[2,3-c]quinolin-4(5H)-one;
(101): 9-(4-(aminomethyl)phenyl)-8-hydroxy-2-(morpholinomethyl)thieno[2,3-c]quinolin-4(5H)-one;

(102): 9-(1H-benzo[d]imidazol-5-yl)-8-hydroxythieno[2,3-c]quinolin-4(5H)-one;
(103): 9-(4-(difluoromethyl)phenyl)-8-methoxythieno[2,3-c]quinolin-4(5H)-one;
(104): 9-(4-(aminomethyl)phenyl)-8-methoxy-2-(morpholinomethyl)thieno[2,3-c]quinolin-4(5H)-one;
(105): 8-hydroxy-9-(4-(2-(piperidin-1-yl)ethylamino)phenyl)thieno[2,3-c]quinolin-4(5H)-one;
(106): 8-hydroxy-9-(4-(piperazin-1-yl)phenyl)thieno[2,3-c]quinolin-4(5H)-one;
(107): 8-methoxy-2,3-dihydro-1H-cyclopenta[c]quinolin-4(5H)-one;
(108): 8-hydroxy-2,3-dihydro-1H-cyclopenta[c]quinolin-4(5H)-one;
(109): 5-(8-hydroxy-4-oxo-4,5-dihydrothieno[2,3-c]quinolin-9-yl)benzo[d]oxazol-2(3H)-one;
(110): tert-butyl 4-(2-(hydroxy-4-oxo-4,5-dihydrothieno[2,3-c]quinolin-9-yl)benzylamino)ethyl)piperidin-1-carboxylate;
(111): 8-methoxy-9-(4-(piperazin-1-yl)phenyl)thieno[2,3-c]quinolin-4(5H)-one;
(112): 8-hydroxy-9-(4-(4-(methylsulfonyl)piperazin-1-yl)phenyl)thieno[2,3-c]quinolin-4(5H)-one;
(113): 8-hydroxy-9-(4-((piperidin-3-ylamino)methyl)phenyl)thieno[2,3-c]quinolin-4(5H)-one;
(114): N-(2-(dimethylamino)ethyl)-4-(8-hydroxy-4-oxo-4,5-dihydrothieno[2,3-c]quinolin-9-yl)benzamide;
(115): 9-(4-(3-(dimethylamino)propoxy)phenyl)-8-methoxythieno[2,3-c]quinolin-(5H)-one;
(116): 8-methoxy-9-(1-(piperidin-4-yl)-1H-pyrazol-4-yl)thieno[2,3-c]quinolin-4(5H)-one;
(117): 8-hydroxy-9-(1-(piperidin-4-yl)-1H-pyrazol-4-yl)thieno[2,3-c]quinolin-4(5H)-one;
(118): 8-methoxythiazolo[4,5-c]quinolin-4(5H)-one;
(119): 2-((4-(aminomethyl)piperidin-1-yl)methyl)-8-hydroxythieno[2,3-c]quinolin-4(5H)-one;
(120): N-(2-(dimethylamino)ethyl)-4-(8-methoxy-4-oxo-4,5-dihydrothieno[2,3-c]quinolin-9-yl)benzamide;
(121): 9-(4-(aminomethyl)phenyl)-8-hydroxy-2,3-dihydro-1H-cyclopenta[c]quinolin-4(5H)-one;
(122): (E)-butyl 3-(8-hydroxy-4-oxo-4,5-dihydrothieno[2,3-c]quinolin-9-yl)acrylate;
(123): 8-methoxy-9-(1H-pyrrolo[2,3-b]pyridin-5-yl)thieno[2,3-c]quinolin-4(5H)-one;
(124): 8-hydroxy-9-(1H-pyrrolo[2,3-b]pyridin-5-yl)thieno[2,3-c]quinolin-4(5H)-one;
(125): N-(methoxy-4-oxo-4,5-dihydrothieno[2,3-c]quinolin-9-yl)phenethyl)acetamide;
(126): N-(2-aminoethyl)-4-(8-hydroxy-4-oxo-4,5-dihydrothieno[2,3-c]quinolin-9-yl)benzamide;
(127): N-(2-aminoethyl)-4-(8-methoxy-4-oxo-4,5-dihydrothieno[2,3-c]quinolin-9-yl)benzamide;
(128): N-(hydroxy-4-oxo-4,5-dihydrothieno[2,3-c]quinolin-9-yl)phenethyl)acetamide;
(129): 4-(8-hydroxy-4-oxo-2,3,4,5-tetrahydro-1H-cyclopenta[c]quinolin-9-yl)benzenesulfonamide;
(130): 8-hydroxy-9-(4-(4-methylpiperazine-1-carbonyl)phenyl)thieno[2,3-c]quinolin-4(5H)-one;
(131): 8-methoxy-9-(4-(4-methylpiperazine-1-carbonyl)phenyl)thieno[2,3-c]quinolin-4(5H)-one;
(132): 8-hydroxy-9-(4-((4-methylpiperazin-1-yl)methyl)phenyl)thieno[2,3-c]quinolin-4(5H)-one;
(133): 8-methoxy-9-(4-((4-methylpiperazin-1-yl)methyl)phenyl)thieno[2,3-c]quinolin-4(5H)-one;
(134): (E)-9-(3-(diethylamino)prop-1-enyl)-8-methoxythieno[2,3-c]quinolin-4(5H)-one;
(135): (E)-9-(3-(4-(aminomethyl)piperidin-1-yl)prop-1-enyl)-8-methoxythieno[2,3-c]quinolin-4(5H)-one;
(136): (E)-9-(3-(2-(diethylamino)ethylamino)prop-1-enyl)-8-hydroxythieno[2,3-c]quinolin-4(5H)-one;
(137): N-(4-(8-hydroxy-4-oxo-2,3,4,5-tetrahydro-1H-cyclopenta[c]quinolin-9-yl)phenyl)methanesulfonamide;
(138): 9-(2-(dimethylamino)pyrimidin-5-yl)-8-hydroxythieno[2,3-c]quinolin-4(5H)-one;
(139): tert-butyl (1-(methoxy-4-oxo-4,5-dihydrothieno[2,3-c]quinolin-9-yl)benzyl)piperidin-4-yl)methylcarbamate;
(140): 8-hydroxy-9-(4-(4-methylpiperazin-1-yl)phenyl)thieno[2,3-c]quinolin-4(5H)-one;
(141): 8-methoxy-9-(4-(4-methylpiperazin-1-yl)phenyl)thieno[2,3-c]quinolin-4(5H)-one;
(142): 8-methoxy-9-(1-(methylsulfonyl)-1,2,3,6-tetrahydropyridin-4-yl)thieno[2,3-c]quinolin-4(5H)-one;
(143): (E)-9-(3-(diethylamino)prop-1-enyl)-8-hydroxythieno[2,3-c]quinolin-4(5H)-one;
(144): 9-(3-(4-(aminomethyl)piperidin-1-yl)propyl)-8-methoxythieno[2,3-c]quinolin-4(5H)-one;
(145): 9-(4-(3-(2-(diethylamino)ethylamino)propoxy)phenyl)-8-methoxythieno[2,3-c]quinolin-4(5H)-one;
(146): 9-(4-(3-(diethylamino)propoxy)phenyl)-8-methoxythieno[2,3-c]quinolin-4(5H)-one;
(147): 9-(4-(3-(2-(diethylamino)ethylamino)propoxy)phenyl)-8-hydroxythieno[2,3-c]quinolin-4(5H)-one;
(148): (E)-9-(3-(4-(aminomethyl)piperidin-1-yl)prop-1-enyl)-8-hydroxythieno[2,3-c]quinolin-4(5H)-one;
(149): 9-(4-(3-(dimethylamino)propoxy)phenyl)-8-hydroxythieno[2,3-c]quinolin-4(5H)-one;
(150): 8-hydroxy-9-(4-(2-(piperidin-1-yl)ethoxy)phenyl)thieno[2,3-c]quinolin-4(5H)-one;
(151): 9-(4-(2-(ethylamino)ethoxy)phenyl)-8-hydroxythieno[2,3-c]quinolin-(5H)-one;
(152): (E)-9-(3-(4-aminopiperidin-1-yl)prop-1-enyl)-8-methoxythieno[2,3-c]quinolin-4(5H)-one;
(153): 9-(1-(2-aminoethyl)-1,2,3,6-tetrahydropyridin-4-yl)-8-methoxythieno[2,3-c]quinolin-4(5H)-one;
(154): 9-(4-(2-(ethylamino)ethoxy)phenyl)-8-methoxythieno[2,3-c]quinolin-4(5H)-one;
(155): 9-(4-(2-(diethylamino)ethoxy)phenyl)-8-hydroxythieno[2,3-c]quinolin-4(5H)-one;
(156): 9-(4-(2-(diethylamino)ethoxy)phenyl)-8-methoxythieno[2,3-c]quinolin-4(5H)-one;
(157): 9-(4-(2-(dimethylamino)ethoxy)phenyl)-8-hydroxythieno[2,3-c]quinolin-4(5H)-one;
(158): 9-(4-(2-(dimethylamino)ethoxy)phenyl)-8-methoxythieno[2,3-c]quinolin-4(5H)-one;
(159): 8-methoxy-9-(4-(2-(piperidin-1-yl)ethoxy)phenyl)thieno[2,3-c]quinolin-4(5H)-one;
(160): 8-methoxy-9-(3-(2-(4-methylpiperazin-1-yl)ethoxy)phenyl)thieno[2,3-c]quinolin-4(5H)-one;
(161): 9-(3-(2-(diethylamino)ethoxy)phenyl)-8-methoxythieno[2,3-c]quinolin-4(5H)-one;
(162): 9-(3-(3-(diethylamino)propoxy)phenyl)-8-methoxythieno[2,3-c]quinolin-4(5H)-one;
(163): 9-(4-(2-(dimethylamino)ethyl)phenyl)-8-methoxythieno[2,3-c]quinolin-4(5H)-one;
(164): 9-(4-((dimethylamino)methyl)phenyl)-8-methoxythieno[2,3-c]quinolin-4(5H)-one;
(165): 9-(4-((dimethylamino)methyl)phenyl)-8-hydroxythieno[2,3-c]quinolin-4(5H)-one;
(166): 9-(3-(2-(diethylamino)ethoxy)phenyl)-8-hydroxythieno[2,3-c]quinolin-4(5H)-one;
(167): 8-hydroxy-9-(3-(2-(4-methylpiperazin-1-yl)ethoxy)phenyl)thieno[2,3-c]quinolin-4(5H)-one;

(168): N-ethyl-N-(2-(4-(8-methoxy-4-oxo-4,5-dihydrothieno[2,3-c]quinolin-9-yl)phenylmethoxy-4-oxo-4,5-dihydrothieno[2,3-c]quinolin-9-yl)phenoxy)ethyl)methanesulfonamide;
(169): 9-(4-(2-aminoethyl)phenyl)-8-methoxythieno[2,3-c]quinolin-4(5H)-one;
(170): 2-(3-(8-hydroxy-4-oxo-4,5-dihydrothieno[2,3-c]quinolin-9-yl)phenyl)acetonitrile;
(171): 2-(3-(8-methoxy-4-oxo-4,5-dihydrothieno[2,3-c]quinolin-9-yl)phenyl)acetonitrile;
(172): 9-(1-(2-(dimethylamino)ethyl)-1,2,3,6-tetrahydropyridin-4-yl)-8-hydroxythieno[2,3-c]quinolin-4(5H)-one;
(173): N-(hydroxy-4-oxo-4,5-dihydrothieno[2,3-c]quinolin-9-yl)phenethyl)methanesulfonamide;
(174): 9-(1-(2-(diethylamino)ethyl)-1,2,3,6-tetrahydropyridin-4-yl)-8-hydroxythieno[2,3-c]quinolin-4(5H)-one;
(175): 9-(4-(2-aminoethyl)phenyl)-8-hydroxythieno[2,3-c]quinolin-4(5H)-one;
(176): 9-(4-(2-aminoethyl)phenyl)-8-hydroxythieno[2,3-c]quinolin-4(5H)-one;
(177): N-(methoxy-4-oxo-4,5-dihydrothieno[2,3-c]quinolin-9-yl)phenethyl)methanesulfonamide;
(178): N-(methoxy-4-oxo-4,5-dihydrothieno[2,3-c]quinolin-9-yl)phenethyl)methanesulfonamide;
(179): N-(2-aminoethyl)-4-(8-hydroxy-4-oxo-4,5-dihydrothieno[2,3-c]quinolin-9-yl)benzenesulfonamide;
(180): 8-hydroxy-9-(1,2,3,6-tetrahydropyridin-4-yl)-2,3-dihydro-1H-cyclopenta[c]quinolin-4(5H)-one;
(181): 9-(4-(1-(dimethylamino)ethyl)phenyl)-8-hydroxy-2,3-dihydro-1H-cyclopenta[c]quinolin-4(5H)-one;
(182): 9-(4-(2-(dimethylamino)ethyl)phenyl)-8-methoxy-2,3-dihydro-1H-cyclopenta[c]quinolin-4(5H)-one;
(183): 9-(4-((diethylamino)methyl)phenyl)-8-methoxythieno[2,3-c]quinolin-4(5H)-one;
(184): 9-(4-((diethylamino)methyl)phenyl)-8-hydroxythieno[2,3-c]quinolin-4(5H)-one;
(185): 9-(3-(2-(dimethylamino)ethyl)phenyl)-8-hydroxythieno[2,3-c]quinolin-4(5H)-one;
(186): 9-(3-(2-aminoethyl)phenyl)-8-hydroxythieno[2,3-c]quinolin-4(5H)-one;
(187): 8-hydroxy-9-(4-((methylamino)methyl)phenyl)thieno[2,3-c]quinolin-4(5H)-one;
(188): 8-methoxy-9-(4-((methylamino)methyl)phenyl)thieno[2,3-c]quinolin-4(5H)-one;
(189): 9-(4-amino-3-methoxyphenyl)-8-methoxythieno[2,3-c]quinolin-4(5H)-one;
(190): 3-(8-hydroxy-4 oxo-4,5-dihydrothieno[2,3-c]quinolin-9-yl)benzonitrile;
(191): 9-(4-(1-(dimethylamino)ethyl)phenyl)-8-hydroxythieno[2,3-c]quinolin-4(5H)-one;
(192): 9-(4-(1-(dimethylamino)ethyl)phenyl)-8-hydroxythieno[2,3-c]quinolin-4(5H)-one;
(193): N-(1-(4-(8-hydroxy-4-oxo-4,5-dihydrothieno[2,3-c]quinolin-9-yl)phenyl)ethyl)methanesulfonamide;
(194): 8-hydroxy-9-(4-(1-(pyrrolidin-1-yl)ethyl)phenyl)thieno[2,3-c]quinolin-4(5H)-one;
(195): 9-(4-(1-aminoethyl)phenyl)-8-hydroxythieno[2,3-c]quinolin-4(5H)-one;
(196): 9-(4-(1-(diethylamino)ethyl)phenyl)-8-hydroxythieno[2,3-c]quinolin-4(5H)-one;
(197): N-(2-aminoethyl)-4-(8-methoxy-4-oxo-4,5-dihydrothieno[2,3-c]quinolin-9-yl)benzenesulfonamide;
(198): N-(2-(dimethylamino)ethyl)-4-(8-methoxy-4-oxo-4,5-dihydrothieno[2,3-c]quinolin-9-yl)benzenesulfonamide;
(199): 4-(8-hydroxy-4-oxo-4,5-dihydrothieno[2,3-c]quinolin-9-yl)-N-(pyrrolidin-3-yl)benzenesulfonamide;
(200): N-(azetidin-3-yl)-4-(8-hydroxy-4-oxo-4,5-dihydrothieno[2,3-c]quinolin-9-yl)benzenesulfonamide;
(201): 9-(4-(2-(diethylamino)ethyl)phenyl)-8-hydroxythieno[2,3-c]quinolin-4(5H)-one;
(202): 2-amino-N-(3-(8-methoxy-4-oxo-4,5-dihydrothieno[2,3-c]quinolin-9-yl)phenyl)ethanesulfonamide;
(203): 4-(8-hydroxy-4 oxo-4,5-dihydrothieno[2,3-c]quinolin-9-yl)benzonitrile;
(204): 4-(8-methoxy-4 oxo-4,5-dihydrothieno[2,3-c]quinolin-9-yl)benzonitrile;
(205): (E)-9-(3-(3-aminopyrrolidin-1-yl)prop-1-enyl)-8-methoxythieno[2,3-c]quinolin-4(5H)-one;
(206): N-(2-hydroxyethyl)-4-(8-methoxy-4-oxo-4,5-dihydrothieno[2,3-c]quinolin-9-yl)benzensulfonamide;
(207): 8-methoxy-9-(5-methoxypyridin-3-yl)thieno[2,3-c]quinolin-4(5H)-one;
(208): 8-methoxy-9-(5-methoxypyridin-3-yl)-2,3-dihydro-1H-cyclopenta[c]quinolin-4(5H)-one;
(209): 9-(4-(3-aminopyrrolidin-1-ylsulfonyl)phenyl)-8-hydroxythieno[2,3-c]quinolin-4(5H)-one;
(210): N-(2-bromoethyl)-4-(8-hydroxy-4-oxo-4,5-dihydrothieno[2,3-c]quinolin-9-yl)benzensulfonamide;
(211): 9-(4-((diisopropylamino)methyl)phenyl)-8-methoxythieno[2,3-c]quinolin-4(5H)-one;
(212): N-(hydroxy-4-oxo-4,5-dihydrothieno[2,3-c]quinolin-9-yl)benzyl)methanesulfonamide;
(213): 9-(4-((isopropylamino)methyl)phenyl)-8-methoxythieno[2,3-c]quinolin-4(5H)-one;
(214): 2-(dimethylamino)-N-(3-(8-hydroxy-4-oxo-4,5-dihydrothieno[2,3-c]quinolin-9-yl)phenyl)ethanesulfonamide;
(215): 2-amino-N-(3-(8-hydroxy-4-oxo-4,5-dihydrothieno[2,3-c]quinolin-9-yl)phenyl)ethanesulfonamide;
(216): 8-methoxy-9-(4-(1-(pyrrolidin-1-yl)ethyl)phenyl)thieno[2,3-c]quinolin-4(5H)-one;
(217): 9-(4-amino-3-hydroxyphenyl)-8-hydroxythieno[2,3-c]quinolin-4(5H)-one;
(218): N-(2-methoxy-4-(8-methoxy-4-oxo-4,5-dihydrothieno[2,3-c]quinolin-9-yl)phenyl)methanesulfonamide;
(219): 9-(3,5-difluoro-4-hydroxyphenyl)-8-methoxythieno[2,3-c]quinolin-4(5H)-one;
(220): N-(2-hydroxy-4-(8-hydroxy-4-oxo-4,5-dihydrothieno[2,3-c]quinolin-9-yl)phenyl)methanesulfonamide;
(221): 9-(4-((4-(aminomethyl)piperidin-1-yl)methyl)-3-fluorophenyl)-8-methoxythieno[2,3-c]quinolin-4(5H)-one;
(222): 9-(4-(2-(dimethylamino)ethyl)phenyl)-6-fluoro-8-methoxythieno[2,3-c]quinolin-4(5H)-one;
(223): 9-(3,5-difluoro-4-hydroxyphenyl)-8-hydroxythieno[2,3-c]quinolin-4(5H)-one;
(224): 6-fluoro-8-methoxy-9-(1,2,3,6-tetrahydropyridin-4-yl)thieno[2,3-c]quinolin-4(5H)-one;
(225): 9-(4-(1-(dimethylamino)ethyl)phenyl)-6-fluoro-8-hydroxythieno[2,3-c]quinolin-(5H)-one;
(226): 9-(4-((diethylamino)methyl)-3-fluorophenyl)-8-methoxythieno[2,3-c]quinolin-4(5H)-one;
(227): (E)-9-(3-(3-hydroxypyrrolidin-1-yl)prop-1-enyl)-8-methoxythieno[2,3-c]quinolin-4(5H)-one;
(228): (E)-8-hydroxy-9-(3-(3-hydroxypyrrolidin-1-yl)prop-1-enyl)thieno[2,3-c]quinolin-4(5H)-one
(229): 8-hydroxy-9-(4-((isopropylamino)methyl)phenyl)thieno[2,3-c]quinolin-4(5H)-one;
(230): (E)-9-(3-(3-aminoazetidin-1-yl)prop-1-enyl)-8-hydroxythieno[2,3-c]quinolin-4(5H)-one;
(231): (E)-8-methoxy-9-(3-(2-(methylsulfonyl)ethylamino)prop-1-enyl)thieno[2,3-c]quinolin-4(5H)-one;

(232): (S)-9-(4-(1-aminoethyl)phenyl)-8-methoxythieno[2,3-c]quinolin-4(5H)-one;
(233): (S)-9-(4-(1-aminoethyl)phenyl)-8-hydroxythieno[2,3-c]quinolin-4(5H)-one;
(234): 8-hydroxy-9-(5-hydroxypyridin-3-yl)-2,3-dihydro-1H-cyclopenta[c]quinolin-4(5H)-one;
(235): 9-(4-((4-(aminomethyl)piperidin-1-yl)methyl)-3-fluorophenyl)-8-hydroxythieno[2,3-c]quinolin-4(5H)-one;
(236): 8-methoxy-9-(4-(1-(2-(methylsulfonyl)ethylamino)ethyl)phenyl)thieno[2,3-c]quinolin-4(5H)-one;
(237): 9-(4-((3-aminopyrrolidin-1-yl)methyl)-3-fluorophenyl)-8-methoxythieno[2,3-c]quinolin-4(5H)-one;
(238): (E)-9-(3-(3-aminoazetidin-1-yl)prop-1-enyl)-8-methoxythieno[2,3-c]quinolin-4(5H)-one;
(239): (E)-9-(3-(ethylamino)prop-1-enyl)-8-hydroxythieno[2,3-c]quinolin-4(5H)-one;
(240): 9-(4-((3-aminopiperidin-1-yl)methyl)-3-fluorophenyl)-8-hydroxythieno[2,3-c]quinolin-4(5H)-one;
(241): 9-(4-((3-aminopyrrolidin-1-yl)methyl)-3-fluorophenyl)-8-hydroxythieno[2,3-c]quinolin-4(5H)-one;
(242): 9-(4-((3-aminopiperidin-1-yl)methyl)-3-fluorophenyl)-8-methoxythieno[2,3-c]quinolin-4(5H)-one;
(243): 8-hydroxy-9-(4-(1-(2-(methylsulfonyl)ethylamino)ethyl)phenyl)thieno[2,3-c]quinolin-4(5H)-one;
(244): (E)-9-(3-(3-aminopiperidin-1-yl)prop-1-enyl)-8-methoxythieno[2,3-c]quinolin-4(5H)-one;
(245): (E)-9-(3-(3-aminopyrrolidin-1-yl)prop-1-enyl)-8-hydroxythieno[2,3-c]quinolin-4(5H)-one;
(246): (E)-9-(3-(3-aminopiperidin-1-yl)prop-1-enyl)-8-hydroxythieno[2,3-c]quinolin-4(5H)-one;
(247): (E)-8-hydroxy-9-(3-(2-(methylsulfonyl)ethylamino)prop-1-enyl)thieno[2,3-c]quinolin-4(5H)-one;
(248): 8-methoxy-9-(4-(2-(2-(methylsulfonyl)ethylamino)ethyl)phenyl)thieno[2,3-c]quinolin-(5H)-one;
(249): 2-(2-fluoro-4-(8-methoxy-4-oxo-4,5-dihydrothieno[2,3-c]quinolin-9-yl)phenyl)acetonitrile;
(250): (E)-N-(1-(3-(8-methoxy-4-oxo-4,5-dihydrothieno[2,3-c]quinolin-9-yl)allyl)azetidin-3-yl)methanesulfonamide;
(251): 4-(8-methoxy-4-oxo-4,5-dihydrothieno[2,3-c]quinolin-9-yl)-N,N-dimethylbenzenesulfonamide;
(252): 4-(8-hydroxy-4-oxo-4,5-dihydrothieno[2,3-c]quinolin-9-yl)-N-methylbenzenesulfonamide;
(253): tert-butyl (5-(8-methoxy-4-oxo-4,5-dihydrothieno[2,3-c]quinolin-9-yl)furan-2-yl)methylcarbamate;
(254): N-(4-(8-hydroxy-4-oxo-4,5-dihydrothieno[2,3-c]quinolin-9-yl)-2-methylphenyl)methanesulfonamide;
(255): N-(4-(8-methoxy-4-oxo-4,5-dihydrothieno[2,3-c]quinolin-9-yl)-2-methylphenyl)methanesulfonamide;
(256): 9-(4-(aminomethyl)phenyl)-6-fluoro-8-hydroxythieno[2,3-c]quinolin-4(5H)-one;
(257): 9-(4-(aminomethyl)phenyl)-6-fluoro-8-methoxythieno[2,3-c]quinolin-4(5H)-one;
(258): 6-fluoro-8-hydroxy-9-(1,2,3,6-tetrahydropyridin-4-yl)thieno[2,3-c]quinolin-4(5H)-one;
(259): 9-(4-((diethylamino)methyl)-3-fluorophenyl)-8-hydroxythieno[2,3-c]quinolin-4(5H)-one;
(260): 8-methoxy-9-(4-(1-(piperidin-1-yl)ethyl)phenyl)thieno[2,3-c]quinolin-4(5H)-one;
(261): 2-(2-fluoro-4-(8-hydroxy-4-oxo-4,5-dihydrothieno[2,3-c]quinolin-9-yl)phenyl)acetonitrile;
(262): 8-hydroxy-9-(4-(1-(piperidin-1-yl)ethyl)phenyl)thieno[2,3-c]quinolin-4(5H)-one;
(263): (E)-9-(3-(3-(dimethylamino)piperidin-1-yl)prop-1-enyl)-8-hydroxythieno[2,3-c]quinolin-4(5H)-one;
(264): (E)-9-(3-(3-(dimethylamino)pyrrolidin-1-yl)prop-1-enyl)-8-hydroxythieno[2,3-c]quinolin-4(5H)-one;
(265): 9-(4-(2-aminoethyl)-3-fluorophenyl)-8-methoxythieno[2,3-c]quinolin-4(5H)-one;
(266): 9-(5-(aminomethyl)thiophen-2-yl)-8-hydroxythieno[2,3-c]quinolin-4(5H)-one;
(267): 9-(4-((ethylamino)methyl)phenyl)-8-hydroxythieno[2,3-c]quinolin-4(5H)-one;
(268): (E)-9-(3-(4-aminopiperidin-1-yl)prop-1-enyl)-8-hydroxythieno[2,3-c]quinolin-4(5H)-one;
(269): 9-(4-((ethylamino)methyl)phenyl)-8-methoxythieno[2,3-c]quinolin-4(5H)-one;
(270): 9-(4-(aminomethyl)phenyl)-6-bromo-8-hydroxythieno[2,3-c]quinolin-4(5H)-one;
(271): 9-(3-chloro-4-((diethylamino)methyl)phenyl)-8-methoxythieno[2,3-c]quinolin-4(5H)-one;
(272): (R)-9-(4-(1-(dimethylamino)ethyl)phenyl)-8-hydroxythieno[2,3-c]quinolin-4(5H)-one;
(273): 9-(4-(3-aminopropyl)phenyl)-8-hydroxythieno[2,3-c]quinolin-4(5H)-one;
(274): (R)-9-(4-(1-aminoethyl)phenyl)-8-methoxythieno[2,3-c]quinolin-4(5H)-one;
(275): (R)-9-(4-(1-aminoethyl)phenyl)-8-hydroxythieno[2,3-c]quinolin-4(5H)-one;
(276): 9-(4-(2-aminoethyl)-3-fluorophenyl)-8-hydroxythieno[2,3-c]quinolin-4(5H)-one;
(277): 9-(4-(1-amino-2-methylpropan-2-yl)phenyl)-8-hydroxythieno[2,3-c]quinolin-4(5H)-one;
(278): 9-(3-fluoro-4-((3-hydroxypyrrolidin-1-yl)methyl)phenyl)-8-hydroxythieno[2,3-c]quinolin-4(5H)-one;
(279): 9-(3-fluoro-4-((3-hydroxypyrrolidin-1-yl)methyl)phenyl)-8-methoxythieno[2,3-c]quinolin-4(5H)-one;
(280): 4-(8-methoxy-4-oxo-4,5-dihydrothieno[2,3-c]quinolin-9-yl)-N-(2,2,2-trifluoroethyl)benzenesulfonamide;
(281): 4-(8-hydroxy-4-oxo-4,5-dihydrothieno[2,3-c]quinolin-9-yl)-N-(2,2,2-trifluoroethyl)benzene sulfonamide;
(282): N-(2-(dimethylamino)ethyl)-4-(8-hydroxy-4-oxo-4,5-dihydrothieno[2,3-c]quinolin-9-yl)benzenesulfonamide;
(283): 8-hydroxy-9-(4-((2-(methylsulfonyl)ethylamino)methyl)phenyl)thieno[2,3-c]quinolin-4(5H)-one;
(284): 9-(3-(3-(dimethylamino)pyrrolidin-1-yl)propyl)-8-hydroxythieno[2,3-c]quinolin-4(5H)-one;
(285): 9-(1-(2-aminoethyl)-1H-pyrazol-4-yl)-8-methoxythieno[2,3-c]quinolin-4(5H)-one;
(286): 9-(3-chloro-4-((diethylamino)methyl)phenyl)-8-hydroxythieno[2,3-c]quinolin-4(5H)-one;
(287): 4-(7-fluoro-8-methoxy-4-oxo-4,5-dihydrothieno[2,3-c]quinolin-9-yl)-N-(2-hydroxyethyl)benzenesulfonamide;
(288): 9-(3-acetylphenyl)-8-methoxythieno[2,3-c]quinolin-4(5H)-one;
(289): 2-fluoro-4-(8-hydroxy-4-oxo-4,5-dihydrothieno[2,3-c]quinolin-9-yl)-N-(2-hydroxyethyl)benzamide;
(290): 3-(4-(8-hydroxy-4-oxo-4,5-dihydrothieno[2,3-c]quinolin-9-yl)phenyl)propanenitrile;
(291): 9-(4-acetylphenyl)-8-methoxythieno[2,3-c]quinolin-4(5H)-one;
(292): 2-fluoro-N-(2-hydroxyethyl)-4-(8-methoxy-4-oxo-4,5-dihydrothieno[2,3-c]quinolin-9-yl)benzamide;
(293): 4-(8-hydroxy-4-oxo-4,5-dihydrothieno[2,3-c]quinolin-9-yl)-N-(2-hydroxyethyl)benzamide;
(294): 1,1-diethyl-3-(hydroxy-4-oxo-4,5-dihydrothieno[2,3-c]quinolin-9-yl)benzyl)urea;
(295): N-(2-hydroxyethyl)-4-(8-methoxy-4-oxo-4,5-dihydrothieno[2,3-c]quinolin-9-yl)benzamide;

(296): 9-(4-acetylphenyl)-8-hydroxythieno[2,3-c]quinolin-4 (5H)-one;
(297): N-(2-bromoethyl)-2-fluoro-4-(8-hydroxy-4-oxo-4,5-dihydrothieno[2,3-c]quinolin-9-yl)benzenesulfonamide;
(298): 9-(3-(3-(dimethylamino)piperidin-1-yl)propyl)-8-hydroxythieno[2,3-c]quinolin-4(5H)-one;
(299): N-(2-fluoro-4-(8-hydroxy-4-oxo-4,5-dihydrothieno[2,3-c]quinolin-9-yl)phenethyl)methanesulfonamide;
(300): 9-(3-fluoro-4-(2-(methylsulfonamido)ethyl)phenyl)-4-oxo-4,5-dihydrothieno[2,3-c]quinolin-8-yl methanesulfonate;
(301): (R)—N-(1-(4-(8-hydroxy-4-oxo-4,5-dihydrothieno[2,3-c]quinolin-9-yl)phenyl)ethyl)methanesulfonamide;
(302): (R)-9-(4-(1-(methylsulfonamido)ethyl)phenyl)-4-oxo-4,5-dihydrothieno[2,3-c]quinolin-8-yl methanesulfonate;
(303): 2-fluoro-N-(2-hydroxyethyl)-4-(8-methoxy-4-oxo-4,5-dihydrothieno[2,3-c]quinolin-9-yl)benzenesulfonamide;
(304): 4-(8-hydroxy-4-oxo-4,5-dihydrothieno[2,3-c]quinolin-9-yl)-N,N-dimethylbenzenesulfonamide;
(305): 9-(4-(2-(dimethylamino)ethyl)phenyl)-7-fluoro-8-methoxythieno[2,3-c]quinolin-4(5H)-one;
(306): N-(2-bromoethyl)-4-(7-fluoro-8-hydroxy-4-oxo-4,5-dihydrothieno[2,3-c]quinolin-9-yl)benzenesulfonamide;
(307): 4-(7-fluoro-8-hydroxy-4-oxo-4,5-dihydrothieno[2,3-c]quinolin-9-yl)-N-(2-hydroxyethyl)benzenesulfonamide;
(308): 9-(4-(1-(dimethylamino)-2-methylpropan-2-yl)phenyl)-8-hydroxythieno[2,3-c]quinolin-4(5H)-one;
(309): N-(2-chloro-4-(8-methoxy-4-oxo-4,5-dihydrothieno[2,3-c]quinolin-9-yl)benzyl)-N-methyl methanesulfonamide;
(310): 4-(8-hydroxy-4 oxo-4,5-dihydrothieno[2,3-c]quinolin-9-yl)-N-(2-methoxyethyl)benzenesulfonamide;
(3H): (E)-3-(8-methoxy-4-oxo-4,5-dihydrothieno[2,3-c]quinolin-9-yl)-2-methylacrylonitrile;
(312): N-(2-fluoro-4-(8-methoxy-4-oxo-4,5-dihydrothieno[2,3-c]quinolin-9-yl)phenethyl)methanesulfonamide;
(313): 8-hydroxy-9-(4-(1-hydroxyethyl)phenyl)thieno[2,3-c]quinolin-4(5H)-one;
(314): 9-(4-(1-(cyclopentylamino)ethyl)phenyl)-8-hydroxythieno[2,3-c]quinolin-4(5H)-one;
(315): 9-(4-(1-(cyclopentylamino)ethyl)phenyl)-8-methoxythieno[2,3-c]quinolin-4(5H)-one;
(316): 4-(8-hydroxy-4-oxo-4,5-dihydrothieno[2,3-c]quinolin-9-yl)-N-(2-hydroxyethyl)benzenesulfonamide;
(317): 9-(5-(aminomethyl)furan-2-yl)-8-hydroxythieno[2,3-c]quinolin-4(5H)-one;
(318): 9-(3-chloro-4-((methylamino)methyl)phenyl)-8-methoxythieno[2,3-c]quinolin-4(5H)-one;
(319): 9-(4-(2-aminopropan-2-yl)phenyl)-8-hydroxythieno[2,3-c]quinolin-4(5H)-one;
(320): N-(3-hydroxypropyl)-4-(8-methoxy-4-oxo-4,5-dihydrothieno[2,3-c]quinolin-9-yl)benzenesulfonamide;
(321): 2-fluoro-4-(8-hydroxy-4-oxo-4,5-dihydrothieno[2,3-c]quinolin-9-yl)-N-(2-hydroxyethyl)benzenesulfonamide;
(322): 4-(8-hydroxy-4-oxo-4,5-dihydrothieno[2,3-c]quinolin-9-yl)-N-(3-hydroxypropyl)benzenesulfonamide;
(323): N-(3-bromopropyl)-4-(8-hydroxy-4-oxo-4,5-dihydrothieno[2,3-c]quinolin-9-yl)benzenesulfonamide;
(324): 2-fluoro-4-(8-hydroxy-4-oxo-4,5-dihydrothieno[2,3-c]quinolin-9-yl)-N-(2-methoxyethyl)benzenesulfonamide;
(325): 9-(3-chloro-4-((methylamino)methyl)phenyl)-8-hydroxythieno[2,3-c]quinolin-4(5H)-one;
(326): 9-(4-(aminomethyl)phenyl)-4 oxo-4,5-dihydrothieno[2,3-c]quinoline-8-carbonitrile;
(327): 9-(4-(2-(dimethylamino)ethyl)-3-fluorophenyl)-8-hydroxythieno[2,3-c]quinolin-(5H)-one;
(328): 9-(4-(aminomethyl)phenyl)-6,7-dichloro-8-hydroxythieno[2,3-c]quinolin-4(5H)-one;
(329): 9-(4-(aminomethyl)phenyl)-6-chloro-8-hydroxythieno[2,3-c]quinolin-4(5H)-one;
(330): 9-(4-(aminomethyl)phenyl)-4-oxo-4,5-dihydrothieno[2,3-c]quinolin-8-yl trifluoromethanesulfonate;
(331): 9-(4-(2-(dimethylamino)ethyl)phenyl)-8-methoxythieno[2,3-c]quinolin-4(5H)-one;
(332): N-(2-chloroethyl)-4-(8-hydroxy-4-oxo-4,5-dihydrothieno[2,3-c]quinolin-9-yl)benzenesulfonamide;
(333): N-(2-fluoroethyl)-4-(8-methoxy-4-oxo-4,5-dihydrothieno[2,3-c]quinolin-9-yl)benzenesulfonamide;
(334): 9-(4-(2-aminopropan-2-yl)phenyl)-6-chloro-8-hydroxythieno[2,3-c]quinolin-4(5H)-one;
(335): (S)-9-(4-(1-(dimethylamino)ethyl)phenyl)-8-hydroxythieno[2,3-c]quinolin-4(5H)-one;
(336): 9-(4-(1-aminopropyl)phenyl)-8-hydroxythieno[2,3-c]quinolin-4(5H)-one;
(337): 9-(4-(1-aminopropyl)phenyl)-8-methoxythieno[2,3-c]quinolin-4(5H)-one;
(338): 9-(4-(1-(diethylamino)propyl)phenyl)-8-hydroxythieno[2,3-c]quinolin-4(5H)-one;
(339): 9-(4-(1-(dimethylamino)propyl)phenyl)-8-hydroxythieno[2,3-c]quinolin-4(5H)-one;
(340): 9-amino-8-methoxythieno[2,3-c]quinolin-4(5H)-one;
(341): 9-(4-(1-(dimethylamino)ethyl)phenyl)-6,7-difluoro-8-hydroxythieno[2,3-c]quinolin-4(5H)-one;
(342): 9-(4-(1-(dimethylamino)ethyl)phenyl)-6,7-difluoro-8-methoxythieno[2,3-c]quinolin-4(5H)-one;
(343): N-cyclopropyl-4-(8-methoxy-4-oxo-4,5-dihydrothieno[2,3-c]quinolin-9-yl)benzenesulfonamide;
(344): N-cyclopropyl-4-(8-hydroxy-4-oxo-4,5-dihydrothieno[2,3-c]quinolin-9-yl)benzenesulfonamide;
(345): 9-(2-amino-2,3-dihydro-1H-inden-5-yl)-8-hydroxythieno[2,3-c]quinolin-4(5H)-one;
(346): 9-(4-(1-(dimethylamino)ethyl)phenyl)thieno[2,3-c]quinolin-4(5H)-one;
(347): (S)—N-(1-(4-(8-hydroxy-4-oxo-4,5-dihydrothieno[2,3-c]quinolin-9-yl)phenyl)ethyl)methanesulfonamide;
(348): 9-(4-(1-(aminomethyl)cyclopropyl)phenyl)-8-hydroxythieno[2,3-c]quinolin-4(5H)-one;
(349): 9-(4-(1-(dimethylamino)ethyl)-3-fluorophenyl)-8-hydroxythieno[2,3-c]quinolin-4(5H)-one;
(350): N-(1-(hydroxymethyl)cyclopentyl)-4-(8-methoxy-4-oxo-4,5-dihydrothieno[2,3-c]quinolin-9-yl)benzenesulfonamide;
(351): 9-(2-(diethylamino)-2,3-dihydro-1H-inden-5-yl)-8-hydroxythieno[2,3-c]quinolin-4(5H)-one
(352): 9-(2-(dimethylamino)-2,3-dihydro-1H-inden-5-yl)-8-hydroxythieno[2,3-c]quinolin-4(5H)-one;
(353): 8-hydroxy-9-(1,2,3,4-tetrahydroisoquinolin-7-yl)thieno[2,3-c]quinolin-4(5H)-one;
(354): 8-methoxy-9-(1,2,3,4-tetrahydroisoquinolin-7-yl)thieno[2,3-c]quinolin-4(5H)-one;
(355): 3-(3-(8-hydroxy-4-oxo-4,5-dihydrothieno[2,3-c]quinolin-9-yl)phenyl)propanenitrile;
(356): 9-(4-(1-(diethylamino)ethyl)-3-fluorophenyl)-8-hydroxythieno[2,3-c]quinolin-4(5H)-one;

(357): 1-(4-(8-methoxy 4-oxo-4,5-dihydrothieno[2,3-c]quinolin-9-yl)phenyl)cyclopropanecarbonitrile;
(358): 9-(2-ethyl-1,2,3,4-tetrahydroisoquinolin-7-yl)-8-hydroxythieno[2,3-c]quinolin-4(5H)-one;
(359): 9-(4-(1-aminoethyl)-3-fluorophenyl)-8-hydroxythieno[2,3-c]quinolin-4(5H)-one;
(360): 3-(3-(8-methoxy-4-oxo-4,5-dihydrothieno[2,3-c]quinolin-9-yl)phenyl)propanenitrile;
(361): 1-(4-(8-hydroxy-4-oxo-4,5-dihydrothieno[2,3-c]quinolin-9-yl)phenyl)cyclopropanecarbonitrile;
(362): 9-(2-amino-2,3-dihydro-1H-inden-5-yl)-8-methoxythieno[2,3-c]quinolin-4(5H)-one;
(363): N-isopentyl-4-(8-methoxy-4-oxo-4,5-dihydrothieno[2,3-c]quinolin-9-yl)benzenesulfonamide;
(364): 9-(2-(dimethylamino)-2,3-dihydro-1H-inden-5-yl)-8-methoxythieno[2,3-c]quinolin-4(5H)-one;
(365): 9-(4-(1-(ethylamino)ethyl)phenyl)-8-methoxythieno[2,3-c]quinolin-4(5H)-one;
(366): 6-chloro-9-(4-(1-(dimethylamino)ethyl)phenyl)-8-hydroxythieno[2,3-c]quinolin-4(5H)-one;
(367): 9-(4-(cyclopropanecarbonyl)phenyl)-8-methoxythieno[2,3-c]quinolin-4(5H)-one;
(368): 9-(4-(aminomethyl)phenyl)-4-oxo-4,5-dihydrothieno[2,3-c]quinoline-8-carboxamide;
(369): 9-(2-aminoethyl)-8-methoxythieno[2,3-c]quinolin-4(5H)-one;
(370): 8-hydroxy-9-(4-(2-hydroxyethylsulfonyl)phenyl)thieno[2,3-c]quinolin-4(5H)-one;
(371): 9-(4-(2-hydroxyethylsulfonyl)phenyl)-8-methoxythieno[2,3-c]quinolin-4(5H)-one;
(372): 9-(1-ethylindolin-5-yl)-8-hydroxythieno[2,3-c]quinolin-4(5H)-one;
(373): 9-(4-(1-aminopropan-2-yl)phenyl)-8-methoxythieno[2,3-c]quinolin-4(5H)-one;
(374): 8-hydroxy-9-(2-methyl-1,2,3,4-tetrahydroisoquinolin-7-yl)thieno[2,3-c]quinolin-4(5H)-one;
(375): 9-(4-(1-aminoethyl)-3-fluorophenyl)-8-methoxythieno[2,3-c]quinolin-4(5H)-one;
(376): 8-hydroxy-9-(1-methylindolin-5-yl)thieno[2,3-c]quinolin-4(5H)-one;
(377): 8-hydroxy-9-(indolin-5-yl)thieno[2,3-c]quinolin-4(5H)-one;
(378): 9-(indolin-5-yl)-8-methoxythieno[2,3-c]quinolin-4(5H)-one;
(379): 9-(4-(1-((dimethylamino)methyl)cyclopropyl)phenyl)-8-hydroxythieno[2,3-c]quinolin-4(5H)-one;
(380): 4-(8-methoxy-4 oxo-4,5-dihydrothieno[2,3-c]quinolin-9-yl)-N-propylbenzenesulfonamide;
(381): N-(cyclopropylmethyl)-4-(8-methoxy-4-oxo-4,5-dihydrothieno[2,3-c]quinolin-9-yl)benzene sulfonamide;
(382): N-(3,3-dimethylbutyl)-4-(8-methoxy-4-oxo-4,5-dihydrothieno[2,3-c]quinolin-9-yl)benzenesulfonamide;
(383): 4-(8-hydroxy-4-oxo-4,5-dihydrothieno[2,3-c]quinolin-9-yl)-N-isopentylbenzenesulfonamide;
(384): N-(3,3-dimethylbutyl)-4-(8-hydroxy-4-oxo-4,5-dihydrothieno[2,3-c]quinolin-9-yl)benzenesulfonamide;
(385): 9-(4-(1-(ethylamino)ethyl)phenyl)-8-hydroxythieno[2,3-c]quinolin-4(5H)-one;
(386): 3-(4-(8-methoxy-4-oxo-4,5-dihydrothieno[2,3-c]quinolin-9-yl)phenyl)-3-oxopropanenitrile;
(387): (E)-9-(2-ethoxyvinyl)-8-methoxythieno[2,3-c]quinolin-4(5H)-one;
(388): N-(1-(4-(8-hydroxy-4-oxo-4,5-dihydrothieno[2,3-c]quinolin-9-yl)phenyl)ethyl)acetamide;
(389): 4-(8-methoxy-4-oxo-4,5-dihydrothieno[2,3-c]quinolin-9-yl)-N-(3,3,3-trifluoropropyl)benzenesulfonamide;
(390): 4-(8-hydroxy-4-oxo-4,5-dihydrothieno[2,3-c]quinolin-9-yl)-N-(1-(hydroxymethyl)cyclopentyl)benzenesulfonamide;
(391): N-(2,2-difluoroethyl)-4-(8-methoxy-4-oxo-4,5-dihydrothieno[2,3-c]quinolin-9-yl)benzenesulfonamide;
or a pharmaceutically acceptable salt thereof.

121. A pharmaceutical composition comprising at least one compound of any one of above 101-120 or a pharmaceutically acceptable salt thereof, and a pharmaceutically acceptable carrier.

122. The pharmaceutical composition of above 121 which is available for preventing or treating a PBK dependent disease.

123. The pharmaceutical composition of above 122, wherein the PBK dependent disease is cancer.

124. A PBK inhibitor comprising at least one compound of any one of above 101-120, or a pharmaceutically acceptable salt thereof.

125. A method for treating a PBK dependent disease in a subject, comprising administering to said subject an effective amount of a compound or a pharmaceutically acceptable salt thereof of any one of above 101-120.

126. A compound or a pharmaceutically acceptable salt thereof of any one of above 101-120 for use in a treatment of a PBK dependent disease.

127. Use of a compound of any one of above 101-120 or a pharmaceutically acceptable salt thereof in manufacturing a pharmaceutical composition for treating a PBK dependent disease.

Preferred compounds include those selected from the group consisting of: Example Nos. 1-391 listed in Table 1 below; and the pharmaceutically acceptable salts, prodrugs, hydrates and solvates of the forgoing compounds.

TABLE 1

(Examples 1-391)

| Example | Structure | Name |
|---------|-----------|------|
| 1 | 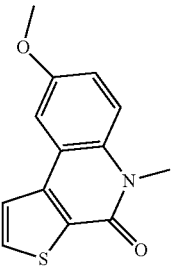 [SMILES: COc1ccc2c(c1)c1ccsc1c(=O)n2C] | 8-methoxy-5-methylthieno[2,3-c]quinolin-4(5H)-one |

TABLE 1-continued
| | | |
|---|---|---|
| 2 | 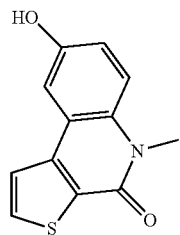 [SMILES: Cn1c(=O)c2sccc2c2cc(O)ccc21] | 8-hydroxy-5-methylthieno[2,3-c]quinolin-4(5H)-one |
| 3 | 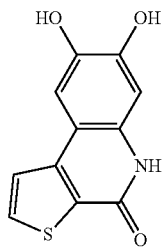 [SMILES: O=c1[nH]c2cc(O)c(O)cc2c2ccsc12] | 7,8-dihydroxythieno[2,3-c]quinolin-4(5H)-one |
| 4 | 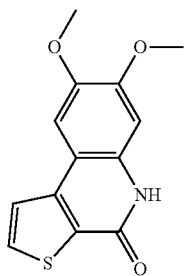 [SMILES: COc1cc2[nH]c(=O)c3sccc3c2cc1OC] | 7,8-dimethoxythieno[2,3-c]quinolin-4(5H)-one |
| 5 | 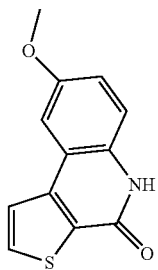 [SMILES: COc1ccc2[nH]c(=O)c3sccc3c2c1] | 8-methoxythieno[2,3-c]quinolin-4(5H)-one |
| 6 | 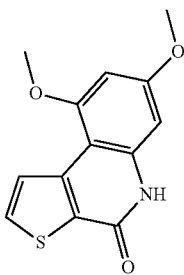 [SMILES: COc1cc(OC)c2c(c1)[nH]c(=O)c1sccc12] | 7,9-dimethoxythieno[2,3-c]quinolin-4(5H)-one |
| 7 | 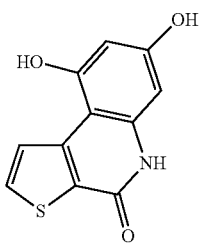 [SMILES: O=c1[nH]c2cc(O)cc(O)c2c2ccsc12] | 7,9-dihydroxythieno[2,3-c]quinolin-4(5H)-one |

TABLE 1-continued
| | | |
|---|---|---|
| 8 | 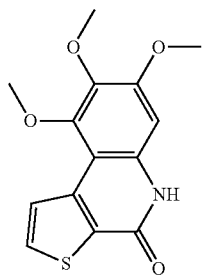 | 7,8,9-trimethoxythieno[2,3-c]quinolin-4(5H)-one |
| 9 | 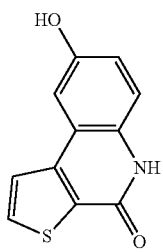 [SMILES: O=c1[nH]c2ccc(O)cc2c2ccsc12] | 8-hydroxythieno[2,3-c]quinolin-4(5H)-one |
| 10 | 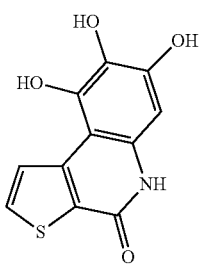 [SMILES: O=c1[nH]c2cc(O)c(O)c(O)c2c2ccsc12] | 7,8,9-trihydroxythieno[2,3-c]quinolin-4(5H)-one |
| 11 | 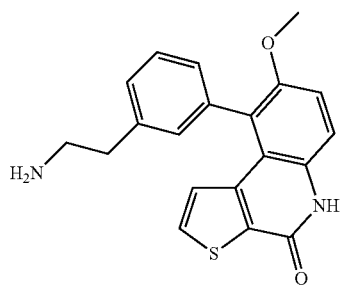 [SMILES: COc1ccc2[nH]c(=O)c3sccc3c2c1-c1cccc(CCN)c1] | 9-(3-(2-aminoethyl)phenyl)-8-methoxythieno[2,3-c]quinolin-4(5H)-one |
| 12 | 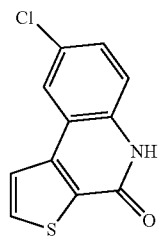 [SMILES: O=c1[nH]c2ccc(Cl)cc2c2ccsc12] | 8-chlorothieno[2,3-c]quinolin-4(5H)-one |
| 13 | 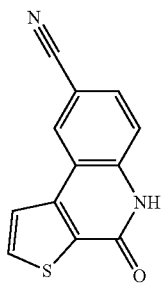 [SMILES: N#Cc1ccc2[nH]c(=O)c3sccc3c2c1] | 4-oxo-4,5-dihydrothieno[2,3-c]quinoline-8-carbonitrile |

TABLE 1-continued
| | | |
|---|---|---|
| 14 | 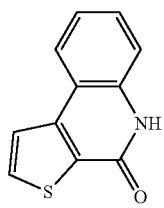 [SMILES: O=c1[nH]c2ccccc2c2ccsc12] | thieno[2,3-c]quinolin-4(5H)-one |
| 15 | 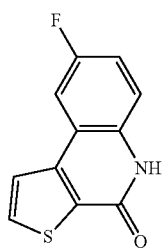 [SMILES: O=c1[nH]c2ccc(F)cc2c2ccsc12] | 8-fluorothieno[2,3-c]quinolin-4(5H)-one |
| 16 | 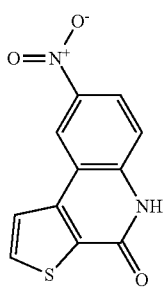 [SMILES: O=c1[nH]c2ccc([N+](=O)[O-])cc2c2ccsc12] | 8-nitrothieno[2,3-c]quinolin-4(5H)-one |
| 17 | 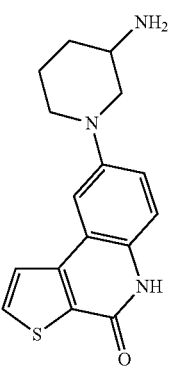 [SMILES: NC1CCCN(c2ccc3[nH]c(=O)c4sccc4c3c2)C1] | 8-(3-aminopiperidin-1-yl)thieno[2,3-c]quinolin-4(5H)-one |
| 18 | 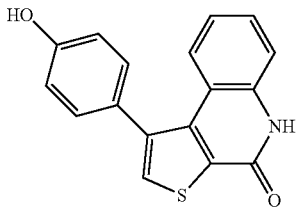 [SMILES: O=c1[nH]c2ccccc2c2c(-c3ccc(O)cc3)csc12] | 1-(4-hydroxyphenyl)thieno[2,3-c]quinolin-4(5H)-one |
| 19 | 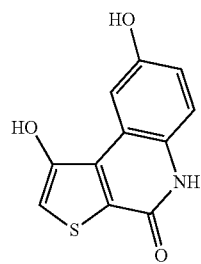 [SMILES: O=c1[nH]c2ccc(O)cc2c2c(O)csc12] | 1,8-dihydroxythieno[2,3-c]quinolin-4(5H)-one |

TABLE 1-continued
| 20 | 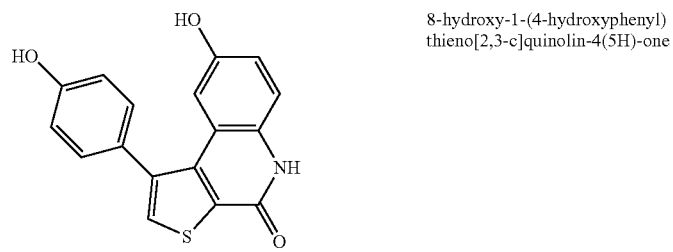 | 8-hydroxy-1-(4-hydroxyphenyl)thieno[2,3-c]quinolin-4(5H)-one |
| 21 | 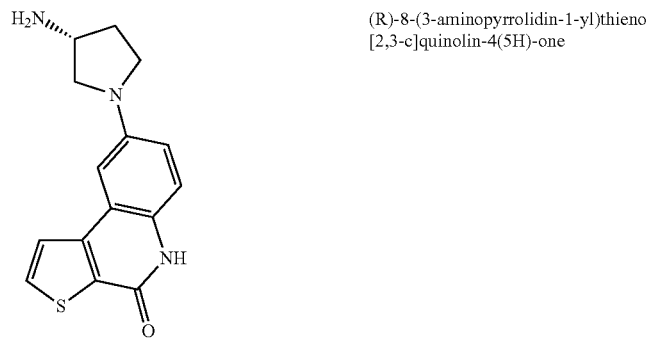 | (R)-8-(3-aminopyrrolidin-1-yl)thieno[2,3-c]quinolin-4(5H)-one |
| 22 | 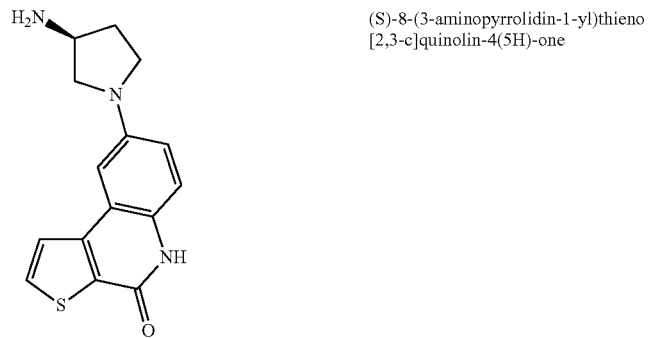 | (S)-8-(3-aminopyrrolidin-1-yl)thieno[2,3-c]quinolin-4(5H)-one |
| 23 | 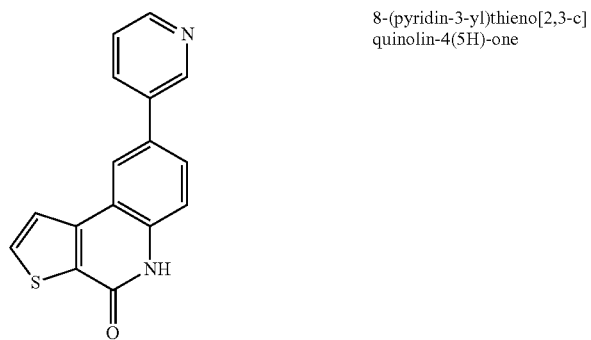 | 8-(pyridin-3-yl)thieno[2,3-c]quinolin-4(5H)-one |

TABLE 1-continued
| | | |
|---|---|---|
| 24 | 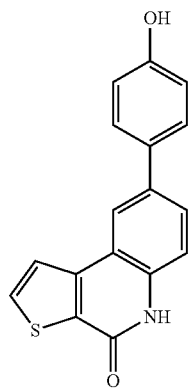 [SMILES: O=c1[nH]c2ccc(-c3ccc(O)cc3)cc2c2ccsc12] | 8-(4-hydroxyphenyl)thieno[2,3-c]quinolin-4(5H)-one |
| 25 | 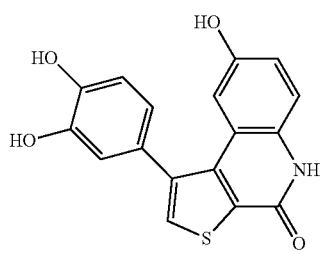 [SMILES: O=c1[nH]c2ccc(O)cc2c2c(-c3ccc(O)c(O)c3)csc12] | 1-(3,4-dihydroxyphenyl)-8-hydroxy thieno[2,3-c]quinolin-4(5H)-one |
| 26 | 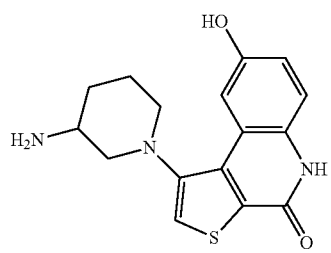 [SMILES: NC1CCCN(c2csc3c(=O)[nH]c4ccc(O)cc4c23)C1] | 1-(3-aminopiperidin-1-yl)-8-hydroxy thieno[2,3-c]quinolin-4(5H)-one |
| 27 | 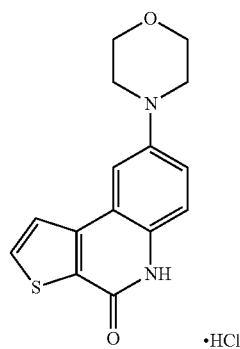 [SMILES: O=c1[nH]c2ccc(N3CCOCC3)cc2c2ccsc12 ; Cl] | 8-morpholinothieno[2,3-c]quinolin-4(5H)-one hydrochloride |
| 28 | 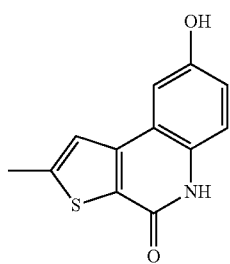 [SMILES: Cc1cc2c(s1)c(=O)[nH]c1ccc(O)cc12] | 8-hydroxy-2-methylthieno[2,3-c]quinolin-4(5H)-one |

TABLE 1-continued
| | | |
|---|---|---|
| 29 | 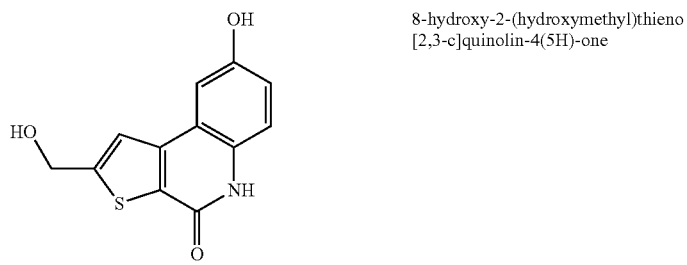 | 8-hydroxy-2-(hydroxymethyl)thieno[2,3-c]quinolin-4(5H)-one |
| 30 | 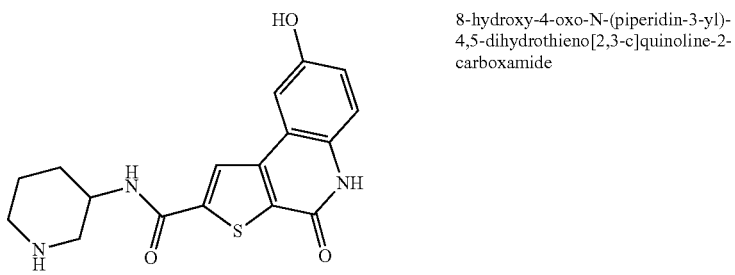 | 8-hydroxy-4-oxo-N-(piperidin-3-yl)-4,5-dihydrothieno[2,3-c]quinoline-2-carboxamide |
| 31 | 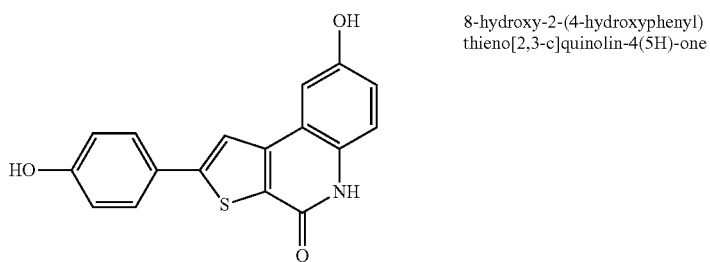 | 8-hydroxy-2-(4-hydroxyphenyl)thieno[2,3-c]quinolin-4(5H)-one |
| 32 | 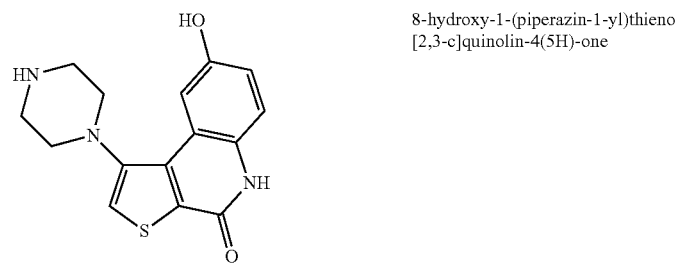 | 8-hydroxy-1-(piperazin-1-yl)thieno[2,3-c]quinolin-4(5H)-one |
| 33 | 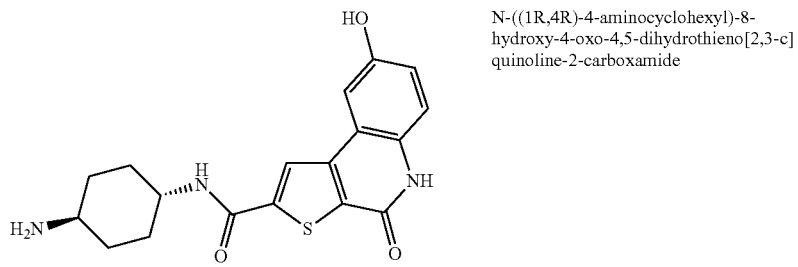 | N-((1R,4R)-4-aminocyclohexyl)-8-hydroxy-4-oxo-4,5-dihydrothieno[2,3-c]quinoline-2-carboxamide |
| 34 | 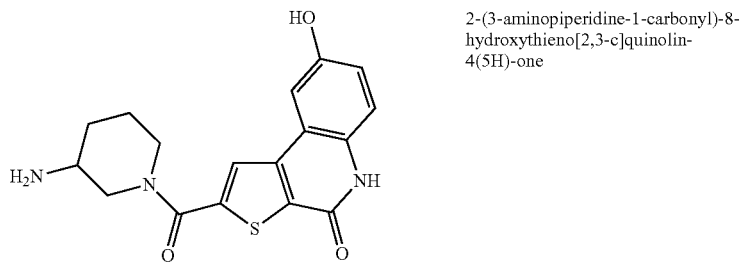 | 2-(3-aminopiperidine-1-carbonyl)-8-hydroxythieno[2,3-c]quinolin-4(5H)-one |

TABLE 1-continued
| | | |
|---|---|---|
| 35 | 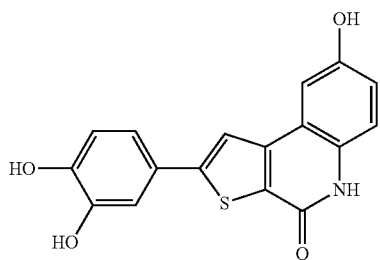 [SMILES: O=c1[nH]c2ccc(O)cc2c2cc(-c3ccc(O)c(O)c3)sc12] | 2-(3,4-dihydroxyphenyl)-8-hydroxy thieno[2,3-c]quinolin-4(5H)-one |
| 36 | 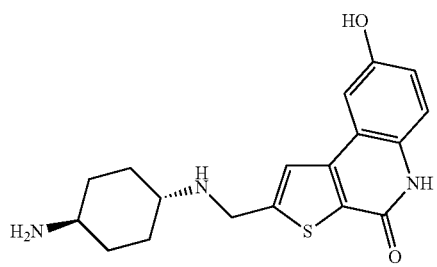 [SMILES: N[C@H]1CC[C@H](NCc2cc3c(s2)c(=O)[nH]c2ccc(O)cc23)CC1] | 2-(((1R,4R)-4-aminocyclohexylamino) methyl)-8-hydroxythieno[2,3-c] quinolin-4(5H)-one |
| 37 | 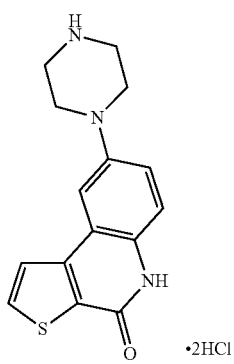 [SMILES: O=c1[nH]c2ccc(N3CCNCC3)cc2c2ccsc12 ; "·2HCl"] | 8-(piperazin-1-yl)thieno[2,3-c] quinolin-4(5H)-one dihydrochloride |
| 38 | 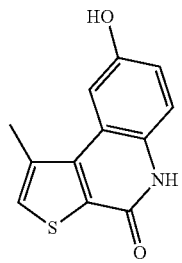 [SMILES: Cc1csc2c(=O)[nH]c3ccc(O)cc3c12] | 8-hydroxy-1-methylthieno[2,3-c] quinolin-4(5H)-one |
| 39 | 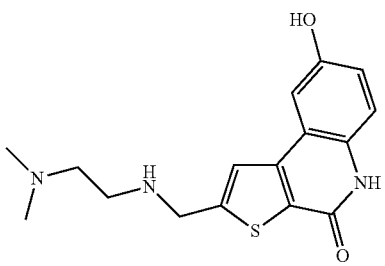 [SMILES: CN(C)CCNCc1cc2c(s1)c(=O)[nH]c1ccc(O)cc12] | 2-((2-(dimethylamino)ethylamino) methyl)-8-hydroxythieno[2,3-c] quinolin-4(5H)-one |

TABLE 1-continued
| | | |
|---|---|---|
| 40 | 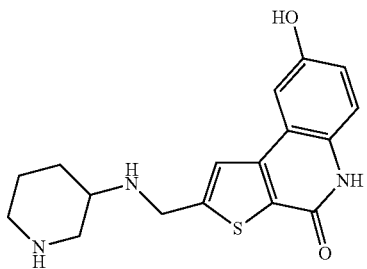 [SMILES: O=c1[nH]c2ccc(O)cc2c2cc(CNC3CCCNC3)sc12] | 8-hydroxy-2-((piperidin-3-ylamino)methyl)thieno[2,3-c]quinolin-4(5H)-one |
| 41 | 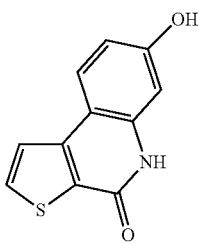 [SMILES: O=c1[nH]c2cc(O)ccc2c2ccsc12] | 7-hydroxythieno[2,3-c]quinolin-4(5H)-one |
| 42 | 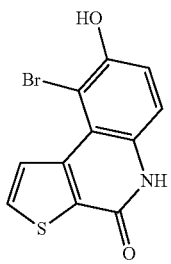 [SMILES: O=c1[nH]c2ccc(O)c(Br)c2c2ccsc12] | 9-bromo-8-hydroxythieno[2,3-c]quinolin-4(5H)-one |
| 43 | 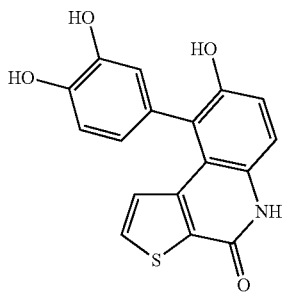 [SMILES: O=c1[nH]c2ccc(O)c(-c3ccc(O)c(O)c3)c2c2ccsc12] | 9-(3,4-dihydroxyphenyl)-8-hydroxythieno[2,3-c]quinolin-4(5H)-one |
| 44 | 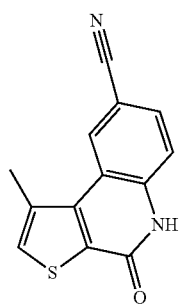 [SMILES: Cc1csc2c(=O)[nH]c3ccc(C#N)cc3c12] | 1-methyl-4-oxo-4,5-dihydrothieno[2,3-c]quinoline-8-carbonitrile |

TABLE 1-continued
| | | |
|---|---|---|
| 45 | 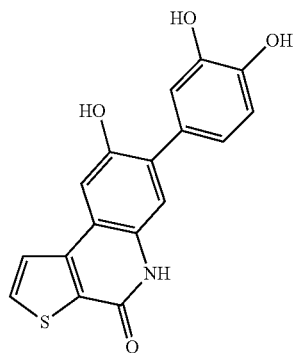 [SMILES: O=c1[nH]c2cc(-c3ccc(O)c(O)c3)c(O)cc2c2ccsc12] | 7-(3,4-dihydroxyphenyl)-8-hydroxy thieno[2,3-c]quinolin-4(5H)-one |
| 46 | 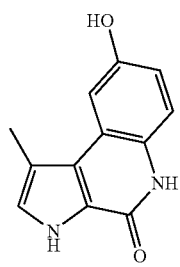 [SMILES: Cc1c[nH]c2c(=O)[nH]c3ccc(O)cc3c12] | 8-hydroxy-1-methyl-3H-pyrrolo[2,3-c]quinolin-4(5H)-one |
| 47 | 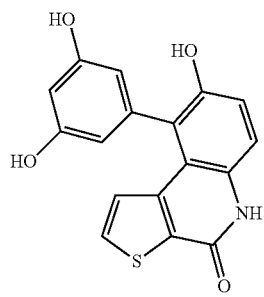 [SMILES: O=c1[nH]c2ccc(O)c(-c3cc(O)cc(O)c3)c2c2ccsc12] | 9-(3,5-dihydroxyphenyl)-8-hydroxy thieno[2,3-c]quinolin-4(5H)-one |
| 48 | 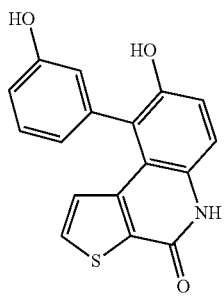 [SMILES: O=c1[nH]c2ccc(O)c(-c3cccc(O)c3)c2c2ccsc12] | 8-hydroxy-9-(3-hydroxyphenyl)thieno[2,3-c]quinolin-4(5H)-one |
| 49 | 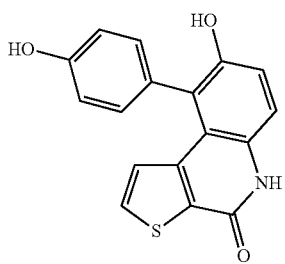 [SMILES: O=c1[nH]c2ccc(O)c(-c3ccc(O)cc3)c2c2ccsc12] | 8-hydroxy-9-(4-hydroxyphenyl)thieno[2,3-c]quinolin-4(5H)-one |

TABLE 1-continued
| | | |
|---|---|---|
| 50 | 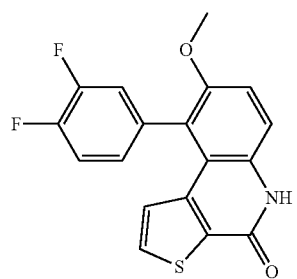 [SMILES: COc1ccc2[nH]c(=O)c3sccc3c2c1-c1ccc(F)c(F)c1] | 9-(3,4-difluorophenyl)-8-methoxy thieno[2,3-c]quinolin-4(5H)-one |
| 51 | 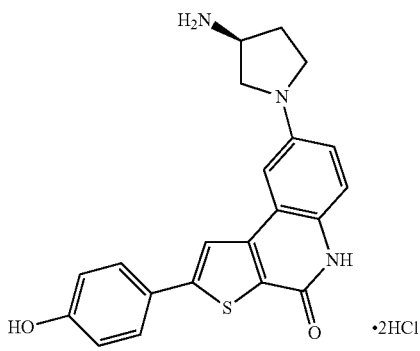 [SMILES: N[C@H]1CCN(c2ccc3[nH]c(=O)c4sc(-c5ccc(O)cc5)cc4c3c2)C1 ; "·2HCl"] •2HCl | (S)-8-(3-aminopyrrolidin-1-yl)-2-(4-hydroxyphenyl)thieno[2,3-c]quinolin-4(5H)-one dihydrochloride |
| 52 | 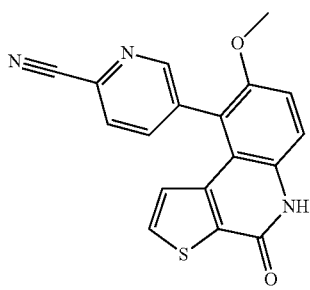 [SMILES: COc1ccc2[nH]c(=O)c3sccc3c2c1-c1ccc(C#N)nc1] | 5-(8-methoxy-4-oxo-4,5-dihydro thieno[2,3-c]quinolin-9-yl) picolinonitrile |
| 53 | 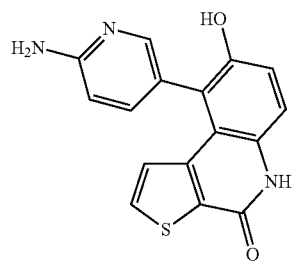 [SMILES: Nc1ccc(-c2c(O)ccc3[nH]c(=O)c4sccc4c23)cn1] | 9-(6-aminopyridin-3-yl)-8-hydroxy thieno[2,3-c]quinolin-4(5H)-one |
| 54 | 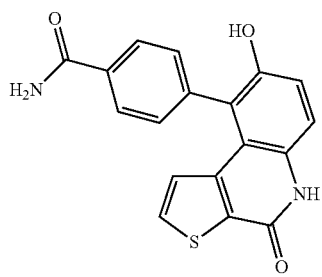 [SMILES: NC(=O)c1ccc(-c2c(O)ccc3[nH]c(=O)c4sccc4c23)cc1] | 4-(8-hydroxy-4-oxo-4,5-dihydro thieno[2,3-c]quinolin-9-yl)benzamide |

TABLE 1-continued
| | | |
|---|---|---|
| 55 | 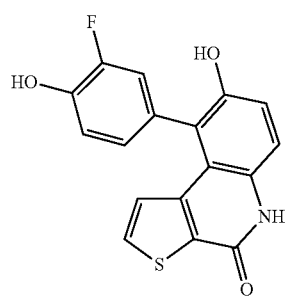 [SMILES: O=c1[nH]c2ccc(O)c(-c3ccc(O)c(F)c3)c2c2ccsc12] | 9-(3-fluoro-4-hydroxyphenyl)-8-hydroxythieno[2,3-c]quinolin-4(5H)-one |
| 56 | 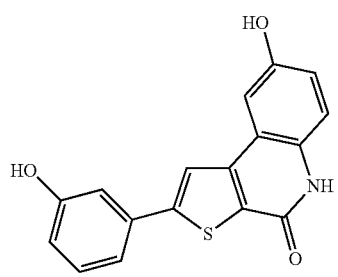 [SMILES: O=c1[nH]c2ccc(O)cc2c2cc(-c3cccc(O)c3)sc12] | 8-hydroxy-2-(3-hydroxyphenyl)thieno[2,3-c]quinolin-4(5H)-one |
| 57 | 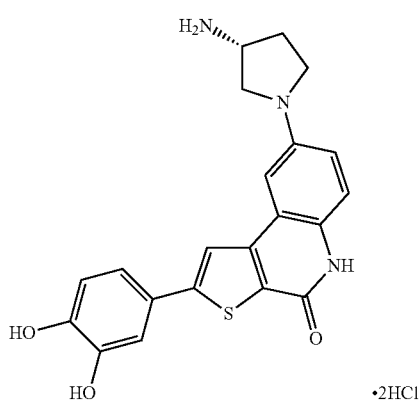 •2HCl | (R)-8-(3-aminopyrrolidin-1-yl)-2-(3,4-dihydroxyphenyl)thieno[2,3-c]quinolin-4(5H)-one dihydrochloride |
| 58 | 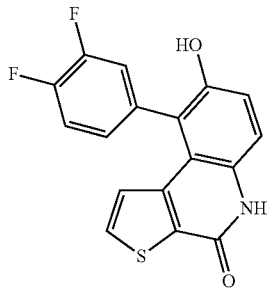 [SMILES: O=c1[nH]c2ccc(O)c(-c3ccc(F)c(F)c3)c2c2ccsc12] | 9-(3,4-difluorophenyl)-8-hydroxythieno[2,3-c]quinolin-4(5H)-one |
| 59 | 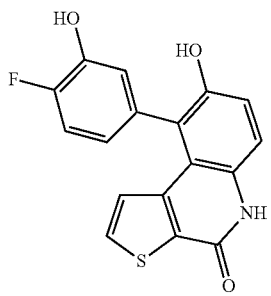 [SMILES: O=c1[nH]c2ccc(O)c(-c3ccc(F)c(O)c3)c2c2ccsc12] | 9-(4-fluoro-3-hydroxyphenyl)-8-hydroxythieno[2,3-c]quinolin-4(5H)-one |

TABLE 1-continued
| | | |
|---|---|---|
| 60 | 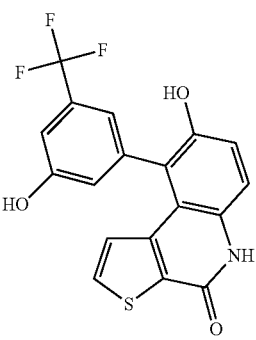 [SMILES: O=c1[nH]c2ccc(O)c(-c3cc(O)cc(C(F)(F)F)c3)c2c2ccsc12] | 8-hydroxy-9-(3-hydroxy-5-(trifluoro methyl)phenyl)thieno[2,3-c] quinolin-4(5H)-one |
| 61 | 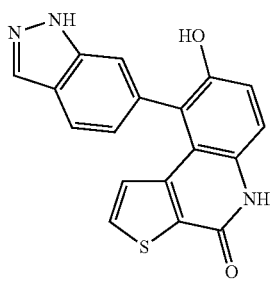 [SMILES: O=c1[nH]c2ccc(O)c(-c3ccc4cn[nH]c4c3)c2c2ccsc12] | 8-hydroxy-9-(1H-indazol-6-yl)thieno [2,3-c]quinolin-4(5H)-one |
| 62 | 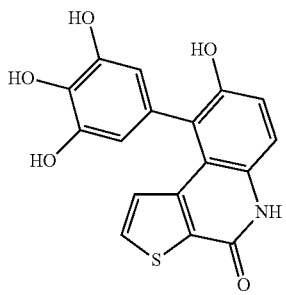 [SMILES: O=c1[nH]c2ccc(O)c(-c3cc(O)c(O)c(O)c3)c2c2ccsc12] | 8-hydroxy-9-(3,4,5-trihydroxy phenyl)thieno[2,3-c]quinolin-4(5H)-one |
| 63 | 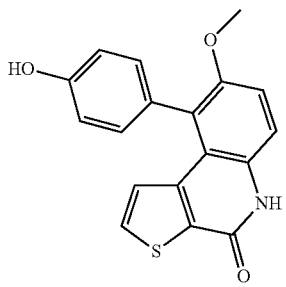 [SMILES: COc1ccc2[nH]c(=O)c3sccc3c2c1-c1ccc(O)cc1] | 9-(4-hydroxyphenyl)-8-methoxy thieno[2,3-c]quinolin-4(5H)-one |
| 64 | 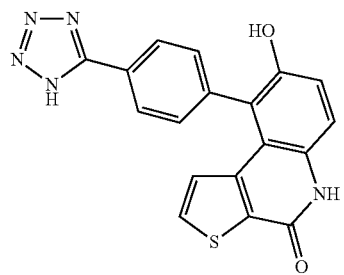 [SMILES: O=c1[nH]c2ccc(O)c(-c3ccc(-c4nnn[nH]4)cc3)c2c2ccsc12] | 9-(4-(1H-tetrazol-5-yl)phenyl)-8-hydroxythieno[2,3-c] quinolin-4(5H)-one |

TABLE 1-continued
| | | |
|---|---|---|
| 65 | 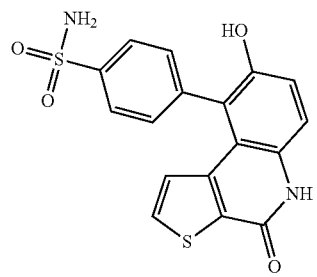 [SMILES: NS(=O)(=O)c1ccc(-c2c(O)ccc3[nH]c(=O)c4sccc4c23)cc1] | 4-(8-hydroxy-4-oxo-4,5-dihydro thieno[2,3-c]quinolin-9-yl) benzenesulfonamide |
| 66 | 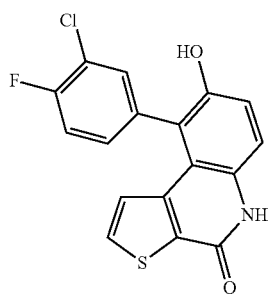 | 9-(3-chloro-4-fluorophenyl)-8-hydroxythieno[2,3-c]quinolin-4(5H)-one |
| 67 | 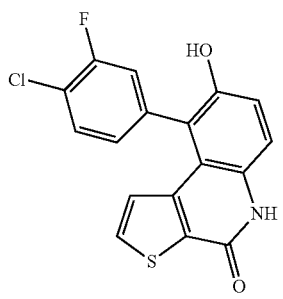 [SMILES: O=c1[nH]c2ccc(O)c(-c3ccc(Cl)c(F)c3)c2c2ccsc12] | 9-(4-chloro-3-fluorophenyl)-8-hydroxythieno[2,3-c]quinolin-4(5H)-one |
| 68 | 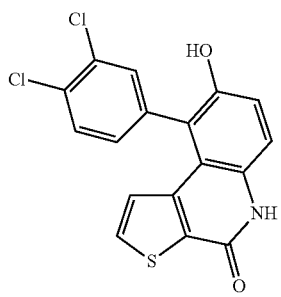 [SMILES: O=c1[nH]c2ccc(O)c(-c3ccc(Cl)c(Cl)c3)c2c2ccsc12] | 9-(3,4-dichlorophenyl)-8-hydroxy thieno[2,3-c]quinolin-4(5H)-one |
| 69 | 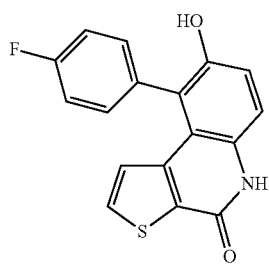 [SMILES: O=c1[nH]c2ccc(O)c(-c3ccc(F)cc3)c2c2ccsc12] | 9-(4-fluorophenyl)-8-hydroxythieno [2,3-c]quinolin-4(5H)-one |

TABLE 1-continued
| | | |
|---|---|---|
| 70 | 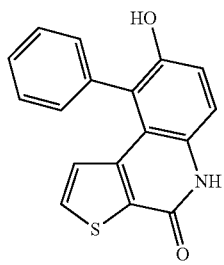 [SMILES: O=c1[nH]c2ccc(O)c(-c3ccccc3)c2c2ccsc12] | 8-hydroxy-9-phenylthieno[2,3-c]quinolin-4(5H)-one |
| 71 | 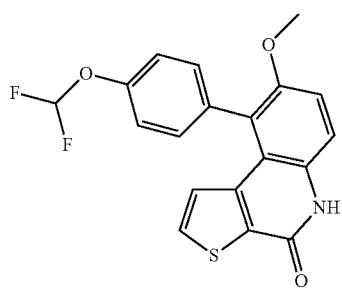 [SMILES: COc1ccc2[nH]c(=O)c3sccc3c2c1-c1ccc(OC(F)F)cc1] | 9-(4-(difluoromethoxy)phenyl)-8-methoxythieno[2,3-c]quinolin-4(5H)-one |
| 72 | 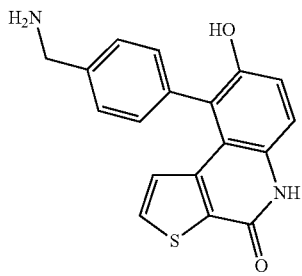 [SMILES: NCc1ccc(-c2c(O)ccc3[nH]c(=O)c4sccc4c23)cc1] | 9-(4-(aminomethyl)phenyl)-8-hydroxythieno[2,3-c]quinolin-4(5H)-one |
| 73 | 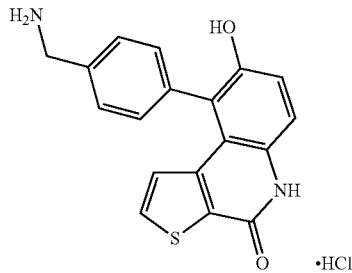 [SMILES: NCc1ccc(-c2c(O)ccc3[nH]c(=O)c4sccc4c23)cc1 ; Cl] | 9-(4-(aminomethyl)phenyl)-8-hydroxythieno[2,3-c]quinolin-4(5H)-one hydrochloride |
| 74 | 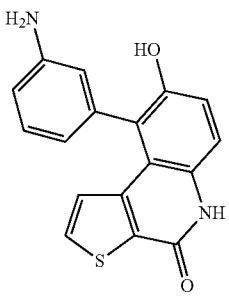 [SMILES: Nc1cccc(-c2c(O)ccc3[nH]c(=O)c4sccc4c23)c1] | 9-(3-aminophenyl)-8-hydroxythieno[2,3-c]quinolin-4(5H)-one |

TABLE 1-continued
| | | |
|---|---|---|
| 75 | 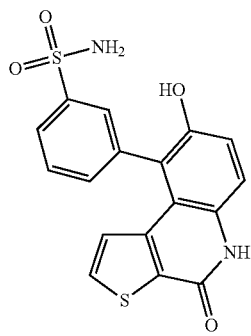 [SMILES: NS(=O)(=O)c1cccc(-c2c(O)ccc3[nH]c(=O)c4sccc4c23)c1] | 3-(8-hydroxy-4-oxo-4,5-dihydro thieno[2,3-c]quinolin-9-yl) benzenesulfonamide |
| 76 | 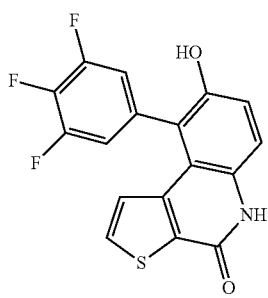 [SMILES: O=c1[nH]c2ccc(O)c(-c3cc(F)c(F)c(F)c3)c2c2ccsc12] | 8-hydroxy-9-(3,4,5-trifluorophenyl) thieno[2,3-c]quinolin-4(5H)-one |
| 77 | 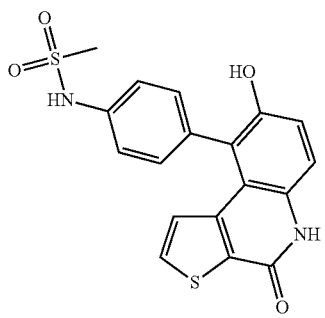 [SMILES: CS(=O)(=O)Nc1ccc(-c2c(O)ccc3[nH]c(=O)c4sccc4c23)cc1] | N-(4-(8-hydroxy-4-oxo-4,5-dihydro thieno[2,3-c]quinolin-9-yl)phenyl) methanesulfonamide |
| 78 | 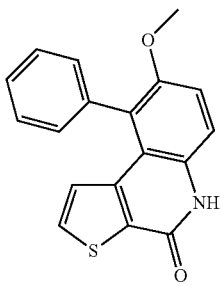 [SMILES: COc1ccc2[nH]c(=O)c3sccc3c2c1-c1ccccc1] | 8-methoxy-9-phenylthieno[2,3-c] quinolin-4(5H)-one |
| 79 | 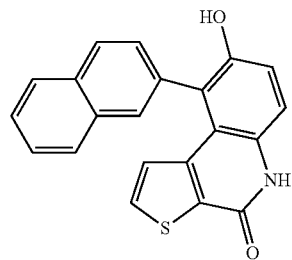 [SMILES: O=c1[nH]c2ccc(O)c(-c3ccc4ccccc4c3)c2c2ccsc12] | 8-hydroxy-9-(naphthalen-2-yl)thieno [2,3-c]quinolin-4(5H)-one |

TABLE 1-continued
| | | |
|---|---|---|
| 80 | 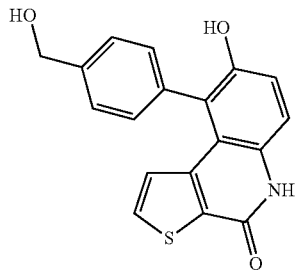 [SMILES: O=c1[nH]c2ccc(O)c(-c3ccc(CO)cc3)c2c2ccsc12] | 8-hydroxy-9-(4-(hydroxymethyl)phenyl)thieno[2,3-c]quinolin-4(5H)-one |
| 81 | 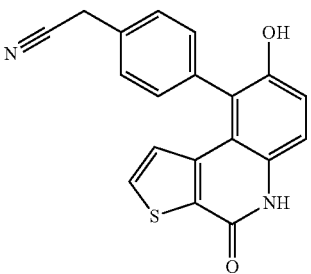 [SMILES: N#CCc1ccc(-c2c(O)ccc3[nH]c(=O)c4sccc4c23)cc1] | 2-(4-(8-hydroxy-4-oxo-4,5-dihydrothieno[2,3-c]quinolin-9-yl)phenyl)acetonitrile |
| 82 | 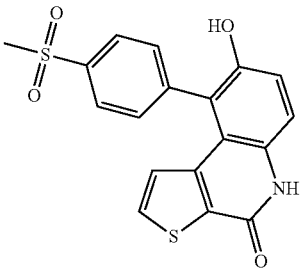 [SMILES: CS(=O)(=O)c1ccc(-c2c(O)ccc3[nH]c(=O)c4sccc4c23)cc1] | 8-hydroxy-9-(4-(methylsulfonyl)phenyl)thieno[2,3-c]quinolin-4(5H)-one |
| 83 | 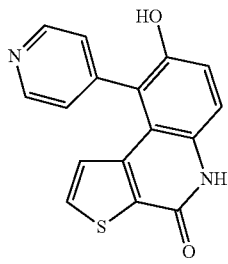 [SMILES: O=c1[nH]c2ccc(O)c(-c3ccncc3)c2c2ccsc12] | 8-hydroxy-9-(pyridin-4-yl)thieno[2,3-c]quinolin-4(5H)-one |
| 84 | 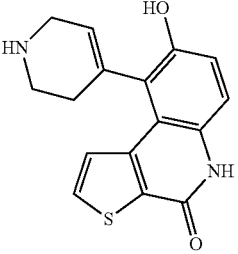 [SMILES: O=c1[nH]c2ccc(O)c(C3=CCNCC3)c2c2ccsc12] | 8-hydroxy-9-(1,2,3,6-tetrahydropyridin-4-yl)thieno[2,3-c]quinolin-4(5H)-one |

TABLE 1-continued
| | | |
|---|---|---|
| 85 | 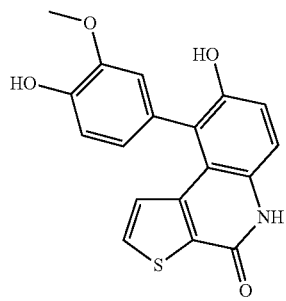 [SMILES: COc1cc(-c2c(O)ccc3[nH]c(=O)c4sccc4c23)ccc1O] | 8-hydroxy-9-(4-hydroxy-3-methoxy phenyl)thieno[2,3-c]quinolin-4(5H)-one |
| 86 | 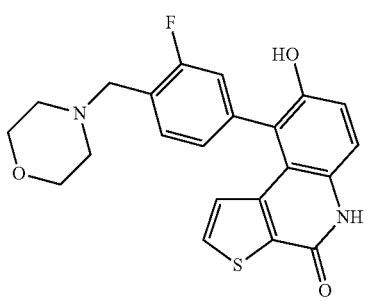 [SMILES: O=c1[nH]c2ccc(O)c(-c3ccc(CN4CCOCC4)c(F)c3)c2c2ccsc12] | 9-(3-fluoro-4-(morpholinomethyl) phenyl)-8-hydroxythieno[2,3-c] quinolin-4(5H)-one |
| 87 | 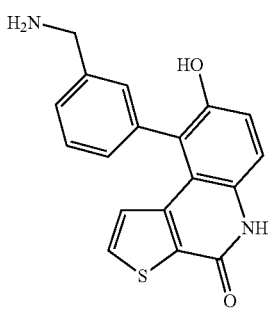 [SMILES: NCc1cccc(-c2c(O)ccc3[nH]c(=O)c4sccc4c23)c1] | 9-(3-(aminomethyl)phenyl)-8-hydroxythieno[2,3-c]quinolin-4(5H)-one |
| 88 | 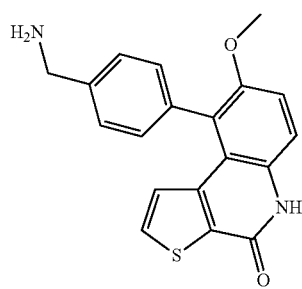 [SMILES: COc1ccc2[nH]c(=O)c3sccc3c2c1-c1ccc(CN)cc1] | 9-(4-(aminomethyl)phenyl)-8-methoxythieno[2,3-c]quinolin-4(5H)-one |
| 89 | 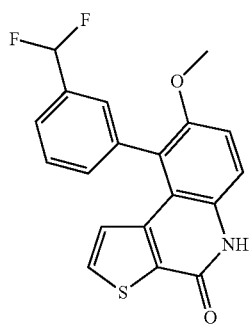 [SMILES: COc1ccc2[nH]c(=O)c3sccc3c2c1-c1cccc(C(F)F)c1] | 9-(3-(difluoromethyl)phenyl)-8-methoxythieno[2,3-c]quinolin-4(5H)-one |

TABLE 1-continued
| 90 | 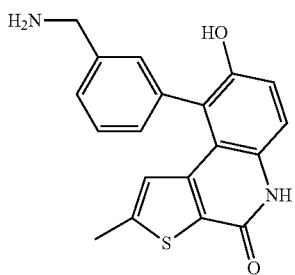 [SMILES: Cc1cc2c(s1)c(=O)[nH]c1ccc(O)c(-c3cccc(CN)c3)c12] | 9-(3-(aminomethyl)phenyl)-8-hydroxy-2-methylthieno[2,3-c]quinolin-4(5H)-one |
| --- | --- | --- |
| 91 | 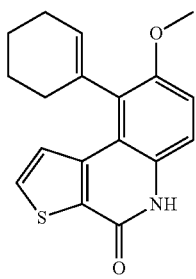 [SMILES: COc1ccc2[nH]c(=O)c3sccc3c2c1C1=CCCCC1] | 9-cyclohexenyl-8-methoxythieno[2,3-c]quinolin-4(5H)-one |
| 92 | 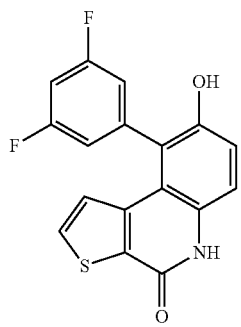 [SMILES: O=c1[nH]c2ccc(O)c(-c3cc(F)cc(F)c3)c2c2ccsc12] | 9-(3,5-difluorophenyl)-8-hydroxythieno[2,3-c]quinolin-4(5H)-one |
| 93 | 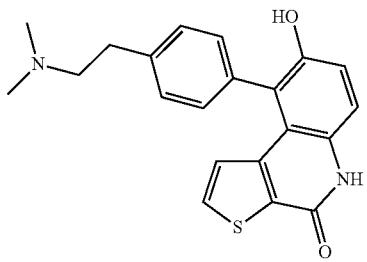 [SMILES: CN(C)CCc1ccc(-c2c(O)ccc3[nH]c(=O)c4sccc4c23)cc1] | 9-(4-(2-(dimethylamino)ethyl)phenyl)-8-hydroxythieno[2,3-c]quinolin-4(5H)-one |
| 94 | 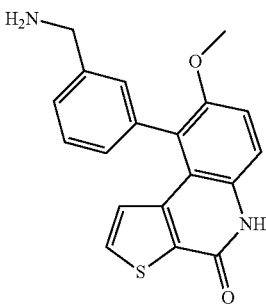 [SMILES: COc1ccc2[nH]c(=O)c3sccc3c2c1-c1cccc(CN)c1] | 9-(3-(aminomethyl)phenyl)-8-methoxythieno[2,3-c]quinolin-4(5H)-one |

TABLE 1-continued
| | | |
|---|---|---|
| 95 | 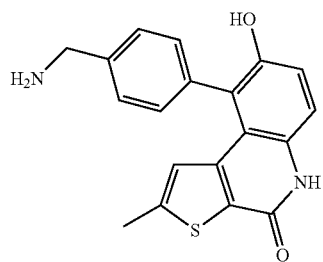 [SMILES: Cc1cc2c(s1)c(=O)[nH]c1ccc(O)c(-c3ccc(CN)cc3)c12] | 9-(4-(aminomethyl)phenyl)-8-hydroxy-2-methylthieno[2,3-c]quinolin-4(5H)-one |
| 96 | 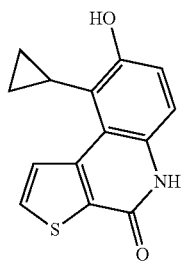 [SMILES: O=c1[nH]c2ccc(O)c(C3CC3)c2c2ccsc12] | 9-cyclopropyl-8-hydroxythieno[2,3-c]quinolin-4(5H)-one |
| 97 | 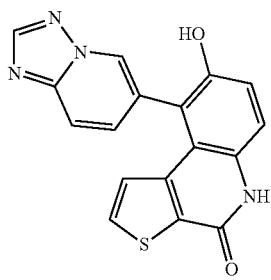 [SMILES: O=c1[nH]c2ccc(O)c(-c3ccc4ncnn4c3)c2c2ccsc12] | 9-([1,2,4]triazolo[1,5-a]pyridin-6-yl)-8-hydroxythieno[2,3-c]quinolin-4(5H)-one |
| 98 | 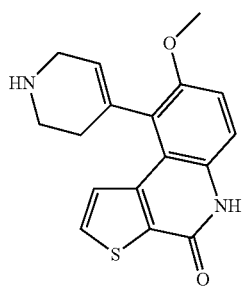 [SMILES: COc1ccc2[nH]c(=O)c3sccc3c2c1C1=CCNCC1] | 8-methoxy-9-(1,2,3,6-tetrahydropyridin-4-yl)thieno[2,3-c]quinolin-4(5H)-one |
| 99 | 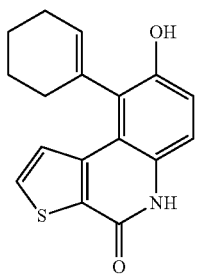 [SMILES: O=c1[nH]c2ccc(O)c(C3=CCCCC3)c2c2ccsc12] | 9-cyclohexenyl-8-hydroxythieno[2,3-c]quinolin-4(5H)-one |

TABLE 1-continued
| | | |
|---|---|---|
| 100 | 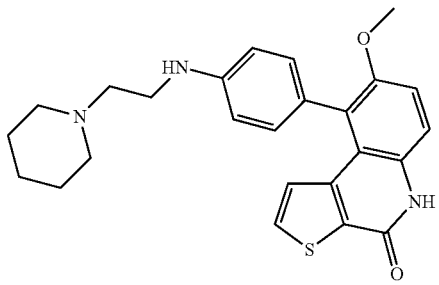 [SMILES: COc1ccc2[nH]c(=O)c3sccc3c2c1-c1ccc(NCCN2CCCCC2)cc1] | 8-methoxy-9-(4-(2-(piperidin-1-yl) ethylamino)phenyl)thieno[2,3-c] quinolin-4(5H)-one |
| 101 | 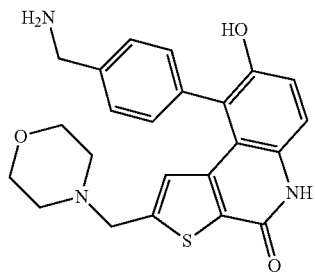 [SMILES: NCc1ccc(-c2c(O)ccc3[nH]c(=O)c4sc(CN5CCOCC5)cc4c23)cc1] | 9-(4-(aminomethyl)phenyl)-8-hydroxy-2-(morpholinomethyl) thieno[2,3-c]quinolin-4(5H)-one |
| 102 | 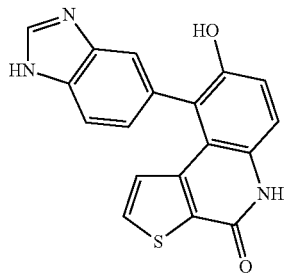 [SMILES: O=c1[nH]c2ccc(O)c(-c3ccc4[nH]cnc4c3)c2c2ccsc12] | 9-(1H-benzo[d]imidazol-5-yl)-8-hydroxythieno[2,3-c]quinolin-4(5H)-one |
| 103 | 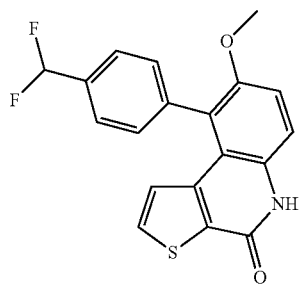 [SMILES: COc1ccc2[nH]c(=O)c3sccc3c2c1-c1ccc(C(F)F)cc1] | 9-(4-(difluoromethyl)phenyl)-8-methoxythieno[2,3-c]quinolin-4(5H)-one |
| 104 | 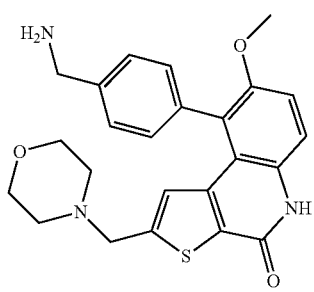 [SMILES: COc1ccc2[nH]c(=O)c3sc(CN4CCOCC4)cc3c2c1-c1ccc(CN)cc1] | 9-(4-(aminomethyl)phenyl)-8-methoxy-2-(morpholinomethyl) thieno[2,3-c]quinolin-4(5H)-one |

TABLE 1-continued
| | | |
|---|---|---|
| 105 | 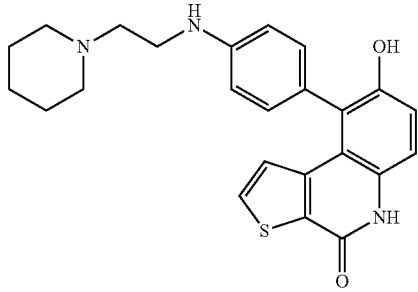 [SMILES: O=c1[nH]c2ccc(O)c(-c3ccc(NCCN4CCCCC4)cc3)c2c2ccsc12] | 8-hydroxy-9-(4-(2-(piperidin-1-yl)ethylamino)phenyl)thieno[2,3-c]quinolin-4(5H)-one |
| 106 | 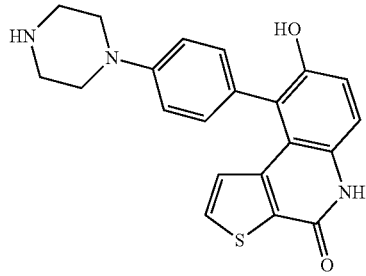 [SMILES: O=c1[nH]c2ccc(O)c(-c3ccc(N4CCNCC4)cc3)c2c2ccsc12] | 8-hydroxy-9-(4-(piperazin-1-yl)phenyl)thieno[2,3-c]quinolin-4(5H)-one |
| 107 | 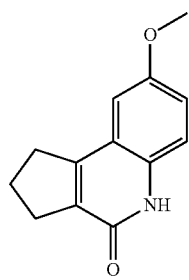 [SMILES: COc1ccc2[nH]c(=O)c3c(c2c1)CCC3] | 8-methoxy-2,3-dihydro-1H-cyclopenta[c]quinolin-4(5H)-one |
| 108 | 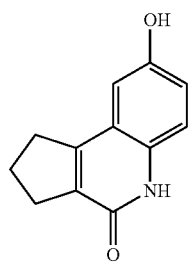 [SMILES: O=c1[nH]c2ccc(O)cc2c2c1CCC2] | 8-hydroxy-2,3-dihydro-1H-cyclopenta[c]quinolin-4(5H)-one |
| 109 | 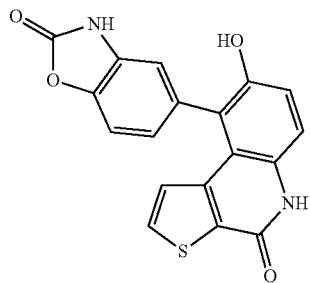 [SMILES: O=c1[nH]c2cc(-c3c(O)ccc4[nH]c(=O)c5sccc5c34)ccc2o1] | 5-(8-hydroxy-4-oxo-4,5-dihydrothieno[2,3-c]quinolin-9-yl)benzo[d]oxazol-2(3H)-one |

TABLE 1-continued

| | | |
|---|---|---|
| 110 | 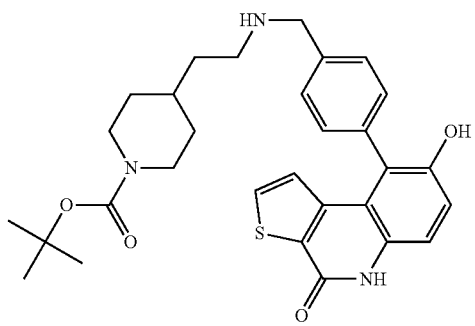 [SMILES: CC(C)(C)OC(=O)N1CCC(CCNCc2ccc(-c3c(O)ccc4[nH]c(=O)c5sccc5c34)cc2)CC1] | tert-butyl 4-(2-(hydroxy-4-oxo-4,5-dihydrothieno[2,3-c]quinolin-9-yl)benzylamino)ethyl)piperidine-1-carboxylate |
| 111 | 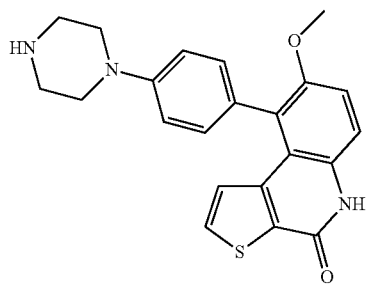 [SMILES: COc1ccc2[nH]c(=O)c3sccc3c2c1-c1ccc(N2CCNCC2)cc1] | 8-methoxy-9-(4-(piperazin-1-yl)phenyl)thieno[2,3-c]quinolin-4(5H)-one |
| 112 | 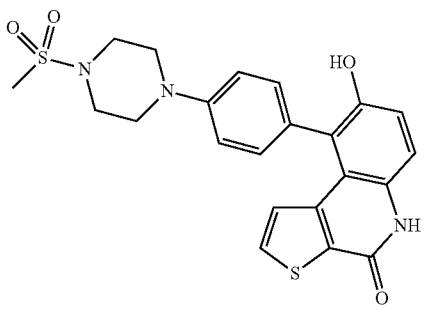 [SMILES: CS(=O)(=O)N1CCN(c2ccc(-c3c(O)ccc4[nH]c(=O)c5sccc5c34)cc2)CC1] | 8-hydroxy-9-(4-(4-(methylsulfonyl)piperazin-1-yl)phenyl)thieno[2,3-c]quinolin-4(5H)-one |
| 113 | 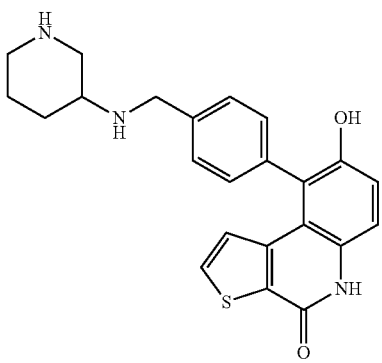 [SMILES: O=c1[nH]c2ccc(O)c(-c3ccc(CNC4CCCNC4)cc3)c2c2ccsc12] | 8-hydroxy-9-(4-((piperidin-3-ylamino)methyl)phenyl)thieno[2,3-c]quinolin-4(5H)-one |
| 114 | 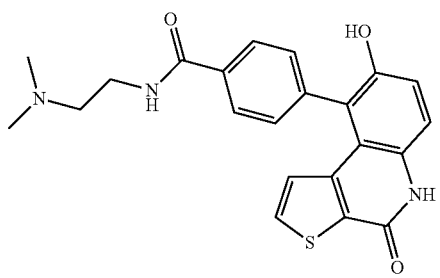 [SMILES: CN(C)CCNC(=O)c1ccc(-c2c(O)ccc3[nH]c(=O)c4sccc4c23)cc1] | N-(2-(dimethylamino)ethyl)-4-(8-hydroxy-4-oxo-4,5-dihydrothieno[2,3-c]quinolin-9-yl)benzamide |

TABLE 1-continued
| | | |
|---|---|---|
| 115 | 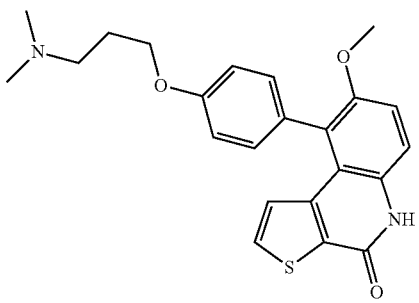 [SMILES: COc1ccc2[nH]c(=O)c3sccc3c2c1-c1ccc(OCCCN(C)C)cc1] | 9-(4-(3-(dimethylamino)propoxy)phenyl)-8-methoxythieno[2,3-c]quinolin-4(5H)-one |
| 116 | 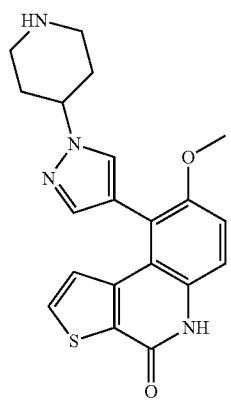 [SMILES: COc1ccc2[nH]c(=O)c3sccc3c2c1-c1cnn(C2CCNCC2)c1] | 8-methoxy-9-(1-(piperidin-4-yl)-1H-pyrazol-4-yl)thieno[2,3-c]quinolin-4(5H)-one |
| 117 | 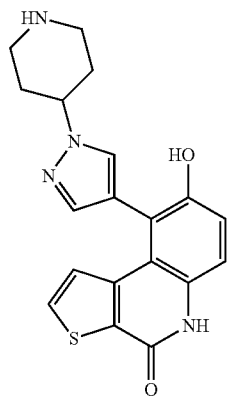 [SMILES: O=c1[nH]c2ccc(O)c(-c3cnn(C4CCNCC4)c3)c2c2ccsc12] | 8-hydroxy-9-(1-(piperidin-4-yl)-1H-pyrazol-4-yl)thieno[2,3-c]quinolin-4(5H)-one |
| 118 | 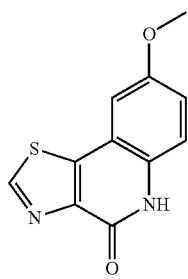 [SMILES: COc1ccc2[nH]c(=O)c3ncsc3c2c1] | 8-methoxythiazolo[4,5-c]quinolin-4(5H)-one |
| 119 | 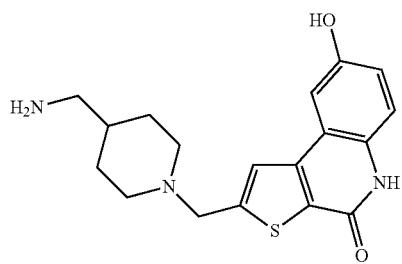 [SMILES: NCC1CCN(Cc2cc3c(s2)c(=O)[nH]c2ccc(O)cc23)CC1] | 2-((4-(aminomethyl)piperidin-1-yl)methyl)-8-hydroxythieno[2,3-c]quinolin-4(5H)-one |

TABLE 1-continued
| | | |
|---|---|---|
| 120 | 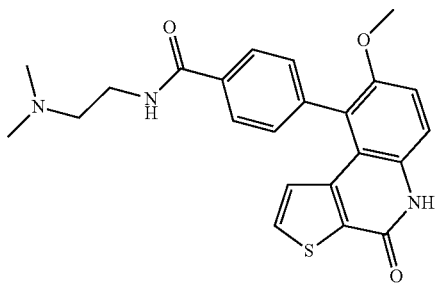 [SMILES: COc1ccc2[nH]c(=O)c3sccc3c2c1-c1ccc(C(=O)NCCN(C)C)cc1] | N-(2-(dimethylamino)ethyl)-4-(8-methoxy-4-oxo-4,5-dihydrothieno[2,3-c]quinolin-9-yl)benzamide |
| 121 | 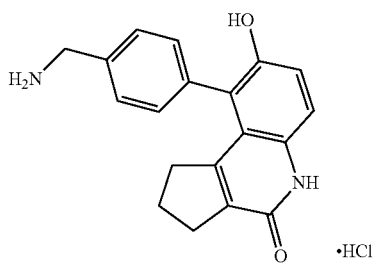 [SMILES: NCc1ccc(-c2c(O)ccc3[nH]c(=O)c4c(c23)CCC4)cc1 ; Cl] | 9-(4-(aminomethyl)phenyl)-8-hydroxy-2,3-dihydro-1H-cyclopenta[c]quinolin-4(5H)-one hydrochloride |
| 122 | 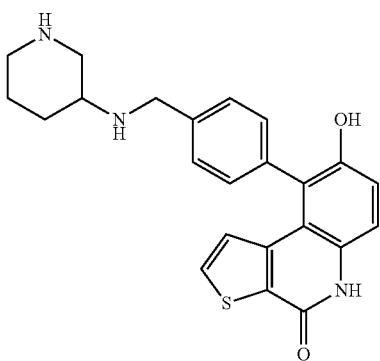 [SMILES: O=c1[nH]c2ccc(O)c(-c3ccc(CNC4CCCNC4)cc3)c2c2ccsc12] | (E)-butyl 3-(8-hydroxy-4-oxo-4,5-dihydrothieno[2,3-c]quinolin-9-yl)acrylate |
| 123 | 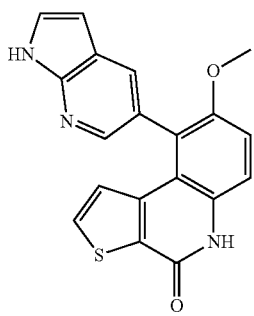 | 8-methoxy-9-(1H-pyrrolo[2,3-b]pyridin-5-yl)thieno[2,3-c]quinolin-4(5H)-one |
| 124 | 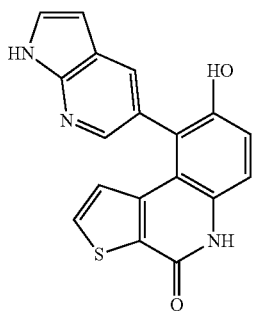 [SMILES: O=c1[nH]c2ccc(O)c(-c3cnc4[nH]ccc4c3)c2c2ccsc12] | 8-hydroxy-9-(1H-pyrrolo[2,3-b]pyridin-5-yl)thieno[2,3-c]quinolin-4(5H)-one |

TABLE 1-continued
| 125 | 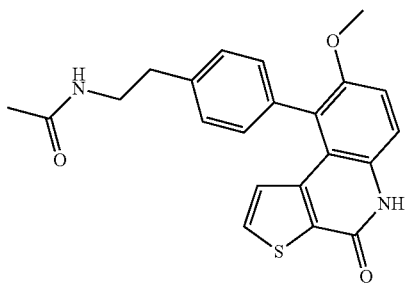 [SMILES: COc1ccc2[nH]c(=O)c3sccc3c2c1-c1ccc(CCNC(C)=O)cc1] | N-(methoxy-4-oxo-4,5-dihydrothieno[2,3-c]quinolin-9-yl)phenethyl)acetamide |
| 126 | 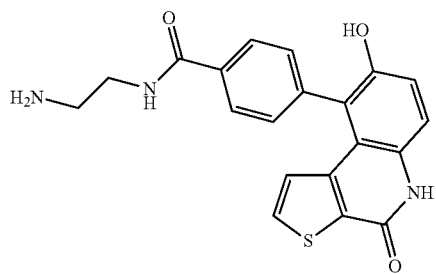 [SMILES: NCCNC(=O)c1ccc(-c2c(O)ccc3[nH]c(=O)c4sccc4c23)cc1] | N-(2-aminoethyl)-4-(8-hydroxy-4-oxo-4,5-dihydrothieno[2,3-c]quinolin-9-yl)benzamide |
| 127 | 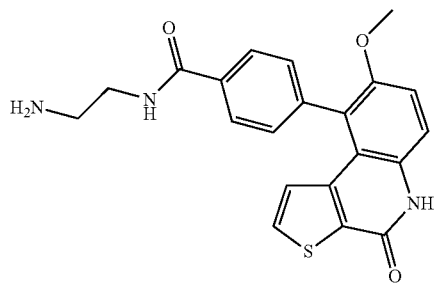 [SMILES: COc1ccc2[nH]c(=O)c3sccc3c2c1-c1ccc(C(=O)NCCN)cc1] | N-(2-aminoethyl)-4-(8-methoxy-4-oxo-4,5-dihydrothieno[2,3-c]quinolin-9-yl)benzamide |
| 128 | 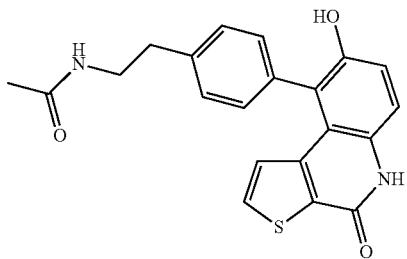 [SMILES: CC(=O)NCCc1ccc(-c2c(O)ccc3[nH]c(=O)c4sccc4c23)cc1] | N-(hydroxy-4-oxo-4,5-dihydrothieno[2,3-c]quinolin-9-yl)phenethyl)acetamide |
| 129 | 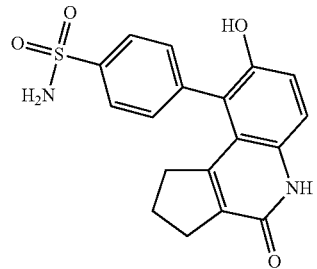 [SMILES: NS(=O)(=O)c1ccc(-c2c(O)ccc3[nH]c(=O)c4c(c23)CCC4)cc1] | 4-(8-hydroxy-4-oxo-2,3,4,5-tetrahydro-1H-cyclopenta[c]quinolin-9-yl)benzenesulfonamide |

TABLE 1-continued
| | | |
|---|---|---|
| 130 | 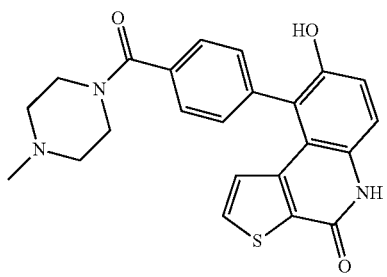 [SMILES: CN1CCN(C(=O)c2ccc(-c3c(O)ccc4[nH]c(=O)c5sccc5c34)cc2)CC1] | 8-hydroxy-9-(4-(4-methylpiperazine-1-carbonyl)phenyl)thieno[2,3-c]quinolin-4(5H)-one |
| 131 | 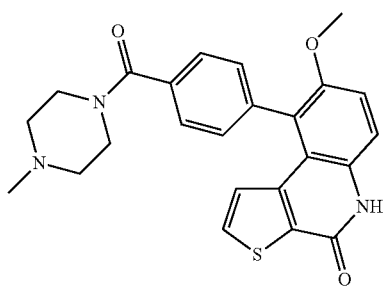 [SMILES: COc1ccc2[nH]c(=O)c3sccc3c2c1-c1ccc(C(=O)N2CCN(C)CC2)cc1] | 8-methoxy-9-(4-(4-methylpiperazine-1-carbonyl)phenyl)thieno[2,3-c]quinolin-4(5H)-one |
| 132 | 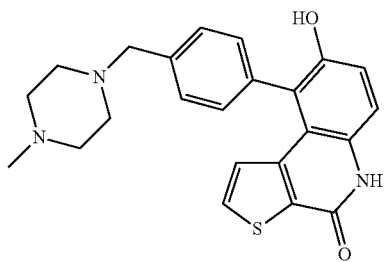 [SMILES: CN1CCN(Cc2ccc(-c3c(O)ccc4[nH]c(=O)c5sccc5c34)cc2)CC1] | 8-hydroxy-9-(4-((4-methylpiperazin-1-yl)methyl)phenyl)thieno[2,3-c]quinolin-4(5H)-one |
| 133 | 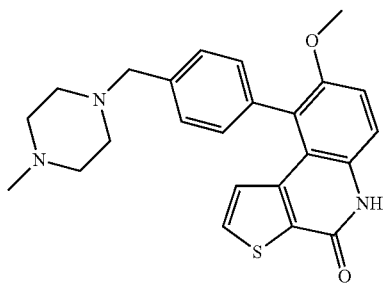 [SMILES: COc1ccc2[nH]c(=O)c3sccc3c2c1-c1ccc(CN2CCN(C)CC2)cc1] | 8-methoxy-9-(4-((4-methylpiperazin-1-yl)methyl)phenyl)thieno[2,3-c]quinolin-4(5H)-one |
| 134 | 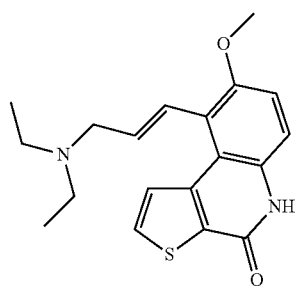 [SMILES: CCN(CC)C/C=C/c1c(OC)ccc2[nH]c(=O)c3sccc3c12] | (E)-9-(3-(diethylamino)prop-1-enyl)-8-methoxythieno[2,3-c]quinolin-4(5H)-one |

TABLE 1-continued

| | | |
|---|---|---|
| 135 | 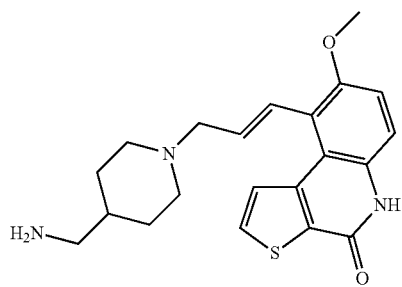 [SMILES: COc1ccc2[nH]c(=O)c3sccc3c2c1/C=C/CN1CCC(CN)CC1] | (E)-9-(3-(4-(aminomethyl)piperidin-1-yl)prop-1-enyl)-8-methoxythieno[2,3-c]quinolin-4(5H)-one |
| 136 | 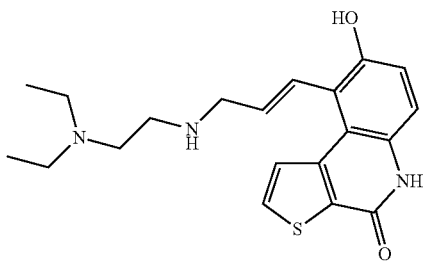 [SMILES: CCN(CC)CCNC/C=C/c1c(O)ccc2[nH]c(=O)c3sccc3c12] | (E)-9-(3-(2-(diethylamino)ethylamino)prop-1-enyl)-8-hydroxythieno[2,3-c]quinolin-4(5H)-one |
| 137 | 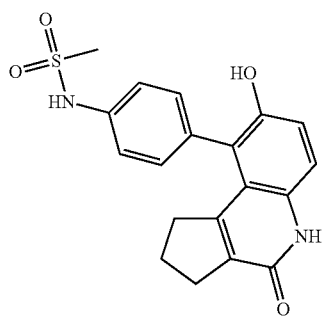 [SMILES: CS(=O)(=O)Nc1ccc(-c2c(O)ccc3[nH]c(=O)c4c(c23)CCC4)cc1] | N-(4-(8-hydroxy-4-oxo-2,3,4,5-tetrahydro-1H-cyclopenta[c]quinolin-9-yl)phenyl)methanesulfonamide |
| 138 | 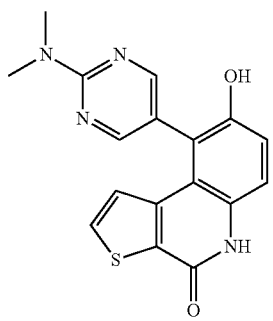 [SMILES: CN(C)c1ncc(-c2c(O)ccc3[nH]c(=O)c4sccc4c23)cn1] | 9-(2-(dimethylamino)pyrimidin-5-yl)-8-hydroxythieno[2,3-c]quinolin-4(5H)-one |
| 139 | 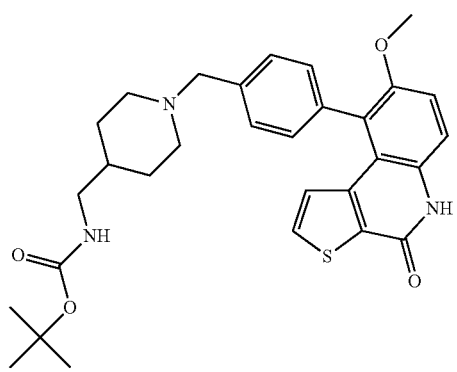 [SMILES: COc1ccc2[nH]c(=O)c3sccc3c2c1-c1ccc(CN2CCC(CNC(=O)OC(C)(C)C)CC2)cc1] | tert-butyl (1-(methoxy-4-oxo-4,5-dihydrothieno[2,3-c]quinolin-9-yl)benzyl)piperidin-4-yl)methyl carbamate |

TABLE 1-continued
| | | |
|---|---|---|
| 140 | 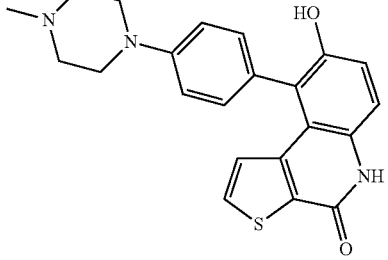 | 8-hydroxy-9-(4-(4-methylpiperazin-1-yl)phenyl)thieno[2,3-c]quinolin-4(5H)-one |
| 141 | 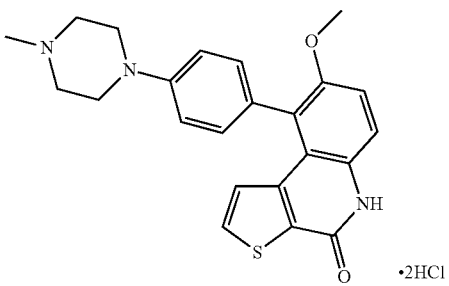 [SMILES: COc1ccc2[nH]c(=O)c3sccc3c2c1-c1ccc(N2CCN(C)CC2)cc1 ; "·2HCl"] ·2HCl | 8-methoxy-9-(4-(4-methylpiperazin-1-yl)phenyl)thieno[2,3-c]quinolin-4(5H)-one diydrochloride |
| 142 | 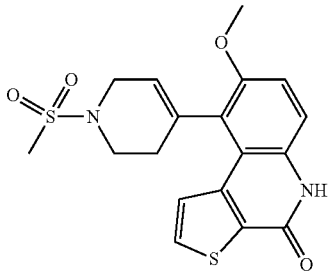 [SMILES: COc1ccc2[nH]c(=O)c3sccc3c2c1C1=CCN(S(C)(=O)=O)CC1] | 8-methoxy-9-(1-(methylsulfonyl)-1,2,3,6-tetrahydropyridin-4-yl)thieno[2,3-c]quinolin-4(5H)-one |
| 143 | 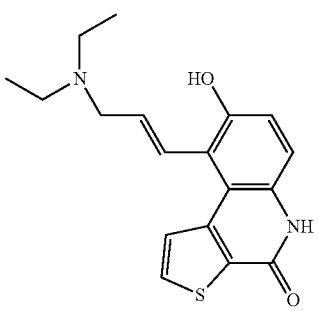 [SMILES: CCN(CC)C/C=C/c1c(O)ccc2[nH]c(=O)c3sccc3c12] | (E)-9-(3-(diethylamino)prop-1-enyl)-8-hydroxythieno[2,3-c]quinolin-4(5H)-one |
| 144 | 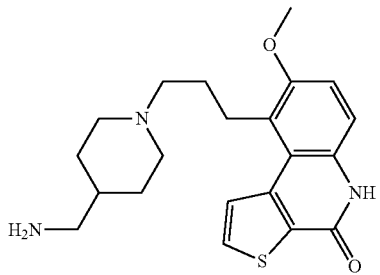 [SMILES: COc1ccc2[nH]c(=O)c3sccc3c2c1CCCN1CCC(CN)CC1] | 9-(3-(4-(aminomethyl)piperidin-1-yl)propyl)-8-methoxythieno[2,3-c]quinolin-4(5H)-one |

TABLE 1-continued

| 145 | | 9-(4-(3-(2-(diethylamino)ethylamino)propoxy)phenyl)-8-methoxythieno[2,3-c]quinolin-4(5H)-one |
| --- | --- | --- |
| 146 | | 9-(4-(3-diethylamino)propoxy)phenyl)-8-methoxythieno[2,3-c]quinolin-4(5H)-one |
| 147 | | 9-(4-(3-(2-(diethylamino)ethylamino)propoxy)phenyl)-8-hydroxythieno[2,3-c]quinolin-4(5H)-one |
| 148 | | (E)-9-(3-(4-(aminomethyl)piperidin-1-yl)prop-1-enyl)-8-hydroxythieno[2,3-c]quinolin-4(5H)-one |
| 149 | | 9-(4-(3-(dimethylamino)propoxy)phenyl)-8-hydroxythieno[2,3-c]quinolin-4(5H)-one |

TABLE 1-continued
| 150 | 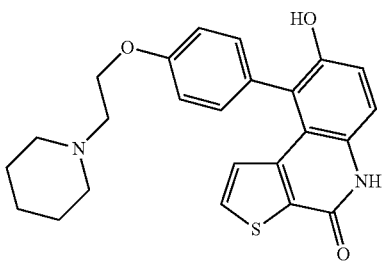 [SMILES: O=c1[nH]c2ccc(O)c(-c3ccc(OCCN4CCCCC4)cc3)c2c2ccsc12] | 8-hydroxy-9-(4-(2-(piperidin-1-yl)ethoxy)phenyl)thieno[2,3-c]quinolin-4(5H)-one |
| 151 | 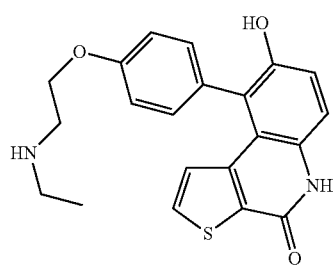 [SMILES: CCNCCOc1ccc(-c2c(O)ccc3[nH]c(=O)c4sccc4c23)cc1] | 9-(4-(2-(ethylamino)ethoxy)phenyl)-8-hydroxythieno[2,3-c]quinolin-4(5H)-one |
| 152 | 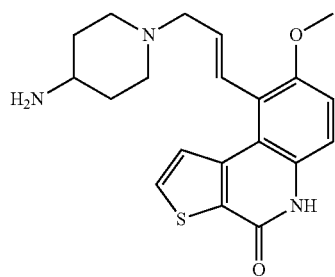 [SMILES: COc1ccc2[nH]c(=O)c3sccc3c2c1/C=C/CN1CCC(N)CC1] | (E)-9-(3-(4-aminopiperidin-1-yl)prop-1-enyl)-8-methoxythieno[2,3-c]quinolin-4(5H)-one |
| 153 | 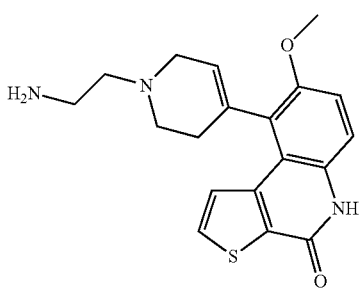 [SMILES: COc1ccc2[nH]c(=O)c3sccc3c2c1C1=CCN(CCN)CC1] | 9-(1-(2-aminoethyl)-1,2,3,6-tetrahydropyridin-4-yl)-8-methoxythieno[2,3-c]quinolin-4(5H)-one |
| 154 | 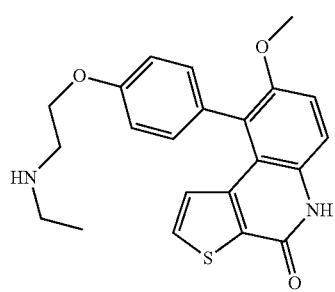 [SMILES: CCNCCOc1ccc(-c2c(OC)ccc3[nH]c(=O)c4sccc4c23)cc1] | 9-(4-(2-(ethylamino)ethoxy)phenyl)-8-methoxythieno[2,3-c]quinolin-4(5H)-one |

TABLE 1-continued
| | | |
|---|---|---|
| 155 | 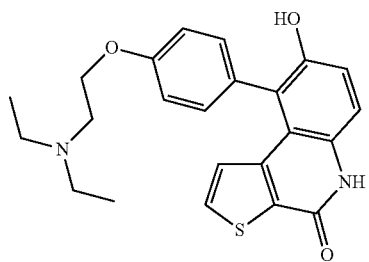 [SMILES: CCN(CC)CCOc1ccc(-c2c(O)ccc3[nH]c(=O)c4sccc4c23)cc1] | 9-(4-(2-(diethylamino)ethoxy)phenyl)-8-hydroxythieno[2,3-c]quinolin-4(5H)-one |
| 156 | 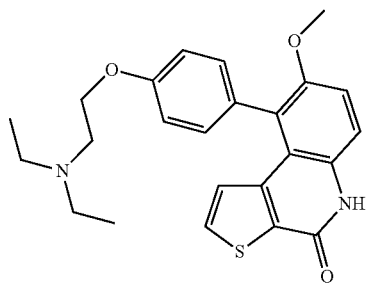 [SMILES: CCN(CC)CCOc1ccc(-c2c(OC)ccc3[nH]c(=O)c4sccc4c23)cc1] | 9-(4-(2-(diethylamino)ethoxy)phenyl)-8-methoxythieno[2,3-c]quinolin-4(5H)-one |
| 157 | 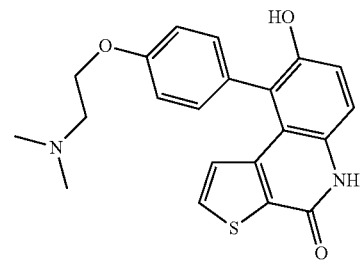 [SMILES: CN(C)CCOc1ccc(-c2c(O)ccc3[nH]c(=O)c4sccc4c23)cc1] | 9-(4-(2-(dimethylamino)ethoxy)phenyl)-8-hydroxythieno[2,3-c]quinolin-4(5H)-one |
| 158 | 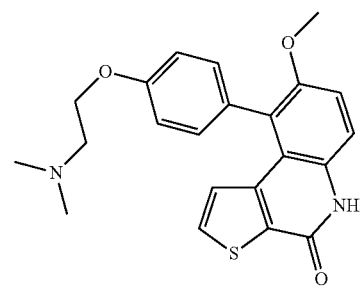 [SMILES: COc1ccc2[nH]c(=O)c3sccc3c2c1-c1ccc(OCCN(C)C)cc1] | 9-(4-(2-(dimethylamino)ethoxy)phenyl)-8-methoxythieno[2,3-c]quinolin-4(5H)-one |
| 159 | 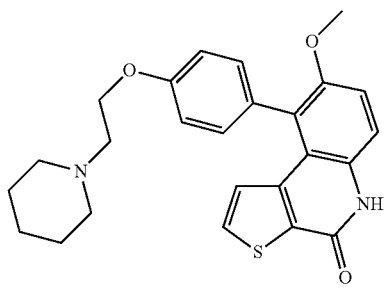 [SMILES: COc1ccc2[nH]c(=O)c3sccc3c2c1-c1ccc(OCCN2CCCCC2)cc1] | 8-methoxy-9-(4-(2-(piperidin-1-yl)ethoxy)phenyl)thieno[2,3-c]quinolin-4(5H)-one |

TABLE 1-continued
| | | |
|---|---|---|
| 160 | 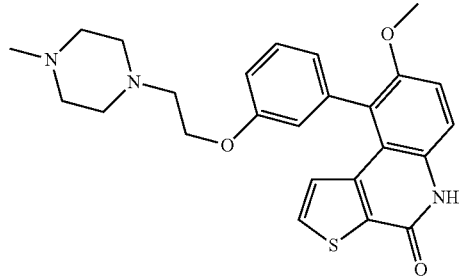 [SMILES: COc1ccc2[nH]c(=O)c3sccc3c2c1-c1cccc(OCCN2CCN(C)CC2)c1] | 8-methoxy-9-(3-(2-(4-methyl piperazin-1-yl)ethoxy)phenyl) thieno[2,3-c]quinolin-4(5H)-one |
| 161 | 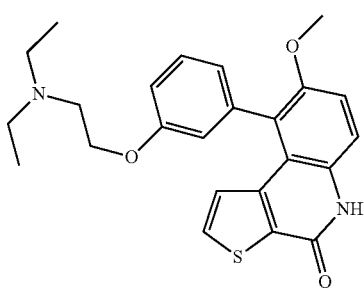 [SMILES: CCN(CC)CCOc1cccc(-c2c(OC)ccc3[nH]c(=O)c4sccc4c23)c1] | 9-(3-(2-(diethylamino)ethoxy)phenyl)-8-methoxythieno[2,3-c]quinolin-4(5H)-one |
| 162 | 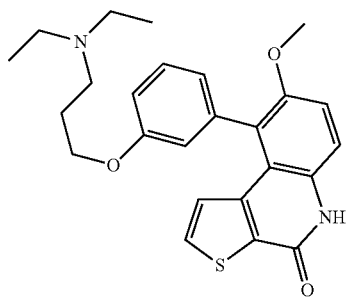 [SMILES: CCN(CC)CCCOc1cccc(-c2c(OC)ccc3[nH]c(=O)c4sccc4c23)c1] | 9-(3-(3-(diethylamino)propoxy)phenyl)-8-methoxythieno[2,3-c]quinolin-4(5H)-one |
| 163 | 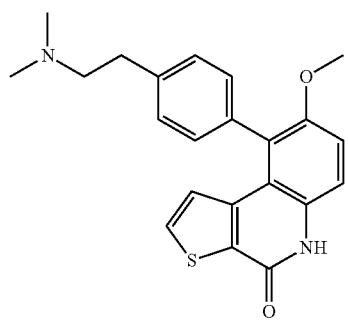 | 9-(4-(2-(dimethylamino)ethyl)phenyl)-8-methoxythieno[2,3-c]quinolin-4(5H)-one |
| 164 | 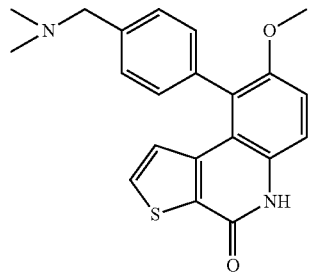 | 9-(4-((dimethylamino)methyl)phenyl)-8-methoxythieno[2,3-c]quinolin-4(5H)-one |

TABLE 1-continued

| | | |
|---|---|---|
| 165 | 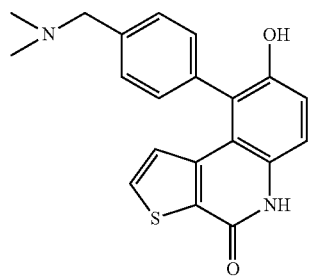 [SMILES: CN(C)Cc1ccc(-c2c(O)ccc3[nH]c(=O)c4sccc4c23)cc1] | 9-(4-((dimethylamino)methyl)phenyl)-8-hydroxythieno[2,3-c]quinolin-4(5H)-one |
| 166 | 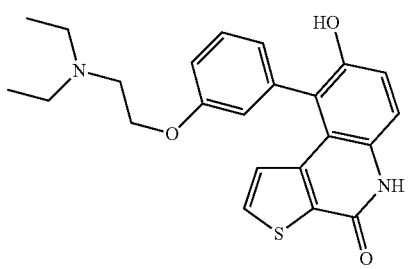 [SMILES: CCN(CC)CCOc1cccc(-c2c(O)ccc3[nH]c(=O)c4sccc4c23)c1] | 9-(3-(2-(diethylamino)ethoxy)phenyl)-8-hydroxythieno[2,3-c]quinolin-4(5H)-one |
| 167 | 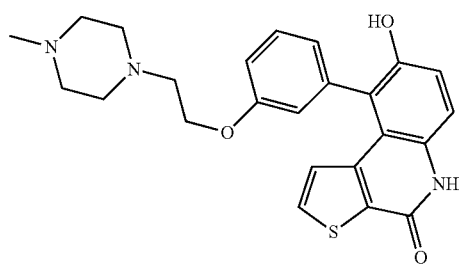 [SMILES: CN1CCN(CCOc2cccc(-c3c(O)ccc4[nH]c(=O)c5sccc5c34)c2)CC1] | 8-hydroxy-9-(3-(2-(4-methylpiperazin-1-yl)ethoxy)phenyl)thieno[2,3-c]quinolin-4(5H)-one |
| 168 | 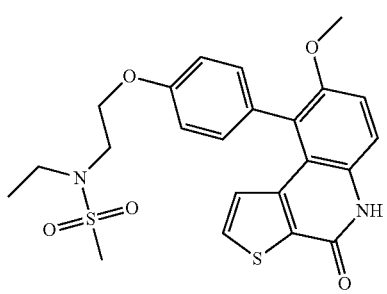 [SMILES: CCN(CCOc1ccc(-c2c(OC)ccc3[nH]c(=O)c4sccc4c23)cc1)S(C)(=O)=O] | N-ethyl-N-(2-(4-(8-methoxy-4-oxo-4,5-dihydrothieno[2,3-c]quinolin-9-yl)phenylmethoxy-4-oxo-4,5-dihydrothieno[2,3-c]quinolin-9-yl)phenoxy)ethyl)methanesulfonamide |
| 169 | 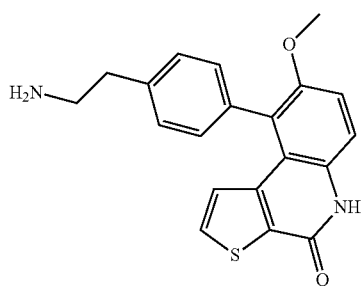 [SMILES: COc1ccc2[nH]c(=O)c3sccc3c2c1-c1ccc(CCN)cc1] | 9-(4-(2-aminoethyl)phenyl)-8-methoxythieno[2,3-c]quinolin-4(5H)-one |

| | | |
|---|---|---|
| 170 | 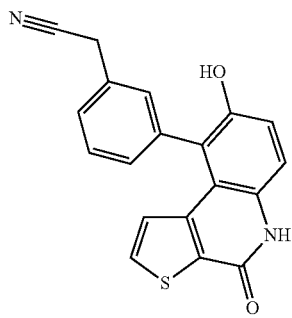 [SMILES: N#CCc1cccc(-c2c(O)ccc3[nH]c(=O)c4sccc4c23)c1] | 2-(3-(8-hydroxy-4-oxo-4,5-dihydro thieno[2,3-c]quinolin-9-yl)phenyl) acetonitrile |
| 171 | 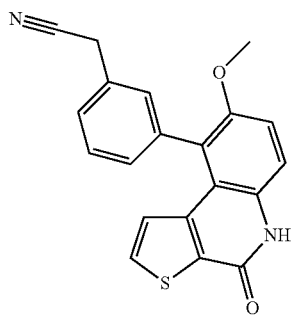 [SMILES: COc1ccc2[nH]c(=O)c3sccc3c2c1-c1cccc(CC#N)c1] | 2-(3-(8-methoxy-4-oxo-4,5-dihydro thieno[2,3-c]quinolin-9-yl)phenyl) acetonitrile |
| 172 | 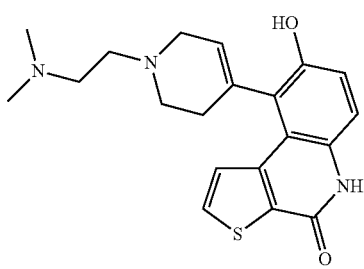 [SMILES: CN(C)CCN1CC=C(c2c(O)ccc3[nH]c(=O)c4sccc4c23)CC1] | 9-(1-(2-(dimethylamino)ethyl)-1,2,3, 6-tetrahydropyridin-4-yl)-8-hydroxy thieno[2,3-c]quinolin-4(5H)-one |
| 173 | 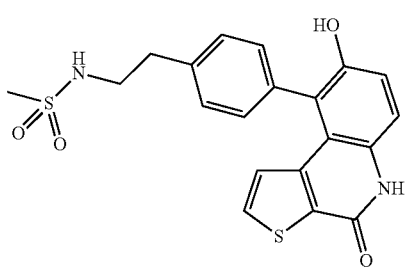 [SMILES: CS(=O)(=O)NCCc1ccc(-c2c(O)ccc3[nH]c(=O)c4sccc4c23)cc1] | N-(hydroxy-4-oxo-4,5-dihydrothieno [2,3-c]quinolin-9-yl)phenethyl) methanesulfonamide |
| 174 | 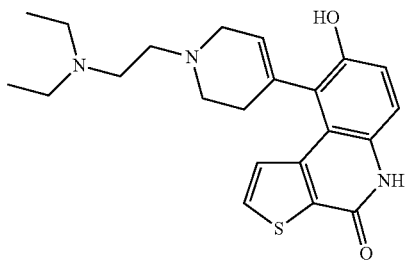 [SMILES: CCN(CC)CCN1CC=C(c2c(O)ccc3[nH]c(=O)c4sccc4c23)CC1] | 9-(1-(2-(diethylamino)ethyl)-1,2,3,6-tetrahydropyridin-4-yl)-8-hydroxy thieno[2,3-c]quinolin-4(5H)-one |

TABLE 1-continued

| | | |
|---|---|---|
| 175 | 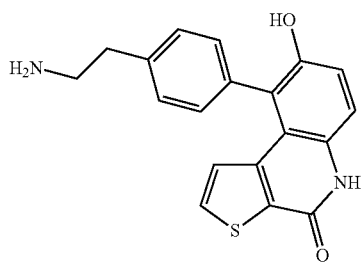 [SMILES: NCCc1ccc(-c2c(O)ccc3[nH]c(=O)c4sccc4c23)cc1] | 9-(4-(2-aminoethyl)phenyl)-8-hydroxythieno[2,3-c]quinolin-4(5H)-one |
| 176 | 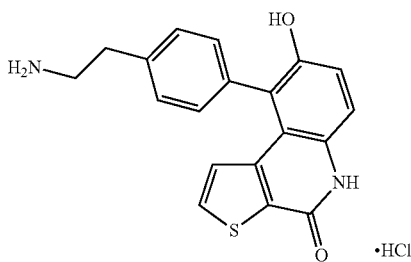 [SMILES: NCCc1ccc(-c2c(O)ccc3[nH]c(=O)c4sccc4c23)cc1 ; Cl] | 9-(4-(2-aminoethyl)phenyl)-8-hydroxythieno[2,3-c]quinolin-4(5H)-one hydrochloride |
| 177 | 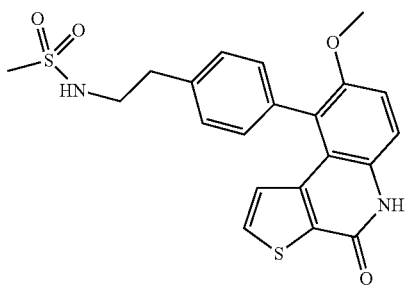 [SMILES: COc1ccc2[nH]c(=O)c3sccc3c2c1-c1ccc(CCNS(C)(=O)=O)cc1] | N-(methoxy-4-oxo-4,5-dihydrothieno[2,3-c]quinolin-9-yl)phenethyl)methanesulfonamide |
| 178 | 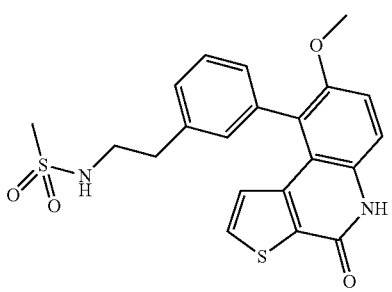 [SMILES: COc1ccc2[nH]c(=O)c3sccc3c2c1-c1cccc(CCNS(C)(=O)=O)c1] | N-(methoxy-4-oxo-4,5-dihydrothieno[2,3-c]quinolin-9-yl)phenethyl)methanesulfonamide |
| 179 | 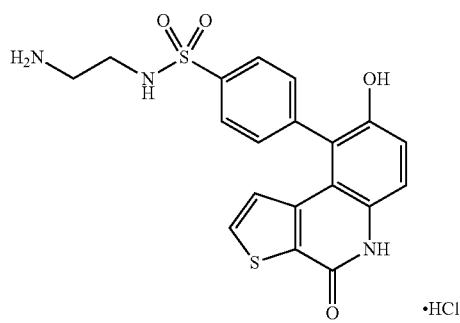 [SMILES: NCCNS(=O)(=O)c1ccc(-c2c(O)ccc3[nH]c(=O)c4sccc4c23)cc1 ; Cl] | N-(2-aminoethyl)-4-(8-hydroxy-4-oxo-4,5-dihydrothieno[2,3-c]quinolin-9-yl)benzenesulfonamide hydrochloride |

TABLE 1-continued

| | | |
|---|---|---|
| 180 | 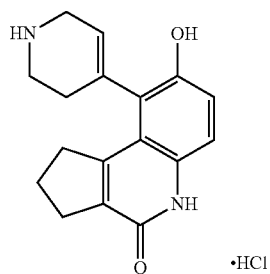 [SMILES: O=c1[nH]c2ccc(O)c(C3=CCNCC3)c2c2c1CCC2 ; Cl] | 8-hydroxy-9-(1,2,3,6-tetrahydro pyridin-4-yl)-2,3-dihydro-1H-cyclo penta[c]quinolin-4(5H)-one hydrochloride |
| 181 | 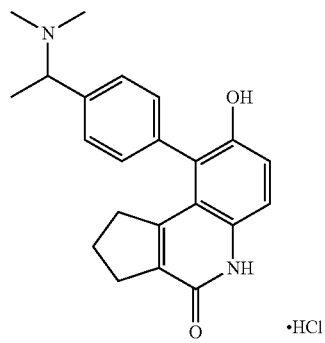 [SMILES: CC(c1ccc(-c2c(O)ccc3[nH]c(=O)c4c(c23)CCC4)cc1)N(C)C ; Cl] | 9-(4-(1-(dimethylamino)ethyl)phenyl)-8-hydroxy-2,3-dihydro-1H-cyclo penta[c]quinolin-4(5H)-one hydrochloride |
| 182 | 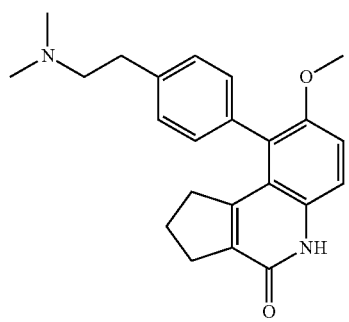 | 9-(4-(2-(dimethylamino)ethyl)phenyl)-8-methoxy-2,3-dihydro-1H-cyclo penta[c]quinolin-4(5H)-one |
| 183 | 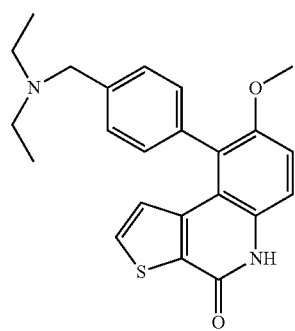 [SMILES: CCN(CC)Cc1ccc(-c2c(OC)ccc3[nH]c(=O)c4sccc4c23)cc1] | 9-(4-((diethylamino)methyl)phenyl)-8-methoxythieno[2,3-c]quinolin-4(5H)-one |
| 184 | 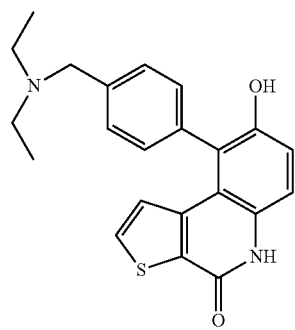 [SMILES: CCN(CC)Cc1ccc(-c2c(O)ccc3[nH]c(=O)c4sccc4c23)cc1] | 9-(4-((diethylamino)methyl)phenyl)-8-hydroxythieno[2,3-c]quinolin-4(5H)-one |

TABLE 1-continued
| | | |
|---|---|---|
| 185 | 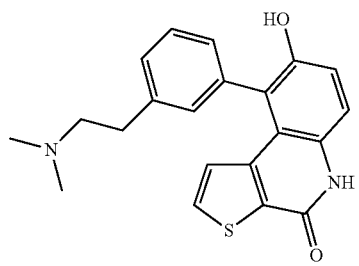 [SMILES: CN(C)CCc1cccc(-c2c(O)ccc3[nH]c(=O)c4sccc4c23)c1] | 9-(3-(2-(dimethylamino)ethyl)phenyl)-8-hydroxythieno[2,3-c]quinolin-4(5H)-one |
| 186 | 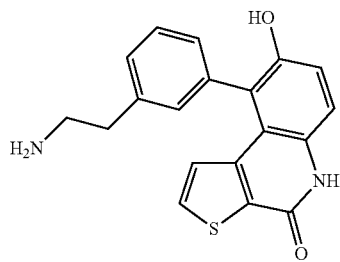 [SMILES: NCCc1cccc(-c2c(O)ccc3[nH]c(=O)c4sccc4c23)c1] | 9-(3-(2-aminoethyl)phenyl)-8-hydroxythieno[2,3-c]quinolin-4(5H)-one |
| 187 | 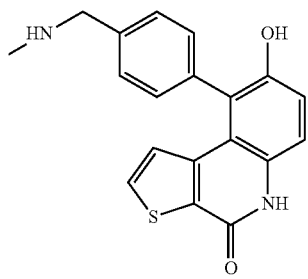 [SMILES: CNCc1ccc(-c2c(O)ccc3[nH]c(=O)c4sccc4c23)cc1] | 8-hydroxy-9-(4-((methylamino)methyl)phenyl)thieno[2,3-c]quinolin-4(5H)-one |
| 188 | 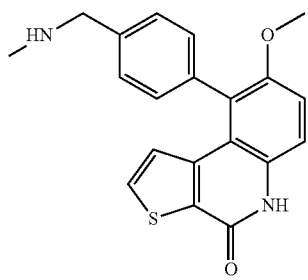 | 8-methoxy-9-(4-((methylamino)methyl)phenyl)thieno[2,3-c]quinolin-4(5H)-one |
| 189 | 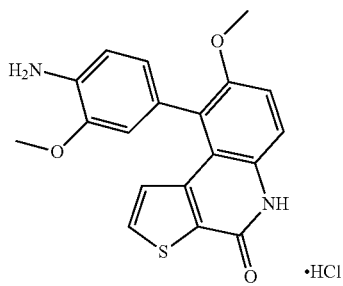 [SMILES: COc1cc(-c2c(OC)ccc3[nH]c(=O)c4sccc4c23)ccc1N ; Cl] | 9-(4-amino-3-methoxyphenyl)-8-methoxythieno[2,3-c]quinolin-4(5H)-one hydrochloride |

TABLE 1-continued
| | | |
|---|---|---|
| 190 | 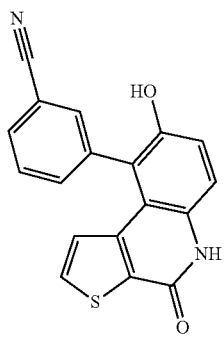 [SMILES: N#Cc1cccc(-c2c(O)ccc3[nH]c(=O)c4sccc4c23)c1] | 3-(8-hydroxy-4-oxo-4,5-dihydro thieno[2,3-c]quinolin-9-yl) benzonitrile |
| 191 | 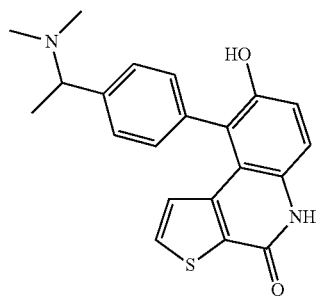 [SMILES: CC(c1ccc(-c2c(O)ccc3[nH]c(=O)c4sccc4c23)cc1)N(C)C] | 9-(4-(1-(dimethylamino)ethyl) phenyl)-8-hydroxythieno[2,3-c] quinolin-4(5H)-one |
| 192 | 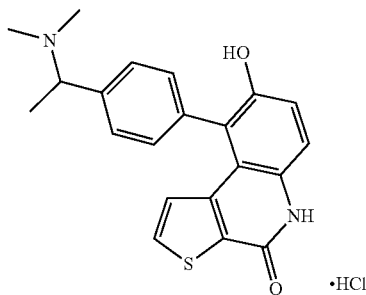 | 9-(4-(1-(dimethylamino)ethyl) phenyl)-8-hydroxythieno[2,3-c] quinolin-4(5H)-one hydrochloride |
| 193 | 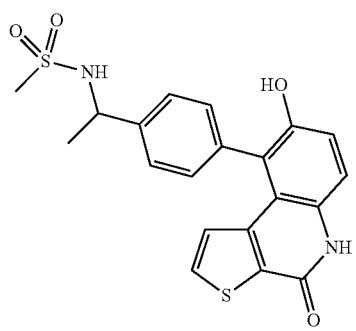 [SMILES: CC(NS(C)(=O)=O)c1ccc(-c2c(O)ccc3[nH]c(=O)c4sccc4c23)cc1] | N-(1-(4-(8-hydroxy-4-oxo-4,5-dihydrothieno[2,3-c]quinolin-9-yl) phenyl)ethyl)methanesulfonamide |
| 194 | 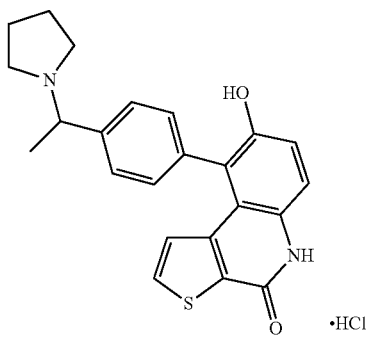 [SMILES: CC(c1ccc(-c2c(O)ccc3[nH]c(=O)c4sccc4c23)cc1)N1CCCC1 ; Cl] | 8-hydroxy-9-(4-(1-(pyrrolidin-1-yl) ethyl)phenyl)thieno[2,3-c]quinolin-4(5H)-one hydrochloride |

TABLE 1-continued

| | | |
|---|---|---|
| 195 | 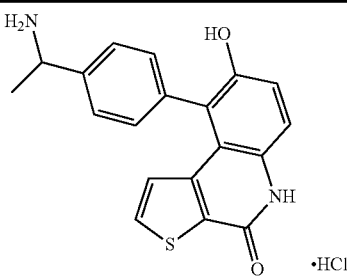 | 9-(4-(1-aminoethyl)phenyl)-8-hydroxythieno[2,3-c]quinolin-4(5H)-one hydrochloride |
| 196 | 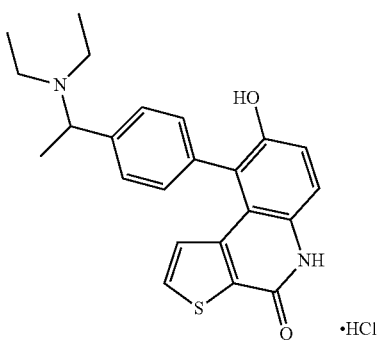 [SMILES: CCN(CC)C(C)c1ccc(-c2c(O)ccc3[nH]c(=O)c4sccc4c23)cc1 ; Cl] | 9-(4-(1-(diethylamino)ethyl)phenyl)-8-hydroxythieno[2,3-c]quinolin-4(5H)-one hydrochloride |
| 197 | 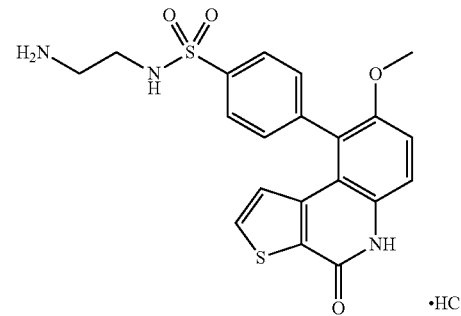 | N-(2-aminoethyl)-4-(8-methoxy-4-oxo-4,5-dihydrothieno[2,3-c]quinolin-9-yl)benzenesulfonamide hydrochloride |
| 198 | 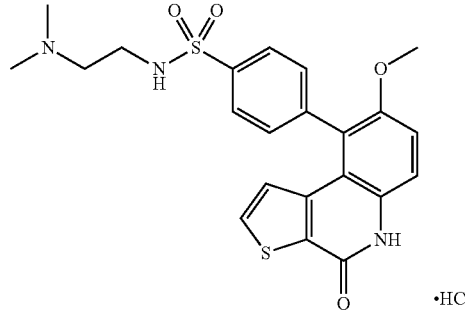 | N-(2-(dimethylamino)ethyl)-4-(8-methoxy-4-oxo-4,5-dihydrothieno[2,3-c]quinolin-9-yl)benzenesulfonamide hydrochloride |
| 199 | 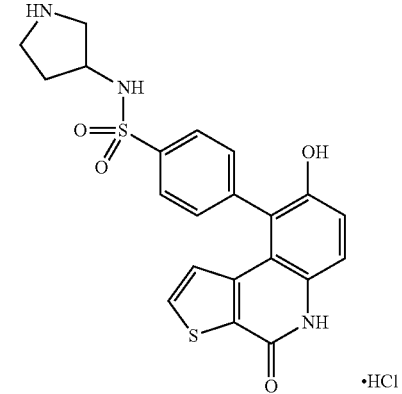 [SMILES: O=c1[nH]c2ccc(O)c(-c3ccc(S(=O)(=O)NC4CCNC4)cc3)c2c2ccsc12 ; Cl] | 4-(8-hydroxy-4-oxo-4,5-dihydrothieno[2,3-c]quinolin-9-yl)-N-(pyrrolidin-3-yl)benzenesulfonamide hydrochloride |

TABLE 1-continued
| | | |
|---|---|---|
| 200 | 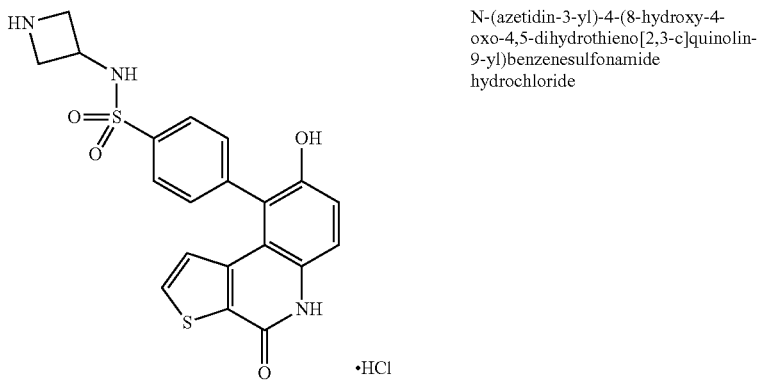 | N-(azetidin-3-yl)-4-(8-hydroxy-4-oxo-4,5-dihydrothieno[2,3-c]quinolin-9-yl)benzenesulfonamide hydrochloride |
| 201 | 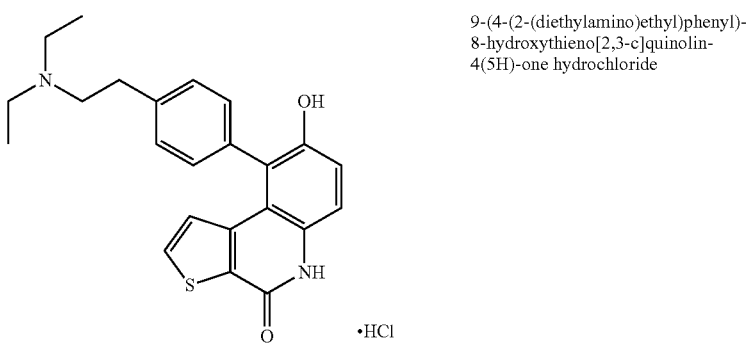 | 9-(4-(2-(diethylamino)ethyl)phenyl)-8-hydroxythieno[2,3-c]quinolin-4(5H)-one hydrochloride |
| 202 | 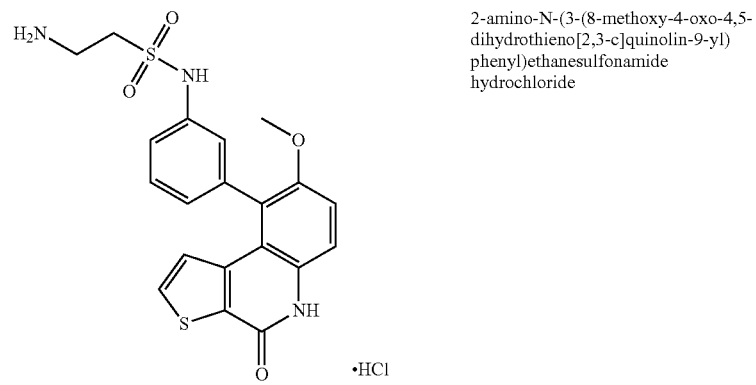 | 2-amino-N-(3-(8-methoxy-4-oxo-4,5-dihydrothieno[2,3-c]quinolin-9-yl)phenyl)ethanesulfonamide hydrochloride |
| 203 | 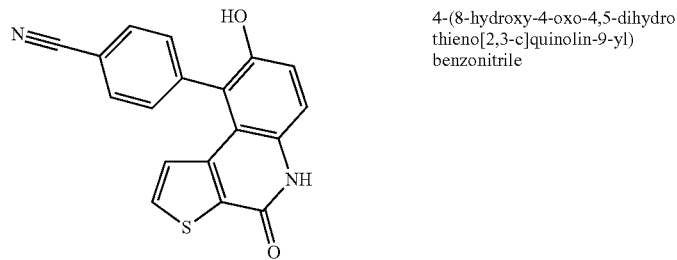 | 4-(8-hydroxy-4-oxo-4,5-dihydrothieno[2,3-c]quinolin-9-yl)benzonitrile |

TABLE 1-continued

| | | |
|---|---|---|
| 204 | 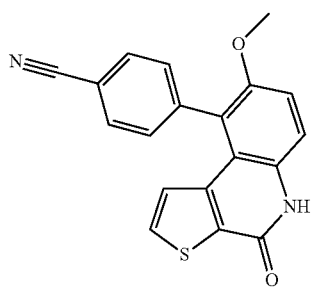 [SMILES: COc1ccc2[nH]c(=O)c3sccc3c2c1-c1ccc(C#N)cc1] | 4-(8-methoxy-4-oxo-4,5-dihydro thieno[2,3-c]quinolin-9-yl) benzonitrile |
| 205 | 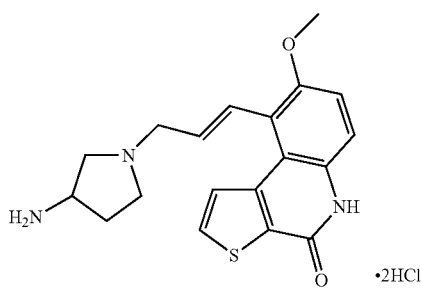 [SMILES: COc1ccc2[nH]c(=O)c3sccc3c2c1/C=C/CN1CCC(N)C1 ; "·2HCl"] | (E)-9-(3-(3-aminopyrrolidin-1-yl) prop-1-enyl)-8-methoxythieno[2,3-c] quinolin-4(5H)-one dihydrochloride |
| 206 | 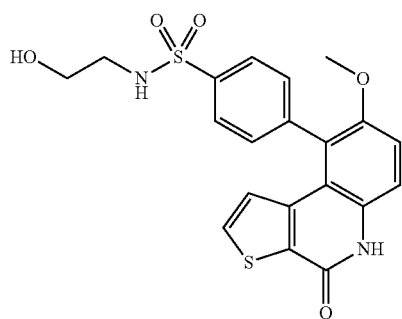 [SMILES: COc1ccc2[nH]c(=O)c3sccc3c2c1-c1ccc(S(=O)(=O)NCCO)cc1] | N-(2-hydroxyethyl)-4-(8-methoxy-4-oxo-4,5-dihydrothieno[2,3-c]quinolin-9-yl)benzenesulfonamide |
| 207 | 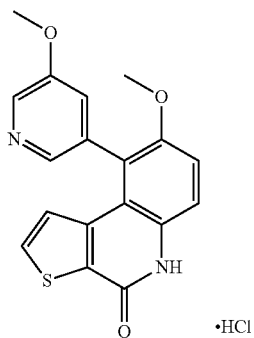 [SMILES: COc1cncc(-c2c(OC)ccc3[nH]c(=O)c4sccc4c23)c1 ; Cl] | 8-methoxy-9-(5-methoxypyridin-3-yl)thieno[2,3-c]quinolin-4(5H)-one hydrochloride |
| 208 | 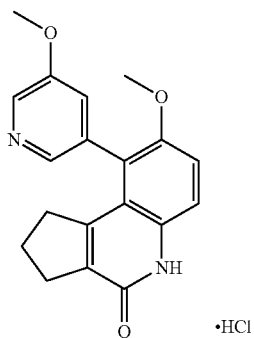 [SMILES: COc1cncc(-c2c(OC)ccc3[nH]c(=O)c4c(c23)CCC4)c1 ; Cl] | N-methoxy-9-(5-methoxypyridin-3-yl)-2,3-dihydro-1H-cyclopenta[c] quinolin-4(5H)-one hydrochloride |

TABLE 1-continued

| 209 | 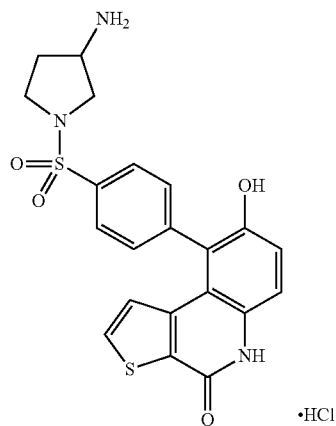 [SMILES: NC1CCN(S(=O)(=O)c2ccc(-c3c(O)ccc4[nH]c(=O)c5sccc5c34)cc2)C1 ; Cl] | 9-(4-(3-aminopyrrolidin-1-ylsulfonyl)phenyl)-8-hydroxythieno[2,3-c]quinolin-4(5H)-one hydrochloride |
| 210 | 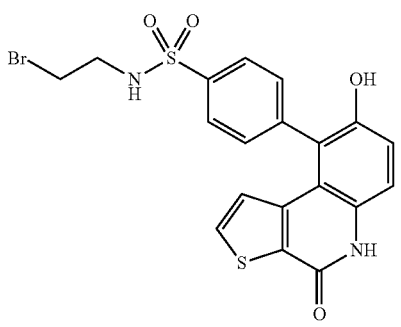 [SMILES: O=c1[nH]c2ccc(O)c(-c3ccc(S(=O)(=O)NCCBr)cc3)c2c2ccsc12] | N-(2-bromoethyl)-4-(8-hydroxy-4-oxo-4,5-dihydrothieno[2,3-c]quinolin-9-yl)benzenesulfonamide |
| 211 | 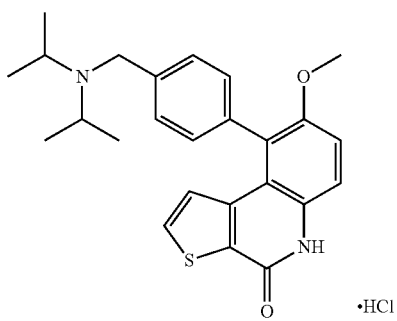 [SMILES: COc1ccc2[nH]c(=O)c3sccc3c2c1-c1ccc(CN(C(C)C)C(C)C)cc1 ; Cl] | 9-(4-((diisopropylamino)methyl)phenyl)-8-methoxythieno[2,3-c]quinolin-4(5H)-one hydrochloride |
| 212 | 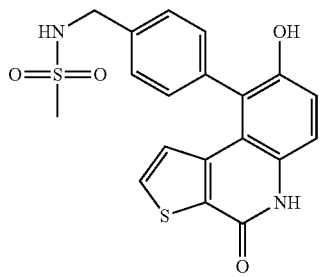 [SMILES: CS(=O)(=O)NCc1ccc(-c2c(O)ccc3[nH]c(=O)c4sccc4c23)cc1] | N-(hydroxy-4-oxo-4,5-dihydrothieno[2,3-c]quinolin-9-yl)benzyl)methanesulfonamide |
| 213 | 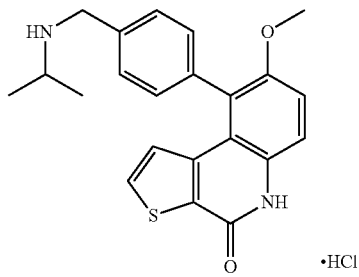 [SMILES: COc1ccc2[nH]c(=O)c3sccc3c2c1-c1ccc(CNC(C)C)cc1 ; Cl] | 9-(4-((isopropylamino)methyl)phenyl)-8-methoxythieno[2,3-c]quinolin-4(5H)-one hydrochloride |

TABLE 1-continued
| | | |
|---|---|---|
| 214 | 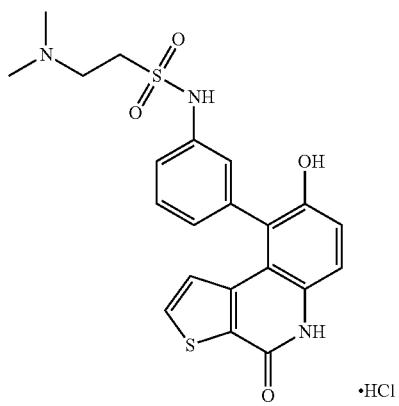 [SMILES: CN(C)CCS(=O)(=O)Nc1cccc(-c2c(O)ccc3[nH]c(=O)c4sccc4c23)c1 ; Cl] | 2-(dimethylamino)-N-(3-(8-hydroxy-4-oxo-4,5-dihydrothieno[2,3-c]quinolin-9-yl)phenyl)ethane sulfonamide hydrochloride |
| 215 | 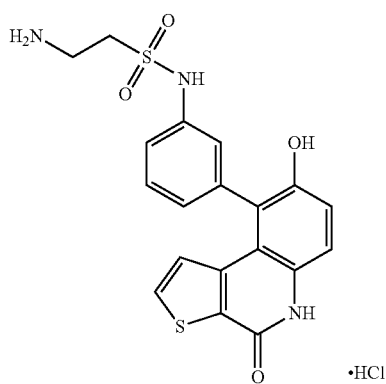 [SMILES: NCCS(=O)(=O)Nc1cccc(-c2c(O)ccc3[nH]c(=O)c4sccc4c23)c1 ; Cl] | 2-amino-N-(3-(8-hydroxy-4-oxo-4,5-dihydrothieno[2,3-c]quinolin-9-yl)phenyl)ethanesulfonamide hydrochloride |
| 216 | 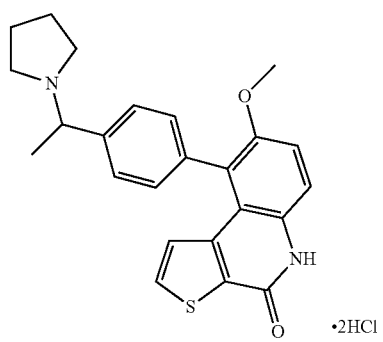 [SMILES: COc1ccc2[nH]c(=O)c3sccc3c2c1-c1ccc(C(C)N2CCCC2)cc1 ; "·2HCl"] | 8-methoxy-9-(4-(1-(pyrrolidin-1-yl)ethyl)phenyl)thieno[2,3-c]quinolin-4(5H)-one hydrochloride |
| 217 | 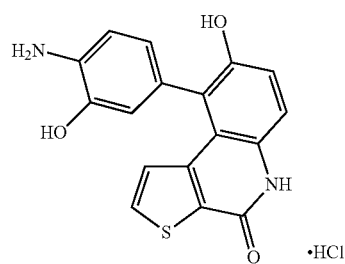 [SMILES: Nc1ccc(-c2c(O)ccc3[nH]c(=O)c4sccc4c23)cc1O ; Cl] | 9-(4-amino-3-hydroxyphenyl)-8-hydroxythieno[2,3-c]quinolin-4(5H)-one hydrochloride |

| | | |
|---|---|---|
| 218 | 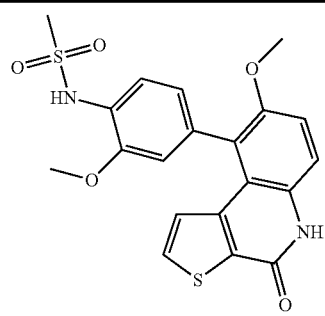 | N-(2-methoxy-4-(8-methoxy-4-oxo-4,5-dihydrothieno[2,3-c]quinolin-9-yl)phenyl)methanesulfonamide |
| 219 | 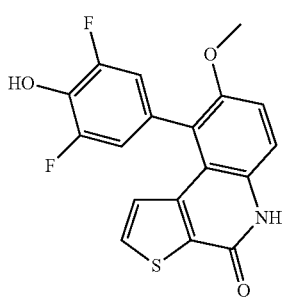 [SMILES: COc1ccc2[nH]c(=O)c3sccc3c2c1-c1cc(F)c(O)c(F)c1] | 9-(3,5-difluoro-4-hydroxyphenyl)-8-methoxythieno[2,3-c]quinolin-4(5H)-one |
| 220 | 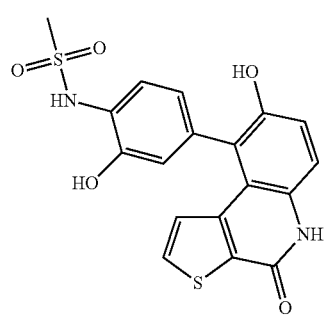 [SMILES: CS(=O)(=O)Nc1ccc(-c2c(O)ccc3[nH]c(=O)c4sccc4c23)cc1O] | N-(2-hydroxy-4-(8-hydroxy-4-oxo-4,5-dihydrothieno[2,3-c]quinolin-9-yl)phenyl)methanesulfonamide |
| 221 | 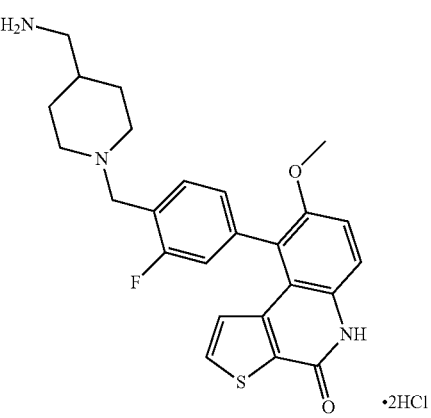 [SMILES: COc1ccc2[nH]c(=O)c3sccc3c2c1-c1ccc(CN2CCC(CN)CC2)c(F)c1 ; "·2HCl"] | 9-(4-((4-(aminomethyl)piperidin-1-yl)methyl)-3-fluorophenyl)-8-methoxythieno[2,3-c]quinolin-4(5H)-one dihydrochloride |
| 222 | 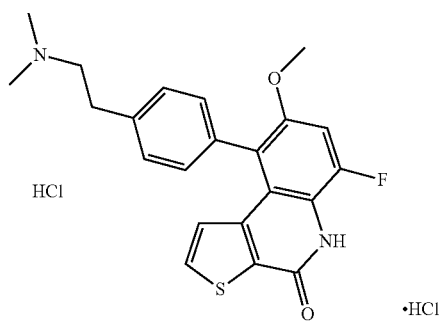 [SMILES: COc1cc(F)c2[nH]c(=O)c3sccc3c2c1-c1ccc(CCN(C)C)cc1 ; Cl ; Cl] | 9-(4-(2-(dimethylamino)ethyl)phenyl)-6-fluoro-8-methoxythieno[2,3-c]quinolin-4(5H)-one hydrochloride |

TABLE 1-continued

| | | |
|---|---|---|
| 223 | 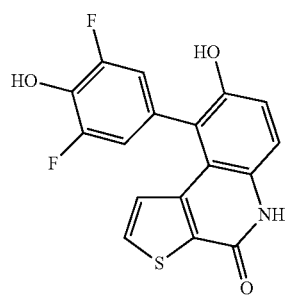 [SMILES: O=c1[nH]c2ccc(O)c(-c3cc(F)c(O)c(F)c3)c2c2ccsc12] | 9-(3,5-difluoro-4-hydroxyphenyl)-8-hydroxythieno[2,3-c]quinolin-4(5H)-one |
| 224 | 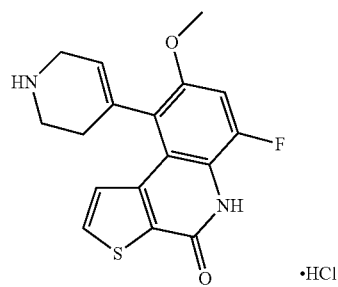 [SMILES: COc1cc(F)c2[nH]c(=O)c3sccc3c2c1C1=CCNCC1 ; Cl] | 6-fluoro-8-methoxy-9-(1,2,3,6-tetra hydropyridin-4-yl)thieno[2,3-c]quinolin-4(5H)-one hydrochloride |
| 225 | 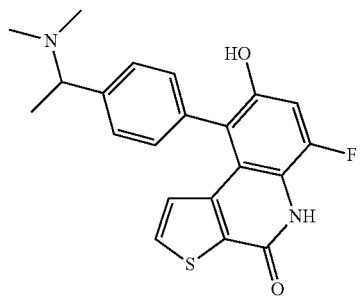 [SMILES: CC(c1ccc(-c2c(O)cc(F)c3[nH]c(=O)c4sccc4c23)cc1)N(C)C] | 9-(4-(1-(dimethylamino)ethyl)phenyl)-6-fluoro-8-hydroxythieno[2,3-c]quinolin-4(5H)-one |
| 226 | 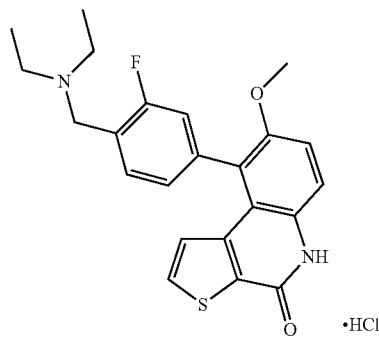 [SMILES: CCN(CC)Cc1ccc(-c2c(OC)ccc3[nH]c(=O)c4sccc4c23)cc1F ; Cl] | 9-(4-((diethylamino)methyl)-3-fluoro phenyl)-8-methoxythieno[2,3-c]quinolin-4(5H)-one hydrochloride |
| 227 | 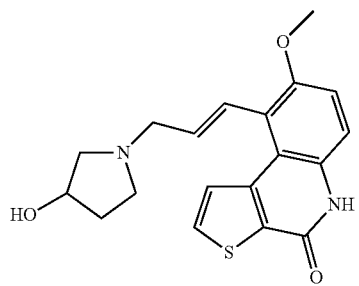 [SMILES: COc1ccc2[nH]c(=O)c3sccc3c2c1/C=C/CN1CCC(O)C1] | (E)-9-(3-(3-hydroxypyrrolidin-1-yl)prop-1-enyl)-8-methoxythieno[2,3-c]quinolin-4(5H)-one |

TABLE 1-continued

| | | |
|---|---|---|
| 228 | 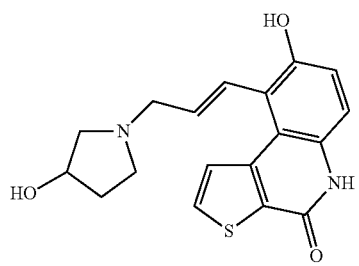 [SMILES: O=c1[nH]c2ccc(O)c(/C=C/CN3CCC(O)C3)c2c2ccsc12] | (E)-8-hydroxy-9-(3-(3-hydroxy pyrrolidin-1-yl)prop-1-enyl)thieno[2,3-c]quinolin-4(5H)-one |
| 229 | 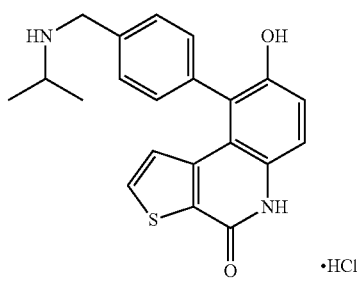 [SMILES: CC(C)NCc1ccc(-c2c(O)ccc3[nH]c(=O)c4sccc4c23)cc1 ; Cl] | 8-hydroxy-9-(4-((isopropylamino)methyl)phenyl)thieno[2,3-c]quinolin-4(5H)-one hydrochloride |
| 230 | 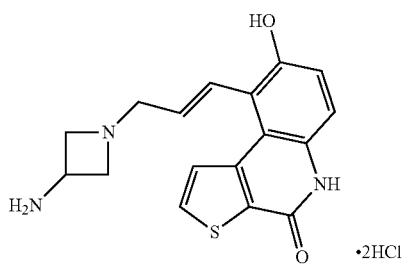 [SMILES: NC1CN(C/C=C/c2c(O)ccc3[nH]c(=O)c4sccc4c23)C1 ; "·2HCl"] | (E)-9-(3-(3-aminoazetidin-1-yl)prop-1-enyl)-8-hydroxythieno[2,3-c]quinolin-4(5H)-one dihydrochloride |
| 231 | 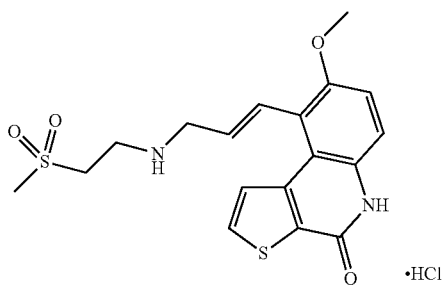 [SMILES: COc1ccc2[nH]c(=O)c3sccc3c2c1/C=C/CNCCS(C)(=O)=O ; Cl] | (E)-8-methoxy-9-(3-(2-(methylsulfonyl)ethylamino)prop-1-enyl)thieno[2,3-c]quinolin-4(5H)-one hydrochloride |
| 232 | 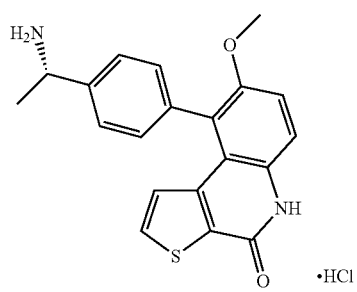 [SMILES: COc1ccc2[nH]c(=O)c3sccc3c2c1-c1ccc([C@H](C)N)cc1 ; Cl] | (S)-9-(4-(1-aminoethyl)phenyl)-8-methoxythieno[2,3-c]quinolin-4(5H)-one hydrochloride |

| | | |
|---|---|---|
| 233 | 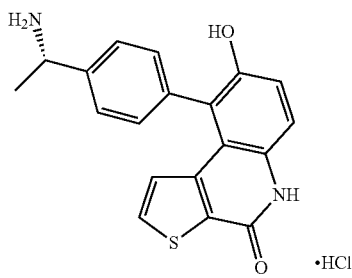 •HCl | (S)-9-(4-(1-aminoethyl)phenyl)-8-hydroxythieno[2,3-c]quinolin-4(5H)-one hydrochloride |
| 234 | 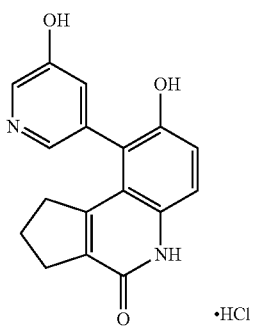 [SMILES: O=c1[nH]c2ccc(O)c(-c3cncc(O)c3)c2c2c1CCC2 ; Cl] •HCl | 8-hydroxy-9-(5-hydroxypyridin-3-yl)-2,3-dihydro-1H-cyclopenta[c]quinolin-4(5H)-one hydrochloride |
| 235 | 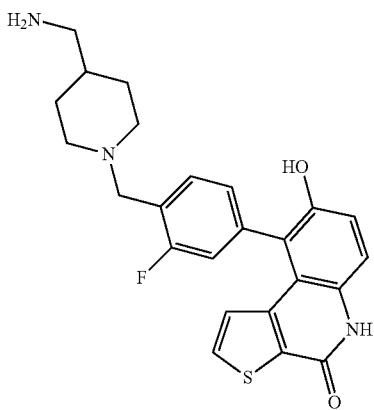 [SMILES: NCC1CCN(Cc2ccc(-c3c(O)ccc4[nH]c(=O)c5sccc5c34)cc2F)CC1] | 9-(4-((4-(aminomethyl)piperidin-1-yl)methyl)-3-fluorophenyl)-8-hydroxythieno[2,3-c]quinolin-4(5H)-one |
| 236 | 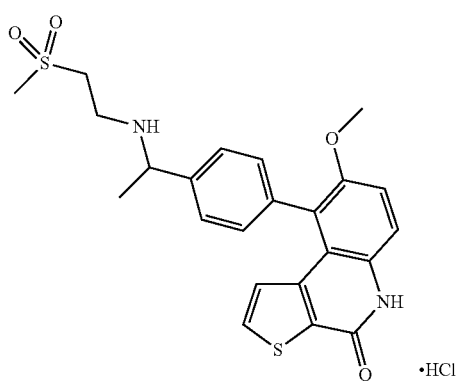 [SMILES: COc1ccc2[nH]c(=O)c3sccc3c2c1-c1ccc(C(C)NCCS(C)(=O)=O)cc1 ; Cl] •HCl | 8-methoxy-9-(4-(1-(2-(methylsulfonyl)ethylamino)ethyl)phenyl)thieno[2,3-c]quinolin-4(5H)-one hydrochloride |

TABLE 1-continued

| | | |
|---|---|---|
| 237 | 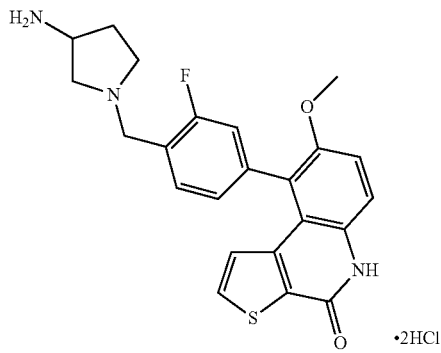 [SMILES: COc1ccc2[nH]c(=O)c3sccc3c2c1-c1ccc(CN2CCC(N)C2)c(F)c1 ; "·2HCl"] •2HCl | 9-(4-((3-aminopyrrolidin-1-yl)methyl)-3-fluorophenyl)-8-methoxythieno[2,3-c]quinolin-4(5H)-one dihydrochloride |
| 238 | 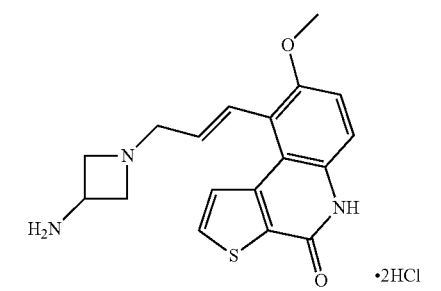 [SMILES: COc1ccc2[nH]c(=O)c3sccc3c2c1/C=C/CN1CC(N)C1 ; "·2HCl"] •2HCl | (E)-9-(3-(3-aminoazetidin-1-yl)prop-1-enyl)-8-methoxythieno[2,3-c]quinolin-4(5H)-one dihydrochloride |
| 239 | 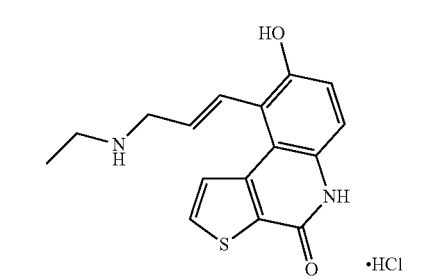 [SMILES: CCNC/C=C/c1c(O)ccc2[nH]c(=O)c3sccc3c12 ; Cl] •HCl | (E)-9-(3-(ethylamino)prop-1-enyl)-8-hydroxythieno[2,3-c]quinolin-4(5H)-one hydrochloride |
| 240 | 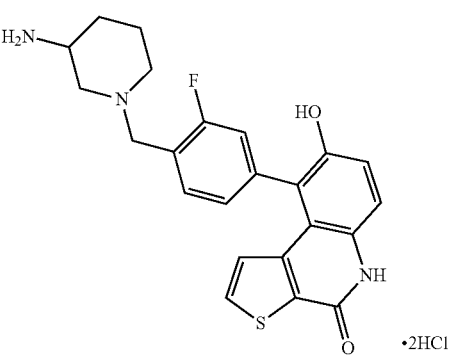 [SMILES: NC1CCCN(Cc2ccc(-c3c(O)ccc4[nH]c(=O)c5sccc5c34)cc2F)C1 ; "·2HCl"] •2HCl | 9-(4-((3-aminopiperidin-1-yl)methyl)-3-fluorophenyl)-8-hydroxythieno[2,3-c]quinolin-4(5H)-one dihydrochloride |
| 241 | 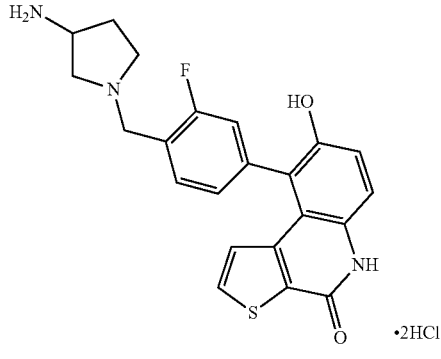 [SMILES: NC1CCN(Cc2ccc(-c3c(O)ccc4[nH]c(=O)c5sccc5c34)cc2F)C1 ; "·2HCl"] •2HCl | 9-(4-((3-aminopyrrolidin-1-yl)methyl)-3-fluorophenyl)-8-hydroxythieno[2,3-c]quinolin-4(5H)-one dihydrochloride |

TABLE 1-continued

| | | |
|---|---|---|
| 242 | 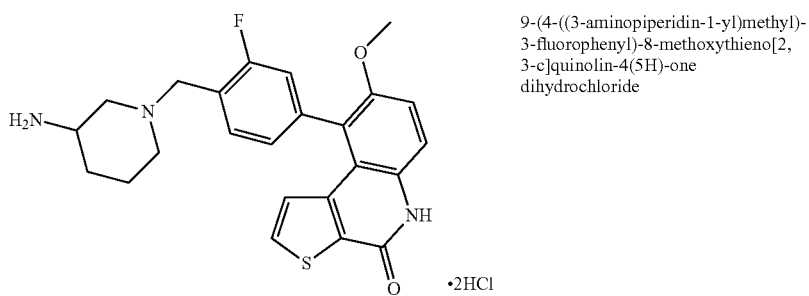 | 9-(4-((3-aminopiperidin-1-yl)methyl)-3-fluorophenyl)-8-methoxythieno[2,3-c]quinolin-4(5H)-one dihydrochloride |
| 243 | 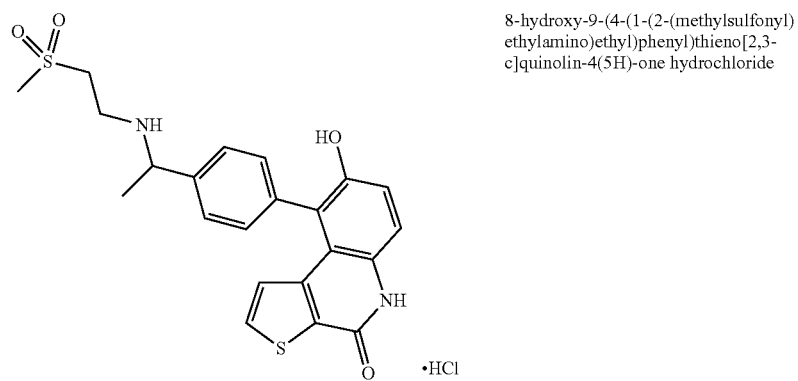 | 8-hydroxy-9-(4-(1-(2-(methylsulfonyl)ethylamino)ethyl)phenyl)thieno[2,3-c]quinolin-4(5H)-one hydrochloride |
| 244 | 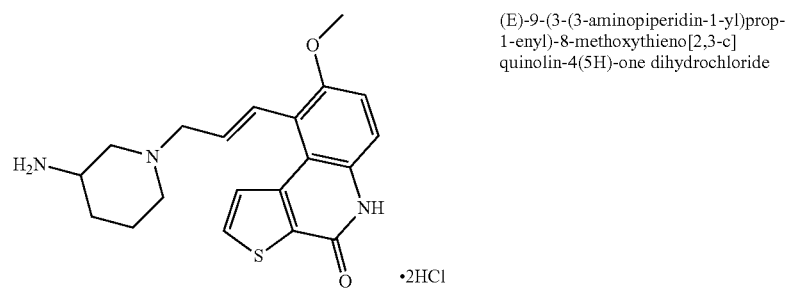 | (E)-9-(3-(3-aminopiperidin-1-yl)prop-1-enyl)-8-methoxythieno[2,3-c]quinolin-4(5H)-one dihydrochloride |
| 245 | 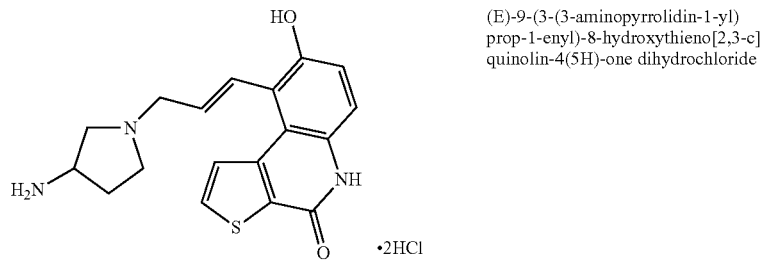 | (E)-9-(3-(3-aminopyrrolidin-1-yl)prop-1-enyl)-8-hydroxythieno[2,3-c]quinolin-4(5H)-one dihydrochloride |
| 246 | 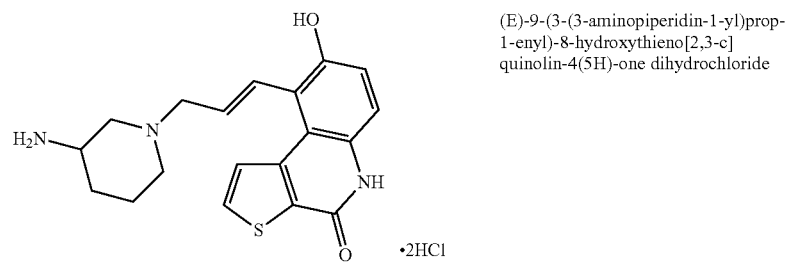 | (E)-9-(3-(3-aminopiperidin-1-yl)prop-1-enyl)-8-hydroxythieno[2,3-c]quinolin-4(5H)-one dihydrochloride |

TABLE 1-continued

| | | |
|---|---|---|
| 247 | 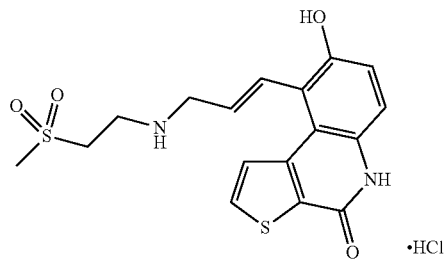 [SMILES: CS(=O)(=O)CCNC/C=C/c1c(O)ccc2[nH]c(=O)c3sccc3c12 ; Cl] | (E)-8-hydroxy-9-(3-(2-(methyl sulfonyl)ethylamino)prop-1-enyl) thieno[2,3-c]quinolin-4(5H)-one hydrochloride |
| 248 | 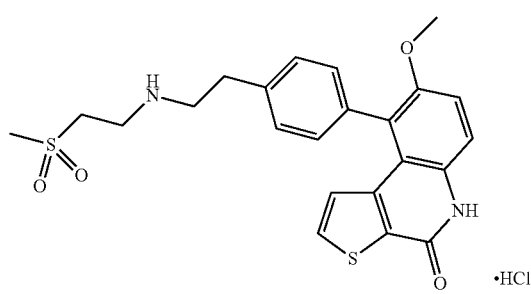 [SMILES: COc1ccc2[nH]c(=O)c3sccc3c2c1-c1ccc(CCNCCS(C)(=O)=O)cc1 ; Cl] | 8-methoxy-9-(4-(2-(2-(methyl sulfonyl)ethylamino)ethyl)phenyl) thieno[2,3-c]quinolin-4(5H)-one hydrochloride |
| 249 | 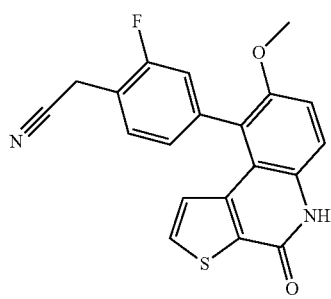 [SMILES: COc1ccc2[nH]c(=O)c3sccc3c2c1-c1ccc(CC#N)c(F)c1] | 2-(2-fluoro-4-(8-methoxy-4-oxo-4,5-dihydrothieno[2,3-c]quinolin-9-yl) phenyl)acetonitrile |
| 250 | 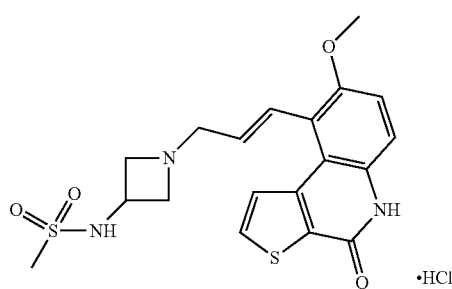 [SMILES: COc1ccc2[nH]c(=O)c3sccc3c2c1/C=C/CN1CC(NS(C)(=O)=O)C1 ; Cl] | (E)-N-(1-(3-(8-methoxy-4-oxo-4,5-dihydrothieno[2,3-c]quinolin-9-yl)allyl) azetidin-3-yl)methanesulfonamide hydrochloride |
| 251 | 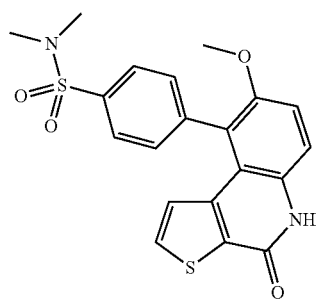 [SMILES: COc1ccc2[nH]c(=O)c3sccc3c2c1-c1ccc(S(=O)(=O)N(C)C)cc1] | 4-(8-methoxy-4-oxo-4,5-dihydro thieno[2,3-c]quinolin-9-yl)-N,N-dimethylbenzenesulfonamide |

| | | |
|---|---|---|
| 252 | 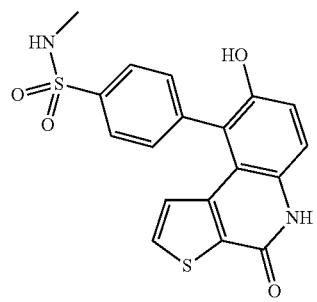 [SMILES: CNS(=O)(=O)c1ccc(-c2c(O)ccc3[nH]c(=O)c4sccc4c23)cc1] | 4-(8-hydroxy-4-oxo-4,5-dihydro thieno[2,3-c]quinolin-9-yl)-N-methyl benzenesulfonamide |
| 253 | 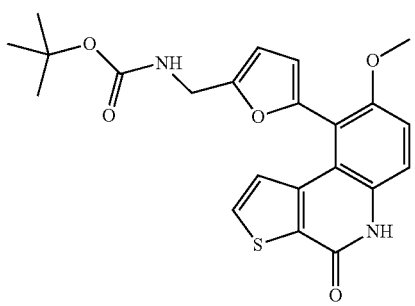 [SMILES: COc1ccc2[nH]c(=O)c3sccc3c2c1-c1ccc(CNC(=O)OC(C)(C)C)o1] | tert-butyl (5-(8-methoxy-4-oxo-4,5-dihydro thieno[2,3-c]quinolin-9-yl)furan-2-yl) methylcarbamate |
| 254 | 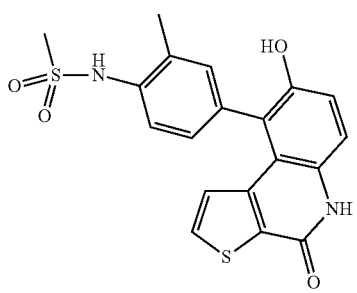 [SMILES: Cc1cc(-c2c(O)ccc3[nH]c(=O)c4sccc4c23)ccc1NS(C)(=O)=O] | N-(4-(8-hydroxy-4-oxo-4,5-dihydro thieno[2,3-c]quinolin-9-yl)-2-methyl phenyl)methanesulfonamide |
| 255 | 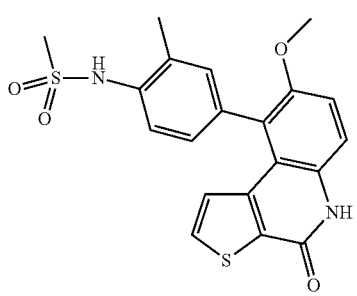 [SMILES: COc1ccc2[nH]c(=O)c3sccc3c2c1-c1ccc(NS(C)(=O)=O)c(C)c1] | N-(4-(8-methoxy-4-oxo-4,5-dihydro thieno[2,3-c]quinolin-9-yl)-2-methyl phenyl)methanesulfonamide |
| 256 | 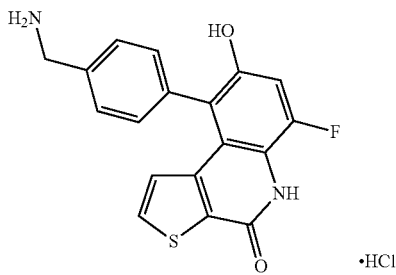 [SMILES: NCc1ccc(-c2c(O)cc(F)c3[nH]c(=O)c4sccc4c23)cc1 ; Cl] | 9-(4-(aminomethyl)phenyl)-6-fluoro-8-hydroxythieno[2,3-c]quinolin-4(5H)-one hydrochloride |

| | | |
|---|---|---|
| 257 | 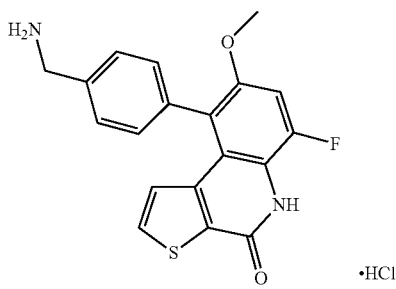 [SMILES: COc1cc(F)c2[nH]c(=O)c3sccc3c2c1-c1ccc(CN)cc1 ; Cl] | 9-(4-(aminomethyl)phenyl)-6-fluoro-8-methoxythieno[2,3-c]quinolin-4(5H)-one hydrochloride |
| 258 | 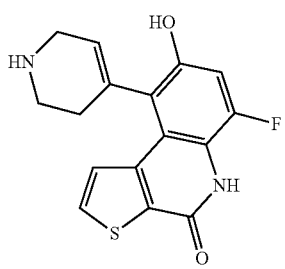 [SMILES: O=c1[nH]c2c(F)cc(O)c(C3=CCNCC3)c2c2ccsc12] | 6-fluoro-8-hydroxy-9-(1,2,3,6-tetra hydropyridin-4-yl)thieno[2,3-c]quinolin-4(5H)-one |
| 259 | 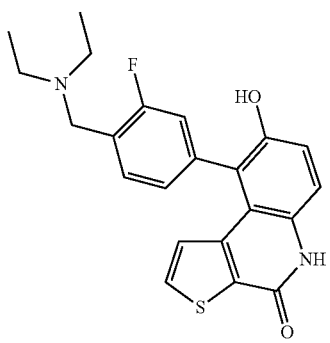 [SMILES: CCN(CC)Cc1ccc(-c2c(O)ccc3[nH]c(=O)c4sccc4c23)cc1F] | 9-(4-((diethylamino)methyl)-3-fluoro phenyl)-8-hydroxythieno[2,3-c]quinolin-4(5H)-one |
| 260 | 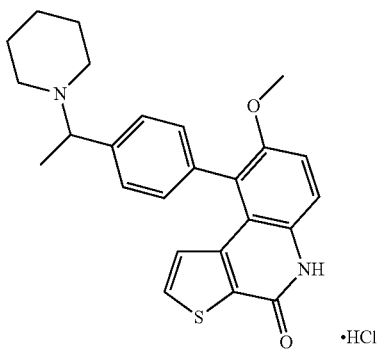 [SMILES: COc1ccc2[nH]c(=O)c3sccc3c2c1-c1ccc(C(C)N2CCCCC2)cc1 ; Cl] | 8-methoxy-9-(4-(1-(piperidin-1-yl)ethyl)phenyl)thieno[2,3-c]quinolin-4(5H)-one hydrochloride |
| 261 | 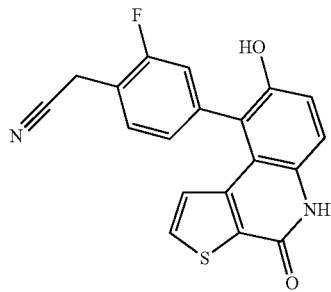 [SMILES: N#CCc1ccc(-c2c(O)ccc3[nH]c(=O)c4sccc4c23)cc1F] | 2-(2-fluoro-4-(8-hydroxy-4-oxo-4,5-dihydrothieno[2,3-c]quinolin-9-yl)phenyl)acetonitrile |

TABLE 1-continued

| | | |
|---|---|---|
| 262 | 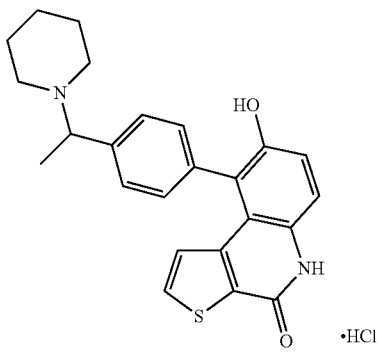 [SMILES: CC(c1ccc(-c2c(O)ccc3[nH]c(=O)c4sccc4c23)cc1)N1CCCCC1 ; Cl] | 8-hydroxy-9-(4-(1-(piperidin-1-yl)ethyl)phenyl)thieno[2,3-c]quinolin-4(5H)-one hydrochloride |
| 263 | 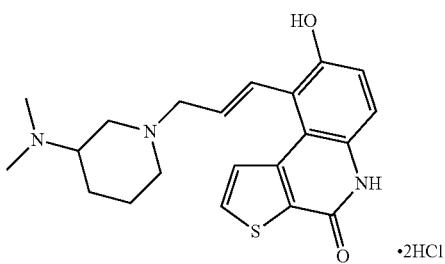 [SMILES: CN(C)C1CCCN(C/C=C/c2c(O)ccc3[nH]c(=O)c4sccc4c23)C1 ; "·2HCl"] | (E)-9-(3-(3-(dimethylamino)piperidin-1-yl)prop-1-enyl)-8-hydroxythieno[2,3-c]quinolin-4(5H)-one dihydrochloride |
| 264 | 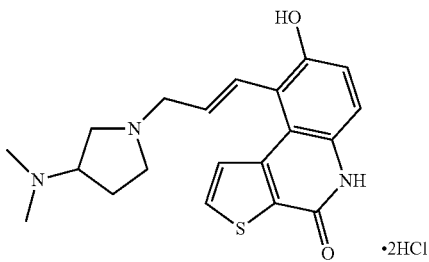 [SMILES: CN(C)C1CCN(C/C=C/c2c(O)ccc3[nH]c(=O)c4sccc4c23)C1 ; "·2HCl"] | (E)-9-(3-(3-(dimethylamino)pyrrolidin-1-yl)prop-1-enyl)-8-hydroxythieno[2,3-c]quinolin-4(5H)-one dihydrochloride |
| 265 | 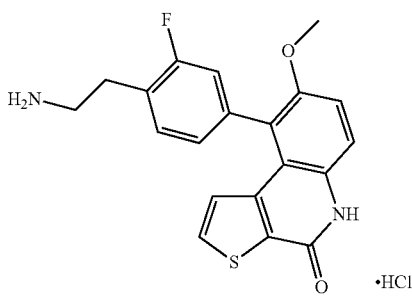 [SMILES: COc1ccc2[nH]c(=O)c3sccc3c2c1-c1ccc(CCN)c(F)c1 ; Cl] | 9-(4-(2-aminoethyl)-3-fluorophenyl)-8-methoxythieno[2,3-c]quinolin-4(5H)-one hydrochloride |
| 266 | 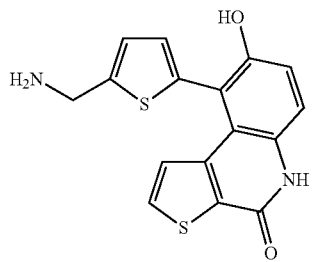 [SMILES: NCc1ccc(-c2c(O)ccc3[nH]c(=O)c4sccc4c23)s1] | 9-(5-(aminomethyl)thiophen-2-yl)-8-hydroxythieno[2,3-c]quinolin-4(5H)-one |

TABLE 1-continued

| 267 | 9-(4-((ethylamino)methyl)phenyl)-8-hydroxythieno[2,3-c]quinolin-4(5H)-one hydrochloride |
| 268 | (E)-9-(3-(4-aminopiperidin-1-yl)prop-1-enyl)-8-hydroxythieno[2,3-c]quinolin-4(5H)-one dihydrochloride |
| 269 | 9-(4-((ethylamino)methyl)phenyl)-8-methoxythieno[2,3-c]quinolin-4(5H)-one hydrochloride |
| 270 | 9-(4-(aminomethyl)phenyl)-6-bromo-8-hydroxythieno[2,3-c]quinolin-4(5H)-one hydrochloride |
| 271 | 9-(3-chloro-4-((diethylamino)methyl)phenyl)-8-methoxythieno[2,3-c]quinolin-4(5H)-one hydrochloride |

TABLE 1-continued

| | | |
|---|---|---|
| 272 | 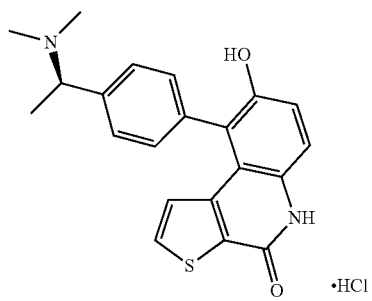 [SMILES: C[C@H](c1ccc(-c2c(O)ccc3[nH]c(=O)c4sccc4c23)cc1)N(C)C ; Cl] | (R)-9-(4-(1-(dimethylamino)ethyl)phenyl)-8-hydroxythieno[2,3-c]quinolin-4(5H)-one hydrochloride |
| 273 | 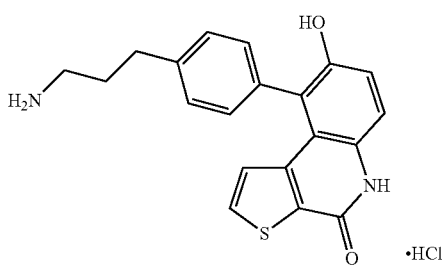 [SMILES: NCCCc1ccc(-c2c(O)ccc3[nH]c(=O)c4sccc4c23)cc1 ; Cl] | 9-(4-(3-aminopropyl)phenyl)-8-hydroxythieno[2,3-c]quinolin-4(5H)-one hydrochloride |
| 274 | 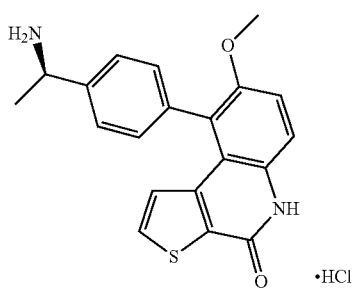 [SMILES: COc1ccc2[nH]c(=O)c3sccc3c2c1-c1ccc([C@@H](C)N)cc1 ; Cl] | (R)-9-(4-(1-aminoethyl)phenyl)-8-methoxythieno[2,3-c]quinolin-4(5H)-one hydrochloride |
| 275 | 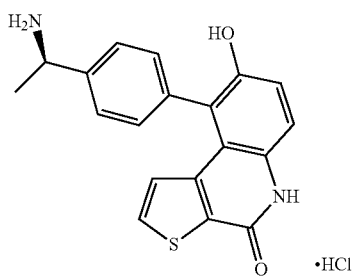 | (R)-9-(4-(1-aminoethyl)phenyl)-8-hydroxythieno[2,3-c]quinolin-4(5H)-one hydrochloride |
| 276 | 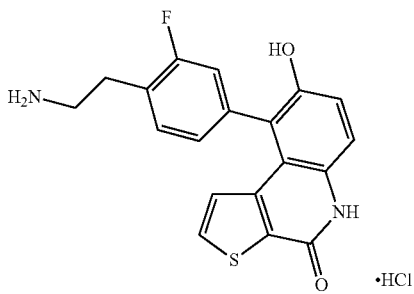 [SMILES: NCCc1ccc(-c2c(O)ccc3[nH]c(=O)c4sccc4c23)cc1F ; Cl] | 9-(4-(2-aminoethyl)-3-fluorophenyl)-8-hydroxythieno[2,3-c]quinolin-4(5H)-one hydrochloride |

TABLE 1-continued

| | | |
|---|---|---|
| 277 | 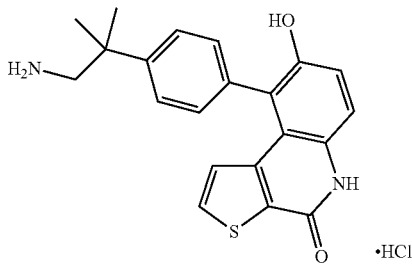 [SMILES: CC(C)(CN)c1ccc(-c2c(O)ccc3[nH]c(=O)c4sccc4c23)cc1 ; Cl] | 9-(4-(1-amino-2-methylpropan-2-yl)phenyl)-8-hydroxythieno[2,3-c]quinolin-4(5H)-one hydrochloride |
| 278 | 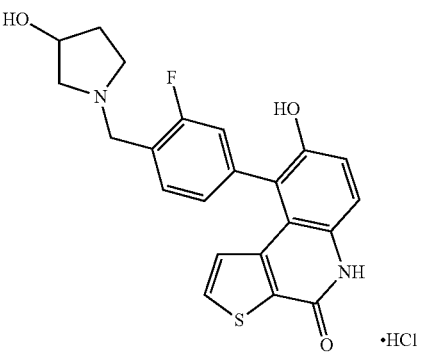 [SMILES: O=c1[nH]c2ccc(O)c(-c3ccc(CN4CCC(O)C4)c(F)c3)c2c2ccsc12 ; Cl] | 9-(3-fluoro-4-((3-hydroxypyrrolidin-1-yl)methyl)phenyl)-8-hydroxythieno[2,3-c]quinolin-4(5H)-one hydrochloride |
| 279 | 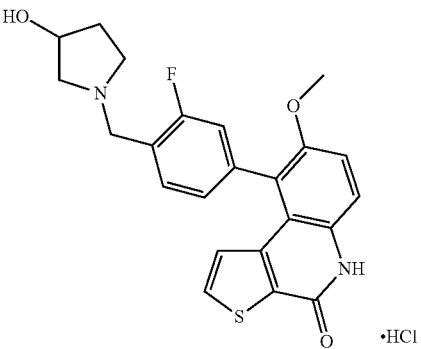 [SMILES: COc1ccc2[nH]c(=O)c3sccc3c2c1-c1ccc(CN2CCC(O)C2)c(F)c1 ; Cl] | 9-(3-fluoro-4-((3-hydroxypyrrolidin-1-yl)methyl)phenyl)-8-methoxythieno[2,3-c]quinolin-4(5H)-one hydrochloride |
| 280 | 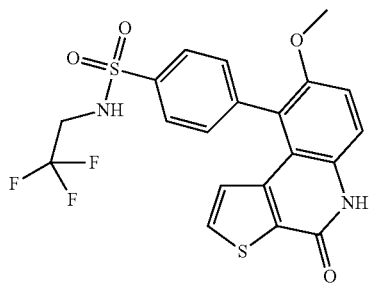 [SMILES: COc1ccc2[nH]c(=O)c3sccc3c2c1-c1ccc(S(=O)(=O)NCC(F)(F)F)cc1] | 4-(8-methoxy-4-oxo-4,5-dihydrothieno[2,3-c]quinolin-9-yl)-N-(2,2,2-trifluoroethyl)benzenesulfonamide |
| 281 | 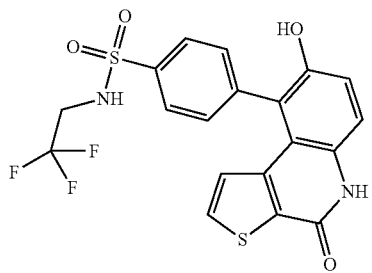 [SMILES: O=c1[nH]c2ccc(O)c(-c3ccc(S(=O)(=O)NCC(F)(F)F)cc3)c2c2ccsc12] | 4-(8-hydroxy-4-oxo-4,5-dihydrothieno[2,3-c]quinolin-9-yl)-N-(2,2,2-trifluoroethyl)benzenesulfonamide |

TABLE 1-continued

| | | |
|---|---|---|
| 282 | 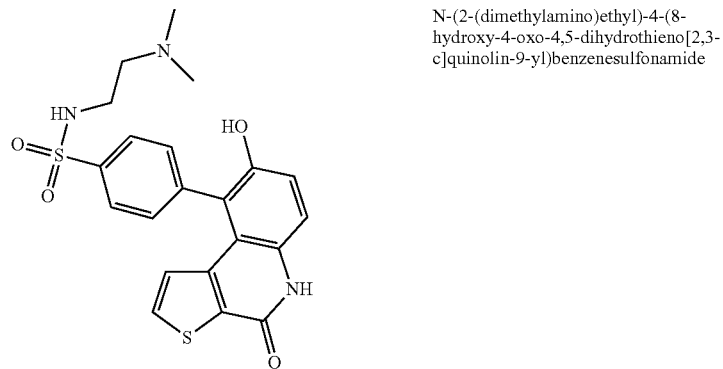 | N-(2-(dimethylamino)ethyl)-4-(8-hydroxy-4-oxo-4,5-dihydrothieno[2,3-c]quinolin-9-yl)benzenesulfonamide |
| 283 | 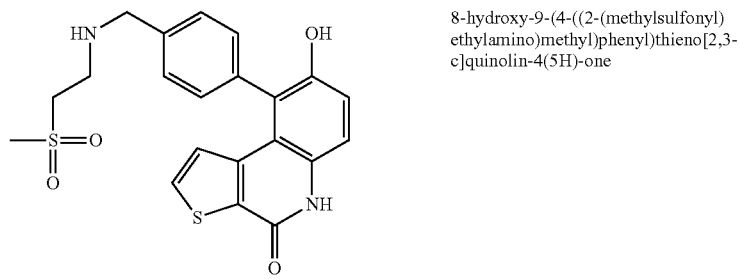 | 8-hydroxy-9-(4-((2-(methylsulfonyl)ethylamino)methyl)phenyl)thieno[2,3-c]quinolin-4(5H)-one |
| 284 | 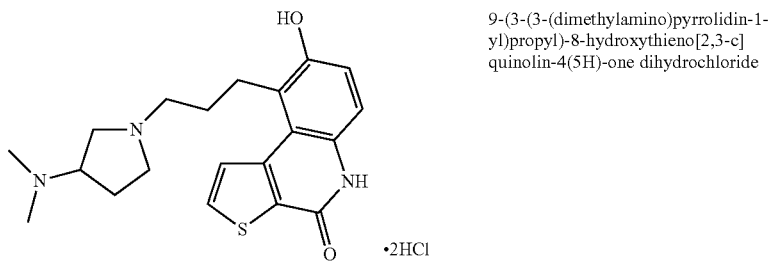 | 9-(3-(3-(dimethylamino)pyrrolidin-1-yl)propyl)-8-hydroxythieno[2,3-c]quinolin-4(5H)-one dihydrochloride |
| 285 | 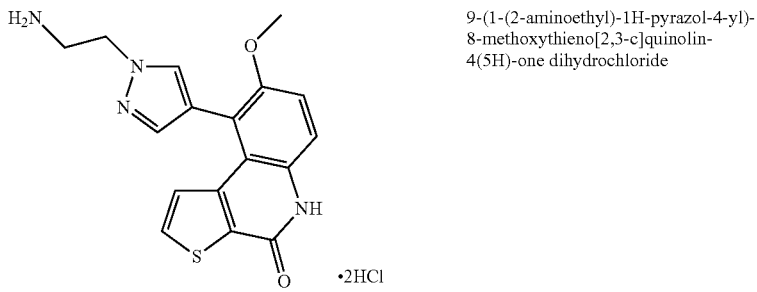 | 9-(1-(2-aminoethyl)-1H-pyrazol-4-yl)-8-methoxythieno[2,3-c]quinolin-4(5H)-one dihydrochloride |
| 286 | 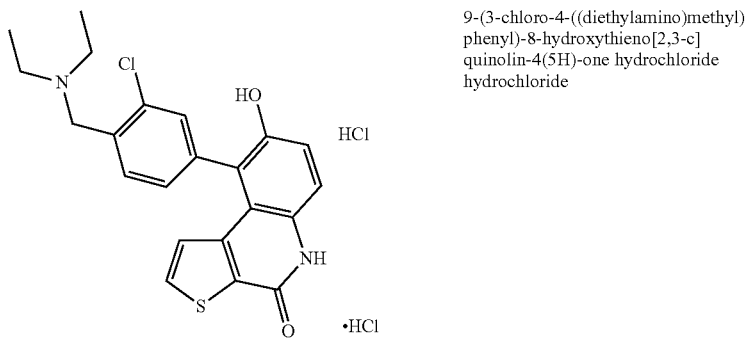 | 9-(3-chloro-4-((diethylamino)methyl)phenyl)-8-hydroxythieno[2,3-c]quinolin-4(5H)-one hydrochloride hydrochloride |

TABLE 1-continued
| 287 | 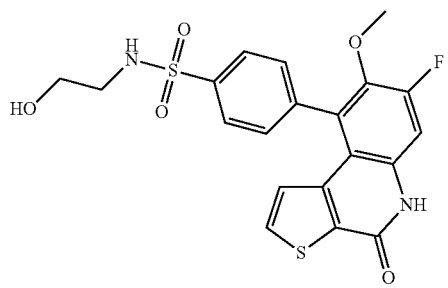 [SMILES: COc1c(F)cc2[nH]c(=O)c3sccc3c2c1-c1ccc(S(=O)(=O)NCCO)cc1] | 4-(7-fluoro-8-methoxy-4-oxo-4,5-dihydrothieno[2,3-c]quinolin-9-yl)-N-(2-hydroxyethyl)benzenesulfonamide |
| 288 | 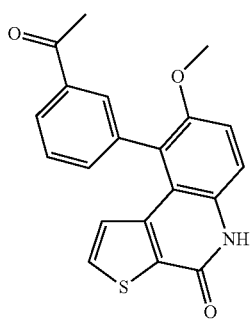 [SMILES: COc1ccc2[nH]c(=O)c3sccc3c2c1-c1cccc(C(C)=O)c1] | 9-(3-acetylphenyl)-8-methoxythieno[2,3-c]quinolin-4(5H)-one |
| 289 | 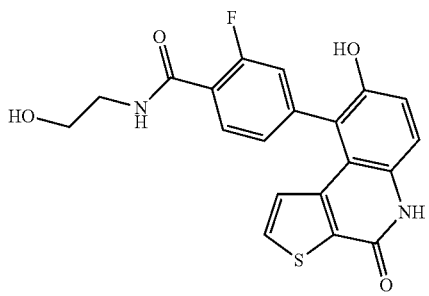 [SMILES: O=C(NCCO)c1ccc(-c2c(O)ccc3[nH]c(=O)c4sccc4c23)cc1F] | 2-fluoro-4-(8-hydroxy-4-oxo-4,5-dihydrothieno[2,3-c]quinolin-9-yl)-N-(2-hydroxyethyl)benzamide |
| 290 | 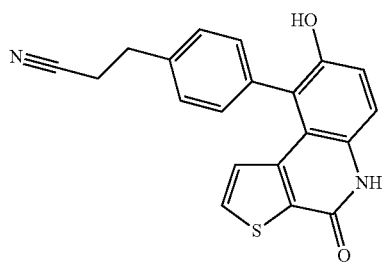 [SMILES: N#CCCc1ccc(-c2c(O)ccc3[nH]c(=O)c4sccc4c23)cc1] | 3-(4-(8-hydroxy-4-oxo-4,5-dihydrothieno[2,3-c]quinolin-9-yl)phenyl)propanenitrile |
| 291 | 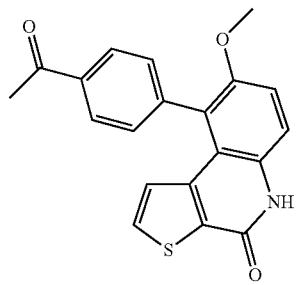 [SMILES: COc1ccc2[nH]c(=O)c3sccc3c2c1-c1ccc(C(C)=O)cc1] | 9-(4-acetylphenyl)-8-methoxythieno[2,3-c]quinolin-4(5H)-one |

| | | |
|---|---|---|
| 292 | 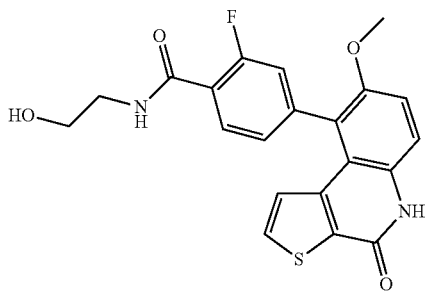 [SMILES: COc1ccc2[nH]c(=O)c3sccc3c2c1-c1ccc(C(=O)NCCO)c(F)c1] | 2-fluoro-N-(2-hydroxyethyl)-4-(8-methoxy-4-oxo-4,5-dihydrothieno[2,3-c]quinolin-9-yl)benzamide |
| 293 | 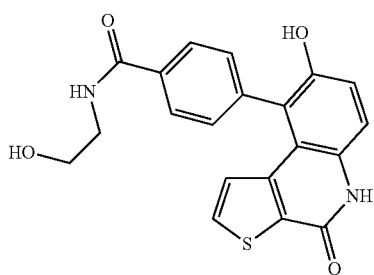 [SMILES: O=C(NCCO)c1ccc(-c2c(O)ccc3[nH]c(=O)c4sccc4c23)cc1] | 4-(8-hydroxy-4-oxo-4,5-dihydrothieno[2,3-c]quinolin-9-yl)-N-(2-hydroxyethyl)benzamide |
| 294 | 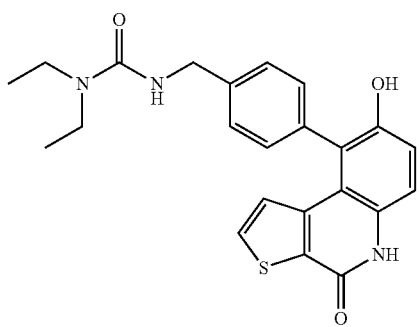 [SMILES: CCN(CC)C(=O)NCc1ccc(-c2c(O)ccc3[nH]c(=O)c4sccc4c23)cc1] | 1,1-diethyl-3-(hydroxy-4-oxo-4,5-dihydrothieno[2,3-c]quinolin-9-yl)benzyl)urea |
| 295 | 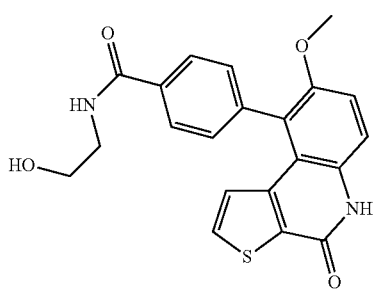 [SMILES: COc1ccc2[nH]c(=O)c3sccc3c2c1-c1ccc(C(=O)NCCO)cc1] | N-(2-hydroxyethyl)-4-(8-methoxy-4-oxo-4,5-dihydrothieno[2,3-c]quinolin-9-yl)benzamide |
| 296 | 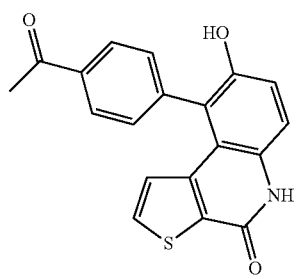 [SMILES: CC(=O)c1ccc(-c2c(O)ccc3[nH]c(=O)c4sccc4c23)cc1] | 9-(4-acetylphenyl)-8-hydroxythieno[2,3-c]quinolin-4(5H)-one |

TABLE 1-continued

| | | |
|---|---|---|
| 297 | 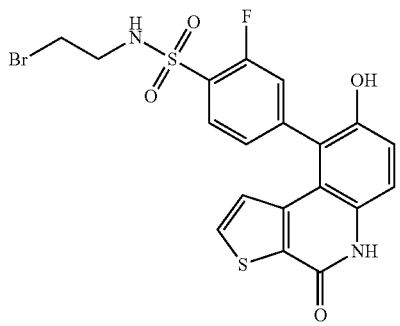 [SMILES: O=c1[nH]c2ccc(O)c(-c3ccc(S(=O)(=O)NCCBr)c(F)c3)c2c2ccsc12] | N-(2-bromoethyl)-2-fluoro-4-(8-hydroxy-4-oxo-4,5-dihydrothieno[2,3-c]quinolin-9-yl)benzenesulfonamide |
| 298 | 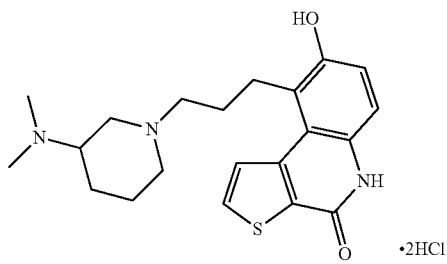 [SMILES: CN(C)C1CCCN(CCCc2c(O)ccc3[nH]c(=O)c4sccc4c23)C1 ; "·2HCl"] | 9-(3-(3-(dimethylamino)piperidin-1-yl)propyl)-8-hydroxythieno[2,3-c]quinolin-4(5H)-one dihydrochloride |
| 299 | 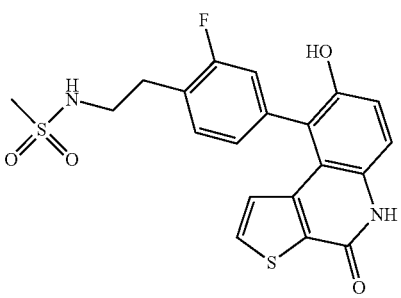 [SMILES: CS(=O)(=O)NCCc1ccc(-c2c(O)ccc3[nH]c(=O)c4sccc4c23)cc1F] | N-(2-fluoro-4-(8-hydroxy-4-oxo-4,5-dihydrothieno[2,3-c]quinolin-9-yl)phenethyl)methanesulfonamide |
| 300 | 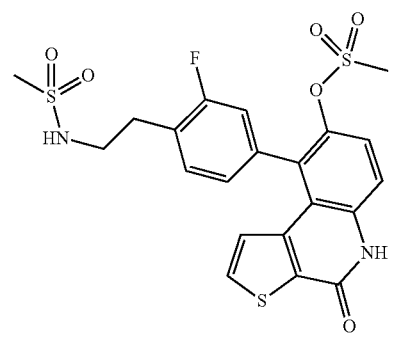 | 9-(3-fluoro-4-(2-(methylsulfonamido)ethyl)phenyl)-4-oxo-4,5-dihydrothieno[2,3-c]quinolin-8-yl methanesulfonate |
| 301 | 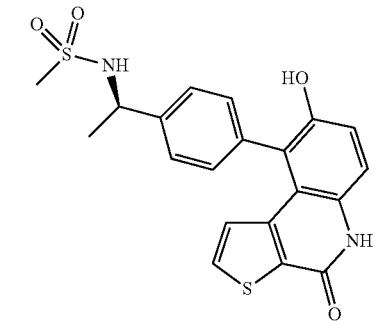 [SMILES: C[C@@H](NS(C)(=O)=O)c1ccc(-c2c(O)ccc3[nH]c(=O)c4sccc4c23)cc1] | (R)-N-(1-(4-(8-hydroxy-4-oxo-4,5-dihydrothieno[2,3-c]quinolin-9-yl)phenyl)ethyl)methanesulfonamide |

TABLE 1-continued
| | | |
|---|---|---|
| 302 | 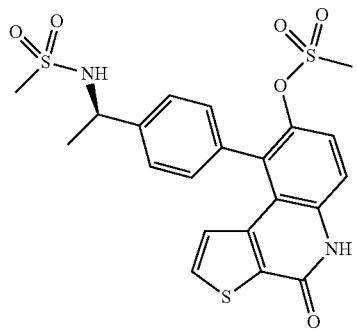 | (R)-9-(4-(1-(methylsulfonamido)ethyl)phenyl)-4-oxo-4,5-dihydrothieno[2,3-c]quinolin-8-yl methanesulfonate |
| 303 | 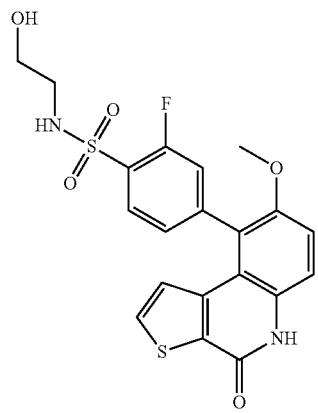 [SMILES: COc1ccc2[nH]c(=O)c3sccc3c2c1-c1ccc(S(=O)(=O)NCCO)c(F)c1] | 2-fluoro-N-(2-hydroxyethyl)-4-(8-methoxy-4-oxo-4,5-dihydrothieno[2,3-c]quinolin-9-yl)benzenesulfonamide |
| 304 | 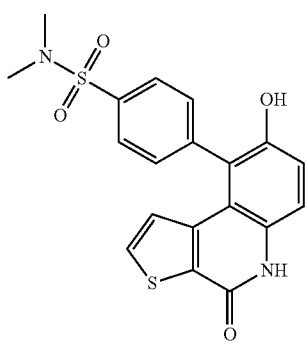 [SMILES: CN(C)S(=O)(=O)c1ccc(-c2c(O)ccc3[nH]c(=O)c4sccc4c23)cc1] | 4-(8-hydroxy-4-oxo-4,5-dihydrothieno[2,3-c]quinolin-9-yl)-N,N-dimethylbenzenesulfonamide |
| 305 | 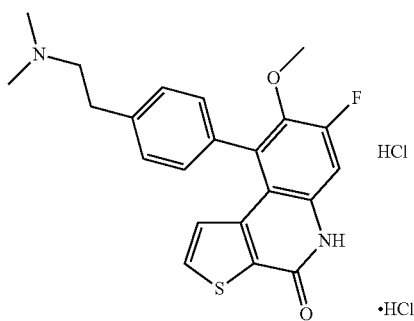 [SMILES: COc1c(F)cc2[nH]c(=O)c3sccc3c2c1-c1ccc(CCN(C)C)cc1 ; Cl ; Cl] | 9-(4-(2-(dimethylamino)ethyl)phenyl)-7-fluoro-8-methoxythieno[2,3-c]quinolin-4(5H)-one hydrochloride |

TABLE 1-continued
| | | |
|---|---|---|
| 306 | 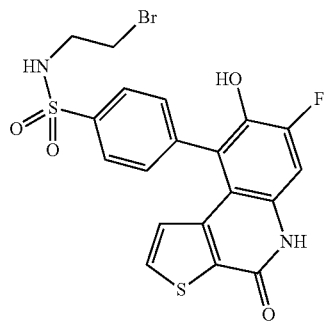 [SMILES: O=c1[nH]c2cc(F)c(O)c(-c3ccc(S(=O)(=O)NCCBr)cc3)c2c2ccsc12] | N-(2-bromoethyl)-4-(7-fluoro-8-hydroxy-4-oxo-4,5-dihydrothieno[2,3-c]quinolin-9-yl)benzenesulfonamide |
| 307 | 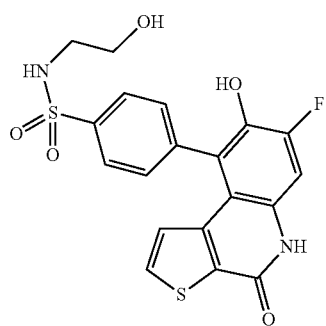 [SMILES: O=c1[nH]c2cc(F)c(O)c(-c3ccc(S(=O)(=O)NCCO)cc3)c2c2ccsc12] | 4-(7-fluoro-8-hydroxy-4-oxo-4,5-dihydrothieno[2,3-c]quinolin-9-yl)-N-(2-hydroxy ethyl)benzene sulfonamide |
| 308 | 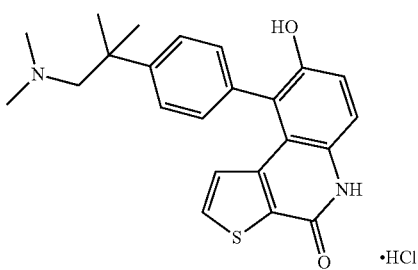 [SMILES: CN(C)CC(C)(C)c1ccc(-c2c(O)ccc3[nH]c(=O)c4sccc4c23)cc1 ; Cl] | 9-(4-(1-(dimethylamino)-2-methylpropan-2-yl)phenyl)-8-hydroxy thieno[2,3-c]quinolin-4(5H)-one hydrochloride |
| 309 | 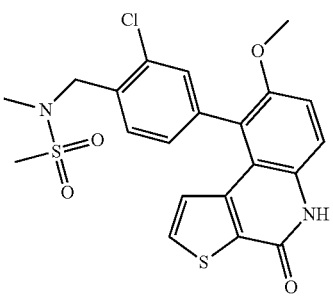 [SMILES: COc1ccc2[nH]c(=O)c3sccc3c2c1-c1ccc(CN(C)S(C)(=O)=O)c(Cl)c1] | N-(2-chloro-4-(8-methoxy-4-oxo-4,5-dihydrothieno[2,3-c]quinolin-9-yl)benzyl)-N-methylmethane sulfonamide |

TABLE 1-continued

| | | |
|---|---|---|
| 310 | 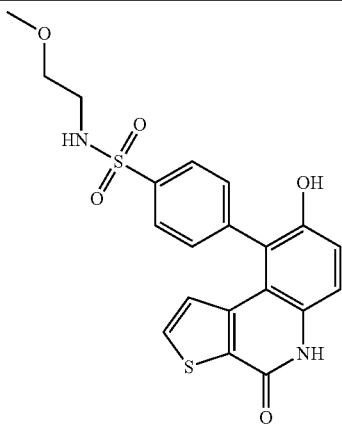 | 4-(8-hydroxy-4-oxo-4,5-dihydro thieno[2,3-c]quinolin-9-yl)-N-(2-methoxyethyl)benzenesulfonamide |
| 311 | 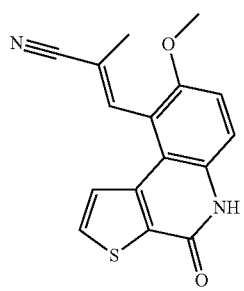 [SMILES: COc1ccc2[nH]c(=O)c3sccc3c2c1/C=C(\C)C#N] | (E)-3-(8-methoxy-4-oxo-4,5-dihydro thieno[2,3-c]quinolin-9-yl)-2-methyl acrylonitrile |
| 312 | 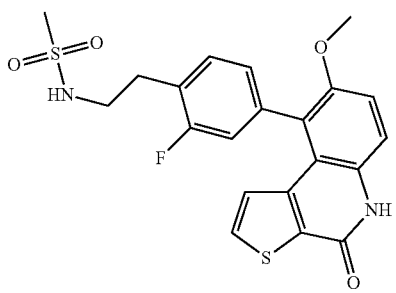 [SMILES: COc1ccc2[nH]c(=O)c3sccc3c2c1-c1ccc(CCNS(C)(=O)=O)c(F)c1] | N-(2-fluoro-4-(8-methoxy-4-oxo-4,5-dihydrothieno[2,3-c]quinolin-9-yl) phenethyl)methanesulfonamide |
| 313 | 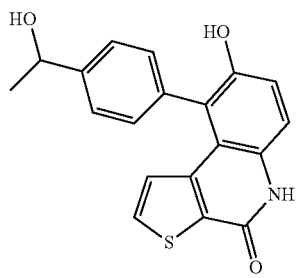 [SMILES: CC(O)c1ccc(-c2c(O)ccc3[nH]c(=O)c4sccc4c23)cc1] | 8-hydroxy-9-(4-(1-hydroxyethyl) phenyl)thieno[2,3-c]quinolin-4(5H)-one |
| 314 | 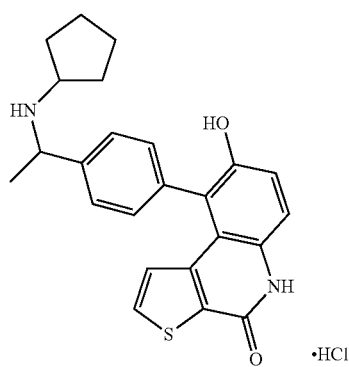 [SMILES: CC(NC1CCCC1)c1ccc(-c2c(O)ccc3[nH]c(=O)c4sccc4c23)cc1 ; Cl] | 9-(4-(1-(cyclopentylamino)ethyl) phenyl)-8-hydroxythieno[2,3-c] quinolin-4(5H)-one hydrochloride |

TABLE 1-continued

| | | |
|---|---|---|
| 315 | 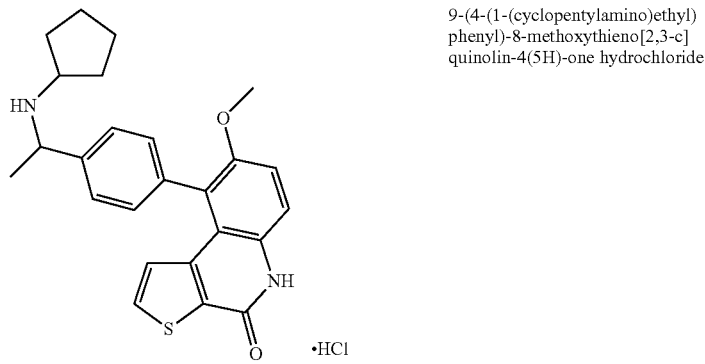 | 9-(4-(1-(cyclopentylamino)ethyl)phenyl)-8-methoxythieno[2,3-c]quinolin-4(5H)-one hydrochloride |
| 316 | 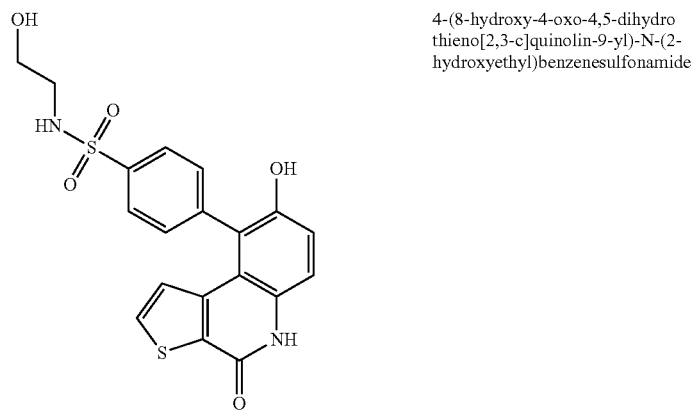 | 4-(8-hydroxy-4-oxo-4,5-dihydrothieno[2,3-c]quinolin-9-yl)-N-(2-hydroxyethyl)benzenesulfonamide |
| 317 | 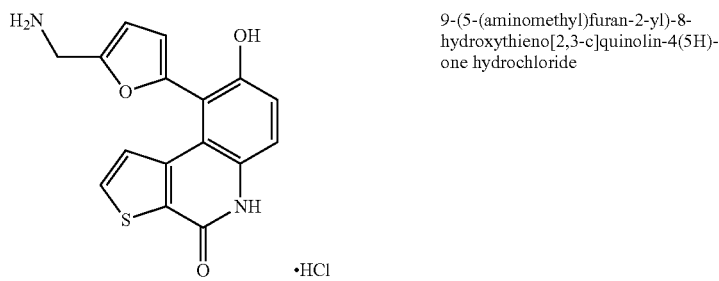 | 9-(5-(aminomethyl)furan-2-yl)-8-hydroxythieno[2,3-c]quinolin-4(5H)-one hydrochloride |
| 318 | 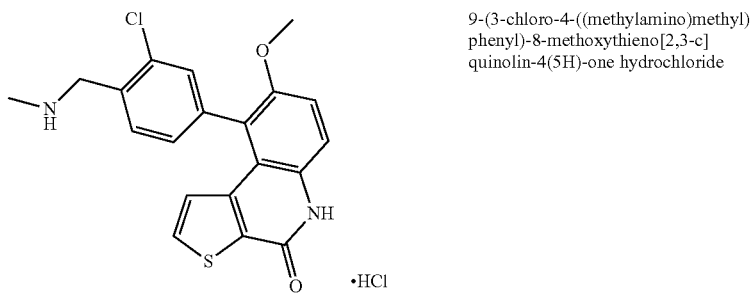 | 9-(3-chloro-4-((methylamino)methyl)phenyl)-8-methoxythieno[2,3-c]quinolin-4(5H)-one hydrochloride |
| 319 | 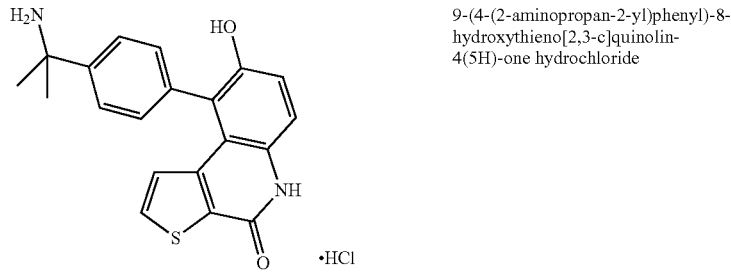 | 9-(4-(2-aminopropan-2-yl)phenyl)-8-hydroxythieno[2,3-c]quinolin-4(5H)-one hydrochloride |

| | | |
|---|---|---|
| 320 | 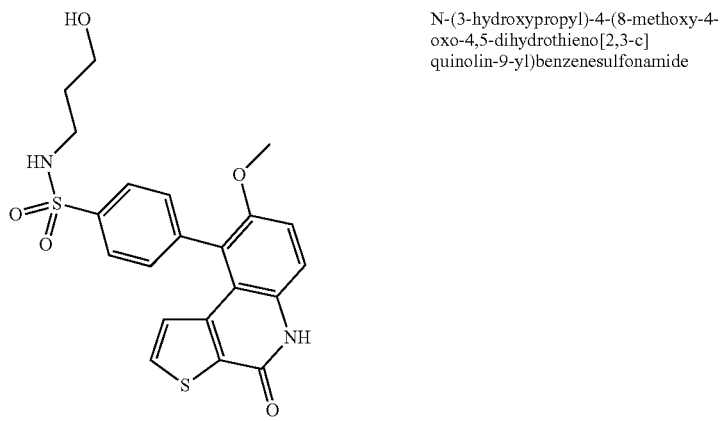 | N-(3-hydroxypropyl)-4-(8-methoxy-4-oxo-4,5-dihydrothieno[2,3-c]quinolin-9-yl)benzenesulfonamide |
| 321 | 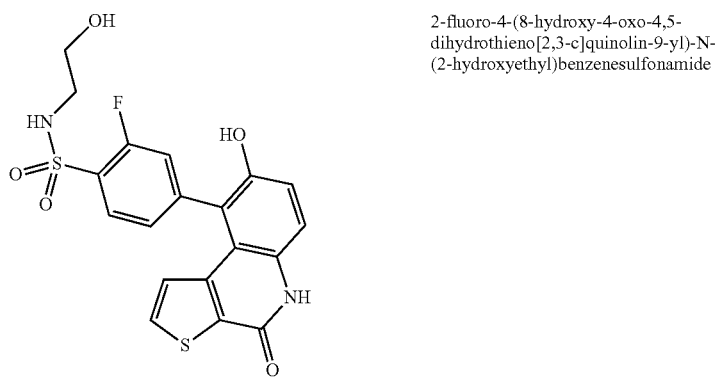 | 2-fluoro-4-(8-hydroxy-4-oxo-4,5-dihydrothieno[2,3-c]quinolin-9-yl)-N-(2-hydroxyethyl)benzenesulfonamide |
| 322 | 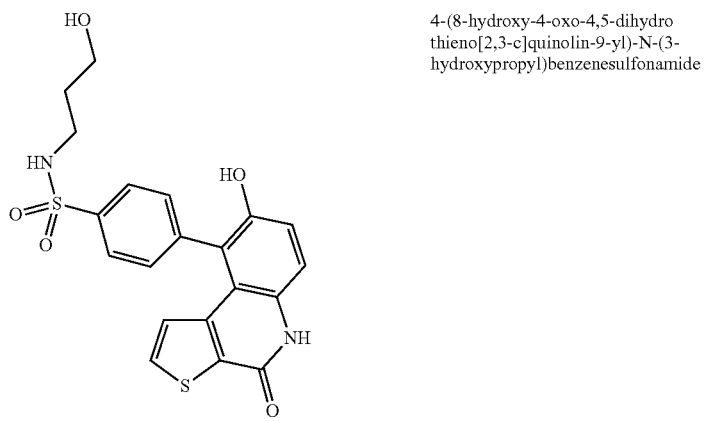 | 4-(8-hydroxy-4-oxo-4,5-dihydrothieno[2,3-c]quinolin-9-yl)-N-(3-hydroxypropyl)benzenesulfonamide |
| 323 | 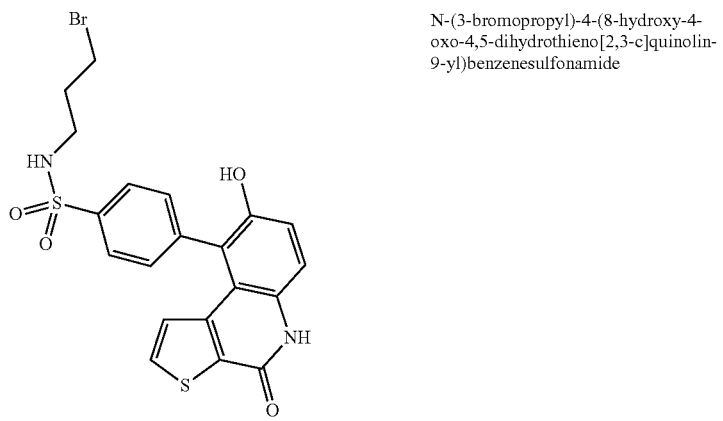 | N-(3-bromopropyl)-4-(8-hydroxy-4-oxo-4,5-dihydrothieno[2,3-c]quinolin-9-yl)benzenesulfonamide |

TABLE 1-continued

| | | |
|---|---|---|
| 324 | 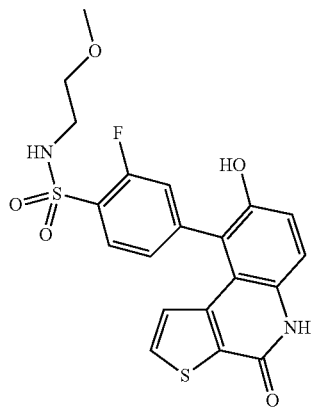 [SMILES: COCCNS(=O)(=O)c1ccc(-c2c(O)ccc3[nH]c(=O)c4sccc4c23)cc1F] | 2-fluoro-4-(8-hydroxy-4-oxo-4,5-dihydrothieno[2,3-c]quinolin-9-yl)-N-(2-methoxyethyl)benzenesulfonamide |
| 325 | 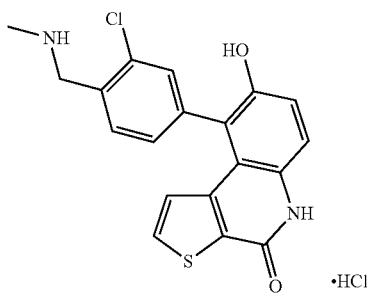 [SMILES: CNCc1ccc(-c2c(O)ccc3[nH]c(=O)c4sccc4c23)cc1Cl ; Cl] | 9-(3-chloro-4-((methylamino)methyl)phenyl)-8-hydroxythieno[2,3-c]quinolin-4(5H)-one hydrochloride |
| 326 | 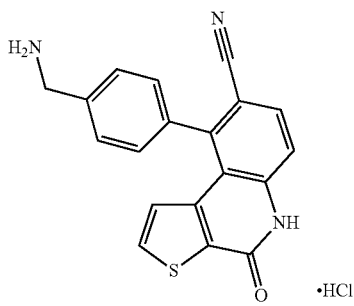 [SMILES: N#Cc1ccc2[nH]c(=O)c3sccc3c2c1-c1ccc(CN)cc1 ; Cl] | 9-(4-(aminomethyl)phenyl)-4-oxo-4,5-dihydrothieno[2,3-c]quinoline-8-carbonitrile hydrochloride |
| 327 | 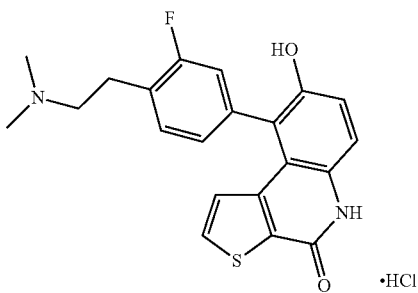 [SMILES: CN(C)CCc1ccc(-c2c(O)ccc3[nH]c(=O)c4sccc4c23)cc1F ; Cl] | 9-(4-(2-(dimethylamino)ethyl)-3-fluorophenyl)-8-hydroxythieno[2,3-c]quinolin-4(5H)-one hydrochloride |
| 328 | 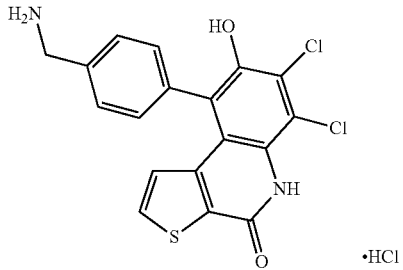 [SMILES: NCc1ccc(-c2c(O)c(Cl)c(Cl)c3[nH]c(=O)c4sccc4c23)cc1 ; Cl] | 9-(4-(aminomethyl)phenyl)-6,7-dichloro-8-hydroxythieno[2,3-c]quinolin-4(5H)-one hydrochloride |

TABLE 1-continued

| | | |
|---|---|---|
| 329 | | 9-(4-(aminomethyl)phenyl)-6-chloro-8-hydroxythieno[2,3-c]quinolin-4(5H)-one hydrochloride |
| 330 | | 9-(4-(aminomethyl)phenyl)-4-oxo-4,5-dihydrothieno[2,3-c]quinolin-8-yl trifluoromethanesulfonate hydrochloride |
| 331 | | 9-(4-(2-(dimethylamino)ethyl)phenyl)-8-methoxythieno[2,3-c]quinolin-4(5H)-one hydrochloride |
| 332 | | N-(2-chloroethyl)-4-(8-hydroxy-4-oxo-4,5-dihydrothieno[2,3-c]quinolin-9-yl)benzenesulfonamide |
| 333 | | N-(2-fluoroethyl)-4-(8-methoxy-4-oxo-4,5-dihydrothieno[2,3-c]quinolin-9-yl)benzenesulfonamide |

TABLE 1-continued

| | | |
|---|---|---|
| 334 | 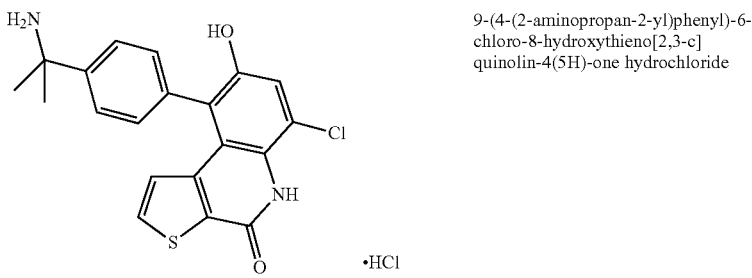 | 9-(4-(2-aminopropan-2-yl)phenyl)-6-chloro-8-hydroxythieno[2,3-c]quinolin-4(5H)-one hydrochloride |
| 335 | 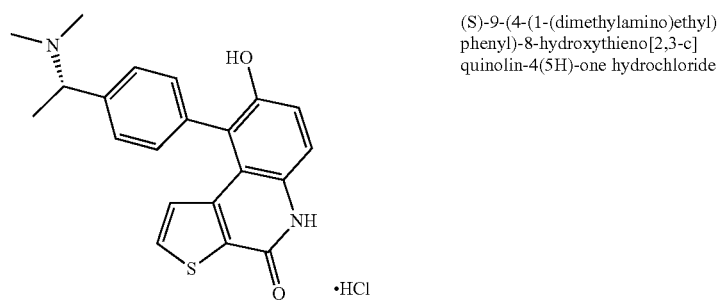 | (S)-9-(4-(1-(dimethylamino)ethyl)phenyl)-8-hydroxythieno[2,3-c]quinolin-4(5H)-one hydrochloride |
| 336 | 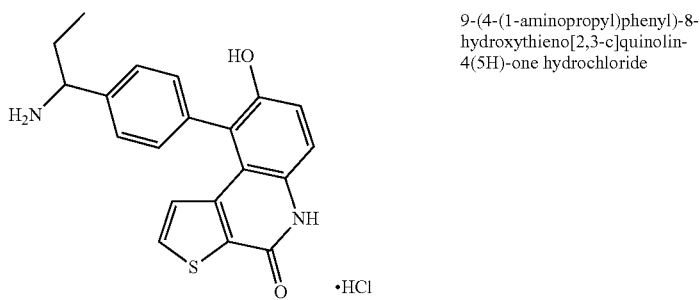 | 9-(4-(1-aminopropyl)phenyl)-8-hydroxythieno[2,3-c]quinolin-4(5H)-one hydrochloride |
| 337 | 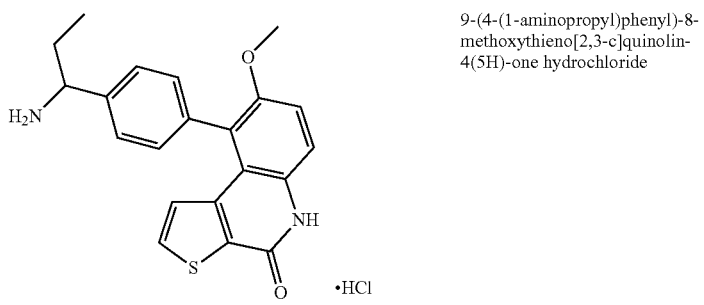 | 9-(4-(1-aminopropyl)phenyl)-8-methoxythieno[2,3-c]quinolin-4(5H)-one hydrochloride |
| 338 | 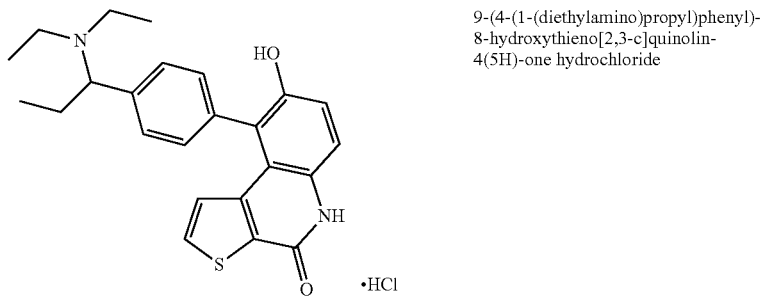 | 9-(4-(1-(diethylamino)propyl)phenyl)-8-hydroxythieno[2,3-c]quinolin-4(5H)-one hydrochloride |

| | | |
|---|---|---|
| 339 | 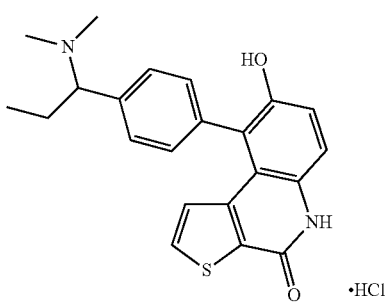 [SMILES: CCC(c1ccc(-c2c(O)ccc3[nH]c(=O)c4sccc4c23)cc1)N(C)C ; Cl] | 9-(4-(1-(dimethylamino)propyl)phenyl)-8-hydroxythieno[2,3-c]quinolin-4(5H)-one hydrochloride |
| 340 | 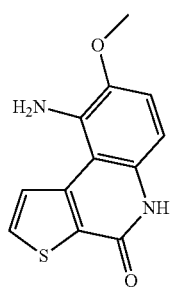 [SMILES: COc1ccc2[nH]c(=O)c3sccc3c2c1N] | 9-amino-8-methoxythieno[2,3-c]quinolin-4(5H)-one |
| 341 | 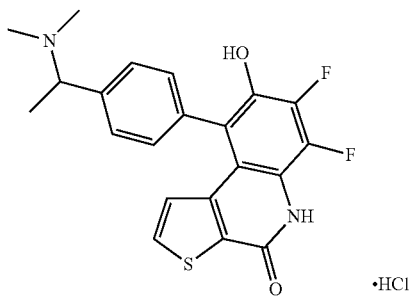 [SMILES: CC(c1ccc(-c2c(O)c(F)c(F)c3[nH]c(=O)c4sccc4c23)cc1)N(C)C ; Cl] | 9-(4-(1-(dimethylamino)ethyl)phenyl)-6,7-difluoro-8-hydroxythieno[2,3-c]quinolin-4(5H)-one hydrochloride |
| 342 | 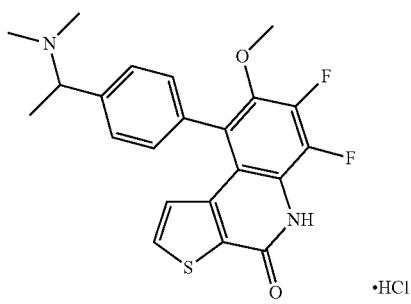 [SMILES: COc1c(F)c(F)c2[nH]c(=O)c3sccc3c2c1-c1ccc(C(C)N(C)C)cc1 ; Cl] | 9-(4-(1-(dimethylamino)ethyl)phenyl)-6,7-difluoro-8-methoxythieno[2,3-c]quinolin-4(5H)-one hydrochloride |
| 343 | 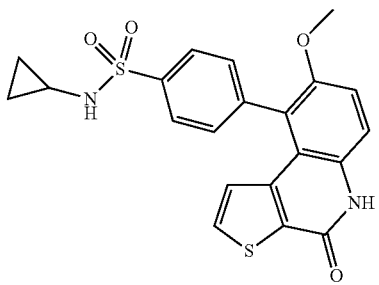 [SMILES: COc1ccc2[nH]c(=O)c3sccc3c2c1-c1ccc(S(=O)(=O)NC2CC2)cc1] | N-cyclopropyl-4-(8-methoxy-4-oxo-4,5-dihydrothieno[2,3-c]quinolin-9-yl)benzenesulfonamide |

| | | |
|---|---|---|
| 344 | 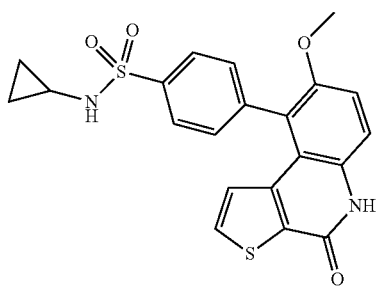 [SMILES: COc1ccc2[nH]c(=O)c3sccc3c2c1-c1ccc(S(=O)(=O)NC2CC2)cc1] | N-cyclopropyl-4-(8-hydroxy-4-oxo-4,5-dihydrothieno[2,3-c]quinolin-9-yl)benzenesulfonamide |
| 345 | 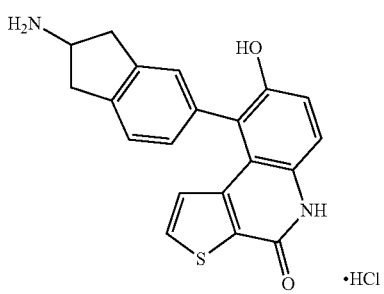 [SMILES: NC1Cc2ccc(-c3c(O)ccc4[nH]c(=O)c5sccc5c34)cc2C1 ; Cl] | 9-(2-amino-2,3-dihydro-1H-inden-5-yl)-8-hydroxythieno[2,3-c]quinolin-4(5H)-one hydrochloride |
| 346 | 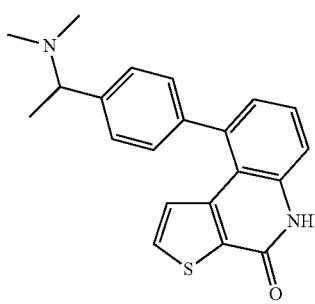 [SMILES: CC(c1ccc(-c2cccc3[nH]c(=O)c4sccc4c23)cc1)N(C)C] | 9-(4-(1-(dimethylamino)ethyl)phenyl)thieno[2,3-c]quinolin-4(5H)-one |
| 347 | 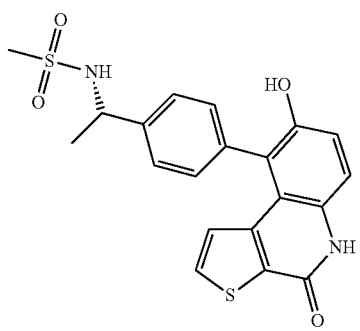 | (S)-N-(1-(4-(8-hydroxy-4-oxo-4,5-dihydrothieno[2,3-c]quinolin-9-yl)phenyl)ethyl)methanesulfonamide |
| 348 | 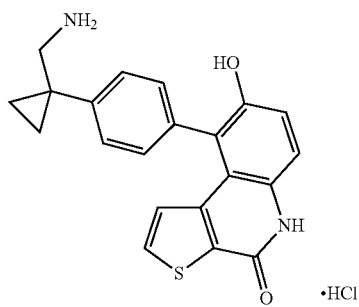 [SMILES: NCC1(c2ccc(-c3c(O)ccc4[nH]c(=O)c5sccc5c34)cc2)CC1 ; Cl] | 9-(4-(1-(aminomethyl)cyclopropyl)phenyl)-8-hydroxythieno[2,3-c]quinolin-4(5H)-one hydrochloride |

TABLE 1-continued

| | | |
|---|---|---|
| 349 | 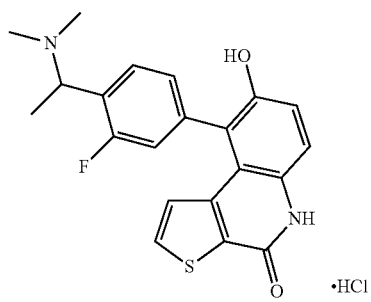 [SMILES: CC(c1ccc(-c2c(O)ccc3[nH]c(=O)c4sccc4c23)cc1F)N(C)C ; Cl] | 9-(4-(1-(dimethylamino)ethyl)-3-fluorophenyl)-8-hydroxythieno[2,3-c]quinolin-4(5H)-one hydrochloride |
| 350 | 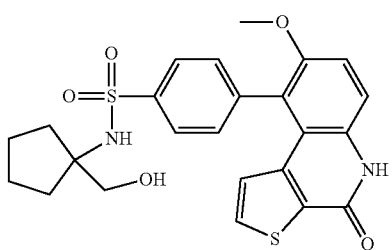 [SMILES: COc1ccc2[nH]c(=O)c3sccc3c2c1-c1ccc(S(=O)(=O)NC2(CO)CCCC2)cc1] | N-(1-(hydroxymethyl)cyclopentyl)-4-(8-methoxy-4-oxo-4,5-dihydrothieno[2,3-c]quinolin-9-yl)benzene sulfonamide |
| 351 | 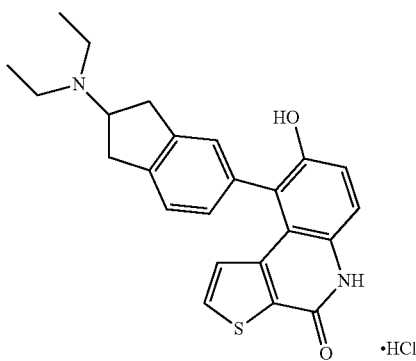 [SMILES: CCN(CC)C1Cc2ccc(-c3c(O)ccc4[nH]c(=O)c5sccc5c34)cc2C1 ; Cl] | 9-(2-(diethylamino)-2,3-dihydro-1H-inden-5-yl)-8-hydroxythieno[2,3-c]quinolin-4(5H)-one hydrochloride |
| 352 | 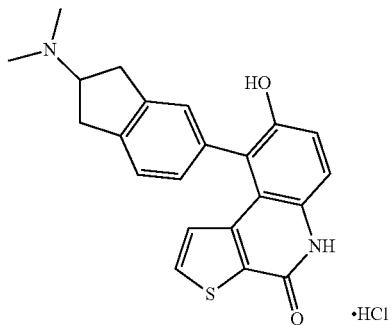 [SMILES: CN(C)C1Cc2ccc(-c3c(O)ccc4[nH]c(=O)c5sccc5c34)cc2C1 ; Cl] | 9-(2-(dimethylamino)-2,3-dihydro-1H-inden-5-yl)-8-hydroxythieno[2,3-c]quinolin-4(5H)-one hydrochloride |
| 353 | 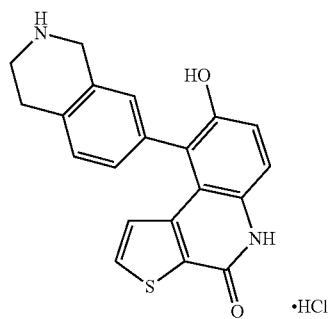 [SMILES: O=c1[nH]c2ccc(O)c(-c3ccc4c(c3)CNCC4)c2c2ccsc12 ; Cl] | 8-hydroxy-9-(1,2,3,4-tetrahydroisoquinolin-7-yl)thieno[2,3-c]quinolin-4(5H)-one hydrochloride |

TABLE 1-continued
| | | |
|---|---|---|
| 354 | 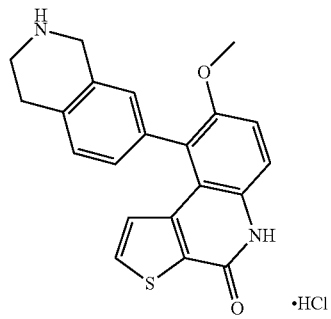 [SMILES: COc1ccc2[nH]c(=O)c3sccc3c2c1-c1ccc2c(c1)CNCC2 ; Cl] | 8-methoxy-9-(1,2,3,4-tetrahydroiso quinolin-7-yl)thieno[2,3-c]quinolin-4(5H)-one hydrochloride |
| 355 | 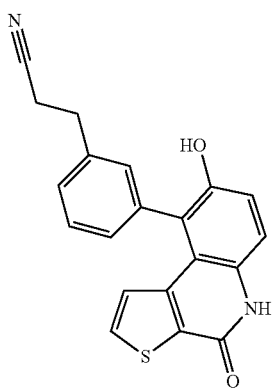 [SMILES: N#CCCc1cccc(-c2c(O)ccc3[nH]c(=O)c4sccc4c23)c1] | 3-(3-(8-hydroxy-4-oxo-4,5-dihydro thieno[2,3-c]quinolin-9-yl)phenyl) propanenitrile |
| 356 | 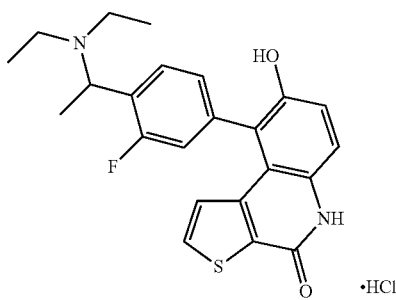 [SMILES: CCN(CC)C(C)c1ccc(-c2c(O)ccc3[nH]c(=O)c4sccc4c23)cc1F ; Cl] | 9-(4-(1-(diethylamino)ethyl)-3-fluoro phenyl)-8-hydroxythieno[2,3-c] quinolin-4(5H)-one hydrochloride |
| 357 | 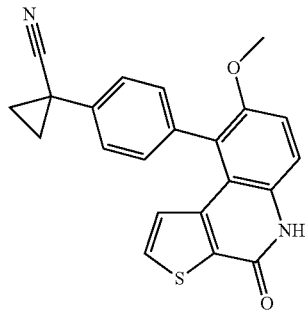 [SMILES: COc1ccc2[nH]c(=O)c3sccc3c2c1-c1ccc(C2(C#N)CC2)cc1] | 1-(4-(8-methoxy-4-oxo-4,5-dihydro thieno[2,3-c]quinolin-9-yl)phenyl) cyclopropanecarbonitrile |

TABLE 1-continued
| | | |
|---|---|---|
| 358 | 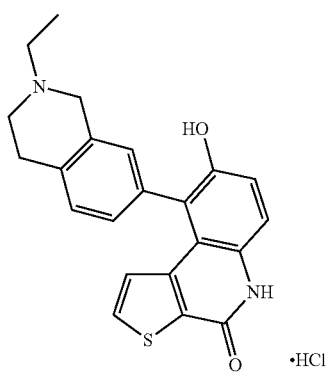 [SMILES: CCN1CCc2ccc(-c3c(O)ccc4[nH]c(=O)c5sccc5c34)cc2C1 ; Cl] | 9-(2-ethyl-1,2,3,4-tetrahydroiso quinolin-7-yl)-8-hydroxythieno[2,3-c] quinolin-4(5H)-one hydrochloride |
| 359 | 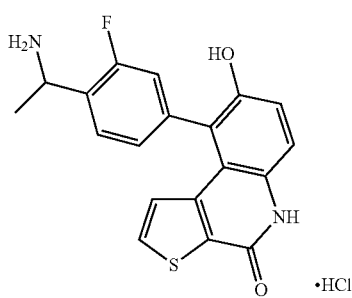 [SMILES: CC(N)c1ccc(-c2c(O)ccc3[nH]c(=O)c4sccc4c23)cc1F ; Cl] | 9-(4-(1-aminoethyl)-3-fluorophenyl)-8-hydroxythieno[2,3-c]quinolin-4(5H)-one hydrochloride |
| 360 | 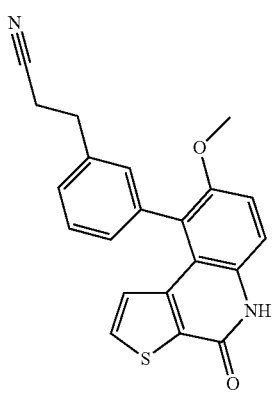 [SMILES: COc1ccc2[nH]c(=O)c3sccc3c2c1-c1cccc(CCC#N)c1] | 3-(3-(8-methoxy-4-oxo-4,5-dihydro thieno[2,3-c]quinolin-9-yl)phenyl) propanenitrile |
| 361 | 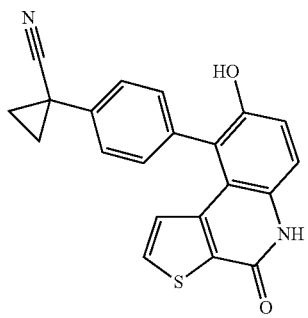 [SMILES: N#CC1(c2ccc(-c3c(O)ccc4[nH]c(=O)c5sccc5c34)cc2)CC1] | 1-(4-(8-hydroxy-4-oxo-4,5-dihydro thieno[2,3-c]quinolin-9-yl)phenyl) cyclopropanecarbonitrile |

TABLE 1-continued

| | | |
|---|---|---|
| 362 | 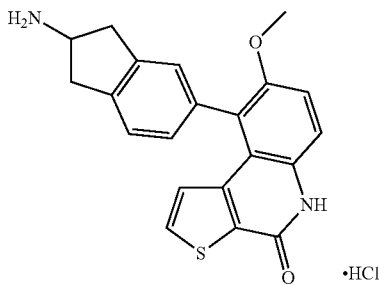 [SMILES: COc1ccc2[nH]c(=O)c3sccc3c2c1-c1ccc2c(c1)CC(N)C2 ; Cl] | 9-(2-amino-2,3-dihydro-1H-inden-5-yl)-8-methoxythieno[2,3-c]quinolin-4(5H)-one hydrochloride |
| 363 | 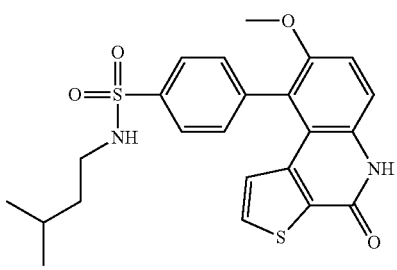 [SMILES: COc1ccc2[nH]c(=O)c3sccc3c2c1-c1ccc(S(=O)(=O)NCCC(C)C)cc1] | N-isopentyl-4-(8-methoxy-4-oxo-4,5-dihydrothieno[2,3-c]quinolin-9-yl)benzenesulfonamide |
| 364 | 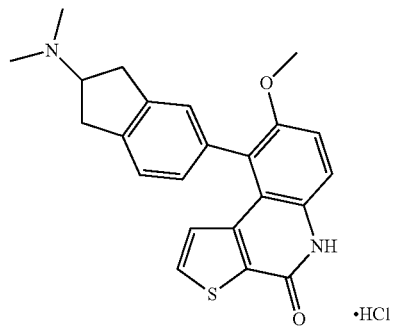 [SMILES: COc1ccc2[nH]c(=O)c3sccc3c2c1-c1ccc2c(c1)CC(N(C)C)C2 ; Cl] | 9-(2-(dimethylamino)-2,3-dihydro-1H-inden-5-yl)-8-methoxythieno[2,3-c]quinolin-4(5H)-one hydrochloride |
| 365 | 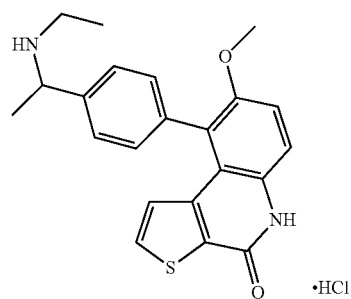 [SMILES: CCNC(C)c1ccc(-c2c(OC)ccc3[nH]c(=O)c4sccc4c23)cc1 ; Cl] | 9-(4-(1-(ethylamino)ethyl)phenyl)-8-methoxythieno[2,3-c]quinolin-4(5H)-one hydrochloride |
| 366 | 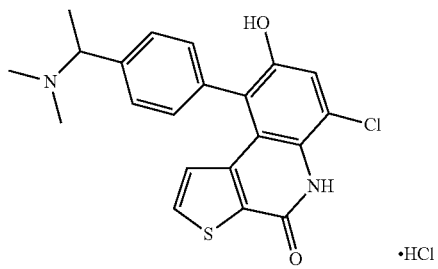 [SMILES: CC(c1ccc(-c2c(O)cc(Cl)c3[nH]c(=O)c4sccc4c23)cc1)N(C)C ; Cl] | 6-chloro-9-(4-(1-(dimethylamino)ethyl)phenyl)-8-hydroxythieno[2,3-c]quinolin-4(5H)-one hydrochloride |

| | | |
|---|---|---|
| 367 | 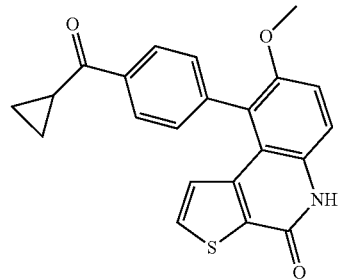 [SMILES: COc1ccc2[nH]c(=O)c3sccc3c2c1-c1ccc(C(=O)C2CC2)cc1] | 9-(4-(cyclopropanecarbonyl)phenyl)-8-methoxythieno[2,3-c]quinolin-4(5H)-one |
| 368 | 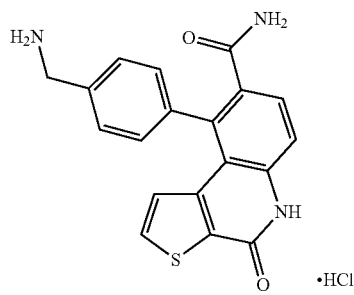 [SMILES: NCc1ccc(-c2c(C(N)=O)ccc3[nH]c(=O)c4sccc4c23)cc1 ; Cl] | 9-(4-(aminomethyl)phenyl)-4-oxo-4,5-dihydrothieno[2,3-c]quinoline-8-carboxamide hydrochloride |
| 369 | 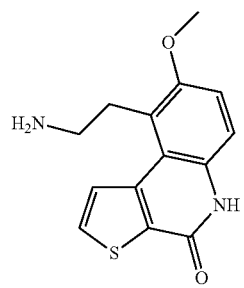 [SMILES: COc1ccc2[nH]c(=O)c3sccc3c2c1CCN] | 9-(2-aminoethyl)-8-methoxythieno[2,3-c]quinolin-4(5H)-one |
| 370 | 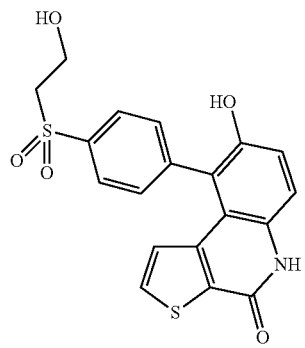 [SMILES: O=c1[nH]c2ccc(O)c(-c3ccc(S(=O)(=O)CCO)cc3)c2c2ccsc12] | 8-hydroxy-9-(4-(2-hydroxyethylsulfonyl)phenyl)thieno[2,3-c]quinolin-4(5H)-one |
| 371 | 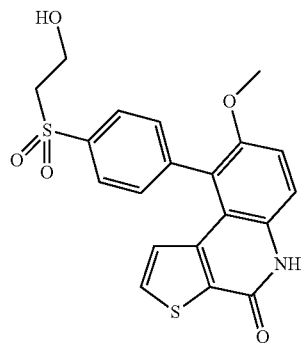 [SMILES: COc1ccc2[nH]c(=O)c3sccc3c2c1-c1ccc(S(=O)(=O)CCO)cc1] | 9-(4-(2-hydroxyethylsulfonyl)phenyl)-8-methoxythieno[2,3-c]quinolin-4(5H)-one |

| | | |
|---|---|---|
| 372 | 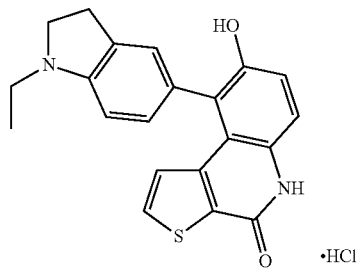 [SMILES: CCN1CCc2cc(-c3c(O)ccc4[nH]c(=O)c5sccc5c34)ccc21 ; Cl] | 9-(1-ethylindolin-5-yl)-8-hydroxy thieno[2,3-c]quinolin-4(5H)-one hydrochloride |
| 373 | 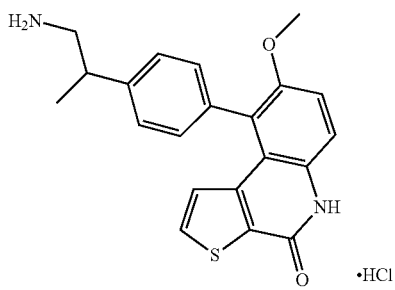 [SMILES: COc1ccc2[nH]c(=O)c3sccc3c2c1-c1ccc(C(C)CN)cc1 ; Cl] | 9-(4-(1-aminopropan-2-yl)phenyl)-8-methoxythieno[2,3-c]quinolin-4(5H)-one hydrochloride |
| 374 | 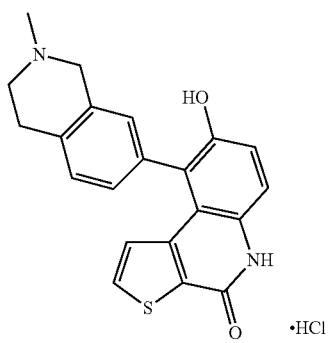 [SMILES: CN1CCc2ccc(-c3c(O)ccc4[nH]c(=O)c5sccc5c34)cc2C1 ; Cl] | 8-hydroxy-9-(2-methyl-1,2,3,4-tetra hydroisoquinolin-7-yl)thieno[2,3-c] quinolin-4(5H)-one hydrochloride |
| 375 | 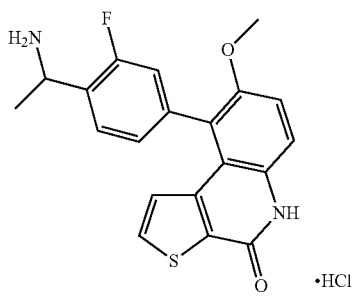 [SMILES: COc1ccc2[nH]c(=O)c3sccc3c2c1-c1ccc(C(C)N)c(F)c1 ; Cl] | 9-(4-(1-aminoethyl)-3-fluorophenyl)-8-methoxythieno[2,3-c]quinolin-4(5H)-one hydrochloride |
| 376 | 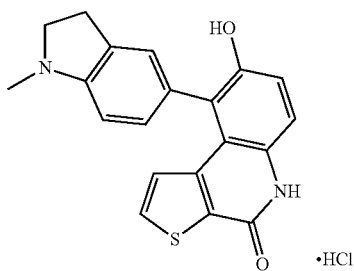 [SMILES: CN1CCc2cc(-c3c(O)ccc4[nH]c(=O)c5sccc5c34)ccc21 ; Cl] | 8-hydroxy-9-(1-methylindolin-5-yl) thieno[2,3-c]quinolin-4(5H)-one hydrochloride |

| | | |
|---|---|---|
| 377 | 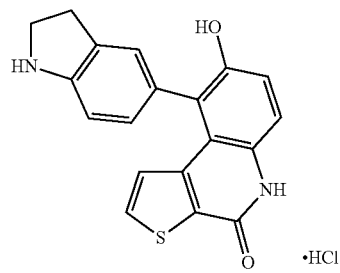 [SMILES: O=c1[nH]c2ccc(O)c(-c3ccc4c(c3)CCN4)c2c2ccsc12 ; Cl] | 8-hydroxy-9-(indolin-5-yl)thieno[2,3-c]quinolin-4(5H)-one hydrochloride |
| 378 | 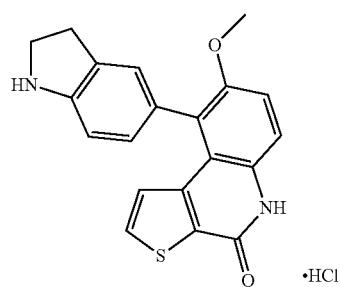 [SMILES: COc1ccc2[nH]c(=O)c3sccc3c2c1-c1ccc2c(c1)CCN2 ; Cl] | 9-(indolin-5-yl)-8-methoxythieno[2,3-c]quinolin-4(5H)-one hydrochloride |
| 379 | 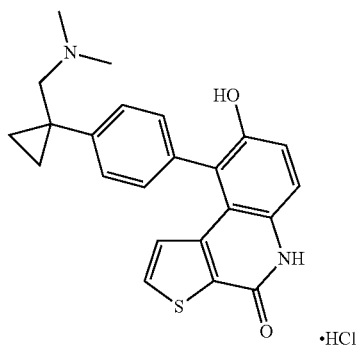 [SMILES: CN(C)CC1(c2ccc(-c3c(O)ccc4[nH]c(=O)c5sccc5c34)cc2)CC1 ; Cl] | 9-(4-(1-((dimethylamino)methyl)cyclopropyl)phenyl)-8-hydroxythieno[2,3-c]quinolin-4(5H)-one hydrochloride |
| 380 | 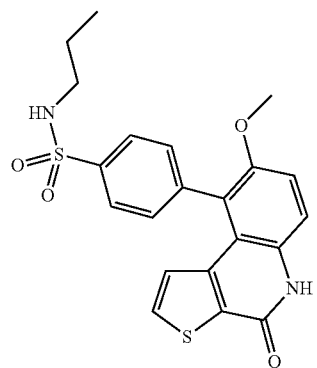 [SMILES: CCCNS(=O)(=O)c1ccc(-c2c(OC)ccc3[nH]c(=O)c4sccc4c23)cc1] | 4-(8-methoxy-4-oxo-4,5-dihydrothieno[2,3-c]quinolin-9-yl)-N-propyl benzenesulfonamide |

TABLE 1-continued
| | | |
|---|---|---|
| 381 | 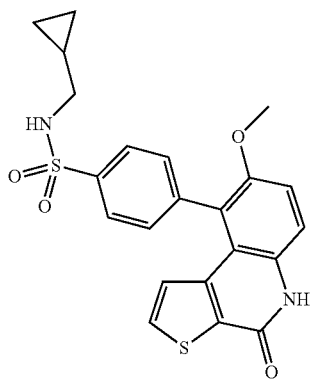 [SMILES: COc1ccc2[nH]c(=O)c3sccc3c2c1-c1ccc(S(=O)(=O)NCC2CC2)cc1] | N-(cyclopropylmethyl)-4-(8-methoxy-4-oxo-4,5-dihydrothieno[2,3-c]quinolin-9-yl)benzenesulfonamide |
| 382 | 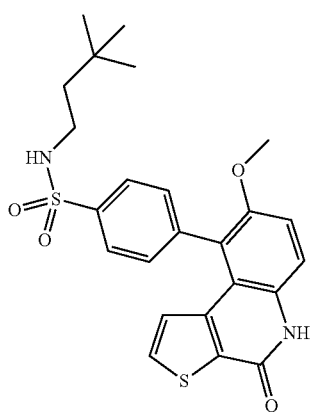 [SMILES: COc1ccc2[nH]c(=O)c3sccc3c2c1-c1ccc(S(=O)(=O)NCCC(C)(C)C)cc1] | N-(3,3-dimethylbutyl)-4-(8-methoxy-4-oxo-4,5-dihydrothieno[2,3-c]quinolin-9-yl)benzenesulfonamide |
| 383 | 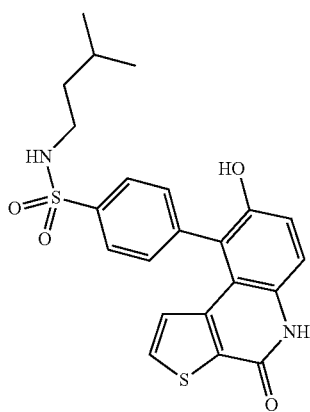 [SMILES: CC(C)CCNS(=O)(=O)c1ccc(-c2c(O)ccc3[nH]c(=O)c4sccc4c23)cc1] | 4-(8-hydroxy-4-oxo-4,5-dihydrothieno[2,3-c]quinolin-9-yl)-N-isopentyl benzenesulfonamide |
| 384 | 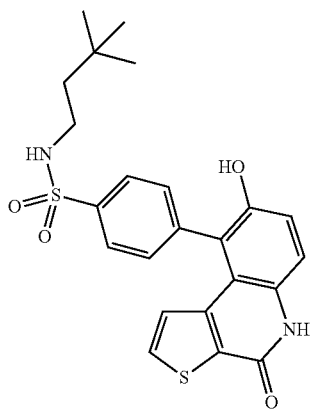 [SMILES: CC(C)(C)CCNS(=O)(=O)c1ccc(-c2c(O)ccc3[nH]c(=O)c4sccc4c23)cc1] | N-(3,3-dimethylbutyl)-4-(8-hydroxy-4-oxo-4,5-dihydrothieno[2,3-c]quinolin-9-yl)benzenesulfonamide |

| | | |
|---|---|---|
| 385 | 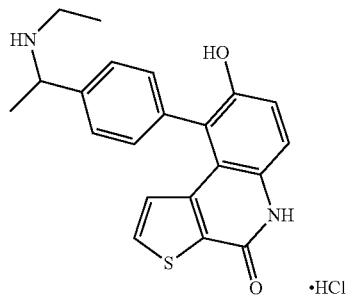 [SMILES: CCNC(C)c1ccc(-c2c(O)ccc3[nH]c(=O)c4sccc4c23)cc1 ; Cl] •HCl | 9-(4-(1-(ethylamino)ethyl)phenyl)-8-hydroxythieno[2,3-c]quinolin-4(5H)-one hydrochloride |
| 386 | 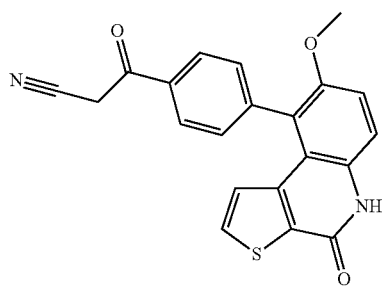 [SMILES: COc1ccc2[nH]c(=O)c3sccc3c2c1-c1ccc(C(=O)CC#N)cc1] | 3-(4-(8-methoxy-4-oxo-4,5-dihydro thieno[2,3-c]quinolin-9-yl)phenyl)-3-oxopropanenitrile |
| 387 | 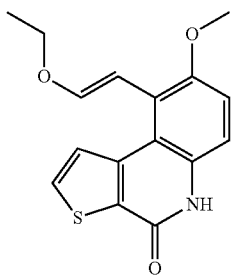 [SMILES: CCO/C=C/c1c(OC)ccc2[nH]c(=O)c3sccc3c12] | (E)-9-(2-ethoxyvinyl)-8-methoxy thieno[2,3-c]quinolin-4(5H)-one |
| 388 | 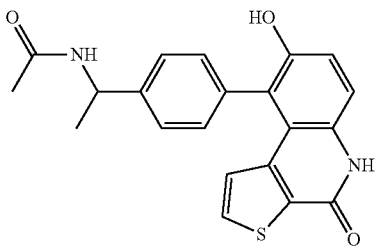 [SMILES: CC(=O)NC(C)c1ccc(-c2c(O)ccc3[nH]c(=O)c4sccc4c23)cc1] | N-(1-(4-(8-hydroxy-4-oxo-4,5-dihydrothieno[2,3-c]quinolin-9-yl)phenyl)ethyl)acetamide |
| 389 | 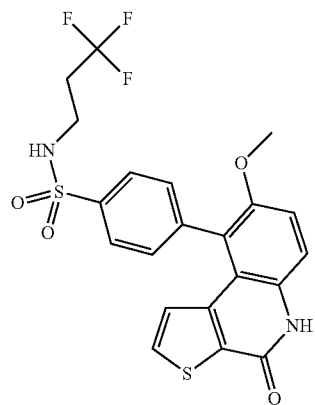 [SMILES: COc1ccc2[nH]c(=O)c3sccc3c2c1-c1ccc(S(=O)(=O)NCCC(F)(F)F)cc1] | 4-(8-methoxy-4-oxo-4,5-dihydro thieno[2,3-c]quinolin-9-yl)-N-(3,3,3-trifluoropropyl)benzenesulfonamide |

TABLE 1-continued
| | | |
|---|---|---|
| 390 | 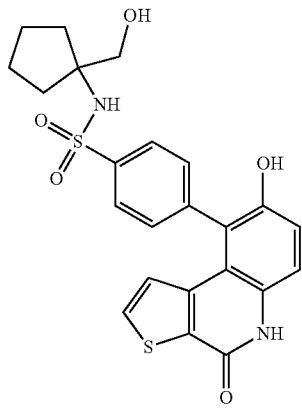 [SMILES: O=c1[nH]c2ccc(O)c(-c3ccc(S(=O)(=O)NC4(CO)CCCC4)cc3)c2c2ccsc12] | 4-(8-hydroxy-4-oxo-4,5-dihydro thieno[2,3-c]quinolin-9-yl)-N-(1-(hydroxymethyl)cyclopentyl) benzenesulfonamide |
| 391 | 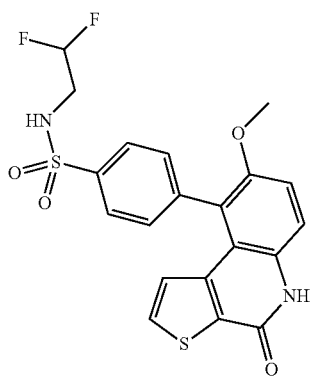 [SMILES: COc1ccc2[nH]c(=O)c3sccc3c2c1-c1ccc(S(=O)(=O)NCC(F)F)cc1] | N-(2,2-difluoroethyl)-4-(8-methoxy-4-oxo-4,5-dihydrothieno[2,3-c]quinolin-9-yl)benzenesulfonamide |
| (Examples 1031-1438) | | |
|---|---|---|
| No. | Molecule | Name |
| 1031 | 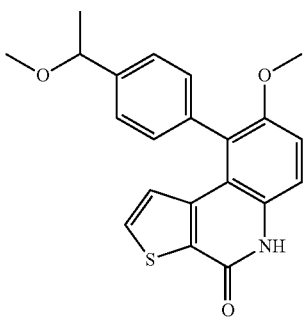 | 8-methoxy-9-(4-(1-methoxyethyl)phenyl)thieno[2,3-c]quinolin-4(5H)-one |
| 1032 | 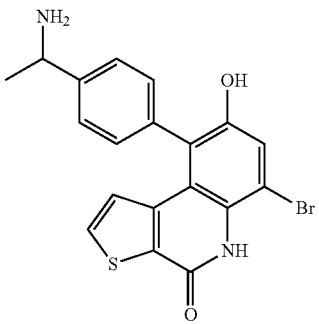 [SMILES: CC(N)c1ccc(-c2c(O)cc(Br)c3[nH]c(=O)c4sccc4c23)cc1] | 9-(4-(1-aminoethyl)phenyl)-6-bromo-8-hydroxythieno[2,3-c]quinolin-4(5H)-one |

TABLE 1-continued

| | | |
|---|---|---|
| 1033 | | 8-methoxy-9-(2-((piperidin-3-ylmethyl)amino)ethyl)thieno[2,3-c]quinolin-4(5H)-one |
| 1034 | | 9-(2-(4-((dimethylamino)methyl)piperidin-1-yl)ethyl)-8-methoxythieno[2,3-c]quinolin-4(5H)-one |
| 1035 | | tert-butyl 4-((2-(8-methoxy-4-oxo-4,5-dihydrothieno[2,3-c]quinolin-9-yl)ethyl)amino)piperidine-1-carboxylate |
| 1036 | | 8-methoxy-9-(2-(piperidin-4-yl amino)ethyl)thieno[2,3-c]quinolin-4(5H)-one |
| 1037 | | 4-(8-hydroxy-4-oxo-4,5-dihydrothieno[2,3-c]quinolin-9-yl)-N-(3,3,3-trifluoropropyl)benzenesulfonamide |

TABLE 1-continued
| 1038 |  | 3H-pyrrolo[2,3-c]quinolin-4(5H)-one |
| 1039 | 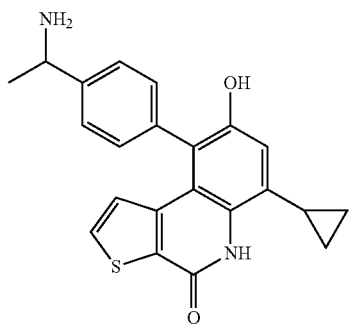 [SMILES: CC(N)c1ccc(-c2c(O)cc(C3CC3)c3[nH]c(=O)c4sccc4c23)cc1] | 9-(4-(1-aminoethyl)phenyl)-6-cyclopropyl-8-hydroxythieno[2,3-c]quinolin-4(5H)-one |
| 1040 | 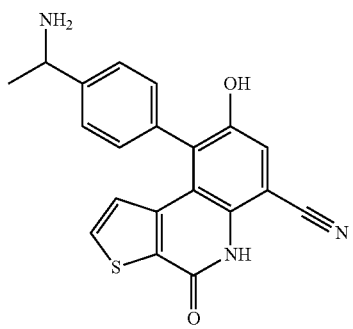 [SMILES: CC(N)c1ccc(-c2c(O)cc(C#N)c3[nH]c(=O)c4sccc4c23)cc1] | 9-(4-(1-aminoethyl)phenyl)-8-hydroxy-4-oxo-4,5-dihydrothieno[2,3-c]quinoline-6-carbonitrile |
| 1041 | 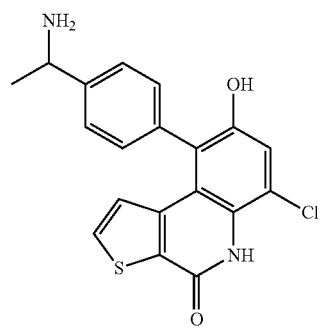 [SMILES: CC(N)c1ccc(-c2c(O)cc(Cl)c3[nH]c(=O)c4sccc4c23)cc1] | 9-(4-(1-aminoethyl)phenyl)-6-chloro-8-hydroxythieno[2,3-c]quinolin-4(5H)-one |
| 1042 | 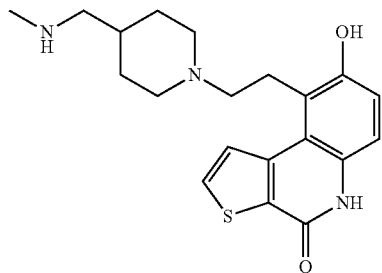 [SMILES: CNCC1CCN(CCc2c(O)ccc3[nH]c(=O)c4sccc4c23)CC1] | 8-hydroxy-9-(2-(4-((methylamino)methyl)piperidin-1-yl)ethyl)thieno[2,3-c]quinolin-4(5H)-one |

TABLE 1-continued

| | | |
|---|---|---|
| 1043 | | 8-methoxy-9-(2-(4-((methylamino)methyl)piperidin-1-yl)ethyl)thieno[2,3-c]quinolin-4(5H)-one |
| 1044 | | 9-(2-(4-((dimethylamino)methyl)piperidin-1-yl)ethyl)-8-hydroxythieno[2,3-c]quinolin-4(5H)-one |
| 1045 | | 9-(4-(1-hydroxypropyl)phenyl)-8-methoxythieno[2,3-c]quinolin-4(5H)-one |
| 1046 | | (R)-8-methoxy-9-(4-(1-(methylamino)ethyl)phenyl)thieno[2,3-c]quinolin-4(5H)-one |
| 1047 | | (R)-8-(4-(1-aminoethyl)phenyl)thieno[2,3-c]quinolin-4(5H)-one |

TABLE 1-continued
| | | |
|---|---|---|
| 1048 | 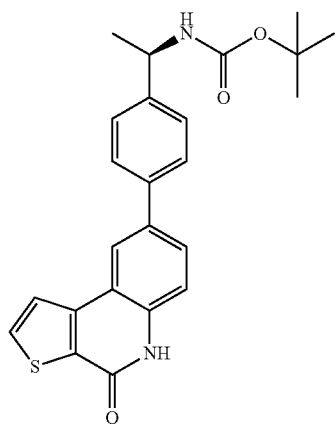 [SMILES: C[C@@H](NC(=O)OC(C)(C)C)c1ccc(-c2ccc3[nH]c(=O)c4sccc4c3c2)cc1] | (R)-tert-butyl (1-(4-(4-oxo-4,5-dihydrothieno [2,3-c]quinolin-8-yl)phenyl) ethyl)carbamate |
| 1049 | 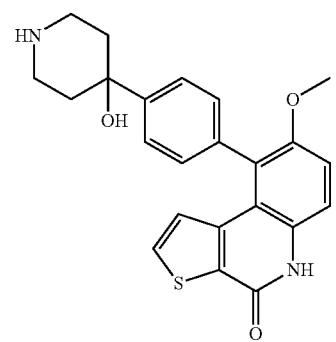 [SMILES: COc1ccc2[nH]c(=O)c3sccc3c2c1-c1ccc(C2(O)CCNCC2)cc1] | 9-(4-(4-hydroxypiperidin-4-yl) phenyl)-8-methoxythieno[2,3-c]quinolin-4(5H)-one |
| 1050 | 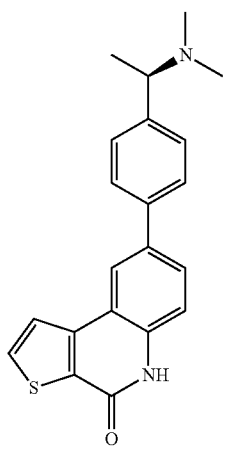 [SMILES: C[C@H](c1ccc(-c2ccc3[nH]c(=O)c4sccc4c3c2)cc1)N(C)C] | (R)-8-(4-(1-(dimethylamino) ethyl)phenyl)thieno[2,3-c]quinolin-4(5H)-one |
| 1051 | 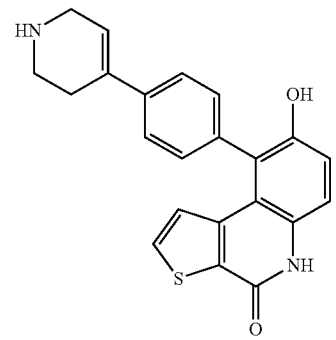 [SMILES: O=c1[nH]c2ccc(O)c(-c3ccc(C4=CCNCC4)cc3)c2c2ccsc12] | 8-hydroxy-9-(4-(1,2,3,6-tetrahydropyridin-4-yl) phenyl)thieno[2,3-c] quinolin-4(5H)-one |

TABLE 1-continued
| | | |
|---|---|---|
| 1052 | 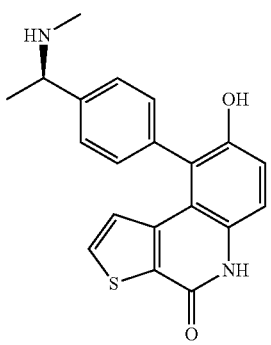 [SMILES: CN[C@H](C)c1ccc(-c2c(O)ccc3[nH]c(=O)c4sccc4c23)cc1] | (R)-8-hydroxy-9-(4-(1-(methyl amino)ethyl)phenyl)thieno[2,3-c]quinolin-4(5H)-one |
| 1053 | 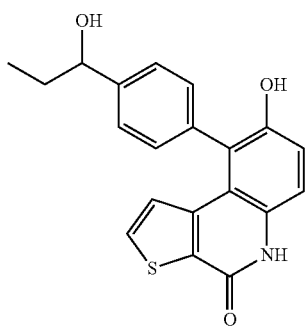 [SMILES: CCC(O)c1ccc(-c2c(O)ccc3[nH]c(=O)c4sccc4c23)cc1] | 8-hydroxy-9-(4-(1-hydroxypropyl)phenyl)thieno [2,3-c]quinolin-4(5H)-one |
| 1054 | 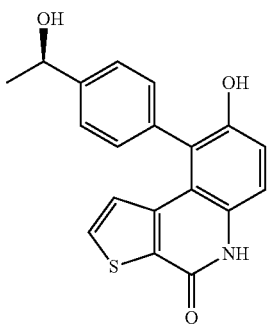 [SMILES: C[C@@H](O)c1ccc(-c2c(O)ccc3[nH]c(=O)c4sccc4c23)cc1] | (R)-8-hydroxy-9-(4-(1-hydroxy ethyl)phenyl)thieno[2,3-c] quinolin-4(5H)-one |
| 1055 | 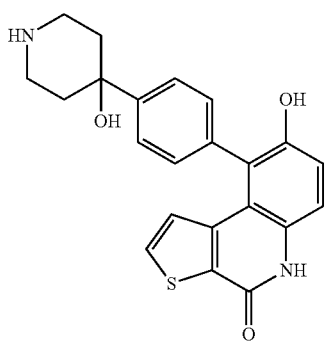 [SMILES: O=c1[nH]c2ccc(O)c(-c3ccc(C4(O)CCNCC4)cc3)c2c2ccsc12] | 8-hydroxy-9-(4-(4-hydroxypiperidin-4-yl)phenyl)thieno[2,3-c]quinolin-4(5H)-one |

TABLE 1-continued
| | | |
|---|---|---|
| 1056 | 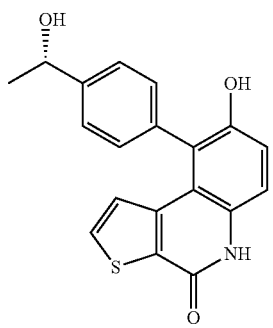 [SMILES: C[C@H](O)c1ccc(-c2c(O)ccc3[nH]c(=O)c4sccc4c23)cc1] | (S)-8-hydroxy-9-(4-(1-hydroxy ethyl)phenyl)thieno[2,3-c]quinolin-4(5H)-one |
| 1057 | 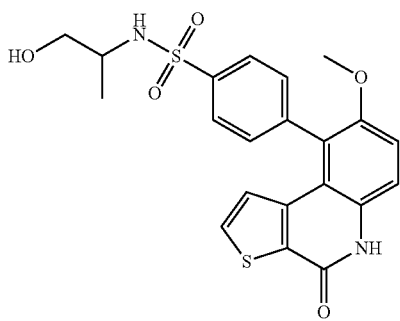 [SMILES: COc1ccc2[nH]c(=O)c3sccc3c2c1-c1ccc(S(=O)(=O)NC(C)CO)cc1] | N-(1-hydroxypropan-2-yl)-4-(8-methoxy-4-oxo-4,5-dihydrothieno[2,3-c]quinolin-9-yl)benzenesulfonamide |
| 1058 | 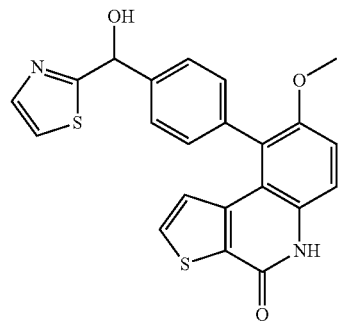 [SMILES: COc1ccc2[nH]c(=O)c3sccc3c2c1-c1ccc(C(O)c2nccs2)cc1] | 9-(4-(hydroxy(thiazol-2-yl)methyl)phenyl)-8-methoxythieno[2,3-c]quinolin-4(5H)-one |
| 1059 | 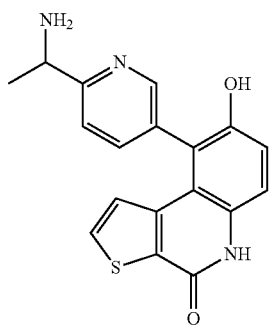 [SMILES: CC(N)c1ccc(-c2c(O)ccc3[nH]c(=O)c4sccc4c23)cn1] | 9-(6-(1-aminoethyl)pyridin-3-yl)-8-hydroxythieno[2,3-c]quinolin-4(5H)-one |
| 1060 | 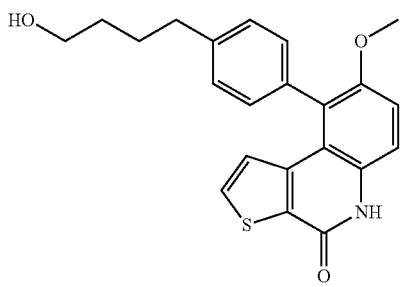 [SMILES: COc1ccc2[nH]c(=O)c3sccc3c2c1-c1ccc(CCCCO)cc1] | 9-(4-(4-hydroxybutyl)phenyl)-8-methoxythieno[2,3-c]quinolin-4(5H)-one |

TABLE 1-continued

| | | |
|---|---|---|
| 1061 | | 2-(4-(8-hydroxy-4-oxo-4,5-dihydrothieno[2,3-c]quinolin-9-yl)phenyl)-2-methylpropanamide |
| 1062 | | N-(1-bromopropan-2-yl)-4-(8-hydroxy-4-oxo-4,5-dihydrothieno[2,3-c]quinolin-9-yl)benzenesulfonamide |
| 1063 | | 8-hydroxy-9-(4-(hydroxy(thiazol-2-yl)methyl)phenyl)thieno[2,3-c]quinolin-4(5H)-one |
| 1064 | | (S)-8-methoxy-9-(4-(1-(methylamino)ethyl)phenyl)thieno[2,3-c]quinolin-4(5H)-one |
| 1065 | | 9-(6-(1-(diethylamino)ethyl)pyridin-3-yl)-8-hydroxythieno[2,3-c]quinolin-4(5H)-one |

TABLE 1-continued
| | | |
|---|---|---|
| 1066 | 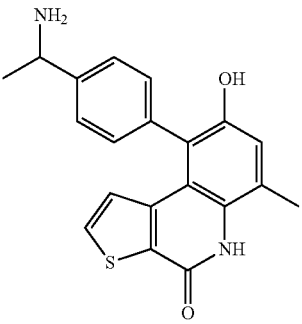 [SMILES: Cc1cc(O)c(-c2ccc(C(C)N)cc2)c2c1[nH]c(=O)c1sccc12] | 9-(4-(1-aminoethyl)phenyl)-8-hydroxy-6-methylthieno[2,3-c]quinolin-4(5H)-one |
| 1067 | 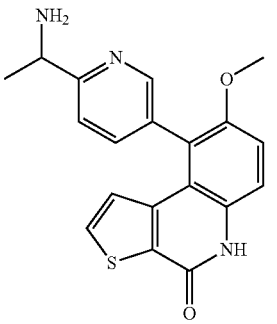 [SMILES: COc1ccc2[nH]c(=O)c3sccc3c2c1-c1ccc(C(C)N)nc1] | 9-(6-(1-aminoethyl)pyridin-3-yl)-8-methoxythieno[2,3-c]quinolin-4(5H)-one |
| 1068 | 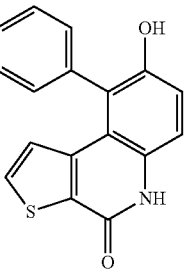 | 8-hydroxy-9-(4-(4-hydroxybutyl)phenyl)thieno[2,3-c]quinolin-4(5H)-one |
| 1069 | 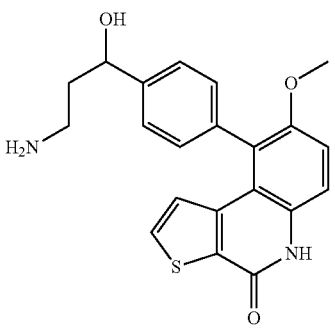 [SMILES: COc1ccc2[nH]c(=O)c3sccc3c2c1-c1ccc(C(O)CCN)cc1] | 9-(4-(3-amino-1-hydroxypropyl)phenyl)-8-methoxythieno[2,3-c]quinolin-4(5H)-one |
| 1070 | 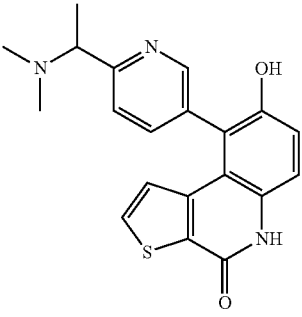 [SMILES: CC(c1ccc(-c2c(O)ccc3[nH]c(=O)c4sccc4c23)cn1)N(C)C] | 9-(6-(1-(dimethylamino)ethyl)pyridin-3-yl)-8-hydroxythieno[2,3-c]quinolin-4(5H)-one |

TABLE 1-continued

| | | |
|---|---|---|
| 1071 | | 9-(6-(1-(dimethylamino)ethyl)pyridin-3-yl)-8-methoxythieno[2,3-c]quinolin-4(5H)-one |
| 1072 | | 4-((4-(8-methoxy-4-oxo-4,5-dihydrothieno[2,3-c]quinolin-9-yl)-1H-pyrazol-1-yl)methyl)benzonitrile |
| 1073 | | 8-aminothieno[2,3-c]quinolin-4(5H)-one |
| 1074 | | 9-(4-((1H-pyrazol-1-yl)methyl)phenyl)-8-methoxythieno[2,3-c]quinolin-4(5H)-one |
| 1075 | | 9-(6-(1-aminoethyl)pyridin-3-yl)-8-methoxythieno[2,3-c]quinolin-4(5H)-one |

TABLE 1-continued

| | | |
|---|---|---|
| 1076 | | 9-(4-(1-aminoethyl)phenyl)-4-oxo-4,5-dihydrothieno[2,3-c]quinolin-8-yl dimethylcarbamate |
| 1077 | | 9-(4-(1-aminoethyl)phenyl)-4-oxo-4,5-dihydrothieno[2,3-c]quinolin-8-yl isopropyl carbonate |
| 1078 | | 9-(4-((1H-imidazol-1-yl)methyl)phenyl)-8-methoxythieno[2,3-c]quinolin-4(5H)-one |
| 1079 | | N-(2-bromopropyl)-4-(8-hydroxy-4-oxo-4,5-dihydrothieno[2,3-c]quinolin-9-yl)benzenesulfonamide |
| 1080 | | (R)-9-(4-(1-aminoethyl)phenyl)-6,7-dichloro-8-hydroxythieno[2,3-c]quinolin-4(5H)-one |

TABLE 1-continued
| | | |
|---|---|---|
| 1081 | 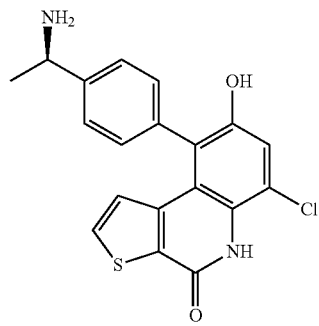 [SMILES: C[C@@H](N)c1ccc(-c2c(O)cc(Cl)c3[nH]c(=O)c4sccc4c23)cc1] | (R)-9-(4-(1-aminoethyl)phenyl)-6-chloro-8-hydroxythieno[2,3-c]quinolin-4(5H)-one |
| 1082 | 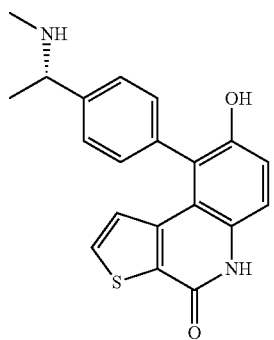 [SMILES: CN[C@@H](C)c1ccc(-c2c(O)ccc3[nH]c(=O)c4sccc4c23)cc1] | (S)-8-hydroxy-9-(4-(1-(methylamino)ethyl)phenyl)thieno[2,3-c]quinolin-4(5H)-one |
| 1083 | 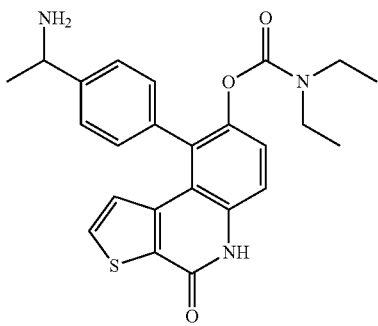 [SMILES: CCN(CC)C(=O)Oc1ccc2[nH]c(=O)c3sccc3c2c1-c1ccc(C(C)N)cc1] | 9-(4-(1-aminoethyl)phenyl)-4-oxo-4,5-dihydrothieno[2,3-c]quinolin-8-yl diethylcarbamate |
| 1084 | 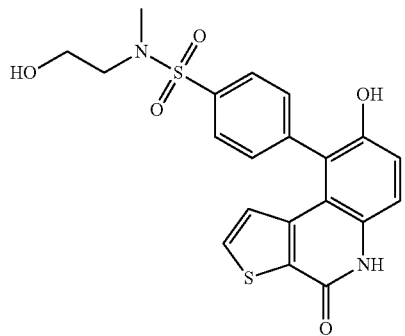 [SMILES: CN(CCO)S(=O)(=O)c1ccc(-c2c(O)ccc3[nH]c(=O)c4sccc4c23)cc1] | 4-(8-hydroxy-4-oxo-4,5-dihydrothieno[2,3-c]quinolin-9-yl)-N-(2-hydroxyethyl)-N-methylbenzenesulfonamide |

TABLE 1-continued

| 1085 | N-(2-hydroxyethyl)-4-(8-methoxy-4-oxo-4,5-dihydrothieno[2,3-c]quinolin-9-yl)-N-methylbenzenesulfonamide |
| 1086 | 9-(4-((1H-pyrazol-1-yl(methyl)phenyl)-8-hydroxythieno[2,3-c]quinolin-4(5H)-one |
| 1087 | (S)-6-chloro-8-hydroxy-9-(4-(1-(methylamino)ethyl)phenyl)thieno[2,3-c]quinolin-4(5H)-one |
| 1088 | 9-(4-(1-aminopropyl)phenyl)-6-chloro-8-hydroxythieno[2,3-c]quinolin-4(5H)-one |
| 1089 | 9-(4-(1-aminoethyl)phenyl)-4-oxo-4,5-dihydrothieno[2,3-c]quinolin-8-yl morpholine-4-carboxylate |

TABLE 1-continued

| | | |
|---|---|---|
| 1090 | | N-(2-hydroxyethyl)-4-(8-methoxy-4-oxo-2,3,4,5-tetrahydro-1H-cyclopenta[c]quinolin-9-yl)benzenesulfonamide |
| 1091 | | 8-bromothieno[2,3-c]quinolin-4(5H)-one |
| 1092 | | 9-(4-(2-(dimethylamino)propyl)phenyl)-8-hydroxythieno[2,3-c]quinolin-4(5H)-one |
| 1093 | | 9-(4-(2-aminopropyl)phenyl)-8-methoxythieno[2,3-c]quinolin-4(5H)-one |
| 1094 | | N-(2-bromoethyl)-4-(8-hydroxy-4-oxo-2,3,4,5-tetrahydro-1H-cyclopenta[c]quinolin-9-yl)benzenesulfonamide |

TABLE 1-continued

| # | Structure | Name |
|---|---|---|
| 1095 | 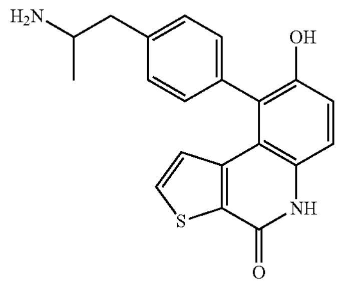 [SMILES: CC(N)Cc1ccc(-c2c(O)ccc3[nH]c(=O)c4sccc4c23)cc1] | 9-(4-(2-aminopropyl)phenyl)-8-hydroxythieno[2,3-c]quinolin-4(5H)-one |
| 1096 | 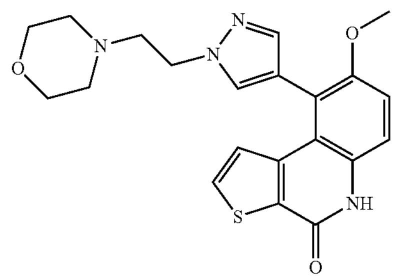 [SMILES: COc1ccc2[nH]c(=O)c3sccc3c2c1-c1cnn(CCN2CCOCC2)c1] | 8-methoxy-9-(1-(2-morpholinoethyl)-1H-pyrazol-4-yl)thieno[2,3-c]quinolin-4(5H)-one |
| 1097 | 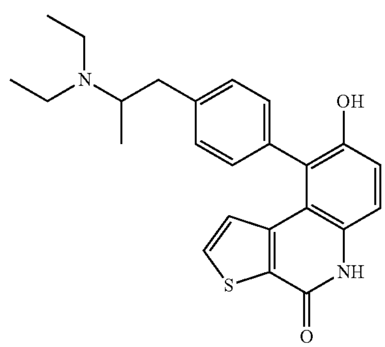 [SMILES: CCN(CC)C(C)Cc1ccc(-c2c(O)ccc3[nH]c(=O)c4sccc4c23)cc1] | 9-(4-(2-(diethylamino)propyl)phenyl)-8-hydroxythieno[2,3-c]quinolin-4(5H)-one |
| 1098 | 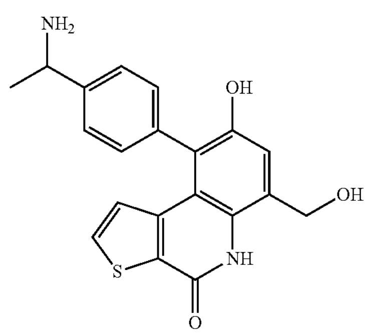 [SMILES: CC(N)c1ccc(-c2c(O)cc(CO)c3[nH]c(=O)c4sccc4c23)cc1] | 9-(4-(1-aminoethyl)phenyl)-8-hydroxy-6-(hydroxymethyl)thieno[2,3-c]quinolin-4(5H)-one |
| 1099 | 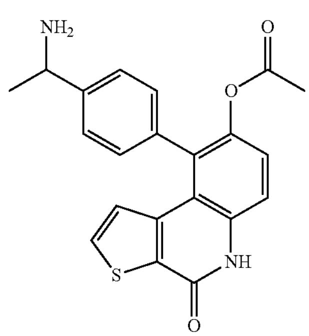 [SMILES: CC(=O)Oc1ccc2[nH]c(=O)c3sccc3c2c1-c1ccc(C(C)N)cc1] | 9-(4-(1-aminoethyl)phenyl)-4-oxo-4,5-dihydrothieno[2,3-c]quinolin-8-yl acetate |

TABLE 1-continued

| | | |
|---|---|---|
| 1100 | | 9-(1-(1-(dimethylamino)propan-2-yl)-1H-pyrazol-4-yl)-8-methoxythieno[2,3-c]quinolin-4(5H)-one |
| 1101 | | 9-(4-((1H-imidazol-1-yl)methyl)phenyl)-8-hydroxythieno[2,3-c]quinolin-4(5H)-one |
| 1102 | | 9-(4-(aminomethyl)phenyl)-8-(2-morpholinoethoxy)thieno[2,3-c]quinolin-4(5H)-one |
| 1103 | | 8-hydroxy-9-(1-(2-morpholinoethyl)-1H-pyrazol-4-yl)thieno[2,3-c]quinolin-4(5H)-one |
| 1104 | | N-(2-(1H-pyrazol-1-yl)ethyl)-4-(8-hydroxy-4-oxo-4,5-dihydrothieno[2,3-c]quinolin-9-yl)benzenesulfonamide |

TABLE 1-continued
| | | |
|---|---|---|
| 1105 | 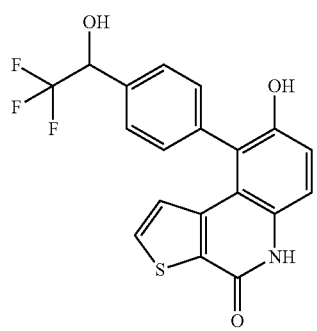 [SMILES: O=c1[nH]c2ccc(O)c(-c3ccc(C(O)C(F)(F)F)cc3)c2c2ccsc12] | 8-hydroxy-9-(4-(2,2,2-trifluoro-1-hydroxyethyl)phenyl)thieno[2,3-c]quinolin-4(5H)-one |
| 1106 | 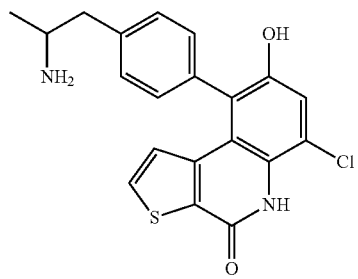 [SMILES: CC(N)Cc1ccc(-c2c(O)cc(Cl)c3[nH]c(=O)c4sccc4c23)cc1] | 9-(4-(2-aminopropyl)phenyl)-6-chloro-8-hydroxythieno[2,3-c]quinolin-4(5H)-one |
| 1107 | 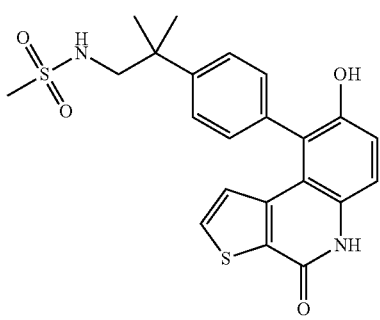 [SMILES: CC(C)(CNS(C)(=O)=O)c1ccc(-c2c(O)ccc3[nH]c(=O)c4sccc4c23)cc1] | N-(2-(4-(8-hydroxy-4-oxo-4,5-dihydrothieno[2,3-c]quinolin-9-yl)phenyl)-2-methylpropyl)methanesulfonamide |
| 1108 | 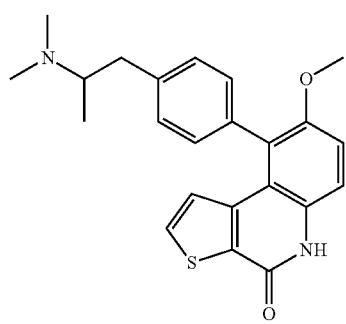 | 9-(4-(2-(dimethylamino)propyl)phenyl)-8-methoxythieno[2,3-c]quinolin-4(5H)-one |
| 1109 | 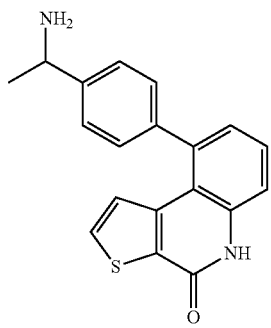 [SMILES: CC(N)c1ccc(-c2cccc3[nH]c(=O)c4sccc4c23)cc1] | 9-(4-(1-aminoethyl)phenyl)thieno[2,3-c]quinolin-4(5H)-one |

TABLE 1-continued
| 1110 | 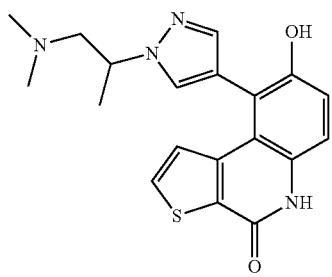 [SMILES: CC(CN(C)C)n1cc(-c2c(O)ccc3[nH]c(=O)c4sccc4c23)cn1] | 9-(1-(1-(dimethylamino)propan-2-yl)-1H-pyrazol-4-yl)-8-hydroxythieno[2,3-c]quinolin-4(5H)-one |
| 1111 | 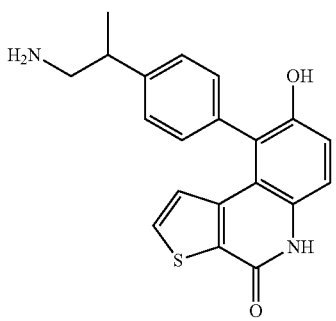 [SMILES: CC(CN)c1ccc(-c2c(O)ccc3[nH]c(=O)c4sccc4c23)cc1] | 9-(4-(1-aminopropan-2-yl)phenyl)-8-hydroxythieno[2,3-c]quinolin-4(5H)-one |
| 1112 | 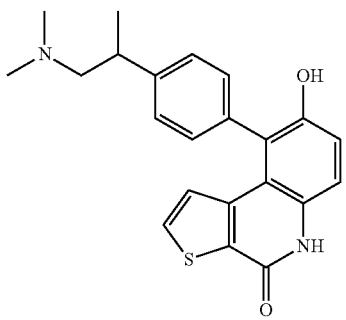 | 9-(4-(1-(dimethylamino)propan-2-yl)phenyl)-8-hydroxythieno[2,3-c]quinolin-4(5H)-one |
| 1113 | 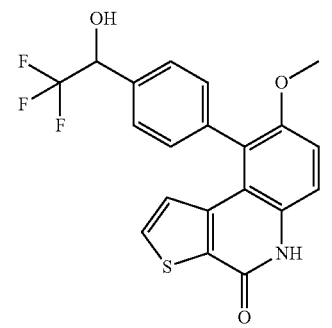 [SMILES: COc1ccc2[nH]c(=O)c3sccc3c2c1-c1ccc(C(O)C(F)(F)F)cc1] | 8-methoxy-9-(4-(2,2,2-trifluoro-1-hydroxyethyl)phenyl)thieno[2,3-c]quinolin-4(5H)-one |
| 1114 | 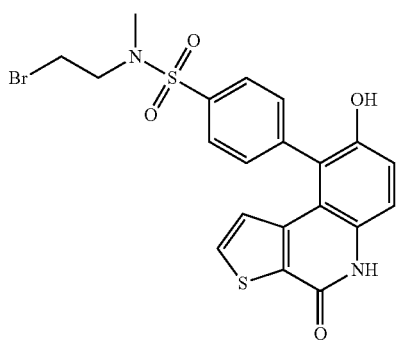 [SMILES: CN(CCBr)S(=O)(=O)c1ccc(-c2c(O)ccc3[nH]c(=O)c4sccc4c23)cc1] | N-(2-bromoethyl)-4-(8-hydroxy-4-oxo-4,5-dihydrothieno[2,3-c]quinolin-9-yl)-N-methylbenzenesulfonamide |

TABLE 1-continued

| | | |
|---|---|---|
| 1115 | | N-(2-(1H-imidazol-1-yl)ethyl)-4-(8-hydroxy-4-oxo-4,5-dihydrothieno[2,3-c]quinolin-9-yl)benzenesulfonamide |
| 1116 | | 9-(4-(1-(aminomethyl)cyclopropyl)phenyl)-6-chloro-8-hydroxythieno[2,3-c]quinolin-4(5H)-one |
| 1117 | | 3-(4-(8-(2-(dimethylamino)ethoxy)-4-oxo-4,5-dihydrothieno[2,3-c]quinolin-9-yl)phenyl)propanenitrile |
| 1118 | | (R)-9-(4-(1-aminopropyl)phenyl)-8-methoxythieno[2,3-c]quinolin-4(5H)-one |
| 1119 | | N-(2-chloroethyl)-4-(8-hydroxy-4-oxo-4,5-dihydrothieno[2,3-c]quinolin-9-yl)-N-methylbenzenesulfonamide |

TABLE 1-continued
| | | |
|---|---|---|
| 1120 | 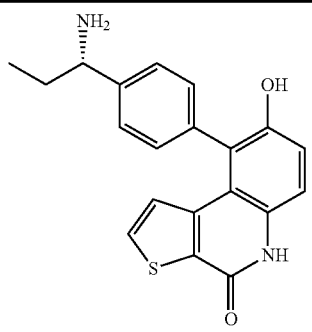 | (S)-9-(4-(1-aminopropyl)phenyl)-8-hydroxythieno[2,3-c]quinolin-4(5H)-one |
| 1121 | 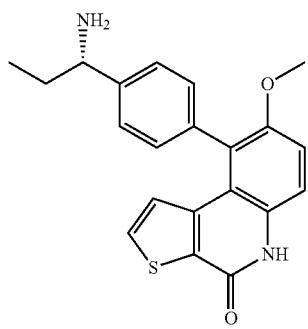 [SMILES: CC[C@H](N)c1ccc(-c2c(OC)ccc3[nH]c(=O)c4sccc4c23)cc1] | (S)-9-(4-(1-aminopropyl)phenyl)-8-methoxythieno[2,3-c]quinolin-4(5H)-one |
| 1122 | 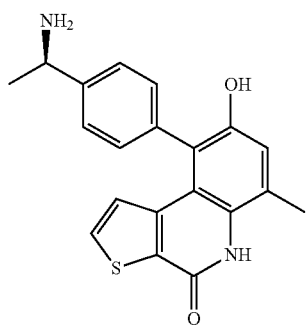 | (R)-9-(4-(1-aminoethyl)phenyl)-8-hydroxy-6-methylthieno[2,3-c]quinolin-4(5H)-one |
| 1123 | 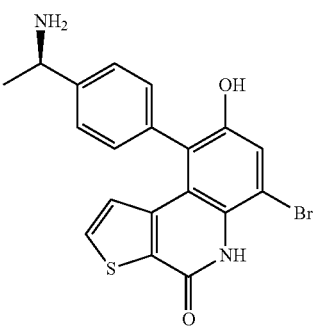 [SMILES: C[C@@H](N)c1ccc(-c2c(O)cc(Br)c3[nH]c(=O)c4sccc4c23)cc1] | (R)-9-(4-(1-aminoethyl)phenyl)-6-bromo-8-hydroxythieno[2,3-c]quinolin-4(5H)-one |
| 1124 | 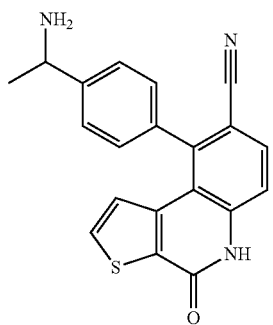 [SMILES: CC(N)c1ccc(-c2c(C#N)ccc3[nH]c(=O)c4sccc4c23)cc1] | 9-(4-(1-aminoethyl)phenyl)-4-oxo-4,5-dihydrothieno[2,3-c]quinoline-8-carbonitrile |

TABLE 1-continued
| | | |
|---|---|---|
| 1125 | 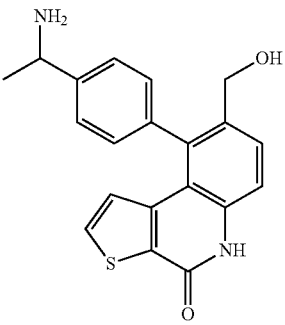 [SMILES: CC(N)c1ccc(-c2c(CO)ccc3[nH]c(=O)c4sccc4c23)cc1] | 9-(4-(1-aminoethyl)phenyl)-8-(hydroxymethyl)thieno[2,3-c]quinolin-4(5H)-one |
| 1126 | 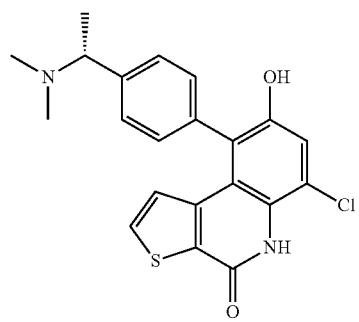 [SMILES: C[C@H](c1ccc(-c2c(O)cc(Cl)c3[nH]c(=O)c4sccc4c23)cc1)N(C)C] | (R)-6-chloro-9-(4-(1-(dimethylamino)ethyl)phenyl)-8-hydroxythieno[2,3-c]quinolin-4(5H)-one |
| 1127 | 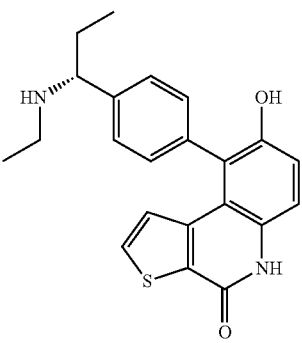 [SMILES: CCN[C@H](CC)c1ccc(-c2c(O)ccc3[nH]c(=O)c4sccc4c23)cc1] | (S)-9-(4-(1-(ethylamino)propyl)phenyl)-8-hydroxythieno[2,3-c]quinolin-4(5H)-one |
| 1128 | 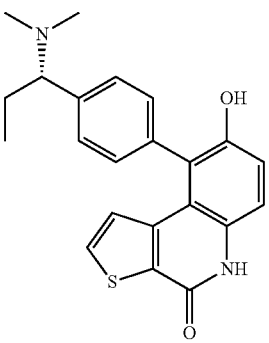 [SMILES: CC[C@@H](c1ccc(-c2c(O)ccc3[nH]c(=O)c4sccc4c23)cc1)N(C)C] | (S)-9-(4-(1-(dimethylamino)propyl)phenyl)-8-hydroxythieno[2,3-c]quinolin-4(5H)-one |
| 1129 | 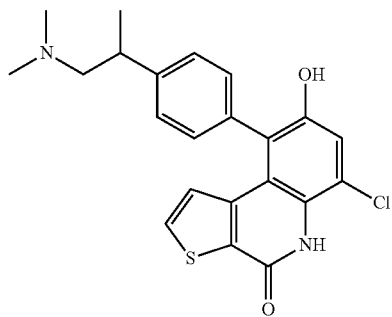 | 6-chloro-9-(4-(1-(dimethylamino)propan-2-yl)phenyl)-8-hydroxythieno[2,3-c]quinolin-4(5H)-one |

TABLE 1-continued
| | | |
|---|---|---|
| 1130 | 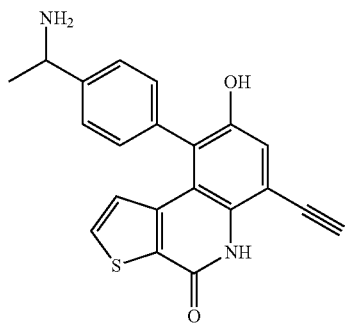 [SMILES: C#Cc1cc(O)c(-c2ccc(C(C)N)cc2)c2c1[nH]c(=O)c1sccc12] | 9-(4-(1-aminoethyl)phenyl)-6-ethynyl-8-hydroxythieno[2,3-c]quinolin-4(5H)-one |
| 1131 | 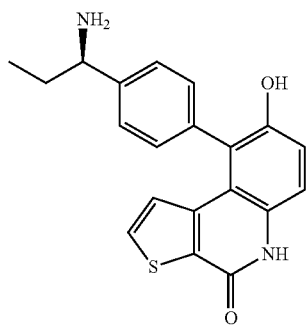 [SMILES: CC[C@@H](N)c1ccc(-c2c(O)ccc3[nH]c(=O)c4sccc4c23)cc1] | (R)-9-(4-(1-aminopropyl)phenyl)-8-hydroxythieno[2,3-c]quinolin-4(5H)-one |
| 1132 | 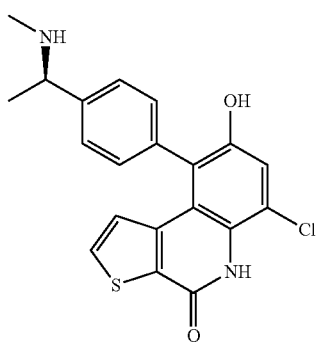 [SMILES: CN[C@H](C)c1ccc(-c2c(O)cc(Cl)c3[nH]c(=O)c4sccc4c23)cc1] | (R)-6-chloro-8-hydroxy-9-(4-(1-(methylamino)ethyl)phenyl)thieno[2,3-c]quinolin-4(5H)-one |
| 1133 | 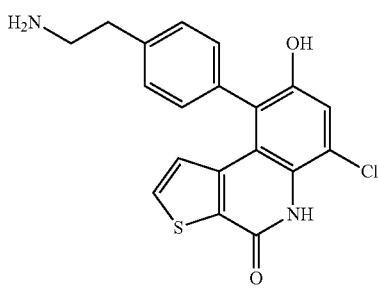 | 9-(4-(2-aminoethyl)phenyl)-6-chloro-8-hydroxythieno[2,3-c]quinolin-4(5H)-one |
| 1134 | 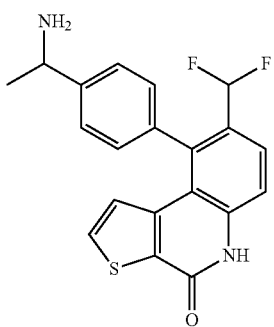 [SMILES: CC(N)c1ccc(-c2c(C(F)F)ccc3[nH]c(=O)c4sccc4c23)cc1] | 9-(4-(1-aminoethyl)phenyl)-8-(difluoromethyl)thieno[2,3-c]quinolin-4(5H)-one |

TABLE 1-continued
| | | |
|---|---|---|
| 1135 | 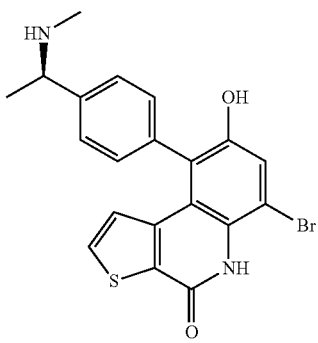 [SMILES: CN[C@H](C)c1ccc(-c2c(O)cc(Br)c3[nH]c(=O)c4sccc4c23)cc1] | (R)-6-bromo-8-hydroxy-9-(4-(1-(methylamino)ethyl)phenyl)thieno[2,3-c]quinolin-4(5H)-one |
| 1136 | 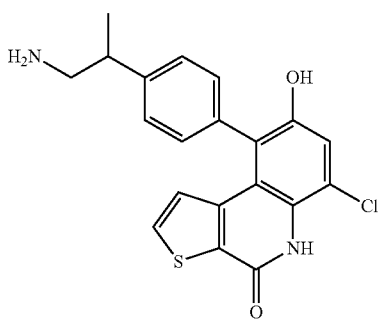 | 9-(4-(1-aminopropan-2-yl)phenyl)-6-chloro-8-hydroxythieno[2,3-c]quinolin-4(5H)-one |
| 1137 | 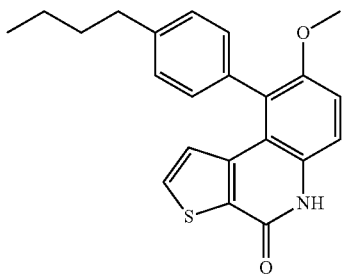 [SMILES: CCCCc1ccc(-c2c(OC)ccc3[nH]c(=O)c4sccc4c23)cc1] | 9-(4-butylphenyl)-8-methoxythieno[2,3-c]quinolin-4(5H)-one |
| 1138 | 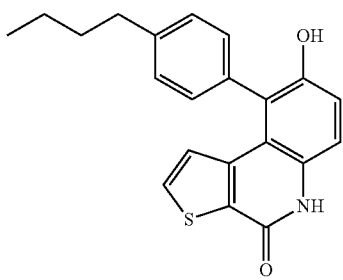 [SMILES: CCCCc1ccc(-c2c(O)ccc3[nH]c(=O)c4sccc4c23)cc1] | 9-(4-butylphenyl)-8-hydroxythieno[2,3-c]quinolin-4(5H)-one |
| 1139 | 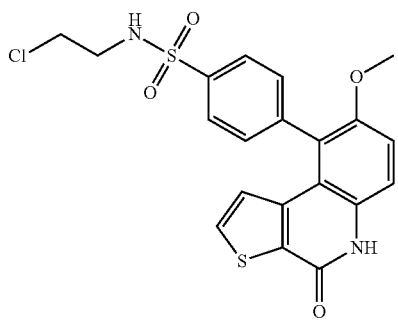 [SMILES: COc1ccc2[nH]c(=O)c3sccc3c2c1-c1ccc(S(=O)(=O)NCCCl)cc1] | N-(2-chloroethyl)-4-(8-methoxy-4-oxo-4,5-dihydrothieno[2,3-c]quinolin-9-yl)benzenesulfonamide |

TABLE 1-continued
| | | |
|---|---|---|
| 1140 | 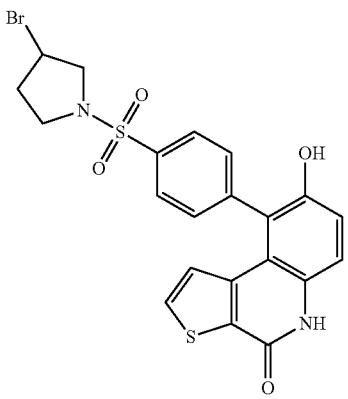 [SMILES: O=c1[nH]c2ccc(O)c(-c3ccc(S(=O)(=O)N4CCC(Br)C4)cc3)c2c2ccsc12] | 9-(4-((3-bromopyrrolidin-1-yl)sulfonyl)phenyl)-8-hydroxythieno[2,3-c]quinolin-4(5H)-one |
| 1141 | 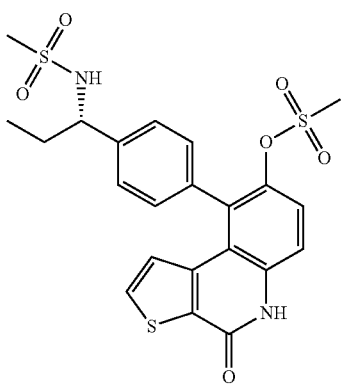 [SMILES: CC[C@H](NS(C)(=O)=O)c1ccc(-c2c(OS(C)(=O)=O)ccc3[nH]c(=O)c4sccc4c23)cc1] | (S)-9-(4-(1-(methylsulfonamido)propyl)phenyl)-4-oxo-4,5-dihydrothieno[2,3-c]quinolin-8-yl methanesulfonate |
| 1142 | 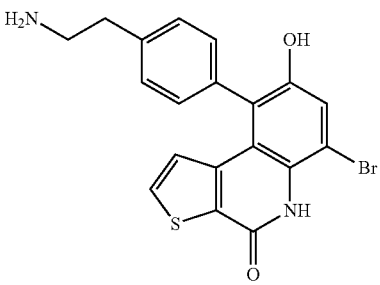 [SMILES: NCCc1ccc(-c2c(O)cc(Br)c3[nH]c(=O)c4sccc4c23)cc1] | 9-(4-(2-aminoethyl)phenyl)-6-bromo-8-hydroxythieno[2,3-c]quinolin-4(5H)-one |
| 1143 | 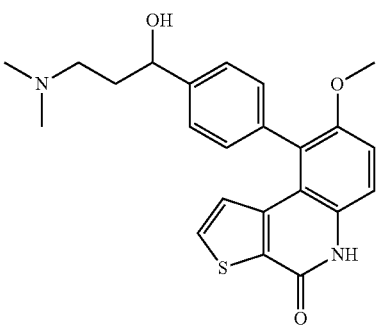 | 9-(4-(3-(dimethylamino)-1-hydroxypropyl)phenyl)-8-methoxythieno[2,3-c]quinolin-4(5H)-one |

TABLE 1-continued

| | | |
|---|---|---|
| 1144 | 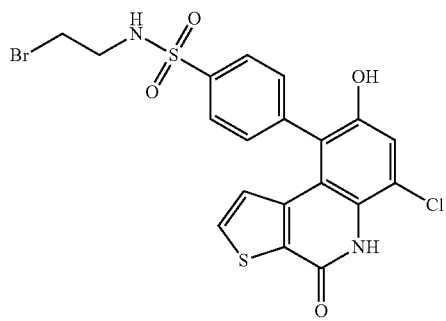 [SMILES: O=c1[nH]c2c(Cl)cc(O)c(-c3ccc(S(=O)(=O)NCCBr)cc3)c2c2ccsc12] | N-(2-bromoethyl)-4-(6-chloro-8-hydroxy-4-oxo-4,5-dihydrothieno[2,3-c]quinolin-9-yl)benzenesulfonamide |
| 1145 | 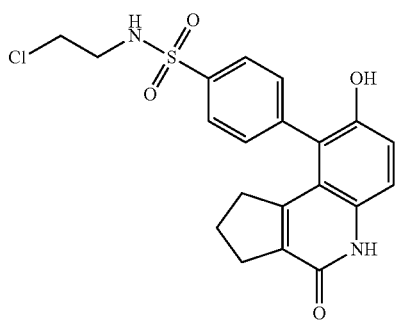 [SMILES: O=c1[nH]c2ccc(O)c(-c3ccc(S(=O)(=O)NCCCl)cc3)c2c2c1CCC2] | N-(2-chloroethyl)-4-(8-hydroxy-4-oxo-2,3,4,5-tetrahydro-1H-cyclopenta[c]quinolin-9-yl)benzenesulfonamide |
| 1146 | 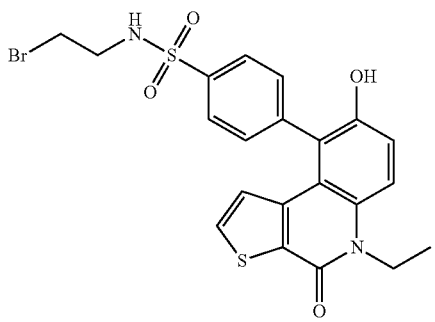 [SMILES: CCn1c(=O)c2sccc2c2c(-c3ccc(S(=O)(=O)NCCBr)cc3)c(O)ccc21] | N-(2-bromoethyl)-4-(5-ethyl-8-hydroxy-4-oxo-4,5-dihydrothieno[2,3-c]quinolin-9-yl)benzenesulfonamide |
| 1147 | 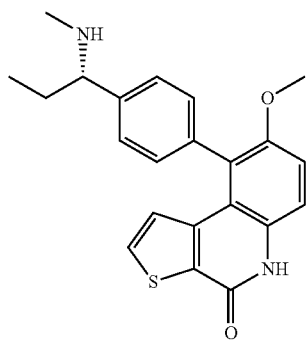 [SMILES: CC[C@H](NC)c1ccc(-c2c(OC)ccc3[nH]c(=O)c4sccc4c23)cc1] | (S)-8-methoxy-9-(4-(1-(methylamino)propyl)phenyl)thieno[2,3-c]quinolin-4(5H)-one |
| 1148 | 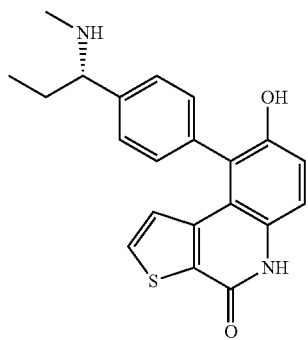 [SMILES: CC[C@H](NC)c1ccc(-c2c(O)ccc3[nH]c(=O)c4sccc4c23)cc1] | (S)-8-hydroxy-9-(4-(1-(methylamino)propyl)phenyl)thieno[2,3-c]quinolin-4(5H)-one |

TABLE 1-continued
| | | |
|---|---|---|
| 1149 | 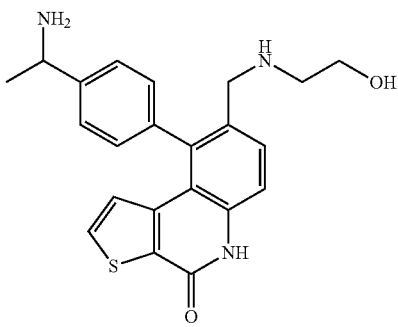 [SMILES: CC(N)c1ccc(-c2c(CNCCO)ccc3[nH]c(=O)c4sccc4c23)cc1] | 9-(4-(1-aminoethyl)phenyl)-8-((((2-hydroxyethyl)amino)methyl)thieno[2,3-c]quinolin-4(5H)-one |
| 1150 | 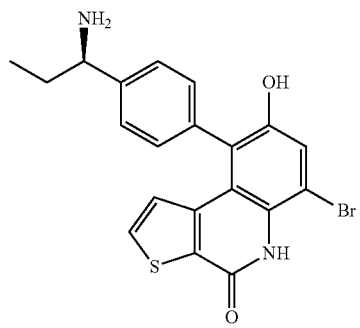 [SMILES: CC[C@@H](N)c1ccc(-c2c(O)cc(Br)c3[nH]c(=O)c4sccc4c23)cc1] | (R)-9-(4-(1-aminopropyl)phenyl)-6-bromo-8-hydroxythieno[2,3-c]quinolin-4(5H)-one |
| 1151 | 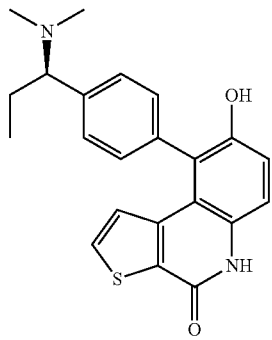 [SMILES: CC[C@H](c1ccc(-c2c(O)ccc3[nH]c(=O)c4sccc4c23)cc1)N(C)C] | (R)-9-(4-(1-(dimethylamino)propyl)phenyl)-8-hydroxythieno[2,3-c]quinolin-4(5H)-one |
| 1152 | 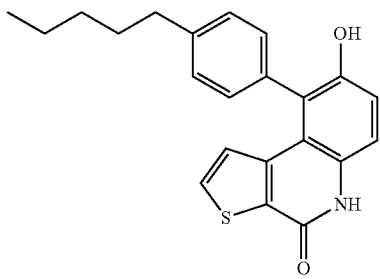 [SMILES: CCCCCc1ccc(-c2c(O)ccc3[nH]c(=O)c4sccc4c23)cc1] | 8-hydroxy-9-(4-pentylphenyl)thieno[2,3-c]quinolin-4(5H)-one |
| 1153 | 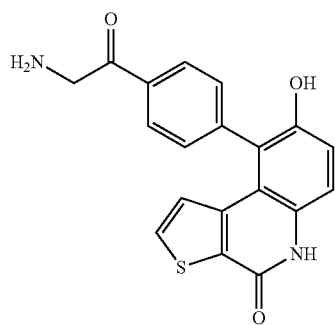 [SMILES: NCC(=O)c1ccc(-c2c(O)ccc3[nH]c(=O)c4sccc4c23)cc1] | 9-(4-(2-aminoacetyl)phenyl)-8-hydroxythieno[2,3-c]quinolin-4(5H)-one |

TABLE 1-continued
| | | |
|---|---|---|
| 1154 | 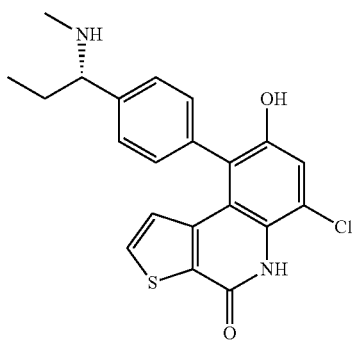 [SMILES: CC[C@H](NC)c1ccc(-c2c(O)cc(Cl)c3[nH]c(=O)c4sccc4c23)cc1] | (S)-6-chloro-8-hydroxy-9-(4-(1-(methylamino)propyl)phenyl)thieno[2,3-c]quinolin-4(5H)-one |
| 1155 | 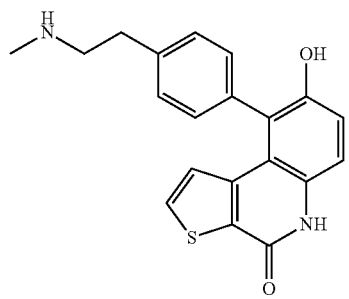 [SMILES: CNCCc1ccc(-c2c(O)ccc3[nH]c(=O)c4sccc4c23)cc1] | 8-hydroxy-9-(4-(2-(methylamino)ethyl)phenyl)thieno[2,3-c]quinolin-4(5H)-one |
| 1156 | 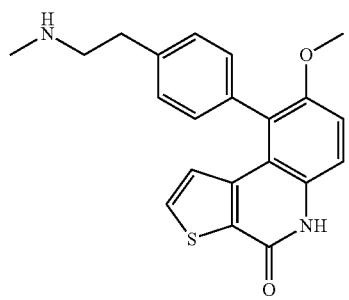 | 8-methoxy-9-(4-(2-(methylamino)ethyl)phenyl)thieno[2,3-c]quinolin-4(5H)-one |
| 1157 | 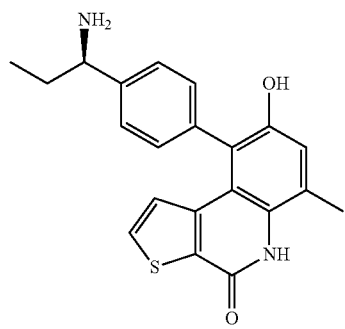 [SMILES: CC[C@@H](N)c1ccc(-c2c(O)cc(C)c3[nH]c(=O)c4sccc4c23)cc1] | (R)-9-(4-(1-aminopropyl)phenyl)-8-hydroxy-6-methylthieno[2,3-c]quinolin-4(5H)-one |
| 1158 | 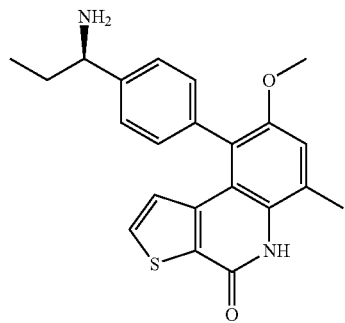 [SMILES: CC[C@@H](N)c1ccc(-c2c(OC)cc(C)c3[nH]c(=O)c4sccc4c23)cc1] | (R)-9-(4-(1-aminopropyl)phenyl)-8-methoxy-6-methylthieno[2,3-c]quinolin-4(5H)-one |

TABLE 1-continued
| | | |
|---|---|---|
| 1159 | 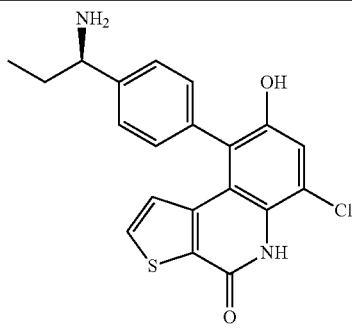 | (R)-9-(4-(1-aminopropyl)phenyl)-6-chloro-8-hydroxythieno[2,3-c]quinolin-4(5H)-one |
| 1160 | 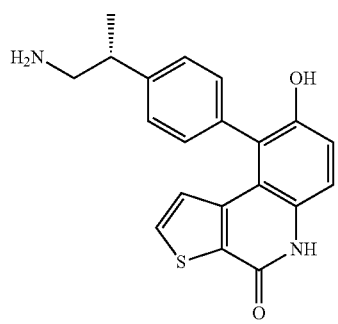 [SMILES: C[C@@H](CN)c1ccc(-c2c(O)ccc3[nH]c(=O)c4sccc4c23)cc1] | (R)-9-(4-(1-aminopropan-2-yl)phenyl)-8-hydroxythieno[2,3-c]quinolin-4(5H)-one |
| 1161 | 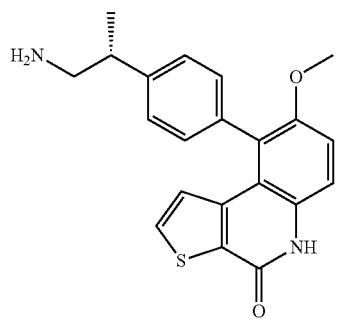 [SMILES: COc1ccc2[nH]c(=O)c3sccc3c2c1-c1ccc([C@@H](C)CN)cc1] | (R)-9-(4-(1-aminopropan-2-yl)phenyl)-8-methoxythieno[2,3-c]quinolin-4(5H)-one |
| 1162 | 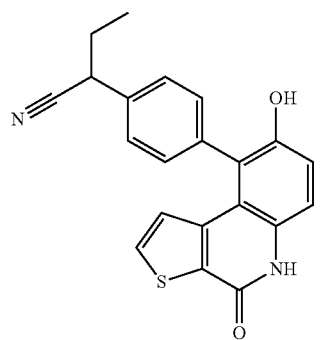 [SMILES: CCC(C#N)c1ccc(-c2c(O)ccc3[nH]c(=O)c4sccc4c23)cc1] | 2-(4-(8-hydroxy-4-oxo-4,5-dihydrothieno[2,3-c]quinolin-9-yl)phenyl)butanenitrile |
| 1163 | 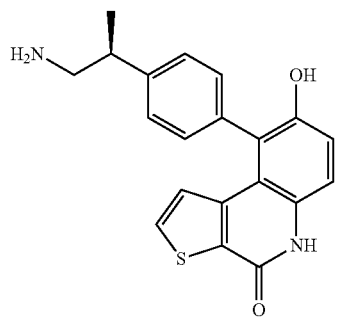 [SMILES: C[C@H](CN)c1ccc(-c2c(O)ccc3[nH]c(=O)c4sccc4c23)cc1] | (S)-9-(4-(1-aminopropan-2-yl)phenyl)-8-hydroxythieno[2,3-c]quinolin-4(5H)-one |

TABLE 1-continued
| | | |
|---|---|---|
| 1164 | 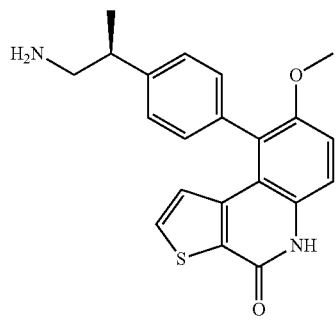 [SMILES: COc1ccc2[nH]c(=O)c3sccc3c2c1-c1ccc([C@H](C)CN)cc1] | (S)-9-(4-(1-aminopropan-2-yl)phenyl)-8-methoxythieno[2,3-c]quinolin-4(5H)-one |
| 1165 | 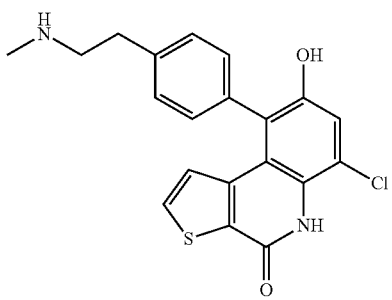 [SMILES: CNCCc1ccc(-c2c(O)cc(Cl)c3[nH]c(=O)c4sccc4c23)cc1] | 6-chloro-8-hydroxy-9-(4-(2-(methylamino)ethyl)phenyl)thieno[2,3-c]quinolin-4(5H)-one |
| 1166 | 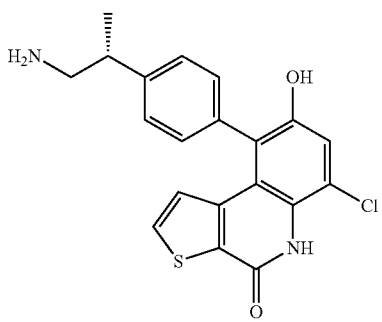 [SMILES: C[C@@H](CN)c1ccc(-c2c(O)cc(Cl)c3[nH]c(=O)c4sccc4c23)cc1] | (R)-9-(4-(1-aminopropan-2-yl)phenyl)-6-chloro-8-hydroxythieno[2,3-c]quinolin-4(5H)-one |
| 1167 | 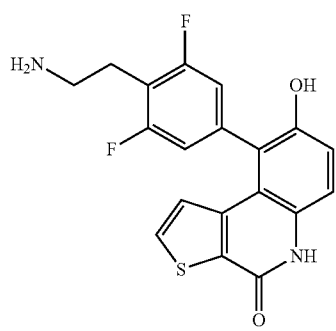 [SMILES: NCCc1c(F)cc(-c2c(O)ccc3[nH]c(=O)c4sccc4c23)cc1F] | 9-(4-(2-aminoethyl)-3,5-difluorophenyl)-8-hydroxythieno[2,3-c]quinolin-4(5H)-one |
| 1168 | 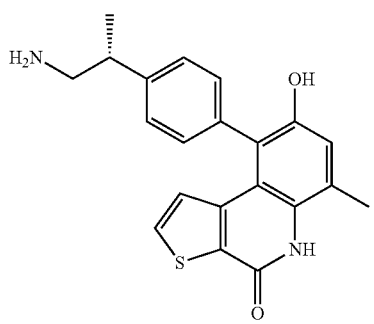 | (R)-9-(4-(1-aminopropan-2-yl)phenyl)-8-hydroxy-6-methylthieno[2,3-c]quinolin-4(5H)-one |

| | | |
|---|---|---|
| 1169 | 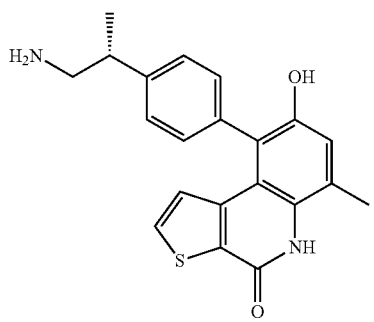 | (R)-9-(4-(1-aminopropan-2-yl)phenyl)-8-hydroxy-6-methylthieno[2,3-c]quinolin-4(5H)-one |
| 1170 | 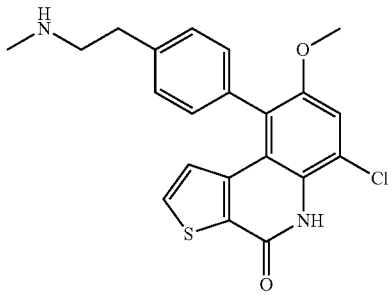 [SMILES: CNCCc1ccc(-c2c(OC)cc(Cl)c3[nH]c(=O)c4sccc4c23)cc1] | 6-chloro-8-methoxy-9-(4-(2-(methylamino)ethyl)phenyl)thieno[2,3-c]quinolin-4(5H)-one |
| 1171 | 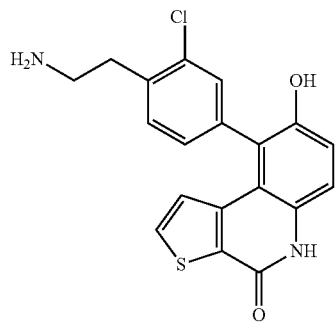 [SMILES: NCCc1ccc(-c2c(O)ccc3[nH]c(=O)c4sccc4c23)cc1Cl] | 9-(4-(2-aminoethyl)-3-chlorophenyl)-8-hydroxythieno[2,3-c]quinolin-4(5H)-one |
| 1172 | 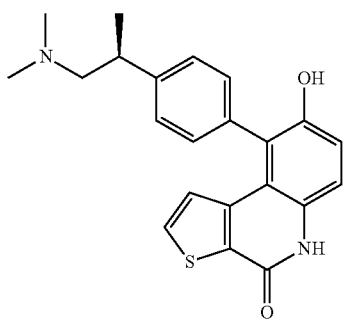 [SMILES: C[C@H](CN(C)C)c1ccc(-c2c(O)ccc3[nH]c(=O)c4sccc4c23)cc1] | (S)-9-(4-(1-(dimethylamino)propan-2-yl)phenyl)-8-hydroxythieno[2,3-c]quinolin-4(5H)-one |
| 1173 | 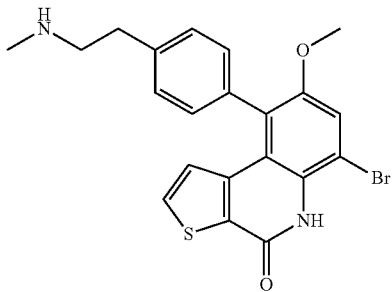 [SMILES: CNCCc1ccc(-c2c(OC)cc(Br)c3[nH]c(=O)c4sccc4c23)cc1] | 6-bromo-8-methoxy-9-(4-(2-(methylamino)ethyl)phenyl)thieno[2,3-c]quinolin-4(5H)-one |

TABLE 1-continued
| | | |
|---|---|---|
| 1174 | 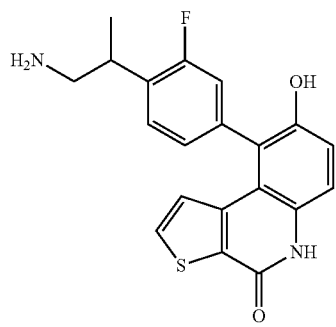 [SMILES: CC(CN)c1ccc(-c2c(O)ccc3[nH]c(=O)c4sccc4c23)cc1F] | 9-(4-(1-aminopropan-2-yl)-3-fluorophenyl)-8-hydroxythieno[2,3-c]quinolin-4(5H)-one |
| 1175 | 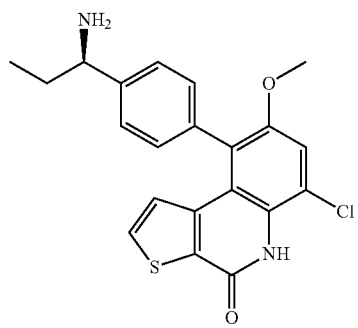 [SMILES: CC[C@@H](N)c1ccc(-c2c(OC)cc(Cl)c3[nH]c(=O)c4sccc4c23)cc1] | (R)-9-(4-(1-aminopropyl)phenyl)-6-chloro-8-methoxythieno[2,3-c]quinolin-4(5H)-one |
| 1176 | 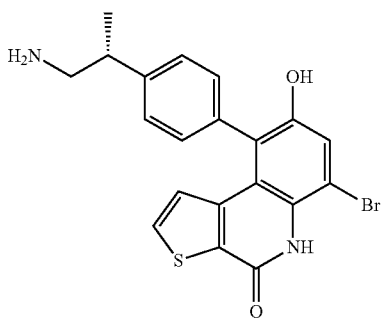 [SMILES: C[C@@H](CN)c1ccc(-c2c(O)cc(Br)c3[nH]c(=O)c4sccc4c23)cc1] | (R)-9-(4-(1-aminopropan-2-yl)phenyl)-6-bromo-8-hydroxythieno[2,3-c]quinolin-4(5H)-one |
| 1177 | 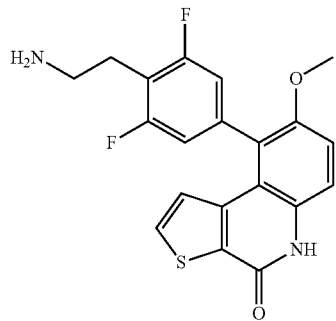 [SMILES: COc1ccc2[nH]c(=O)c3sccc3c2c1-c1cc(F)c(CCN)c(F)c1] | 9-(4-(2-aminoethyl)-3,5-difluorophenyl)-8-methoxythieno[2,3-c]quinolin-4(5H)-one |
| 1178 | 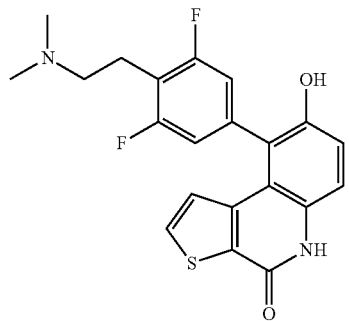 [SMILES: CN(C)CCc1c(F)cc(-c2c(O)ccc3[nH]c(=O)c4sccc4c23)cc1F] | 9-(4-(2-(dimethylamino)ethyl)-3,5-difluorophenyl)-8-hydroxythieno[2,3-c]quinolin-4(5H)-one |

TABLE 1-continued
| | | |
|---|---|---|
| 1179 | 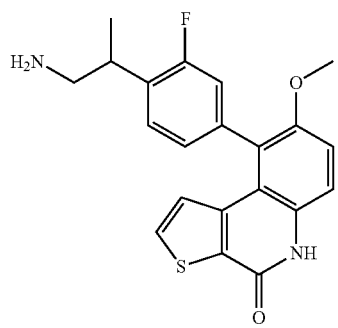 [SMILES: COc1ccc2[nH]c(=O)c3sccc3c2c1-c1ccc(C(C)CN)c(F)c1] | 9-(4-(1-aminopropan-2-yl)-3-fluorophenyl)-8-methoxythieno[2,3-c]quinolin-4(5H)-one |
| 1180 | 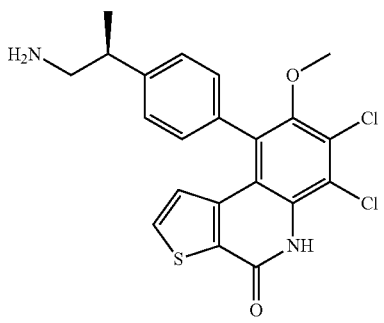 [SMILES: COc1c(Cl)c(Cl)c2[nH]c(=O)c3sccc3c2c1-c1ccc([C@H](C)CN)cc1] | (S)-9-(4-(1-aminopropan-2-yl)phenyl)-6,7-dichloro-8-methoxythieno[2,3-c]quinolin-4(5H)-one |
| 1181 | 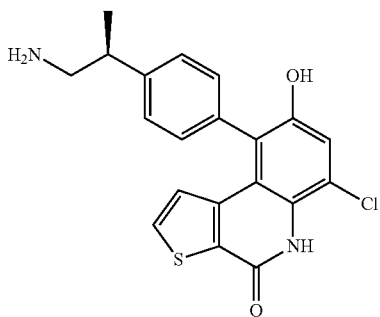 [SMILES: C[C@H](CN)c1ccc(-c2c(O)cc(Cl)c3[nH]c(=O)c4sccc4c23)cc1] | (S)-9-(4-(1-aminopropan-2-yl)phenyl)-6-chloro-8-hydroxythieno[2,3-c]quinolin-4(5H)-one |
| 1182 | 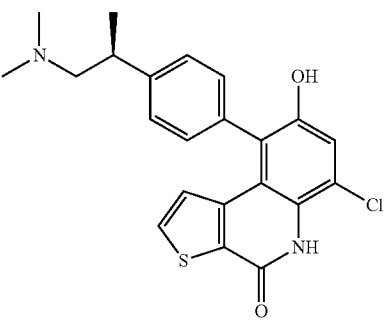 [SMILES: C[C@H](CN(C)C)c1ccc(-c2c(O)cc(Cl)c3[nH]c(=O)c4sccc4c23)cc1] | (S)-6-chloro-9-(4-(1-(dimethylamino)propan-2-yl)phenyl)-8-hydroxythieno[2,3-c]quinolin-4(5H)-one |
| 1183 | 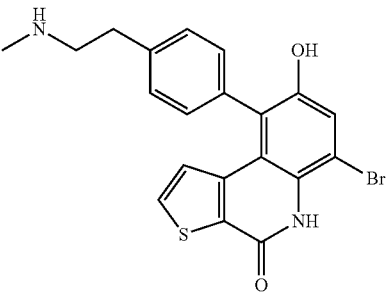 [SMILES: CNCCc1ccc(-c2c(O)cc(Br)c3[nH]c(=O)c4sccc4c23)cc1] | 6-bromo-8-hydroxy-9-(4-(2-(methylamino)ethyl)phenyl)thieno[2,3-c]quinolin-4(5H)-one |

TABLE 1-continued
| | | |
|---|---|---|
| 1185 | 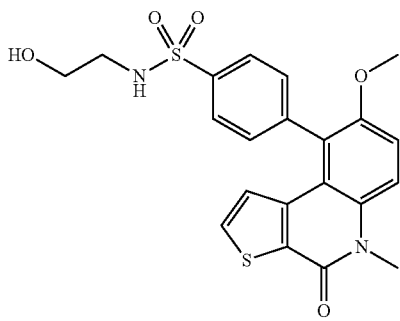 [SMILES: COc1ccc2c(c1-c1ccc(S(=O)(=O)NCCO)cc1)c1ccsc1c(=O)n2C] | N-(2-hydroxyethyl)-4-(8-methoxy-5-methyl-4-oxo-4,5-dihydrothieno[2,3-c]quinolin-9-yl)benzenesulfonamide |
| 1186 | 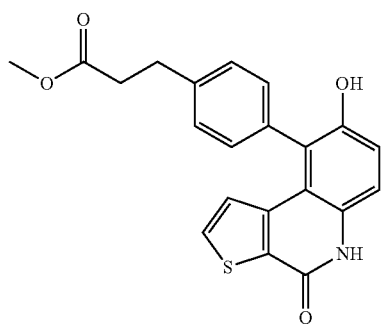 [SMILES: COC(=O)CCc1ccc(-c2c(O)ccc3[nH]c(=O)c4sccc4c23)cc1] | methyl 3-(4-(8-hydroxy-4-oxo-4,5-dihydrothieno[2,3-c]quinolin-9-yl)phenyl)propanoate |
| 1187 | 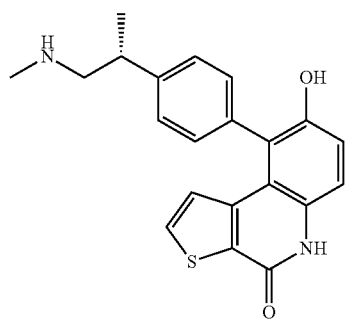 [SMILES: CNC[C@H](C)c1ccc(-c2c(O)ccc3[nH]c(=O)c4sccc4c23)cc1] | (R)-8-hydroxy-9-(4-(1-(methylamino)propan-2-yl)phenyl)thieno[2,3-c]quinolin-4(5H)-one |
| 1188 | 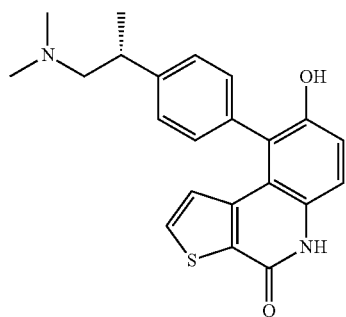 [SMILES: C[C@@H](CN(C)C)c1ccc(-c2c(O)ccc3[nH]c(=O)c4sccc4c23)cc1] | (R)-9-(4-(1-(dimethylamino)propan-2-yl)phenyl)-8-hydroxythieno[2,3-c]quinolin-4(5H)-one |
| 1189 | 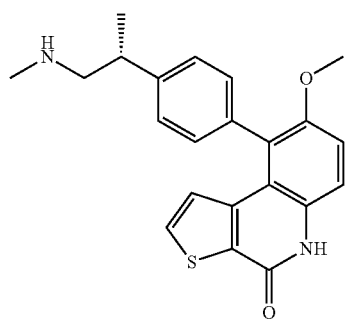 | (R)-8-methoxy-9-(4-(1-(methylamino)propan-2-yl)phenyl)thieno[2,3-c]quinolin-4(5H)-one |

TABLE 1-continued

| | | |
|---|---|---|
| 1190 | [structure] | 9-(4-(1-aminopropan-2-yl)-3-fluorophenyl)-8-hydroxy-6-methylthieno[2,3-c]quinolin-4(5H)-one |
| 1191 | [structure] | 9-(4-(2-aminoethyl)phenyl)-8-hydroxy-6-methylthieno[2,3-c]quinolin-4(5H)-one |
| 1192 | [structure] | 9-(4-(2-aminoethyl)phenyl)-8-methoxy-6-methylthieno[2,3-c]quinolin-4(5H)-one |
| 1193 | [structure] | 9-(4-(1-(dimethylamino)propan-2-yl)-3-fluorophenyl)-8-hydroxy-6-methylthieno[2,3-c]quinolin-4(5H)-one |
| 1194 | [structure] | (S)-6-chloro-8-hydroxy-9-(4-(1-(methylamino)propan-2-yl)phenyl)thieno[2,3-c]quinolin-4(5H)-one |

TABLE 1-continued

| | | |
|---|---|---|
| 1195 | 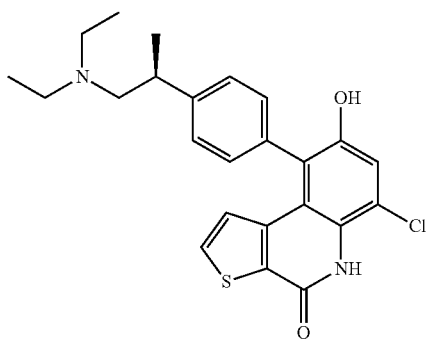 [SMILES: CCN(CC)C[C@@H](C)c1ccc(-c2c(O)cc(Cl)c3[nH]c(=O)c4sccc4c23)cc1] | (S)-6-chloro-9-(4-(1-(diethylamino) propan-2-yl)phenyl)-8-hydroxythieno[2,3-c]quinolin-4(5H)-one |
| 1196 | 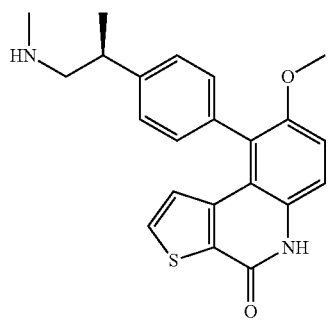 [SMILES: CNC[C@@H](C)c1ccc(-c2c(OC)ccc3[nH]c(=O)c4sccc4c23)cc1] | (S)-8-methoxy-9-(4-(1-(methyl amino)propan-2-yl)phenyl) thieno[2,3-c]quinolin-4(5H)-one |
| 1197 | 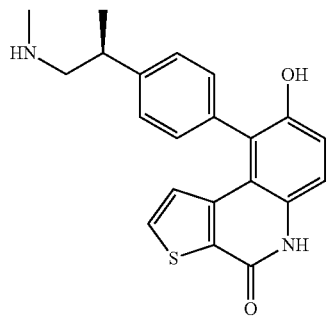 [SMILES: CNC[C@@H](C)c1ccc(-c2c(O)ccc3[nH]c(=O)c4sccc4c23)cc1] | (S)-8-hydroxy-9-(4-(1-(methylamino)propan-2-yl) phenyl)thieno[2,3-c]quinolin-4(5H)-one |
| 1198 | 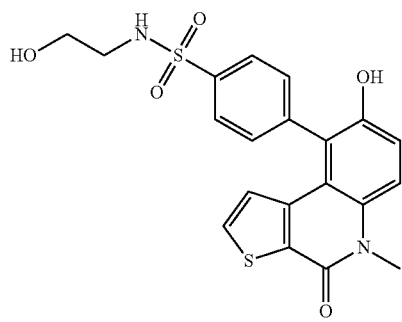 [SMILES: Cn1c(=O)c2sccc2c2c(-c3ccc(S(=O)(=O)NCCO)cc3)c(O)ccc21] | 4-(8-hydroxy-5-methyl-4-oxo-4,5-dihydrothieno[2,3-c]quinolin-9-yl)-N-(2-hydroxyethyl) benzenesulfonamide |
| 1199 | 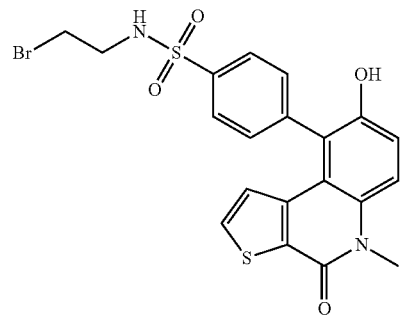 [SMILES: Cn1c(=O)c2sccc2c2c(-c3ccc(S(=O)(=O)NCCBr)cc3)c(O)ccc21] | N-(2-bromoethyl)-4-(8-hydroxy-5-methyl-4-oxo-4,5-dihydrothieno[2,3-c]quinolin-9-yl) benzenesulfonamide |

TABLE 1-continued

| | | |
|---|---|---|
| 1200 | | (R)-6-chloro-9-(4-(1-(dimethyl amino)propan-2-yl)phenyl)-8-methoxythieno[2,3-c]quinolin-4(5H)-one |
| 1201 | | (R)-9-(4-(1-aminopropan-2-yl) phenyl)-6-chloro-8-methoxythieno [2,3-c]quinolin-4(5H)-one |
| 1202 | | 9-(4-(1-aminobutan-2-yl)phenyl)-8-methoxythieno[2,3-c]quinolin-4(5H)-one |
| 1203 | | 9-(4-(2-aminopropan-2-yl) phenyl)-8-hydroxy-2-(phenylsulfonyl) thieno[2,3-c]quinolin-4(5H)-one |
| 1204 | | N-(1-chloropropan-2-yl)-4-(8-hydroxy-4-oxo-4,5-dihydrothieno [2,3-c]quinolin-9-yl) benzenesulfonamide |

| | | |
|---|---|---|
| 1205 | 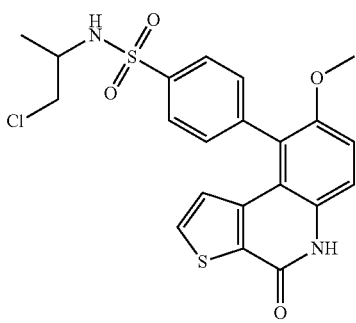 [SMILES: COc1ccc2[nH]c(=O)c3sccc3c2c1-c1ccc(S(=O)(=O)NC(C)CCl)cc1] | N-(1-chloropropan-2-yl)-4-(8-methoxy-4-oxo-4,5-dihydrothieno[2,3-c]quinolin-9-yl)benzenesulfonamide |
| 1206 | 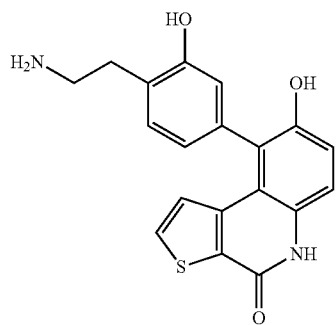 | 9-(4-(2-aminoethyl)-3-hydroxyphenyl)-8-hydroxythieno[2,3-c]quinolin-4(5H)-one |
| 1207 | 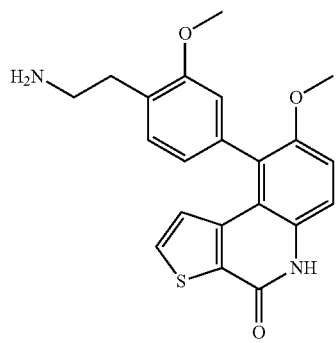 [SMILES: COc1cc(-c2c(OC)ccc3[nH]c(=O)c4sccc4c23)ccc1CCN] | 9-(4-(2-aminoethyl)-3-methoxyphenyl)-8-methoxythieno[2,3-c]quinolin-4(5H)-one |
| 1208 | 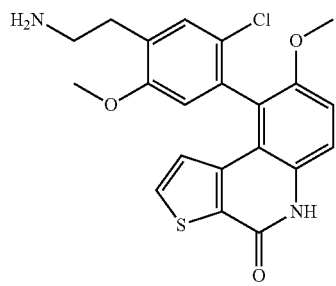 [SMILES: COc1cc(-c2c(OC)ccc3[nH]c(=O)c4sccc4c23)c(Cl)cc1CCN] | 9-(4-(2-aminoethyl)-2-chloro-5-methoxyphenyl)-8-methoxythieno[2,3-c]quinolin-4(5H)-one |
| 1209 | 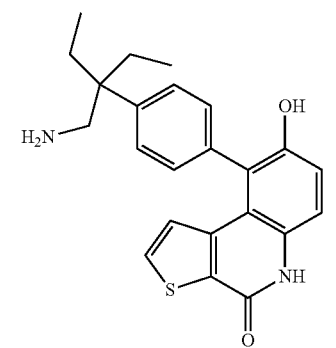 [SMILES: CCC(CC)(CN)c1ccc(-c2c(O)ccc3[nH]c(=O)c4sccc4c23)cc1] | 9-(4-(3-(aminomethyl)pentan-3-yl)phenyl)-8-hydroxythieno[2,3-c]quinolin-4(5H)-one |

TABLE 1-continued
| | | |
|---|---|---|
| 1210 | 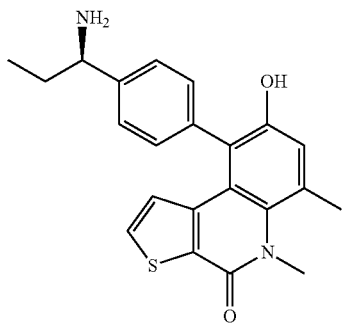 [SMILES: CC[C@@H](N)c1ccc(-c2c(O)cc(C)c3c2c2ccsc2c(=O)n3C)cc1] | (R)-9-(4-(1-aminopropy)phenyl)-8-hydroxy-5,6-dimethylthieno[2,3-c]quinolin-4(5H)-one |
| 1211 | 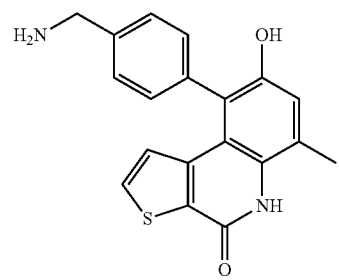 [SMILES: Cc1cc(O)c(-c2ccc(CN)cc2)c2c1[nH]c(=O)c1sccc12] | 9-(4-(2-aminoethyl)-2-chloro-5-hydroxyphenyl)-6-chloro-8-hydroxythieno[2,3-c]quinolin-4(5H)-one |
| 1212 | 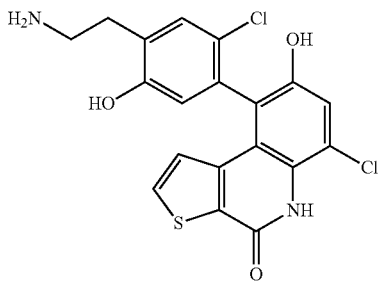 [SMILES: NCCc1cc(Cl)c(-c2c(O)cc(Cl)c3[nH]c(=O)c4sccc4c23)cc1O] | 9-(4-(aminomethyl)phenyl)-8-hydroxy-6-methylthieno[2,3-c]quinolin-4(5H)-one |
| 1213 | 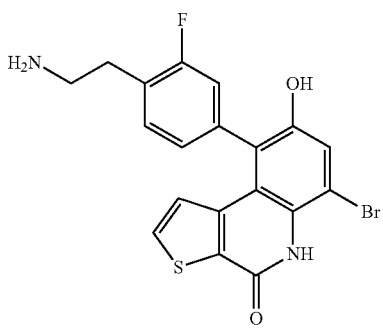 [SMILES: NCCc1ccc(-c2c(O)cc(Br)c3[nH]c(=O)c4sccc4c23)cc1F] | 9-(4-(2-aminoethyl)-3-fluorophenyl)-6-bromo-8-hydroxythieno[2,3-c]quinolin-4(5H)-one |
| 1214 | 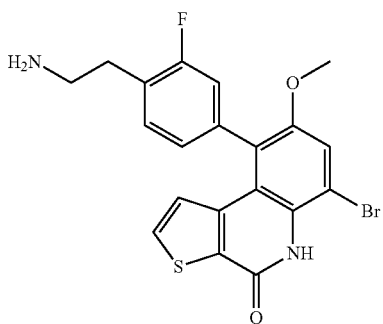 [SMILES: COc1cc(Br)c2[nH]c(=O)c3sccc3c2c1-c1ccc(CCN)c(F)c1] | 9-(4-(2-aminoethyl)-3-fluorophenyl)-6-bromo-8-methoxythieno[2,3-c]quinolin-4(5H)-one |

TABLE 1-continued

| | | |
|---|---|---|
| 1215 | | (S)-8-hydroxy-6-methyl-9-(4-(1-(methylamino)propan-2-yl)phenyl)thieno[2,3-c]quinolin-4(5H)-one |
| 1216 | | 9-(4-(2-aminoethyl)-3-fluorophenyl)-8-methoxy-6-methylthieno[2,3-c]quinolin-4(5H)-one |
| 1217 | | 9-(4-(2-aminoethyl)-3-fluorophenyl)-8-hydroxy-6-methylthieno[2,3-c]quinolin-4(5H)-one |
| 1218 | | 9-(4-(2-aminoethyl)-3-fluorophenyl)-6-chloro-8-methoxythieno[2,3-c]quinolin-4(5H)-one |
| 1219 | | 9-(4-(2-aminoethyl)-3-fluorophenyl)-6-chloro-8-hydroxythieno[2,3-c]quinolin-4(5H)-one |

TABLE 1-continued
| | | |
|---|---|---|
| 1220 | 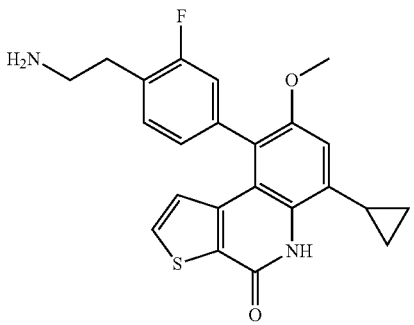 [SMILES: COc1cc(C2CC2)c2[nH]c(=O)c3sccc3c2c1-c1ccc(CCN)c(F)c1] | 9-(4-(2-aminoethyl)-3-fluorophenyl)-6-cyclopropyl-8-methoxy thieno[2,3-c]quinolin-4(5H)-one |
| 1221 | 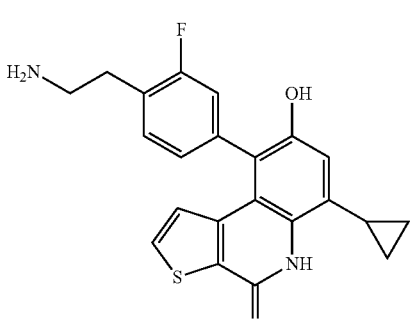 | 9-(4-(2-aminoethyl)-3-fluorophenyl)-6-cyclopropyl-8-hydroxythieno[2,3-c] quinolin-4(5H)-one |
| 1222 | 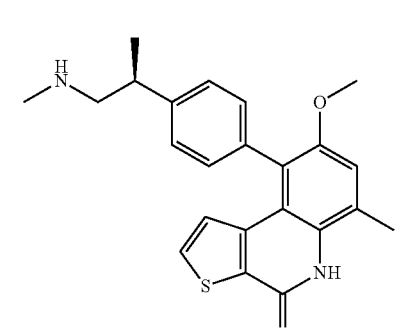 | (S)-8-methoxy-6-methyl-9-(4-(1-(methylamino)propan-2-yl) phenyl)thieno[2,3-c]quinolin-4(5H)-one |
| 1223 | 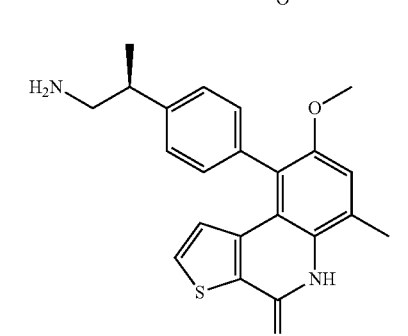 | (S)-9-(4-(1-aminopropan-2-yl) phenyl)-8-methoxy-6-methylthieno [2,3-c]quinolin-4(5H)-one |
| 1224 | 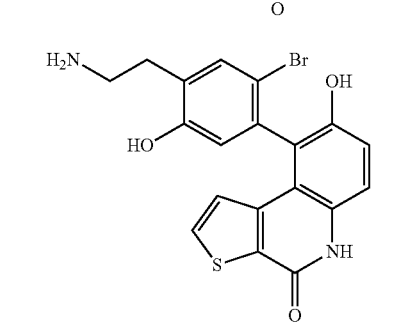 | 9-(4-(2-aminoethyl)-2-bromo-5-hydroxyphenyl)-8-hydroxythieno [2,3-c]quinolin-4(5H)-one |

TABLE 1-continued

| | | |
|---|---|---|
| 1225 | 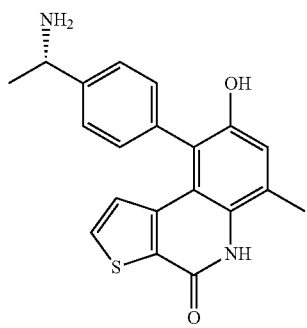 [SMILES: Cc1cc(O)c(-c2ccc([C@H](C)N)cc2)c2c1[nH]c(=O)c1sccc12] | (S)-9-(4-(1-aminoethyl)phenyl)-8-hydroxy-6-methylthieno[2,3-c]quinolin-4(5H)-one |
| 1226 | 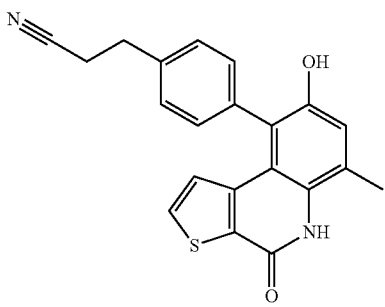 [SMILES: Cc1cc(O)c(-c2ccc(CCC#N)cc2)c2c1[nH]c(=O)c1sccc12] | 3-(4-(8-hydroxy-6-methyl-4-oxo-4,5-dihydrothieno[2,3-c]quinolin-9-yl)phenyl)propanenitrile |
| 1227 | 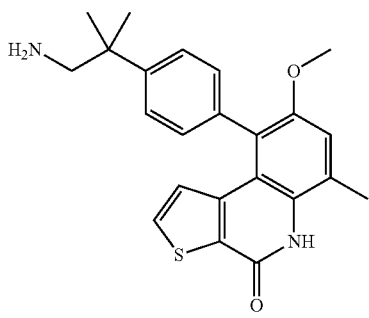 [SMILES: COc1cc(C)c2[nH]c(=O)c3sccc3c2c1-c1ccc(C(C)(C)CN)cc1] | 9-(4-(1-amino-2-methylpropan-2-yl)phenyl)-8-methoxy-6-methylthieno[2,3-c]quinolin-4(5H)-one |
| 1228 | 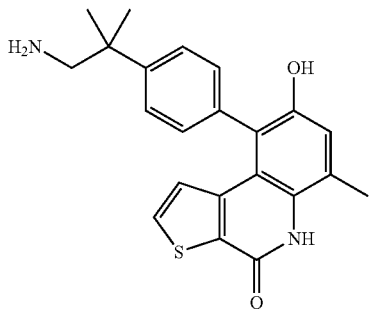 [SMILES: Cc1cc(O)c(-c2ccc(C(C)(C)CN)cc2)c2c1[nH]c(=O)c1sccc12] | 9-(4-(1-amino-2-methylpropan-2-yl)phenyl)-8-hydroxy-6-methylthieno[2,3-c]quinolin-4(5H)-one |
| 1229 | 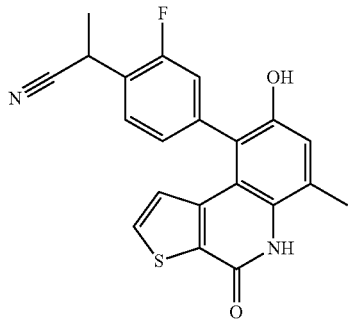 [SMILES: Cc1cc(O)c(-c2ccc(C(C)C#N)c(F)c2)c2c1[nH]c(=O)c1sccc12] | 2-(2-fluoro-4-(8-hydroxy-6-methyl-4-oxo-4,5-dihydrothieno[2,3-c]quinolin-9-yl)phenyl)propanenitrile |

TABLE 1-continued

| | | |
|---|---|---|
| 1230 | 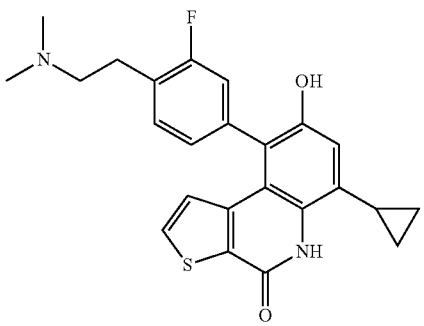 [SMILES: CN(C)CCc1ccc(-c2c(O)cc(C3CC3)c3[nH]c(=O)c4sccc4c23)cc1F] | 6-cyclopropyl-9-(4-(2-(dimethylamino)ethyl)-3-fluorophenyl)-8-hydroxythieno[2,3-c]quinolin-4(5H)-one |
| 1231 | 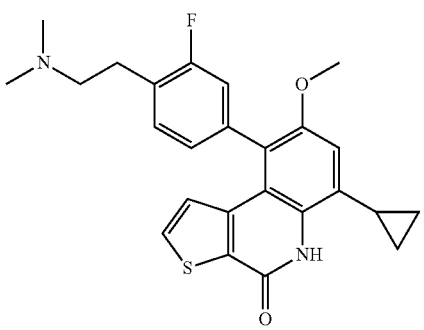 [SMILES: COc1cc(C2CC2)c2[nH]c(=O)c3sccc3c2c1-c1ccc(CCN(C)C)c(F)c1] | 6-cyclopropyl-9-(4-(2-(dimethylamino)ethyl)-3-fluorophenyl)-8-methoxythieno[2,3-c]quinolin-4(5H)-one |
| 1232 | 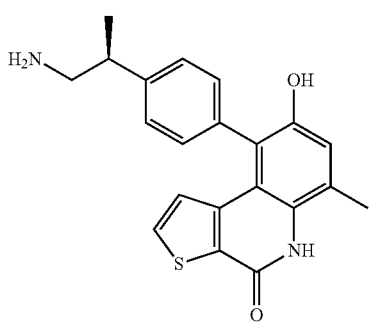 [SMILES: Cc1cc(O)c(-c2ccc([C@H](C)CN)cc2)c2c1[nH]c(=O)c1sccc12] | (S)-9-(4-(1-aminopropan-2-yl)phenyl)-8-hydroxy-6-methylthieno[2,3-c]quinolin-4(5H)-one |
| 1233 | 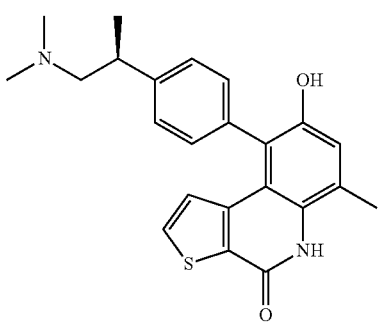 | (S)-9-(4-(1-(dimethylamino)propan-2-yl)phenyl)-8-hydroxy-6-methylthieno[2,3-c]quinolin-4(5H)-one |
| 1234 | 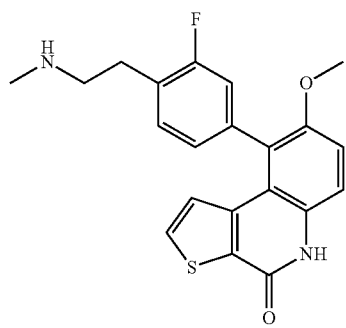 | 9-(3-fluoro-4-(2-(methylamino)ethyl)phenyl)-8-methoxythieno[2,3-c]quinolin-4(5H)-one |

TABLE 1-continued

| | | |
|---|---|---|
| 1235 | | 9-(3-fluoro-4-(2-(methylamino)ethyl)phenyl)-8-hydroxythieno[2,3-c]quinolin-4(5H)-one |
| 1236 | | 9-(4-(2-amino-1-cyclopentylethyl)phenyl)-8-hydroxythieno[2,3-c]quinolin-4(5H)-one |
| 1237 | | 9-(4-(2-amino-1,1-dicyclopentylethyl)phenyl)-8-methoxythieno[2,3-c]quinolin-4(5H)-one |
| 1238 | | 3-(4-(8-methoxy-6-methyl-4-oxo-4,5-dihydrothieno[2,3-c]quinolin-9-yl)phenyl)propanenitrile |
| 1239 | | 9-(4-(2-amino-1-cyclopentylethyl)phenyl)-8-methoxythieno[2,3-c]quinolin-4(5H)-one |

TABLE 1-continued
| | | |
|---|---|---|
| 1240 | 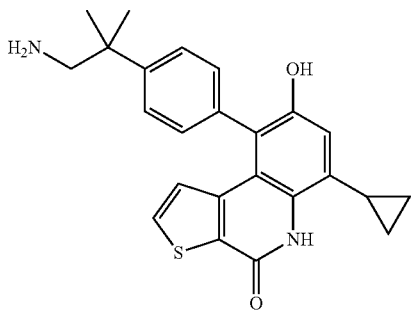 [SMILES: CC(C)(CN)c1ccc(-c2c(O)cc(C3CC3)c3[nH]c(=O)c4sccc4c23)cc1] | 9-(4-(1-amino-2-methylpropan-2-yl)phenyl)-6-cyclopropyl-8-hydroxythieno[2,3-c]quinolin-4(5H)-one |
| 1241 | 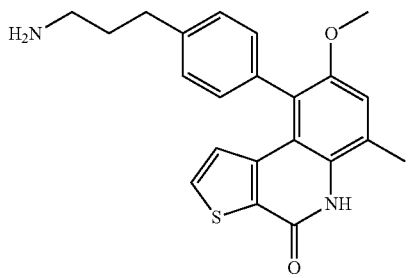 [SMILES: COc1cc(C)c2[nH]c(=O)c3sccc3c2c1-c1ccc(CCCN)cc1] | 9-(4-(3-aminopropyl)phenyl)-8-methoxy-6-methylthieno[2,3-c]quinolin-4(5H)-one |
| 1242 | 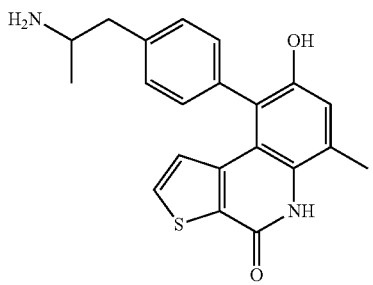 | 9-(4-(2-aminopropyl)phenyl)-8-hydroxy-6-methylthieno[2,3-c]quinolin-4(5H)-one |
| 1243 | 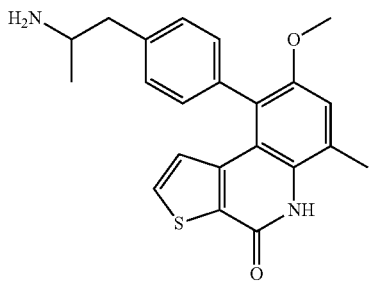 | 9-(4-(2-aminopropyl)phenyl)-8-methoxy-6-methylthieno[2,3-c]quinolin-4(5H)-one |
| 1244 | 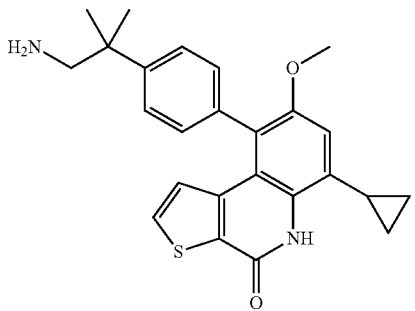 [SMILES: COc1cc(C2CC2)c2[nH]c(=O)c3sccc3c2c1-c1ccc(C(C)(C)CN)cc1] | 9-(4-(1-amino-2-methylpropan-2-yl)phenyl)-6-cyclopropyl-8-methoxythieno[2,3-c]quinolin-4(5H)-one |

TABLE 1-continued

| | | |
|---|---|---|
| 1245 | | 6-bromo-9-(3-fluoro-4-(2-(methylamino)ethyl)phenyl)-8-hydroxythieno[2,3-c]quinolin-4(5H)-one |
| 1246 | | 6-bromo-9-(3-fluoro-4-(2-(methylamino)ethyl)phenyl)-8-methoxythieno[2,3-c]quinolin-4(5H)-one |
| 1247 | | 9-(4-(1-amino-2-methylpropan-2-yl)phenyl)-6-bromo-8-hydroxythieno[2,3-c]quinolin-4(5H)-one |
| 1248 | | 9-(4-(1-amino-2-methylpropan-2-yl)phenyl)-6-bromo-8-methoxythieno[2,3-c]quinolin-4(5H)-one |
| 1249 | | (R)-9-(4-(1-aminopropan-2-yl)phenyl)-6-methyl-4-oxo-4,5-dihydrothieno[2,3-c]quinoline-8-carbonitrile |

TABLE 1-continued
| | | |
|---|---|---|
| 1250 | 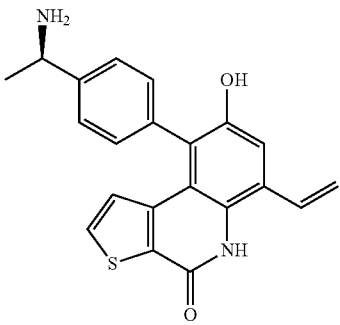 [SMILES: C=Cc1cc(O)c(-c2ccc([C@@H](C)N)cc2)c2c1[nH]c(=O)c1sccc12] | (R)-9-(4-(1-aminoethyl)phenyl)-8-hydroxy-6-vinylthieno[2,3-c]quinolin-4(5H)-one |
| 1251 | 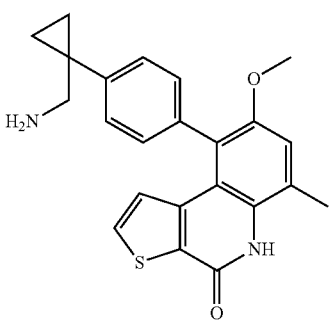 [SMILES: COc1cc(C)c2[nH]c(=O)c3sccc3c2c1-c1ccc(C2(CN)CC2)cc1] | 9-(4-(1-(aminomethyl)cyclopropyl)phenyl)-8-methoxy-6-methylthieno[2,3-c]quinolin-4(5H)-one |
| 1252 | 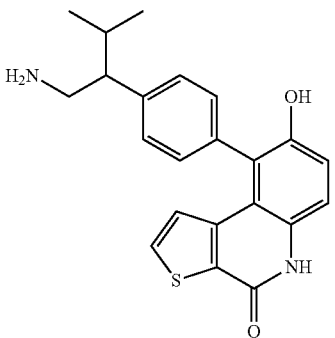 [SMILES: CC(C)C(CN)c1ccc(-c2c(O)ccc3[nH]c(=O)c4sccc4c23)cc1] | 9-(4-(1-amino-3-methylbutan-2-yl)phenyl)-8-hydroxythieno[2,3-c]quinolin-4(5H)-one |
| 1253 | 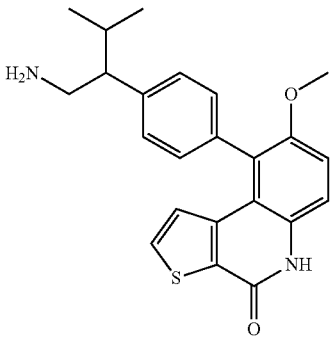 [SMILES: COc1ccc2[nH]c(=O)c3sccc3c2c1-c1ccc(C(CN)C(C)C)cc1] | 9-(4-(1-amino-3-methylbutan-2-yl)phenyl)-8-methoxythieno[2,3-c]quinolin-4(5H)-one |
| 1254 | 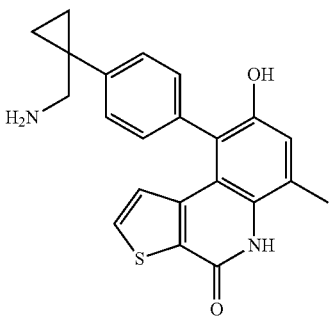 [SMILES: Cc1cc(O)c(-c2ccc(C3(CN)CC3)cc2)c2c1[nH]c(=O)c1sccc12] | 9-(4-(1-(aminomethyl)cyclopropyl)phenyl)-8-hydroxy-6-methylthieno[2,3-c]quinolin-4(5H)-one |

TABLE 1-continued

| | | |
|---|---|---|
| 1255 | 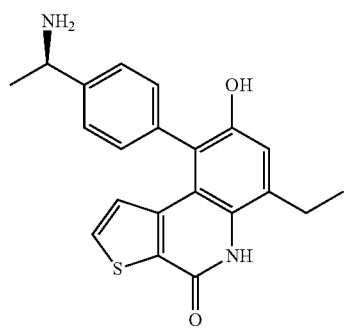 [SMILES: CCc1cc(O)c(-c2ccc([C@@H](C)N)cc2)c2c1[nH]c(=O)c1sccc12] | (R)-9-(4-(1-aminoethyl)phenyl)-6-ethyl-8-hydroxythieno[2,3-c]quinolin-4(5H)-one |
| 1256 | 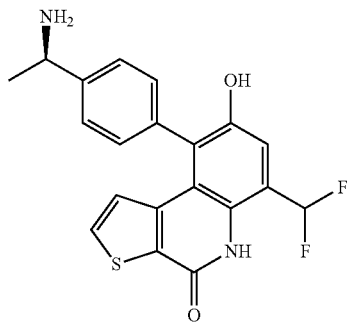 [SMILES: C[C@@H](N)c1ccc(-c2c(O)cc(C(F)F)c3[nH]c(=O)c4sccc4c23)cc1] | (R)-9-(4-(1-aminoethyl)phenyl)-6-(difluoromethyl)-8-hydroxythieno[2,3-c]quinolin-4(5H)-one |
| 1257 | 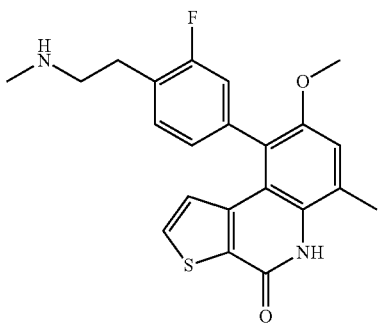 | 9-(3-fluoro-4-(2-(methylamino)ethyl)phenyl)-8-methoxy-6-methylthieno[2,3-c]quinolin-4(5H)-one |
| 1258 | 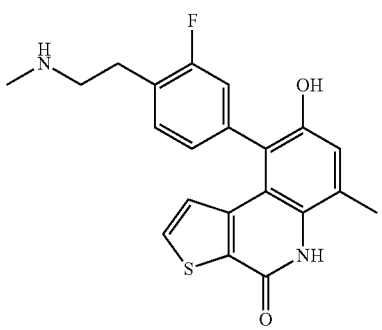 | 9-(3-fluoro-4-(2-(methylamino)ethyl)phenyl)-8-hydroxy-6-methylthieno[2,3-c]quinolin-4(5H)-one |
| 1259 | 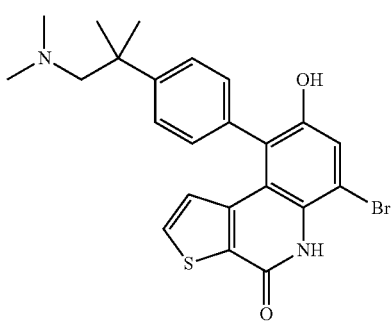 [SMILES: CN(C)CC(C)(C)c1ccc(-c2c(O)cc(Br)c3[nH]c(=O)c4sccc4c23)cc1] | 6-bromo-9-(4-(1-(dimethylamino)-2-methylpropan-2-yl)phenyl)-8-hydroxythieno[2,3-c]quinolin-4(5H)-one |

TABLE 1-continued
| 1260 | 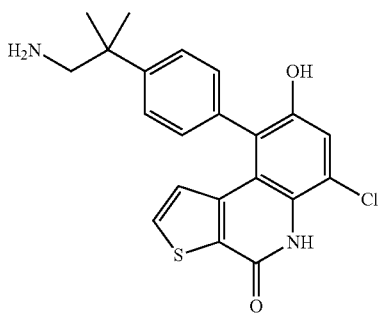 [SMILES: CC(C)(CN)c1ccc(-c2c(O)cc(Cl)c3[nH]c(=O)c4sccc4c23)cc1] | 9-(4-(1-amino-2-methylpropan-2-yl)phenyl)-6-chloro-8-hydroxythieno[2,3-c]quinolin-4(5H)-one |
| 1261 | 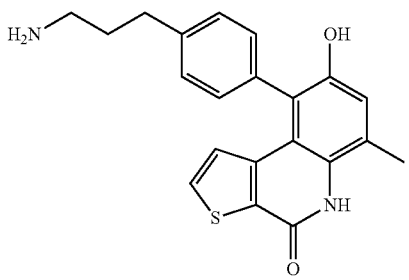 [SMILES: Cc1cc(O)c(-c2ccc(CCCN)cc2)c2c1[nH]c(=O)c1sccc12] | 9-(4-(3-aminopropyl)phenyl)-8-hydroxy-6-methylthieno[2,3-c]quinolin-4(5H)-one |
| 1262 | 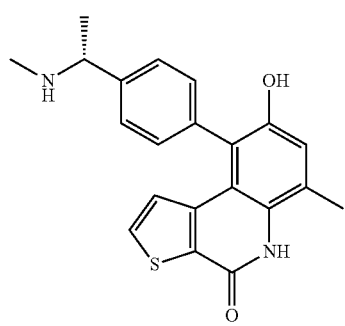 | (R)-8-hydroxy-6-methyl-9-(4-(1-(methylamino)ethyl)phenyl)thieno[2,3-c]quinolin-4(5H)-one |
| 1263 | 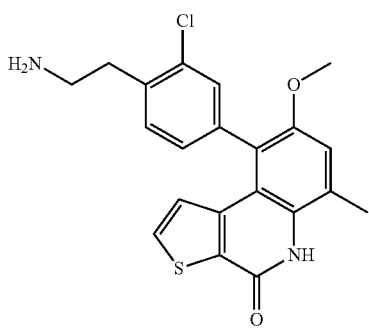 | 9-(4-(2-aminoethyl)-3-chlorophenyl)-8-methoxy-6-methylthieno[2,3-c]quinolin-4(5H)-one |
| 1264 | 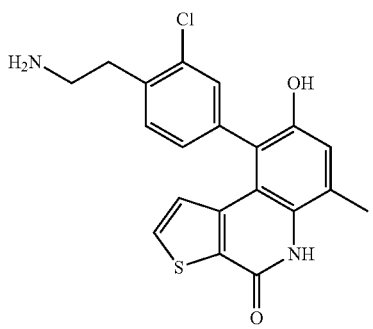 [SMILES: Cc1cc(O)c(-c2ccc(CCN)c(Cl)c2)c2c1[nH]c(=O)c1sccc12] | 9-(4-(2-aminoethyl)-3-chlorophenyl)-8-hydroxy-6-methylthieno[2,3-c]quinolin-4(5H)-one |

TABLE 1-continued

| | | |
|---|---|---|
| 1265 | | (R)-8-methoxy-6-methyl-9-(4-(1-(methylamino)ethyl)phenyl)thieno[2,3-c]quinolin-4(5H)-one |
| 1266 | | 9-(4-(2-aminopropyl)phenyl)-6-ethyl-8-hydroxythieno[2,3-c]quinolin-4(5H)-one |
| 1267 | | (R)-9-(4-(1-aminoethyl)phenyl)-6-butyl-8-hydroxythieno[2,3-c]quinolin-4(5H)-one |
| 1268 | | 9-(4-(2-aminoethyl)-3-chlorophenyl)-6-chloro-8-hydroxythieno[2,3-c]quinolin-4(5H)-one |
| 1269 | | 9-(4-(2-aminopropyl)phenyl)-6-ethyl-8-methoxythieno[2,3-c]quinolin-4(5H)-one |

TABLE 1-continued
| | | |
|---|---|---|
| 1270 | 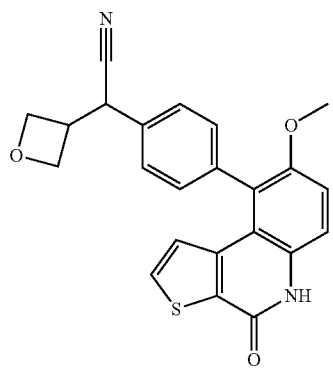 [SMILES: COc1ccc2[nH]c(=O)c3sccc3c2c1-c1ccc(C(C#N)C2COC2)cc1] | 2-(4-(8-methoxy-4-oxo-4,5-dihydrothieno[2,3-c]quinolin-9-yl)phenyl)-2-(oxetan-3-yl)acetonitrile |
| 1271 | 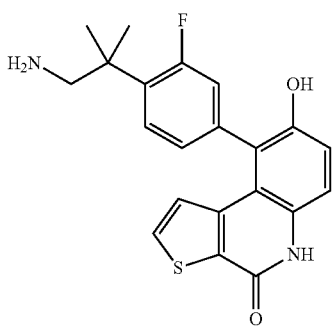 [SMILES: CC(C)(CN)c1ccc(-c2c(O)ccc3[nH]c(=O)c4sccc4c23)cc1F] | 9-(4-(1-amino-2-methylpropan-2-yl)-3-fluorophenyl)-8-hydroxythieno[2,3-c]quinolin-4(5H)-one |
| 1272 | 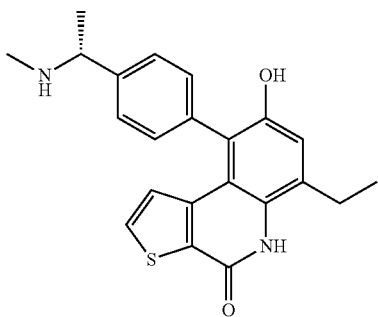 [SMILES: CCc1cc(O)c(-c2ccc([C@@H](C)NC)cc2)c2c1[nH]c(=O)c1sccc12] | (R)-6-ethyl-8-hydroxy-9-(4-(1-(methylamino)ethyl)phenyl)thieno[2,3-c]quinolin-4(5H)-one |
| 1273 | 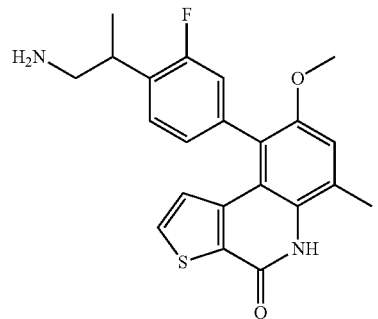 [SMILES: COc1cc(C)c2[nH]c(=O)c3sccc3c2c1-c1ccc(C(C)CN)c(F)c1] | 9-(4-(1-aminopropan-2-yl)-3-fluorophenyl)-8-methoxy-6-methylthieno[2,3-c]quinolin-4(5H)-one |

TABLE 1-continued
| | | |
|---|---|---|
| 1274 | 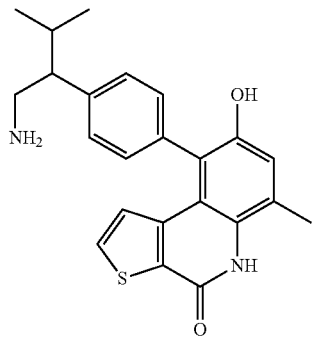 [SMILES: Cc1cc(O)c(-c2ccc(C(CN)C(C)C)cc2)c2c1[nH]c(=O)c1sccc12] | 9-(4-(1-amino-3-methylbutan-2-yl)phenyl)-8-hydroxy-6-methylthieno[2,3-c]quinolin-4(5H)-one |
| 1275 | 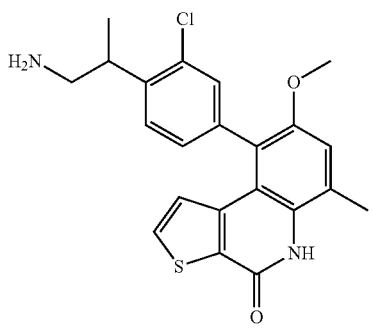 | 9-(4-(1-aminopropan-2-yl)-3-chlorophenyl)-8-methoxy-6-methylthieno[2,3-c]quinolin-4(5H)-one |
| 1276 | 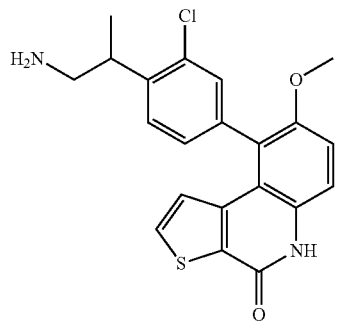 [SMILES: COc1ccc2[nH]c(=O)c3sccc3c2c1-c1ccc(C(C)CN)c(Cl)c1] | 9-(4-(1-aminopropan-2-yl)-3-chlorophenyl)-8-methoxythieno[2,3-c]quinolin-4(5H)-one |
| 1277 | 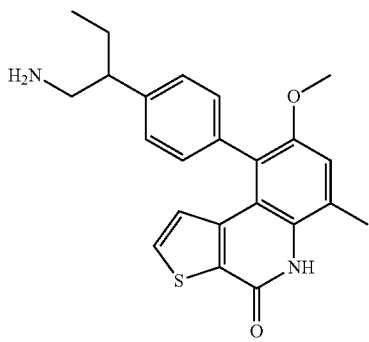 [SMILES: CCC(CN)c1ccc(-c2c(OC)cc(C)c3[nH]c(=O)c4sccc4c23)cc1] | 9-(4-(1-aminobutan-2-yl)phenyl)-8-methoxy-6-methylthieno[2,3-c]quinolin-4(5H)-one |

TABLE 1-continued

| | | |
|---|---|---|
| 1278 | | 9-(4-(1-amino-2-methylpropan-2-yl)-3-fluorophenyl)-8-hydroxy-6-methylthieno[2,3-c]quinolin-4(5H)-one |
| 1279 | | 9-(4-(1-aminopropan-2-yl)-3-chlorophenyl)-8-hydroxy-6-methylthieno[2,3-c]quinolin-4(5H)-one |
| 1280 | | 9-(4-(1-aminopropan-2-yl)-3-chlorophenyl)-8-hydroxythieno[2,3-c]quinolin-4(5H)-one |
| 1281 | | 9-(4-(2-amino-2-methylpropyl)phenyl)-8-methoxythieno[2,3-c]quinolin-4(5H)-one |
| 1282 | | 9-(4-(2-amino-2-methylpropyl)phenyl)-8-hydroxythieno[2,3-c]quinolin-4(5H)-one |

TABLE 1-continued
| | | |
|---|---|---|
| 1283 | 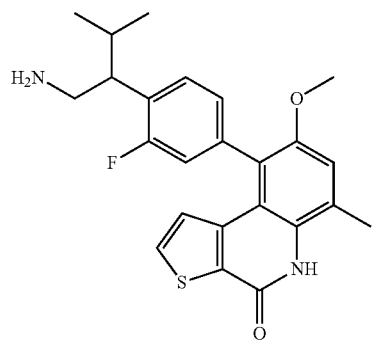 | 9-(4-(1-amino-3-methylbutan-2-yl)-3-fluorophenyl)-8-methoxy-6-methylthieno[2,3-c]quinolin-4(5H)-one |
| 1284 | 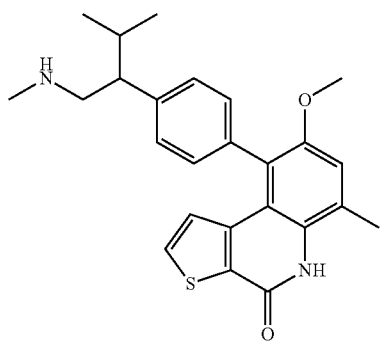 | 8-methoxy-6-methyl-9-(4-(3-methyl-1-(methylamino)butan-2-yl)phenyl)thieno[2,3-c]quinolin-4(5H)-one |
| 1285 | 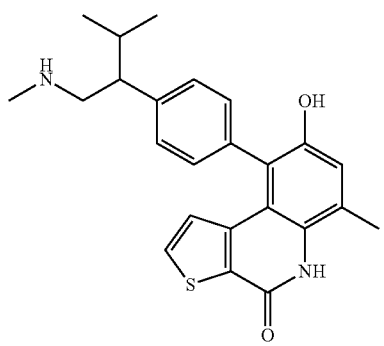 | 8-hydroxy-6-methyl-9-(4-(3-methyl-1-(methylamino)butan-2-yl)phenyl)thieno[2,3-c]quinolin-4(5H)-one |
| 1286 | 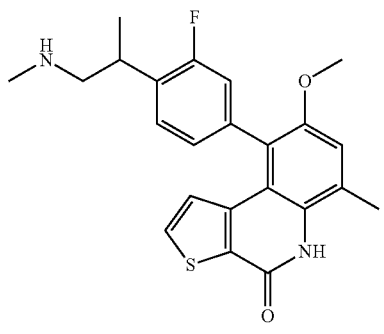 | 9-(3-fluoro-4-(1-(methylamino)propan-2-yl)phenyl)-8-methoxy-6-methylthieno[2,3-c]quinolin-4(5H)-one |

TABLE 1-continued

| | | |
|---|---|---|
| 1287 | | 9-(4-(1-amino-2-methylpropan-2-yl)-3-fluorophenyl)-8-methoxythieno[2,3-c]quinolin-4(5H)-one |
| 1288 | | 9-(4-(1-amino-3-methylbutan-2-yl)-3-fluorophenyl)-8-hydroxy-6-methylthieno[2,3-c]quinolin-4(5H)-one |
| 1289 | | 9-(4-(2-amino-2-methylpropyl)phenyl)-6-bromo-8-methoxythieno[2,3-c]quinolin-4(5H)-one |
| 1290 | | 9-(4-(1-(aminomethyl)cyclobutyl)phenyl)-8-hydroxy-6-methylthieno[2,3-c]quinolin-4(5H)-one |
| 1291 | | 9-(4-(1-aminobutan-2-yl)phenyl)-8-hydroxy-6-methylthieno[2,3-c]quinolin-4(5H)-one |

TABLE 1-continued

| # | Structure | Name |
|---|---|---|
| 1292 | 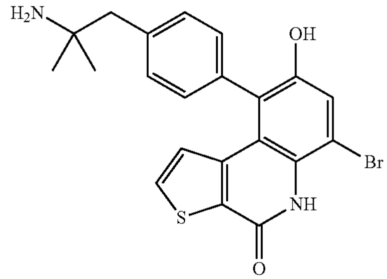 [SMILES: CC(C)(N)Cc1ccc(-c2c(O)cc(Br)c3[nH]c(=O)c4sccc4c23)cc1] | 9-(4-(2-amino-2-methylpropyl)phenyl)-6-bromo-8-hydroxythieno[2,3-c]quinolin-4(5H)-one |
| 1293 | 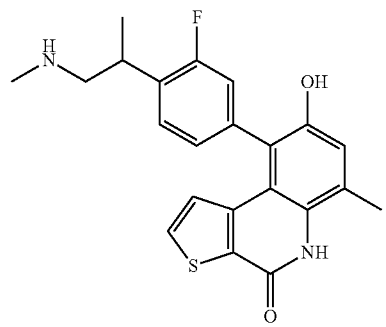 | 9-(3-fluoro-4-(1-(methylamino)propan-2-yl)phenyl)-8-hydroxy-6-methylthieno[2,3-c]quinolin-4(5H)-one |
| 1294 | 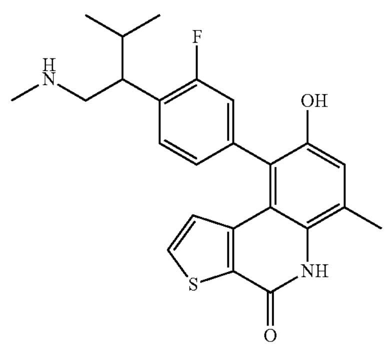 | 9-(3-fluoro-4-(3-methyl-1-(methylamino)butan-2-yl)phenyl)-8-hydroxy-6-methylthieno[2,3-c]quinolin-4(5H)-one |
| 1295 | 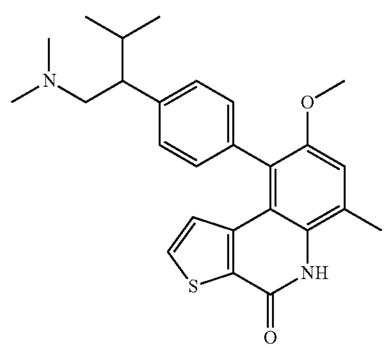 | 9-(4-(1-(dimethylamino)-3-methylbutan-2-yl)phenyl)-8-methoxy-6-methylthieno[2,3-c]quinolin-4(5H)-one |
| 1296 | 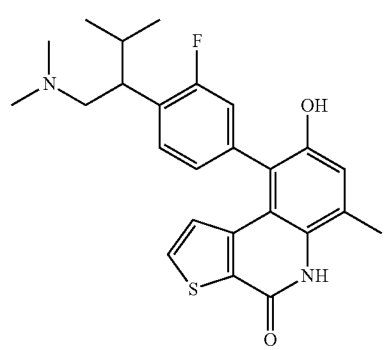 | 9-(4-(1-(dimethylamino)-3-methylbutan-2-yl)-3-fluorophenyl)-8-hydroxy-6-methylthieno[2,3-c]quinolin-4(5H)-one |

TABLE 1-continued
| | | |
|---|---|---|
| 1297 | 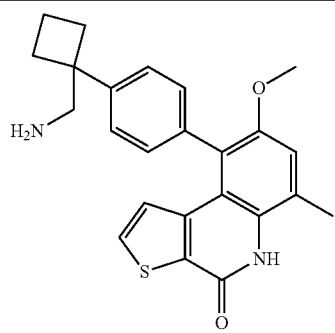 | 9-(4-(1-(aminomethyl)cyclobutyl)phenyl)-8-methoxy-6-methyl thieno[2,3-c]quinolin-4(5H)-one |
| 1298 | 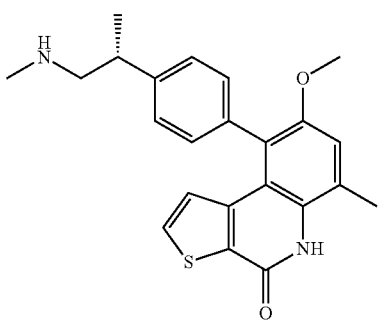 | (R)-8-methoxy-6-methyl-9-(4-(1-(methylamino)propan-2-yl)phenyl)thieno[2,3-c]quinolin-4(5H)-one |
| 1299 | 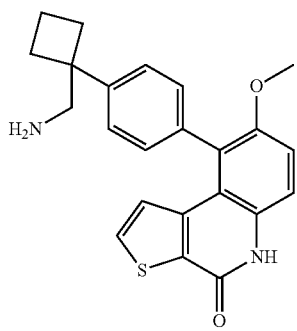 [SMILES: COc1ccc2[nH]c(=O)c3sccc3c2c1-c1ccc(C2(CN)CCC2)cc1] | 9-(4-(1-(aminomethyl)cyclobutyl)phenyl)-8-methoxythieno[2,3-c]quinolin-4(5H)-one |
| 1300 | 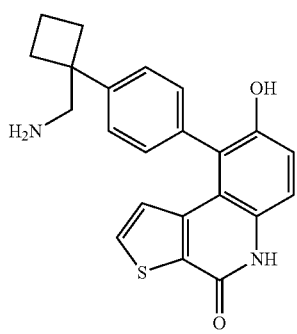 [SMILES: NCC1(c2ccc(-c3c(O)ccc4[nH]c(=O)c5sccc5c34)cc2)CCC1] | 9-(4-(1-(aminomethyl)cyclobutyl)phenyl)-8-hydroxythieno[2,3-c]quinolin-4(5H)-one |
| 1301 | 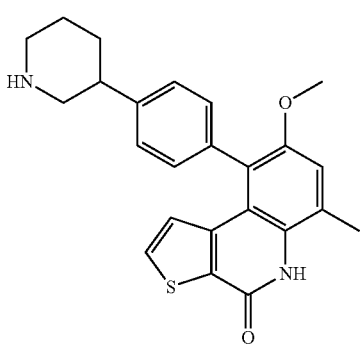 [SMILES: COc1cc(C)c2[nH]c(=O)c3sccc3c2c1-c1ccc(C2CCCNC2)cc1] | 8-methoxy-6-methyl-9-(4-(piperidin-3-yl)phenyl)thieno[2,3-c]quinolin-4(5H)-one |

TABLE 1-continued
| | | |
|---|---|---|
| 1302 | 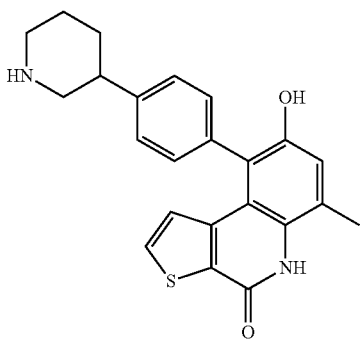 | 8-hydroxy-6-methyl-9-(4-(piperidin-3-yl)phenyl)thieno[2,3-c]quinolin-4(5H)-one |
| 1303 | 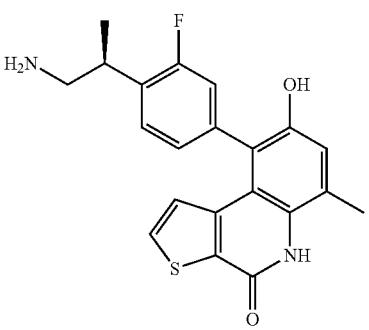 | (S)-9-(4-(1-aminopropan-2-yl)-3-fluorophenyl)-8-hydroxy-6-methylthieno[2,3-c]quinolin-4(5H)-one |
| 1304 | 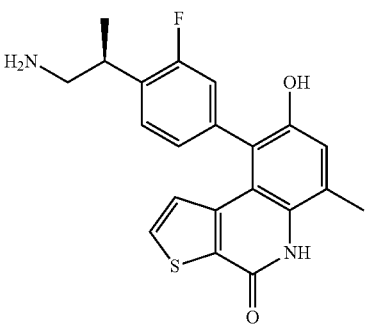 [SMILES: Cc1cc(O)c(-c2ccc([C@H](C)CN)c(F)c2)c2c1[nH]c(=O)c1sccc12] | (S)-9-(4-(1-aminopropan-2-yl)-3-fluorophenyl)-8-hydroxy-6-methylthieno[2,3-c]quinolin-4(5H)-one |
| 1305 | 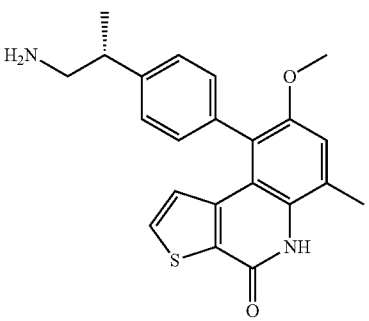 [SMILES: COc1cc(C)c2[nH]c(=O)c3sccc3c2c1-c1ccc([C@@H](C)CN)cc1] | (R)-9-(4-(1-aminopropan-2-yl)phenyl)-8-methoxy-6-methylthieno[2,3-c]quinolin-4(5H)-one |
| 1306 | 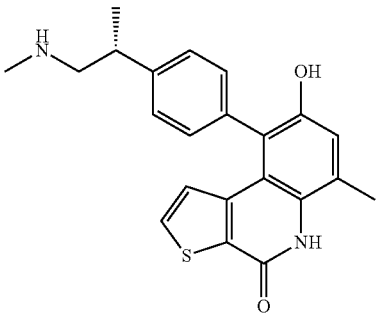 | (R)-8-hydroxy-6-methyl-9-(4-(1-(methylamino)propan-2-yl)phenyl)thieno[2,3-c]quinolin-4(5H)-one |

TABLE 1-continued
| | | |
|---|---|---|
| 1307 | 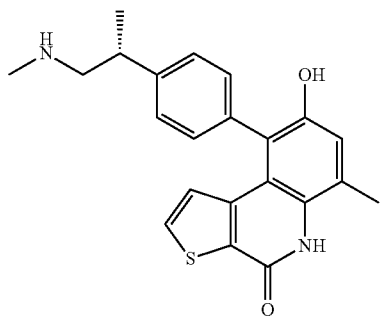 | (R)-8-hydroxy-6-methyl-9-(4-(1-(methylamino)propan-2-yl)phenyl)thieno[2,3-c]quinolin-4(5H)-one |
| 1308 | 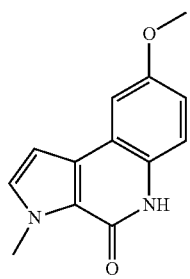 [SMILES: COc1ccc2[nH]c(=O)c3c(ccn3C)c2c1] | 8-methoxy-3-methyl-3H-pyrrolo[2,3-c]quinolin-4(5H)-one |
| 1309 | 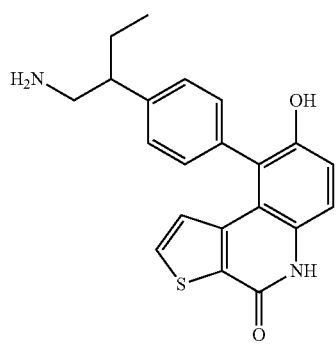 [SMILES: CCC(CN)c1ccc(-c2c(O)ccc3[nH]c(=O)c4sccc4c23)cc1] | 9-(4-(1-aminobutan-2-yl)phenyl)-8-hydroxythieno[2,3-c]quinolin-4(5H)-one |
| 1310 | 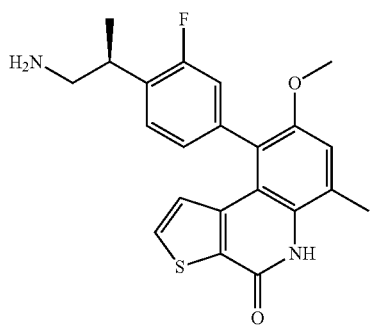 [SMILES: COc1cc(C)c2[nH]c(=O)c3sccc3c2c1-c1ccc([C@H](C)CN)c(F)c1] | (S)-9-(4-(1-aminopropan-2-yl)-3-fluorophenyl)-8-methoxy-6-methylthieno[2,3-c]quinolin-4(5H)-one |
| 1311 | 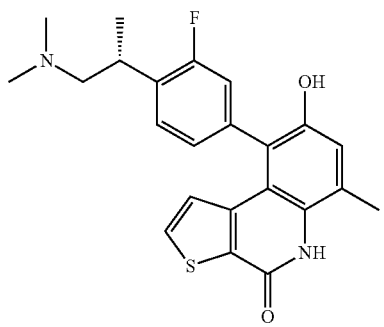 | (R)-9-(4-(1-(dimethylamino)propan-2-yl)-3-fluorophenyl)-8-hydroxy-6-methylthieno[2,3-c]quinolin-4(5H)-one |

TABLE 1-continued

| | | |
|---|---|---|
| 1312 | | 9-(4-(1-aminobutan-2-yl)phenyl)-6-chloro-8-hydroxythieno[2,3-c]quinolin-4(5H)-one |
| 1313 | | 8-hydroxy-3-methyl-3H-pyrrolo[2,3-c]quinolin-4(5H)-one |
| 1314 | | 9-amino-8-methoxy-6-methylthieno[2,3-c]quinolin-4(5H)-one |
| 1315 | | (R)-9-(3-fluoro-4-(1-(methylamino)propan-2-yl)phenyl)-8-hydroxy-6-methylthieno[2,3-c]quinolin-4(5H)-one |
| 1316 | | (R)-9-(3-fluoro-4-(1-(methylamino)propan-2-yl)phenyl)-8-methoxy-6-methylthieno[2,3-c]quinolin-4(5H)-one |

TABLE 1-continued
| | | |
|---|---|---|
| 1317 | 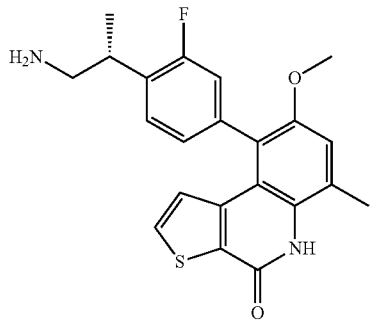 [SMILES: COc1cc(C)c2[nH]c(=O)c3sccc3c2c1-c1ccc([C@@H](C)CN)c(F)c1] | (R)-9-(4-(1-aminopropan-2-yl)-3-fluorophenyl)-8-methoxy-6-methylthieno[2,3-c]quinolin-4(5H)-one |
| 1318 | 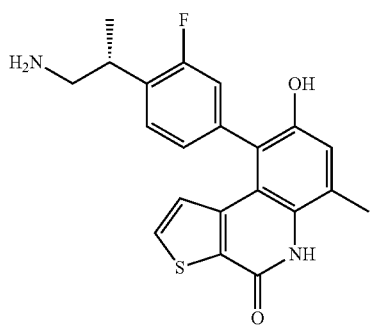 | (R)-9-(4-(1-aminopropan-2-yl)-3-fluorophenyl)-8-hydroxy-6-methylthieno[2,3-c]quinolin-4(5H)-one |
| 1319 | 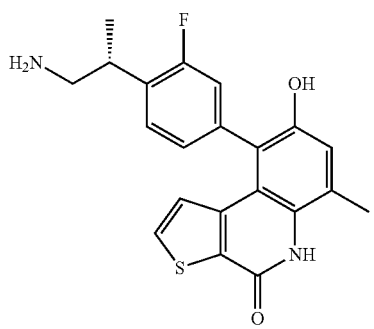 | (R)-9-(4-(1-aminopropan-2-yl)-3-fluorophenyl)-8-hydroxy-6-methylthieno[2,3-c]quinolin-4(5H)-one |
| 1320 | 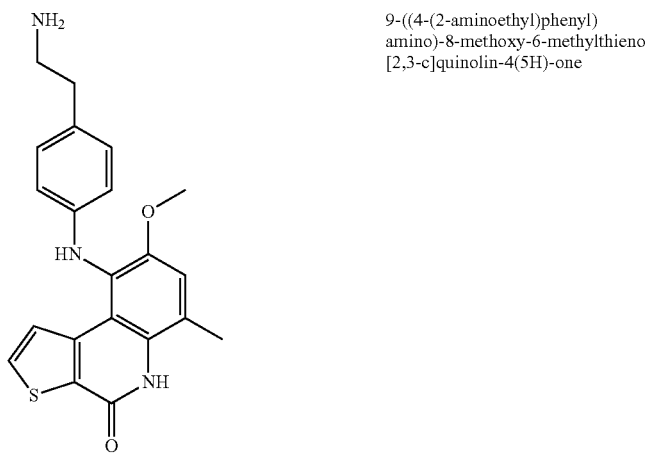 | 9-((4-(2-aminoethyl)phenyl)amino)-8-methoxy-6-methylthieno[2,3-c]quinolin-4(5H)-one |

TABLE 1-continued
| | | |
|---|---|---|
| 1321 | 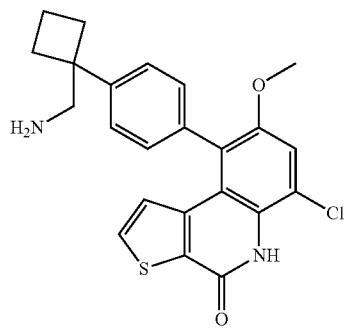 [SMILES: COc1cc(Cl)c2[nH]c(=O)c3sccc3c2c1-c1ccc(C2(CN)CCC2)cc1] | 9-(4-(1-(aminomethyl)cyclobutyl)phenyl)-6-chloro-8-methoxythieno[2,3-c]quinolin-4(5H)-one |
| 1322 | 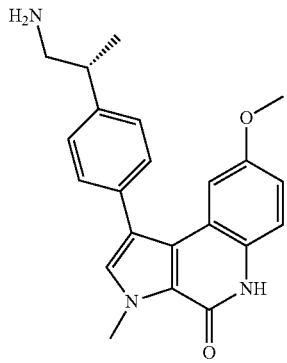 [SMILES: COc1ccc2[nH]c(=O)c3c(c(-c4ccc([C@@H](C)CN)cc4)cn3C)c2c1] | (R)-1-(4-(1-aminopropan-2-yl)phenyl)-8-methoxy-3-methyl-3H-pyrrolo[2,3-c]quinolin-4(5H)-one |
| 1323 | 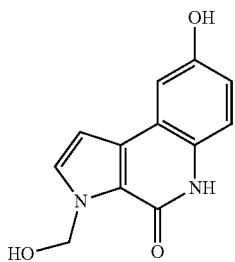 [SMILES: O=c1[nH]c2ccc(O)cc2c2ccn(CO)c12] | 8-hydroxy-3-(hydroxymethyl)-3H-pyrrolo[2,3-c]quinolin-4(5H)-one |
| 1324 | 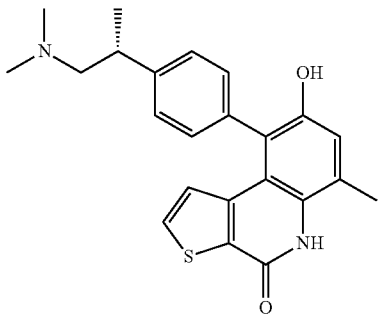 | (R)-9-(4-(1-(dimethylamino)propan-2-yl)phenyl)-8-hydroxy-6-methylthieno[2,3-c]quinolin-4(5H)-one |

TABLE 1-continued
| | | |
|---|---|---|
| 1325 | 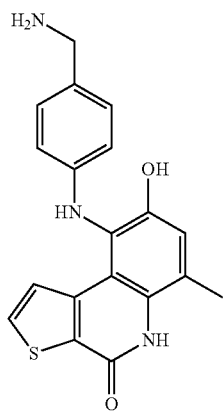 [SMILES: Cc1cc(O)c(Nc2ccc(CN)cc2)c2c1[nH]c(=O)c1sccc12] | 9-((4-(aminomethyl)phenyl)amino)-8-hydroxy-6-methylthieno[2,3-c]quinolin-4(5H)-one |
| 1326 | 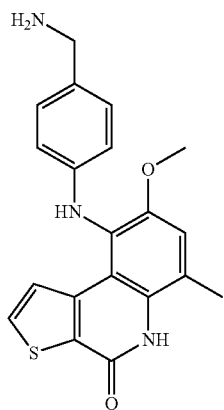 [SMILES: COc1cc(C)c2[nH]c(=O)c3sccc3c2c1Nc1ccc(CN)cc1] | 9-((4-(aminomethyl)phenyl)amino)-8-methoxy-6-methylthieno[2,3-c]quinolin-4(5H)-one |
| 1327 | 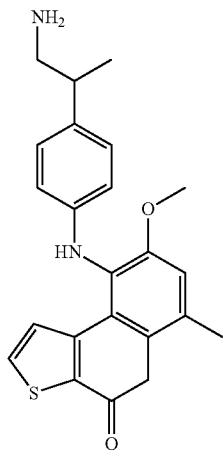 [SMILES: COc1cc(C)c2c(c1Nc1ccc(C(C)CN)cc1)-c1ccsc1C(=O)C2] | 9-((4-(1-aminopropan-2-yl)phenyl)amino)-8-methoxy-6-methylthieno[2,3-c]quinolin-4(5H)-one |

TABLE 1-continued
| | | |
|---|---|---|
| 1328 | 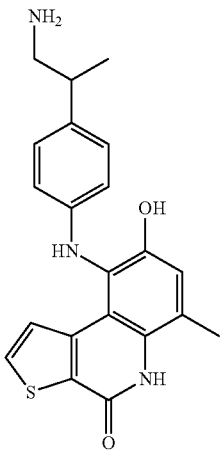 [SMILES: Cc1cc(O)c(Nc2ccc(C(C)CN)cc2)c2c1[nH]c(=O)c1sccc12] | 9-((4-(1-aminopropan-2-yl)phenyl)amino)-8-hydroxy-6-methylthieno[2,3-c]quinolin-4(5H)-one |
| 1329 | 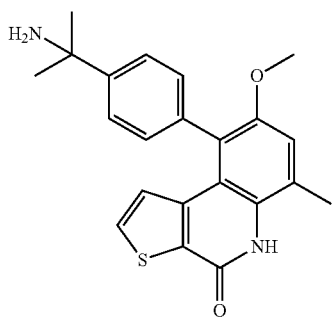 [SMILES: COc1cc(C)c2[nH]c(=O)c3sccc3c2c1-c1ccc(C(C)(C)N)cc1] | 9-(4-(2-aminopropan-2-yl)phenyl)-8-methoxy-6-methylthieno[2,3-c]quinolin-4(5H)-one |
| 1330 | 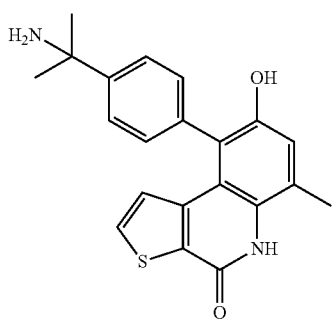 [SMILES: Cc1cc(O)c(-c2ccc(C(C)(C)N)cc2)c2c1[nH]c(=O)c1sccc12] | 9-(4-(2-aminopropan-2-yl)phenyl)-8-hydroxy-6-methylthieno[2,3-c]quinolin-4(5H)-one |
| 1331 | 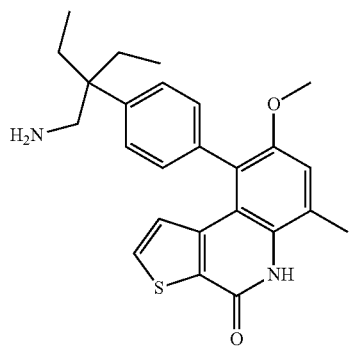 [SMILES: CCC(CC)(CN)c1ccc(-c2c(OC)cc(C)c3[nH]c(=O)c4sccc4c23)cc1] | 9-(4-(3-(aminomethyl)pentan-3-yl)phenyl)-8-methoxy-6-methylthieno[2,3-c]quinolin-4(5H)-one |

TABLE 1-continued
| | | |
|---|---|---|
| 1332 | 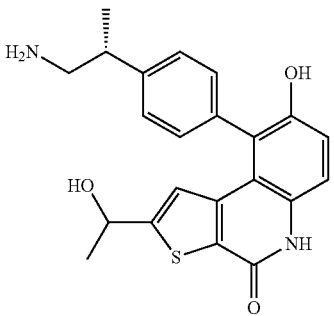 [SMILES: CC(O)c1cc2c(s1)c(=O)[nH]c1ccc(O)c(-c3ccc([C@@H](C)CN)cc3)c12] | 9-(4-((R)-1-aminopropan-2-yl)phenyl)-8-hydroxy-2-(1-hydroxyethyl)thieno[2,3-c]quinolin-4(5H)-one |
| 1333 | 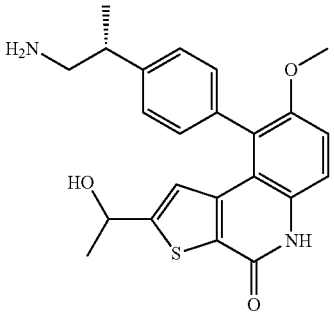 [SMILES: COc1ccc2[nH]c(=O)c3sc(C(C)O)cc3c2c1-c1ccc([C@@H](C)CN)cc1] | 9-(4-((R)-1-aminopropan-2-yl)phenyl)-2-(1-hydroxyethyl)-8-methoxythieno[2,3-c]quinolin-4(5H)-one |
| 1334 | 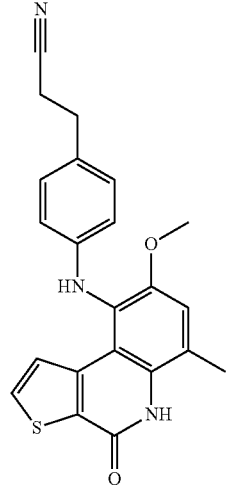 [SMILES: COc1cc(C)c2[nH]c(=O)c3sccc3c2c1Nc1ccc(CCC#N)cc1] | 3-(4-((8-methoxy-6-methyl-4-oxo-4,5-dihydrothieno[2,3-c]quinolin-9-yl)amino)phenyl)propanenitrile |
| 1335 | 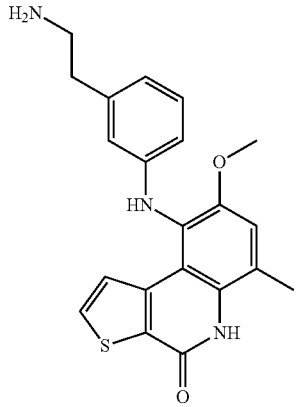 [SMILES: COc1cc(C)c2[nH]c(=O)c3sccc3c2c1Nc1cccc(CCN)c1] | 9-((3-(2-aminoethyl)phenyl)amino)-8-methoxy-6-methylthieno[2,3-c]quinolin-4(5H)-one |

TABLE 1-continued
| | | |
|---|---|---|
| 1336 | 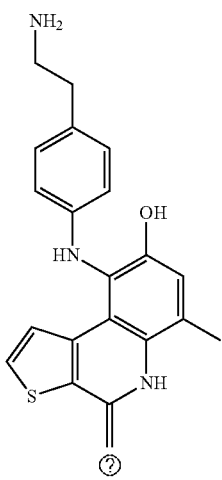 [SMILES: C=C1Nc2c(C)cc(O)c(Nc3ccc(CCN)cc3)c2-c2ccsc21] | 9-((4-(2-aminoethyl)phenyl)amino)-8-hydroxy-6-methylthieno[2,3-c]quinolin-4(5H)-one |
| 1337 | 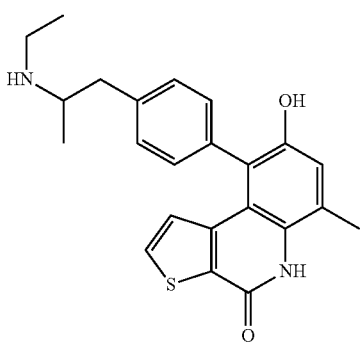 [SMILES: CCNC(C)Cc1ccc(-c2c(O)cc(C)c3[nH]c(=O)c4sccc4c23)cc1] | 9-(4-(2-(ethylamino)propyl)phenyl)-8-hydroxy-6-methylthieno[2,3-c]quinolin-4(5H)-one |
| 1338 | 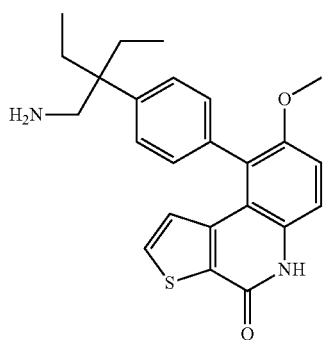 [SMILES: CCC(CC)(CN)c1ccc(-c2c(OC)ccc3[nH]c(=O)c4sccc4c23)cc1] | 9-(4-(3-(aminomethyl)pentan-3-yl)phenyl)-8-methoxythieno[2,3-c]quinolin-4(5H)-one |
| 1339 | 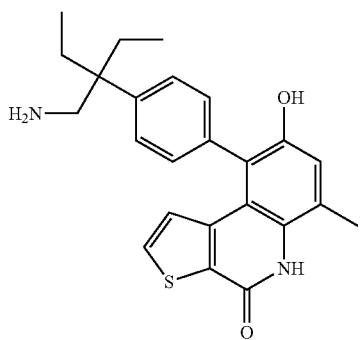 [SMILES: CCC(CC)(CN)c1ccc(-c2c(O)cc(C)c3[nH]c(=O)c4sccc4c23)cc1] | 9-(4-(3-(aminomethyl)pentan-3-yl)phenyl)-8-hydroxy-6-methylthieno[2,3-c]quinolin-4(5H)-one |

TABLE 1-continued

| | | |
|---|---|---|
| 1340 | 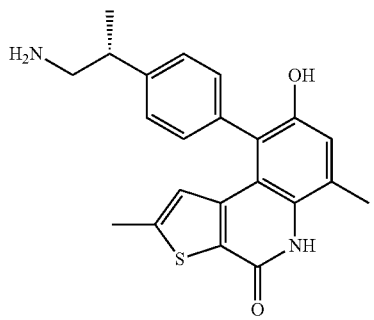 [SMILES: Cc1cc2c(s1)c(=O)[nH]c1c(C)cc(O)c(-c3ccc([C@@H](C)CN)cc3)c12] | (R)-9-(4-(1-aminopropan-2-yl)phenyl)-8-hydroxy-2,6-dimethylthieno[2,3-c]quinolin-4(5H)-one |
| 1341 | 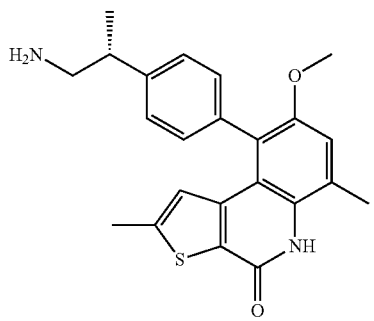 [SMILES: COc1cc(C)c2[nH]c(=O)c3sc(C)cc3c2c1-c1ccc([C@@H](C)CN)cc1] | (R)-9-(4-(1-aminopropan-2-yl)phenyl)-8-methoxy-2,6-dimethylthieno[2,3-c]quinolin-4(5H)-one |
| 1342 | 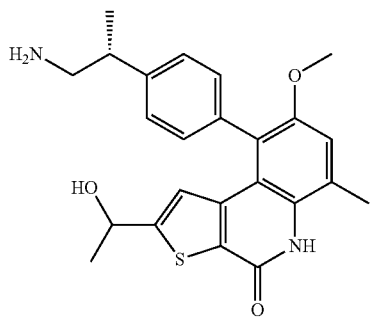 [SMILES: COc1cc(C)c2[nH]c(=O)c3sc(C(C)O)cc3c2c1-c1ccc([C@@H](C)CN)cc1] | 9-(4-((R)-1-aminopropan-2-yl)phenyl)-2-(1-hydroxyethyl)-8-methoxy-6-methylthieno[2,3-c]quinolin-4(5H)-one |
| 1343 | 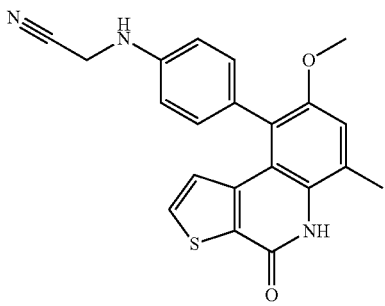 [SMILES: COc1cc(C)c2[nH]c(=O)c3sccc3c2c1-c1ccc(NCC#N)cc1] | 2-((4-(8-methoxy-6-methyl-4-oxo-4,5-dihydrothieno[2,3-c]quinolin-9-yl)phenyl)amino)acetonitrile |
| 1344 | 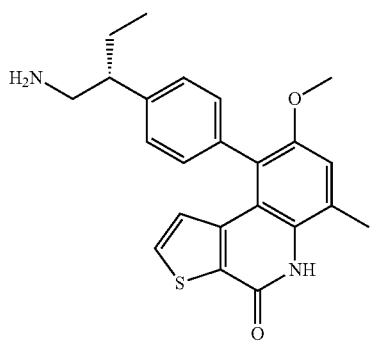 [SMILES: CC[C@@H](CN)c1ccc(-c2c(OC)cc(C)c3[nH]c(=O)c4sccc4c23)cc1] | (R)-9-(4-(1-aminobutan-2-yl)phenyl)-8-methoxy-6-methylthieno[2,3-c]quinolin-4(5H)-one |

| | | |
|---|---|---|
| 1345 | 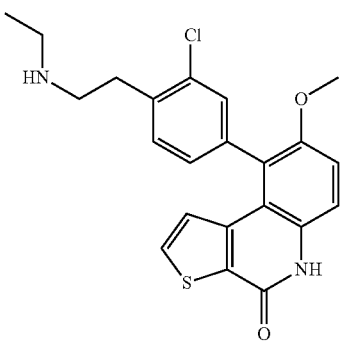 [SMILES: CCNCCc1ccc(-c2c(OC)ccc3[nH]c(=O)c4sccc4c23)cc1Cl] | 9-(3-chloro-4-(2-(ethylamino)ethyl)phenyl)-8-methoxythieno[2,3-c]quinolin-4(5H)-one |
| 1346 | 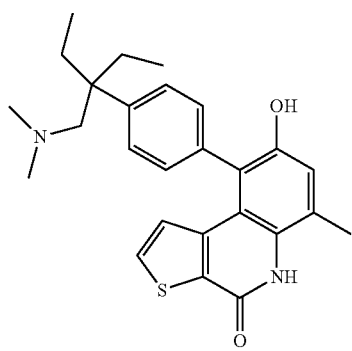 | 9-(4-(3-((dimethylamino)methyl)pentan-3-yl)phenyl)-8-hydroxy-6-methylthieno[2,3-c]quinolin-4(5H)-one |
| 1347 | 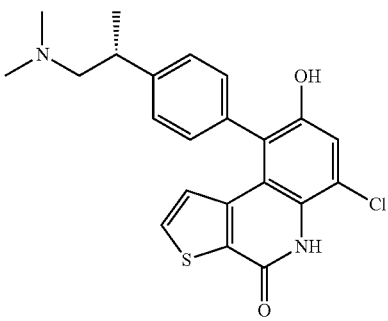 [SMILES: C[C@@H](CN(C)C)c1ccc(-c2c(O)cc(Cl)c3[nH]c(=O)c4sccc4c23)cc1] | (R)-6-chloro-9-(4-(1-(dimethylamino)propan-2-yl)phenyl)-8-hydroxythieno[2,3-c]quinolin-4(5H)-one |
| 1348 | 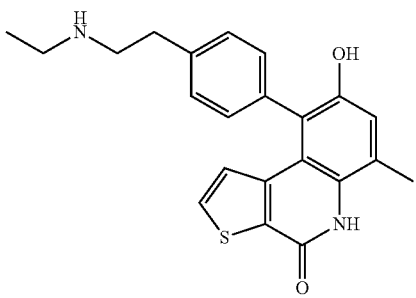 [SMILES: CCNCCc1ccc(-c2c(O)cc(C)c3[nH]c(=O)c4sccc4c23)cc1] | 9-(4-(2-(ethylamino)ethyl)phenyl)-8-hydroxy-6-methylthieno[2,3-c]quinolin-4(5H)-one |
| 1349 | 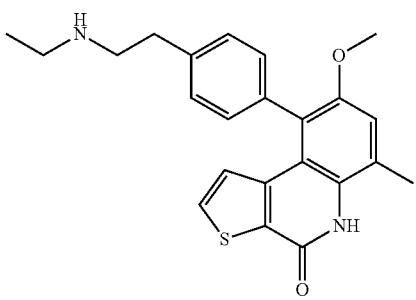 [SMILES: CCNCCc1ccc(-c2c(OC)cc(C)c3[nH]c(=O)c4sccc4c23)cc1] | 9-(4-(2-(ethylamino)ethyl)phenyl)-8-methoxy-6-methylthieno[2,3-c]quinolin-4(5H)-one |

TABLE 1-continued
| | | |
|---|---|---|
| 1350 | 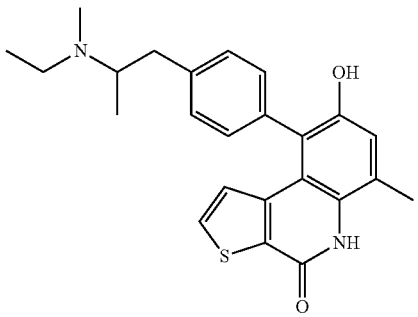 [SMILES: CCN(C)C(C)Cc1ccc(-c2c(O)cc(C)c3[nH]c(=O)c4sccc4c23)cc1] | 9-(4-(2-(ethyl(methyl)amino)propyl)phenyl)-8-hydroxy-6-methylthieno[2,3-c]quinolin-4(5H)-one |
| 1351 | 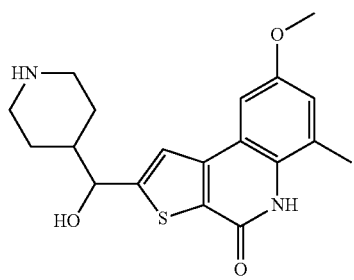 [SMILES: COc1cc(C)c2[nH]c(=O)c3sc(C(O)C4CCNCC4)cc3c2c1] | 2-(hydroxy(piperidin-4-yl)methyl)-8-methoxy-6-methylthieno[2,3-c]quinolin-4(5H)-one |
| 1352 | 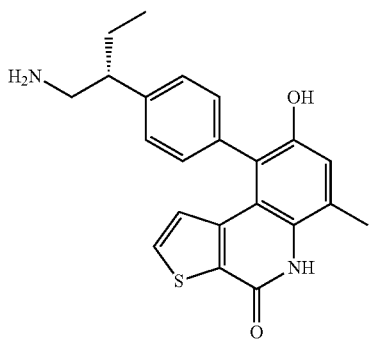 [SMILES: CC[C@@H](CN)c1ccc(-c2c(O)cc(C)c3[nH]c(=O)c4sccc4c23)cc1] | (R)-9-(4-(1-aminobutan-2-yl)phenyl)-8-hydroxy-6-methylthieno[2,3-c]quinolin-4(5H)-one |
| 1353 | 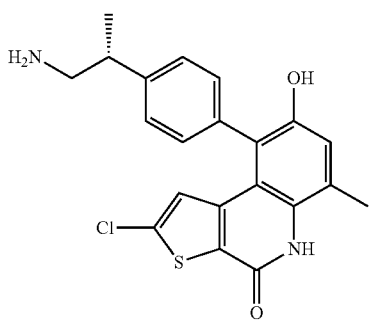 [SMILES: Cc1cc(O)c(-c2ccc([C@@H](C)CN)cc2)c2c1[nH]c(=O)c1sc(Cl)cc12] | (R)-9-(4-(1-aminopropan-2-yl)phenyl)-2-chloro-8-hydroxy-6-methylthieno[2,3-c]quinolin-4(5H)-one |
| 1354 | 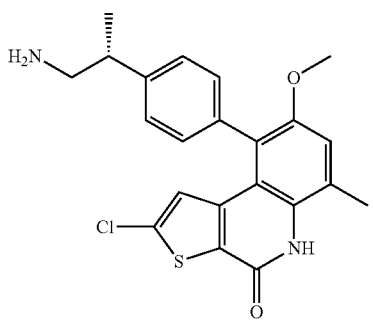 | (R)-9-(4-(1-aminopropan-2-yl)phenyl)-2-chloro-8-methoxy-6-methylthieno[2,3-c]quinolin-4(5H)-one |

TABLE 1-continued

| # | Name |
|---|---|
| 1355 | 8-methoxy-6-methyl-9-(4-(2-(methylamino)ethyl)phenyl)thieno[2,3-c]quinolin-4(5H)-one |
| 1356 | 9-(4-(2-(ethyl(methyl)amino)ethyl)phenyl)-8-hydroxy-6-methylthieno[2,3-c]quinolin-4(5H)-one |
| 1357 | 9-(4-(3-(aminomethyl)pentan-3-yl)phenyl)-6-chloro-8-methoxythieno[2,3-c]quinolin-4(5H)-one |
| 1358 | 9-(4-(3-((dimethylamino)methyl)pentan-3-yl)phenyl)-8-hydroxythieno[2,3-c]quinolin-4(5H)-one |
| 1359 | 9-(6-(dimethylamino)pyridin-3-yl)-8-methoxy-6-methylthieno[2,3-c]quinolin-4(5H)-one |

TABLE 1-continued

| | | |
|---|---|---|
| 1360 | 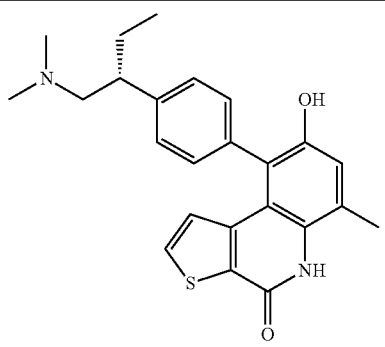 | (R)-9-(4-(1-(dimethylamino)butan-2-yl)phenyl)-8-hydroxy-6-methylthieno[2,3-c]quinolin-4(5H)-one |
| 1361 | 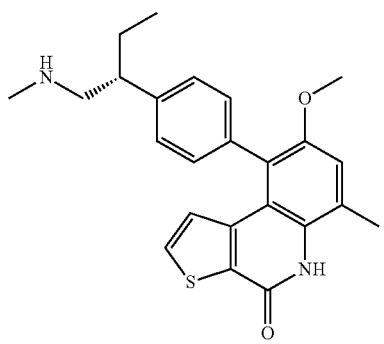 | (R)-8-methoxy-6-methyl-9-(4-(1-(methylamino)butan-2-yl)phenyl)thieno[2,3-c]quinolin-4(5H)-one |
| 1362 | 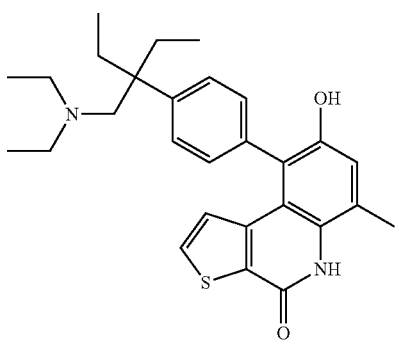 [SMILES: CCN(CC)CC(CC)(CC)c1ccc(-c2c(O)cc(C)c3[nH]c(=O)c4sccc4c23)cc1] | 9-(4-(3-((diethylamino)methyl)pentan-3-yl)phenyl)-8-hydroxy-6-methylthieno[2,3-c]quinolin-4(5H)-one |
| 1363 | 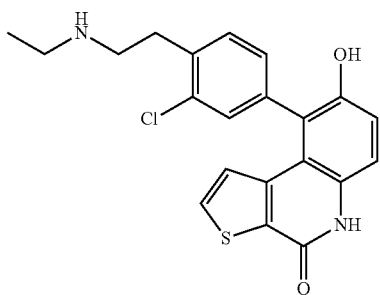 [SMILES: CCNCCc1ccc(-c2c(O)ccc3[nH]c(=O)c4sccc4c23)cc1Cl] | 9-(3-chloro-4-(2-(ethylamino)ethyl)phenyl)-8-hydroxythieno[2,3-c]quinolin-4(5H)-one |
| 1364 | 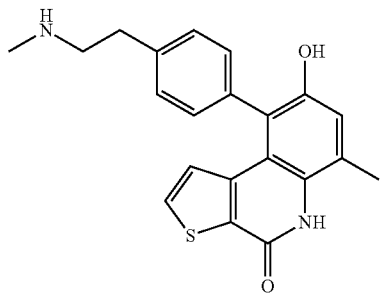 | 8-hydroxy-6-methyl-9-(4-(2-(methylamino)ethyl)phenyl)thieno[2,3-c]quinolin-4(5H)-one |

TABLE 1-continued
| | | |
|---|---|---|
| 1365 | 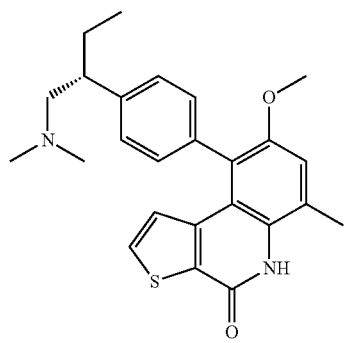 | (R)-9-(4-(1-(dimethylamino)butan-2-yl)phenyl)-8-methoxy-6-methylthieno[2,3-c]quinolin-4(5H)-one |
| 1366 | 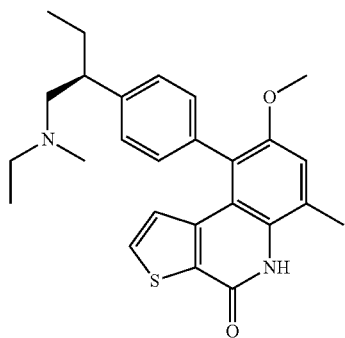 [SMILES: CC[C@H](CN(C)CC)c1ccc(-c2c(OC)cc(C)c3[nH]c(=O)c4sccc4c23)cc1] | (R)-9-(4-(1-(ethyl(methyl)amino)butan-2-yl)phenyl)-8-methoxy-6-methylthieno[2,3-c]quinolin-4(5H)-one |
| 1367 | 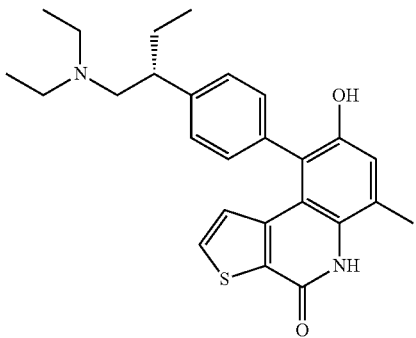 [SMILES: CC[C@@H](CN(CC)CC)c1ccc(-c2c(O)cc(C)c3[nH]c(=O)c4sccc4c23)cc1] | (R)-9-(4-(1-(diethylamino)butan-2-yl)phenyl)-8-hydroxy-6-methylthieno[2,3-c]quinolin-4(5H)-one |
| 1368 | 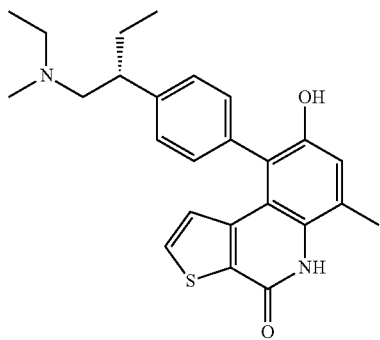 | (R)-9-(4-(1-(ethyl(methyl)amino)butan-2-yl)phenyl)-8-hydroxy-6-methylthieno[2,3-c]quinolin-4(5H)-one |

TABLE 1-continued

| | | |
|---|---|---|
| 1369 | | 2-((4-(8-methoxy-6-methyl-4-oxo-4,5-dihydrothieno[2,3-c]quinolin-9-yl)phenyl)(methyl)amino)acetonitrile |
| 1370 | | 2-((4-(8-hydroxy-6-methyl-4-oxo-4,5-dihydrothieno[2,3-c]quinolin-9-yl)phenyl)(methyl)amino)acetonitrile |
| 1371 | | 9-(3-chloro-4-(2-(ethyl(methyl)amino)ethyl)phenyl)-8-hydroxythieno[2,3-c]quinolin-4(5H)-one |
| 1372 | | 9-(4-(1-((dimethylamino)methyl)cyclobutyl)phenyl)-8-hydroxy-6-methylthieno[2,3-c]quinolin-4(5H)-one |
| 1373 | | (R)-9-(4-(1-aminopropyl)phenyl)-6-bromo-8-methoxythieno[2,3-c]quinolin-4(5H)-one |

TABLE 1-continued
| | | |
|---|---|---|
| 1374 | 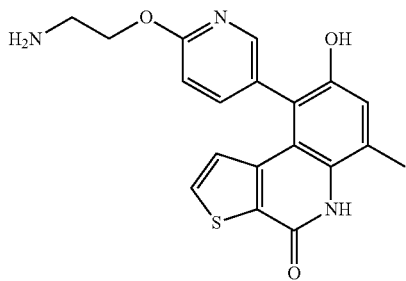 [SMILES: Cc1cc(O)c(-c2ccc(OCCN)nc2)c2c1[nH]c(=O)c1sccc12] | 9-(6-(2-aminoethoxy)pyridin-3-yl)-8-hydroxy-6-methylthieno[2,3-c]quinolin-4(5H)-one |
| 1375 | 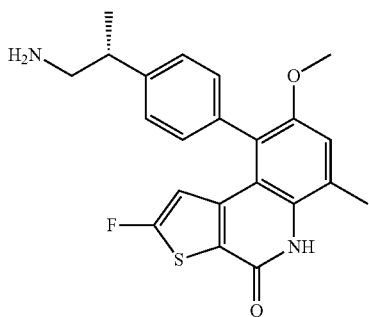 | (R)-9-(4-(1-aminopropan-2-yl)phenyl)-2-fluoro-8-methoxy-6-methylthieno[2,3-c]quinolin-4(5H)-one |
| 1376 | 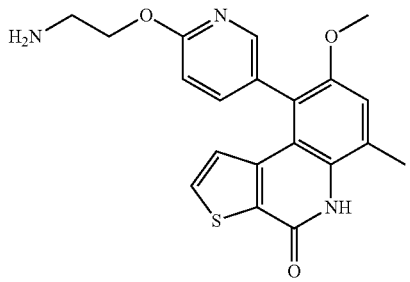 [SMILES: COc1cc(C)c2[nH]c(=O)c3sccc3c2c1-c1ccc(OCCN)nc1] | 9-(6-(2-aminoethoxy)pyridin-3-yl)-8-methoxy-6-methylthieno[2,3-c]quinolin-4(5H)-one |
| 1377 | 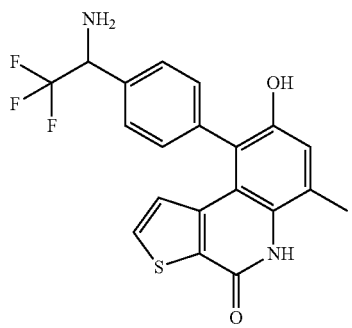 [SMILES: Cc1cc(O)c(-c2ccc(C(N)C(F)(F)F)cc2)c2c1[nH]c(=O)c1sccc12] | 9-(4-(1-amino-2,2,2-trifluoroethyl)phenyl)-8-hydroxy-6-methylthieno[2,3-c]quinolin-4(5H)-one |
| 1378 | 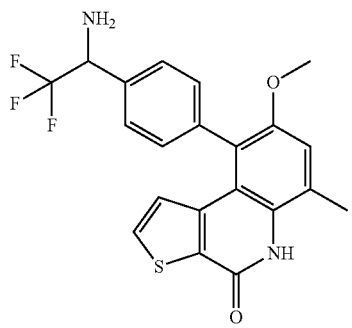 [SMILES: COc1cc(C)c2[nH]c(=O)c3sccc3c2c1-c1ccc(C(N)C(F)(F)F)cc1] | 9-(4-(1-amino-2,2,2-trifluoroethyl)phenyl)-8-methoxy-6-methylthieno[2,3-c]quinolin-4(5H)-one |

TABLE 1-continued
| | | |
|---|---|---|
| 1379 | 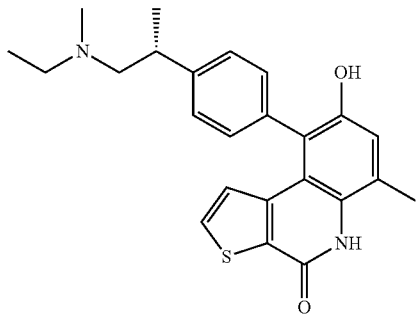 [SMILES: CCN(C)C[C@H](C)c1ccc(-c2c(O)cc(C)c3[nH]c(=O)c4sccc4c23)cc1] | (R)-9-(4-(1-(ethyl(methyl)amino)propan-2-yl)phenyl)-8-hydroxy-6-methylthieno[2,3-c]quinolin-4(5H)-one |
| 1380 | 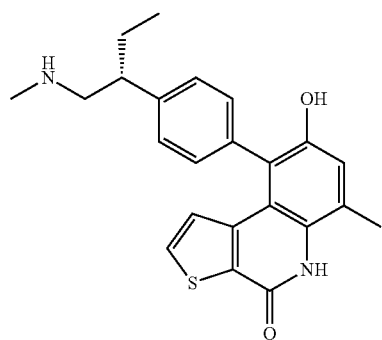 | (R)-8-hydroxy-6-methyl-9-(4-(1-(methylamino)butan-2-yl)phenyl)thieno[2,3-c]quinolin-4(5H)-one |
| 1381 | 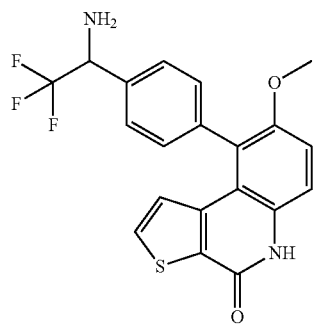 [SMILES: COc1ccc2[nH]c(=O)c3sccc3c2c1-c1ccc(C(N)C(F)(F)F)cc1] | 9-(4-(1-amino-2,2,2-trifluoroethyl)phenyl)-8-methoxythieno[2,3-c]quinolin-4(5H)-one |
| 1382 | 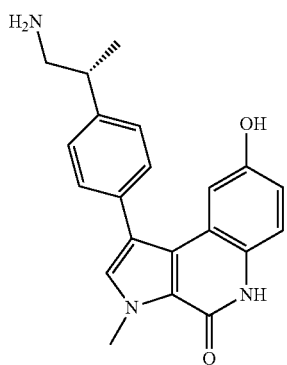 [SMILES: C[C@@H](CN)c1ccc(-c2cn(C)c3c(=O)[nH]c4ccc(O)cc4c23)cc1] | (R)-1-(4-(1-aminopropan-2-yl)phenyl)-8-hydroxy-3-methyl-3H-pyrrolo[2,3-c]quinolin-4(5H)-one |

TABLE 1-continued

| | | |
|---|---|---|
| 1383 | | (R)-9-(4-(1-aminopropan-2-yl)phenyl)-2-fluoro-8-hydroxy-6-methylthieno[2,3-c]quinolin-4(5H)-one |
| 1384 | | 9-(6-((2-aminoethyl)amino)pyridin-3-yl)-8-hydroxy-6-methylthieno[2,3-c]quinolin-4(5H)-one |
| 1385 | | 9-(6-((2-aminoethyl)amino)pyridin-3-yl)-8-methoxy-6-methylthieno[2,3-c]quinolin-4(5H)-one |
| 1386 | | (S)-6-chloro-9-(4-(1-(ethyl(methyl)amino)propan-2-yl)phenyl)-8-hydroxythieno[2,3-c]quinolin-4(5H)-one |
| 1387 | | (S)-9-(4-(1-(dimethylamino)propan-2-yl)-3-fluorophenyl)-8-methoxy-6-methylthieno[2,3-c]quinolin-4(5H)-one |

TABLE 1-continued

| | | |
|---|---|---|
| 1388 | 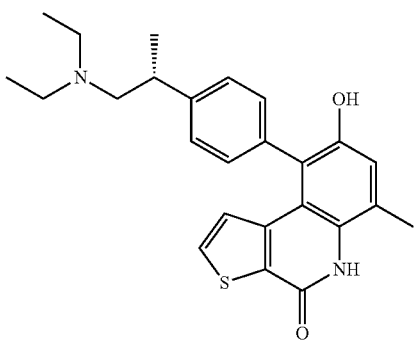 [SMILES: CCN(CC)C[C@H](C)c1ccc(-c2c(O)cc(C)c3[nH]c(=O)c4sccc4c23)cc1] | (R)-9-(4-(1-(diethylamino)propan-2-yl)phenyl)-8-hydroxy-6-methylthieno[2,3-c]quinolin-4(5H)-one |
| 1389 | 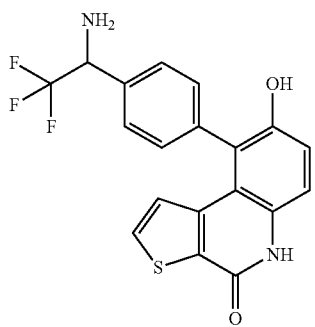 [SMILES: NC(c1ccc(-c2c(O)ccc3[nH]c(=O)c4sccc4c23)cc1)C(F)(F)F] | 9-(4-(1-amino-2,2,2-trifluoroethyl)phenyl)-8-hydroxythieno[2,3-c]quinolin-4(5H)-one |
| 1390 | 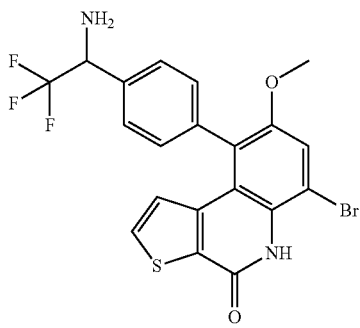 [SMILES: COc1cc(Br)c2[nH]c(=O)c3sccc3c2c1-c1ccc(C(N)C(F)(F)F)cc1] | 9-(4-(1-amino-2,2,2-trifluoroethyl)phenyl)-6-bromo-8-methoxythieno[2,3-c]quinolin-4(5H)-one |
| 1391 | 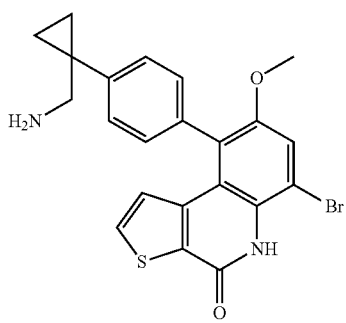 [SMILES: COc1cc(Br)c2[nH]c(=O)c3sccc3c2c1-c1ccc(C2(CN)CC2)cc1] | 9-(4-(1-(aminomethyl)cyclopropyl)phenyl)-6-bromo-8-methoxythieno[2,3-c]quinolin-4(5H)-one |
| 1392 | 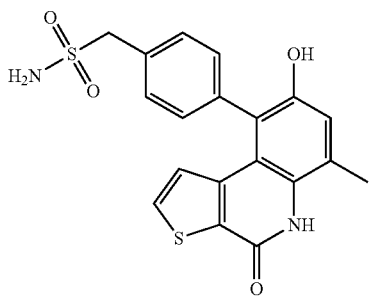 [SMILES: Cc1cc(O)c(-c2ccc(CS(N)(=O)=O)cc2)c2c1[nH]c(=O)c1sccc12] | (4-(8-hydroxy-6-methyl-4-oxo-4,5-dihydrothieno[2,3-c]quinolin-9-yl)phenyl)methanesulfonamide |

| | | |
|---|---|---|
| 1393 | 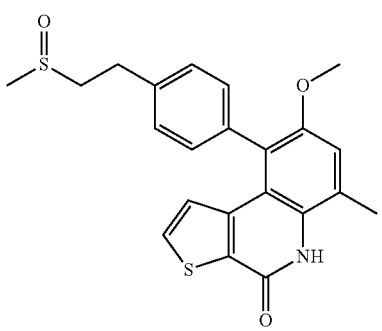 | 8-methoxy-6-methyl-9-(4-(2-(methylsulfinyl)ethyl)phenyl)thieno[2,3-c]quinolin-4(5H)-one |
| 1394 | 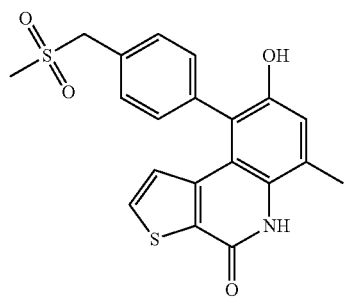 | 8-hydroxy-6-methyl-9-(4-((methylsulfonyl)methyl)phenyl)thieno[2,3-c]quinolin-4(5H)-one |
| 1395 | 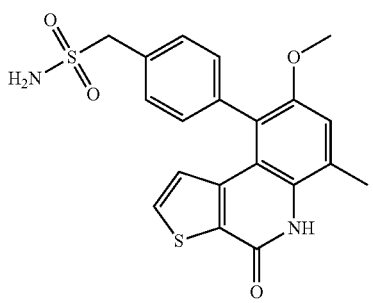 [SMILES: COc1cc(C)c2[nH]c(=O)c3sccc3c2c1-c1ccc(CS(N)(=O)=O)cc1] | (4-(8-methoxy-6-methyl-4-oxo-4,5-dihydrothieno[2,3-c]quinolin-9-yl)phenyl)methanesulfonamide |
| 1396 | 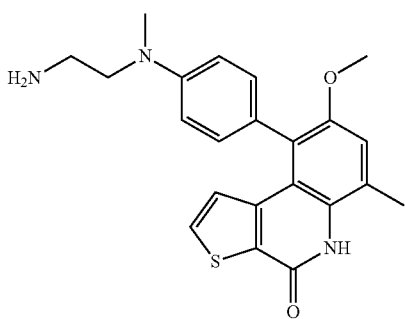 [SMILES: COc1cc(C)c2[nH]c(=O)c3sccc3c2c1-c1ccc(N(C)CCN)cc1] | 9-(4-((2-aminoethyl)(methyl)amino)phenyl)-8-methoxy-6-methylthieno[2,3-c]quinolin-4(5H)-one |
| 1397 | 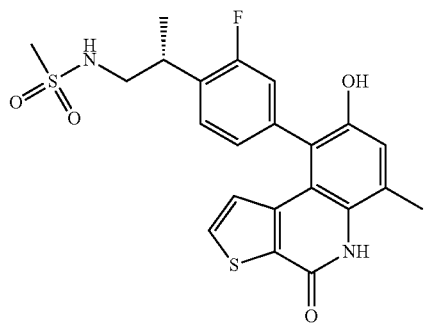 [SMILES: Cc1cc(O)c(-c2ccc([C@@H](C)CNS(C)(=O)=O)c(F)c2)c2c1[nH]c(=O)c1sccc12] | (R)-N-(2-(2-fluoro-4-(8-hydroxy-6-methyl-4-oxo-4,5-dihydrothieno[2,3-c]quinolin-9-yl)phenyl)propyl)methanesulfonamide |

TABLE 1-continued

| | | |
|---|---|---|
| 1398 | 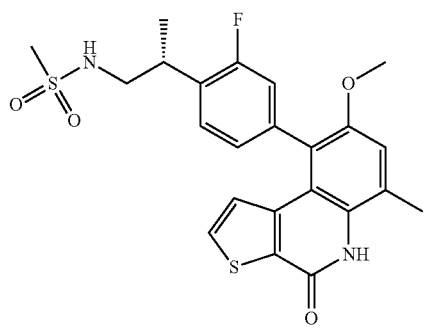 [SMILES: COc1cc(C)c2[nH]c(=O)c3sccc3c2c1-c1ccc([C@@H](C)CNS(C)(=O)=O)c(F)c1] | (R)-N-(2-(2-fluoro-4-(8-methoxy-6-methyl-4-oxo-4,5-dihydrothieno[2,3-c]quinolin-9-yl)phenyl)propyl)methanesulfonamide |
| 1399 | 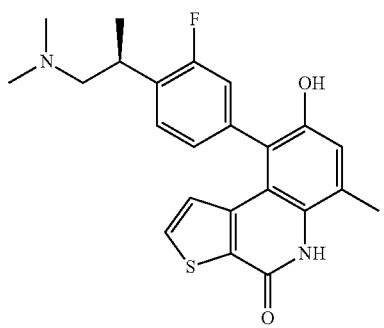 | (S)-9-(4-(1-(dimethylamino)propan-2-yl)-3-fluorophenyl)-8-hydroxy-6-methylthieno[2,3-c]quinolin-4(5H)-one |
| 1400 | 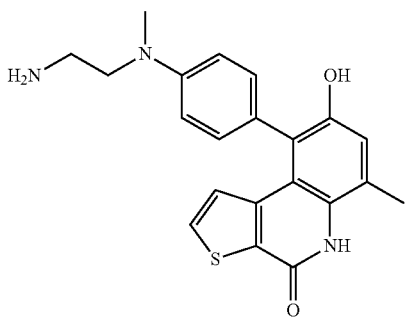 [SMILES: Cc1cc(O)c(-c2ccc(N(C)CCN)cc2)c2c1[nH]c(=O)c1sccc12] | 9-(4-((2-aminoethyl)(methyl)amino)phenyl)-8-hydroxy-6-methylthieno[2,3-c]quinolin-4(5H)-one |
| 1401 | 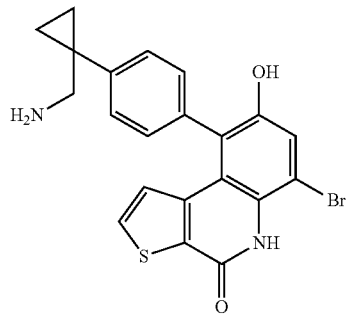 [SMILES: NCC1(c2ccc(-c3c(O)cc(Br)c4[nH]c(=O)c5sccc5c34)cc2)CC1] | 9-(4-(1-(aminomethyl)cyclopropyl)phenyl)-6-bromo-8-hydroxythieno[2,3-c]quinolin-4(5H)-one |
| 1402 | 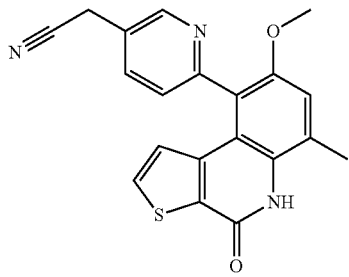 [SMILES: COc1cc(C)c2[nH]c(=O)c3sccc3c2c1-c1ccc(CC#N)cn1] | 2-(6-(8-methoxy-6-methyl-4-oxo-4,5-dihydrothieno[2,3-c]quinolin-9-yl)pyridin-3-yl)acetonitrile |

TABLE 1-continued
| | | |
|---|---|---|
| 1403 | 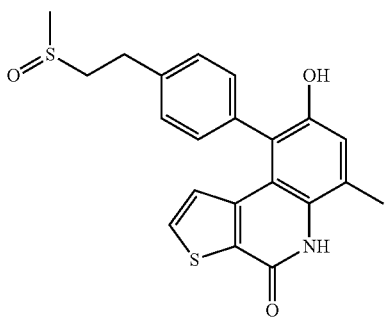 [SMILES: Cc1cc(O)c(-c2ccc(CCS(C)=O)cc2)c2c1[nH]c(=O)c1sccc12] | 8-hydroxy-6-methyl-9-(4-(2-(methylsulfinyl)ethyl)phenyl)thieno[2,3-c]quinolin-4(5H)-one |
| 1404 | 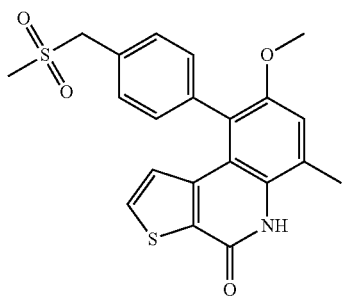 | 8-methoxy-6-methyl-9-(4-((methylsulfonyl)methyl)phenyl)thieno[2,3-c]quinolin-4(5H)-one |
| 1405 | 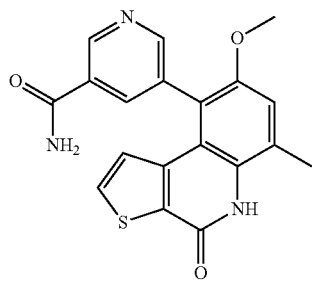 [SMILES: COc1cc(C)c2[nH]c(=O)c3sccc3c2c1-c1cncc(C(N)=O)c1] | 5-(8-methoxy-6-methyl-4-oxo-4,5-dihydrothieno[2,3-c]quinolin-9-yl)nicotinamide |
| 1406 | 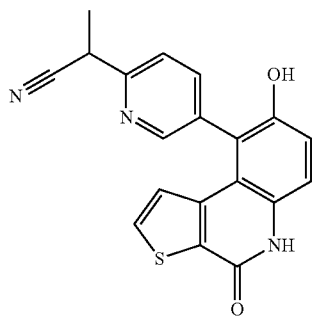 [SMILES: CC(C#N)c1ccc(-c2c(O)ccc3[nH]c(=O)c4sccc4c23)cn1] | 2-(5-(8-hydroxy-4-oxo-4,5-dihydrothieno[2,3-c]quinolin-9-yl)pyridin-2-yl)propanenitrile |
| 1407 | 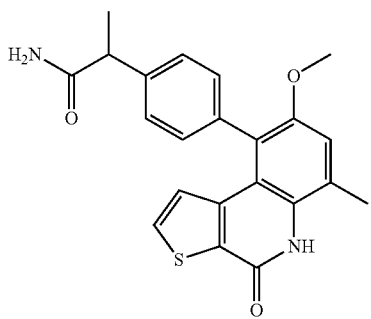 [SMILES: COc1cc(C)c2[nH]c(=O)c3sccc3c2c1-c1ccc(C(C)C(N)=O)cc1] | 2-(4-(8-methoxy-6-methyl-4-oxo-4,5-dihydrothieno[2,3-c]quinolin-9-yl)phenyl)propanamide |

TABLE 1-continued

| | | |
|---|---|---|
| 1408 | | 9-(6-(1-aminopropan-2-yl)pyridin-3-yl)-8-methoxy-6-methylthieno[2,3-c]quinolin-4(5H)-one |
| 1409 | | 2-(5-(8-methoxy-6-methyl-4-oxo-4,5-dihydrothieno[2,3-c]quinolin-9-yl)pyridin-2-yl)-2-methylpropanenitrile |
| 1410 | | 2-hydroxy-2-(4-(8-hydroxy-4-oxo-4,5-dihydrothieno[2,3-c]quinolin-9-yl)phenyl)propane-1-sulfonamide |
| 1411 | | N-(tert-butyl)-2-hydroxy-2-(4-(8-methoxy-4-oxo-4,5-dihydrothieno[2,3-c]quinolin-9-yl)phenyl)propane-1-sulfonamide |
| 1412 | | 2-(4-(8-hydroxy-6-methyl-4-oxo-4,5-dihydrothieno[2,3-c]quinolin-9-yl)phenyl)propanamide |

TABLE 1-continued

| | | |
|---|---|---|
| 1413 | 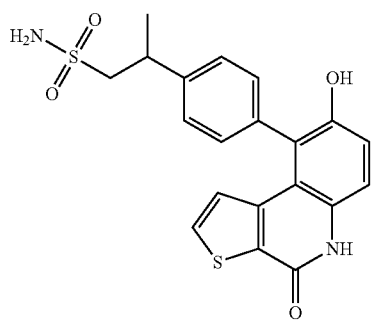 [SMILES: CC(CS(N)(=O)=O)c1ccc(-c2c(O)ccc3[nH]c(=O)c4sccc4c23)cc1] | 2-(4-(8-hydroxy-4-oxo-4,5-dihydrothieno[2,3-c]quinolin-9-yl)phenyl)propane-1-sulfonamide |
| 1414 | 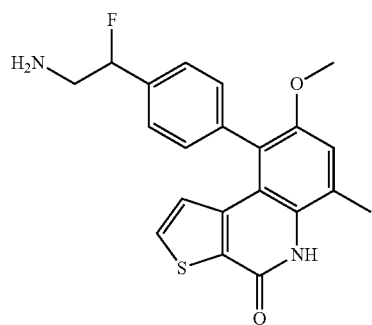 | 9-(4-(2-amino-1-fluoroethyl)phenyl)-8-methoxy-6-methylthieno[2,3-c]quinolin-4(5H)-one |
| 1415 | 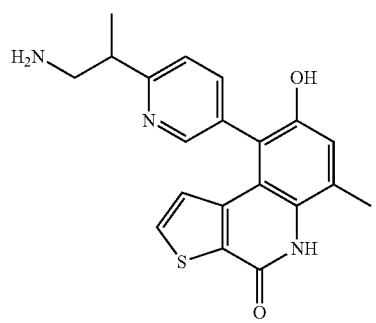 [SMILES: Cc1cc(O)c(-c2ccc(C(C)CN)nc2)c2c1[nH]c(=O)c1sccc12] | 9-(6-(1-aminopropan-2-yl)pyridin-3-yl)-8-hydroxy-6-methylthieno[2,3-c]quinolin-4(5H)-one |
| 1416 | 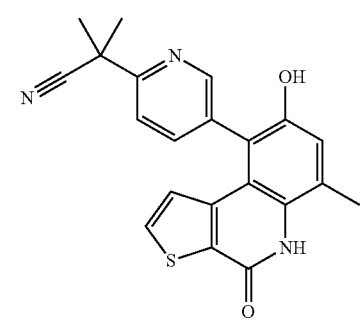 [SMILES: Cc1cc(O)c(-c2ccc(C(C)(C)C#N)nc2)c2c1[nH]c(=O)c1sccc12] | 2-(5-(8-hydroxy-6-methyl-4-oxo-4,5-dihydrothieno[2,3-c]quinolin-9-yl)pyridin-2-yl)-2-methylpropanenitrile |
| 1417 | 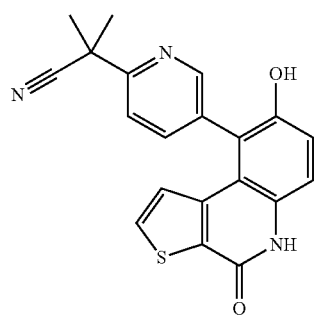 [SMILES: CC(C)(C#N)c1ccc(-c2c(O)ccc3[nH]c(=O)c4sccc4c23)cn1] | 2-(5-(8-hydroxy-4-oxo-4,5-dihydrothieno[2,3-c]quinolin-9-yl)pyridin-2-yl)-2-methylpropanenitrile |

TABLE 1-continued

| | | |
|---|---|---|
| 1418 | 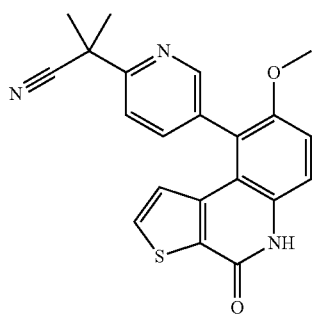 [SMILES: COc1ccc2[nH]c(=O)c3sccc3c2c1-c1ccc(C(C)(C)C#N)nc1] | 2-(5-(8-methoxy-4-oxo-4,5-dihydrothieno[2,3-c]quinolin-9-yl)pyridin-2-yl)-2-methylpropanenitrile |
| 1419 | 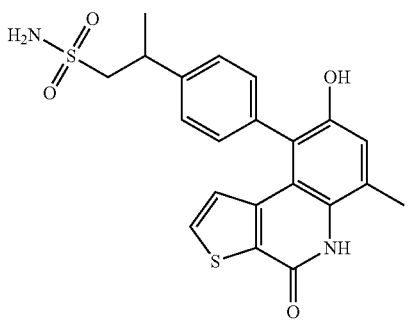 [SMILES: Cc1cc(O)c(-c2ccc(C(C)CS(N)(=O)=O)cc2)c2c1[nH]c(=O)c1sccc12] | 2-(4-(8-hydroxy-6-methyl-4-oxo-4,5-dihydrothieno[2,3-c]quinolin-9-yl)phenyl)propane-1-sulfonamide |
| 1420 | 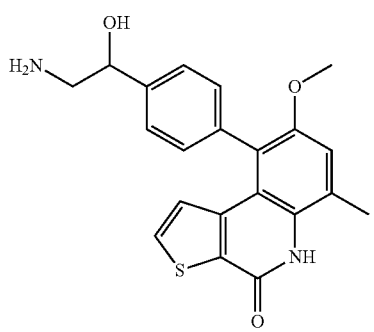 | 9-(4-(2-amino-1-hydroxyethyl)phenyl)-8-methoxy-6-methylthieno[2,3-c]quinolin-4(5H)-one |
| 1421 | 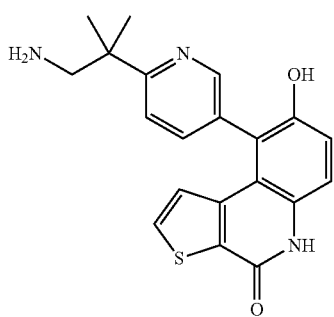 [SMILES: CC(C)(CN)c1ccc(-c2c(O)ccc3[nH]c(=O)c4sccc4c23)cn1] | 9-(6-(1-amino-2-methylpropan-2-yl)pyridin-3-yl)-8-hydroxythieno[2,3-c]quinolin-4(5H)-one |
| 1422 | 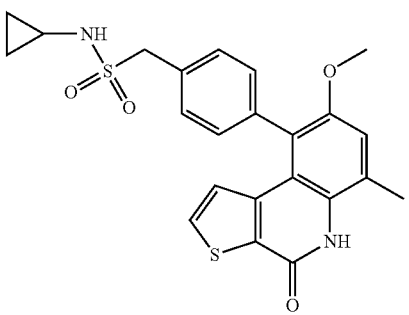 [SMILES: COc1cc(C)c2[nH]c(=O)c3sccc3c2c1-c1ccc(CS(=O)(=O)NC2CC2)cc1] | N-cyclopropyl-1-(4-(8-methoxy-6-methyl-4-oxo-4,5-dihydrothieno[2,3-c]quinolin-9-yl)phenyl)methanesulfonamide |

TABLE 1-continued

| | | |
|---|---|---|
| 1423 | 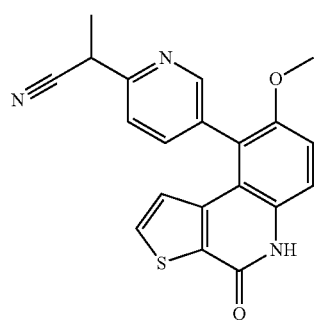 [SMILES: COc1ccc2[nH]c(=O)c3sccc3c2c1-c1ccc(C(C)C#N)nc1] | 2-(5-(8-methoxy-4-oxo-4,5-dihydrothieno[2,3-c]quinolin-9-yl)pyridin-2-yl)propanenitrile |
| 1424 | 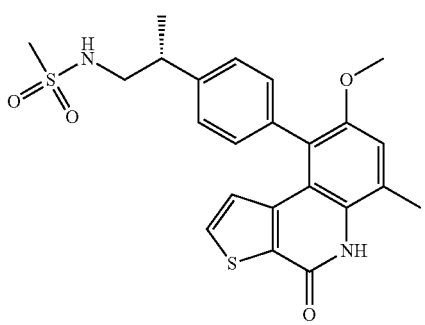 [SMILES: COc1cc(C)c2[nH]c(=O)c3sccc3c2c1-c1ccc([C@@H](C)CNS(C)(=O)=O)cc1] | (R)-N-(2-(4-(8-methoxy-6-methyl-4-oxo-4,5-dihydrothieno[2,3-c]quinolin-9-yl)phenyl)propyl)methanesulfonamide |
| 1425 | 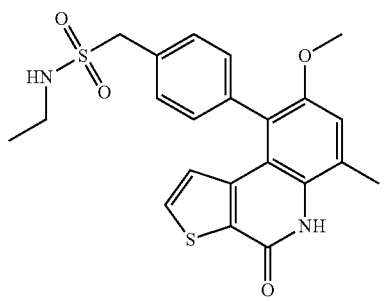 [SMILES: CCNS(=O)(=O)Cc1ccc(-c2c(OC)cc(C)c3[nH]c(=O)c4sccc4c23)cc1] | N-ethyl-1-(4-(8-methoxy-6-methyl-4-oxo-4,5-dihydrothieno[2,3-c]quinolin-9-yl)phenyl)methanesulfonamide |
| 1426 | 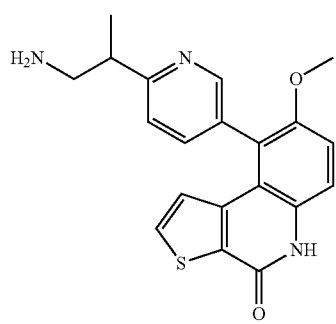 [SMILES: COc1ccc2[nH]c(=O)c3sccc3c2c1-c1ccc(C(C)CN)nc1] | 9-(6-(1-aminopropan-2-yl)pyridin-3-yl)-8-methoxythieno[2,3-c]quinolin-4(5H)-one |
| 1427 | 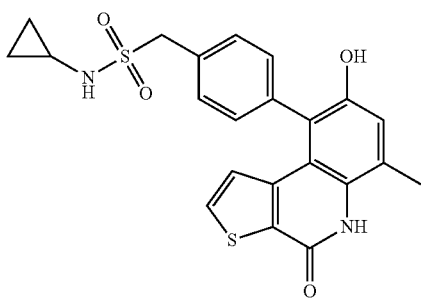 [SMILES: Cc1cc(O)c(-c2ccc(CS(=O)(=O)NC3CC3)cc2)c2c1[nH]c(=O)c1sccc12] | N-cyclopropyl-1-(4-(8-hydroxy-6-methyl-4-oxo-4,5-dihydrothieno[2,3-c]quinolin-9-yl)phenyl)methanesulfonamide |

TABLE 1-continued

| | | |
|---|---|---|
| 1428 | 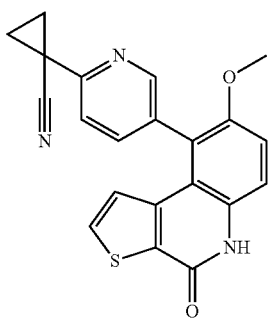 [SMILES: COc1ccc2[nH]c(=O)c3sccc3c2c1-c1ccc(C2(C#N)CC2)nc1] | 1-(5-(8-methoxy-4-oxo-4,5-dihydrothieno[2,3-c]quinolin-9-yl)pyridin-2-yl)cyclopropanecarbonitrile |
| 1429 | 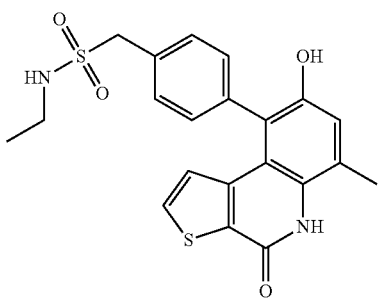 [SMILES: CCNS(=O)(=O)Cc1ccc(-c2c(O)cc(C)c3[nH]c(=O)c4sccc4c23)cc1] | N-ethyl-1-(4-(8-hydroxy-6-methyl-4-oxo-4,5-dihydrothieno[2,3-c]quinolin-9-yl)phenyl)methanesulfonamide |
| 1430 | 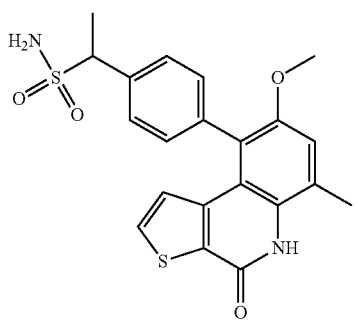 [SMILES: COc1cc(C)c2[nH]c(=O)c3sccc3c2c1-c1ccc(C(C)S(N)(=O)=O)cc1] | 1-(4-(8-methoxy-6-methyl-4-oxo-4,5-dihydrothieno[2,3-c]quinolin-9-yl)phenyl)ethanesulfonamide |
| 1431 | 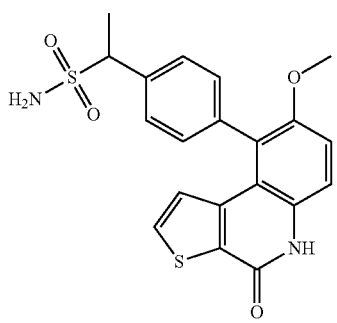 [SMILES: COc1ccc2[nH]c(=O)c3sccc3c2c1-c1ccc(C(C)S(N)(=O)=O)cc1] | 1-(4-(8-methoxy-4-oxo-4,5-dihydrothieno[2,3-c]quinolin-9-yl)phenyl)ethanesulfonamide |
| 1432 | 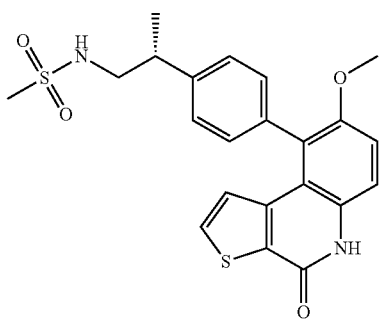 | (R)-N-(2-(4-(8-methoxy-4-oxo-4,5-dihydrothieno[2,3-c]quinolin-9-yl)phenyl)propyl)methanesulfonamide |

TABLE 1-continued

| 1433 | 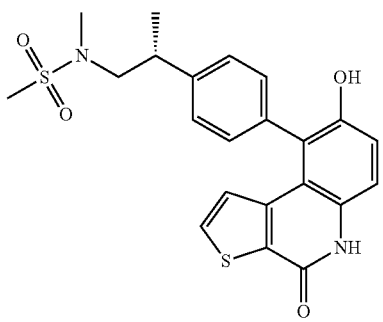 [SMILES: C[C@@H](CN(C)S(C)(=O)=O)c1ccc(-c2c(O)ccc3[nH]c(=O)c4sccc4c23)cc1] | (R)-N-(2-(4-(8-hydroxy-4-oxo-4,5-dihydrothieno[2,3-c]quinolin-9-yl)phenyl)propyl)-N-methylmethanesulfonamide |
| 1434 | 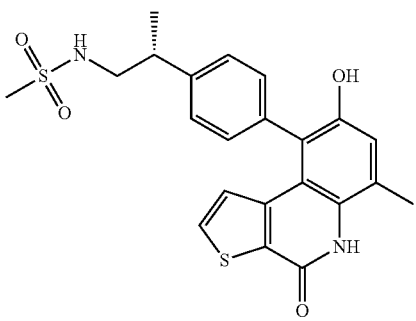 | (R)-N-(2-(4-(8-hydroxy-6-methyl-4-oxo-4,5-dihydrothieno[2,3-c]quinolin-9-yl)phenyl)propyl)methanesulfonamide |
| 1435 | 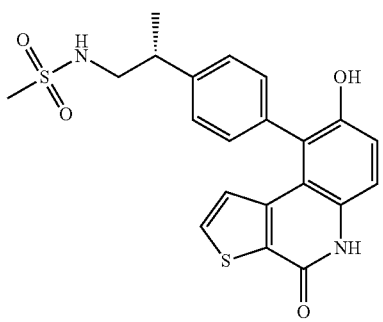 [SMILES: C[C@@H](CNS(C)(=O)=O)c1ccc(-c2c(O)ccc3[nH]c(=O)c4sccc4c23)cc1] | (R)-N-(2-(4-(8-hydroxy-4-oxo-4,5-dihydrothieno[2,3-c]quinolin-9-yl)phenyl)propyl)methanesulfonamide |
| 1436 | 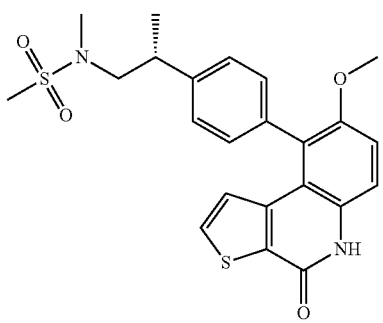 | (R)-N-(2-(4-(8-methoxy-4-oxo-4,5-dihydrothieno[2,3-c]quinolin-9-yl)phenyl)propyl)-N-methylmethanesulfonamide |
| 1437 | 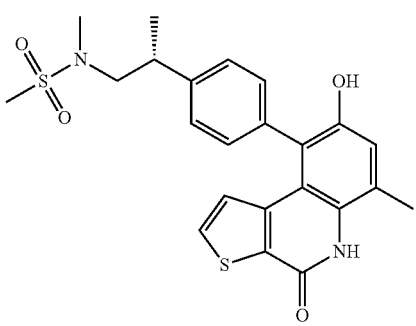 | (R)-N-(2-(4-(8-hydroxy-6-methyl-4-oxo-4,5-dihydrothieno[2,3-c]quinolin-9-yl)phenyl)propyl)-N-methylmethanesulfonamide |

TABLE 1-continued

| | | |
|---|---|---|
| 1438 | 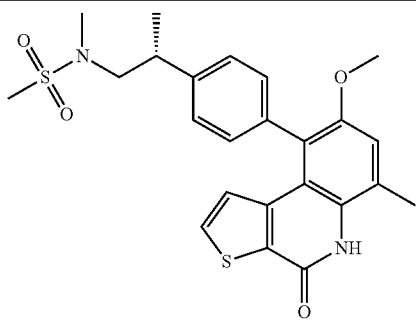 | (R)-N-(2-(4-(8-methoxy-6-methyl-4-oxo-4,5-dihydrothieno[2,3-c]quinolin-9-yl)phenyl)propyl)-N-methylmethanesulfonamide |

The compound of formula (I) of the present invention may be in the form of a pharmaceutically acceptable salt derived from an inorganic or organic acid. Representative examples of the pharmaceutically acceptable salt derived from an inorganic or organic acid include salts obtained by adding to the compound of formula (I) an inorganic acid including, but not limited to hydrochloric acid, hydrobromic acid, phosphoric acid or sulfonic acid, or organic carboxylic acids such as acetic acid, trifluoroacetic acid, citric acid, formic acid, maleic acid, oxalic acid, succinic acid, benzoic acid, tartaric acid, fumaric acid, mandelic acid, ascorbic acid or malic acid, methanesulfonic acid, or para toluenesulfonic acid, which do not limit its scope. Such acids may be prepared by the conventional processes, and other acids, which themselves are not pharmaceutically acceptable, including oxalic acid may be employed in the preparation of the salts.

Alternatively, the compound of formula (I) of the present invention may also be in the form of a pharmaceutically acceptable salt derived from an inorganic or organic base include salts obtained by adding an inorganic or organic base. For example, alkalis including sodium hydroxide or potassium hydroxide, or alkaline earth metal hydroxides including calcium hydroxide, magnesium hydroxide, aluminum hydroxide or ammonium hydroxide may be used for the preparation of inorganic salt of the compound. Further, organic bases including triethylamine or diisopropylethylamine may also be used for the preparation of organic salt of the compound.

The compounds of formula (I) may be prepared as in Scheme (I) and (II).

Scheme (I)

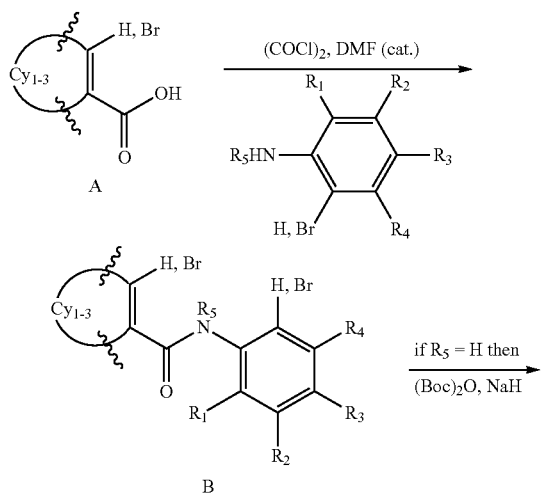

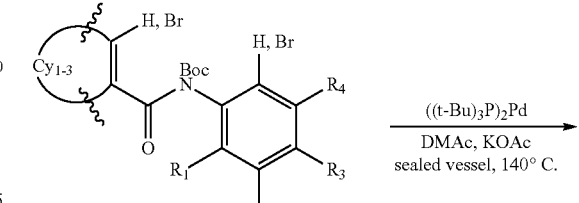

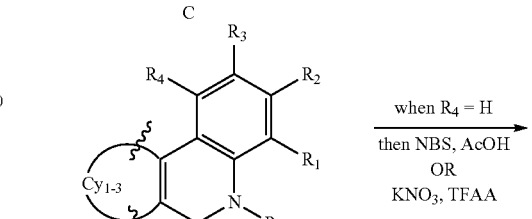

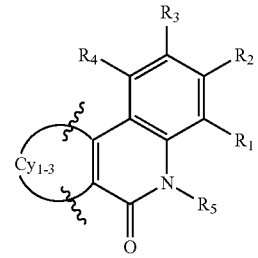

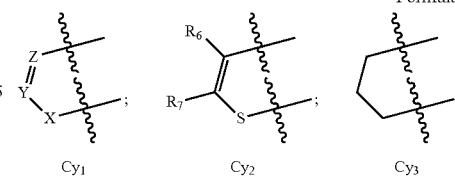

A variety of acids A whose structure is defined by the cycles (Cy$_{1-3}$) shown in Scheme I, were converted to the corresponding acid chloride and then coupled with the requisite aniline to afford coupled products B. In the case where R$_5$=H, the amide was protected to obtain intermediates C which subsequently underwent the key intramolecular Heck cyclization using bis-tri-t-butyl phosphine as the catalyst of choice. This provided tricycles D which included some compounds of Formula I, II and III. In some instances tricycles D were brominated using NBS or nitrated using potassium nitrate and trifluoroacetic anhydride to provide products E (Scheme I).

pounds were treated with boron tribromide or aluminum chloride to provide the de-methylated compounds I. Finally, compounds with $R_1$=Br were reacted with trimethylboroxine and palladium catalyst to afford compounds J of formula I, II

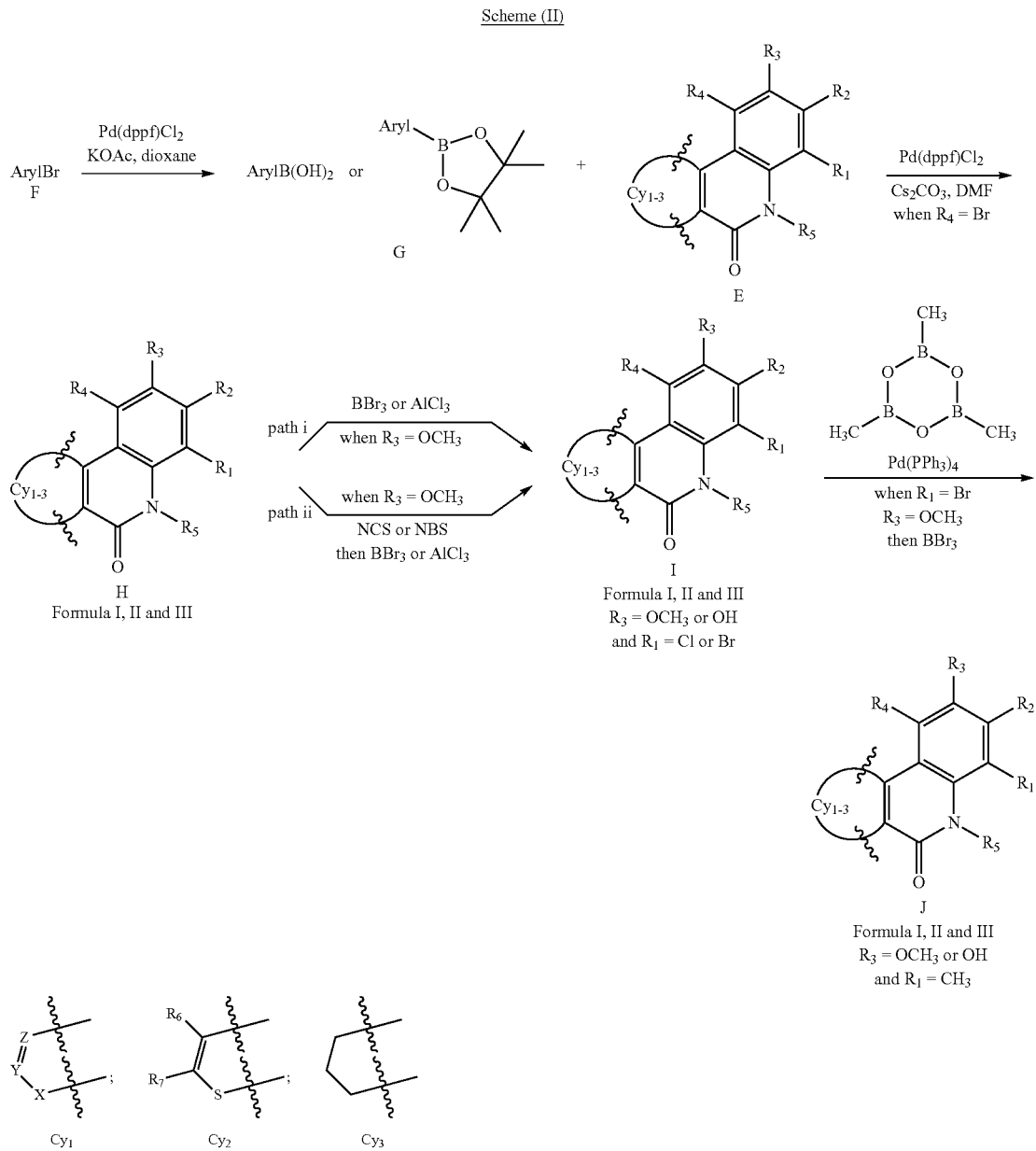

The aryl bromides F were either purchased or prepared and then converted to the corresponding boronic acids or boronate esters G via standard conditions. Bromides E underwent Suzuki or Buchwald type cross-coupling reactions with the requisite boronate esters or boronic acids G to afford compounds H some of which are compounds of Formula I, II and III. In cases where $R_3$=OCH$_3$, treatment of compounds H (via path i) with boron tribromide or aluminum chloride provided the de-methylated compounds I which includes compounds of Formula I, II and III (Scheme II). Additionally, treatment of compounds H (via path ii) with NCS or NBS afforded compounds I containing a halogen at $R_1$. These halogenated compounds were treated with boron tribromide afforded compounds of formula I, II and III where $R_1$=CH$_3$. Treatment of these compounds with boron tribromide afforded compounds of formula I, II and III.

A salt, hydrate, solvate and isomer of the inventive compound of formula (I) or (II) may be prepared by employing any of the known methods. The inventive compound of formula (I) or (II), or a salt, hydrate, solvate or isomer thereof, may be used for the treatment of PBK-dependent diseases such as cancer. The treatment of PBK-dependent diseases can be accomplished by way of inhibiting PBK activity. The inventive compound typically have an IC$_{50}$ value (micro M) in the range of 0.0001 to 100, for example 0.001 to 50, preferably 0.001 to 10, more preferably 0.001 to 5.

Accordingly, the present invention includes a pharmaceutical composition that includes a therapeutically effective amount of the compound of formula (I) or (II), a salt, hydrate, solvate or isomer thereof as an active ingredient and a pharmaceutically acceptable carrier. The pharmaceutical composition of the present invention can be used to treat or prevent PBK-dependent diseases.

A pharmaceutical formulation may be prepared in accordance with any of the conventional procedures. In preparing the formulation, the active ingredient is preferably admixed or diluted with a carrier, or enclosed within a carrier, sachet or other container. The carrier may be a solid, semi-solid or liquid material acting as a vehicle, excipient or medium for the active ingredient. The formulations may be in the form of a tablet, pill, powder, sachet, elixir, suspension, emulsion, solution, syrup, aerosol, soft and hard gelatin capsule, sterile injectable solution, sterile packaged powder and the like.

Examples of suitable carriers, excipients, and diluents are lactose, dextrose, sucrose, sorbitol, mannitol, calcium silicate, cellulose, methyl cellulose, microcrystalline cellulose, polyvinylpyrrolidone, water, and mineral oil. The formulations may additionally include fillers, antiemulsifiers, preservatives and the like. The compositions of the invention may be formulated to provide immediate, sustained or delayed release of the active ingredient after their administration to a mammal by employing any of the procedures well known in the art.

The pharmaceutical composition of the present invention can be administered via various routes including oral, transdermal, subcutaneous, intravenous and intramuscular administration.

In addition to the above, the present composition may contain other pharmaceutical active ingredients so long as they do not inhibit the in vivo function of the compound of the present invention. The compounds as disclosed herein can be co-administered with a second therapeutic agent, such as a chemotherapeutic agent. The term "co-administer" means to administer more than one active agent, such that the duration of physiological effect of one active agent overlaps with the physiological effect of a second active agent. For systematic agents, the term co-administer means that more than one active agent is present in the bloodstream during at least one time point. Co-administration includes administering two active agents simultaneously, approximately simultaneously, or sequentially in any order. In some embodiments, co-administration can be accomplished by co-formulation, i.e., preparing a single dosage unit including both active agents.

"Treating" the disease includes one or more of: addressing a physiological cause of the disease, addressing a physiological cause of a disease symptom, reducing the severity of the disease, ameliorating a symptom of the disease, and shortening the duration of the disease. "Preventing" the disease includes eliminating or delaying the onset of a disease or its symptoms.

The compounds disclosed herein can be used to treat or prevent PBK-dependent diseases, including cancer. It has been shown that PBK is a target for treating cancers, such as breast cancer (Example 504 of the present specification), bladder cancer (WO2006/085684), and small cell lung cancer (WO2007/013665). Accordingly, cancers to be targeted include, but are not limited to, breast cancer, bladder cancer, and small cell lung cancer. For example, the present invention provides methods for treating or preventing PBK-dependent diseases, including cancer, in a subject by administering to said subject the compounds disclosed herein.

In a preferred embodiment, such compound can be administered to the subject in the form of pharmaceutical composition including the compound of the present invention and pharmaceutically or physiologically acceptable carrier. The pharmaceutical composition of the present invention can be administered via various routes including oral, transdermal, subcutaneous, intravenous and intramuscular introduction for treating PBK dependent diseases, including cancer, in a subject.

In another embodiment, the present invention also provides the use of the compound of the present invention in manufacturing a pharmaceutical composition for treating a PBK dependent diseases including cancer. For example, the present invention relates to a use of the compound of the present invention for manufacturing a pharmaceutical composition for treating PBK dependent diseases, including cancer. In another embodiment, the compounds of the present invention can be used in treating PBK dependent diseases, including cancer.

In another embodiment, the present invention also provides a method or process for manufacturing a pharmaceutical composition for treating a PBK dependent diseases including cancer, wherein the method or process includes a step for admixing an active ingredient with a pharmaceutically or physiologically acceptable carrier, wherein the active ingredient is the compound of the present invention.

The dosage and method of administration vary according to the body weight, age, and symptoms of the patient; however, one skilled in the art can suitably select them.

For example, the dose is generally about 0.1 mg to about 100 mg per day, preferably about 1.0 mg to about 50 mg per day and more preferably about 1.0 mg to about 20 mg per day, when administered orally to a normal adult human (weight 60 kg).

When administering the compound parenterally, in the form of an injection to a normal adult human (weight 60 kg), although there are some differences according to the patient, target organ, symptoms and method of administration, it is convenient to intravenously inject a dose of about 0.01 mg to about 30 mg per day, preferably about 0.1 to about 20 mg per day and more preferably about 0.1 to about 10 mg per day. In the case of other animals, the appropriate dosage amount may be routinely calculated by converting to 60 kg of body weight.

EXAMPLES

The following examples are intended to further illustrate the present invention without limiting its scope.

General Procedure A (Scheme I):

Step 1: To a suspension of the requisite carboxylic acid A (1 mol) in $CH_2Cl_2$ (0.1-0.5 M) at room temperature was added $(COCl)_2$ (2 mol) followed by the addition of catalytic DMF. The reaction mixture was stirred at room temperature for 18 h, concentrated and dried under high vacuum to obtain the intermediate acid chloride. The acid chloride was dissolved in $CH_2Cl_2$ (0.1-0.3 M) followed by the addition of $Et_3N$ (1.5-2 mol) and the requisite aniline (1.1 mol) and the reaction was stirred at room temperature for 18 h. The reaction mixture was concentrated, triturated with an appropriate solvent or purified by flash chromatography to obtain amide B as a solid.

Step 2: To a solution of amide B (1 mol) in THF (0.1-0.3 M) at 0° C. was added NaH (1.2 mol) and the reaction was warmed up to 45° C. for 15 min and cooled to 0° C. followed by the addition of $(Boc)_2O$ (2 mol). The reaction mixture was warmed to room temperature and stirred for 18 h. The reaction mixture was quenched by slowly pouring it into a stirred solution of water and satd aq $NaHCO_3$ at 0° C. The mixture was extracted with ethyl acetate and the combined organic layers were washed with brine, dried over $Na_2SO_4$ and concentrated. The residue was triturated with an appropriate solvent or purified by flash chromatography to obtain C as a solid.

Step 3: Intermediate C (1 mol), bis(tri-tert-butylphosphine) palladium (5 mol %) and potassium acetate (4 mol) were added to a Parr pressure reactor followed by the addition of dimethyl acetamide (0.3 M). The reaction mixture was sparged with nitrogen for 30 min followed by heating at 140-150° C. for 4 h. The reaction mixture was cooled and quenched by pouring into brine at 0° C. The resulting precipitate was filtered and the filter cake was washed with water and ether to obtain crude D as a solid.

Step 4: To a solution of crude D (1 mol) in $CH_2Cl_2$:AcOH (1:1) was added NBS (1 mol) and the reaction mixture was stirred at room temperature for 18 h. The reaction mixture was quenched by pouring slowly into a stirred solution of ice and satd aq $Na_2CO_3$. Once the aqueous layer was at pH 8 the layers were separated and the $CH_2Cl_2$ layer was concentrated, triturated with acetonitrile and filtered to obtain E as solid.

Example 392

4-(tert-Butyldimethylsilyloxy)aniline

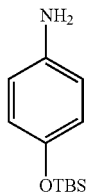

To a solution of 4-aminophenol (11 g, 100 mmol) and imidazole (10 g, 150 mmol) in THF (250 mL) was added tert-butyldimethylsilyl chloride (18 g, 120 mmol) and the reaction was stirred at room temperature for 18 h. The reaction mixture was poured into water and extracted with diethyl ether. The combined organic layers were dried over $Na_2SO_4$, filtered, concentrated and the residue was purified by column chromatography to afford the desired product (15 g, 67%): ESI MS m/z 224 $[C_{12}H_{21}NOSi+H]^+$.

Example 393

3-Bromo-N-[4-(tert-butyldimethylsilyloxy)phenyl]thiophene-2-carboxamide

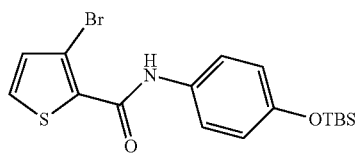 [SMILES: CC(C)(C)[Si](C)(C)Oc1ccc(NC(=O)c2sccc2Br)cc1]

Following Step 1 from General Procedure A, 5-bromothiophene-2-carboxylic acid (3.0 g, 14 mmol) was reacted with 4-(tert-butyldimethylsilyloxy)aniline (4.2 g, 19 mmol) to afford the desired product (4.4 g, 73%) as a solid: ESI MS m/z 413 $[C_{17}H_{22}BrNO_2SSi+H]^+$.

Example 394 tert-Butyl 3-Bromothiophene-2-carbonyl[4-(tert-butyldimethylsilyloxy)phenyl]carbamate

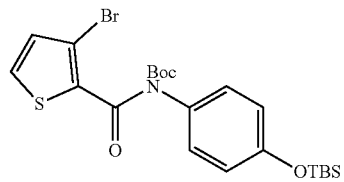 [SMILES: CC(C)(C)OC(=O)N(C(=O)c1sccc1Br)c1ccc(O[Si](C)(C)C(C)(C)C)cc1]

Following Step 2 from General Procedure A, 3-bromo-N-[4-(tert-butyldimethylsilyloxy)phenyl]thiophene-2-carboxamide (4.4 g, 11 mmol) was reacted with di-tert-butyl dicarbonate (4.6 g, 21 mmol) to afford the desired product (1.5 g, 28%) as a solid: ESI MS m/z 513 $[C_{22}H_{30}BrNO_4SSi+H]^+$.

Example 395

8-(tert-Butyldimethylsilyloxy)thieno[2,3-c]quinolin-4(5H)-one

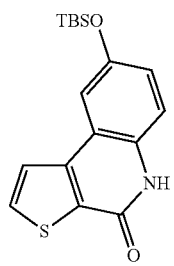 [SMILES: CC(C)(C)[Si](C)(C)Oc1ccc2[nH]c(=O)c3sccc3c2c1]

Following Step 3 from General Procedure A, tert-butyl 3-bromothiophene-2-carbonyl[4-(tert-butyldimethylsilyloxy)phenyl]carbamate (1.0 g, 2.0 mmol) was reacted with bis(tri-tert-butylphosphine)palladium (50 mg, 0.098 mmol) to afford the desired product (740 mg, quant.) as a solid: ESI MS m/z 332 $[C_{17}H_{21}NO_2SSi+H]^+$.

Example 396

9-Bromo-8-(tert-butyldimethylsilyloxy)thieno[2,3-c]quinolin-4(5H)-one

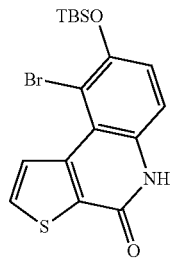 [SMILES: CC(C)(C)[Si](C)(C)Oc1ccc2[nH]c(=O)c3sccc3c2c1Br]

Following Step 4 from General Procedure A, 8-(tert-butyldimethylsilyloxy)thieno[2,3-c]quinolin-4(5H)-one (740 mg, 2.2 mmol) was reacted with N-bromosuccinimide (480 mg, 2.7 mmol) to afford the desired product (340 mg, 37%) as a brown solid: ESI MS m/z 411 [C$_{17}$H$_{20}$BrNO$_2$SSi+H]$^+$.

Example 397

N-(2-Bromo-4-methoxyphenyl)-5-methyl-N-(5-methylthiophene-2-carbonyl)thiophene-2-carboxamide

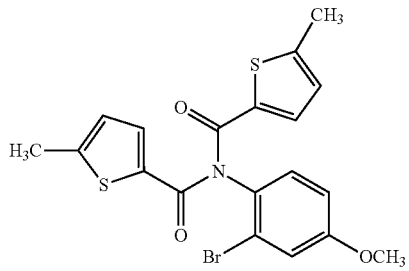 [SMILES: COc1ccc(N(C(=O)c2ccc(C)s2)C(=O)c2ccc(C)s2)c(Br)c1]

Following Step 1 from General Procedure A, 5-methylthiophene-2-carboxylic acid (8.5 g, 60 mmol) was reacted with 2-bromo-4-methoxyaniline (6.7 g, 30 mmol) to afford the desired product (5.0 g, 57%) as a solid: ESI MS m/z 327 [C$_{13}$H$_{12}$BrNO$_2$S+H]$^+$.

Example 398

8-Methoxy-2-methylthieno[2,3-c]quinolin-4(5H)-one

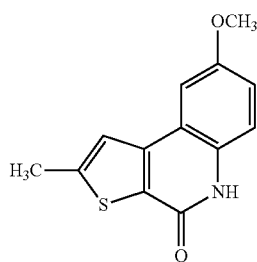 [SMILES: COc1ccc2[nH]c(=O)c3sc(C)cc3c2c1]

Following Step 3 from General Procedure A, N-(2-bromo-4-methoxyphenyl)-5-methyl-N-(5-methylthiophene-2-carbonyl)thiophene-2-carboxamide (500 mg, 1.1 mmol) was reacted with bis(tri-tert-butylphosphine)palladium (45 mg, 0.089 mmol) to afford the desired product (1.3 g, 48%) as a green solid: ESI MS m/z 246 [C$_{13}$H$_{11}$NO$_2$S+H]$^+$.

Example 399

9-Bromo-8-methoxy-2-methylthieno[2,3-c]quinolin-4(5H)-one

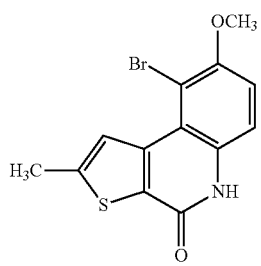 [SMILES: COc1ccc2[nH]c(=O)c3sc(C)cc3c2c1Br]

Following Step 4 from General Procedure A, 8-methoxy-2-methylthieno[2,3-c]quinolin-4(5H)-one (1.4 g, 5.7 mmol) was reacted with N-bromosuccinimide (1.2 g, 6.9 mmol) to afford the desired product (740 mg, 40%) as a brown solid: ESI MS m/z 325 [C$_{13}$H$_{10}$BrNO$_2$S+H]$^+$.

Example 400

3-bromo-N-(2-fluoro-4-methoxyphenyl)thiophene-2-carboxamide

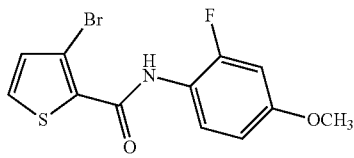 [SMILES: COc1ccc(NC(=O)c2sccc2Br)c(F)c1]

Following Step 1 from General Procedure A, 3-bromothiophene-2-carboxylic acid (7.3 g, 35 mmol) was reacted with 2-fluoro-4-methoxyaniline (5.0 g, 35 mmol) to afford the desired product (10 g, 90%) as an orange solid: ESI MS m/z 331 [C$_{12}$H$_1$FNO$_2$S+H]$^+$.

Example 401 tert-butyl 3-bromothiophene-2-carbonyl(2-fluoro-4-methoxyphenyl)carbamate

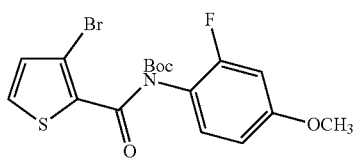 [SMILES: COc1ccc(N(C(=O)OC(C)(C)C)C(=O)c2sccc2Br)c(F)c1]

Following Step 2 from General Procedure A, 3-bromo-N-(2-fluoro-4-methoxyphenyl)thiophene-2-carboxamide (12 g, 35 mmol) was reacted with di-tert-butyl dicarbonate (12 g, 53 mmol) to afford the desired product (14 g, >99%) as an orange solid: ESI MS m/z 331 [C$_{12}$H$_{10}$FNO$_2$S+H]$^+$.

Example 402

6-Fluoro-8-methoxythieno[2,3-c]quinolin-4(5H)-one

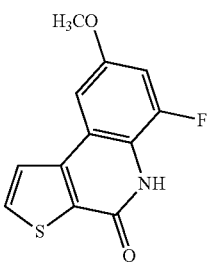 [SMILES: COc1cc(F)c2[nH]c(=O)c3sccc3c2c1]

Following Step 3 from General Procedure A, tert-butyl 3-bromothiophene-2-carbonyl(2-fluoro-4-methoxyphenyl)carbamate (2.0 g, 4.6 mmol) was reacted with bis(tri-tert-butylphosphine)palladium (100 mg, 0.20 mmol) to afford the desired product (950 mg, 80%) as a dark brown solid: ESI MS m/z 250 [C$_{12}$H$_8$FNO$_2$S+H]$^+$.

Example 403

9-Bromo-6-fluoro-8-methoxythieno[2,3-c]quinolin-4 (5H)-one

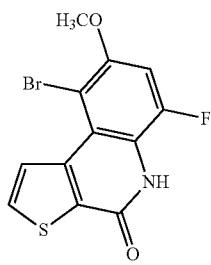 [SMILES: COc1cc(F)c2[nH]c(=O)c3sccc3c2c1Br]

Following Step 4 from General Procedure A, 6-fluoro-8-methoxythieno[2,3-c]quinolin-4(5H)-one (1.0 g, 4.0 mmol) was reacted with N-bromosuccinimide (570 mg, 4.8 mmol) to afford the desired product (800 mg, 61%) as a brown solid: ESI MS m/z 329 $[C_{12}H_7BrFNO_2S+H]^+$.

Example 404

3-Bromo-N-(2,3-difluoro-4-methoxyphenyl) thiophene-2-carboxamide

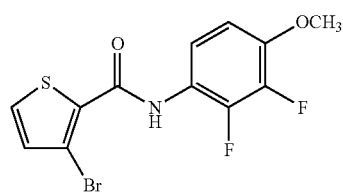 [SMILES: COc1ccc(NC(=O)c2sccc2Br)c(F)c1F]

Following Step 1 from General Procedure A, 3-bromothiophene-2-carboxylic acid (1.3 g, 6.3 mmol) was reacted with 2,3-difluoro-4-methoxyaniline (960 mg, 7.5 mmol) to afford the desired product (2.2 g, >99%): ESI MS m/z 349 $[C_{12}H_8BrF_2NO_2S+H]^+$.

Example 405 tert-Butyl 3-Bromothiophene-2-carbonyl(2,3-difluoro-4-methoxyphenyl)carbamate

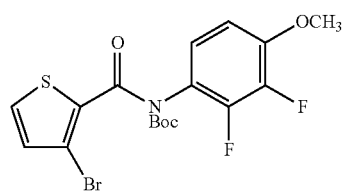 [SMILES: COc1ccc(N(C(=O)OC(C)(C)C)C(=O)c2sccc2Br)c(F)c1F]

Following Step 2 from General Procedure A, 3-bromo-N-(2,3-difluoro-4-methoxyphenyl)thiophene-2-carboxamide (2.4 g, 7.00 mmol) was reacted with di-tert-butyl dicarbonate (330 mg, 14 mmol) to afford the desired product (2.1 g, 67%) as a white solid: ESI MS m/z 448 $[C_{17}H_{16}BrF_2NO_4S+H]^+$.

Example 406

6,7-Difluoro-8-methoxythieno[2,3-c]quinolin-4(5H)-one

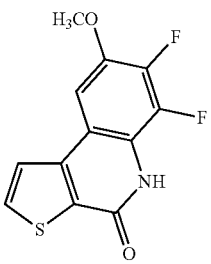 [SMILES: COc1cc2c([nH]c(=O)c3sccc32)c(F)c1F]

Following Step 3 from General Procedure A, tert-butyl 3-bromothiophene-2-carbonyl(2,3-difluoro-4-methoxyphenyl)carbamate (1.4 g, 3.1 mmol) was reacted with bis(tri-tert-butylphosphine)palladium (80 mg, 0.15 mmol) to afford the desired product (58 mg, 65%) as a brown solid: ESI MS m/z 268 $[C_{12}H_7F_2NO_2S+H]^+$.

Example 407

9-Bromo-6,7-difluoro-8-methoxythieno[2,3-c]quinolin-4(5H)-one

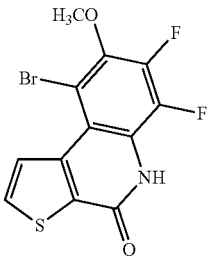 [SMILES: COc1c(F)c(F)c2[nH]c(=O)c3sccc3c2c1Br]

Following Step 4 from General Procedure A, 6,7-difluoro-8-methoxythieno[2,3-c]quinolin-4(5H)-one (300 mg, 1.1 mmol) was reacted with N-bromosuccinimide (400 mg, 2.2 mmol) to afford the desired product (200 mg, 57%) as a yellow solid: ESI MS m/z 347 $[C_{12}H_6BrF_2NO_2S+H]^+$.

Example 510

3-bromo-N-(4-methoxy-2-methylphenyl)thiophene-2-carboxamide

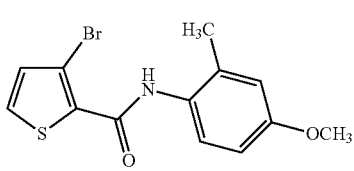 [SMILES: COc1ccc(NC(=O)c2sccc2Br)c(C)c1]

Following Step 1 from General Procedure A, 3-bromothiophene-2-carboxylic acid (6.7 g, 49 mol) was reacted with 2-methyl-4-methoxyaniline (12 g, 53 mmol) to afford the desired product (13 g, 80%) as an orange solid: ESI MS m/z 331 $[C_{12}H_{10}FNO_2S+H]^+$.

Example 511 tert-butyl 3-bromothiophene-2-carbonyl(4-methoxy-2-methylphenyl)carbamate

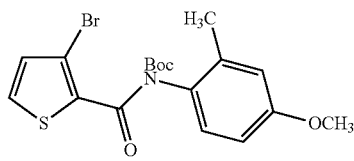 [SMILES: COc1ccc(N(C(=O)OC(C)(C)C)C(=O)c2sccc2Br)c(C)c1]

Following Step 2 from General Procedure A, 3-bromo-N-(4-methoxy-2-methylphenyl)thiophene-2-carboxamide (12 g, 37 mmol) was reacted with di-tert-butyl dicarbonate (9.6 g, 44 mmol) to afford the desired product (15 g, 96%) as an orange solid: ESI MS m/z 331 $[C_{12}H_{10}FNO_2S+H]^+$.

Example 512

8-methoxy-6-methylthieno[2,3-c]quinolin-4(5H)-one

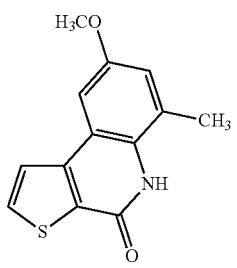 [SMILES: COc1cc(C)c2[nH]c(=O)c3sccc3c2c1]

Following Step 3 from General Procedure A, tert-butyl 3-bromothiophene-2-carbonyl(4-methoxy-2-methylphenyl)carbamate (14 g, 33 mmol) was reacted with bis(tri-tert-butylphosphine)palladium (750 mg, 1.5 mmol) to afford the desired product (7.0 g, 85%) as a dark brown solid: ESI MS m/z 250 $[C_{12}H_8FNO_2S+H]^+$.

Example 513

9-bromo-8-methoxy-6-methylthieno[2,3-c]quinolin-4(5H)-one

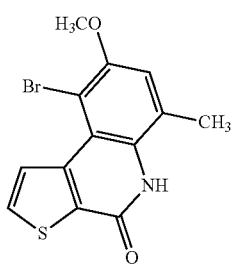 [SMILES: COc1cc(C)c2[nH]c(=O)c3sccc3c2c1Br]

Following Step 4 from General Procedure A, 8-methoxy-6-methylthieno[2,3-c]quinolin-4(5H)-one (6.4 g, 26 mmol) was reacted with N-bromosuccinimide (5.0 g, 26 mmol) to afford the desired product (7.0 g, 82%) as a brown solid: ESI MS m/z 329 $[C_{12}H_7BrFNO_2S+H]^+$.

Example 514

3-Bromo-N-(4-methoxyphenyl)thiophene-2-carboxamide

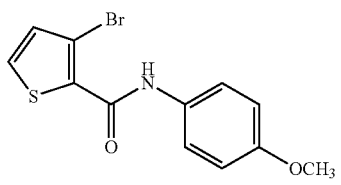

Following Step 1 from General Procedure A, 5-bromothiophene-2-carboxylic acid (75 g, 360 mmol) was reacted with 4-methoxyaniline (54 g, 430 mmol) to afford the desired product (110 g, 93%) as a solid: ESI MS m/z 313 $[C_{12}H_{10}BrNO_2S+H]^+$.

Example 515 tert-Butyl 3-bromothiophene-2-carbonyl(4-methoxyphenyl)carbamate

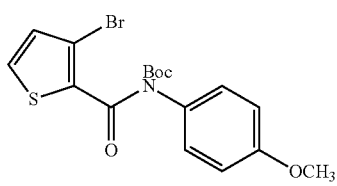 [SMILES: COc1ccc(N(C(=O)OC(C)(C)C)C(=O)c2sccc2Br)cc1]

Following Step 2 from General Procedure A, 3-Bromo-N-(4-methoxyphenyl)thiophene-2-carboxamide (60 g, 190 mmol) was reacted with di-tert-butyl dicarbonate (83 g, 380 mmol) to afford the desired product (65 g, 82%) as a solid: ESI MS m/z 413 $[C_{17}H_{18}BrNO_4S+H]^+$.

Example 516

8-Methoxythieno[2,3-c]quinolin-4(5H)-one

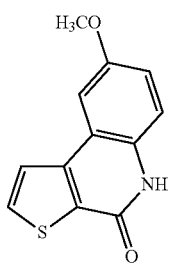

Following Step 3 from General Procedure A, tert-butyl 3-bromothiophene-2-carbonyl(4-methoxyphenyl)carbamate (62 g, 150 mmol) was reacted with bis(tri-tert-butylphosphine) palladium (3.7 g, 5 mol %) to afford the crude desired product (26 g) as a grey-brown solid: ESI MS m/z 232 $[C_2H_9NO_2S+H]^+$.

Example 517

9-Bromo-8-methoxythieno[2,3-c]quinolin-4(5H)-one

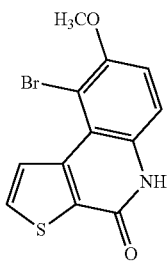 [SMILES: COc1ccc2[nH]c(=O)c3sccc3c2c1Br]

General Procedure B (Scheme II):

To a solution of bromides E (1 mmol) in DMF was added Cs$_2$CO$_3$ (3 mmol), Pd(dppf)Cl$_2$ (0.1 mmol) and boronate esters or acids G (1-2 mmol) and the reaction was heated at 80° C. for 18 h. The reaction mixture was cooled, concentrated and the residue was purified by column chromatography (silica, ethyl acetate/hexanes gradient) or preparatory HPLC (C18 silica, acetonitrile/water with 0.05% TFA gradient) to obtain the desired products H. In some instances the desired product was dissolved in aqueous HCl, concentrated and dried under high vacuum to afford the desired product as a hydrochloride salt.

General Procedure C (Scheme II):

The compound from General Procedure B (1 mmol) was dissolved in TFA (10 mmol) and stirred at room temperature for 2 h and concentrated. The residue was eluted through an ion-exchange column (using methanol and 7 N methanol in ammonia) to obtain the desired product as the free base. In some instances the desired product was dissolved in aqueous HCl, concentrated and dried under high vacuum to afford the desired product as a hydrochloride salt.

General Procedure D-1 (Scheme II):

The requisite compound (1 mmol) was dissolved in methanol followed by the addition of 2 N HCl in diethylether (100 mmol). The reaction mixture was stirred at room temperature for 2 h and filtered or concentrated to obtain the desired product as the hydrochloride salt.

General Procedure D-2 (Scheme II):

The requisite compound was dissolved in aqueous HCl, concentrated and dried under high vacuum to afford the desired product as a hydrochloride salt.

General Procedure D-3 (Scheme II):

The requisite compound (1 mmol) was dissolved in aqueous HCl (100 mmol) and stirred concentrated at room temperature for 2 h, concentrated and dried under high vacuum to afford the desired product as a hydrochloride salt.

General Procedure E—One Pot (Scheme II):

To a solution of aryl bromides F (1 mmol) in dioxane was added KOAc (2 mmol), Pd(dppf)Cl$_2$ (0.1 mmol) and bis(pinacolato)diboron (1.5 mmol) and the reaction was heated at 90° C. until the aryl bromide was consumed. To the reaction mixture was added Cs$_2$CO$_3$ (2 mmol) and bromides E (0.5 mmol) and heating was continued for 18 h. The reaction mixture was cooled, concentrated and purified by chromatography (silica, ethyl acetate/hexanes gradient) or preparatory HPLC (C18 silica, acetonitrile/water with 0.05% TFA gradient) to obtain the desired products I. In some instances the desired product was dissolved in aqueous HCl, concentrated and dried under high vacuum to afford the desired product as a hydrochloride salt.

General Procedure F (Scheme II):

To a solution or suspension of compounds H, I, or J (R$_3$=OCH$_3$) (1 mmol) in CH$_2$Cl$_2$ at 0° C. was added BBr$_3$ (6-10 mmol) and the reaction was warmed to room temperature for 18 h or until the starting material disappeared by LCMS analysis. The reaction was quenched by pouring onto ice-water and the resulting mixture was concentrated and purified by preparatory HPLC (C18 silica, acetonitrile/water (with 0.05% TFA) gradient). The desired fractions were combined, concentrated and eluted through an ion-exchange column (using methanol and 7 N methanol in ammonia) to obtain the desired product. In some instances the desired product was dissolved in aqueous HCl, concentrated and dried under high vacuum to afford the desired product as a hydrochloride salt.

General Procedure G (Scheme II):

To a solution of aryl bromides F (1 mmol) in dioxane was added KOAc (2 mmol), Pd(dppf)Cl$_2$ (0.1 mmol) and bis(pinacolato)diboron (1.5 mmol) and the reaction was heated at 90° C. for 18 h. The reaction mixture was cooled, concentrated and the residue was purified by column chromatography (silica, ethyl acetate/hexanes gradient) to obtain the desired product.

General Procedure H (Scheme II):

To a solution requisite compound H (1.0 mmol) in DMF was added N-chlorosuccinimide (1.2 mmol) and the reaction was stirred at room temperature for 30 min and heated at 60° C. for 2 h. The reaction mixture was concentrated and the residue purified by column chromatography (silica, 0-30% ethyl acetate/heptane) to afford the desired product I.

General Procedure I (Scheme II):

To a solution requisite compound H (1.0 mmol) in DMF was added N-bromosuccinimide (1.2 mmol) and the reaction was stirred at room temperature for 30 min and heated at 50° C. for 2 h. The reaction mixture was concentrated and the residue purified by column chromatography (silica, 0-30% ethyl acetate/heptane) to afford the desired product I.

General Procedure J (Scheme II):

To a solution requisite compound I (1.0 mmol) in toluene, was added tripotassium phosphate (4.0 mmol), trimethylboroxine (3.0 mmol), water (0.60 M) and Pd(PPh$_3$)$_4$ (0.10 mmol) the reaction mixture degassed and heated at 120° C. for 2 hr. The reaction mixture was cooled, concentrated and the residue was purified by column chromatography (silica, ethyl acetate/hexanes gradient) to afford the desired product J.

Example 518

(S)-tert-Butyl 1-(4-(8-methoxy-4-oxo-4,5-dihydrothieno[2,3-c]quinolin-9-yl)phenyl)propyl(methyl)carbamate

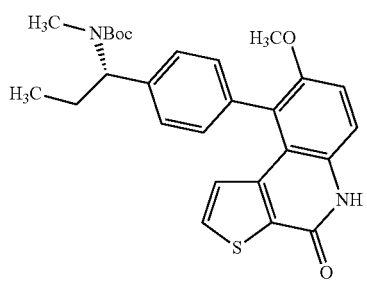 [SMILES: CC[C@@H](c1ccc(-c2c(OC)ccc3[nH]c(=O)c4sccc4c23)cc1)N(C)C(=O)OC(C)(C)C]

Following General Procedure B, 9-bromo-8-methoxythieno[2,3-c]quinolin-4(5H)-1)-one (670 mg, 2.2 mmol) was reacted with (S)-tert-butyl methyl(1-(4-(4,4,5,5-tetramethyl-1,3,2-dioxaborolan-2-yl)phenyl)propyl)carbamate (1.3 g, 3.4 mmol) to afford the desired product (700 mg, 48%) as a light brown solid: ESI MS m/z 479 $[C_{27}H_{30}N_2O_4S+H]^+$.

Example 519

(S)-tert-Butyl 2-(4-(8-methoxy-4-oxo-4,5-dihydrothieno[2,3-c]quinolin-9-yl)phenyl)propylcarbamate

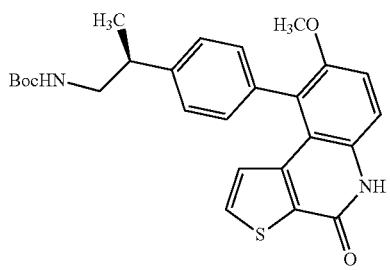 [SMILES: COc1ccc2[nH]c(=O)c3sccc3c2c1-c1ccc([C@H](C)CNC(=O)OC(C)(C)C)cc1]

Following General Procedure B, 9-bromo-8-methoxythieno[2,3-c]quinolin-4(5H)-one (240 mg, 0.32 mmol) was reacted with (S)-tert-butyl 2-(4-(4,4,5,5-tetramethyl-1,3,2-dioxaborolan-2-yl)phenyl)propylcarbamate (3.5 g, 9.7 mmol) to afford the desired product (1.4 g, 32%) as a light brown solid: ESI MS m/z 465 $[C_{26}H_{28}N_2O_4S+H]^+$.

Example 520 tert-Butyl(1-(4-(8-methoxy-4-oxo-4,5-dihydrothieno[2,3-c]quinolin-9-yl)phenyl)cyclopropyl)methylcarbamate

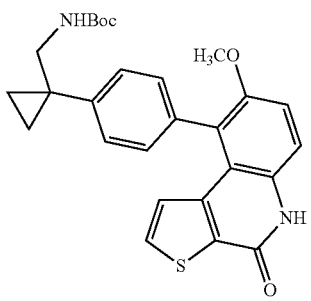 [SMILES: COc1ccc2[nH]c(=O)c3sccc3c2c1-c1ccc(C2(CNC(=O)OC(C)(C)C)CC2)cc1]

Following General Procedure B, 9-bromo-8-methoxythieno[2,3-c]quinolin-4(5H)-one (830 mg, 2.7 mmol) was reacted with tert-butyl(1-(4-(4,4,5,5-tetramethyl-1,3,2-dioxaborolan-2-yl)phenyl)cyclopropyl)methylcarbamate (1.5 g, 4.0 mmol) to afford the desired product (670 mg, 52%) as a light brown solid: ESI MS m/z 477 $[C_{27}H_{28}N_2O_4S+H]^+$.

Example 521 tert-Butyl (1-(4-(8-methoxy-6-methyl-4-oxo-4,5-dihydrothieno[2,3-c]quinolin-9-yl)phenyl)cyclopropyl)methylcarbamate

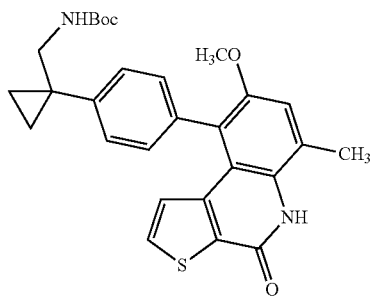 [SMILES: COc1cc(C)c2[nH]c(=O)c3sccc3c2c1-c1ccc(C2(CNC(=O)OC(C)(C)C)CC2)cc1]

Following General Procedure B, 9-bromo-8-methoxy-6-methylthieno[2,3-c]quinolin-4(5H)-one (150 mg, 0.46 mmol) was reacted with tert-butyl(1-(4-(4,4,5,5-tetramethyl-1,3,2-dioxaborolan-2-yl)phenyl)cyclopropyl)methylcarbamate (260 mg, 0.69 mmol) to afford the desired product (150 mg, 68%) as a light brown solid: ESI MS m/z 491 $[C_{28}H_{30}N_2O_4S+H]^+$.

Example 522

(S)-tert-Butyl 2-(4-(8-methoxy-4-oxo-4,5-dihydrothieno[2,3-c]quinolin-9-yl)phenyl)propyl(methyl)carbamate

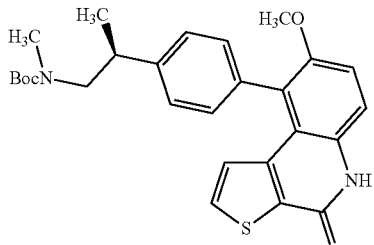

Following General Procedure B, 9-bromo-8-methoxythieno[2,3-c]quinolin-4(5H)-one (2.5 g, 8.1 mmol) was reacted with (S)-tert-butylmethyl(2-(4-(4,4,5,5-tetramethyl-1,3,2-dioxaborolan-2-yl)phenyl)propyl)carbamate (4.6 g, 12

Example 523

(S)-tert-Butyl 2-(4-(8-methoxy-6-methyl-4-oxo-4,5-dihydrothieno[2,3-c]quinolin-9-yl)phenyl)propylcarbamate

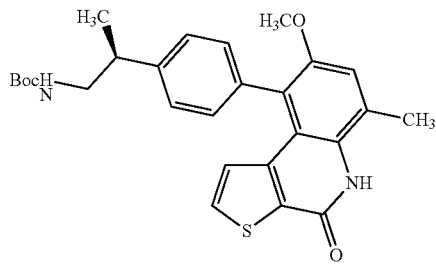 [SMILES: COc1cc(C)c2[nH]c(=O)c3sccc3c2c1-c1ccc([C@H](C)CNC(=O)OC(C)(C)C)cc1]

Following General Procedure B, 9-bromo-8-methoxy-6-methylthieno[2,3-c]quinolin-4(5H)-one (150 mg, 0.46 mmol) was reacted with (S)-tert-butyl-2-(4-(4,4,5,5-tetramethyl-1,3,2-dioxaborolan-2-yl)phenyl)propylcarbamate (251 mg, 0.69 mmol) to afford the desired product (140 mg, 62%) as a light brown solid: ESI MS m/z 479 $[C_{27}H_{30}N_2O_4S+H]^+$.

Example 524

(S)-tert-Butyl 2-(4-(8-methoxy-6-methyl-4-oxo-4,5-dihydrothieno[2,3-c]quinolin-9-yl)phenyl)propylcarbamate

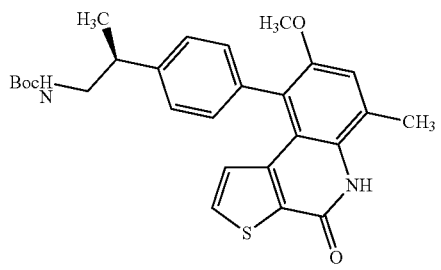 [SMILES: COc1cc(C)c2[nH]c(=O)c3sccc3c2c1-c1ccc([C@H](C)CNC(=O)OC(C)(C)C)cc1]

Following General Procedure B, 9-bromo-8-methoxy-6-methylthieno[2,3-c]quinolin-4(5H)-one (150 mg, 0.46 mmol) was reacted with (S)-tert-butyl2-(4-(4,4,5,5-tetramethyl-1,3,2-dioxaborolan-2-yl)phenyl)propylcarbamate (251 mg, 0.69 mmol) to afford the desired product (135 mg, 62%) as a light brown solid: ESI MS m/z 479 $[C_{27}H_{30}N_2O_4S+H]^+$.

Example 525 tert-Butyl 2-chloro-4-(8-methoxy-4-oxo-4,5-dihydrothieno[2,3-c]quinolin-9-yl)phenethylcarbamate

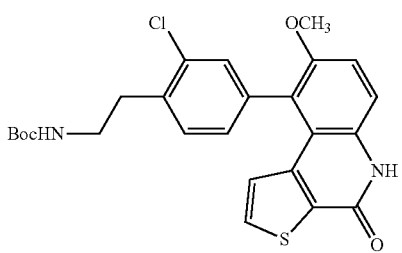 [SMILES: COc1ccc2[nH]c(=O)c3sccc3c2c1-c1ccc(CCNC(=O)OC(C)(C)C)c(Cl)c1]

Following General Procedure B, 9-bromo-8-methoxythieno[2,3-c]quinolin-4(5H)-one (3.0 g, 9.7 mmol) was reacted with tert-butyl 2-chloro-4-(4,4,5,5-tetramethyl-1,3,2-dioxaborolan-2-yl)phenethylcarbamate (5.53 g, 14.5 mmol) to afford the desired product (2.65 g, 57%) as a light brown solid. ESI MS m/z 485 $[C_{25}H_{25}ClN_2O_4S+H]^+$.

Example 526

(R)-tert-Butyl 1-(4-(8-methoxy-6-methyl-4-oxo-4,5-dihydrothieno[2,3-c]quinolin-9-yl)phenyl)ethyl(methyl)carbamate

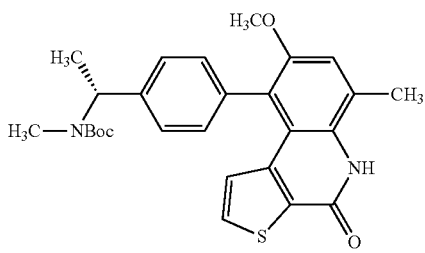

Following General Procedure B, 9-bromo-8-methoxy-6-methylthieno[2,3-c]quinolin-4(5H)-one (150 mg, 0.46 mmol) was reacted with (R)-tert-butylmethyl(1-(4-(4,4,5,5-tetramethyl-1,3,2-dioxaborolan-2-yl)phenyl)ethyl)carbamate (250 mg, 0.69 mmol to afford the desired product (145 mg, 66%) as a light brown solid: ESI MS m/z 479 $[C_{27}H_{30}N_2O_4S+H]^+$.

Example 527

(R)-tert-Butyl 1-(4-(8-methoxy-4-oxo-4,5-dihydrothieno[2,3-c]quinolin-9-yl)phenyl)ethyl(methyl)carbamate

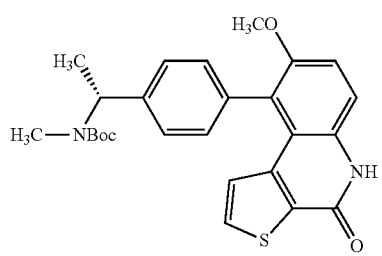 [SMILES: COc1ccc2[nH]c(=O)c3sccc3c2c1-c1ccc([C@@H](C)N(C)C(=O)OC(C)(C)C)cc1]

Following General Procedure B, 9-bromo-8-methoxythieno[2,3-c]quinolin-4(5H)-one 1.4 g, 4.4 mmol) was reacted with (R)-tert-butylmethyl(1-(4-(4,4,5,5-tetramethyl-1,3,2-dioxaborolan-2-yl)phenyl)ethyl)carbamate (2.4 g, 6.6 mmol) to afford the desired product (1.4 g, 66%) as a light brown solid: ESI MS m/z 465 $[C_{26}H_{28}N_2O_4S+H]^+$.

Example 528 tert-Butyl 2-(2-fluoro-4-(8-methoxy-1-oxo-4,5-dihydrothieno[2,3-c]quinolin-9-yl)phenyl)-2-methylpropylcarbamate

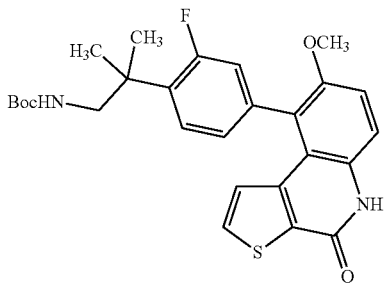 [SMILES: COc1ccc2[nH]c(=O)c3sccc3c2c1-c1ccc(C(C)(C)CNC(=O)OC(C)(C)C)c(F)c1]

Following General Procedure B, 9-bromo-8-methoxythieno[2,3-c]quinolin-4(5H)-one (1.4 g, 4.3 mmol) was reacted with tert-butyl2-(2-fluoro-4-(4,4,5,5-tetramethyl-1,3,2-dioxaborolan-2-yl)phenyl)-2-methylpropylcarbamate (2.5 g, 6.4 mmol) to afford the desired product (1.7 g, 79%) as a light brown solid. ESI MS m/z 497 $[C_{27}H_{21}FN_2O_4S+H]^+$.

Example 529 tert-Butyl 2-(2-fluoro-4-(8-methoxy-6-methyl-4-oxo-4,5-dihydrothieno[2,3-c]quinolin-9-yl)phenyl)-2-methylpropylcarbamate

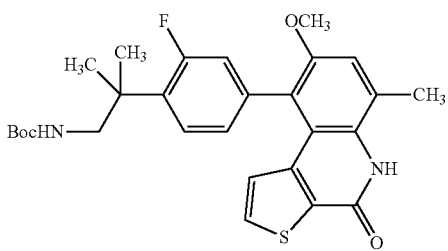 [SMILES: COc1cc(C)c2[nH]c(=O)c3sccc3c2c1-c1ccc(C(C)(C)CNC(=O)OC(C)(C)C)c(F)c1]

Following General Procedure B, 9-bromo-8-methoxy-6-methylthieno[2,3-c]quinolin-4(5H)-one (150 mg, 0.46 mmol) was reacted with tert-butyl 2-(2-fluoro-4-(4,4,5,5-tetramethyl-1,3,2-dioxaborolan-2-yl)phenyl)-2-methylpropylcarbamate (270 mg, 0.64 mmol) to afford the desired product (130 mg, 56%) as a light brown solid: ESI MS m/z 511 $[C_{28}H_{31}FN_2O_4S+H]^+$.

Example 530 tert-Butyl 2-(4-(8-methoxy-6-methyl-4-oxo-4,5-dihydrothieno[2,3-c]quinolin-9-yl)phenyl)butylcarbamate

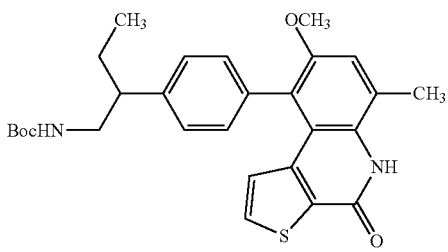 [SMILES: CCC(CNC(=O)OC(C)(C)C)c1ccc(-c2c(OC)cc(C)c3[nH]c(=O)c4sccc4c23)cc1]

Following General Procedure B, 9-brom-8-methoxy-6-methylthieno[2,3-c]quinolin-4(5H)-one (150 mg, 0.46 mmol) was reacted with tert-butyl 2-(4-(4,4,5,5-tetramethyl-1,3,2-dioxaborolan-2-yl)phenyl)butylcarbamate (240 mg, 0.64 mmol) to afford the desired product (75 mg, 33%) as a light brown solid: ESI MS m/z 493 $[C_{28}H_{12}N_2O_4S+H]^+$.

Example 531

(S)-tert-Butyl 1-(4-(8-Methoxy-4-oxo-4,5-dihydrothieno[2,3-c]quinolin-9-yl)phenyl)propylcarbamate

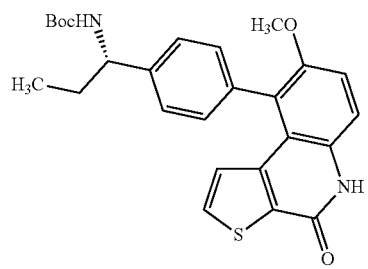 [SMILES: CC[C@H](NC(=O)OC(C)(C)C)c1ccc(-c2c(OC)ccc3[nH]c(=O)c4sccc4c23)cc1]

Following General Procedure B, 9-bromo-8-methoxythieno[2,3-c]quinolin-4(5H)-one (640 mg, 2.1 mmol) was reacted with (S)-tert-butyl 1-(4-(4,4,5,5-tetramethyl-1,3,2-dioxaborolan-2-yl)phenyl)propylcarbamate (1.13 g, 3.12 mmol) to afford the desired product (680 mg, 71%) as a light brown solid: ESI MS m/z 465 $[C_{26}H_{28}N_2O_4S+H]^+$.

Example 532 tert-Butyl(1-(4-(8-methoxy-6-methyl-4-oxo-4,5-dihydrothieno[2,3-c]quinolin-9-yl)phenyl)cyclobutyl)methylcarbamate

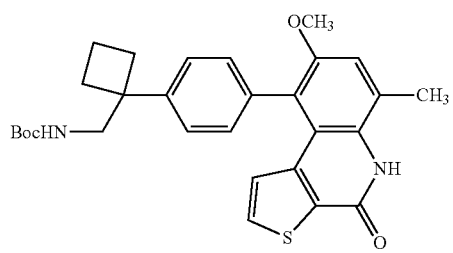 [SMILES: COc1cc(C)c2[nH]c(=O)c3sccc3c2c1-c1ccc(C2(CNC(=O)OC(C)(C)C)CCC2)cc1]

Following General Procedure B, 9-bromo-8-methoxy-6-methylthieno[2,3-c]quinolin-4(5H)-one (150 mg, 0.46 mmol) was reacted with tert-butyl (1-(4-(4,4,5,5-tetramethyl-1,3,2-dioxaborolan-2-yl)phenyl)cyclobutyl)methylcarbamate (270 mg, 0.70 mmol to afford the desired product (105 mg, 45%) as a light brown solid: ESI MS m/z 505 $[C_{29}H_{32}N_2O_4S+H]^+$.

Example 533 tert-Butyl(1-(4-(8-methoxy-4-oxo-4,5-dihydrothieno[2,3-c]quinolin-9-yl)phenyl)cyclobutyl)methylcarbamate

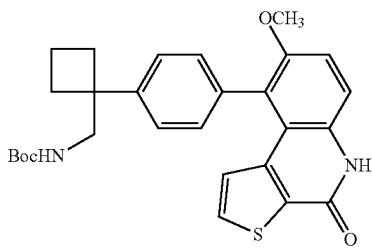 [SMILES: COc1ccc2[nH]c(=O)c3sccc3c2c1-c1ccc(C2(CNC(=O)OC(C)(C)C)CCC2)cc1]

Following General Procedure B, 9-bromo-8-methoxythieno[2,3-c]quinolin-4(5H)-one (1.9 g, 6.0 mmol) was reacted with tert-butyl (1-(4-(4,4,5,5-tetramethyl-1,3,2-dioxaborolan-2-yl)phenyl)cyclobutyl)methylcarbamate (3.5 g, 9.0 mmol) to afford the desired product (1.5 g, 33%) as a light brown solid: ESI MS m/z 491 $[C_{28}H_{30}N_2O_4S+H]^+$.

Example 534 tert-Butyl 2-(4-(8-methoxy-4-oxo-4,5-dihydrothieno[2,3-c]quinolin-9-yl)phenyl)butylcarbamate

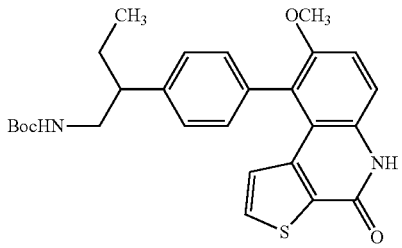 [SMILES: CCC(CNC(=O)OC(C)(C)C)c1ccc(-c2c(OC)ccc3[nH]c(=O)c4sccc4c23)cc1]

Following General Procedure B, 9-bromo-8-methoxythieno[2,3-c]quinolin-4(5H)-one (840 mg, 2.7 mmol) was reacted with tert-butyl 2-(4-(4,4,5,5-tetramethyl-1,3,2-dioxaborolan-2-yl)phenyl)butylcarbamate (1.5 g, 4.0 mmol) to afford the desired product (820 mg, 43%) as a light brown solid: ESI MS m/z 479 $[C_{27}H_{30}N_2O_4S+H]^+$.

Example 535 tert-Butyl ethyl(1-((8-methoxy-4-oxo-4,5-dihydrothieno[2,3-c]quinolin-9-yl)phenyl)ethyl)carbamate

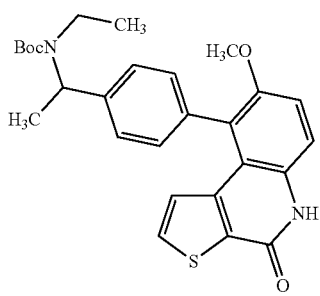 [SMILES: CCN(C(=O)OC(C)(C)C)C(C)c1ccc(-c2c(OC)ccc3[nH]c(=O)c4sccc4c23)cc1]

Following General Procedure B, 9-bromo-8-methoxythieno[2,3-c]quinolin-4(5H)-one (770 mg, 2.5 mmol) was reacted with tert-butyl ethyl(1-(4-(4,4,5,5-tetramethyl-1,3,2-dioxaborolan-2-yl)phenyl)ethyl)carbamate (1.4 g, 3.7 mmol) to afford the desired product (450 mg, 40%) as a light brown solid: ESI MS m/z 479 $[C_{27}H_{30}N_2O_4S+H]^+$.

Example 536 tert-Butyl 4-(8-methoxy-4-oxo-4,5-dihydrothieno[2,3-c]quinolin-9-yl)phenethyl(methyl)carbamate

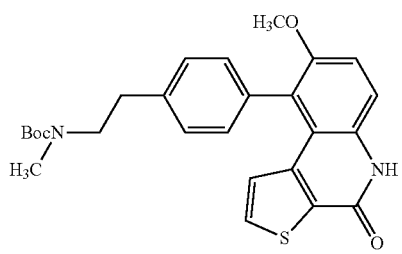 [SMILES: COc1ccc2[nH]c(=O)c3sccc3c2c1-c1ccc(CCN(C)C(=O)OC(C)(C)C)cc1]

Following General Procedure B, 9-bromo-8-methoxythieno[2,3-c]quinolin-4(5H)-one (2.4 g, 7.6 mmol) was reacted with tert-butyl methyl(4-(4,4,5,5-tetramethyl-1,3,2-dioxaborolan-2-yl)phenethyl)carbamate (4.2 g, 11 mmol) to afford the desired product (2.1 g, 40%) as a light brown solid: ESI MS m/z 465 $[C_{26}H_{28}N_2O_4S+H]^+$.

Example 537

(S)-tert-Butyl 2-(4-(8-methoxy-4-oxo-4,5-dihydrothieno[2,3-c]quinolin-9-yl)phenyl)propyl(methyl)carbamate

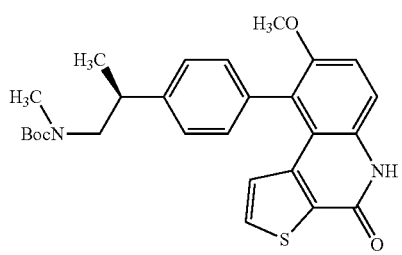 [SMILES: COc1ccc2[nH]c(=O)c3sccc3c2c1-c1ccc([C@H](C)CN(C)C(=O)OC(C)(C)C)cc1]

Following General Procedure B, 9-bromo-8-methoxythieno[2,3-c]quinolin-4(5H)-one (2.6 g, 8.2 mmol) was reacted with (S)-tert-butyl methyl(2-(4-(4,4,5,5-tetramethyl-1,3,2-dioxaborolan-2-yl)phenyl)propyl)carbamate (4.6 g, 12 mmol) to afford the desired product (1.9 g, 50%) as a light brown solid: ESI MS m/z 479 $[C_{27}H_{30}N_2O_4S+H]^+$.

Example 538

(S)-tert-Butyl 2-(2-fluoro-4-(8-methoxy-6-methyl-4-oxo-4,5-dihydrothieno[2,3-c]quinolin-9-yl)phenyl)propylcarbamate

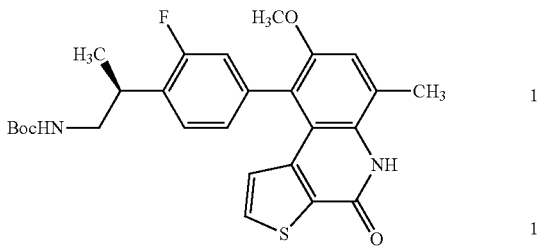

Following General Procedure B, 9-bromo-8-methoxy-6-methylthieno[2,3-c]quinolin-4(5H)-one) (380 mg, 1.2 mmol) was reacted with (S)-tert-butyl2-(2-fluoro-4-(4,4,5,5-tetramethyl-1,3,2-dioxaborolan-2-yl)phenyl)propylcarbamate (400 mg, 1.1 mmol) to afford the desired product (190 mg, 36%) as a yellow solid: ESI MS m/z 497 $[C_{27}H_{29}FN_2O_4S+H]^+$.

Example 539 tert-Butyl 2-(4-(8-methoxy-4-oxo-4,5-dihydrothieno[2,3-c]quinolin-9-yl)phenyl)-3-methylbutylcarbamate

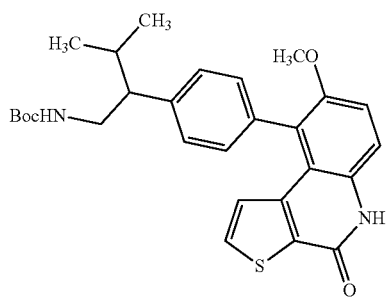 [SMILES: COc1ccc2[nH]c(=O)c3sccc3c2c1-c1ccc(C(CNC(=O)OC(C)(C)C)C(C)C)cc1]

Following General Procedure B, 9-bromo-8-methoxythieno[2,3-c]quinolin-4(5H)-one) (800 mg, 2.58 mmol) was reacted with tert-butyl 3-methyl-2-(4-(4,4,5,5-tetramethyl-1,3,2-dioxaborolan-2-yl)phenyl)butylcarbamate (1.2 g, 3.09 mmol) to afford the desired product (250 mg, 20%) as a yellow solid: ESI MS m % z 493 $[C_{28}H_{32}N_2O_4S+H]^+$.

Example 540 tert-Butyl 2-(4-(8-methoxy-6-methyl-4-oxo-4,5-dihydrothieno[2,3-c]quinolin-9-yl)phenyl)-3-methylbutylcarbamate

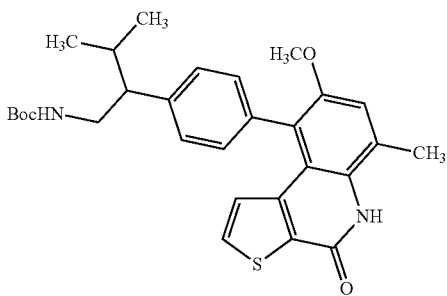 [SMILES: COc1cc(C)c2[nH]c(=O)c3sccc3c2c1-c1ccc(C(CNC(=O)OC(C)(C)C)C(C)C)cc1]

Following General Procedure B, 9-bromo-8-methoxy-6-methylthieno[2,3-c]quinolin-4(5H)-one) (500 mg, 1.54 mmol) was reacted with tert-butyl 3-methyl-2-(4-(4,4,5,5-tetramethyl-1,3,2-dioxaborolan-2-yl)phenyl)butylcarbamate (590 mg, 1.9 mmol) to afford the desired product (120 mg, 15%) as a yellow solid: ESI MS m/z 507 $[C_{29}H_{34}N_2O_4S+H]^+$.

Example 541

(R)-tert-Butyl 2-(2-fluoro-4-(8-methoxy-6-methyl-4-oxo-4,5-dihydrothieno[2,3-c]quinolin-9-yl)phenyl)propylcarbamate

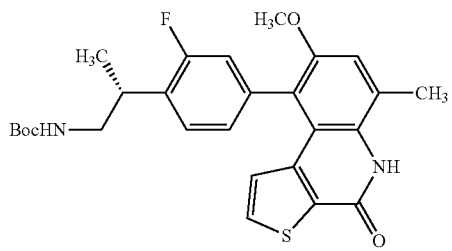 [SMILES: COc1cc(C)c2[nH]c(=O)c3sccc3c2c1-c1ccc([C@@H](C)CNC(=O)OC(C)(C)C)c(F)c1]

Following General Procedure B, 9-bromo-8-methoxy-6-methylthieno[2,3-c]quinolin-4(5H)-one) (770 mg, 2.4 mmol) was reacted with (R)-tert-butyl 2-(2-fluoro-4-(4,4,5,5-tetramethyl-1,3,2-dioxaborolan-2-yl)phenyl)propylcarbamate (770 mg, 2.0 mmol) to afford the desired product (500 mg, 49%) as a yellow solid: ESI MS m/z 497 $[C_{27}H_{29}FN_2O_4S+H]^+$.

Example 542

(R)-tert-Butyl 2-(2-fluoro-4-(8-methoxy-6-methyl-4-oxo-4,5-dihydrothieno[2,3-c]quinolin-9-yl)phenyl)propyl(methyl)carbamate

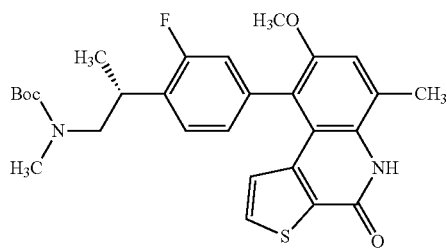

Following General Procedure B, 9-bromo-8-methoxy-6-methylthieno[2,3-c]quinolin-4(5H)-one) (180 mg, 0.57 mmol) was reacted with (R)-tert-butyl 2-(2-fluoro-4-(4,4,5,5-tetramethyl-1,3,2-dioxaborolan-2-yl)phenyl)propyl(methyl)carbamate (150 mg, 0.38 mmol) to afford the desired product (190 mg, 36%) as a yellow solid: ESI MS m/z 511 $[C_{28}H_{31}FN_2O_4S+H]^+$.

Example 543

(R)-tert-Butyl 2-(4-(8-methoxy-6-methyl-4-oxo-4,5-dihydrothieno[2,3-c]quinolin-9-yl)phenyl)butylcarbamate

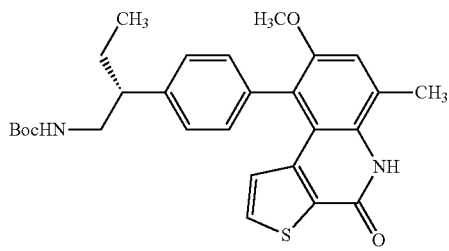 [SMILES: CC[C@@H](CNC(=O)OC(C)(C)C)c1ccc(-c2c(OC)cc(C)c3[nH]c(=O)c4sccc4c23)cc1]

Following General Procedure B, 9-bromo-8-methoxy-6-methylthieno[2,3-c]quinolin-4(5H)-one) (900 mg, 2.9 mmol) was reacted with (R)-tert-butyl 2-(4-(4,4,5,5-tetramethyl-1,3,2-dioxaborolan-2-yl)phenyl)butylcarbamate (900 mg, 2.7 mmol) to afford the desired product (190 mg, 15%) as a yellow solid: ESI MS m % z 493 $[C_{28}H_{32}N_2O_4S+H]^+$.

Example 544 tert-Butyl 2-(2-fluoro-4-(8-methoxy-6-methyl-4-oxo-4,5-dihydrothieno[2,3-c]quinolin-9-yl)phenyl)propylcarbamate

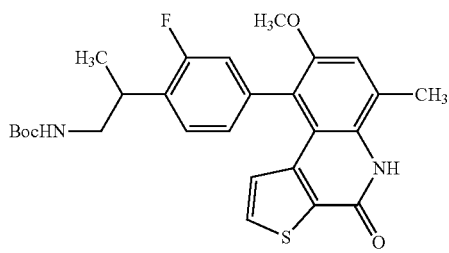 [SMILES: COc1cc(C)c2[nH]c(=O)c3sccc3c2c1-c1ccc(C(C)CNC(=O)OC(C)(C)C)c(F)c1]

Following General Procedure B, 9-bromo-8-methoxy-6-methylthieno[2,3-c]quinolin-4(5H)-one) (900 mg, 2.8 mmol) was reacted with ter-butyl 2-(2-fluoro-4-(4,4,5,5-tetramethyl-1,3,2-dioxaborolan-2-yl)phenyl)propylcarbamate (1.3 g, 3.3 mmol) to afford the desired product (200 mg, 27%) as a yellow solid: ESI MS m/z 497 $[C_{27}H_{29}FN_2O_4S+H]^+$.

Example 545 tert-Butyl 2-(2-fluoro-4-(8-methoxy-6-methyl-4-oxo-4,5-dihydrothieno[2,3-c]quinolin-9-yl)phenyl)-3-methyl butylcarbamate

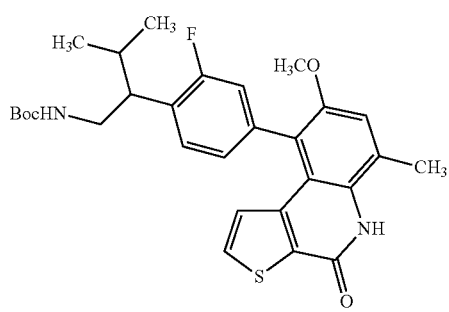 [SMILES: COc1cc(C)c2[nH]c(=O)c3sccc3c2c1-c1ccc(C(CNC(=O)OC(C)(C)C)C(C)C)c(F)c1]

Following General Procedure B, 9-bromo-8-methoxy-6-methylthieno[2,3-c]quinolin-4(5H)-one) (170 mg, 0.50 mmol) was reacted with tert-butyl 2-(2-fluoro-4-(4,4,5,5-tetramethyl-1,3,2-dioxaborolan-2-yl)phenyl)-3-methylbutylcarbamate (200 mg, 0.50 mmol) to afford the desired product (65 mg, 25%) as a yellow solid: ESI MS m/z 525 $[C_{29}H_{33}FN_2O_4S+H]^+$.

Example 546 tert-Butyl 2-(2-fluoro-4-(8-methoxy-6-methyl-4-oxo-4,5-dihydrothieno[2,3-c]quinolin-9-yl)phenyl)propyl(methyl)carbamate

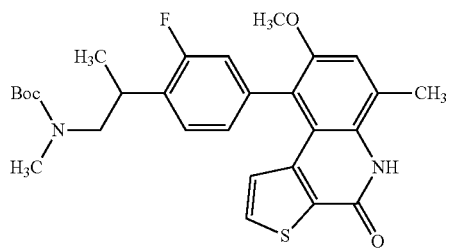

Following General Procedure B, 9-bromo-8-methoxy-6-methylthieno[2,3-c]quinolin-4(5H)-one) (380 mg, 1.16 mmol) was reacted with tert-butyl 2-(2-fluoro-4-(4,4,5,5-tetramethyl-1,3,2-dioxaborolan-2-yl)phenyl)propyl(methyl)carbamate (400 mg, 1.1 mmol) to afford the desired product (190 mg, 36%) as a yellow solid: ESI MS m/z 511 $[C_{28}H_{31}FN_2O_4S+H]^+$.

Example 547 tert-Butyl 2-(2-fluoro-4-(8-methoxy-6-methyl-4-oxo-4,5-dihydrothieno[2,3-c]quinolin-9-yl)phenyl-3-methylbutyl(methyl)carbamate

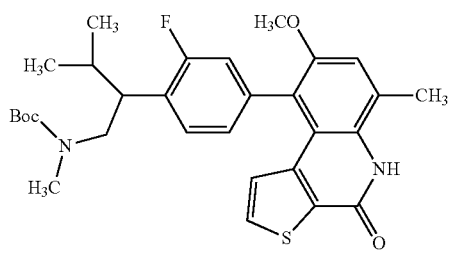 [SMILES: COc1cc(C)c2[nH]c(=O)c3sccc3c2c1-c1ccc(C(CN(C)C(=O)OC(C)(C)C)C(C)C)c(F)c1]

Following General Procedure, 9-bromo-8-methoxy-6-methylthieno[2,3-c]quinolin-4(5H)-one) (265 mg, 0.81 mmol) was reacted with tert-butyl 2-(2-fluoro-4-(4,4,5,5-tetramethyl-1,3,2-dioxaborolan-2-yl)phenyl)-3-methylbutyl(methyl)carbamate (300 mg, 0.89 mmol) to afford the desired product (80 mg, 18%) as a yellow solid: ESI MS m/z 539 $[C_{30}H_{35}FN_2O_4S+H]^+$.

Example 548

(R)-tert-Butyl 2-(2-fluoro-4-(8-methoxy-6-methyl-4-oxo-4,5-dihydrothieno[2,3-c]quinolin-9-yl)phenyl)propylcarbamate

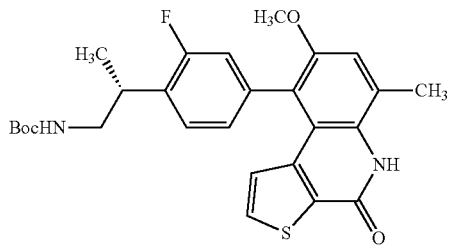 [SMILES: COc1cc(C)c2[nH]c(=O)c3sccc3c2c1-c1ccc([C@@H](C)CNC(=O)OC(C)(C)C)c(F)c1]

Following General Procedure B, 9-bromo-8-methoxy-6-methylthieno[2,3-c]quinolin-4(5H)-one) (1.0 g, 3.3 mmol) was reacted with (R)-tert-butyl 2-(2-fluoro-4-(4,4,5,5-tetramethyl-1,3,2-dioxaborolan-2-yl)phenyl)propylcarbamate (1.1 g, 3.0 mmol) to afford the desired product (510 mg, 34%) as a yellow solid: ESI MS m/z 497 $[C_{27}H_{19}FN_2O_4S+H]^+$.

Example 549 tert-Butyl 2-(4-(8-methoxy-6-methyl-4-oxo-4,5-dihydrothieno[2,3-c]quinolin-9-yl)phenyl)-3-methylbutyl(methyl)carbamate

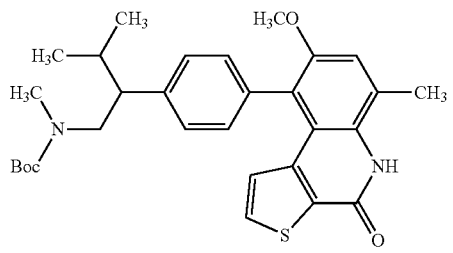

Following General Procedure B, 9-bromo-8-methoxy-6-methylthieno[2,3-c]quinolin-4(5H)-one) (440 mg, 1.4 mmol) was reacted with tert-butyl methyl(3-methyl-2-(4-(4,4,5,5-tetramethyl-1,3,2-dioxaborolan-2-yl)phenyl)butyl)carbamate (600 mg, 1.5 mmol) to afford the desired product (100 mg, 14%) as a yellow solid: ESI MS m/z 521 $[C_{30}H_{36}N_2O_4S+H]^+$.

Example 550

(S)-tert-Butyl 2-(2-fluoro-4-(8-methoxy-6-methyl-4-oxo-4,5-dihydrothieno[2,3-c]quinolin-9-yl)phenyl)propylcarbamate

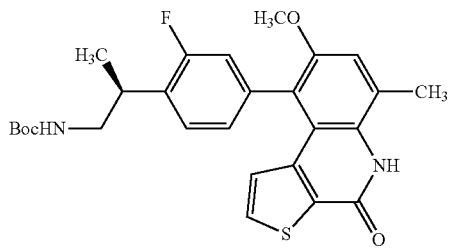 [SMILES: COc1cc(C)c2[nH]c(=O)c3sccc3c2c1-c1ccc([C@H](C)CNC(=O)OC(C)(C)C)c(F)c1]

Following General Procedure B, 9-bromo-8-methoxy-methylthieno[2,3-c]quinolin-4(5H)-one) (840 mg, 2.6 mmol) was reacted with (S)-tert-butyl 2-(2-fluoro-4-(4,4,5,5-tetramethyl-1,3,2-dioxaborolan-2-yl)phenyl)propylcarbamate (900 mg, 2.4 mmol) to afford the desired

Example 551

(R)-tert-Butyl 2-(4-(8-methoxy-4-oxo-4,5-dihydrothieno[2,3-c]quinolin-9-yl)phenyl)propylcarbamate

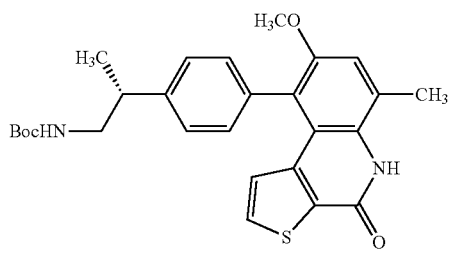 [SMILES: COc1cc(C)c2[nH]c(=O)c3sccc3c2c1-c1ccc([C@@H](C)CNC(=O)OC(C)(C)C)cc1]

Following General Procedure B, 9-bromo-8-methoxythieno[2,3-c]quinolin-4(5H)-one (1.2 g, 4.0 mmol) was reacted with (R)-tert-butyl 2-(4-(4,4,5,5-tetramethyl-1,3,2-dioxaborolan-2-yl)phenyl)propylcarbamate (2.2 g, 6.1 mmol) to afford the desired product (900 mg, 48%) as a yellow solid: ESI MS m/z 465 $[C_{26}H_{28}N_2O_4S+H]^+$.

Example 1057

N-(1-Hydroxypropan-2-yl)-4-(8-methoxy-4-oxo-4,5-dihydrothieno[2,3-c]quinolin-9-yl)benzenesulfonamide

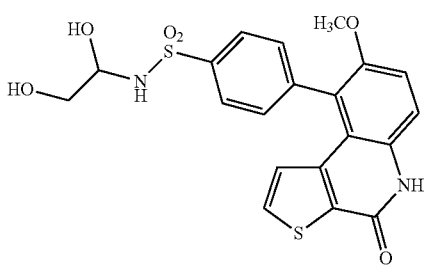 [SMILES: COc1ccc2[nH]c(=O)c3sccc3c2c1-c1ccc(S(=O)(=O)NC(O)CO)cc1]

Following General Procedure B, 9-bromo-8-methoxythieno[2,3-c]quinolin-4(5H)-one) (530 mg, 1.8 mmol) was reacted with N-(1-hydroxypropan-2-yl)-4-(4,4,5,5-tetramethyl-1,3,2-dioxaborolan-2-yl)benzenesulfonamide (750 mg, 2.02 mmol) to afford the desired product (150 mg, 20%) as a yellow solid: ESI MS m/z 445 $[C_{21}H_{20}N_2O_5S_2+H]^+$.

Example 1238

3-(4-(8-Methoxy-6-methyl-4-oxo-4,5-dihydrothieno)[2,3-c]quinolin-9-yl)phenyl)propanenitrile

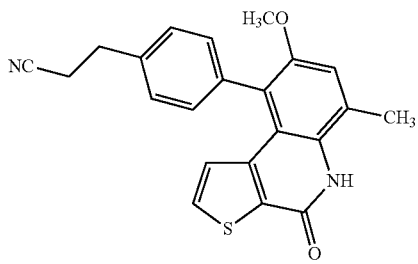 [SMILES: COc1cc(C)c2[nH]c(=O)c3sccc3c2c1-c1ccc(CCC#N)cc1]

Following General Procedure B, 9-bromo-8-methoxy-6-methylthieno[2,3-c]quinolin-4(5H)-one) (325 mg, 1.0 mmol) was reacted 3-(4-(4,4,5,5-tetramethyl-1,3,2-dioxaborolan-2-yl)propanenitrile (330 mg, 1.3 mmol) to afford the desired product (140 mg, 37%) as a yellow solid: ESI MS m/z 375 $[C_{22}H_{18}N_2O_2S+H]^+$.

Example 552 tert-Butyl 2-cyclopentyl-2-(4-(8-methoxy-4-oxo-4,5-dihydrothieno[2,3-c]quinolin-9-yl)phenyl)ethylcarbamate

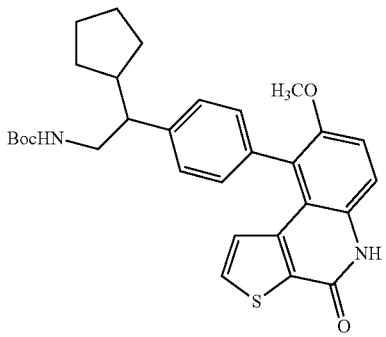 [SMILES: COc1ccc2[nH]c(=O)c3sccc3c2c1-c1ccc(C(CNC(=O)OC(C)(C)C)C2CCCC2)cc1]

Following General Procedure B, 9-bromo-8-methoxy-thieno[2,3-c]quinolin-4(5H)-one) (500 mg, 1.6 mmol) was reacted with tert-butyl 2-cyclopentyl-2-(4-(4,4,5,5-tetramethyl-1,3,2-dioxaborolan-2-yl)phenyl)ethylcarbamate (1.3 g, 3.2 mmol) to afford the desired product (150 mg, 19%) as a yellow solid: ESI MS m/z 519 $[C_{30}H_{34}N_2O_4S+H]^+$.

Example 553 tert-Butyl 3-(4-(8-methoxy-6-methyl-4-oxo-4,5-dihydrothieno[2,3-c]quinolin-9-yl)phenyl)piperidine-1-carboxylate

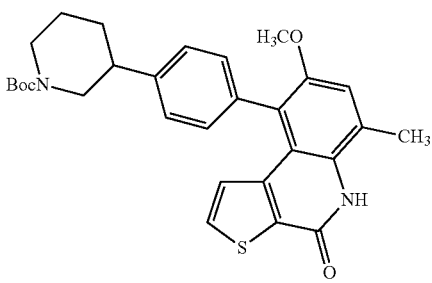 [SMILES: COc1cc(C)c2[nH]c(=O)c3sccc3c2c1-c1ccc(C2CCCN(C(=O)OC(C)(C)C)C2)cc1]

Following General Procedure B, 9-bromo-8-methoxy-thieno[2,3-c]quinolin-4(5H)-one) (190 mg, 0.58 mmol) was reacted with tert-butyl 3-(4-(4,4,5,5-tetramethyl-1,3,2-dioxaborolan-2-yl)phenyl)piperidine-1-carboxylate (180 mg, 0.46 mmol) to afford the desired product (79 mg, 34%) as a yellow solid: ESI MS m % z 505 $[C_{29}H_{32}N_2O_4S+H]^+$.

Example 554 tert-Butyl 2-((4-(8-methoxy-6-methyl-4-oxo-4,5-dihydrothieno[2,3-c]quinolin-9-yl)phenyl)(methyl)amino ethylcarbamate

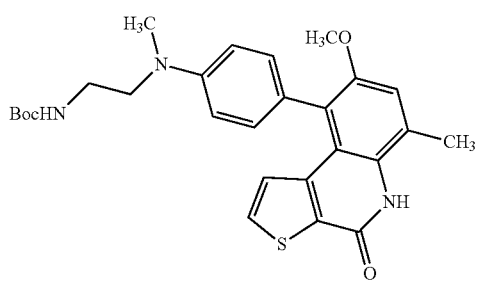 [SMILES: COc1cc(C)c2[nH]c(=O)c3sccc3c2c1-c1ccc(N(C)CCNC(=O)OC(C)(C)C)cc1]

Following General Procedure B, 9-bromo-8-methoxy-6-methylthieno[2,3-c]quinolin-4(5H)-one) (86 mg, 0.26 mmol) was reacted with tert-butyl 2-(methyl(4-(4,4,5,5-tetramethyl-1,3,2-dioxaborolan-2-yl)phenyl)amino)ethylcarbamate (100 mg, 0.26 mmol) to afford the desired product (100 mg, 78%) as a yellow solid: ESI MS m/z 494 $[C_{27}H_{31}N_3O_4S+H]^+$.

Example 1310

(S)-9-(4-(1-Aminopropan-2-yl)-3-fluorophenyl)-8-methoxy-6-methylthieno[2,3-c]quinolin-4(5H)-one Hydrochloride

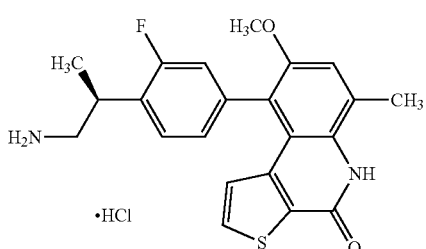

Following General Procedure D1, (S)-tert-butyl 2-(2-fluoro-4-(8-methoxy-6-methyl-4-oxo-4,5-dihydrothieno[2,3-c]quinolin-9-yl)phenyl)propylcarbamate (100 mg, 0.20 mmol) was reacted with HCl in ether (10 mL) to afford the desired product (80 mg, 98%) as an off-white solid: ESI MS m/z 397 $[C_{22}H_{21}FN_2O_2S+H]^+$.

Example 1253

9-(4-(1-Amino-3-methylbutan-2-yl)phenyl)-8-methoxythieno[2,3-c]quinolin-4(5H)-one Hydrochloride

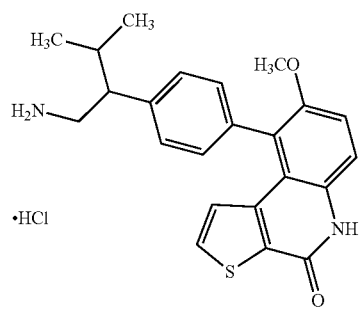 [SMILES: Cl ; COc1ccc2[nH]c(=O)c3sccc3c2c1-c1ccc(C(CN)C(C)C)cc1]

Following General Procedure D1, tert-butyl 2-(4-(8-methoxy-4-oxo-4,5-dihydrothieno[2,3-c]quinolin-9-yl)phenyl)-3-methylbutylcarbamate (30 mg, 0.060 mmol) was reacted with HCl in ether (3 mL) to afford the desired product (22 mg, 97%) as an off-white solid; $^1$H NMR (500 MHz, DMSO-d) δ 7.93 (s, 3H), 7.62 (d, J=5.4 Hz, 1H), 7.53 (d, J=9.1 Hz, 1H), 7.41 (d, J=9.0 Hz, 2H), 7.38-7.33 (m, 1H), 7.24 (d, J=8.2 Hz, 2H), 5.72 (d, J=5.4 Hz, 1H), 3.70 (s, 3H), 3.38-3.26 (m, 2H), 2.87 (dt, J=12.9, 6.3 Hz, 1H), 2.01 (dq, J=13.3, 6.6 Hz, 1H), 0.97 (t, J=7.8 Hz, 3H), 0.82 (t, J=9.9 Hz, 3H); ESI MS m/z 393 $[C_{23}H_{24}N_2O_2S+H]^+$. HPLC 98.4% (AUC), $t_R$=11.65 min.

Example 555

9-(4-(1-Amino-3-methylbutan-2-yl)phenyl)-8-methoxy-6-methylthieno[2,3-c]quinolin-4(5H)-one Hydrochloride

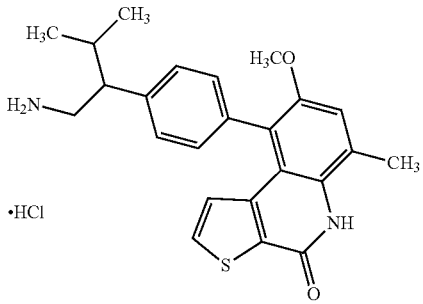 [SMILES: Cl ; COc1cc(C)c2[nH]c(=O)c3sccc3c2c1-c1ccc(C(CN)C(C)C)cc1]

Following General Procedure D1, tert-butyl 2-(4-(8-methoxy-6-methyl-4-oxo-4,5-dihydrothieno[2,3-c]quinolin-9-yl)phenyl)-3-methylbutylcarbamate (50 mg, 0.060 mmol) was reacted with HCl in ether (3 mL) to afford the desired product (37 mg, 92%) as an off-white solid: ESI MS m/1407 $[C_{24}H_{26}N_2O_2S+H]^+$.

Example 1317

(R)-9-(4-(1-Aminopropan-2-yl)-3-fluorophenyl)-8-methoxy-6-methylthieno[2,3-c]quinolin-4(5H)-one Hydrochloride

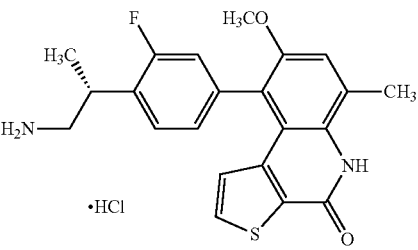 [SMILES: COc1cc(C)c2[nH]c(=O)c3sccc3c2c1-c1ccc([C@@H](C)CN)c(F)c1 ; Cl]

Following General Procedure D1, (R)-tert-butyl 2-(2-fluoro-4-(8-methoxy-6-methyl-4-oxo-4,5-dihydrothieno[2,3-c]quinolin-9-yl)phenyl)propylcarbamate (150 mg, 0.30 mmol) was reacted with HCl in ether (15 mL) to afford the desired product (105 mg, 81%) as an off-white solid: $^1$H NMR (500 MHz, MeOD) δ 7.63 (dd, J=5.4, 2.4 Hz, 1H), 7.52 (dt, J=24.8, 7.8 Hz, 1H), 7.30 (s, 1H), 7.09 (m, 2H), 6.11 (dd, J=26.4, 5.4 Hz, 1H), 3.76 (s, 3H), 3.63-3.43 (m, 1H), 3.42-3.16 (m, 2H), 2.64 (s, 3H), 1.51 (d, J=7.0 Hz, 3H). ESI MS m/z 397 $[C_{22}H_{21}FN_2O_2S+H]^+$; HPLC >99% (AUC), $t_R$=11.57 min.

Example 1316

(R)-9-(3-Fluoro-4-(1-(methylamino)propan-2-yl)phenyl)-8-methoxy-6-methylthieno[2,3-c]quinolin-4(5H)-one Hydrochloride

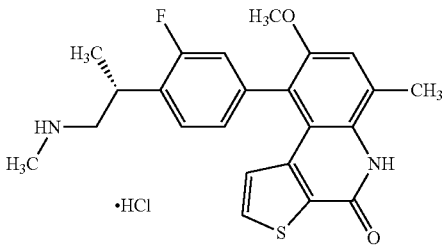

Following General Procedure D1, (R)-tert-butyl 2-(2-fluoro-4-(8-methoxy-6-methyl-4-oxo-4,5-dihydrothieno[2,3-c]quinolin-9-yl)phenyl)propyl(methyl)carbamate (50 mg, 0.10 mmol) was reacted with HCl in ether (5 mL) to afford the desired product (35 mg, 85%) as an yellow solid; $^1$H NMR (500 MHz, CD$_3$OD) δ 7.63 (d, J=5.4 Hz, 1H), 7.53 (dt, J=28.7, 7.8 Hz, 1H), 7.29 (s, 1H), 7.17-7.04 (m, 2H), 6.10 (dd, J=31.6, 5.4 Hz, 1H), 3.75 (s, 3H), 3.68-3.24 (m, 3H), 2.78 (d, J=13.3 Hz, 3H), 2.64 (s, 3H), 1.52 (dd, J=7.0, 3.2 Hz, 3H); ESI MS m/z 411 $[C_{23}H_{23}FN_2O_2S+H]^+$; HPLC 98.2% (AUC), $t_R$=11.79 min.

Example 1344

(R)-9-(4-(1-Aminobutan-2-yl)phenyl)-8-methoxy-6-methylthieno[2,3-c]quinolin-4(5H)-one Hydrochloride

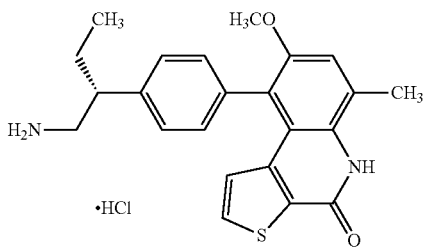 [SMILES: CC[C@@H](CN)c1ccc(-c2c(OC)cc(C)c3[nH]c(=O)c4sccc4c23)cc1 ; Cl]

Following General Procedure D1, (R)-tert-butyl 2-(4-(8-methoxy-6-methyl-4-oxo-4,5-dihydrothieno[2,3-c]quinolin-9-yl)phenyl)butylcarbamate (100 mg, 0.20 mmol) was reacted with HCl in ether (10 mL) to afford the desired product (75 mg, 94%) as an off-white solid: ESI MS m/z 393 $[C_{23}H_{24}N_2O_2S+H]^+$.

Example 1273

9-(4-(1-Aminopropan-2-yl)-3-fluorophenyl)-8-methoxy-6-methylthieno[2,3-c]quinolin-4(5H)-one Hydrochloride

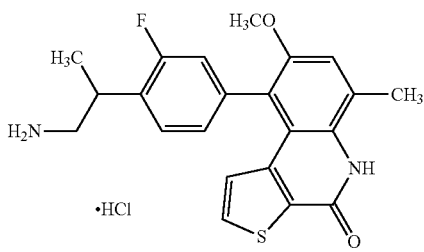 [SMILES: COc1cc(C)c2[nH]c(=O)c3sccc3c2c1-c1ccc(C(C)CN)c(F)c1 ; Cl]

Following General Procedure D1, tert-butyl 2-(2-fluoro-4-(8-methoxy-6-methyl-4-oxo-4,5-dihydrothieno[2,3-c]quinolin-9-yl)phenyl)propylcarbamate (200 mg, 0.40 mmol) was reacted with HCl in ether (20 mL) to afford the desired product (145 mg, 91%) as an off-white solid: $^1$H NMR (500 MHz, DMSO-$d_6$) δ 10.80 (s, 1H), 8.06 (s, 3H), 7.74 (dd, J=14.6, 5.4 Hz, 1H), 7.52 (t, J=7.9 Hz, 1H), 7.30 (s, 1H), 7.16-7.02 (m, 2H), 5.87 (dd, J=43.2, 5.4 Hz, 1H), 3.70 (s, 3H), 3.51-3.40 (m, 1H), 3.26-3.07 (m, 2H), 2.59 (s, 3H), 1.39 (t, J=7.6 Hz, 3H); ESI MS m/z 397 $[C_{22}H_{21}FN_2O_2S+H]^+$; HPLC 98.8% (AUC), $t_R$=11.60 min.

Example 1283

9-(4-(1-Amino-3-methylbutan-2-yl)-3-fluorophenyl)-8-methoxy-6-methylthieno[2,3-c]quinolin-4(5H)-one Hydrochloride

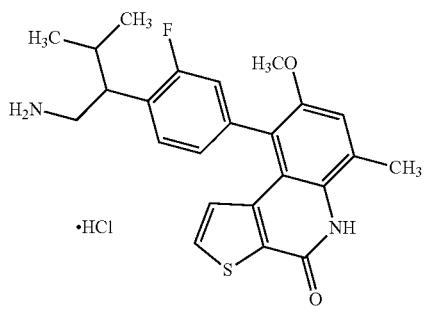 [SMILES: COc1cc(C)c2[nH]c(=O)c3sccc3c2c1-c1ccc(C(CN)C(C)C)c(F)c1 ; Cl]

Following General Procedure D1, tert-butyl 2-(2-fluoro-4-(%-methoxy-6-methyl-4-oxo-4,5-dihydrothieno[2,3-c]quinolin-9-yl)phenyl)-3-methylbutylcarbamate (52 mg, 0.10 mmol) was reacted with HCl in ether (5 mL) to afford the desired product (25 mg, 59%) as an off-white solid; $^1$H NMR (500 MHz, DMSO-$d_6$) δ 7.69 (dd, J=16.1, 5.4 Hz, 1H), 7.41 (dt, J=13.3, 8.0 Hz, 1H), 7.29 (d, J=3.4 Hz, 1H), 7.10-6.98 (m, 2H), 5.89-5.72 (m, 1H), 3.71 (t, J=6.8 Hz, 3H), 3.19-2.83 (m, 3H), 2.59 (s, 3H), 2.03 (dt, J=13.5, 6.7 Hz, 1H), 0.99 (t, J=10.0 Hz, 3H), 0.82 (dd, J=9.9, 6.8 Hz, 3H): ESI MS m/z 425 $[C_{24}H_{25}FN_2O_2S+H]^+$; HPLC 93.4% (AUC), $t_R$=11.20 min.

Example 556

8-Methoxy-6-methyl-9-(4-(3-methyl-1-(methylamino)butan-2-yl)phenyl)thieno[2,3-c]quinolin-4(5H)-one Hydrochloride

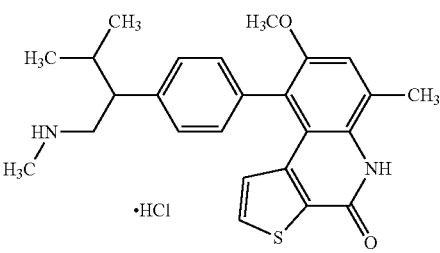

Following General Procedure D1, tert-butyl 2-(4-(8-methoxy-6-methyl-4-oxo-4,5-dihydrothieno[2,3-c]quinolin-9-yl)phenyl)-3-methylbutyl(methyl)carbamate (100 mg, 0.2 mmol) was reacted with HCl in ether (8 mL) to afford the desired product (40 mg, 47%) as an off-white solid: ESI MS m/z 421 $[C_{25}H_{28}N_2O_2S+H]^+$

Example 1286

9-(3-Fluoro-4-(1-(methylamino)propan-2-yl)phenyl)-8-methoxy-6-methylthieno[2,3-c]quinolin-4(5H)-one Hydrochloride

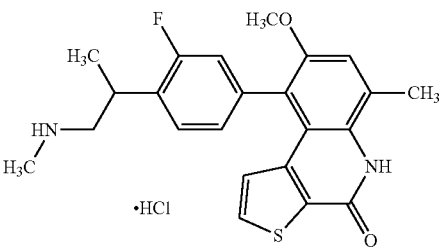

Following General Procedure D1, tert-butyl 2-(2-fluoro-4-(8-methoxy-6-methyl-4-oxo-4,5-dihydrothieno[2,3-c]quinolin-9-yl)phenyl)propyl(methyl carbamate (100 mg, 0.20 mmol) was reacted with HCl in ether (5 mL) to afford the desired product (75 mg, 93%) as an off-white solid: $^1$H NMR (500 MHz, DMSO-$d_6$) δ 10.80 (s, 1H), 7.75 (dd, J=11.7, 5.4 Hz, 1H), 7.52 (t, J=7.8 Hz, 1H), 7.30 (s, 1H), 7.17-7.04 (m, 2H), 5.87 (dd, J=35.8, 5.4 Hz, 1H), 3.71 (s, 3H), 3.55 (dd, J=14.0, 6.8 Hz, 1H), 3.28 (m, 2H), 2.63 (d, J=5.5 Hz, 3H), 2.59 (s, 3H), 1.39 (dt, J=17.4, 7.6 Hz, 3H); ESI MS m/z 411 $[C_{23}H_{23}FN_2O_2S+H]^+$; HPLC 98.9% (AUC), $t_R$=10.75 min.

Example 557

9-(3-Fluoro-4-(3-methyl-1-(methylamino)butan-2-yl)phenyl)-8-methoxy-6-methylthieno[2,3-c]quinolin-4(5H)-one Hydrochloride

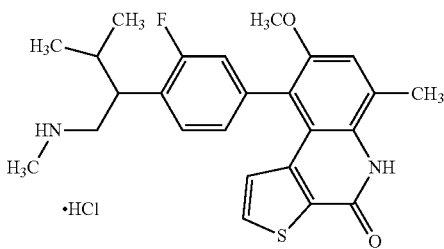

Following General Procedure D1, tert-butyl 2-(2-fluoro-4-(8-methoxy-6-methyl-4-oxo-4,5-dihydrothieno[2,3-c]quinolin-9-yl)phenyl)-3-methylbutyl(methyl)carbamate (100 mg, 0.18 mmol) was reacted with HCl in ether (6 mL) to afford the desired product (55 mg, 70%) as an off-white solid: ESI MS m/z 439 $[C_{25}H_{27}FN_2O_2S+H]^+$

Example 1317

(R)-9-(4-(1-aminopropan-2-yl)-3-fluorophenyl)-8-methoxy-6-methylthieno[2,3-c]quinolin-4(5H)-one Hydrochloride

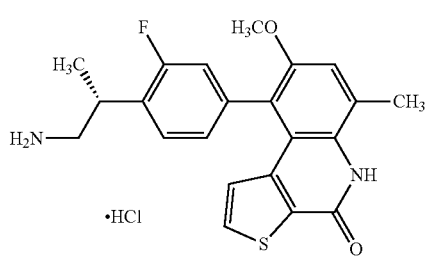 [SMILES: COc1cc(C)c2[nH]c(=O)c3sccc3c2c1-c1ccc([C@@H](C)CN)c(F)c1 ; Cl]

Following General Procedure D1, (R)-tert-butyl 2-(2-fluoro-4-(8-methoxy-6-methyl-4-oxo-4,5-dihydrothieno[2,3-c]quinolin-9-yl)phenyl)propylcarbamate (510 mg, 1.1 mmol) was reacted with HCl in ether (25 mL) to afford the desired product (312 mg, 78%) as an off-white solid: ESI MS m/z 397 $[C_{22}H_{21}FN_2O_2S+H]^+$

Example 1310

(S)-9-(4-(1-Aminopropan-2-yl)-3-fluorophenyl)-8-methoxy-6-methylthieno[2,3-c]quinolin-4(5H)-one Hydrochloride

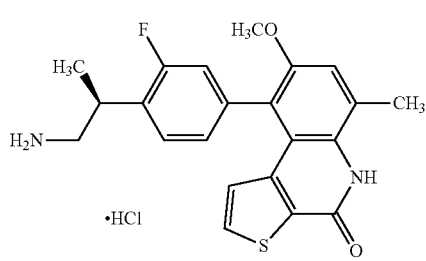 [SMILES: COc1cc(C)c2[nH]c(=O)c3sccc3c2c1-c1ccc([C@H](C)CN)c(F)c1 ; Cl]

Following General Procedure D1, (S)-tert-butyl 2-(2-fluoro-4-(8-methoxy-6-methyl-4-oxo-4,5-dihydrothieno[2,3-c]quinolin-9-yl)phenyl)propylcarbamate (520 mg, 1.1 mmol) was reacted with HCl (25 ml) to afford desire product (300 mg, 74%) as an off-white solid: $^1$H NMR (500 MHz, MeOD) δ 7.63 (d, J=5.4 Hz, 1H), 7.51 (dt, J=23.5, 7.8 Hz, 1H), 7.29 (s, 1H), 7.14-7.02 (m, 2H), 6.16-6.05 (m, 1H), 3.76 (s, 3H), 3.54 (ddd, J=46.9, 14.5, 7.3 Hz, 1H), 3.43-3.20 (m, 2H), 1.51 (d, J=7.0 Hz, 3H); ESI MS m/z 397 $[C_{22}H_{21}FN_2O_2S+H]^+$; HPLC 98.9% (AUC), $t_R$=10.75 min.

Example 1387

(S)-9-(4-(1-(dimethylamino)propan-2-yl)-3-fluorophenyl)-8-methoxy-6-methylthieno[2,3-c]quinolin-4(5H)-one Hydrochloride

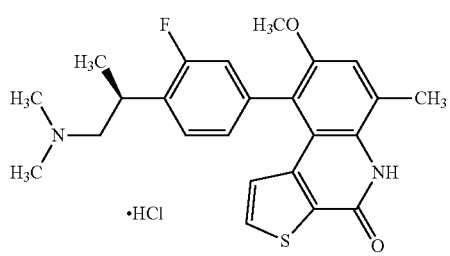

To a solution of (S)-9-(4-(1-aminopropan-2-yl)-3-fluorophenyl)-8-methoxy-6-methylthieno[2,3-c]quinolin-4(5H)-one hydrochloride (110 mg, 0.27 mmol)) in a 1:1 mixture of MeOH/THF (3 mL) was added paraformaldehyde (7.5 mg, 0.24 mmol) followed by NaCNBH$_3$ (70 mg 1.2 mmol) and stirred at rt for 16 h. The reaction mixture was quenched by the addition of 2 N NaHCO$_3$ (1 mL), eluted through an SCX ion-exchange column and converted to HCl salt using General Procedure D-2 (Scheme II) to obtain the desired product (67 mg, 60%) as a white solid: ESI MS m/z 425 $[C_{24}H_{25}FN_2O_2S+H]^+$;

Example 558

(R)-9-(4-(1-Aminopropan-2-yl)phenyl)-8-methoxythieno[2,3-c]quinolin-4(5H)-one

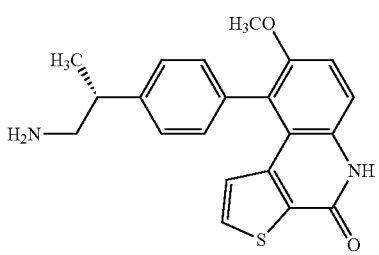 [SMILES: COc1ccc2[nH]c(=O)c3sccc3c2c1-c1ccc([C@@H](C)CN)cc1]

Following General Procedure C (R)-tert-butyl 2-(4-(8-methoxy-4-oxo-4,5-dihydrothieno[2,3-c]quinolin-9-yl)phenyl)propylcarbamate (2.5 g, 5.4 mmol) was reacted with TFA (10 mL) to afford the desired product (1.6 g, 81%) as an off-white solid: ESI MS m/z 365 $[C_{21}H_{20}N_2O_2S+H]^+$

Example 1205

N-(1-Chloropropan-2-yl)-4-(8-methoxy-4-oxo-4,5-dihydrothieno[2,3-c]quinolin-9-yl)benzenesulfonamide

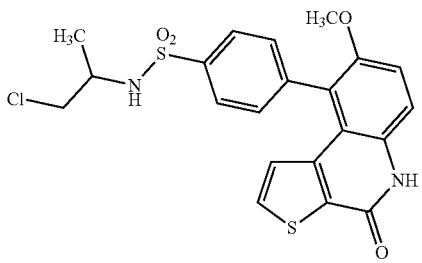 [SMILES: COc1ccc2[nH]c(=O)c3sccc3c2c1-c1ccc(S(=O)(=O)NC(C)CCl)cc1]

To a mixture of N-(1-hydroxypropan-2-yl)-4-(8-methoxy-4-oxo-4,5-dihydrothieno[2,3-c]quinolin-9-yl)benzenesulfonamide (140 mg, 0.30 mmol) and triphenylphosphine (160 mg, 0.62 mmol) in DMF/CCl$_4$ (1 mL/3 mL) was added NCS (41 mg, 0.31 mmol) and the reaction mixture was stirred at room temperature for 15 h. The reaction mixture was diluted with water (ca. 20 mL), and extracted with DCM (1×50 mL). The extract was washed with water (2×20 mL), brine (1×10 mL), dried over sodium sulfate, and evaporated under vacuum. The residue was purified by flash chromatography to afford the desired product (100 mg, 74%) as light yellow solid; ESI MS m/z 464 [C$_{21}$H$_{19}$ClN$_2$O$_4$S+H]$^+$

Example 1239

9-(4-(2-Amino-1-cyclopentylethyl)phenyl)-8-methoxythieno[2,3-c]quinolin-4(5H)-one Hydrochloride

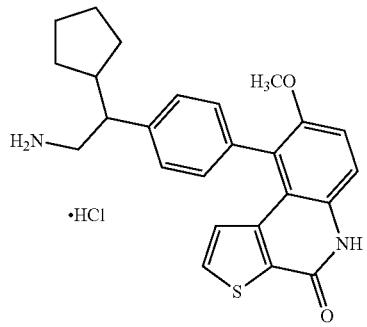 [SMILES: COc1ccc2[nH]c(=O)c3sccc3c2c1-c1ccc(C(CN)C2CCCC2)cc1 ; Cl]

Following General Procedure D, tert-butyl 2-cyclopentyl-2-(4-(8-methoxy-4-oxo-4,5-dihydrothieno[2,3-c]quinolin-9-yl)phenyl)ethylcarbamate (50 mg, 0.10 mmol) was reacted with HCl in ether (5 mL) to afford the desired product (29 mg, 69%) as an off-white solid: ESI MS m/z 419 [C25H$_{26}$N$_2$O$_2$S+H]$^+$; $^1$H NMR (500 MHz, DMSO-d$_6$) δ 7.59 (d, J=5.4 Hz, 1H), 7.59 (d, J=5.4 Hz, 1H), 7.54 (d, J=9.0 Hz, 1H), 7.54 (d, J=9.0 Hz, 1H), 7.48 (d, J=7.9 Hz, 1H), 7.48 (d, J=7.9 Hz, 1H), 7.44-7.36 (m, 2H), 7.45-7.35 (m, 2H), 7.28-7.19 (m, 2H), 7.28-7.19 (m, 2H), 5.72 (d, J=5.4 Hz, 1H), 5.72 (d, J=5.4 Hz, 1H), 3.70 (s, 3H), 3.33-3.20 (m, 2H), 2.84 (td, J=9.2, 6.0 Hz, 1H), 2.20-2.03 (m, 1H), 1.98-1.84 (m, 1H), 1.76-1.35 (m, 5H), 1.28 (dq, J=18.0, 8.9 Hz, 1H), 1.18-1.02 (m, 1H). HPLC >99% (AUC), t$_R$=12.45 min.

Example 1301

8-Methoxy-6-methyl-9-(4-(piperidin-3-yl)phenyl)thieno[2,3-c]quinolin-4(5H)-one Hydrochloride

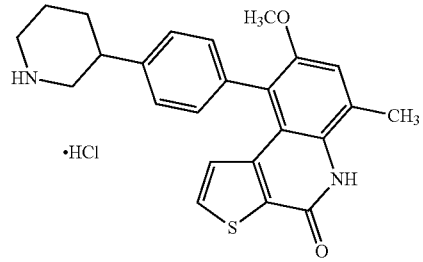 [SMILES: COc1cc(C)c2[nH]c(=O)c3sccc3c2c1-c1ccc(C2CCCNC2)cc1 ; Cl]

Following General Procedure D1, tert-butyl 3-(4-(8-methoxy-6-methyl-4-oxo-4,5-dihydrothieno[2,3-c]quinolin-9-yl)phenyl)piperidine-1-carboxylate (50 mg, 0.10 mmol) was reacted with HCl in ether (2.5 mL) to afford the desired product (31 mg, 77%) as an off-white solid: ESI MS m/z 405 [C$_{24}$H$_{24}$N$_2$O$_2$S+H]$^+$

Example 1396

9-(4-((2-aminoethyl)(methyl)amino)phenyl)-8-methoxy-6-methylthieno[2,3-c]quinolin-4(5H)-one Hydrochloride

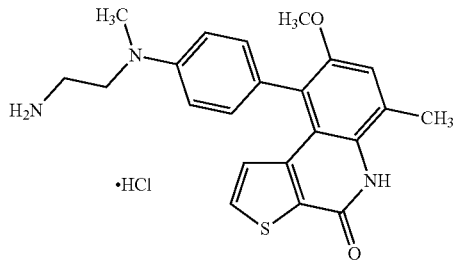 [SMILES: COc1cc(C)c2[nH]c(=O)c3sccc3c2c1-c1ccc(N(C)CCN)cc1 ; Cl]

Following General Procedure D1, tert-butyl 2-((4-(8-methoxy-6-methyl-4-oxo-4,5-dihydrothieno[2,3-c]quinolin-9-yl)phenyl)methyl)amino)ethylcarbamate (100 mg, 0.20 mmol) was reacted with HCl in ether (10 mL) to afford the desired product (65 mg, 83%) as an off-white solid: ESI MS m/z 394 [C$_{22}$H$_{23}$N$_3$O$_2$S+H]$^+$

Example 559 tert-Butyl 1-(4-(8-methoxy-4-oxo-4,5-dihydrothieno[2,3-c]quinolin-9-yl)phenyl)ethylcarbamate

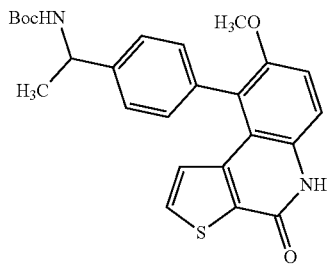 [SMILES: COc1ccc2[nH]c(=O)c3sccc3c2c1-c1ccc(C(C)NC(=O)OC(C)(C)C)cc1]

Following General Procedure B, 9-bromo-8-methoxythieno[2,3-c]quinolin-4(5H)-one (600 mg, 1.9 mmol) was reacted with tert-butyl 1-(4-(4,4,5,5-tetramethyl-1,3,2-dioxaborolan-2-yl)phenyl)ethylcarbamate (1.34 g, 3.87 mmol) to afford the desired product (340 mg, 39%) as a brown solid: ESI MS m/z 451 $[C_{25}H_{26}N_2O_4S+H]^+$.

Example 560

(R)-tert-Butyl 1-(4-(8-methoxy-4-oxo-4,5-dihydrothieno[2,3-c]quinolin-9-yl)phenyl)ethyl(methyl)carbamate

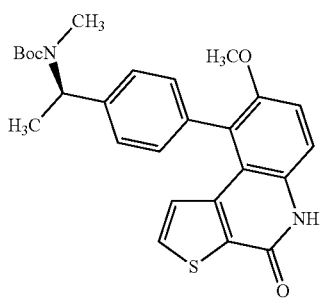 [SMILES: COc1ccc2[nH]c(=O)c3sccc3c2c1-c1ccc([C@@H](C)N(C)C(=O)OC(C)(C)C)cc1]

Following General Procedure B, 9-bromo-8-methoxythieno[2,3-c]quinolin-4(5H)-one (300 mg, 0.97 mmol) was reacted with (R)-tert-butyl methyl(1-(4-(4,4,5,5-tetramethyl-1,3,2-dioxaborolan-2-yl)phenyl)ethyl)carbamate (520 mg, 1.45 mmol) to afford the desired product (120 mg, 27%) as a brown solid: ESI MS m/z 465 $[C_{26}H_{28}N_2O_4S+H]^+$.

Example 561 tert-butyl 1-(4-(8-methoxy-4-oxo-4,5-dihydrothieno[2,3-c]quinolin-9-yl)phenyl)propan-2-ylcarbamate

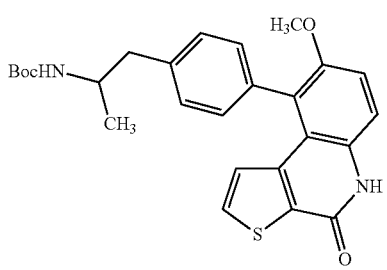 [SMILES: COc1ccc2[nH]c(=O)c3sccc3c2c1-c1ccc(CC(C)NC(=O)OC(C)(C)C)cc1]

Following General Procedure B, 9-bromo-8-methoxythieno[2,3-c]quinolin-4(5H)-one (1.5 g, 4.4 mmol) was reacted with tert-butyl 1-(4-(4,4,5,5-tetramethyl-1,3,2-dioxaborolan-2-yl)phenyl)propan-2-ylcarbamate (2.6 g, 7.3 mmol) to afford the desired product (1.1 g, 50%) as a brown solid: ESI MS m/z 465 $[C_{26}H_{28}N_2O_4S+H]^+$.

Example 562 tert-butyl 2-(2-chloro-4-(8-methoxy-4-oxo-4,5-dihydrothieno[2,3-c]quinolin-9-yl)phenyl)propylcarbamate

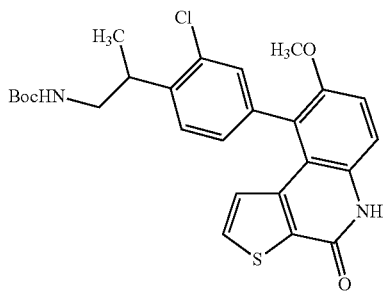 [SMILES: COc1ccc2[nH]c(=O)c3sccc3c2c1-c1ccc(C(C)CNC(=O)OC(C)(C)C)c(Cl)c1]

Following General Procedure B, 9-bromo-8-methoxythieno[2,3-c]quinolin-4(5H)-on (3.0 g, 9.7 mmol) was reacted with tert-butyl 2-(2-chloro-4-(4,4,5,5-tetramethyl-1,3,2-dioxaborolan-2-yl)phenyl)propylcarbamate (5.7 g, 14 mmol) to afford the desired product (2.7 g, 56%) as a brown solid: ESI MS m/z 499 $[C_{26}H_{27}ClN_2O_4S+H]^+$.

Example 563

2-(4-(8-Methoxy-4-oxo-4,5-dihydrothieno[2,3-c]quinolin-9-yl)phenyl)propanenitrile

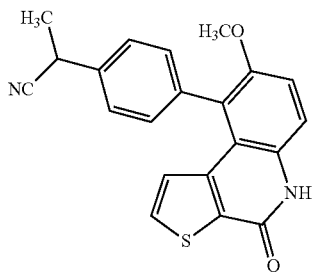 [SMILES: COc1ccc2[nH]c(=O)c3sccc3c2c1-c1ccc(C(C)C#N)cc1]

Following General Procedure B, 9-bromo-8-methoxythieno[2,3-c]quinolin-4(5H)-one (500 mg, 1.6 mmol) was reacted with 2-(4-(4,4,5,5-tetramethyl-1,3,2-dioxaborolan-2-yl)phenyl)propanenitrile (600 g, 2.2 mmol) to afford the desired product (350 mg, 62%) as a brown solid: ESI MS m/z 361 $[C_{21}H_{16}N_2O_2S+H]^+$.

Example 564 tert-Butyl 2-(4-(8-methoxy-4-oxo-4,5-dihydrothieno[2,3-c]quinolin-9-yl)phenyl)-2-methylpropylcarbamate

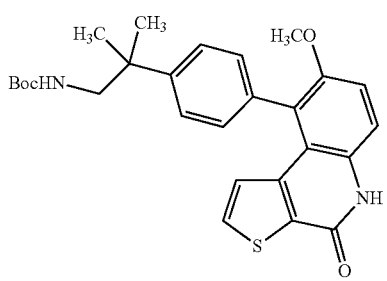 [SMILES: COc1ccc2[nH]c(=O)c3sccc3c2c1-c1ccc(C(C)(C)CNC(=O)OC(C)(C)C)cc1]

Following General Procedure B, 9-bromo-8-methoxythieno[2,3-c]quinolin-4(5H)-one (2.0 g, 6.4 mmol) was reacted with tert-butyl 2-methyl-2-(4-(4,4,5,5-tetramethyl-1,3,2-dioxaborolan-2-yl)phenyl)propylcarbamate (3.6 g, 9.7 mmol) to afford the desired product (864 mg, 28%) as a brown solid: ESI MS m/z 479 $[C_{27}H_{30}N_2O_4S+H]^+$.

Example 565

(R)-tert-Butyl 1-(4-(8-methoxy-4-oxo-4,5-dihydrothieno[2,3-c]quinolin-9-yl)phenyl)ethylcarbamate

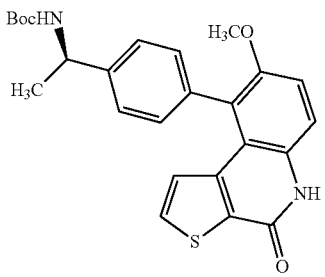 [SMILES: COc1ccc2[nH]c(=O)c3sccc3c2c1-c1ccc([C@@H](C)NC(=O)OC(C)(C)C)cc1]

Following General Procedure B, 9-bromo-8-methoxythieno[2,3-c]quinolin-4(5H)-one (3.0 g, 9.7 mmol) was reacted with (R)-tert-butyl 1-(4-(4,4,5,5-tetramethyl-1,3,2-dioxaborolan-2-yl)phenyl)ethylcarbamate (5.0 g, 14 mmol) to afford the desired product (2.0 g, 47%) as a brown solid: ESI MS m/z 451 $[C_{25}H_{26}N_2O_4S+H]^+$.

Example 566 tert-Butyl 2-ethyl-2-(4-(8-methoxy-4-oxo-4,5-dihydrothieno[2,3-c]quinolin-9-yl)phenyl)butylcarbamate

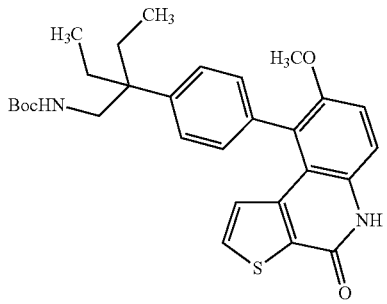 [SMILES: CCC(CC)(CNC(=O)OC(C)(C)C)c1ccc(-c2c(OC)ccc3[nH]c(=O)c4sccc4c23)cc1]

Following General Procedure B, 9-bromo-8-methoxythieno[2,3-c]quinolin-4(5H)-one (120 mg, 0.39 mmol) was reacted with 2-ethyl-2-(4-(4,4,5,5-tetramethyl-1,3,2-dioxaborolan-2-yl)phenyl)butan-1-amine (220 mg, 0.58 mmol) to afford the desired product (50 mg, 27%) as a brown solid: ESI MS m/z 507 $[C_{29}H_{34}N_2O_4S+H]^+$.

Example 567 tert-Butyl 2-fluoro-4-(8-methoxy-4-oxo-4,5-dihydrothieno[2,3-c]quinolin-9-yl)phenethylcarbamate

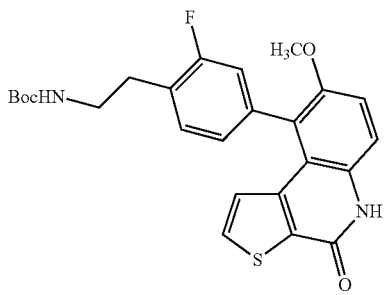 [SMILES: COc1ccc2[nH]c(=O)c3sccc3c2c1-c1ccc(CCNC(=O)OC(C)(C)C)c(F)c1]

Following General Procedure B, 9-bromo-8-methoxythieno[2,3-c]quinolin-4(5H)-one (1.5 g, 4.8 mmol) was reacted with tert-butyl 2-fluoro-4-(4,4,5,5-tetramethyl-1,3,2-dioxaborolan-2-yl)phenethylcarbamate (2.6 g, 7.3 mmol) to afford the desired product (1.5 g, 65%) as a brown solid: ESI MS m/z 469 $[C_{25}H_{25}FN_2O_4S+H]^+$.

Example 568

(R)-tert-Butyl 2-(4-(8-methoxy-4-oxo-4,5-dihydrothieno[2,3-c]quinolin-9-yl)phenyl)propylcarbamate

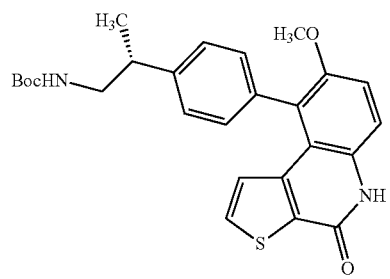 [SMILES: COc1ccc2[nH]c(=O)c3sccc3c2c1-c1ccc([C@@H](C)CNC(=O)OC(C)(C)C)cc1]

Following General Procedure B, 9-bromo-8-methoxythieno[2,3-c]quinolin-4(5H)-one (1.5 g, 4.4 mmol) was reacted with (R)-tert-butyl 2-(4-(4,4,5,5-tetramethyl-1,3,2-dioxaborolan-2-yl)phenyl)propylcarbamate (2.0 g, 6.4 mmol) to afford the desired product (1.4 g, 48%) as a brown solid: ESI MS m/z 465 $[C_{26}H_{28}N_2O_4S+H]^+$.

Example 569 tert-Butyl 2-(2-fluoro-4-(8-methoxy-4-oxo-4,5-dihydrothieno[2,3-c]quinolin-9-yl)phenyl)propylcarbamate

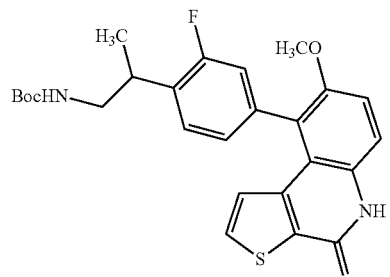

Following General Procedure B, 9-bromo-8-methoxythieno[2,3-c]quinolin-4(5H)-one (1.2 g, 3.8 mmol) was reacted with tert-butyl 2-(2-fluoro-4-(4,4,5,5-tetramethyl-1,3,2-dioxaborolan-2-yl)phenyl)propylcarbamate (2.2 g, 5.8 mmol) to afford the desired product (905 mg, 51%) as a brown solid: ESI MS m/z 483 $[C_{26}H_{27}FN_2O_4S+H]^+$.

Example 570

(R)-tert-Butyl 2-(4-(8-methoxy-4-oxo-4,5-dihydrothieno[2,3-c]quinolin-9-yl)phenyl)propyl(methyl)carbamate

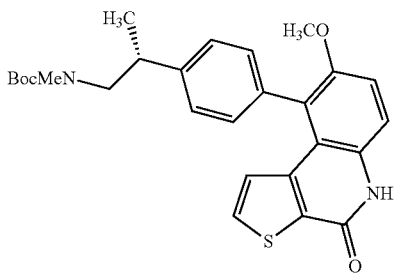

Following General Procedure B, 9-bromo-8-methoxythieno[2,3-c]quinolin-4(5H)-one (700 mg, 2.3 mmol) was reacted with (R)-tert-butyl methyl(2-(4-(4,4,5,5-tetramethyl-1,3,2-dioxaborolan-2-yl)phenyl)propyl)carbamate (1.3 g, 3.4 mmol) to afford the desired product (383 mg, 38%) as a yellow solid: ESI MS m/z 479 $[C_{27}H_{30}N_2O_4S+H]^+$.

Example 571 tert-Butyl 4-(8-methoxy-4-oxo-4,5-dihydrothieno[2,3-c]quinolin-9-yl)phenethylcarbamate

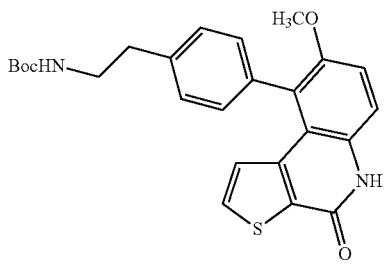 [SMILES: COc1ccc2[nH]c(=O)c3sccc3c2c1-c1ccc(CCNC(=O)OC(C)(C)C)cc1]

Following General Procedure B, 9-bromo-8-methoxythieno[2,3-c]quinolin-4(5-1H)-one (2.0 g, 6.4 mmol) was reacted with tert-butyl 4-(4,4,5,5-tetramethyl-1,3,2-dioxaborolan-2-yl)phenethylcarbamate (3.4 g, 9.4 mmol) to afford the desired product (1.93 g, 65%) as a brown solid: ESI MS m/z 451 $[(C_{25}H_{26}N_2O_4S+H]^+$.

Example 572

2-(4-(8-Methoxy-4-oxo-4,5-dihydrothieno[2,3-c]quinolin-9-yl)phenyl)propanenitrile

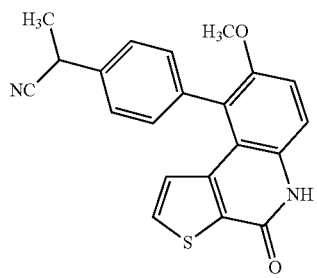 [SMILES: COc1ccc2[nH]c(=O)c3sccc3c2c1-c1ccc(C(C)C#N)cc1]

Following General Procedure B, 9-bromo-8-methoxythieno[2,3-c]quinolin-4(5H)-one (1.5 g, 4.84 mmol) was reacted with 2-(4-(4,4,5,5-tetramethyl-1,3,2-dioxaborolan-2-yl)phenyl)propanenitrile (1.87 g, 7.26 mmol) to afford the desired product (1.45 g, 82%) as a brown solid: ESI MS m/z 361 $[C_{21}H_{16}N_2O_2S+H]^+$.

Example 573

(R)-tert-Butyl 2-(4-(8-methoxy-6-methyl-4-oxo-4,5-dihydrothieno[2,3-c]quinolin-9-yl)phenyl)propylcarbamate

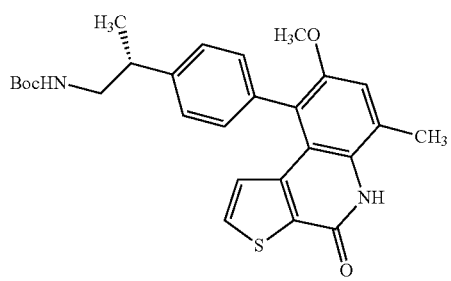 [SMILES: COc1cc(C)c2[nH]c(=O)c3sccc3c2c1-c1ccc([C@@H](C)CNC(=O)OC(C)(C)C)cc1]

Following General Procedure B, 9-bromo-8-methoxy-6-methylthieno[2,3-c]quinolin-4(5H)-one (3.0 g, 9.26 mmol) was reacted with (R)-tert-butyl 2-(4-(4,4,5,5-tetramethyl-1,3,2-dioxaborolan-2-yl)phenyl)propylcarbamate (5.2 g, 13.89 mmol) to afford the desired product (1.60 g, 35%) as a brown solid: ESI MS m/z 479 $[C_{27}H_{30}N_2O_4S+H]^+$.

Example 574 tert-Butyl 2-(4-(8-methoxy-4-oxo-4,5-dihydrothieno[2,3-c]quinolin-9-yl)phenyl)propylcarbamate

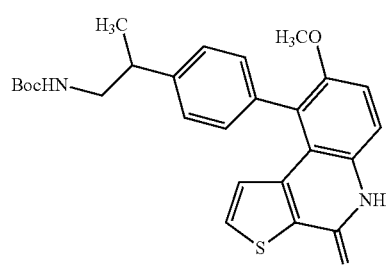

Following General Procedure B, 9-bromo-8-methoxythieno[2,3-c]quinolin-4(5H)-one (800 mg, 4.84 mmol) was reacted with tert-butyl 2-(4-(4,4,5,5-tetramethyl-1,3,2-dioxaborolan-2-yl)phenyl)propylcarbamate (1.5 g, 4.16 mmol) to afford the desired product (550 mg, 46%) as a brown solid: ESI MS m/z 465 $[C_{26}H_{28}N_2O_4S+H]^+$.

Example 575 tert-Butyl 2-(4-(8-methoxy-6-methyl-4-oxo-4,5-dihydrothieno[2,3-c]quinolin-9-yl)phenyl)-2-methylpropylcarbamate

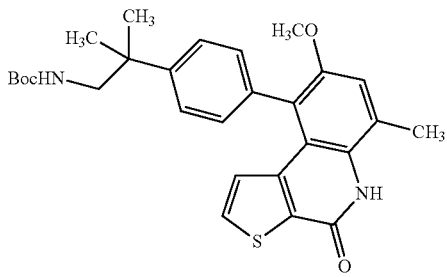 [SMILES: COc1cc(C)c2[nH]c(=O)c3sccc3c2c1-c1ccc(C(C)(C)CNC(=O)OC(C)(C)C)cc1]

Following General Procedure B, 9-bromo-8-methoxy-6-methylthieno[2,3-c]quinolin-4(5H)-one (200 mg, 0.62 mmol) was reacted with tert-butyl 2-methyl-2-(4-(4,4,5,5-tetramethyl-1,3,2-dioxaborolan-2-yl)phenyl)propylcarbamate (350 mg, 0.93 mmol) to afford the desired product (95 mg, 62%) as a brown solid: ESI MS m/z 493 $[C_{28}H_{32}N_2O_4S+H]^+$.

Example 576 tert-Butyl 1-(4-(8-methoxy-6-methyl-4-oxo-4,5-dihydrothieno[2,3-c]quinolin-9-yl)phenyl)propan-2-ylcarbamate

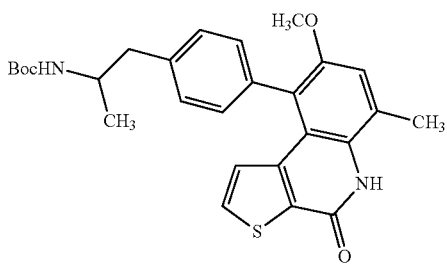 [SMILES: COc1cc(C)c2[nH]c(=O)c3sccc3c2c1-c1ccc(CC(C)NC(=O)OC(C)(C)C)cc1]

Following General Procedure B, 9-bromo-8-methoxy-6-methylthieno[2,3-c]quinolin-4(5H)-one (260 mg, 0.80 mmol) was reacted with tert-butyl 1-(4-(4,4,5,5-tetramethyl-1,3,2-dioxaborolan-2-yl)phenyl)propan-2-ylcarbamate (430 g, 1.2 mmol) to afford the desired product (212 mg, 55%) as a yellow oil: ESI MS m/z 479 $[C_{27}H_{30}N_2O_4S+H]^+$.

Example 577 tert-Butyl 1-(4-(6-chloro-%-methoxy-4-oxo-4,5-dihydrothieno[2,3-c]quinolin-9-yl)phenyl)ethylcarbamate

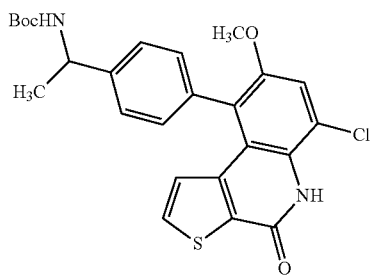 [SMILES: COc1cc(Cl)c2[nH]c(=O)c3sccc3c2c1-c1ccc(C(C)NC(=O)OC(C)(C)C)cc1]

Following General Procedure H, tert-butyl 1-(4-(8-methoxy-4-oxo-4,5-dihydrothieno[2,3-c]quinolin-9-yl)phenylethylcarbamate) (130 mg, 0.37 mmol) was reacted with NCS (64 mg, 0.48 mmol) to afford the desired product (58 mg, 32%) as a yellow solid. ESI MS m/z 485 $[C_{25}H_{25}ClN_2O_4S+H]^+$.

Example 578

(S)-tert-Butyl 1-(4-(6-chloro-8-methoxy-4-oxo-4,5-dihydrothieno[2,3-c]quinolin-9-yl)phenyl)propyl(methyl)carbamate

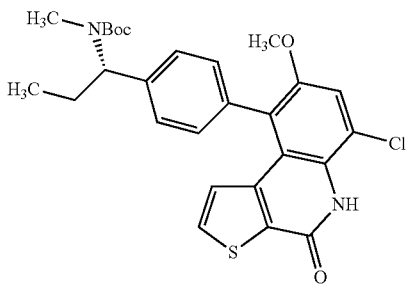 [SMILES: CC[C@@H](c1ccc(-c2c(OC)cc(Cl)c3[nH]c(=O)c4sccc4c23)cc1)N(C)C(=O)OC(C)(C)C]

Following General Procedure H, ((S)-tert-butyl 1-(4-(8-methoxy-4-oxo-4,5-dihydrothieno[2,3-c]quinolin-9-yl)phenyl)propyl(methyl)carbamate) (200 mg, 0.41 mmol) was reacted with NCS (68 mg, 0.50 mmol) to afford the desired product (130 mg, 61%) as a yellow solid: ESI MS m/z 513 $[C_{27}H_{29}ClN_2O_4S+H]^+$.

Example 579

(S)-tert-Butyl 2-(4-(6-chloro-8-methoxy-4-oxo-4,5-dihydrothieno[2,3-c]quinolin-9-yl)phenyl)propylcarbamate

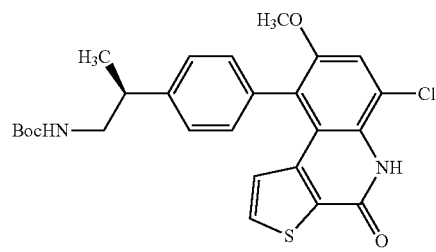 [SMILES: COc1cc(Cl)c2[nH]c(=O)c3sccc3c2c1-c1ccc([C@H](C)CNC(=O)OC(C)(C)C)cc1]

Following General Procedure H, (S)-tert-butyl 2-(4-(8-methoxy-4-oxo-4,5-dihydrothieno[2,3-c]quinolin-9-yl)phenyl)propylcarbamate (500 mg, 1.08 mmol) was reacted with NCS (175 mg, 1.29 mmol)) to afford the desired product (310 mg, 58%) as a yellow solid: ESI MS m/z 499 $[C_{26}H_{27}ClN_2O_4S+H]^+$.

Example 580 tert-Butyl (1-(4-(6-chloro-8-methoxy-4-oxo-4,5-dihydrothieno[2,3-c]quinolin-9-yl)phenyl)cyclopropyl)methylcarbamate

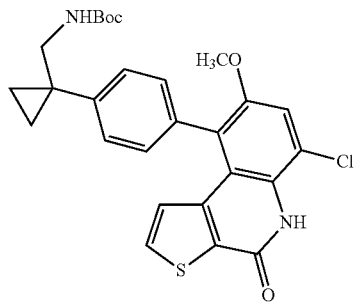 [SMILES: COc1cc(Cl)c2[nH]c(=O)c3sccc3c2c1-c1ccc(C2(CNC(=O)OC(C)(C)C)CC2)cc1]

Following General Procedure H, tert-butyl (1-(4-(8-methoxy-4-oxo-4,5-dihydrothieno[2,3-c]quinolin-9-yl phenyl)cyclopropyl)methylcarbamate (300 mg, 0.629 mmol) was reacted with NCS (85 mg, 0.629 mmol) to afford the desired product (250 mg, 78%) as a yellow solid: ESI MS m/z 511 $[C_{27}H_{27}ClN_2O_4S+H]^+$.

Example 581 tert-Butyl 2-chloro-4-(6-chloro-8-methoxy-4-oxo-4,5-dihydrothieno[2,3-c]quinolin-9-yl)phenethylcarbamate

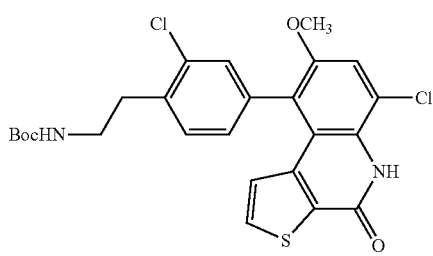 [SMILES: COc1cc(Cl)c2[nH]c(=O)c3sccc3c2c1-c1ccc(CCNC(=O)OC(C)(C)C)c(Cl)c1]

Following General Procedure H, tert-butyl 2-chloro-4-(8-methoxy-4-oxo-4,5-dihydrothieno[2,3-c]quinolin-9-yl)phenethylcarbamate (127 mg, 0.26 mmol) was reacted with NCS (43 mg, 0.312 mmol) to afford the desired product (70 mg, 52%) as a yellow solid: ESI MS m/z 519 $[C_{25}H_{24}Cl_2N_2O_4S+H]^+$.

Example 582 tert-Butyl 2-(4-(6-chloro-8-methoxy-4-oxo-4,5-dihydrothieno[2,3-c]quinolin-9-yl)phenyl)butylcarbamate

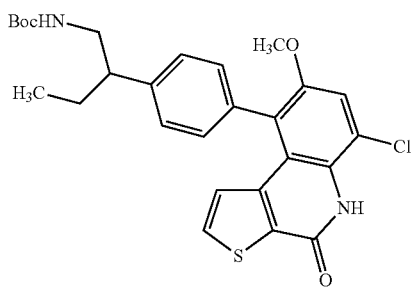 [SMILES: CCC(CNC(=O)OC(C)(C)C)c1ccc(-c2c(OC)cc(Cl)c3[nH]c(=O)c4sccc4c23)cc1]

Following General Procedure H, tert-butyl 2-(4-(8-methoxy-4-oxo-4,5-dihydrothieno[2,3-c]quinolin-9-yl)phenyl)butylcarbamate (100 mg, 0.21 mmol) in (DMF) was reacted with NCS (34 mg, 0.25 mmol) to afford the desired product (65 mg, 61%) as a yellow solid: ESI MS m/z 513 $[C_{27}H_{29}ClN_2O_4S+H]^+$.

Example 583 tert-Butyl 4-(6-chloro-8-methoxy-4-oxo-4,5-dihydrothieno[2,3-c]quinolin-9-yl)phenethyl(methyl)carbamate

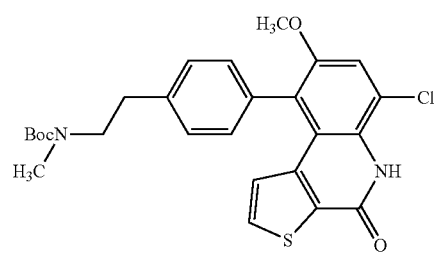 [SMILES: COc1cc(Cl)c2[nH]c(=O)c3sccc3c2c1-c1ccc(CCN(C)C(=O)OC(C)(C)C)cc1]

Following General Procedure H, tert-butyl 4-(8-methoxy-4-oxo-4,5-dihydrothieno[2,3-c]quinolin-9-yl)phenethyl(methyl)carbamate (200 mg, 0.43 mmol) in (DMF) was reacted with NCS (70 mg, 0.50 mmol) to afford the desired product (120 mg, 55%) as a yellow solid: ESI MS m/z 500 $[C_{26}H_{27}ClN_2O_4S+H]^+$.

Example 584

(R)-tert-Butyl 1-(4-(6-chloro-8-methoxy-4-oxo-4,5-dihydrothieno[2,3-c]quinolin-9-yl)phenyl)ethylcarbamate

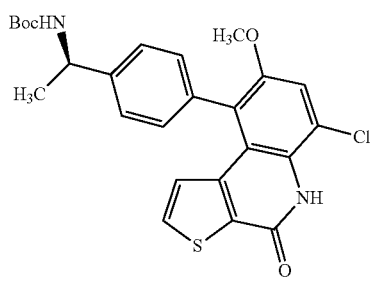 [SMILES: COc1cc(Cl)c2[nH]c(=O)c3sccc3c2c1-c1ccc([C@@H](C)NC(=O)OC(C)(C)C)cc1]

Following General Procedure H, (R)-tert-butyl 1-(4-(8-methoxy-4-oxo-4,5-dihydrothieno[2,3-c]quinolin-9-yl)phenyl)ethylcarbamate (300 mg, 0.67 mmol) was reacted with NCS (110 mg, 0.87 mmol) to afford the desired product (27 mg, 11%) as a yellow solid: ESI MS m/z 485 $[C_{25}H_{25}ClN_2O_4S+H]^+$.

Example 585 tert-Butyl 4-(6-chloro-8-methoxy-4-oxo-4,5-dihydrothieno[2,3-c]quinolin-9-yl)-2-fluorophenethylcarbamate

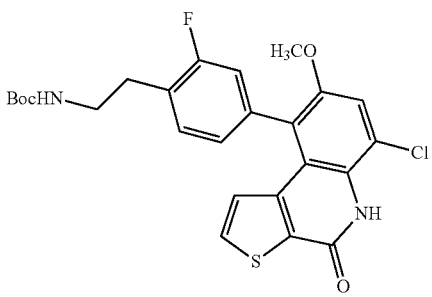 [SMILES: COc1cc(Cl)c2[nH]c(=O)c3sccc3c2c1-c1ccc(CCNC(=O)OC(C)(C)C)c(F)c1]

Following General Procedure H, tert-butyl 2-fluoro-4-(8-methoxy-4-oxo-4,5-dihydrothieno[2,3-c]quinolin-9-yl)phenethylcarbamate (300 mg, 0.64 mmol) was reacted with NCS (94 mg, 0.71 mmol) to afford the desired product (150 mg, 46%) as a yellow solid. ESI MS m/z 503 $[C_{25}H_{21}ClFN_2O_4S+H]^+$.

Example 586 tert-Butyl 1-(4-(6-chloro-8-methoxy-4-oxo-4,5-dihydrothieno[2,3-c]quinolin-9-yl)phenyl)propan-2-ylcarbamate

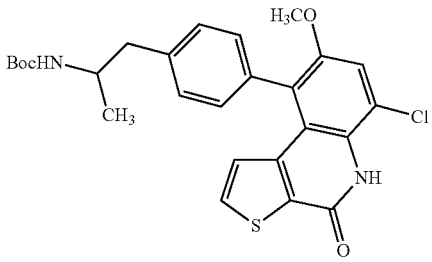 [SMILES: COc1cc(Cl)c2[nH]c(=O)c3sccc3c2c1-c1ccc(CC(C)NC(=O)OC(C)(C)C)cc1]

Following General Procedure H, tert-butyl 1-(4-(8-methoxy-4-oxo-4-oxo-4,5-dihydrothieno[2,3-c]quinolin-9-yl)phenyl)propan-2-ylcarbamate (220 mg, 0.47 mmol) was reacted with NCS (69 mg, 0.52 mmol) to afford the desired product (60 mg, 26%) as a brown solid. ESI MS m/z 499 $[C_{26}H_{27}ClN_2O_4S+H]^+$.

Example 1041

9-(4-(1-Aminoethyl)phenyl)-6-chloro-8-hydroxythieno[2,3-c]quinolin-4(5H)-one Hydrochloride

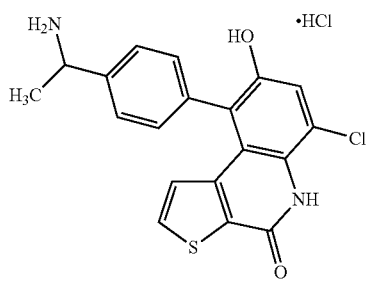 [SMILES: Cl ; CC(N)c1ccc(-c2c(O)cc(Cl)c3[nH]c(=O)c4sccc4c23)cc1]

Following General Procedure F, tert-butyl 1-(4-(6-chloro-8-methoxy-4-oxo-4,5-dihydrothieno[2,3-c]quinolin-9-yl)phenyl)ethylcarbamate (50 mg, 0.10 mmol) was treated with BBr$_3$ (1.0 M in CH$_2$Cl$_2$, 2 mL, 2 mmol) to afford the desired product (21 mg, 58%) as a light yellow solid (21 mg, 58%): $^1$H NMR (500 MHz, CD$_4$OD) δ 7.65 (dt, J=5.2, 3.4 Hz, 2H), 7.59 (d, J=5.4 Hz, 1H), 7.41 (dt, J=4.0, 2.6 Hz, 2H), 7.30 (s, 1H), 6.07 (d, J=: 5.4 Hz, 1H), 4.62 (q, J=6.8 Hz, 1H), 1.76 (d, J=6.9 Hz, 3H); ESI MS m/z 371 $[C_{19}H_{15}ClN_1O_2S+H]^+$; HPLC 97.8% (AUC), $t_R$=9.72 min.

Example 1052

(R)-8-Hydroxy-9-(4-(1-(methylamino)ethyl)phenyl)thieno[2,3-c]quinolin-4(5)-one Hydrochloride

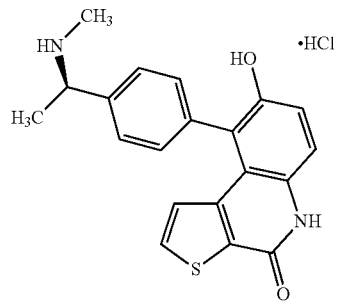 [SMILES: CN[C@H](C)c1ccc(-c2c(O)ccc3[nH]c(=O)c4sccc4c23)cc1 ; Cl]

Following General Procedure F, (R)-tert-butyl 1-(4-(8-methoxy-4-oxo-4,5-dihydrothieno[2,3-c]quinolin-9-yl)phenyl)ethyl(methyl)carbamate (120 mg, 0.25 mmol was treated with BBr$_3$ (1.0 M in CH$_2$Cl$_2$, 3 mL, 3 mmol) to afford the desired product (50 mg, 56%) as a light yellow solid: $^1$H NMR (500 MHz, CD$_3$OD) δ 7.64 (ddd, J=7.1, 5.6, 2.3 Hz, 2H), 7.57 (d, J=5.4 Hz, 1H), 7.49-7.39 (m, 3H), 7.18 (d, J=8.9 Hz, 1H), 6.04 (d, J=5.4 Hz, 1H), 4.48 (q, J=7.0 Hz, 1H), 2.72 (s, 3H), 1.80 (d, J=6.9 Hz, 3H); ESI MS m/z 351 $[C_{20}H_{18}N_2O_2S+H]^+$; HPLC 97.6% (AUC), $t_R$=7.82 min.

Example 1081

(R)-9-(4-(1-Aminoethyl)phenyl)-6-chloro-8-hydroxythieno[2,3-c]quinolin-4(5H)-one Hydrochloride

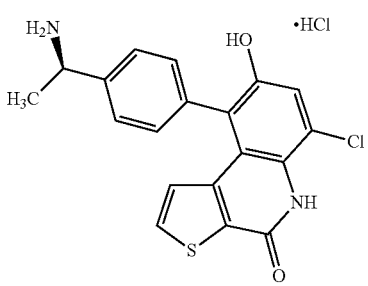 [SMILES: Cl ; C[C@@H](N)c1ccc(-c2c(O)cc(Cl)c3[nH]c(=O)c4sccc4c23)cc1]

Following General Procedure F, tert-butyl 1-(4-(6-chloro-8-methoxy-4-oxo-4,5-dihydrothieno[2,3-c]quinolin-9-yl)phenyl)ethylcarbamate (0.35 mg, 0.07 mmol) was treated with BBr$_3$ (1.0 M in CH$_2$Cl$_2$, 2 mL, 2 mmol) to afford the desired product (23 mg, 84%) as a light yellow solid: $^1$H NMR (500 MHz, CD$_3$OD) δ 7.67-7.61 (m, 2H), 7.59 (d, J=5.4 Hz, 1H), 7.44-7.39 (m, 2H), 7.30 (s, 1H), 6.07 (d, J=5.4 Hz, 1H), 4.62 (q, J=6.8 Hz, 1H), 1.76 (d, J=6.9 Hz, 3H); ESI MS m/z 371 [C$_{19}$H$_{15}$ClN$_2$O$_2$S+H]$^+$; HPLC 97.2% (AUC), t$_R$=9.58 min.

Example 1209

9-(4-(3-(Aminomethyl)pentan-3-yl)phenyl)-8-hydroxythieno[2,3-c]quinolin-4(5H)-one Hydrochloride

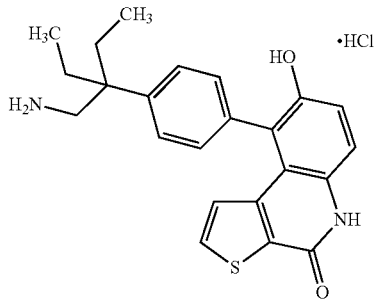 [SMILES: CCC(CC)(CN)c1ccc(-c2c(O)ccc3[nH]c(=O)c4sccc4c23)cc1 ; Cl]

Following General Procedure F, tert-butyl 2-ethyl-2-(4-(8-methoxy-4-oxo-4,5-dihydrothieno[2,3-c]quinolin-9-yl)phenyl)butyl)butylcarbamate (20 mg, 0.05 mmol) was treated with BBr$_3$ (1.0 M in CH$_2$Cl$_2$, 3 mL, 3 mmol) to afford the desired product (7.0 mg, 36%) as a light yellow solid: $^1$H NMR (500 MHz, CD$_3$OD) δ 7.63 (d, J=8.4 Hz, 2H), 7.54 (d, J=5.4 Hz, 1H), 7.45-7.37 (m, 3H), 7.19 (dd, J=8.9, 2.2 Hz, 1H), 6.08 (d, J=5.4 Hz, 1H), 3.29 (s, 2H), 1.97 (dt, J=14.6, 7.2 Hz, 4H), 0.93 (t, J=7.4 Hz, 6H). ESI MS m/z 393 [C$_{23}$H$_{24}$N$_2$O$_2$S+H]$^+$; HPLC 99.6% (AUC), t$_R$=9.47 min.

Example 1213

9-(4-(2-Aminoethyl)-3-fluorophenyl)-6-bromo-8-hydroxythieno[2,3-c]quinolin-4(5H)-one Hydrochloride

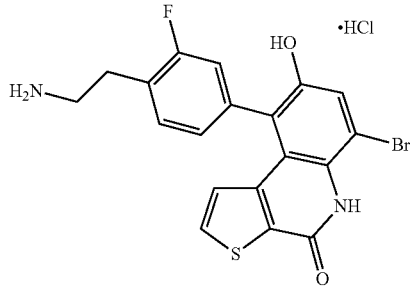 [SMILES: NCCc1ccc(-c2c(O)cc(Br)c3[nH]c(=O)c4sccc4c23)cc1F ; Cl]

Following General Procedure F, tert-butyl 4-(6-bromo-8-methoxy-4-oxo-4,5-dihydrothieno[2,3-c]quinolin-9-yl)-2-fluorophenethylcarbamate (100 mg, 0.18 mmol) was treated with BBr$_3$ (1.0 M in CH$_2$Cl$_2$, 5 mL, 5 mmol) to afford the desired product as an off-white solid (24 mg, 30%): $^1$H NMR (500 MHz, CD$_3$OD) δ 7.69 (d, J=5.4 Hz, 1H), 7.51 (t, J=7.7 Hz, 1H), 7.48 (s, 1H), 7.14 (d, J=9.0 Hz, 2H), 6.18 (d, J=5.4 Hz, 1H), 3.37-3.20 (m, 3H), 3.14-3.04 (m, 1H); ESI MS m/z 433 [C$_{19}$H$_{14}$BrFN$_2$O$_2$S+H]$^+$; HPLC 98.6% (AUC), t$_R$=9.12 min.

Example 1217

9-(4-(2-Aminoethyl)-3-fluorophenyl)-8-hydroxy-6-methylthieno[2,3-c]quinolin-4(5H)-one Hydrochloride

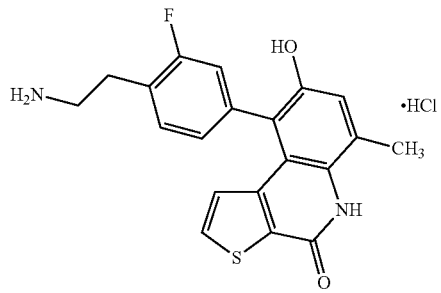 [SMILES: Cc1cc(O)c(-c2ccc(CCN)c(F)c2)c2c1[nH]c(=O)c1sccc12 ; Cl]

Following General Procedure F, tert-butyl 2-fluoro-4-(8-methoxy-6-methyl-4-oxo-4,5-dihydrothieno[2,3-c]quinolin-9-yl)phenethylcarbamate (78 mg, 0.16 mmol) was treated with BBr$_3$ (1.0 M in CH$_2$Cl$_2$, 3 mL, 3 mmol) to afford the desired product as a yellow solid (16 mg, 27%): $^1$H NMR (500 MHz, CD$_3$OD) δ 7.62 (d, J=5.4 Hz, 1H), 7.49 (t, J=7.9 Hz, 1H), 7.14-7.05 (m, 3H), 6.21 (d, J=5.4 Hz, 1H), 3.36-3.21 (m, 2H), 3.13-3.04 (m, 1H), 2.57 (s, 3H); ESI MS m/z 369 [C$_{20}$H$_{17}$FN$_2$O$_2$S+H]$^+$; HPLC 97.3% (AUC), t$_R$=8.47 min.

Example 1166

(R)-9-(4(1-Aminopropan-2-yl)phenyl)-6-chloro-8-hydroxythieno[2,3-c]quinolin-4(5H)-one Hydrochloride

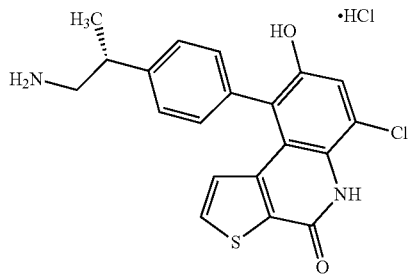 [SMILES: Cl ; C[C@@H](CN)c1ccc(-c2c(O)cc(Cl)c3[nH]c(=O)c4sccc4c23)cc1]

Following General Procedure F, (R)-tert-butyl 2-(4-(6-chloro-8-methoxy-4-oxo-4,5-dihydrothieno[2,3-c]quinolin-9-yl)phenyl)propylcarbamate (100 mg, 0.20 mmol) was treated with BBr$_3$ (1.0 M in CH$_2$Cl$_2$, 5 mL, 5 mmol) to afford the desired product as a white solid (23 mg, 30%): $^1$H NMR (500 MHz, CD$_3$OD) δ 7.63 (d, J=5.4 Hz, 1H), 7.56 (dd, J=7.9, 1.9 Hz, 1H), 7.47 (dd, J=7.8, 1.9 Hz, 1H), 7.39-7.28 (m, 3H),

Example 1174

9-(4-(1-Aminopropan-2-yl)-3-fluorophenyl)-8-hydroxythieno[2,3-c]quinolin-4(5H)-one Hydrochloride

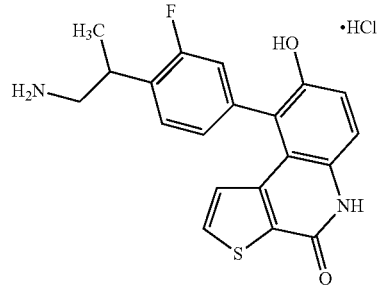 [SMILES: CC(CN)c1ccc(-c2c(O)ccc3[nH]c(=O)c4sccc4c23)cc1F ; Cl]

Following General Procedure F, tert-butyl 2-(2-fluoro-4-(8-methoxy-4-oxo-4,5-dihydrothieno[2,3-c]quinolin-9-yl)phenyl)propylcarbamate (120 mg, 0.25 mmol) was treated with BBr$_3$ (1.0 M in CH$_2$Cl$_2$, 5 mL, 5 mmol) to afford the desired product as an off-white solid (35 mg, 37%). $^1$H NMR (500 MHz, CD$_3$OD) δ 7.65 (dd, J=5.4, 3.4 Hz, 1H), 7.59 (s, 1H), 7.51 (s, 1H), 7.43 (dd, J=8.9, 2.3 Hz, 1H), 7.24-7.09 (m, 2H), 6.22 (dd, J=9.4, 5.4 Hz, 1H), 3.62 (d, J=7.2 Hz, 1H), 3.49-3.25 (m, 2H), 1.52 (t, J=6.7 Hz, 3H); ESI MS m/z 369 [C$_{20}$H$_{17}$FN$_2$O$_2$S+H]$^+$; HPLC 99.3% (AUC), $t_R$=8.37 min.

Example 1187

(R)-8-Hydroxy-9-(4-(1-(methylamino)propan-2-yl)phenyl)thieno[2,3-c]quinolin-4(5H)-one Hydrochloride

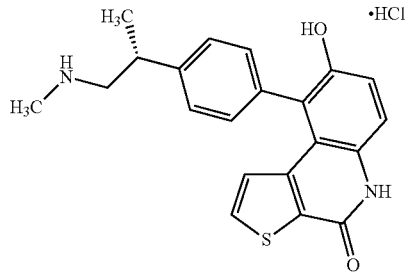 [SMILES: Cl ; CNC[C@H](C)c1ccc(-c2c(O)ccc3[nH]c(=O)c4sccc4c23)cc1]

Following General Procedure F (R)-tert-butyl 2-(4-(8-methoxy-4-oxo-4,5-dihydrothieno[2,3-c]quinolin-9-yl)phenyl)propyl(methyl)carbamate (250 mg, 0.52 mmol) was treated with BBr$_3$ (1.0 M in CH$_2$Cl$_2$, 4 mL, 4 mmol) to afford the desired product as an light yellow solid (39 mg, 42%). $^1$H NMR (500 MHz, CD$_3$OD) δ 7.58 (dd, J=10.8, 3.6 Hz, 2H), 7.50-7.46 (m, 1H), 7.42 (d, J=8.9 Hz, 1H), 7.38 (dd, J=7.9, 1.8 Hz, 1H), 7.32 (dd, J=7.7, 1.7 Hz, 1H), 7.18 (d, J=8.9 Hz, 1H), 6.14 (d, J=5.4 Hz, 1H), 3.37-3.28 (m, 3H), 2.75 (s, 3H), 1.50 (d, J=6.7 Hz, 3H); ESI MS m/z 365 [C$_{21}$H$_{20}$N$_2$O$_2$S+H]$^+$; HPLC 97.1% (AUC), $t_R$=8.43 min.

Example 1190

9-(4-(1-Aminopropan-2-yl)-3-fluorophenyl)-8-hydroxy-6-methylthieno[2,3-c]quinolin-4(5H)-one Hydrochloride

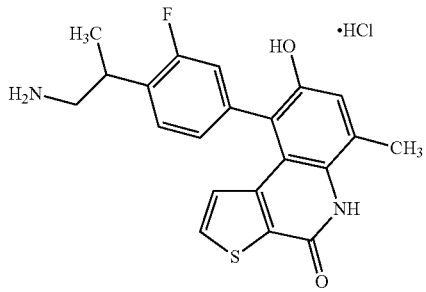 [SMILES: Cc1cc(O)c(-c2ccc(C(C)CN)c(F)c2)c2c1[nH]c(=O)c1sccc12 ; Cl]

Following General Procedure F, tert-butyl 2-(2-fluoro-4-(8-methoxy-6-methyl-4-oxo-4,5-dihydrothieno[2,3-e]quinolin-9-yl)phenyl)propylcarbamate (120 mg, 0.25 mmol) was treated with BBr$_3$ (1.0 M in CH$_2$Cl$_2$, 5 mL, 5 mmol) to afford the desired product as an off-white solid (39 mg, 42%). $^1$H NMR (500 MHz, CD$_3$OD) δ 7.64 (dd, J=5.4, 4.6 Hz, 1H), 7.57 (t, J=7.8 Hz, 1H), 7.48 (t, J=7.8 Hz, 1H), 7.22-7.05 (m, 3H), 6.23 (dd, J=8.4, 5.4 Hz, 1H), 3.61 (dd, J=14.4, 7.2 Hz, 1H), 3.51-3.23 (m, 2H), 2.57 (s, 3H), 1.52 (t, J=7.0 Hz, 3H); ESI MS m/z 383 [C$_{21}$H$_{19}$FN$_2$O$_2$S+H]$^+$; HPLC 96.1% (AUC), $t_R$=8.85 min.

Example 1133

9-(4-(2-Aminoethyl)phenyl)-6-chloro-8-hydroxythieno[2,3-c]quinolin-4(5H)-one hydrochloride

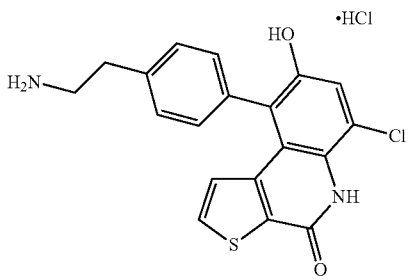 [SMILES: Cl ; NCCc1ccc(-c2c(O)cc(Cl)c3[nH]c(=O)c4sccc4c23)cc1]

Following General Procedure F, tert-butyl 4-(6-chloro-8-methoxy-4-oxo-4,5-dihydrothieno[2,3-c]quinolin-9-yl)phenethylcarbamate (79 mg, 0.25 mmol) was treated with BBr$_3$ (1.0 M in CH$_2$Cl$_2$, 9 mL, 9 mmol) to afford the desired product as a yellow solid (12 mg, 20%). $^1$H NMR (500 MHz, CD$_3$OD) δ 7.61 (d, J=5.4 Hz, 1H), 7.49 (d, J=8.1 Hz, 2H), 7.31 (d, J=7.0 Hz, 3H), 6.10 (d, J=5.4 Hz, 1H), 3.37-3.27 (m, 2H), 3.12 (t, J=7.6 Hz, 2H); ESI MS m/z 371 [$C_{19}H_{15}ClN_2O_2S+H$]$^+$; HPLC 96.9% (AUC), $t_R$=8.83 min.

Example 1142

9-(4-(2-Aminoethyl)phenyl)-6-bromo-8-hydroxythieno[2,3-c]quinolin-4(5H)-one Hydrochloride

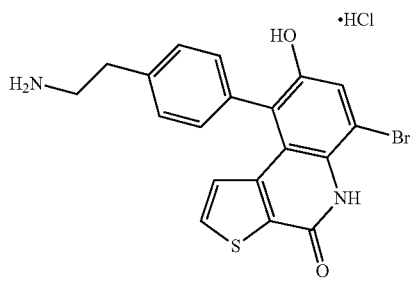 [SMILES: Cl ; NCCc1ccc(-c2c(O)cc(Br)c3[nH]c(=O)c4sccc4c23)cc1]

Following General Procedure F, tert-butyl 4-(6-chloro-8-methoxy-4-oxo-4,5-dihydrothieno[2,3-c]quinolin-9-yl)phenethylcarbamate (410 mg, 0.76 mmol) was treated with BBr$_3$ (1.0 M in CH$_2$Cl$_2$, 10 mL, 10 mmol) to afford the desired product as an off-white solid (58 mg, 18%): $^1$H NMR (500 MHz, CD$_3$OD) δ 7.62 (d, J=5.4 Hz, 1H), 7.53-7.45 (m, 3H), 7.31 (d, J=8.1 Hz, 2H), 6.10 (d, J=5.4 Hz, 1H), 3.31-3.28 (m, 2H), 3.11 (t, J=7.6 Hz, 2H); ESI MS m/z 415 [$C_{19}H_{15}BrN_2O_2S+H$]$^+$; HPLC 94.9% (AUC), $t_R$=9.02 min.

Example 1176

(R)-9-(4-(1-Aminopropan-2-yl)phenyl)-6-bromo-8-hydroxythieno[2,3-c]quinolin-4(5H)-one Hydrochloride

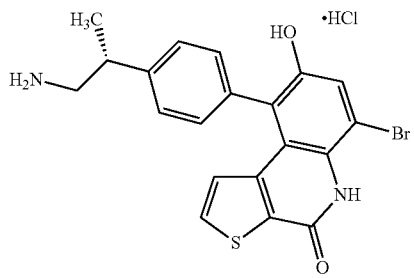 [SMILES: Cl ; C[C@@H](CN)c1ccc(-c2c(O)cc(Br)c3[nH]c(=O)c4sccc4c23)cc1]

Following General Procedure F, (R)-tert-butyl 2-(4-(8-methoxy-4-oxo-4,5-dihydrothieno[2,3-c]quinolin-9-yl)phenyl)propylcarbamate (60 mg, 0.11 mmol) was reacted with BBr$_3$ (1.0 M in CH$_2$Cl$_2$, 6 mL, 6 mmol) to afford the desired product as an off-white solid (24 mg, 51%): $^1$HNMR (500 MHz, CD$_3$OD) δ 7.64 (d, J=5.4 Hz, 1H), 7.56 (dd, J=7.9, 1.9 Hz, 1H), 7.50-7.45 (m, 2H), 7.37 (dd, J=7.9, 1.8 Hz, 1H), 7.32 (dd, J=7.7, 1.7 Hz, 1H), 6.12 (d, J=5.4 Hz, 1H), 3.36-3.18 (m, 3H), 1.49 (d, J=6.5 Hz, 3H): ESI MS m/z 429 [$C_{20}H_{17}BrN_2O_2S+H$]$^+$; HPLC >99% (AUC), $t_R$=9.30 min.

Example 1136

9-(4-(1-Aminopropan-2-yl)phenyl)-6-chloro-8-hydroxythieno[2,3-c]quinolin-4(5H)-one Hydrochloride

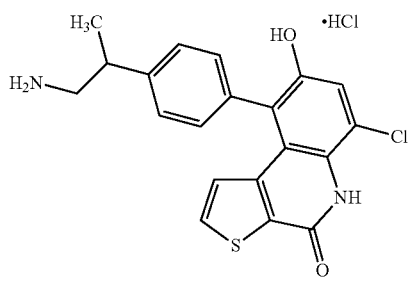 [SMILES: Cl ; CC(CN)c1ccc(-c2c(O)cc(Cl)c3[nH]c(=O)c4sccc4c23)cc1]

Following General Procedure F, tert-butyl 2-(4-(6-chloro-8-methoxy-4-oxo-4,5-dihydrothieno[2,3-c]quinolin-9-yl)phenyl)propylcarbamate (40 mg, 0.08 mmol) was treated with BBr$_3$ (1.0 M in CH$_2$Cl$_2$, 3 mL, 3 mmol) to afford the desired product as an yellow solid (13 mg, 40%): $^1$H NMR (500 MHz, CD$_3$OD) δ 7.63 (d, J=5.4 Hz, 1H), 7.56 (dd, J=7.9, 1.8 Hz, 1H), 7.48 (dd, J=7.8, 1.8 Hz, 1H), 7.40-7.28 (m, 3H), 6.12 (d, J=5.4 Hz, 1H), 3.29-3.19 (m, 3H), 1.49 (d, J=6.3 Hz, 3H); ESI MS m/z 385 [$C_{20}H_{17}ClN_2O_2S+H$]$^+$; HPLC 99% (AUC), $t_R$=8.12 min.

Example 1132

(R)-6-Chloro-8-hydroxy-9-(4-(1-(methylamino)ethyl)phenyl)thieno[2,3-c]quinolin-4(5H)-one Hydrochloride

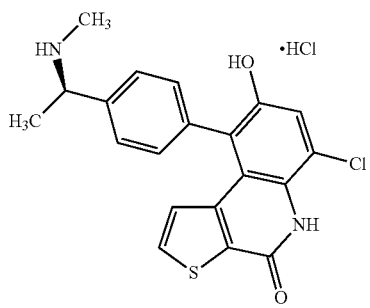 [SMILES: CN[C@H](C)c1ccc(-c2c(O)cc(Cl)c3[nH]c(=O)c4sccc4c23)cc1 ; Cl]

Following General Procedure F, (R)-tert-butyl 1-(4-(6-chloro-8-methoxy-4-oxo-4,5-dihydrothieno[2,3-c]quinolin-9-yl)phenyl)ethyl(methyl)carbamate (43 mg, 0.09 mmol) was treated with BBr$_3$ (1.0 M in CH$_2$Cl$_2$, 4 mL, 4 mmol) to afford the desired product as a white solid (15 mg, 45%): $^1$H NMR (500 MHz, CD$_3$OD) δ 7.69-7.59 (m, 3H), 7.45 (ddd, J=7.0, 5.8, 2.1 Hz, 2H), 7.30 (s, 1H), 6.03 (d, J=5.4 Hz, 1H), 4.48 (q, J=6.9 Hz, 1H), 2.72 (s, 3H), 1.79 (d, J=6.9 Hz, 3H); ESI MS m/z 385 [C$_{20}$H$_{17}$ClN$_2$O$_2$S+H]$^+$; HPLC 97.1% (AUC), t$_R$=8.85 min.

Example 1219

9-(4-(2-Aminoethyl)-3-fluorophenyl)-6-chloro-8-hydroxythieno[2,3-c]quinolin-4(5H)-one Hydrochloride

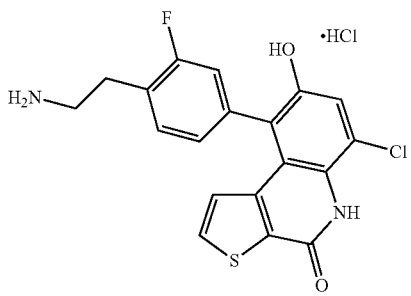 [SMILES: NCCc1ccc(-c2c(O)cc(Cl)c3[nH]c(=O)c4sccc4c23)cc1F ; Cl]

Following General Procedure F, tert-butyl 4-(6-chloro-8-methoxy-4-oxo-4,5-dihydrothieno[2,3-c]quinolin-9-yl)-2-fluorophenethylcarbamate (70 mg, 0.14 mmol) was treated with BBr$_3$ (1.0 M in CH$_2$Cl$_2$, 6 mL, 6 mmol) to afford the desired product as a white solid (26 mg, 48%); $^1$H NMR (500 MHz, CD$_3$OD) δ 7.67 (d, J=5.4 Hz, 1H), 7.51 (t, J=7.7 Hz, 1H), 7.30 (s, 1H), 7.17-7.11 (m, 2H), 6.18 (d, J=5.4 Hz, 1H), 3.35-3.20 (m, 2H), 3.14-3.04 (m, 1H); ESI MS m/z 389 [C$_{19}$H$_{14}$ClFN$_2$O$_2$S+H]$^+$; HPLC >99% (AUC), t$_R$=8.93 min.

Example 1228

9-(4-(1-Amino-2-methylpropan-2-yl)phenyl)-8-hydroxy-6-methylthieno[2,3-c]quinolin-4(5H)-one Hydrochloride

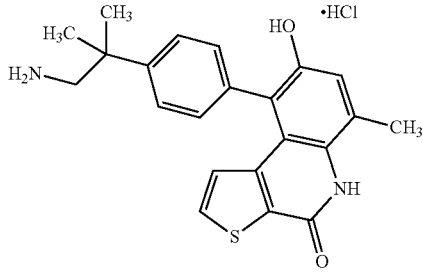 [SMILES: Cc1cc(O)c(-c2ccc(C(C)(C)CN)cc2)c2c1[nH]c(=O)c1sccc12 ; Cl]

Following General Procedure F, tert-butyl 2-(4-(8-methoxy-6-methyl-4-oxo-4,5-dihydrothieno[2,3-c]quinolin-9-yl)phenyl)-2-methylpropylcarbamate (40 mg, 0.08 mmol) was treated with BBr$_3$ (1.0 M in CH$_2$Cl$_2$, 4 mL, 4 mmol) to afford the desired product as a brown solid (21 mg, 67%); $^1$H NMR (500 MHz, CD$_3$OD) δ 7.64 (d, J=8.4 Hz, 2H), 7.58 (d, J=5.4 Hz, 1H), 7.36 (d, J=8.3 Hz, 2H), 7.09 (s, 1H), 6.18 (d, J=5.4 Hz, 1H), 3.28 (s, 2H), 2.58 (s, 3H), 1.58 (s, 6H); ESI MS m/z 379 [C$_{22}$H$_{22}$N$_2$O$_2$S+H]$^+$; HPLC 96.5% (AUC), t$_R$=9.04 min.

Example 1242

9-(4-(2-Aminopropyl)phenyl)-8-hydroxy-6-methylthieno[2,3-c]quinolin-4(5H)-one Hydrochloride

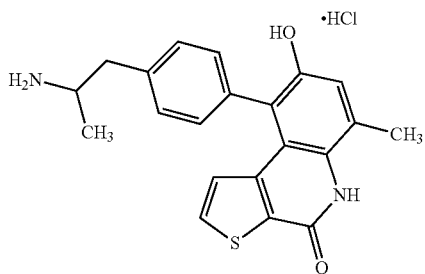 [SMILES: Cl ; Cc1cc(O)c(-c2ccc(CC(C)N)cc2)c2c1[nH]c(=O)c1sccc12]

Following General Procedure F, tert-butyl 1-(4-(8-methoxy-6-methyl-4-oxo-4,5-dihydrothieno[2,3-c]quinolin-9-yl)phenyl)propan-2-ylcarbamate (90 mg, 0.19 mmol) was treated with BBr$_3$ (1.0 M in CH$_2$Cl$_2$, 8 mL, 8 mmol) to afford the desired product as a light brown solid (25 mg, 53%): $^1$H NMR (500 MHz, CD$_3$OD) δ 7.57 (d, J=5.4 Hz, 1H), 7.45 (dd, J=20.6, 7.8 Hz, 2H), 7.32-7.26 (m, 2H), 7.09 (s, 1H), 6.12 (d, J=5.4 Hz, 1H), 3.65 (dd, J=13.7, 6.9 Hz, 1H), 3.14-2.99 (m, 2H), 2.57 (s, 3H), 1.41 (d, J=6.6 Hz, 3H); ESI MS m/z 365 [C$_{21}$H$_{20}$N$_2$O$_2$S+H]$^+$; HPLC 98.6% (AUC), t$_R$=8.68 min.

Example 1191

9-(4-(2-Aminoethyl)phenyl)-8-hydroxy-6-methylthieno[2,3-c]quinolin-4(5H)-one Hydrochloride

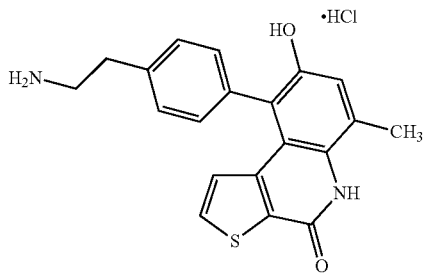 [SMILES: Cl ; Cc1cc(O)c(-c2ccc(CCN)cc2)c2c1[nH]c(=O)c1sccc12]

Following General Procedure F, tert-butyl 4-(8-methoxy-6-methyl-4-oxo-4,5-dihydrothieno[2,3-c]quinolin-9-yl)phenethylcarbamate (30 mg, 0.06 mmol) was treated with BBr$_3$ (1.0 M in CH$_2$Cl$_2$, 4 mL, 4 mmol) to afford the desired product as a light yellow solid (20 mg, 90%): $^1$H NMR (500 MHz, CD$_3$OD) δ 7.55 (d, J=5.4 Hz, 1H), 7.47 (d, J=8.1 Hz, 2H), 7.30 (d, J=8.1 Hz, 2H), 7.07 (d, J=0.8 Hz, 1H), 6.14 (d, J=5.4 Hz, 1H), 3.34-3.27 (m, 2H), 3.11 (t, J=7.5 Hz, 2H), 2.57 (s, 3H); ESI MS m/z 351 [C$_{20}$H$_{18}$N$_2$O$_2$S+H]$^+$; HPLC 98.4% (AUC), t$_R$=8.32 min.

Example 1364

8-Hydroxy-6-methyl-9-(4-(2-(methylamino)ethyl)phenyl)thieno[2,3-c]quinolin-4(5H)-one Hydrochloride

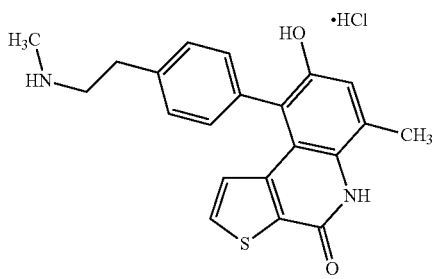

Following General Procedure F, 8-methoxy-6-methyl-9-(4-(2-(methylamino)ethyl)phenyl)thieno[2,3-c]quinolin-4(5H)-one (32 mg, 0.06 mmol) was treated with BBr$_3$ (1.0 M in CH$_2$Cl$_2$, 3 mL, 3 mmol) to afford the desired product as a light yellow solid (15 mg, 62%): $^1$H NMR (500 MHz, CD$_3$OD) δ 7.55 (d, J=5.4 Hz, 1H), 7.47 (d, J=8.1 Hz, 2H), 7.34-7.27 (m, 2H), 7.07 (d, J=0.7 Hz, 1H), 6.12 (d, J=5.4 Hz, 1H), 3.39 (t, J=7.6 Hz, 2H), 3.18-3.10 (m, 2H), 2.79 (s, 3H), 2.57 (s, 3H); ESI MS m/z 365 [(C$_{21}$H$_{20}$N$_2$O$_2$S+H]$^+$; HPLC >99% (AUC), t$_R$=8.41 min.

Example 1307

(R)-8-Hydroxy-6-methyl-9-(4-(1-(methylamino)propan-2-yl)phenyl)thieno[2,3-c]quinolin-4(5H)-one Hydrobromide

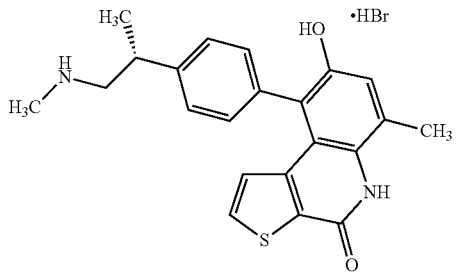

Following General Procedure F, (R)-tert-butyl 2-(4-(8-methoxy-6-methyl-4-oxo-4,5-dihydrothieno[2,3-c]quinolin-9-yl)phenyl)propyl(methyl)carbamate (2.08 g, 4.23 mmol) was treated with BBr$_3$ (1.0 M in CH$_2$Cl$_2$, 40 mL, 40 mmol) to afford the desired product as a yellow solid (1.05 g, 65%); $^1$H NMR (500 MHz, CD$_3$OD) δ 7.60-7.54 (m, 2H), 7.46 (dd, J=7.8, 1.9 Hz, 1H), 7.37 (dd, J=7.9, 1.8 Hz, 1H), 7.31 (dd, J=7.7, 1.7 Hz, 1H), 7.08 (d, J=0.8 Hz, 1H), 6.16 (d, J=5.4 Hz, 1H), 3.37-3.24 (m, 3H), 2.74 (s, 3H), 2.57 (s, 3H), 1.50 (d, J=6.8 Hz, 3H); ESI MS m/z 379 [C$_{22}$H$_{22}$N$_2$O$_2$S+H]$^+$; HPLC >99% (AUC), t$_R$=8.74 min.

Example 1169

(R)-9-(4-(1-Aminopropan-2-yl)phenyl)-8-hydroxy-6-methylthieno[2,3-c]quinolin-4(5H)-one Hydrobromide

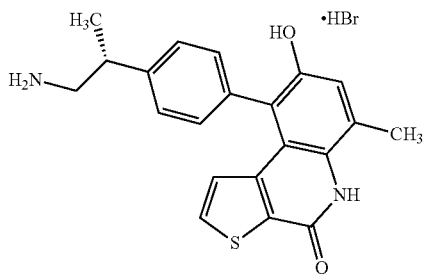 [SMILES: Br ; Cc1cc(O)c(-c2ccc([C@@H](C)CN)cc2)c2c1[nH]c(=O)c1sccc12]

Following General Procedure F, (R)-tert-butyl 2-(4-(8-methoxy-6-methyl-4-oxo-4,5-dihydrothieno[2,3-c]quinolin-9-yl)phenyl)propyl(methyl)carbamate (2.20 g, 4.60 mmol) was treated with BBr$_3$ (1.0 M in CH$_2$Cl$_2$, 50 mL, 50 mmol) to afford the desired product as a yellow solid (1.50 g, 73%): $^1$H NMR (500 MHz, CD$_3$OD) δ 7.58 (d, J=5.4 Hz, 1H), 7.55 (dd, J=7.9, 1.8 Hz, 1H), 7.45 (dd, J=7.8, 1.9 Hz, 1H), 7.35 (dd, J=7.9, 1.7 Hz, 1H), 7.30 (dd, J=7.7, 1.6 Hz, 1H), 7.08 (d, J=0.8 Hz, 1H), 6.17 (d, J=5.4 Hz, 1H), 3.36-3.19 (m, 3H), 2.57 (d, J=0.6 Hz, 3H), 1.50 (d, J=6.4 Hz, 3H); ESI MS m/z 365 [C$_{21}$H$_{20}$N$_2$O$_2$S+H]$^+$; HPLC 98.3% (AUC), t$_R$=8.64 min.

Example 587 tert-Butyl 4-(6-bromo-8-methoxy-4-oxo-4,5-dihydrothieno[2,3-c]quinolin-9-yl)-2-fluorophenethylcarbamate

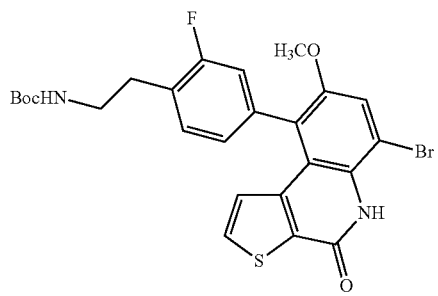

Following General Procedure I, tert-butyl 2-fluoro-4-(8-methoxy-4-oxo-4,5-dihydrothieno[2,3-c]quinolin-9-yl)phenethylcarbamate (1.1 g, 2.3 mmol) was reacted with NBS (540 mg, 3.1 mmol) to afford the desired product (920 mg, 70%) as a brown solid. ESI MS m/z 547 [C$_{25}$H$_{24}$BrFN$_2$O$_4$S+H]$^+$.

Example 588 tert-Butyl 2-(4-(6-bromo-8-methoxy-4-oxo-4,5-dihydrothieno[2,3-c]quinolin-9-yl)phenyl)-2-methylpropylcarbamate

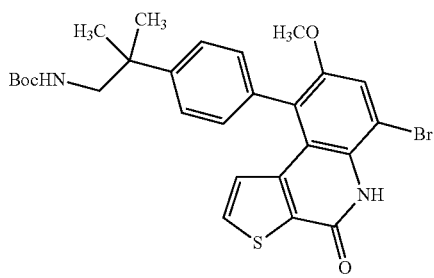 [SMILES: COc1cc(Br)c2[nH]c(=O)c3sccc3c2c1-c1ccc(C(C)(C)CNC(=O)OC(C)(C)C)cc1]

Following General Procedure I, tert-butyl 2-(4-(8-methoxy-4-oxo-4,5-dihydrothieno[2,3-c]quinolin-9-yl)phenyl)-2-methylpropylcarbamate (600 mg, 1.3 mmol) was reacted with NBS (330 mg, 1.9 mmol) to afford the desired product (350 mg, 51%) as a yellow solid: ESI MS m/z 557 $[C_{27}H_{29}BrN_2O_4S+H]^+$.

Example 589 tert-Butyl 2-(4-(6-bromo-8-methoxy-4-oxo-4,5-dihydrothieno[2,3-c]quinolin-9-yl)-2-fluorophenyl)propylcarbamate

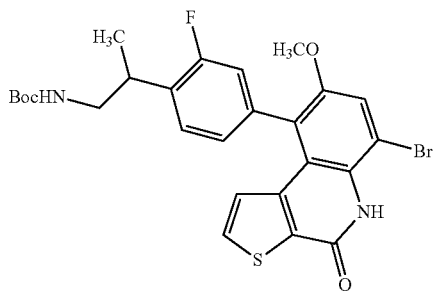 [SMILES: COc1cc(Br)c2[nH]c(=O)c3sccc3c2c1-c1ccc(C(C)CNC(=O)OC(C)(C)C)c(F)c1]

Following General Procedure I, tert-butyl 2-(2-fluoro-4-(8-methoxy-4-oxo-4,5-dihydrothieno[2,3-c]quinolin-9-yl)phenyl)propylcarbamate (500 mg, 1.0 mmol) was reacted with NBS (220 mg, 1.2 mmol) to afford the desired product (280 mg, 48%) as a brown oil. ESI MS m/z 561 $[C_{26}H_{26}BrFN_2O_4S+H]^+$.

Example 590 tert-Butyl 4-(6-bromo-8-methoxy-4-oxo-4,5-dihydrothieno[2,3-c]quinolin-9-yl)phenethylcarbamate

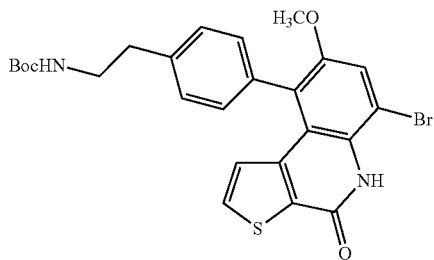 [SMILES: COc1cc(Br)c2[nH]c(=O)c3sccc3c2c1-c1ccc(CCNC(=O)OC(C)(C)C)cc1]

Following General Procedure I, tert-butyl 4-(8-methoxy-4-oxo-4,5-dihydrothieno[2,3-c]quinolin-9-yl)phenethylcarbamate (600 mg, 1.3 mmol) was reacted with NBS (280 mg, 1.5 mmol) to afford the desired product (410 mg, 60%) as a reddish brown solid. ESI MS m/z 529 $[C_{25}H_{25}BrN_2O_4S\,H]^+$.

Example 59

(R)-tert-Butyl 2-(4-(6-bromo-8-methoxy-4-oxo-4,5-dihydrothieno[2,3-c]quinolin-9-yl)phenyl)propylcarbamate

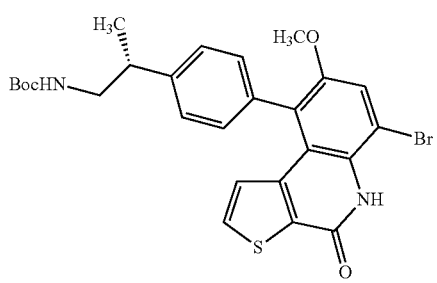 [SMILES: COc1cc(Br)c2[nH]c(=O)c3sccc3c2c1-c1ccc([C@@H](C)CNC(=O)OC(C)(C)C)cc1]

Following General Procedure I, (R)-tert-butyl 2-(4-(8-methoxy-4-oxo-4,5-dihydrothieno[2,3-c]quinolin-9-yl)phenyl)propylcarbamate (220 mg, 0.39 mmol) was reacted with NBS (90 mg, 0.51 mmol) to afford the desired product (60 mg, 28%) as a reddish oil: ESI MS m/z 543 $[C_{26}H_{27}BrN_2O_4S+H]^+$.

Example 592 tert-Butyl 2-fluoro-4-(8-methoxy-6-methyl-4-oxo-4,5-dihydrothieno[2,3-c]quinolin-9-yl)phenethylcarbamate

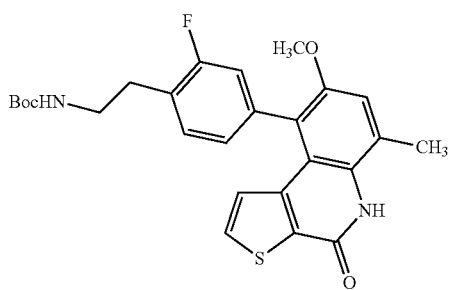 [SMILES: COc1cc(C)c2[nH]c(=O)c3sccc3c2c1-c1ccc(CCNC(=O)OC(C)(C)C)c(F)c1]

Following General Procedure I, tert-butyl 4-(6-bromo-8-methoxy-4-oxo-4,5-dihydrothieno[2,3-c]quinolin-9-yl)-2-fluorophenethylcarbamate (300 mg, 0.55 mmol) was reacted with trimethylboroxine (207 mg, 1.65 mmol) and Pd(pph$_3$)$_4$ (63 mg, 0.05 mmol) to afford the desired product (155 mg, 58%) as a brown solid. ESI MS m/z 483 $[C_{26}H_{27}FN_2O_4S+H]^+$.

Example 593 tert-Butyl 2-(2-fluoro-4-(8-methoxy-6-methyl-4-oxo-4,5-dihydrothieno[2,3-c]quinolin-9-yl)phenyl)propylcarbamate

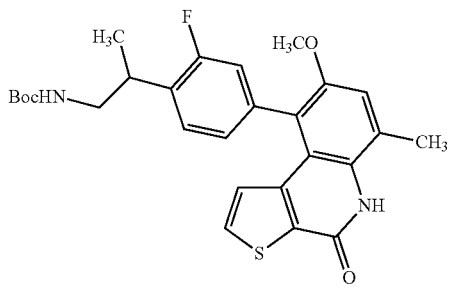 [SMILES: COc1cc(C)c2[nH]c(=O)c3sccc3c2c1-c1ccc(C(C)CNC(=O)OC(C)(C)C)c(F)c1]

Following General Procedure I, tert-butyl 2-(4-(6-bromo-8-methoxy-4-oxo-4,5-dihydrothieno[2,3-c]quinolin-9-yl)-2-fluorophenyl)propylcarbamate (282 mg, 0.50 mmol) was reacted with trimethylboroxine (170 mg, 1.35 mmol) and Pd(pph$_3$)$_4$ (50 mg, 0.04 mmol) to afford the desired product (130 mg, 52%) as a yellow solid. ESI MS m/z 497 [C$_{27}$H$_{29}$FN$_2$O$_4$S+H]$^+$.

Example 1216

9-(4-(2-Aminoethyl)-3-fluorophenyl)-8-methoxy-6-methylthieno[2,3-c]quinolin-4(5H)-one Hydrochloride

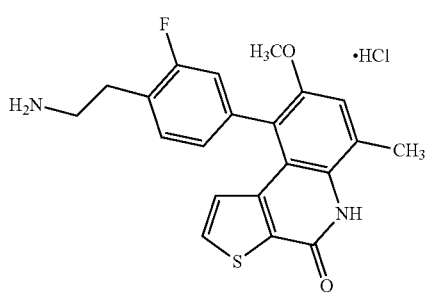 [SMILES: COc1cc(C)c2[nH]c(=O)c3sccc3c2c1-c1ccc(CCN)c(F)c1 ; Cl]

Following General Procedure C, tert-butyl 2-fluoro-4-(8-methoxy-6-methyl-4-oxo-4,5-dihydrothieno[2,3-c]quinolin-9-yl)phenethylcarbamate (50 mg, 0.10 mmol) was reacted with TFA (2 mL) to afford the desired product (32 mg, 80%) as a yellow solid: $^1$H NMR (500 MHz, CD$_3$OD) δ 7.62 (d, J=5.4 Hz, 1H), 7.48 (dd, J=9.7, 6.1 Hz, 1H), 7.29 (s, 1H), 7.08 (ddd, J=9.0, 6.2, 1.6 Hz, 2H), 6.12 (d, J=5.4 Hz, 1H), 3.75 (s, 3H), 3.34-3.27 (m, 1H), 3.27-3.06 (m, 3H), 2.64 (s, 3H); ESI MS m/z 383 [C$_{21}$H$_{19}$FN$_2$O$_2$S+H]$^+$; HPLC 97.6% (AUC), t$_R$=9.22 min.

Example 1161

(R)-9-(4-(1-Aminopropan-2-yl)phenyl)-8-methoxythieno[2,3-c]quinolin-4(5H)-one Hydrochloride

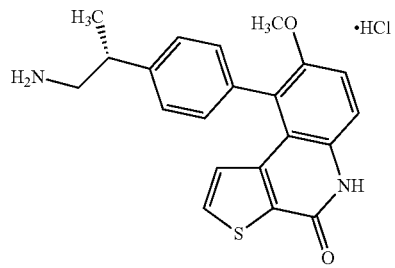 [SMILES: COc1ccc2[nH]c(=O)c3sccc3c2c1-c1ccc([C@@H](C)CN)cc1 ; Cl]

Following General Procedure C, (R)-tert-butyl 2-(4-(8-methoxy-4-oxo-4,5-dihydrothieno[2,3-c]quinolin-9-yl)phenyl)propylcarbamate (200 mg, 0.55 mmol) was reacted with TFA (10 mL) to afford the desired product (51 mg, 26%) as a white solid: $^1$H NMR (500 MHz, CD$_3$OD) δ 7.61-7.44 (m, 4H), 7.39 (d, J=9.1 Hz, 1H), 7.30 (ddd, J=13.2, 7.9, 1.7 Hz, 2H), 6.00 (d, J=5.4 Hz, 1H), 3.33-3.18 (m, 3H), 1.49 (d, J=6.6 Hz, 3H); ESI MS m/z 365 [C$_{21}$H$_{20}$N$_2$O$_2$S+H]$^+$; HPLC 97.6% (AUC), t$_R$=8.88 min

Example 1305

(R)-9-(4-(1-Aminopropan-2-yl)phenyl)-8-methoxy-6-methylthieno[2,3-c]quinolin-4(5H)-one Hydrochloride

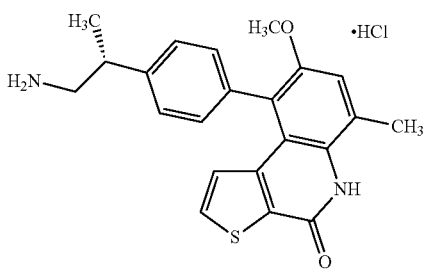 [SMILES: COc1cc(C)c2[nH]c(=O)c3sccc3c2c1-c1ccc([C@@H](C)CN)cc1 ; Cl]

Following General Procedure C, (R)-tert-butyl 2-(4-(8-methoxy-6-methyl-4-oxo-4,5-dihydrothieno[2,3-c]quinolin-9-yl)phenyl)propylcarbamate (1.5 g, 3.1 mmol) was reacted with TFA (30 mL) to afford the desired product (520 mg, 47%) as a yellow solid: $^1$H NMR (500 MHz, CD$_3$OD) δ 7.56 (d, J=5.4 Hz, 1H), 7.50 (dd, J=7.8, 1.8 Hz, 1H), 7.45 (dd, J=7.7, 1.9 Hz, 1H), 7.28 (ddd, J=9.4, 7.0, 1.7 Hz, 3H), 6.01 (d, J=5.4 Hz, 1H), 3.75 (s, 3H), 3.36-3.18 (m, 3H), 2.64 (s, 3H), 1.48 (d, J=6.6 Hz, 3H); ESI MS m/z 379 [C$_{22}$H$_{12}$N$_2$O$_2$S+H]$^+$; HPLC 99% (AUC), t$_R$=8.81 min.

Example 1201

(R)-9-(4-(1-Aminopropan-2-yl)phenyl)-6-chloro-8-methoxythieno[2,3-c]quinolin-4(5H)-one Hydrochloride

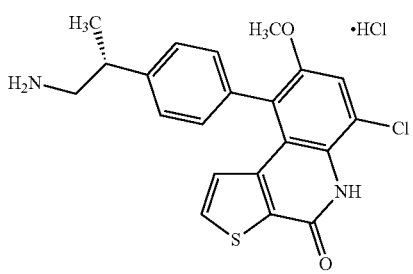 [SMILES: COc1cc(Cl)c2[nH]c(=O)c3sccc3c2c1-c1ccc([C@@H](C)CN)cc1 ; Cl]

Following General Procedure C, (R)-tert-butyl 2-(4-(6-chloro-8-methoxy-4-oxo-4,5-dihydrothieno[2,3-c]quinolin-9-yl)phenyl)propylcarbamate (60 mg, 0.12 mmol) was reacted with TFA (4 mL) to afford the desired product (28 mg, 52%) as a yellow solid: $^1$H NMR (500 MHz, CD$_3$OD) δ 7.61 (d, J=5.4 Hz, 1H), 7.54-7.50 (m, 2H), 7.48 (dd, J=7.8, 1.7 Hz, 1H), 7.32-7.25 (m, 2H), 5.97 (d, J=5.4 Hz, 1H), 3.76 (s, 1H), 3.29-3.17 (m, 3H), 1.48 (d, J=6.5 Hz, 2H); ESI MS m/z 399 [C$_{21}$H$_{19}$ClN$_2$O$_2$S+H]$^+$; HPLC >99% (AUC), t$_R$=9.65 min.

Example 1298

(R)-8-Methoxy-6-methyl-9-(4-(1-(methylamino)propan-2-yl)phenyl)thieno[2,3-c]quinolin-4(5H)-one Hydrochloride

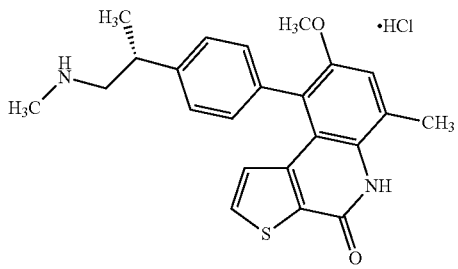

Following General Procedure C, (R)-tert-butyl 2-(4-(8-methoxy-6-methyl-4-oxo-4,5-dihydrothieno[2,3-c]quinolin-9-yl)phenyl)propyl(methyl)carbamate (600 mg, 1.2 mmol) was reacted with TFA (20 mL) to afford the desired product (330 mg, 69%) as a light yellow solid: $^1$H NMR (500 MHz, CD$_3$OD) δ 7.56 (d, J=5.4 Hz, 1H), 7.52 (dd, J=7.9, 1.9 Hz, 1H), 7.47 (dd, J=7.7, 1.9 Hz, 1H), 7.28 (ddd, J=14.7, 7.9, 1.7 Hz, 3H), 6.00 (d, J=5.4 Hz, 1H), 3.36-3.26 (m, 3H), 2.76 (s, 3H), 2.64 (s, 3H), 1.48 (d, J=6.7 Hz, 3H); ESI MS m/z 393 [(C$_{23}$H$_{24}$N$_2$O$_2$S+H]$^+$; HPLC 98.6% (AUC), t$_R$=8.96 min.

Example 594

(R)-tert-Butyl 2-(4-(6-chloro-8-methoxy-4-oxo-4,5-dihydrothieno[2,3-c]quinolin-9-yl)phenyl)propylcarbamate

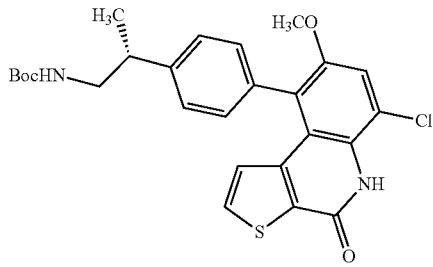 [SMILES: COc1cc(Cl)c2[nH]c(=O)c3sccc3c2c1-c1ccc([C@@H](C)CNC(=O)OC(C)(C)C)cc1]

Following General Procedure H, (R)-tert-butyl 2-(4-(8-methoxy-4-oxo-4,5-dihydrothieno[2,3-c]quinolin-9-yl)phenylpropylcarbamate (400 mg, 0.86 mmol) was reacted with NCS (138 mg, 1.03 mmol) to afford the desired product (210 mg, 49%) as a brown solid. ESI MS m/z 499 [C$_{26}$H$_{27}$ClN$_2$O$_4$S+H]$^+$.

Example 595 tert-Butyl 4-(6-chloro-8-methoxy-4-oxo-4,5-dihydrothieno[2,3-c]quinolin-9-yl)phenethylcarbamate

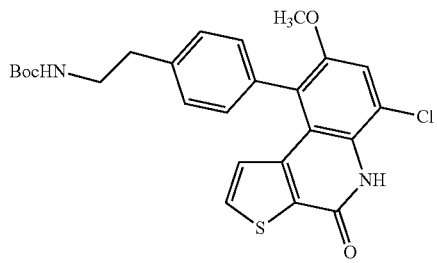 [SMILES: COc1cc(Cl)c2[nH]c(=O)c3sccc3c2c1-c1ccc(CCNC(=O)OC(C)(C)C)cc1]

Following General Procedure 1H, tert-butyl 4-(8-methoxy-4-oxo-4,5-dihydrothieno[2,3-c]quinolin-9-yl)phenethylcarbamate (200 mg, 0.43 mmol) was reacted with NCS (68 mg, 0.52 mmol) to afford the desired product (79 mg, 38%) as a brown solid. ESI MS m/z 485 [C$_{25}$H$_{25}$ClN$_2$O$_4$S+H]$^+$.

Example 596 tert-Butyl 2-(4-(6-chloro-8-methoxy-4-oxo-4,5-dihydrothieno[2,3-c]quinolin-9-yl)phenyl)propylcarbamate

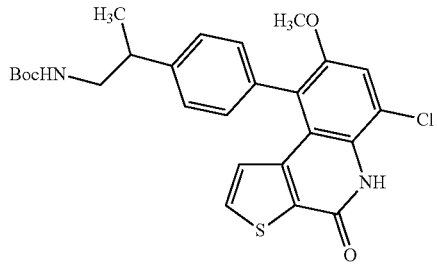 [SMILES: COc1cc(Cl)c2[nH]c(=O)c3sccc3c2c1-c1ccc(C(C)CNC(=O)OC(C)(C)C)cc1]

Following General Procedure H, tert-butyl 2-(4-(8-methoxy-4-oxo-4,5-dihydrothieno[2,3-c]quinolin-9-yl)phenyl)propylcarbamate (180 mg, 0.39 mmol) was reacted with NCS (57 mg, 0.42 mmol) to afford the desired product (110 mg, 56%) as a yellowish solid. ESI MS m/z 499 [C$_{26}$H$_{27}$ClN$_2$O$_4$S+H]$^+$.

Example 597

(R)-tert-Butyl 1-(4-(6-chloro-8-methoxy-4-oxo-4,5-dihydrothieno[2,3-c]quinolin-9-yl)phenyl)ethyl(methyl)carbamate

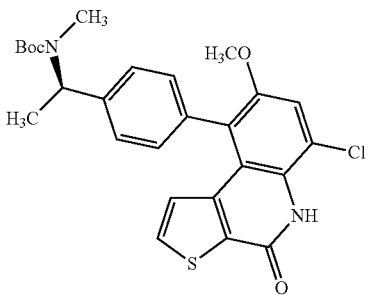 [SMILES: COc1cc(Cl)c2[nH]c(=O)c3sccc3c2c1-c1ccc([C@@H](C)N(C)C(=O)OC(C)(C)C)cc1]

Following General Procedure H, (R)-tert-butyl 1-(4-(8-methoxy-4-oxo-4,5-dihydrothieno[2,3-c]quinolin-9-yl)phenyl)ethyl(methyl)carbamate (200 mg, 0.43 mmol) was reacted with NCS (69 mg, 0.52 mmol) to afford the desired product (43 mg, 20%) as a yellowish solid. ESI MS m/z 499 $[C_{26}H_{27}ClN_2O_4S+H]^+$.

Example 598 tert-Butyl 4-(6-chloro-8-methoxy-4-oxo-4,5-dihydrothieno[2,3-c]quinolin-9-yl)-2-fluorophenethylcarbamate

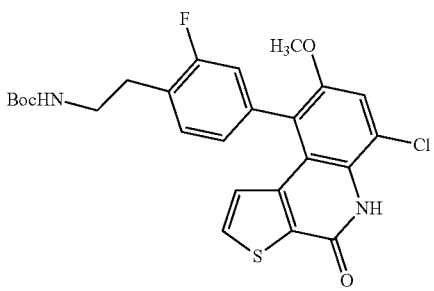 [SMILES: COc1cc(Cl)c2[nH]c(=O)c3sccc3c2c1-c1ccc(CCNC(=O)OC(C)(C)C)c(F)c1]

Following General Procedure H, tert-butyl 2-fluoro-4-(8-methoxy-4-oxo-4,5-dihydrothieno[2,3-c]quinolin-9-yl)phenethylcarbamate (300 mg, 0.64 mmol) was reacted with NCS (94 mg, 0.71 mmol) to afford the desired product (150 mg, 46%) as a yellow solid. ESI MS m/z 503 $[C_{25}H_{24}ClFN_2O_4S+H]^+$.

Example 373

9-(4-(1-aminopropan-2-yl)phenyl)-8-methoxythieno[2,3-c]quinolin-4(5H)-one Hydrochloride

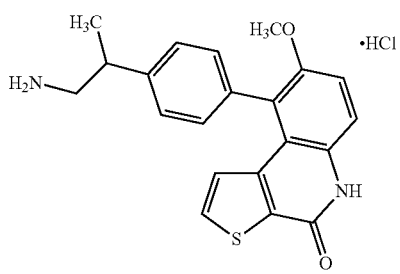 [SMILES: COc1ccc2[nH]c(=O)c3sccc3c2c1-c1ccc(C(C)CN)cc1 ; Cl]

To a solution of 2-(4-(8-methoxy-4-oxo-4,5-dihydrothieno[2,3-c]quinolin-9-yl)phenyl)propanenitrile (1.4 g, 4.0 mmol) in toluene (10 mL) at 0° C. was added BH$_3$.THF (1.0 M in THF, 10 mL, 10 mmol) and the reaction was warmed to room temperature and heated at reflux for 4 h. The reaction was quenched by adding methanol (1 mL) at 0° C. The resulting mixture was concentrated and purified by preparatory HPLC (C18 silica, acetonitrile/water (with 0.05% TFA) gradient).

The desired product was dissolved in aqueous HCl, concentrated and dried under high vacuum to afford the desired product (352 mg, 24%) as a brown solid: ESI MS m/z 365 $[CH_{21}H_{20}N_2O_2S+H]^+$.

Example 1112

9-(4-(1-(Dimethylamino)propan-2-yl)phenyl)-8-hydroxythieno[2,3-c]quinolin-4(5H)-one Hydrochloride

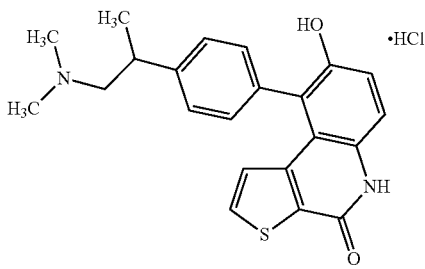 [SMILES: CC(CN(C)C)c1ccc(-c2c(O)ccc3[nH]c(=O)c4sccc4c23)cc1 ; Cl]

Following the procedure outlined for Example 1387, 9-(4-(1-aminopropan-2-yl)phenyl-8-hydroxythieno[2,3-c]quinolin-4(5H)-one hydrochloride (15 mg, 0.040 mmol) was reacted with paraformaldehyde (4.0 mg, 0.13 mmol) and after purification the resulting material was converted to the hydrochloride salt as outlined in General Procedure D-2 to afford the desired product (12 mg, 75%) as a light yellow solid: $^1$H NMR (500 MHz, CD$_3$OD) δ 7.66-7.51 (m, 3H), 7.47-7.30 (m, 3H), 7.18 (d, J=8.9 Hz, 1H), 6.12 (d, J=5.4 Hz, 1H), 3.67-3.57 (m, 1H), 3.51-3.38 (m, 2H), 2.95 (d, J=16.0 Hz, 6H), 1.49 (d, J=6.5 Hz, 3H); ESI MS m/z 379 $[C_{22}H_{22}N_2O_2S+H]^+$; HPLC >99% (AUC), $t_R$=8.46 min.

Example 1126

(R)-6-Chloro-9-(4-(1-(dimethylamino)ethyl)phenyl)-8-hydroxythieno[2,3-c]quinolin-4(5H)-one Hydrochloride

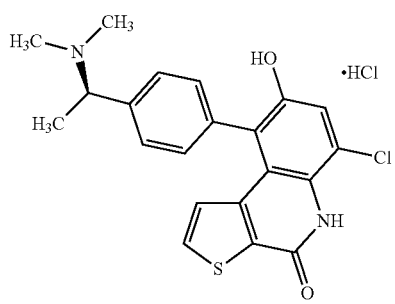 [SMILES: C[C@H](c1ccc(-c2c(O)cc(Cl)c3[nH]c(=O)c4sccc4c23)cc1)N(C)C ; Cl]

Following the procedure outlined for Example 1387, (R)-9-(4-(1-aminoethyl)phenyl)-6-chloro-8-hydroxythieno[2,3-c]quinolin-4(5H)-one hydrochloride (120 mg, 0.32 mmol) was reacted with paraformaldehyde (29 mg, 0.97 mmol) and after purification the resulting material was converted to the hydrochloride salt as outlined in General Procedure D-2 to afford the desired product (21 mg, 16%) as a light yellow solid: $^1$H NMR (500 MHz, CD$_3$OD) δ 7.71 (dd, J=10.5, 7.8 Hz, 2H), 7.64 (d, J=5.4 Hz, 1H), 7.47 (t, J=7.1 Hz, 2H), 7.31 (s, 1H), 6.01 (d, J=5.4 Hz, 1H), 4.66 (q, J=6.9 Hz, 1H), 2.97

(s, 3H), 2.86 (s, 3H), 1.86 (d, J=7.0 Hz, 3H). ESI MS m/z 399 [C$_{21}$H$_{19}$ClN$_2$O$_2$S+H]$^+$; HPLC 97.5% (AUC), t$_R$=9.96 min.

Example 1188

(R)-9-(4-(1-(dimethylamino)propan-2-yl)phenyl)-8-hydroxythieno[2,3-c]quinolin-4(5H)-one Hydrochloride

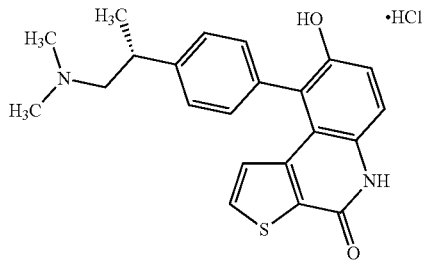 [SMILES: C[C@@H](CN(C)C)c1ccc(-c2c(O)ccc3[nH]c(=O)c4sccc4c23)cc1 ; Cl]

Following the procedure outlined for Example 1387, (R)-8-methoxy-9-(4-(1-(methylamino)propan-2-yl)phenyl)thieno[2,3-c]quinolin-4(5H)-one hydrochloride (40 mg, 0.11 mmol) was reacted with paraformaldehyde (7 mg, 0.21 mmol) and after purification the resulting material was converted to the hydrochloride salt as outlined in General Procedure D-2 to afford the desired product (28 mg, 67%) as a white solid: $^1$H NMR (500 MHz, CD$_3$OD) δ 7.65-7.52 (m, 3H), 7.44-7.32 (m, 3H), 7.18 (d, J=8.9 Hz, 1H), 6.12 (d, J=5.4 Hz, 1H), 3.62 (d, J=3.1 Hz, 1H), 3.46 (dd, J=13.2, 4.7 Hz, 2H), 2.97 (s, 3H), 2.94 (s, 3H), 1.49 (d, J=6.6 Hz, 3H); ESI MS m/z 379 [C$_{22}$H$_{22}$N$_2$O$_2$S+H]$^+$; HPLC >99% (AUC), t$_R$=8.57 min.

Example 1193

9-(4-(1-(Dimethylamino)propan-2-yl)-3-fluorophenyl)-8-hydroxy-6-methylthieno[2,3-c]quinolin-4(5H)-one Hydrochloride

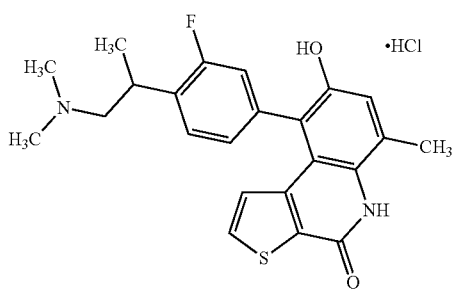

Following the procedure outlined for Example 1387, 9-(4-(1-Aminopropan-2-yl)-3-fluorophenyl)-8-hydroxy-6-methylthieno[2,3-c]quinolin-4(5H)-one Hydrochloride (30 mg, 0.08 mmol) was reacted with paraformaldehyde (9 mg, 0.31 mmol) and after purification the resulting material was converted to the Hydrochloride salt as outlined in General Procedure D-2 to afford the desired product (25 mg, 75(%) as a light yellow solid: $^1$H NMR (500 MHz, CD$_3$OD) δ 7.67-7.51 (m, 2H), 7.26-7.10 (m, 2H), 7.08 (dd, J=1.6, 0.8 Hz, 1H), 6.20 (dd, J=8.1, 5.4 Hz, 1H), 3.88-3.40 (m, 3H), 3.0-2.96 (m, 6H), 2.57 (s, 3H), 1.57-1.46 (m, 3H); ESI MS m/z 411 [C$_{23}$H$_{23}$FN$_2$O$_2$S+H]$^+$; HPLC >99% (AUC), t$_R$=9.14 min.

Example 1347

(R)-6-chloro-9-(4-(1-(dimethylamino)propan-2-yl)phenyl)-8-hydroxythieno[2,3-c]quinolin-4(5H)-one Hydrochloride

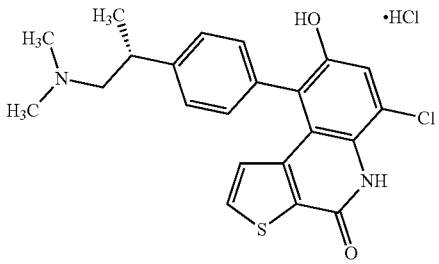 [SMILES: C[C@@H](CN(C)C)c1ccc(-c2c(O)cc(Cl)c3[nH]c(=O)c4sccc4c23)cc1 ; Cl]

Following the procedure outlined for Example 1387, (R)-9-(4-(1-aminopropan-2-yl)phenyl)-6-chloro-8-hydroxythieno[2,3-c]quinolin-4(5H)-one hydrochloride (30 mg, 0.10 mmol) was reacted with paraformaldehyde (6 mg, 0.20 mmol) and after purification the resulting material was converted to the hydrochloride salt as outlined in General Procedure D-2 to afford the desired product (12 mg, 29%) as a yellow solid: $^1$H NMR (500 MHz, CD$_3$OD) δ 7.66-7.57 (m, 2H), 7.55 (d, J=7.8 Hz, 1H), 7.40-7.27 (m, 3H), 6.07 (d, J=5.4 Hz, 1H), 3.62 (dd, J=12.2, 8.9 Hz, 1H), 3.46 (ddd, J=11.7, 9.3, 6.3 Hz, 2H), 2.98 (s, 3H), 2.94 (s, 3H), 1.48 (d, J=6.5 Hz, 3H); ESI MS m/z 413 [C$_{22}$H$_{21}$ClN$_2$O$_2$S+H]$^+$; HPLC >99% (AUC), t$_R$=9.46 min.

Example 1379

(R)-9-(4-(1-(ethyl(methyl)amino)propan-2-yl)phenyl)-8-hydroxy-6-methylthieno[2,3-c]quinolin-4(5H)-one Hydrochloride

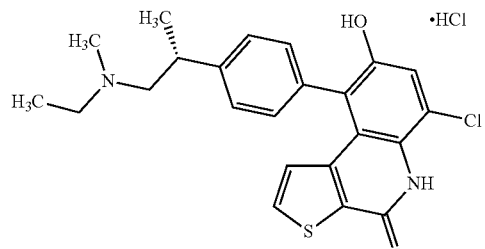

Following the procedure outlined for Example 1387, ((R)-8-hydroxy-6-methyl-9-(4-(1-(methylamino)propan-2-yl)phenyl)thieno[2,3-c]quinolin-4(5H)-one hydrochloride (15 mg, 0.04 mmol) was reacted with acetaldehyde (5 uL, 0.08 mmol) and after purification the resulting material was converted to the hydrochloride salt as outlined in General Procedure D-2 to afford the desired product (8 mg, 50%) as a yellow solid: $^1$H NMR (500 MHz, CD$_3$OD) δ 7.66-7.49 (m, 3H), 7.42-7.27 (m, 2H), 7.08 (s, 1H), 6.13 (dd, J=19.9, 5.4 Hz, 1H), 3.70 (dd, J=12.8, 10.3 Hz, 1H), 3.58-3.14 (m, 4H), 2.91 (d, J=23.4 Hz, 3H), 2.57 (s, 3H), 1.49 (dd, J=6.8, 3.3 Hz, 3H), 1.36 (dt, J=12.8, 7.3 Hz, 3H); ESI MS m/z 407 [C$_{24}$H$_{11}$N$_2$O$_2$S+H]$^+$; HPLC >99% (AUC), t$_R$=9.16 min.

Example 1324

(R)-9-(4-(1-(Dimethylamino)propan-2-yl)phenyl)-8-hydroxy-6-methylthieno[2,3-c]quinolin-4(5H)-one Hydrochloride

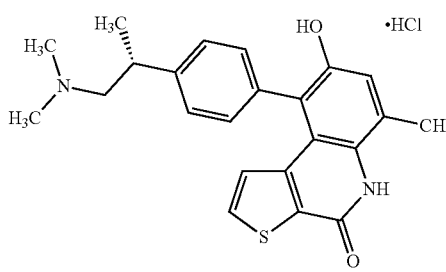

Following the procedure outlined for Example 1387, (R)-9-(4-(1-aminopropan-2-yl)phenyl)-8-hydroxy-6-methylthieno[2,3-c]quinolin-4(5H)-one hydrobromide (100 mg, 0.26 mmol) was reacted with paraformaldehyde (24 mg, 0.80 mmol) and after purification the resulting material was converted to the hydrochloride salt as outlined in General Procedure D-2 to afford the desired product (34 mg, 34%) as a white solid: $^1$H NMR (500 MHz, CD$_3$OD) δ 7.61-7.55 (m, 1H), 7.53 (dd, J=7.8, 1.8 Hz, 1H), 7.36 (dd, J=7.9, 1.7 Hz, 1H), 7.31 (dd, J=7.7, 1.7 Hz, 1H), 7.08 (s, 1H), 6.12 (d, J=5.4 Hz, 1H), 3.61 (dd, J=12.3, 9.3 Hz, 1H), 3.45 (dt, J=9.1, 6.2 Hz, 2H), 2.97 (s, 1H), 2.94 (s, 1H), 2.57 (s, 1H), 1.48 (d, J=6.6 Hz, 1H); ESI MS m/z 393 [C$_{23}$H$_{24}$N$_2$O$_2$S+H]$^+$; HPLC >99% (AUC), t$_R$=8.90 min.

Example 1306

(R)-8-Hydroxy-6-methyl-9-(4-(1-(methylamino)propan-2-yl)phenyl)thieno[2,3-c]quinolin-4(5H)-one Hydrochloride

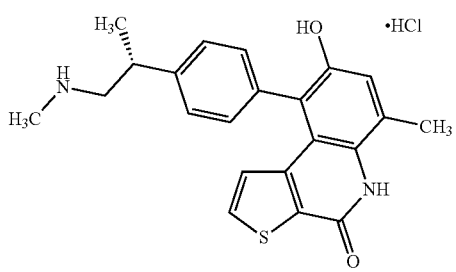

Following General Procedure D-3, (R)-8-hydroxy-6-methyl-9-(4-(1-(methylamino)propan-2-yl)phenyl)thieno[2,3-c]quinolin-4(5H)-one hydrobromide (120 mg, 0.26 mmol) was dissolved in aqueous HCl (100 mmol) and stirred concentrated at room temperature for 2 h, concentrated and dried under high vacuum to afford the desired product as a hydrochloride salt. The desired product was dried under high vacuum to afford the desired product as a light yellow solid (27 mg, 28%): $^1$H NMR (500 M Hz, CD$_3$OD) δ 7.61-7.53 (m, 2H), 7.46 (dd, J=7.8, 1.8 Hz, 1H), 7.36 (dd, J=7.9, 1.6 Hz, 1H), 7.31 (dd, J=7.7, 1.7 Hz, 1H), 7.08 (s, 1H), 6.16 (d, J=5.4 Hz, 1H), 3.41-3.24 (m, 3H), 2.74 (s, 3H), 2.57 (s, 3H), 1.50 (d, J=6.8 Hz, 3H); ESI MS m/z 379 [C$_{22}$H$_{22}$N$_2$O$_2$S+H]$^+$; HPLC 98.7% (AUC), t$_R$=8.82 min.

Example 408

N-tert-Butyl-4-(8-methoxy-4-oxo-4,5-dihydrothieno[2,3-c]quinolin-9-yl)benzenesulfonamide

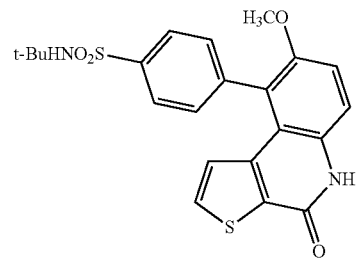

Following General Procedure B, 9-bromo-8-methoxythieno[2,3-c]quinolin-4(5H)-one (5.0 g, 16 mmol) was reacted with 4-(N-tert-butylsulfamoyl)phenylboronic acid (5.4 g, 21 mmol) to afford the desired product (4.3 g, 60%) as a yellow solid: ESI MS m/z [C$_{22}$H$_{22}$N$_2$O$_4$S$_2$+H]$^+$.

Example 409

9-(1H-Indazol-6-yl)-8-methoxythieno[2,3-c]quinolin-4(5H)-one

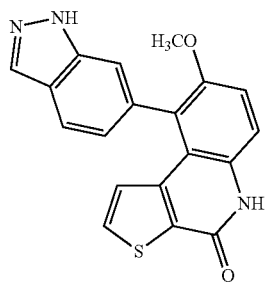 [SMILES: COc1ccc2[nH]c(=O)c3sccc3c2c1-c1ccc2cn[nH]c2c1]

Following General Procedure B, 9-bromo-8-methoxythieno[2,3-c]quinolin-4(5H)-one (100 mg, 0.32 mmol) was reacted with 6-(4,4,5,5-tetramethyl-1,3,2-dioxaborolan-2-yl)-1H-indazole (120 mg, 0.48 mmol) to afford the desired product (35 mg, 31%) as brown solid: ESI MS m/z 348 [C$_{18}$H$_{11}$N$_3$O$_2$S+H]$^+$.

Example 169

9-[4-(2-Aminoethyl)phenyl]-8-methoxythieno[2,3-c]quinolin-4(5H)-one

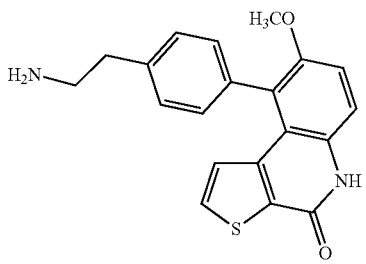 [SMILES: COc1ccc2[nH]c(=O)c3sccc3c2c1-c1ccc(CCN)cc1]

Following General Procedure C, tert-butyl 4-(8-methoxy-4-oxo-4,5-dihydrothieno[2,3-c]quinolin-9-yl)phenethylcarbamate (310 mg, 0.69 mmol) was reacted with TFA (2 mL) to afford the desired product (220 mg, 90%) as an off-white solid: $^1$H NMR (500 MHz, DMSO-d) δ 7.91 (s, 1H), 7.91 (br s, 2H), 7.71 (d, J=5.4 Hz, 1H), 7.52 (d, J=9.1 Hz, 1H), 7.40 (m, 3H), 7.22 (d, J=8.1 Hz, 2H), 5.80 (d, J=5.4 Hz, 1H), 3.68 (s, 3H), 3.20-3.17 (m, 2H), 3.02-2.99 (m, 2H); ESI MS m/z 351 $[C_{20}H_{18}N_2O_2S+H]^+$; HPLC 98.8% (AUC), $t_R$=8.32 min.

Example 145

9-(4-{3-[2-(Diethylamino)ethylamino]propoxy}phenyl)-8-methoxythieno[2,3-c]quinolin-4(5H)-one

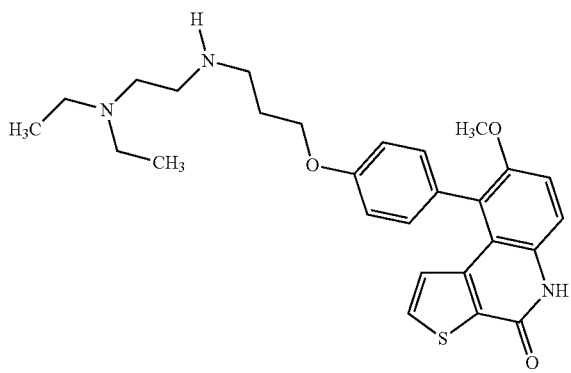 [SMILES: CCN(CC)CCNCCCOc1ccc(-c2c(OC)ccc3[nH]c(=O)c4sccc4c23)cc1]

Following General Procedure B, 9-bromo-8-methoxythieno[2,3-c]quinolin-4(5H)-one (100 mg, 0.33 mmol) was reacted with N',N'-diethyl-N$^2$-{3-[4-(4,4,5,5-tetramethyl-1,3,2-dioxaborolan-2-yl)phenoxy]propyl}ethane-1,2-diamine (250 mg, 0.67 mmol) to afford the desired product (58 mg, 37%) as a brown solid: $^1$H NMR (500 MHz, CD$_3$OD) δ 7.56 (d, J=5.4 Hz, 1H), 7.52 (d, J=9.1 Hz, 1H), 7.36 (d, J=9.1 Hz, 1H), 7.18 (d, J=8.6 Hz, 2H), 7.12 (d, J=8.6 Hz, 2H), 6.11 (d, J=5.4 Hz, 1H), 4.25 (t, J=5.7 Hz, 2H), 3.74 (s, 3H), 3.74-3.43 (m, 4H), 3.42 (t, J=7.4 Hz, 2H), 3.34-3.33 (m, 4H), 2.35-2.25 (m, 2H), 1.37 (t, J=7.3 Hz, 6H); ESI MS m/z 480 $[C_{27}H_{33}N_3O_3S+H]^+$; HPLC 98.6%, $t_R$=8.42 min.

Example 410 tert-Butyl 4-[4-(8-Methoxy-4-oxo-4,5-dihydrothieno[2,3-c]quinolin-9-yl)phenyl]piperazine-1-carboxylate

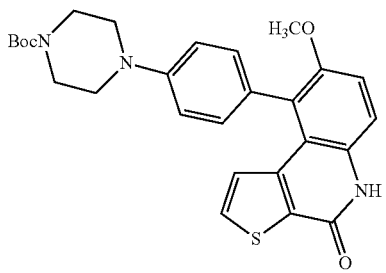 [SMILES: COc1ccc2[nH]c(=O)c3sccc3c2c1-c1ccc(N2CCN(C(=O)OC(C)(C)C)CC2)cc1]

Following General Procedure B, 9-bromo-8-methoxythieno[2,3-c]quinolin-4(5H)-one (80 mg, 0.26 mmol) was reacted with tert-butyl 4-[4-(4,4,5,5-tetramethyl-1,3,2-dioxaborolan-2-yl)phenyl]piperazine-1-carboxylate (170 mg, 0.44 mmol) to afford the desired product (68 mg, 32%) as a yellow solid: ESI MS m/z 492 $[C_{27}H_{29}N_3O_4S+H]^+$.

Example 411

8-Methoxy-9-[4-(piperazin-1-yl)phenyl]thieno[2,3-c]quinolin-4(5H)-one

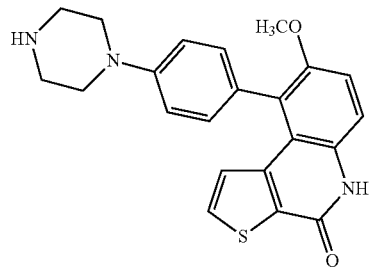 [SMILES: COc1ccc2[nH]c(=O)c3sccc3c2c1-c1ccc(N2CCNCC2)cc1]

Following General Procedure C, tert-butyl 4-[4-(8-methoxy-4-oxo-4,5-dihydrothieno[2,3-c]quinolin-9-yl)phenyl]piperazine-1-carboxylate (160 mg, 0.33 mmol) was reacted with TFA (4 mL) to afford the desired product (23 mg, 22%) as a light yellow solid: $^1$H NMR (500 MHz, DMSO-d$_6$) δ 11.84 (s, 1H), 8.72 (s, 2H), 7.76 (d, J=5.4 Hz, 1H), 7.49 (d, J=9.0 Hz, 1H), 7.37 (d, J=9.1 Hz, 1H), 7.20-7.03 (m, 4H), 5.95 (d, J=5.4 Hz, 1H), 3.68 (s, 3H), 3.52-3.41 (m, 4H), 3.31 (s, 4H).

Example 412

8-Methoxy-9-{4-[4-(methylsulfonyl)piperazin-1-yl]phenyl}thieno[2,3-c]quinolin-4(5H)-one

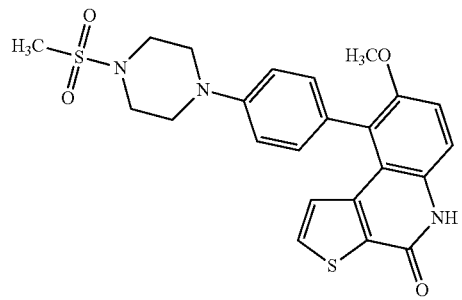 [SMILES: COc1ccc2[nH]c(=O)c3sccc3c2c1-c1ccc(N2CCN(S(C)(=O)=O)CC2)cc1]

To a solution of 8-methoxy-9-[4-(piperazin-1-yl)phenyl]thieno[2,3-c]quinolin-4(5H)-one (89 mg, 0.23 mmol) in methylene chloride (2 mL) was added N,N-diisopropylethylamine (0.42 mL, 0.68 mmol) and methanesulfonyl chloride (45 μL, 0.27 mmol) and the reaction mixture was stirred for 1 h. The reaction mixture was quenched with water and the layers were separated. The aqueous layer was extracted with ethyl acetate and the combined organic layers were dried over Na$_2$SO$_4$, filtered, concentrated and the residue was purified by preparatory HPLC (C18 silica, acetonitrile/water w/0.05%

TFA gradient) to afford the desired product (72 mg, 68%) as a brown solid: ESI MS m/z 470 $[C_{23}H_{23}N_3O_4S_2+H]^+$.

Example 413 tert-Butyl 4-(8-Methoxy-2-methyl-4-oxo-4,5-dihydrothieno[2,3-c]quinolin-9-yl)benzylcarbamate

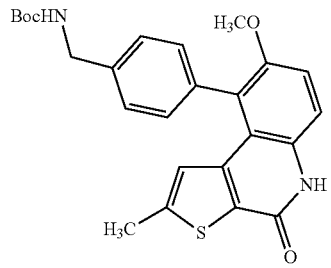 [SMILES: COc1ccc2[nH]c(=O)c3sc(C)cc3c2c1-c1ccc(CNC(=O)OC(C)(C)C)cc1]

Following General Procedure B A, 9-bromo-8-methoxy-2-methylthieno[2,3-c]quinolin-4(5H)-one (100 mg, 0.31 mmol) was reacted with 4-[(tert-butoxycarbonylamino)methyl]phenylboronic acid (120 mg, 0.40 mmol) to afford desired product (80 mg, 55%) as a brown solid: ESI MS m/z 451 $[C_{25}H_{26}N_2O_4S+H]^+$.

Example 414

N-[4-(8-Methoxy-4-oxo-4,5-dihydrothieno[2,3-c]quinolin-9-yl)phenyl]methanesulfonamide

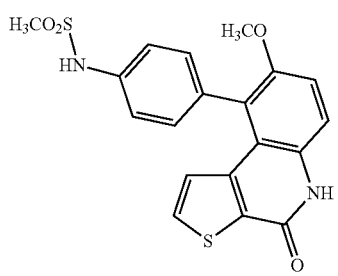

Following Step 1 from General Procedure B, 9-bromo-8-methoxythieno[2,3-c]quinolin-4(5H)-one (50 mg, 0.10 mmol) was reacted with 4-(methylsulfonamido)phenylboronic acid (52 mg, 0.24 mmol) to afford the desired product (40 mg, 62%) as a brown solid: ESI MS m/z 400 $[C_{19}H_{16}N_2O_4S_2+H]^+$.

Example 415 tert-Butyl 1-[4-(8-Methoxy-4-oxo-4,5-dihydrothieno[2,3-c]quinolin-9-yl)phenyl]ethylcarbamate

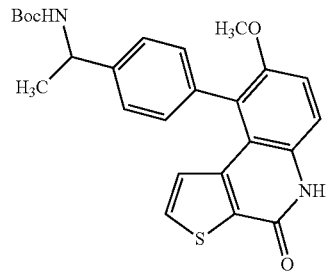 [SMILES: COc1ccc2[nH]c(=O)c3sccc3c2c1-c1ccc(C(C)NC(=O)OC(C)(C)C)cc1]

Following General Procedure B, 9-bromo-8-methoxythieno[2,3-c]quinolin-4(5H)-one (600 mg, 2.0 mmol) was reacted with tert-butyl 1-[4-(4,4,5,5-tetramethyl-1,3,2-dioxaborolan-2-yl)phenyl]ethylcarbamate (340 mg, 39%) as a brown solid: ESI MS m/z 451 $[C_{25}H_{26}N_2O_4S+H]^+$.

Example 416

8-Methoxy-9-{4-[1-(piperidin-1-yl)ethyl]phenyl}thieno[2,3-c]quinolin-4(5H)-one

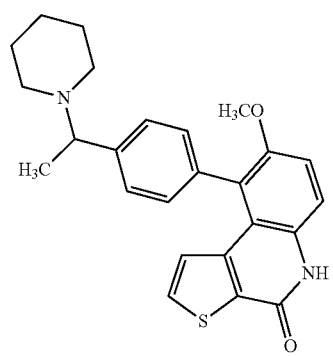 [SMILES: COc1ccc2[nH]c(=O)c3sccc3c2c1-c1ccc(C(C)N2CCCCC2)cc1]

Following General Procedure B, 9-bromo-8-methoxythieno[2,3-c]quinolin-4(5H)-one (150 mg, 0.48 mmol) was reacted with 4-[1-(piperidin-1-yl)ethyl]phenylboronic acid (170 mg, 0.73 mmol) to afford the desired product (10 mg, 5%) as a yellow solid: $^1$H NMR (500 MHz, CD$_3$OD) δ 7.74-7.66 (m, 2H), 7.62-7.53 (m, 2H), 7.49-7.34 (m, 3H), 5.94 (d, J=5.4 Hz, 1H), 4.61 (q, J=6.9 Hz, 1H), 3.86-3.78 (m, 1H), 3.76 (s, 1H), 3.47 (d, J=12.6 Hz, 1H), 3.10-2.98 (m, 1H), 2.96-2.82 (m, 1H), 2.11-1.91 (m, 2H), 1.89 (d, J=7.0 Hz, 2H), 1.85-1.70 (m, 1H).

Example 417

2-[2-Fluoro-4-(8-methoxy-4-oxo-4,5-dihydrothieno[2,3-c]quinolin-9-yl)phenyl]acetonitrile

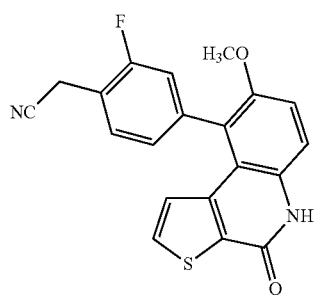 [SMILES: COc1ccc2[nH]c(=O)c3sccc3c2c1-c1ccc(CC#N)c(F)c1]

Following General Procedure B, 9-bromo-8-methoxythieno[2,3-c]quinolin-4(5H)-one (350 mg, 1.1 mmol) was reacted with 2-[2-fluoro-4-(4,4,5,5-tetramethyl-1,3,2-dioxaborolan-2-yl)phenyl]acetonitrile (440 mg, 1.7 mmol) to afford the desired product (400 mg, >99%) as a brown solid: ESI MS m/z 365 $[C_{20}H_{13}FN_2O_2S+H]^+$.

Example 265

9-[4-(2-Aminoethyl)-3-fluorophenyl]-8-methoxythieno[2,3-c]quinolin-4(5H)-one Hydrochloride

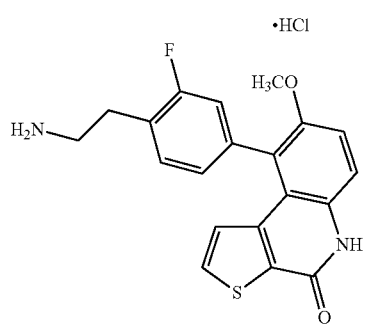 [SMILES: Cl ; COc1ccc2[nH]c(=O)c3sccc3c2c1-c1ccc(CCN)c(F)c1]

To a solution of 2-[2-fluoro-4-(8-methoxy-4-oxo-4,5-dihydrothieno[2,3-c]quinolin-9-yl)phenyl]acetonitrile (49 mg, 0.14 mmol) in toluene (3 mL) was added borane (1.0 M in THF, 3.0 mL, 0.30 mmol) and the reaction was stirred at reflux for 3 h. The reaction mixture was cooled to room temperature, concentrated and the residue was purified by preparatory HPLC. The residue was dissolved in aqueous HCl, concentrated and dried under high vacuum to afford the hydrochloride salt (4.5 mg, 9%) as a brown solid: $^1$H NMR (500 MHz, CD$_3$OD) δ 7.63 (d, J=5.4 Hz, 1H), 7.56 (d, J=9.0 Hz, 1H), 7.50 (t, J=7.8 Hz, 1H), 7.40 (d, J=9.1 Hz, 1H), 7.11-7.05 (m, 2H), 6.11 (d, J=5.4 Hz, 1H), 3.76 (s, 3H), 3.25-3.08 (m, 4H), 2.75 (br s, 3H); ESI MS m/z 369 [C$_{20}$H$_{17}$FN$_2$O$_2$S+H]$^+$; HPLC 95.0% (AUC), t$_R$=7.89 min.

Example 418

(S)-tert-Butyl 1-[4-(8-Methoxy-4-oxo-4,5-dihydrothieno[2,3-c]quinolin-9-yl)phenyl]ethylcarbamate

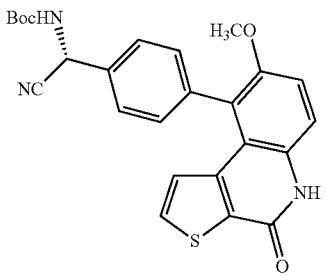 [SMILES: COc1ccc2[nH]c(=O)c3sccc3c2c1-c1ccc([C@H](C#N)NC(=O)OC(C)(C)C)cc1]

Following General Procedure B, 9-bromo-8-methoxythieno[2,3-c]quinolin-4(5H)-one (280 mg, 0.89 mmol) was reacted with (S)-tert-butyl 1-[4-(4,4,5,5-tetramethyl-1,3,2-dioxaborolan-2-yl)phenyl]ethylcarbamate (320 mg, 1.1 mmol) to afford the desired product (220 mg, 55%) as a white solid: ESI MS m/z 351 [C$_{25}$H$_{26}$N$_2$O$_4$S-Boc]$^+$.

Example 232

(S)-9-[4-(1-Aminoethyl)phenyl]-8-methoxythieno[2,3-c]quinolin-4(5H)-one Hydrochloride

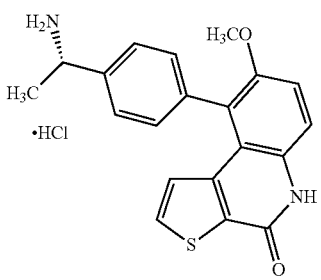 [SMILES: COc1ccc2[nH]c(=O)c3sccc3c2c1-c1ccc([C@H](C)N)cc1 ; Cl]

Following General Procedure C, (S)-tert-butyl 1-[4-(8-methoxy-4-oxo-4,5-dihydrothieno[2,3-c]quinolin-9-yl)phenyl]ethylcarbamate (90 mg, 0.12 mmol) was reacted with TFA (3 mL) to afford the desired product (11 mg, 15%) as an off-white solid: $^1$H NMR (500 MHz, CD$_3$OD) δ 7.65-7.62 (m, 2H), 7.56-7.54 (m, 2H), 7.40-7.38 (m, 3H), 6.04 (d, J=5.5 Hz, 1H), 4.62 (q, J=7.0 Hz, 1H), 7.73 (s, 3H), 1.77 (d, J=6.9 Hz, 3H); ESI MS m/z 351[C$_{20}$H$_{18}$N$_2$O$_2$S+H]$^+$; HPLC 97.6% (AUC), t$_R$=8.33 min.

Example 216

8-Methoxy-9-{4-[1-(pyrrolidin-1-yl)ethyl]phenyl}thieno[2,3-c]quinolin-4(5H)-one Hydrochloride

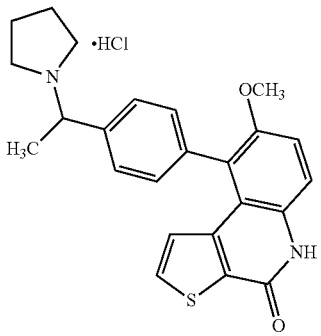 [SMILES: COc1ccc2[nH]c(=O)c3sccc3c2c1-c1ccc(C(C)N2CCCC2)cc1 ; Cl]

Following General Procedure B, 9-bromo-8-methoxythieno[2,3-c]quinolin-4(5H)-one (120 mg, 0.39 mmol) was reacted with 4-[1-(pyrrolidin-1-yl)ethyl]phenylboronic acid (170 mg, 0.77 mmol) to afford the desired product (70 mg, 45%) as a white solid: $^1$H NMR (500 MHz, CD$_3$OD) δ 7.69-7.67 (m, 2H), 7.60 (d, J=5.4 Hz, 1H), 7.56 (d, J=9.0 Hz, 1H), 7.44-7.40 (m, 3H), 5.96 (d, J=5.4 Hz, 1H), 4.54 (q, J=6.8 Hz, 1H), 3.89-3.84 (m, 1H), 3.76 (s, 3H), 3.38-3.16 (m, 3H),

Example 419

8-Methoxy-9-{4-[1-(piperidin-1-yl)ethyl]phenyl}thieno[2,3-c]quinolin-4(5H)-one

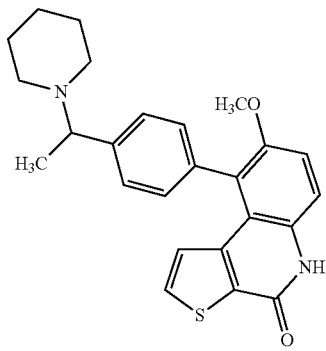 [SMILES: COc1ccc2[nH]c(=O)c3sccc3c2c1-c1ccc(C(C)N2CCCCC2)cc1]

Following General Procedure B, 9-bromo-8-methoxythieno[2,3-c]quinolin-4(5H)-one (150 mg, 0.48 mmol) was reacted with 4-[1-(piperidin-1-yl)ethyl]phenylboronic acid (170 mg, 0.73 mmol) to afford the desired product (10 mg, 5%) as a yellow solid: $^1$H NMR (500 MHz, CD$_3$OD) δ 7.74-7.66 (m, 2H), 7.62-7.53 (m, 2H), 7.49-7.34 (m, 3H), 5.94 (d, J=5.4 Hz, 1H), 4.61 (q, J=6.9 Hz, 1H), 3.86-3.78 (m, 1H), 3.76 (s, 1H), 3.47 (d, J=12.6 Hz, 1H), 3.10-2.98 (m, 1H), 2.96-2.82 (m, 1H), 2.11-1.91 (m, 2H), 1.89 (d, J=7.0 Hz, 2H), 1.85-1.70 (m, 1H).

Example 420

2-[2-Fluoro-4-(8-methoxy-4-oxo-4,5-dihydrothieno[2,3-c]quinolin-9-yl)phenyl]acetonitrile

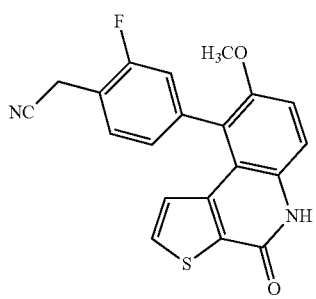 [SMILES: COc1ccc2[nH]c(=O)c3sccc3c2c1-c1ccc(CC#N)c(F)c1]

Following Step 1 from General Procedure B, 9-bromo-8-methoxythieno[2,3-c]quinolin-4(5H)-one (350 mg, 1.1 mmol) was reacted with 2-[2-fluoro-4-(4,4,5,5-tetramethyl-1,3,2-dioxaborolan-2-yl)phenyl]acetonitrile (440 mg, 1.7 mmol) to afford the desired product (400 mg, >99%) as a brown solid: ESI MS m/z 365 [C$_{20}$H$_{13}$FN$_2$O$_2$S+H]$^+$.

Example 421

9-[4-(3-Aminopropyl)phenyl]-8-methoxythieno[2,3-c]quinolin-4(5H)-one

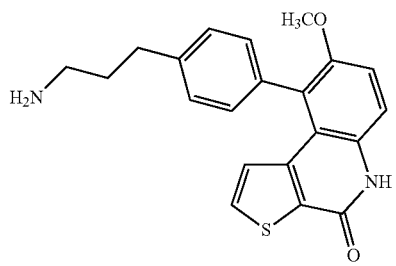 [SMILES: COc1ccc2[nH]c(=O)c3sccc3c2c1-c1ccc(CCCN)cc1]

Following the procedure outlined for Example 265, 3-[4-(8-methoxy-4-oxo-4,5-dihydrothieno[2,3-c]quinolin-9-yl)phenyl]propanenitrile (250 mg, 0.69 mmol) was reacted with borane (1.0 M in THF, 10 mL, 10 mmol) to afford the desired product (150 mg, 60%) as a brown oil: ESI MS m/z 365 [C$_{21}$H$_{20}$N$_2$O$_2$S+H]$^+$.

Example 274

(R)-9-[4-(1-Aminoethyl)phenyl]-8-methoxythieno[2,3-c]quinolin-4(5H)-one Hydrochloride

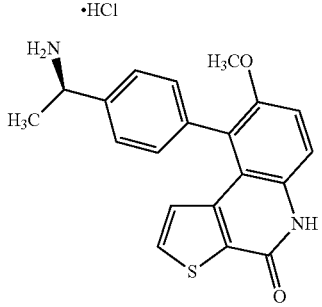 [SMILES: Cl ; COc1ccc2[nH]c(=O)c3sccc3c2c1-c1ccc([C@@H](C)N)cc1]

Following General Procedure C, (R)-tert-butyl 1-[4-(8-methoxy-4-oxo-4,5-dihydrothieno[2,3-c]quinolin-9-yl)phenyl]ethylcarbamate (50 mg, 0.11 mmol) was reacted with TFA (3 mL) to afford the desired product (11 mg, 26%) as an off-white solid: $^1$H NMR (500 MHz, CD$_3$OD) δ 7.63-7.62 (m, 2H), 7.56-7.55 (m, 2H), 7.40-7.37 (m, 3H), 6.04 (d, J=5.4 Hz, 1H), 4.62 (q, J=6.9 Hz, 1H), 3.79 (s, 3H), 2.77 (br s, 3H), 1.76 (d, J=6.9 Hz, 3H); ESI MS m/z 351 [C$_{20}$H$_{18}$N$_2$O$_2$S+H]$^+$; HPLC 98.7% (AUC), $t_R$=8.24 min.

Example 422

(R)-tert-Butyl 1-[4-(8-Methoxy-4-oxo-4,5-dihydrothieno[2,3-c]quinolin-9-yl)phenyl]ethylcarbamate

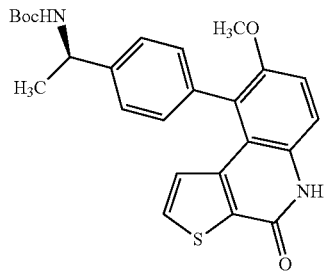 [SMILES: COc1ccc2[nH]c(=O)c3sccc3c2c1-c1ccc([C@@H](C)NC(=O)OC(C)(C)C)cc1]

Following Step 1 from General Procedure B, 9-bromo-8-methoxythieno[2,3-c]quinolin-4(5H)-one (480 mg, 1.5 mmol) was reacted with (R)-tert-butyl 1-[4-(4,4,5,5-tetramethyl-1,3,2-dioxaborolan-2-yl)phenyl]ethylcarbamate (800 mg, 2.3 mmol) to afford the desired product (410 mg, 59%) as a brown solid: ESI MS m/z 451 [C$_{25}$H$_{26}$N$_2$O$_4$S+H]$^+$.

Example 423

2-[4-(8-Methoxy-4-oxo-4,5-dihydrothieno[2,3-c]quinolin-9-yl)phenyl]-2-methylpropanenitrile

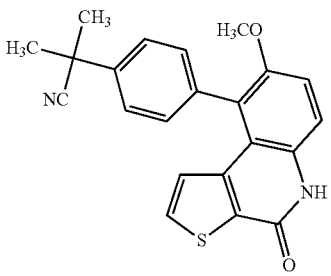 [SMILES: COc1ccc2[nH]c(=O)c3sccc3c2c1-c1ccc(C(C)(C)C#N)cc1]

Following General Procedure B, 9-bromo-8-methoxythieno[2,3-c]quinolin-4(5H)-one (380 mg, 1.2 mmol) was reacted with 2-methyl-2-[4-(4,4,5,5-tetramethyl-1,3,2-dioxaborolan-2-yl)phenyl]propanenitrile (500 mg, 1.9 mmol) to afford the desired product (260 mg, 56%) as a brown solid: ESI MS m/z 375 [C$_{22}$H$_{18}$N$_2$O$_2$S+H]$^+$.

Example 424

9-[4-(1-Amino-2-methylpropa-2-yl)phenyl]-8-methoxythieno[2,3-c]quinolin-4(5H)-one

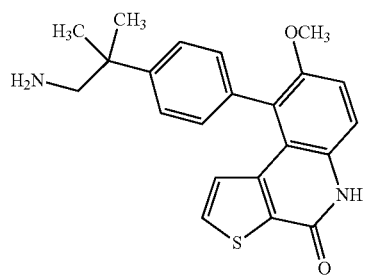 [SMILES: COc1ccc2[nH]c(=O)c3sccc3c2c1-c1ccc(C(C)(C)CN)cc1]

Following the procedure outlined for Example 265, 2-[4-(8-methoxy-4-oxo-4,5-dihydrothieno[2,3-c]quinolin-9-yl)phenyl]-2-methylpropanenitrile (250 mg, 0.67 mmol) was reacted with borane (1.0 M in THF, 10 mL, 10.0 mmol) to afford the desired product (100 mg, 40%) as a yellow solid: ESI MS m/z 379 [C$_{22}$H$_{22}$N$_2$O$_2$S+H]$^+$.

Example 425

9-{3-Fluoro-4-[(3-hydroxypyrrolidin-1-yl)methyl]phenyl}-8-methoxythieno[2,3-c]quinolin-4(5H)-one

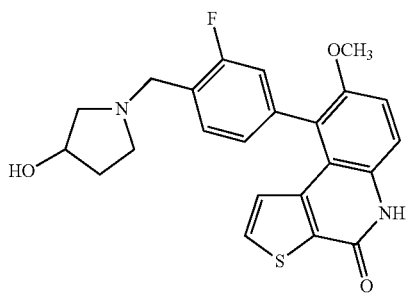 [SMILES: COc1ccc2[nH]c(=O)c3sccc3c2c1-c1ccc(CN2CCC(O)C2)c(F)c1]

Following General Procedure B, 9-bromo-8-methoxythieno[2,3-c]quinolin-4(5H)-one (180 mg, 0.58 mmol) was reacted with 1-[2-fluoro-4-(4,4,5,5-tetramethyl-1,3,2-dioxaborolan-2-yl)benzyl]pyrrolidin-3-ol (280 mg, 0.87 mmol) to afford the desired product (130 mg, 48%) as a brown solid: $^1$H NMR (500 MHz, CD$_3$OD) δ 7.79-7.72 (m, 1H), 7.66 (d, J=5.4 Hz, 1H), 7.58 (d, J=9.1 Hz, 1H), 7.42 (d, J=9.1 Hz, 1H), 7.33-7.21 (m, 2H), 6.09 (td, J=5.3, 2.4 Hz, 1H), 4.75-4.53 (m, 3H), 3.91-3.66 (m, 4H), 3.66-3.34 (m, 3H), 2.55-2.44 (m, 1H), 2.28-2.15 (m, 1H), 2.14-2.04 (m, 1H).

Example 426 tert-Butyl 5-(8-Methoxy-4-oxo-4,5-dihydrothieno[2,3-c]quinolin-9-yl)-2,3-dihydro-1H-inden-2-ylcarbamate

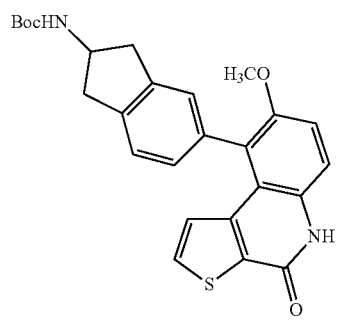 [SMILES: COc1ccc2[nH]c(=O)c3sccc3c2c1-c1ccc2c(c1)CC(NC(=O)OC(C)(C)C)C2]

Following General Procedure B, 9-bromo-8-methoxythieno[2,3-c]quinolin-4(5H)-one (1.1 g, 3.6 mmol) was reacted with tert-butyl 5-bromo-2,3-dihydro-1H-inden-2-ylcarbamate (2.0 g, 5.6 mmol) to afford the desired product (250 mg, 15%) as a brown solid: ESI MS m/z 363 [C$_{26}$H$_{26}$N$_2$O$_4$S+H-100]$^+$.

Example 427

1-[4-(8-Methoxy-4-oxo-4,5-dihydrothieno[2,3-c]quinolin-9-yl)phenyl]cyclopropanecarbonitrile

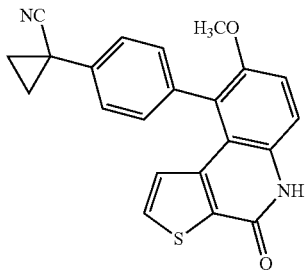 [SMILES: COc1ccc2[nH]c(=O)c3sccc3c2c1-c1ccc(C2(C#N)CC2)cc1]

Following General Procedure B, 1-(4-bromophenyl)cyclopropanecarbonitrile (1.5 g, 7.1 mmol) was reacted with bis(pinacolato)diboron (2.7 g, 10 mmol) to afford the crude boronic ester which was reacted with 9-bromo-8-methoxythieno[2,3-c]quinolin-4(5H)-one (1.3 g, 4.2 mmol) to afford the desired product (378 mg, 29%) as a white solid: ESI MS m/z 373 $[C_{22}H_{16}N_2O_2S+H]^+$.

Example 428 tert-Butyl 7-(8-Methoxy-4-oxo-4,5-dihydrothieno[2,3-c]quinolin-9-yl)-3,4-dihydroisoquinoline-2(1H)-carboxylate

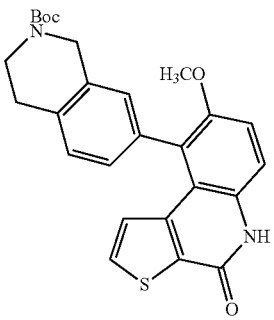 [SMILES: COc1ccc2[nH]c(=O)c3sccc3c2c1-c1ccc2c(c1)CN(C(=O)OC(C)(C)C)CC2]

Following General Procedure B, 9-bromo-8-methoxythieno[2,3-c]quinolin-4(5H)-one (1 g, 3.3 mmol) was reacted with tert-butyl 7-(4,4,5,5-tetramethyl-1,3,2-dioxaborolan-2-yl)-3,4-dihydroisoquinoline-2(1H)-carboxylate (1.8 g, 5.0 mmol) to afford the desired product (720 mg, 48%) as a brown solid: ESI MS m/z 463 $[C_{26}H_{26}N_2O_4S+H]^+$.

Example 429

8-Methoxy-9-(1,2,3,4-tetrahydroisoquinolin-7-yl)thieno[2,3-c]quinolin-4(5H)-one

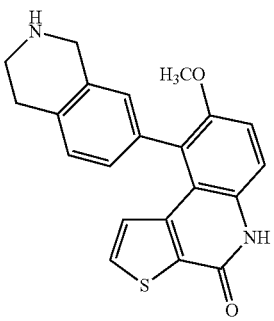 [SMILES: COc1ccc2[nH]c(=O)c3sccc3c2c1-c1ccc2c(c1)CNCC2]

Following General Procedure C, tert-Butyl 7-(8-Methoxy-4-oxo-4,5-dihydrothieno[2,3-c]quinolin-9-yl)-3,4-dihydroisoquinoline-2(1H)-carboxylate (260 mg, 0.53 mmol) was reacted with TFA (5 mL) afford the desired product (180 mg, 20%) as a white solid: $^1$H NMR (500 MHz, CD$_3$OD) δ 7.61-7.56 (m, 1H), 7.55 (dd, J=9.0, 3.2 Hz, 1H), 7.44 (d, J=7.8 Hz, 1H), 7.41-7.36 (m, 1H), 7.22 (d, J=7.8 Hz, 1H), 7.16 (s, 1H), 6.13 (d, J=5.4 Hz, 1H), 4.42 (s, 2H), 3.73 (s, 3H), 3.68-3.54 (m, 2H), 3.29-3.20 (m, 2H).

Example 430 tert-Butyl 1-[2-Fluoro-4-(8-methoxy-4-oxo-4,5-dihydrothieno[2,3-c]quinolin-9-yl)phenyl]ethylcarbamate

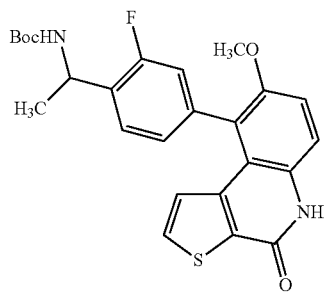 [SMILES: COc1ccc2[nH]c(=O)c3sccc3c2c1-c1ccc(C(C)NC(=O)OC(C)(C)C)c(F)c1]

Following General Procedure B, 9-bromo-8-methoxythieno[2,3-c]quinolin-4(5H)-one (800 mg, 2.6 mmoL) was reacted with tert-butyl 1-[2-fluoro-4-(4,4,5,5-tetramethyl-1,3,2-dioxaborolan-2-yl)phenyl]ethylcarbamate (1.4 g, 3.9 mmol) to afford the desired product (480 mg, 40%) as a brown solid: ESI MS m/z 469 $[C_{25}H_2FN_2O_4S+H]^+$.

Example 431

3-[4-(8-Methoxy-4-oxo-4,5-dihydrothieno[2,3-c]quinolin-9-yl)phenyl]propanenitrile

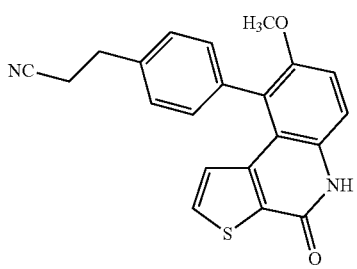 [SMILES: COc1ccc2[nH]c(=O)c3sccc3c2c1-c1ccc(CCC#N)cc1]

Following General Procedure B, 9-bromo-8-methoxythieno[2,3-c]quinolin-4(5H)-one (400 mg, 1.3 mmol) was reacted with 3-[4-(4,4,5,5-tetramethyl-1,3,2-dioxaborolan-2-yl)phenyl]propanenitrile (600 mg, 1.9 mmol) to afford the desired product (320 mg, 69%) as a brown solid: ESI MS m/z 361 $[C_{21}H_{16}N_2O_2S+H]^+$.

Example 432

9-(4-Acetylphenyl-8-methoxythieno[2,3-c]quinolin-4(5H)-one

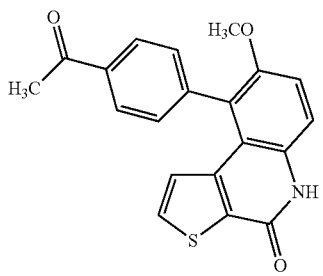 [SMILES: COc1ccc2[nH]c(=O)c3sccc3c2c1-c1ccc(C(C)=O)cc1]

Following General Procedure B, 9-bromo-8-methoxythieno[2,3-c]quinolin-4(5H)-one (1.0 g, 3.2 mmol) was reacted with 1-[4-(4,4,5,5-tetramethyl-1,3,2-dioxaborolan-2-yl)phenyl]ethanone (1.2 g, 4.8 mmol) to afford the desired product (520 mg, 46%) as a brown solid: $^1$H NMR (500 MHz, CD$_3$OD) δ 8.16 (d, J=8.1 Hz, 2H), 7.61-7.54 (m, 2H), 7.45-7.39 (m, 3H), 6.05 (d, J=5.4 Hz, 1H), 3.75 (s, 3H), 2.71 (s, 3H).

Example 433

9-{4-[1-(Cyclopentylamino)ethyl]phenyl}-8-methoxythieno[2,3-c]quinolin-4(5H)-one

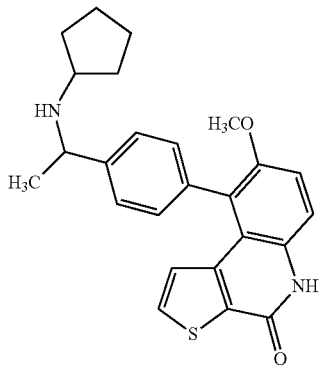 [SMILES: COc1ccc2[nH]c(=O)c3sccc3c2c1-c1ccc(C(C)NC2CCCC2)cc1]

Following General Procedure E, N-[1-(4-bromophenyl)ethyl]cyclopentanamine (600 mg, 2.3 mmol) was reacted with bis(pinacolato)diboron (410 mg, 1.6 mmol) to afford the crude boronic ester which was reacted with 9-bromo-8-methoxythieno[2,3-c]quinolin-4(5H)-one (250 mg, 0.81 mmol) to afford the desired product (330 mg, 97%) as a brown solid: $^1$H NMR (300 MHz, CD$_3$OD) δ 7.73-7.64 (m, 2H), 7.60-7.50 (m, 2H), 7.47-7.34 (m, 3H), 6.01 (d, J=5.4 Hz, 1H), 4.57 (q, J=6.8 Hz, 1H), 3.74 (s, 3H), 3.62-3.45 (m, 1H), 2.30-2.02 (m, 2H), 1.93-1.85 (m, 2H), 1.81 (d, J=6.7 Hz, 3H), 1.77-1.51 (m, 4H).

Example 434 tert-Butyl 1-[4-(8-Methoxy-4-oxo-4,5-dihydrothieno[2,3-c]quinolin-9-yl)phenyl]propylcarbamate

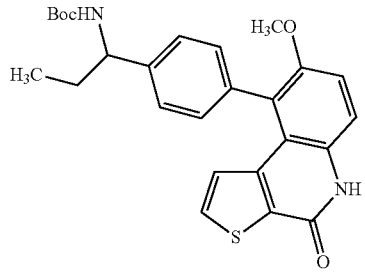 [SMILES: CCC(NC(=O)OC(C)(C)C)c1ccc(-c2c(OC)ccc3[nH]c(=O)c4sccc4c23)cc1]

Following General Procedure B, 9-bromo-8-methoxythieno[2,3-c]quinolin-4(5H)-one (1.1 g, 3.7 mmol) was reacted with tert-butyl 1-[4-(4,4,5,5-tetramethyl-1,3,2-dioxaborolan-2-yl)phenyl]propylcarbamate (2.0 g, 5.5 mmol) to afford the desired product (1.2 g, 68%) as a white solid: ESI MS m/z 465 [C$_{26}$H$_{28}$N$_2$O$_4$S+H]$^+$.

Example 337

9-[4-(1-Aminopropyl)phenyl]-8-methoxythieno[2,3-c]quinolin-4(5H)-one Hydrochloride

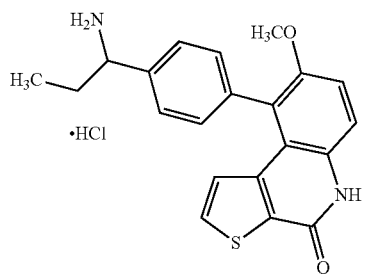 [SMILES: CCC(N)c1ccc(-c2c(OC)ccc3[nH]c(=O)c4sccc4c23)cc1 ; Cl]

Following General Procedure C, tert-butyl 1-[4-(8-methoxy-4-oxo-4,5-dihydrothieno[2,3-c]quinolin-9-yl)phenyl]propylcarbamate (30 mg, 0.064 mmol) was reacted with TFA (2 mL) to afford the desired product (17 mg, 72%) as a white solid: $^1$H NMR (500 MHz, CD$_3$OD) δ 7.64-7.57 (m, 2H), 7.54 (d, J=2.0 Hz, 1H), 7.53 (d, J=1.6 Hz, 1H), 7.39-7.35 (m, 3H), 5.98 (d, J=5.4 Hz, 1H), 4.32 (q, J=5.1 Hz, 1H), 5.53 (s, 3H), 2.17-2.07 (m, 2H), 1.03 (t, J=7.4 Hz, 3H); ESI MS m/z 365 [C$_{21}$H$_{20}$N$_2$O$_2$S+H]$^+$; HPLC >99% (AUC), t$_R$=9.47 min.

Example 435

(S)-tert-Butyl 1-[4-(8-Methoxy-4-oxo-4,5-dihydrothieno[2,3-c]quinolin-9-yl)phenyl]ethylcarbamate

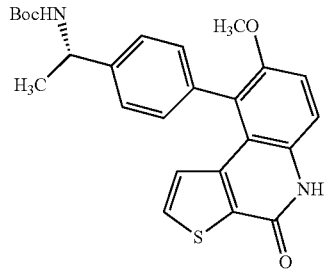

Following General Procedure B, 9-bromo-8-methoxythieno[2,3-c]quinolin-4(5H)-one (760 mg, 2.4 mmol) was reacted with (S)-tert-butyl 1-[4-(4,4,5,5-tetramethyl-1,3,2-dioxaborolan-2-yl)phenyl]ethylcarbamate (1.3 g, 3.7 mmol) to afford the desired product (730 mg, 66%) as a light yellow solid: ESI MS m/z 451 [$C_{25}H_{26}N_2O_4S+H$]+.

Example 436

9-{4-[1-(Dimethylamino)ethyl]-phenyl}-8-methoxythieno[2,3-c]quinolin-4(5H)-one

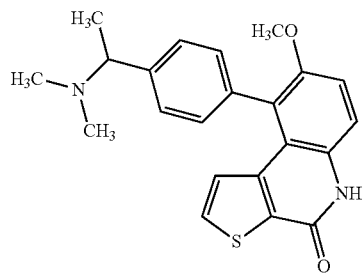 [SMILES: COc1ccc2[nH]c(=O)c3sccc3c2c1-c1ccc(C(C)N(C)C)cc1]

Following General Procedure B, 9-bromo-8-methoxythieno[2,3-c]quinolin-4(5H)-one (1.5 g, 4.8 mmol) was reacted with 4-[1-(dimethylamino)ethyl]phenylboronic acid (1.5 g, 6.3 mmol) to afford the desired product (1.1 g, 58%) as a white solid: ESI MS m/z 379 [$C_{22}H_{22}N_2O_2S+H$]+.

Example 139 tert-Butyl {1-[4-(8-Methoxy-4-oxo-4,5-dihydrothieno[2,3-c]quinolin-9-yl)benzyl]piperidin-4-yl}methylcarbamate

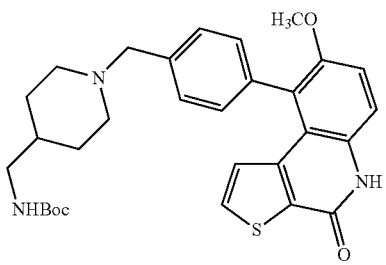 [SMILES: COc1ccc2[nH]c(=O)c3sccc3c2c1-c1ccc(CN2CCC(CNC(=O)OC(C)(C)C)CC2)cc1]

Following General Procedure B, 9-bromo-8-methoxythieno[2,3-c]quinolin-4(5H)-one (110 mg, 0.31 mmol) was reacted with 4-({4-[(tert-butoxycarbonylamino)methyl]piperidin-1-yl}methyl)phenylboronic acid (80 mg, 0.26 mol) to afford the desired product (25 mg, 20%) as a yellow glass: 1H NMR (500 MHz, CD3OD) δ 7.69-7.66 (m, 2H), 7.57-7.54 (m, 2H), 7.41-7.38 (m, 3H), 5.96-5.95 (m, 1H), 4.48-4.44 (m, 2H), 3.75 (s, 3H), 3.70-3.64 (m, 2H), 3.27-2.91 (m, 4H), 2.25-1.95 (m, 2H), 1.57 (s, 1H), 1.52-1.42 (m, 10H); ESI MS m/z 534 [$C_{30}H_{35}N_3O_4S+H$]+; HPLC 97.6% (AUC), $t_R$=14.10 min.

Example 437

(E)-tert-Butyl 1-[3-(8-Methoxy-4-oxo-4,5-dihydrothieno[2,3-c]quinolin-9-yl)allyl]piperidin-4-ylcarbamate

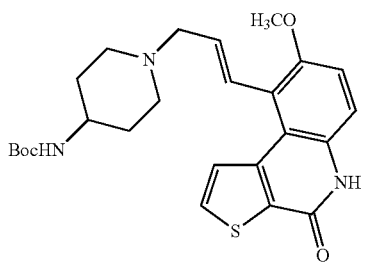 [SMILES: COc1ccc2[nH]c(=O)c3sccc3c2c1/C=C/CN1CCC(NC(=O)OC(C)(C)C)CC1]

Following General Procedure B, 9-bromo-8-methoxythieno[2,3-c]quinolin-4(5H)-one (180 mg, 0.48 mmol) was reacted with (E)-tert-butyl 1-[3-(4,4,5,5-tetramethyl-1,3,2-dioxaborolan-2-yl)allyl]piperidin-4-ylcarbamate (100 mg, 0.32 mmol) to afford the desired product (86 mg, 57%) as a brown solid: ESI MS m/z 470 [$C_{25}H_{31}N_3O_4S+H$]+.

Example 152

(E)-9-[3-(4-Aminopiperidin-1-yl)prop-1-enyl]-8-methoxythieno[2,3-c]quinolin-4(5H)-one

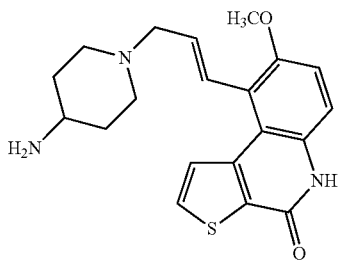 [SMILES: COc1ccc2[nH]c(=O)c3sccc3c2c1/C=C/CN1CCC(N)CC1]

Following General Procedure C, (E)-tert-butyl 1-[3-(8-methoxy-4-oxo-4,5-dihydrothieno[2,3-c]quinolin-9-yl)allyl]piperidin-4-ylcarbamate (40 mg, 0.085 mmol) was reacted with TFA (1 mL) to afford the desired product (15 mg, 86%) as a yellow solid: 1H NMR (500 MHz, CD3OD) δ 7.94 (d, J=5.3 Hz, 1H), 7.86 (d, J=5.3 Hz, 1H), 7.34 (d, J=9.1 Hz, 1H), 7.24 (d, J=9.1 Hz, 1H), 7.06 (d, J=16.0 Hz, 1H), 6.14-6.08 (m, 1H), 4.12 (d, J=7.1 Hz, 2H), 3.84 (br s, 2H), 3.55 (br s, 1H), 3.26 (br s, 3H), 2.38 (d, J=13.3 Hz, 2H), 2.12-2.07 (m, 2H), 1.35-1.31 (m, 1H), 0.96-0.90 (m, 1H); ESI MS m/z 370 [C$_{20}$H$_{23}$N$_3$O$_2$S+H]$^+$; HPLC 95.6% (AUC), t$_R$=6.78 min.

Example 164

9-{4-[(Dimethylamino)methyl]phenyl}-8-methoxythieno[2,3-c]quinolin-4(5H)-one

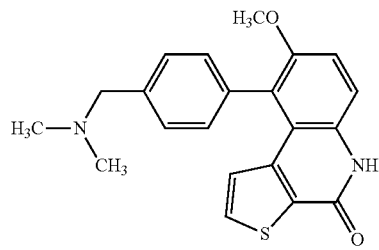 [SMILES: COc1ccc2[nH]c(=O)c3sccc3c2c1-c1ccc(CN(C)C)cc1]

Following the procedure outlined for Example 460, 9-[4-(aminomethyl)phenyl]-8-methoxythieno[2,3-c]quinolin-4(5H)-one (100 mg, 0.27 mmol) was reacted with formaldehyde (37% in water, 20 mg, 0.67 mmol) to afford the desired product (45 mg, 47%): $^1$H NMR (500 MHz, CD$_3$OD) δ 7.67 (d, J=8.2 Hz, 2H), 7.58-7.54 (m, 2H), 7.42-7.38 (m, 3H), 5.96 (d, J=5.5 Hz, 1H), 4.47 (s, 2H), 3.75 (s, 3H), 2.98 (s, 6H); ESI MS m/z 365 [C$_{21}$H$_{20}$N$_2$O$_2$S+H]$^+$; HPLC >99% (AUC), t$_R$=8.50 min.

Example 438

9-{4-[(Diethylamino)methyl]phenyl}-8-methoxythieno[2,3-c]quinolin-4(5H)-one

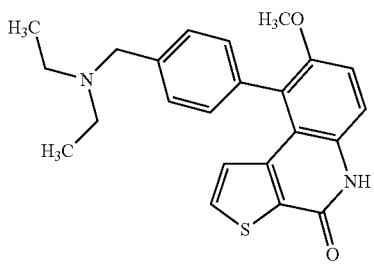 [SMILES: CCN(CC)Cc1ccc(-c2c(OC)ccc3[nH]c(=O)c4sccc4c23)cc1]

Following General Procedure E, N-(4-bromobenzyl)-N-ethylethanamine (200 mg, 0.83 mmol) was reacted with bis(pinacolato)diboron (230 mg, 0.91 mmol) to afford the crude boronic ester which was reacted with 9-bromo-8-methoxythieno[2,3-c]quinolin-4(5H)-one (260 mg, 0.83 mmol) to afford the desired product (58 mg, 25%) as a white solid: $^1$H NMR (500 MHz, CD$_3$OD) δ 7.69 (d, J=8.2 Hz, 2H), 7.60-7.54 (m, 2H), 7.46-7.43 (m, 2H), 7.41 (d, J=9.1 Hz, 1H), 5.99 (d, J=5.4 Hz, 1H), 4.50 (s, 2H), 3.75 (s, 3H), 3.41-3.32 (m, 4H), 1.44 (t, J=7.3 Hz, 6H).

Example 188

8-Methoxy-9-{4-[(methylamino)methyl]phenyl}thieno[2,3-c]quinolin-4(5H)-one

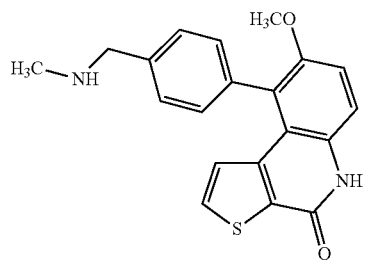 [SMILES: CNCc1ccc(-c2c(OC)ccc3[nH]c(=O)c4sccc4c23)cc1]

Following General Procedure E, 1-(4-bromophenyl)-N-methylmethanamine (200 mg, 1.0 mmol) was reacted to bis(pinacoato)diboron (280 mg, 1.1 mmol) to afford the crude boronic ester which was reacted with 9-bromo-8-methoxythieno[2,3-c]quinolin-4(5H)-one (310 mg, 1.0 mmol) to afford the desired product (145 mg, 42%) as a white solid: $^1$H NMR (500 MHz, CD$_3$OD) δ 7.65 (d, J=8.1 Hz, 2H), 7.58-7.52 (m, 2H), 7.42-7.35 (m, 3H), 6.02 (d, J=5.4 Hz, 1H), 4.33 (s, 2H), 3.73 (s, 3H), 2.83 (s, 3H).

Example 439 tert-Butyl 4-(8-Methoxy-4-oxo-4,5-dihydrothieno[2,3-c]quinolin-9-yl)benzylcarbamate

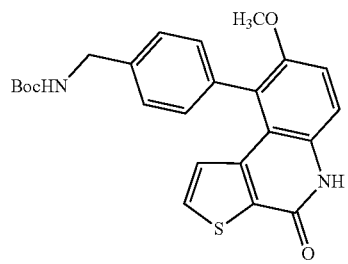 [SMILES: COc1ccc2[nH]c(=O)c3sccc3c2c1-c1ccc(CNC(=O)OC(C)(C)C)cc1]

Following General Procedure B, 9-bromo-8-methoxythieno[2,3-c]quinolin-4(5H)-one (150 mg, 0.48 mmol) was reacted with 4-[(tert-butoxycarbonylamino)methyl]phenylboronic acid (180 mg, 0.73 mmol) to afford the desired product (180 mg, 83%) as a brown solid: ESI MS m/z 437 [C$_{24}$H$_{24}$N$_2$O$_4$S+H]$^+$.

Example 440

9-{4-[(Isopropylamino)methyl]phenyl}-8-methoxythieno[2,3-c]quinolin-4(5H)-one

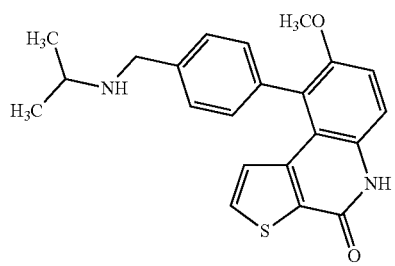 [SMILES: COc1ccc2[nH]c(=O)c3sccc3c2c1-c1ccc(CNC(C)C)cc1]

Following General Procedure E, N-(4-bromobenzyl)propan-2-amine (200 mg, 0.88 mmol) was reacted with bis(pinacolato)diboron (240 mg, 0.96 mmol) to afford the crude boronic ester which was reacted with 9-bromo-8-methoxythieno[2,3-c]quinolin-4(5H)-one (270 mg, 0.88 mmol) to afford the desired product (190 mg, 57%) as a light brown solid: $^1$H NMR (500 MHz, CD$_3$CD$_2$OD) δ 7.68-7.63 (m, 2H), 7.56-7.49 (m, 2H), 7.41-7.34 (m, 3H), 6.04 (dd, J=5.4, 2.4 Hz, 1H), 4.33 (s, 2H), 3.72-3.67 (m, 3H), 3.56-3.50 (m, 1H), 1.45 (dd, J=6.6, 2.2 Hz, 6H).

Example 269

9-{4-[(Ethylamino)methyl]phenyl}-8-methoxythieno[2,3-c]quinolin-4(5H)-one Hydrochloride

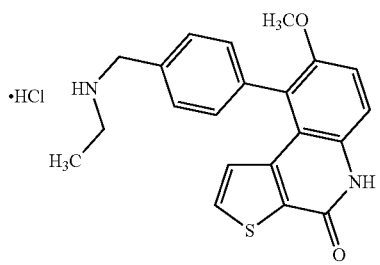 [SMILES: Cl ; CCNCc1ccc(-c2c(OC)ccc3[nH]c(=O)c4sccc4c23)cc1]

Following General Procedure E, N-(4-bromobenzyl)ethanamine (300 mg, 1.4 mmol) was reacted with bis(pinacolato)diboron (390 mg, 1.5 mmol) to afford the crude boronic ester which was reacted with 9-bromo-8-methoxythieno[2,3-c]quinolin-4(5H)-one (430 mg, 1.4 mmol) to afford the desired product (160 mg, 31%) as a brown solid: $^1$H NMR (500 MHz, CD$_3$OD) δ 7.67 (d, J=8.1 Hz, 2H), 7.57-7.54 (m, 2H), 7.39-7.36 (m, 3H), 4.34 (s, 2H), 3.72 (s, 3H), 3.23 (q, J=7.3 Hz, 2H), 1.97 (s, 2H), 1.42 (t, J=7.3 Hz, 3H); ESI MS m/z 365 [C$_{21}$H$_{20}$N$_2$O$_2$S+H]$^+$; HPLC >99% (AUC), t$_R$=8.61 min.

Example 441

(E)-tert-Butyl 1-[3-(8-Methoxy-4-oxo-4,5-dihydrothieno[2,3-c]quinolin-9-yl)allyl]piperidin-3-ylcarbamate

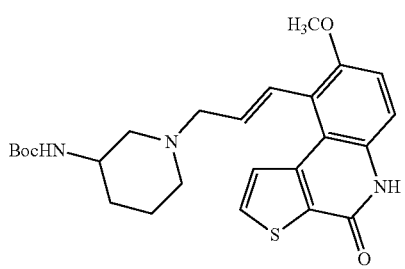 [SMILES: COc1ccc2[nH]c(=O)c3sccc3c2c1/C=C/CN1CCCC(NC(=O)OC(C)(C)C)C1]

Following General Procedure B, 9-bromo-8-methoxythieno[2,3-c]quinolin-4(5H)-one (530 mg, 1.7 mmol) was reacted with (E)-tert-Butyl 1-[3-(4,4,5,5-tetramethyl-1,3,2-dioxaborolan-2-yl)allyl]piperidin-3-ylcarbamate (320 mg, 0.88 mmol) to afford the desired product (190 mg, 47%) as a light brown solid: ESI MS m/z 456 [C$_{24}$H$_{29}$N$_3$O$_4$S+H]$^+$.

Example 442 tert-Butyl 4-(6-Fluoro-8-methoxy-4-oxo-4,5-dihydrothieno[2,3-c]quinolin-9-yl)benzylcarbamate

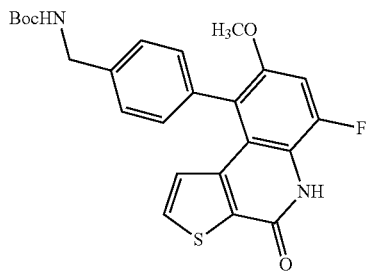 [SMILES: COc1cc(F)c2[nH]c(=O)c3sccc3c2c1-c1ccc(CNC(=O)OC(C)(C)C)cc1]

Following General Procedure B, 9-bromo-6-fluoro-8-methoxythieno[2,3-c]quinolin-4(5H)-one (150 mg, 0.50 mmol) was reacted with tert-butyl 4-(4,4,5,5-tetramethyl-1,3,2-dioxaborolan-2-yl)benzylcarbamate (200 mg, 0.60 mmol) to afford the desired product (100 mg, 48%) as a brown solid: ESI MS m/z 455 [C$_{24}$H$_{23}$FN$_2$O$_4$S+H]$^+$.

Example 257

9-[4-(Aminomethyl)phenyl]-6-fluoro-8-methoxythieno[2,3-c]quinolin-4(5H)-one Hydrochloride

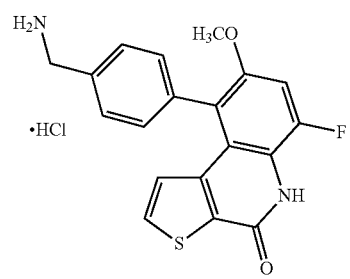 [SMILES: Cl ; COc1cc(F)c2[nH]c(=O)c3sccc3c2c1-c1ccc(CN)cc1]

Following General Procedure D-1, tert-butyl 4-(6-fluoro-8-methoxy-4-oxo-4,5-dihydrothieno[2,3-c]quinolin-9-yl)benzylcarbamate (15 mg, 0.030 mmol) was reacted with HCl (2 N in diethyl ether, 1.5 mL) to afford the desired product (10 mg, 90%) as a white solid: $^1$H NMR (500 MHz, CD$_3$OD) δ 7.63 (d, J=8.1 Hz, 2H), 7.58 (d, J=5.4 Hz, 1H), 7.36 (d, J=8.1 Hz, 2H), 7.32 (d, J=12.7 Hz, 1H), 6.04 (d, J=5.4 Hz, 1H), 4.27 (s, 2H), 3.72 (s, 3H); ESI MS m/z 355 [C$_{19}$H$_{15}$FN$_2$O$_2$S+H]$^+$; HPLC 99% (AUC), t$_R$=10.64 min.

Example 443

9-{4-[1-(Dimethylamino)ethyl]phenyl}-6,7-difluoro-8-methoxythieno[2,3-c]quinolin-4(5H)-one

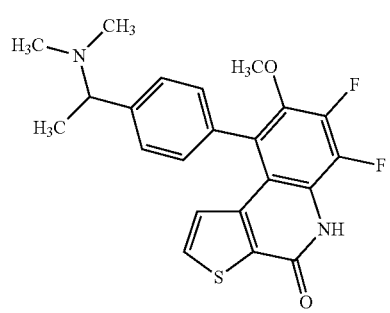 [SMILES: COc1c(F)c(F)c2[nH]c(=O)c3sccc3c2c1-c1ccc(C(C)N(C)C)cc1]

Following General Procedure B, 9-bromo-6,7-difluoro-8-methoxythieno[2,3-c]quinolin-4(5H)-one (150 mg, 0.40 mmol) was reacted with 4-[1-(dimethylamino)ethyl]phenylboronic acid (120 mg, 0.50 mmol) to afford the desired product (55 mg, 35%) as an off-white solid: ESI MS m/z 415 [C$_{22}$H$_{20}$F$_2$N$_2$O$_2$S+H]$^+$.

Example 444

9-{4-[2-(Dimethylamino)ethyl]phenyl}-8-methoxythieno[2,3-c]quinolin-4(5H)-one

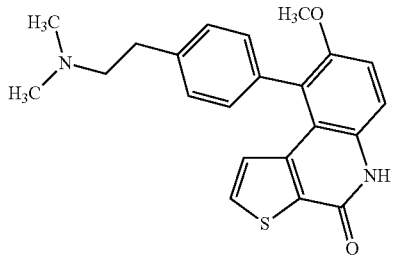 [SMILES: COc1ccc2[nH]c(=O)c3sccc3c2c1-c1ccc(CCN(C)C)cc1]

Following the procedure outlined for Example 460, 9-[4-(2-aminoethyl)phenyl]-8-methoxythieno[2,3-c]quinolin-4(5H)-one (100 mg, 0.30 mmol) was reacted with formaldehyde (100 mg, 1.0 mmol) to afford the desired product (85 mg, 84%) as a white solid: $^1$H NMR (500 MHz, CD$_3$CN+D$_2$O) δ 7.54-7.50 (m, 2H), 7.42 (d, J=7.8 Hz, 2H), 7.32 (d, J=9.1 Hz, 1H), 7.13 (d, 7.8 Hz, 2H), 5.83 (d, J=5.3 Hz, 1H), 3.69 (s, 3H), 3.43-3.40 (m, 2H), 3.16-3.13 (m, 2H), 2.92 (s, 6H).

Example 445

9-(4-Amino-3-methoxyphenyl)-8-methoxythieno[2,3-c]quinolin-4(5H)-one

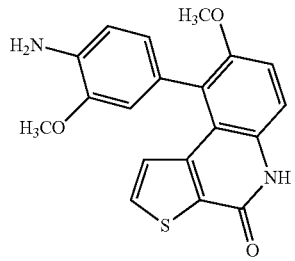 [SMILES: COc1cc(-c2c(OC)ccc3[nH]c(=O)c4sccc4c23)ccc1N]

Following General Procedure B, 9-bromo-8-methoxythieno[2,3-c]quinolin-4(5H)-one (100 mg, 0.30 mmol) was reacted with 2-methoxy-4-(4,4,5,5-tetramethyl-1,3,2-dioxaborolan-2-yl)aniline (150 mg, 0.50 mmol) to afford the desired product (64 mg, 60%) as a brown solid: $^1$H NMR (500 MHz, CD$_3$OD) δ 7.61 (d, J=5.3 Hz, 1H), 7.58-7.53 (m, 2H), 7.41 (d, J=5.3 Hz, 1H), 7.16 (s, 1H), 7.01 (d, J=5.3 Hz, 1H), 6.09 (d, J=5.1 Hz, 1H), 3.93 (s, 3H), 3.77 (s, 3H).

Example 222

9-{4-[1-(Dimethylamino)ethyl]phenyl}-6-fluoro-8-methoxythieno[2,3-c]quinolin-4(5H)-one Hydrochloride

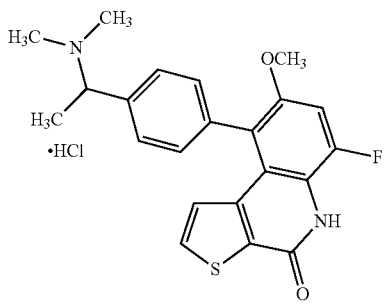 [SMILES: COc1cc(F)c2[nH]c(=O)c3sccc3c2c1-c1ccc(C(C)N(C)C)cc1 ; Cl]

Following General Procedure B, 9-bromo-6-fluoro-8-methoxythieno[2,3-c]quinolin-4(5H)-one (100 mg, 0.30 mmol) was reacted with 4-[1-(dimethylamino)ethyl]phenylboronic acid (100 mg, 0.45 mmol) to afford the desired product (49 mg, 41%) as a white solid: $^1$H NMR (500 MHz, DMSO-d$_6$) δ 10.28 (s, 1H), 7.77 (d, J=5.4 Hz, 1H), 7.71 (q, J=8.0 Hz, 2H), 7.46 (d, J=12.8 Hz, 1H), 7.38 (d, J=8.2 Hz, 2H), 5.69 (d, J=5.4 Hz, 1H), 4.64 (t, J=6.0 Hz, 1H), 3.71 (s, 3H), 2.82 (d, J=4.2 Hz, 3H), 2.70 (d, J=4.4 Hz, 3H), 1.74 (d, J=6.8 Hz, 3H); ESI MS m/z 397 [C$_{22}$H$_{21}$FN$_2$O$_2$S+H]$^+$; HPLC >99% (AUC), t$_R$=9.85 min.

Example 446 tert-Butyl{(1-[2-Fluoro-4-(8-methoxy-4-oxo-4,5-dihydrothieno[2,3-c]quinolin-9-yl)benzyl]piperidin-4-yl}methylcarbamate

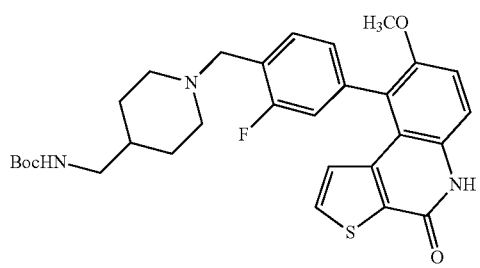 [SMILES: COc1ccc2[nH]c(=O)c3sccc3c2c1-c1ccc(CN2CCC(CNC(=O)OC(C)(C)C)CC2)c(F)c1]

Following General Procedure B, 9-bromo-8-methoxythieno[2,3-c]quinolin-4(5H)-one (100 mg, 0.30 mmol) was reacted with tert-butyl{1-[2-fluoro-4-(4,4,5,5-tetramethyl-1,3,2-dioxaborolan-2-yl)benzyl]piperidin-4-yl}methylcarbamate (150 mg, 0.36 mmol) to afford the desired product (81 mg, 49% 0 was a yellow solid: ESI MS m/z 552 [C$_{30}$H$_{34}$FN$_3$O$_4$S+H]$^+$.

Example 447 tert-Butyl[5-(8-Methoxy-4-oxo-4,5-dihydrothieno[2,3-c]quinolin-9-yl)thiophen-2-yl]methylcarbamate

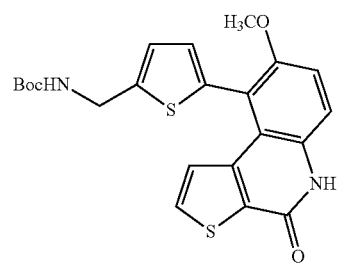 [SMILES: COc1ccc2[nH]c(=O)c3sccc3c2c1-c1ccc(CNC(=O)OC(C)(C)C)s1]

Following General Procedure B, 9-bromo-8-methoxythieno[2,3-c]quinolin-4(5H)-one (150 mg, 0.48 mmol) was reacted with 5-[(tert-butoxycarbonylamino)methyl]thiophen-2-ylboronic acid (130 mg, 0.53 mmol) to afford the desired product (30 mg, 18%) as an off-white solid: $^1$H NMR (500 MHz, CD$_3$OD) δ 7.74 (d, J=5.4 Hz, 1H), 7.56 (d, J=9.1 Hz, 1H), 7.36 (d, J=9.1 Hz, 1H), 6.49 (d, J=3.1 Hz, 1H), 6.40 (br s, 1H), 6.01 (d, J=5.4 Hz, 1H), 4.27 (s, 2H), 3.82 (s, 3H), 1.39 (s, 9H).

Example 448

2-Fluoro-N-(2-hydroxyethyl)-4-(8-methoxy-4-oxo-4,5-dihydrothieno[2,3-c]quinolin-9-yl)benzenesulfonamide

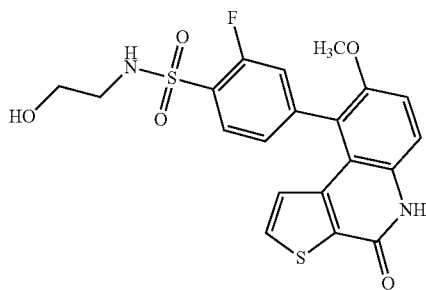 [SMILES: COc1ccc2[nH]c(=O)c3sccc3c2c1-c1ccc(S(=O)(=O)NCCO)c(F)c1]

Following General Procedure E, 4-bromo-2-fluoro-N-(2-hydroxyethyl)benzenesulfonamide (3.30 mg, 1.1 mmol) was reacted with bis(pinacolato)diborane (300 mg, 1.2 mmol) to afford the crude boronic ester which was reacted with 9-bromo-8-methoxythieno[2,3-c]quinolin-4(5H)-one (310 mg, 1.0 mmol) to afford the desired product (68 mg, 13%) as an off-white solid: $^1$H NMR (300 MHz, DMSO-d$_6$) δ 11.95 (s, 1H), 8.04 (t, J=5.8 Hz, 1H), 7.93 (t, J=7.8 Hz, 1H), 7.93 (d, J=5.4 Hz, 1H), 7.57 (d, J=9.1 Hz, 1H), 7.49-7.43 (m, 2H), 7.30 (dd, J=8.0, 1.5 Hz, 1H), 5.89 (d, J=5.4 Hz, 1H), 4.78 (t, J=5.6 Hz, 1H), 3.72 (s, 3H), 3.46 (q, J=6.2 Hz, 2H), 3.05 (m, 2H).

Example 449

4-(8-Methoxy-4-oxo-4,5-dihydrothieno[2,3-c]quinolin-9-yl)-N,N-dimethylbenzenesulfonamide

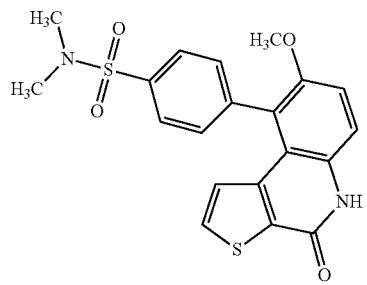 [SMILES: COc1ccc2[nH]c(=O)c3sccc3c2c1-c1ccc(S(=O)(=O)N(C)C)cc1]

Following General Procedure B, 9-bromo-8-methoxythieno[2,3-c]quinolin-4(5H)-one (100 mg, 0.32 mmol) was reacted with N,N-dimethyl-4-(4,4,5,5-tetramethyl-1,3,2-dioxaborolan-2-yl)benzenesulfonamide (110 mg, 0.35 mmol) to afford the desired product (33 mg, crude) as a brown solid: ESI MS m/z 415 [C$_{20}$H$_{8}$N$_2$O$_4$S$_2$+H]$^+$.

Example 450

N-(2-Hydroxyethyl)-4-(8-methoxy-4-oxo-4,5-dihydrothieno[2,3-c]quinolin-9-yl)benzenesulfonamide

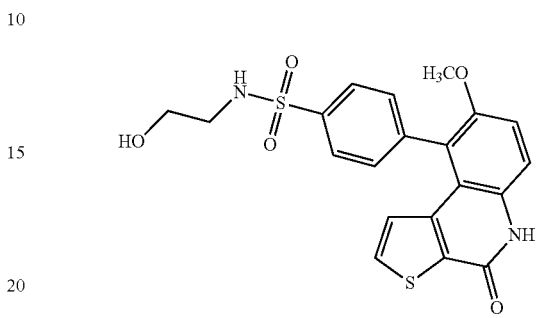

Following General Procedure B, 9-bromo-8-methoxythieno[2,3-c]quinolin-4(5H)-one (500 mg, 1.5 mmol) was reacted with N-(2-hydroxyethyl)-4-(4,4,5,5-tetramethyl-1,3,2-dioxaborolan-2-yl)benzenesulfonamide (450 mg, 1.5 mmol) to afford the desired product (130 mg, 20%) as an off-white solid: $^1$H NMR (300 MHz, DMSO-d$_6$) δ 11.93 (s, 1H), 7.94 (d, J=8.4 Hz, 2H), 7.78-7.74 (m, 2H), 7.58-7.42 (m, 4H), 5.74 (d, J=5.4 Hz, 1H), 4.78 (t, J=5.6 Hz, 1H), 3.71 (s, 3H), 3.45 (q, J=6.1 Hz, 2H), 2.93 (q, J=6.2 Hz, 2H).

Example 333

N-(2-Fluoroethyl)-4-(8-methoxy-4-oxo-4,5-dihydrothieno[2,3-c]quinolin-9-yl)benzenesulfonamide

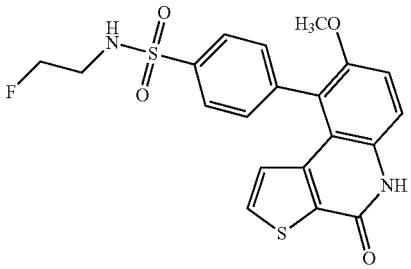 [SMILES: COc1ccc2[nH]c(=O)c3sccc3c2c1-c1ccc(S(=O)(=O)NCCF)cc1]

To a solution of N-(2-hydroxyethyl)-4-(8-methoxy-4-oxo-4,5-dihydrothieno[2,3-c]quinolin-9-yl)benzenesulfonamide (120 mg, 0.28 mmol) in methylene chloride (10 mL) and THF (6 mL) under nitrogen at −78° C. was added DAST (89 mg, 0.56 mmol) and the reaction mixture was stirred at −78° C. for 2 h and warmed to room temperature and stirred for 16 h. The reaction mixture was concentrated and the residue was purified by column chromatography (silica gel, ethyl acetate/hexanes gradient). The resulting crude residue was triturated in methylene chloride and filtered to afford the desired product (90 mg, 75%) as a off-white solid: $^1$H NMR (500 MHz, DMSO-d$_6$) δ 11.92 (s, 1H), 8.10 (t, J=5.9 Hz, 1H), 7.95 (d, J=8.4 Hz, 2H), 7.76 (d, J=5.4 Hz, 1H), 7.56 (d, J=9.1 Hz, 1H), 7.51 (d, J=8.4 Hz, 2H), 7.43 (d, J=9.2 Hz, 1H), 5.75 (d, J=5.4 Hz, 1H), 4.51 (t, J=4.9 Hz, 1H), 4.42 (t, J=4.9 Hz, 1H), 3.71

(s, 3H), 3.24 (q, J=5.2 Hz, 1H), 3.19 (q, J=5.2 Hz, 1H); ESI MS m/z 433 $[C_{20}H_{17}FN_2O_4S_2+H]^+$; HPLC 93.4% (AUC), $t_R$=15.64 min.

Example 451 tert-Butyl 4-(8-Methoxy-4-oxo-4,5-dihydrothieno[2,3-c]quinolin-9-yl)benzylcarbamate

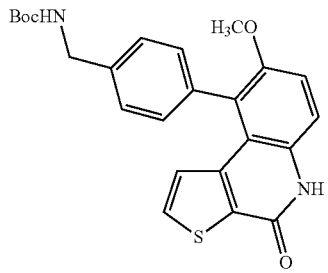 [SMILES: COc1ccc2[nH]c(=O)c3sccc3c2c1-c1ccc(CNC(=O)OC(C)(C)C)cc1]

Following General Procedure E, tert-butyl 4-bromobenzylcarbamate (2.9 g, 10 mmol) was reacted with bis(pinacolato)diborane (2.8 g, 11 mmol) to afford the crude boronic ester which was reacted with 9-bromo-8-methoxythieno[2,3-c]quinolin-4(5H)-one (2.8 g, 9.0 mmol) to afford the desired product (2.7 g, 68%) as a brown solid: ESI MS m/z 437 $[C_{24}H_{24}N_2O_4S+H]^+$.

Example 452 tert-Butyl 4-(6-Bromo-8-methoxy-4-oxo-4,5-dihydrothieno[2,3-c]quinolin-9-yl)benzylcarbamate

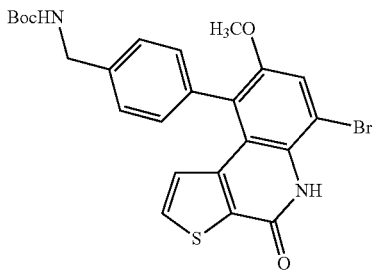 [SMILES: COc1cc(Br)c2[nH]c(=O)c3sccc3c2c1-c1ccc(CNC(=O)OC(C)(C)C)cc1]

To a solution of tert-butyl 4-(8-methoxy-4-oxo-4,5-dihydrothieno[2,3-c]quinolin-9-yl)benzylcarbamate (29 mg, 0.055 mmol) in DMF (1 mL) was added N-bromosuccinimide (12 mg, 0.066 mmol) and the reaction was stirred at room temperature for 1 h and heated at 50° C. for 2 h. The reaction mixture was concentrated and the residue was purified by preparatory TLC (silica, methanol/methylene chloride gradient) to afford the desired product (10 mg, 35%): ESI MS m/z 516 $[C_{24}H_{23}BrN_2O_4S+H]^+$.

Example 453 tert-Butyl 2-[4-(8-Methoxy-4-oxo-4,5-dihydrothieno[2,3-c]quinolin-9-yl)phenyl]propan-2-ylcarbamate

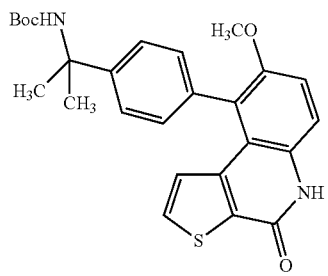

Following General Procedure E, tert-butyl 2-(4-bromophenyl)propan-2-ylcarbamate (160 mg, 0.50 mmol) was reacted with bis(pinacolato)diboron (140 mg, 0.55 mmol) to afford the crude boronic ester which was reacted with 9-bromo-8-methoxythieno[2,3-c]quinolin-4(5H)-one (140 mg, 0.45 mmol) to afford the desired product (110 mg, 47%) as a brown solid: ESI MS m/z 465 $[C_{26}H_{28}N_2O_4S+H]^+$.

Example 454 tert-Butyl 4-(6-Chloro-8-methoxy-4-oxo-4,5-dihydrothieno[2,3-c]quinolin-9-yl)benzylcarbamate

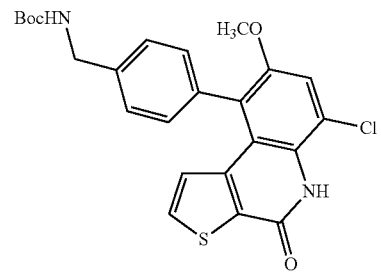 [SMILES: COc1cc(Cl)c2[nH]c(=O)c3sccc3c2c1-c1ccc(CNC(=O)OC(C)(C)C)cc1]

A solution of tert-butyl 4-(8-methoxy-4-oxo-4,5-dihydrothieno[2,3-c]quinolin-9-yl)benzylcarbamate (45 mg, 0.10 mmol) and N-chlorosuccinimide (17 mg, 0.13 mmol) in DMF (1 mL) was heated at 50° C. for 3 h. The reaction mixture was concentrated under reduced pressure. The residue was purified by preparatory HPLC (water/acetonitrile w 0.05% TFA gradient) to afford the desired product (15 mg, 32%) as a brown solid: ESI MS m/z 471 $[C_{24}H_{23}ClN_2O_4S+H]^+$.

Example 455 tert-Butyl 2-[4-(6-Chloro-8-methoxy-4-oxo-4,5-dihydrothieno[2,3-c]quinolin-9-yl)phenyl]propan-2-ylcarbamate

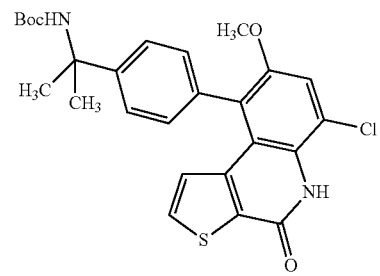 [SMILES: COc1cc(Cl)c2[nH]c(=O)c3sccc3c2c1-c1ccc(C(C)(C)NC(=O)OC(C)(C)C)cc1]

A solution of tert-butyl 2-[4-(8-methoxy-4-oxo-4,5-dihydrothieno[2,3-c]quinolin-9-yl)phenyl]propan-2-ylcarbamate (130 mg, 0.27 mmol) and N-chlorosuccinimide (47 mg, 0.35 mmol) in DMF (3 mL) was heated at 70° C. for 2 h. The reaction mixture was cooled to room temperature, quenched with water and the aqueous layer was extracted with methylene chloride/methanol (9:1). The combined organic layers were dried over sodium sulfate, filtered, concentrated and the residue was purified by column chromatography (silica, methanol/methylene chloride gradient) to afford the desired product (42 mg, 31%) as a brown solid: ESI MS m/z 500 $[C_{26}H_{27}ClN_2O_4S+H]^+$.

Example 456

N-[4-(8-Methoxy-4-oxo-4,5-dihydrothieno[2,3-c]quinolin-9-yl)-2-methylphenyl]methanesulfonamide

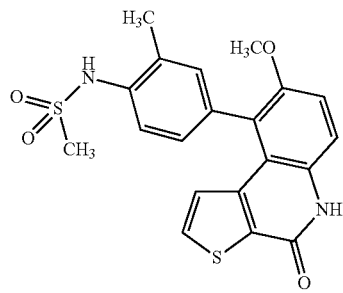 [SMILES: COc1ccc2[nH]c(=O)c3sccc3c2c1-c1ccc(NS(C)(=O)=O)c(C)c1]

Following General Procedure E, N-(4-bromo-2-methylphenyl)methanesulfonamide (130 mg, 0.50 mmol) was reacted with bis(pinacolato)diboron (140 mg, 0.55 mmol) to afford the crude boronic ester which was reacted with 9-bromo-8-methoxythieno[2,3-c]quinolin-4(5H)-one (140 mg, 0.45 mmol) to afford the desired product (51 mg, 27%) as a brown solid: ESI MS m/z 415 $[C_{20}H_{18}N_2O_4S_2+H]^+$.

Example 599

(R)-tert-butyl 2-(4-(8-methoxy-6-methyl-4-oxo-4,5-dihydrothieno[2,3-c]quinolin-9-yl)phenyl)propylcarbamate

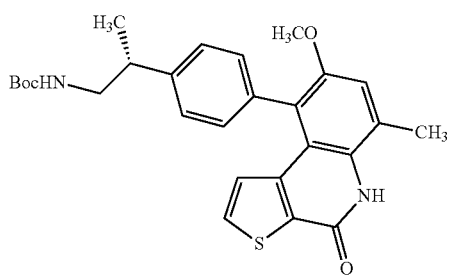 [SMILES: COc1cc(C)c2[nH]c(=O)c3sccc3c2c1-c1ccc([C@@H](C)CNC(=O)OC(C)(C)C)cc1]

Following General Procedure E, (R)-tert-butyl 2-(4-bromophenyl)propylcarbamate (60 mg, 0.20 mmol) was reacted with 9-bromo-8-methoxy-6-methylthieno[2,3-c]quinolin-4 (5H)-one (60 mg, 0.20 mmol) to afford the desired product (52 mg, 62%) as a brown solid: ESI MS m/z 479 $[C_{27}H_{30}N_2O_4S]^+$

Example 600 tert-butyl 2-(4-(8-methoxy-6-methyl-4-oxo-4,5-dihydrothieno[2,3-c]quinolin-9-yl)phenyl)propan-2-ylcarbamate

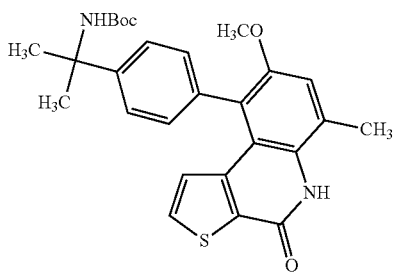 [SMILES: COc1cc(C)c2[nH]c(=O)c3sccc3c2c1-c1ccc(C(C)(C)NC(=O)OC(C)(C)C)cc1]

Following General Procedure E, tert-butyl 2-(4-bromophenyl)propan-2-ylcarbamate (0.44 g, 1.4 mmol) was reacted with 9-bromo-8-methoxy-6-methylthieno[2,3-c]quinolin-4 (5H)-one (0.45 g, 1.4 mmol) to afford the desired product (0.53 g, 79%) as a brown solid: ESI MS m/z 479 $[C_{27}H_{30}N_2O_4S+H]^+$.

Example 601 tert-butyl 4-(8-methoxy-4-oxo-4,5-dihydrothieno[2,3-c]quinolin-9-yl)benzylcarbamate

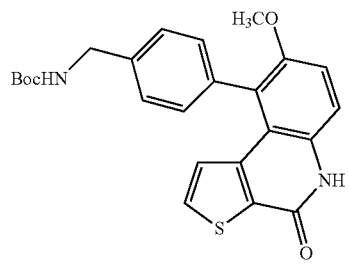 [SMILES: COc1ccc2[nH]c(=O)c3sccc3c2c1-c1ccc(CNC(=O)OC(C)(C)C)cc1]

Following General Procedure E, tert-butyl 4-bromobenzylcarbamate (0.78 g, 2.7 mmol) was reacted with 9-bromo-8-methoxythieno[2,3-c]quinolin-4(5H)-one (0.76 g, 2.5 mmol) to afford the desired product (0.66 g, 62%) as a brown solid: ESI MS m/z 437 $[C_{24}H_{24}N_2O_4S+H]^+$.

Example 602

(R)-tert-Butyl 1-(4-(8-methoxy-6-methyl-4-oxo-4,5-dihydrothieno[2,3-c]quinolin-9-yl)phenyl)ethylcarbamate

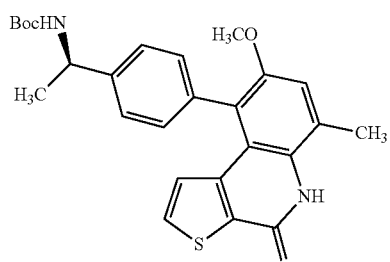

Following General Procedure E, (R1-tert-butyl 1-(4-bromophenyl)ethylcarbamate (60 mg, 0.20 mmol) was reacted with 9-bromo-8-methoxy-6-methylthieno[2,3-c]quinolin-4 (5H)-one (60 mg, 0.20 mmol) to afford the desired product (52 mg, 62%) as a brown solid:

Example 603

(R)-tert-Butyl 1-(4-(8-methoxy-4-oxo-4,5-dihydrothieno[2,3-c]quinolin-9-yl)phenyl)ethylcarbamate

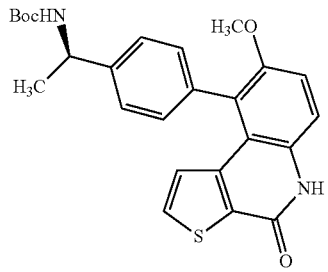 [SMILES: COc1ccc2[nH]c(=O)c3sccc3c2c1-c1ccc([C@@H](C)NC(=O)OC(C)(C)C)cc1]

Following General Procedure E, (R1-tert-butyl 1-(4-bromophenyl)ethylcarbamate (1.5 g, 5 mmol) was reacted with 9-bromo-8-methoxythieno[2,3-c]quinolin-4(5H)-one (1.4 g, 4.6 mmol) to afford the desired product (0.90 g, 43%) as a brown solid: ESI MS m/z 451 $[C_{25}H_{26}N_2O_4S+H]^+$.

Example 604

(S)-tert-Butyl 1-(4-(8-methoxy-6-methyl-4-oxo-4,5-dihydrothieno[2,3-c]quinolin-9-yl)phenyl)ethylcarbamate

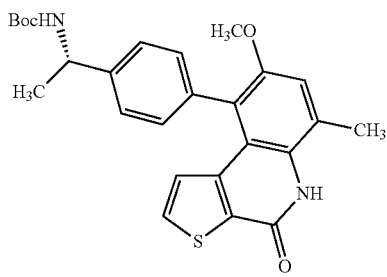 [SMILES: COc1cc(C)c2[nH]c(=O)c3sccc3c2c1-c1ccc([C@H](C)NC(=O)OC(C)(C)C)cc1]

Following General Procedure E, (S)-tert-butyl 1-(4-bromophenyl)ethylcarbamate (60 mg, 0.20 mmol) was reacted with 9-bromo-8-methoxy-6-methylthieno[2,3-c]quinolin-4(5H)-one (60 mg, 0.20 mmol) to afford the desired product (52 mg, 62%) as a brown solid: ESI MS m/z 465 $[C_{26}H_{28}N_2O_4S+H]^+$.

Example 605 tert-Butyl 1-(4-(8-methoxy-4-oxo-4,5-dihydrothieno[2,3-c]quinolin-9-yl)phenyl)ethylcarbamate

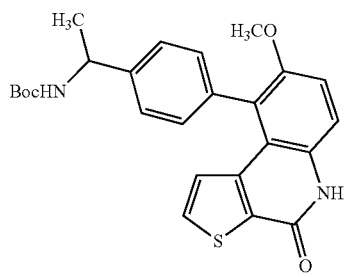 [SMILES: COc1ccc2[nH]c(=O)c3sccc3c2c1-c1ccc(C(C)NC(=O)OC(C)(C)C)cc1]

Following General Procedure E, tert-butyl 1-(4-bromophenyl)ethylcarbamate (3.0 g, 10 mmol) was reacted with 9-bromo-8-methoxythieno[2,3-c]quinolin-4(5H)-one (2.8 g, 9.0 mmol) to afford the desired product (2.0 g, 50%) as a brown solid: ESI MS m/z 451 $[C_{25}H_{26}N_2O_4S+H]^+$.

Example 606

(R)-tert-Butyl 1-(4-(6-chloro-8-methoxy-4-oxo-4,5-dihydrothieno[2,3-c]quinolin-9-yl)phenyl)propylcarbamate

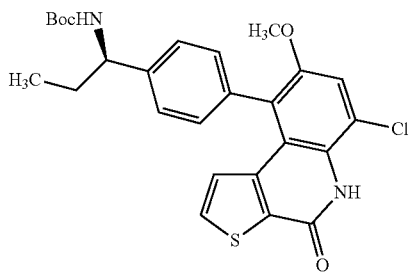 [SMILES: CC[C@@H](NC(=O)OC(C)(C)C)c1ccc(-c2c(OC)cc(Cl)c3[nH]c(=O)c4sccc4c23)cc1]

Following General Procedure H, (R)-tert-butyl 1-(4-(8-methoxy-4-oxo-4,5-dihydrothieno[2,3-c]quinolin-9-yl)phenyl)propylcarbamate (0.67 g, 1.5 mmol) was reacted with N-chlorosuccinimide (0.29 g, 1.6 mmol) in DMF (10 mL) to afford the desired product (0.28 g, 35%) as a brown solid: ESI MS m/z 499 $[C_{26}H_{27}ClN_2O_4S+H]^+$.

Example 607 tert-Butyl 1-(4-(6-bromo-8-methoxy-4-oxo-4,5-dihydrothieno[2,3-c]quinolin-9-yl)phenyl)ethylcarbamate

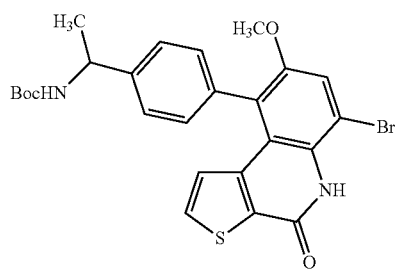 [SMILES: COc1cc(Br)c2[nH]c(=O)c3sccc3c2c1-c1ccc(C(C)NC(=O)OC(C)(C)C)cc1]

Following General Procedure I, tert-butyl 1-(4-(8-methoxy-4-oxo-4,5-dihydrothieno[2,3-c]quinolin-9-yl)phenyl)ethylcarbamate (1.0 g, 2.2 mmol) was reacted with N-bromosuccinimide (0.45 g, 2.5 mmol) in DMF (10 mL) to afford the desired product (0.35 g, 29%) as a brown solid: ESI MS m/z 529 $[C_{25}H_{25}BrN_2O_4S+H]^+$.

Example 608 tert-Butyl 4-(6-bromo-8-methoxy-4-oxo-4,5-dihydrothieno[2,3-c]quinolin-9-yl)benzylcarbamate

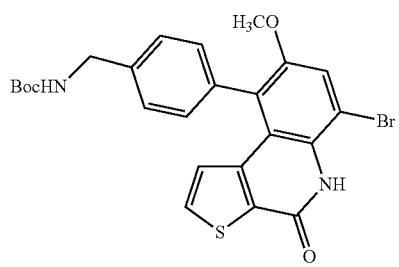 [SMILES: COc1cc(Br)c2[nH]c(=O)c3sccc3c2c1-c1ccc(CNC(=O)OC(C)(C)C)cc1]

Following General Procedure I, tert-butyl 4-(8-methoxy-4-oxo-4,5-dihydrothieno[2,3-c]quinolin-9-yl)benzylcarbamate (0.66 g, 1.5 mmol) was reacted with N-bromosuccinimide (0.30 g, 1.7 mmol) in DMF (10 mL) to afford the desired product (0.39 g, 51%) as a brown solid: ESI MS m/z 515 $[C_{24}H_{23}BrN_2O_4S+H]^+$.

Example 609 tert-Butyl 4-(8-methoxy-6-methyl-4-oxo-4,5-dihydrothieno[2,3-c]quinolin-9-yl)benzylcarbamate

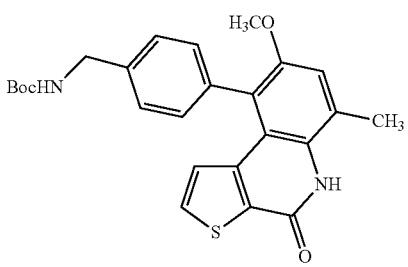 [SMILES: COc1cc(C)c2[nH]c(=O)c3sccc3c2c1-c1ccc(CNC(=O)OC(C)(C)C)cc1]

Following General Procedure J, tert-butyl 4-(6-bromo-8-methoxy-4-oxo-4,5-dihydrothieno[2,3-c]quinolin-9-yl)benzylcarbamate (52 mg, 0.10 mmol) was reacted with trimethylboroxine (13 mg, 0.10 mmol) to afford the desired product (43 mg, 95%) as a grey solid: ESI MS m/z 451 $[C_{25}H_{26}N_2O_4S+H]^+$.

Example 610 tert-Butyl 1-(4-(8-methoxy-6-methyl-4-oxo-4,5-dihydrothieno[2,3-c]quinolin-9-yl)phenyl)ethylcarbamate

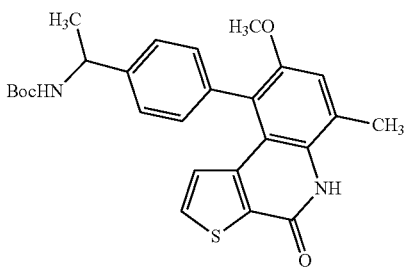 [SMILES: COc1cc(C)c2[nH]c(=O)c3sccc3c2c1-c1ccc(C(C)NC(=O)OC(C)(C)C)cc1]

Following General Procedure J, tert-butyl 1-(4-(6-bromo-8-methoxy-4-oxo-4,5-dihydrothieno[2,3-c]quinolin-9-yl)phenyl)ethylcarbamate (32 mg, 0.060 mmol) was reacted with trimethylboroxine (8 mg, 0.060 mmol) to afford the desired product (20 mg, 61%) as a grey solid: ESI MS m/z 465 $[C_{26}H_{28}N_2O_4S+H]^+$.

Example 1168

(R)-9-(4-(1-aminopropan-2-yl)phenyl)-8-hydroxy-6-methylthieno[2,3-c]quinolin-4(5H)-one

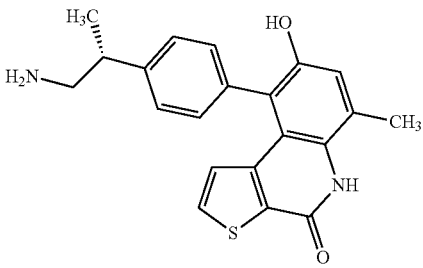 [SMILES: Cc1cc(O)c(-c2ccc([C@@H](C)CN)cc2)c2c1[nH]c(=O)c1sccc12]

Following General Procedure F, (R)-tert-butyl 2-(4-(8-methoxy-6-methyl-4-oxo-4,5-dihydrothieno[2,3-c]quinolin-9-yl)phenyl)propylcarbamate (43 mg, 0.095 mmol) was reacted with tribromoborane (1.0 M in methylene chloride, 1.0 mL, 1.0 mmol) to afford the desired product (18 mg, 51%) as a grey solid: $^1$H NMR (300 MHz, DMSO-$d_6$) δ 10.75-10.65 (m, 1H), 9.14 (s, 1H), 8.09 (s, 3H), 7.68 (d, J=5.4 Hz, 1H), 7.43 (d, J=8.4 Hz, 2H), 7.21 (d, J=8.3 Hz, 2H), 7.05 (s, 1H), 5.86 (d, J=5.4 Hz, 1H), 3.27-2.95 (m, 3H), 1.38 (d, J=6.6 Hz, 3H); ESI MS m/z 365 $[C_{21}H_{20}N_2O_2S+H]^+$; HPLC 98.6%, $t_R$=8.42 min.

Example 1122

(R)-9-(4-(1-Aminoethyl)phenyl)-8-hydroxy-6-methylthieno[2,3-c]quinolin-4(5H)-one

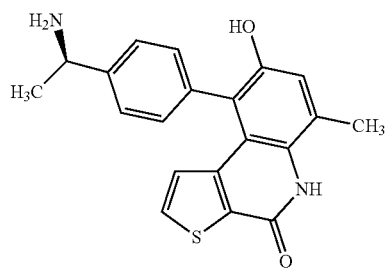 [SMILES: Cc1cc(O)c(-c2ccc([C@@H](C)N)cc2)c2c1[nH]c(=O)c1sccc12]

Following General Procedure F, (R)-tert-butyl 1-(4-(8-methoxy-6-methyl-4-oxo-4,5-dihydrothieno[2,3-c]quinolin-9-yl)phenyl)ethylcarbamate (43 mg, 0.095 mmol) was reacted with tribromoborane (1.0 M in methylene chloride, 1.0 mL, 1.0 mmol) to afford the desired product (18 mg, 51%) as a grey solid: $^1$H NMR (300 MHz, DMSO-$d_6$) δ 10.72 (s, 1H), 8.52 (s, 3H), 7.65 (dd, J=13.3, 6.8 Hz, 3H), 7.30 (d, J=8.2 Hz, 2H), 7.06 (s, 1H), 5.87 (d, J=5.4 Hz, 1H), 4.64-4.45 (m, 1H), 2.50 (s, 3H), 1.63 (d, J=6.8 Hz, 3H); ESI MS m/z 480 [C$_{27}$H$_{33}$N$_3$O$_3$S+H]$^+$; HPLC 98.6%, t$_R$=8.42 min.

Example 1212

9-(4-(Aminomethyl)phenyl)-8-hydroxy-6-methylthieno[2,3-c]quinolin-4(5H)-one Hydrochloride

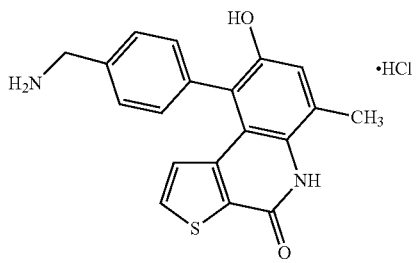 [SMILES: Cc1cc(O)c(-c2ccc(CN)cc2)c2c1[nH]c(=O)c1sccc12 ; Cl]

Following General Procedure F, tert-butyl 4-(8-methoxy-6-methyl-4-oxo-4,5-dihydrothieno[2,3-c]quinolin-9-yl)benzylcarbamate (43 mg, 0.095 mmol) was reacted with tribromoborane (1.0 M in methylene chloride, 1.0 mL, 1.0 mmol) to afford the desired product (18 mg, 51%) as a grey solid: $^1$H NMR (500 MHz, CD$_3$OD) δ 7.62 (d, J=8.1 Hz, 2H), 7.53 (d, J=5.4 Hz, 1H), 7.39 (d, J=8.0 Hz, 2H), 7.07 (s, 1H), 6.10 (d, J=5.4 Hz, 1H), 4.26 (s, 1H), 2.57 (s, 3H); ESI MS m/z 335 [C$_{19}$H$_{16}$N$_2$O$_2$S−H]$^−$; HPLC 96.7%, t$_R$=7.99 min.

Example 1225

(S)-9-(4-(1-Aminoethyl)phenyl)-8-hydroxy-6-methylthieno[2,3-c]quinolin-4(5H)-one

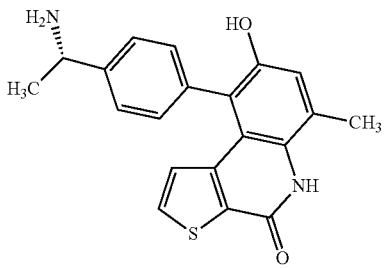 [SMILES: Cc1cc(O)c(-c2ccc([C@H](C)N)cc2)c2c1[nH]c(=O)c1sccc12]

Following General Procedure F, (S)-9-(4-(1-aminoethyl)phenyl)-8-hydroxy-6-methylthieno[2,3-c]quinolin-4(5H)-one (52 mg, 0.11 mmol) was reacted with tribromoborane (1.0 M in methylene chloride, 1.0 mL, 1.0 mmol) to afford the desired product (20 mg, 46%) as an off-white solid: $^1$H NMR (500 MHz, CD$_3$OD) δ 7.62 (d, J=7.4 Hz, 2H), 7.54 (d, J=5.4 Hz, 1H), 7.39 (d, J=7.4 Hz, 2H), 7.07 (s, 1H), 6.09 (d, J=5.4 Hz, 1H), 4.61 (q, J=6.9 Hz, 1H), 2.57 (s, 3H), 1.76 (d, J=6.9 Hz, 3H): ESI MS m/z 351 [C$_{20}$H$_{18}$N$_2$O$_2$S+H]$^+$; HPLC >99%, t$_R$=8.40 min.

Example 1032

9-(4-(1-Aminoethyl)phenyl)-6-bromo-8-hydroxythieno[2,3-c]quinolin-4(5H)-one hydrochloride

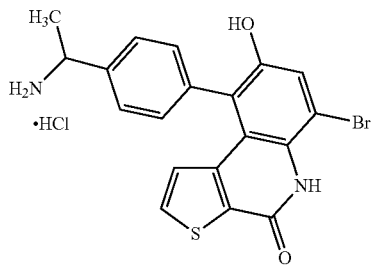 [SMILES: Cl ; CC(N)c1ccc(-c2c(O)cc(Br)c3[nH]c(=O)c4sccc4c23)cc1]

Following General Procedure F, tert-butyl 1-(4-(6-bromo-8-methoxy-4-oxo-4,5-dihydrothieno[2,3-c]quinolin-9-yl)phenyl ethylcarbamate (17 mg, 0.032 mmol) was reacted with tribromoborane (1.0 M in methylene chloride, 1.0 mL, 1.0 mmol) to afford the desired product (8 mg, 55%) as a light yellow solid: 1H NMR (500 MHz, MeOD) δ 7.62 (d, J=7.4 Hz, 2H), 7.54 (d, J=5.4 Hz, 1H), 7.42-7.37 (m, 2H), 7.07 (d, J=0.7 Hz, 1H), 6.09 (d, J=5.4 Hz, 1H), 4.67-4.56 (m, 1H), 2.57 (s, 3H), 1.76 (d, J=6.9 Hz, 3H); ESI MS m/z 415 [C$_{19}$H$_{15}$BrN$_2$O$_2$S+H]$^+$; HPLC 95.0%, t$_R$=12.16 min.

Example 1066

9-(4-(1-Aminoethyl)phenyl)-8-hydroxy-6-methylthieno[2,3-c]quinolin-4(5H)-one

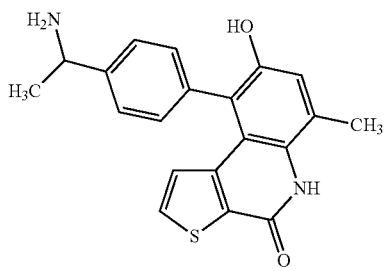 [SMILES: Cc1cc(O)c(-c2ccc(C(C)N)cc2)c2c1[nH]c(=O)c1sccc12]

Following General Procedure F, 9-(4-(1-aminoethyl)phenyl)-8-hydroxy-6-methylthieno[2,3-c]quinolin-4(5H)-one (20 mg, 0.043 mmol) was reacted with tribromoborane (1.0 M in methylene chloride, 1.0 mL, 1.0 mmol) to afford the desired product (10 mg, 60%) as a light grey solid: $^1$H NMR (500 MHz, MeOD) δ 7.62 (d, J=7.4 Hz, 2H), 7.54 (d, J=5.4 Hz, 1H), 7.42-7.37 (m, 2H), 7.07 (d, J=0.7 Hz, 1H), 6.09 (d, J=5.4 Hz, 1H), 4.67-4.56 (m, 1H), 2.57 (s, 3H), 1.76 (d, J=6.9 Hz, 3H); ESI MS m/z 351 [C$_{20}$H$_{18}$N$_2$O$_2$S+H]$^+$; HPLC >99%, t$_R$=8.40 min.

Example 1123

(R)-9-(4-(1-Aminoethyl)phenyl)-6-bromo-8-hydroxythieno[2,3-c]quinolin-4(5H)-one

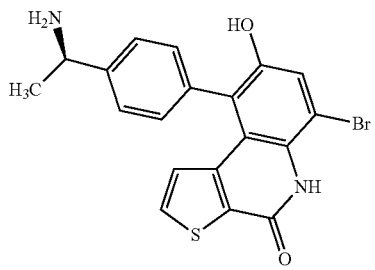 [SMILES: C[C@@H](N)c1ccc(-c2c(O)cc(Br)c3[nH]c(=O)c4sccc4c23)cc1]

Following General Procedure F, (R)-tert-butyl 1-(4-(6-bromo-8-methoxy-4-oxo-4,5-dihydrothieno[2,3-c]quinolin-9-yl phenyl)ethylcarbamate (24 mg, 0.045 mmol) was reacted with tribromoborane (1.0 M in methylene chloride, 1.0 mL, 1.0 mmol) to afford the desired product (18 mg, 88%) as a light grey solid: $^1$H NMR (500 MHz, MeOD) δ 7.64 (dd, J=10.4, 3.5 Hz, 31H), 7.61 (d, J=5.4 Hz, 1H), 7.47 (s, 1H), 7.42 (d, J=7.5 Hz, 2H), 6.07 (d, J=5.4 Hz, 1H), 4.65-4.59 (m, 1H), 1.76 (d, J=6.9 Hz, 3H); ESI MS m/z 415 $[C_{19}H_{15}BrN_2O_2S+H]^+$; HPLC 97.0%, $t_R$=8.74 min.

Example 1159

(R)-9-(4-(1-Aminopropyl)phenyl)-6-chloro-8-hydroxythieno[2,3-c]quinolin-4(5H)-one hydrochloride

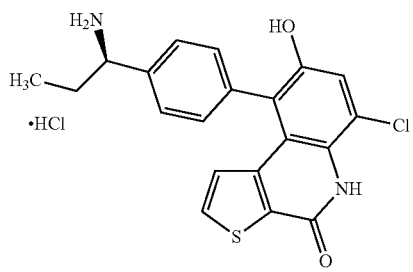 [SMILES: Cl ; CC[C@@H](N)c1ccc(-c2c(O)cc(Cl)c3[nH]c(=O)c4sccc4c23)cc1]

Following General Procedure F, (R)-tert-butyl 1-(4-(6-chloro-8-methoxy-4-oxo-4,5-dihydrothieno[2,3-c]quinolin-9-yl)phenyl)propylcarbamate (30 mg, 0.063 mmol) was reacted with tribromoborane (1.0 M in methylene chloride, 1.0 mL, 1.0 mmol) to afford the desired product (22 mg, 87%) as a light yellow solid: $^1$H NMR (500 MHz, CD$_3$OD) δ 7.63-7.56 (m, 2H), 7.53 (d, J=5.4 Hz, 1H), 7.40 (t, J=6.6 Hz, 3H), 7.08 (s, 1H), 6.04 (d, J=5.4 Hz, 1H), 4.31 (dd, J=9.2, 5.9 Hz, 1H), 2.57 (s, 3H), 2.21-2.01 (m, 2H), 1.03 (t, J=7.4 Hz, 3H); ESI MS m/z 383 $[C_{20}H_{17}ClN_2O_2S-H]^-$; HPLC 96.9%, $t_R$=8.69 min.

Example 1157

(R)-9-(4-(1-Aminopropyl)phenyl)-8-hydroxy-6-methylthieno[2,3-c]quinolin-4(5H)-one hydrochloride

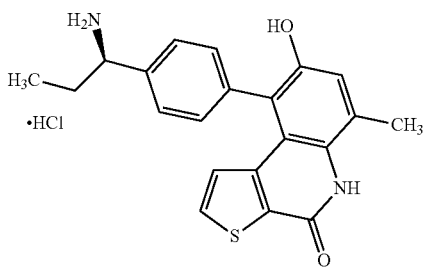 [SMILES: Cl ; CC[C@@H](N)c1ccc(-c2c(O)cc(C)c3[nH]c(=O)c4sccc4c23)cc1]

Following General Procedure F, (R)-tert-butyl 1-(4-(8-methoxy-6-methyl-4-oxo-4,5-dihydrothieno[2,3-c]quinolin-9-yl)phenyl)propylcarbamate (30 mg, 0.063 mmol) was reacted with tribromoborane (1.0 M in methylene chloride, 1.0 mL, 1.0 mmol) to afford the desired product (22 mg, 87%) as a light grey solid: $^1$H NMR, (500 MHz, CD$_3$OD) δ 7.63-7.56 (m, 2H), 7.53 (d, J=5.4 Hz, 1H), 7.40 (t, J=6.6 Hz, 3H), 7.08 (s, 1H), 6.04 (d, J=5.4 Hz, 1H), 4.31 (dd, J=9.2, 5.9 Hz, 1H), 2.57 (s, 3H), 2.21-2.01 (m, 2H), 1.03 (t, J=7.4 Hz, 3H); ESI MS m/z 365 $[C_{21}H_{20}N_2O_2S+H]^+$; HPLC >99%, $t_R$=8.69 min.

Example 1330

9-(4-(2-Aminopropan-2-yl)phenyl)-8-hydroxy-6-methylthieno[2,3-c]quinolin-4(5)-one

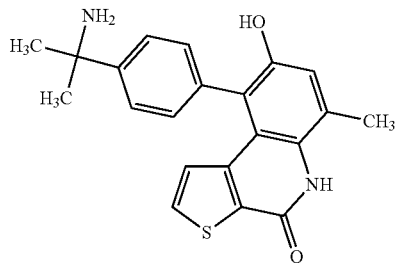 [SMILES: Cc1cc(O)c(-c2ccc(C(C)(C)N)cc2)c2c1[nH]c(=O)c1sccc12]

Following General Procedure F, (S)-9-(4-(1-aminoethyl)phenyl-8-hydroxy-6-methylthieno[2,3-c]quinolin-4(5H)-one (52 mg, 0.11 mmol) was reacted with tribromoborane (1.0 M in methylene chloride, 1.0 mL, 1.0 mmol) to afford the desired product (20 mg, 46%) as an off-white solid: $^1$H NMR (500 MHz, CD$_3$OD) δ 7.68 (d, J=8.4 Hz, 2H), 7.54 (d, J=5.4 Hz, 1H), 7.41 (d, J=8.4 Hz, 2H), 7.07 (s, 1H), 6.08 (d, J=5.4 Hz, 1H), 2.57 (s, 3H), 1.86 (s, 6H); ESI MS m/z 363 $[C_{21}H_{20}N_2O_2S-H]^-$; HPLC 98.7%, $t_R$=8.51 min.

Example 611 982

9-bromo-8-methoxy-6-methyl-5-((2-(trimethylsilyl)ethoxy)methyl)thieno[2,3-c]quinolin-4(5H)-one

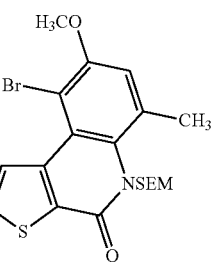

To a suspension of 9-bromo-8-methoxy-6-methylthieno[2,3-c]quinolin-4(5H)-one (2.2 g, 6.8 mmol) in a mixture of DMF (15 mL) and THF (15 mL) at 0° C. was added sodium hydride (60%, 0.54 g, 13.6 mmol). The reaction mixture was stirred at 0° C. for 30 min before (2-(chloromethoxy)ethyl)trimethylsilane (3.4 g, 20 mmol) was added. The resulting mixture was stirred at rt overnight and then poured into ice-water (50 mL). The resulting precipitate was filtered and purified by column chromatography (silica, heptane/ethyl acetate) to afford the desired product (2.7 g, 87%) as a light yellow solid: ESI MS m/z 454 $[C_{19}H_{24}BrNO_3SSi+H]^+$.

Example 612

9-Bromo-8-methoxy-2,6-dimethyl-5-((2-(trimethylsilyl)ethoxy)methyl)thieno[2,3-c]quinolin-4(5H)-one

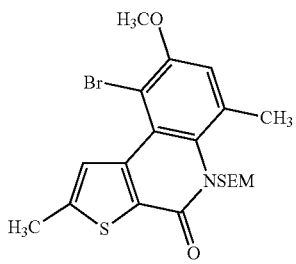

To a stirred solution of diidopropylamine (85 µL, 0.6 mmol) in THF (2.5 mL) at −78° C. was added n-BuLi (2.5 M, 0.24 mL, 0.60 mmol) and the reaction mixture was stirred at 0° C. for 10 min then cooled to −78° C. A solution of 9-bromo-8-methoxy-6-methyl-5-((2-(trimethylsilyl)ethoxy) methyl)thieno[2,3-c]quinolin-4(5H)-one (0.23 g, 0.50 mmol) in THF (1 mL) was added dropwise and the reaction mixture was stirred at −78° C. for 30 min. Iodomethane (93 µL, 1.5 mmol) was added and the reaction mixture was stirred at −78° C. for 2 h and quenched by the addition of satd. aq. ammonium chloride and extracted with dichloromethane. The organics were dried over $Na_2SO_4$, filtered, concentrated in vacuo and the residue was purified by column chromatography (silica, heptane/ethyl acetate) to afford the desired product (0.13 g, 55%) as a white solid: ESI MS m/z 468 $[C_{20}H_{26}BrNO_3SSi+H]^+$.

Example 613

(R)-tert-Butyl 2-(4-(8-methoxy-2,6-dimethyl-4-oxo-5-((2-(trimethylsilyl)ethoxy)methyl)-4,5-dihydrothieno[2,3-c]quinolin-9-yl)phenyl)propylcarbamate

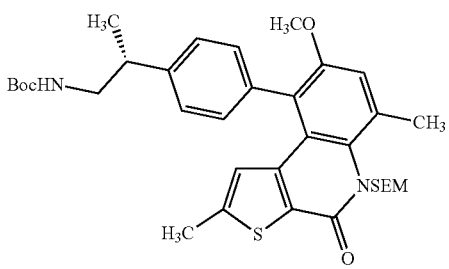 [SMILES: COc1cc(C)c2c(c1-c1ccc([C@@H](C)CNC(=O)OC(C)(C)C)cc1)c1cc(C)sc1c(=O)n2COCC[Si](C)(C)C]

Following General Procedure B, (R)-tert-butyl 2-(4-(4,4,5,5-tetramethyl-1,3,2-dioxaborolan-2-yl)phenyl)propylcarbamate (0.12 g, 0.33 mmol) was reacted with 9-bromo-8-methoxy-2,6-dimethyl-5-((2-(trimethylsilyl)ethoxy)methyl) thieno[2,3-c]quinolin-4(5H)-one (0.12 g, 0.33 mmol) to afford the desired product (78 mg, 45%) as a solid: ESI MS m/z 623 $[C_{34}H_{46}N_2O_5SSi+H]^+$.

Example 1341

(R)-9-(4-(1-Aminopropan-2-yl)phenyl)-8-methoxy-2,6-dimethylthieno[2,3-c]quinolin-4(5H)-one hydrochloride

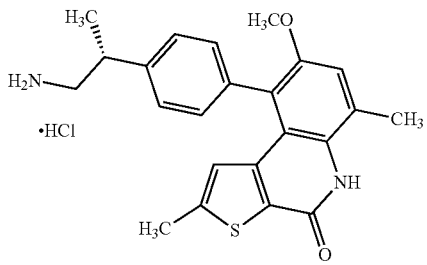 [SMILES: COc1cc(C)c2[nH]c(=O)c3sc(C)cc3c2c1-c1ccc([C@@H](C)CN)cc1 ; Cl]

To a solution of (R)-tert-butyl 2-(4-(8-methoxy-2,6-dimethyl-4-oxo-5-((2-(trimethylsilyl)ethoxy)methyl)-4,5-dihydrothieno[2,3-c]quinolin-9-yl)phenyl)propylcarbamate (24 mg, 0.039 mmol) in $CH_2Cl_2$ (1 mL) at rt was added trifluoroacetic acid (1.0 mL) and the reaction was stirred at that temperature for 2 h. The mixture was concentrated and the residue was dissolved methanol (2 mL) and treated with $NH_4OH$ (2 mL). The resulting mixture was stirred at rt for 2 h and purified by preparatory HPLC (C18 silica, acetonitrile/water (with 0.05% TFA) gradient). The desired fractions were combined, concentrated and the residue was dissolved in aqueous HCl, concentrated and dried under high vacuum to afford the desired product (5 mg, 30%) as a hydrochloride salt: $^1$H NMR (500 MHz, $CD_3OD$) δ 7.52 (dd, J=7.8, 1.5 Hz, 1H), 7.47 (dd, J=7.7, 1.5 Hz, 1H), 7.32 (s, 1H), 7.31-7.22 (m, 2H), 5.30 (d, J=2.7 Hz, 1.1H), 3.29-3.18 (m, 3H), 2.63 (s, 3H), 1.47 (d, J=6.1 Hz, 3H): ESI MS m/z 392 $[C_{23}H_{24}N_2O_4S+H]^+$.

Example 1340

(R)-9-(4-(1-Aminopropan-2-yl)phenyl)-8-hydroxy-2,6-dimethylthieno[2,3-c]quinolin-4(5H)-one

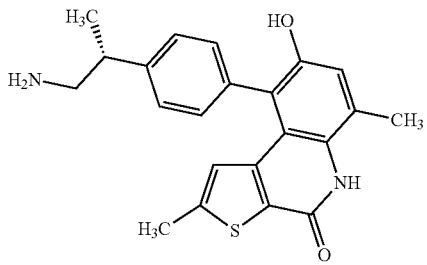 [SMILES: Cc1cc2c(s1)c(=O)[nH]c1c(C)cc(O)c(-c3ccc([C@@H](C)CN)cc3)c12]

To a solution of (R)-tert-butyl 2-(4-(8-methoxy-2,6-dimethyl-4-oxo-5-((2-(trimethylsilyl)ethoxy)methyl)-4,5-dihydrothieno[2,3-c]quinolin-9-yl)phenyl)propylcarbamate (40 mg, 0.064 mmol) in $CH_2C_2$ (1 mL) at 0° C. was added $BBr_3$ (1.0 M in methylene chloride, 1.0 mL, 1.0 mmol) and the reaction was stirred at that temperature for 1 h and quenched by pouring onto water or ice-water. The resulting mixture was concentrated and the residue was dissolved methanol (2 mL)

and treated with NH₄OH (2 mL). The resulting mixture was stirred at rt for 2 h and purified by preparatory HPLC (C18 silica, acetonitrile/water (with 0.05% TFA) gradient). The desired fractions were combined, concentrated and the residue was dissolved in aqueous HCl, concentrated and dried under high vacuum to afford the desired product as a hydrochloride salt: $^1$H NMR (500 MHz, CD₃OD) δ 7.55 (dd, J=7.9, 1.9 Hz, 1H), 7.45 (dd, J=7.7, 1.9 Hz, 1H), 7.34 (dd, J=7.9, 1.8 Hz, 1H), 7.28 (dd, J=7.7, 1.7 Hz, 1H), 7.06 (d, J=0.7 Hz, 1H), 5.70 (d, J=1.1 Hz, 1H), 3.29-3.13 (m, 3H), 2.55 (s, 3H), 2.30 (d, J=1.0 Hz, 3H), 1.50 (d, J=6.5 Hz, 3H); ESI MS m/z 378 [C₂₂H₂₂N₂O₂S+H]⁺.

Example 614

9-Bromo-2-chloro-8-methoxy-6-methyl-5-((2-(trimethylsilyl)ethoxy)methyl)thieno[2,3-c]quinolin-4(5H)-one

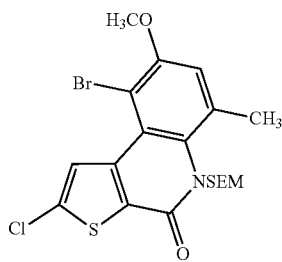 [SMILES: COc1cc(C)c2c(c1Br)c1cc(Cl)sc1c(=O)n2COCC[Si](C)(C)C]

To a stirred solution of diidopropylamine (85 μL, 0.6 mmol) in THF (2.5 mL) at −78° C. was added n-BuLi (2.5M, 0.24 mL, 0.6 mmol). The resulting mixture was stirred at 0° C. for 10 min and then cooled at −78° C. A solution of 9-bromo-8-methoxy-6-methyl-5-((2-(trimethylsilyl)ethoxy)methyl) thienio[2,3-c]quinolin-4(5H)-one (0.23 g, 0.50 mmol) in T-IF (1 mL) was added dropwise and the resulting mixture was stirred at −78° C. for 30 min. Hexachloroethane (0.24 g, 1.0 mmol) was added dropwise and the mixture was stirred at −78° C. for 2 h and allowed to warm to rt. The reaction was quenched by adding saturated ammonium chloride and extracted with dichloromethane (2×). The combined extracts were dried over Na₂SO₄, filtered and concentrated in vacuo. The residue was purified by column chromatography (heptane/ethyl acetate) to afford the desired product (0.13 g, 52%) as a white solid: ESI MS m/z 488 [C₁₉H₂₃BrClNO₃SSi+H]⁺.

Example 615

(R)-tert-Butyl 2-(4-(2-chloro-8-methoxy-6-methyl-4-oxo-5-((2-(trimethylsilyl)ethoxy)methyl)-4,5-dihydrothieno[2,3-c]quinolin-9-yl)phenyl)propylcarbamate

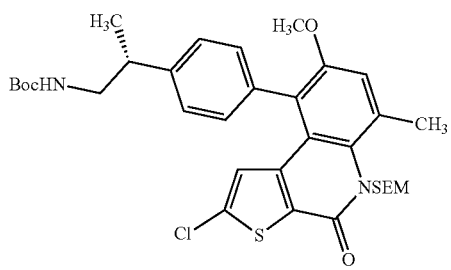 [SMILES: COc1cc(C)c2c(c1-c1ccc([C@@H](C)CNC(=O)OC(C)(C)C)cc1)c1cc(Cl)sc1c(=O)n2COCC[Si](C)(C)C]

Following General Procedure E, (R)-tert-butyl 2-(4-bromophenyl)propylcarbamate (97 mg, 0.31 mmol) was reacted with 9-bromo-8-methoxy-2,6-dimethyl-5-((2-(trimethylsilyl)ethoxy)methyl)thieno[2,3-c]quinolin-4(5H)-one (0.10 g, 0.21 mmol) to afford the desired product (62 mg, 46%) as a solid: ESI MS m/z 643 [C₃₃H₄₃ClN₂O₅SSi+H]⁺.

Example 1354

(R)-9-(4-(1-Aminopropan-2-yl)phenyl)-2-chloro-8-methoxy-6-methylthieno[2,3-c]quinolin-4(5H)-one hydrochloride

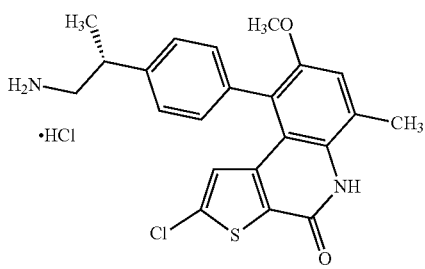 [SMILES: COc1cc(C)c2[nH]c(=O)c3sc(Cl)cc3c2c1-c1ccc([C@@H](C)CN)cc1 ; Cl]

To a solution of (R)-tert-butyl 2-(4-(2-chloro-8-methoxy-6-methyl-4-oxo-5-((2-(trimethylsilyl)ethoxy)methyl)-4,5-dihydrothieno[2,3-c]quinolin-9-yl)phenyl)propylcarbamate (11 mg, 0.017 mmol) in CH₂Cl₂ (1 mL) at rt was added trifluoroacetic acid (1.0 mL) and the reaction was stirred at that temperature for 2 h. The mixture was concentrated and the residue was dissolved methanol (2 mL) and treated with NH₄OH (2 mL). The resulting mixture was stirred at rt for 2 h and purified by preparatory HPLC (C18 silica, acetonitrile/water (with 0.05% TFA) gradient). The desired fractions were combined, concentrated and the residue was dissolved in aqueous HCl, concentrated and dried under high vacuum to afford the desired product (7 mg, 92%) as a hydrochloride salt: $^1$H NMR (500 MHz, CD₃OD) δ 7.52 (dd, J=7.8, 1.5 Hz, 1H), 7.47 (dd, J=7.7, 1.5 Hz, 1H), 7.32 (s, 1H), 7.31-7.22 (m, 2H), 5.30 (d, J=2.7 Hz, 1H), 3.29-3.18 (m, 3H), 2.63 (s, 3H), 1.47 (d, J=6.1 Hz, 3H); ESI MS m/z 413 [C₂₂H₂₁ClN₂O₂S I H]⁺.

Example 1353

(R)-9-(4-(1-Aminopropan-2-yl)phenyl)-2-chloro-8-hydroxy-6-methylthieno[2,3-c]quinolin-4(5H)-one hydrochloride

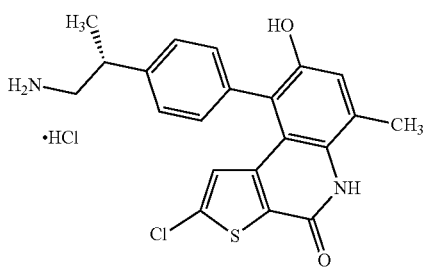 [SMILES: Cc1cc(O)c(-c2ccc([C@@H](C)CN)cc2)c2c1[nH]c(=O)c1sc(Cl)cc12 ; Cl]

To a solution of (R)-tert-butyl 2-(4-(2-chloro-8-methoxy-6-methyl-4-oxo-5-((2-(trimethylsilyl)ethoxy)methyl)-4,5-dihydrothieno[2,3-c]quinolin-9-yl)phenyl)propylcarbamate (32 mg, 0.050 mmol) in CH$_2$Cl$_2$ at 0° C. was added BBr$_3$ (1.0 M in methylene chloride, 1.0 mL, 1.0 mmol) and the reaction was stirred at that temperature for 1 h and quenched by pouring onto water or ice-water. The resulting mixture was concentrated and the residue was dissolved methanol (2 mL) and treated with NH$_4$OH (2 mL). The resulting mixture was stirred at rt for 2 h and purified by preparatory HPLC (C18 silica, acetonitrile/water (with 0.05% TFA) gradient). The desired fractions were combined, concentrated and the residue was dissolved in aqueous HCl, concentrated and dried under high vacuum to afford the desired product as a hydrochloride salt: 1H NMR (500 MHz, MeOD) δ 7.57 (dd, J=7.9, 1.8 Hz, 1H), 7.48 (dd, J=7.8, 1.8 Hz, 1H), 7.35 (dd, J=7.9, 1.7 Hz, 1H), 7.29 (dd, J=7.8, 1.6 Hz, 1H), 7.10 (d, J=0.7 Hz, 1H), 5.75 (s, 1H), 3.28-3.19 (m, 3H), 2.55 (s, 3H), 1.50 (d, J=6.4 Hz, 3H). ESI MS m/z 399 [C$_{21}$H$_{19}$ClN$_2$O$_2$S+H]$^+$.

Example 616

9-Bromo-2-fluoro-8-methoxy-6-methyl-5-((2-(trimethylsilyl)ethoxy)methyl)thieno[2,3-c]quinolin-4(5H)-one

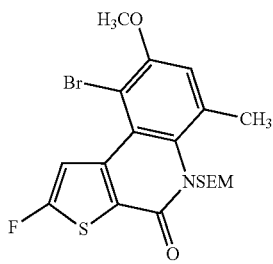 [SMILES: COc1cc(C)c2c(c1Br)c1cc(F)sc1c(=O)n2COCC[Si](C)(C)C]

To a stirred solution of diidopropylamine (84 µL 0.6 mmol) in THF (2.5 mL) at −78° C. was added n-BuLi (2.5M, 0.24 mL, 0.6 mmol). The resulting mixture was stirred at 0° C. for 10 min and then cooled at −78° C. A solution of 9-bromo-8-methoxy-6-methyl-5-((2-(trimethylsilyl ethoxy)methyl)thieno[2,3-c]quinolin-4(5H)-one (0.23 g, 0.50 mmol) in THF (1 mL) was added dropwise and the resulting mixture was stirred at −78° C. for 30 min. A solution of N-fluorobenzenesulfonimide (0.32, 1.0 mmol) in THF (1 mL) was added and the mixture was stirred at −78° C. for 2 h. The reaction was quenched by adding saturated ammonium chloride and extracted with dichloromethane (2×). The combined extracts were dried over Na$_2$SO$_4$, filtered and concentrated in vacuo. The residue was purified by column chromatography (heptane/ethyl acetate) to afford the desired product (98 mg, 41%) as a white solid: ESI MS m/z 472 [C$_{19}$H$_{23}$BrFNO$_3$SSi+H]$^+$.

Example 617

(R)-tert-butyl 2-(4-(2-fluoro)-8-methoxy-6-methyl-4-oxo-5-((2-(trimethylsilyl)ethoxy)methyl)-4,5-dihydrothieno[2,3-c]quinolin-9-yl)phenyl)propylcarbamate

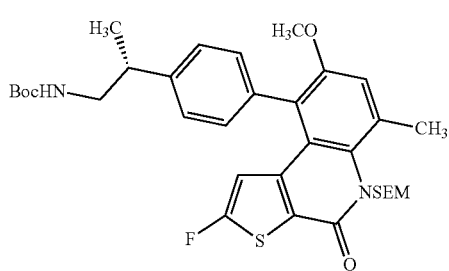 [SMILES: COc1cc(C)c2c(c1-c1ccc([C@@H](C)CNC(=O)OC(C)(C)C)cc1)c1cc(F)sc1c(=O)n2COCC[Si](C)(C)C]

Following General Procedure B, (R)-tert-butyl 2-(4-(4,4,5,5-tetramethyl-1,3,2-dioxaborolan-2-yl)phenyl)propylcarbamate (0.11 g, 0.31 mmol) was reacted with 9-bromo-2-fluoro-8-methoxy-6-methyl-5-((2-(trimethylsilyl)ethoxy)methyl)thieno[2,3-c]quinolin-4(5H)-one (98 mg, 0.21 mmol) to afford the desired product (0.11 g, 85%) as a solid: ESI MS m/z 627 [C$_{33}$H$_{43}$FN$_2$O$_2$SSi+H]$^+$.

Example 1375

(R)-9-(4-(1-Aminopropan-2-yl)phenyl)-2-fluoro-8-methoxy-6-methylthieno[2,3-c]quinolin-4(5H)-one

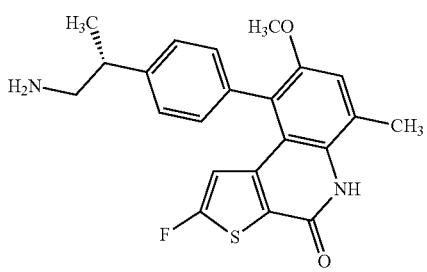 [SMILES: COc1cc(C)c2[nH]c(=O)c3sc(F)cc3c2c1-c1ccc([C@@H](C)CN)cc1]

To a solution (R)-tert-butyl 2-(4-(2-fluoro-8-methoxy-6-methyl-4-oxo-5-((2-(trimethylsilyl)ethoxy)methyl)-4,5-dihydrothieno[2,3-c]quinolin-9-yl)phenyl)propylcarbamate (17 mg, 0.027 mmol) in CH$_2$C2 (1 mL) at rt was added trifluoroacetic acid (1.0 mL) and the reaction was stirred at that temperature for 2 h. The mixture was concentrated and the residue was dissolved methanol (2 mL) and treated with NH$_4$OH (2 mL). The resulting mixture was stirred at rt for 2 h and purified by preparatory HPLC (C18 silica, acetonitrile/water (with 0.05% TFA) gradient). The desired fractions were combined, concentrated and the residue was dissolved in aqueous HCl, concentrated and dried under high vacuum to afford the desired product (5 mg, 43%) as a hydrochloride salt: $^1$H NMR (500 MHz, CD$_3$OD) δ 7.52 (dd, J=7.8, 1.5 Hz, 1H), 7.47 (dd, J=7.7, 1.5 Hz, 1H), 7.32 (s, 1H), 7.31-7.22 (m, 2H), 5.30 (d, J=2.7 Hz, 1H), 3.29-3.18 (m, 3H), 2.63 (s, 3H), 1.47 (d, J=6.1 Hz, 3H): ESI MS m/z 397 [C$_{22}$H$_{21}$FN$_2$O$_2$S+H]$^+$.

Example 1383

(R)-9-(4-(1-Aminopropan-2-yl)phenyl)-2-fluoro-8-hydroxy-6-methylthieno[2,3-c]quinolin-4(5H)-one

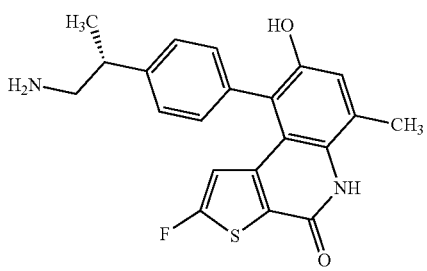 [SMILES: Cc1cc(O)c(-c2ccc([C@@H](C)CN)cc2)c2c1[nH]c(=O)c1sc(F)cc12]

To a solution of (R)-tert-butyl 2-(4-(2-fluoro-8-methoxy-6-methyl-4-oxo-5-((2-(trimethylsilyl)ethoxy)methyl)-4,5-dihydrothieno[2,3-c]quinolin-9-yl)phenyl)propylcarbamate (60 mg, 0.096 mmol) in CH$_2$Cl$_2$ (1 mL) at 0° C. was added BBr$_3$ (1.0 M in methylene chloride, 1.0 mL, 1.0 mmol) and the reaction was stirred at that temperature for 1 h and quenched by pouring onto water or ice-water. The resulting mixture was concentrated and the residue was dissolved methanol (2 mL) and treated with NH$_4$OH (2 mL). The resulting mixture was stirred at rt for 2 h and purified by preparatory HPLC (C18 silica, acetonitrile/water (with 0.05% TFA) gradient). The desired fractions were combined, concentrated and the residue was dissolved in aqueous HCl, concentrated and dried under high vacuum to afford the desired product as a hydrochloride salt: $^1$H NMR (500 MHz, CD$_3$OD) δ 7.55 (dd, J=7.9, 1.7 Hz, 1H), 7.46 (dd, J=7.8, 1.8 Hz, 1H), 7.32 (dd, J=23.9, 7.9 Hz, 2H), 7.10 (s, 1H), 5.46 (d, J=2.9 Hz, 1H), 3.28-3.15 (m, 3H), 2.55 (s, 3H), 1.49 (d, J=6.3 Hz, 3H); ESI MS m/z 383 [C$_{21}$H$_{19}$FN$_2$O$_2$S+H]$^+$.

Example 618 tert-butyl 1-(4-(8-hydroxy-4-oxo-4,5-dihydrothieno[2,3-c]quinolin-9-yl)phenyl)ethylcarbamate

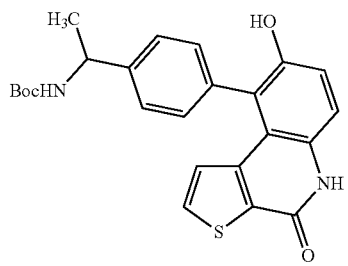 [SMILES: CC(NC(=O)OC(C)(C)C)c1ccc(-c2c(O)ccc3[nH]c(=O)c4sccc4c23)cc1]

To a solution of tert-butyl 1-(4-(8-methoxy-4-oxo-4,5-dihydrothieno[2,3-c]quinolin-9-yl)phenyl)ethylcarbamate (0.96 g, 2.1 mmol) in dichloromethane (15 mL) at 0° C. was added BBr$_3$ (1.0 M in methylene chloride, 15 mL, 15 mmol) and the reaction was stirred at that temperature for 1 h and quenched by pouring onto water or ice-water. The precipitate was filtered and suspended in DMF (8 mL). Di-tert-butyl dicarbonate (0.85 g, 3.9 mmol) and triethylamine (1.1 mL, 7.8 mmol) were added and the mixture was stirred at rt for 2 h. Water was added and the precipitate was filtered and purified by column chromatography to afford the desired product as a solid: ESI MS m/z 437 [C$_{24}$H$_{24}$N$_2$O$_4$S+H]$^+$.

Example 619 tert-butyl 1-(4-(8-(isopropoxycarbonyloxy)-4-oxo-4,5-dihydrothieno[2,3-c]quinolin-9-yl)phenyl)ethylcarbamate

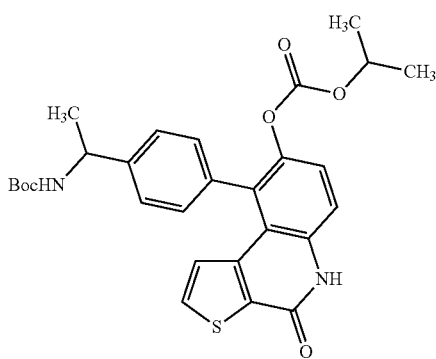 [SMILES: CC(C)OC(=O)Oc1ccc2[nH]c(=O)c3sccc3c2c1-c1ccc(C(C)NC(=O)OC(C)(C)C)cc1]

To a solution of tert-butyl 1-(4-(8-hydroxy-4-oxo-4,5-dihydrothieno[2,3-c]quinolin-9-yl)phenyl)ethylcarbamate (44 mg, 0.10 mmol) in THF (2 mL) at 0° C. was added NaH (60%, 6 mg, 0.15 mmol) and the reaction was stirred at that temperature for 1 h. Isopropyl chloroformate (21 μL, 0.15 mmol) was added and the resulting mixture was stirred at rt for 3 h. Water was added and the mixture was extracted with dichloromethane (2×15 mL). The combined extracts were dried over Na$_2$SO$_4$, filtered and concentrated in vacuo. The residue was purified by column chromatography (heptane/ethyl acetate) to afford the desired product (26 mg, 50%) as a solid: ESI MS m/z 523 [C$_{28}$H$_{30}$N$_2$O$_6$S+H]$^+$.

Example 1077

9-(4-(1-Aminoethyl)phenyl)-4-oxo-4,5-dihydrothieno[2,3-c]quinolin-8-yl isopropyl carbonate Hydrochloride

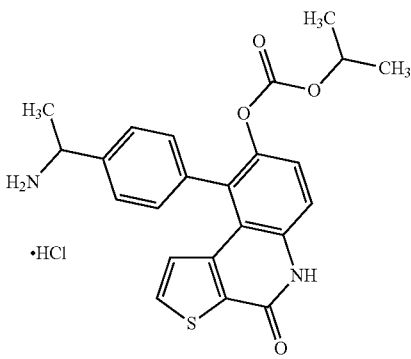 [SMILES: Cl ; CC(C)OC(=O)Oc1ccc2[nH]c(=O)c3sccc3c2c1-c1ccc(C(C)N)cc1]

Following General Procedure C, tert-butyl 1-(4-(8-(isopropoxycarbonyloxy)-4-oxo-4,5-dihydrothieno[2,3-c]quinolin-9-yl)phenyl)ethylcarbamate (20 mg, 0.038 mmol) was reacted with trifluoroacetic acid (3 mL) to afford the desired product (18 mg, quant.) as a light yellow solid: ESI MS m/z 423 [C$_{23}$H$_{22}$N$_2$O$_4$S+H]$^+$.

Example 620

9-(4-(1-(tert-Butoxycarbonylamino)ethyl)phenyl)-4-oxo-4,5-dihydrothieno[2,3-c]quinolin-8-yl acetate

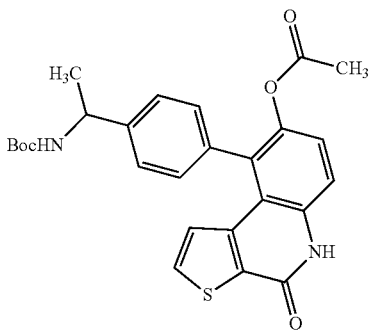 [SMILES: CC(=O)Oc1ccc2[nH]c(=O)c3sccc3c2c1-c1ccc(C(C)NC(=O)OC(C)(C)C)cc1]

Following Procedure Preparing tert-butyl 1-(4-(8-(isopropoxycarbonyloxy)-4-oxo-4,5-dihydrothieno[2,3-c]quinolin-9-yl)phenyl)ethylcarbamate, (44 mg, 0.10 mmol) was reacted with acetic anhydride (11 μL, 0.12 mmol) to afford the desired product (30 mg, 63%) as a solid: ESI MS m/z 479 [C$_{26}$H$_{26}$N$_2$O$_5$S+H]$^+$.

Example 1099

9-(4-(1-Aminoethyl)phenyl)-4-oxo-4,5-dihydrothieno[2,3-c]quinolin-8-yl acetate Hydrochloride

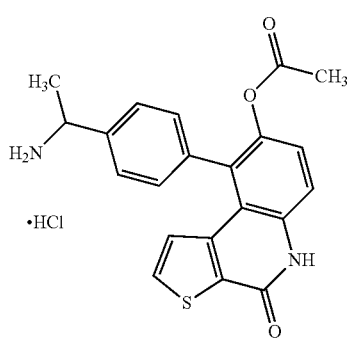 [SMILES: Cl ; CC(=O)Oc1ccc2[nH]c(=O)c3sccc3c2c1-c1ccc(C(C)N)cc1]

Example 621

2-(4-(8-methoxy-6-methyl-4-oxo-4,5-dihydrothieno[2,3-c]quinolin-9-yl)phenyl)propane-1-sulfonamide

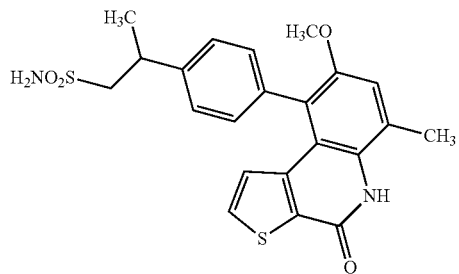 [SMILES: COc1cc(C)c2[nH]c(=O)c3sccc3c2c1-c1ccc(C(C)CS(N)(=O)=O)cc1]

Following General Procedure E, 2-(4-bromophenyl)propane-1-sulfonamide (0.12 g, 0.43 mmol) was reacted with 9-bromo-8-methoxy-6-methylthieno[2,3-c]quinolin-4(5H)-one (0.14 g, 0.44 mmol) to afford the desired product (16 mg, 8%) as a brown solid: ESI MS m/z 443 $[C_{22}H_{22}N_2O_4S_2+H]^+$.

Example 1419

2-(4-(8-hydroxy-6-methyl-4-oxo-4,5-dihydrothieno[2,3-c]quinolin-9-yl)phenyl)propane-1-sulfonamide

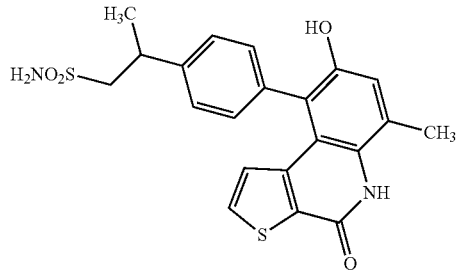 [SMILES: Cc1cc(O)c(-c2ccc(C(C)CS(N)(=O)=O)cc2)c2c1[nH]c(=O)c1sccc12]

Following General Procedure F, 2-(4-(8-methoxy-6-methyl-4-oxo-4,5-dihydrothieno[2,3-c]quinolin-9-yl)phenyl) propane-1-sulfonamide (16 mg, 0.036 mmol) was reacted with tribromoborane (1.0 M in methylene chloride, 1.0 mL, 1.0 mmol) to afford the desired product (7.0 mg, 44%) as a light brown solid: $^1$H NMR (500 MHz, $CD_3OD$) δ 7.68 (d, J=8.4 Hz, 2H), 7.54 (d, J=5.4 Hz, 1H), 7.41 (d, J=8.4 Hz, 2H), 7.07 (s, 1H), 6.08 (d, J=5.4 Hz, 1H), 2.57 (s, 3H), 1.86 (s, 6H); ESI MS m/z 429 $[C_{21}H_{20}N_2O_4S_2+H]^+$; HPLC 98.7%, $t_R$=8.51 min.

Example 1057

N-(1-hydroxypropan-2-yl)-4-(8-methoxy-4-oxo-4,5-dihydrothieno[2,3-c]quinolin-9-yl)benzenesulfonamide

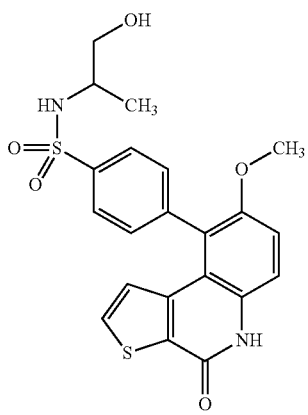 [SMILES: COc1ccc2[nH]c(=O)c3sccc3c2c1-c1ccc(S(=O)(=O)NC(C)CO)cc1]

Following General Procedure B, N-(1-hydroxypropan-2-yl)-4-(4,4,5,5-tetramethyl-1,3,2-dioxaborolan-2-yl)benzenesulfonamide (570 mg, 1.7 mmol) was reacted with 9-bromo-8-methoxythieno[2,3-c]quinolin-4(5H)-one, (471 mg, 1.5 mmol) to afford the desired product (109 mg, 16%) as an off-white powder. ESI MS m/z 445 $[C_{21}H_{20}N_2O_5S_2+H]^+$;

Example 1062

N-(1-bromopropan-2-yl)-4-(8-hydroxy-4-oxo-4,5-dihydrothieno[2,3-c]quinolin-9-yl)benzenesulfonamide

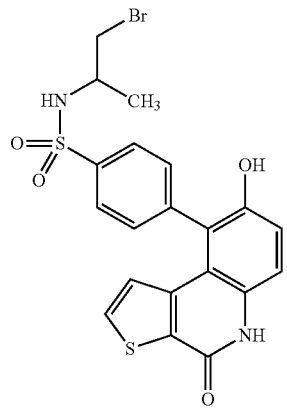 [SMILES: CC(CBr)NS(=O)(=O)c1ccc(-c2c(O)ccc3[nH]c(=O)c4sccc4c23)cc1]

Following General Procedure F, N-(1-hydroxypropan-2-yl)-4-(8-methoxy-4-oxo-4,5-dihydrothieno[2,3-c]quinolin- 9-yl)benzenesulfonamide (55 mg, 0.12 mmol) was reacted with tribromoborane (0.2 mL) to afford the desired product (48 mg, 79%) as an off-white solid: $^1$H NMR (500 MHz, CD$_3$OD); ESI MS m/z 494 [C$_{20}$H$_{17}$BrN$_2$O$_4$S$_2$+H]$^+$; HPLC 99.0% (AUC), t$_R$=11.39 min;

Example 1090

N-(2-Hydroxyethyl)-4-(8-methoxy-4-oxo-2,3,4,5-tetrahydro-1H-cyclopenta[c]quinolin-9-yl benzenesulfonamide

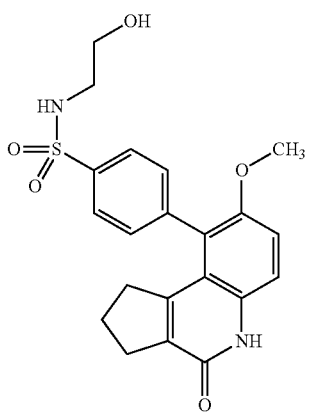 [SMILES: COc1ccc2[nH]c(=O)c3c(c2c1-c1ccc(S(=O)(=O)NCCO)cc1)CCC3]

Following General Procedure B, N-(2-hydroxyethyl)-4-(4,4,5,5-tetramethyl-1,3,2-dioxaborolan-2-yl)benzenesulfonamide (268 mg, 0.82 mmol) was reacted with 9-bromo-8-methoxy-2,3-dihydro-1H-cyclopenta[c]quinolin-4(5H)-one, (268 mg, 0.68 mmol) to afford the desired product (68 mg, 16%) as an off-white solid: $^1$H NMR: (300 MHz, DMSO-d6) ESI MS m/z 415 [C$_{21}$H$_{22}$O$_3$S+H]$^+$; HPLC >99% (AUC), t$_R$=11.73 min;

Example 1094

N-(2-Bromoethyl)-4-(8-hydroxy-4-oxo-2,3,4,5-tetrahydro-1H-cyclopenta[c]quinolin-9-yl)benzenesulfonamide

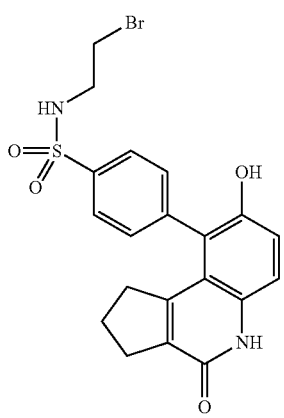 [SMILES: O=c1[nH]c2ccc(O)c(-c3ccc(S(=O)(=O)NCCBr)cc3)c2c2c1CCC2]

Following General Procedure F, N-(2-hydroxyethyl-4-(8-methoxy-4-oxo-2,3,4,5-tetrahydro-1H-cyclopenta[c]quinolin-9-yl)benzenesulfonamide (55 mg, 0.13 mmol) was reacted with tribromoborane (0.2 mL) to afford the desired product (11 mg, 18%) as an off-white solid: $^1$H NMR (500 MHz, CD$_3$OD) ESI MS m/z 464 [C$_{20}$H$_{19}$BrN$_2$O$_4$S+H]$^+$; HPLC 94.9% (AUC), t$_R$=14.88 min;

Example 622

2-(4-(8-Methoxy-4-oxo-2,3,4,5-tetrahydro-1H-cyclopenta[c]quinolin-9-yl)phenylsulfonamido)ethyl methanesulfonate

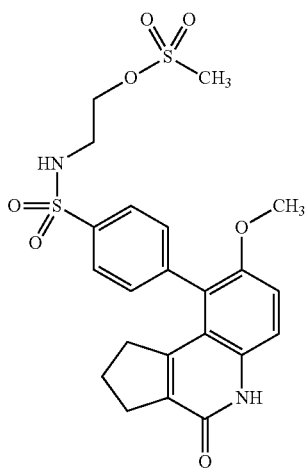 [SMILES: COc1ccc2[nH]c(=O)c3c(c2c1-c1ccc(S(=O)(=O)NCCOS(C)(=O)=O)cc1)CCC3]

To a stirred solution of N-(2-hydroxyethyl)-4-(8-methoxy-4-oxo-2,3,4,5-tetrahydro-1H-cyclopenta[c]quinolin-9-yl) benzenesulfonamide (230 mg, 0.555 mmol) and triethylamine (168 mg, 1.66 mmol) in anhydrous tetrahydrofuran (10 mL) was added methane sulfonyl chloride (88 mg, 0.666 mmol). The reaction mixture was stirred for 20 h at room temperature. After this time the reaction mixture was filtered to remove a white precipitate, which was washed with tetrahydrofuran (30 mL). The filtrate was concentrated under reduced pressure to an orange solid. The residue was purified by flash chromatography to afford the desired product as a brown solid (141 mg, 51%). ESI MS m/z 493 [C$_{22}$H$_{24}$N$_2$O$_7$S$_2$+H]$^+$ Example 1145

N-(2-chloroethyl)-4-(8-hydroxy-4-oxo-2,3,45-tetrahydro-1H-cyclopenta[c]quinolin-9-yl)benzenesulfonamide

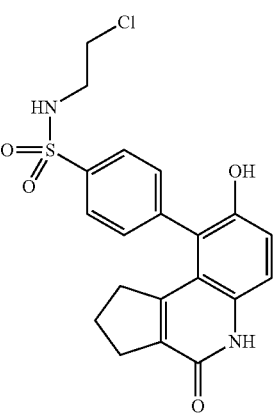 [SMILES: O=c1[nH]c2ccc(O)c(-c3ccc(S(=O)(=O)NCCCl)cc3)c2c2c1CCC2]

To a stirred solution of 2-(4-(8-methoxy-4-oxo-2,3,4,5-tetrahydro-1H-cyclopenta[c]quinolin-9-yl)phenylsulfonamido)ethyl methanesulfonate (141 mg, 0.286 mmol) in anhydrous dichloroethane (10 mL) was added aluminum chloride (190 mg, 1.43 mmol). The reaction mixture was stirred at reflux for 20 h. After this time the reaction was cooled to room temperature and concentrated under reduced pressure. The residue was treated with methanol (10 mL) and allowed to stand at room temperature for 1 h. Upon standing a precipitate formed and was subsequently filtered from the mother liquor. The precipitate was purified by preparatory HPLC (C18 silica, acetonitrile/water with 0.05% TFA gradient) to obtain the desired product (9 mg, 7.5%) as an off-white solid: $^1$H NMR (500 MHz, DMSO-d) ESI MS m/z 419 $[C_{20}H_{19}N_2O_4S+H]^+$; HPLC 97.6% (AUC), $t_R$=15.94 min.

Example 1154

(S)-6-chloro-8-hydroxy-9-(4-(1-(methylamino)propyl)phenyl)thieno[2,3-c]quinolin-4(5H)-one Hydrochloride

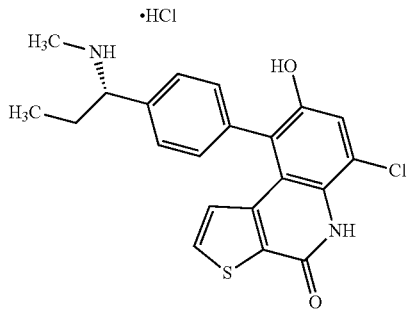 [SMILES: Cl ; CC[C@H](NC)c1ccc(-c2c(O)cc(Cl)c3[nH]c(=O)c4sccc4c23)cc1]

Following General Procedure F, (S)-tert-butyl 1-(4-(6-chloro-%-methoxy-4-oxo-4,5-dihydrothieno[2,3-c]quinolin-9-yl)phenyl)propyl(methyl)carbamate (100 mg, 0.194 mmol was reacted with tribromoborane (1.0 M in methylene chloride 1.16 mL, 1.16 mmol) to afford the desired product (35 mg, 45%) as a white solid: $^1$H NMR (500 MHz, DMSO) δ 10.81 (d, J=10.5 Hz, 1H), 9.83 (s, 1H), 9.70-9.45 (m, 1H), 9.28 (s, 1H), 7.73 (d, J=5.4 Hz, 1H), 7.70-7.60 (m, 2H), 7.38 (dd, J=12.4, 4.7 Hz, 3H), 5.70 (d, J=5.4 Hz, 1H), 4.19 (dt, J=12.1, 6.0 Hz, 1H), 2.51 (s, 3H), 2.20 (ddd, J=14.4, 9.5, 5.9 Hz, 1H), 2.02-1.89 (m, 1H), 0.84 (t, J=7.4 Hz, 31); ESI MS m/z 399 $[C_{22}H_{22}N_2O_2S+H]^+$; HPLC 96.9% (AUC), $t_R$=9.36 min.

Example 1148

(S)-8-hydroxy-9-(4-(1-(methylamino)propyl)phenyl)thieno[2,3-c]quinolin-4(5H)-one Hydrochloride

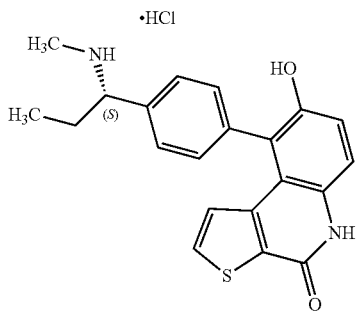

Following General Procedure F, (S)-tert-butyl 1-(4-(8-methoxy-4-oxo-4,5-dihydrothieno[2,3-c]quinolin-9-yl)phenyl)propyl(methyl)carbamate (135 mg, 0.282 mmol) was reacted with tribromoborane (1.0 M in methylene chloride, 1.69 mL, 1.69 mmol) to afford the desired product (48 mg, 47%) as a white solid: $^1$H NMR (500 MHz, MeOD) δ 7.62 (ddd, J=11.7, 8.0, 1.7 Hz, 2H), 7.56 (d, J=5.4 Hz, 1H), 7.51-7.40 (m, 3H), 7.19 (d, J=8.9 Hz, 1H), 5.97 (d, J=5.4 Hz, 1H), 4.22 (dd, J=10.7, 4.6 Hz, 1H), 2.70 (s, 3H), 2.34-2.02 (m, 2H), 1.04-0.96 (m, 3H); ESI MS m/z 365 $[C_{21}H_{20}N_2O_2S+H]^+$; HPLC 95.9% (AUC), $t_R$=8.38 min.

Example 1181

(S)-9-(4-(1-aminopropan-2-yl)phenyl)-6-chloro-8-hydroxythieno[2,3-c]quinolin-4(5H)-one Hydrochloride

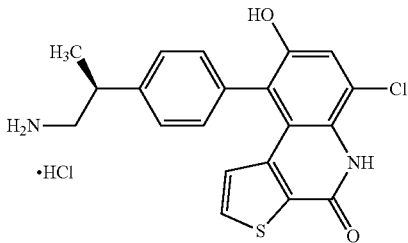 [SMILES: C[C@H](CN)c1ccc(-c2c(O)cc(Cl)c3[nH]c(=O)c4sccc4c23)cc1 ; Cl]

Following General Procedure F, (S)-tert-butyl 2-(4-(6-chloro-8-methoxy-4-oxo-4,5-dihydrothieno[2,3-c]quinolin-9-yl)phenyl)propylcarbamate (100 mg, 0.20 mmol) was reacted with tribromoborane (1.0 M in methylene chloride, 1.2 mL, 1.2 mmol) to afford the desired product (35 mg, 46%) as a white solid: $^1$H NMR (500 MHz, MeOD) δ 7.62 (d, J=5.4 Hz, 1H), 7.56 (dd, J=7.9, 1.9 Hz, 1H), 7.48 (dd, J=7.8, 1.9 Hz, 1H), 7.36 (dd, J=7.9, 1.7 Hz, 1H), 7.34-7.29 (m, 2H), 6.12 (d, J=5.4 Hz, 1H), 3.29-3.15 (m, 3H), 1.49 (d, J=6.5 Hz, 3H); ESI MS m/z 385 $[C_{20}H_{17}ClN_2O_2S+H]^+$; HPLC >99% (AUC), $t_R$=8.74 min.

Example 1163

(S)-9-(4-(1-Aminopropan-2-yl)phenyl)-8-hydroxythieno[2,3-c]quinolin-4(5H)-one Hydrochloride

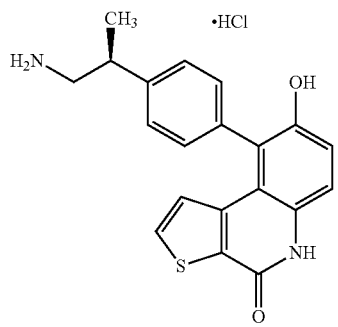 [SMILES: C[C@H](CN)c1ccc(-c2c(O)ccc3[nH]c(=O)c4sccc4c23)cc1 ; Cl]

Following General Procedure F, (S)-tert-butyl 2-(4-(8-methoxy-4-oxo-4,5-dihydrothieno[2,3-c]quinolin-9-yl)phenyl)propylcarbamate (110 mg, 0.236 mmol) was reacted with tribromoborane (1.0 M in methylene chloride, 1.42 mL, 1.42 mmol) to afford the desired product (38 mg, 47%) as a white solid: $^1$H NMR (500 MHz, MeOD) δ 7.61-7.53 (m, 2H), 7.47 (dd, J=7.8, 1.9 Hz, 1H), 7.41 (dd, J=10.9, 6.1 Hz, 1H), 7.37 (dd, J=7.9, 1.7 Hz, 1H), 7.32 (dd, J=7.7, 1.7 Hz, 1H), 7.18 (d, J=8.9 Hz, 1H), 6.15 (d, J=5.4 Hz, 1H), 3.29-3.17 (m, 3H), 1.50 (d, J=6.4 Hz, 3H); ESI MS m/z 351 $[C_{20}H_{18}N_2O_2S+H]^+$; HPLC >99% (AUC), $t_R$=8.58 min.

Example 1116

9-(4-(1-(Aminomethyl)cyclopropyl)phenyl)-6-chloro-8-hydroxythieno[2,3-c]quinolin-4(5H)-one Hydrochloride

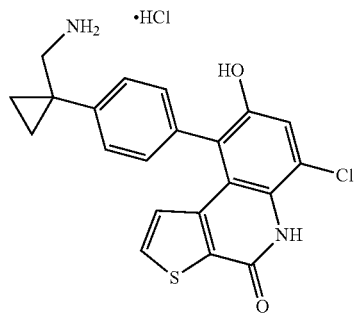 [SMILES: Cl ; NCC1(c2ccc(-c3c(O)cc(Cl)c4[nH]c(=O)c5sccc5c34)cc2)CC1]

Following General Procedure F, tert-butyl (1-(4-(6-chloro-8-methoxy-4-oxo-4,5-dihydrothieno[2,3-c]quinolin-9-yl)phenyl)cyclopropyl)methylcarbamate (50 mg, 0.09 mmol) was reacted with tribromoborane (1.0 M in methylene chloride, 0.58 mL, 0.58 mmol) to afford the desired product (19 mg, 48%) as a white solid: $^1$H NMR; (500 MHz, MeOD) δ 7.66-7.58 (m, 3H), 7.38-7.27 (m, 3H), 6.14 (d, J=5.4 Hz, 1H), 3.26 (s, 2H), 1.19 (t, J=5.5 Hz, 2H), 1.11 (t, J=5.5 Hz, 2H); ESI MS m/z 397 $[C_{21}H_{17}ClN_2O_2S+H]^+$; HPLC 98.4% (AUC), $t_R$=9.24 min.

Example 1401

9-(4-(1-(Aminomethyl)cyclopropyl)phenyl)-6-bromo-8-hydroxythieno[2,3-c]quinolin-4(5H)-one Hydrochloride

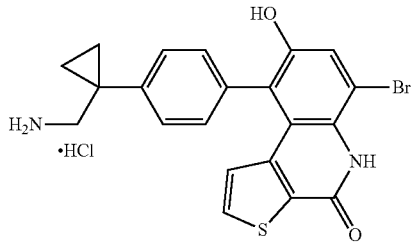 [SMILES: NCC1(c2ccc(-c3c(O)cc(Br)c4[nH]c(=O)c5sccc5c34)cc2)CC1 ; Cl]

Following General Procedure F, 9-(4-(1-(aminomethyl)cyclopropyl)phenyl)-6-bromo-8-methoxythieno[2,3-c]quinolin-4(5H)-one hydrochloride (100 mg, 0.22 mmol was reacted with tribromoborane (1.0 M in methylene chloride, 1.32 mL, 1.32 mmol) to afford the desired product (52 mg, 54%) as a white solid: $^1$H NMR (500 MHz, MeOD) δ 7.63 (t, J=6.8 Hz, 3H), 7.48 (s, 1H), 7.33 (d, J=8.2 Hz, 2H), 6.14 (d, J=5.4 Hz, 1H), 3.26 (s, 2H), 1.19 (t, J=5.6 Hz, 2H), 1.12 (t, J=5.5 Hz, 2H); ESI MS m/z 442 $[C_{21}H_{17}BrN_2O_2S+H]^+$; HPLC >99% (AUC), $t_R$=9.25 min.

Example 1254

9-(4-(1-(aminomethyl)cyclopropyl)phenyl)-8-hydroxy-6-methylthieno[2,3-c]quinolin-4(5H)-one Hydrochloride

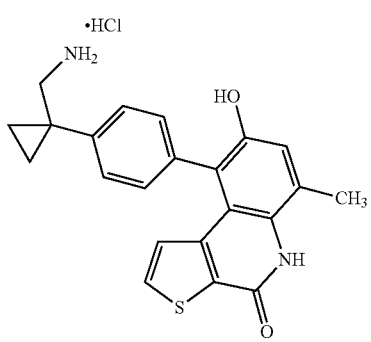 [SMILES: Cl ; Cc1cc(O)c(-c2ccc(C3(CN)CC3)cc2)c2c1[nH]c(=O)c1sccc12]

Following General Procedure F, tert-butyl(1-(4-(8-methoxy-6-methyl-4-oxo-4,5-dihydrothieno[2,3-c]quinolin-9-yl)phenyl)cyclopropyl)methylcarbamate (120 mg, 0.24 mmol) was reacted with tribromoborane (1.0 M in methylene chloride, 1.46 mL, 1.46 mmol) to afford the desired product (38 mg, 42%) as a white solid: $^1$H NMR (500 MHz, MeOD) δ 7.60 (ddd, J=12.3, 7.1, 3.6 Hz, 3H), 7.34-7.29 (m, 2H), 7.08 (d, J=0.6 Hz, 1H), 6.19 (d, J=5.4 Hz, 1H), 3.25 (s, 2H), 2.57 (s, 3H), 1.22-1.06 (m, 4H); ESI MS m/z 377 $[C_{23}H_{22}N_2O_2S+H]^+$; HPLC 98.6% (AUC), $t_R$=8.97 min.

Example 1215

(S)-8-Hydroxy-6-methyl-9-(4-(1-(methylamino)propan-2-yl)phenyl)thieno[2,3-c]quinolin-4(5H)-one Hydrochloride

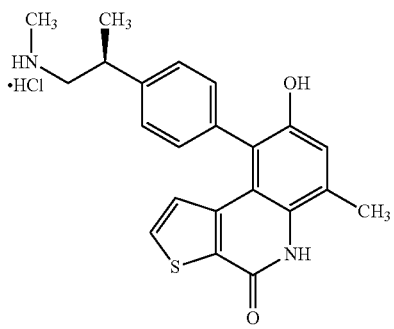 [SMILES: Cl ; CNC[C@@H](C)c1ccc(-c2c(O)cc(C)c3[nH]c(=O)c4sccc4c23)cc1]

Following General Procedure F, (S)-tert-butyl 2-(4-(8-methoxy-6-methyl-4-oxo-4,5-dihydrothieno[2,3-c]quinolin-9-yl)phenyl)propyl(methyl carbamate (50 mg, 0.10 mmol) was reacted with tribromoborane (1.0 M in methylene chloride, 0.61 mL, 0.61 mmol) to afford the desired product (12 mg, 32%) as a light yellow solid: $^1$H NMR (500 MHz, MeOD) δ 7.60-7.53 (m, 2H), 7.47 (dd, J=7.8, 1.8 Hz, 1H), 7.35 (dd, J=7.9, 1.7 Hz, 1H), 7.30 (dd, J=7.7, 1.7 Hz, 1H), 7.08 (s, 1H), 6.15 (d, J=5.4 Hz, 1H), 3.40-3.27 (m, 3H), 2.74 (s, 3H), 2.57 (s, 3H), 1.50 (d, J=6.6 Hz, 3H); ESI MS m/z 379 $[C_{22}H_{22}N_2O_2S+H]^+$; HPLC >99% (AUC), $t_R$=8.88 min.

Example 1232

(S)-9-(4-(1-aminopropan-2-yl)phenyl)-8-hydroxy-6-methylthieno[2,3-c]quinolin-4(5H)-one Hydrochloride

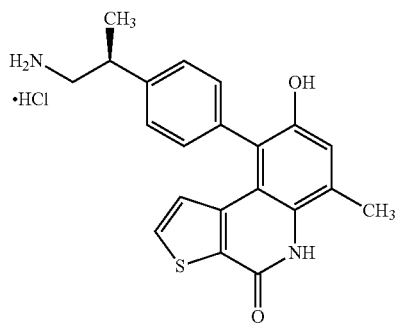 [SMILES: Cl ; Cc1cc(O)c(-c2ccc([C@H](C)CN)cc2)c2c1[nH]c(=O)c1sccc12]

Following General Procedure F, (S)-tert-butyl 2-(4-(8-methoxy-6-methyl-4-oxo-4,5-dihydrothieno[2,3-c]quinolin-9-yl)phenyl)propylcarbamate (100 mg, 0.209 mmol) was reacted with tribromoborane (1.0 M in methylene chloride, 1.25 mL, 1.25 mmol) to afford the desired product (38 mg, 52%) as a white solid: $^1$H NMR (500 MHz, MeOD) δ 7.60-7.52 (m, 2H), 7.45 (dd, J=7.8, 1.9 Hz, 1H), 7.35 (dd, J=7.9, 1.7 Hz, 1H), 7.29 (dd, J=7.7, 1.7 Hz, 1H), 7.08 (s, 1H), 6.16 (d, J=5.4 Hz, 1H), 3.29-3.17 (m, 3H), 2.57 (s, 3H), 1.50 (d, J=6.4 Hz, 3H); ESI MS m/z 365 $[C_{21}H_{20}N_2O_2S+H]^+$; HPLC 98.0% (AUC), $t_R$=8.63 min.

Example 1264

9-(4-(2-aminoethyl)-3-chlorophenyl)-8-hydroxy-6-methylthieno[2,3-c]quinolin-4(5H)-one Hydrochloride

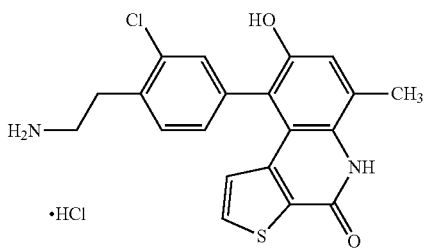 [SMILES: Cc1cc(O)c(-c2ccc(CCN)c(Cl)c2)c2c1[nH]c(=O)c1sccc12 ; Cl]

Following General Procedure F, tert-butyl 2-chloro-4-(8-methoxy-6-methyl-4-oxo-4,5-dihydrothieno[2,3-c]quinolin-9-yl)phenethylcarbamate (120 mg, 0.24 mmol) was reacted with tribromoborane (1.0 M in methylene chloride, 1.45 mL, 1.45 mmol) to afford the desired product (52 mg, 57%) as a white solid: $^1$H NMR (500 MHz, MeOD) δ 7.64 (d, J=5.4 Hz, 1H), 7.54 (d, J=7.8 Hz, 1H), 7.37 (d, J=1.4 Hz, 1H), 7.23 (dd, J=7.7, 1.4 Hz, 1H), 7.08 (s, 1H), 6.19 (d, J=5.4 Hz, 1H), 3.42-3.14 (m, 4H), 2.56 (s, 3H); ESI MS m/z 385 $[C_{20}H_{17}ClN_2O_2S+H]^+$; HPLC 98.2% (AUC), $t_R$=8.55 min.

Example 1268

9-(4-(2-aminoethyl)-3-chlorophenyl)-6-chloro-8-hydroxythieno[2,3-c]quinolin-4(5H)-one Hydrochloride

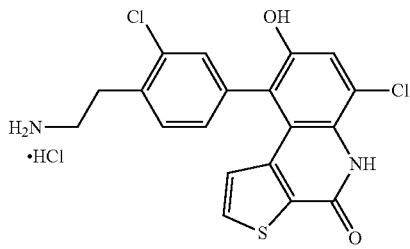 [SMILES: Cl ; NCCc1ccc(-c2c(O)cc(Cl)c3[nH]c(=O)c4sccc4c23)cc1Cl]

Following General Procedure F, tert-butyl 2-chloro-4-(6-chloro-8-methoxy-4-oxo-4,5-dihydrothieno[2,3-c]quinolin-9-yl)phenethylcarbamate (80 mg, 0.154 mmol) was reacted with tribromoborane (1.0 M in methylene chloride, 0.92 mL, 0.92 mmol) to afford the desired product (37 mg, 59%) as a white solid: $^1$H NMR (500 MHz, MeOD) δ 7.68 (d, J=5.4 Hz, 1H), 7.56 (d, J=7.8 Hz, 1H), 7.42 (d, J=1.7 Hz, 1H), 7.30 (s, 1H), 7.27 (dd, J=7.8, 1.7 Hz, 1H), 6.17 (d, J=5.4 Hz, 1H), 3.39-3.25 (m, 4H); ESI MS m/z 405 $[C_{19}H_{14}Cl_2N_2O_2S+H]^+$; HPLC 98.1% (AUC), $t_R$=9.17 min.

Example 1262

(R)-8-hydroxy-6-methyl-9-(4-(1-(methylamino)ethyl)phenyl)thieno[2,3-c]quinolin-4(5H)-one Hydrochloride

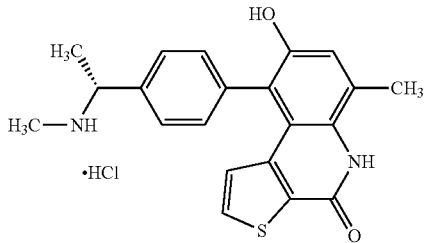

Following General Procedure F, (R)-tert-butyl 1-(4-(8-methoxy-6-methyl-4-oxo-4,5-dihydrothieno[2,3-c]quinolin-9-yl)phenyl)ethyl(methyl)carbamate (150 mg, 0.313 mmol) was reacted with tribromoborane (1.0 M in methylene chloride, 1.9 mL, 1.9 mmol) to afford the desired product (85 mg, 74%) as a white solid: $^1$H NMR (500 MHz, MeOD) δ 7.63 (ddd, J=7.0, 5.5, 2.2 Hz, 2H), 7.57 (d, J=5.4 Hz, 1H), 7.43 (ddd, J=7.4, 6.1, 2.1 Hz, 2H), 7.08 (s, 1H), 6.05 (d, J=5.4 Hz, 1H), 4.47 (q, J=6.9 Hz, 1H), 2.71 (s, 3H), 2.57 (s, 3H), 1.79 (d, J=6.9 Hz, 3H); ESI MS m/z 365 $[C_{21}H_{20}N_2O_2S+H]^+$; HPLC >99% (AUC), $t_R$=8.40 min.

Example 1135

(R)-6-bromo-8-hydroxy-9-(4-(1-(methylamino)ethyl)phenyl)thieno[2,3-c]quinolin-4(5H)-one Hydrochloride

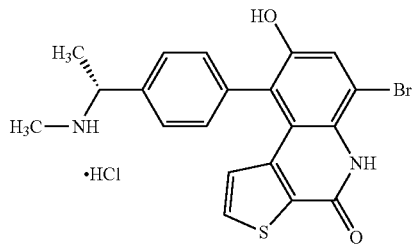 [SMILES: CN[C@H](C)c1ccc(-c2c(O)cc(Br)c3[nH]c(=O)c4sccc4c23)cc1 ; Cl]

Following General Procedure F, (R)-tert-butyl 1-(4-(6-bromo-8-methoxy-4-oxo-4,5-dihydrothieno[2,3-c]quinolin-9-yl)phenyl)ethyl(methyl)carbamate (100 mg, 0.18 mmol) was reacted with tribromoborane (1.0 M in methylene chloride, 1.1 mL, 1.1 mmol) to afford the desired product (38 mg, 48%) as a white solid: $^1$H NMR (500 MHz, DMSO) δ 10.20 (s, 1H), 9.88 (s, 1H), 9.76-9.59 (m, 1H), 9.37-9.21 (m, 1H), 7.78 (d, J=5.4 Hz, 1H), 7.74-7.64 (m, 2H), 7.54 (s, 1H), 7.40-7.33 (m, 2H), 5.77 (d, J=5.4 Hz, 1H), 4.44 (dd, J=12.5, 6.4 Hz, 1H), 2.50 (s, 3H), 1.68 (d, J=6.8 Hz, 3H); ESI MS m/z 429 $[C_{20}H_{17}BrN_2O_2S+H]^+$; HPLC >99% (AUC), $t_R$=9.00 min.

Example 1271

9-(4-(1-Amino-2-methylpropan-2-yl)-3-fluorophenyl)-8-hydroxythieno[2,3-c]quinolin-4(5H)-one Hydrochloride

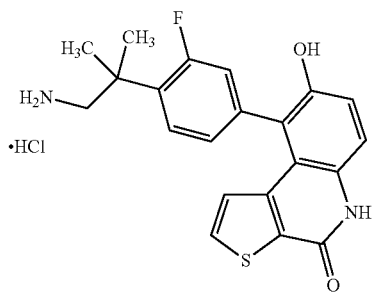 [SMILES: Cl ; CC(C)(CN)c1ccc(-c2c(O)ccc3[nH]c(=O)c4sccc4c23)cc1F]

Following General Procedure F, tert-butyl 2-(2-fluoro-4-(8-methoxy-4-oxo-4,5-dihydrothieno[2,3-c]quinolin-9-yl)phenyl)-2-methylpropylcarbamate (130 mg, 0.26 mmol) was reacted with tribromoborane (1.0 M in methylene chloride, 1.57 mL, 1.57 mmol) to afford the desired product (35 mg, 35%) as a white solid: $^1$H NMR (500 MHz, DMSO) δ 11.81 (s, 1H), 9.34 (s, 1H), 7.98 (s, 3H), 7.72 (d, J=5.4 Hz, 1H), 7.49 (t, J=8.5 Hz, 1H), 7.40 (d, J=8.9 Hz, 1H), 7.17 (t, J=9.0 Hz, 1H), 7.12 (ddd, J=10.7, 9.7, 1.7 Hz, 2H), 6.02 (d, J=5.4 Hz, 1H), 3.25 (s, 2H), 1.51 (d, J=9.1 Hz, 6H); ESI MS m/z 383 $[C_{21}H_{19}FN_2O_2S+H]^+$; HPLC >99% (AUC), $t_R$=8.77 min.

Example 1278

9-(4-(1-Amino-2-methylpropan-2-yl)-3-fluorophenyl)-8-hydroxy-6-methylthieno[2,3-c]quinolin-4(5H)-one Hydrochloride

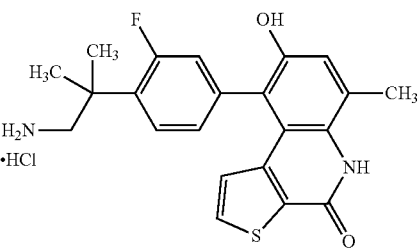 [SMILES: Cl ; Cc1cc(O)c(-c2ccc(C(C)(C)CN)c(F)c2)c2c1[nH]c(=O)c1sccc12]

Following General Procedure F, tert-butyl 2-(2-fluoro-4-(8-methoxy-6-methyl-4-oxo-4,5-dihydrothieno[2,3-c]quinolin-9-yl)phenyl)-2-methylpropylcarbamate (50 mg, 0.10 mmol) was reacted with tribromoborane (1.0 M in methylene chloride, 0.58 mL, 0.58 mmol) to afford the desired product (22 mg, 58%) as a white solid: $^1$H NMR (500 MHz, MeOD) δ 7.64 (d, J=5.4 Hz, 1H), 7.57 (t, J=8.4 Hz, 1H), 7.15 (ddd, J=15.1, 10.7, 1.7 Hz, 2H), 7.08 (d, J=0.7 Hz, 1H), 6.26 (d, J=5.4 Hz, 1H), 3.31 (s, 2H), 2.57 (s, 3H), 1.62 (d, J=5.6 Hz, 6H); ESI MS m/z 397 $[C_{22}H_{21}FN_2O_2S+H]^+$; HPLC >99% (AUC), $t_R$=9.07 min.

Example 1291

9-(4-(1-Aminobutan-2-yl)phenyl)-8-hydroxy-6-methylthieno[2,3-c]quinolin-4(5H)-one Hydrochloride

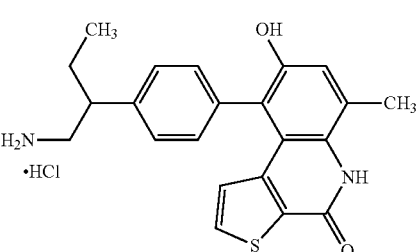

Following General Procedure F, tert-butyl 2-(4-(8-methoxy-6-methyl-4-oxo-4,5-dihydrothieno[2,3-c]quinolin-9-yl)phenyl)butylcarbamate (100 mg, 0.23 mmol) was reacted with tribromoborane (1.0 M in methylene chloride, 1.4 mL, 1.4 mmol)) to afford the desired product (42 mg, 55%) as a white solid: $^1$H NMR (500 MHz, MeOD) δ 7.57-7.50 (m, 2H), 7.40 (ddd, J=18.8, 7.8, 1.8 Hz, 2H), 7.31 (dd, J=7.7, 1.7 Hz, 1H), 7.09 (d, J=0.8 Hz, 1H), 6.13 (d, J=5.4 Hz, 1H), 3.25 (ddd, J=26.6, 13.1, 7.1 Hz, 2H), 2.93 (dq, J, J=15.3, 5.2 Hz, 1H), 2.57 (d, J=0.6 Hz, 3H), 1.97-1.74 (m, 2H), 0.99 (t, J=7.4 Hz, 3H); ESI MS m/z 379 [$C_{22}H_{22}N_2O_2S$+H]$^+$; HPLC >99% (AUC), $t_R$=9.21 min.

Example 1120

(S)-9-(4-(1-aminopropyl)phenyl)-8-hydroxythieno[2,3-c]quinolin-4(5H)-one Hydrochloride

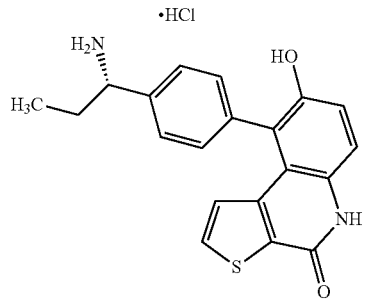 [SMILES: Cl ; CC[C@H](N)c1ccc(-c2c(O)ccc3[nH]c(=O)c4sccc4c23)cc1]

Following General Procedure F, (S)-tert-butyl 1-(4-(8-methoxy-4-oxo-4,5-dihydrothieno[2,3-c]quinolin-9-yl)phenyl)propylcarbamate (100 mg, 0.22 mmol) was reacted with tribromoborane (1.0 M in methylene chloride, 1.3 mL, 1.3 mmol) to afford the desired product (28 mg, 38%) as a white solid: $^1$H NMR (500 MHz, MeOD) δ 7.65-7.58 (m, 2H), 7.54 (d, J=5.4 Hz, 1H), 7.46-7.40 (m, 3H), 7.18 (d, J=8.9 Hz, 1H), 6.03 (d, J=5.4 Hz, 1H), 4.32 (dd, J=9.2, 5.9 Hz, 1H), 2.21-2.03 (m, 2H), 1.04 (t, J=7.4 Hz, 3H); ESI MS m/z 351 [$C_{20}H_{18}N_2O_2S$+H]$^+$; HPLC >99% (AUC), $t_R$=8.24 min.

Example 1290

9-(4-(1-(Aminomethyl)cyclobutyl)phenyl)-8-hydroxy-6-methylthieno[2,3-c]quinolin-4(5H)-one Hydrochloride

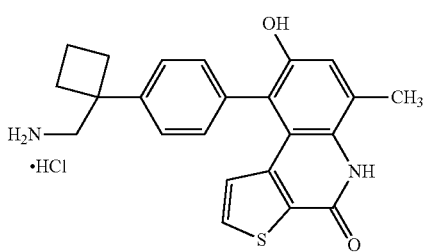 [SMILES: Cl ; Cc1cc(O)c(-c2ccc(C3(CN)CCC3)cc2)c2c1[nH]c(=O)c1sccc12]

Following General Procedure F, tert-butyl (1-(4-(8-methoxy-6-methyl-4-oxo-4,5-dihydrothieno[2,3-c]quinolin-9-yl)phenyl)cyclobutyl)methylcarbamate (130 mg, 0.32 mmol was reacted with tribromoborane (1.0 M in methylene chloride, 1.9 mL, 1.9 mmol to afford the desired product (82 mg, 65%) as a white solid: $^1$H NMR (500 MHz, MeOD) δ 7.63 (d, J=5.4 Hz, 1H), 7.46-7.41 (m, 2H), 7.38-7.32 (m, 2H), 7.09 (d, J=0.7 Hz, 1H), 6.26 (d, J=5.4 Hz, 1H), 3.36-3.33 (m, 2H), 2.65 (dd, J=21.2, 9.3 Hz, 2H), 2.58 (s, 3H), 2.45-2.37 (m, 2H), 2.27 (ddd, J=17.7, 11.5, 8.6 Hz, 1H), 2.12-2.01 (m, 1H); ESI MS m/z 391 [$C_{23}H_{22}N_2O_2S$+H]$^+$; HPLC >99% (AUC), $t_R$=9.37 min.

Example 1300

9-(4-(1-(Aminomethyl)cyclobutyl)phenyl)-8-hydroxythieno[2,3-c]quinolin-4(5H)-one Hydrochloride

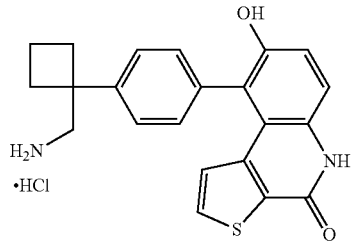 [SMILES: Cl ; NCC1(c2ccc(-c3c(O)ccc4[nH]c(=O)c5sccc5c34)cc2)CCC1]

Following General Procedure F, tert-butyl (1-(4-(8-methoxy-4-oxo-4,5-dihydrothieno[2,3-c]quinolin-9-yl)phenyl)cyclobutyl)methylcarbamate (100 mg, 0.20 mmol) was reacted with tribromoborane (1.0 M in methylene chloride, 1.23 mL, 1.23 mmol) to afford the desired product (52 mg, 68%) as a white solid: $^1$H NMR (500 MHz, MeOD) δ 7.64 (d, J=5.4 Hz, 1H), 7.44 (ddd, J=17.8, 10.5, 3.8 Hz, 3H), 7.39-7.35 (m, 2H), 7.19 (d, J=8.9 Hz, 1H), 6.25 (d, J=5.4 Hz, 1H), 3.44 (s, 2H), 2.65 (dd, J=21.3, 9.4 Hz, 2H), 2.46-2.36 (m, 2H), 2.33-2.20 (m, 1H), 2.14-2.00 (m, 1H); ESI MS m/z 377 [$C_{22}H_{20}N_2O_2S$+H]$^+$; HPLC >99% (AUC), $t_R$=9.00 min.

Example 1309

9-(4-(1-Aminobutan-2-yl)phenyl)-8-hydroxythieno[2,3-c]quinolin-4(5H)-one Hydrochloride

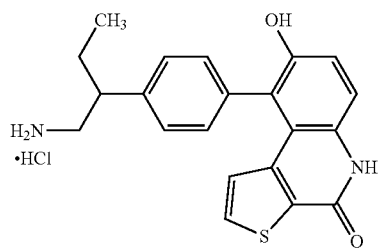 [SMILES: Cl ; CCC(CN)c1ccc(-c2c(O)ccc3[nH]c(=O)c4sccc4c23)cc1]

Following General Procedure F, tert-butyl 2-(4-(8-methoxy-4-oxo-4,5 dihydrothieno[2,3-c]quinolin-9-yl)phenyl)butylcarbamate (100 mg, 0.21 mmol) was reacted with tribromoborane (1.0 M in methylene chloride, 1.25 mL, 1.25 mmol) to afford the desired product (45 mg, 60%) as a white solid: $^1$H NMR (500 MHz, MeOD) δ 7.58-7.50 (m, 2H), 7.46-7.36 (m, 3H), 7.32 (dt, J=12.4, 6.2 Hz, 1H), 7.19 (d, J=8.9 Hz, 1H), 6.11 (d, J=5.4 Hz, 1H), 3.40-3.19 (m, 2H), 2.95 (dq, J=15.3, 5.2 Hz, 1H), 1.98-1.85 (m, 1H), 1.86-1.71

(m, 1H), 1.06-0.91 (m, 3H); ESI MS m/z 365 [C$_{21}$H$_{20}$N$_2$O$_2$S+H]$^+$; HPLC >99% (AUC), t$_R$=8.15 min.

Example 1312

9-(4-(1-Aminobutan-2-yl)phenyl)-6-chloro-8-hydroxythieno[2,3-c]quinolin-4(5H)-one Hydrochloride

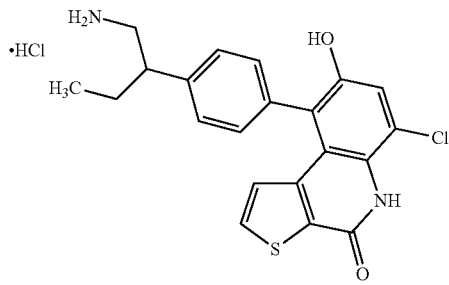 [SMILES: Cl ; CCC(CN)c1ccc(-c2c(O)cc(Cl)c3[nH]c(=O)c4sccc4c23)cc1]

Following General Procedure F, tert-butyl 2-(4-(6-chloro-8-methoxy-4-oxo-4,5-dihydrothieno[2,3-c]quinolin-9-yl)phenyl)butylcarbamate (65 mg, 0.13 mmol) was reacted with tribromoborane (1.0 M in methylene chloride, 0.76 mL, 0.76 mmol) to afford the desired product (28 mg, 56%) as a white solid: $^1$H NMR (500 MHz, MeOD) δ 7.60 (d, J=5.4 Hz, 1H), 7.54 (dd, J=7.9, 1.8 Hz, 1H), 7.44 (dd, J=7.7, 1.8 Hz, 1H), 7.39 (dd, J=7.9, 1.8 Hz, 1H), 7.35-7.30 (m, 2H), 6.08 (d, J=5.4 Hz, 1H), 3.38-3.22 (m, 2H), 2.98-2.89 (m, 1H), 1.97-1.85 (m, 1H), 1.85-1.72 (m, 1H), 0.98 (t, J=7.4 Hz, 3H); ESI MS m/z 399 [C$_{21}$H$_{19}$ClN$_2$O$_2$S+H]$^+$; HPLC >99%, (AUC), t$_R$=10.29 min.

Example 385

9-(4-(1-(Ethylamino)ethyl)phenyl)-8-hydroxythieno[2,3-c]quinolin-4(5H)-one Hydrochloride

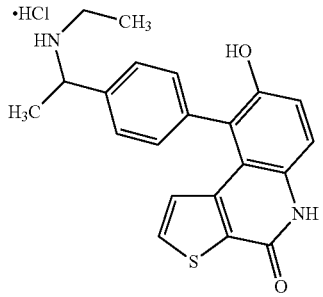 [SMILES: Cl ; CCNC(C)c1ccc(-c2c(O)ccc3[nH]c(=O)c4sccc4c23)cc1]

Following General Procedure F, tert-butyl ethyl(1-(4-(8-methoxy-4-oxo-4,5-dihydrothieno[2,3-c]quinolin-9-yl)phenyl)ethyl)carbamate (150 mg, 0.31 mmol) was reacted with tribromoborane (1.0 M in methylene chloride, 1.9 mL, 1.9 mmol) to afford the desired product (37 mg, 33%) as a white glass: $^1$H NMR (500 MHz, MeOD); δ 7.65 (dd, J=13.2, 4.9 Hz, 2H), 7.57 (d, J=5.4 Hz, 1H), 7.48-7.39 (m, 3H), 7.18 (d, J=8.9 Hz, 1H), 6.04 (d, J=5.4 Hz, 1H), 4.53 (q, J=6.8 Hz, 1H), 3.20-3.08 (m, 1H), 3.08-2.96 (m, 1H), 1.79 (d, J=6.9 Hz, 3H), 1.36 (t, J=7.3 Hz, 3H). ESI MS m/z 365 [+H]$^+$; HPLC >99% (AUC), t$_R$=12.05 min.

Example 1165

6-chloro-8-hydroxy-9-(4-(2-(methylamino)ethyl)phenyl)thieno[2,3-c]quinolin-4(5H)-one Hydrochloride

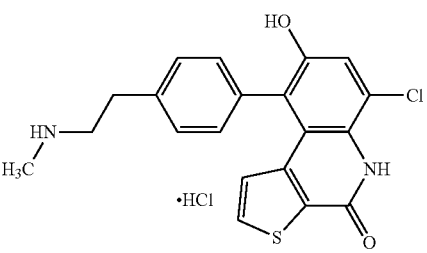 [SMILES: CNCCc1ccc(-c2c(O)cc(Cl)c3[nH]c(=O)c4sccc4c23)cc1 ; Cl]

Following General Procedure F, tert-butyl 4-(6-chloro-8-methoxy-4-oxo-4,5-dihydrothieno[2,3-c]quinolin-9-yl)phenethyl(methyl)carbamate (60 mg, 0.12 mmol) was reacted with tribromoborane (1.0 M in methylene chloride, 0.72 mL, 0.72 mmol) to afford the desired product (22 mg, 50%) as a white solid: $^1$H NMR (500 MHz, DMSO-d$_6$) δ 10.77 (s, 1H), 9.72 (s, 1H), 8.72 (s, 1H), 7.76 (d, J=5.4 Hz, 1H), 7.42 (d, J=8.1 Hz, 2H), 7.31 (s, 1H), 7.24 (d, J=8.1 Hz, 2H), 5.85 (d, J=5.4 Hz, 1H), 3.30-3.23 (m, 2H), 3.09-3.02 (m, 2H), 2.65 (s, 3H); ESI MS m/z 385 [C$_{20}$H$_{17}$ClN$_2$O$_2$S+H]$^+$; HPLC >99% (AUC), t$_R$=9.03 min.

Example 1197

(S)-8-hydroxy-9-(4-(1-(methylamino)propan-2-yl)phenyl)thieno[2,3-c]quinolin-4(5H)-one Hydrochloride

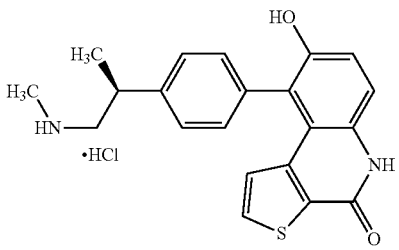 [SMILES: CNC[C@@H](C)c1ccc(-c2c(O)ccc3[nH]c(=O)c4sccc4c23)cc1 ; Cl]

Following General Procedure F, (S)-tert-butyl 2-(4-(8-methoxy-4-oxo-4,5-dihydrothieno[2,3-c]quinolin-9-yl)phenyl)propyl(methyl)carbamate (100 mg, 0.21 mmol) was reacted with tribromoborane (1.0 M in methylene chloride, 1.25 mL, 1.25 mmol) to afford the desired product (31 mg, 41%) as a white solid: $^1$H NMR (500 MHz, MeOD) δ 7.61-7.53 (m, 2H), 7.48 (dd, J=7.8, 1.9 Hz, 1H), 7.44-7.37 (m, 2H), 7.33 (dd, J=7.7, 1.7 Hz, 1H), 7.18 (d, J=8.9 Hz, 1H), 6.14 (d, J=5.4 Hz, 1H), 3.41-3.25 (m, 3H), 2.75 (s, 3H), 1.50 (d, J=6.8 Hz, 3H); ESI MS m/z 365 [C$_{21}$H$_{20}$N$_2$O$_2$S+H]$^+$; HPLC >99% (AUC), t$_R$=8.36 min.

Example 1224

9-(4-(2-aminoethyl)-2-bromo-5-hydroxyphenyl)-8-hydroxythieno[2,3-c]quinolin-4(5H)-one Hydrochloride

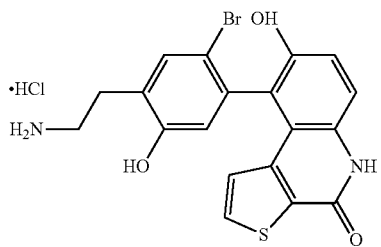 [SMILES: Cl ; NCCc1cc(Br)c(-c2c(O)ccc3[nH]c(=O)c4sccc4c23)cc1O]

Following General Procedure F, (tert-butyl 5-bromo-2-hydroxy-4-(8-methoxy-4-oxo-4,5-dihydrothieno[2,3-c]quinolin-9-yl)phenethylcarbamate (50 mg, 0.90 mmol) was reacted with tribromoborane (1.0 M in methylene chloride, 0.54 mL, 0.54 mmol) to afford the desired product (18 mg, 48%) as a white solid: $^1$H NMR (500 MHz, MeOD) δ 7.68 (d, J=5.5 Hz, 1H), 7.58 (s, 1H), 7.44 (d, J=9.0 Hz, 1H), 7.18 (d, J=9.0 Hz, 1H), 6.82 (s, 1H), 6.33 (d, J=5.5 Hz, 1H), 3.25 (m, 2H), 2.95 (m, 2H); ESI MS m/z 432 [C$_{19}$H$_{15}$BrN$_2$O$_3$S+H]$^+$; HPLC 96.9% (AUC), t$_R$=8.10 min.

Example 1082

(S)-8-hydroxy-9-(4-(1-(methylamino)ethyl)phenyl)thieno[2,3-c]quinolin-4(5H)-one Hydrochloride

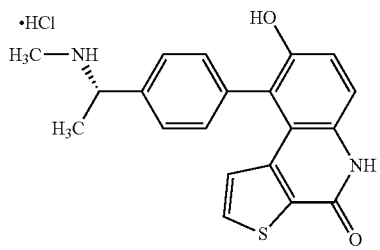 [SMILES: Cl ; CN[C@@H](C)c1ccc(-c2c(O)ccc3[nH]c(=O)c4sccc4c23)cc1]

Following General Procedure F, (S)-tert-butyl 1-(4-(8-methoxy-4-oxo-4,5-dihydrothieno[2,3-c]quinolin-9-yl)phenyl)ethyl(methyl)carbamate (100 mg, 0.22 mmol) was reacted with tribromoborane (1.0 M in methylene chloride, 1.30 mL, 13.0 mmol) to afford the desired product (50 mg, 66%) as a white solid: $^1$H NMR (500 MHz, MeOD) δ 7.68-7.61 (m, 2H), 7.57 (d, J=5.4 Hz, 1H), 7.49-7.39 (m, 3H), 7.18 (d, J=8.9 Hz, 1H), 6.04 (d, J=5.4 Hz, 1H), 4.48 (q, J=6.8 Hz, 1H), 2.72 (s, 3H), 1.80 (d, J=6.9 Hz, 3H); ESI MS m/z 351 [C$_{20}$H$_{18}$N$_2$O$_2$S+H]$^+$; HPLC 96.9% (AUC), t$_R$=7.68 min.

Example 1088

9-(4-(1-aminopropyl)phenyl)-6-chloro-8-hydroxythieno[2,3-c]quinolin-4(5H)-one Hydrochloride

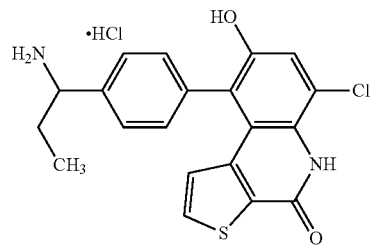 [SMILES: CCC(N)c1ccc(-c2c(O)cc(Cl)c3[nH]c(=O)c4sccc4c23)cc1 ; Cl]

Following General Procedure F, tert-butyl 1-(4-(6-chloro-8-methoxy-4-oxo-4,5-dihydrothieno[2,3-c]quinolin-9-yl)phenyl)propylcarbamate (40 mg, 0.08 mmol) was reacted with tribromoborane (1.0 M in methylene chloride, 0.48 mL, 0.48 mmol) to afford the desired product (12 mg, 40%) as a white solid: $^1$H NMR (500 MHz, MeOD) δ 7.65-7.56 (m, 3H), 7.46-7.39 (m, 2H), 7.30 (s, 1H), 6.02 (d, J=5.4 Hz, 1H), 4.32 (dd, J=9.1, 6.0 Hz, 1H), 2.21-2.02 (m, 2H), 1.03 (t, J=7.4 Hz, 3H); ESI MS m/z 385 [C$_{20}$H$_{17}$N$_2$O$_2$S+H]$^+$; HPLC 95.9% (AUC), t$_R$=9.15 min.

Example 1087

(S)-6-chloro-8-hydroxy-9-(4-(1-(methylamino)ethyl)phenyl)thieno[2,3-c]quinolin-4(5H)-one Hydrochloride

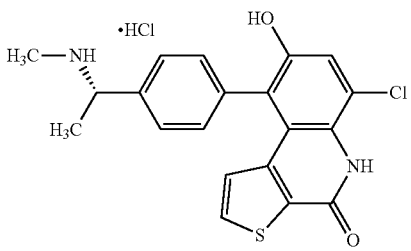 [SMILES: CN[C@@H](C)c1ccc(-c2c(O)cc(Cl)c3[nH]c(=O)c4sccc4c23)cc1 ; Cl]

Following General Procedure F, (S)-tert-butyl 1-(4-(6-chloro-8-methoxy-4-oxo-4,5-dihydrothieno[2,3-c]quinolin-9-yl)phenyl)ethyl(methyl)carbamate (40 mg, 0.08 mmol) was reacted with tribromoborane (1.0 M in methylene chloride, 0.48 mL, 0.48 mmol) to afford the desired product (18 mg, 60%) as a white solid: $^1$H NMR (500 MHz, MeOD) δ 7.72-7.60 (m, 3H), 7.49-7.39 (m, 2H), 7.30 (s, 1H), 6.03 (d, J=5.4 Hz, 1H), 4.49 (q, J=6.9 Hz, 1H), 2.73 (d, J=4.3 Hz, 3H), 1.80 (d, J=6.9 Hz, 3H); ESI MS m/z 385 [C₂₀H₁₇ClN₂O₂S+H]⁺; HPLC >99% (AUC), t_R=13.60 min.

Example 1209

9-(4-(3-(aminomethyl)pentan-3-yl)phenyl)-8-hydroxythieno[2,3-c]quinolin-4(5H)-one Hydrochloride

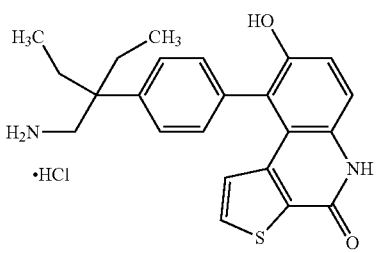 [SMILES: CCC(CC)(CN)c1ccc(-c2c(O)ccc3[nH]c(=O)c4sccc4c23)cc1 ; Cl]

Following General Procedure F, tert-butyl 2-ethyl-2-(4-(8-methoxy-4-oxo-4,5-dihydrothieno[2,3-c]quinolin-9-yl)phenyl)butylcarbamate (200 mg, 0.40 mmol) was reacted with tribromoborane (1.0 M in methylene chloride, 2.37 mL, 2.37 mmol) to afford the desired product (120 mg, 78%) as a white solid: ¹H NMR (500 MHz, MeOD) δ 7.62 (d, J=8.4 Hz, 2H), 7.54 (d, J=5.4 Hz, 1H), 7.41 (dd, J=15.2, 8.6 Hz, 3H), 7.19 (d, J=8.9 Hz, 1H), 6.08 (d, J=5.4 Hz, 1H), 3.34 (s, 2H), 2.05-1.88 (m, 4H), 0.93 (t, J=7.4 Hz, 6H); ESI MS m/z 393 [C₂₁H₂₄N₂O₂S+H]⁺; HPLC >99% (AUC), t_R=9.38 min.

Example 1271

9-(4-(1-amino-2-methylpropan-2-yl)-3-fluorophenyl)-8-hydroxythieno[2,3-c]quinolin-4(5H)-one Hydrochloride

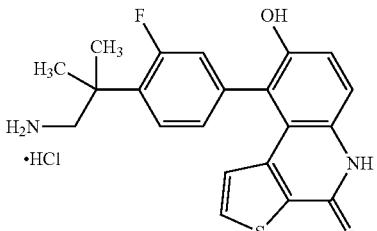

Following General Procedure F, tert-butyl 2-(2-fluoro-4-(8-methoxy-4-oxo-4,5-dihydrothieno[2,3-c]quinolin-9-yl)phenyl)-2-methylpropylcarbamate (80 mg, 0.16 mmol) was reacted with tribromoborane (1.0 M in methylene chloride, 1.0 mL, 1.0 mmol) to afford the desired product (35 mg, 56%) as a yellow glass: ¹H NMR (500 MHz, MeOD) δ 7.67 (d, J=5.4 Hz, 1H), 7.59 (t, J=8.4 Hz, 1H), 7.44 (d, J=8.9 Hz, 1H), 7.20 (d, J=8.9 Hz, 3H), 6.25 (d, J=5.4 Hz, 1H), 3.54 (d, J=13.0 Hz, 2H), 3.28 (s, 1H), 1.63 (d, J=4.6 Hz, 6H); ESI MS m/z 383 [C₂₁H₁₉FN₂O₂S+H]⁺; HPLC >99% (AUC), t_R=8.89 min.

Example 623 tert-butyl (1-(4-(6-bromo-8-methoxy-4-oxo-4,5-dihydrothieno[2,3-c]quinolin-9-yl)phenyl)cyclopropyl)methylcarbamate

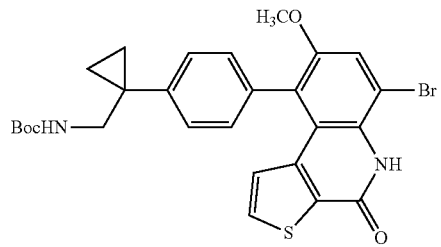 [SMILES: COc1cc(Br)c2[nH]c(=O)c3sccc3c2c1-c1ccc(C2(CNC(=O)OC(C)(C)C)CC2)cc1]

Following General Procedure I, tert-butyl (1-(4-(8-methoxy-4-oxo-4,5-dihydrothieno[2,3-c]quinolin-9-yl)phenyl)cyclopropyl)methylcarbamate (750 mg, 1.57 mmol) was reacted with NBS (280 mg, 1.57 mmol)) to afford the desired product (473 mg, 54%) as a yellow solid: ESI MS m/z 555 [C₂₇H₂₇BrN₂O₄S+H]⁺.

Example 624

(S)-tert-butyl 2-(4-(6-bromo-8-methoxy-4-oxo-4,5-dihydrothieno[2,3-c]quinolin-9-yl)phenyl)propyl(methyl)carbamate

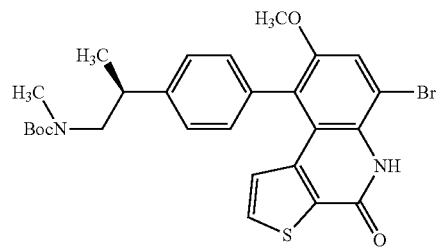 [SMILES: COc1cc(Br)c2[nH]c(=O)c3sccc3c2c1-c1ccc([C@H](C)CN(C)C(=O)OC(C)(C)C)cc1]

Following General Procedure I, (S)-tert-butyl 2-(4-(8-methoxy-4-oxo-4,5-dihydrothieno[2,3-c]quinolin-9-yl)phenyl)propyl(methyl)carbamate (1.0 g, 2.0 mmol was reacted with NBS (446 mg, 2.5 mmol) to afford the desired product (500 mg, 43%) as a yellow solid: ESI MS m/z 557 [C₂₇H₂₉BrN₂O₄S+H]⁺.

Example 625

(R)-tert-butyl 1-(4-(6-bromo-8-methoxy-4-oxo-4,5-dihydrothieno[2,3-c]quinolin-9-yl)phenyl)ethyl(methyl)carbamate

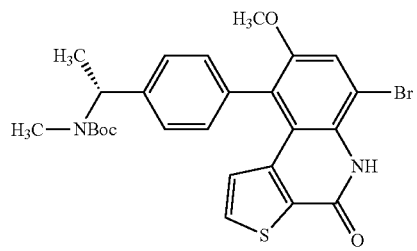 [SMILES: COc1cc(Br)c2[nH]c(=O)c3sccc3c2c1-c1ccc([C@@H](C)N(C)C(=O)OC(C)(C)C)cc1]

Following General Procedure I, (R)-tert-butyl 1-(4-(8-methoxy-4-oxo-4,5-dihydrothieno[2,3-c]quinolin-9-yl)phenyl)ethyl(methyl)carbamate (400 mg, 0.86 mmol) was reacted with NBS (184 mg, 1.03 mmol) to afford the desired product (285 mg, 61%) as a yellow solid: ESI MS m/z 543 $[C_{26}H_{30}BrN_2O_4S+H]^+$.

Example 1263

9-(4-(2-aminoethyl)-3-chlorophenyl)-8-methoxy-6-methylthieno[2,3-c]quinolin-4(5H)-one Hydrochloride

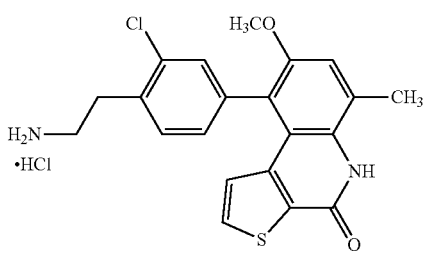 [SMILES: Cl ; COc1cc(C)c2[nH]c(=O)c3sccc3c2c1-c1ccc(CCN)c(Cl)c1]

Following General Procedure C, tert-butyl 2-chloro-4-(8-methoxy-6-methyl-4-oxo-4,5-dihydrothieno[2,3-c]quinolin-9-yl)phenethylcarbamate (50 mg, 0.10 mmol) was reacted with TFA (3.0 mL) to afford the desired product as a light yellow solid (27 mg, 68%): $^1$H NMR (500 MHz, MeOD) δ 7.62 (t, J=5.8 Hz, 1H), 7.53 (d, J=7.8 Hz, 1H), 7.35 (d, J=1.6 Hz, 1H), 7.29 (s, 1H), 7.21 (dd, J=7.7, 1.7 Hz, 1H), 6.11 (d, J=5.4 Hz, 1H), 3.75 (d, J=7.4 Hz, 3H), 3.38-3.16 (m, 4H), 2.64 (s, 3H); ESI MS m/z 399 $[C_{21}H_{19}ClN_2O_2S+H]^+$; HPLC 98.8% (AUC), $t_R$=9.50 min.

Example 1265

(R)-8-methoxy-6-methyl-9-(4-(1-(methylamino)ethyl)phenyl)thieno[2,3-c]quinolin-4(5H)-one Hydrochloride

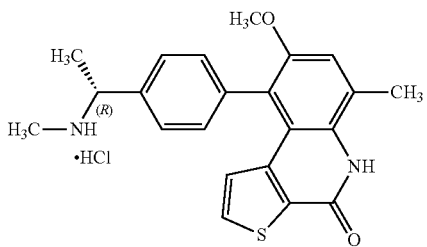

Following General Procedure C, (R)-tert-butyl 1-(4-(8-methoxy-6-methyl-4-oxo-4,5-dihydrothieno[2,3-c]quinolin-9-yl)phenyl)ethyl(methyl)carbamate (50 mg, 0.10 mmol) was reacted with TFA (3.0 mL) to afford the desired product as a yellow solid 25 mg, 63%): $^1$H NMR (500 MHz, MeOD) δ 7.64 (d, J=8.4 Hz, 2H), 7.57 (d, J=5.4 Hz, 1H), 7.38 (d, J=8.6 Hz, 2H), 7.29 (s, 1H), 5.99 (d, J=5.4 Hz, 1H), 4.48 (q, J=6.8 Hz, 1H), 3.73 (s, 3H), 2.72 (s, 3H), 2.64 (s, 3H), 1.80 (d, J=6.9 Hz, 3H). ESI MS m/z 379 $[C_{22}H_{21}N_2O_2S+H]^+$; HPLC 98.0% (AUC), $t_R$=9.51 min.

Example 1277

9-(4-(1-aminobutan-2-yl)phenyl)-8-methoxy-6-methylthieno[2,3-c]quinolin-4(5H)-one Hydrochloride

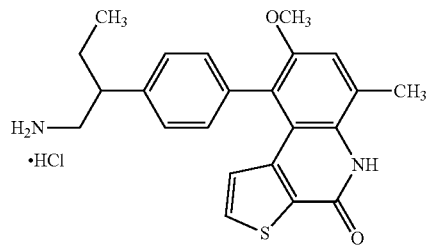 [SMILES: Cl ; CCC(CN)c1ccc(-c2c(OC)cc(C)c3[nH]c(=O)c4sccc4c23)cc1]

Following General Procedure C, tert-butyl 2-(4-(8-methoxy-6-methyl-4-oxo-4,5-dihydrothieno[2,3-c]quinolin-9-yl)phenyl)butylcarbamate (40 mg, 0.08 mmol) was reacted with TFA (3.0 mL) to afford the desired product as a white solid 14 mg, 44%): $^1$H NMR (500 MHz, MeOD) δ 7.54-7.47 (m, 2H), 7.42 (dd, J: 7.7, 1.8 Hz, 1H), 7.35-7.25 (m, 3H), 5.96 (d, J=5.4 Hz, 1H), 3.75 (s, 3H), 3.37-3.26 (m, 2H), 3.02-2.89 (m, 1H), 2.64 (s, 3H), 1.97-1.85 (m, 1H), 1.81-1.67 (m, 1H), 0.96 (t, J=7.3 Hz, 3H); ESI MS m/z 39.3 $[C_{23}H_{24}N_2O_2S+H]^+$; HPLC >99% (AUC), $L_R$=9.74 min.

Example 1064

(S)-8-methoxy-9-(4-(1-(methylamino)ethyl)phenyl)thieno[2,3-c]quinolin-4(5H)-one Hydrochloride

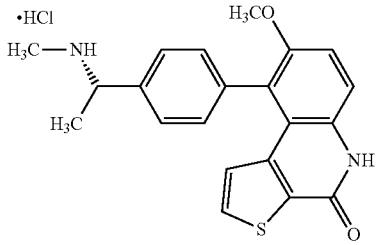

Following General Procedure C, (S)-tert-butyl 1-(4-(8-methoxy-4-oxo-4,5-dihydrothieno[2,3-c]quinolin-9-yl)phenyl)ethyl(methyl)carbamate (30 mg, 0.06 mmol) was reacted with TFA (1.5 mL) to afford the desired product (15 mg, 65%) as a white solid: $^1$H NMR (500 MHz, MeOD); δ 7.64 (d, J=8.5 Hz, 2H), 7.61-7.52 (m, 2H), 7.45-7.36 (m, 3H), 5.98 (d, J=5.4 Hz, 1H), 4.48 (q, J=6.8 Hz, 1H), 3.74 (s, 3H), 2.73 (s, 3H), 1.79 (t, J=8.0 Hz, 3H). ESI MS m/z 365 [C$_{21}$H$_{20}$N$_2$O$_2$S+H]$^+$; HPLC >99% (AUC), t$_R$=13.69 min.

Example 1121

(S)-9-(4-(1-aminopropyl)phenyl)-8-methoxythieno [2,3-c]quinolin-4(5H)-one Hydrochloride

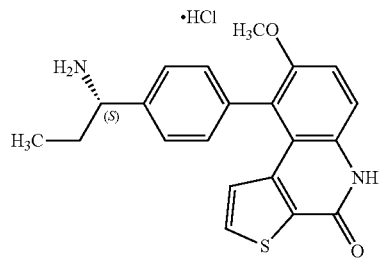

Following General Procedure C, (S)-tert-butyl 1-(4-(8-methoxy-4-oxo-4,5-dihydrothieno[2,3-c]quinolin-9-yl)phenyl)propylcarbamate (40 mg, 0.09 mmol) was reacted with TFA (2.0 mL) to afford the desired product (15 mg, 49%) as a light yellow glass: $^1$H NMR (500 MHz, MeOD)) δ 7.60 (tt, J=7.1, 3.6 Hz, 2H), 7.57-7.51 (m, 2H), 7.42-7.36 (m, 3H), 6.00 (d, J=5.4 Hz, 1H), 4.32 (dd, J=9.2, 6.0 Hz, 1H), 3.73 (s, 3H), 2.11 (qdd, J=13.6, 8.3, 6.7 Hz, 3H), 1.08-0.98 (m, 3H); ESI MS m/z 365 [C$_{21}$H$_{20}$N$_2$O$_2$S+H]$^+$; HPLC >99% (AUC), t$_R$=8.74 min.

Example 1391

9-(4-(1-(aminomethyl)cyclopropyl)phenyl)-6-bromo-8-methoxythieno[2,3-c]quinolin-4(5H)-one Hydrochloride

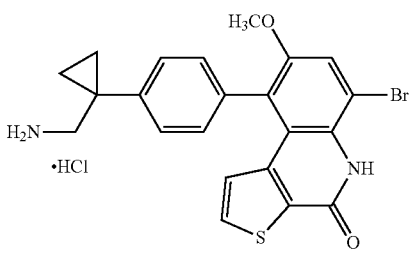 [SMILES: COc1cc(Br)c2[nH]c(=O)c3sccc3c2c1-c1ccc(C2(CN)CC2)cc1 ; Cl]

Following General Procedure C, tert-butyl (1-(4-(6-bromo-8-methoxy-4-oxo-4,5-dihydrothieno[2,3-c]quinolin-9-yl)phenyl)cyclopropyl)methylcarbamate (50 mg, 0.09 mmol) was reacted with TFA (5.0 mL) to afford the desired product (19 mg, 47%) as a white solid: $^1$H NMR (500 MHz, MeOD) δ 7.71-7.65 (m, 1H), 7.65-7.57 (m, 3H), 7.32-7.27 (m, 2H), 5.99 (t, J=6.4 Hz, 1H), 3.75 (s, 3H), 3.29 (s, 2H), 1.21-1.10 (m, 4H); ESI MS m/z 456 [C$_{22}$H$_{19}$BrN$_2$O$_2$S+H]$^+$; HPLC >99% (AUC), t$_R$=10.83 min.

Example 1251

9-(4-(1-(aminomethyl)cyclopropyl)phenyl)-8-methoxy-6-methylthieno[2,3-c]quinolin-4(5H)-one Hydrochloride

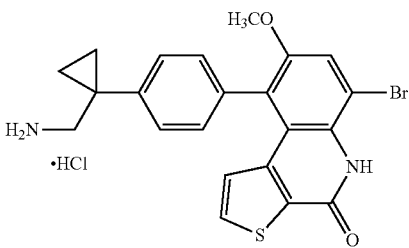 [SMILES: COc1cc(Br)c2[nH]c(=O)c3sccc3c2c1-c1ccc(C2(CN)CC2)cc1 ; Cl]

Following General Procedure C, tert-butyl (1-(4-(8-methoxy-6-methyl-4-oxo-4,5-dihydrothieno[2,3-c]quinolin-9-yl)phenyl)cyclopropyl)methylcarbamate (70 mg, 0.14 mmol) was reacted with TFA (4.0 mL) to afford the desired product (32 mg, 56%) as a white solid: $^1$H NMR (500 MHz, MeOD) δ 7.63-7.51 (m, 3H), 7.32-7.23 (m, 3H), 6.02 (d, J=5.4 Hz, 1H), 3.74 (s, 3H), 3.28 (s, 2H), 2.64 (s, 3H), 1.21-1.08 (m, 4H); ESI MS m/z 391 [C$_{23}$H$_{22}$N$_2$O$_2$S+H]$^+$; HPLC 95.7% (AUC), t$_R$=9.15 min.

Example 1297

9-(4-(1-(aminomethyl)cyclobutyl)phenyl)-8-methoxy-6-methylthieno[2,3-c]quinolin-4(5H)-one Hydrochloride

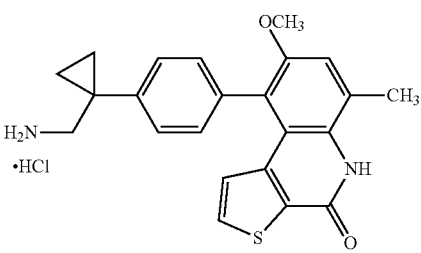 [SMILES: Cl ; COc1cc(C)c2[nH]c(=O)c3sccc3c2c1-c1ccc(C2(CN)CC2)cc1]

Following General Procedure C, tert-butyl(1-(4-(8-methoxy-6-methyl-4-oxo-4,5-dihydrothieno[2,3-c]quinolin-9-yl)phenyl)cyclobutyl)methylcarbamate (200 mg, 0.42 mmol) was reacted with TFA (5.0 mL) to afford the desired product (150 mg, 89%) as a white solid: $^1$H NMR (500 MHz, MeOD) δ 7.61 (d, J=5.4 Hz, 1H), 7.47-7.41 (m, 2H), 7.35-7.30 (m, 3H), 6.07 (d, J=5.4 Hz, 1H), 3.76 (s, 3H), 3.46 (s, 2H), 2.65 (s, 3H), 2.64-2.57 (m, 2H), 2.47-2.37 (m, 2H), 2.32-2.15 (m, 1H), 2.12-1.97 (m, 1H); ESI MS m/z 405 [$C_{24}H_{24}N_2O_2S$+H]$^+$; HPLC >99% (AUC), $t_R$=12.27 min.

Example 1321

9-(4-(1-(aminomethyl)cyclobutyl)phenyl)-6-chloro-8-methoxythieno[2,3-c]quinolin-4(5H)-one Hydrochloride

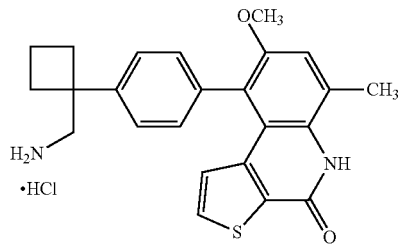 [SMILES: Cl ; COc1cc(C)c2[nH]c(=O)c3sccc3c2c1-c1ccc(C2(CN)CCC2)cc1]

Following General Procedure C, tert-butyl(1-(4-(6-chloro-8-methoxy-4-oxo-4,5-dihydrothieno[2,3-c]quinolin-9-yl)phenyl)cyclobutyl)methylcarbamate (25 mg, 0.05 mmol) was reacted with TFA (2.5 mL) to afford the desired product (16 mg, 80%) as a white solid: $^1$H NMR (500 MHz, MeOD) δ 7.66 (s, 1H), 7.55 (s, 1H), 7.47 (s, 2H), 7.34 (s, 2H), 6.04 (s, 1H), 3.77 (s, 3H), 3.47 (s, 2H), 2.68-2.54 (m, 2H), 2.47-2.35 (m, 2H), 2.31-2.20 (m, 1H), 2.12-2.02 (m, 1H); ESI MS m/z 426 [$C_{23}H_{21}ClN_2O_2S$+H]$^+$; HPLC >99% (AUC), $t_R$=9.87 min.

Example 1154

(S)-6-chloro-8-hydroxy-9-(4-(1-(methylamino)propyl)phenyl)thieno[2,3-c]quinolin-4(5H)-one Hydrochloride

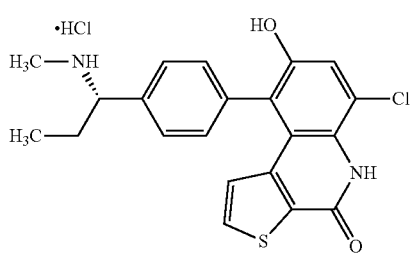 [SMILES: CC[C@H](NC)c1ccc(-c2c(O)cc(Cl)c3[nH]c(=O)c4sccc4c23)cc1 ; Cl]

Following General Procedure F, (S)-tert-butyl 1-(4-(6-chloro-8-methoxy-4-oxo-4,5-dihydrothieno[2,3-c]quinolin-9-yl)phenyl)propyl(methyl)carbamate (100 mg, 0.194 mmol was reacted with tribromoborane (1.0 M in methylene chloride 1.2 mL, 1.16 mmol) to afford the desired product (35 mg, 45%) as a white solid: $^1$H NMR (500 MHz, DMSO) δ 10.81 (d, J=10.5 Hz, 1H), 9.83 (s, 1H), 9.70-9.45 (m, 1H), 9.28 (s, 1H), 7.73 (d, J=5.4 Hz, 1H), 7.70-7.60 (m, 2H), 7.38 (dd, J=12.4, 4.7 Hz, 3H), 5.70 (d, J=5.4 Hz, 1H), 4.19 (dt, J=12.1, 6.0 Hz, 1H), 2.51 (s, 3H), 2.20 (ddd, J=14.4, Z

Example 626

(S)-tert-butyl 2-(4-(8-methoxy-6-methyl-4-oxo-4,5-dihydrothieno[2,3-c]quinolin-9-yl)phenyl)propyl(methyl)carbamate

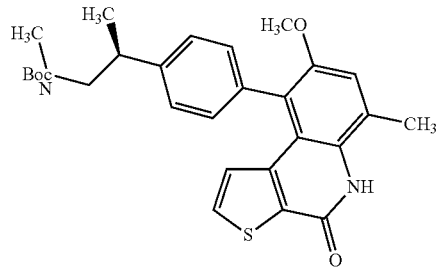

Following General Procedure J, (S)-tert-butyl 2-(4-(6-bromo-8-methoxy-4-oxo-4,5-dihydrothieno[2,3-c]quinolin-9-yl)phenyl)propyl(methyl)carbamate (150 mg, 0.269 mmol) was reacted with trimethyl boroxine (102 mg, 0.8 mmol) to afford the desired product (95 mg, 75%) as a brown solid: ESI MS m/z 493 [$C_{28}H_{32}BrN_2O_4S$+H]$^+$.

Example 1372

9-(4-(1-((dimethylamino)methyl)cyclobutyl)phenyl)-8-hydroxy-6-methylthieno[2,3-c]quinolin-4(5H)-one Hydrochloride

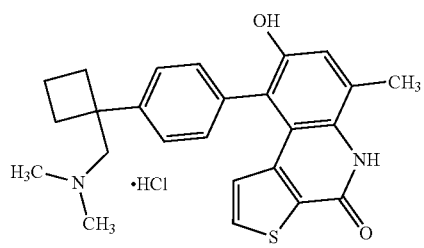

Following the procedure outlined for Example 460, 9-(4-(1-(aminomethyl)cyclobutyl)phenyl)-8-hydroxy-6-methylthieno[2,3-c]quinolin-4(5H)-one hydrochloride (110 mg, 0.28 mmol)) was reacted with formaldehyde (37% in water, 22 mg, 0.70 mmol) to afford the desired product as a white solid (28 mg, 25%): $^1$H NMR (500 MHz, MeOD) δ 7.65 (t, J=7.4 Hz, 3H), 7.43 (d, J=8.1 Hz, 2H), 7.12 (s, 1H), 6.24 (d, J=5.3 Hz, 1H), 3.80 (s, 2H), 2.86 (s, 6H), 2.77-2.67 (m, 2H), 2.60 (s, 3H), 2.52 (dt, J=11.9, 8.8 Hz, 2H), 2.30-2.17 (m, 1H), 2.17-2.05 (m, 1H); ESI MS m/z 419 $[C_{25}H_{26}N_2O_2S+H]^+$; HPLC >99% (AUC), $t_R$=9.51 min.

Example 1172

(S)-9-(4-(1-(dimethylamino)propan-2-yl)phenyl)-8-hydroxythieno[2,3-c]quinolin-4(5H)-one Hydrochloride

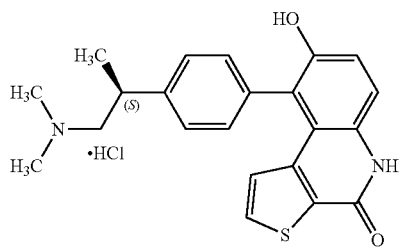

Following the procedure outlined for Example 460, (S)-9-(4-(1-aminopropan-2-yl)phenyl)-8-hydroxythieno[2,3-c]quinolin-4(5H)-one hydrochloride (20 mg, 0.06 mmol)) was reacted with formaldehyde (37% in water, 5.0 mg, 0.15 mmol) to afford the desired product as a white solid (15 mg, 70%): $^1$H NMR (500 MHz, MeOD) δ 7.64-7.51 (m, 3H), 7.45-7.37 (m, 2H), 7.34 (dd, J=7.7, 1.7 Hz, 1H), 7.19 (t, J=7.7 Hz, 1H), 6.12 (d, J=5.4 Hz, 1H), 3.62 (td, J=11.5, 2.6 Hz, 1H), 3.50-3.40 (m, 2H), 2.97 (s, 3H), 2.94 (s, 3H), 1.48 (d, J=6.6 Hz, 3H); ESI MS m/z 379 $[C_{22}H_{22}N_2O_2S+H]^+$; HPLC >99% (AUC), $t_R$=8.63 min.

Example 1128

(S)-9-(4-(1-(dimethylamino)propyl)phenyl)-8-hydroxythieno[2,3-c]quinolin-4(5H)-one Hydrochloride

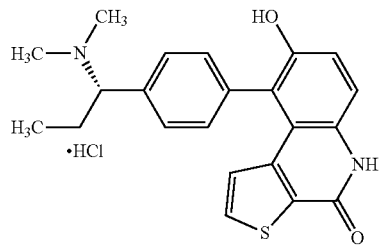 [SMILES: CC[C@@H](c1ccc(-c2c(O)ccc3[nH]c(=O)c4sccc4c23)cc1)N(C)C ; Cl]

Following the procedure outlined for Example 460, (S)-9-(4-(1-aminopropyl)phenyl)-8-hydroxythieno[2,3-c]quinolin-4(5H)-one hydrochloride (25 mg, 0.07 mmol)) was reacted with formaldehyde (37% in water, 5.5 mg, 0.18 mmol) to afford the desired product as a white solid (12 mg, 45%): $^1$H NMR (500 MHz, MeOD) δ 7.66 (ddd, J=19.7, 7.7, 1.6 Hz, 2H), 7.55 (d, J=5.4 Hz, 1H), 7.52-7.45 (m, 2H), 7.43 (d, J=8.9 Hz, 1H), 7.20 (d, J=8.9 Hz, 1H), 5.95 (d, J=5.4 Hz, 1H), 4.38 (dd, J=11.3, 4.4 Hz, 1H), 2.99 (d, J=2.1 Hz, 3H), 2.85 (d, J=3.2 Hz, 3H), 2.40-2.18 (m, 2H), 1.03-0.93 (m, 3H); ESI MS m/z 379 $[C_{22}H_{22}N_2O_2S+H]^+$; HPLC 98.4% (AUC), $t_R$=8.14 min.

Example 1127

(S)-9-(4-(1-(ethylamino)propyl)phenyl)-8-hydroxythieno[2,3-c]quinolin-4(5H)-one Hydrochloride

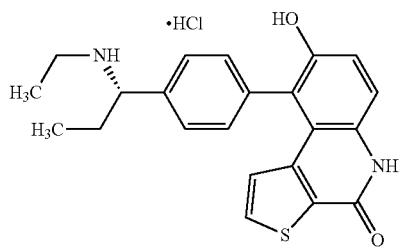 [SMILES: CCN[C@@H](CC)c1ccc(-c2c(O)ccc3[nH]c(=O)c4sccc4c23)cc1 ; Cl]

Following the procedure outlined for Example 460, (S)-9-(4-(1-aminopropyl)phenyl)-8-hydroxythieno[2,3-c]quinolin-4(5H)-one hydrochloride (30 mg, 0.09 mmol)) was reacted with formaldehyde (37% in water, 9.5 mg, 0.21 mmol) to afford the desired product as a white solid (15 mg, 46%): $^1$H NMR (500 MHz, MeOD) δ 7.68-7.57 (m, 2H), 7.54 (d, J=5.4 Hz, 1H), 7.45 (ddd, J=17.0, 10.1, 5.3 Hz, 3H), 7.19 (d, J=8.9 Hz, 1H), 5.97 (d. J=15.4 Hz, 1H), 4.26 (dd, J=11.1, 4.3 Hz, 1H), 3.11 (tt, J=14.6, 7.3 Hz, 1H), 3.05-2.95 (m, 1H), 2.25 (ddd, J=13.0, 7.4, 4.4 Hz, 1H), 2.09 (ddd, J=13.1, 11.2, 7.4 Hz, 1H), 1.35 (t, J=7.3 Hz, 3H); ESI MS m/z 379 $[C_{22}H_{22}N_2O_2S+H]^+$; HPLC 98.4% (AUC), $t_R$=8.51 min.

Example 1095

9-(4-(2-aminopropyl)phenyl)-8-hydroxythieno[2,3-c]quinolin-4(5H)-one Hydrochloride

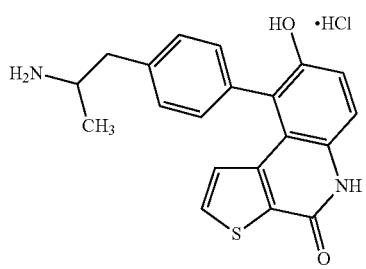 [SMILES: Cl ; CC(N)Cc1ccc(-c2c(O)ccc3[nH]c(=O)c4sccc4c23)cc1]

Following General Procedure F, tert-butyl 1-(4-(8-methoxy-4-oxo-4,5-dihydrothieno[2,3-c]quinolin-9-yl)phenyl)propan-2-ylcarbamate (650 mg, 1.40 mmol) was reacted with BBr$_3$ (1.0 M in CH$_2$Cl$_2$, 10 mL, 10 mmol) to afford the desired product (152 mg, 31%) as a light yellow solid: $^1$H NMR (500 MHz, CD$_3$OD) δ 7.56 (d, J=5.4 Hz, 1H), 7.49 (d, J=7.9 Hz, 1H), 7.43 (dd, J=13.3, 8.3 Hz, 2H), 7.34 (d, J=7.9 Hz, 2H), 7.18 (d, J=8.9 Hz, 1H), 6.11 (d, J=5.4 Hz, 1H), 3.71-3.60 (m, 1H), 3.05 (dd, J=7.2, 2.2 Hz, 2H), 1.40 (d, J=6.6 Hz, 3H): ESI MS m/z 351 [C$_{20}$H$_{18}$N$_2$O$_2$S+H]$^+$; HPLC 98.6% (AUC), t$_R$=8.08 min.

Example 1106

9-(4-(2-aminopropyl)phenyl)-6-chloro-8-hydroxythieno[2,3-c]quinolin-4(5H)-one Hydrochloride

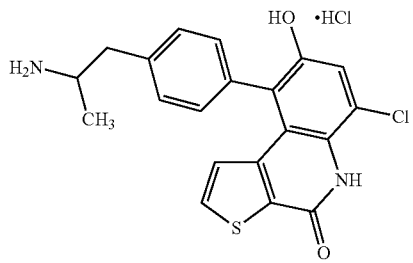 [SMILES: Cl ; CC(N)Cc1ccc(-c2c(O)cc(Cl)c3[nH]c(=O)c4sccc4c23)cc1]

Following General Procedure F, a tert-butyl 1-(4-(6-chloro-8-methoxy-4-oxo-4,5-dihydrothieno[2,3-c]quinolin-9-yl)phenyl)propan-2-ylcarbamate (55 mg, 0.11 mmol) was reacted with BBr$_3$ (1.0 M in CH$_2$Cl$_2$, 2 mL, 2 mmol) to afford the desired product (28 mg, 66%) as a white solid: $^1$H NMR (500 MHz, CD$_3$OD) δ 7.61 (d, J=5.4 Hz, 1H), 7.47 (dd, J=22.8, 7.8 Hz, 2H), 7.36-7.29 (m, 3H), 6.08 (d, J=5.4 Hz, 1H), 3.65 (dd, J=13.7, 6.9 Hz, 1H), 3.05 (ddd, J=34.9, 13.6, 7.3 Hz, 2H), 1.39 (d, J=6.6 Hz, 3H): ESI MS m/z 385 [C$_{20}$H$_{17}$ClN$_2$O$_2$S+H]$^+$; HPLC >99% (AUC), t$_R$=8.77 min.

Example 379

9-(4-(1-((dimethylamino)methyl)cyclopropyl)phenyl)-8-hydroxythieno[2,3-c]quinolin-4(5H)-one Hydrochloride

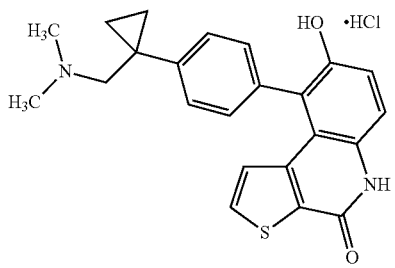 [SMILES: CN(C)CC1(c2ccc(-c3c(O)ccc4[nH]c(=O)c5sccc5c34)cc2)CC1 ; Cl]

Following the procedure outlined for Example 1387, 9-(4-(1-(aminomethyl)cyclopropyl)phenyl)-8-hydroxythieno[2,3-c]quinolin-4(5H)-one hydrochloride (10 mg, 0.03 mmol) was reacted with paraformaldehyde (8 mg, 0.11 mmol) and after purification the resulting material was converted to the hydrochloride salt as outlined in General Procedure D-2 to afford the desired product (7.0 mg, 87%) as a light yellow solid: $^1$H NMR (500 MHz, CD$_3$OD) δ 7.70 (d, J=7.9 Hz, 2H), 7.58 (d, J=5.4 Hz, 1H), 7.39 (dd, J=25.8, 8.4 Hz, 3H), 7.18 (d, J=8.9 Hz, 1H), 6.12 (d, J=5.4 Hz, 1H), 2.94 (s, 6H), 1.34-1.25 (m, 2H), 1.23-1.14 (m, 2H); ESI MS m/z 391 [C$_{23}$H$_{22}$N$_2$O$_2$S+H]$^+$; HPLC 96.7% (AUC), t$_R$=8.72 min.

Example 373

9-(4-(1-aminopropan-2-yl)phenyl)-8-methoxythieno[2,3-c]quinolin-4(5H)-one Hydrochloride

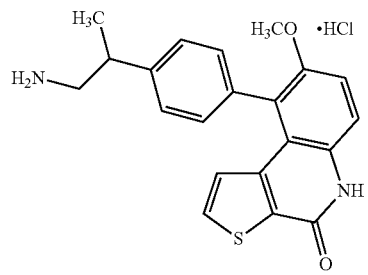 [SMILES: COc1ccc2[nH]c(=O)c3sccc3c2c1-c1ccc(C(C)CN)cc1 ; Cl]

To a solution of 2-(4-(8-methoxy-4-oxo-4,5-dihydrothieno[2,3-c]quinolin-9-yl)phenyl)propanenitrile (50 mg, 0.14 mmol) in toluene (13 mL) at 0° C. was added BH$_3$.THF (1.0 M, 13 mL, 13 mmol) and the reaction was warmed to room temperature and heated at reflux for 4 h. The reaction was quenched by pouring onto water or ice-water and the resulting mixture was concentrated and purified by preparatory HPLC (C18 silica, acetonitrile/water (with 0.05% TFA) gradient). The desired product was dissolved in aqueous HCl, concentrated and dried under high vacuum to afford the desired product as a light yellow solid (5.4 mg, 10%): $^1$H NMR (500 MHz, CD$_3$OD) δ 7.60-7.49 (m, 3H), 7.47 (dd, J=7.7, 1.7 Hz, 1H), 7.39 (d, J=9.1 Hz, 1H), 7.34-7.25 (m, 2H), 6.00 (d, J=5.4 Hz, 1H), 3.75 (s, 3H), 3.30-3.18 (m, 3H), 1.49 (d, J=6.5 Hz, 3H): ESI MS m/z 365 [C$_{21}$H$_{20}$N$_2$O$_2$S+H]$^+$; HPLC 99% (AUC), t$_R$=8.76 min.

Example 1218

9-(4-(2-aminoethyl)-3-fluorophenyl)-6-chloro-8-methoxythieno[2,3-c]quinolin-4(5H)-one Hydrochloride

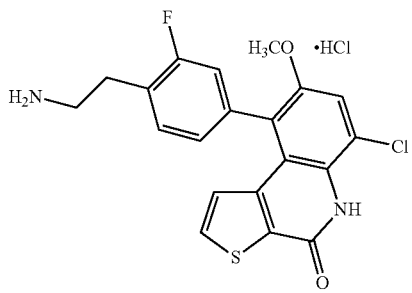 [SMILES: COc1cc(Cl)c2[nH]c(=O)c3sccc3c2c1-c1ccc(CCN)c(F)c1 ; Cl]

Following General Procedure F, tert-butyl 2-fluor-4-(8-methoxy-4-oxo-4,5-dihydrothieno[2,3-c]quinolin-9-yl)phenethylcarbamate (70 mg, 0.14 mmol) was treated with BBr$_3$ (1.0 M in CH$_2$Cl$_2$, 5 mL, 5 mmol) to afford the desired product as a white solid (17 mg, 30%): $^1$H NMR (500 MHz, CD$_3$OD) δ 7.66 (d, J=5.4 Hz, 1H), 7.54 (s, 1H), 7.50 (t, J=7.9 Hz, 1H), 7.10 (d, J=7.9 Hz, 2H), 6.09 (d, J=5.4 Hz, 1H), 3.76

(s, 3H), 3.25-3.06 (m, 4H); ESI MS m/z 403 [$C_{20}H_{16}ClFN_2O_2S+H$]$^+$; HPLC 97.9% (AUC), $t_R$=9.63 min.

Example 1247

9-(4-(1-amino-2-methylpropan-2-yl)phenyl)-6-bromo-8-hydroxythieno[2,3-c]quinolin-4(5H)-one Hydrochloride

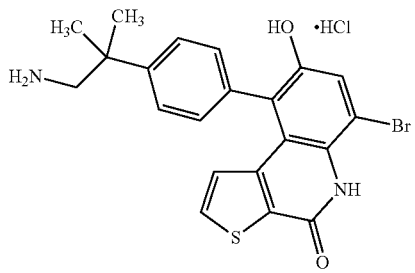 [SMILES: CC(C)(CN)c1ccc(-c2c(O)cc(Br)c3[nH]c(=O)c4sccc4c23)cc1 ; Cl]

Following General Procedure F, tert-butyl 2-(4-(6-bromo-8-methoxy-4-oxo-4,5-dihydrothieno[2,3-c]quinolin-9-yl)phenyl)-2-methylpropylcarbamate (110 mg, 0.20 mmol) was treated with BBr$_3$ (1.0 M in CH$_2$Cl$_2$, 10 mL, 10 mmol) to afford the desired product as a brown solid (39 mg, 45%): ESI MS m/z 443 [$C_{21}H_{19}BrN_2O_2S+H$]$^+$; HPLC 96.3% (AUC), $t_R$=9.56 min.

Example 1245

6-bromo-9-(3-fluoro-4-(2-(methylamino)ethyl)phenyl)-8-hydroxythieno[2,3-c]quinolin-4(5H)-one Hydrochloride

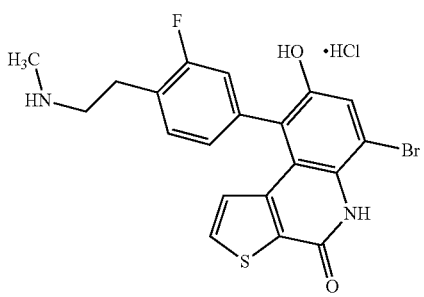 [SMILES: CNCCc1ccc(-c2c(O)cc(Br)c3[nH]c(=O)c4sccc4c23)cc1F ; Cl]

Following General Procedure F, tert-butyl 4-(6-bromo-8-methoxy-4-oxo-4,5-dihydrothieno[2,3-c]quinolin-9-yl)-2-fluorophenethyl(methyl)carbamate (90 mg, 0.16 mmol) in CH$_2$Cl$_2$ at 0° C. was added BBr$_3$ (1.0 M in CH$_2$Cl$_2$, 6 mL, 6 mmol) and the reaction was warmed to room temperature for 4 h. The reaction was quenched by pouring onto water or ice-water and the resulting mixture was concentrated and purified by preparatory HPLC (C18 silica, acetonitrile/water (with 0.05% TFA) gradient). The desired product was dissolved in aqueous HCl, concentrated and dried under high vacuum to afford the desired product as a white solid (15 mg, 21%): ESI MS m/z 447 [$C_{20}H_{16}BrFN_2O_2S+H$]$^+$; HPLC >99% (AUC), $t_R$=9.26 min.

Example 1258

9-(3-fluoro-4-(2-(methylamino)ethyl)phenyl)-8-hydroxy-6-methylthieno[2,3-c]quinolin-4(5H)-one Hydrochloride

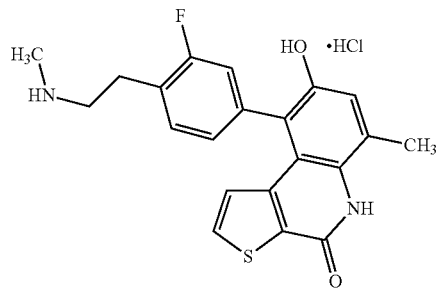

Following General Procedure F, tert-butyl 2-fluoro-4-(8-methoxy-6-methyl-4-oxo-4,5-dihydrothieno[2,3-c]quinolin-9-yl)phenethyl(methyl)carbamate (60 mg, 0.12 mmol) in CH$_2$Cl$_2$ at 0° C. was added BBr$_3$ (1.0 M in CH$_2$Cl$_2$, 6 mL, 6 mmol) and the reaction was warmed to room temperature for 4 h. The reaction was quenched by pouring onto water or ice-water and the resulting mixture was concentrated and purified by preparatory HPLC (C18 silica, acetonitrile/water (with 0.05% TFA) gradient). The desired product was dissolved in aqueous HCl, concentrated and dried under high vacuum to afford the desired product as a off-white solid (31 mg, 67%): $^1$H NMR (500 MHz, (CD$_3$OD) 7.63 (d, J=5.4 Hz, 1H), 7.51 (t, J=7.9 Hz, 1H), 7.15-7.06 (m, 3H), 6.20 (d, J=5.4 Hz, 1H), 3.42-3.35 (m, 2H), 3.30-3.10 (m, 2H), 2.80 (s, 3H), 2.57 (s, 3H); ESI MS m/z 383 [$C_{21}H_{11}FN_2O_2S+H$]$^+$, HPLC >99% (AUC), $t_R$=8.65 min.

Example 1260

9-(4-(1-amino-2-methylpropan-2-yl)phenyl)-6-chloro-8-hydroxythieno[2,3-c]quinolin-4(5H)-one Hydrochloride

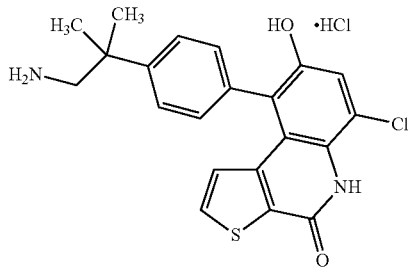 [SMILES: CC(C)(CN)c1ccc(-c2c(O)cc(Cl)c3[nH]c(=O)c4sccc4c23)cc1 ; Cl]

Following General Procedure F, tert-butyl 2-(4-(8-methoxy-4-oxo-4,5-dihydrothieno[2,3-c]quinolin-9-yl)phenyl)-2-methylpropylcarbamate (70 mg, 0.14 mmol) in CH$_2$C$_2$ at 0° C. was added BBr$_3$ (1.0 M in CH$_2$Cl$_2$, 5 mL, 5 mmol) and the reaction was warmed to room temperature for 4 h. The reaction was quenched by pouring onto water or ice-water and the resulting mixture was concentrated and purified by preparatory HPLC (C18 silica, acetonitrile/water (with 0.05% TFA) gradient). The desired product was dissolved in aqueous HCl, concentrated and dried under high vacuum to afford the desired product as a brown solid (12 mg, 38%): $^1$H NMR (500 MHz, CD$_3$OD) δ 7.66 (d, J=8.4 Hz, 2H), 7.63 (d, J=5.4 Hz, 1H), 7.36 (d, J=8.4 Hz, 2H), 7.32 (s, 1H), 6.13 (d, J=5.4 Hz, 1H), 3.29 (s, 2H), 1.58 (s, 6H); ESI MS m/z 399 [C$_{21}$H$_{19}$ClN$_2$O$_2$S+H]$^+$; HPLC 98.8% (AUC), t$_R$=9.26 min.

Example 1280

9-(4-(1-aminopropan-2-yl)-3-chlorophenyl)-8-hydroxythieno[2,3-c]quinolin-4(5H)-one Hydrochloride

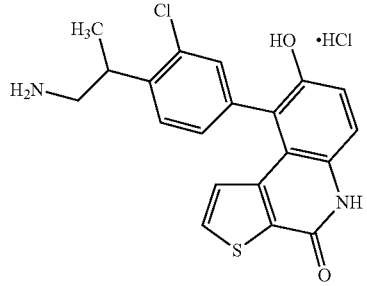 [SMILES: CC(CN)c1ccc(-c2c(O)ccc3[nH]c(=O)c4sccc4c23)cc1Cl ; Cl]

Following General Procedure F, tert-butyl 2-(2-chloro-4-(8-methoxy-4-oxo-4,5-dihydrothieno[2,3-c]quinolin-9-yl)phenyl)propylcarbamate (120 mg, 0.24 mmol) in CH$_2$Cl$_2$ at 0° C. was added BBr$_3$ (1.0 M in CH$_2$Cl$_2$, 15 mL, 15 mmol) and the reaction was warmed to room temperature for 4 h. The reaction was quenched by pouring onto water or ice-water and the resulting mixture was concentrated and purified by preparatory HPLC (C18 silica, acetonitrile/water (with 0.05% TFA) gradient). The desired product was dissolved in aqueous HCl, concentrated and dried under high vacuum to afford the desired product as a brown solid (40 mg, 43%): $^1$H NMR (500 MHz, CD$_3$OD) δ 7.65 (ddd, J=9.9, 9.3, 6.1 Hz, 2H), 7.46-7.36 (m, 2H), 7.33-7.27 (m, 1H), 7.18 (t, J=9.0 Hz, 1H), 6.10 (dd, J=28.8, 5.4 Hz, 1H), 3.86-3.66 (m, 1H), 3.29-3.12 (m, 2H), 1.44-1.28 (m, 3H); ESI MS m/z 385 [C$_{20}$H$_{17}$ClN$_2$O$_2$S+H]$^+$; HPLC >99% (AUC), t$_R$=9.07 min.

Example 1111

9-(4-(1-aminopropan-2-yl)phenyl)-8-hydroxythieno[2,3-c]quinolin-4(5H)-one Hydrochloride

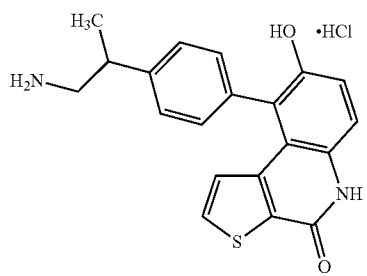 [SMILES: CC(CN)c1ccc(-c2c(O)ccc3[nH]c(=O)c4sccc4c23)cc1 ; Cl]

Following General Procedure F, 9-(4-(1-aminopropan-2-yl)phenyl)-8-methoxythieno[2,3-c]quinolin-4(5H)-one (120 mg, 0.33 mmol) in CH$_2$Cl$_2$ at 0° C. was added BBr$_3$ (1.0 M in CH$_2$Cl$_2$, 5 mL, 5 mmol) and the reaction was warmed to room temperature for 4 h. The reaction was quenched by pouring onto water or ice-water and the resulting mixture was concentrated and purified by preparatory HPLC (C18 silica, acetonitrile/water (with 0.05% TFA) gradient). The desired product was dissolved in aqueous HCl, concentrated and dried under high vacuum to afford the desired product as a light yellow solid (48 mg, 42%): $^1$H NMR (500 MHz, CD$_3$OD) δ 7.57 (dd, J=12.7, 6.7 Hz, 2H), 7.47 (d, J=6.9 Hz, 1H), 7.42 (d, J=8.9 Hz, 1H), 7.37 (d, J=7.9 Hz, 1H), 7.32 (d, J=7.7 Hz, 1H), 7.18 (d, J=8.9 Hz, 1H), 6.15 (d, J=5.4 Hz, 1H), 3.28-3.17 (m, 3H), 1.50 (d, J=6.1 Hz, 3H); ESI MS m/z 351 [C$_{20}$H$_{18}$N$_2$O$_2$S+H]$^+$; HPLC >99% (AUC), t$_R$=8.25 min.

Example 1151

(R)-9-(4-(1-(dimethylamino)propyl)phenyl)-8-hydroxythieno[2,3-c]quinolin-4(5H)-one Hydrochloride

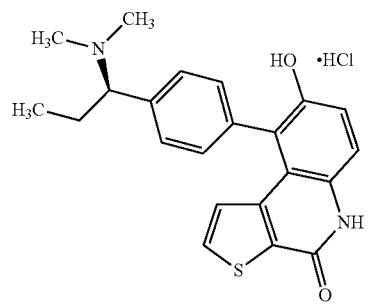 [SMILES: CC[C@H](c1ccc(-c2c(O)ccc3[nH]c(=O)c4sccc4c23)cc1)N(C)C ; Cl]

Following the procedure outlined for Example 1387, (R)-9-(4-(1-aminopropyl)phenyl)-8-methoxythieno[2,3-c]quinolin-4(5H)-one hydrochloride (20 mg, 0.06 mmol) was reacted with paraformaldehyde (10 mg, 0.17 mmol) and after purification the resulting material was converted to the hydrochloride salt as outlined in General Procedure D-2 to afford the desired product (5 mg, 24%) as a light yellow solid: $^1$H NMR (500 MHz, CD$_3$OD) δ 7.71 (dd, J=10.5, 7.8 Hz, 2H), 7.64 (d, J=5.4 Hz, 1H), 7.47 (t, J=7.1 Hz, 2H), 7.31 (d, J=8.9 Hz, 2H), 6.01 (d, J=5.4 Hz, 1H), 4.66 (q, J=6.9 Hz, 1H), 2.97 (s, 3H), 2.86 (s, 3H), 2.20-2.00 (m, 2H), 1.86 (d, J=7.0 Hz, 3H); ESI MS m/z 379 [C$_{12}$H$_{22}$N$_2$O$_2$S+H]$^+$; HPLC 95.6% (AUC), t$_R$=8.92 min.

Example 1162

2-(4-(8-hydroxy-4-oxo-4,5-dihydrothieno[2,3-c]quinolin-9-yl)phenyl)butanenitrile

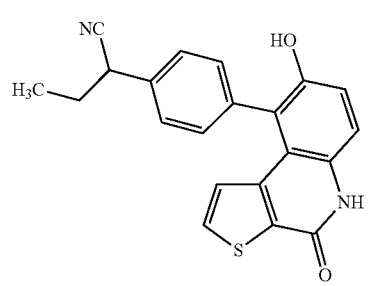 [SMILES: CCC(C#N)c1ccc(-c2c(O)ccc3[nH]c(=O)c4sccc4c23)cc1]

Following General Procedure F, 2-(4-(8-methoxy-4-oxo-4,5-dihydrothieno[2,3-c]quinolin-9-yl phenyl)butanenitrile (80 mg, 0.21 mmol) in CH$_2$Cl$_2$ at 0° C. was added BBr$_3$ (1.0 M in CH$_2$Cl$_2$, 3 mL, 3 mmol) and the reaction was warmed to room temperature for 4 h. The reaction was quenched by pouring onto water or ice-water and the resulting mixture was concentrated and purified by preparatory HPLC (C18 silica, acetonitrile/water (with 0.05% TFA) gradient). The desired product was dissolved in aqueous HCl, concentrated and dried under high vacuum to afford the desired product as a light yellow solid (4.3 mg, 6%): $^1$H NMR (500 MHz, CD$_3$OD) δ 7.56 (dd, J=10.8, 4.6 Hz, 3H), 7.43-7.31 (m, 3H), 7.17 (d, J=8.9 Hz, 1H), 6.00 (d, J=5.4 Hz, 1H), 4.15 (t, J=7.2 Hz, 1H), 2.07 (p, J=7.3 Hz, 2H), 1.16 (t, J=7.4 Hz, 3H): ESI MS m/z 361 [C$_{21}$H$_{16}$N$_2$O$_2$S+H]$^+$; HPLC 98.5% (AUC), t$_R$=12.2 min.

Example 1174

9-(4-(1-aminopropan-2-yl)-3-fluorophenyl)-8-hydroxythieno[2,3-c]quinolin-4(5H)-one Hydrochloride

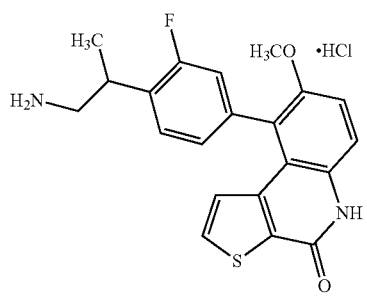 [SMILES: COc1ccc2[nH]c(=O)c3sccc3c2c1-c1ccc(C(C)CN)c(F)c1 ; Cl]

Following General Procedure C tert-butyl 2-(2-fluoro-4-(8-methoxy-4-oxo-4,5-dihydrothieno[2,3-c]quinolin-9-yl)phenyl)propylcarbamate (120 mg, 0.25 mmol) was reacted with TFA (10 mL) to afford the desired product (35 mg, 37%) as a off-white solid: $^1$H NMR (500 MHz, CD$_3$OD) δ 7.64 (dd, J=5.4, 3.1 Hz, 1H), 7.54 (ddd, J=25.0, 11.7, 5.2 Hz, 2H), 7.40 (dd, J=9.1, 1.1 Hz, 1H), 7.18-7.06 (m, 2H), 6.10 (dd, J=27.5, 5.4 Hz, 1H), 3.77 (s, 3H), 3.64-3.43 (m, 1H), 3.42-3.22 (m, 2H), 1.51 (d, J=7.0 Hz, 3H): ESI MS m/z 383 [C$_{21}$H$_{19}$FN$_2$O$_2$S+H]$^+$; HPLC 96.5% (AUC), t$_R$=−9.07 min.

Example 1189

(R)-8-methoxy-9-(4-(1-(methylamino)propan-2-yl)phenyl)thieno[2,3-c]quinolin-4(5H)-one Hydrochloride

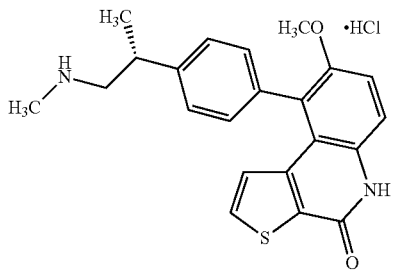 [SMILES: CNC[C@H](C)c1ccc(-c2c(OC)ccc3[nH]c(=O)c4sccc4c23)cc1 ; Cl]

Following General Procedure C (R)-tert-butyl 2-(4-(8-methoxy-4-oxo-4,5-dihydrothieno[2,3-c]quinolin-9-yl)phenyl)propyl(methyl)carbamate (120 mg, 0.25 mmol) was reacted with TFA (8 mL) to afford the desired product (56 mg, 59%) as a white solid: $^1$H NMR (500 MHz, CD$_3$OD) δ 7.60-7.51 (m, 3H), 7.48 (dd, J=7.8, 1.9 Hz, 1H), 7.39 (d, J=9.1 Hz, 1H), 7.31 (ddd, J=15.8, 7.8, 1.8 Hz, 2H), 5.99 (d, J=5.4 Hz, 1H), 3.75 (s, 3H), 3.46-3.36 (m, 1H), 3.37-3.24 (m, 2H), 2.76 (s, 3H), 1.49 (d, J=6.7 Hz, 3H); ESI MS m/z 379 [C$_{22}$H$_{22}$N$_2$O$_2$S+H]$^+$; HPLC >99% (AUC), t$_R$=8.96 min.

Example 1131

(R)-9-(4-(1-aminopropyl)phenyl)-8-hydroxythieno[2,3-c]quinolin-4(5H)-one Hydrochloride

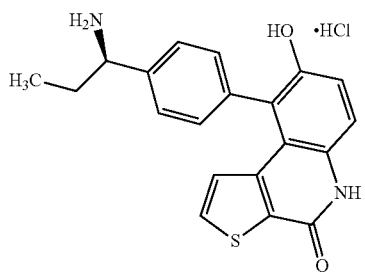 [SMILES: CC[C@@H](N)c1ccc(-c2c(O)ccc3[nH]c(=O)c4sccc4c23)cc1 ; Cl]

Following General Procedure F, (R)-tert-butyl 1-(4-(8-methoxy-4-oxo-4,5-dihydrothieno[2,3-c]quinolin-9-yl)phenyl)propylcarbamate (70 mg, 0.15 mmol) in CH$_2$Cl$_2$ at 0° C. was added BBr$_3$ (1.0 M in CH$_2$Cl$_2$, 3 mL, 3 mmol) and the reaction was warmed to room temperature for 4 h. The reaction was quenched by pouring onto water or ice-water and the resulting mixture was concentrated and purified by preparatory HPLC (C18 silica, acetonitrile/water (with 0.05% TFA) gradient). The desired product was dissolved in aqueous HCl, concentrated and dried under high vacuum to afford the desired product as a light yellow solid (35 mg, 67%): $^1$H NMR (500 MHz, CD$_3$OD) δ 7.61 (s, 2H), 7.55 (d, J=5.4 Hz, 1H), 7.45-7.40 (m, 3H), 7.18 (d, J=8.9 Hz, 1H), 6.03 (d, J=5.4 Hz, 1H), 4.32 (dd, J=9.2, 5.9 Hz, 1H), 2.23-2.01 (m, 2H), 1.04 (t, J=7.4 Hz, 3H); ESI MS m/z 351 [C$_{20}$H$_{18}$N$_2$O$_2$S+H]$^+$; HPLC >99% (AUC), t$_R$=8.06 min.

Example 1150

(R)-9-(4-(1-aminopropyl)phenyl)-6-bromo-8-hydroxythieno[2,3-c]quinolin-4(5H)-one Hydrochloride

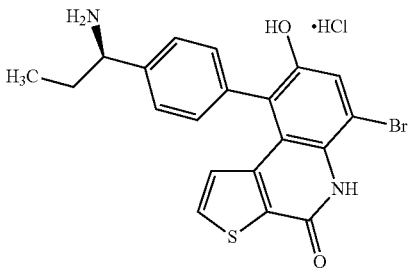 [SMILES: CC[C@@H](N)c1ccc(-c2c(O)cc(Br)c3[nH]c(=O)c4sccc4c23)cc1 ; Cl]

Following General Procedure F, (R-tert-butyl 1-(4-(6-bromo-8-methoxy-4-oxo-4,5-dihydrothieno[2,3-c]quinolin-9-yl)phenyl)propylcarbamate (50 mg, 0.09 mmol) in CH$_2$Cl$_2$

Example 254

N-[4-(8-Hydroxy-4-oxo-4,5-dihydrothieno[2,3-c]quinolin-9-yl)-2-methylphenyl]methanesulfonamide

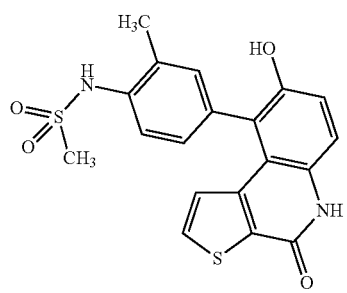 [SMILES: Cc1cc(-c2c(O)ccc3[nH]c(=O)c4sccc4c23)ccc1NS(C)(=O)=O]

Following General Procedure F, N-[4-(8-methoxy-4-oxo-4,5-dihydrothieno[2,3-c]quinolin-9-yl)-2-methylphenyl]methanesulfonamide (47 mg, 0.11 mmol) was reacted with tribromoborane (1.0 M in methylene chloride, 3.0 mL, 3.0 mmol) to afford the desired product (17 mg, 39%) as an off-white solid: $^1$H NMR (500 MHz, CD$_3$OD) δ 7.58 (d, J=5.4 Hz, 1H), 7.55 (d, J=8.1 Hz, 1H), 7.39 (d, J=8.9 Hz, 1H), 7.21 (s, 1H), 7.17-7.14 (m, 2H), 6.10 (d, J=5.4 Hz, 1H), 3.40 (s, 3H), 2.43 (s, 3H); ESI MS m/z 401 [C$_{19}$H$_6$N$_2$O$_4$S$_2$+H]$^+$; HPLC 96.4% (AUC), t$_R$=10.23 min.

Example 334

9-[4-(2-Aminopropan-2-yl)phenyl]-6-chloro-8-hydroxythieno[2,3-c]quinolin-4(5H)-one Hydrochloride

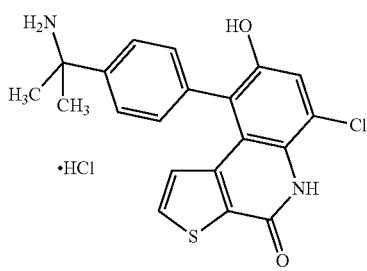 [SMILES: CC(C)(N)c1ccc(-c2c(O)cc(Cl)c3[nH]c(=O)c4sccc4c23)cc1 ; Cl]

Following General Procedure F, tert-butyl 2-[4-(6-chloro-8-methoxy-4-oxo-4,5-dihydrothieno[2,3-c]quinolin-9-yl)phenyl]propan-2-ylcarbamate (10 mg, 0.020 mmol) was reacted with tribromoborane (1.0 M in methylene chloride, 1.0 mL, 1.0 mmol) to afford the desired product (9.7 mg, 97%) as an off-white solid: $^1$H NMR (500 MHz, CD$_3$OD) δ 7.71 (d, J=8.4 Hz, 2H), 7.60 (d, J=5.4 Hz, 1H), 7.42 (d, J=8.4 Hz, 2H), 7.30 (s, 1H), 6.06 (d, J=5.4 Hz, 1H), 1.86 (s, 6H); ESI MS m/z 385 [C$_{20}$H$_{17}$ClN$_2$O$_2$S+H]$^+$; HPLC >99% (AUC), t$_R$=10.89 min

Example 329

9-[4-(Aminomethyl)phenyl]-6-chloro-8-hydroxythieno[2,3-c]quinolin-4(5H)-one Hydrochloride

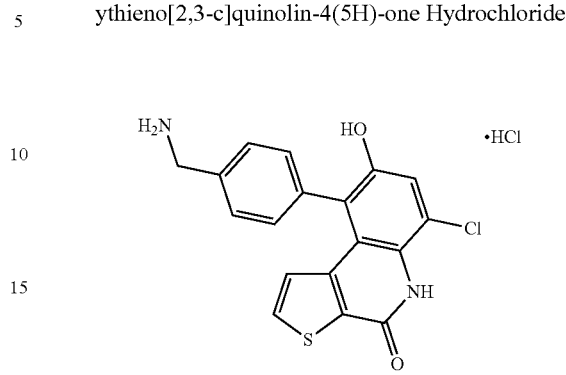

Following General Procedure F, tert-butyl 4-(6-chloro-8-methoxy-4-oxo-4,5-dihydrothieno[2,3-c]quinolin-9-yl)benzylcarbamate (15 mg, 0.032 mmol) was reacted with tribromoborane (1.0 M in methylene chloride, 1 mL, 1 mmol) to afford the desired product (10 mg, 80%) as a brown solid: $^1$H NMR (500 MHz, CD$_3$OD) δ 7.64 (d, J=8.2 Hz, 2H), 7.59 (d, J=5.4 Hz, 1H), 7.43-7.38 (m, 2H), 7.30 (s, 1H), 6.08 (d, J=5.4 at 0° C. was added BBr$_3$ (1.0 M in CH$_2$Cl$_2$, 5 mL, 5 mmol) and the reaction was warmed to room temperature for 4 h. The reaction was quenched by pouring onto water or ice-water and the resulting mixture was concentrated and purified by preparatory HPLC (C18 silica, acetonitrile/water (with 0.05% TFA) gradient). The desired product was dissolved in aqueous HCl, concentrated and dried under high vacuum to afford the desired product as a light yellow solid (36 mg, 92%): $^1$H NMR (500 MHz, CD$_3$OD) δ 7.65-7.57 (m, 3H), 7.50-7.46 (m, 1H), 7.45-7.39 (m, 2H), 6.02 (d, J=5.4 Hz, 1H), 4.32 (dd, J=9.2, 6.0 Hz, 1H), 2.20-2.00 (m, 2H), 1.03 (t, J=7.4 Hz, 3H); ESI MS m/z 429 [C$_{20}$H$_{17}$BrN$_2$O$_2$S+H]$^+$; HPLC >99% (AUC), t$_R$=9.17 min. Hz, 1H), 4.27 (s, 2H); ESI MS m/z 357 [C$_{18}$H$_{13}$ClN$_2$O$_2$S+H]$^+$; ESI MS m/z 357 [C$_{18}$H$_{13}$ClN$_2$O$_2$S+H]$^+$; HPLC 98.4% (AUC), t$_R$=8.62 min.

Example 457 tert-Butyl 4-(8-Hydroxy-4-oxo-4,5-dihydrothieno[2,3-c]quinolin-9-yl)benzylcarbamate

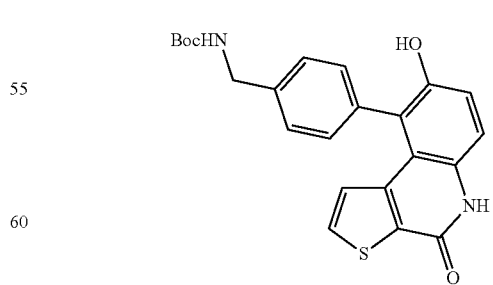

Following the procedure from Example 463, 9-[4-(aminomethyl)phenyl]-8-hydroxythieno[2,3-c]quinolin-4(5H)-one (320 mg, 1.0 mmol) was reacted with di-tert-butyl dicarbonate (260 mg, 1.2 mmol) to afford the desired product (150 mg, 36%): ESI MS m/z 323 [C₂₃H₂₂N₂O₄S+H]⁺.

Example 319

9-[4-(2-Aminopropan-2-yl)phenyl]-8-hydroxythieno[2,3-c]quinolin-4(5H)-one Hydrochloride

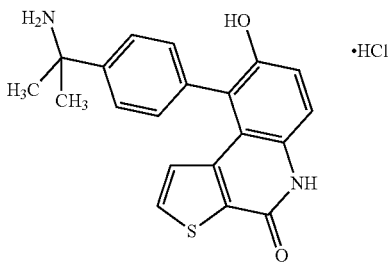 [SMILES: CC(C)(N)c1ccc(-c2c(O)ccc3[nH]c(=O)c4sccc4c23)cc1 ; Cl]

Following General Procedure F, tert-butyl 2-[4-(8-methoxy-4-oxo-4,5-dihydrothieno[2,3-c]quinolin-9-yl)phenyl]propan-2-ylcarbamate (29 mg, 0.063 mmol) was reacted with tribromoborane (1.0 M, 1.0 mL, 0.10 mmol) to afford the desired product (12 mg, 52%) as a white solid: ¹H NMR (500 MHz, CD₃OD) δ 7.70 (d, J=8.4 Hz, 2H), 7.55 (d, J=5.4 Hz, 1H), 7.46-7.37 (m, J=8.6, 7.7 Hz, 3H), 7.17 (d, J=8.9 Hz, 1H), 6.07 (d, J=5.4 Hz, 1H), 1.86 (s, 6H); ESI MS m/z 351 [C₂₀H₁₈N₂O₂S+H]⁺; HPLC 98.3% (AUC), t$_R$=10.48 min.

Example 270

9-[4-(Aminomethyl)phenyl]-6-bromo-8-hydroxythieno[2,3-c]quinolin-4(5H)-one Hydrochloride

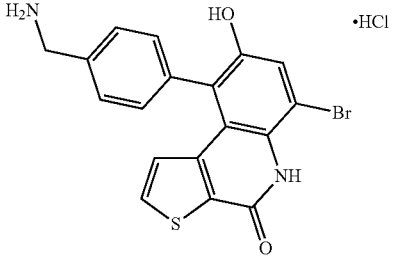 [SMILES: NCc1ccc(-c2c(O)cc(Br)c3[nH]c(=O)c4sccc4c23)cc1 ; Cl]

Following General Procedure F, tert-butyl 4-(6-bromo-8-methoxy-4-oxo-4,5-dihydrothieno[2,3-c]quinolin-9-yl)benzylcarbamate (10 mg, 0.019 mmol) was reacted with tribromoborane (1.0 M in methylene chloride, 1.0 mL, 1.0 mmol) to afford the desired product (3.9 mg, 47%) as a white solid: ¹H NMR (500 MHz, CD₃OD) δ 7.64 (d, J=8.1 Hz, 2H), 7.60 (d, J=5.4 Hz, 1H), 7.47 (s, 1H), 7.42-7.40 (m, 2H), 6.08 (d, J=5.5 Hz, 1H), 4.27 (s, 2H); ESI MS m/z 403 [(C₁₈H₁₃BrN₂O₂S+2)+H]⁺; HPLC 97.1% (AUC), t$_R$=7.90 min.

Example 210

N-(2-Bromoethyl)-4-(8-hydroxy-4-oxo-4,5-dihydrothieno[2,3-c]quinolin-9-yl)benzenesulfonamide

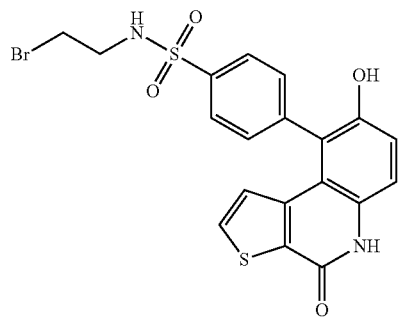

Following General Procedure F, N-(2-hydroxyethyl)-4-(8-methoxy-4-oxo-4,5-dihydrothieno[2,3-c]quinolin-9-yl)benzenesulfonamide (1.7 g, 3.9 mmol) was reacted with tribromoborane (3.7 mL, 24 mmol) to afford the desired product (1.7 g, 91%) as an off-white solid: ¹H NMR (500 MHz, DMSO-d₆) δ 11.84 (s, 1H), 9.43 (s, 1H), 8.16 (t, J=5.9 Hz, 1H), 7.94 (d, J=8.3 Hz, 2H), 7.75 (d, J=5.4 Hz, 1H), 7.52 (d, J=8.3 Hz, 2H), 7.41 (d, J=8.9 Hz, 1H), 7.19 (d, J=8.9 Hz, 1H), 5.83 (d, J=5.4 Hz, 1H), 3.51 (t, J=6.4 Hz, 2H), 3.28 (q, J=6.2 Hz, 2H); ESI MS m/z 478 [C₁₉H₁₅BrN₂O₄S₂+H]⁺; HPLC 98.5% (AUC), t$_R$=15.23 min.

Example 458

2-{4-[8-Hydroxy-4-oxo-4,5-dihydrothieno[2,3-c]quinolin-9-yl]phenylsulfonamido}ethyl methanesulfonate

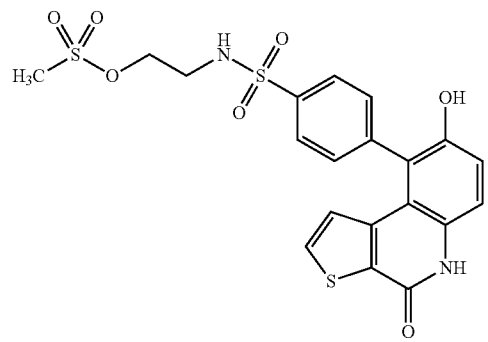 [SMILES: CS(=O)(=O)OCCNS(=O)(=O)c1ccc(-c2c(O)ccc3[nH]c(=O)c4sccc4c23)cc1]

To a solution of N-(2-hydroxyethyl)-4-(8-methoxy-4-oxo-4,5-dihydrothieno[2,3-c]quinolin-9-yl)benzenesulfonamide (390 mg, 0.90 mmol) and triethylamine (450 mg, 4.5 mmol) in anhydrous THF (20 mL) was added methane sulfonyl chloride (0.21 mL, 2.7 mmol) and the reaction mixture was stirred for 20 h at room temperature. The resulting precipitate was filtered and the filter cake was washed with THF (50 mL). The filtrate was concentrated and the residue was purified by flash chromatography (silica, ethyl acetate/hexanes gradient) to afford the desired product as a brown solid (250 mg, 55%).

¹H NMR (300 MHz, DMSO-d$_6$) δ 11.93 (s, 1H), 8.14 (t, J=11.7 Hz, 1H), 7.95 (d, J=8.4 Hz, 2H), 7.79 (d, J=5.4 Hz, 1H), 7.56 (d, J=9.0 Hz, 1H), 7.53 (d, J=8.4 Hz, 2H), 7.43 (d, J=9.0 Hz, 1H), 5.74 (d, J=5.4 Hz, 1H), 4.24 (t, J=10.5 Hz, 2H), 3.71 (s, 3H), 3.20 (q, J=11.7 Hz, 2H) ESI MS m/z 509 [C$_{21}$H$_{20}$N$_2$O$_7$S$_3$+H]$^+$

Example 332

N-(2-Chloroethyl)-4-(8-hydroxy-4-oxo-4,5-dihydrothieno[2,3-c]quinolin-9-yl)benzenesulfonamide

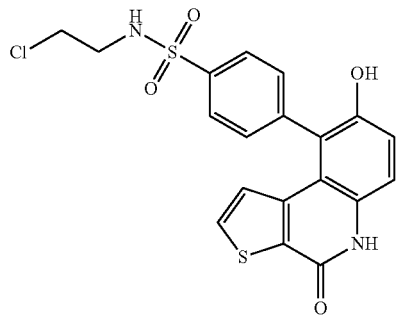 [SMILES: O=c1[nH]c2ccc(O)c(-c3ccc(S(=O)(=O)NCCCl)cc3)c2c2ccsc12]

To a solution of 2-(4-(8-methoxy-4-oxo-4,5-dihydrothieno[2,3-c]quinolin-9-yl)phenylsulfonamido)ethyl methanesulfonate (250 mg, 0.49 mmol) in anhydrous dichloroethane was added aluminum chloride (330 mg, 2.5 mmol) and the reaction mixture was heated at reflux for 20 h. The reaction was cooled to room temperature, concentrated and quenched with methanol (10 mL). The resulting mixture was allowed to stand at room temperature for 1 h and the resulting precipitate was filtered and dried to afford the desired product (88 mg, 41%) as an off-white solid: ¹H NMR (500 MHz, DMSO-d) δ 11.83 (s, 1H), 9.42 (s, 1H), 8.13 (t, J=7.2 Hz, 1H), 7.94 (d, J=5.1 Hz, 2H), 7.74 (d, J=3.3 Hz, 1H), 7.51 (d, J=5.1 Hz, 2H), 7.41 (d, J=5.4 Hz, 1H), 7.18 (d, J=5.4 Hz, 1H), 5.82 (d, J=3.3 Hz, 1H), 3.65 (t, J=3.9 Hz, 2H), 3.22 (q, J=3.6 Hz, 2H); ESI MS m/z 435 [C$_{19}$H$_{15}$ClN$_2$O$_4$S$_2$+H]$^+$; HPLC 97.2% (AUC), t$_R$=14.98 min, Example 304

4-(8-Hydroxy-4-oxo-4,5-dihydrothieno[2,3-c]quinolin-9-yl)-N,N-dimethylbenzenesulfonamide

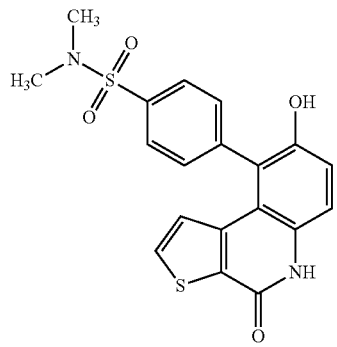 [SMILES: CN(C)S(=O)(=O)c1ccc(-c2c(O)ccc3[nH]c(=O)c4sccc4c23)cc1]

Following General Procedure F, the crude material from Example 74, 4-(8-methoxy-4-oxo-4,5-dihydrothieno[2,3-c]quinolin-9-yl)-N,N-dimethylbenzenesulfonamide (33 mg, 0.080 mmol), was reacted with tribromoborane (0.2 mL) to afford the desired product (9 mg, 7% over 2 steps) as a brown solid: ¹H NMR (500 MHz, DMSO-d$_6$) δ 11.85 (s, 1H), 9.44 (s, 1H), 7.88 (dd, J=6.8, 1.6 Hz, 2H), 7.79 (d, J=5.4 Hz, 1H), 7.57 (dd, J=6.6, 1.7 Hz, 2H), 7.42 (d, J=8.9 Hz, 1H), 7.20 (d, J=8.9 Hz, 1H), 5.69 (d, J=5.4 Hz, 1H), 2.71 (s, 6H); ESI MS m/z 401 [C$_{19}$H$_6$N$_2$O$_4$S$_2$+H]$^+$; HPLC 94.5% (AUC), t$_R$=14.84 min.

Example 297

N-(2-Bromoethyl)-2-fluoro-4-(8-hydroxy-4-oxo-4,5-dihydrothieno[2,3-c]quinolin-9-yl)benzenesulfonamide

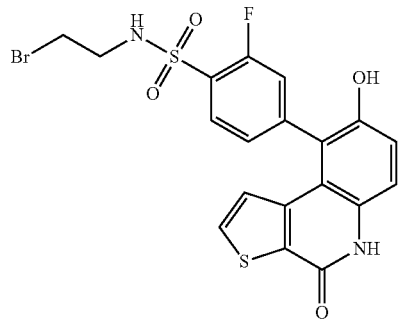 [SMILES: O=c1[nH]c2ccc(O)c(-c3ccc(S(=O)(=O)NCCBr)c(F)c3)c2c2ccsc12]

Following General Procedure F, 2-fluoro-N-(2-hydroxyethyl)-4-(8-methoxy-4-oxo-4,5-dihydrothieno[2,3-c]quinolin-9-yl)benzenesulfonamide (52 mg, 0.12 mmol) was reacted with tribromoborane (0.80 mL, 0.23 mmol) to afford the desired product (47 mg, 81%) as a white solid: ¹H NMR (500 MHz, DMSO-d$_6$) δ 11.86 (s, 1H), 9.52 (s, 1H), 8.45 (t, J=5.7 Hz, 1H), 7.92 (t, J=7.8 Hz, 1H), 7.80 (d, J=5.5 Hz, 1H), 7.46 (d, J=10.9 Hz, 1H), 7.42 (d, J=8.9 Hz, 1H), 7.30 (dd, J=8.0, 1.4 Hz, 1H), 7.19 (d, J=9.0 Hz, 1H), 6.00 (d, J=5.4 Hz, 1H), 3.53 (t, J=6.3 Hz, 2H), 3.42 (q, J=6.0 Hz, 2H); ESI MS m/z 499 [C$_{19}$H$_{14}$BrFN$_2$O$_4$S$_2$+H]$^+$; HPLC 98.3% (AUC), t$_R$=15.61 min.

Example 266

9-[5-(Aminomethyl)thiophen-2-yl]-8-hydroxythieno[2,3-c]quinolin-4(5H)-one

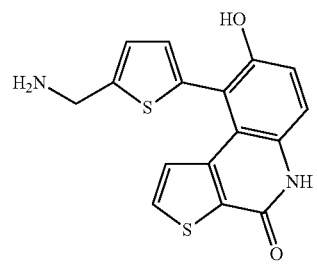 [SMILES: NCc1ccc(-c2c(O)ccc3[nH]c(=O)c4sccc4c23)s1]

Following General Procedure F, tert-butyl [5-(8-methoxy-4-oxo-4,5-dihydrothieno[2,3-c]quinolin-9-yl)thiophen-2-yl]

methylcarbamate (30 mg, 0.067 mmol) was reacted with tribromoborane (0.50 mL) to afford the desired product (25 mg, 91%) as a off-white solid: $^1$H NMR (500 MHz, CD$_3$OD) δ 7.67 (d, J=5.4 Hz, 1H), 7.43 (d, J=9.0 Hz, 1H), 7.16-7.14 (m, 2H), 6.86 (d, J=3.5 Hz, 1H), 6.35 (d, J=5.4 Hz, 1H), 4.12 (s, 2H); ESI MS m/z 329 [C$_{16}$H$_{12}$N$_2$O$_2$S$_2$+H]$^+$; HPLC 95.6% (AUC), t$_R$=9.59 min.

Example 235

9-{4-[(4-(Aminomethyl)piperidin-1-yl)methyl]-3-fluorophenyl-8-hydroxythieno[2,3-c]quinolin-4(5H)-one

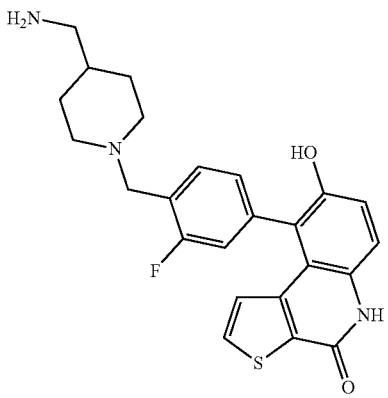 [SMILES: NCC1CCN(Cc2ccc(-c3c(O)ccc4[nH]c(=O)c5sccc5c34)cc2F)CC1]

Following General Procedure F, tert-Butyl {1-[2-Fluoro-4-(8-methoxy-4-oxo-4,5-dihydrothieno[2,3-c]quinolin-9-yl)benzyl]piperidin-4-yl}methylcarbamate (10 mg, 0.020 mmol) was reacted with tribromoborane (1.0 M in methylene chloride, 0.20 mL, 0.20 mmol) to afford the desired product (6.0 mg, 65%) as a light yellow solid: $^1$H NMR (500 MHz, CD$_3$CN+D$_2$O) δ 7.73 (t, J=7.8 Hz, 1H), 7.63 (d, J=5.4 Hz, 1H), 7.46 (d, J=8.9 Hz, 1H), 7.24 (d, J=8.9 Hz, 1H), 7.21-7.18 (m, 2H), 6.07 (d, J=5.4 Hz, 1H), 4.45 (q, 14.0 Hz, 2H), 3.15-3.11 (m, 2H), 2.94-2.90 (m, 2H), 2.51 (s, 2H), 2.09-2.06 (m, 3H), 2.00-1.96 (m, 4H); ESI MS m/z 438 [C$_{24}$H$_{24}$FN$_3$O$_2$S+H]$^+$; HPLC 94.6% (AUC), t$_R$=7.26 min.

Example 225

9-{4-[2-(Dimethylamino)ethyl]phenyl}-6-fluoro-8-hydroxythieno[2,3-c]quinolin-4(5H)-one

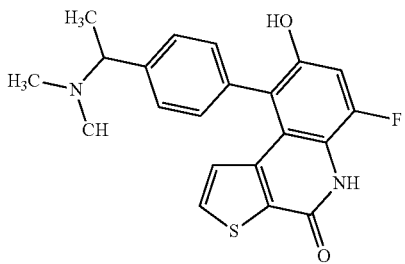 [SMILES: CC(c1ccc(-c2c(O)cc(F)c3[nH]c(=O)c4sccc4c23)cc1)N(C)C]

Following General Procedure F, 9-{4-[1-(dimethylamino)ethyl]phenyl}-6-fluoro-8-methoxythieno[2,3-c]quinolin-4(5H)-one (6.0 mg, 0.015 mmol) was reacted with tribromoborane (1.0 M in methylene chloride, 0.10 mL, 0.075 mmol) to afford the desired product (5.2 mg, 90%) as an off-white solid: $^1$H NMR (500 MHz, CD$_3$OD) δ 7.72 (t, J=9.4 Hz, 2H), 7.63 (d, J=5.4 Hz, 1H), 7.46 (t, J=7.6 Hz, 2H), 7.04 (d, J=12.0 Hz, 1H), 6.02 (d, J=5.4 Hz, 1H), 4.68 (q, J=4.3 Hz, 1H), 2.98 (s, 3H), 2.87 (s, 3H), 1.87 (d, J=7.0 Hz, 3H); ESI MS m/z 383 [C$_{21}$H$_{19}$FN$_2$O$_2$S+H]$^+$; HPLC 96.0% (AUC), t$_R$=9.97 min.

Example 217

9-(4-Amino-3-hydroxyphenyl)-8-hydroxythieno[2,3-c]quinolin-4(5H)-one Hydrochloride

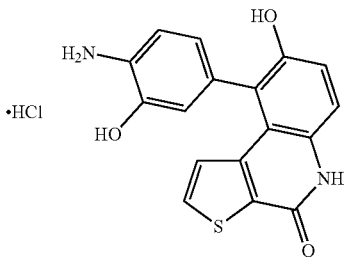 [SMILES: Cl ; Nc1ccc(-c2c(O)ccc3[nH]c(=O)c4sccc4c23)cc1O]

Following General Procedure F, 9-(4-Amino-3-methoxyphenyl)-8-methoxythieno[2,3-c]quinolin-4(5H)-one (20 mg, 0.060 mmol) was reacted with tribromoborane (1.0 M in methylene chloride, 0.20 mL, 0.18 mmol) to afford the desired product (16 mg, 84%) as an off-white solid: $^1$H NMR (500 MHz, CD$_3$OD) δ 7.62 (d, J=5.4 Hz, 1H), 7.48 (d, J=8.0 Hz, 1H), 7.42 (d, J=8.9 Hz, 1H), 7.18 (d, J=8.9 Hz, 1H), 6.97 (d, J=1.7 Hz, 1H), 6.91 (dd, J=8.0, 1.7 Hz, 1H), 6.21 (d, J=5.4 Hz, 1H); ESI MS m/z 325 [C$_{17}$H$_{12}$N$_2$O$_3$S+H]$^+$; HPLC 94.3% (AUC), t$_R$=8.17 min.

Example 93

9-{4-[2-(Dimethylamino)ethyl]phenyl}-8-hydroxythieno[2,3-c]quinolin-4(5H)-one

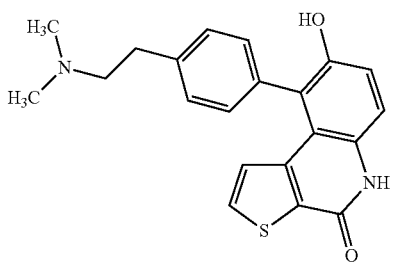 [SMILES: CN(C)CCc1ccc(-c2c(O)ccc3[nH]c(=O)c4sccc4c23)cc1]

Following General Procedure F, 9-{4-[2-(dimethylamino)ethyl]phenyl}-8-methoxythieno[2,3-c]quinolin-4(5H)-one (25 mg, 0.060 mmol) was reacted with tribromoborane (1.0 M in methylene chloride, 0.20 mL, 0.18 mmol) to afford the desired product (20 mg, 89%) as a yellow solid: $^1$H NMR (500 MHz, CD$_3$CN+D$_2$O) δ 7.55 (d, J=5.4 Hz, 1H), 7.43-7.41 (m, 3H), 7.22-7.18 (m, 3H), 5.99 (d, J=5.4 Hz, 1H), 3.00 (s, 4H), 2.56 (s, 6H); ESI MS m/z 365 [C$_{21}$H$_{20}$N$_2$O$_2$S+H]$^+$; HPLC 98.3% (AUC), t$_R$=9.24 min.

Example 341

9-{4-[1-(Dimethylamino)ethyl]phenyl}-6,7-difluoro-8-hydroxythieno[2,3-c]quinolin-4(5H)-one Hydrochloride

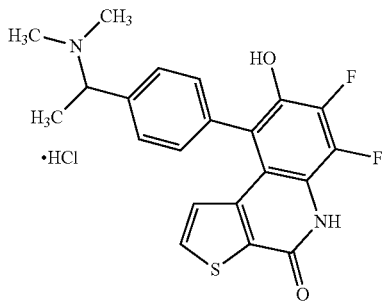 [SMILES: CC(c1ccc(-c2c(O)c(F)c(F)c3[nH]c(=O)c4sccc4c23)cc1)N(C)C ; Cl]

Following General Procedure F, 9-{4-[1-(dimethylamino)ethyl]phenyl})-6,7-difluoro-8-methoxythieno[2,3-c]quinolin-4(5H)-one (20 mg, 0.050 mmol) was reacted with tribromoborane (1.0 M in methylene chloride, 0.50 mL, 0.50 mmol) to afford the desired product (15 mg, 72%) as an off-white solid: $^1$H NMR (500 MHz, CD$_3$CN+D$_2$O) δ 7.68-7.67 (m, 2H), 7.61-7.59 (m, 1H), 7.43-7.41 (m, 2H), 5.86-5.84 (m, 1H), 4.58-4.54 (m, 1H), 2.86 (s, 3H), 2.76 (s, 3H), 1.79-1.77 (m, 3H); ESI MS m/z 401[C$_{21}$H$_{18}$F$_2$N$_2$O$_2$S+H]$^+$; HPLC 97.8% (AUC), t$_R$=9.35 min.

Example 256

9-[4-(Aminomethyl)phenyl]-6-fluoro-8-hydroxythieno[2,3-c]quinolin-4(5H)-one Hydrochloride

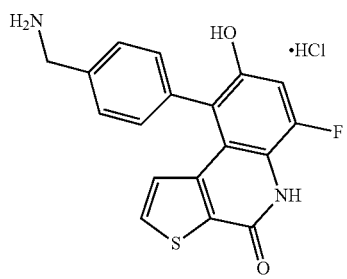 [SMILES: NCc1ccc(-c2c(O)cc(F)c3[nH]c(=O)c4sccc4c23)cc1 ; Cl]

Following General Procedure F, tert-butyl 4-(6-fluoro-8-methoxy-4-oxo-4,5-dihydrothieno[2,3-c]quinolin-9-yl)benzylcarbamate (30 mg, 0.075 mmol) was reacted with tribromoborane (1.0 M in methylene chloride, 0.75 mL, 0.75 mmol) to afford the desired product (22 mg, 88%) as an off-white solid: $^1$H NMR (500 MHz, CD$_3$OD) δ 7.64 (d, J=8.0 Hz, 2H), 7.58 (d, J=5.4 Hz, 1H), 7.39 (d, J=8.0 Hz, 2H), 7.02 (d, J=12.0 Hz, 1H), 6.07 (d, J=5.4 Hz, 1H), 4.28 (s, 2H); ESI MS m/z 341 [C$_{18}$H$_{13}$FN$_2$O$_2$S+H]$^+$; HPLC >99% (AUC), t$_R$=8.34 min.

Example 335

(S)-9-{4-[1-(Dimethylamino)ethyl]phenyl}-8-hydroxythieno[2,3-c]quinolin-4(5H)-one Hydrochloride

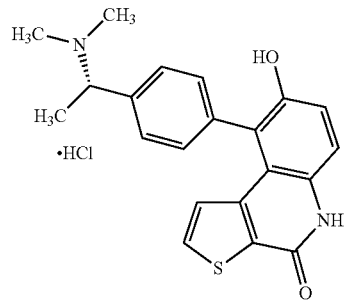 [SMILES: C[C@@H](c1ccc(-c2c(O)ccc3[nH]c(=O)c4sccc4c23)cc1)N(C)C ; Cl]

Following the procedure outlined for Example 460, (S)-9-[4-(1-aminoethyl)phenyl]-8-hydroxythieno[2,3-c]quinolin-4(5H)-one (100 mg, 0.30 mmol) was reacted with formaldehyde (37% in water, 27 mg, 0.89 mmol) and after purification the resulting material was converted to the hydrochloride salt as outlined in General Procedure D-2 to afford the desired product (43 mg, 40%) as a white solid: $^1$H NMR (500 MHz, CD$_3$OD) δ 7.69 (q, J=7.8 Hz, 2H), 7.58 (d, J=5.4 Hz, 1H), 7.48-7.42 (m, 3H), 7.18 (d, J=8.9 Hz, 1H), 6.01 (d, J=5.4 Hz, 1H), 4.65 (q, J=6.6 Hz, 1H), 2.97 (s, 3H), 2.87 (s, 3H), 1.86 (d, J=7.0 Hz, 3H); ESI MS m/z 365 [C$_{21}$H$_{20}$N$_2$O$_2$S+H]$^+$; HPLC >99% (AUC), t$_R$=9.30 min.

Example 459

(E)-9-[3-(3-Aminopiperidin-1-yl)prop-1-enyl]-8-hydroxythieno[2,3-c]quinolin-4(5H)-one

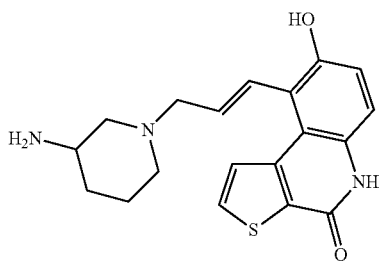 [SMILES: NC1CCCN(C/C=C/c2c(O)ccc3[nH]c(=O)c4sccc4c23)C1]

Following General Procedure F, (E)-tert-Butyl 1-[3-(8-Methoxy-4-oxo-4,5-dihydrothieno[2,3-c]quinolin-9-yl)allyl]piperidin-3-ylcarbamate (320 mg, 0.88 mmol) was reacted with tribromoborane (1.0 M in methylene chloride, 4.0 mL, 4.0 mmol) to afford the desired product (100 mg, 41%) as a yellow solid: $^1$H NMR (500 MHz, CD$_3$OD) δ 8.00 (dd, J=19.3, 5.4 Hz, 2H), 7.32 (d, J=8.9 Hz, 1H), 7.24 (d, J=16.0 Hz, 1H), 7.12 (d, J=8.9 Hz, 1H), 6.39-6.25 (m, 1H), 4.25 (d, J=6.8 Hz, 1H), 3.94 (d, J=11.4 Hz, 1H), 3.83 (d, J=11.9 Hz, 1H), 3.76-3.65 (m, 1H), 3.28-3.10 (m, 2H), 2.24 (dd, J=35.1, 13.6 Hz, 2H), 2.06-1.98 (m, 1H), 1.81-1.68 (m, 1H).

Example 460

(E)-9-{3-[3-(Dimethylamino)piperidin-1-yl]prop-1-enyl}-8-hydroxythieno[2,3-c]quinolin-4(5H)-one

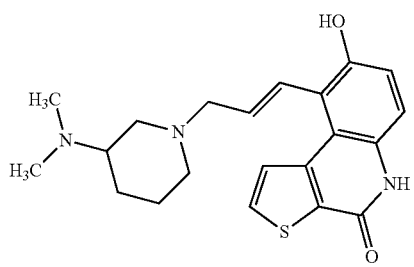 [SMILES: CN(C)C1CCCN(C/C=C/c2c(O)ccc3[nH]c(=O)c4sccc4c23)C1]

A solution of (E)-9-[3-(3-aminopiperidin-1-yl)prop-1-enyl]-8-hydroxythieno[2,3-c]quinolin-4(5H)-one (60 mg, 0.15 mmol) and formaldehyde (37% in water, 13 mg, 0.44 mmol) in methanol (1 mL) was stirred at room temperature for 30 min followed by the addition of sodium cyanoborohydride (28 mg, 0.44 mmol). The reaction mixture was stirred at room temperature overnight, concentrated and partitioned between water and ethyl acetate. The layers were separated and the aqueous layer was extracted with methylene chloride. The combined organic layers were washed with brine, dried over sodium sulfate, filtered, and concentrated. The residue was purified by preparatory HPLC (C18 silica, water/acetonitrile w/0.05% TFA gradient) to afford the desired product (30 mg, 53%) as a yellow solid: $^1$H NMR (500 MHz, CD$_3$OD) δ 7.97 (dd, J=19.4, 5.3 Hz, 2H), 7.30 (d, J=8.9 Hz, 1H), 7.23 (d, J=15.9 Hz, 1H), 7.07 (d, J=8.9 Hz, 1H), 6.33-6.22 (m, 1H), 4.32-4.18 (m, 3H), 3.90-3.77 (m, 2H), 3.47 (t, J=11.6 Hz, 1H), 3.18 (t, J=11.3 Hz, 1H), 3.01 (s, 6H), 2.40-2.23 (m, 2H), 2.10-1.84 (m, 2H).

Example 298

9-{3-[3-(Dimethylamino)piperidin-1-yl]propyl}-8-hydroxythieno[2,3-c]quinolin-4(5H)-one Hydrochloride

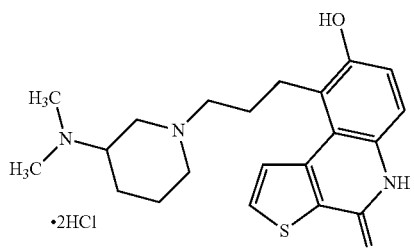

To a solution of (E)-9-{3-[3-(dimethylamino)piperidin-1-yl]prop-1-enyl}-8-hydroxythieno[2,3-c]quinolin-4(5H)-one (20 mg, 0.052 mmol) in methanol (10 mL) under nitrogen was added Pd on carbon (10 wt %, 12 mg) and the reaction mixture was placed in a Parr shaker for 18 h under an atmosphere of hydrogen (40 psi). The reaction mixture was filtered over diatomaceous earth and the filtrate was concentrated. The residue was purified by preparatory HPLC (C18 Silica, water/acetonitrile w/0.05% TFA gradient) and the resulting material was converted to the hydrochloride salt as outlined in General Procedure D-2 to afford the desired product (5.6 mg, 40%) as a white solid: $^1$H NMR (500 MHz, CD$_3$OD) δ 8.08 (d, J=5.4 Hz, 1H), 8.03 (d, J=5.4 Hz, 1H), 7.27 (d, J=8.8 Hz, 1H), 7.11 (d, J=8.8 Hz, 1H), 3.94-3.87 (m, 1H), 3.72-3.61 (m, 2H), 3.45-3.35 (m, 4H), 2.99-2.94 (m, 1H), 2.94 (s, 6H), 2.26-2.14 (m, 4H), 1.90-1.72 (m, 2H), 1.24 (s, 2H), 1.20 (s, 1H); ESI MS m/z 386 [C$_{21}$H$_{27}$N$_3$O$_2$S+H]$^+$; HPLC >99% (AUC), t$_R$=6.71 min.

Example 267

9-{4-[(Ethylamino)methyl]phenyl}-8-hydroxythieno[2,3-c]quinolin-4(5H)-one Hydrochloride

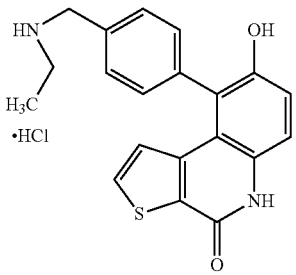 [SMILES: Cl ; CCNCc1ccc(-c2c(O)ccc3[nH]c(=O)c4sccc4c23)cc1]

Following General Procedure F, 9-{4-[(ethylamino)methyl]phenyl}-8-methoxythieno[2,3-c]quinolin-4(5H)-one (70 mg, 0.19 mmol) was reacted with tribromoborane (1.0 M in methylene chloride, 1.2 mL, 1.2 mmol) to afford the desired product (42 mg, 63%) as a yellow solid: $^1$H NMR (500 MHz, CD$_3$OD) δ 7.66 (d, J=8.2 Hz, 2H), 7.55 (d, J=5.4 Hz, 1H), 7.43-7.41 (m, 3H), 7.17 (d, J=8.9 Hz, 1H), 6.08 (d, J=5.4 Hz, 1H), 4.34 (s, 2H), 3.22 (q, J=7.3 Hz, 2H), 1.41 (t, J=7.3 Hz, 3H); ESI MS m/z 351 [C$_{20}$H$_{18}$N$_2$O$_2$S+H]$^+$; HPLC >99% (AUC), t$_R$=8.01 min.

Example 229

8-Hydroxy-9-{4-[(isopropylamino)methyl]phenyl}thieno[2,3-c]quinolin-4(5H)-one Hydrochloride

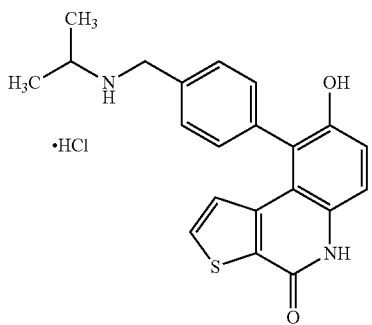 [SMILES: CC(C)NCc1ccc(-c2c(O)ccc3[nH]c(=O)c4sccc4c23)cc1 ; Cl]

Following General Procedure F, 9-{4-[(isopropylamino)methyl]phenyl}-8-methoxythieno[2,3-c]quinolin-4(5H)-one was reacted with tribromoborane (1.0 M in methylene chloride, 1.6 mL, 1.6 mmol) to afford the desired product (48 mg, 50%) as a light brown glass: $^1$H NMR (500 MHz, CD$_3$OD) δ 7.70 (d, J=7.6 Hz, 2H), 7.58 (d, J=9.7 Hz, 1H), 7.44-7.41 (m, 3H), 7.18 (d, J=8.9 Hz, 1H), 6.12 (d, J=5.1 Hz, 1H), 4.37 (s, 2H), 3.59-3.55 (m, 1H), 1.48 (d, J=6.5 Hz, 6H); ESI MS m/z 365 [C$_{21}$H$_{20}$N$_2$O$_2$S+H]$^+$; HPLC >97.8% (AUC), t$_R$=7.93 min.

Example 212

N-[4-(8-Hydroxy-4-oxo-4,5-dihydrothieno[2,3-c]quinolin-9-yl)benzyl]methanesulfonamide

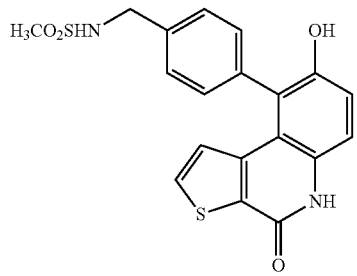

A solution of 9-[4-(aminomethyl)phenyl]-8-hydroxythieno[2,3-c]quinolin-4(5H)-one (50 mg, 0.16 mmol) and methanesulfonyl chloride (43 mg, 0.37 mmol) in methylene chloride (5 mL) was stirred at room temperature for 10 min. N,N-diisopropylethylamine (48 mg, 0.37 mmol) was added and the reaction mixture was stirred for 1.5 h, concentrated under reduced pressure and the residue was purified by preparatory HPLC (C18 silica, water/acetonitrile w/0.05% TFA gradient) to afford the desired product (28 mg, 45%) as a white solid: $^1$H NMR (500 MHz, DMSO-d$_6$) δ 11.77 (s, 1H), 9.22 (s, 1H), 7.70-7.67 (m, 2H), 7.49 (d, J=8.0 Hz, 2H), 7.36 (d, J=8.9 Hz, 1H), 7.23 (d, J=8.0 Hz, 2H), 7.15 (d, J=8.9 Hz, 1H), 5.89 (d, J=5.4 Hz, 1H), 4.29 (d, J=6.4 Hz, 2H), 2.94 (s, 3H); ESI MS m/z 401 [C$_{19}$H$_{16}$N$_2$O$_4$S+H]$^+$; HPLC >99% (AUC), t$_R$=12.12 min.

Example 187

8-Hydroxy-9-{4-[(methylamino)methyl]phenyl}thieno[2,3-c]quinolin-4(5H)-one

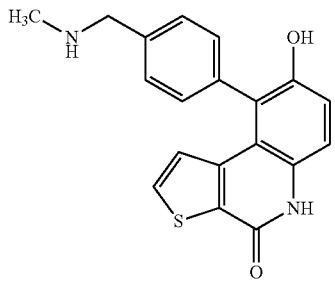 [SMILES: CNCc1ccc(-c2c(O)ccc3[nH]c(=O)c4sccc4c23)cc1]

Following General Procedure F, 8-methoxy-9-{4-[(methylamino)methyl]phenyl}thieno[2,3-c]quinolin-4(5H)-one (100 mg, 0.29 mmol) was reacted with tribromoborane (1.0 M in methylene chloride, 1.7 mL, 1.7 mmol) to afford the desired product (28 mg, 30%) as a white solid: $^1$H NMR (500 MHz, CD$_3$OD) δ 7.65 (d, J=8.1 Hz, 2H), 7.55 (d, J=5.4 Hz, 1H), 7.44-7.41 (m, 3H), 7.17 (d, J=8.9 Hz, 1H), 6.05 (d, J=5.4 Hz, 1H), 4.33 (s, 2H), 2.83 (s, 3H); ESI MS m/z 337 [C$_{19}$H$_{16}$N$_2$O$_2$S+H]$^+$; HPLC >99% (AUC), t$_R$=10.02 min.

Example 184

9-{4-[(Diethylamino)methyl]phenyl}-8-hydroxythieno[2,3-c]quinolin-4(5H)-one

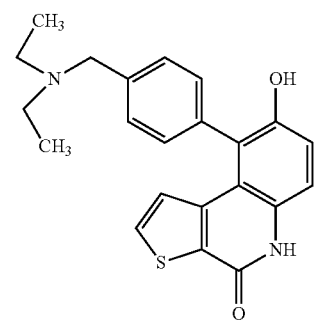 [SMILES: CCN(CC)Cc1ccc(-c2c(O)ccc3[nH]c(=O)c4sccc4c23)cc1]

Following General Procedure F, 9-{4-[(diethylamino)methyl]phenyl}-8-methoxythieno[2,3-c]quinolin-4(5H)-one (30 mg, 0.076 mmol) was reacted with tribromoborane (1.0 M in methylene chloride, 0.46 mL, 0.46 mmol) to afford the desired product (12 mg, 42%) as a white solid: $^1$H NMR (500 MHz, CD$_3$OD) δ 7.69 (d, J=8.1 Hz, 2H), 7.56 (d, J=5.4 Hz, 1H), 7.48-7.42 (m, 3H), 7.18 (d, J=8.9 Hz, 1H), 6.03 (d, J=5.4 Hz, 1H), 4.50 (s, 2H), 3.36-3.31 (m, 4H), 1.43 (t, J=7.3 Hz, 6H); ESI MS m/z 379 [C$_{22}$H$_{22}$N$_2$O$_2$S+H]$^+$; HPLC 97.2% (AUC), t$_R$=8.27 min.

Example 165

9-{4-[(Dimethylamino)methyl]phenyl}hydroxythieno[2,3-c]quinolin-4(5H)-one

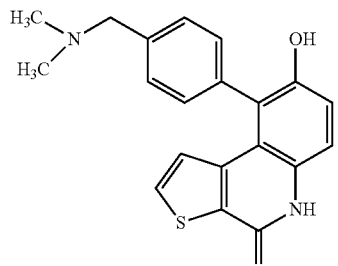

Following General Procedure F, 9-{4-[(dimethylamino)methyl]phenyl}-8-methoxythieno[2,3-c]quinolin-4(5H)-one (30 mg, 0.082 mmol) was reacted with tribromoborane (1.0 M in methylene chloride, 0.49 mL, 0.49 mmol) to afford the desired product (11 mg, 40%) as a white solid: $^1$H NMR (500 MHz, CD$_3$OD) δ 7.54-7.50 (m, 3H), 7.39 (d, J=8.9 Hz, 1H), 7.29 (d, J=8.0 Hz, 2H), 7.18 (d, J=8.9 Hz, 1H), 5.99 (d, J=5.5

Hz, 1H), 3.64 (s, 2H), 2.36 (s, 6H); ESI MS m/z 351 [C$_{20}$H$_{18}$N$_2$O$_2$S+H]$^+$; HPLC 98.5% (AUC), t$_R$=7.71 min.

Example 191

9-{4-[1-(Dimethylamino)ethyl]phenyl}-8-hydroxythieno[2,3-c]quinolin-4(5H)-one

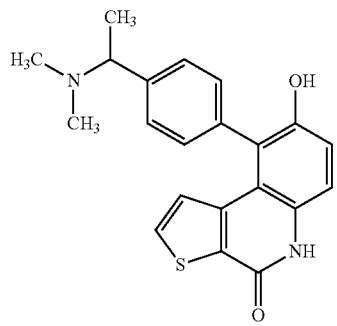 [SMILES: CC(c1ccc(-c2c(O)ccc3[nH]c(=O)c4sccc4c23)cc1)N(C)C]

Following the procedure outlined for Example 460, 9-[4-(1-Aminoethyl)phenyl]-8-hydroxythieno[2,3-c]quinolin-4(5H)-one (40 mg, 0.12 mmol) was reacted with formaldehyde (37% in water, 14 mg, 0.50 mmol) and after purification the resulting material was converted to the hydrochloride salt as outlined in General Procedure D-2 to afford the desired product (20 mg, 42%) as a white solid: $^1$H NMR (500 MHz, CD$_3$OD) δ 7.71-7.67 (m, 2H), 7.58 (d, J=4.4 Hz, 1H), 7.48-7.41 (m, 3H), 7.18 (d, J=8.9 Hz, 1H), 6.01 (d, J=5.4 Hz, 1H), 4.65 (q, J=7.0 Hz, 1H), 2.97 (s, 3H), 2.87 (s, 3H), 1.86 (d, J=7.0 Hz, 3H); ESI MS m/z 365 [C$_{21}$H$_{20}$N$_2$O$_2$S+H]$^+$; HPLC >99% (AUC), t$_R$=7.86 min.

Example 192

9-(4-(1-(dimethylamino)ethyl)phenyl)-8-hydroxythieno[2,3-c]quinolin-4(5H)-one Hydrochloride

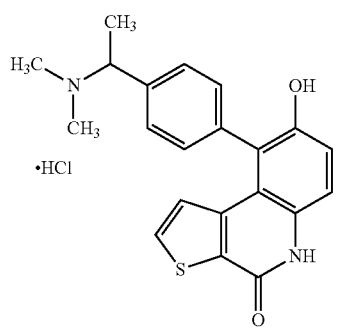 [SMILES: CC(c1ccc(-c2c(O)ccc3[nH]c(=O)c4sccc4c23)cc1)N(C)C ; Cl]

Following General Procedure F, 9-{4-[1-(dimethylamino)ethyl]phenyl}-8-methoxythieno[2,3-c]quinolin-4(5H)-one (3.2 g, 7.1 mmol) was reacted with tribromoborane (1.0 M in methylene chloride, 43 mL, 43 mmol) and the resulting material was converted to the hydrochloride salt as outlined in General Procedure D-2 to afford the desired product (1.3 g, 92%) as a white solid: $^1$H NMR (500 MHz, CD$_3$OD) δ 7.71-7.67 (m, 2H), 7.58 (d, J=4.4 Hz, 1H), 7.48-7.41 (m, 3H), 7.18 (d, J=8.9 Hz, 1H), 6.01 (d, J=5.4 Hz, 1H), 4.65 (q, J=7.0 Hz, 1H), 2.97 (s, 3H), 2.87 (s, 3H), 1.86 (d, J=7.0 Hz, 3H); ESI MS m/z 365 [C$_{21}$H$_{20}$N$_2$O$_2$S+H]$^+$; HPLC >99% (AUC), t$_R$=7.86 min.

Example 72

9-[4-(Aminomethyl)phenyl]-8-hydroxythieno[2,3-c]quinolin-4(5H)-one

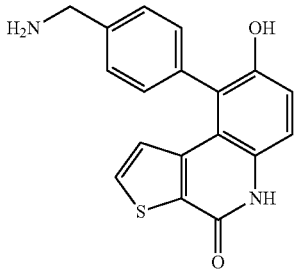 [SMILES: NCc1ccc(-c2c(O)ccc3[nH]c(=O)c4sccc4c23)cc1]

Following General Procedure F, tert-Butyl 4-(8-Methoxy-4-oxo-4,5-dihydrothieno[2,3-c]quinolin-9-yl)benzylcarbamate (70 mg, 0.16 mmol) was reacted with tribromoborane (1.0 M in methylene chloride, 0.96 mL, 0.96 mmol) to afford the desired product (37 mg, 60%) as a white solid: $^1$H NMR (500 MHz, DMSO-d$_6$) δ 11.80 (s, 1H), 9.28 (s, 1H), 8.25 (br s, 2H), 7.68 (d, J=5.4 Hz, 1H), 7.60 (d, J=8.0 Hz, 2H), 7.39 (d, J=8.9 Hz, 1H), 7.33 (d, J=8.1 Hz, 2H), 7.17 (d, J=8.8 Hz, 1H), 5.92 (d, J=5.4 Hz, 1H), 4.18 (m, 2H); ESI MS m/z 323 [C$_{18}$H$_{14}$N$_2$O$_2$S+H]$^+$; HPLC 98.3% (AUC), t$_R$=10.74 min.

Example 73

9-[4-(Aminomethyl)phenyl]-8-hydroxythieno[2,3-c]quinolin-4(5H)-one Hydrochloride

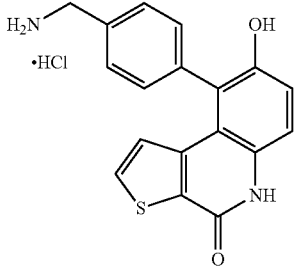 [SMILES: NCc1ccc(-c2c(O)ccc3[nH]c(=O)c4sccc4c23)cc1 ; Cl]

Following General Procedure F, tert-butyl 4-(8-methoxy-4-oxo-4,5-dihydrothieno[2,3-c]quinolin-9-yl)benzylcarbamate (260 mg, 0.60 mmol) was reacted with tribromoborane (1.0 M in methylene chloride, 3.6 mL, 3.6 mmol) and the resulting material was converted to the hydrochloride salt as outlined in General Procedure D-2 to afford the desired product (120 mg, 50%) as a off-white solid: $^1$H NMR (500 MHz, DMSO-d$_6$) δ 11.80 (s, 1H), 9.28 (s, 1H), 8.25 (br s, 2H), 7.68

(d, J=5.4 Hz, 1H), 7.60 (d, J=8.0 Hz, 2H), 7.39 (d, J=8.9 Hz, 1H), 7.33 (d, J=8.1 Hz, 2H), 7.17 (d, J=8.8 Hz, 1H), 5.92 (d, J=5.4 Hz, 1H), 4.18 (m, 2H); ESI MS m/z 323 $[C_{18}H_{14}N_2O_2S+H]^+$; HPLC 98.3% (AUC), $t_R$=10.74 min.

Example 233

(S)-9-[4-(1-Aminoethyl)phenyl]-8-hydroxythieno[2,3-c]quinolin-4(5H)-one Hydrochloride

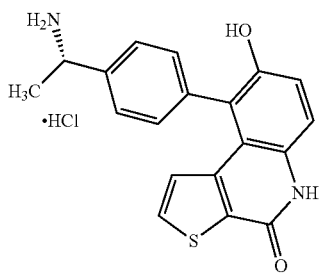 [SMILES: C[C@H](N)c1ccc(-c2c(O)ccc3[nH]c(=O)c4sccc4c23)cc1 ; Cl]

Following General Procedure F, (S)-9-[4-(1-aminoethyl)phenyl]-8-methoxythieno[2,3-c]quinolin-4(5H)-one (100 mg, 0.22 mmol) was reacted with tribromoborane (3.0 mL) to afford the desired product (16 mg, 22%) as a yellow solid: $^1$H NMR (500 MHz, CD$_3$OD) δ 7.63-7.61 (m, 2H), 7.56-7.55 (m, 1H), 7.43-7.41 (m, 3H), 7.17 (d, J=8.9 Hz, 1H), 6.08 (d, J=5.4 Hz, 1H), 4.61 (q, J=4.7 Hz, 1H), 1.76 (d, J=6.9 Hz, 3H); ESI MS m/z 337 $[C_{19}H_{16}N_2O_2S+H]^+$; HPLC 98.6% (AUC), $t_R$=7.62 min.

Example 347

(S)—N-{1-[4-(8-Hydroxy-4-oxo-4,5-dihydrothieno[2,3-c]quinolin-9-yl)phenyl]ethyl}methanesulfonamide

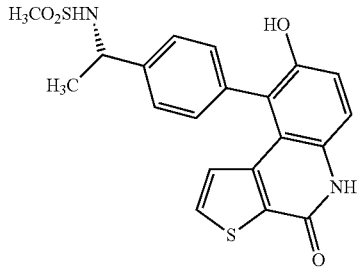

Following the procedure outlined for Example 301, (S)-9-[4-(1-aminoethyl)phenyl]-8-hydroxythieno[2,3-c]quinolin-4(5H)-one (100 mg, 0.30 mmol) was reacted with methanesulfonyl chloride (100 mg, 0.89 mmol) to afford the desired product (70 mg, 56%) as a light brown solid: $^1$H NMR (500 MHz, CD$_3$OD) δ 5.89-7.55 (m, 2H), 7.52 (d, J=5.4 Hz, 1H), 7.38 (d J=8.9 Hz, 1H), 7.30-7.28 (m, 2H), 7.15 (d, J=8.9 Hz, 1H), 6.00 (d, J=5.4 Hz, 1H), 4.71 (q, J=7.1 Hz, 1H), 2.82 (s, 3H), 1.61 (d, J=7.0 Hz, 3H); ESI MS m/z 415 $[C_{20}H_{18}N_2O_4S_2+H]^+$; HPLC >99% (AUC), $t_R$=12.43 min.

Example 339

9-{4-[1-(Dimethylamino)propyl]phenyl}-8-hydroxythieno[2,3-c]quinolin-4(5H)-one Hydrochloride

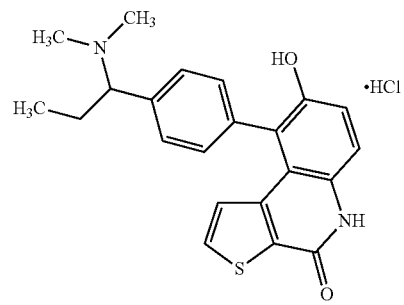 [SMILES: CCC(c1ccc(-c2c(O)ccc3[nH]c(=O)c4sccc4c23)cc1)N(C)C ; Cl]

Following the procedure outlined for Example 460, 9-[4-(1-aminopropyl)phenyl]-8-hydroxythieno[2,3-c]quinolin-4(5H)-one (100 mg, 0.29 mmol) was reacted with formaldehyde (26 mg, 0.86 mmol) and the resulting material was converted to the hydrochloride salt as outlined in General Procedure D-2 to afford the desired product (62 mg, 58%) as a white solid: $^1$H NMR (500 MHz, CD$_3$OD) δ 7.69-7.64 (m, 2H), 7.56 (d, J=5.4 Hz, 1H), 7.51-7.47 (m, 2H), 7.43 (d, J=8.9 Hz, 1H), 7.19 (d, J=8.0 Hz, 1H), 5.95 (d, J=5.4 Hz, 1H), 4.38 (dd, J=11.3, 4.3 Hz, 1H), 2.99 (s, 3H), 2.85 (s, 3H), 2.32-2.25 (m, 2H), 0.98 (t, J=7.3 Hz, 3H); ESI MS m/z 379 $[C_{22}H_{22}N_2O_2S+H]^+$; HPLC 97.2% (AUC), $t_R$=9.45 min.

Example 338

9-{4-[1-(Diethylamino)propyl]phenyl}-8-hydroxythieno[2,3-c]quinolin-4(5H)-one Hydrochloride

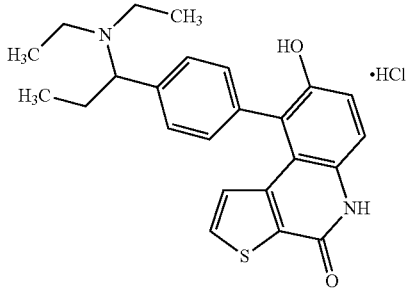 [SMILES: CCC(c1ccc(-c2c(O)ccc3[nH]c(=O)c4sccc4c23)cc1)N(CC)CC ; Cl]

Following the procedure outlined for Example 460, (9-[4-(1-aminopropyl)phenyl]-8-hydroxythieno[2,3-c]quinolin-4(5H)-one (100 mg, 0.29 mmol) was reacted with formaldehyde (38 mg, 0.86 mmol) and the resulting material was converted to the hydrochloride salt as outlined in General Procedure D-2 to afford the desired product (52 mg, 45%) as a light brown solid: $^1$H NMR (500 MHz, CD$_3$OD) δ 7.71 (dd, J=7.7, 1.8 Hz, 1H), 7.66 (dd, J=7.9 Hz, 1.9 Hz, 1H), 7.54 (d, J=5.5 Hz, 1H), 7.49-7.45 (m, 2H), 7.42 (d, J=5.5 Hz, 1H), 7.19 (d, J=4.2 Hz, 1H), 5.95 (d, J=5.4 Hz, 1H), 4.48 (dd, J=11.7, 3.8 Hz, 1H), 3.47-3.40 (m, 3H), 3.12-3.08 (m, 1H), 2.35-2.21 (m, 2H), 1.45 (t, J=7.3 Hz, 3H), 1.35 (t, J=7.3 Hz, 3H), 0.95 (t, J=7.3 Hz, 3H); ESI MS m/z 407 [C$_{24}$H$_{26}$N$_2$O$_2$S+H]$^+$; HPLC 96.3% (AUC), t$_R$=10.74 min.

Example 336

9-[4-(1-Aminopropyl)phenyl]-8-hydroxythieno[2,3-c]quinolin-4(5H)-one Hydrochloride

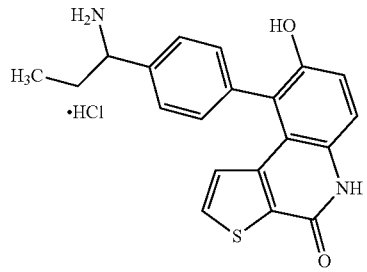 [SMILES: CCC(N)c1ccc(-c2c(O)ccc3[nH]c(=O)c4sccc4c23)cc1 ; Cl]

Following General Procedure F, tert-butyl 1-[4-(8-methoxy-4-oxo-4,5-dihydrothieno[2,3-c]quinolin-9-yl)phenyl]propylcarbamate (70 mg, 0.15 mmol) was reacted with tribromoborane (1.0 M in methylene chloride, 0.90 mL, 0.90 mmol) to afford the desired product (35 mg, 52%) as a light yellow solid: $^1$H NMR (500 MHz, CD$_3$OD) δ 7.63-7.58 (m, 2H), 7.53 (d, J=5.4 Hz, 1H), 7.42-7.39 (m, 3H), 7.17 (d, J=8.9 Hz, 1H), 6.02 (d, J=5.4 Hz, 1H), 4.32 (q, J=5.9 Hz, 1H), 2.17-2.08 (m, 2H), 1.03 (t, J=7.4 Hz, 3H); ESI MS m/z 351 [C$_{20}$H$_{18}$N$_2$O$_2$S+H]$^+$; HPLC >99% (AUC), t$_R$=9.39 min.

Example 314

9-{4-[1-(Cyclopentylamino)ethyl]phenyl}-8-hydroxythieno[2,3-c]quinolin-4(5H)-one Hydrochloride

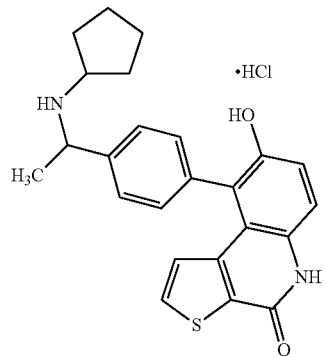 [SMILES: CC(NC1CCCC1)c1ccc(-c2c(O)ccc3[nH]c(=O)c4sccc4c23)cc1 ; Cl]

Following General Procedure F, 9-{4-[1-(cyclopentylamino)ethyl]phenyl}-8-methoxythieno[2,3-c]quinolin-4(5H)-one (200 mg, 0.48 mmol) was reacted with tribromoborane (15 mL) to afford the desired product (25 mg, 13%) as a brown solid: $^1$H NMR (300 MHz, CD$_3$OD) δ 7.71-7.64 (m, 2H), 7.56 (d, J=5.4 Hz, 1H), 7.48-7.41 (m, 3H), 7.18 (d, J=8.9 Hz, 1H), 6.06 (d, J=5.4 Hz, 1H), 4.57 (q, J=6.8 Hz, 1H), 3.59-3.49 (m, 1H), 2.26-2.08 (m, 2H), 1.87-1.62 (m, 9H); ESI MS m/z 405 [C$_{24}$H$_{24}$N$_2$O$_2$S+H]$^+$; HPLC >99% (AUC), t$_R$=8.84 min.

Example 313

8-Hydroxy-9-[4-(1-hydroxyethyl)phenyl]thieno[2,3-c]quinolin-4(5H)-one

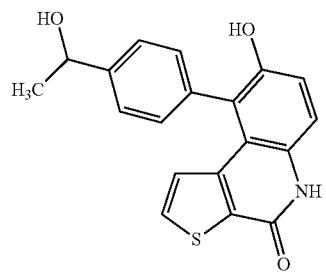 [SMILES: CC(O)c1ccc(-c2c(O)ccc3[nH]c(=O)c4sccc4c23)cc1]

A solution of 9-(4-acetylphenyl)-8-hydroxythieno[2,3-c]quinolin-4(5H)-one (200 mg, 0.59 mmol) in ethanol (4 mL) was cooled to 0° C. and sodium borohydride (45 mg, 1.2 mmol) was added. The reaction mixture was stirred at room temperature for 18 h however starting material was present. The reaction was cooled to 0° C. and lithium aluminum hydride (1.0 M in THF, 1.2 mL, 1.2 mmol) was added and the reaction mixture was stirred at room temperature for 2 h. The reaction was cooled to 0° C., quenched with methanol and concentrated. The residue was purified by preparatory HPLC (C18 silica, water/acetonitrile w/0.05% TFA gradient) to afford the desired product (2.6 mg, 1%) as a light brown solid: $^1$H NMR (300 MHz, CD$_3$OD) δ 7.59-7.52 (m, 3H), 7.39 (d, J=8.9 Hz, 1H), 7.29-7.25 (m, 2H), 7.16 (d, J=8.9 Hz, 1H), 6.03 (d, J=5.4 Hz, 1H), 4.97 (q, J=6.4 Hz, 1H), 1.56 (d, J=6.5 Hz, 3H); ESI MS m/z 338 [C$_{19}$H$_{15}$NO$_3$S+H]$^+$; HPLC 98.6% (AUC), t$_R$=9.78 min.

Example 308

9-{4-[1-(Dimethylamino)-2-methylpropan-2-yl]phenyl}-8-hydroxythieno[2,3-c]quinolin-4(5H)-one Hydrochloride

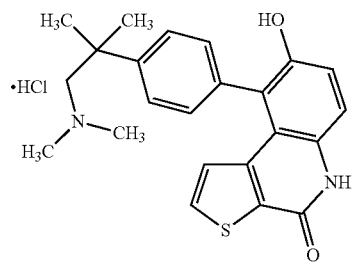 [SMILES: Cl ; CN(C)CC(C)(C)c1ccc(-c2c(O)ccc3[nH]c(=O)c4sccc4c23)cc1]

Following the procedure outlined for Example 460, 9-[4-(1-amino-2-methylpropan-2-yl)phenyl]-8-hydroxythieno[2,3-c]quinolin-4(5H)-one (30 mg, 0.082 mmol) was reacted with formaldehyde (7.4 mL, 0.25 mmol) and the resulting material was converted to the hydrochloride salt as outlined in General Procedure D-2 to afford the desired product (7 mg, 22%) as a light yellow solid: $^1$H NMR (500 MHz, CD$_3$OD) δ

7.71 (d, J=8.3 Hz, 2H), 7.56 (d, J=5.4 Hz, 1H), 7.40 (q, J=6.6 Hz, 3H), 7.17 (d, J=8.9 Hz, 1H), 6.07 (d, J=5.4 Hz, 1H), 3.68 (s, 2H), 2.81 (s, 6H), 1.62 (s, 6H); ESI MS m/z 393 [C$_{23}$H$_{24}$N$_2$O$_2$S+H]$^+$; HPLC 97.5% (AUC), t$_R$=8.46 min.

Example 301

(R)—N-{1-[4-(8-Hydroxy-4-oxo-4,5-dihydrothieno[2,3-c]quinolin-9-yl)phenyl]ethyl}methanesulfonamide

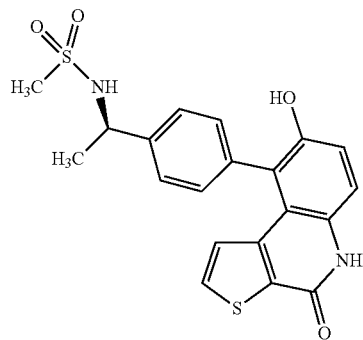 [SMILES: C[C@@H](NS(C)(=O)=O)c1ccc(-c2c(O)ccc3[nH]c(=O)c4sccc4c23)cc1]

A solution of (R)-9-[4-(1-aminoethyl)phenyl]-8-hydroxythieno[2,3-c]quinolin-4(5H)-one (28 mg, 0.83 mmol) and methanesulfonyl chloride (82 µL, 1.0 mmol) in 1:1 methylene chloride/THF (6 mL) and DMF (1.5 mL) was stirred at room temperature for 10 min followed by the addition of N,N-diisopropylethylamine (170 µL, 1.0 mmol). The reaction mixture was stirred for 1.5 h, concentrated and purified by preparatory HPLC (C18 silica, water/acetonitrile w/0.05% TFA gradient) to afford the desired product (8.9 mg, 2%) as a light brown solid: $^1$H NMR (500 MHz, CD$_3$OD) δ 7.59-7.55 (m, 2H), 7.53 (d, J=5.5 Hz, 1H), 7.39 (d, J=8.9 Hz, 1H), 7.31-7.30 (m, 2H), 7.16 (d, J=8.9 Hz, 1H), 6.02 (d, J=5.4 Hz, 1H), 4.71 (q, J=4.6 Hz, 1H), 2.82 (s, 3H), 1.62 (d, J=7.0 Hz, 3H); ESI MS m/z 415 [C$_{20}$H$_{18}$N$_2$O$_4$S$_2$+H]$^+$; HPLC 96.4% (AUC), t$_R$=10.14 min.

Example 296

9-(4-Acetylphenyl)-8-hydroxythieno[2,3-c]quinolin-4(5H)-one

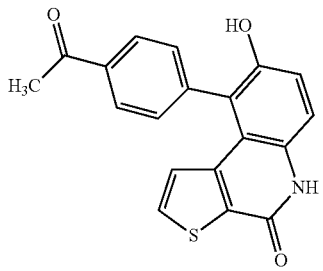 [SMILES: CC(=O)c1ccc(-c2c(O)ccc3[nH]c(=O)c4sccc4c23)cc1]

Following General Procedure F, 9-(4-acetylphenyl)-8-methoxythieno[2,3-c]quinolin-4(5H)-one (450 mg, 1.3 mmol) was reacted with tribromoborane (15 mL) to afford the desired product (320 mg, 74%) as a light brown solid: $^1$H NMR (500 MHz, DMSO-d$_6$) δ 11.82 (s, 1H), 9.38 (s, 1H), 8.10 (d, J=8.3 Hz, 2H), 7.74 (d, J=5.4 Hz, 1H), 7.44-7.39 (m, 3H), 7.18 (d, J=8.9 Hz, 1H), 5.90 (d, J=5.4 Hz, 1H), 2.68 (s, 3H); ESI MS m/z 336 [C$_{19}$H$_{13}$NO$_3$S+H]$^+$; HPLC 98.3% (AUC), t$_R$=10.59 min.

Example 290

3-[4-(8-Hydroxy-4-oxo-4,5-dihydrothieno[2,3-c]quinolin-9-yl)phenyl]propanenitrile

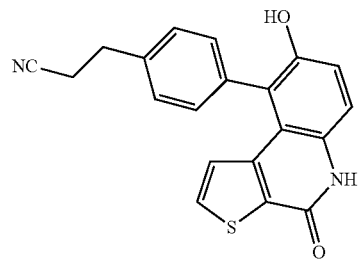 [SMILES: N#CCCc1ccc(-c2c(O)ccc3[nH]c(=O)c4sccc4c23)cc1]

Following General Procedure F, 3-[4-(8-methoxy-4-oxo-4,5-dihydrothieno[2,3-c]quinolin-9-yl)phenyl]propanenitrile (45 mg, 0.13 mmol) was reacted with tribromoborane (3 mL) to afford the desired product (5.6 mg, 13%) as a white solid: $^1$H NMR (500 MHz, CD$_3$OD) δ 7.53 (d, J=5.4 Hz, 1H), 7.48 (d, J=7.9 Hz, 2H), 7.39 (d, J=8.9 Hz, 1H), 7.28 (d, J=7.9 Hz, 2H), 7.16 (d, J=8.9 Hz, 1H), 5.96 (d, J=5.4 Hz, 1H), 3.10 (t, J=3.8 Hz, 2H), 2.89 (t, J=7.1 Hz, 2H); ESI MS m/z 347 [C$_{20}$H$_{14}$N$_2$O$_2$S+H]$^+$; HPLC >99% (AUC), t$_R$=10.99 min.

Example 356

9-{4-[1-(Diethylamino)ethyl]-3-fluorophenyl}-8-hydroxythieno[2,3-c]quinolin-4(5H)-one Hydrochloride

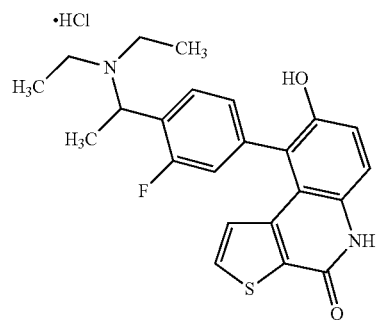 [SMILES: Cl ; CCN(CC)C(C)c1ccc(-c2c(O)ccc3[nH]c(=O)c4sccc4c23)cc1F]

A solution of 9-(4-(1-aminoethyl)-3-fluorophenyl)-8-hydroxythieno[2,3-c]quinolin-4(5H)-one (40 mg, 0.11 mmol) and acetaldehyde (25 mg, 0.45 mmol) in methanol (2 mL) was stirred at room temperature for 30 min followed by the addition of sodium cyanoborohydride (28 mg, 0.452 mmol) and the reaction mixture was stirred at room temperature for 18 h. The reaction mixture was concentrated, partitioned between water and ethyl acetate and the layers were separated. The aqueous layer was extracted with methylene chloride and the combined organic layers were washed with brine, dried over anhydrous sodium sulfate, filtered, and concentrated. The residue was purified by preparatory HPLC (C18 silica, water/acetonitrile w/0.05% TFA gradient) and the resulting material was converted to the hydrochloride salt as outlined in General Procedure D-2 to afford the desired product (30 mg, 65%) as a yellow solid: $^1$H NMR (500 MHz, CD$_3$OD) δ 7.84-7.82 (m, 1H), 7.67-7.65 (m, 1H), 7.44 (dd, J=9.1, 1.5 Hz, 1H), 7.34-7.28 (m, 2H), 7.19 (dd, J=8.9, 2.5 Hz, 1H), 6.14 (t, J=5.1 Hz, 1H), 5.16-5.06 (m, 1H), 3.46-3.35 (m, 3H), 3.30-3.15 (m, 1H), 2.79 (s, 1H), 1.88 (t, J=6.2 Hz, 3H), 1.48-1.37 (m, 6H); ESI MS m/z 411 [C$_{23}$H$_{23}$FN$_2$O$_2$S+H]$^+$; HPLC >99% (AUC), t$_R$=8.57 min.

Example 359

9-[4-(1-Aminoethyl)-3-fluorophenyl]-8-hydroxythieno[2,3-c]quinolin-4(5H)-one Hydrochloride

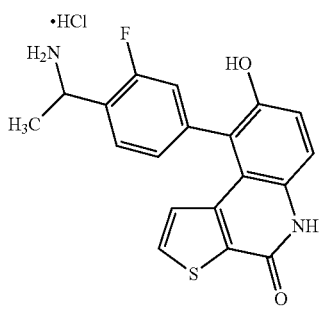 [SMILES: Cl ; CC(N)c1ccc(-c2c(O)ccc3[nH]c(=O)c4sccc4c23)cc1F]

Following General Procedure F, tert-butyl 1-[2-fluoro-4-(8-methoxy-4-oxo-4,5-dihydrothieno[2,3-c]quinolin-9-yl)phenyl]ethylcarbamate (400 mg, 0.856 mmol) was reacted with tribromoborane (4 mL) to afford the desired product (99 mg, 33%) as a white solid: $^1$H NMR (300 MHz, CD$_3$OD) δ 7.70-7.60 (m, 2H), 7.43 (d, J=8.9 Hz, 1H), 7.27-7.15 (m, 3H), 6.18 (q, J=3.0 Hz, 1H), 1.78 (t, J=6.5 Hz, 3H); ESI MS m/z 355 [C$_{19}$H$_{15}$FN$_2$O$_2$S+H]$^+$; HPLC >99% (AUC), t$_R$=7.84 min.

Example 353

8-Hydroxy-9-(1,2,3,4-tetrahydroisoquinolin-7-yl)thieno[2,3-c]quinolin-4(5H)-one Hydrochloride

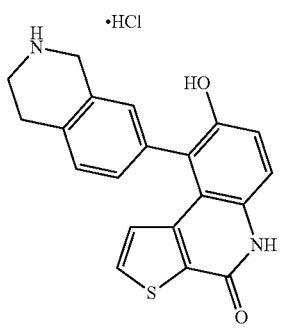 [SMILES: Cl ; O=c1[nH]c2ccc(O)c(-c3ccc4c(c3)CNCC4)c2c2ccsc12]

Following General Procedure F, 8-methoxy-9-(1,2,3,4-tetrahydroisoquinolin-7-yl)thieno[2,3-c]quinolin-4(5H)-one (40 mL, 0.11 mmol) was reacted with tribromoborane (2 mL) to afford the desired product (26 mg, 68%) as an off-white solid: $^1$H NMR (500 MHz, CD$_3$OD) δ 7.56 (d, J=5.5 Hz, 1H), 7.45 (d, J=8.0 Hz, 1H), 7.40 (d, J=8.9 Hz, 1H), 7.27-7.25 (m, 1H), 7.19 (br s, 1H), 7.16 (d, J=8.9 Hz, 1H), 6.17 (d, J=5.4 Hz, 1H), 4.12 (s, 2H), 3.67-3.57 (m, 2H), 3.29-3.22 (m, 2H); ESI MS m/z 349 [C$_{20}$H$_{16}$N$_2$O$_2$S+H]$^+$; HPLC >99% (AUC), t$_R$=7.82 min.

Example 349

9-{4-[1-(Dimethylamino)ethyl]-3-fluorophenyl}-8-hydroxythieno[2,3-c]quinolin-4(5H)-one Hydrochloride

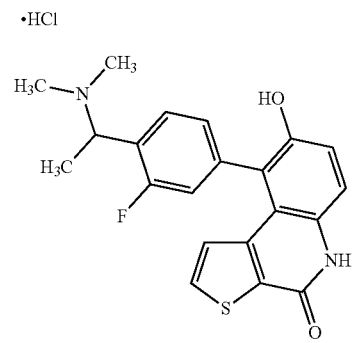 [SMILES: Cl ; CC(c1ccc(-c2c(O)ccc3[nH]c(=O)c4sccc4c23)cc1F)N(C)C]

Following the procedure outlined for Example 460, 9-[4-(1-aminoethyl)-3-fluorophenyl]-8-hydroxythieno[2,3-c]quinolin-4(5H)-one (40 mg, 0.11 mmol) was reacted with formaldehyde (14 mg, 0.45 mmol) to afford the desired product (23 mg, 53%) as a yellow solid: $^1$H NMR (500 MHz, CD$_3$OD) δ 7.81-7.73 (m, 1H), 7.66 (q, J=4.3 Hz, 1H), 7.44 (dd, J=8.9, 2.3 Hz, 1H), 7.34-7.29 (m, 2H), 7.20-7.18 (m, 1H), 6.14 (t, J=6.0 Hz, 1H), 5.03-4.92 (m, 1H), 3.03-2.86 (m, 6H), 2.78 (br s, 1H), 1.88 (dd, J=7.0, 2.4 Hz, 3H); ESI MS m/z 383 [C$_{21}$H$_{19}$FN$_2$O$_2$S+H]$^+$; HPLC >99% (AUC), t$_R$=8.04 min.

Example 361

1-[4-(8-Hydroxy-4-oxo-4,5-dihydrothieno[2,3-c]quinolin-9-yl)phenyl]cyclopropanecarbonitrile

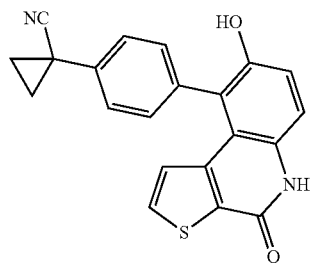 [SMILES: N#CC1(c2ccc(-c3c(O)ccc4[nH]c(=O)c5sccc5c34)cc2)CC1]

Following General Procedure F, 1-[4-(8-methoxy-4-oxo-4,5-dihydrothieno[2,3-c]quinolin-9-yl)phenyl]cyclopropanecarbonitrile (340 mg, 0.91 mmol) was reacted with tribromoborane (1.3 mL) to afford the desired product (90 mg, 28%) as a light brown solid: ESI MS m/z 359 [C$_{21}$H$_{14}$N$_2$O$_2$S+H]$^+$.

Example 348

9-{4-[1-(Aminomethyl)cyclopropyl]phenyl}-8-hydroxythieno[2,3-c]quinolin-4(5H)-one Hydrochloride

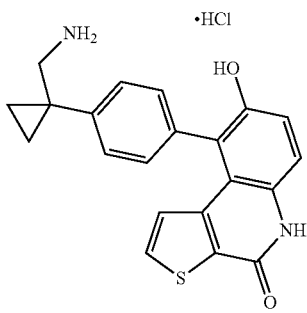 [SMILES: Cl ; NCC1(c2ccc(-c3c(O)ccc4[nH]c(=O)c5sccc5c34)cc2)CC1]

Following the procedure outlined for Example 265, 1-[4-(8-hydroxy-4-oxo-4,5-dihydrothieno[2,3-c]quinolin-9-yl)phenyl]cyclopropanecarbonitrile (80 mg, 0.11 mmol) was reacted with borane (3 mL) and the resulting material was converted to the hydrochloride salt as outlined in General Procedure D-2 to afford the desired product (20 mg, 28%) as a brown solid: $^1$H NMR (500 MHz, CD$_3$OD) δ 7.62 (d, J=8.1 Hz, 2H), 7.58 (d, J=5.4 Hz, 1H), 7.41 (d, J=8.9 Hz, 1H), 7.34 (d, J=8.0 Hz, 2H), 7.18 (d, J=8.9 Hz, 1H), 6.17 (d, J=5.4 Hz, 1H), 3.25 (s, 2H), 1.21-1.12 (m, 4H); ESI MS m/z 363 [C$_{21}$H$_{18}$N$_2$O$_2$S+H]$^+$; HPLC 97.3% (AUC), t$_R$=8.38 min.

Example 345

9-(2-Amino-2,3-dihydro-1H-inden-5-yl)-8-hydroxythieno[2,3-c]quinolin-4(5H)-one Hydrochloride

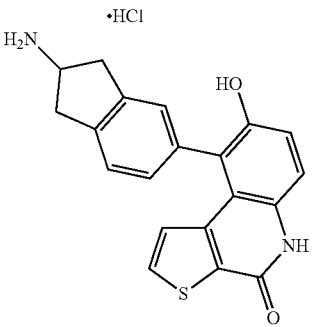 [SMILES: Cl ; NC1Cc2ccc(-c3c(O)ccc4[nH]c(=O)c5sccc5c34)cc2C1]

Following General Procedure F, tert-butyl 5-(8-methoxy-4-oxo-4,5-dihydrothieno[2,3-c]quinolin-9-yl)-2,3-dihydro-1H-inden-2-ylcarbamate (210 mg, 0.59 mmol) was reacted tribromoborane (10 mL) to afford the desired product (55 mg, 27%) as a yellow solid:

Major Isomer: $^1$H NMR (500 MHz, CD$_3$OD) δ 7.56 (d, J=2.4 Hz, 1H), 7.49 (d, J=7.7 Hz, 1H), 7.39 (d, J=1.3 Hz, 1H), 7.26 (s, 1H), 7.19-7.15 (m, 2H), 6.14 (d, J=5.4 Hz, 1H), 4.24-4.20 (m, 1H), 3.62-3.49 (m, 2H), 3.22-3.07 (m, 2H); ESI MS m/z 349 [C$_{20}$H$_{16}$N$_2$O$_2$S+H]$^+$; HPLC 60.4% (AUC), t$_R$=7.89 min;

Minor Isomer: $^1$H NMR (500 MHz, CD$_3$OD) δ 7.55 (d, J=2.4 Hz, 1H), 7.46 (d, J=7.7 Hz, 1H), 7.41 (d, J=1.3 Hz, 1H), 7.24 (s, 1H), 7.19-7.15 (m, 2H), 6.26 (d, J=5.4 Hz, 1H), 4.24-4.20 (m, 1H), 3.62-3.49 (m, 2H), 3.22-3.07 (m, 2H); ESI MS m/z 349 [C$_{20}$H$_{16}$N$_2$O$_2$S+H]$^+$; HPLC 39.5% (AUC), t$_R$=7.65 min.

Example 327

9-{4-[2-(Dimethylamino)ethyl]-3-fluorophenyl}-8-hydroxythieno[2,3-c]quinolin-4(5H)-one Hydrochloride

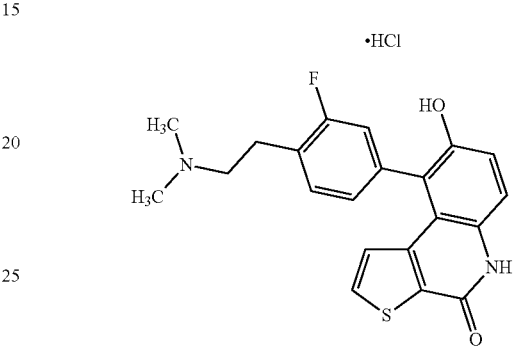

Following General Procedure F, 9-[4-(2-aminoethyl)-3-fluorophenyl]-8-hydroxythieno[2,3-c]quinolin-4(5H)-one (25 mg, 0.063 mmol) was reacted with tribromoborane (3 mL) to afford the desired product (3.5 mg, 13%) as a brown solid: $^1$H NMR (500 MHz, CD$_3$OD) δ 7.62 (d, J=5.4 Hz, 1H), 7.55 (t, J=7.9 Hz, 1H), 7.42 (d, J=8.9 Hz, 1H), 7.18-7.11 (m, 3H), 6.15 (d, J=5.4 Hz, 1H), 3.52 (t, J=8.2 Hz, 2H), 3.26-3.19 (m, 1H), 3.04 (s, 6H); ESI MS m/z 383 [C$_{21}$H$_{19}$FN$_2$O$_2$S+H]$^+$; HPLC 96.2% (AUC), t$_R$=8.06 min.

Example 278

9-{3-Fluoro-4-[(3-hydroxypyrrolidin-1-yl)methyl]phenyl}-8-hydroxythieno[2,3-c]quinolin-4(5H)-one Hydrochloride

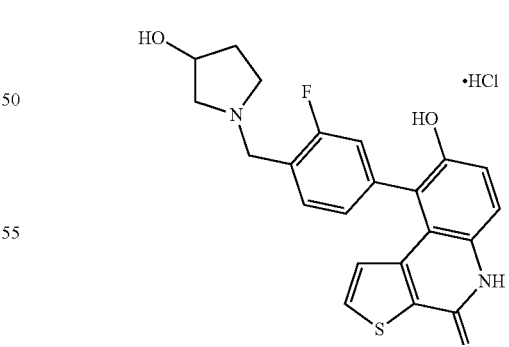

Following General Procedure F, 9-{3-fluoro-4-[(3-hydroxypyrrolidin-1-yl)methyl]phenyl}-8-methoxythieno[2,3-c]quinolin-4(5H)-one (90 mg, 0.21 mmol) was reacted with tribromoborane (2 mL) to afford the desired product (32 mg, 34%) as a light yellow solid: $^1$H NMR (500 MHz, CD$_3$OD) δ 7.78-7.75 (m, 1H), 7.65 (d, J=5.3 Hz, 1H), 7.44 (d, J=8.9 Hz, 1H), 7.30-7.27 (m, 2H), 7.19 (d, J=8.9 Hz, 1H), 6.15-6.13 (m, 1H), 4.76-4.57 (m, 3H), 3.86-3.72 (m, 1H), 3.62-3.53 (m, 1H), 3.49-3.40 (m, 1H), 2.78 (br s, 1H), 2.54-2.46 (m, 1H), 2.22-2.20 (m, 1H), 2.15-2.05 (m, 1H); ESI MS m/z 411 $[C_{22}H_{19}FN_2O_3S+H]^+$; HPLC >99% (AUC), $t_R$=7.58 min.

Example 277

9-[4-(1-Amino-2-methylpropan-2-yl)phenyl]-8-hydroxythieno[2,3-c]quinolin-4(5H)-one Hydrochloride

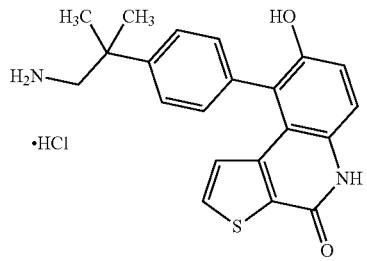 [SMILES: Cl ; CC(C)(CN)c1ccc(-c2c(O)ccc3[nH]c(=O)c4sccc4c23)cc1]

Following General Procedure F, 9-[4-(1-amino-2-methylpropan-2-yl)phenyl]-8-methoxythieno[2,3-c]quinolin-4(5H)-one (100 mg, 0.27 mmol) was reacted with tribromoborane (3 mL) to afford the desired product (25 mg, 22%) as an off-white solid: $^1$H NMR (500 MHz, CD$_3$OD) δ 7.66 (d, J=8.4 Hz, 2H), 7.59 (d, J=5.4 Hz, 1H), 7.42 (d, J=8.9 Hz, 1H), 7.37 (d, J=8.3 Hz, 2H), 7.19 (d, J=8.9 Hz, 1H), 6.16 (d, J=5.4 Hz, 1H), 3.28 (s, 2H), 1.59 (s, 6H); ESI MS m/z 365 $[C_{21}H_{20}N_2O_2S+H]^+$; HPLC 96.9% (AUC), $t_R$=9.47 min.

Example 276

9-[4-(2-Aminoethyl)-3-fluorophenyl]-8-hydroxythieno[2,3-c]quinolin-4(5H)-one Hydrochloride

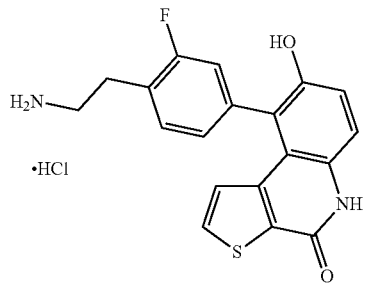 [SMILES: Cl ; NCCc1ccc(-c2c(O)ccc3[nH]c(=O)c4sccc4c23)cc1F]

Following General Procedure F, 9-[4-(2-aminoethyl)-3-fluorophenyl]-8-methoxythieno[2,3-c]quinolin-4(5H)-one (260 mg, 0.71 mmol) was reacted with tribromoborane (6 mL) to afford the desired product (12 mg, 12%) as a light yellow solid: $^1$H NMR (500 MHz, CD$_3$OD) δ 7.63 (d, J=5.4 Hz, 1H), 7.52-7.49 (m, 1H), 7.42 (d, J=8.9 Hz, 1H), 7.17 (d, J=8.9 Hz, 1H), 7.15-7.12 (m, 2H), 6.20 (d, J=5.4 Hz, 1H), 3.30-3.23 (m, 2H), 3.12-3.06 (m, 2H), 2.79 (br s, 3H); ESI MS m/z 355 $[C_{19}H_{15}FN_2O_2S+H]^+$; HPLC 94.9% (AUC), $t_R$=7.80 min.

Example 275

(R)-9-[4-(1-Aminoethyl)phenyl]-8-hydroxythieno[2,3-c]quinolin-4(5H)-one Hydrochloride

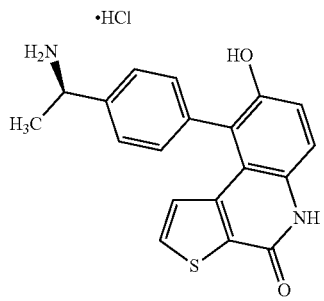 [SMILES: Cl ; C[C@@H](N)c1ccc(-c2c(O)ccc3[nH]c(=O)c4sccc4c23)cc1]

Following General Procedure F, (R)-tert-butyl 1-[4-(8-methoxy-4-oxo-4,5-dihydrothieno[2,3-c]quinolin-9-yl)phenyl]ethylcarbamate (350 mg, 0.78 mmol) was reacted with tribromoborane (15 mL) to afford the desired product (120 mg, 42%) as an off-white solid: $^1$H NMR (500 MHz, CD$_3$OD) δ 7.65-7.62 (m, 2H), 7.55 (d, J=5.4 Hz, 1H), 7.42-7.41 (m, 3H), 7.17 (d, J=8.9 Hz, 1H), 6.08 (d, J=5.4 Hz, 1H), 4.61 (q, J=4.5 Hz, 1H), 2.78 (br s, 3H), 1.76 (d, J=6.9 Hz, 3H); ESI MS m/z 337$[C_{19}H_{16}N_2O_2S+H]^+$; HPLC >99% (AUC), $t_R$=7.49 min.

Example 273

9-[4-(3-Aminopropyl)phenyl]-8-hydroxythieno[2,3-c]quinolin-4(5H)-one Hydrochloride

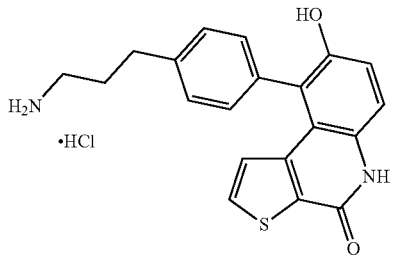 [SMILES: NCCCc1ccc(-c2c(O)ccc3[nH]c(=O)c4sccc4c23)cc1 ; Cl]

Following General Procedure F, 9-[4-(3-aminopropyl)phenyl]-8-methoxythieno[2,3-c]quinolin-4(5H)-one (140 mg, 0.39 mmol) was reacted with tribromoborane (6 mL) to afford the desired product (18 mg, 12%) as a light yellow solid: $^1$H NMR (500 MHz, CD$_3$OD) δ 7.53 (d, J=5.5 Hz, 1H), 7.43 (d, J=8.0 Hz, 2H), 7.39 (d, J=8.9 Hz, 1H), 7.26 (d, J=8.1 Hz, 2H), 7.16 (d, J=8.9 Hz, 1H), 6.02 (d, J=5.5 Hz, 1H), 3.04 (t, J=7.7

Hz, 2H), 2.88 (t, J=7.7 Hz, 2H), 2.11-2.08 (m, 2H); ESI MS m/z 351 [$C_{20}H_{18}N_2O_2S$+H]$^+$; HPLC 96.2%, $t_R$=8.91 min.

Example 65

4-(8-Hydroxy-4-oxo-4,5-dihydrothieno[2,3-c]quinolin-9-yl)benzenesulfonamide

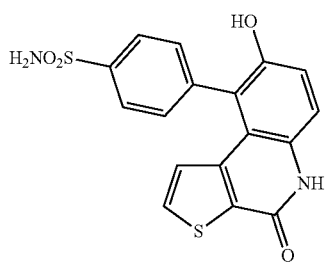 [SMILES: NS(=O)(=O)c1ccc(-c2c(O)ccc3[nH]c(=O)c4sccc4c23)cc1]

Following General Procedure F, N-tert-butyl-4-(8-methoxy-4-oxo-4,5-dihydrothieno[2,3-c]quinolin-9-yl)benzenesulfonamide (4.3 g, 9.9 mmol) was reacted with tribromoborane (1.0 M in methylene chloride, 48 mL, 48 mmol) to afford the desired product (3.4 g, 94%) as a light red solid: $^1$H NMR (300 MHz, DMSO-$d_6$) δ 11.83 (s, 1H), 9.12 (s, 1H), 7.96-7.95 (m, 2H), 7.76 (d, J=5.4 Hz, 1H), 7.48-7.47 (m, 4H), 7.41 (d, J=8.9 Hz, 1H), 7.18 (d, J=8.9 Hz, 1H), 5.91 (d, J=5.4 Hz, 1H); ESI MS m/z 373 [$C_{17}H_{12}N_2O_4S_2$+H]$^+$; HPLC 98.1% (AUC), $t_R$=10.29 min.

Example 61

8-Hydroxy-9-(1H-indazol-6-yl)thieno[2,3-c]quinolin-4(5H)-one

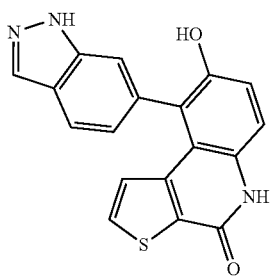 [SMILES: O=c1[nH]c2ccc(O)c(-c3ccc4cn[nH]c4c3)c2c2ccsc12]

Following General Procedure F, 9-(1H-indazol-6-yl)-8-methoxythieno[2,3-c]quinolin-4(5H)-one (35 mg, 0.10 mmol) was reacted with tribromoborane (1.5 mL, 0.15 mmol) to afford the desired product (3.6 mg, 11%) as a light brown solid: $^1$H NMR (500 MHz, CD$_3$OD) δ 8.17 (s, 1H), 7.75-7.73 (m, 2H), 7.48 (d, J=5.5 Hz, 1H), 7.42 (d, J=8.9 Hz, 1H), 7.34 (d, J=9.2 Hz, 1H), 7.19 (d, J=8.9 Hz, 1H), 5.91 (d, J=5.5 Hz, 1H); ESI MS m/z 334 [$C_{18}H_{11}N_3O_2S$+H]$^+$; HPLC 96.3% (AUC), $t_R$=9.20 min.

Example 193

N-{1-[4-(8-Hydroxy-4-oxo-4,5-dihydrothieno[2,3-c]quinolin-9-yl)phenyl]ethyl}methanesulfonamide

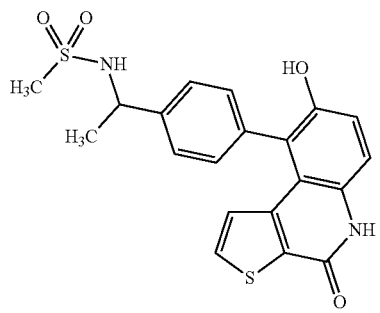 [SMILES: CC(NS(C)(=O)=O)c1ccc(-c2c(O)ccc3[nH]c(=O)c4sccc4c23)cc1]

A solution of 9-[4-(1-aminoethyl)phenyl]-8-hydroxythieno[2,3-c]quinolin-4(5H)-one (30 mg, 0.089 mmol) and methanesulfonyl chloride (9.0 µL, 0.11 mmol) in 2:1 methylene chloride/THF (3 mL) was stirred at room temperature for 10 min followed by the addition of N,N-diisopropylethylamine (19 µL, 0.11 mmol). The reaction mixture was stirred for 1.5 h, concentrated and purified by preparatory HPLC (C18 silica, water/acetonitrile w/0.05% TFA gradient) to afford the desired product (7.2 mg, 20%) as an amorphous brown solid: $^1$H NMR (500 MHz, CD$_3$OD) δ 7.57-7.56 (m, 2H), 7.53 (d, J=5.4 Hz, 1H), 7.39 (d, J=8.9 Hz, 1H), 7.32-7.30 (m, 2H), 7.16 (d, J=8.9 Hz, 1H), 6.02 (d, J=5.4 Hz, 1H), 4.71 (q, J=4.6 Hz, 1H), 2.82 (s, 3H), 1.62 (d, J=7.0 Hz, 3H); ESI MS m/z 415 [$C_{20}H_{18}N_2O_4S_2$+H]$^+$; HPLC >99%, $t_R$=10.18 min.

Example 175

9-[4-(2-Aminoethyl)phenyl]-8-hydroxythieno[2,3-c]quinolin-4(5H)-one

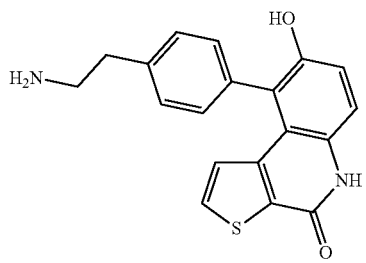 [SMILES: NCCc1ccc(-c2c(O)ccc3[nH]c(=O)c4sccc4c23)cc1]

Following General Procedure F, 9-[4-(2-aminoethyl)phenyl]-8-methoxythieno[2,3-c]quinolin-4(5H)-one (800 mg, 1.8 mmol) was reacted with tribromoborane (10 mL) to afford the desired product (520 mg, 88%) as an off-white solid: $^1$H NMR (500 MHz, DMSO-$d_6$) δ 11.78 (s, 1H), 9.20 (s, 1H), 7.88 (br s, 2H), 7.69 (d, J=5.4 Hz, 1H), 7.41-7.36 (m, 3H), 7.22 (d, J=8.1 Hz, 2H), 7.15 (d, J=8.9 Hz, 1H), 5.88 (d, J=5.4

Hz, 1H), 3.21-3.14 (m, 2H), 3.01-2.98 (m, 2H); ESI MS m/z 337 [$C_{19}H_{16}N_2O_2S$+H]$^+$; HPLC >99% (AUC), $t_R$=7.72 min.

Example 176

9-[4-(2-Aminoethyl)phenyl]-8-hydroxythieno[2,3-c]quinolin-4(5H)-one Hydrochloride

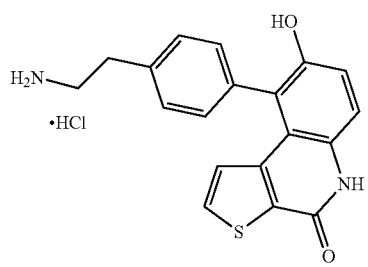 [SMILES: NCCc1ccc(-c2c(O)ccc3[nH]c(=O)c4sccc4c23)cc1 ; Cl]

Following General Procedure F, 9-[4-(2-aminoethyl)phenyl]-8-methoxythieno[2,3-c]quinolin-4(5H)-one (800 mg, 1.8 mmol) was reacted with tribromoborane (10 mL) and the resulting material was converted to the hydrochloride salt as outlined in General Procedure D-2 to afford the desired product (520 mg, 88%) as an off-white solid: $^1$H NMR (500 MHz, DMSO-$d_6$) δ 11.78 (s, 1H), 9.20 (s, 1H), 7.88 (br s, 2H), 7.69 (d, J=5.4 Hz, 1H), 7.41-7.36 (m, 3H), 7.22 (d, J=8.1 Hz, 2H), 7.15 (d, J=8.9 Hz, 1H), 5.88 (d, J=5.4 Hz, 1H), 3.21-3.14 (m, 2H), 3.01-2.98 (m, 2H); ESI MS m/z 337 [$C_{19}H_{16}N_2O_2S$+H]$^+$; HPLC >99% (AUC), $t_R$=7.72 min.

Example 112

8-Hydroxy-9-{4-[4-(methylsulfonyl)piperazin-1-yl]phenyl}thieno[2,3-c]quinolin-4(5H)-one

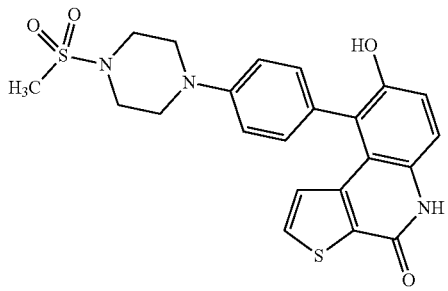 [SMILES: CS(=O)(=O)N1CCN(c2ccc(-c3c(O)ccc4[nH]c(=O)c5sccc5c34)cc2)CC1]

Following General Procedure F, 8-methoxy-9-{4-[4-(methylsulfonyl)piperazin-1-yl]phenyl}thieno[2,3-c]quinolin-4(5H)-one (32 mg, 0.068 mmol) was reacted with tribromoborane (1.0 mL) to afford the desired product (5.2 mg, 17%) as an off-white solid: $^1$H NMR (500 MHz, CD$_3$OD) δ 7.58 (d, J=5.4 Hz, 1H), 7.37 (d, J=8.9 Hz, 1H), 7.20 (s, 4H), 7.15 (d, J=8.9 Hz, 1H), 6.16 (d, J=5.4 Hz, 1H), 3.44-3.43 (m, 8H), 2.92 (s, 3H); ESI MS m/z 456[$C_{22}H_{21}N_3O_4S_2$+H]$^+$; HPLC >99%, $t_R$=10.47 min.

Example 95

9-[4-(Aminomethyl)phenyl]-8-hydroxy-2-methylthieno[2,3-c]quinolin-4(5H)-one

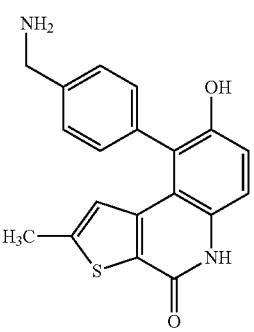 [SMILES: Cc1cc2c(s1)c(=O)[nH]c1ccc(O)c(-c3ccc(CN)cc3)c12]

Following General Procedure F, tert-butyl 4-(8-methoxy-2-methyl-4-oxo-4,5-dihydrothieno[2,3-c]quinolin-9-yl)benzylcarbamate (80 mg, 0.17 mmol) was reacted with tribromoborane (2.0 mL) to afford the desired product (20 mg, 37%) as an off-white solid: $^1$H NMR (500 MHz, CD$_3$OD) δ 7.63 (d, J=8.9 Hz, 2H), 7.40-7.37 (m, 3H), 7.15 (d, J=8.1 Hz, 1H), 5.76 (s, 1H), 4.28 (s, 2H), 2.33 (s, 3H); ESI MS m/z 337 [$C_{19}H_{16}N_2O_2S$+H]$^+$; HPLC >99%, $t_R$=5.91 min.

Example 84

8-Hydroxy-9-(1,2,3,6-tetrahydropyridin-4-yl)thieno[2,3-c]quinolin-4(5H)-one

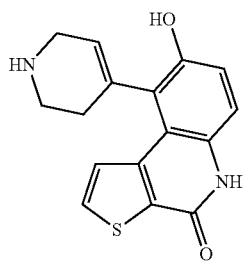 [SMILES: O=c1[nH]c2ccc(O)c(C3=CCNCC3)c2c2ccsc12]

Following General Procedure B, 9-bromo-8-(tert-butyldimethylsilyloxy)thieno[2,3-c]quinolin-4(5H)-one (80 mg, 0.20 mmol) was reacted with tert-butyl 4-(4,4,5,5-tetramethyl-1,3,2-dioxaborolan-2-yl)cyclohex-3-enylcarbamate (90 mg, 0.29 mmol) to afford the desired product (140 mg, 23%) as an off-white solid: $^1$H NMR (500 MHz, CD$_3$OD) δ 8.01-7.98 (m, 2H), 7.35 (d, J=8.9 Hz, 1H), 7.12 (d, J=8.9 Hz, 1H), 5.80 (s, 1H), 4.01-3.91 (m, 2H), 3.63-3.60 (m, 2H), 2.88-2.84 (m, 1H), 2.57-2.53 (m, 1H); ESI MS m/z 299 [$C_{16}H_{14}N_2O_2S$+H]$^+$; HPLC >99% (AUC), $t_R$=6.70 min.

Example 77

N-[4-(8-Hydroxy-4-oxo-4,5-dihydrothieno[2,3-c]quinolin-9-yl)phenyl]methanesulfonamide

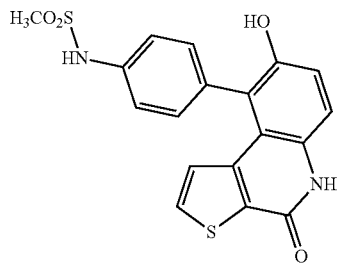

Following General Procedure F, N-[4-(8-methoxy-4-oxo-4,5-dihydrothieno[2,3-c]quinolin-9-yl)phenyl]methanesulfonamide (40 mg, 0.10 mmol) was reacted with tribromoborane (3.0 mL) to afford the desired product (3.8 mg, 10%) as an off-white solid: $^1$H NMR (500 MHz, CD$_3$OD) δ 7.61 (d, J=5.4 Hz, 1H), 7.44-7.43 (m, 2H), 7.39 (d, J=5.4 Hz, 1H), 7.29-7.27 (m, 2H), 7.16 (d, J=8.4 Hz, 1H), 6.12 (d, J=5.0 Hz, 1H), 3.09 (s, 3); ESI MS m/z 387 [$C_{18}H_{14}N_2O_4S_2$+H]$^+$; HPLC >99%, $t_R$=9.69 min.

Example 196

9-{4-[1-(Diethylamino)ethyl]phenyl}-8-hydroxythieno[2,3-c]quinolin-4(5H)-one Hydrochloride

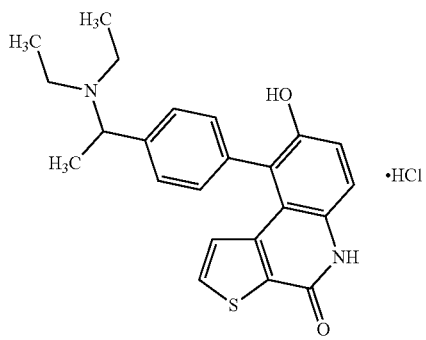 [SMILES: CCN(CC)C(C)c1ccc(-c2c(O)ccc3[nH]c(=O)c4sccc4c23)cc1 ; Cl]

Following the procedure outlined for Example 460, 9-[4-(1-aminoethyl)phenyl]-8-hydroxythieno[2,3-c]quinolin-4(5H)-one (30 mg, 0.081 mmol) was reacted with formaldehyde (37% in water, 15 mg, 0.26 mmol) and the resulting material was converted to the hydrochloride salt as outlined in General Procedure D-2 to afford the desired product (7.2 mg, 21%) as a light brown solid: $^1$H NMR (500 MHz, CD$_3$OD) δ 7.73 (q, J=6.9 Hz, 2H), 7.58 (d, J=5.4 Hz, 1H), 7.48-7.45 (m, 2H), 7.43 (d, J=8.9 Hz, 1H), 7.19 (d, J=8.9 Hz, 1H), 6.02 (d, J=5.4 Hz, 1H), 4.78 (q, J=4.7 Hz, 1H), 3.51-3.34 (m, 3H), 3.19-3.12 (m, 1H), 1.86 (d, J=6.9 Hz, 3H), 1.43 (t, J=7.3 Hz, 3H), 1.37 (t, J=7.3 Hz, 3H); ESI MS m/z 393 [$C_{23}H_{24}N_2O_2S$+H]$^+$; HPLC >99% (AUC), $t_R$=8.29 min.

Example 195

9-[4-(1-Aminoethyl)phenyl]-8-hydroxythieno[2,3-c]quinolin-4(5H)-one Hydrochloride

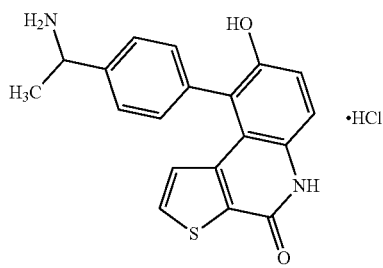 [SMILES: CC(N)c1ccc(-c2c(O)ccc3[nH]c(=O)c4sccc4c23)cc1 ; Cl]

Following General Procedure F, tert-butyl 1-[4-(8-methoxy-4-oxo-4,5-dihydrothieno[2,3-c]quinolin-9-yl)phenyl]ethylcarbamate (320 mg, 0.71 mmol) was reacted with tribromoborane (10 mL) to afford the desired product (160 mg, 59%) as a light brown solid: $^1$H NMR (500 MHz, CD$_3$OD) δ 7.64-7.63 (m, 2H), 7.55 (d, J=5.4 Hz, 1H), 7.43-7.40 (m, 3H), 7.17 (d, J=8.9 Hz, 1H), 6.08 (d, J=5.4 Hz, 1H), 4.61 (q, J=6.9 Hz, 1H), 1.76 (d, J=6.9 Hz, 3H); ESI MS m/z 337 [$C_{19}H_{16}N_2O_2S$+H]$^+$; HPLC 98.1% (AUC), $t_R$=7.63 min.

Example 194

8-Hydroxy-9-{4-[1-(pyrrolidin-1-yl)ethyl]phenyl}thieno[2,3-c]quinolin-4(5H)-one Hydrochloride

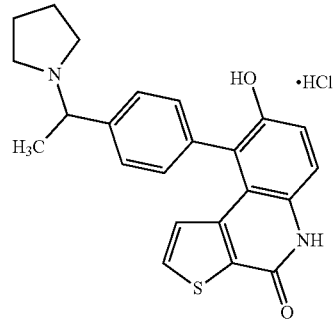 [SMILES: CC(c1ccc(-c2c(O)ccc3[nH]c(=O)c4sccc4c23)cc1)N1CCCC1 ; Cl]

Following General Procedure F, 8-methoxy-9-{4-[1-(pyrrolidin-1-yl)ethyl]phenyl}thieno[2,3-c]quinolin-4(5H)-one (70 mg, 0.17 mmol) was reacted with tribromoborane (2.0 mL) to afford the desired product (43 mg, 58%) as an off-white solid: $^1$H NMR (500 MHz, CD$_3$OD) δ 7.70-7.66 (m, 2H), 7.59 (d, J=5.4 Hz, 1H), 7.48-7.44 (m, 2H), 7.42 (d, J=8.9 Hz, 1H), 7.18 (d, J=8.9 Hz, 1H), 6.01 (d, J=5.4 Hz, 1H), 4.53 (q, J=6.8 Hz, 1H), 3.45 (br s, 1H), 3.20-3.10 (m, 1H), 2.20-

2.00 (m, 4H), 1.87 (d, J=6.9 Hz, 3H); ESI MS m/z 391 [C$_{23}$H$_{22}$N$_2$O$_2$S+H]$^+$; HPLC >99%, t$_R$=8.21 min.

Example 272

(R)-9-{4-[1-(Dimethylamino)ethyl]phenyl}-8-hydroxythieno[2,3-c]quinolin-4(5H)-one Hydrochloride

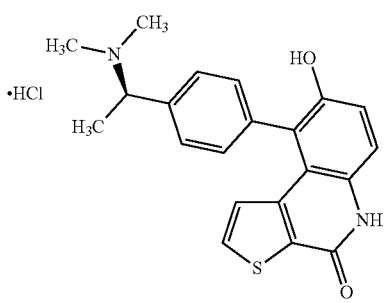 [SMILES: Cl ; C[C@H](c1ccc(-c2c(O)ccc3[nH]c(=O)c4sccc4c23)cc1)N(C)C]

Following the procedure outlined for Example 460, (R)-9-[4-(1-aminoethyl)phenyl]-8-hydroxythieno[2,3-c]quinolin-4(5H)-one (50 mg, 0.15 mmol) was reacted with formaldehyde (14 mL, 0.45 mmol) and the resulting material was converted to the hydrochloride salt as outlined in General Procedure D-2 to afford the desired product (12 mg, 20%) as an off-white solid: $^1$H NMR (500 MHz, CD$_3$OD) δ 7.71 (q, J=2.6 Hz, 2H), 7.59 (d, J=5.4 Hz, 1H), 7.48 (t, J=7.5 Hz, 2H), 7.43 (d, J=8.9 Hz, 1H), 7.19 (d, J=8.9 Hz, 1H), 6.02 (d, J=5.4 Hz, 1H), 4.66 (q, J=7.1 Hz, 1H), 2.97 (s, 3H), 2.87 (s, 3H), 1.86 (d, J=7.0 Hz, 3H); ESI MS m/z 365 [C$_{21}$H$_{20}$N$_2$O$_2$S+H]$^+$; HPLC 97.1% (AUC), t$_R$=8.57 min.

Example 262

8-Hydroxy-9-{4-[1-(piperidin-1-yl)ethyl]phenyl}thieno[2,3-c]quinolin-4(5H)-one Hydrochloride

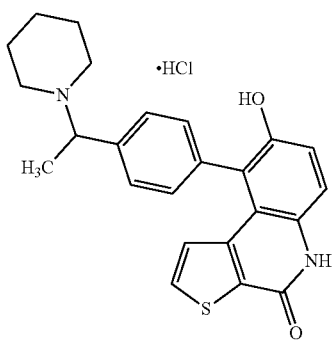 [SMILES: CC(c1ccc(-c2c(O)ccc3[nH]c(=O)c4sccc4c23)cc1)N1CCCCC1 ; Cl]

Following General Procedure F, 8-methoxy-9-{4-[1-(piperidin-1-yl)ethyl]phenyl}thieno[2,3-c]quinolin-4(5H)-one (40 mg, 0.096 mmol) was reacted with tribromoborane (1.0 mL) to afford the desired product (4.9 mg, 13%) as a yellow solid: $^1$H NMR (500 MHz, CD$_3$OD) δ 7.73 (d, J=8.4 Hz, 1H), 7.68 (d, J=7.8 Hz, 1H), 7.58 (d, J=5.5 Hz, 1H), 7.48-7.42 (m, 3H), 7.19 (d, J=8.9 Hz, 1H), 6.01 (d, J=5.4 Hz, 1H), 4.60 (q, J=4.5 Hz, 1H), 3.79 (d, J=12.0 Hz, 1H), 3.50 (d, J=11.7 Hz, 1H), 3.02 (t, J=11.3 Hz, 1H), 2.89 (t, J=6.0 Hz, 1H), 2.09-1.72 (m, 8H), 1.55-1.45 (m, 1H); ESI MS m/z 405 [C$_{24}$H$_{24}$N$_2$O$_2$S+H]$^+$; HPLC 95.0% (AUC), t$_R$=7.83 min.

Example 261

2-[2-Fluoro-4-(8-hydroxy-4-oxo-4,5-dihydrothieno[2,3-c]quinolin-9-yl)phenyl]acetonitrile

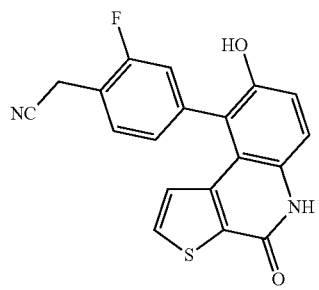 [SMILES: N#CCc1ccc(-c2c(O)ccc3[nH]c(=O)c4sccc4c23)cc1F]

Following General Procedure F, 2-[2-fluoro-4-(8-hydroxy-4-oxo-4,5-dihydrothieno[2,3-c]quinolin-9-yl)phenyl]acetonitrile (42 mg, 1.2 mmol) was reacted with tribromoborane (12 mL, 12 mmol) to afford the desired product (22 mg, 55%) as a light brown solid: $^1$H NMR (500 MHz, CD$_3$OD) δ 7.65 (m, 2H), 7.42 (d, J=8.9 Hz, 1H), 7.19-7.14 (m, 3H), 6.16 (d, J=5.5 Hz, 1H), 4.07 (s, 2H); ESI MS m/z 351 [C$_{19}$H$_{11}$FN$_2$O$_2$S+H]$^+$; HPLC 97.1% (AUC), t$_R$=13.67 min.

Example 81

2-[4-(8-Hydroxy-4-oxo-4,5-dihydrothieno[2,3-c]quinolin-9-yl)phenyl]acetonitrile

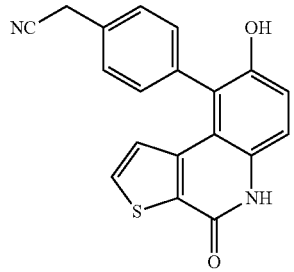 [SMILES: N#CCc1ccc(-c2c(O)ccc3[nH]c(=O)c4sccc4c23)cc1]

Following General Procedure B, 9-bromo-8-(tert-butyldimethylsilyloxy)thieno[2,3-c]quinolin-4(5H)-one (50 mg, 0.12 mmol) was reacted with 4-(cyanomethyl)phenylboronic acid (26 mg, 0.18 mmol) to afford the TBS protected intermediate which was treated with aqueous lithium hydroxide to afford the desired product (20 mg, 50%) as an off-white solid: $^1$H NMR (500 MHz, DMSO-d$_6$) δ 9.28 (s, 1H), 7.73 (d, J=5.4 Hz, 1H), 7.50 (d, J=8.1 Hz, 2H), 7.38 (d, J=8.9 Hz, 1H), 7.29 (d, J=8.1 Hz, 2H), 7.18 (m, 1H), 5.90 (d, J=5.4 Hz, 1H), 4.19 (s, 2H); ESI MS m/z 333 [C$_{19}$H$_{12}$N$_2$O$_2$S+H]$^+$; HPLC 96.2% (AUC), t$_R$=12.07 min.

Example 346

9-{4-[1-(Dimethylamino)ethyl]phenyl}thieno[2,3-c]quinolin-4(5H)-one

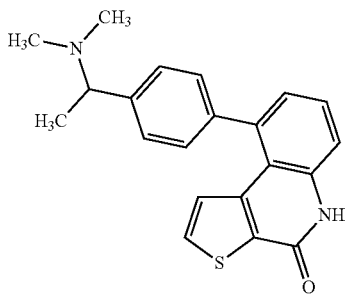 [SMILES: CC(c1ccc(-c2cccc3[nH]c(=O)c4sccc4c23)cc1)N(C)C]

To a solution of 9-{4-[1-(dimethylamino)ethyl]phenyl}-8-hydroxythieno[2,3-c]quinolin-4(5H)-one (350 mg, 1.0 mmol) in anhydrous THF (20 mL) at 0° C. was added sodium hydride (60 wt %, 160 mg, 5.0 mmol) and the reaction mixture was heated to 60° C. for 1 h. The reaction mixture was cooled to 0° C. and trifluoro-N-phenyl-N-[(trifluoromethyl)sulfonyl]methanesulfonamide (450 mg, 1.1 mmol) was added and the reaction mixture was warmed to room temperature and stirred for 1 h. The reaction mixture was quenched with satd. aq. ammonium chloride and the layers were separated. The aqueous layer was extracted with 3:1 chloroform/isopropanol and the combined organic layers were dried over anhydrous sodium sulfate, filtered, and concentrated to afford the crude triflate (400 mg) as a brown solid. The crude triflate was dissolved in anhydrous DMF (30 mL) was degassed for 10 min followed by the addition of triethylamine (1.7 mL, 12 mmol), 1,1'-bis(diphenylphosphino)ferrocene dichloropalladium(II) (70 mg, 0.080 mmol), and formic acid (0.3 mL, 8.00 mmol). The reaction mixture was heated at 100° C. for 24 h, cooled, concentrated, and the residue was purified by preparatory HPLC (C18 silica, water/acetonitrile w/0.05% TFA gradient) to afford the desired product (60 mg, 21% for two steps) as a white solid: $^1$H NMR (500 MHz, CDCl$_3$) δ 12.00 (s, 1H), 7.61 (d, J=8.0 Hz, 1H), 7.51 (t, J=7.7 Hz, 1H), 7.45-7.42 (m, 3H), 7.35-7.34 (m, 2H), 7.16 (d, J=7.2 Hz, 1H), 6.30 (d, J=5.4 Hz, 1H), 3.45 (d, J=6.3 Hz, 1H), 2.32 (s, 6H), 1.50 (d, J=6.6 Hz, 3H); ESI MS m/z 349 [C$_{21}$H$_{20}$N$_2$OS+H]$^+$; HPLC 98.5% (AUC), t$_R$=10.86 min.

Example 461

9-{4-[(tert-Butoxycarbonylamino)methyl]phenyl}-4-oxo-4,5-dihydrothieno[2,3-c]quinolin-8-yl Trifluoromethanesulfonate

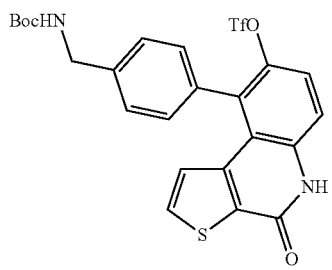 [SMILES: CC(C)(C)OC(=O)NCc1ccc(-c2c(OS(=O)(=O)C(F)(F)F)ccc3[nH]c(=O)c4sccc4c23)cc1]

To a solution of tert-butyl 4-(8-hydroxy-4-oxo-4,5-dihydrothieno[2,3-c]quinolin-9-yl)benzylcarbamate (150 mg, 0.36 mmol) in THF (3 mL) at 0° C. was added sodium hydride (60 wt %, 18 mg, 0.44 mmol) and the reaction mixture was stirred at 0° C. for 1 h. N-Phenyl-bis(trifluoromethanesulfonimide) (160 mg, 0.44 mmol) was added and the reaction mixture was warmed to room temperature and stirred for 18 h. The reaction mixture was quenched with water and the aqueous layer was extracted with methylene chloride. The combined organic layers were dried over anhydrous sodium sulfate, filtered, concentrated and the residue was purified by column chromatography (silica, methanol/methylene chloride gradient) to afford the desired product (200 mg, 98%): ESI MS m/z 555 [C$_{24}$H$_{21}$F$_3$N$_2$O$_6$S$_2$+H]$^+$.

Example 462 tert-Butyl 4-(8-Cyano-4-oxo-4,5-dihydrothieno[2,3-c]quinolin-9-yl)benzylcarbamate

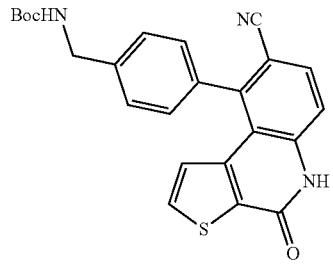 [SMILES: CC(C)(C)OC(=O)NCc1ccc(-c2c(C#N)ccc3[nH]c(=O)c4sccc4c23)cc1]

A solution of 9-{4-[(tert-butoxycarbonylamino)methyl]phenyl}-4-oxo-4,5-dihydrothieno[2,3-c]quinolin-8-yl trifluoromethanesulfonate (176 mg, 0.320 mmol), zinc chloride (75 mg, 0.640 mmol), 1,1'-bis(diphenylphosphino)ferrocene (18 mg, 0.032 mmol), and tris(dibenzylideneacetone)dipalladium(0) (15 mg, 0.016 mmol) in anhydrous DMF (4 mL) was heated at 130° C. for 3 h. The reaction mixture was cooled, quenched with water and the resulting precipitate was filtered and purified by column chromatography (silica, methanol/methylene chloride gradient) to afford the desired product (120 mg, 87%) as a brown solid: ESI MS m/z 432 [C$_{24}$H$_{21}$N$_3$O$_3$S+H]$^+$.

Example 326

9-[4-(Aminomethyl)phenyl]-4-oxo-4,5-dihydrothieno[2,3-c]quinoline-8-carbonitrile Hydrochloride

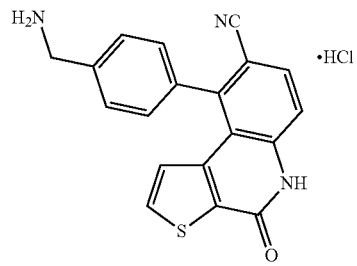 [SMILES: N#Cc1ccc2[nH]c(=O)c3sccc3c2c1-c1ccc(CN)cc1 ; Cl]

Following General Procedure D-3, tert-butyl 4-(8-cyano-4-oxo-4,5-dihydrothieno[2,3-c]quinolin-9-yl)benzylcarbamate (10 mg, 0.023 mmol) was reacted with 4 N HCl (3 mL) to afford the desired product (7.4 mg, 74%) as a dark brown solid: $^1$H NMR (500 MHz, CD$_3$OD) δ 7.89 (d, J=8.6 Hz, 1H), 7.74 (t, J=9.5 Hz, 2H), 7.65 (dd, J=14.4, 7.0 Hz, 2H), 7.55-7.53 (m, 2H), 6.08 (d, J=5.4 Hz, 1H), 4.32 (s, 2H); ESI MS m/z 330 [C$_{19}$H$_{13}$N$_3$OS–H]$^-$; HPLC 98.3% (AUC), t$_R$=9.36 min.

Example 627

(S)-4-benzyl-3-(2-(4-bromo-2-fluorophenyl)acetyl)oxazolidin-2-one

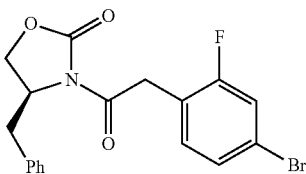 [SMILES: O=C(Cc1ccc(Br)cc1F)N1C(=O)OC[C@@H]1Cc1ccccc1]

To a solution of (2-(4-bromo-2-fluorophenyl)acetic acid) (3 g, 13 mmol) and triethylamine (2.5 mL, 14 mmol) in toluene (50 mL) at 0° C. was added trimethylacetyl chloride (6.1 mL, 65 mmol) dropwise. After 10 mins the reaction mixture was cooled to −78° C. In a separate flask, to a solution of (S-(+)-4-benzyl-2-oxazolidinone (2.5 g, 14 mmol) in tetrahydrofuran (50 mL) at −78° C. was added LiHMDS (1 M in hexane, 17 mL, 17 mmol)) until yellowish color persisted. After 10 mins the resulting solution was transferred through a cannula into the suspension of mixed anhydride prepared as described above. The reaction mixture was allowed to reach rt over the period of 4 h, then diluted with saturated aqueous sodium bisulfate (ca. 20 mL), and extracted with ethyl acetate (ca. 100 mL). The extract was washed with brine (2×50 mL), dried over sodium sulfate, and evaporated under vacuum. Flash chromatography of the residue followed by trituration (hexanes) afforded the desired product (2.1 g, 42%) as white solid. ESI MS m/z 393 $[C_{18}H_{15}BrFNO_3+H]^+$

Example 628

(R)-4-benzyl-3-(2-(4-bromo-2-fluorophenyl)acetyl)oxazolidin-2-one

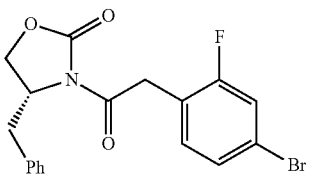 [SMILES: O=C(Cc1ccc(Br)cc1F)N1C(=O)OC[C@H]1Cc1ccccc1]

Following the procedure outlined for Example 627, (2-(4-bromo-2-fluorophenyl)acetic acid) (10.8 g, 30.7 mmol) reacted with (S)-(+)-4-benzyl-2-oxazolidinone (5.44 g, 30.7 mmol) to obtain the desired product (4.5 g, 36%) as white solid. ESI MS nm/393 $[C_{18}H_{15}BrFNO_3+H]^+$

Example 629

(S)-4-benzyl-3-((S)-2-(4-bromo-2-fluorophenyl)propanoyl)oxazolidin-2-one

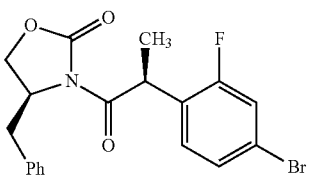 [SMILES: C[C@H](C(=O)N1C(=O)OC[C@@H]1Cc1ccccc1)c1ccc(Br)cc1F]

To a solution of (S)-4-benzyl-3-(2-(4-bromo-2-fluorophenyl)acetyl)oxazolidin-2-one (3.6 g, 9.2 mmol) in THF (40 mL) was added a solution of methyl iodide (1 M solution in toluene, 9.6 mL, 9.6 mmol). The mixture was cooled to −78° C. and a solution of sodium bis(trimethylsilyl)amide (1 M in THF, 9.6 mL, 9.6 mmol) was added dropwise. The resultant dark red mixture was stirred for 15 min at ca. −78° C. and allowed to warm up to room temperature. After 3.5 h the reaction mixture was diluted with saturated aqueous sodium bisulfate (ca. 20 mL), and extracted with ethyl acetate (1×50 mL). The extract was washed with brine (2×50 mL), dried over sodium sulfate, and evaporated under vacuum. Flash chromatography of the residue afforded the desired product (1.7 g, 45%) as light yellow solid: ESI MS m/z 407 $[C_{19}H_{17}BrFNO_3+H]+$

Example 630

(R)-4-benzyl-3-((R)-2-(4-bromo-2-fluorophenyl)propanoyl)oxazolidin-2-one

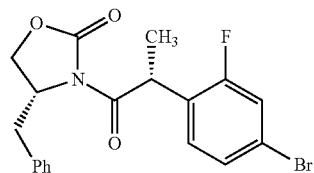 [SMILES: C[C@@H](C(=O)N1C(=O)OC[C@H]1Cc1ccccc1)c1ccc(Br)cc1F]

Following the procedure outlined for Example 628, (R)-4-benzyl-3-(2-(4-bromo-2-fluorophenyl)acetyl)oxazolidin-2-one (4.6 g, 12 mmol) was reacted with methyl iodide (1M solution in toluene, 12.3 mL, 12.3 mmol) to obtain the desired product (3.0 g, 60%) as light yellow solid: ESI MS m/z 407 $[C_{19}H_{17}BrFNO_3+H]^+$

Example 631

(S)-2-(4-bromo-2-fluorophenyl)propan-1-ol

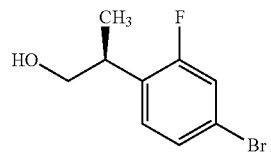

To a solution of ((S)-4-benzyl-3-((S)-2-(4-bromo-2-fluorophenyl)propanoyl)oxazolidin-2-one) (1.7 g, 4.2 mmol) in THF (12 mL) was added a solution of sodium borohydride (700 mg, 21 mmol) in water (2 mL). The reaction mixture was stirred for 3 h at room temperature. The excess hydride was quenched by slow addition of aqueous hydrochloric acid (1 N, ca. 2.9 mL). The mixture was further diluted with water (10 mL) and extracted with ethyl acetate (1×30 mL). The combined organics were washed with brine (2×10 mL), dried over sodium sulfate, and evaporated under vacuum. The residue was purified by flash chromatography of the residue afforded the desired product (0.8 g, 82%) as light yellow oil: ESI MS m/z 234 $[C_9H_{10}BrFO+H]^+$

Example 632

(R)-2-(4-bromo-2-fluorophenyl)propan-1-ol

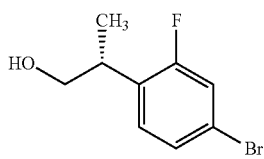

Following the procedure outlined for Example 630, (R)-4-benzyl-3-((R)-2-(4-bromo-2-fluorophenyl)propanoyl)oxazolidin-2-one (3 g, 7.4 mmol) was reacted with sodium borohydride (1.2 g, 37 mmol) to obtain the desired product (1.5 g, 87%) as light yellow oil; ESI MS m/z 234 $[C_{11}H_{10}BrFO+H]^+$

Example 633

(S)-2-(2-(4-bromo-2-fluorophenyl)propyl)isoindoline-1,3-dione

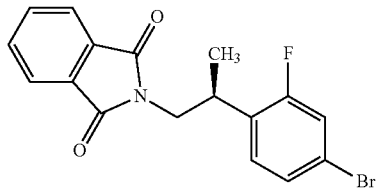 [SMILES: C[C@H](CN1C(=O)c2ccccc2C1=O)c1ccc(Br)cc1F]

To a solution of (S)-2-(4-bromo-2-fluorophenyl)propan-1-ol (800 mg, 3.43 mmol), phthalimide (554 mg, 3.77 mmol), and triphenylphosphine (1.34 g, 5.14 mmol) in THF (2 mL) was added DIAD (1 mL, 5.14 mmol) dropwise. The reaction mixture was stirred at room temperature for 18 h and evaporated under vacuum. Flash chromatography of the residue afforded the desired product (1 g, 81%) as a white solid ESI MS m/z 363 $[C_{17}H_{13}BrFNO_2+H]^+$

Example 634

(R)-2-(2-(4-bromo-2-fluorophenyl)propyl)isoindoline-1,3-dione

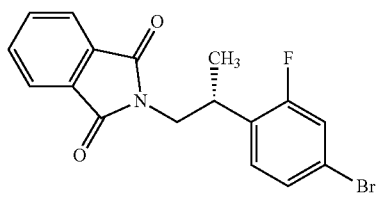 [SMILES: C[C@@H](CN1C(=O)c2ccccc2C1=O)c1ccc(Br)cc1F]

Following the procedure described for Example 633, (R)-2-(4-bromo-2-fluorophenyl)propan-1-ol (1.5 mg, 6.4 mmol) was reacted with phthalimide (1.0 mg, 7.008 mmol) to obtain the desired product (1.6 g, 69%) as a white solid: ESI MS m/z 363 $[C_{17}H_{13}BrFNO_2+H]^+$

Example 635

(S)-tert-butyl 2-(2-fluoro-4-(4,4,5,5-tetramethyl-1,3,2-dioxaborolan-2-yl)phenyl)propylcarbamate

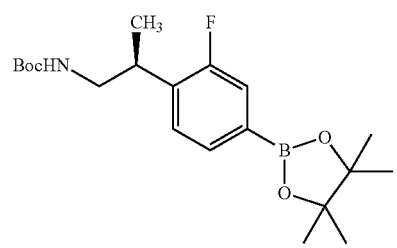 [SMILES: C[C@H](CNC(=O)OC(C)(C)C)c1ccc(B2OC(C)(C)C(C)(C)O2)cc1F]

To a solution of (S)-2-(2-(4-bromo-2-fluorophenyl)propyl)isoindoline-1,3-dione) (1.0 g, 2.8 mmol) in toluene (10 mL) was added hydrazine (1.3 mL, 41.5 mmol) dropwise. The reaction mixture was heated at 80-90° C. for 1 h and cooled to room temperature. The supernatant was decanted, and the residual solid was washed with toluene. The combined solution was evaporated under vacuum, dissolved in DCM (10 mL) and cooled to 0° C. Next, Boc$_2$O (870 mg, 4 mmol) and Et$_3$N (0.5 mL, 4 mmol) were added and the reaction mixture stirred for 30 min at room temperature. The reaction mixture diluted with DCM (20 mL) and washed with 1N HCl (1×10 mL), water (1×20 mL) followed by brine (1×10 mL), dried over sodium sulfate, and evaporated under vacuum to afford the desire product (860 mg, 99%) which was taken to next step without further purification. ESI MS m/n 333 $[C_{14}H_{19}BrFNO_2+H]^+$ The next step carried out following the procedure G (Scheme II): (S)-tert-butyl 2-(4-bromo-2-fluorophenyl)propylcarbamate (860 mg, 2.66) was reacted with KOAc (833 mg, 8.5 mmol), Pd(dppf)Cl$_2$ (200 mg, 0.26 mmol) and bis (pinacolato)diboron (863 mg, 3.4 mmol) to afford (S)-tert-butyl 2-(2-fluoro-4-(4,4,5,5-tetramethyl-1,3,2-dioxaborolan-2-yl)phenyl)propylcarbamate as a colourless paste (900 mg, 89%): ESI MS m/z 380 $[C_{20}H_{31}BFNO_4+H]^+$

Example 636

(R)-tert-butyl 2-(2-fluoro-4-(4,4,5,5-tetramethyl-1,3,2-dioxaborolan-2-yl)phenyl)propylcarbamate

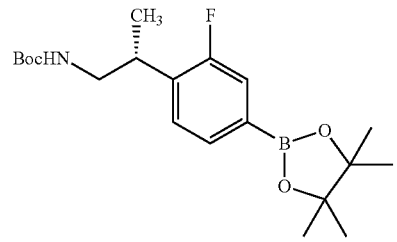 [SMILES: C[C@@H](CNC(=O)OC(C)(C)C)c1ccc(B2OC(C)(C)C(C)(C)O2)cc1F]

Followed the procedure outlined for Example 635 (R)-2-(2-(4-bromo-2-fluorophenyl)propyl)isoindoline-1,3-dione) (1.6 g, 4.42 mmol) was reacted with hydrazine (2.1 g, 66 mmol), Boc$_2$O (2.0 g, 8.8 mmol) followed by bis(pinacolato)diboron (1.0 g, 4.0 mmol) to obtain the desired product (1.1 g, 80%) as a colourless paste: ESI MS m/z 380 [C$_{20}$H$_{31}$BFNO$_4$+H]$^+$ Example 637

(R)-tert-butyl 2-(2-fluoro-4-(4,4,5,5-tetramethyl-1,3,2-dioxaborolan-2-yl)phenyl)propyl(methyl)carbamate

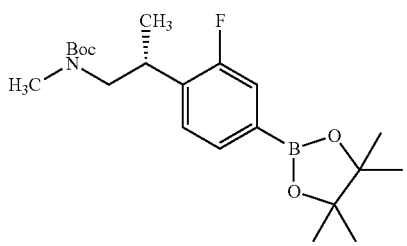

Following the procedure described for Example 647, (R)-tert-butyl 2-(2-fluoro-4-(4,4,5,5-tetramethyl-1,3,2-dioxaborolan-2-yl)phenyl)propylcarbamate (400 mg, 1 mmol) was reacted with methyl iodide (1M solution in toluene, 2 mL, 2 mmol) and NaHMDS (1 M solution, 2 mL, 2 mmol) to afford the desired product (330 mg, 82%) as viscous mass. ESI MS m/z 394 [C$_{21}$H$_{38}$BFNO$_4$+H]$^+$ Example 638 tert-butyl 3-methyl-2-(4-(4,4,5,5-tetramethyl-1,3,2-dioxaborolan-2-yl)phenyl)butylcarbamate

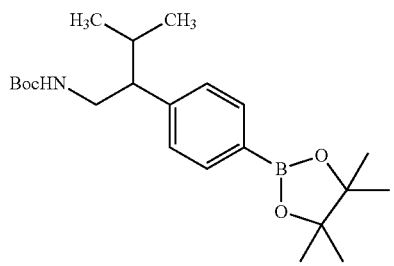 [SMILES: CC(C)C(CNC(=O)OC(C)(C)C)c1ccc(B2OC(C)(C)C(C)(C)O2)cc1]

Following the procedure described for Example 647, 2-(4-(4,4,5,5-tetramethyl-1,3,2-dioxaborolan-2-yl)phenyl)acetonitrile (5.6 g, 23 mmol) was reacted with iso propyl iodide (4 g, 24 mmol) NaHMDS (1 M solution, 24 m L, 24 mmol) to afford the desired product (2.1 g, 23%) as viscous mass. ESI MS not 390 [C$_{22}$H$_{36}$BNO$_4$+H]$^+$.

Example 639 tert-butyl 2-(2-fluoro-4-(4,4,5,5-tetramethyl-1,3,2-dioxaborolan-2-yl)phenyl)-3-methylbutylcarbamate

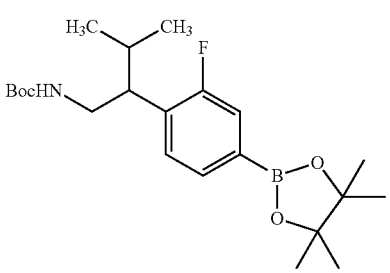 [SMILES: CC(C)C(CNC(=O)OC(C)(C)C)c1ccc(B2OC(C)(C)C(C)(C)O2)cc1F]

Following the procedure described for Example 647, 2-(2-fluoro-4-(4,4,5,5-tetramethyl-1,3,2-dioxaborolan-2-yl)phenyl)acetonitrile (1.7 g, 6.5 mmol) was reacted with iso propyl iodide (1.1 g, 6.8 mmol) NaHMDS (1 M solution, 7.1 mL, 7.1 mmol) to afford the desired product (0.65 g, 24%) as viscous mass. ESI MS m/z 408 [C$_{22}$H$_{36}$FBNO$_4$+H]$^+$ Example 640 tert-butyl 2-cyclopentyl-2-(4-(4,4,5,5-tetramethyl-1,3,2-dioxaborolan-2-yl)phenyl)ethylcarbamate

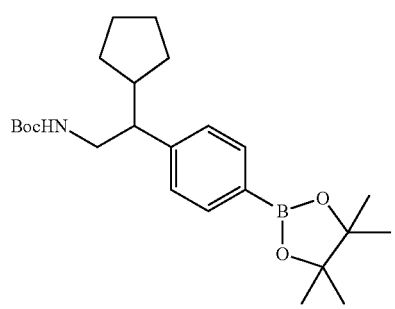 [SMILES: CC(C)(C)OC(=O)NCC(c1ccc(B2OC(C)(C)C(C)(C)O2)cc1)C1CCCC1]

Following the procedure described for Example 647, 2-(4-(4,4,5,5-tetramethyl-1,3,2-dioxaborolan-2-yl)phenyl)acetonitrile (1.7 g, 7.16 mmol) was reacted with cyclopentyl iodide (1 M solution in toluene, 7.16 mL, 7.16 mmol) and NaHMDS (M solution, 7.16 mL, 7.16 mmol) to afford the desired product (1.6 g, 53%) as viscous mass. ESI MS m/z 415 [C$_{24}$H$_{38}$BNO$_4$+H]$^+$.

Example 641 tert-butyl methyl(3-methyl-2-(4-(4-(4,4,5,5-tetramethyl-1,3,2-dioxaborolan-2-yl)phenyl)butyl)carbamate

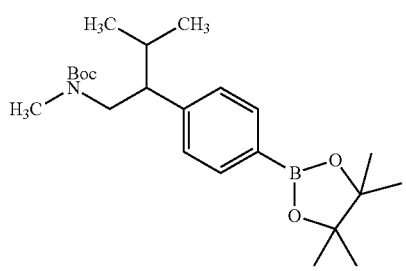

Example 642

Following the procedure described for Example 647, tert-butyl 3-methyl-2-(4-(4,4,5,5-tetramethyl-1,3,2-dioxaborolan-2-yl)phenyl)butylcarbamate (400 mg, 1 mmol) was reacted with methyl iodide (1M solution in toluene, 2 mL, 2 mmol) and NaHMDS (1 M solution, 2 mL, 2 mmol) to afford the desired product (350 mg, 84%) as viscous mass. ESI MS m/z 403 [C$_{23}$H$_{38}$BNO$_4$+H]$^+$.

Example 643 tert-butyl 2-(2-fluoro-4-(4,4,5,5-tetramethyl-1,3,2-dioxaborolan-2-yl)phenyl)-3-methylbutyl(methyl)carbamate

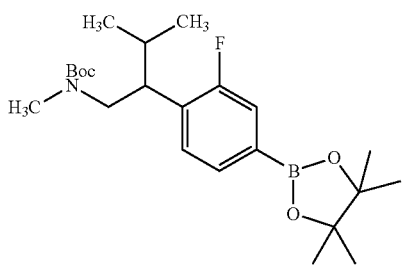

Following the procedure described for Example 647, tert-butyl 2-(2-fluoro-4-(4,4,5,5-tetramethyl-1,3,2-dioxaborolan-2-yl)phenyl)-3-methylbutylcarbamate (650 mg, 1.6 mmol) was reacted with methyl iodide (1M solution in toluene, 3.2 mL, 3.2 mmol) and NaHMDS (1 M solution, 4.8 mL, 4.8 mmol) to afford the desired product (650 mg, 94%) as viscous mass. ESI MS m/z 421 $[C_{23}H_{38}FNO_4+H]^+$

Example 644 tert-butyl 3-(4-bromophenyl)piperidine-1-carboxylate

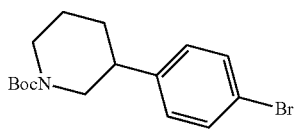 [SMILES: CC(C)(C)OC(=O)N1CCCC(c2ccc(Br)cc2)C1]

To a solution of 3-(4-bromophenyl)pyridine (0.4 g, 1.68 mmol) and HCl (1.0 N solution in water, 1.7 mL, 1.7 mmol) in MeOH (20 mL) was added PtO$_2$ (0.5 g) and stirred for 24 h at room temperature under H$_2$ atmosphere (50 psi) in a Parr hydrogenation apparatus. The mixture was filtered through Celite, and the filtrate was evaporated under reduced pressure. The resulting white solid was dissolved in EtOAc (50 mL) and washed with 1 N NaOH (10 mL). The aqueous phase was extracted with EtOAc (3×50 mL), and the combined organic phase was dried (Na$_2$SO$_4$). Evaporation of the solvent gave a white solid which was redissolved in DCM and added Boc$_2$O followed by Et$_3$N at 0° C. After stirring the reaction mixture for 1 h at room temperature diluted with DCM and washed sequentially with 1 N HCl, water and brine, dried over sodium sulfate, and evaporated under vacuum. Flash chromatography of the residue afforded the desired product as viscous mass (350 mg, 61%) ESI MS m/z 341 $[C_{16}H_{22}BrNO_2+H]^+$.

Example 645 tert-butyl 3-(4-(4,4,5,5-tetramethyl-1,3,2-dioxaborolan-2-yl)phenyl)piperidine-1-carboxylate

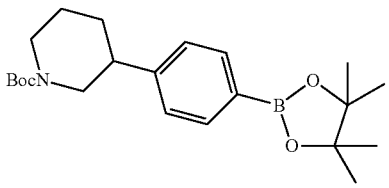 [SMILES: CC(C)(C)OC(=O)N1CCCC(c2ccc(B3OC(C)(C)C(C)(C)O3)cc2)C1]

General Procedure G, tert-butyl 3-(4-bromophenyl)piperidine-1-carboxylate (350 mg, 1) was reacted with bis(pinacolato)diboron (275, 1.2 mmol) to to afford the desired product (190 mg, 48%) as a viscous mass: ESI MS m/z 388 $[C_{22}H_{34}BNO_4+H]^+$.

Example 646

3-(4-(4,4,5,5-tetramethyl-1,3,2-dioxaborolan-2-yl)phenyl)propanenitrile

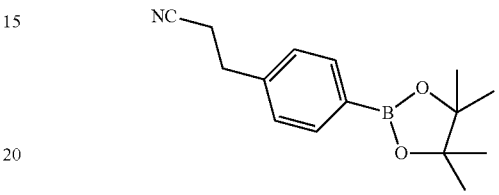

General Procedure G, tert-butyl 3-(4-bromophenyl)piperidine-1-carboxylate (350 mg, 1) was reacted with bis(pinacolato)diboron (275, 1.2 mmol) to to afford the desired product (190 mg, 48%) as a viscous mass: ESI MS m/z 388 $[C_{22}H_{34}BNO_4+H]^+$.

Example 647

N-methyl(R)-tert-butyl methyl(1-(4-(4,4,5,5-tetramethyl-1,3,2-dioxaborolan-2-yl)phenyl)ethyl)carbamate

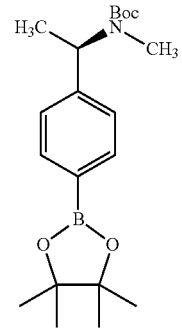

To a solution of (R)-tert-butyl 1-(4-(4,4,5,5-tetramethyl-1,3,2-dioxaborolan-2-yl)phenyl)ethylcarbamate (1.0 g, 2.88 mmol) in anhydrous THF (20 mL) was cooled to 0° C. and sodium hydride (60 wt %, 330 mg, 8.64 mmol) added portion wise. The mixture was stirred for min and then heated at 60° C. for 1 h. The flask was then cooled down to room temperature and methyl iodide (277 mL, 4.32 mmol) was added. The mixture was heated again at 60° C. for 12 h. LCMS showed completion of reaction. The reaction mixture was quenched with water and diluted with ethyl acetate (200 mL). The layers were separated and the organic layer was dried over anhydrous sodium sulfate, filtered, concentrated and the residue purified by column chromatography (silica, 0-30% ethyl acetate/heptane) to afford the desired product (520 mg, 43%) as a white solid: ESI MS m/z 306 $[C_{20}H_{32}BNO_4+H]^+$.

Example 648

(R)-tert-butyl methyl(2-(4-(4,4,5,5-tetramethyl-1,3,2-dioxaborolan-2-yl)phenyl)propyl)carbamate

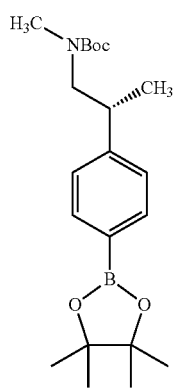

A solution of (R)-tert-butyl 2-(4-(4,4,5,5-tetramethyl-1,3,2-dioxaborolan-2-yl)phenyl)propylcarbamate (9.0 g, 24.93 mmol) in anhydrous THF (120 mL) was cooled to 0° C. and NaHMDS (30 mL, 29.9 mmol) was added. The mixture was stirred for 1 h, methyl iodide (1.9 mL, 29.9) in THF (40 mL) added and stirred for 14 h. The reaction mixture was quenched with water (20 mL) and diluted with ethyl acetate (250 mL). The layers were separated and the organic layer was dried over anhydrous sodium sulfate, filtered, concentrated and the residue purified by column chromatography (silica, 0-30% ethyl acetate/heptane) to afford the desired product (6.2 g, 66%) as light yellow oil: ESI MS m/z 376 $[C_{21}H_{13}NO_4+H]^+$.

Example 649

2-(4-bromophenyl)propanenitrile

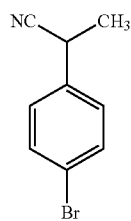

To a solution of 2-(4-bromophenyl)acetonitrile (5.0 g, 25.5 mmol) in anhydrous THF (70 mL) was cooled to 0° C. and sodium hydride (60 wt %, 1.5 g, 38.3 mmol) added portion wise. The mixture was stirred at room temperature for 1 h. After which methyl iodide (1.$ mL, 28.1 mmol) was added and the mixture stirred for 14 h. The reaction mixture was carefully quenched with water at 0° C. and diluted with ethyl acetate (200 mL). The layers were separated and the organic layer was dried over anhydrous sodium sulfate, filtered, concentrated and the residue purified by column chromatography (silica, 0-30% ethyl acetate/heptane) to afford the desired product (3.8 g, 72%) as a yellow oil: ESI MS m/z 210 $[C_9H_8BrN+H]^+$.

Example 650

2-(2-chlorophenyl)propanenitrile

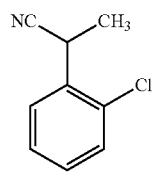

Following the procedure outlined for Example 649, 2-(2-chlorophenyl)acetonitrile (15 g, 98.9 mmol) was reacted with NaHMDS (118 mL, 118 mmol), and methyl iodie (7.0 mL, 108 mmol) to afford the desired product (14 g, 87%) as a brown oil: ESI MS m/z 166 $[C_9H_8ClN+H]^+$.

Example 651

2-(2-chlorophenyl)propan-1-amine

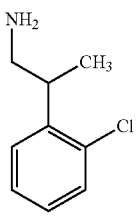

To a solution of 2-(2-chlorophenyl)propanenitrile (14 g, 84.8 mmol) in toluene at 0° C. was added BH$_3$.THF (127, 255 mmol) and the reaction was warmed to room temperature and heated at reflux for 4 h. The reaction mixture was cooled; quenched with water, concentrated and the residue was purified by column chromatography (silica, ethyl acetate/hexanes gradient) to obtain the desired product (13.9 g, 97%) as a reddish oil: ESI MS m/z 170 $[C_9H_{12}ClN+H]^+$.

Example 652

N-(2-(4-bromo-2-chlorophenyl)propyl)-2,2,2-trifluoroacetamide

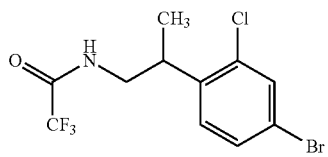

A solution of trifluoro acetic anhydride (12.8 mL, 90.1 mmol) in anhydrous methylene chloride (82 mL) was cooled to 0° C. and 2-(2-chlorophenyl)propan-1-amine (14 g, 82.8 mmol) in anhydrous methylene chloride (30 mL) was added dropwise. The mixture was stirred at room temperature for 1.5 h. The flask was again cooled to 0° C. and methane sulfonic acid (13 mL) followed by 1,3-Dibromo-5,5-Dimethylhydantoin (11.8 g, 41.4 mmol) was added in one portion. The mixture was stirred for 14 h and quenched with water (30 mL) and diluted with methylene chloride (150 mL). The layers were separated and the organic layer was dried over anhydrous sodium sulfate, filtered, concentrated and the residue purified by column chromatography (silica, 0-30% ethyl acetate/heptane) to afford the desired product (14 g, 50%) as a yellowish oil: ESI MS m/z 344 $[C_{11}H_{10}BrClF_3NO+H]^+$.

Example 653 tert-butyl 2-(2-chloro-4-(4,4,5,5-tetramethyl-1,3,2-dioxaborolan-2-yl)phenyl)propylcarbamate

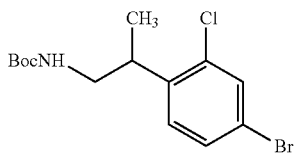 [SMILES: CC(CNC(=O)OC(C)(C)C)c1ccc(Br)cc1Cl]

A mixture of N-(2-(4-bromo-2-chlorophenyl)propyl)-2,2,2-trifluoroacetamide (14 g, 40.6 mmol), methanol (200 mL) and sodium hydroxide (2M, 200 mL, 81.2 mmol) was stirred at room temperature for 14 h. LCMS showed completion of the reaction. The solvent was removed, extraction with methylene chloride (200 mL) and concentrated to give an oil. The residue was dissolved in methylene chloride (100 mL) and cooled to 0° C. Triethylamine (8.3 mL, 61.0 mmol) and di-tert-butyl dicarbonate (13.3 g, 61.0 mmol) and the reaction mixture stirred at room temperature for 18 h. The reaction mixture concentrated and the residue was purified by column chromatography (silica, ethyl acetate/hexanes gradient) to obtain the desired product (13.8 g, 90%) as white solid: ESI MS m/z 293 $[C_{14}H_{11}BrClNO_2-56]^+$.

Example 654 tert-butyl 2-(2-chloro-4-(4,4,5,5-tetramethyl-1,3,2-dioxaborolan-2-yl)phenyl)propylcarbamate

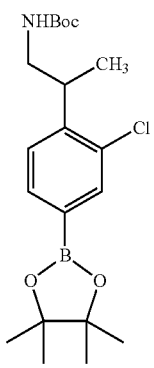 [SMILES: CC(CNC(=O)OC(C)(C)C)c1ccc(B2OC(C)(C)C(C)(C)O2)cc1Cl]

Following General Procedure G, tert-butyl 2-(4-bromo-2-chlorophenyl)propylcarbamate (12.0 g, 34.5 mmol) was reacted with bis(pinacolata)diboron (13.2 g, 51.7 mmol) to afford the desired product (8.0 g, 58%) as a amorphous reddish oil: ESI MS m/z 396 $[C_{20}H_{31}BClNO_4+H]^+$.

Example 655

2-(4-(4,4,5,5-tetramethyl-1,3,2-dioxaborolan-2-yl)phenyl)propanenitrile

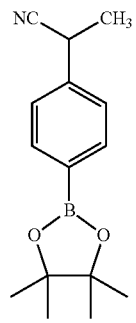

Following General Procedure G, 2-(4-bromophenyl)propanenitrile (3.5 g, 18.2 mmol) was reacted with bis(pinacolata)diboron (4.6 g, 27.1 mmol) to afford the desired product (2.5 g, 53%) as a brown solid: ESI MS m/z 258 $[C_{15}H_{20}BNO_2+H]^+$.

Example 656

2-ethyl-2-(4-(4,4,5,5-tetramethyl-1,3,2-dioxaborolan-2-yl)phenyl)butanenitrile

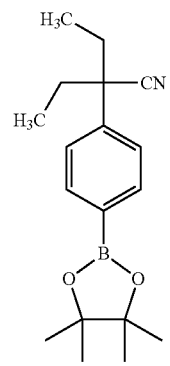 [SMILES: CCC(C#N)(CC)c1ccc(B2OC(C)(C)C(C)(C)O2)cc1]

To a solution of 2-(4-(4,4,5,5-tetramethyl-1,3,2-dioxaborolan-2-yl)phenyl)acetonitrile (2.0 g, 8.23 mmol) in DMF (40 mL) was cooled to 0° C. and sodium hydride (60 wt %, 1.2 g, 32.9 mmol) added portion wise. The mixture was stirred for 10 min and ethyl iodide (0.74 mL, 9.05 mmol) in THF (10 mL) was added. The mixture was stirred at room temperature for 12 h. The reaction mixture was quenched with water and diluted with ethyl acetate. The layers were separated and the organic layer was dried over anhydrous sodium sulfate, filtered, concentrated and the residue purified by column chromatography (silica, 0-30% ethyl acetate/heptane) to afford the desired product (950 mg, 38%) as a brown solid: ESI MS m/z 300 $[C_{18}H_{26}BNO_2+H]^+$.

Example 657

2-(4-(4,4,5,5-tetramethyl-1,3,2-dioxaborolan-2-yl)phenyl)propanenitrile

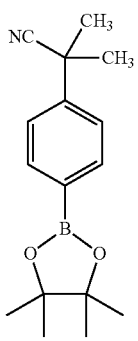

Following General Procedure G, 2-(4-bromophenyl)propanenitrile (5.0 g, 22.3 mmol) was reacted with bis(pinacolata)diboron (8.7 g, 33.5 mmol) to afford the desired product (5.8 g, 95%) as a white solid: ESI MS m/z 272 $[C_{16}H_{22}BNO_2+H]^+$.

Example 658

(R)—N-(2-(4-bromophenyl)propyl)-2,2,2-trifluoroacetamide

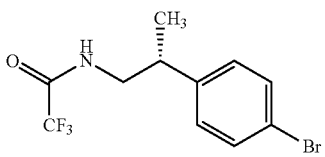 [SMILES: C[C@@H](CNC(=O)C(F)(F)F)c1ccc(Br)cc1]

A solution of trifluoro acetic anhydride (11.4 mL, 81.4 mmol) in anhydrous methylene chloride (73 mL) was cooled to 0° C. and (R)-2-phenylpropan-1-amine (10 g, 73.9 mmol) in anhydrous methylene chloride (20 mL) was added dropwise. The mixture was stirred at room temperature for 1.5 h. The flask was again cooled to 0° C. and methane sulfonic acid (12 mL) followed by 1,3-Dibromo-5,5-Dimethylhydantoin (11 g, 36.9 mmol) was added in one portion. The mixture was stirred for 14 h and quenched with water (30 mL) and diluted with methylene chloride (100 mL). The layers were separated and the organic layer was dried over anhydrous sodium sulfate, filtered, concentrated and the residue purified by column chromatography (silica, 0-30% ethyl acetate/heptane) to afford the desired product (21 g, 91%) as a yellow solid: ESI MS m/z 310 $[C_{11}H_{11}BrF_3NO+H]^+$.

Example 659

(R)-tert-butyl 2-(4-bromophenyl)propylcarbamate

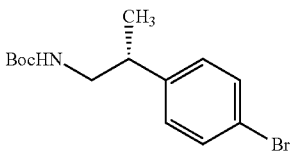 [SMILES: C[C@@H](CNC(=O)OC(C)(C)C)c1ccc(Br)cc1]

A mixture of (R)—N-(2-(4-bromophenyl)propyl)-2,2,2-trifluoroacetamide (21 g, 68.3 mmol), methanol (40 mL) and sodium hydroxide (2M, 68 mL, 136 mmol) was stirred at room temperature for 14 h. LCMS showed completion of the reaction. The solvent was removed, extraction with methylene chloride (250 mL) and concentrated to give an oil. The residue was dissolved in methylene chloride (100 mL) and cooled to 0° C. Triethylamine (14 mL, 102 mmol) and di-tert-butyl dicarbonate (22 g, 102 mmol) and the reaction mixture stirred at room temperature for 18 h. The reaction mixture concentrated and the residue was purified by column chromatography (silica, ethyl acetate/hexanes gradient) to obtain the desired product (19 g, 91%) as yellow oil: ESI MS m/z 257 $[C_{14}H_{20}BrNO_2-56]^+$.

Example 660

(R)-tert-butyl 2-(4-(4,4,5,5-tetramethyl-1,3,2-dioxaborolan-2-yl)phenyl)propylcarbamate

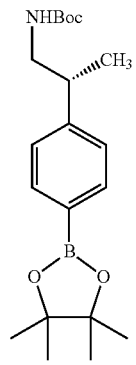

Following General Procedure G, (R)-tert-butyl 2-(4-bromophenyl)propylcarbamate (19 g, 60.5 mmol) was reacted with bis(pinacolata)diboron (24 g, 94.4 mmol) to afford the desired product (22 g, 99%) as a light yellow solid: ESI MS m/z 362 $[C_{20}H_{32}BNO_4+H]^+$.

Example 661

(R)—N-(1-(4-bromophenyl)propyl)-2,2,2-trifluoroacetamide

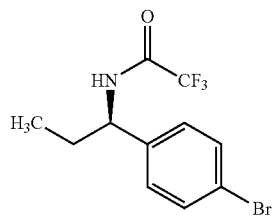 [SMILES: CC[C@@H](NC(=O)C(F)(F)F)c1ccc(Br)cc1]

A solution of trifluoro acetic anhydride (5.7 mL, 40.7 mmol) in anhydrous methylene chloride (40 mL) was cooled to 0° C. and (R)-1-phenylpropan-1-amine (5 g, 36.9 mmol) in anhydrous methylene chloride (10 mL) was added dropwise. The mixture was stirred at room temperature for 1.5 h. The flask was again cooled to 0° C. and methane sulfonic acid (6.3 mL) followed by 1,3-dibromo-5,5-dimethylhydantoin (5.3 g, 18.5 mmol) was added in one portion. The mixture was stirred for 14 h and quenched with water (30 mL) and diluted with methylene chloride (50 mL). The layers were separated and the organic layer was dried over anhydrous sodium sulfate, filtered, concentrated and the residue purified by column chromatography (silica, 0-30% ethyl acetate/heptane) to afford the desired product (8.1 g, 73%) as a white solid: ESI MS m/z 310 $[C_{11}H_{11}BrF_3NO+H]^+$.

Example 662

(R)-tert-butyl 1-(4-bromophenyl)propylcarbamate

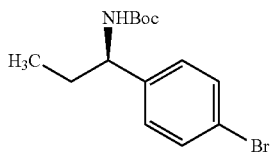 [SMILES: CC[C@@H](NC(=O)OC(C)(C)C)c1ccc(Br)cc1]

A mixture of (R)—N-(1-(4-bromophenyl)propyl)-2,2,2-trifluoroacetamide (8.1 g, 68.3 mmol), methanol (20 mL) and sodium hydroxide (2M, 15 mL, 30.6 mmol) was stirred at room temperature for 14 h. LCMS showed completion of the reaction. The solvent was removed, extraction with methylene chloride (150 mL) and concentrated to give an oil. The residue was dissolved in methylene chloride (100 mL) and cooled to 0° C. Triethylamine (2.2 mL, 15.3 mmol) and di-tert-butyl dicarbonate (3.3 g, 15.3 mmol) and the reaction mixture stirred at room temperature for 18 h. The reaction mixture concentrated and the residue was purified by column chromatography (silica, ethyl acetate/hexanes gradient) to obtain the desired product (5.8 g, 70%) as off-white solid: ESI MS m/z 257 $[C_{14}H_{20}BrNO_2-56]^+$.

Example 663

(R)-tert-butyl 1-(4-(4,4,5,5-tetramethyl-1,3,2-dioxaborolan-2-yl)phenyl)propylcarbamate

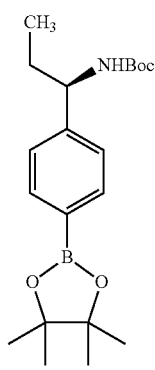

Following General Procedure G, (R)-tert-butyl 1-(4-bromophenyl)propylcarbamate (5.8 g, 18.4 mmol) was reacted with bis(pinacolata)diboron (7.03 g, 27.7 mmol) to afford the desired product (6.18 g, 92%) as yellow oil: ESI MS m/z 362 $[C_{20}H_{32}BNO_4+H]^+$.

Example 664 tert-butyl 1-(4-bromophenyl)propan-2-ylcarbamate

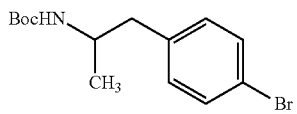

To a solution of 1-(4-bromophenyl)propan-2-one (5.0 g, 23.4 mmol) in ethanol (115 mL) was added ammonia in methanol (9 N, 20.2 mL, 140 mmol) followed by Titanium isoperoxide (13.3 mL, 46.9 mmol). The mixture was heated at 50° C. overnight. The flask was cooled to 0° C. and NaBH$_4$ (142 mg, 3.76 mmol) was added in portions. After stirring for 1 h, NH$_4$OH (2 N, 4.0 mL) was added and the mixture stirred for 1 h. The white solid was filtered off and the filtrate extracted with methylene chloride. Solvent was removed and oil obtained was dissolved in methylene chloride (100 mL) and cooled to 0° C. Triethylamine (4.8 mL, 35.2 mmol) and di-tert-butyl dicarbonate (10.2 g, 46.9 mmol) and the reaction mixture stirred at room temperature for 18 h. The reaction mixture concentrated and the residue was purified by column chromatography (silica, ethyl acetate/hexanes gradient) to obtain the desired product (4.2 g, 57%) as white solid: ESI MS m/z 257 $[C_{14}H_{20}BrNO_2-56]^+$.

Example 665 tert-butyl 1-(4-(4,4,5,5-tetramethyl-1,3,2-dioxaborolan-2-yl)phenyl)propan-2-ylcarbamate

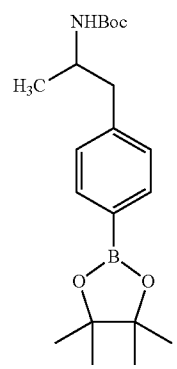 [SMILES: CC(Cc1ccc(B2OC(C)(C)C(C)(C)O2)cc1)NC(=O)OC(C)(C)C]

Following General Procedure G, tert-butyl 1-(4-bromophenyl)propan-2-ylcarbamate (8.8 g, 28.03 mmol) was reacted with bis(pinacolata)diboron (10.7 g, 42.0 mmol) to afford the desired product (10.5 g, 99%) as a brown oil: ESI MS m/z 362 $[C_{20}H_{32}BNO_4+H]^+$.

Example 666 tert-butyl 2-ethyl-2-(4-(4,4,5,5-tetramethyl-1,3,2-dioxaborolan-2-yl)phenyl)butylcarbamate

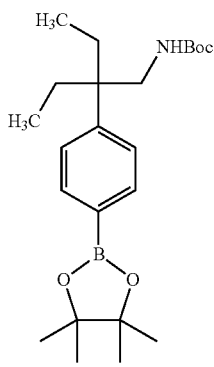 [SMILES: CCC(CC)(CNC(=O)OC(C)(C)C)c1ccc(B2OC(C)(C)C(C)(C)O2)cc1]

To a solution of cyano compound (500 mg, 1.67 mmol) in toluene (10 mL) at 0° C. was added BH₃.THF (1.0 M in THF, 16 mL, 10 mmol) and the reaction was warmed to room temperature and heated at reflux for 4 h. The reaction mixture was cooled; quenched with water, concentrated. The residue was dissolved in methylene chloride (30 mL) and cooled to 0° C. Triethylamine (0.36 mL, 2.51 mmol) and di-tert-butyl dicarbonate (547 mg, 2.51 mmol) and the reaction mixture stirred at room temperature for 18 h. The reaction mixture concentrated and the residue was purified by column chromatography (silica, ethyl acetate/hexanes gradient) to obtain the desired product (480 mg, 71%) as a brown solid: ESI MS m/z 404 $[C_{23}H_{38}BNO_4+H]^+$.

Example 667 tert-butyl 2-methyl-2-(4-(4,4,5,5-tetramethyl-1,3,2-dioxaborolan-2-yl)phenyl)propylcarbamate

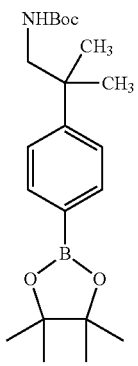

Following the procedure outlined for Example 666, 2-(4-(4,4,5,5-tetramethyl-1,3,2-dioxaborolan-2-yl)phenyl)propanenitrile (5.8 g, 21.4 mmol) was reacted with BH₃.THF (1.0 M in THF, 64 mL, 64 mmol) and di-tert-butyl dicarbonate (7.0 g, 32.1 mmol) to give the desired product (6.9 g, 86%) as a white solid: ESI MS m/z 310 $[C_{21}H_{34}BNO_4-56]^+$.

Example 668

1-(4-(4,4,5,5-tetramethyl-1,3,2-dioxaborolan-2-yl)phenyl)cyclobutanecarbonitrile

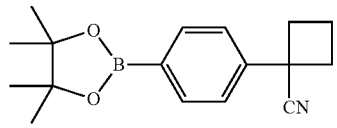

To a solution of 2-(4-(4,4,5,5-tetramethyl-1,3,2-dioxaborolan-2-yl)phenyl)acetonitrile (7.0 g, 29 mmol) in THF at 0° C. was added NaHMDS (1.0 M, 120 mL, 120 mmol). After stirring for 20 min 1,3-diiodopropane (26 g, 86 mmol) was added and the reaction mixture was stirred at room temperature for 2 h. The reaction mixture was cooled to 0° C., quenched with MeOH (5.0 mL) and the residue was purified by column chromatography (silica, ethyl acetate/hexanes gradient) to afford the desired product (4.0 g, 47%) as a yellow oil: ESI MS m/z 286 $[C_{17}H_{22}BNO_2+H]^+$.

Example 669

(1-(4-(4,4,5,5-tetramethyl-1,3,2-dioxaborolan-2-yl)phenyl)cyclobutyl)methanamine

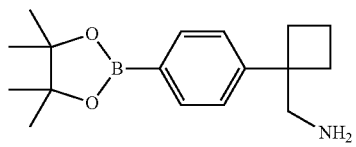 [SMILES: CC1(C)OB(c2ccc(C3(CN)CCC3)cc2)OC1(C)C]

Following the procedure outlined for Example 666, 1-(4-(4,4,5,5-tetramethyl-1,3,2-dioxaborolan-2-yl)phenyl)cyclobutane carbonitrile (4.0 g, 14 mmol) was reacted with BH₃.THF (1.0 M in THF, 60 mL, 60 mmol) to afford the desired product (3.7 g, 91%) as a yellow oil: ESI MS m/z 288 $[C_{11}H_2BNO_2+H]^+$.

Example 670 tert-butyl (1-(4-(4,4,5,5-tetramethyl-1,3,2-dioxaborolan-2-yl)phenyl)cyclobutyl)methylcarbamate

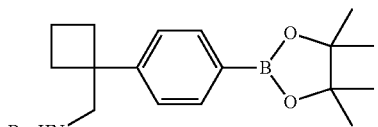

Following the procedure outlined for Example 463, (1-(4-(4,4,5,5-tetramethyl-1,3,2-dioxaborolan-2-yl)phenyl)cyclobutyl)methanamine (3.7 g, 13 mmol)) was reacted with di-tert-butyl dicarbonate (3.4 g, 16 mmol) to afford the desired product (3.5 g, 71%) as a yellow oil: ESI MS m/z 388 $[C_{22}H_{34}BNO_4+H]^+$.

Example 671

4-bromo-2-chloro-1-(2-nitrovinyl)benzene

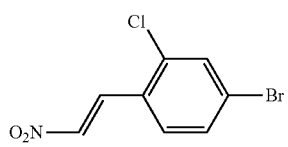

To a solution of 4-bromo-2-chlorobenzaldehyde (7.5 g, 34 mmol) in nitromethane was added methylamine hydrochloride (1.3 g, 22 mmol), NaOAc (1.8 g, 22 mmol). The mixture was vigorously stirred for 18 h at room temperature. The reaction mixture was diluted with water (60 mL) and extracted with CH₂Cl₂ (3×100 mL), organic phases dried Example 672

2-(4-bromo-2-chlorophenyl)ethanamine

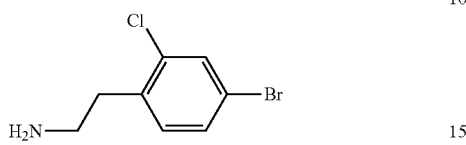

To a stirred suspension of LiBH$_4$ (2.0 M, 73 mL, 145 mmol) in THF (60 mL) at room temperature was added chlorotrimethylsilane (32 g, 290 mmol), dropwise over 10 min. After stirring at room temperature for 20 min, nitrogen gas was bubbled through the mixture for 5 min to remove the remaining trimethylsilane that had formed. A solution of 4-bromo-2-chloro-1-(2-nitrovinyl)benzene (9.5 g, 36.2 mmol) in THF (60 mL) was added dropwise over 10 min with stirring at room temperature. The resulting mixture was heated at reflux for 1 h. The reaction mixture was cooled in an ice bath and carefully quenched with MeOH (100 mL). The solvent was evaporated and the residue was partitioned between 20% KOH (120 mL) and CH$_2$Cl$_2$ (60 mL). The organic layer was dried, concentrated, purified by column chromatography (silica, ethyl acetate/hexanes gradient) to obtain the desired product (8.5 g, 95%) as a light yellow oil: ESI MS m/z 234 [C$_8$H$_9$BrClN+H]$^+$.

Example 673 tert-butyl 4-bromo-2-chlorophenethyl carbamate

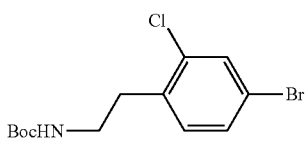

Following the procedure outlined for Example 463, 2-(4-bromo-2-chlorophenyl)ethanamine (7.5 g, 32 mmol) was reacted with di-tert-butyl dicarbonate (8.3 g, 38 mmol) to afford the desired product (9.7 g, 90%) as a white solid: ESI MS m/z 334 [C$_{13}$H$_{17}$BrClNO$_2$+H]$^+$.

Example 674 tert-butyl 2-chloro-4-(4,4,5,5-tetramethyl-1,3,2-dioxaborolan-2-yl)phenethylcarbamate

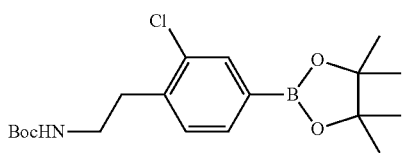 [SMILES: CC(C)(C)OC(=O)NCCc1ccc(B2OC(C)(C)C(C)(C)O2)cc1Cl]

(Na$_2$SO$_4$), evaporated to afford the desired product (8.5 g, 95%) as a light yellow oil: ESI MS m/z 262 [C$_8$H$_5$BrClNO$_2$+H]$^+$.

Following General Procedure G, tert-butyl 4-bromo-2-chlorophenethylcarbamate (9.6 g, 30 mmol) was reacted with bis(pinacolato)diboron (11 g, 45 mmol to afford the desired product (8.2 g, 73%) as a colorless oil: ESI MS m/z 382 [C$_{19}$H$_{29}$BClNO$_2$+H]$^+$.

Example 675

2-(4-(4,4,5,5-tetramethyl-1,3,2-dioxaborolan-2-yl)phenyl)butanenitrile

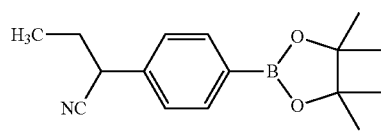 [SMILES: CCC(C#N)c1ccc(B2OC(C)(C)C(C)(C)O2)cc1]

Following the procedure outlined for Example 649, 2-(4-(4,4,5,5-tetramethyl-1,3,2-dioxaborolan-2-yl)phenyl)acetonitrile (5.2 g, 21 mmol)) was reacted with ethyl bromide (2.6 g, 24 mmol) to afford the desired product (3.4 g, 59%) as colorless oil: ESI MS m/z 272 [C$_{16}$H$_{22}$BNO$_2$+H]$^+$.

Example 676

2-(4-(4,4,5,5-tetramethyl-1,3,2-dioxaborolan-2-yl)phenyl)butan-1-amine

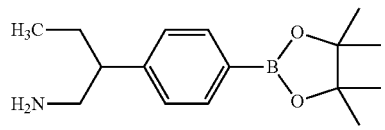 [SMILES: CCC(CN)c1ccc(B2OC(C)(C)C(C)(C)O2)cc1]

Following the procedure outlined for Example 666, 2-(4-(4,4,5,5-tetramethyl-1,3,2-dioxaborolan-2-yl)phenyl)butanenitrile (3.4 g, 12.5 mmol) was reacted with BH$_3$.THF (1.0 M in THF, 64 mL, 64 mmol) to afford the desired product (3.2 g, 93%) as light yellow oil: ESI MS m/z 276 [C$_{16}$H$_{26}$BNO$_2$+H]$^+$.

Example 677

(1-(4-bromophenyl)cyclopropyl)methanamine

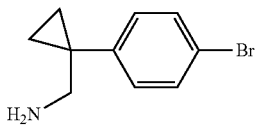 [SMILES: NCC1(c2ccc(Br)cc2)CC1]

Following the procedure outlined for Example 666, 1-(4-bromophenyl)cyclopropane carbonitrile (2.0 g, 9.0 mmol) was reacted with BH$_3$.THF (1.0 M in THF, 50 mL, 50 mmol)

to afford the desired product (1.9 g, 94%) as a yellow oil: ESI MS m/z 226 $[C_{10}H_{12}BrN+H]^+$.

Example 678 tert-butyl 2-(4-(4,4,5,5-tetramethyl-1,3,2-dioxaborolan-2-yl)phenyl)butylcarbamate

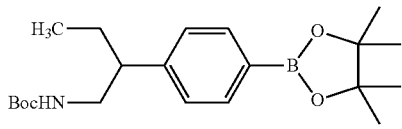

Following the procedure outlined for Example 463, 2-(4-(4,4,5,5-tetramethyl-1,3,2-dioxaborolan-2-yl)phenyl)butan-1-amine (2.9 g, 10.5 mmol) was reacted with di-tert-butyl dicarbonate (2.8 g, 12.6 mmol) to afford the desired product (2.4 g, 62%) as a light yellow oil: ESI MS m/z 376 $[C_{12}H_{34}BNO_4+H]^+$.

Example 679 tert-butyl (1-(4-bromophenyl)cyclopropyl)methylcarbamate

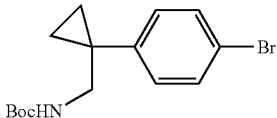

Following the procedure outlined for Example 463, (1-(4-bromophenyl)cyclopropyl)methanamine (2.2 g, 9.5 mmol) was reacted with di-tert-butyl dicarbonate (2.5 g, 12 mmol) to afford the desired product (1.5 g, 52%) as a yellow oil: ESI MS m/z 326 $[C_{15}H_{20}BrNO_2+H]^+$.

Example 680 tert-butyl (1-(4-(4,4,5,5-tetramethyl-1,3,2-dioxaborolan-2-yl)phenyl)cyclopropyl)methylcarbamate

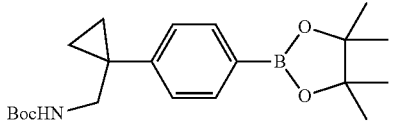

Following General Procedure G, tert-butyl (1-(4-bromophenyl)cyclopropyl)methyl carbamate (1.3 g, 4.0 mmol) was reacted with bis(pinacolato)diboron (1.55 g, 6.1 mmol) to afford the desired product (1.8 g, 60%) as a colorless oil: ESI MS m/z 374 $[C_{21}H_{32}BNO_4+H]^+$.

Example 463 tert-Butyl 4-Bromophenethylcarbamate

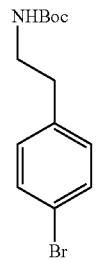

To a solution of 2-(4-bromophenyl)ethanamine (3.0 g, 15 mmol) in methylene chloride (75 mL) at 0° C. was added triethylamine (2.5 mL, 18 mmol) and di-tert-butyl dicarbonate (3.9 g, 18 mmol) and the reaction mixture was stirred at room temperature for 18 h. The reaction mixture was concentrated and the residue was triturated with acetonitrile and filtered to afford the desired product (3.5 g, 75%) as a yellow solid: ESI MS m/z 301 $[C_{13}H_{18}BrNO_2+H]^+$.

Example 464 tert-Butyl 4-(4,4,5,5-Tetramethyl-1,3,2-dioxaborolan-2-yl)phenethylcarbamate

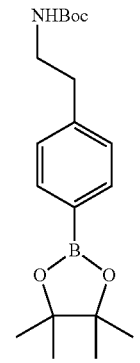

Following General Procedure G, tert-butyl 4-bromophenethylcarbamate (1.3 g, 4.3 mmol) was reacted with bis(pinacolato)diboron (1.3 g, 5.1 mmol) to afford the desired product (1.1 g, 70%) as a light brown solid: ESI MS m/z 348 $[C_{19}H_{30}BNO_4+H]^+$.

Example 465 tert-Butyl 4-(8-Methoxy-4-oxo-4,5-dihydrothieno[2,3-c]quinolin-9-yl)phenethylcarbamate

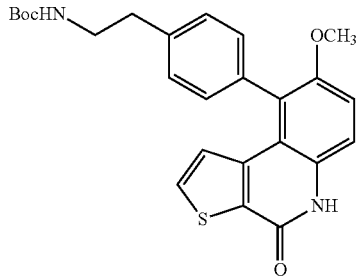 [SMILES: COc1ccc2[nH]c(=O)c3sccc3c2c1-c1ccc(CCNC(=O)OC(C)(C)C)cc1]

Following General Procedure B, 9-bromo-8-methoxythieno[2,3-c]quinolin-4(5H)-one (780 mg, 2.5 mmol) was reacted with tert-butyl 4-(4,4,5,5-tetramethyl-1,3,2-dioxaborolan-2-yl)phenethylcarbamate (1.5 g, 4.3 mmol) to afford the desired product (1.0 g, 90%) as a brown solid: ESI MS m/z 451 $[C_{25}H_{26}N_2O_4S+H]^+$.

Example 466

2-[4-(3-Bromopropoxy)phenyl]-4,4,5,5-tetramethyl-1,3,2-dioxaborolane

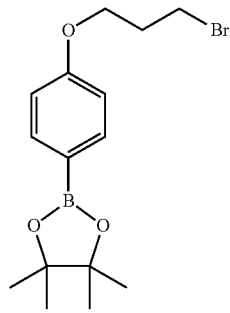 [SMILES: CC1(C)OB(c2ccc(OCCCBr)cc2)OC1(C)C]

To a solution of 4-(3-bromopropoxy)phenylboronic acid (1.0 g, 3.9 mmol) in diethyl ether (40 mL) was added pinacol (1.4 g, 12 mmol) and the reaction mixture was stirred for 18 h and concentrated to afford the desired product (1.5 g, crude) as a light brown oil which carried onto the next step without further purification: ESI MS m/z 247 $[C_{15}H_{22}BBrO_3-94]^+$.

Example 467

$N^1,N^1$-Diethyl-$N^2$-{3-[4-(4,4,5,5-tetramethyl-1,3,2-dioxaborolan-2-yl)phenoxy]propyl}ethane-1,2-diamine

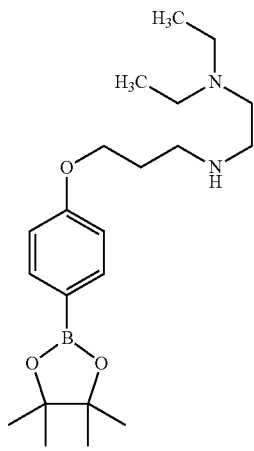 [SMILES: CCN(CC)CCNCCCOc1ccc(B2OC(C)(C)C(C)(C)O2)cc1]

A solution of 2-[4-(3-bromopropoxy)phenyl]-4,4,5,5-tetramethyl-1,3,2-dioxaborolane (500 mL, 2.02 mmol), $N^1,N^1$-diethylethane-1,2-diamine (0.87 mL, 6.1 mmol), and potassium carbonate (550 mg, 4.0 mmol) in acetonitrile (15 mL) was heated to 50° C. for 3 h. The reaction mixture was cooled, filtered and the filtrate was concentrated to afford the desired product (400 mg, 53%) as a yellow oil: ESI MS m/z 377 $[C_{21}H_{37}BN_2O_3+H]^+$.

Example 468 tert-Butyl 1-(4-Bromophenyl)ethylcarbamate

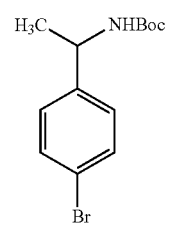

Following the procedure outlined for Example 463, 1-(4-bromophenyl)ethanamine (3.0 g, 15 mmol) was reacted with di-tert-butyl dicarbonate (3.9 g, 18 mmol) to afford the desired product (4.2 g, 93%) as a white solid: ESI MS m/z 301 $[C_{13}H_{18}BrNO_2+H]^+$.

Example 469 tert-Butyl 1-[4-(4,4,5,5-Tetramethyl-1,3,2-dioxaborolan-2-yl)phenyl]ethylcarbamate

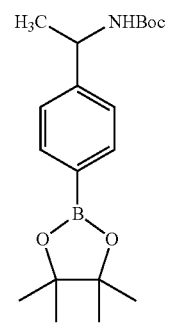

Following General Procedure G, tert-butyl 1-(4-bromophenyl)ethylcarbamate (2.2 g, 7.3 mmol) was reacted with bis(pinacolata)diboron (3.9 g, 11 mmol) to afford the desired product (1.3 g, 53%) as an off-white solid: ESI MS m/z 247 $[C_{19}H_{30}BNO_4+H]^+$.

Example 470

(S)-tert-Butyl 1-(4-Bromophenyl)ethylcarbamate

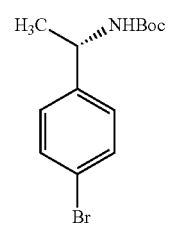

Following the procedure outlined for Example 463, (S)-1-(4-bromophenyl)ethanamine (500 mg, 2.5 mmol) was reacted with di-tert-butyl dicarbonate (650 mg, 3.0 mmol) to afford the desired product (640 mg, 82%) as a white solid: ESI MS m/z 247 $[C_{13}H_{18}BrNO_2+H]^+$.

Example 471

(S)-tert-Butyl 1-[4-(4,4,5,5-Tetramethyl-1,3,2-dioxaborolan-2-yl)phenyl]ethylcarbamate

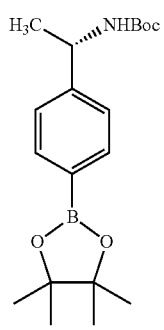

Following General Procedure G, (S)-tert-butyl 1-(4-bromophenyl)ethylcarbamate (630 mg, 2.1 mmol) was reacted with bis(pinacolato)diboron (1.1 g, 3.1 mmol) to afford the desired product (320 mg, 44%) as a brown solid: ESI MS m/z 347 $[C_{19}H_{30}BNO_4-Boc]^+$.

Example 472

2-[2-Fluoro-4-(4,4,5,5-tetramethyl-1,3,2-dioxaborolan-2-yl)phenyl]acetonitrile

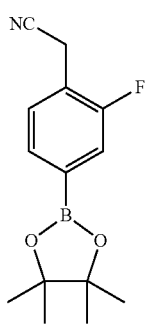 [SMILES: CC1(C)OB(c2ccc(CC#N)c(F)c2)OC1(C)C]

Following General Procedure G, 2-(4-bromo-2-fluorophenyl)acetonitrile (4.0 g, 19 mmol) was reacted with bis(pinacolato)diboron (7.1 g, 28 mmol) to afford the desired product (2.5 g, 57%) as a brown solid: ESI MS m/z 232 $[C_{14}H_{17}BFNO_2+H]^+$.

Example 473

(R)-tert-Butyl 1-(4-Bromophenyl)ethylcarbamate

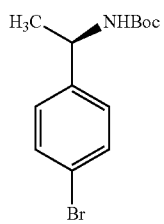

Following the procedure outlined for Example 463, (R)-1-(4-bromophenyl)ethanamine (1.0 g, 5.0 mmol) was reacted with di-tert-butyl dicarbonate (1.3 g, 5.9 mmol) to afford the desired product (1.2 g, 86%) as an off-white solid: ESI MS m/z 301 $[C_{13}H_{18}BrNO_2+H]^+$.

Example 474

(R)-tert-Butyl 1-[4-(4,4,5,5-Tetramethyl-1,3,2-dioxaborolan-2-yl)phenyl]ethylcarbamate

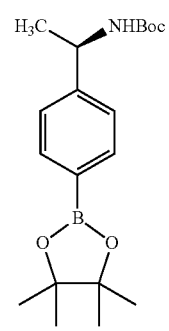

Following General Procedure G, (R)-tert-butyl 1-(4-bromophenyl)ethylcarbamate (1.2 g, 4.0 mmol) was reacted with bis(pinacolato)diboron (1.5 g, 6.0 mmol) to afford the desired product (1.0 g, 77%) as a colorless oil: ESI MS m/z 292 $[C_{19}H_{30}BNO_4-55]^+$.

Example 475

2-Methyl-2-[4-(4,4,5,5-tetramethyl-1,3,2-dioxaborolan-2-yl)phenyl]propanenitrile

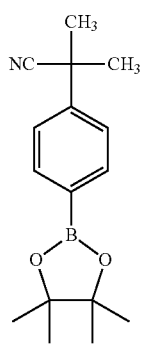

Following General Procedure G, 2-(4-bromophenyl)-2-methylpropanenitrile (1.0 g, 4.5 mmol) was reacted with bis(pinacolato)diboron (1.7 g, 6.7 mmol) to afford the desired product (980 mg, 81%) as an off-white solid: ESI MS m/z 272 $[C_{16}H_{22}BNO_2+H]^+$.

Example 476

1-[2-Fluoro-4-(4,4,5,5-tetramethyl-1,3,2-dioxaborolan-2-yl)benzyl]pyrrolidin-3-ol

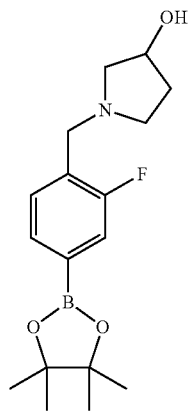 [SMILES: CC1(C)OB(c2ccc(CN3CCC(O)C3)c(F)c2)OC1(C)C]

A solution of 2-[4-(bromomethyl)-3-fluorophenyl]-4,4,5,5-tetramethyl-1,3,2-dioxaborolane (300 mg, 0.95 mmol), pyrrolidin-3-ol (99 mg, 1.1 mmol), and potassium carbonate (160 mg, 1.1 mmol) in acetonitrile (5 mL) was heated to 50° C. for 3 h. The reaction mixture was cooled, filtered and the filtrate was concentrated to afford the desired product (280 mg, 92%) as a red oil: ESI MS m/z 322 $[C_{17}H_{25}BFNO_3+H]^+$.

Example 477 tert-Butyl 5-Bromo-2,3-dihydro-1H-inden-2-ylcarbamate

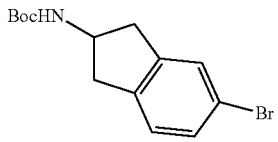 [SMILES: CC(C)(C)OC(=O)NC1Cc2ccc(Br)cc2C1]

Following the procedure outlined for Example 463, 5-bromo-2,3-dihydro-1H-inden-2-amine (2.5 g, 8.5 mmol) was reacted with di-tert-butyl dicarbonate (2.8 g, 13 mmol) to afford the desired product (2.5 g, 96%) as a white solid: ESI MS m/z 313 $[C_{14}H_{18}BrNO_2+H]^+$.

Example 478 tert-Butyl 5-(4,4,5,5-Tetramethyl-1,3,2-dioxaborolan-2-yl)-2,3-dihydro-1H-inden-2-ylcarbamate

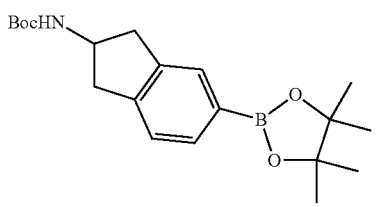 [SMILES: CC(C)(C)OC(=O)NC1Cc2ccc(B3OC(C)(C)C(C)(C)O3)cc2C1]

Following General Procedure G, tert-butyl 5-bromo-2,3-dihydro-1H-inden-2-ylcarbamate (2.5 g, 8.0 mmol) was reacted with bis(pinacolato)diboron (3.0 g, 12 mmol) to afford the desired product (2.1 g, 72%) as a colorless oil: ESI MS m/z 360 $[C_{20}H_{30}BNO_4+H]^+$.

Example 479 tert-Butyl 7-(4,4,5,5-Tetramethyl-1,3,2-dioxaborolan-2-yl)-3,4-dihydroisoquinoline-2(1H)-carboxylate

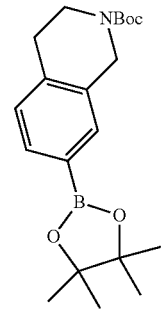 [SMILES: CC(C)(C)OC(=O)N1CCc2ccc(B3OC(C)(C)C(C)(C)O3)cc2C1]

Following General Procedure G, tert-butyl 7-bromo-3,4-dihydroisoquinoline-2(1H)-carboxylate (1.3 g, 4.4 mmol) was reacted with bis(pinacolato)diboron (1.7 g, 6.6 mmol) to afford the desired product (1.1 g, 72%) as a colorless oil: ESI MS m/z 360 $[C_{20}H_{30}BNO_4+H]^+$.

Example 480

1-(4-Bromo-2-fluorophenyl)ethanamine

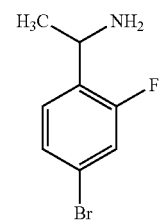

To a solution of 1-(4-bromo-2-fluorophenyl)ethanone (2.0 g, 9.2 mmol) in methanol (50 mL) was added ammonia (7 N in methanol, 8.0 mL, 55 mmol) and titanium(IV) isopropoxide (5.4 mL, 18 mmol). The reaction mixture was stirred at room temperature for 18 h, cooled to 0° C. and sodium borohydride (520 mg, 14 mmol) was added. The reaction mixture was warmed to room temperature, stirred for 20 min, quenched with 2 M ammonium hydroxide and filtered. The reaction mixture was extracted with methylene chloride and the combined organic layers were dried over sodium sulfate, filtered, and concentrated to afford the desired product (1.2 g, 63%) as an oil: ESI MS m/z 219 $[C_8H_9BrFN+H]^+$.

Example 481 tert-Butyl 1-(4-Bromo-2-fluorophenyl)ethylcarbamate

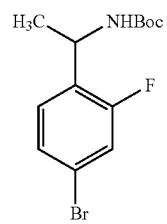

Following the procedure outlined for Example 463, 1-(4-bromo-2-fluorophenyl)ethanamine (1.2 g, 5.6 mmol) was reacted with di-tert-butyl dicarbonate (1.4 g, 6.7 mmol) to afford the desired product (1.3 g, 73%) as a white solid: ESI MS m/z 219 $[C_{13}H_{17}BrFNO_2+H-100]^+$.

Example 482 tert-Butyl 1-[2-Fluoro-4-(4,4,5,5-tetramethyl-1,3,2-dioxaborolan-2-yl)phenyl]ethylcarbamate

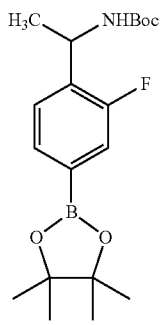

Following General Procedure G, tert-butyl 1-(4-bromo-2-fluorophenyl)ethylcarbamate (1.3 g, 4.4 mmol) was reacted with bis(pinacolato)diboron (1.7 g, 6.6 mmol) to afford the desired product (1.5 g, 93%) as a white solid: ESI MS m/z 266 [$C_{19}H_{29}BFNO_4$+H−100].

Example 483

3-[4-(4,4,5,5-Tetramethyl-1,3,2-dioxaborolan-2-yl)phenyl]propanenitrile

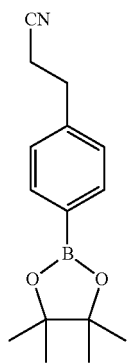

Following General Procedure G, 3-(4-bromophenyl)propanenitrile (1.0 g, 4.8 mmol) was reacted with bis(pinacolato)diboron (1.8 g, 7.1 mmol) to afford the desired product (1.1 g, 97%) as a light brown solid: ESI MS m/z 258 [$C_{15}H_{20}BNO_2$+H]$^+$.

Example 484

N-(1-[4-Bromophenyl]ethyl)cyclopentanamine

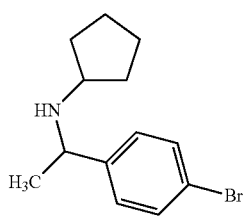

To a solution of 1-(4-bromophenyl)ethanone (500 mg, 2.5 mmol) in ethanol (16 mL) was added cyclopentanamine (320 mg, 3.8 mmol) and the reaction mixture was heated at 50° C. for 18 h. The reaction mixture was cooled to 0° C. and sodium borohydride (140 mg, 3.8 mmol) was added and the reaction mixture was warmed to room temperature and stirred for 30 min. The reaction mixture was quenched with 2 M aqueous ammonium hydroxide and extracted with methylene chloride. The combined organic layers were dried over sodium sulfate, filtered and concentrated to afford the desired product (600 mg, 90%) as a red oil: ESI MS m/z 269 [$C_{13}H_{18}BrN$+H]$^+$.

Example 485 tert-Butyl 1-[4-(4,4,5,5-Tetramethyl-1,3,2-dioxaborolan-2-yl)phenyl]propylcarbamate

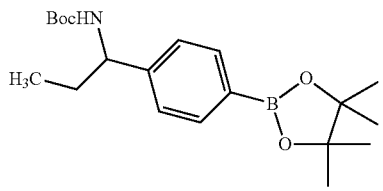 [SMILES: CCC(NC(=O)OC(C)(C)C)c1ccc(B2OC(C)(C)C(C)(C)O2)cc1]

Following General Procedure G, tert-butyl 1-(4-bromophenyl)propylcarbamate (2.0 g, 6.4 mmol) was reacted with bis(pinacolato)diboron (2.4 g, 9.6 mmol) to afford the desired product (2.1 g, 93%) as a yellow solid: ESI MS m/z 305 [$C_{20}H_{32}BNO_4$−56]$^+$.

Example 486

(S)-tert-Butyl 1-(4-Bromophenyl)ethylcarbamate

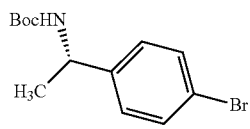 [SMILES: C[C@H](NC(=O)OC(C)(C)C)c1ccc(Br)cc1]

Following the procedure outlined for Example 463, (S)-1-(4-bromophenyl)ethanamine (1.0 g, 5.0 mmol) was reacted with di-tert-butyl dicarbonate (1.3 g, 6.0 mmol) to afford the desired product (1.3 g, 88%) as a white solid: ESI MS m/z 300 [$C_{13}H_{18}BrNO_2$+H]$^+$.

Example 487

(S)-tert-Butyl 1-[4-(4,4,5,5-Tetramethyl-1,3,2-dioxaborolan-2-yl)phenyl]ethylcarbamate

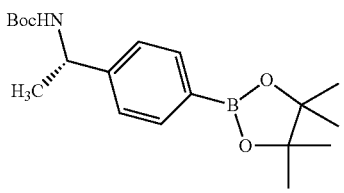 [SMILES: C[C@H](NC(=O)OC(C)(C)C)c1ccc(B2OC(C)(C)C(C)(C)O2)cc1]

Following General Procedure G, (S)-tert-butyl 1-(4-bromophenyl)ethylcarbamate (1.3 g, 4.4 mmol) was reacted with bis(pinacolato)diboron (1.7 g, 6.6 mmol) to afford the desired product (1.4 g, 96%) as a brown solid: ESI MS m/z 348 [$C_{19}H_{30}BNO_4$+H]$^+$.

Example 488

N-(4-Bromobenzyl)propan-2-amine

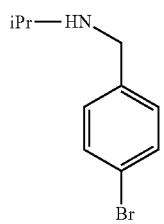 [SMILES: CC(C)NCc1ccc(Br)cc1]

A solution of 1-bromo-4-(bromomethyl)benzene (2.0 g, 8.0 mmol), isopropylamine (950 mg, 16 mmol) and potassium carbonate (2.2 g, 16 mmol) in acetonitrile (40 mL) was stirred at room temperature for 18 h. The reaction mixture was quenched with water and extracted with ethyl acetate. The combined organic layers were washed with brine, dried over anhydrous sodium sulfate, filtered, and concentrated. The residue was purified by column chromatography (silica, 0-100% methylene chloride/methanol) to afford the desired product (1.4 g, 78%) as a brown solid: ESI MS m/z 228 $[C_{10}H_{14}BrN+H]^+$.

Example 489

4-({4-[(tert-Butoxycarbonylamino)methyl]piperidin-1-yl}methyl)phenylboronic acid

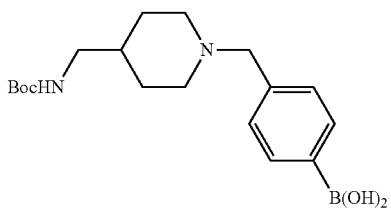 [SMILES: CC(C)(C)OC(=O)NCC1CCN(Cc2ccc(B(O)O)cc2)CC1]

Following the procedure outlined for Example 488, 4-formylphenylboronic acid (100 mg, 0.47 mmol) was reacted with tert-butyl piperidin-4-ylmethylcarbamate (70 mg, 0.47 mmol) to afford the desired product (120 mg, 77%) as a brown solid: ESI MS m/z 349 $[C_{18}H_{29}BN_2O_4+H]^+$.

Example 490

(E)-tert-Butyl 1-[3-(4,4,5,5-Tetramethyl-1,3,2-dioxaborolan-2-yl)allyl]piperidin-4-ylcarbamate

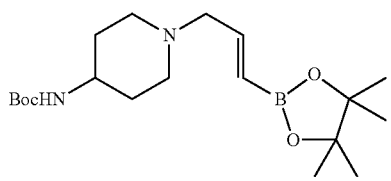 [SMILES: CC(C)(C)OC(=O)NC1CCN(C/C=C/B2OC(C)(C)C(C)(C)O2)CC1]

Following the procedure outlined for Example 488, (Z)-2-(3-chloroprop-1-enyl)-4,4,5,5-tetramethyl-1,3,2-dioxaborolane (210 mg, 1.1 mmol) was reacted with tert-butyl piperidin-4-ylcarbamate (640 mg, 3.2 mmol) to afford the desired product (100 mg, 30%) as a brown solid: ESI MS m/z 367 $[C_{14}H_{27}BN_2O_2+H]^+$.

Example 491

1-(4-Bromophenyl)-N-methylmethanamine

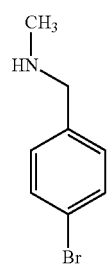

Following the procedure outlined for Example 488, 1-bromo-4-(bromomethyl)benzene (1.0 g, 4.0 mmol) was reacted with methanamine (620 mg, 20 mmol) to afford the desired product (750 mg, 93%) as a brown solid: ESI MS m/z 201 $[C_8H_{10}BrN+H]^+$.

Example 492

N-(4-Bromobenzyl)ethanamine

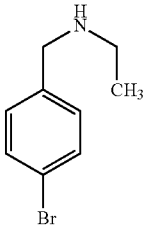

Following the procedure outlined for Example 488, 1-bromo-4-(bromomethyl)benzene (2.0 g, 8.0 mmol) was reacted with ethanamine (720 mg, 16 mmol) to afford the desired product (1.3 g, 75%) as a brown solid: ESI MS m/z 215 $[C_9H_{12}BrN+H]^+$.

Example 493

(E)-2-(3-Chloroprop-1-enyl)-4,4,5,5-tetramethyl-1,3,2-dioxaborolane

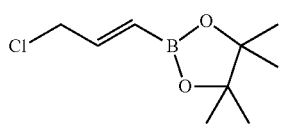

A solution of (E)-3-chloroprop-1-enylboronic acid (5 g, 41 mmol), pinacol (4.9 g, 41 mmol), and magnesium sulfate (15 g, 120 mmol) in methylene chloride (100 mL) was stirred at room temperature for 18 h. The reaction mixture was filtered

Example 494

(E)-tert-Butyl 1-[3-(4,4,5,5-Tetramethyl-1,3,2-dioxaborolan-2-yl)allyl]piperidin-3-ylcarbamate

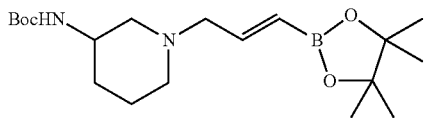 [SMILES: CC(C)(C)OC(=O)NC1CCCN(C/C=C/B2OC(C)(C)C(C)(C)O2)C1]

Following the procedure outlined for Example 488, (E)-2-(3-chloroprop-1-enyl)-4,4,5,5-tetramethyl-1,3,2-dioxaborolane (500 mg, 2.5 mmol) was reacted with tert-butyl piperidin-3-ylcarbamate (740 mg, 3.7 mmol) to afford the desired product (320 mg, 24%) as a yellow oil: ESI MS m/z 367 $[C_{19}H_{35}BN_2O_4+H]^+$.

Example 495

4-Bromo-2-fluoro-N-(2-hydroxyethyl)benzenesulfonamide

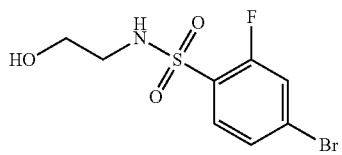 [SMILES: O=S(=O)(NCCO)c1ccc(Br)cc1F]

To a solution of 2-aminoethanol (0.24 mL, 4.0 mmol), and triethylamine (1.5 mL, 11 mmol) in anhydrous THF (15 mL) was added 4-bromo-2-fluorobenzene-1-sulfonyl chloride (1.0 g, 3.7 mmol) portion wise and the reaction mixture stirred at room temperature for 16 h. The reaction was filtered, the filtrate was concentrated and the residue was purified by column chromatography (silica, ethyl acetate/hexanes gradient) to afford the desired product (850 mg, 77%): ESI MS m/z 298 $[C_8H_9BrFNO_3S+H]^+$.

Example 496

4-Bromo-N-(2-hydroxyethyl)benzenesulfonamide

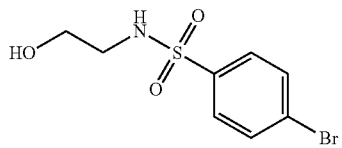 [SMILES: O=S(=O)(NCCO)c1ccc(Br)cc1]

To a solution of 2-aminoethanol (2.3 mL, 39 mmol), and triethylamine (16 mL, 120 mmol) in anhydrous THF (100 mL) was added 4-bromobenzene-1-sulfonyl chloride (10 g, 39 mmol) portion wise and the reaction mixture stirred at room temperature for 16 h. The reaction was filtered, the filtrate was concentrated and the residue was purified by column chromatography (silica, ethyl acetate/hexanes gradient) to afford the desired product (5.5 g, 50%): $^1$H NMR (500 MHz, CDCl$_3$) δ 7.74 (td, J=9.0, 2.1 Hz, 2H), 7.67 (td, J=9.0, 2.1 Hz, 2H), 5.08 (s, 1H), 3.72 (t, J=5.1 Hz, 2H), 3.12 (t, J=4.8 Hz, 2H), 1.83 (s, 1H).

Example 497

N-(2-Hydroxyethyl)-4-(4,4,5,5-tetramethyl-1,3,2-dioxaborolan-2-yl)benzenesulfonamide

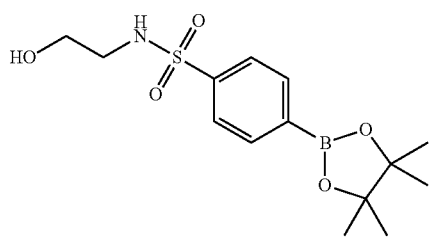 [SMILES: CC1(C)OB(c2ccc(S(=O)(=O)NCCO)cc2)OC1(C)C]

Following General Procedure G, 4-bromo-N-(2-hydroxyethyl)benzenesulfonamide (5.0 g, 18 mmol) was reacted with bis(pinacolato)diboron (4.9 g, 20 mmol) to afford the desired product (4.2 g, 40%) as a yellow solid: $^1$H NMR (300 MHz, CDCl$_3$) δ 7.95 (d, J=8.3 Hz, 2H), 7.85 (d, J=8.3 Hz, 2H), 5.14 (t, J=6.1 Hz, 1H), 3.68 (t, J=5.0 Hz, 2H), 3.09 (q, J=5.4 Hz, 2H), 1.36 (s, 12H).

Example 498

(S)-tert-Butyl 1-(3-Bromo-4-nitrophenyl)pyrrolidin-3-ylcarbamate

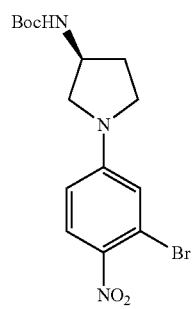

A solution of 2-bromo-4-fluoro-1-nitrobenzene (1.5 g, 6.8 mmol), (S)-tert-butyl pyrrolidin-3-ylcarbamate (1.9 g, 10 mmol), and sodium bicarbonate (1.7 g, 20 mmol) in DMSO (40 mL) was heated at 80° C. for 1 h. The reaction mixture was cooled to room temperature, poured into excess water and the resulting precipitate was filtered. The solids were washed with aqueous ammonium chloride, brine and water to afford the desired product (2.5 g, 96%) as a yellow solid: 387 $[C_{15}H_{20}BrN_3O_4+H]^+$.

Example 499

(S)-tert-Butyl 1-(4-Amino-3-bromophenyl)pyrrolidin-3-ylcarbamate

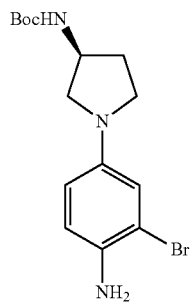 [SMILES: CC(C)(C)OC(=O)N[C@H]1CCN(c2ccc(N)c(Br)c2)C1]

A solution of (S)-tert-butyl 1-(3-bromo-4-nitrophenyl)pyrrolidin-3-ylcarbamate (2.5 g, 6.5 mmol), ammonium chloride (380 mg, 7.1 mmol), and iron (1.8 g, 32 mmol) in ethanol (20 mL) and water (10 mL) was heated to reflux for 1 h. The reaction mixture was cooled to room temperature and filtered through diatomaceous earth. The filtrate was concentrated to afford the desired product (2.3 g, >99%) as a blue solid: ESI MS m/z 357 $[C_{15}H_{22}BrN_3O_2+H]^+$.

Example 500

Methyl 5-Bromothiophene-2-carboxylate

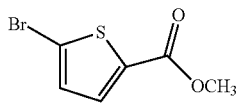

A solution of 5-bromothiophene-2-carboxylic acid (5.0 g, 24 mmol), methyl iodide (5.1 g, 30 mmol), and potassium carbonate (6.7 g, 48 mmol) in DMF (50 mL) was stirred at room temperature for 64 h. The reaction was quenched with water and the aqueous layer was extracted multiple times with ethyl acetate. The combined organic layers were washed with aqueous lithium chloride and brine, dried over anhydrous sodium sulfate, filtered, and concentrated. The residue was purified by column chromatography (silica, ethyl acetate/hexanes gradient) to afford the desired product (4.2 g, 79%): $^1$H NMR (500 MHz, CDCl$_3$) δ 7.54 (d, J=4.0 Hz, 1H), 7.07 (d, J=4.0 Hz, 1H), 3.87 (s, 3H).

Example 501

Methyl 5-(4-Methoxyphenyl)thiophene-2-carboxylate

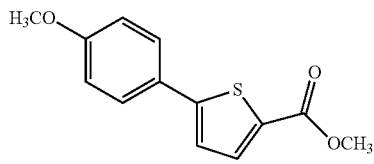 [SMILES: COC(=O)c1ccc(-c2ccc(OC)cc2)s1]

Following General Procedure B, 4-methoxyphenylboronic acid (2.7 g, 18 mmol) was reacted with methyl 5-bromothiophene-2-carboxylate (2.0 g, 9.0 mmol) to afford the desired product (1.4 g, 61%): $^1$H NMR (300 MHz, CDCl$_3$) δ 7.71 (d, J=3.9 Hz, 1H), 7.53 (td, J=9.7, 2.5 Hz, 2H), 7.14 (d, J=3.9 Hz, 1H), 6.89 (td, J=9.7, 2.5 Hz, 2H), 3.87 (s, 3H), 3.80 (s, 3H).

Example 502

5-(4-Methoxyphenyl)thiophene-2-carboxylic Acid

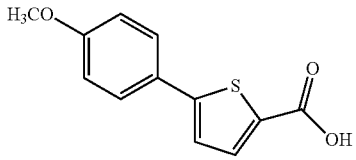 [SMILES: COc1ccc(-c2ccc(C(=O)O)s2)cc1]

A solution of methyl 5-(4-methoxyphenyl)thiophene-2-carboxylate (1.4 g, 5.6 mmol), and 1 M sodium hydroxide (55 mL) in methanol (55 mL) was heated at 80° C. for 18 h. The reaction mixture was cooled to room temperature and diluted with ethyl acetate. The organic layer was washed with 1 N hydrochloric acid and aqueous sodium chloride, dried over anhydrous sodium sulfate, filtered, and concentrated to afford the desired product (1.2 g, 93%) as an off-white solid: ESI MS m/z 325 $[C_{12}H_{10}O_3S+H]^+$.

Example 503

5-(4-Methoxyphenyl)thiophene-2-carbonyl chloride

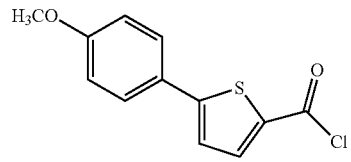 [SMILES: COc1ccc(-c2ccc(C(=O)Cl)s2)cc1]

To a solution of 5-(4-methoxyphenyl)thiophene-2-carboxylic acid (0.60 g, 2.5 mmol) in toluene (4 mL) was added thionylchloride (560 mL, 7.7 mmol) and the reaction mixture was heated at 100° C. for 18 h. The reaction mixture was cooled to room temperature and concentrated to afford the desire product (642 mg, crude): ESI MS m/z 253 $[C_{12}H_9ClO_2S+H]^+$.

Example 504

(S)-tert-Butyl 1-{3-Bromo-4-[5-(4-methoxyphenyl)thiophene-2-carboxamido]phenyl}pyrrolidin-3-ylcarbamate

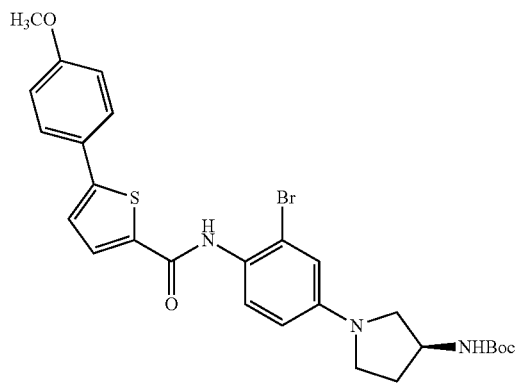 [SMILES: COc1ccc(-c2ccc(C(=O)Nc3ccc(N4CC[C@H](NC(=O)OC(C)(C)C)C4)cc3Br)s2)cc1]

Following Step 1 from General Procedure A, 5-(4-methoxyphenyl)thiophene-2-carbonyl chloride (640 mg, 2.5 mmol) was reacted with (S)-tert-butyl 1-(4-amino-3-bromophenyl)pyrrolidin-3-ylcarbamate (800 mg, 2.2 mmol) to afford the desired product (500 mg, 39%) as a light yellow solid: ESI MS m/z 573 $[C_{27}H_{30}BrN_3O_4S+H]^+$.

Example 505

(S)-tert-Butyl 1-{3-Bromo-4-[5-(4-methoxyphenyl)-N-{[2-(trimethylsilyl)ethoxy]methyl}thiophene-2-carboxamido]phenyl}pyrrolidin-3-ylcarbamate

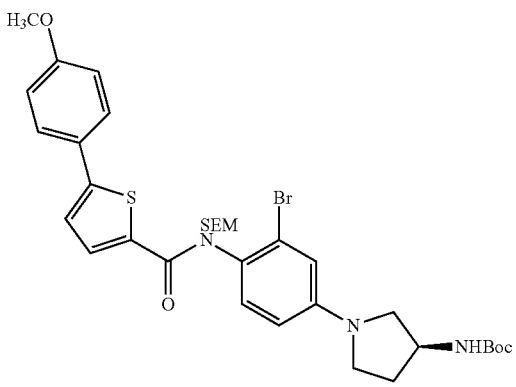 [SMILES: COc1ccc(-c2ccc(C(=O)N(COCC[Si](C)(C)C)c3ccc(N4CC[C@H](NC(=O)OC(C)(C)C)C4)cc3Br)s2)cc1]

A solution of (S)-tert-butyl 1-{3-bromo-4-[5-(4-methoxyphenyl)thiophene-2-carboxamido]phenyl}pyrrolidin-3-ylcarbamate (400 mg, 0.69 mmol) in THF (20 mL) was cooled to 0° C. and sodium hydride (60 wt %, 140 mg, 3.5 mmol) was added. The reaction was warmed to room temperature followed by the addition of 2-(trimethylsilyl)ethoxymethyl chloride (370 mL, 2.1 mmol) and the reaction mixture was stirred at room temperature for 18 h. The reaction mixture was quenched with water and diluted with ethyl acetate. The layers were separated and the organic layer was dried over anhydrous sodium sulfate, filtered, concentrated and the residue was purified by column chromatography (silica, 0-30% ethyl acetate/heptane) to afford the desired product (400 mg, 87%): ESI MS m/z 703 $[C_{33}H_{44}BrN_3O_5SSi+H]^+$.

Example 506

(S)-8-(3-Aminopyrrolidin-1-yl)-2-(4-methoxyphenyl)-5-{[2-(trimethylsilyl)ethoxy]methyl}thieno[2,3-c]quinolin-4(5H)-one

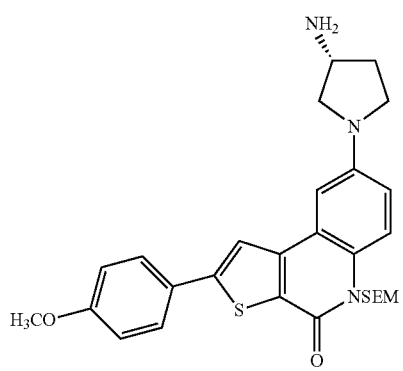 [SMILES: COc1ccc(-c2cc3c(s2)c(=O)n(COCC[Si](C)(C)C)c2ccc(N4CC[C@@H](N)C4)cc32)cc1]

Following Step 3 from General Procedure A, (S)-tert-butyl 1-{3-bromo-4-[5-(4-methoxyphenyl)-N-{[2-(trimethylsilyl)ethoxy]methyl}thiophene-2-carboxamido]phenyl}pyrrolidin-3-ylcarbamate (210 mg, 0.29 mmol) was reacted with bis(tri-tert-butylphosphine)palladium (15 mg, 0.029 mmol) to afford the desired product (25 mg, 14%): ESI MS m/z 622 $[C_{28}H_{35}N_3O_3SSi+H]^+$.

Example 51

(S)-8-(3-Aminopyrrolidin-1-yl)-2-(4-hydroxyphenyl)thieno[2,3-c]quinolin-4(5H)-one Hydrochloride

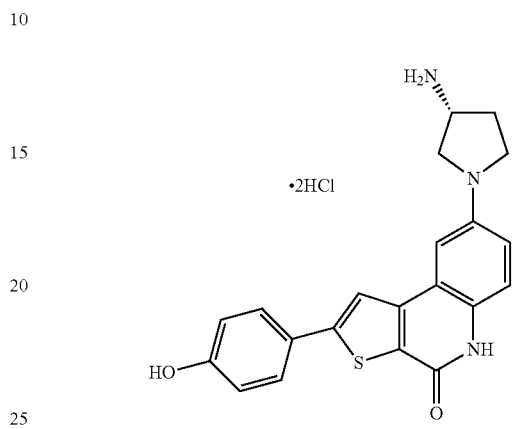

Following General Procedure F, (S)-8-(3-aminopyrrolidin-1-yl)-2-(4-methoxyphenyl)-5-{[2-(trimethylsilyl)ethoxy]methyl}thieno[2,3-c]quinolin-4(5H)-one (25 mg, 0.040 mmol) was reacted with tribromoborane (38 mL, 0.40 mmol) to afford the desired product (6.4 mg, 43%) as a yellow-green solid: $^1$H NMR (500 MHz, CD$_3$OD) δ 8.06 (s, 1H), 7.71 (d, J=8.6 Hz, 2H), 7.36 (d, J=9.0 Hz, 1H), 7.26 (s, 1H), 6.99 (d, J=8.4 Hz, 1H), 6.90 (d, J=8.5 Hz, 2H), 4.09 (s, 1H), 3.74-3.69 (m, 2H), 3.59-3.57 (m, 1H), 3.48-3.39 (m, 1H), 2.57-2.52 (m, 1H), 2.25-2.23 (m, 1H); ESI MS m/z 378 $[C_{21}H_{19}N_3O_2S+H]^+$; HPLC 97.1% (AUC), $t_R$=10.89 min.

Compounds of the invention of this application that the specific procedure for producing the compound was not particularly described in the Examples above were also synthesized by the similar or analogous methods by referring to the above-mentioned general procedures for producing the present compounds, Examples and such.

Examples 507

Kinase Assay

PBK activity was determined in the presence or absence of compounds using fluorescein isothiocyanate-labeled (FITC-labeled) histone H3 peptide as a substrate. The extent of FITC-labeled histone H3 peptide phosphorylation was measured by immobilized metal ion affinity-based fluorescence polarization (IMAP) technology (Sportsman J R, et al., Assay Drug Dev. Technol. 2: 205-14, 2004) using IMAP FP Progressive Binding System (Molecular Devices Corporation). Test compounds were dissolved in DMSO at 12.5 mM and then serially diluted as the DMSO concentration in the assays to be 1%. The serially diluted compounds, 0.8 ng/micro-L PBK (Carna Biosciences) and 100 nM FITC-labeled histone H3 peptide were reacted in a reaction buffer (20 mM HEPES, 0.01% Tween-20, 0.3 mM MgCl$_2$, 2 mM dithiothreitol, 50 micro-M ATP, pH 7.4) at room temperature for 1 hour. The reaction was stopped by the addition of three fold assay volume of progressive binding solution. Following 0.5 hour incubation at room temperature, fluorescence polarization was measured by Wallac EnVision 2103 multilabel reader (PerkinElmer). IC50 values were calculated by nonlinear four parameter fit using SigmaPlot, version 10.0 (Systat Software, Inc.).

$IC_{50}$ values of the typical compounds of the present invention are shown in following table 2:

TABLE 2

| ID. | Compound | IC50 (microM) (kinase assay) |
|---|---|---|
| 51 | (S)-8-(3-Aminopyrrolidin-1-yl)-2-(4-hydroxyphenyl)thieno[2,3-c]quinolin-4(5H)-one Dihydrochloride | 0.078 |
| 61 | 8-Hydroxy-9-(1H-indazol-6-yl)thieno[2,3-c]quinolin-4(5H)-one | 0.0035 |
| 65 | 4-(8-Hydroxy-4-oxo-4,5-dihydrothieno[2,3-c]quinolin-9-yl)benzenesulfonamide | 0.0018 |
| 72 | 9-[4-(Aminomethyl)phenyl]-8-hydroxythieno[2,3-c]quinolin-4(5H)-one | 0.00063 |
| 73 | 9-[4-(Aminomethyl)phenyl]-8-hydroxythieno[2,3-c]quinolin-4(5H)-one Hydrochloride | 0.00038 |
| 77 | N-[4-(8-Hydroxy-4-oxo-4,5-dihydrothieno[2,3-c]quinolin-9-yl)phenyl]methanesulfonamide | 0.0026 |
| 81 | 2-[4-(8-Hydroxy-4-oxo-4,5-dihydrothieno[2,3-c]quinolin-9-yl)phenyl]acetonitrile | 0.012 |
| 84 | 8-Hydroxy-9-(1,2,3,6-tetrahydropyridin-4-yl)thieno[2,3-c]quinolin-4(5H)-one | 0.00078 |
| 93 | 9-{4-4[2-(Dimethylamino)ethyl[phenyl}-8-hydroxythieno[2,3-c]quinolin-4(5H)-one | 0.0054 |
| 95 | 9-[4-(Aminomethyl)phenyl]-8-hydroxy-2-methylthieno][2,3-c]quinolin-4(5H)-one | 0.0044 |
| 112 | 8-Hydroxy-9-{4-[4-(methylsulfonyl)piperazin-1-yl]phenyl}thieno[2,3-c]quinolin-4(5H)-one | 0.012 |
| 139 | tert-Butyl {1-[4-(8-Methoxy-4-oxo-4,5-dihydrothieno[2,3-c]quinolin-9-yl)benzyl]piperidin-4-yl}methylcarbamate | 0.0094 |
| 145 | 9-(4-{3-[2-Diethylamino)ethylamino]propoxy}phenyl)-8-methoxythieno[2,3-c]quinolin-4(5H)-one | 0.047 |
| 152 | (E)-9-[3-(4-Aminopiperidin-1-yl)prop-1-enyl]-8-methoxythieno[2,3-c]quinolin-4(5H)-one | 0.031 |
| 164 | 9-{4-[(Dimethylamino)methyl]phenyl}-8-methoxythieno[2,3-c]quinolin-4(5H)-one | 0.011 |
| 165 | 9-{4-[(Dimethylamino)methyl]phenyl}-8-hydroxythieno[2,3-c]quinolin-4(5H)-one | 0.0069 |
| 169 | 9-[4-(2-Aminoethyl)phenyl]-8-methoxythieno[2,3-c]quinolin-4(5H)-one | 0.022 |
| 175 | 9-[4-(2-Aminoethyl)phenyl]-8-hydroxythieno[2,3-c]quinolin-4(5H)-one | 0.0012 |
| 176 | 9-[4-(2-Aminoethyl)phenyl]-8-hydroxythieno[2,3-c]quinolin-4(5H)-one Hydrochloride | 0.0011 |
| 184 | 9-{4-[(Diethylamino)methyl]phenyl}-8-hydroxythieno[2,3-c]quinolin-4(5H)-one | 0.0077 |
| 187 | 8-Hydroxy-9-{4-[(methylamino)methyl]phenyl}thieno[2,3-c]quinolin-4(5H)-one | 0.0009 |
| 188 | 8-Methoxy-9-{4-[(methylamino)methyl]phenyl}thieno[2,3-c]quinolin-4(5H)-one | 0.0078 |
| 192 | 9-(4-(1-(dimethylamino)ethyl)phenyl)-8-hydroxythieno[2,3-c]quinolin-4(5H)-one Hydrochloride | 0.0016 |
| 191 | 9-{4-[1-(Dimethylamino)ethyl]phenyl}-8-hydroxythieno[2,3-c]quinolin-4(5H)-one | 0.0019 |
| 193 | N-{1-[4-(8-Hydroxy-4-oxo-4,5-dihydrothieno[2,3-c]quinolin-9-yl)phenyl]ethyl}methanesulfonamide | 0.0037 |
| 194 | 8-Hydroxy-9-{4-[1-(pyrrolidin-1-yl)ethyl]phenyl}thieno[2,3-c]quinolin-4(5H)-one Hydrochloride | 0.0028 |
| 195 | 9-[4-(1-Aminoethyl)phenyl]-8-hydroxythieno[2,3-c]quinolin-4(5H)-one Hydrochloride | 0.00073 |
| 196 | 9-{4-(1-(dimethylamino)ethyl]phenyl}-8-hydroxythieno[2,3-c]quinolin-4(5H)-one Hydrochloride | 0.0045 |
| 210 | N-(2-Bromoethyl)-4-(8-hydroxy-4-oxo-4,5-dihydrothieno[2,3-c]quinolin-9-yl)benzenesulfonamide | 0.0113 |
| 212 | N-[4-(8-Hydroxy-4-oxo-4,5-dihydrothieno[2,3-c]quinolin-9-yl)benzyl]methanesulfonamide | 0.0055 |
| 216 | 8-Methoxy-9-{4-[1-(pyrrolidin-1-yl)ethyl]phenyl}thieno[2,3-c]quinolin-4(5H)-one Hydrochloride | 0.021 |
| 217 | 9-(4-Amino-3-hydroxyphenyl)-8-hydroxythieno[2,3-c]quinolin-4(5H)-one Hydrochloride | 0.0023 |
| 222 | 9-{4-[1-(Dimethylamino)ethyl]phenyl}-6-fluoro-8-methoxythieno[2,3-c]quinolin-4(5H)-one Hydrochloride | 0.082 |
| 225 | 9-{4-[2-(Dimethylamino)ethyl]phenyl}-6-fluoro-8-hydroxythieno[2,3-c]quinolin-4(5H)-one | 0.023 |
| 229 | 8-Hydroxy-9-{4-[(isopropylamino)methyl]phenyl}thieno[2,3-c]quinolin-4(5H)-one Hydrochloride | 0.0042 |
| 232 | (S)-9-[4-(1-Aminoethyl)phenyl]-8-methoxythieno[2,3-c]quinolin-4(5H)-one Hydrochloride | 0.0074 |

TABLE 2-continued

| ID. | Compound | IC50 (microM) (kinase assay) |
|---|---|---|
| 233 | (S)-9-[4-(1-Aminoethyl)phenyl]-8-hydroxythieno[2,3-c]quinolin-4(5H)-one Hydrochloride | 0.00081 |
| 235 | 9-(4-{[4-(Aminomethyl)piperidin-1-yl]methyl}-3-fluorophenyl)-8-hydroxythieno[2,3-c]quinolin-4(5H)-one | 0.00057 |
| 254 | N-[4-(8-Hydroxy-4-oxo-4,5-dihydrothieno[2,3-c]quinolin-9-yl)-2-methylphenyl]methanesulfonamide | 0.003 |
| 256 | 9-[4-(Aminomethyl)phenyl]-6-fluoro-8-hydroxythieno[2,3-c]quinolin-4(5H)-one Hydrochloride | 0.0025 |
| 257 | 9-[4-(Aminomethyl)phenyl]-6-fluoro-8-methoxythieno[2,3-c]quinolin-4(5H)-one Hydrochloride | 0.026 |
| 261 | 2-[2-Fluoro-4-(8-hydroxy-4-oxo-4,5-dihydrothieno[2,3-c]quinolin-9-yl)phenyl]acetonitrile | 0.015 |
| 262 | 8-Hydroxy-9-{4-[1-(piperidin-1-yl)ethyl]phenyl}thieno[2,3-c]quinolin-4(5H)-one Hydrochloride | 0.0043 |
| 265 | 9-[4-(2-Aminoethyl)-3-fluorophenyl]-8-methoxythieno[2,3-c]quinolin-4(5H)-one Hydrochloride | 0.0038 |
| 266 | 9-[5-(Aminomethyl)thiophen-2-yl]-8-hydroxythieno[2,3-c]quinolin-4(5H)-one | 0.00078 |
| 267 | 9-{4-[(Ethylamino)methyl]phenyl}-8-hydroxythieno[2,3-c]quinolin-4(5H)-one Hydrochloride | 0.002 |
| 269 | 9-{4-[(Ethylamino)methyl]phenyl}-8-methoxythieno[2,3-c]quinolin-4(5H)-one Hydrochloride | 0.006 |
| 270 | 9-[4-(Aminomethyl)phenyl]-6-bromo-8-hydroxythieno[2,3-c]quinolin-4(5H)-one Hydrochloride | 0.031 |
| 272 | (R)-9-{4-[1-(Dimethylamino)ethyl]phenyl}-8-hydroxythieno[2,3-c]quinolin-4(5H)-one Hydrochloride | 0.00088 |
| 273 | 9-[4-(3-Aminopropyl)phenyl]-8-hydroxythieno[2,3-c]quinolin-4(5H)-one Hydrochloride | 0.00074 |
| 274 | (R)-9-[4-(1-Aminoethyl)phenyl]-8-methoxythieno[2,3-c]quinolin-4(5H)-one Hydrochloride | 0.0038 |
| 275 | (R)-9-[4-(1-Aminoethyl)phenyl]-8-hydroxythieno[2,3-c]quinolin-4(5H)-one Hydrochloride | 0.00054 |
| 276 | 9-[4-(2-Aminoethyl)-3-fluorophenyl]-8-hydroxythieno[2,3-c]quinolin-4(5H)-one Hydrochloride | 0.0005 |
| 277 | 9-[4-(1-Amino-2-methylpropan-2-yl)phenyl]-8-hydroxythieno[2,3-c]quinolin-4(5H)-one Hydrochloride | 0.00067 |
| 278 | 9-{3-Fluoro-4-[(3-hydroxypyrrolidin-1-yl)methyl]phenyl}-8-hydroxythieno[2,3-c]quinolin-4(5H)-one Hydrochloride | 0.00097 |
| 290 | 3-[4-(8-Hydroxy-4-oxo-4,5-dihydrothieno[2,3-c]quinolin-9-yl)phenyl]propanenitrile | 0.0032 |
| 296 | 9-(4-Acetylphenyl)-8-hydroxythieno[2,3-c]quinolin-4(5H)-one | 0.023 |
| 297 | N-(2-Bromoethyl)-2-fluoro-4-(8-hydroxy-4-oxo-4,5-dihydrothieno[2,3-c]quinolin-9-yl)benzenesulfonamide | 0.013 |
| 298 | 9-{3-[3-(Dimethylamino)piperidin-1-yl]propyl}-8-hydroxythieno[2,3-c]quinolin-4(5H)-one Dihydrochloride | 0.083 |
| 301 | (R)-N-{1-[4-(8-Hydroxy-4-oxo-4,5-dihydrothieno[2,3-c]quinolin-9-yl)phenyl]ethyl}methanesulfonamide | 0.0032 |
| 304 | 4-(8-Hydroxy-4-oxo-4,5-dihydrothieno[2,3-c]quinolin-9-yl)-N,N-dimethylbenzenesulfonamide | 0.045 |
| 308 | 9-{4-[1-(Dimethylamino)-2-methylpropan-2-yl]phenyl}-8-hydroxythieno[2,3-c]quinolin-4(5H)-one Hydrochloride | 0.0028 |
| 313 | 8-Hydroxy-9-[4-(1-hydroxyethyl)phenyl]thieno[2,3-c]quinolin-4(5H)-one | 0.002 |
| 314 | 9-{4-[1-(Cyclopentylamino)ethyl]phenyl}-8-hydroxythieno[2,3-c]quinolin-4(5H)-one Hydrochloride | 0.0028 |
| 319 | 9-[4-(2-Aminopropan-2-yl)phenyl]-8-hydroxythieno[2,3-c]quinolin-4(5H)-one Hydrochloride | 0.00043 |
| 326 | 9-[4-(Aminomethyl)phenyl]-4-oxo-4,5-dihydrothieno[2,3-c]quinoline-8-carbonitrile Hydrochloride | 0.013 |
| 327 | 9-{4-[2-(Dimethylamino)ethyl]-3-fluorophenyl}-8-hydroxythieno[2,3-c]quinolin-4(5H)-one Hydrochloride | 0.0019 |
| 329 | 9-[4-(Aminomethyl)phenyl]-6-chloro-8-hydroxythieno[2,3-c]quinolin-4(5H)-one Hydrochloride | 0.016 |
| 332 | N-(2-Chloroethyl)-4-(8-hydroxy-4-oxo-4,5-dihydrothieno[2,3-c]quinolin-9-yl)benzenesulfonamide | 0.023 |
| 333 | N-(2-Fluoroethyl)-4-(8-methoxy-4-oxo-4,5-dihydrothieno[2,3-c]quinolin-9-yl)benzenesulfonamide | 0.031 |
| 334 | 9-[4-(2-Aminopropan-2-yl)phenyl]-6-chloro-8-hydroxythieno[2,3-c]quinolin-4(5H)-one Hydrochloride | 0.01 |
| 335 | (S)-9-{4-[1-(Dimethylamino)ethyl]phenyl}-8-hydroxythieno[2,3-c]quinolin-4(5H)-one Hydrochloride | 0.0029 |
| 336 | 9-[4-(1-Aminopropyl)phenyl]-8-hydroxythieno[2,3-c]quinolin-4(5H)-one Hydrochloride | 0.00082 |
| 337 | 9-[4-(1-Aminopropyl)phenyl]-8-methoxythieno[2,3-c]quinolin-4(5H)-one Hydrochloride | 0.0052 |
| 338 | 9-{4-[1-(Diethylamino)propyl]phenyl}-8-hydroxythieno[2,3-c]quinolin-4(5H)-one Hydrochloride | 0.0037 |
| 339 | 9-{4-[1-(Dimethylamino)propyl]phenyl}-8-hydroxythieno[2,3-c]quinolin-4(5H)-one Hydrochloride | 0.0019 |

TABLE 2-continued

| ID. | Compound | IC50 (microM) (kinase assay) |
|---|---|---|
| 341 | 9-{4-[1-(Dimethylamino)ethyl]phenyl}-6,7-difluoro-8-hydroxythieno[2,3-c]quinolin-4(5H)-one Hydrochloride | 0.034 |
| 345 | 9-(2-Amino-2,3-dihydro-1H-inden-5-yl)-8-hydroxythieno[2,3-c]quinolin-4(5H)-one Hydrochloride | 0.0012 |
| 346 | 9-{4-[1-(Dimethylamino)ethyl]phenyl}thieno[2,3-c]quinolin-4(5H)-one | 0.0092 |
| 347 | (S)-N-{1-[4-(8-Hydroxy-4-oxo-4,5-dihydrothieno[2,3-c]quinolin-9-yl)phenyl]ethyl}methanesulfonamide | 0.002 |
| 348 | 9-{4-[1-(Aminomethyl)cyclopropyl]phenyl}-8-hydroxythieno[2,3-c]quinolin-4(5H)-one Hydrochloride | 0.0019 |
| 349 | 9-{4-[1-(Dimethylamino)ethyl]-3-fluorophenyl}-8-hydroxythieno[2,3-c]quinolin-4(5H)-one Hydrochloride | 0.0019 |
| 353 | 8-Hydroxy-9-(1,2,3,4-tetrahydroisoquinolin-7-yl)thieno[2,3-c]quinolin-4(5H)-one Hydrochloride | 0.002 |
| 356 | 9-{4-[1-(Diethylamino)ethyl]-3-fluorophenyl}-8-hydroxythieno[2,3-c]quinolin-4(5H)-one Hydrochloride | 0.0036 |
| 359 | 9-[4-(1-Aminoethyl)-3-fluorophenyl]-8-hydroxythieno[2,3-c]quinolin-4(5H)-one Hydrochloride | 0.00092 |
| 361 | 1-[4-(8-Hydroxy-4-oxo-4,5-dihydrothieno[2,3-c]quinolin-9-yl)phenyl]cyclopropanecarbonitrile | 0.032 |
| 373 | 9-(4-(1-aminopropan-2-yl)phenyl)-8-methoxythieno[2,3-c]quinolin-4(5H)-one hydrochloride | 0.0032 |
| 379 | 9-(4-(1-((dimethylamino)methyl)cyclopropyl)phenyl)-8-hydroxythieno[2,3-c]quinolin-4(5H)-one hydrochloride | 0.0036 |
| 385 | 9-(4-(1-(ethylamino)ethyl)phenyl)-8-hydroxythieno[2,3-c]quinolin-4(5H)-one hydrochloride | 0.0039 |
| 1032 | 9-(4-(1-aminoethyl)phenyl)-6-bromo-8-hydroxythieno[2,3-c]quinolin-4(5H)-one hydrochloride | 0.047 |
| 1041 | 9-(4-(1-aminoethyl)phenyl)-6-chloro-8-hydroxythieno[2,3-c]quinolin-4(5H)-one hydrochloride | 0.012 |
| 1052 | (R)-8-hydroxy-9-(4-(1-(methylamino)ethyl)phenyl)thieno[2,3-c]quinolin-4(5H)-one hydrochloride | 0.0013 |
| 1062 | N-(1-bromopropan-2-yl)-4-(8-hydroxy-4-oxo-4,5-dihydrothieno[2,3-c]quinolin-9-yl)benzenesulfonamide | 0.031 |
| 1064 | (S)-8-methoxy-9-(4-(1-(methylamino)ethyl)phenyl)thieno[2,3-c]quinolin-4(5H)-one hydrochloride | 0.0025 |
| 1066 | 9-(4-(1-aminoethyl)phenyl)-8-hydroxy-6-methylthieno[2,3-c]quinolin-4(5H)-one hydrochloride | 0.012 |
| 1077 | 9-(4-(1-aminoethyl)phenyl)-4-oxo-4,5-dihydrothieno[2,3-c]quinolin-8-yl isopropyl carbonate hydrochloride | 0.076 |
| 1081 | (R)-9-(4-(1-aminoethyl)phenyl)-6-chloro-8-hydroxythieno[2,3-c]quinolin-4(5H)-one hydrochloride | 0.0086 |
| 1082 | (S)-8-hydroxy-9-(4-(1-(methylamino)ethyl)phenyl)thieno[2,3-c]quinolin-4(5H)-one hydrochloride | 0.0011 |
| 1087 | (S)-6-chloro-8-hydroxy-9-(4-(1-(methylamino)ethyl)phenyl)thieno[2,3-c]quinolin-4(5H)-one hydrochloride | 0.019 |
| 1088 | 9-(4-(1-aminopropyl)phenyl)-6-chloro-8-hydroxythieno[2,3-c]quinolin-4(5H)-one hydrochloride | 0.016 |
| 1094 | N-(2-bromoethyl)-4-(8-hydroxy-4-oxo-2,3,4,5-tetrahydro-1H-cyclopenta[c]quinolin-9-yl)benzenesulfonamide | 0.01 |
| 1095 | 9-(4-(2-aminopropyl)phenyl)-8-hydroxythieno[2,3-c]quinolin-4(5H)-one hydrochloride | 0.0013 |
| 1099 | 9-(4-(1-aminoethyl)phenyl)-4-oxo-4,5-dihydrothieno[2,3-c]quinolin-8-yl acetate hydrochloride | 0.033 |
| 1106 | 9-(4-(2-aminopropyl)phenyl)-6-chloro-8-hydroxythieno[2,3-c]quinolin-4(5H)-one hydrochloride | 0.041 |
| 1111 | 9-(4-(1-aminopropan-2-yl)phenyl)-8-hydroxythieno[2,3-c]quinolin-4(5H)-one hydrochloride | 0.0013 |
| 1112 | 9-(4-(1-(dimethylamino)propan-2-yl)phenyl)-8-hydroxythieno[2,3-c]quinolin-4(5H)-one hydrochloride | 0.0033 |
| 1116 | 9-(4-(1-(aminomethyl)cyclopropyl)phenyl)-6-chloro-8-hydroxythieno[2,3-c]quinolin-4(5H)-one hydrochloride | 0.022 |
| 1120 | (S)-9-(4-(1-aminopropyl)phenyl)-8-hydroxythieno[2,3-c]quinolin-4(5H)-one hydrochloride | 0.00088 |
| 1121 | (S)-9-(4-(1-aminopropyl)phenyl)-8-methoxythieno[2,3-c]quinolin-4(5H)-one hydrochloride | 0.0029 |
| 1122 | (R)-9-(4-(1-aminoethyl)phenyl)-8-hydroxy-6-methylthieno[2,3-c]quinolin-4(5H)-one hydrochloride | 0.0059 |
| 1123 | (R)-9-(4-(1-aminoethyl)phenyl)-6-bromo-8-hydroxythieno[2,3-c]quinolin-4(5H)-one hydrochloride | 0.033 |
| 1126 | (R)-6-chloro-9-(4-(1-(dimethylamino)ethyl)phenyl)-8-hydroxythieno[2,3-c]quinolin-4(5H)-one hydrochloride | 0.042 |
| 1127 | (S)-9-(4-(1-(ethylamino)propyl)phenyl)-8-hydroxythieno[2,3-c]quinolin-4(5H)-one hydrochloride | 0.0014 |
| 1128 | (S)-9-(4-(1-(dimethylamino)propyl)phenyl)-8-hydroxythieno[2,3-c]quinolin-4(5H)-one hydrochloride | 0.0022 |
| 1131 | (R)-9-(4-(1-aminopropyl)phenyl)-8-hydroxythieno[2,3-c]quinolin-4(5H)-one hydrochloride | 0.0013 |

TABLE 2-continued

| ID. | Compound | IC50 (microM) (kinase assay) |
|---|---|---|
| 1132 | (R)-6-chloro-8-hydroxy-9-(4-(1-(methylamino)ethyl)phenyl)thieno[2,3-c]quinolin-4(5H)-one hydrochloride | 0.014 |
| 1133 | 9-(4-(2-aminoethyl)phenyl)-6-chloro-8-hydroxythieno[2,3-c]quinolin-4(5H)-one hydrochloride | 0.02 |
| 1135 | (R)-6-bromo-8-hydroxy-9-(4-(1-(methylamino)ethyl)phenyl)thieno[2,3-c]quinolin-4(5H)-one hydrochloride | 0.03 |
| 1136 | 9-(4-(1-aminopropan-2-yl)phenyl)-6-chloro-8-hydroxythieno[2,3-c]quinolin-4(5H)-one hydrochloride | 0.0086 |
| 1139 | N-(2-chloroethyl)-4-(8-methoxy-4-oxo-4,5-dihydrothieno[2,3-c]quinolin-9-yl)benzenesulfonamide | 0.07 |
| 1142 | 9-(4-(2-aminoethyl)phenyl)-6-bromo-8-hydroxythieno[2,3-c]quinolin-4(5H)-one hydrochloride | 0.045 |
| 1145 | N-(2-chloroethyl)-4-(8-hydroxy-4-oxo-2,3,4,5-tetrahydro-1H-cyclopenta[c]quinolin-9-yl)benzenesulfonamide | 0.013 |
| 1148 | (S)-8-hydroxy-9-(4-(1-(methylamino)propyl)phenyl)thieno[2,3-c]quinolin-4(5H)-one hydrochloride | 0.0013 |
| 1150 | (R)-9-(4-(1-aminopropyl)phenyl)-6-bromo-8-hydroxythieno[2,3-c]quinolin-4(5H)-one hydrochloride | 0.047 |
| 1151 | (R)-9-(4-(1-(dimethylamino)propyl)phenyl)-8-hydroxythieno[2,3-c]quinolin-4(5H)-one hydrochloride | 0.0025 |
| 1154 | (S)-6-chloro-8-hydroxy-9-(4-(1-(methylamino)propyl)phenyl)thieno[2,3-c]quinolin-4(5H)-one hydrochloride | 0.0094 |
| 1157 | (R)-9-(4-(1-aminopropyl)phenyl)-8-hydroxy-6-methylthieno[2,3-c]quinolin-4(5H)-one hydrochloride | 0.018 |
| 1159 | (R)-9-(4-(1-aminopropyl)phenyl)-6-chloro-8-hydroxythieno[2,3-c]quinolin-4(5H)-one hydrochloride | 0.026 |
| 1160 | (R)-9-(4-(1-aminopropan-2-yl)phenyl)-8-hydroxythieno[2,3-c]quinolin-4(5H)-one hydrochloride | 0.00064 |
| 1161 | (R)-9-(4-(1-aminopropan-2-yl)phenyl)-8-methoxythieno[2,3-c]quinolin-4(5H)-one hydrochloride | 0.002 |
| 1162 | 2-(4-(8-hydroxy-4-oxo-4,5-dihydrothieno[2,3-c]quinolin-9-yl)phenyl)butanenitrile | 0.013 |
| 1163 | (S)-9-(4-(1-aminopropan-2-yl)phenyl)-8-hydroxythieno[2,3-c]quinolin-4(5H)-one hydrochloride | 0.0013 |
| 1165 | 6-chloro-8-hydroxy-9-(4-(2-(methylamino)ethyl)phenyl)thieno[2,3-c]quinolin-4(5H)-one hydrochloride | 0.058 |
| 1166 | (R)-9-(4-(1-aminopropan-2-yl)phenyl)-6-chloro-8-hydroxythieno[2,3-c]quinolin-4(5H)-one hydrochloride | 0.0044 |
| 1168 | (R)-9-(4-(1-aminopropan-2-yl)phenyl)-8-hydroxy-6-methylthieno[2,3-c]quinolin-4(5H)-one hydrochloride | 0.0026 |
| 1169 | (R)-9-(4-(1-aminopropan-2-yl)phenyl)-8-hydroxy-6-methylthieno[2,3-c]quinolin-4(5H)-one hydrobromide | 0.0089 |
| 1172 | (S)-9-(4-(1-(dimethylamino)propan-2-yl)phenyl)-8-hydroxythieno[2,3-c]quinolin-4(5H)-one hydrochloride | 0.004 |
| 1174 | 9-(4-(1-aminopropan-2-yl)-3-fluorophenyl)-8-hydroxythieno[2,3-c]quinolin-4(5H)-one hydrochloride | 0.0015 |
| 1176 | (R)-9-(4-(1-aminopropan-2-yl)phenyl)-6-bromo-8-hydroxythieno[2,3-c]quinolin-4(5H)-one hydrochloride | 0.017 |
| 1179 | 9-(4-(1-aminopropan-2-yl)-3-fluorophenyl)-8-methoxythieno[2,3-c]quinolin-4(5H)-one hydrochloride | 0.003 |
| 1181 | (S)-9-(4-(1-aminopropan-2-yl)phenyl)-6-chloro-8-hydroxythieno[2,3-c]quinolin-4(5H)-one hydrochloride | 0.033 |
| 1187 | (R)-8-hydroxy-9-(4-(1-(methylamino)propan-2-yl)phenyl)thieno[2,3-c]quinolin-4(5H)-one hydrochloride | 0.0013 |
| 1188 | (R)-9-(4-(1-(dimethylamino)propan-2-yl)phenyl)-8-hydroxythieno[2,3-c]quinolin-4(5H)-one hydrochloride | 0.0025 |
| 1189 | (R)-8-methoxy-9-(4-(1-(methylamino)propan-2-yl)phenyl)thieno[2,3-c]quinolin-4(5H)-one hydrochloride | 0.003 |
| 1190 | 9-(4-(1-aminopropan-2-yl)-3-fluorophenyl)-8-hydroxy-6-methylthieno[2,3-c]quinolin-4(5H)-one hydrochloride | 0.0051 |
| 1191 | 9-(4-(2-aminoethyl)phenyl)-8-hydroxy-6-methylthieno[2,3-c]quinolin-4(5H)-one hydrochloride | 0.019 |
| 1193 | 9-(4-(1-(dimethylamino)propan-2-yl)-3-fluorophenyl)-8-hydroxy-6-methylthieno[2,3-c]quinolin-4(5H)-one hydrochloride | 0.046 |
| 1197 | (S)-8-hydroxy-9-(4-(1-(methylamino)propan-2-yl)phenyl)thieno[2,3-c]quinolin-4(5H)-one hydrochloride | 0.0028 |
| 1201 | (R)-9-(4-(1-aminopropan-2-yl)phenyl)-6-chloro-8-methoxythieno[2,3-c]quinolin-4(5H)-one hydrochloride | 0.02 |
| 1204 | N-(1-chloropropan-2-yl)-4-(8-hydroxy-4-oxo-4,5-dihydrothieno[2,3-c]quinolin-9-yl)benzenesulfonamide | 0.015 |
| 1209 | 9-(4-(3-(aminomethyl)pentan-3-yl)phenyl)-8-hydroxythieno[2,3-c]quinolin-4(5H)-one hydrochloride | 0.0018 |
| 1212 | 9-(4-(aminomethyl)phenyl)-8-hydroxy-6-methylthieno[2,3-c]quinolin-4(5H)-one hydrochloride | 0.016 |
| 1213 | 9-(4-(2-aminoethyl)-3-fluorophenyl)-6-bromo-8-hydroxythieno[2,3-c]quinolin-4(5H)-one hydrochloride | 0.019 |

TABLE 2-continued

| ID. | Compound | IC50 (microM) (kinase assay) |
|---|---|---|
| 1215 | (S)-8-hydroxy-6-methyl-9-(4-(1-(methylamino)propan-2-yl)phenyl)thieno[2,3-c]quinolin-4(5H)-one hydrochloride | 0.06 |
| 1216 | 9-(4-(2-aminoethyl)-3-fluorophenyl)-8-methoxy-6-methylthieno[2,3-c]quinolin-4(5H)-one hydrochloride | 0.057 |
| 1217 | 9-(4-(2-aminoethyl)-3-fluorophenyl)-8-hydroxy-6-methylthieno[2,3-c]quinolin-4(5H)-one hydrochloride | 0.0047 |
| 1218 | 9-(4-(2-aminoethyl)-3-fluorophenyl)-6-chloro-8-methoxythieno[2,3-c]quinolin-4(5H)-one hydrochloride | 0.087 |
| 1219 | 9-(4-(2-aminoethyl)-3-fluorophenyl)-6-chloro-8-hydroxythieno[2,3-c]quinolin-4(5H)-one hydrochloride | 0.0055 |
| 1224 | 9-(4-(2-aminoethyl)-2-bromo-5-hydroxyphenyl)-8-hydroxythieno[2,3-c]quinolin-4(5H)-one hydrochloride | 0.0064 |
| 1225 | (S)-9-(4-(1-aminoethyl)phenyl)-8-hydroxy-6-methylthieno[2,3-c]quinolin-4(5H)-one hydrochloride | 0.016 |
| 1226 | 3-(4-(8-hydroxy-6-methyl-4-oxo-4,5-dihydrothieno[2,3-c]quinolin-9-yl)phenyl)propanenitrile | 0.092 |
| 1228 | 9-(4-(1-amino-2-methylpropan-2-yl)phenyl)-8-hydroxy-6-methylthieno[2,3-c]quinolin-4(5H)-one hydrochloride | 0.039 |
| 1232 | (S)-9-(4-(1-aminopropan-2-yl)phenyl)-8-hydroxy-6-methylthieno[2,3-c]quinolin-4(5H)-one hydrochloride | 0.016 |
| 1236 | 9-(4-(2-amino-1-cyclopentylethyl)phenyl)-8-hydroxythieno[2,3-c]quinolin-4(5H)-one | 0.0046 |
| 1239 | 9-(4-(2-amino-1-cyclopentylethyl)phenyl)-8-methoxythieno[2,3-c]quinolin-4(5H)-one hydrochloride | 0.023 |
| 1242 | 9-(4-(2-aminopropyl)phenyl)-8-hydroxy-6-methylthieno[2,3-c]quinolin-4(5H)-one hydrochloride | 0.037 |
| 1245 | 6-bromo-9-(3-fluoro-4-(2-(methylamino)ethyl)phenyl)-8-hydroxythieno[2,3-c]quinolin-4(5H)-one hydrochloride | 0.045 |
| 1247 | 9-(4-(1-amino-2-methylpropan-2-yl)phenyl)-6-bromo-8-hydroxythieno[2,3-c]quinolin-4(5H)-one hydrochloride | 0.072 |
| 1251 | 9-(4-(1-(aminomethyl)cyclopropyl)phenyl)-8-methoxy-6-methylthieno[2,3-c]quinolin-4(5H)-one hydrochloride | 0.055 |
| 1252 | 9-(4-(1-amino-3-methylbutan-2-yl)phenyl)-8-hydroxythieno[2,3-c]quinolin-4(5H)-one | 0.0014 |
| 1253 | 9-(4-(1-amino-3-methylbutan-2-yl)phenyl)-8-methoxythieno[2,3-c]quinolin-4(5H)-one hydrochloride | 0.0041 |
| 1254 | 9-(4-(1-(aminomethyl)cyclopropyl)phenyl)-8-hydroxy-6-methylthieno[2,3-c]quinolin-4(5H)-one hydrochloride | 0.0096 |
| 1258 | 9-(3-fluoro-4-(2-(methylamino)ethyl)phenyl)-8-hydroxy-6-methylthieno[2,3-c]quinolin-4(5H)-one hydrochloride | 0.025 |
| 1260 | 9-(4-(1-amino-2-methylpropan-2-yl)phenyl)-6-chloro-8-hydroxythieno[2,3-c]quinolin-4(5H)-one hydrochloride | 0.075 |
| 1262 | (R)-8-hydroxy-6-methyl-9-(4-(1-(methylamino)ethyl)phenyl)thieno[2,3-c]quinolin-4(5H)-one hydrochloride | 0.012 |
| 1263 | 9-(4-(2-aminoethyl)-3-chlorophenyl)-8-methoxy-6-methylthieno[2,3-c]quinolin-4(5H)-one hydrochloride | 0.033 |
| 1264 | 9-(4-(2-aminoethyl)-3-chlorophenyl)-8-hydroxy-6-methylthieno[2,3-c]quinolin-4(5H)-one hydrochloride | 0.003 |
| 1265 | (R)-8-methoxy-6-methyl-9-(4-(1-(methylamino)ethyl)phenyl)thieno[2,3-c]quinolin-4(5H)-one hydrochloride | 0.067 |
| 1268 | 9-(4-(2-aminoethyl)-3-chlorophenyl)-6-chloro-8-hydroxythieno[2,3-c]quinolin-4(5H)-one hydrochloride | 0.0039 |
| 1271 | 9-(4-(1-amino-2-methylpropan-2-yl)-3-fluorophenyl)-8-hydroxythieno[2,3-c]quinolin-4(5H)-one hydrochloride | 0.001 |
| 1273 | 9-(4-(1-aminopropan-2-yl)-3-fluorophenyl)-8-methoxy-6-methylthieno[2,3-c]quinolin-4(5H)-one hydrochloride | 0.04 |
| 1274 | 9-(4-(1-amino-3-methylbutan-2-yl)phenyl)-8-hydroxy-6-methylthieno[2,3-c]quinolin-4(5H)-one | 0.018 |
| 1277 | 9-(4-(1-aminobutan-2-yl)phenyl)-8-methoxy-6-methylthieno[2,3-c]quinolin-4(5H)-one hydrochloride | 0.063 |
| 1278 | 9-(4-(1-amino-2-methylpropan-2-yl)-3-fluorophenyl)-8-hydroxy-6-methylthieno[2,3-c]quinolin-4(5H)-one hydrochloride | 0.022 |
| 1280 | 9-(4-(1-aminopropan-2-yl)-3-chlorophenyl)-8-hydroxythieno[2,3-c]quinolin-4(5H)-one hydrochloride | 0.01 |
| 1283 | 9-(4-(1-amino-3-methylbutan-2-yl)-3-fluorophenyl)-8-methoxy-6-methylthieno[2,3-c]quinolin-4(5H)-one hydrochloride | 0.047 |
| 1285 | 8-hydroxy-6-methyl-9-(4-(3-methyl-1-(methylamino)butan-2-yl)phenyl)thieno[2,3-c]quinolin-4(5H)-one | 0.05 |
| 1286 | 9-(3-fluoro-4-(1-(methylamino)propan-2-yl)phenyl)-8-methoxy-6-methylthieno[2,3-c]quinolin-4(5H)-one hydrochloride | 0.043 |
| 1288 | 9-(4-(1-amino-3-methylbutan-2-yl)-3-fluorophenyl)-8-hydroxy-6-methylthieno[2,3-c]quinolin-4(5H)-one | 0.02 |
| 1290 | 9-(4-(1-(aminomethyl)cyclobutyl)phenyl)-8-hydroxy-6-methylthieno[2,3-c]quinolin-4(5H)-one hydrochloride | 0.01 |
| 1291 | 9-(4-(1-aminobutan-2-yl)phenyl)-8-hydroxy-6-methylthieno[2,3-c]quinolin-4(5H)-one hydrochloride | 0.015 |

TABLE 2-continued

| ID. | Compound | IC50 (microM) (kinase assay) |
|---|---|---|
| 1293 | 9-(3-fluoro-4-(1-(methylamino)propan-2-yl)phenyl)-8-hydroxy-6-methylthieno[2,3-c]quinolin-4(5H)-one | 0.0089 |
| 1294 | 9-(3-fluoro-4-(3-methyl-1-(methylamino)butan-2-yl)phenyl)-8-hydroxy-6-methylthieno[2,3-c]quinolin-4(5H)-one | 0.017 |
| 1297 | 9-(4-(1-(aminomethyl)cyclobutyl)phenyl)-8-methoxy-6-methylthieno[2,3-c]quinolin-4(5H)-one hydrochloride | 0.035 |
| 1298 | (R)-8-methoxy-6-methyl-9-(4-(1-(methylamino)propan-2-yl)phenyl)thieno[2,3-c]quinolin-4(5H)-one hydrochloride | 0.032 |
| 1300 | 9-(4-(1-(aminomethyl)cyclobutyl)phenyl)-8-hydroxythieno[2,3-c]quinolin-4(5H)-one hydrochloride | 0.0017 |
| 1302 | 8-hydroxy-6-methyl-9-(4-(piperidin-3-yl)phenyl)thieno[2,3-c]quinolin-4(5H)-one hydrochloride | 0.075 |
| 1303 | (S)-9-(4-(1-aminopropan-2-yl)-3-fluorophenyl)-8-hydroxy-6-methylthieno[2,3-c]quinolin-4(5H)-one | 0.014 |
| 1304 | (S)-9-(4-(1-aminopropan-2-yl)-3-fluorophenyl)-8-hydroxy-6-methylthieno[2,3-c]quinolin-4(5H)-one hydrobromide | 0.013 |
| 1305 | (R)-9-(4-(1-aminopropan-2-yl)phenyl)-8-methoxy-6-methylthieno[2,3-c]quinolin-4(5H)-one hydrochloride | 0.015 |
| 1306 | (R)-8-hydroxy-6-methyl-9-(4-(1-(methylamino)propan-2-yl)phenyl)thieno[2,3-c]quinolin-4(5H)-one hydrochloride | 0.0073 |
| 1307 | (R)-8-hydroxy-6-methyl-9-(4-(1-(methylamino)propan-2-yl)phenyl)thieno[2,3-c]quinolin-4(5H)-one hydrobromide | 0.018 |
| 1309 | 9-(4-(1-aminobutan-2-yl)phenyl)-8-hydroxythieno[2,3-c]quinolin-4(5H)-one hydrochloride | 0.00074 |
| 1310 | (S)-9-(4-(1-aminopropan-2-yl)-3-fluorophenyl)-8-methoxy-6-methylthieno[2,3-c]quinolin-4(5H)-one hydrochloride | 0.054 |
| 1311 | (R)-9-(4-(1-(dimethylamino)propan-2-yl)-3-fluorophenyl)-8-hydroxy-6-methylthieno[2,3-c]quinolin-4(5H)-one hydrochloride | 0.017 |
| 1312 | 9-(4-(1-aminobutan-2-yl)phenyl)-6-chloro-8-hydroxythieno[2,3-c]quinolin-4(5H)-one hydrochloride | 0.019 |
| 1315 | (R)-9-(3-fluoro-4-(1-(methylamino)propan-2-yl)phenyl)-8-hydroxy-6-methylthieno[2,3-c]quinolin4(5H)-one hydrochloride | 0.0081 |
| 1316 | (R)-9-(3-fluoro-4-(1-(methylamino)propan-2-yl)phenyl)-8-methoxy-6-methylthieno[2,3-c]quinolin-4(5H)-one hydrochloride | 0.033 |
| 1317 | (R)-9-(4-(1-aminopropan-2-yl)-3-fluorophenyl)-8-methoxy-6-methylthieno[2,3-c]quinolin-4(5H)-one hydrochloride | 0.022 |
| 1318 | (R)-9-(4-(1-aminopropan-2-yl)-3-fluorophenyl)-8-hydroxy-6-methylthieno[2,3-c]quinolin-4(5H)-one hydrochloride | 0.0036 |
| 1319 | (R)-9-(4-(1-aminopropan-2-yl)-3-fluorophenyl)-8-hydroxy-6-methylthieno[2,3-c]quinolin-4(5H)-one hydrobromide | 0.0034 |
| 1321 | 9-(4-(1-(aminomethyl)cyclobutyl)phenyl)-6-chloro-8-methoxythieno[2,3-c]quinolin-4(5H)-one hydrochloride | 0.096 |
| 1324 | (R)-9-(4-(1-(dimethylamino)propan-2-yl)phenyl)-8-hydroxy-6-methylthieno[2,3-c]quinolin-4(5H)-one hydrochloride | 0.032 |
| 1330 | 9-(4-(2-aminopropan-2-yl)phenyl)-8-hydroxy-6-methylthieno[2,3-c]quinolin-4(5H)-one hydrochloride | 0.0083 |
| 1340 | (R)-9-(4-(1-aminopropan-2-yl)phenyl)-8-hydroxy-2,6-dimethylthieno[2,3-c]quinolin-4(5H)-one hydrochloride | 0.012 |
| 1341 | (R)-9-(4-(1-aminopropan-2-yl)phenyl)-8-methoxy-2,6-dimethylthieno[2,3-c]quinolin-4(5H)-one hydrochloride | 0.038 |
| 1347 | (R)-6-chloro-9-(4-(1-(dimethylamino)propan-2-yl)phenyl)-8-hydroxythieno[2,3-c]quinolin-4(5H)-one hydrochloride | 0.043 |
| 1352 | (R)-9-(4-(1-aminobutan-2-yl)phenyl)-8-hydroxy-6-methylthieno[2,3-c]quinolin-4(5H)-one hydrochloride | 0.04 |
| 1353 | (R)-9-(4-(1-aminopropan-2-yl)phenyl)-2-chloro-8-hydroxy-6-methylthieno[2,3-c]quinolin-4(5H)-one hydrochloride | 0.004 |
| 1354 | (R)-9-(4-(1-aminopropan-2-yl)phenyl)-2-chloro-8-methoxy-6-methylthieno[2,3-c]quinolin-4(5H)-one hydrochloride | 0.011 |
| 1364 | 8-hydroxy-6-methyl-9-(4-(2-(methylamino)ethyl)phenyl)thieno[2,3-c]quinolin-4(5H)-one hydrochloride | 0.055 |
| 1372 | 9-(4-(1-((dimethylamino)methyl)cyclobutyl)phenyl)-8-hydroxy-6-methylthieno[2,3-c]quinolin-4(5H)-one hydrochloride | 0.042 |
| 1375 | (R)-9-(4-(1-aminopropan-2-yl)phenyl)-2-fluoro-8-methoxy-6-methylthieno[2,3-c]quinolin-4(5H)-one hydrochloride | 0.022 |
| 1379 | (R)-9-(4-(1-(ethyl(methyl)amino)propan-2-yl)phenyl)-8-hydroxy-6-methylthieno[2,3-c]quinolin-4(5H)-one hydrochloride | 0.076 |
| 1380 | (R)-8-hydroxy-6-methyl-9-(4-(1-(methylamino)butan-2-yl)phenyl)thieno[2,3-c]quinolin-4(5H)-one hydrochloride | 0.085 |
| 1383 | (R)-9-(4-(1-aminopropan-2-yl)phenyl)-2-fluoro-8-hydroxy-6-methylthieno[2,3-c]quinolin-4(5H)-one hydrochloride | 0.0037 |
| 1391 | 9-(4-(1-(aminomethyl)cyclopropyl)phenyl)-6-bromo-8-methoxythieno[2,3-c]quinolin-4(5H)-one hydrochloride | 0.07 |
| 1399 | (S)-9-(4-(1-(dimethylamino)propan-2-yl)-3-fluorophenyl)-8-hydroxy-6-methylthieno[2,3-c]quinolin-4(5H)-one hydrochloride | 0.058 |
| 1400 | 9-(4-((2-aminoethyl)(methyl)amino)phenyl)-8-hydroxy-6-methylthieno[2,3-c]quinolin-4(5H)-one hydrochloride | 0.06 |

TABLE 2-continued

| ID. | Compound | IC50 (microM) (kinase assay) |
|---|---|---|
| 1401 | 9-(4-(1-(aminomethyl)cyclopropyl)phenyl)-6-bromo-8-hydroxythieno[2,3-c]quinolin-4(5H)-one hydrochloride | 0.051 |
| 1419 | 2-(4-(8-hydroxy-6-methyl-4-oxo-4,5-dihydrothieno[2,3-c]quinolin-9-yl)phenyl)propane-1-sulfonamide | 0.082 |

Examples 508

Western Blot Analysis

To evaluate the expression status of PBK in several cell lines, western blot analysis was performed using crude cell lysate collected from those cells. Anti-PBK antibody (clone 31, BD Biosciences) was used to visualize the expression. Breast cancer cell lines, T47D and BT-549 expressed PBK significantly although Bladder cancer cell line and HT-1197 showed no expression of PBK.

Examples 509

Cell-Based Assay

Active candidate inhibitors against PBK were evaluated for their target-specific cytotoxicity using T47D, A549, BT-549, and HT-1197 cells was used for negative control. 100 micro-L of cell suspension was seeded onto 96-well microtiter plate (ViewPlate-96FTC, PerkinElmer). The initial cell concentration of T47D, BT-549 and HT-1197 were 3,000 cells/well, 2,000 cells/well and 2,500 cells/well, respectively. Cellular growth was determined using Cell Counting Kit-8 (DOJINDO) at 72 hours after the exposure of the candidate inhibitors. IC50 was used as an indicator of the anti-proliferative activity of the inhibitors, and calculated by serial dilution method (0, 1.5625, 3.125, 6.25, 12.5, 25, 50, and 100 micro-M). Accurate IC50 values were calculated as described previously.

$IC_{50}$ values of the typical compounds of the present invention are shown in following table 3:

TABLE 3

| ID | Compound | IC50 (microM) (BT549) | IC50 (microM) (T47D) | IC50 (microM) (A549) | IC50 (microM) (HT1197) |
|---|---|---|---|---|---|
| 51 | (S)-8-(3-Aminopyrrolidin-1-yl)-2-(4-hydroxyphenyl)thieno[2,3-c]quinolin-4(5H)-one Dihydrochloride | 14 | 2.1 | 21 | 62 |
| 61 | 8-Hydroxy-9-(1H-indazol-6-yl)thieno[2,3-c]quinolin-4(5H)-one | 1.8 | 3.7 | 2.6 | 5.1 |
| 65 | 4-(8-Hydroxy-4-oxo-4,5-dihydrothieno[2,3-c]quinolin-9-yl)benzenesulfonamide | 3.3 | 4.4 | 100 | 100 |
| 72 | 9-[4-(Aminomethyl)phenyl]-8-hydroxythieno[2,3-c]quinolin-4(5H)-one | 1.1 | 1.2 | 3.2 | 12 |
| 73 | 9-[4-(Aminomethyl)phenyl]-8-hydroxy-thieno[2,3-c]quinolin-4(5H)-one Hydrochloride | 0.67 | 0.65 | 1.2 | 11 |
| 77 | N-[4-(8-Hydroxy-4-oxo-4,5-dihydrothieno[2,3-c]quinolin-9-yl)phenyl]methanesulfonamide | 7.9 | 3.2 | 46 | 100 |
| 81 | 2-[4-(8-Hydroxy-4-oxo-4,5-dihydrothieno[2,3-c]quinolin-9-yl)phenyl]acetonitrile | 3.5 | 6.2 | 7.7 | 27 |
| 84 | 8-Hydroxy-9-(1,2,3,6-tetrahydropyridin-4-yl)thieno[2,3-c]quinolin-4(5H)-one | 5.4 | 4.8 | 11 | 7.1 |
| 93 | 9-{4-[2-(Dimethylamino)ethyl]phenyl}-8-hydroxythieno[2,3-c]quinolin-4(5H)-one | 2.5 | 4.7 | 3 | 7 |
| 95 | 9-[4-(Aminomethyl)phenyl]-8-hydroxy-2-methylthieno[2,3-c]quinolin-4(5H)-one | 4.1 | 2.9 | 8.1 | 22 |
| 112 | 8-Hydroxy-9-{4-[4-(methylsulfonyl)piperazin-1-yl]phenyl}thieno[2,3-c]quinolin-4(5H)-one | 3.9 | 6.9 | 6.6 | 6.8 |
| 139 | tert-Butyl {1-[4-(8-Methoxy-4-oxo-4,5-dihydrothieno[2,3-c]quinolin-9-yl)benzyl]piperidin-4-yl}methylcarbamate | 3.8 | 4.3 | 5 | 3.9 |
| 145 | 9-(4-{3-[2-(Diethylamino)ethyl-amino]propoxy}phenyl)-8-methoxythieno[2,3-c]quinolin-4(5H)-one | 7.7 | 4.8 | 8.2 | 9.2 |
| 152 | (E)-9-[3-(4-Aminopiperidin-1-yl)prop-1-enyl]-8-methoxythieno[2,3-c]quinolin-4(5H)-one | 5.8 | 4.4 | 12 | 6.5 |
| 164 | 9-{4-[(Dimethylamino)methyl]phenyl}-8-methoxythieno[2,3-c]quinolin-4(5H)-one | 2.9 | 4.9 | 2.4 | 7 |
| 165 | 9-{4-[(Dimethylamino)methyl]phenyl}-8-hydroxythieno[2,3-c]quinolin-4(5H)-one | 3.2 | 6.2 | 3 | 6.5 |
| 169 | 9-[4-(2-Aminoethyl)phenyl]-8-methoxythieno[2,3-c]quinolin-4(5H)-one | 2.4 | 4.2 | 3.7 | 6.1 |
| 175 | 9-[4-(2-Aminoethyl)phenyl]-8-hydroxy-thieno[2,3-c]quinolin-4(5H)-one | 0.7 | 0.67 | 0.85 | 1.5 |

TABLE 3-continued

| | | | | | |
|---|---|---|---|---|---|
| 176 | 9-[4-(2-Aminoethyl)phenyl]-8-hydroxy-thieno[2,3-c]quinolin-4(5H)-one Hydrochloride | 0.64 | 0.49 | 0.64 | 1.1 |
| 184 | 9-{4-[(Diethylamino)methyl]phenyl}-8-hydroxythieno[2,3-c]quinolin-4(5H)-one | 2.9 | 6.1 | 2.7 | 7.1 |
| 187 | 8-Hydroxy-9-{4-[(methyl-amino)methyl]phenyl}thieno[2,3-c]quinolin-4(5H)-one | 1.3 | 1.4 | 1.6 | 2 |
| 188 | 8-Methoxy-9-{4-[(methyl-amino)methyl]phenyl}thieno[2,3-c]quinolin-4(5H)-one | 3.5 | 7.9 | 3.8 | 8 |
| 192 | 9-(4-(1-(dimethylamino)ethyl)phenyl)-8-hydroxythieno[2,3-c]quinolin-4(5H)-one Hydrochloride | 0.34 | 0.67 | 0.3 | 0.66 |
| 191 | 9-{4-[1-(Dimethylamino)ethyl]phenyl}-8-hydroxythieno[2,3-c]quinolin-4(5H)-one | 0.4 | 0.78 | 0.35 | 0.87 |
| 193 | N-{1-[4-(8-Hydroxy-4-oxo-4,5-di-hydrothieno[2,3-c]quinolin-9-yl)phenyl]ethyl}methanesulfonamide | 2.4 | 1.7 | 13 | 39 |
| 194 | 8-Hydroxy-9-{4-[1-(pyrrolidin-1-yl)ethyl]phenyl}thieno[2,3-c]quinolin-4(5H)-one Hydrochloride | 0.46 | 1 | 0.49 | 1.2 |
| 195 | 9-[4-(1-Aminoethyl)phenyl]-8-hydroxythieno[2,3-c]quinolin-4(5H)-one Hydrochloride | 0.37 | 0.4 | 0.61 | 2.4 |
| 196 | 9-{4-[1-(Diethylamino)ethyl]phenyl}-8-hydroxythieno[2,3-c]quinolin-4(5H)-one Hydrochloride | 1.1 | 2.3 | 1 | 2.7 |
| 210 | N-(2-Bromoethyl)-4-(8-hydroxy-4-oxo-4,5-dihydrothieno[2,3-c]quinolin-9-yl)benzenesulfonamide | 0.006 | 0.25 | 0.028 | 14 |
| 212 | N-[4-(8-Hydroxy-4-oxo-4,5-dihydro-thieno[2,3-c]quinolin-9-yl)benzyl]methane-sulfonamide | 5.5 | 1.4 | 17 | 40 |
| 216 | 8-Methoxy-9-{4-[1-(pyrrolidin-1-yl)ethyl]phenyl}thieno[2,3-c]quinolin-4(5H)-one Hydrochloride | 2.9 | 5.8 | 2.6 | 7.4 |
| 217 | 9-(4-Amino-3-hydroxyphenyl)-8-hydroxythieno[2,3-c]quinolin-4(5H)-one Hydrochloride | 2.8 | 6.8 | 5.6 | 48 |
| 222 | 9-{4-[1-(Dimethylamino)ethyl]phenyl}-6-fluoro-8-methoxythieno[2,3-c]quinolin-4(5H)-one Hydrochloride | 3.8 | 7 | 3.5 | 8.7 |
| 225 | 9-{4-[2-(Dimethylamino)ethyl]phenyl}-6-fluoro-8-hydroxythieno[2,3-c]quinolin-4(5H)-one | 1.2 | 3 | 1.2 | 3.4 |
| 229 | 8-Hydroxy-9-{4-[(isopropyl-amino)methyl]phenyl}thieno[2,3-c]quinolin-4(5H)-one Hydrochloride | 1.9 | 4 | 2.1 | 4.2 |
| 232 | (S)-9-[4-(1-Aminoethyl)phenyl]-8-me-thoxythieno[2,3-c]quinolin-4(5H)-one Hydrochloride | 2.1 | 5 | 2 | 7.3 |
| 233 | (S)-9-[4-(1-Aminoethyl)phenyl]-8-hydroxythieno[2,3-c]quinolin-4(5H)-one Hydrochloride | 0.28 | 0.38 | 0.36 | 1.1 |
| 235 | 9-(4-{[4-(Aminomethyl)piperidin-1-yl]methyl}-3-fluorophenyl)-8-hydroxythieno[2,3-c]quinolin-4(5H)-one | 3.2 | 2.2 | 7.1 | 10 |
| 254 | N-[4-(8-Hydroxy-4-oxo-4,5-dihydro-thieno[2,3-c]quinolin-9-yl)-2-methyl-phenyl]methanesulfonamide | 4.8 | 5.2 | 14 | 32 |
| 256 | 9-[4-(Aminomethyl)phenyl]-6-fluoro-8-hydroxythieno[2,3-c]quinolin-4(5H)-one Hydrochloride | 0.57 | 0.99 | 0.75 | 3.3 |
| 257 | 9-[4-(Aminomethyl)phenyl]-6-fluoro-8-methoxythieno[2,3-c]quinolin-4(5H)-one Hydrochloride | 3.4 | 8.2 | 3.7 | 100 |
| 261 | 2-[2-Fluoro-4-(8-hydroxy-4-oxo-4,5-dihydrothieno[2,3-c]quinolin-9-yl)phenyl]acetonitrile | 0.69 | 1.1 | 1.3 | 6.6 |
| 262 | 8-Hydroxy-9-{4-[1-(piperidin-1-yl)ethyl]phenyl}thieno[2,3-c]quinolin-4(5H)-one Hydrochloride | 1.2 | 2.7 | 1 | 2.6 |
| 265 | 9-[4-(2-Aminoethyl)-3-fluorophenyl]-8-methoxythieno[2,3-c]quinolin-4(5H)-one Hydrochloride | 3 | 5.6 | 4.4 | 7.7 |
| 266 | 9-[5-(Aminomethyl)thiophen-2-yl]-8-hydroxythieno[2,3-c]quinolin-4(5H)-one | 1.3 | 1.5 | 2.7 | 13 |
| 267 | 9-{4-[(Ethylamino)methyl]phenyl}-8-hydroxythieno[2,3-c]quinolin-4(5H)-one Hydrochloride | 1.9 | 3.1 | 2 | 3.3 |

TABLE 3-continued

| | | | | | |
|---|---|---|---|---|---|
| 269 | 9-{4-[(Ethylamino)methyl]phenyl}-8-methoxythieno[2,3-c]quinolin-4(5H)-one Hydrochloride | 3 | 6.9 | 2.3 | 6.7 |
| 270 | 9-[4-(Aminomethyl)phenyl]-6-bromo-8-hydroxythieno[2,3-c]quinolin-4(5H)-one Hydrochloride | 0.36 | 0.65 | 0.44 | 2.4 |
| 272 | (R)-9-{4-[1-Dimethylamino)ethyl]phenyl}-8-hydroxythieno[2,3-c]quinolin-4(5H)-one Hydrochloride | 0.19 | 0.36 | 0.17 | 0.49 |
| 273 | 9-[4-(3-Aminopropyl)phenyl]-8-hydroxy-thieno[2,3-c]quinolin-4(5H)-one Hydrochloride | 3.8 | 2.1 | 6.4 | 5.3 |
| 274 | (R)-9-[4-(1-Aminoethyl)phenyl]-8-methoxythieno[2,3-c]quinolin-4(5H)-one Hydrochloride | 1.3 | 2.8 | 1.6 | 5.1 |
| 275 | (R)-9-[4-(1-Aminoethyl)phenyl]-8-hydroxythieno[2,3-c]quinolin-4(5H)-one Hydrochloride | 0.32 | 0.34 | 0.57 | 5.2 |
| 276 | 9-[4-(2-Aminoethyl)-3-fluorophenyl]-8-hydroxythieno[2,3-c]quinolin-4(5H)-one Hydrochloride | 0.81 | 0.57 | 1.3 | 2.1 |
| 277 | 9-[4-(1-Amino-2-methylpropan-2-yl)phenyl]-8-hydroxythieno[2,3-c]quinolin-4(5H)-one Hydrochloride | 0.53 | 0.74 | 0.69 | 2.1 |
| 278 | 9-{3-Fluoro-4-[(3-hydroxypyrrolidin-1-yl)methyl]phenyl}-8-hydroxythieno[2,3-c]quinolin-4(5H)-one Hydrochloride | 2.5 | 2.7 | 5 | 10 |
| 290 | 3-[4-(8-Hydroxy-4-oxo-4,5-dihydrothieno[2,3-c]quinolin-9-yl)phenyl]propanenitrile | 0.63 | 0.96 | 0.76 | 2.8 |
| 296 | 9-(4-Acetylphenyl)-8-hydroxythieno[2,3-c]quinolin-4(5H)-one | 5.4 | 7.4 | 3.5 | 14 |
| 297 | N-(2-Bromoethyl)-2-fluoro-4-(8-hydroxy-4-oxo-4,5-dihydrothieno[2,3-c]quinolin-9-yl)benzenesulfonamide | 0.21 | 1.2 | 0.47 | 32 |
| 298 | 9-{3-[3-(Dimethylamino)piperidin-1-yl]propyl}-8-hydroxythieno[2,3-c]quinolin-4(5H)-one Dihydrochloride | 6.2 | 6.9 | 4.4 | 11 |
| 301 | (R)-N-{1-[4-(8-Hydroxy-4-oxo-4,5-dihydrothieno[2,3-c]quinolin-9-yl)phenyl]ethyl}methanesulfonamide | 7.2 | 3 | 14 | 28 |
| 304 | 4-(8-Hydroxy-4-oxo-4,5-dihydrothieno[2,3-c]quinolin-9-yl)-N,N-dimethylbenzene-sulfonamide | 4.6 | 6.9 | 5.2 | 100 |
| 308 | 9-{4-[1-(Dimethylamino)-2-methylpropan-2-yl]phenyl}-8-hydroxythieno[2,3-c]quinolin-4(5H)-one Hydrochloride | 1.8 | 3.8 | 1.4 | 4.2 |
| 313 | 8-Hydroxy-9-[4-(1-hydroxy-ethyl)phenyl]thieno[2,3-c]quinolin-4(5H)-one | 1.7 | 3 | 2.6 | 11 |
| 314 | 9-{4-[1-(Cyclopentylamino)ethyl]phenyl}-8-hydroxythieno[2,3-c]quinolin-4(5H)-one Hydrochloride | 1.9 | 4.1 | 1.5 | 3.7 |
| 319 | 9-[4-(2-Aminopropan-2-yl)phenyl]-8-hydroxythieno[2,3-c]quinolin-4(5H)-one Hydrochloride | 0.55 | 0.9 | 0.64 | 2.3 |
| 326 | 9-[4-(Aminomethyl)phenyl]-4-oxo-4,5-dihydrothieno[2,3-c]quinoline-8-carbonitrile Hydrochloride | 4.3 | 5.9 | 7.9 | 10 |
| 327 | 9-{4-[2-(Dimethylamino)ethyl]-3-fluorophenyl}-8-hydroxythieno[2,3-c]quinolin-4(5H)-one Hydrochloride | 3.3 | 6.4 | 3.7 | 7.8 |
| 329 | 9-[4-(Aminomethyl)phenyl]-6-chloro-8-hydroxythieno[2,3-c]quinolin-4(5H)-one Hydrochloride | 0.32 | 0.63 | 0.36 | 1.4 |
| 332 | N-(2-Chloroethyl)-4-(8-hydroxy-4-oxo-4,5-dihydrothieno[2,3-c]quinolin-9-yl)benzenesulfonamide | 0.012 | 0.31 | 0.034 | 24 |
| 333 | N-(2-Fluoroethyl)-4-(8-methoxy-4-oxo-4,5-dihydrothieno[2,3-c]quinolin-9-yl)benzenesulfonamide | 2.5 | 9.3 | 2 | 24 |
| 334 | 9-[4-(2-Aminopropan-2-yl)phenyl]-6-chloro-8-hydroxythieno[2,3-c]quinolin-4(5H)-one Hydrochloride | 0.48 | 1.1 | 0.49 | 1.3 |
| 335 | (S)-9-{4-[1-(Dimethylamino)ethyl]phenyl}-8-hydroxythieno[2,3-c]quinolin-4(5H)-one Hydrochloride | 1.1 | 2.4 | 1.2 | 3.3 |
| 336 | 9-[4-(1-Aminopropyl)phenyl]-8-hydroxy-thieno[2,3-c]quinolin-4(5H)-one Hydrochloride | 0.21 | 0.35 | 0.32 | 0.97 |
| 337 | 9-[4-(1-Aminopropyl)phenyl]-8-methoxythieno[2,3-c]quinolin-4(5H)-one Hydrochloride | 1.5 | 3.4 | 1.4 | 3.9 |

TABLE 3-continued

| ID | Compound | | | | |
|---|---|---|---|---|---|
| 338 | 9-{4-[1-(Diethylamino)propyl]phenyl}-8-hydroxythieno[2,3-c]quinolin-4(5H)-one Hydrochloride | 2 | 7.1 | 1.8 | 4.5 |
| 339 | 9-{4-[1-(Dimethylamino)propyl]phenyl}-8-hydroxythieno[2,3-c]quinolin-4(5H)-one Hydrochloride | 0.35 | 0.79 | 0.36 | 0.98 |
| 341 | 9-{4-[1-(Dimethylamino)ethyl]phenyl}-6,7-difluoro-8-hydroxythieno[2,3-c]quinolin-4(5H)-one Hydrochloride | 1.4 | 2.9 | 1.5 | 3.3 |
| 345 | 9-(2-Amino-2,3-dihydro-1H-inden-5-yl)-8-hydroxythieno[2,3-c]quinolin-4(5H)-one Hydrochloride | 3.1 | 4.4 | 5.7 | 7.1 |
| 346 | 9-{4-[1-(Dimethyl-amino)ethyl]phenyl}thieno[2,3-c]quinolin-4(5H)-one | 2.5 | 7.2 | | 6.8 |
| 347 | (S)-N-{1-[4-(8-Hydroxy-4-oxo-4,5-dihydrothieno[2,3-c]quinolin-9-yl)phenyl]ethyl}methanesulfonamide | 1 | 0.75 | 5.6 | 29 |
| 348 | 9-{4-[1-(Aminomethyl)cyclopropyl]phenyl}-8-hydroxythieno[2,3-c]quinolin-4(5H)-one Hydrochloride | 0.31 | 3.2 | 0.38 | 1.2 |
| 349 | 9-{4-[1-(Dimethylamino)ethyl]-3-fluorophenyl}-8-hydroxythieno[2,3-c]quinolin-4(5H)-one Hydrochloride | 0.58 | 1.3 | 0.48 | 1.3 |
| 353 | 8-Hydroxy-9-(1,2,3,4-tetrahydroisoquinolin-7-yl)thieno[2,3-c]quinolin-4(5H)-one Hydrochloride | 1.9 | 3.7 | 3.2 | 4.2 |
| 356 | 9-{4-[1-(Diethylamino)ethyl]-3-fluoro-phenyl}-8-hydroxythieno[2,3-c]quinolin-4(5H)-one Hydrochloride | 1.5 | 3.3 | 1.3 | 3.5 |
| 359 | 9-[4-(1-Aminoethyl)-3-fluorophenyl]-8-hydroxythieno[2,3-c]quinolin-4(5H)-one Hydrochloride | 0.35 | 0.64 | 0.62 | 4 |
| 361 | 1-[4-(8-Hydroxy-4-oxo-4,5-dihydrothieno[2,3-c]quinolin-9-yl)phenyl]cyclopropanecarbonitrile | 0.94 | 2.5 | 0.96 | 2.7 |

| ID | Compound | IC50 (microM) (BT549) | IC50 (microM) (T47D) | IC50 (microM) (A549) | IC50 (microM) (HT1197) | IC50 (microM) (22Rv1) |
|---|---|---|---|---|---|---|
| 373 | 9-(4-(1-aminopropan-2-yl)phenyl)-8-methoxythieno[2,3-c]quinolin-4(5H)-one hydrochloride | 0.46 | 0.82 | 0.58 | 1.5 | — |
| 379 | 9-(4-(1-((dimethylamino)methyl)cyclo-propyl)phenyl)-8-hydroxythieno[2,3-c]quinolin-4(5H)-one hydrochloride | 0.52 | 1 | 0.46 | 1.4 | — |
| 385 | 9-(4-(1-(ethylamino)ethyl)phenyl)-8-hydroxythieno[2,3-c]quinolin-4(5H)-one hydrochloride | 0.8 | 1.8 | 0.94 | 2.6 | — |
| 1032 | 9-(4-(1-aminoethyl)phenyl)-6-bromo-8-hydroxythieno[2,3-c]quinolin-4(5H)-one hydrochloride | 0.27 | 0.53 | 0.3 | 1.2 | — |
| 1041 | 9-(4-(1-aminoethyl)phenyl)-6-chloro-8-hydroxythieno[2,3-c]quinolin-4(5H)-one hydrochloride | 0.19 | 0.34 | 0.16 | 0.65 | — |
| 1052 | (R)-8-hydroxy-9-(4-(1-(methyl-amino)ethyl)phenyl)thieno[2,3-c]quinolin-4(5H)-one hydrochloride | 0.17 | 0.32 | 0.17 | 0.45 | — |
| 1062 | N-(1-bromopropan-2-yl)-4-(8-hydroxy-4-oxo-4,5-dihydrothieno[2,3-c]quinolin-9-yl)benzenesulfonamide | 0.15 | 1.9 | 0.88 | 12 | — |
| 1064 | (S)-8-methoxy-9-(4-(1-(methyl-amino)ethyl)phenyl)thieno[2,3-c]quinolin-4(5H)-one hydrochloride | 1 | 2.2 | 0.89 | 2.9 | — |
| 1066 | 9-(4-(1-aminoethyl)phenyl)-8-hydroxy-6-methylthieno[2,3-c]quinolin-4(5H)-one hydrochloride | 0.065 | 0.13 | 0.12 | 0.34 | — |
| 1077 | 9-(4-(1-aminoethyl)phenyl)-4-oxo-4,5-dihydrothieno[2,3-c]quinolin-8-yl isopropyl carbonate hydrochloride | 0.41 | 0.45 | 0.66 | 2.5 | — |
| 1081 | (R)-9-(4-(1-aminoethyl)phenyl)-6-chloro-8-hydroxythieno[2,3-c]quinolin-4(5H)-one hydrochloride | 0.086 | 0.17 | 0.1 | 0.39 | — |
| 1082 | (S)-8-hydroxy-9-(4-(1-(methyl-amino)ethyl)phenyl)thieno[2,3-c]quinolin-4(5H)-one hydrochloride | 0.36 | 0.6 | 0.43 | 1 | — |
| 1087 | (S)-6-chloro-8-hydroxy-9-(4-(1-(methyl-amino)ethyl)phenyl)thieno[2,3-c]quinolin-4(5H)-one hydrochloride | 0.23 | 0.5 | 0.26 | 0.66 | — |

TABLE 3-continued

| | | | | | | |
|---|---|---|---|---|---|---|
| 1088 | 9-(4-(1-aminopropyl)phenyl)-6-chloro-8-hydroxythieno[2,3-c]quinolin-4(5H)-one hydrochloride | 0.24 | 0.52 | 0.24 | 0.66 | — |
| 1094 | N-(2-bromoethyl)-4-(8-hydroxy-4-oxo-2,3,4,5-tetrahydro-1H-cyclopenta[c]quinolin-9-yl)benzenesulfonamide | 0.0071 | 0.29 | 0.028 | 21 | — |
| 1095 | 9-(4-(2-aminopropyl)phenyl)-8-hydroxythieno[2,3-c]quinolin-4(5H)-one hydrochloride | 0.81 | 0.54 | 0.95 | 0.93 | — |
| 1099 | 9-(4-(1-aminoethyl)phenyl)-4-oxo-4,5-dihydrothieno[2,3-c]quinolin-8-yl acetate hydrochloride | 0.46 | 0.37 | 0.54 | 1.9 | — |
| 1106 | 9-(4-(2-aminopropyl)phenyl)-6-chloro-8-hydroxythieno[2,3-c]quinolin-4(5H)-one hydrochloride | 0.13 | 0.26 | 0.15 | 0.62 | — |
| 1111 | 9-(4-(1-aminopropan-2-yl)phenyl)-8-hydroxythieno[2,3-c]quinolin-4(5H)-one hydrochloride | 0.12 | 0.072 | 0.12 | 0.37 | — |
| 1112 | 9-(4-(1-(dimethylamino)propan-2-yl)phenyl)-8-hydroxythieno[2,3-c]quinolin-4(5H)-one hydrochloride | 0.21 | 0.47 | 0.25 | 0.64 | — |
| 1116 | 9-(4-(1-(aminomethyl)cyclopropyl)phenyl)-6-chloro-8-hydroxythieno[2,3-c]quinolin-4(5H)-one hydrochloride | 0.098 | 0.17 | 0.12 | 0.54 | — |
| 1120 | (S)-9-(4-(1-aminopropyl)phenyl)-8-hydroxythieno[2,3-c]quinolin-4(5H)-one hydrochloride | 0.093 | 0.15 | 0.13 | 0.33 | — |
| 1121 | (S)-9-(4-(1-aminopropyl)phenyl)-8-methoxythieno[2,3-c]quinolin-4(5H)-one hydrochloride | 0.42 | 0.7 | 0.36 | 1.5 | — |
| 1122 | (R)-9-(4-(1-aminoethyl)phenyl)-8-hydroxy-6-methylthieno[2,3-c]quinolin-4(5H)-one hydrochloride | — | 0.065 | 0.049 | 0.17 | 0.065 |
| 1123 | (R)-9-(4-(1-aminoethyl)phenyl)-6-bromo-8-hydroxythieno[2,3-c]quinolin-4(5H)-one hydrochloride | 0.18 | 0.34 | 0.16 | 0.76 | — |
| 1126 | (R)-6-chloro-9-(4-(1-(dimethylamino)ethyl)phenyl)-8-hydroxythieno[2,3-c]quinolin-4(5H)-one hydrochloride | 0.14 | 0.29 | 0.11 | 0.32 | — |
| 1127 | (S)-9-(4-(1-(ethylamino)propyl)phenyl)-8-hydroxythieno[2,3-c]quinolin-4(5H)-one hydrochloride | 0.3 | 0.63 | 0.22 | 0.65 | — |
| 1128 | (S)-9-(4-(1-(dimethylamino)propyl)phenyl)-8-hydroxythieno[2,3-c]quinolin-4(5H)-one hydrochloride | 0.43 | 1 | 0.37 | 1.2 | — |
| 1131 | (R)-9-(4-(1-aminopropyl)phenyl)-8-hydroxythieno[2,3-c]quinolin-4(5H)-one hydrochloride | 0.51 | 0.71 | 0.68 | 4.8 | — |
| 1132 | (R)-6-chloro-8-hydroxy-9-(4-(1-(methylamino)ethyl)phenyl)thieno[2,3-c]quinolin-4(5H)-one hydrochloride | 0.097 | 0.19 | 0.09 | 0.32 | — |
| 1133 | 9-(4-(2-aminoethyl)phenyl)-6-chloro-8-hydroxythieno[2,3-c]quinolin-4(5H)-one hydrochloride | 0.15 | 0.23 | 0.18 | 0.87 | — |
| 1135 | (R)-6-bromo-8-hydroxy-9-(4-(1-(methylamino)ethyl)phenyl)thieno[2,3-c]quinolin-4(5H)-one hydrochloride | 0.14 | 0.28 | 0.13 | 0.41 | — |
| 1136 | 9-(4-(1-aminopropan-2-yl)phenyl)-6-chloro-8-hydroxythieno[2,3-c]quinolin-4(5H)-one hydrochloride | 0.032 | 0.057 | 0.035 | 0.18 | — |
| 1139 | N-(2-chloroethyl)-4-(8-methoxy-4-oxo-4,5-dihydrothieno[2,3-c]quinolin-9-yl)benzenesulfonamide | 0.017 | 0.2 | 0.023 | 14 | — |
| 1142 | 9-(4-(2-aminoethyl)phenyl)-6-bromo-8-hydroxythieno[2,3-c]quinolin-4(5H)-one hydrochloride | 0.17 | 0.25 | 0.21 | 1 | — |
| 1145 | N-(2-chloroethyl)-4-(8-hydroxy-4-oxo-2,3,4,5-tetrahydro-1H-cyclopenta[c]quinolin-9-yl)benzenesulfonamide | 0.01 | 0.18 | 0.051 | 31 | — |
| 1148 | (S)-8-hydroxy-9-(4-(1-(methylamino)propyl)phenyl)thieno[2,3-c]quinolin-4(5H)-one hydrochloride | 0.13 | 0.25 | 0.12 | 0.26 | — |
| 1150 | (R)-9-(4-(1-aminopropyl)phenyl)-6-bromo-8-hydroxythieno[2,3-c]quinolin-4(5H)-one hydrochloride | — | 1.1 | 0.51 | 1.3 | 0.88 |

TABLE 3-continued

| | | | | | | |
|---|---|---|---|---|---|---|
| 1151 | (R)-9-(4-(1-(dimethyl-amino)propyl)phenyl)-8-hydroxythieno[2,3-c]quinolin-4(5H)-one hydrochloride | 0.39 | 0.85 | 0.32 | 1 | — |
| 1154 | (S)-6-chloro-8-hydroxy-9-(4-(1-(methyl-amino)propyl)phenyl)thieno[2,3-c]quinolin-4(5H)-one hydrochloride | 0.14 | 0.29 | 0.13 | 0.32 | |
| 1157 | (R)-9-(4-(1-aminopropyl)phenyl)-8-hydroxy-6-methylthieno[2,3-c]quinolin-4(5H)-one hydrochloride | 0.16 | 0.32 | 0.22 | 0.58 | — |
| 1159 | (R)-9-(4-(1-aminopropyl)phenyl)-6-chloro-8-hydroxythieno[2,3-c]quinolin-4(5H)-one hydrochloride | 0.38 | 0.76 | 0.4 | 1.1 | — |
| 1160 | (R)-9-(4-(1-aminopropan-2-yl)phenyl)-8-hydroxythieno[2,3-c]quinolin-4(5H)-one hydrochloride | 0.054 | 0.057 | 0.056 | 0.23 | 0.069 |
| 1161 | (R)-9-(4-(1-aminopropan-2-yl)phenyl)-8-methoxythieno[2,3-c]quinolin-4(5H)-one hydrochloride | 0.22 | 0.45 | 0.27 | 0.82 | — |
| 1162 | 2-(4-(8-hydroxy-4-oxo-4,5-di-hydrothieno[2,3-c]quinolin-9-yl)phenyl)butanenitrile | 0.51 | 1.2 | 0.65 | 1.3 | — |
| 1163 | (S)-9-(4-(1-aminopropan-2-yl)phenyl)-8-hydroxythieno[2,3-c]quinolin-4(5H)-one hydrochloride | 0.33 | 0.24 | 0.32 | 0.96 | — |
| 1165 | 6-chloro-8-hydroxy-9-(4-(2-(methyl-amino)ethyl)phenyl)thieno[2,3-c]quinolin-4(5H)-one hydrochloride | 0.37 | 0.65 | 0.41 | 1.2 | — |
| 1166 | (R)-9-(4-(1-aminopropan-2-yl)phenyl)-6-chloro-8-hydroxythieno[2,3-c]quinolin-4(5H)-one hydrochloride | 0.013 | 0.026 | 0.017 | 0.12 | — |
| 1168 | (R)-9-(4-(1-aminopropan-2-yl)phenyl)-8-hydroxy-6-methylthieno[2,3-c]quinolin-4(5H)-one hydrochloride | — | 0.0084 | 0.0065 | 0.027 | 0.008 |
| 1169 | (R)-9-(4-(1-aminopropan-2-yl)phenyl)-8-hydroxy-6-methylthieno[2,3-c]quinolin-4(5H)-one hydrobromide | 0.013 | 0.024 | 0.023 | 0.079 | 0.022 |
| 1172 | (S)-9-(4-(1-(dimethylamino)propan-2-yl)phenyl)-8-hydroxythieno[2,3-c]quinolin-4(5H)-one hydrochloride | 0.31 | 0.65 | 0.33 | 0.65 | — |
| 1174 | 9-(4-(1-aminopropan-2-yl)-3-fluorophenyl)-8-hydroxythieno[2,3-c]quinolin-4(5H)-one hydrochloride | 0.16 | 0.12 | 0.27 | 1.2 | — |
| 1176 | (R)-9-(4-(1-aminopropan-2-yl)phenyl)-6-bromo-8-hydroxythieno[2,3-c]quinolin-4(5H)-one hydrochloride | 0.024 | 0.038 | 0.027 | 0.1 | — |
| 1179 | 9-(4-(1-aminopropan-2-yl)-3-fluorophenyl)-8-methoxythieno[2,3-c]quinolin-4(5H)-one hydrochloride | 0.45 | 0.86 | 0.63 | 1.9 | — |
| 1181 | (S)-9-(4-(1-aminopropan-2-yl)phenyl)-6-chloro-8-hydroxythieno[2,3-c]quinolin-4(5H)-one hydrochloride | 0.1 | 0.21 | 0.11 | 0.6 | — |
| 1187 | (R)-8-hydroxy-9-(4-(1-(methyl-amino)propan-2-yl)phenyl)thieno[2,3-c]quinolin-4(5H)-one hydrochloride | 0.19 | 0.19 | 0.2 | 0.32 | — |
| 1188 | (R)-9-(4-(1-(dimethylamino)propan-2-yl)phenyl)-8-hydroxythieno[2,3-c]quinolin-4(5H)-one hydrochloride | 0.16 | 0.29 | 0.16 | 0.43 | — |
| 1189 | (R)-8-methoxy-9-(4-(1-(methyl-amino)propan-2-yl)phenyl)thieno[2,3-c]quinolin-4(5H)-one hydrochloride | 0.69 | 1.3 | 0.59 | 1.3 | — |
| 1190 | 9-(4-(1-aminopropan-2-yl)-3-fluorophenyl)-8-hydroxy-6-methyl-thieno[2,3-c]quinolin-4(5H)-one hydrochloride | 0.015 | 0.019 | 0.021 | 0.11 | |
| 1191 | 9-(4-(2-aminoethyl)phenyl)-8-hydroxy-6-methylthieno[2,3-c]quinolin-4(5H)-one hydrochloride | 0.064 | 0.073 | 0.12 | 0.48 | — |
| 1193 | 9-(4-(1-(dimethylamino)propan-2-yl)-3-fluorophenyl)-8-hydroxy-6-methyl-thieno[2,3-c]quinolin-4(5H)-one hydrochloride | 0.14 | 0.24 | 0.13 | 0.33 | — |
| 1197 | (S)-8-hydroxy-9-(4-(1-(methyl-amino)propan-2-yl)phenyl)thieno[2,3-c]quinolin-4(5H)-one hydrochloride | 0.43 | 0.54 | 0.62 | 1 | — |
| 1201 | (R)-9-(4-(1-aminopropan-2-yl)phenyl)-6-chloro-8-methoxythieno[2,3-c]quinolin-4(5H)-one hydrochloride | 0.053 | 0.12 | 0.046 | 0.14 | — |

TABLE 3-continued

| | | | | | | |
|---|---|---|---|---|---|---|
| 1204 | N-(1-chloropropan-2-yl)-4-(8-hydroxy-4-oxo-4,5-dihydrothieno[2,3-c]quinolin-9-yl)benzenesulfonamide | 0.16 | 1.9 | 0.71 | 15 | — |
| 1209 | 9-(4-(3-(aminomethyl)pentan-3-yl)phenyl)-8-hydroxythieno[2,3-c]quinolin-4(5H)-one hydrochloride | 0.49 | 1 | 0.48 | 1.2 | — |
| 1212 | 9-(4-(aminomethyl)phenyl)-8-hydroxy-6-methylthieno[2,3-c]quinolin-4(5H)-one hydrochloride | 0.12 | 0.2 | 0.15 | 0.63 | — |
| 1213 | 9-(4-(2-aminoethyl)-3-fluorophenyl)-6-bromo-8-hydroxythieno[2,3-c]quinolin-4(5H)-one hydrochloride | 0.23 | 0.38 | 0.36 | 1.7 | — |
| 1215 | (S)-8-hydroxy-6-methyl-9-(4-(1-(methylamino)propan-2-yl)phenyl)thieno[2,3-c]quinolin-4(5H)-one hydrochloride | 0.14 | 0.26 | 0.15 | 0.5 | — |
| 1216 | 9-(4-(2-aminoethyl)-3-fluorophenyl)-8-methoxy-6-methylthieno[2,3-c]quinolin-4(5H)-one hydrochloride | 0.21 | 0.46 | 0.28 | 0.64 | — |
| 1217 | 9-(4-(2-aminoethyl)-3-fluorophenyl)-8-hydroxy-6-methylthieno[2,3-c]quinolin-4(5H)-one hydrochloride | 0.065 | 0.084 | 0.14 | 0.48 | — |
| 1218 | 9-(4-(2-aminoethyl)-3-fluorophenyl)-6-chloro-8-methoxythieno[2,3-c]quinolin-4(5H)-one hydrochloride | 0.55 | 1.2 | 0.62 | 1.3 | — |
| 1219 | 9-(4-(2-aminoethyl)-3-fluorophenyl)-6-chloro-8-hydroxythieno[2,3-c]quinolin-4(5H)-one hydrochloride | 0.1 | 0.18 | 0.17 | 0.88 | — |
| 1224 | 9-(4-(2-aminoethyl)-2-bromo-5-hydroxyphenyl)-8-hydroxythieno[2,3-c]quinolin-4(5H)-one hydrochloride | 0.98 | 0.77 | 0.49 | 1.5 | — |
| 1225 | (S)-9-(4-(1-aminoethyl)phenyl)-8-hydroxy-6-methylthieno[2,3-c]quinolin-4(5H)-one hydrochloride | 0.091 | 0.16 | 0.1 | 0.38 | — |
| 1226 | 3-(4-(8-hydroxy-6-methyl-4-oxo-4,5-dihydrothieno[2,3-c]quinolin-9-yl)phenyl)propanenitrile | 0.59 | 1.2 | 0.49 | 1.3 | — |
| 1228 | 9-(4-(1-amino-2-methylpropan-2-yl)phenyl)-8-hydroxy-6-methyl-thieno[2,3-c]quinolin-4(5H)-one hydrochloride | 0.15 | 0.33 | 0.16 | 0.81 | — |
| 1232 | (S)-9-(4-(1-aminopropan-2-yl)phenyl)-8-hydroxy-6-methylthieno[2,3-c]quinolin-4(5H)-one hydrochloride | 0.037 | 0.062 | 0.041 | 0.2 | — |
| 1236 | 9-(4-(2-amino-1-cyclopentyl-ethyl)phenyl)-8-hydroxythieno[2,3-c]quinolin-4(5H)-one | 0.51 | 0.8 | 0.46 | 1 | — |
| 1239 | 9-(4-(2-amino-1-cyclopentyl-ethyl)phenyl)-8-methoxythieno[2,3-c]quinolin-4(5H)-one hydrochloride | 1.5 | 1.1 | 0.89 | 1.7 | — |
| 1242 | 9-(4-(2-aminopropyl)phenyl)-8-hydroxy-6-methylthieno[2,3-c]quinolin-4(5H)-one hydrochloride | 0.11 | 0.15 | 0.12 | 0.42 | — |
| 1245 | 6-bromo-9-(3-fluoro-4-(2-(methyl-amino)ethyl)phenyl)-8-hydroxy-thieno[2,3-c]quinolin-4(5H)-one hydrochloride | 0.72 | 1.3 | 0.85 | 2.5 | — |
| 1247 | 9-(4-(1-amino-2-methylpropan-2-yl)phenyl)-6-bromo-8-hydroxy-thieno[2,3-c]quinolin-4(5H)-one hydrochloride | 0.52 | 0.94 | 0.47 | 1.3 | — |
| 1251 | 9-(4-(1-(aminomethyl)cyclo-propyl)phenyl)-8-methoxy-6-methyl-thieno[2,3-c]quinolin-4(5H)-one hydrochloride | 0.26 | 0.52 | 0.2 | 0.65 | — |
| 1252 | 9-(4-(1-amino-3-methylbutan-2-yl)phenyl)-8-hydroxythieno[2,3-c]quinolin-4(5H)-one | 0.25 | 0.21 | 0.16 | 0.42 | — |
| 1253 | 9-(4-(1-amino-3-methylbutan-2-yl)phenyl)-8-methoxythieno[2,3-c]quinolin-4(5H)-one hydrochloride | 1.5 | 0.87 | 0.76 | 1.9 | — |
| 1254 | 9-(4-(1-(aminomethyl)cyclo-propyl)phenyl)-8-hydroxy-6-methyl-thieno[2,3-c]quinolin-4(5H)-one hydrochloride | 0.035 | 0.053 | 0.039 | 0.24 | — |
| 1258 | 9-(3-fluoro-4-(2-(methyl-amino)ethyl)phenyl)-8-hydroxy-6-methyl-thieno[2,3-c]quinolin-4(5H)-one hydrochloride | 0.43 | 0.6 | 0.66 | 1.5 | — |

TABLE 3-continued

| | | | | | | |
|---|---|---|---|---|---|---|
| 1260 | 9-(4-(1-amino-2-methylpropan-2-yl)phenyl)-6-chloro-8-hydroxy-thieno[2,3-c]quinolin-4(5H)-one hydrochloride | 0.43 | 0.93 | 0.5 | 1.7 | — |
| 1262 | (R)-8-hydroxy-6-methyl-9-(4-(1-(methylamino)ethyl)phenyl)thieno[2,3-c]quinolin-4(5H)-one hydrochloride | 0.039 | 0.078 | 0.045 | 0.13 | — |
| 1263 | 9-(4-(2-aminoethyl)-3-chlorophenyl)-8-methoxy-6-methylthieno[2,3-c]quinolin-4(5H)-one hydrochloride | 0.2 | 0.41 | 0.23 | 0.58 | — |
| 1264 | 9-(4-(2-aminoethyl)-3-chlorophenyl)-8-hydroxy-6-methylthieno[2,3-c]quinolin-4(5H)-one hydrochloride | 0.032 | 0.046 | 0.075 | 0.17 | — |
| 1265 | (R)-8-methoxy-6-methyl-9-(4-(1-(methylamino)ethyl)phenyl)thieno[2,3-c]quinolin-4(5H)-one hydrochloride | 0.11 | 0.26 | 0.11 | 0.32 | — |
| 1268 | 9-(4-(2-aminoethyl)-3-chlorophenyl)-6-chloro-8-hydroxythieno[2,3-c]quinolin-4(5H)-one hydrochloride | 0.077 | 0.12 | 0.13 | 0.38 | — |
| 1271 | 9-(4-(1-amino-2-methylpropan-2-yl)-3-fluorophenyl)-8-hydroxy-thieno[2,3-c]quinolin-4(5H)-one hydrochloride | 0.3 | 0.57 | 0.47 | 1.6 | — |
| 1273 | 9-(4-(1-aminopropan-2-yl)-3-fluorophenyl)-8-methoxy-6-methyl-thieno[2,3-c]quinolin-4(5H)-one hydrochloride | 0.073 | 0.17 | 0.071 | 0.2 | — |
| 1274 | 9-(4-(1-amino-3-methylbutan-2-yl)phenyl)-8-hydroxy-6-methyl-thieno[2,3-c]quinolin-4(5H)-one | 0.066 | 0.098 | 0.045 | 0.18 | — |
| 1277 | 9-(4-(1-aminobutan-2-yl)phenyl)-8-methoxy-6-methylthieno[2,3-c]quinolin-4(5H)-one hydrochloride | 0.13 | 0.28 | 0.14 | 0.29 | — |
| 1278 | 9-(4-(1-amino-2-methylpropan-2-yl)-3-fluorophenyl)-8-hydroxy-6-methylthieno[2,3-c]quinolin-4(5H)-one hydrochloride | 0.11 | 0.26 | 0.29 | 0.51 | — |
| 1280 | 9-(4-(1-aminopropan-2-yl)-3-chlorophenyl)-8-hydroxy-thieno[2,3-c]quinolin-4(5H)-one hydrochloride | 0.45 | 2.6 | 0.37 | 7 | — |
| 1283 | 9-(4-(1-amino-3-methylbutan-2-yl)-3-fluorophenyl)-8-methoxy-6-methylthieno[2,3-c]quinolin-4(5H)-one hydrochloride | 0.25 | 0.56 | 0.56 | 0.53 | — |
| 1285 | 8-hydroxy-6-methyl-9-(4-(3-methyl-1-(methylamino)butan-2-yl)phenyl)thieno[2,3-c]quinolin-4(5H)-one | 0.11 | 0.21 | 0.23 | 0.28 | — |
| 1286 | 9-(3-fluoro-4-(1-(methylamino)propan-2-yl)phenyl)-8-methoxy-6-methylthieno[2,3-c]quinolin-4(5H)-one hydrochloride | 0.093 | 0.22 | 0.095 | 0.22 | — |
| 1288 | 9-(4-(1-amino-3-methylbutan-2-yl)-3-fluorophenyl)-8-hydroxy-6-methyl-thieno[2,3-c]quinolin-4(5H)-one | 0.047 | 0.074 | 0.11 | 0.14 | — |
| 1290 | 9-(4-(1-(aminomethyl)cyclobutyl)phenyl)-8-hydroxy-6-methylthieno[2,3-c]quinolin-4(5H)-one hydrochloride | 0.025 | 0.044 | 0.021 | 0.096 | — |
| 1291 | 9-(4-(1-aminobutan-2-yl)phenyl)-8-hydroxy-6-methylthieno[2,3-c]quinolin-4(5H)-one hydrochloride | 0.026 | 0.029 | 0.022 | 0.11 | — |
| 1293 | 9-(3-fluoro-4-(1-(methyl-amino)propan-2-yl)phenyl)-8-hydroxy-6-methylthieno[2,3-c]quinolin-4(5H)-one | 0.032 | 0.052 | 0.035 | 0.19 | — |
| 1294 | 9-(3-fluoro-4-(3-methyl-1-(methyl-amino)butan-2-yl)phenyl)-8-hydroxy-6-methylthieno[2,3-c]quinolin-4(5H)-one | 0.085 | 0.18 | 0.078 | 0.34 | — |
| 1297 | 9-(4-(1-(aminomethyl)cyclo-butyl)phenyl)-8-methoxy-6-methyl-thieno[2,3-c]quinolin-4(5H)-one hydrochloride | 0.26 | 0.62 | 0.22 | 0.52 | — |
| 1298 | (R)-8-methoxy-6-methyl-9-(4-(1-(methylamino)propan-2-yl)phenyl)thieno [2,3-c]quinolin-4(5H)-one hydrochloride | 0.064 | 0.14 | 0.068 | 0.16 | — |

TABLE 3-continued

| | | | | | | |
|---|---|---|---|---|---|---|
| 1300 | 9-(4-(1-(aminomethyl)cyclo-butyl)phenyl)-8-hydroxythieno[2,3-c]quinolin-4(5H)-one hydrochloride | 0.1 | 0.12 | 0.077 | 0.23 | — |
| 1302 | 8-hydroxy-6-methyl-9-(4-(piperidin-3-yl)phenyl)thieno[2,3-c]quinolin-4(5H)-one hydrochloride | 0.74 | 0.83 | 0.97 | 1.5 | — |
| 1303 | (S)-9-(4-(1-aminopropan-2-yl)-3-fluorophenyl)-8-hydroxy-6-methyl-thieno[2,3-c]quinolin-4(5H)-one | 0.081 | 0.13 | 0.092 | 0.51 | — |
| 1304 | (S)-9-(4-(1-aminopropan-2-yl)-3-fluorophenyl)-8-hydroxy-6-methyl-thieno[2,3-c]quinolin-4(5H)-one hydrobromide | — | 0.12 | 0.099 | 0.34 | 0.074 |
| 1305 | (R)-9-(4-(1-aminopropan-2-yl)phenyl)-8-methoxy-6-methylthieno [2,3-c]quinolin-4(5H)-one hydrochloride | 0.021 | 0.04 | 0.02 | 0.064 | — |
| 1306 | (R)-8-hydroxy-6-methyl-9-(4-(1-(methylamino)propan-2-yl)phenyl)thieno[2,3-c]quinolin-4(5H)-one hydrochloride | — | 0.035 | 0.02 | 0.073 | 0.033 |
| 1307 | (R)-8-hydroxy-6-methyl-9-(4-(1-(methylamino)propan-2-yl)phenyl)thieno [2,3-c]quinolin-4(5H)-one hydrobromide | 0.042 | 0.085 | 0.057 | 0.15 | 0.073 |
| 1309 | 9-(4-(1-aminobutan-2-yl)phenyl)-8-hydroxythieno[2,3-c]quinolin-4(5H)-one hydrochloride | 0.094 | 0.066 | 0.065 | 0.21 | — |
| 1310 | (S)-9-(4-(1-aminopropan-2-yl)-3-fluorophenyl)-8-methoxy-6-methyl-thieno[2,3-c]quinolin-4(5H)-one hydrochloride | 0.4 | 0.8 | 0.37 | 0.89 | — |
| 1311 | (R)-9-(4-(1-(dimethylamino)propan-2-yl)-3-fluorophenyl)-8-hydroxy-6-methylthieno[2,3-c]quinolin-4(5H)-one hydrochloride | 0.037 | 0.07 | 0.045 | 0.11 | — |
| 1312 | 9-(4-(1-aminobutan-2-yl)phenyl)-6-chloro-8-hydroxythieno[2,3-c]quinolin-4(5H)-one hydrochloride | 0.058 | 0.076 | 0.054 | 0.23 | — |
| 1315 | (R)-9-(3-fluoro-4-(1-(methyl-amino)propan-2-yl)phenyl)-8-hydroxy-6-methylthieno[2,3-c]quinolin-4(5H)-one hydrochloride | 0.024 | 0.041 | 0.034 | 0.1 | — |
| 1316 | (R)-9-(3-fluoro-4-(1-(methyl-amino)propan-2-yl)phenyl)-8-methoxy-6-methylthieno[2,3-c]quinolin-4(5H)-one hydrochloride | 0.083 | 0.16 | 0.086 | 0.23 | — |
| 1317 | (R)-9-(4-(1-aminopropan-2-yl)-3-fluorophenyl)-8-methoxy-6-methyl-thieno[2,3-c]quinolin-4(5H)-one hydrochloride | 0.036 | 0.072 | 0.042 | 0.1 | — |
| 1318 | (R)-9-(4-(1-aminopropan-2-yl)-3-fluorophenyl)-8-hydroxy-6-methyl-thieno[2,3-c]quinolin-4(5H)-one hydrochloride | 0.0084 | 0.015 | 0.015 | 0.063 | — |
| 1319 | (R)-9-(4-(1-aminopropan-2-yl)-3-fluorophenyl)-8-hydroxy-6-methyl-thieno[2,3-c]quinolin-4(5H)-one hydrobromide | — | 0.016 | 0.014 | 0.054 | 0.014 |
| 1321 | 9-(4-(1-(aminomethyl)cyclo-butyl)phenyl)-6-chloro-8-methoxy-thieno[2,3-c]quinolin-4(5H)-one hydrochloride | 1 | 2.2 | 0.8 | 2 | — |
| 1324 | (R)-9-(4-(1-(dimethylamino)propan-2-yl)phenyl)-8-hydroxy-6-methylthieno[2,3-c]quinolin-4(5H)-one hydrochloride | 0.03 | 0.066 | 0.024 | 0.069 | — |
| 1330 | 9-(4-(2-aminopropan-2-yl)phenyl)-8-hydroxy-6-methylthieno[2,3-c]quinolin-4(5H)-one hydrochloride | 0.19 | 0.43 | 0.18 | 0.76 | — |
| 1340 | (R)-9-(4-(1-aminopropan-2-yl)phenyl)-8-hydroxy-2,6-dimethylthieno[2,3-c]quinolin-4(5H)-one hydrochloride | 0.17 | 0.25 | 0.19 | 0.65 | — |
| 1341 | (R)-9-(4-(1-aminopropan-2-yl)phenyl)-8-methoxy-2,6-dimethylthieno[2,3-c]quinolin-4(5H)-one hydrochloride | 0.86 | 0.98 | 0.57 | 0.88 | — |
| 1347 | (R)-6-chloro-9-(4-(1-(dimethyl-amino)propan-2-yl)phenyl)-8-hydroxythieno [2,3-c]quinolin-4(5H)-one hydrochloride | 0.11 | 0.26 | 0.1 | 0.26 | — |

TABLE 3-continued

| | | | | | | |
|---|---|---|---|---|---|---|
| 1352 | (R)-9-(4-(1-aminobutan-2-yl)phenyl)-8-hydroxy-6-methylthieno[2,3-c]quinolin-4(5H)-one hydrochloride | 0.071 | 0.099 | 0.055 | 0.34 | — |
| 1353 | (R)-9-(4-(1-aminopropan-2-yl)phenyl)-2-chloro-8-hydroxy-6-methylthieno[2,3-c]quinolin-4(5H)-one hydrochloride | 0.079 | 0.087 | 0.045 | 0.11 | — |
| 1354 | (R)-9-(4-(1-aminopropan-2-yl)phenyl)-2-chloro-8-methoxy-6-methylthieno[2,3-c]quinolin-4(5H)-one hydrochloride | 0.29 | 0.53 | 0.15 | 0.23 | — |
| 1364 | 8-hydroxy-6-methyl-9-(4-(2-(methylamino)ethyl)phenyl)thieno[2,3-c]quinolin-4(5H)-one hydrochloride | 0.26 | 0.3 | 0.27 | 0.66 | — |
| 1372 | 9-(4-(1-((dimethylamino)methyl)cyclobutyl)phenyl)-8-hydroxy-6-methylthieno[2,3-c]quinolin-4(5H)-one hydrochloride | — | 0.084 | 0.035 | 0.1 | 0.075 |
| 1375 | (R)-9-(4-(1-aminopropan-2-yl)phenyl)-2-fluoro-8-methoxy-6-methylthieno[2,3-c]quinolin-4(5H)-one hydrochloride | — | 0.42 | 0.16 | 0.37 | 0.35 |
| 1379 | (R)-9-(4-(1-(ethyl(methyl)amino)propan-2-yl)phenyl)-8-hydroxy-6-methyl-thieno[2,3-c]quinolin-4(5H)-one hydrochloride | — | 0.28 | 0.11 | 0.31 | 0.22 |
| 1380 | (R)-8-hydroxy-6-methyl-9-(4-(1-(methylamino)butan-2-yl)phenyl)thieno[2,3-c]quinolin-4(5H)-one hydrochloride | — | 0.24 | 0.096 | 0.37 | 0.19 |
| 1383 | (R)-9-(4-(1-aminopropan-2-yl)phenyl)-2-fluoro-8-hydroxy-6-methylthieno[2,3-c]quinolin-4(5H)-one hydrochloride | — | 0.057 | 0.029 | 0.1 | 0.048 |
| 1391 | 9-(4-(1-(aminomethyl)cyclopropyl)phenyl)-6-bromo-8-methoxy-thieno[2,3-c]quinolin-4(5H)-one hydrochloride | — | 1.2 | 0.67 | 1.4 | 0.99 |
| 1399 | (S)-9-(4-(1-(dimethylamino)propan-2-yl)-3-fluorophenyl)-8-hydroxy-6-methylthieno[2,3-c]quinolin-4(5H)-one hydrochloride | — | 0.45 | 0.18 | 0.47 | 0.3 |
| 1400 | 9-(4-((2-aminoethyl)(methyl)amino)phenyl)-8-hydroxy-6-methylthieno[2,3-c]quinolin-4(5H)-one hydrochloride | — | 1.4 | 0.9 | 2.8 | 1.1 |
| 1401 | 9-(4-(1-(aminomethyl)cyclopropyl)phenyl)-6-bromo-8-hydroxy-thieno[2,3-c]quinolin-4(5H)-one hydrochloride | — | 0.4 | 0.3 | 1.2 | 0.34 |
| 1419 | 2-(4-(8-hydroxy-6-methyl-4-oxo-4,5-dihydrothieno[2,3-c]quinolin-9-yl)phenyl)propane-1-sulfonamide | — | — | 0.72 | 6.4 | 0.28 |

">100" in the table means over 100 micro M.

INDUSTRIAL APPLICABILITY

The present invention provides a novel Tricyclic compound having PBK inhibitory effect. The compounds of the present invention may be used for pharmaceutical composition for inhibiting PBK. Such pharmaceutical compositions are suitable for treating or preventing cancer.

The invention claimed is:
1. A compound represented by general formula I:

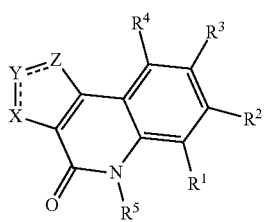

or a pharmaceutically acceptable salt thereof,
wherein $R^1$, $R^2$, and $R^3$ are each independently a group selected from the group consisting of:
hydrogen,
hydroxyl,
halogen,
cyano,
nitro,
amino,
$C_1$-$C_6$ alkyl,
$C_2$-$C_6$ alkenyl,
$C_2$-$C_6$ alkynyl,
$C_3$-$C_{10}$ cycloalkyl,
$C_3$-$C_{10}$ cycloalkenyl,
$C_1$-$C_6$ alkoxy,
$C_6$-$C_{10}$ aryl,
indanyl,
heteroaryl,
3- to 8-membered heterocycloalkyl,
—$OSO_2CH_3$, —OSO$_2$CF$_3$,
—CONH$_2$,
—OCONR$^{101}$R$^{102}$, wherein R$^{101}$ and R$^{102}$ each independently is hydrogen, C$_1$-C$_6$ alkyl, or R$^{101}$ and R$^{102}$ taken together form morpholinyl,
—OCOR$^{103}$, wherein R$^{103}$ represents C$_1$-C$_6$ alkyl, and
—OCOOR$^{104}$, wherein R$^{104}$ represents C$_1$-C$_6$ alkyl,
wherein R$^1$, R$^2$, and R$^3$ are optionally substituted with a substituent independently selected from the group consisting of substituent A;
R$^4$ is selected from the group consisting of hydroxyl, halogen, amino, C$_1$-C$_6$ alkyl, C$_2$-C$_6$ alkenyl, C$_3$-C$_{10}$ cycloalkyl, C$_3$-C$_{10}$ cycloalkenyl, C$_1$-C$_6$ alkoxy, C$_6$-C$_{10}$ aryl, indanyl, heteroaryl, and 3- to 8-membered heterocycloalkyl, and R$^4$ is optionally substituted with substituent A;
wherein substituent A is independently selected from the group consisting of:
hydroxyl;
oxo (=O);
cyano;
halogen;
C$_1$-C$_6$ alkyl optionally substituted with substituent B;
C$_3$-C$_{10}$ cycloalkyl optionally substituted with cyano or C$_1$-C$_6$ alkyl substituted with —NR$^{31}$R$^{32}$, wherein R$^{31}$ and R$^{32}$ each independently represent hydrogen or C$_1$-C$_6$ alkyl;
—NR$^{21}$R$^{22}$, wherein R$^{21}$ and R$^{22}$ each independently represent hydrogen; C$_1$-C$_6$ alkyl optionally substituted with hydroxyl, amino, di(C$_1$-C$_6$ alkyl)amino, —SO$_2$(C$_1$-C$_6$ alkyl), 3- to 8-membered heterocycloalkyl, or cyano; or a 3- to 8-membered heterocycloalkyl optionally substituted with —COOR$^{105}$ wherein R$^{105}$ represents C$_1$-C$_6$ alkyl;
C$_1$-C$_6$ alkoxy optionally substituted with halogen, 3- to 8-membered heterocycloalkyl optionally substituted with C$_1$-C$_6$ alkyl, or —NR$^{33}$R$^{34}$ wherein R$^{33}$ and R$^{34}$ each independently represent hydrogen, C$_1$-C$_6$ alkylsulfonyl, or C$_1$-C$_6$ alkyl optionally substituted with C$_1$-C$_6$ alkylsulfonyl or di(C$_1$-C$_6$ alkyl)amino;
—SO$_2$NR$^{23}$R$^{24}$, wherein R$^{23}$ and R$^{24}$ each independently represent hydrogen; C$_1$-C$_6$ alkyl optionally substituted with hydroxyl, C$_1$-C$_6$ alkoxy, halogen, C$_3$-C$_{10}$ cycloalkyl, heteroaryl, or —NR$^{35}$R$^{36}$ wherein R$^{35}$ and R$^{36}$ each independently represent hydrogen or C$_1$-C$_6$ alkyl; C$_3$-C$_{10}$ cycloalkyl optionally substituted with C$_1$-C$_6$ hydroxyalkyl; 3- to 8-membered heterocycloalkyl; or R$^{23}$ and R$^{24}$ taken together form 3- to 8-membered heterocycloalkyl optionally substituted with amino or halogen;
C$_1$-C$_6$ alkylsulfonyl optionally substituted with hydroxyl;
—NHSO$_2$(C$_1$-C$_6$ alkyl), wherein the carbon atoms are optionally substituted with —NR$^{37}$R$^{38}$ wherein R$^{37}$ and R$^{38}$ each independently represent hydrogen or C$_1$-C$_6$ alkyl;
3- to 8-membered heterocycloalkyl optionally substituted with —NR$^{39}$R$^{40}$, wherein R$^{39}$ and R$^{40}$ each independently represent hydrogen, C$_1$-C$_6$ alkyl, or C$_1$-C$_6$ alkylsulfonyl; C$_1$-C$_6$ alkyl optionally substituted with —NR$^{41}$R$^{42}$, wherein R$^{41}$ and R$^{42}$ each independently represent hydrogen or C$_1$-C$_6$ alkyl; hydroxyl; or C$_1$-C$_6$ alkylsulfonyl;
aryl optionally substituted with C$_1$-C$_6$ alkyl optionally substituted with cyano or amino;
heteroaryl;
—COOR$^{11}$, wherein R$^{11}$ represents hydrogen or C$_1$-C$_6$ alkyl; and
—COR$^{12}$, wherein R$^{12}$ represents C$_1$-C$_6$ alkyl; C$_3$-C$_{10}$ cycloalkyl; cyanomethyl; aminomethyl; —NR$^{25}$R$^{26}$ wherein R$^{25}$ and R$^{26}$ each independently represent hydrogen or C$_1$-C$_6$ alkyl optionally substituted with hydroxyl or —NR$^{43}$R$^{44}$, wherein R$^{43}$ and R$^{44}$ each independently represent hydrogen or C$_1$-C$_6$ alkyl; or 3- to 8-membered heterocycloalkyl optionally substituted with C$_1$-C$_6$ alkyl;
wherein substituent B is independently selected from the group consisting of:
halogen;
hydroxyl;
C$_1$-C$_6$ alkoxy;
cyano;
cycloalkyl;
C$_6$-C$_{10}$ aryl optionally substituted with cyano;
heteroaryl;
3- to 8-membered heterocycloalkyl optionally substituted with C$_1$-C$_6$ alkyl, hydroxyl, amino, C$_1$-C$_6$ aminoalkyl, or C$_1$-C$_6$ alkyl substituted with C$_2$-C$_7$ alkyloxycarbonylamino;
—NR$^{51}$R$^{52}$, wherein R$^{51}$ and R$^{52}$ each independently represent hydrogen; C$_1$-C$_6$ alkyl optionally substituted with C$_1$-C$_6$ alkylsulfonyl or 3- to 8-membered heterocycloalkyl optionally substituted with —COOR$^{53}$ wherein R$^{53}$ represents hydrogen or C$_1$-C$_6$ alkyl; 3- to 8-membered heterocycloalkyl; C$_1$-C$_6$ alkylsulfonyl; C$_3$-C$_{10}$ cycloalkyl; —COR$^{55}$ wherein R$^{55}$ represents C$_1$-C$_6$ alkyl; —COOR$^{56}$ wherein R$^{56}$ represents C$_1$-C$_6$ alkyl; or —CONR$^{57}$R$^{58}$ wherein R$^{57}$ and R$^{58}$ each independently represent hydrogen or C$_1$-C$_6$ alkyl;
—COOR$^{54}$, wherein R$^{54}$ represents hydrogen or C$_1$-C$_6$ alkyl;
—CONH$_2$;
—SO$_2$NR$^{106}$R$^{107}$, wherein R$^{106}$ and R$^{107}$ each independently represent hydrogen, C$_1$-C$_6$ alkyl, or C$_3$-C$_{10}$ cycloalkyl;
C$_1$-C$_6$ alkylsulfinyl; and
C$_1$-C$_6$ alkylsulfonyl;
wherein R$^5$ is hydrogen or C$_1$-C$_6$ alkyl; and
wherein $$—X\!\!=\!\!\!=\!\!Y\!\!=\!\!\!=\!\!Z—$$

is the structure: —S—CR$^7$=CR$^6$—,
wherein R$^6$ is selected from the group consisting of:
hydrogen,
hydroxyl,
C$_1$-C$_6$ alkyl,
C$_6$-C$_{10}$ aryl optionally substituted with hydroxyl, and
3- to 8-membered heterocycloalkyl optionally substituted with —NR$^{61}$R$^{62}$, wherein R$^{61}$ and R$^{62}$ each independently represent hydrogen or C$_1$-C$_6$ alkyl;
wherein R$^7$ is selected from the group consisting of:
hydrogen;
halogen; C$_1$-C$_6$ alkyl optionally substituted with hydroxyl, —NR$^{71}$R$^{72}$ wherein R$^{71}$ and R$^{72}$ each independently represent hydrogen; C$_1$-C$_6$ alkyl optionally substituted with dimethylamino; C$_3$-C$_{10}$ cycloalkyl optionally substituted with amino or 3- to 8-membered heterocycloalkyl; or 3- to 8-membered heterocycloalkyl optionally substituted with $C_1$-$C_6$ aminoalkyl;

$C_6$-$C_{10}$ aryl optionally substituted with hydroxyl;

$C_6$-$C_{10}$ arylsulfonyl; and

—$COR^{73}$, wherein $R^{73}$ represents 3- to 8-membered heterocycloalkyl optionally substituted with amino; or —$NR^{74}R^{75}$ wherein $R^{74}$ and $R^{75}$ each independently represent hydrogen, 3- to 8-membered heterocycloalkyl, or $C_3$-$C_{10}$ cycloalkyl optionally substituted with amino.

2. The compound of claim 1, or a pharmaceutically acceptable salt thereof, wherein $R^1$ is hydrogen, cyano, $C_1$-$C_6$ alkyl optionally substituted with hydroxyl or halogen, $C_3$-$C_{10}$ cycloalkyl, $C_2$-$C_6$ alkenyl, $C_2$-$C_6$ alkynyl, or halogen.

3. The compound of claim 1, or a pharmaceutically acceptable salt thereof, wherein $R^2$ is hydrogen, hydroxyl, halogen, $C_1$-$C_6$ alkoxy, or $C_6$-$C_{10}$ aryl optionally substituted with hydroxyl.

4. The compound of claim 1, or a pharmaceutically acceptable salt, wherein $R^2$ is hydrogen, hydroxyl, halogen, $C_1$-$C_6$ alkoxy, or dihydroxyphenyl.

5. The compound of claim 1, or a pharmaceutically acceptable salt thereof, wherein $R^3$ is selected from the group consisting of: hydrogen; hydroxyl; $C_1$-$C_6$ alkyl optionally substituted with hydroxyl, halogen, or hydroxyethylamino; halogen; $C_1$-$C_6$ alkoxy optionally substituted with dimethylamino or morpholinyl; $C_1$-$C_6$ alkylphenyl, wherein the aliphatic carbons are optionally substituted with —$NR^{51}R^{52}$; cyano; nitro; amino; 3- to 8-membered heterocycloalkyl optionally substituted with amino; heteroaryl; —$OSO_2CH_3$; —$OSO_2CF_3$; —$OCOR^{103}$, wherein $R^{103}$ represents $C_1$-$C_6$ alkyl; —$OCOOR^{104}$ wherein $R^{104}$ represents $C_1$-$C_6$ alkyl; —$OCONR^{101}R^{102}$ wherein $R^{101}$ and $R^{102}$ each independently represent hydrogen or $C_1$-$C_6$ alkyl, or $R^{101}$ and $R^{102}$ taken together form morpholinyl; and —$CONH_2$.

6. The compound of claim 5, or a pharmaceutically acceptable salt thereof, wherein when $R^3$ is a 3- to 8-membered heterocycloalkyl, the 3- to 8-membered heterocycloalkyl is selected from the group consisting of piperidyl, pyrrolidinyl, morpholinyl, or piperazinyl and optionally substituted with amino; and when $R^3$ is heteroaryl, the heteroaryl is pyridyl.

7. The compound of claim 1, or a pharmaceutically acceptable salt thereof, wherein when $R^4$ is heteroaryl, the heteroaryl is selected from the group consisting of pyridyl, 1H-indazolyl, 1H-tetrazolyl, [1,2,4]triazolo[1,5-a]pyridyl, benzoimidazolyl, 2,3-dihydrobenzooxazolyl, pyrazolyl, pyrrolo[2,3-b]pyridyl, pyrimidinyl, indolinyl, furyl, thienyl, and tetrahydroisoquinolyl); and wherein the 3- to 8-membered heterocycloalkyl is selected from the group consisting of aziridinyl, azetidinyl, pyrrolidinyl, imidazolidinyl, piperidyl, piperazinyl, azepanyl, morpholinyl, and 1,2,3,6-tetrahydropyridyl; wherein each of the groups of $R^4$ is optionally substituted with substituent A-1;

wherein substituent A-1 is selected from the group consisting of:
hydroxyl;
oxo;
cyano;
halogen;
$C_1$-$C_6$ alkyl optionally substituted with a substituent selected from the group consisting of substituent B-1;
$C_3$-$C_{10}$ cycloalkyl optionally substituted with cyano, or $C_1$-$C_6$ alkyl substituted with —$NR^{31}R^{32}$;
—$NR^{21A}R^{22A}$, wherein $R^{21A}$ and $R^{22A}$ each independently represent hydrogen; $C_1$-$C_6$ alkyl optionally substituted with amino, di($C_1$-$C_6$ alkyl)amino, —$SO_2$($C_1$-$C_6$ alkyl), piperidyl, or cyano; or piperidyl optionally substituted with —$COOR^{105}$;
$C_1$-$C_6$ alkoxy optionally substituted with halogen; a 3- to 8-membered heterocycloalkyl selected from piperidyl and piperazinyl, either of which is optionally substituted with $C_1$-$C_6$ alkyl; or —$NR^{33}R^{34}$;
—$SO^2NR^{23A}R^{24A}$, wherein $R^{23A}$ and $R^{24A}$ each independently represent hydrogen, $C_1$-$C_6$ alkyl optionally substituted with hydroxyl, $C_1$-$C_6$ alkoxy, halogen, $C_3$-$C_{10}$ cycloalkyl, pyrazolyl, imidazolyl, or —$NR^{35}R^{36}$; $C_3$-$C_{10}$ cycloalkyl optionally substituted with $C_1$-$C_6$ hydroxyalkyl; azetidinyl; pyrrolidinyl, or $R^{23A}$ and $R^{24A}$ taken together form pyrrolidinyl optionally substituted with amino or halogen;
$C_1$-$C_6$ alkylsulfonyl optionally substituted with hydroxyl;
—$NHSO_2$($C_1$-$C_6$ alkyl), wherein the carbon atoms are optionally substituted with —$NR^{37}R^{38}$;
3- to 8-membered heterocycloalkyl selected from the group consisting of azetidinyl, pyrrolidinyl, piperidyl, piperazinyl, and tetrahydropyridyl any of which is optionally substituted with —$NR^{39}R^{40}$; $C_1$-$C_6$ alkyl optionally substituted with —$NR^{41}R^{42}$; hydroxyl; or $C_1$-$C_6$ alkylsulfonyl;
1H-tetrazolyl;
aryl optionally substituted with $C_1$-$C_6$ alkyl, wherein $C_1$-$C_6$ is the aliphatic carbons are optionally substituted with cyano or amino;
—$COOR^{11}$; and
—$COR^{12A}$, wherein $R^{12A}$ represents piperazinyl optionally substituted with $C_1$-$C_6$ alkyl; $C_3$-$C_{10}$ cycloalkyl; cyanomethyl; aminomethyl; —$NR^{25}R^{26}$ wherein $R^{25}$ and $R^{26}$ each independently represent hydrogen or $C_1$-$C_6$ alkyl optionally substituted with hydroxyl or —$NR^{43}R^{44}$; or $C_1$-$C_6$ alkylsulfonyl;

wherein substituent B-1 is selected from the group consisting of:
halogen;
hydroxyl;
$C_1$-$C_6$ alkoxy;
cyano;
cycloalkyl;
phenyl optionally substituted with cyano;
heteroaryl selected from the group consisting of imidazolyl, pyrazolyl, and thiazolyl;
3- to 8-membered heterocycloalkyl selected from the group consisting of pyrrolidinyl, piperidyl, piperazinyl, morpholinyl, and oxetanyl any of which are optionally substituted with hydroxyl, amino, $C_1$-$C_6$ aminoalkyl, or $C_1$-$C_6$ alkyl optionally substituted with $C_2$-$C_7$ alkyloxycarbonylamino;
—$NR^{51A}R^{52A}$, wherein $R^{51A}$ and $R^{52A}$ each independently represent hydrogen; $C_1$-$C_6$ alkyl optionally substituted with $C_1$-$C_6$ alkylsulfonyl or piperidyl optionally substituted with —$COOR^{53}$; piperidyl; $C_1$-$C_6$ alkylsulfonyl; $C_3$-$C_{10}$ cycloalkyl; —$COR^{55}$, —$COOR^{56}$, or —$CONR^{57}R^{58}$;
—$COOR^{54}$;
—$CONH_2$;
—$SO_2NR^{106}R^{107}$;
$C_1$-$C_6$ alkylsulfinyl; and
$C_1$-$C_6$ alkylysulfonyl.

8. The compound of claim 7, or a pharmaceutically acceptable salt thereof, wherein $R^4$ is a group selected from group (p):

wherein group (p) is independently selected from the group consisting of:

hydroxyl,
halogen,
amino optionally substituted with a substituent selected from the group consisting of substituent (g),
$C_1$-$C_6$ alkyl optionally substituted with a substituent selected from the group consisting of substituent (a),
$C_2$-$C_6$ alkenyl optionally substituted with a substituent selected from the group consisting of substituent (b),
$C_3$-$C_{10}$ cycloalkyl,
$C_3$-$C_{10}$ cycloalkenyl,
$C_1$-$C_6$ alkoxy,
$C_6$-$C_{10}$ aryl optionally substituted with a substituent selected from the group consisting of substituent (c),
indanyl optionally substituted with a substituent selected from the group consisting of substituent (d),
heteroaryl selected from the group consisting of pyridyl, 1H-indazolyl, 1H-tetrazolyl, [1,2,4]triazolo[1,5-a]pyridyl, benzoimidazolyl, 2,3-dihydrobenzooxazolyl, pyrazolyl, pyrrolo[2,3-b]pyridyl, pyrimidinyl, indolinyl, furyl, thienyl, and tetrahydroisoquinolyl any of which is optionally substituted with a substituent selected from the group consisting of substituent (e); and
3- to 8-membered heterocycloalkyl selected from the group consisting of pyrrolidinyl, piperidyl, piperazinyl, morpholinyl, and 1,2,3,6-tetrahydropyridyl any of which is optionally substituted with a substituent selected from the group consisting of substituent (f);
wherein substituent (a) is selected from the group consisting of:
$NR^{21A}R^{22A}$, wherein $R^{21A}$ and $R^{22A}$ each independently represent hydrogen; $C_1$-$C_6$ alkyl optionally substituted with piperidyl; or piperidyl optionally substituted with —$COOR^{105}$;
3- to 8-membered heterocycloalkyl selected from the group consisting of pyrrolidinyl and piperidyl either of which is optionally substituted with $C_1$-$C_6$ alkyl optionally substituted with —$NR^{41}R^{42}$ or —$NR^{39}R^{40}$ wherein $R^{39}$ and $R^{40}$ each independently represent hydrogen or $C_1$-$C_6$ alkyl; and
—$NHSO_2(C_1$-$C_6$ alkyl);
wherein substituent (b) is selected from the group consisting of:
—$COOR^{11}$;
—$NR^{21a}R^{22a}$, wherein $R^{21a}$ and $R^{22a}$ each independently represent hydrogen, or $C_1$-$C_6$ alkyl optionally substituted with di($C_1$-$C_6$ alkyl)amino or $C_1$-$C_6$ alkylsulfonyl;
3- to 8-membered heterocycloalkyl selected from the group consisting of azetidinyl, pyrrolidinyl, and piperidyl any of which are optionally substituted with —$NR^{39}R^{40}$, $C_1$-$C_6$ alkyl optionally substituted with —$NR^{41}R^{42}$, hydroxyl, or $C_1$-$C_6$ alkylsulfonyl;
cyano; and
$C_1$-$C_6$ alkoxy;
wherein substituent (c) is selected from the group consisting of:
hydroxyl;
cyano;
halogen;
$C_1$-$C_6$ alkyl optionally substituted with a substituent selected from the group consisting of substituent B-c below;
$C_3$-$C_{10}$ cycloalkyl optionally substituted with cyano, or $C_1$-$C_6$ alkyl substituted with —$NR^{31}R^{32}$;
—$NR^{21c}R^{22c}$, wherein $R^{21c}$ and $R^{22c}$ each independently represent hydrogen or $C_1$-$C_6$ alkyl optionally substituted with amino or cyano;
$C_1$-$C_6$ alkoxy optionally substituted with halogen, 3- to 8-membered heterocycloalkyl selected from the group consisting of piperidyl and piperazinyl either of which are optionally substituted with $C_1$-$C_6$ alkyl, or —$NR^{33}R^{34}$;
—$SO_2NR^{23c}R^{24c}$, wherein $R^{23c}$ and $R^{24c}$ each independently represent hydrogen, $C_1$-$C_6$ alkyl optionally substituted with hydroxyl, $C_1$-$C_6$ alkoxy, halogen, $C_3$-$C_{10}$ cycloalkyl, pyrazolyl, imidazolyl, or —$NR^{35}R^{36}$; $C_3$-$C_{10}$cycloalkyl optionally substituted with $C_1$-$C_6$ hydroxyalkyl; azetidinyl, pyrrolidinyl, or wherein $R^{23c}$ and $R^{24c}$ taken together form pyrrolidinyl which is optionally substituted with amino or halogen;
$C_1$-$C_6$ alkylsulfonyl optionally substituted with hydroxyl;
—$NHSO_2(C_1$-$C_6$ alkyl), wherein the carbon atoms are optionally substituted with —$NR^{37}R^{38}$;
piperazinyl optionally substituted with $C_1$-$C_6$ alkyl or $C_1$-$C_6$ alkylsulfonyl;
piperidyl optionally substituted with hydroxyl;
1H-tetrazolyl;
1,2,3,6-tetrahydropyridyl; and
—$COR^{12c}$, wherein $R^{12c}$ represents piperazinyl which is optionally substituted with $C_1$-$C_6$ alkyl, $C_3$-$C_{10}$ cycloalkyl, cyanomethyl, aminomethyl, —$NR^{25}R^{26}$, or $C_1$-$C_6$ alkyl; and
wherein substituent B-c is selected from the group consisting of:
halogen;
hydroxyl;
methoxy;
cyano;
$C_3$-$C_{10}$ cycloalkyl;
3- to 8-membered heterocycloalkyl selected from the group consisting of pyrrolidinyl, piperidyl, piperazinyl, morpholinyl, and oxetanyl, any of which is optionally substituted with $C_1$-$C_6$ alkyl, hydroxyl, amino, $C_1$-$C_6$ aminoalkyl, or $C_1$-$C_6$ alkyl substituted with $C_2$-$C_7$ alkyloxycarbonylamino;
—$NR^{51c}R^{52c}$, wherein $R^{51c}$ and $R^{52c}$ each independently represent hydrogen; $C_1$-$C_6$ alkyl optionally substituted with $C_1$-$C_6$ alkylsulfonyl, or piperidyl optionally substituted with —$COOR^{53}$; piperidyl; $C_1$-$C_6$alkylsulfonyl; $C_3$-$C_{10}$ cycloalkyl; —$COR^{55}$; or —$CONR^{57}R^{58}$;
heteroaryl selected from the group consisting of imidazolyl, pyrazolyl, and thiazolyl;
—$CONH_2$;
—$SO_2NR^{106}R^{107}$;
$C_1$-$C_6$ alkylsufinyl; and
$C_1$-$C_6$ alkylsulfonyl;
wherein substituent (d) is selected from the group consisting of:
—$NR^{21d}R^{22d}$, wherein $R^{21d}$ and $R^{22d}$ each independently represent hydrogen or $C_1$-$C_6$ alkyl;
wherein substituent (e) is selected from the group consisting of:
hydroxyl;
oxo;
cyano;

$C_3$-$C_{10}$ cycloalkyl optionally substituted with cyano;
—NR$^{21e}$R$^{22e}$, wherein R$^{21e}$ and R$^{22e}$ each independently represent hydrogen or $C_1$-$C_6$ alkyl optionally substituted with amino;
piperidyl;
$C_1$-$C_6$ alkoxy optionally substituted with —NR$^{33}$R$^{34}$;
$C_1$-$C_6$ alkyl optionally substituted with cyano; —NR$^{51e}$R$^{52e}$, wherein R$^{51e}$ and R$^{52e}$ each independently represent hydrogen, $C_1$-$C_6$ alkyl, or —COOR$^{56}$; morpholinyl; or cyanophenyl;
—CONH$_2$;
wherein substituent (f) is selected from the group consisting of:
$C_1$-$C_6$ alkyl optionally substituted with —NR$^{51f}$R$^{52f}$, wherein R$^{51f}$ and R$^{52f}$ each independently represent hydrogen, $C_1$-$C_6$ alkyl, or —COOR$^{56}$; and
$C_1$-$C_6$ alkylsulfonyl;
wherein substituent (g) is aryl optionally substituted with $C_1$-$C_6$ alkyl having the aliphatic carbons optionally substituted with cyano or amino.

9. The compound of claim 1, or a pharmaceutically acceptable salt thereof, wherein R$^6$ is hydrogen; hydroxyl; $C_1$-$C_6$ alkyl; phenyl optionally substituted with 1 to 3 hydroxyls; piperidyl optionally substituted with amino; or piperazinyl.

10. The compound of claim 9, or a pharmaceutically acceptable salt thereof, wherein R$^7$ is hydrogen; $C_1$-$C_6$ alkyl optionally substituted with hydroxyl or piperidyl; or halogen.

11. The compound of claim 1, or a pharmaceutically acceptable salt thereof, wherein R$^7$ is
hydrogen;
$C_1$-$C_6$ alkyl optionally substituted with hydroxyl; —NR$^{71A}$R$^{72A}$ wherein R$^{71A}$ and R$^{72A}$ each independently represent hydrogen, $C_1$-$C_6$ alkyl optionally substituted with dimethylamino, $C_3$-$C_{10}$ cycloalkyl optionally substituted with amino, or piperidyl; or 3- to 8-membered heterocycloalkyl selected from the group consisting of piperidyl and morpholinyl either of which is optionally substituted with $C_1$-$C_6$ aminoalkyl;
phenyl optionally substituted with 1 to 2 hydroxyls; phenylsulfonyl; or
—COR$^{73A}$, wherein R$^{73A}$ represents piperidyl optionally substituted with amino, or —NR$^{74A}$R$^{75A}$, wherein R$^{74A}$ and R$^{75A}$ each independently represent hydrogen, piperidyl, or $C_3$-$C_{10}$ cycloalkyl optionally substituted with amino.

12. A compound selected from the group consisting of:
(6): 7,9-dimethoxythieno[2,3-c]quinolin-4(5H)-one;
(7): 7,9-dihydroxythieno[2,3-c]quinolin-4(5H)-one;
(8): 7,8,9-trimethoxythieno[2,3-c]quinolin-4(5H)-one;
(10): 7,8,9-trihydroxythieno[2,3-c]quinolin-4(5H)-one;
(11): 9-(3-(2-aminoethyl)phenyl)-8-methoxythieno[2,3-c]quinolin-4(5H)-one;
(42): 9-bromo-8-hydroxythieno[2,3-c]quinolin-4(5H)-one;
(43): 9-(3,4-dihydroxyphenyl)-8-hydroxythieno[2,3-c]quinolin-4(5H)-one;
(47): 9-(3,5-dihydroxyphenyl)-8-hydroxythieno[2,3-c]quinolin-4(5H)-one;
(48): 8-hydroxy-9-(3-hydroxyphenyl)thieno[2,3-c]quinolin-4(5H)-one;
(49): 8-hydroxy-9-(4-hydroxyphenyl)thieno[2,3-c]quinolin-4(5H)-one;
(50): 9-(3,4-difluorophenyl)-8-methoxythieno[2,3-c]quinolin-4(5H)-one;
(52): 5-(8-methoxy-4-oxo-4,5-dihydrothieno[2,3-c]quinolin-9-yl)picolinonitrile;
(53): 9-(6-aminopyridin-3-yl)-8-hydroxythieno[2,3-c]quinolin-4(5H)-one;
(54): 4-(8-hydroxy-4-oxo-4,5-dihydrothieno[2,3-c]quinolin-9-yl)benzamide;
(55): 9-(3-fluoro-4-hydroxyphenyl)-8-hydroxythieno[2,3-c]quinolin-4(5H)-one;
(58): 9-(3,4-difluorophenyl)-8-hydroxythieno[2,3-c]quinolin-4(5H)-one;
(59): 9-(4-fluoro-3-hydroxyphenyl)-8-hydroxythieno[2,3-c]quinolin-4(5H)-one;
(60): 8-hydroxy-9-(3-hydroxy-5-(trifluoromethyl)phenyl)thieno[2,3-c]quinolin-4(5H)-one;
(61): 8-hydroxy-9-(1H-indazol-6-yl)thieno[2,3-c]quinolin-4(5H)-one;
(62): 8-hydroxy-9-(3,4,5-trihydroxyphenyl)thieno[2,3-c]quinolin-4(5H)-one;
(63): 9-(4-hydroxyphenyl)-8-methoxythieno[2,3-c]quinolin-4(5H)-one;
(64): 9-(4-(1H-tetrazol-5-yl)phenyl)-8-hydroxythieno[2,3-c]quinolin-4(5H)-one;
(65): 4-(8-hydroxy-4-oxo-4,5-dihydrothieno[2,3-c]quinolin-9-yl)benzenesulfonamide;
(66): 9-(3-chloro-4-fluorophenyl)-8-hydroxythieno[2,3-c]quinolin-4(5H)-one;
(67): 9-(4-chloro-3-fluorophenyl)-8-hydroxythieno[2,3-c]quinolin-4(5H)-one;
(68): 9-(3,4-dichlorophenyl)-8-hydroxythieno[2,3-c]quinolin-4(5H)-one;
(69): 9-(4-fluorophenyl)-8-hydroxythieno[2,3-c]quinolin-4(5H)-one;
(70): 8-hydroxy-9-phenylthieno[2,3-c]quinolin-4(5H)-one;
(71): 9-(4-(difluoromethoxy)phenyl)-8-methoxythieno[2,3-c]quinolin-4(5H)-one;
(72): 9-(4-(aminomethyl)phenyl)-8-hydroxythieno[2,3-c]quinolin-4(5H)-one;
(73): 9-(4-(aminomethyl)phenyl)-8-hydroxythieno[2,3-c]quinolin-4(5H)-one;
(74): 9-(3-aminophenyl)-8-hydroxythieno[2,3-c]quinolin-4(5H)-one;
(75): 3-(8-hydroxy-4-oxo-4,5-dihydrothieno[2,3-c]quinolin-9-yl)benzenesulfonamide;
(76): 8-hydroxy-9-(3,4,5-trifluorophenyl)thieno[2,3-c]quinolin-4(5H)-one;
(77): N-(4-(8-hydroxy-4-oxo-4,5-dihydrothieno[2,3-c]quinolin-9-yl)phenyl)methanesulfonamide;
(78): 8-methoxy-9-phenylthieno[2,3-c]quinolin-4(5H)-one;
(79): 8-hydroxy-9-(naphthalen-2-yl)thieno[2,3-c]quinolin-4(5H)-one;
(80): 8-hydroxy-9-(4-(hydroxymethyl)phenyl)thieno[2,3-c]quinolin-4(5H)-one;
(81): 2-(4-(8-hydroxy-4-oxo-4,5-dihydrothieno[2,3-c]quinolin-9-yl)phenyl)acetonitrile;
(82): 8-hydroxy-9-(4-(methylsulfonyl)phenyl)thieno[2,3-c]quinolin-4(5H)-one;
(83): 8-hydroxy-9-(pyridin-4-yl)thieno[2,3-c]quinolin-4(5H)-one;
(84): 8-hydroxy-9-(1,2,3,6-tetrahydropyridin-4-yl)thieno[2,3-c]quinolin-4(5H)-one;
(85): 8-hydroxy-9-(4-hydroxy-3-methoxyphenyl)thieno[2,3-c]quinolin-4(5H)-one;
(86): 9-(3-fluoro-4-(morpholinomethyl)phenyl)-8-hydroxythieno[2,3-c]quinolin-4(5H)-one;
(87): 9-(3-(aminomethyl)phenyl)-8-hydroxythieno[2,3-c]quinolin-4(5H)-one;

(88): 9-(4-(aminomethyl)phenyl)-8-methoxythieno[2,3-c]quinolin-4(5H)-one;
(89): 9-(3-(difluoromethyl)phenyl)-8-methoxythieno[2,3-c]quinolin-4(5H)-one;
(90): 9-(3-(aminomethyl)phenyl)-8-hydroxy-2-methylthieno[2,3-c]quinolin-4(5H)-one;
(91): 9-cyclohexenyl-8-methoxythieno[2,3-c]quinolin-4(5H)-one;
(92): 9-(3,5-difluorophenyl)-8-hydroxythieno[2,3-c]quinolin-4(5H)-one;
(93): 9-(4-(2-(dimethylamino)ethyl)phenyl)-8-hydroxythieno[2,3-c]quinolin-4(5H)-one;
(94): 9-(3-(aminomethyl)phenyl)-8-methoxythieno[2,3-c]quinolin-4(5H)-one;
(95): 9-(4-(aminomethyl)phenyl)-8-hydroxy-2-methylthieno[2,3-c]quinolin-4(5H)-one;
(96): 9-cyclopropyl-8-hydroxythieno[2,3-c]quinolin-4(5H)-one;
(97): 9-([1,2,4]triazolo[1,5-a]pyridin-6-yl)-8-hydroxythieno[2,3-c]quinolin-4(5H)-one;
(98): 8-methoxy-9-(1,2,3,6-tetrahydropyridin-4-yl)thieno[2,3-c]quinolin-4(5H)-one;
(99): 9-cyclohexenyl-8-hydroxythieno[2,3-c]quinolin-4(5H)-one;
(100): 8-methoxy-9-(4-(2-(piperidin-1-yl)ethylamino)phenyl)thieno[2,3-c]quinolin-4(5H)-one;
(101): 9-(4-(aminomethyl)phenyl)-8-hydroxy-2-(morpholinomethyl)thieno[2,3-c]quinolin-4(5H)-one;
(102): 9-(1H-benzo[d]imidazol-5-yl)-8-hydroxythieno[2,3-c]quinolin-4(5H)-one;
(103): 9-(4-(difluoromethyl)phenyl)-8-methoxythieno[2,3-c]quinolin-4(5H)-one;
(104): 9-(4-(aminomethyl)phenyl)-8-methoxy-2-(morpholinomethyl)thieno[2,3-c]quinolin-4(5H)-one;
(105): 8-hydroxy-9-(4-(2-(piperidin-1-yl)ethylamino)phenyl)thieno[2,3-c]quinolin-4(5H)-one;
(106): 8-hydroxy-9-(4-(piperazin-1-yl)phenyl)thieno[2,3-c]quinolin-4(5H)-one;
(109): 5-(8-hydroxy-4-oxo-4,5-dihydrothieno[2,3-c]quinolin-9-yl)benzo[d]oxazol-2(3H)-one;
(110): tert-butyl 4-(2-(hydroxy-4-oxo-4,5-dihydrothieno[2,3-c]quinolin-9-yl)benzylamino)ethyl)piperidine-1-carboxylate;
(111): 8-methoxy-9-(4-(piperazin-1-yl)phenyl)thieno[2,3-c]quinolin-4(5H)-one;
(112): 8-hydroxy-9-(4-(4-(methylsulfonyl)piperazin-1-yl)phenyl)thieno[2,3-c]quinolin-4(5H)-one;
(113): 8-hydroxy-9-(4-((piperidin-3-ylamino)methyl)phenyl)thieno[2,3-c]quinolin-4(5H)-one;
(114): N-(2-(dimethylamino)ethyl)-4-(8-hydroxy-4-oxo-4,5-dihydrothieno[2,3-c]quinolin-9-yl)benzamide;
(115): 9-(4-(3-(dimethylamino)propoxy)phenyl)-8-methoxythieno[2,3-c]quinolin-4(5H)-one;
(116): 8-methoxy-9-(1-(piperidin-4-yl)-1H-pyrazol-4-yl)thieno[2,3-c]quinolin-4(5H)-one;
(117): 8-hydroxy-9-(1-(piperidin-4-yl)-1H-pyrazol-4-yl)thieno[2,3-c]quinolin-4(5H)-one;
(120): N-(2-(dimethylamino)ethyl)-4-(8-methoxy-4-oxo-4,5-dihydrothieno[2,3-c]quinolin-9-yl)benzamide;
(122): (E)-butyl 3-(8-hydroxy-4-oxo-4,5-dihydrothieno[2,3-c]quinolin-9-yl)acrylate;
(123): 8-methoxy-9-(1H-pyrrolo[2,3-b]pyridin-5-yl)thieno[2,3-c]quinolin-4(5H)-one;
(124): 8-hydroxy-9-(1H-pyrrolo[2,3-b]pyridin-5-yl)thieno[2,3-c]quinolin-4(5H)-one;
(125): N-(methoxy-4-oxo-4,5-dihydrothieno[2,3-c]quinolin-9-yl)phenethyl)acetamide;
(126): N-(2-aminoethyl)-4-(8-hydroxy-4-oxo-4,5-dihydrothieno[2,3-c]quinolin-9-yl)benzamide;
(127): N-(2-aminoethyl)-4-(8-methoxy-4-oxo-4,5-dihydrothieno[2,3-c]quinolin-9-yl)benzamide;
(128): N-(hydroxy-4-oxo-4,5-dihydrothieno[2,3-c]quinolin-9-yl)phenethyl)acetamide;
(130): 8-hydroxy-9-(4-(4-methylpiperazine-1-carbonyl)phenyl)thieno[2,3-c]quinolin-4(5H)-one;
(131): 8-methoxy-9-(4-(4-methylpiperazine-1-carbonyl)phenyl)thieno[2,3-c]quinolin-4(5H)-one;
(132): 8-hydroxy-9-(4-((4-methylpiperazin-1-yl)methyl)phenyl)thieno[2,3-c]quinolin-4(5H)-one;
(133): 8-methoxy-9-(4-((4-methylpiperazin-1-yl)methyl)phenyl)thieno[2,3-c]quinolin-4(5H)-one;
(134): (E)-9-(3-(diethylamino)prop-1-enyl)-8-methoxythieno[2,3-c]quinolin-4(5H)-one;
(135): (E)-9-(3-(4-(aminomethyl)piperidin-1-yl)prop-1-enyl)-8-methoxythieno[2,3-c]quinolin-4(5H)-one;
(136): (E)-9-(3-(2-(diethylamino)ethylamino)prop-1-enyl)-8-hydroxythieno[2,3-c]quinolin-4(5H)-one;
(138): 9-(2-(dimethylamino)pyrimidin-5-yl)-8-hydroxythieno[2,3-c]quinolin-4(5H)-one;
(139): tert-butyl (1-(methoxy-4-oxo-4,5-dihydrothieno[2,3-c]quinolin-9-yl)benzyl)piperidin-4-yl)methylcarbamate;
(140): 8-hydroxy-9-(4-(4-methylpiperazin-1-yl)phenyl)thieno[2,3-c]quinolin-4(5H)-one;
(141): 8-methoxy-9-(4-(4-methylpiperazin-1-yl)phenyl)thieno[2,3-c]quinolin-4(5H)-one;
(142): 8-methoxy-9-(1-(methylsulfonyl)-1,2,3,6-tetrahydropyridin-4-yl)thieno[2,3-c]quinolin-4(5H)-one;
(143): (E)-9-(3-(diethylamino)prop-1-enyl)-8-hydroxythieno[2,3-c]quinolin-4(5H)-one;
(144): 9-(3-(4-(aminomethyl)piperidin-1-yl)propyl)-8-methoxythieno[2,3-c]quinolin-4(5H)-one;
(145): 9-(4-(3-(2-(diethylamino)ethylamino)propoxy)phenyl)-8-methoxythieno[2,3-c]quinolin-4(5H)-one;
(146): 9-(4-(3-(diethylamino)propoxy)phenyl)-8-methoxythieno[2,3-c]quinolin-4(5H)-one;
(147): 9-(4-(3-(2-(diethylamino)ethylamino)propoxy)phenyl)-8-hydroxythieno[2,3-c]quinolin-4(5H)-one;
(148): (E)-9-(3-(4-(aminomethyl)piperidin-1-yl)prop-1-enyl)-8-hydroxythieno[2,3-c]quinolin-4 (5H)-one;
(149): 9-(4-(3-(dimethylamino)propoxy)phenyl)-8-hydroxythieno[2,3-c]quinolin-4(5H)-one;
(150): 8-hydroxy-9-(4-(2-(piperidin-1-yl)ethoxy)phenyl)thieno[2,3-c]quinolin-4(5H)-one;
(151): 9-(4-(2-(ethylamino)ethoxy)phenyl)-8-hydroxythieno[2,3-c]quinolin-4(5H)-one;
(152): (E)-9-(3-(4-aminopiperidin-1-yl)prop-1-enyl)-8-methoxythieno[2,3-c]quinolin-4(5H)-one;
(153): 9-(1-(2-aminoethyl)-1,2,3,6-tetrahydropyridin-4-yl)-8-methoxythieno[2,3-c]quinolin-4(5H)-one;
(154): 9-(4-(2-(ethylamino)ethoxy)phenyl)-8-methoxythieno[2,3-c]quinolin-4(5H)-one;
(155): 9-(4-(2-(diethylamino)ethoxy)phenyl)-8-hydroxythieno[2,3-c]quinolin-4(5H)-one;
(156): 9-(4-(2-(diethylamino)ethoxy)phenyl)-8-methoxythieno[2,3-c]quinolin-4(5H)-one;
(157): 9-(4-(2-(dimethylamino)ethoxy)phenyl)-8-hydroxythieno[2,3-c]quinolin-4(5H)-one;
(158): 9-(4-(2-(dimethylamino)ethoxy)phenyl)-8-methoxythieno[2,3-c]quinolin-4(5H)-one;
(159): 8-methoxy-9-(4-(2-(piperidin-1-yl)ethoxy)phenyl)thieno[2,3-c]quinolin-4(5H)-one;
(160): 8-methoxy-9-(3-(2-(4-methylpiperazin-1-yl)ethoxy)phenyl)thieno[2,3-c]quinolin-4(5H)-one;

(161): 9-(3-(2-(diethylamino)ethoxy)phenyl)-8-methoxythieno[2,3-c]quinolin-4(5H)-one;
(162): 9-(3-(3-(diethylamino)propoxy)phenyl)-8-methoxythieno[2,3-c]quinolin-4(5H)-one;
(163): 9-(4-(2-(dimethylamino)ethyl)phenyl)-8-methoxythieno[2,3-c]quinolin-4(5H)-one;
(164): 9-(4-((dimethylamino)methyl)phenyl)-8-methoxythieno[2,3-c]quinolin-4(5H)-one;
(165): 9-(4-((dimethylamino)methyl)phenyl)-8-hydroxythieno[2,3-c]quinolin-4(5H)-one;
(166): 9-(3-(2-(diethylamino)ethoxy)phenyl)-8-hydroxythieno[2,3-c]quinolin-4(5H)-one;
(167): 8-hydroxy-9-(3-(2-(4-methylpiperazin-1-yl)ethoxy)phenyl)thieno[2,3-c]quinolin-4(5H)-one;
(168): N-ethyl-N-(2-(4-(8-methoxy-4-oxo-4,5-dihydrothieno[2,3-c]quinolin-9-yl)phenylmethoxy-4-oxo-4,5-dihydrothieno[2,3-c]quinolin-9-yl)phenoxy)ethyl)methanesulfonamide;
(169): 9-(4-(2-aminoethyl)phenyl)-8-methoxythieno[2,3-c]quinolin-4(5H)-one;
(170): 2-(3-(8-hydroxy-4-oxo-4,5-dihydrothieno[2,3-c]quinolin-9-yl)phenyl)acetonitrile;
(171): 2-(3-(8-methoxy-4-oxo-4,5-dihydrothieno[2,3-c]quinolin-9-yl)phenyl)acetonitrile;
(172): 9-(1-(2-(dimethylamino)ethyl)-1,2,3,6-tetrahydropyridin-4-yl)-8-hydroxythieno[2,3-c]quinolin-4(5H)-one;
(173): N-(hydroxy-4-oxo-4,5-dihydrothieno[2,3-c]quinolin-9-yl)phenethyl)methanesulfonamide;
(174): 9-(1-(2-(diethylamino)ethyl)-1,2,3,6-tetrahydropyridin-4-yl)-8-hydroxythieno[2,3-c]quinolin-4(5H)-one;
(175): 9-(4-(2-aminoethyl)phenyl)-8-hydroxythieno[2,3-c]quinolin-4(5H)-one;
(176): 9-(4-(2-aminoethyl)phenyl)-8-hydroxythieno[2,3-c]quinolin-4(5H)-one;
(177): N-(methoxy-4-oxo-4,5-dihydrothieno[2,3-c]quinolin-9-yl)phenethyl)methanesulfonamide;
(178): N-(methoxy-4-oxo-4,5-dihydrothieno[2,3-c]quinolin-9-yl)phenethyl)methanesulfonamide;
(179): N-(2-aminoethyl)-4-(8-hydroxy-4-oxo-4,5-dihydrothieno[2,3-c]quinolin-9-yl)benzenesulfonamide;
(183): 9-(4-((diethylamino)methyl)phenyl)-8-methoxythieno[2,3-c]quinolin-4(5H)-one;
(184): 9-(4-((diethylamino)methyl)phenyl)-8-hydroxythieno[2,3-c]quinolin-4(5H)-one;
(185): 9-(3-(2-(dimethylamino)ethyl)phenyl)-8-hydroxythieno[2,3-c]quinolin-4(5H)-one;
(186): 9-(3-(2-aminoethyl)phenyl)-8-hydroxythieno[2,3-c]quinolin-4(5H)-one;
(187): 8-hydroxy-9-(4-((methylamino)methyl)phenyl)thieno[2,3-c]quinolin-4(5H)-one;
(188): 8-methoxy-9-(4-((methylamino)methyl)phenyl)thieno[2,3-c]quinolin-4(5H)-one;
(189): 9-(4-amino-3-methoxyphenyl)-8-methoxythieno[2,3-c]quinolin-4(5H)-one;
(190): 3-(8-hydroxy-4-oxo-4,5-dihydrothieno[2,3-c]quinolin-9-yl)benzonitrile;
(191): 9-(4-(1-(dimethylamino)ethyl)phenyl)-8-hydroxythieno[2,3-c]quinolin-4(5H)-one;
(192): 9-(4-(1-(dimethylamino)ethyl)phenyl)-8-hydroxythieno[2,3-c]quinolin-4(5H)-one;
(193): N-(1-(4-(8-hydroxy-4-oxo-4,5-dihydrothieno[2,3-c]quinolin-9-yl)phenyl)ethyl)methanesulfonamide;
(194): 8-hydroxy-9-(4-(1-(pyrrolidin-1-yl)ethyl)phenyl)thieno[2,3-c]quinolin-4(5H)-one;
(195): 9-(4-(1-aminoethyl)phenyl)-8-hydroxythieno[2,3-c]quinolin-4(5H)-one;
(196): 9-(4-(1-(diethylamino)ethyl)phenyl)-8-hydroxythieno[2,3-c]quinolin-4(5H)-one;
(197): N-(2-aminoethyl)-4-(8-methoxy-4-oxo-4,5-dihydrothieno[2,3-c]quinolin-9-yl)benzenesulfonamide;
(198): N-(2-(dimethylamino)ethyl)-4-(8-methoxy-4-oxo-4,5-dihydrothieno[2,3-c]quinolin-9-yl)benzenesulfonamide;
(199): 4-(8-hydroxy-4-oxo-4,5-dihydrothieno[2,3-c]quinolin-9-yl)-N-(pyrrolidin-3-yl)benzenesulfonamide;
(200): N-(azetidin-3-yl)-4-(8-hydroxy-4-oxo-4,5-dihydrothieno[2,3-c]quinolin-9-yl)benzenesulfonamide;
(201): 9-(4-(2-(diethylamino)ethyl)phenyl)-8-hydroxythieno[2,3-c]quinolin-4(5H)-one;
(202): 2-amino-N-(3-(8-methoxy-4-oxo-4,5-dihydrothieno[2,3-c]quinolin-9-yl)phenyl)ethanesulfonamide;
(203): 4-(8-hydroxy-4-oxo-4,5-dihydrothieno[2,3-c]quinolin-9-yl)benzonitrile;
(204): 4-(8-methoxy-4-oxo-4,5-dihydrothieno[2,3-c]quinolin-9-yl)benzonitrile;
(205): (E)-9-(3-(3-aminopyrrolidin-1-yl)prop-1-enyl)-8-methoxythieno[2,3-c]quinolin-4(5H)-one;
(206): N-(2-hydroxyethyl)-4-(8-methoxy-4-oxo-4,5-dihydrothieno[2,3-c]quinolin-9-yl)benzenesulfonamide;
(207): 8-methoxy-9-(5-methoxypyridin-3-yl)thieno[2,3-c]quinolin-4(5H)-one;
(209): 9-(4-(3-aminopyrrolidin-1-ylsulfonyl)phenyl)-8-hydroxythieno[2,3-c]quinolin-4(5H)-one;
(210): N-(2-bromoethyl)-4-(8-hydroxy-4-oxo-4,5-dihydrothieno[2,3-c]quinolin-9-yl)benzenesulfonamide;
(211): 9-(4-((diisopropylamino)methyl)phenyl)-8-methoxythieno[2,3-c]quinolin-4(5H)-one;
(212): N-(hydroxy-4-oxo-4,5-dihydrothieno[2,3-c]quinolin-9-yl)benzyl)methanesulfonamide;
(213): 9-(4-((isopropylamino)methyl)phenyl)-8-methoxythieno[2,3-c]quinolin-4(5H)-one;
(214): 2-(dimethylamino)-N-(3-(8-hydroxy-4-oxo-4,5-dihydrothieno[2,3-c]quinolin-9-yl)phenyl)ethanesulfonamide;
(215): 2-amino-N-(3-(8-hydroxy-4-oxo-4,5-dihydrothieno[2,3-c]quinolin-9-yl)phenyl)ethanesulfonamide;
(216): 8-methoxy-9-(4-(1-(pyrrolidin-1-yl)ethyl)phenyl)thieno[2,3-c]quinolin-4(5H)-one;
(217): 9-(4-amino-3-hydroxyphenyl)-8-hydroxythieno[2,3-c]quinolin-4(5H)-one;
(218): N-(2-methoxy-4-(8-methoxy-4-oxo-4,5-dihydrothieno[2,3-c]quinolin-9-yl)phenyl)methanesulfonamide;
(219): 9-(3,5-difluoro-4-hydroxyphenyl)-8-methoxythieno[2,3-c]quinolin-4(5H)-one;
(220): N-(2-hydroxy-4-(8-hydroxy-4-oxo-4,5-dihydrothieno[2,3-c]quinolin-9-yl)phenyl)methanesulfonamide;
(221): 9-(4-((4-(aminomethyl)piperidin-1-yl)methyl)-3-fluorophenyl)-8-methoxythieno[2,3-c]quinolin-4(5H)-one;
(222): 9-(4-(2-(dimethylamino)ethyl)phenyl)-6-fluoro-8-methoxythieno[2,3-c]quinolin-4(5H)-one;
(223): 9-(3,5-difluoro-4-hydroxyphenyl)-8-hydroxythieno[2,3-c]quinolin-4(5H)-one;
(224): 6-fluoro-8-methoxy-9-(1,2,3,6-tetrahydropyridin-4-yl)thieno[2,3-c]quinolin-4(5H)-one;
(225): 9-(4-(1-(dimethylamino)ethyl)phenyl)-6-fluoro-8-hydroxythieno[2,3-c]quinolin-4(5H)-one;

(226): 9-(4-((diethylamino)methyl)-3-fluorophenyl)-8-methoxythieno[2,3-c]quinolin-4(5H)-one;
(227): (E)-9-(3-(3-hydroxypyrrolidin-1-yl)prop-1-enyl)-8-methoxythieno[2,3-c]quinolin-4(5H)-one;
(228): (E)-8-hydroxy-9-(3-(3-hydroxypyrrolidin-1-yl)prop-1-enyl)thieno[2,3-c]quinolin-4(5H)-one;
(229): 8-hydroxy-9-(4-((isopropylamino)methyl)phenyl)thieno[2,3-c]quinolin-4(5H)-one;
(230): (E)-9-(3-(3-aminoazetidin-1-yl)prop-1-enyl)-8-hydroxythieno[2,3-c]quinolin-4(5H)-one;
(231): (E)-8-methoxy-9-(3-(2-(methylsulfonyl)ethylamino)prop-1-enyl)thieno[2,3-c]quinolin-4(5H)-one;
(232): (S)-9-(4-(1-aminoethyl)phenyl)-8-methoxythieno[2,3-c]quinolin-4(5H)-one;
(233): (S)-9-(4-(1-aminoethyl)phenyl)-8-hydroxythieno[2,3-c]quinolin-4(5H)-one;
(235): 9-(4-((4-(aminomethyl)piperidin-1-yl)methyl)-3-fluorophenyl)-8-hydroxythieno[2,3-c]quinolin-4(5H)-one;
(236): 8-methoxy-9-(4-(1-(2-(methylsulfonyl)ethylamino)ethyl)phenyl)thieno[2,3-c]quinolin-4(5H)-one;
(237): 9-(4-((3-aminopyrrolidin-1-yl)methyl)-3-fluorophenyl)-8-methoxythieno[2,3-c]quinolin-4(5H)-one;
(238): (E)-9-(3-(3-aminoazetidin-1-yl)prop-1-enyl)-8-methoxythieno[2,3-c]quinolin-4(5H)-one;
(239): (E)-9-(3-(ethylamino)prop-1-enyl)-8-hydroxythieno[2,3-c]quinolin-4(5H)-one;
(240): 9-(4-((3-aminopiperidin-1-yl)methyl)-3-fluorophenyl)-8-hydroxythieno[2,3-c]quinolin-4(5H)-one;
(241): 9-(4-((3-aminopyrrolidin-1-yl)methyl)-3-fluorophenyl)-8-hydroxythieno[2,3-c]quinolin-4(5H)-one;
(242): 9-(4-((3-aminopiperidin-1-yl)methyl)-3-fluorophenyl)-8-methoxythieno[2,3-c]quinolin-4(5H)-one;
(243): 8-hydroxy-9-(4-(1-(2-(methylsulfonyl)ethylamino)ethyl)phenyl)thieno[2,3-c]quinolin-4(5H)-one;
(244): (E)-9-(3-(3-aminopiperidin-1-yl)prop-1-enyl)-8-methoxythieno[2,3-c]quinolin-4(5H)-one;
(245): (E)-9-(3-(3-aminopyrrolidin-1-yl)prop-1-enyl)-8-hydroxythieno[2,3-c]quinolin-4(5H)-one;
(246): (E)-9-(3-(3-aminopiperidin-1-yl)prop-1-enyl)-8-hydroxythieno[2,3-c]quinolin-4(5H)-one;
(247): (E)-8-hydroxy-9-(3-(2-(methylsulfonyl)ethylamino)prop-1-enyl)thieno[2,3-c]quinolin-4(5H)-one;
(248): 8-methoxy-9-(4-(2-(2-(methylsulfonyl)ethylamino)ethyl)phenyl)thieno[2,3-c]quinolin-4(5H)-one;
(249): 2-(2-fluoro-4-(8-methoxy-4-oxo-4,5-dihydrothieno[2,3-c]quinolin-9-yl)phenyl)acetonitrile;
(250): (E)-N-(1-(3-(8-methoxy-4-oxo-4,5-dihydrothieno[2,3-c]quinolin-9-yl)allyl)azetidin-3-yl)methanesulfonamide;
(251): 4-(8-methoxy-4-oxo-4,5-dihydrothieno[2,3-c]quinolin-9-yl)-N,N-dimethylbenzenesulfonamide;
(252): 4-(8-hydroxy-4-oxo-4,5-dihydrothieno[2,3-c]quinolin-9-yl)-N-methylbenzenesulfonamide;
(253): tert-butyl (5-(8-methoxy-4-oxo-4,5-dihydrothieno[2,3-c]quinolin-9-yl)furan-2-yl)methylcarbamate;
(254): N-(4-(8-hydroxy-4-oxo-4,5-dihydrothieno[2,3-c]quinolin-9-yl)-2-methylphenyl)methanesulfonamide;
(255): N-(4-(8-methoxy-4-oxo-4,5-dihydrothieno[2,3-c]quinolin-9-yl)-2-methylphenyl)methanesulfonamide;
(256): 9-(4-(aminomethyl)phenyl)-6-fluoro-8-hydroxythieno[2,3-c]quinolin-4(5H)-one;
(257): 9-(4-(aminomethyl)phenyl)-6-fluoro-8-methoxythieno[2,3-c]quinolin-4(5H)-one;
(258): 6-fluoro-8-hydroxy-9-(1,2,3,6-tetrahydropyridin-4-yl)thieno[2,3-c]quinolin-4(5H)-one;
(259): 9-(4-((diethylamino)methyl)-3-fluorophenyl)-8-hydroxythieno[2,3-c]quinolin-4(5H)-one;
(260): 8-methoxy-9-(4-(1-(piperidin-1-yl)ethyl)phenyl)thieno[2,3-c]quinolin-4(5H)-one;
(261): 2-(2-fluoro-4-(8-hydroxy-4-oxo-4,5-dihydrothieno[2,3-c]quinolin-9-yl)phenyl)acetonitrile;
(262): 8-hydroxy-9-(4-(1-(piperidin-1-yl)ethyl)phenyl)thieno[2,3-c]quinolin-4(5H)-one;
(263): (E)-9-(3-(3-(dimethylamino)piperidin-1-yl)prop-1-enyl)-8-hydroxythieno[2,3-c]quinolin-4(5H)-one;
(264): (E)-9-(3-(3-(dimethylamino)pyrrolidin-1-yl)prop-1-enyl)-8-hydroxythieno[2,3-c]quinolin-4(5H)-one;
(265): 9-(4-(2-aminoethyl)-3-fluorophenyl)-8-methoxythieno[2,3-c]quinolin-4(5H)-one;
(266): 9-(5-(aminomethyl)thiophen-2-yl)-8-hydroxythieno[2,3-c]quinolin-4(5H)-one;
(267): 9-(4-((ethylamino)methyl)phenyl)-8-hydroxythieno[2,3-c]quinolin-4(5H)-one;
(268): (E)-9-(3-(4-aminopiperidin-1-yl)prop-1-enyl)-8-hydroxythieno[2,3-c]quinolin-4(5H)-one;
(269): 9-(4-((ethylamino)methyl)phenyl)-8-methoxythieno[2,3-c]quinolin-4(5H)-one;
(270): 9-(4-(aminomethyl)phenyl)-6-bromo-8-hydroxythieno[2,3-c]quinolin-4(5H)-one;
(271): 9-(3-chloro-4-((diethylamino)methyl)phenyl)-8-methoxythieno[2,3-c]quinolin-4(5H)-one;
(272): (R)-9-(4-(1-(dimethylamino)ethyl)phenyl)-8-hydroxythieno[2,3-c]quinolin-4(5H)-one;
(273): 9-(4-(3-aminopropyl)phenyl)-8-hydroxythieno[2,3-c]quinolin-4(5H)-one;
(274): (R)-9-(4-(1-aminoethyl)phenyl)-8-methoxythieno[2,3-c]quinolin-4(5H)-one;
(275): (R)-9-(4-(1-aminoethyl)phenyl)-8-hydroxythieno[2,3-c]quinolin-4(5H)-one;
(276): 9-(4-(2-aminoethyl)-3-fluorophenyl)-8-hydroxythieno[2,3-c]quinolin-4(5H)-one;
(277): 9-(4-(1-amino-2-methylpropan-2-yl)phenyl)-8-hydroxythieno[2,3-c]quinolin-4(5H)-one;
(278): 9-(3-fluoro-4-((3-hydroxypyrrolidin-1-yl)methyl)phenyl)-8-hydroxythieno[2,3-c]quinolin-4(5H)-one;
(279): 9-(3-fluoro-4-((3-hydroxypyrrolidin-1-yl)methyl)phenyl)-8-methoxythieno[2,3-c]quinolin-4(5H)-one;
(280): 4-(8-methoxy-4-oxo-4,5-dihydrothieno[2,3-c]quinolin-9-yl)-N-(2,2,2-trifluoroethyl)benzenesulfonamide;
(281): 4-(8-hydroxy-4-oxo-4,5-dihydrothieno[2,3-c]quinolin-9-yl)-N-(2,2,2-trifluoroethyl)benzenesulfonamide;
(282): N-(2-(dimethylamino)ethyl)-4-(8-hydroxy-4-oxo-4,5-dihydrothieno[2,3-c]quinolin-9-yl)benzenesulfonamide;
(283): 8-hydroxy-9-(4-((2-(methylsulfonyl)ethylamino)methyl)phenyl)thieno[2,3-c]quinolin-4(5H)-one;
(284): 9-(3-(3-(dimethylamino)pyrrolidin-1-yl)propyl)-8-hydroxythieno[2,3-c]quinolin-4(5H)-one;
(285): 9-(1-(2-aminoethyl)-1H-pyrazol-4-yl)-8-methoxythieno[2,3-c]quinolin-4(5H)-one;
(286): 9-(3-chloro-4-((diethylamino)methyl)phenyl)-8-hydroxythieno[2,3-c]quinolin-4(5H)-one;
(287): 4-(7-fluoro-8-methoxy-4-oxo-4,5-dihydrothieno[2,3-c]quinolin-9-yl)-N-(2-hydroxyethyl)benzenesulfonamide;
(288): 9-(3-acetylphenyl)-8-methoxythieno[2,3-c]quinolin-4(5H)-one;
(289): 2-fluoro-4-(8-hydroxy-4-oxo-4,5-dihydrothieno[2,3-c]quinolin-9-yl)-N-(2-hydroxyethyl)benzamide;

(290): 3-(4-(8-hydroxy-4-oxo-4,5-dihydrothieno[2,3-c]quinolin-9-yl)phenyl)propanenitrile;
(291): 9-(4-acetylphenyl)-8-methoxythieno[2,3-c]quinolin-4(5H)-one;
(292): 2-fluoro-N-(2-hydroxyethyl)-4-(8-methoxy-4-oxo-4,5-dihydrothieno[2,3-c]quinolin-9-yl)benzamide;
(293): 4-(8-hydroxy-4-oxo-4,5-dihydrothieno[2,3-c]quinolin-9-yl)-N-(2-hydroxyethyl)benzamide;
(294): 1,1-diethyl-3-(hydroxy-4-oxo-4,5-dihydrothieno[2,3-c]quinolin-9-yl)benzyl)urea;
(295): N-(2-hydroxyethyl)-4-(8-methoxy-4-oxo-4,5-dihydrothieno[2,3-c]quinolin-9-yl)benzamide;
(296): 9-(4-acetylphenyl)-8-hydroxythieno[2,3-c]quinolin-4(5H)-one;
(297): N-(2-bromoethyl)-2-fluoro-4-(8-hydroxy-4-oxo-4,5-dihydrothieno[2,3-c]quinolin-9-yl)benzenesulfonamide;
(298): 9-(3-(3-(dimethylamino)piperidin-1-yl)propyl)-8-hydroxythieno[2,3-c]quinolin-4(5H)-one;
(299): N-(2-fluoro-4-(8-hydroxy-4-oxo-4,5-dihydrothieno[2,3-c]quinolin-9-yl)phenethyl)methanesulfonamide;
(300): 9-(3-fluoro-4-(2-(methylsulfonamido)ethyl)phenyl)-4-oxo-4,5-dihydrothieno[2,3-c]quinolin-8-yl methanesulfonate;
(301): (R)—N-(1-(4-(8-hydroxy-4-oxo-4,5-dihydrothieno[2,3-c]quinolin-9-yl)phenyl)ethyl)methanesulfonamide;
(302): (R)-9-(4-(1-(methylsulfonamido)ethyl)phenyl)-4-oxo-4,5-dihydrothieno[2,3-c]quinolin-8-yl methanesulfonate;
(303): 2-fluoro-N-(2-hydroxyethyl)-4-(8-methoxy-4-oxo-4,5-dihydrothieno[2,3-c]quinolin-9-yl)benzenesulfonamide;
(304): 4-(8-hydroxy-4-oxo-4,5-dihydrothieno[2,3-c]quinolin-9-yl)-N,N-dimethylbenzenesulfonamide;
(305): 9-(4-(2-(dimethylamino)ethyl)phenyl)-7-fluoro-8-methoxythieno[2,3-c]quinolin-4(5H)-one;
(306): N-(2-bromoethyl)-4-(7-fluoro-8-hydroxy-4-oxo-4,5-dihydrothieno[2,3-c]quinolin-9-yl)benzenesulfonamide;
(307): 4-(7-fluoro-8-hydroxy-4-oxo-4,5-dihydrothieno[2,3-c]quinolin-9-yl)-N-(2-hydroxyethyl)benzenesulfonamide;
(308): 9-(4-(1-(dimethylamino)-2-methylpropan-2-yl)phenyl)-8-hydroxythieno[2,3-c]quinolin-4(5H)-one;
(309): N-(2-chloro-4-(8-methoxy-4-oxo-4,5-dihydrothieno[2,3-c]quinolin-9-yl)benzyl)-N-methylmethanesulfonamide;
(310): 4-(8-hydroxy-4-oxo-4,5-dihydrothieno[2,3-c]quinolin-9-yl)-N-(2-methoxyethyl)benzenesulfonamide;
(311): (E)-3-(8-methoxy-4-oxo-4,5-dihydrothieno[2,3-c]quinolin-9-yl)-2-methylacrylonitrile;
(312): N-(2-fluoro-4-(8-methoxy-4-oxo-4,5-dihydrothieno[2,3-c]quinolin-9-yl)phenethyemethanesulfonamide;
(313): 8-hydroxy-9-(4-(1-hydroxyethyl)phenyl)thieno[2,3-c]quinolin-4(5H)-one;
(314): 9-(4-(1-(cyclopentylamino)ethyl)phenyl)-8-hydroxythieno[2,3-c]quinolin-4(5H)-one;
(315): 9-(4-(1-(cyclopentylamino)ethyl)phenyl)-8-methoxythieno[2,3-c]quinolin-4(5H)-one;
(316): 4-(8-hydroxy-4-oxo-4,5-dihydrothieno[2,3-c]quinolin-9-yl)-N-(2-hydroxyethyl)benzenesulfonamide;
(317): 9-(5-(aminomethyl)furan-2-yl)-8-hydroxythieno[2,3-c]quinolin-4(5H)-one;
(318): 9-(3-chloro-4-((methylamino)methyl)phenyl)-8-methoxythieno[2,3-c]quinolin-4(5H)-one;
(319): 9-(4-(2-aminopropan-2-yl)phenyl)-8-hydroxythieno[2,3-c]quinolin-4(5H)-one;
(320): N-(3-hydroxypropyl)-4-(8-methoxy-4-oxo-4,5-dihydrothieno[2,3-c]quinolin-9-yl)benzenesulfonamide;
(321): 2-fluoro-4-(8-hydroxy-4-oxo-4,5-dihydrothieno[2,3-c]quinolin-9-yl)-N-(2-hydroxyethyl)benzenesulfonamide;
(322): 4-(8-hydroxy-4-oxo-4,5-dihydrothieno[2,3-c]quinolin-9-yl)-N-(3-hydroxypropyl)benzenesulfonamide;
(323): N-(3-bromopropyl)-4-(8-hydroxy-4-oxo-4,5-dihydrothieno[2,3-c]quinolin-9-yl)benzenesulfonamide;
(324): 2-fluoro-4-(8-hydroxy-4-oxo-4,5-dihydrothieno[2,3-c]quinolin-9-yl)-N-(2-methoxyethyl)benzenesulfonamide;
(325): 9-(3-chloro-4-((methylamino)methyl)phenyl)-8-hydroxythieno[2,3-c]quinolin-4(5H)-one;
(326): 9-(4-(aminomethyl)phenyl)-4-oxo-4,5-dihydrothieno[2,3-c]quinoline-8-carbonitrile;
(327): 9-(4-(2-(dimethylamino)ethyl)-3-fluorophenyl)-8-hydroxythieno[2,3-c]quinolin-4(5H)-one;
(328): 9-(4-(aminomethyl)phenyl)-6,7-dichloro-8-hydroxythieno[2,3-c]quinolin-4(5H)-one;
(329): 9-(4-(aminomethyl)phenyl)-6-chloro-8-hydroxythieno[2,3-c]quinolin-4(5H)-one;
(330): 9-(4-(aminomethyl)phenyl)-4-oxo-4,5-dihydrothieno[2,3-c]quinolin-8-yl trifluoromethanesulfonate;
(331): 9-(4-(2-(dimethylamino)ethyl)phenyl)-8-methoxythieno[2,3-c]quinolin-4(5H)-one;
(332): N-(2-chloroethyl)-4-(8-hydroxy-4-oxo-4,5-dihydrothieno[2,3-c]quinolin-9-yl)benzenesulfonamide;
(333): N-(2-fluoroethyl)-4-(8-methoxy-4-oxo-4,5-dihydrothieno[2,3-c]quinolin-9-yl)benzenesulfonamide;
(334): 9-(4-(2-aminopropan-2-yl)phenyl)-6-chloro-8-hydroxythieno[2,3-c]quinolin-4(5H)-one;
(335): (S)-9-(4-(1-(dimethylamino)ethyl)phenyl)-8-hydroxythieno[2,3-c]quinolin-4(5H)-one;
(336): 9-(4-(1-aminopropyl)phenyl)-8-hydroxythieno[2,3-c]quinolin-4(5H)-one;
(337): 9-(4-(1-aminopropyl)phenyl)-8-methoxythieno[2,3-c]quinolin-4(5H)-one;
(338): 9-(4-(1-(diethylamino)propyl)phenyl)-8-hydroxythieno[2,3-c]quinolin-4(5H)-one;
(339): 9-(4-(1-(dimethylamino)propyl)phenyl)-8-hydroxythieno[2,3-c]quinolin-4(5H)-one;
(340): 9-amino-8-methoxythieno[2,3-c]quinolin-4(5H)-one;
(341): 9-(4-(1-(dimethylamino)ethyl)phenyl)-6,7-difluoro-8-hydroxythieno[2,3-c]quinolin-4(5H)-one;
(342): 9-(4-(1-(dimethylamino)ethyl)phenyl)-6,7-difluoro-8-methoxythieno[2,3-c]quinolin-4(5H)-one;
(343): N-cyclopropyl-4-(8-methoxy-4-oxo-4,5-dihydrothieno[2,3-c]quinolin-9-yl)benzenesulfonamide;
(344): N-cyclopropyl-4-(8-hydroxy-4-oxo-4,5-dihydrothieno[2,3-c]quinolin-9-yl)benzenesulfonamide;
(345): 9-(2-amino-2,3-dihydro-1H-inden-5-yl)-8-hydroxythieno[2,3-c]quinolin-4(5H)-one;
(346): 9-(4-(1-(dimethylamino)ethyl)phenyl)thieno[2,3-c]quinolin-4(5H)-one;
(347): (S)—N-(1-(4-(8-hydroxy-4-oxo-4,5-dihydrothieno[2,3-c]quinolin-9-yl)phenyl)ethyl)methanesulfonamide;

(348): 9-(4-(1-(aminomethyl)cyclopropyl)phenyl)-8-hydroxythieno[2,3-c]quinolin-4(5H)-one;
(349): 9-(4-(1-(dimethylamino)ethyl)-3-fluorophenyl)-8-hydroxythieno[2,3-c]quinolin-4(5H)-one;
(350): N-(1-(hydroxymethyl)cyclopentyl)-4-(8-methoxy-4-oxo-4,5-dihydrothieno[2,3-c]quinolin-9-yl)benzenesulfonamide;
(351): 9-(2-(diethylamino)-2,3-dihydro-1H-inden-5-yl)-8-hydroxythieno[2,3-c]quinolin-4(5H)-one;
(352): 9-(2-(dimethylamino)-2,3-dihydro-1H-inden-5-yl)-8-hydroxythieno[2,3-c]quinolin-4(5H)-one;
(353): 8-hydroxy-9-(1,2,3,4-tetrahydroisoquinolin-7-yl)thieno[2,3-c]quinolin-4(5H)-one;
(354): 8-methoxy-9-(1,2,3,4-tetrahydroisoquinolin-7-yl)thieno[2,3-c]quinolin-4(5H)-one;
(355): 3-(3-(8-hydroxy-4-oxo-4,5-dihydrothieno[2,3-c]quinolin-9-yl)phenyl)propanenitrile;
(356): 9-(4-(1-(diethylamino)ethyl)-3-fluorophenyl)-8-hydroxythieno[2,3-c]quinolin-4(5H)-one;
(357): 1-(4-(8-methoxy-4-oxo-4,5-dihydrothieno[2,3-c]quinolin-9-yl)phenyl)cyclopropanecarbonitrile;
(358): 9-(2-ethyl-1,2,3,4-tetrahydroisoquinolin-7-yl)-8-hydroxythieno[2,3-c]quinolin-4(5H)-one;
(359): 9-(4-(1-aminoethyl)-3-fluorophenyl)-8-hydroxythieno[2,3-c]quinolin-4(5H)-one;
(360): 3-(3-(8-methoxy-4-oxo-4,5-dihydrothieno[2,3-c]quinolin-9-yl)phenyl)propanenitrile;
(361): 1-(4-(8-hydroxy-4-oxo-4,5-dihydrothieno[2,3-c]quinolin-9-yl)phenyl)cyclopropanecarbonitrile;
(362): 9-(2-amino-2,3-dihydro-1H-inden-5-yl)-8-methoxythieno[2,3-c]quinolin-4(5H)-one;
(363): N-isopentyl-4-(8-methoxy-4-oxo-4,5-dihydrothieno[2,3-c]quinolin-9-yl)benzenesulfonamide;
(364): 9-(2-(dimethylamino)-2,3-dihydro-1H-inden-5-yl)-8-methoxythieno[2,3-c]quinolin-4(5H)-one;
(365): 9-(4-(1-(ethylamino)ethyl)phenyl)-8-methoxythieno[2,3-c]quinolin-4(5H)-one;
(366): 6-chloro-9-(4-(1-(dimethylamino)ethyl)phenyl)-8-hydroxythieno[2,3-c]quinolin-4(5H)-one;
(367): 9-(4-(cyclopropanecarbonyl)phenyl)-8-methoxythieno[2,3-c]quinolin-4(5H)-one;
(368): 9-(4-(aminomethyl)phenyl)-4-oxo-4,5-dihydrothieno[2,3-c]quinoline-8-carboxamide;
(369): 9-(2-aminoethyl)-8-methoxythieno[2,3-c]quinolin-4(5H)-one;
(370): 8-hydroxy-9-(4-(2-hydroxyethylsulfonyl)phenyl)thieno[2,3-c]quinolin-4(5H)-one;
(371): 9-(4-(2-hydroxyethylsulfonyl)phenyl)-8-methoxythieno[2,3-c]quinolin-4(5H)-one;
(372): 9-(1-ethylindolin-5-yl)-8-hydroxythieno[2,3-c]quinolin-4(5H)-one;
(373): 9-(4-(1-aminopropan-2-yl)phenyl)-8-methoxythieno[2,3-c]quinolin-4(5H)-one;
(374): 8-hydroxy-9-(2-methyl-1,2,3,4-tetrahydroisoquinolin-7-yl)thieno[2,3-c]quinolin-4(5H)-one;
(375): 9-(4-(1-aminoethyl)-3-fluorophenyl)-8-methoxythieno[2,3-c]quinolin-4(5H)-one;
(376): 8-hydroxy-9-(1-methylindolin-5-yl)thieno[2,3-c]quinolin-4(5H)-one;
(377): 8-hydroxy-9-(indolin-5-yl)thieno[2,3-c]quinolin-4(5H)-one;
(378): 9-(indolin-5-yl)-8-methoxythieno[2,3-c]quinolin-4(5H)-one;
(379): 9-(4-(1-((dimethylamino)methyl)cyclopropyl)phenyl)-8-hydroxythieno[2,3-c]quinolin-4(5H)-one;
(380): 4-(8-methoxy-4-oxo-4,5-dihydrothieno[2,3-c]quinolin-9-yl)-N-propylbenzenesulfonamide;
(381): N-(cyclopropylmethyl)-4-(8-methoxy-4-oxo-4,5-dihydrothieno[2,3-c]quinolin-9-yl)benzenesulfonamide;
(382): N-(3,3-dimethylbutyl)-4-(8-methoxy-4-oxo-4,5-dihydrothieno[2,3-c]quinolin-9-yl)benzenesulfonamide;
(383): 4-(8-hydroxy-4-oxo-4,5-dihydrothieno[2,3-c]quinolin-9-yl)-N-isopentylbenzenesulfonamide;
(384): N-(3,3-dimethylbutyl)-4-(8-hydroxy-4-oxo-4,5-dihydrothieno[2,3-c]quinolin-9-yl)benzenesulfonamide;
(385): 9-(4-(1-(ethylamino)ethyl)phenyl)-8-hydroxythieno[2,3-c]quinolin-4(5H)-one;
(386): 3-(4-(8-methoxy-4-oxo-4,5-dihydrothieno[2,3-c]quinolin-9-yl)phenyl)-3-oxopropanenitrile;
(387): (E)-9-(2-ethoxyvinyl)-8-methoxythieno[2,3-c]quinolin-4(5H)-one;
(388): N-(1-(4-(8-hydroxy-4-oxo-4,5-dihydrothieno[2,3-c]quinolin-9-yl)phenyl)ethyl)acetamide;
(389): 4-(8-methoxy-4-oxo-4,5-dihydrothieno[2,3-c]quinolin-9-yl)-N-(3,3,3-trifluoropropyl)benzenesulfonamide;
(390): 4-(8-hydroxy-4-oxo-4,5-dihydrothieno[2,3-c]quinolin-9-yl)-N-(1-(hydroxymethyl)cyclopentyl)benzenesulfonamide;
(391): N-(2,2-difluoroethyl)-4-(8-methoxy-4-oxo-4,5-dihydrothieno[2,3-c]quinolin-9-yl)benzenesulfonamide;
(1031): 8-methoxy-9-(4-(1-methoxyethyl)phenyl)thieno[2,3-c]quinolin-4(5H)-one;
(1032): 9-(4-(1-aminoethyl)phenyl)-6-bromo-8-hydroxythieno[2,3-c]quinolin-4(5H)-one;
(1033): 8-methoxy-9-(2-((piperidin-3-ylmethyl)amino)ethyl)thieno[2,3-c]quinolin-4(5H)-one;
(1034): 9-(2-(4-((dimethylamino)methyl)piperidin-1-yl)ethyl)-8-methoxythieno[2,3-c]quinolin-4(5H)-one;
(1035): tert-butyl 4-((2-(8-methoxy-4-oxo-4,5-dihydrothieno[2,3-c]quinolin-9-yl)ethyl)amino)piperidine-1-carboxylate;
(1036): 8-methoxy-9-(2-(piperidin-4-ylamino)ethyl)thieno[2,3-c]quinolin-4(5H)-one;
(1037): 4-(8-hydroxy-4-oxo-4,5-dihydrothieno[2,3-c]quinolin-9-yl)-N-(3,3,3-trifluoropropyl)benzenesulfonamide;
(1039): 9-(4-(1-aminoethyl)phenyl)-6-cyclopropyl-8-hydroxythieno[2,3-c]quinolin-4(5H)-one;
(1040): 9-(4-(1-aminoethyl)phenyl)-8-hydroxy-4-oxo-4,5-dihydrothieno[2,3-c]quinoline-6-carbonitrile;
(1041): 9-(4-(1-aminoethyl)phenyl)-6-chloro-8-hydroxythieno[2,3-c]quinolin-4(5H)-one;
(1042): 8-hydroxy-9-(2-(4-((methylamino)methyl)piperidin-1-yl)ethyl)thieno[2,3-c]quinolin-4(5H)-one;
(1043): 8-methoxy-9-(2-(4-((methylamino)methyl)piperidin-1-yl)ethyl)thieno[2,3-c]quinolin-4(5H)-one;
(1044): 9-(2-(4-((dimethylamino)methyl)piperidin-1-yl)ethyl)-8-hydroxythieno[2,3-c]quinolin-4(5H)-one;
(1045): 9-(4-(1-hydroxypropyl)phenyl)-8-methoxythieno[2,3-c]quinolin-4(5H)-one;
(1046): (R)-8-methoxy-9-(4-(1-(methylamino)ethyl)phenyl)thieno[2,3-c]quinolin-4(5H)-one;
(1049): 9-(4-(4-hydroxypiperidin-4-yl)phenyl)-8-methoxythieno[2,3-c]quinolin-4(5H)-one;
(1051): 8-hydroxy-9-(4-(1,2,3,6-tetrahydropyridin-4-yl)phenyl)thieno[2,3-c]quinolin-4(5H)-one;
(1052): (R)-8-hydroxy-9-(4-(1-(methylamino)ethyl)phenyl)thieno[2,3-c]quinolin-4(5H)-one;
(1053): 8-hydroxy-9-(4-(1-hydroxypropyl)phenyl)thieno[2,3-c]quinolin-4(5H)-one;

(1054): (R)-8-hydroxy-9-(4-(1-hydroxyethyl)phenyl)thieno[2,3-c]quinolin-4(5H)-one;
(1055): 8-hydroxy-9-(4-(4-hydroxypiperidin-4-yl)phenyl)thieno[2,3-c]quinolin-4(5H)-one;
(1056): (S)-8-hydroxy-9-(4-(1-hydroxyethyl)phenyl)thieno[2,3-c]quinolin-4(5H)-one;
(1057): N-(1-hydroxypropan-2-yl)-4-(8-methoxy-4-oxo-4,5-dihydrothieno[2,3-c]quinolin-9-yl)benzenesulfonamide;
(1058): 9-(4-(hydroxy(thiazol-2-yl)methyl)phenyl)-8-methoxythieno[2,3-c]quinolin-4(5H)-one;
(1059): 9-(6-(1-aminoethyl)pyridin-3-yl)-8-hydroxythieno[2,3-c]quinolin-4(5H)-one;
(1060): 9-(4-(4-hydroxybutyl)phenyl)-8-methoxythieno[2,3-c]quinolin-4(5H)-one;
(1061): 2-(4-(8-hydroxy-4-oxo-4,5-dihydrothieno[2,3-c]quinolin-9-yl)phenyl)-2-methylpropanamide;
(1062): N-(1-bromopropan-2-yl)-4-(8-hydroxy-4-oxo-4,5-dihydrothieno[2,3-c]quinolin-9-yl)benzenesulfonamide;
(1063): 8-hydroxy-9-(4-(hydroxy(thiazol-2-yl)methyl)phenyl)thieno[2,3-c]quinolin-4(5H)-one;
(1064): (S)-8-methoxy-9-(4-(1-(methylamino)ethyl)phenyl)thieno[2,3-c]quinolin-4(5H)-one;
(1065): 9-(6-(1-(diethylamino)ethyl)pyridin-3-yl)-8-hydroxythieno[2,3-c]quinolin-4(5H)-one;
(1066): 9-(4-(1-aminoethyl)phenyl)-8-hydroxy-6-methylthieno[2,3-c]quinolin-4(5H)-one;
(1067): 9-(6-(1-aminoethyl)pyridin-3-yl)-8-methoxythieno[2,3-c]quinolin-4(5H)-one;
(1068): 8-hydroxy-9-(4-(4-hydroxybutyl)phenyl)thieno[2,3-c]quinolin-4(5H)-one;
(1069): 9-(4-(3-amino-1-hydroxypropyl)phenyl)-8-methoxythieno[2,3-c]quinolin-4(5H)-one;
(1070): 9-(6-(1-(dimethylamino)ethyl)pyridin-3-yl)-8-hydroxythieno[2,3-c]quinolin-4(5H)-one;
(1071): 9-(6-(1-(dimethylamino)ethyl)pyridin-3-yl)-8-methoxythieno[2,3-c]quinolin-4(5H)-one;
(1072): 4-((4-(8-methoxy-4-oxo-4,5-dihydrothieno[2,3-c]quinolin-9-yl)-1H-pyrazol-1-yl)methyl)benzonitrile;
(1074): 9-(4-((1H-pyrazol-1-yl)methyl)phenyl)-8-methoxythieno[2,3-c]quinolin-4(5H)-one;
(1075): 9-(6-(1-aminoethyl)pyridin-3-yl)-8-methoxythieno[2,3-c]quinolin-4(5H)-one;
(1076): 9-(4-(1-aminoethyl)phenyl)-4-oxo-4,5-dihydrothieno[2,3-c]quinolin-8-yl dimethylcarbamate;
(1077): 9-(4-(1-aminoethyl)phenyl)-4-oxo-4,5-dihydrothieno[2,3-c]quinolin-8-yl isopropyl carbonate;
(1078): 9-(4-((1H-imidazol-1-yl)methyl)phenyl)-8-methoxythieno[2,3-c]quinolin-4(5H)-one;
(1079): N-(2-bromopropyl)-4-(8-hydroxy-4-oxo-4,5-dihydrothieno[2,3-c]quinolin-9-yl)benzenesulfonamide;
(1080): (R)-9-(4-(1-aminoethyl)phenyl)-6,7-dichloro-8-hydroxythieno[2,3-c]quinolin-4(5H)-one;
(1081): (R)-9-(4-(1-aminoethyl)phenyl)-6-chloro-8-hydroxythieno[2,3-c]quinolin-4(5H)-one;
(1082): (S)-8-hydroxy-9-(4-(1-(methylamino)ethyl)phenyl)thieno[2,3-c]quinolin-4(5H)-one;
(1083): 9-(4-(1-aminoethyl)phenyl)-4-oxo-4,5-dihydrothieno[2,3-c]quinolin-8-yl diethylcarbamate;
(1084): 4-(8-hydroxy-4-oxo-4,5-dihydrothieno[2,3-c]quinolin-9-yl)-N-(2-hydroxyethyl)-N-methylbenzenesulfonamide;
(1085): N-(2-hydroxyethyl)-4-(8-methoxy-4-oxo-4,5-dihydrothieno[2,3-c]quinolin-9-yl)-N-methylbenzenesulfonamide;
(1086): 9-(4-((1H-pyrazol-1-yl)methyl)phenyl)-8-hydroxythieno[2,3-c]quinolin-4(5H)-one;
(1087): (S)-6-chloro-8-hydroxy-9-(4-(1-(methylamino)ethyl)phenyl)thieno[2,3-c]quinolin-4(5H)-one;
(1088): 9-(4-(1-aminopropyl)phenyl)-6-chloro-8-hydroxythieno[2,3-c]quinolin-4(5H)-one;
(1089): 9-(4-(1-aminoethyl)phenyl)-4-oxo-4,5-dihydrothieno[2,3-c]quinolin-8-yl morpholine-4-carboxylate;
(1091): 8-bromothieno[2,3-c]quinolin-4(5H)-one;
(1092): 9-(4-(2-(dimethylamino)propyl)phenyl)-8-hydroxythieno[2,3-c]quinolin-4(5H)-one;
(1093): 9-(4-(2-aminopropyl)phenyl)-8-methoxythieno[2,3-c]quinolin-4(5H)-one;
(1095): 9-(4-(2-aminopropyl)phenyl)-8-hydroxythieno[2,3-c]quinolin-4(5H)-one;
(1096): 8-methoxy-9-(1-(2-morpholinoethyl)-1H-pyrazol-4-yl)thieno[2,3-c]quinolin-4(5H)-one;
(1097): 9-(4-(2-(diethylamino)propyl)phenyl)-8-hydroxythieno[2,3-c]quinolin-4(5H)-one;
(1098): 9-(4-(1-aminoethyl)phenyl)-8-hydroxy-6-(hydroxymethyl)thieno[2,3-c]quinolin-4(5H)-one;
(1099): 9-(4-(1-aminoethyl)phenyl)-4-oxo-4,5-dihydrothieno[2,3-c]quinolin-8-yl acetate;
(1100): 9-(1-(1-(dimethylamino)propan-2-yl)-1H-pyrazol-4-yl)-8-methoxythieno[2,3-c]quinolin-4(5H)-one;
(1101): 9-(4-((1H-imidazol-1-yl)methyl)phenyl)-8-hydroxythieno[2,3-c]quinolin-4(5H)-one;
(1102): 9-(4-(aminomethyl)phenyl)-8-(2-morpholinoethoxy)thieno[2,3-c]quinolin-4(5H)-one;
(1103): 8-hydroxy-9-(1-(2-morpholinoethyl)-1H-pyrazol-4-yl)thieno[2,3-c]quinolin-4(5H)-one;
(1104): N-(2-(1H-pyrazol-1-yl)ethyl)-4-(8-hydroxy-4-oxo-4,5-dihydrothieno[2,3-c]quinolin-9-yl)benzenesulfonamide;
(1105): 8-hydroxy-9-(4-(2,2,2-trifluoro-1-hydroxyethyl)phenyl)thieno[2,3-c]quinolin-4(5H)-one;
(1106): 9-(4-(2-aminopropyl)phenyl)-6-chloro-8-hydroxythieno[2,3-c]quinolin-4(5H)-one;
(1107): N-(2-(4-(8-hydroxy-4-oxo-4,5-dihydrothieno[2,3-c]quinolin-9-yl)phenyl)-2-methylpropyl)methanesulfonamide;
(1108): 9-(4-(2-(dimethylamino)propyl)phenyl)-8-methoxythieno[2,3-c]quinolin-4(5H)-one;
(1109): 9-(4-(1-aminoethyl)phenyl)thieno[2,3-c]quinolin-4(5H)-one;
(1110): 9-(1-(1-(dimethylamino)propan-2-yl)-1H-pyrazol-4-yl)-8-hydroxythieno[2,3-c]quinolin-4(5H)-one;
(1111): 9-(4-(1-aminopropan-2-yl)phenyl)-8-hydroxythieno[2,3-c]quinolin-4(5H)-one;
(1112): 9-(4-(1-(dimethylamino)propan-2-yl)phenyl)-8-hydroxythieno[2,3-c]quinolin-4(5H)-one;
(1113): 8-methoxy-9-(4-(2,2,2-trifluoro-1-hydroxyethyl)phenyl)thieno[2,3-c]quinolin-4(5H)-one;
(1114): N-(2-bromoethyl)-4-(8-hydroxy-4-oxo-4,5-dihydrothieno[2,3-c]quinolin-9-yl)-N-methylbenzenesulfonamide;
(1115): N-(2-(1H-imidazol-1-yl)ethyl)-4-(8-hydroxy-4-oxo-4,5-dihydrothieno[2,3-c]quinolin-9-yl)benzenesulfonamide;
(1116): 9-(4-(1-(aminomethyl)cyclopropyl)phenyl)-6-chloro-8-hydroxythieno[2,3-c]quinolin-4(5H)-one;
(1117): 3-(4-(8-(2-(dimethylamino)ethoxy)-4-oxo-4,5-dihydrothieno[2,3-c]quinolin-9-yl)phenyl)propanenitrile;
(1118): (R)-9-(4-(1-aminopropyl)phenyl)-8-methoxythieno[2,3-c]quinolin-4(5H)-one;

(1119): N-(2-chloroethyl)-4-(8-hydroxy-4-oxo-4,5-dihydrothieno[2,3-c]quinolin-9-yl)-N-methylbenzenesulfonamide;
(1120): (S)-9-(4-(1-aminopropyl)phenyl)-8-hydroxythieno[2,3-c]quinolin-4(5H)-one;
(1121): (S)-9-(4-(1-aminopropyl)phenyl)-8-methoxythieno[2,3-c]quinolin-4(5H)-one;
(1122): (R)-9-(4-(1-aminoethyl)phenyl)-8-hydroxy-6-methylthieno[2,3-c]quinolin-4(5H)-one;
(1123): (R)-9-(4-(1-aminoethyl)phenyl)-6-bromo-8-hydroxythieno[2,3-c]quinolin-4(5H)-one;
(1124): 9-(4-(1-aminoethyl)phenyl)-4-oxo-4,5-dihydrothieno[2,3-c]quinoline-8-carbonitrile;
(1125): 9-(4-(1-aminoethyl)phenyl)-8-(hydroxymethyl)thieno[2,3-c]quinolin-4(5H)-one;
(1126): (R)-6-chloro-9-(4-(1-(dimethylamino)ethyl)phenyl)-8-hydroxythieno[2,3-c]quinolin-4(5H)-one;
(1127): (S)-9-(4-(1-(ethylamino)propyl)phenyl)-8-hydroxythieno[2,3-c]quinolin-4(5H)-one;
(1128): (S)-9-(4-(1-(dimethylamino)propyl)phenyl)-8-hydroxythieno[2,3-c]quinolin-4(5H)-one;
(1129): 6-chloro-9-(4-(1-(dimethylamino)propan-2-yl)phenyl)-8-hydroxythieno[2,3-c]quinolin-4(5H)-one;
(1130): 9-(4-(1-aminoethyl)phenyl)-6-ethynyl-8-hydroxythieno[2,3-c]quinolin-4(5H)-one;
(1131): (R)-9-(4-(1-aminopropyl)phenyl)-8-hydroxythieno[2,3-c]quinolin-4(5H)-one;
(1132): (R)-6-chloro-8-hydroxy-9-(4-(1-(methylamino)ethyl)phenyl)thieno[2,3-c]quinolin-4(5H)-one;
(1133): 9-(4-(2-aminoethyl)phenyl)-6-chloro-8-hydroxythieno[2,3-c]quinolin-4(5H)-one;
(1134): 9-(4-(1-aminoethyl)phenyl)-8-(difluoromethyl)thieno[2,3-c]quinolin-4(5H)-one;
(1135): (R)-6-bromo-8-hydroxy-9-(4-(1-(methylamino)ethyl)phenyl)thieno[2,3-c]quinolin-4(5H)-one;
(1136): 9-(4-(1-aminopropan-2-yl)phenyl)-6-chloro-8-hydroxythieno[2,3-c]quinolin-4(5H)-one;
(1137): 9-(4-butylphenyl)-8-methoxythieno[2,3-c]quinolin-4(5H)-one;
(1138): 9-(4-butylphenyl)-8-hydroxythieno[2,3-c]quinolin-4(5H)-one;
(1139): N-(2-chloroethyl)-4-(8-methoxy-4-oxo-4,5-dihydrothieno[2,3-c]quinolin-9-yl)benzenesulfonamide;
(1140): 9-(4-((3-bromopyrrolidin-1-yl)sulfonyl)phenyl)-8-hydroxythieno[2,3-c]quinolin-4(5H)-one;
(1141): (S)-9-(4-(1-(methylsulfonamido)propyl)phenyl)-4-oxo-4,5-dihydrothieno[2,3-c]quinolin-8-yl methanesulfonate;
(1142): 9-(4-(2-aminoethyl)phenyl)-6-bromo-8-hydroxythieno[2,3-c]quinolin-4(5H)-one;
(1143): 9-(4-(3-(dimethylamino)-1-hydroxypropyl)phenyl)-8-methoxythieno[2,3-c]quinolin-4(5H)-one;
(1144): N-(2-bromoethyl)-4-(6-chloro-8-hydroxy-4-oxo-4,5-dihydrothieno[2,3-c]quinolin-9-yl)benzenesulfonamide;
(1146): N-(2-bromoethyl)-4-(5-ethyl-8-hydroxy-4-oxo-4,5-dihydrothieno[2,3-c]quinolin-9-yl)benzenesulfonamide;
(1147): (S)-8-methoxy-9-(4-(1-(methylamino)propyl)phenyl)thieno[2,3-c]quinolin-4(5H)-one;
(1148): (S)-8-hydroxy-9-(4-(1-(methylamino)propyl)phenyl)thieno[2,3-c]quinolin-4(5H)-one;
(1149): 9-(4-(1-aminoethyl)phenyl)-8-(((2-hydroxyethyl)amino)methyl)thieno[2,3-c]quinolin-4(5H)-one;
(1150): (R)-9-(4-(1-aminopropyl)phenyl)-6-bromo-8-hydroxythieno[2,3-c]quinolin-4(5H)-one;
(1151): (R)-9-(4-(1-(dimethylamino)propyl)phenyl)-8-hydroxythieno[2,3-c]quinolin-4(5H)-one;
(1152): 8-hydroxy-9-(4-pentylphenyl)thieno[2,3-c]quinolin-4(5H)-one;
(1153): 9-(4-(2-aminoacetyl)phenyl)-8-hydroxythieno[2,3-c]quinolin-4(5H)-one;
(1154): (S)-6-chloro-8-hydroxy-9-(4-(1-(methylamino)propyl)phenyl)thieno[2,3-c]quinolin-4(5H)-one;
(1155): 8-hydroxy-9-(4-(2-(methylamino)ethyl)phenyl)thieno[2,3-c]quinolin-4(5H)-one;
(1156): 8-methoxy-9-(4-(2-(methylamino)ethyl)phenyl)thieno[2,3-c]quinolin-4(5H)-one;
(1157): (R)-9-(4-(1-aminopropyl)phenyl)-8-hydroxy-6-methylthieno[2,3-c]quinolin-4(5H)-one;
(1158): (R)-9-(4-(1-aminopropyl)phenyl)-8-methoxy-6-methylthieno[2,3-c]quinolin-4(5H)-one;
(1159): (R)-9-(4-(1-aminopropyl)phenyl)-6-chloro-8-hydroxythieno[2,3-c]quinolin-4(5H)-one;
(1160): (R)-9-(4-(1-aminopropan-2-yl)phenyl)-8-hydroxythieno[2,3-c]quinolin-4(5H)-one;
(1161): (R)-9-(4-(1-aminopropan-2-yl)phenyl)-8-methoxythieno[2,3-c]quinolin-4(5H)-one;
(1162): 2-(4-(8-hydroxy-4-oxo-4,5-dihydrothieno[2,3-c]quinolin-9-yl)phenyl)butanenitrile;
(1163): (S)-9-(4-(1-aminopropan-2-yl)phenyl)-8-hydroxythieno[2,3-c]quinolin-4(5H)-one;
(1164): (S)-9-(4-(1-aminopropan-2-yl)phenyl)-8-methoxythieno[2,3-c]quinolin-4(5H)-one;
(1165): 6-chloro-8-hydroxy-9-(4-(2-(methylamino)ethyl)phenyl)thieno[2,3-c]quinolin-4(5H)-one;
(1166): (R)-9-(4-(1-aminopropan-2-yl)phenyl)-6-chloro-8-hydroxythieno[2,3-c]quinolin-4(5H)-one;
(1167): 9-(4-(2-aminoethyl)-3,5-difluorophenyl)-8-hydroxythieno[2,3-c]quinolin-4(5H)-one;
(1168): (R)-9-(4-(1-aminopropan-2-yl)phenyl)-8-hydroxy-6-methylthieno[2,3-c]quinolin-4(5H)-one;
(1169): (R)-9-(4-(1-aminopropan-2-yl)phenyl)-8-hydroxy-6-methylthieno[2,3-c]quinolin-4(5H)-one;
(1170): 6-chloro-8-methoxy-9-(4-(2-(methylamino)ethyl)phenyl)thieno[2,3-c]quinolin-4(5H)-one;
(1171): 9-(4-(2-aminoethyl)-3-chlorophenyl)-8-hydroxythieno[2,3-c]quinolin-4(5H)-one;
(1172): (S)-9-(4-(1-(dimethylamino)propan-2-yl)phenyl)-8-hydroxythieno[2,3-c]quinolin-4(5H)-one;
(1173): 6-bromo-8-methoxy-9-(4-(2-(methylamino)ethyl)phenyl)thieno[2,3-c]quinolin-4(5H)-one;
(1174): 9-(4-(1-aminopropan-2-yl)-3-fluorophenyl)-8-hydroxythieno[2,3-c]quinolin-4(5H)-one;
(1175): (R)-9-(4-(1-aminopropyl)phenyl)-6-chloro-8-methoxythieno[2,3-c]quinolin-4(5H)-one;
(1176): (R)-9-(4-(1-aminopropan-2-yl)phenyl)-6-bromo-8-hydroxythieno[2,3-c]quinolin-4(5H)-one;
(1177): 9-(4-(2-aminoethyl)-3,5-difluorophenyl)-8-methoxythieno[2,3-c]quinolin-4(5H)-one;
(1178): 9-(4-(2-(dimethylamino)ethyl)-3,5-difluorophenyl)-8-hydroxythieno[2,3-c]quinolin-4(5H)-one;
(1179): 9-(4-(1-aminopropan-2-yl)-3-fluorophenyl)-8-methoxythieno[2,3-c]quinolin-4(5H)-one;
(1180): (S)-9-(4-(1-aminopropan-2-yl)phenyl)-6,7-dichloro-8-methoxythieno[2,3-c]quinolin-4(5H)-one;
(1181): (S)-9-(4-(1-aminopropan-2-yl)phenyl)-6-chloro-8-hydroxythieno[2,3-c]quinolin-4(5H)-one;
(1182): (S)-6-chloro-9-(4-(1-(dimethylamino)propan-2-yl)phenyl)-8-hydroxythieno[2,3-c]quinolin-4(5H)-one;
(1183): 6-bromo-8-hydroxy-9-(4-(2-(methylamino)ethyl)phenyl)thieno[2,3-c]quinolin-4(5H)-one;

(1185): N-(2-hydroxyethyl)-4-(8-methoxy-5-methyl-4-oxo-4,5-dihydrothieno[2,3-c]quinolin-9-yl)benzenesulfonamide;
(1186): methyl 3-(4-(8-hydroxy-4-oxo-4,5-dihydrothieno[2,3-c]quinolin-9-yl)phenyl)propanoate;
(1187): (R)-8-hydroxy-9-(4-(1-(methylamino)propan-2-yl)phenyl)thieno[2,3-c]quinolin-4(5H)-one;
(1188): (R)-9-(4-(1-(dimethylamino)propan-2-yl)phenyl)-8-hydroxythieno[2,3-c]quinolin-4(5H)-one;
(1189): (R)-8-methoxy-9-(4-(1-(methylamino)propan-2-yl)phenyl)thieno[2,3-c]quinolin-4(5H)-one;
(1190): 9-(4-(1-aminopropan-2-yl)-3-fluorophenyl)-8-hydroxy-6-methylthieno[2,3-c]quinolin-4(5H)-one;
(1191): 9-(4-(2-aminoethyl)phenyl)-8-hydroxy-6-methylthieno[2,3-c]quinolin-4(5H)-one;
(1192): 9-(4-(2-aminoethyl)phenyl)-8-methoxy-6-methylthieno[2,3-c]quinolin-4(5H)-one;
(1193): 9-(4-(1-(dimethylamino)propan-2-yl)-3-fluorophenyl)-8-hydroxy-6-methylthieno[2,3-c]quinolin-4(5H)-one;
(1194): (S)-6-chloro-8-hydroxy-9-(4-(1-(methylamino)propan-2-yl)phenyl)thieno[2,3-c]quinolin-4(5H)-one;
(1195): (S)-6-chloro-9-(4-(1-(diethylamino)propan-2-yl)phenyl)-8-hydroxythieno[2,3-c]quinolin-4(5H)-one;
(1196): (S)-8-methoxy-9-(4-(1-(methylamino)propan-2-yl)phenyl)thieno[2,3-c]quinolin-4(5H)-one;
(1197): (S)-8-hydroxy-9-(4-(1-(methylamino)propan-2-yl)phenyl)thieno[2,3-c]quinolin-4(5H)-one;
(1198): 4-(8-hydroxy-5-methyl-4-oxo-4,5-dihydrothieno[2,3-c]quinolin-9-yl)-N-(2-hydroxyethyl)benzenesulfonamide;
(1199): N-(2-bromoethyl)-4-(8-hydroxy-5-methyl-4-oxo-4,5-dihydrothieno[2,3-c]quinolin-9-yl)benzenesulfonamide;
(1200): (R)-6-chloro-9-(4-(1-(dimethylamino)propan-2-yl)phenyl)-8-methoxythieno[2,3-c]quinolin-4(5H)-one;
(1201): (R)-9-(4-(1-aminopropan-2-yl)phenyl)-6-chloro-8-methoxythieno[2,3-c]quinolin-4(5H)-one;
(1202): 9-(4-(1-aminobutan-2-yl)phenyl)-8-methoxythieno[2,3-c]quinolin-4(5H)-one;
(1203): 9-(4-(2-aminopropan-2-yl)phenyl)-8-hydroxy-2-(phenylsulfonyl)thieno[2,3-c]quinolin-4(5H)-one;
(1204): N-(1-chloropropan-2-yl)-4-(8-hydroxy-4-oxo-4,5-dihydrothieno[2,3-c]quinolin-9-yl)benzenesulfonamide;
(1205): N-(1-chloropropan-2-yl)-4-(8-methoxy-4-oxo-4,5-dihydrothieno[2,3-c]quinolin-9-yl)benzenesulfonamide;
(1206): 9-(4-(2-aminoethyl)-3-hydroxyphenyl)-8-hydroxythieno[2,3-c]quinolin-4(5H)-one;
(1207): 9-(4-(2-aminoethyl)-3-methoxyphenyl)-8-methoxythieno[2,3-c]quinolin-4(5H)-one;
(1208): 9-(4-(2-aminoethyl)-2-chloro-5-methoxyphenyl)-8-methoxythieno[2,3-c]quinolin-4(5H)-one;
(1209): 9-(4-(3-(aminomethyl)pentan-3-yl)phenyl)-8-hydroxythieno[2,3-c]quinolin-4(5H)-one;
(1210): (R)-9-(4-(1-aminopropyl)phenyl)-8-hydroxy-5,6-dimethylthieno[2,3-c]quinolin-4(5H)-one;
(1211): 9-(4-(2-aminoethyl)-2-chloro-5-hydroxyphenyl)-6-chloro-8-hydroxythieno[2,3-c]quinolin-4(5H)-one;
(1212): 9-(4-(aminomethyl)phenyl)-8-hydroxy-6-methylthieno[2,3-c]quinolin-4(5H)-one;
(1213): 9-(4-(2-aminoethyl)-3-fluorophenyl)-6-bromo-8-hydroxythieno[2,3-c]quinolin-4(5H)-one;
(1214): 9-(4-(2-aminoethyl)-3-fluorophenyl)-6-bromo-8-methoxythieno[2,3-c]quinolin-4(5H)-one;
(1215): (S)-8-hydroxy-6-methyl-9-(4-(1-(methylamino)propan-2-yl)phenyl)thieno[2,3-c]quinolin-4(5H)-one;
(1216): 9-(4-(2-aminoethyl)-3-fluorophenyl)-8-methoxy-6-methylthieno[2,3-c]quinolin-4(5H)-one;
(1217): 9-(4-(2-aminoethyl)-3-fluorophenyl)-8-hydroxy-6-methylthieno[2,3-c]quinolin-4(5H)-one;
(1218): 9-(4-(2-aminoethyl)-3-fluorophenyl)-6-chloro-8-methoxythieno[2,3-c]quinolin-4(5H)-one;
(1219): 9-(4-(2-aminoethyl)-3-fluorophenyl)-6-chloro-8-hydroxythieno[2,3-c]quinolin-4(5H)-one;
(1220): 9-(4-(2-aminoethyl)-3-fluorophenyl)-6-cyclopropyl-8-methoxythieno[2,3-c]quinolin-4(5H)-one;
(1221): 9-(4-(2-aminoethyl)-3-fluorophenyl)-6-cyclopropyl-8-hydroxythieno[2,3-c]quinolin-4(5H)-one;
(1222): (S)-8-methoxy-6-methyl-9-(4-(1-(methylamino)propan-2-yl)phenyl)thieno[2,3-c]quinolin-4(5H)-one;
(1223): (S)-9-(4-(1-aminopropan-2-yl)phenyl)-8-methoxy-6-methylthieno[2,3-c]quinolin-4(5H)-one;
(1224): 9-(4-(2-aminoethyl)-2-bromo-5-hydroxyphenyl)-8-hydroxythieno[2,3-c]quinolin-4(5H)-one;
(1225): (S)-9-(4-(1-aminoethyl)phenyl)-8-hydroxy-6-methylthieno[2,3-c]quinolin-4(5H)-one;
(1226): 3-(4-(8-hydroxy-6-methyl-4-oxo-4,5-dihydrothieno[2,3-c]quinolin-9-yl)phenyl)propanenitrile;
(1227): 9-(4-(1-amino-2-methylpropan-2-yl)phenyl)-8-methoxy-6-methylthieno[2,3-c]quinolin-4(5H)-one;
(1228): 9-(4-(1-amino-2-methylpropan-2-yl)phenyl)-8-hydroxy-6-methylthieno[2,3-c]quinolin-4(5H)-one;
(1229): 2-(2-fluoro-4-(8-hydroxy-6-methyl-4-oxo-4,5-dihydrothieno[2,3-c]quinolin-9-yl)phenyl)propanenitrile;
(1230): 6-cyclopropyl-9-(4-(2-(dimethylamino)ethyl)-3-fluorophenyl)-8-hydroxythieno[2,3-c]quinolin-4(5H)-one;
(1231): 6-cyclopropyl-9-(4-(2-(dimethylamino)ethyl)-3-fluorophenyl)-8-methoxythieno[2,3-c]quinolin-4(5H)-one;
(1232): (S)-9-(4-(1-aminopropan-2-yl)phenyl)-8-hydroxy-6-methylthieno[2,3-c]quinolin-4(5H)-one;
(1233): (S)-9-(4-(1-(dimethylamino)propan-2-yl)phenyl)-8-hydroxy-6-methylthieno[2,3-c]quinolin-4(5H)-one;
(1234): 9-(3-fluoro-4-(2-(methylamino)ethyl)phenyl)-8-methoxythieno[2,3-c]quinolin-4(5H)-one;
(1235): 9-(3-fluoro-4-(2-(methylamino)ethyl)phenyl)-8-hydroxythieno[2,3-c]quinolin-4(5H)-one;
(1236): 9-(4-(2-amino-1-cyclopentylethyl)phenyl)-8-hydroxythieno[2,3-c]quinolin-4(5H)-one;
(1237): 9-(4-(2-amino-1,1-dicyclopentylethyl)phenyl)-8-methoxythieno[2,3-c]quinolin-4(5H)-one;
(1238): 3-(4-(8-methoxy-6-methyl-4-oxo-4,5-dihydrothieno[2,3-c]quinolin-9-yl)phenyl)propanenitrile;
(1239): 9-(4-(2-amino-1-cyclopentylethyl)phenyl)-8-methoxythieno[2,3-c]quinolin-4(5H)-one;
(1240): 9-(4-(1-amino-2-methylpropan-2-yl)phenyl)-6-cyclopropyl-8-hydroxythieno[2,3-c]quinolin-4(5H)-one;
(1241): 9-(4-(3-aminopropyl)phenyl)-8-methoxy-6-methylthieno[2,3-c]quinolin-4(5H)-one;
(1242): 9-(4-(2-aminopropyl)phenyl)-8-hydroxy-6-methylthieno[2,3-c]quinolin-4(5H)-one;
(1243): 9-(4-(2-aminopropyl)phenyl)-8-methoxy-6-methylthieno[2,3-c]quinolin-4(5H)-one;
(1244): 9-(4-(1-amino-2-methylpropan-2-yl)phenyl)-6-cyclopropyl-8-methoxythieno[2,3-c]quinolin-4(5H)-one;
(1245): 6-bromo-9-(3-fluoro-4-(2-(methylamino)ethyl)phenyl)-8-hydroxythieno[2,3-c]quinolin-4(5H)-one;

(1246): 6-bromo-9-(3-fluoro-4-(2-(methylamino)ethyl) phenyl)-8-methoxythieno[2,3-c]quinolin-4(5H)-one;
(1247): 9-(4-(1-amino-2-methylpropan-2-yl)phenyl)-6-bromo-8-hydroxythieno[2,3-c]quinolin-4(5H)-one;
(1248): 9-(4-(1-amino-2-methylpropan-2-yl)phenyl)-6-bromo-8-methoxythieno[2,3-c]quinolin-4(5H)-one;
(1249): (R)-9-(4-(1-aminopropan-2-yl)phenyl)-6-methyl-4-oxo-4,5-dihydrothieno[2,3-c]quinoline-8-carbonitrile;
(1250): (R)-9-(4-(1-aminoethyl)phenyl)-8-hydroxy-6-vinylthieno[2,3-c]quinolin-4(5H)-one;
(1251): 9-(4-(1-(aminomethyl)cyclopropyl)phenyl)-8-methoxy-6-methylthieno[2,3-c]quinolin-4(5H)-one;
(1252): 9-(4-(1-amino-3-methylbutan-2-yl)phenyl)-8-hydroxythieno[2,3-c]quinolin-4(5H)-one;
(1253): 9-(4-(1-amino-3-methylbutan-2-yl)phenyl)-8-methoxythieno[2,3-c]quinolin-4(5H)-one;
(1254): 9-(4-(1-(aminomethyl)cyclopropyl)phenyl)-8-hydroxy-6-methylthieno[2,3-c]quinolin-4(5H)-one;
(1255): (R)-9-(4-(1-aminoethyl)phenyl)-6-ethyl-8-hydroxythieno[2,3-c]quinolin-4(5H)-one;
(1256): (R)-9-(4-(1-aminoethyl)phenyl)-6-(difluoromethyl)-8-hydroxythieno[2,3-c]quinolin-4(5H)-one;
(1257): 9-(3-fluoro-4-(2-(methylamino)ethyl)phenyl)-8-methoxy-6-methylthieno[2,3-c]quinolin-4(5H)-one;
(1258): 9-(3-fluoro-4-(2-(methylamino)ethyl)phenyl)-8-hydroxy-6-methylthieno[2,3-c]quinolin-4(5H)-one;
(1259): 6-bromo-9-(4-(1-(dimethylamino)-2-methylpropan-2-yl)phenyl)-8-hydroxythieno[2,3-c]quinolin-4(5H)-one;
(1260): 9-(4-(1-amino-2-methylpropan-2-yl)phenyl)-6-chloro-8-hydroxythieno[2,3-c]quinolin-4(5H)-one;
(1261): 9-(4-(3-aminopropyl)phenyl)-8-hydroxy-6-methylthieno[2,3-c]quinolin-4(5H)-one;
(1262): (R)-8-hydroxy-6-methyl-9-(4-(1-(methylamino)ethyl)phenyl)thieno[2,3-c]quinolin-4(5H)-one;
(1263): 9-(4-(2-aminoethyl)-3-chlorophenyl)-8-methoxy-6-methylthieno[2,3-c]quinolin-4(5H)-one;
(1264): 9-(4-(2-aminoethyl)-3-chlorophenyl)-8-hydroxy-6-methylthieno[2,3-c]quinolin-4(5H)-one;
(1265): (R)-8-methoxy-6-methyl-9-(4-(1-(methylamino)ethyl)phenyl)thieno[2,3-c]quinolin-4(5H)-one;
(1266): 9-(4-(2-aminopropyl)phenyl)-6-ethyl-8-hydroxythieno[2,3-c]quinolin-4(5H)-one;
(1267): (R)-9-(4-(1-aminoethyl)phenyl)-6-butyl-8-hydroxythieno[2,3-c]quinolin-4(5H)-one;
(1268): 9-(4-(2-aminoethyl)-3-chlorophenyl)-6-chloro-8-hydroxythieno[2,3-c]quinolin-4(5H)-one;
(1269): 9-(4-(2-aminopropyl)phenyl)-6-ethyl-8-methoxythieno[2,3-c]quinolin-4(5H)-one;
(1270): 2-(4-(8-methoxy-4-oxo-4,5-dihydrothieno[2,3-c]quinolin-9-yl)phenyl)-2-(oxetan-3-yl)acetonitrile;
(1271): 9-(4-(1-amino-2-methylpropan-2-yl)-3-fluorophenyl)-8-hydroxythieno[2,3-c]quinolin-4(5H)-one;
(1272): (R)-6-ethyl-8-hydroxy-9-(4-(1-(methylamino)ethyl)phenyl)thieno[2,3-c]quinolin-4(5H)-one;
(1273): 9-(4-(1-aminopropan-2-yl)-3-fluorophenyl)-8-methoxy-6-methylthieno[2,3-c]quinolin-4(5H)-one;
(1274): 9-(4-(1-amino-3-methylbutan-2-yl)phenyl)-8-hydroxy-6-methylthieno[2,3-c]quinolin-4(5H)-one;
(1275): 9-(4-(1-aminopropan-2-yl)-3-chlorophenyl)-8-methoxy-6-methylthieno[2,3-c]quinolin-4(5H)-one;
(1276): 9-(4-(1-aminopropan-2-yl)-3-chlorophenyl)-8-methoxythieno[2,3-c]quinolin-4(5H)-one;
(1277): 9-(4-(1-aminobutan-2-yl)phenyl)-8-methoxy-6-methylthieno[2,3-c]quinolin-4(5H)-one;

(1278): 9-(4-(1-amino-2-methylpropan-2-yl)-3-fluorophenyl)-8-hydroxy-6-methylthieno[2,3-c]quinolin-4(5H)-one;
(1279): 9-(4-(1-aminopropan-2-yl)-3-chlorophenyl)-8-hydroxy-6-methylthieno[2,3-c]quinolin-4(5H)-one;
(1280): 9-(4-(1-aminopropan-2-yl)-3-chlorophenyl)-8-hydroxythieno[2,3-c]quinolin-4(5H)-one;
(1281): 9-(4-(2-amino-2-methylpropyl)phenyl)-8-methoxythieno[2,3-c]quinolin-4(5H)-one;
(1282): 9-(4-(2-amino-2-methylpropyl)phenyl)-8-hydroxythieno[2,3-c]quinolin-4(5H)-one;
(1283): 9-(4-(1-amino-3-methylbutan-2-yl)-3-fluorophenyl)-8-methoxy-6-methylthieno[2,3-c]quinolin-4(5H)-one;
(1284): 8-methoxy-6-methyl-9-(4-(3-methyl-1-(methylamino)butan-2-yl)phenyl)thieno[2,3-c]quinolin-4(5H)-one;
(1285): 8-hydroxy-6-methyl-9-(4-(3-methyl-1-(methylamino)butan-2-yl)phenyl)thieno[2,3-c]quinolin-4(5H)-one;
(1286): 9-(3-fluoro-4-(1-(methylamino)propan-2-yl)phenyl)-8-methoxy-6-methylthieno[2,3-c]quinolin-4(5H)-one;
(1287): 9-(4-(1-amino-2-methylpropan-2-yl)-3-fluorophenyl)-8-methoxythieno[2,3-c]quinolin-4(5H)-one;
(1288): 9-(4-(1-amino-3-methylbutan-2-yl)-3-fluorophenyl)-8-hydroxy-6-methylthieno[2,3-c]quinolin-4(5H)-one;
(1289): 9-(4-(2-amino-2-methylpropyl)phenyl)-6-bromo-8-methoxythieno[2,3-c]quinolin-4(5H)-one;
(1290): 9-(4-(1-(aminomethyl)cyclobutyl)phenyl)-8-hydroxy-6-methylthieno[2,3-c]quinolin-4(5H)-one;
(1291): 9-(4-(1-aminobutan-2-yl)phenyl)-8-hydroxy-6-methylthieno[2,3-c]quinolin-4(5H)-one;
(1292): 9-(4-(2-amino-2-methylpropyl)phenyl)-6-bromo-8-hydroxythieno[2,3-c]quinolin-4(5H)-one;
(1293): 9-(3-fluoro-4-(1-(methylamino)propan-2-yl)phenyl)-8-hydroxy-6-methylthieno[2,3-c]quinolin-4(5H)-one;
(1294): 9-(3-fluoro-4-(3-methyl-1-(methylamino)butan-2-yl)phenyl)-8-hydroxy-6-methylthieno[2,3-c]quinolin-4(5H)-one;
(1295): 9-(4-(1-(dimethylamino)-3-methylbutan-2-yl)phenyl)-8-methoxy-6-methylthieno[2,3-c]quinolin-4(5H)-one;
(1296): 9-(4-(1-(dimethylamino)-3-methylbutan-2-yl)-3-fluorophenyl)-8-hydroxy-6-methylthieno[2,3-c]quinolin-4(5H)-one;
(1297): 9-(4-(1-(aminomethyl)cyclobutyl)phenyl)-8-methoxy-6-methylthieno[2,3-c]quinolin-4(5H)-one;
(1298): (R)-8-methoxy-6-methyl-9-(4-(1-(methylamino)propan-2-yl)phenyl)thieno[2,3-c]quinolin-4(5H)-one;
(1299): 9-(4-(1-(aminomethyl)cyclobutyl)phenyl)-8-methoxythieno[2,3-c]quinolin-4(5H)-one;
(1300): 9-(4-(1-(aminomethyl)cyclobutyl)phenyl)-8-hydroxythieno[2,3-c]quinolin-4(5H)-one;
(1301): 8-methoxy-6-methyl-9-(4-(piperidin-3-yl)phenyl)thieno[2,3-c]quinolin-4(5H)-one;
(1302): 8-hydroxy-6-methyl-9-(4-(piperidin-3-yl)phenyl)thieno[2,3-c]quinolin-4(5H)-one;
(1303): (S)-9-(4-(1-aminopropan-2-yl)-3-fluorophenyl)-8-hydroxy-6-methylthieno[2,3-c]quinolin-4(5H)-one;
(1304): (S)-9-(4-(1-aminopropan-2-yl)-3-fluorophenyl)-8-hydroxy-6-methylthieno[2,3-c]quinolin-4(5H)-one;
(1305): (R)-9-(4-(1-aminopropan-2-yl)phenyl)-8-methoxy-6-methylthieno[2,3-c]quinolin-4(5H)-one;

(1306): (R)-8-hydroxy-6-methyl-9-(4-(1-(methylamino) propan-2-yl)phenyl)thieno[2,3-c]quinolin-4(5H)-one;
(1307): (R)-8-hydroxy-6-methyl-9-(4-(1-(methylamino) propan-2-yl)phenyl)thieno[2,3-c]quinolin-4(5H)-one;
(1309): 9-(4-(1-aminobutan-2-yl)phenyl)-8-hydroxythieno[2,3-c]quinolin-4(5H)-one;
(1310): (S)-9-(4-(1-aminopropan-2-yl)-3-fluorophenyl)-8-methoxy-6-methylthieno[2,3-c]quinolin-4(5H)-one;
(1311): (R)-9-(4-(1-(dimethylamino)propan-2-yl)-3-fluorophenyl)-8-hydroxy-6-methylthieno[2,3-c]quinolin-4(5H)-one;
(1312): 9-(4-(1-aminobutan-2-yl)phenyl)-6-chloro-8-hydroxythieno[2,3-c]quinolin-4(5H)-one;
(1314): 9-amino-8-methoxy-6-methylthieno[2,3-c]quinolin-4(5H)-one;
(1315): (R)-9-(3-fluoro-4-(1-(methylamino)propan-2-yl) phenyl)-8-hydroxy-6-methylthieno[2,3-c]quinolin-4(5H)-one;
(1316): (R)-9-(3-fluoro-4-(1-(methylamino)propan-2-yl) phenyl)-8-methoxy-6-methylthieno[2,3-c]quinolin-4(5H)-one;
(1317): (R)-9-(4-(1-aminopropan-2-yl)-3-fluorophenyl)-8-methoxy-6-methylthieno[2,3-c]quinolin-4(5H)-one;
(1318): (R)-9-(4-(1-aminopropan-2-yl)-3-fluorophenyl)-8-hydroxy-6-methylthieno[2,3-c]quinolin-4(5H)-one;
(1319): (R)-9-(4-(1-aminopropan-2-yl)-3-fluorophenyl)-8-hydroxy-6-methylthieno[2,3-c]quinolin-4(5H)-one;
(1320): 9-((4-(2-aminoethyl)phenyl)amino)-8-methoxy-6-methylthieno[2,3-c]quinolin-4(5H)-one;
(1321): 9-(4-(1-(aminomethyl)cyclobutyl)phenyl)-6-chloro-8-methoxythieno[2,3-c]quinolin-4(5H)-one;
(1324): (R)-9-(4-(1-(dimethylamino)propan-2-yl)phenyl)-8-hydroxy-6-methylthieno[2,3-c]quinolin-4(5H)-one;
(1325): 9-((4-(aminomethyl)phenyl)amino)-8-hydroxy-6-methylthieno[2,3-c]quinolin-4(5H)-one;
(1326): 9-((4-(aminomethyl)phenyl)amino)-8-methoxy-6-methylthieno[2,3-c]quinolin-4(5H)-one;
(1327): 9-((4-(1-aminopropan-2-yl)phenyl)amino)-8-methoxy-6-methylthieno[2,3-c]quinolin-4(5H)-one;
(1328): 9-((4-(1-aminopropan-2-yl)phenyl)amino)-8-hydroxy-6-methylthieno[2,3-c]quinolin-4(5H)-one;
(1329): 9-(4-(2-aminopropan-2-yl)phenyl)-8-methoxy-6-methylthieno[2,3-c]quinolin-4(5H)-one;
(1330): 9-(4-(2-aminopropan-2-yl)phenyl)-8-hydroxy-6-methylthieno[2,3-c]quinolin-4(5H)-one;
(1331): 9-(4-(3-(aminomethyl)pentan-3-yl)phenyl)-8-methoxy-6-methylthieno[2,3-c]quinolin-4(5H)-one;
(1332): 9-(4-((R)-1-aminopropan-2-yl)phenyl)-8-hydroxy-2-(1-hydroxyethyl)thieno[2,3-c]quinolin-4(5H)-one;
(1333): 9-(4-((R)-1-aminopropan-2-yephenyl)-2-(1-hydroxyethyl)-8-methoxythieno[2,3-c]quinolin-4(5H)-one;
(1334): 3-(4-((8-methoxy-6-methyl-4-oxo-4,5-dihydrothieno[2,3-c]quinolin-9-yl)amino)phenyl)propanenitrile;
(1335): 9-((3-(2-aminoethyl)phenyl)amino)-8-methoxy-6-methylthieno[2,3-c]quinolin-4(5H)-one;
(1336): 9-((4-(2-aminoethyl)phenyl)amino)-8-hydroxy-6-methylthieno[2,3-c]quinolin-4(5H)-one;
(1337): 9-(4-(2-(ethylamino)propyl)phenyl)-8-hydroxy-6-methylthieno[2,3-c]quinolin-4(5H)-one;
(1338): 9-(4-(3-(aminomethyl)pentan-3-yl)phenyl)-8-methoxythieno[2,3-c]quinolin-4(5H)-one;
(1339): 9-(4-(3-(aminomethyl)pentan-3-yl)phenyl)-8-hydroxy-6-methylthieno[2,3-c]quinolin-4(5H)-one;
(1340): (R)-9-(4-(1-aminopropan-2-yl)phenyl)-8-hydroxy-2,6-dimethylthieno[2,3-c]quinolin-4(5H)-one;
(1341): (R)-9-(4-(1-aminopropan-2-yl)phenyl)-8-methoxy-2,6-dimethylthieno[2,3-c]quinolin-4(5H)-one;
(1342): 9-(4-((R)-1-aminopropan-2-yl)phenyl)-2-(1-hydroxyethyl)-8-methoxy-6-methylthieno[2,3-c]quinolin-4(5H)-one;
(1343): 2-((4(4-(8-methoxy-6-methyl-4-oxo-4,5-dihydrothieno[2,3-c]quinolin-9-yl)phenyl)amino)acetonitrile;
(1344): (R)-9-(4-(1-aminobutan-2-yl)phenyl)-8-methoxy-6-methylthieno[2,3-c]quinolin-4(5H)-one;
(1345): 9-(3-chloro-4-(2-(ethylamino)ethyl)phenyl)-8-methoxythieno[2,3-c]quinolin-4(5H)-one;
(1346): 9-(4-(3-((dimethylamino)methyl)pentan-3-yl) phenyl)-8-hydroxy-6-methylthieno[2,3-c]quinolin-4(5H)-one;
(1347): (R)-6-chloro-9-(4-(1-(dimethylamino)propan-2-yl)phenyl)-8-hydroxythieno[2,3-c]quinolin-4(5H)-one;
(1348): 9-(4-(2-(ethylamino)ethyl)phenyl)-8-hydroxy-6-methylthieno[2,3-c]quinolin-4(5H)-one;
(1349): 9-(4-(2-(ethylamino)ethyl)phenyl)-8-methoxy-6-methylthieno[2,3-c]quinolin-4(5H)-one;
(1350): 9-(4-(2-(ethyl(methyl)amino)propyl)phenyl)-8-hydroxy-6-methylthieno[2,3-c]quinolin-4(5H)-one;
(1351): 2-(hydroxy(piperidin-4-yl)methyl)-8-methoxy-6-methylthieno[2,3-c]quinolin-4(5H)-one;
(1352): (R)-9-(4-(1-aminobutan-2-yl)phenyl)-8-hydroxy-6-methylthieno[2,3-c]quinolin-4(5H)-one;
(1353): (R)-9-(4-(1-aminopropan-2-yl)phenyl)-2-chloro-8-hydroxy-6-methylthieno[2,3-c]quinolin-4(5H)-one;
(1354): (R)-9-(4-(1-aminopropan-2-yl)phenyl)-2-chloro-8-methoxy-6-methylthieno[2,3-c]quinolin-4(5H)-one;
(1355): 8-methoxy-6-methyl-9-(4-(2-(methylamino) ethyl)phenyl)thieno[2,3-c]quinolin-4(5H)-one;
(1356): 9-(4-(2-(ethyl(methyl)amino)ethyl)phenyl)-8-hydroxy-6-methylthieno[2,3-c]quinolin-4(5H)-one;
(1357): 9-(4-(3-(aminomethyl)pentan-3-yl)phenyl)-6-chloro-8-methoxythieno[2,3-c]quinolin-4(5H)-one;
(1358): 9-(4-(3-((dimethylamino)methyl)pentan-3-yl) phenyl)-8-hydroxythieno[2,3-c]quinolin-4(5H)-one;
(1359): 9-(6-(dimethylamino)pyridin-3-yl)-8-methoxy-6-methylthieno[2,3-c]quinolin-4(5H)-one;
(1360): (R)-9-(4-(1-(dimethylamino)butan-2-yl)phenyl)-8-hydroxy-6-methylthieno[2,3-c]quinolin-4(5H)-one;
(1361): (R)-8-methoxy-6-methyl-9-(4-(1-(methylamino) butan-2-yl)phenyl)thieno[2,3-c]quinolin-4(5H)-one;
(1362): 9-(4-(3-((diethylamino)methyl)pentan-3-yl)phenyl)-8-hydroxy-6-methylthieno[2,3-c]quinolin-4(5H)-one;
(1363): 9-(3-chloro-4-(2-(ethylamino)ethyl)phenyl)-8-hydroxythieno[2,3-c]quinolin-4(5H)-one;
(1364): 8-hydroxy-6-methyl-9-(4-(2-(methylamino)ethyl) phenyl)thieno[2,3-c]quinolin-4(5H)-one;
(1365): (R)-9-(4-(1-(dimethylamino)butan-2-yl)phenyl)-8-methoxy-6-methylthieno[2,3-c]quinolin-4(5H)-one;
(1366): (R)-9-(4-(1-(ethyl(methyl)amino)butan-2-yl)phenyl)-8-methoxy-6-methylthieno[2,3-c]quinolin-4(5H)-one;
(1367): (R)-9-(4-(1-(diethylamino)butan-2-yl)phenyl)-8-hydroxy-6-methylthieno[2,3-c]quinolin-4(5H)-one;
(1368): (R)-9-(4-(1-(ethyl(methyl)amino)butan-2-yl)phenyl)-8-hydroxy-6-methylthieno[2,3-c]quinolin-4(5H)-one;
(1369): 2-((4-(8-methoxy-6-methyl-4-oxo-4,5-dihydrothieno[2,3-c]quinolin-9-yl)phenyl)(methyl)amino) acetonitrile;

(1370): 2-((4-(8-hydroxy-6-methyl-4-oxo-4,5-dihydrothieno[2,3-c]quinolin-9-yl)phenyl)(methyl)amino)acetonitrile;

(1371): 9-(3-chloro-4-(2-(ethyl(methyl)amino)ethyl)phenyl)-8-hydroxythieno[2,3-c]quinolin-4(5H)-one;

(1372): 9-(4-(1-((dimethylamino)methyl)cyclobutyl)phenyl)-8-hydroxy-6-methylthieno[2,3-c]quinolin-4(5H)-one;

(1373): (R)-9-(4-(1-aminopropyl)phenyl)-6-bromo-8-methoxythieno[2,3-c]quinolin-4(5H)-one;

(1374): 9-(6-(2-aminoethoxy)pyridin-3-yl)-8-hydroxy-6-methylthieno[2,3-c]quinolin-4(5H)-one;

(1375): (R)-9-(4-(1-aminopropan-2-yl)phenyl)-2-fluoro-8-methoxy-6-methylthieno[2,3-c]quinolin-4(5H)-one;

(1376): 9-(6-(2-aminoethoxy)pyridin-3-yl)-8-methoxy-6-methylthieno[2,3-c]quinolin-4(5H)-one;

(1377): 9-(4-(1-amino-2,2,2-trifluoroethyl)phenyl)-8-hydroxy-6-methylthieno[2,3-c]quinolin-4(5H)-one;

(1378): 9-(4-(1-amino-2,2,2-trifluoroethyl)phenyl)-8-methoxy-6-methylthieno[2,3-c]quinolin-4(5H)-one;

(1379): (R)-9-(4-(1-(ethyl(methyl)amino)propan-2-yl)phenyl)-8-hydroxy-6-methylthieno[2,3-c]quinolin-4(5H)-one;

(1380): (R)-8-hydroxy-6-methyl-9-(4-(1-(methylamino)butan-2-yl)phenyl)thieno[2,3-c]quinolin-4(5H)-one;

(1381): 9-(4-(1-amino-2,2,2-trifluoroethyl)phenyl)-8-methoxythieno[2,3-c]quinolin-4(5H)-one;

(1383): (R)-9-(4-(1-aminopropan-2-yl)phenyl)-2-fluoro-8-hydroxy-6-methylthieno[2,3-c]quinolin-4(5H)-one;

(1384): 9-(6-((2-aminoethyl)amino)pyridin-3-yl)-8-hydroxy-6-methylthieno[2,3-c]quinolin-4(5H)-one;

(1385): 9-(6-((2-aminoethyl)amino)pyridin-3-yl)-8-methoxy-6-methylthieno[2,3-c]quinolin-4(5H)-one;

(1386): (S)-6-chloro-9-(4-(1-(ethyl(methyl)amino)propan-2-yl)phenyl)-8-hydroxythieno[2,3-c]quinolin-4(5H)-one;

(1387): (S)-9-(4-(1-(dimethylamino)propan-2-yl)-3-fluorophenyl)-8-methoxy-6-methylthieno[2,3-c]quinolin-4(5H)-one;

(1388): (R)-9-(4-(1-(diethylamino)propan-2-yl)phenyl)-8-hydroxy-6-methylthieno[2,3-c]quinolin-4(5H)-one;

(1389): 9-(4-(1-amino-2,2,2-trifluoroethyl)phenyl)-8-hydroxythieno[2,3-c]quinolin-4(5H)-one;

(1390): 9-(4-(1-amino-2,2,2-trifluoroethyl)phenyl)-6-bromo-8-methoxythieno[2,3-c]quinolin-4(5H)-one;

(1391): 9-(4-(1-(aminomethyl)cyclopropyl)phenyl)-6-bromo-8-methoxythieno[2,3-c]quinolin-4(5H)-one;

(1392): (4-(8-hydroxy-6-methyl-4-oxo-4,5-dihydrothieno[2,3-c]quinolin-9-yl)phenyl)methanesulfonamide;

(1393): 8-methoxy-6-methyl-9-(4-(2-(methylsulfinyl)ethyl)phenyl)thieno[2,3-c]quinolin-4(5H)-one;

(1394): 8-hydroxy-6-methyl-9-(4-((methylsulfonyl)methyl)phenyl)thieno[2,3-c]quinolin-4(5H)-one;

(1395): (4-(8-methoxy-6-methyl-4-oxo-4,5-dihydrothieno[2,3-c]quinolin-9-yl)phenyl)methanesulfonamide;

(1396): 9-(4-((2-aminoethyl)(methyl)amino)phenyl)-8-methoxy-6-methylthieno[2,3-c]quinolin-4(5H)-one;

(1397): (R)—N-(2-(2-fluoro-4-(8-hydroxy-6-methyl-4-oxo-4,5-dihydrothieno[2,3-c]quinolin-9-yl)phenyl)propyl)methanesulfonamide;

(1398): (R)—N-(2-(2-fluoro-4-(8-methoxy-6-methyl-4-oxo-4,5-dihydrothieno[2,3-c]quinolin-9-yl)phenyl)propyl)methanesulfonamide;

(1399): (S)-9-(4-(1-(dimethylamino)propan-2-yl)-3-fluorophenyl)-8-hydroxy-6-methylthieno[2,3-c]quinolin-4(5H)-one;

(1400): 9-(4-((2-aminoethyl)(methyl)amino)phenyl)-8-hydroxy-6-methylthieno[2,3-c]quinolin-4(5H)-one;

(1401): 9-(4-(1-(aminomethyl)cyclopropyl)phenyl)-6-bromo-8-hydroxythieno[2,3-c]quinolin-4(5H)-one;

(1402): 2-(6-(8-methoxy-6-methyl-4-oxo-4,5-dihydrothieno[2,3-c]quinolin-9-yl)pyridin-3-yl)acetonitrile;

(1403): 8-hydroxy-6-methyl-9-(4-(2-(methylsulfinyl)ethyl)phenyl)thieno[2,3-c]quinolin-4(5H)-one;

(1404): 8-methoxy-6-methyl-9-(4-((methylsulfonyl)methyl)phenyl)thieno[2,3-c]quinolin-4(5H)-one;

(1405): 5-(8-methoxy-6-methyl-4-oxo-4,5-dihydrothieno[2,3-c]quinolin-9-yl)nicotinamide;

(1406): 2-(5-(8-hydroxy-4-oxo-4,5-dihydrothieno[2,3-c]quinolin-9-yl)pyridin-2-yl)propanenitrile;

(1407): 2-(4-(8-methoxy-6-methyl-4-oxo-4,5-dihydrothieno[2,3-c]quinolin-9-yl)phenyl)propanamide;

(1408): 9-(6-(1-aminopropan-2-yl)pyridin-3-yl)-8-methoxy-6-methylthieno[2,3-c]quinolin-4(5H)-one;

(1409): 2-(5-(8-methoxy-6-methyl-4-oxo-4,5-dihydrothieno[2,3-c]quinolin-9-yl)pyridin-2-yl)-2-methylpropanenitrile;

(1410): 2-hydroxy-2-(4-(8-hydroxy-4-oxo-4,5-dihydrothieno[2,3-c]quinolin-9-yl)phenyl)propane-1-sulfonamide;

(1411): N-(tert-butyl)-2-hydroxy-2-(4-(8-methoxy-4-oxo-4,5-dihydrothieno[2,3-c]quinolin-9-yl)phenyl)propane-1-sulfonamide;

(1412): 2-(4-(8-hydroxy-6-methyl-4-oxo-4,5-dihydrothieno[2,3-c]quinolin-9-yl)phenyl)propanamide;

(1413): 2-(4-(8-hydroxy-4-oxo-4,5-dihydrothieno[2,3-c]quinolin-9-yl)phenyl)propane-1-sulfonamide;

(1414): 9-(4-(2-amino-1-fluoroethyl)phenyl)-8-methoxy-6-methylthieno[2,3-c]quinolin-4(5H)-one;

(1415): 9-(6-(1-aminopropan-2-yl)pyridin-3-yl)-8-hydroxy-6-methylthieno[2,3-c]quinolin-4(5H)-one;

(1416): 2-(5-(8-hydroxy-6-methyl-4-oxo-4,5-dihydrothieno[2,3-c]quinolin-9-yl)pyridin-2-yl)-2-methylpropanenitrile;

(1417): 2-(5-(8-hydroxy-4-oxo-4,5-dihydrothieno[2,3-c]quinolin-9-yl)pyridin-2-yl)-2-methylpropanenitrile;

(1418): 2-(5-(8-methoxy-4-oxo-4,5-dihydrothieno[2,3-c]quinolin-9-yl)pyridin-2-yl)-2-methylpropanenitrile;

(1419): 2-(4-(8-hydroxy-6-methyl-4-oxo-4,5-dihydrothieno[2,3-c]quinolin-9-yl)phenyl)propane-1-sulfonamide;

(1420): 9-(4-(2-amino-1-hydroxyethyl)phenyl)-8-methoxy-6-methylthieno[2,3-c]quinolin-4(5H)-one;

(1421): 9-(6-(1-amino-2-methylpropan-2-yl)pyridin-3-yl)-8-hydroxythieno[2,3-c]quinolin-4(5H)-one;

(1422): N-cyclopropyl-1-(4-(8-methoxy-6-methyl-4-oxo-4,5-dihydrothieno[2,3-c]quinolin-9-yl)phenyl)methanesulfonamide;

(1423): 2-(5-(8-methoxy-4-oxo-4,5-dihydrothieno[2,3-c]quinolin-9-yl)pyridin-2-yl)propanenitrile;

(1424): (R)—N-(2-(4-(8-methoxy-6-methyl-4-oxo-4,5-dihydrothieno[2,3-c]quinolin-9-yl)phenyl)propyl)methanesulfonamide;

(1425): N-ethyl-1-(4-(8-methoxy-6-methyl-4-oxo-4,5-dihydrothieno[2,3-c]quinolin-9-yl)phenyl)methanesulfonamide;

(1426): 9-(6-(1-aminopropan-2-yl)pyridin-3-yl)-8-methoxythieno[2,3-c]quinolin-4(5H)-one;

(1427): N-cyclopropyl-1-(4-(8-hydroxy-6-methyl-4-oxo-4,5-dihydrothieno[2,3-c]quinolin-9-yl)phenyl)methanesulfonamide;

(1428): 1-(5-(8-methoxy-4-oxo-4,5-dihydrothieno[2,3-c]quinolin-9-yl)pyridin-2-yl)cyclopropanecarbonitrile;

(1429): N-ethyl-1-(4-(8-hydroxy-6-methyl-4-oxo-4,5-dihydrothieno[2,3-c]quinolin-9-yl)phenyl)methanesulfonamide;

(1430): 1-(4-(8-methoxy-6-methyl-4-oxo-4,5-dihydrothieno[2,3-c]quinolin-9-yl)phenyl)ethanesulfonamide;

(1431): 1-(4-(8-methoxy-4-oxo-4,5-dihydrothieno[2,3-c]quinolin-9-yl)phenyl)ethanesulfonamide;

(1432): (R)—N-(2-(4-(8-methoxy-4-oxo-4,5-dihydrothieno[2,3-c]quinolin-9-yl)phenyl)propyl)methanesulfonamide;

(1433): (R)—N-(2-(4-(8-hydroxy-4-oxo-4,5-dihydrothieno[2,3-c]quinolin-9-yl)phenyl)propyl)-N-methylmethanesulfonamide;

(1434): (R)—N-(2-(4-(8-hydroxy-6-methyl-4-oxo-4,5-dihydrothieno[2,3-c]quinolin-9-yl)phenyl)propyl)methanesulfonamide;

(1435): (R)—N-(2-(4-(8-hydroxy-4-oxo-4,5-dihydrothieno[2,3-c]quinolin-9-yl)phenyl)propyl)methanesulfonamide;

(1436): (R)—N-(2-(4-(8-methoxy-4-oxo-4,5-dihydrothieno[2,3-c]quinolin-9-yl)phenyl)propyl)-N-methylmethanesulfonamide;

(1437): (R)—N-(2-(4-(8-hydroxy-6-methyl-4-oxo-4,5-dihydrothieno[2,3-c]quinolin-9-yl)phenyl)propyl)-N-methylmethanesulfonamide;

(1438): (R)—N-(2-(4-(8-methoxy-6-methyl-4-oxo-4,5-dihydrothieno[2,3-c]quinolin-9-yl)phenyl)propyl)-N-methylmethanesulfonamide;

or a pharmaceutically acceptable salt thereof.

13. A pharmaceutical composition comprising at least one compound of claim 1 or a pharmaceutically acceptable salt thereof, and a pharmaceutically acceptable carrier.

14. A method of killing a PBK dependent cancer cell in a subject in need thereof, comprising administering to said subject an effective amount of a compound or a pharmaceutically acceptable salt thereof of claim 1.

* * * * *